(12) United States Patent
Tanaka et al.

(10) Patent No.: US 9,624,215 B2
(45) Date of Patent: Apr. 18, 2017

(54) AMINE DERIVATIVE OR SALT THEREOF

(71) Applicants: TOYAMA CHEMICAL CO., LTD., Shinjuku-ku (JP); FUJIFILM CORPORATION, Minato-ku (JP)

(72) Inventors: Tadashi Tanaka, Toyama (JP); Yoshitake Konishi, Toyama (JP); Daisuke Kubo, Toyama (JP); Masataka Fujino, Toyama (JP); Issei Doi, Toyama (JP); Daisuke Nakagawa, Kaisei (JP); Tatsuya Murakami, Kaisei (JP); Takayuki Yamakawa, Kaisei (JP)

(73) Assignees: TOYAMA CHEMICAL CO., LTD., Shinjuku-ku (JP); FUJIFILM CORPORATION, Minato-ku (JP)

( * ) Notice: Subject to any disclaimer, the term of this patent is extended or adjusted under 35 U.S.C. 154(b) by 0 days.

(21) Appl. No.: 14/440,010

(22) PCT Filed: Oct. 30, 2013

(86) PCT No.: PCT/JP2013/079364
§ 371 (c)(1),
(2) Date: Apr. 30, 2015

(87) PCT Pub. No.: WO2014/069510
PCT Pub. Date: May 8, 2014

(65) Prior Publication Data
US 2015/0299189 A1    Oct. 22, 2015

(30) Foreign Application Priority Data
Oct. 31, 2012    (JP) .................. 2012-240172
Mar. 13, 2013    (JP) .................. 2013-050845

(51) Int. Cl.
A61K 31/455    (2006.01)
A61K 31/4709    (2006.01)
(Continued)

(52) U.S. Cl.
CPC .......... *C07D 471/04* (2013.01); *A61K 31/404* (2013.01); *A61K 31/4035* (2013.01); *A61K 31/416* (2013.01); *A61K 31/4184* (2013.01); *A61K 31/423* (2013.01); *A61K 31/427* (2013.01); *A61K 31/428* (2013.01);
(Continued)

(58) Field of Classification Search
CPC .. A61K 31/455; A61K 31/497; A61K 31/501; A61K 31/506; A61K 31/416; A61K 31/4725; A61K 31/404; A61K 31/498; A61K 31/428; A61K 31/423; A61K 31/427; A61K 31/538; A61K 31/4439; A61K 31/4035; A61K 31/4184; A61K 31/4709; A61K 31/437; A61K 31/454; A61K 31/517; A61K 31/5377; C07D 215/38; C07D 235/26; C07D 209/48; C07D 209/38; C07D 401/06; C07D 209/08; C07D 231/56; C07D 209/46; C07D 213/80; C07D 235/08; C07D 209/12; C07D 417/06; C07D 277/68;
(Continued)

(56) References Cited

U.S. PATENT DOCUMENTS 5,017,706 A    5/1991    Rochat et al.
2002/0035137 A1    3/2002    Liu et al.
(Continued)

FOREIGN PATENT DOCUMENTS

EP    1 990 342 A1    11/2008
EP    2 130 541 A2    12/2009
(Continued)

OTHER PUBLICATIONS

Wuts, Peter GM, and Theodora W. Greene. Greene's protective groups in organic synthesis. Chapter 5, John Wiley & Sons, 2006.*
(Continued)

*Primary Examiner* — Samantha Shterengarts
*Assistant Examiner* — Matt Mauro
(74) *Attorney, Agent, or Firm* — Oblon, McClelland, Maier & Neustadt, L.L.P.

(57) ABSTRACT

A novel amine derivative expressed by general formula (1)

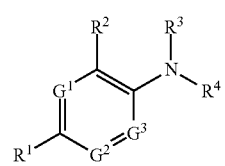

(1)

(in the formula: $G^1$, $G^2$, and $G^3$ are the same or different and represent CH or a nitrogen atom; $R^1$ represents a chlorine atom, an optionally-substituted $C_{3-8}$ cycloalkyl group, or the like; $R^2$ represents —$COOR^5$ (in the formula, $R^5$ represents a hydrogen atom or a carboxyl protective group), or the like; $R^3$ represents a hydrogen atom, or the like; and $R^4$ represents an optionally-substituted condensed bicyclic hydrocarbon group, an optionally-substituted bicyclic heterocyclic group, or the like), or a salt thereof is useful in procedures such as the treatment or prevention of conditions related to excessive keratinocyte proliferation.

20 Claims, No Drawings

(51) Int. Cl.

| | | |
|---|---|---|
| A61K 31/497 | (2006.01) | |
| A61K 31/501 | (2006.01) | |
| C07D 235/26 | (2006.01) | |
| C07D 403/04 | (2006.01) | |
| C07D 413/12 | (2006.01) | |
| C07D 417/04 | (2006.01) | |
| C07D 241/44 | (2006.01) | |
| C07D 263/58 | (2006.01) | |
| C07D 209/08 | (2006.01) | |
| C07D 277/68 | (2006.01) | |
| C07D 471/04 | (2006.01) | |
| C07D 403/12 | (2006.01) | |
| C07D 401/14 | (2006.01) | |
| C07D 405/14 | (2006.01) | |
| A61K 31/4035 | (2006.01) | |
| A61K 31/404 | (2006.01) | |
| A61K 31/416 | (2006.01) | |
| A61K 31/4184 | (2006.01) | |
| A61K 31/423 | (2006.01) | |
| A61K 31/427 | (2006.01) | |
| A61K 31/428 | (2006.01) | |
| A61K 31/437 | (2006.01) | |
| A61K 31/4439 | (2006.01) | |
| A61K 31/454 | (2006.01) | |
| A61K 31/4725 | (2006.01) | |
| A61K 31/498 | (2006.01) | |
| A61K 31/506 | (2006.01) | |
| A61K 31/517 | (2006.01) | |
| A61K 31/5377 | (2006.01) | |
| A61K 31/538 | (2006.01) | |
| C07D 213/80 | (2006.01) | |
| C07D 215/38 | (2006.01) | |
| C07D 217/24 | (2006.01) | |
| C07D 231/56 | (2006.01) | |
| C07D 401/04 | (2006.01) | |
| C07D 235/08 | (2006.01) | |
| C07D 401/06 | (2006.01) | |
| C07D 401/12 | (2006.01) | |
| C07D 417/06 | (2006.01) | |
| C07D 417/12 | (2006.01) | |
| C07D 209/12 | (2006.01) | |
| C07D 209/34 | (2006.01) | |
| C07D 209/38 | (2006.01) | |
| C07D 209/42 | (2006.01) | |
| C07D 209/46 | (2006.01) | |
| C07D 209/48 | (2006.01) | |
| C07C 211/45 | (2006.01) | |
| C07D 209/04 | (2006.01) | |
| C07D 215/227 | (2006.01) | |
| C07D 239/88 | (2006.01) | |
| C07D 265/36 | (2006.01) | |
| C07D 401/10 | (2006.01) | |
| C07D 407/14 | (2006.01) | |
| C07D 413/06 | (2006.01) | |
| C07D 413/10 | (2006.01) | |
| C07D 413/14 | (2006.01) | |

(52) U.S. Cl.
CPC ........ *A61K 31/437* (2013.01); *A61K 31/4439* (2013.01); *A61K 31/454* (2013.01); *A61K 31/455* (2013.01); *A61K 31/4709* (2013.01); *A61K 31/4725* (2013.01); *A61K 31/497* (2013.01); *A61K 31/498* (2013.01); *A61K 31/501* (2013.01); *A61K 31/506* (2013.01); *A61K 31/517* (2013.01); *A61K 31/538* (2013.01); *A61K 31/5377* (2013.01); *C07C 211/45* (2013.01); *C07D 209/04* (2013.01); *C07D 209/08* (2013.01); *C07D 209/12* (2013.01); *C07D 209/34* (2013.01); *C07D 209/38* (2013.01); *C07D 209/42* (2013.01); *C07D 209/46* (2013.01); *C07D 209/48* (2013.01); *C07D 213/80* (2013.01); *C07D 215/227* (2013.01); *C07D 215/38* (2013.01); *C07D 217/24* (2013.01); *C07D 231/56* (2013.01); *C07D 235/08* (2013.01); *C07D 235/26* (2013.01); *C07D 239/88* (2013.01); *C07D 241/44* (2013.01); *C07D 263/58* (2013.01); *C07D 265/36* (2013.01); *C07D 277/68* (2013.01); *C07D 401/04* (2013.01); *C07D 401/06* (2013.01); *C07D 401/10* (2013.01); *C07D 401/12* (2013.01); *C07D 401/14* (2013.01); *C07D 403/04* (2013.01); *C07D 403/12* (2013.01); *C07D 405/14* (2013.01); *C07D 407/14* (2013.01); *C07D 413/06* (2013.01); *C07D 413/10* (2013.01); *C07D 413/12* (2013.01); *C07D 413/14* (2013.01); *C07D 417/04* (2013.01); *C07D 417/06* (2013.01); *C07D 417/12* (2013.01); *Y02P 20/55* (2015.11)

(58) Field of Classification Search
CPC .. C07D 209/42; C07D 241/44; C07D 209/34; C07D 405/14; Y02P 20/55
See application file for complete search history.

(56) References Cited

U.S. PATENT DOCUMENTS

| | | |
|---|---|---|
| 2002/0169157 A1 | 11/2002 | Liu et al. |
| 2003/0078288 A1 | 4/2003 | Haning et al. |
| 2003/0220382 A1 | 11/2003 | Barta et al. |
| 2003/0229113 A1 | 12/2003 | Hashimoto et al. |
| 2005/0137221 A1 | 6/2005 | Tsukida et al. |
| 2008/0312270 A1 | 12/2008 | Brown et al. |
| 2009/0082328 A1 | 3/2009 | Li et al. |
| 2009/0093462 A1 | 4/2009 | Abel et al. |
| 2009/0124596 A1 | 5/2009 | Bonnert et al. |
| 2009/0275534 A1 | 11/2009 | Gerlach et al. |
| 2010/0074898 A1 | 3/2010 | Castro Palomino Laria et al. |
| 2010/0204203 A1 | 8/2010 | Bonnert et al. |
| 2011/0212945 A1 | 9/2011 | Castro Palomino Laria et al. |
| 2012/0101091 A1 | 4/2012 | Beaulieu et al. |

FOREIGN PATENT DOCUMENTS

| | | |
|---|---|---|
| JP | 2-6485 A | 1/1990 |
| JP | 7-330714 A | 12/1995 |
| JP | 8-3049 A | 1/1996 |
| JP | 10-139669 A | 5/1998 |
| JP | 2003-531883 A | 10/2003 |
| JP | 2004-517851 A | 6/2004 |
| JP | 2004-292314 A | 10/2004 |
| JP | 2004-531455 A | 10/2004 |
| JP | 2008-517024 A | 5/2008 |
| JP | 2010-513362 A | 4/2010 |
| JP | 2010-515712 A | 5/2010 |
| JP | 2010-526069 A | 7/2010 |
| JP | 2010-526788 A | 8/2010 |
| JP | 2010-526794 A | 8/2010 |
| JP | 2010-535824 A | 11/2010 |
| JP | 2012-504556 A | 2/2012 |
| WO | 01/70269 A1 | 9/2001 |
| WO | WO 01/83425 A1 | 11/2001 |
| WO | WO 02/18323 A2 | 3/2002 |
| WO | WO 03/018535 A2 | 3/2003 |
| WO | 2004/002959 A1 | 1/2004 |
| WO | 2008/077639 A1 | 7/2008 |

(56) References Cited

FOREIGN PATENT DOCUMENTS

| WO | WO 2008/084223 A2 | 7/2008 |
|----|----|----|
| WO | WO 2008/107661 A1 | 9/2008 |
| WO | 2009/021696 A1 | 2/2009 |
| WO | WO 2010/029300 A1 | 3/2010 |
| WO | WO 2010/037210 A1 | 4/2010 |
| WO | 2011-021678 A1 | 2/2011 |

OTHER PUBLICATIONS

Wuts, Peter GM, and Theodora W. Greene. Greene's protective groups in organic synthesis. Chapter 7, John Wiley & Sons, 2006.*
WO 2011021678 English Machine Translation ProQuest accessed online Mar. 22, 2016. p. 1-428.*
Lowes, M.A.,"Pathogenesis and therapy of psoriasis." Nature 445. 7130 (2007): 866-873.*
Ramu Meesala, et al., "A short route to the synthesis of pyrroloacridines via Ullmann-Goldberg condensation", Tetrahedron Letters, vol. 51, No. 2, pp. 422-424, (2010).
R. W. Baldwin, et al., "Further Studies on the Influence of Peripheral Ring Substitution on the Carcino-Genicity of Tricycloquinazoline", Biochemical Pharmacology, vol. 14, No. 3, pp. 323-331, (1965).
Amy M. Bunker, et al., "1,3-Diaryl-2-Carboxyindoles as Potent Non-Peptide Endothelin Antagonists", Bioorganic & Medicinal Chemistry Letters, vol. 6, No. 9, pp. 1061-1066, (1996).
Michal P. Schon, et al., "Psoriasis", The New England Journal of Medicine, vol. 352, pp. 1899-1912, (2005).
Kunio Matsumoto, et al., "Growth-Inhibitory Effects of 1,25-Dihydroxyvitamin $D_3$ on Normal Human Keratinocytes Cultured in Serum-Free Medium", Biochemical and Biophysical Research Communications, vol. 166, No. 2, pp. 916-923, (Jan. 30, 1990).
International Search Report Issued Dec. 24, 2013 in PCT/JP13/079364 Filed Oct. 30, 2013.
Extended European Search Report issued May 11, 2016 in Patent Application No. 13851612.5.
M. W. Partridge, et al., "492. Cyclic Amidines. Part XV. Derivatives of Tricycloquinazoline." Journal of the Chemical Society, XP055269950, 1962, pp. 2549-2556.
"380. Kurt Brass: Über die Oxydation von Anilido-chinonen zu Benzidin-Derivaten. II." Chemische Berichte, XP055270121, 1913, 6 Pages.

* cited by examiner

AMINE DERIVATIVE OR SALT THEREOF

TECHNICAL FIELD

The present invention relates to novel amine derivatives or salts thereof.

BACKGROUND ART

The skin epidermis plays a role in protecting the inside of the skin from bacteria, viruses, ultraviolet rays, chemical substances and the like. In the epidermis, keratinocytes undergo keratinization and cell death to form the stratum corneum, while other keratinocytes are grown and differentiated repeatedly. Afterwards, the stratum corneum turns into dirt and is exfoliated from the epidermis. Typically, this cycle (turnover) over about 28 days is repeated. However, in skin diseases such as skin cancer, psoriasis, immunologic/allergic skin diseases and chronic wound, it is observed that the control mechanism for the cell proliferation of keratinocytes breaks down and the skin is thickened by the abnormal proliferation of skin epithelial cells (Non Patent Document 1).

Steroid formulations have conventionally been used for therapy of psoriasis. Steroid formulations are active in inhibiting inflammation and in suppressing the immune function and are also highly therapeutically effective. However, it is known that everyday use of steroid formulations causes various side effects such as skin atrophy and skin thinning.

Recently, several compounds have been reported which inhibit the proliferation of keratinocytes. For example, active vitamin D3 or derivatives thereof have been reported to inhibit the proliferation of keratinocytes and to be effective for psoriasis and keratosis (Patent Documents 1 and 2 and Non Patent Document 2). Zearalenone derivatives (Patent Document 3), azasugar derivatives (Patent Document 4), hydroxamic acid derivatives (Patent Document 5) and phosphodiester compounds with ascorbic acid and tocopherol (Patent Document 6) have also been reported to inhibit the proliferation of keratinocytes.

DHODH inhibitors have also been reported as other compounds to inhibit the proliferation of keratinocytes (Patent Documents 7 and 8).

PRIOR ART DOCUMENTS

Patent Documents

Patent Document 1: JP 07-330714 A
Patent Document 2: JP 10-139669 A
Patent Document 3: JP 2004-292314 A
Patent Document 4: WO 2004/002959 pamphlet
Patent Document 5: WO 01/070269 pamphlet
Patent Document 6: JP 08-003049 A
Patent Document 7: WO 2008/077639 pamphlet
Patent Document 8: WO 2009/021696 pamphlet

Non Patent Documents

Non Patent Document 1: N Engl J Med, vol. 352, pp. 1899-18912, 2005

Non Patent Document 2: Biochem. Biophys. Res. Commun., vol. 166, pp. 916-923, 1990

SUMMARY OF INVENTION

Technical Problem

As therapeutic methods for the diseases associated with the cell proliferation of skin epidermis, therapeutic methods to target the molecules involved in cell proliferation have been known. However, any effect of such methods is unsatisfactory, and more effective therapeutic drugs have been desired.

Solution to Problem

As a result of extensive studies under such circumstances, the present inventors have found that a compound as represented by the general formula (1) or a salt thereof has the excellent effect of inhibiting the proliferation of keratinocytes and are useful for treatment such as prevention or therapy of the diseases involved in the overproliferation of keratinocytes. Further, the inventors have also found that the compound represented by the general formula (1) or the salt thereof according to the present invention, which has the excellent effect of inhibiting the production of TNFα, is useful for treatment such as prevention or therapy of the diseases involved in the overproduction of TNFα, and thus completed the present invention.

The present invention provides the following.

[1] A compound as represented by the general formula (1) or a salt thereof.

[Formula 1]

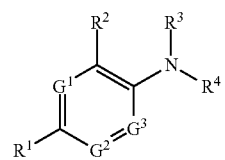

(1)

(wherein
$G^1$, $G^2$ and $G^3$ are identical or different and are CH or a nitrogen atom;

$R^1$ is a chlorine atom, a bromine atom, an iodine atom, an optionally substituted $C_{1-6}$ alkyl group, an optionally substituted $C_{3-8}$ cycloalkyl group, an optionally substituted aryl group, an optionally substituted $C_{1-6}$ alkoxy group, an optionally substituted aryloxy group, an optionally substituted $C_{1-6}$ alkylthio group, an optionally substituted arylthio group, an optionally substituted $C_{1-6}$ alkylamino group, an optionally substituted di($C_{1-6}$ alkyl)amino group or an optionally substituted heterocyclic group;

$R^2$ is —COOR$^5$ (wherein $R^5$ is a hydrogen atom or a carboxyl protecting group) or —C(O)N(R$^6$)SO$_2$R$^7$ (wherein $R^6$ is a hydrogen atom or an imino protecting group; and $R^7$ is an optionally substituted $C_{1-6}$ alkyl group or an optionally substituted $C_{3-8}$ cycloalkyl group);

$R^3$ is a hydrogen atom or an imino protecting group; and $R^4$ is an optionally substituted fused bicyclic hydrocarbon ring group, an optionally substituted fused tricyclic hydrocarbon ring group, an optionally substituted bicyclic heterocyclic group or an optionally substituted tricyclic heterocyclic group, provided that (1) when $R^4$ is an optionally substituted fused bicyclic hydrocarbon ring group, then $G^3$ is a nitrogen atom; and
(2) when $G^1$ is CH, $G^2$ is CH, $G^3$ is CH, $R^1$ is a chlorine atom, a bromine atom, an iodine atom, a $C_{1-4}$ alkyl group, a trifluoromethyl group, a dibutylamino group, a methoxy group or a substituted phenyloxy group, $R^2$ is —COOH and $R^3$ is a hydrogen atom, then $R^4$ is a group as represented by the general formulas (2-1) to (2-4):

[Formula 2]

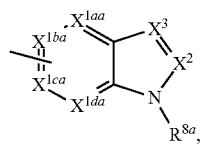

(2-1)

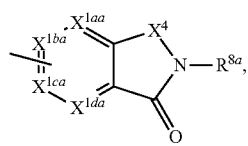

(2-2)

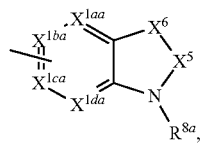

(2-3)

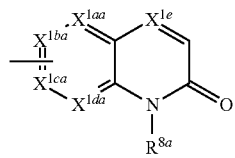

(2-4)

(wherein
$X^{1aa}$, $X^{1ba}$, $X^{1ca}$, $X^{1da}$ and $X^{1e}$ are identical or different and are $CR^{9a}$ (wherein $R^{9a}$ is a hydrogen atom, a halogen atom, an optionally substituted $C_{1-6}$ alkyl group, an optionally substituted $C_{3-8}$ cycloalkyl group or an optionally substituted aryl group) or a nitrogen atom;

$X^2$ is $CR^{10}$ (wherein $R^{10}$ is a hydrogen atom, an optionally protected carboxyl group, an optionally substituted carbamoyl group, an optionally substituted $C_{1-6}$ alkyl group or an optionally substituted aryl group) or a nitrogen atom;

$X^3$ is $CR^{11}$ (wherein $R^{11}$ is a hydrogen atom, an optionally substituted $C_{1-6}$ alkyl group, an optionally substituted $C_{3-8}$ cycloalkyl group, an optionally substituted aryl group, an optionally substituted ar-$C_{1-6}$ alkyl group or an optionally substituted acyl group) or a nitrogen atom;

$X^4$ is $CH_2$, $CH_2$—$CH_2$, C=O, an oxygen atom or a sulfur atom;

$X^5$ is $CH_2$ or C=O;

$X^6$ is $CH_2$, $CH_2$—$CH_2$, C=O, $NR^{12}$ (wherein $R^{12}$ is a hydrogen atom, an imino protecting group, an optionally substituted $C_{1-6}$ alkyl group, an optionally substituted $C_{3-8}$ cycloalkyl group or an optionally substituted $C_{3-8}$ cycloalkyl-$C_{1-6}$ alkyl group), an oxygen atom or a sulfur atom; and $R^{8a}$ is an optionally substituted $C_{3-6}$ alkyl group, an optionally substituted $C_{3-8}$ cycloalkyl group, an optionally substituted $C_{3-8}$ cycloalkyl-$C_{1-6}$ alkyl group, an optionally substituted aryl group, an optionally substituted ar-$C_{1-6}$ alkyl group, an optionally substituted acyl group, an optionally substituted heterocyclic group or an optionally substituted heterocyclic $C_{1-6}$ alkyl group)).

[2] The compound or the salt thereof according to [1], wherein $R^1$ is a chlorine atom, a bromine atom, an optionally substituted $C_{1-6}$ alkyl group, an optionally substituted $C_{3-8}$ cycloalkyl group, an optionally substituted aryl group, an optionally substituted aryloxy group, an optionally substituted $C_{1-6}$ alkylthio group or an optionally substituted heterocyclic group.

[3] The compound or the salt thereof according to [1] or [2], wherein $R^1$ is a chlorine atom, a bromine atom, a $C_{1-6}$ alkyl group, a $C_{3-8}$ cycloalkyl group, an aryl group, an aryloxy group optionally substituted with a methylsulfonyl group, a $C_{1-6}$ alkylthio group or a heterocyclic group.

[4] The compound or the salt thereof according to any of [1] to [3], wherein $R^2$ is —COOH.

[5] The compound or the salt thereof according to any of [1] to [4], wherein $R^3$ is a hydrogen atom.

[6] The compound or the salt thereof according to any of [1] to [5], wherein $R^4$ is an optionally substituted bicyclic heterocyclic group.

[7] The compound or the salt thereof according to any of [1] to [6], wherein $R^1$ is a chlorine atom or a $C_{3-8}$ cycloalkyl group.

[8'] The compound or the salt thereof according to any of [1] to [7], wherein $R^4$ is a group as represented by the general formulas (3-1') to (3-3'):

[Formula 3]

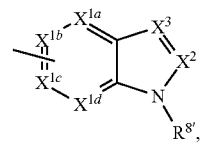

(3-1')

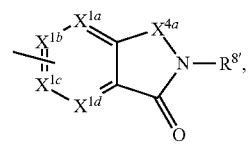

(3-2')

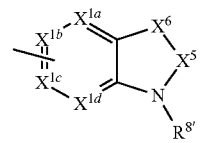

(3-3')

(wherein
$X^{1a}$, $X^{1b}$, $X^{1c}$ and $X^{1d}$ are identical or different and are $CR^{9'}$ (wherein $R^{9'}$ is a hydrogen atom, a halogen atom, an optionally substituted $C_{1-6}$ alkyl group, an optionally substituted $C_{2-6}$ alkenyl group, an optionally substituted $C_{3-8}$ cycloalkyl group, an optionally substituted $C_{4-8}$ cycloalkenyl group, an optionally substituted $C_{3-8}$ cycloalkyl-$C_{1-6}$ alkyl group, an optionally substituted aryl group or an optionally substituted heterocyclic group) or a nitrogen atom;

$X^2$ is $CR^{10}$ (wherein $R^{10}$ is a hydrogen atom, an optionally protected carboxyl group, an optionally substituted carbamoyl group, an optionally substituted $C_{1-6}$ alkyl group or an optionally substituted aryl group) or a nitrogen atom;

$X^3$ is $CR^{11}$ (wherein $R^{11}$ is a hydrogen atom, an optionally substituted $C_{1-6}$ alkyl group, an optionally substituted $C_{3-8}$ cycloalkyl group, an optionally substituted aryl group, an optionally substituted ar-$C_{1-6}$ alkyl group or an optionally substituted acyl group) or a nitrogen atom;

$X^{4a}$ is $CH_2$, $CH_2$—$CH_2$ or C=O;

$X^5$ is $CH_2$ or C=O;

$X^6$ is $CH_2$, $CH_2$—$CH_2$, C=O, $NR^{12}$ (wherein $R^{12}$ is a hydrogen atom, an imino protecting group, an optionally substituted $C_{1-6}$ alkyl group, an optionally substituted $C_{3-8}$ cycloalkyl group or an optionally substituted $C_{3-8}$ cycloalkyl-$C_{1-6}$ alkyl group), an oxygen atom or a sulfur atom; and $R^{8'}$ is a hydrogen atom, an optionally substituted $C_{1-12}$ alkyl group, an optionally substituted $C_{3-8}$ cycloalkyl group, an optionally substituted $C_{3-8}$ cycloalkyl-$C_{1-6}$ alkyl group, an optionally substituted aryl group, an optionally substituted ar-$C_{1-6}$ alkyl group, an optionally substituted acyl group, an optionally substituted heterocyclic group or an optionally substituted heterocyclic $C_{1-6}$ alkyl group, provided that when $G^1$ is CH, $G^2$ is CH, $G^3$ is CH, $R^1$ is a chlorine atom, a bromine atom, an iodine atom, a $C_{1-4}$ alkyl group, a trifluoromethyl group, a dibutylamino group, a methoxy group or a substituted phenyloxy group, $R^2$ is —COOH and $R^3$ is a hydrogen atom, then $R^4$ is a group as represented by the general formulas (3-1a) to (3-3a):

[Formula 4]

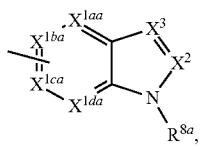

(3-1a)

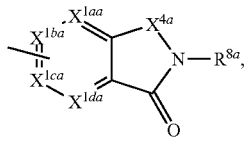

(3-2a)

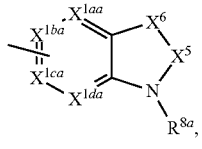

(3-3a)

(wherein $X^{1aa}$, $X^{1ba}$, $X^{1ca}$ and $X^{1da}$ are identical or different and are $CR^{9a}$ (wherein $R^{9a}$ is a hydrogen atom, a halogen atom, an optionally substituted $C_{1-6}$ alkyl group, an optionally substituted $C_{3-8}$ cycloalkyl group or an optionally substituted aryl group) or a nitrogen atom;

$X^2$ is $CR^{10}$ (wherein $R^{10}$ is a hydrogen atom, an optionally protected carboxyl group, an optionally substituted carbamoyl group, an optionally substituted $C_{1-6}$ alkyl group or an optionally substituted aryl group) or a nitrogen atom;

$X^3$ is $CR^{11}$ (wherein $R^{11}$ is a hydrogen atom, an optionally substituted $C_{1-6}$ alkyl group, an optionally substituted $C_{3-8}$ cycloalkyl group, an optionally substituted aryl group, an optionally substituted ar-$C_{1-6}$ alkyl group or an optionally substituted acyl group) or a nitrogen atom;

$X^5$ is $CH_2$ or C=O;

$X^6$ is $CH_2$, $CH_2$—$CH_2$, C=O, $NR^{12}$ (wherein $R^{12}$ is a hydrogen atom, an imino protecting group, an optionally substituted $C_{1-6}$ alkyl group, an optionally substituted $C_{3-8}$ cycloalkyl group or an optionally substituted $C_{3-8}$ cycloalkyl-$C_{1-6}$ alkyl group), an oxygen atom or a sulfur atom;

$R^{8a}$ is an optionally substituted $C_{3-6}$ alkyl group, an optionally substituted $C_{3-8}$ cycloalkyl group, an optionally substituted $C_{3-8}$ cycloalkyl-$C_{1-6}$ alkyl group, an optionally substituted aryl group, an optionally substituted ar-$C_{1-6}$ alkyl group, an optionally substituted acyl group, an optionally substituted heterocyclic group or an optionally substituted heterocyclic $C_{1-6}$ alkyl group; and $X^{4a}$ is as defined above)).

[8] The compound or the salt thereof according to any of [1] to [7], wherein $R^4$ is a group as represented by the general formulas (3-1) to (3-3):

[Formula 5]

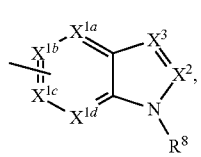

(3-1)

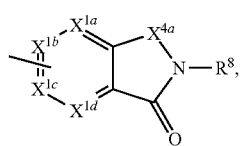

(3-2)

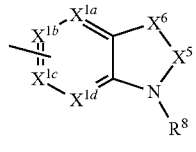

(3-3)

(wherein $X^{1a}$, $X^{1b}$, $X^{1c}$ and $X^{1d}$ are identical or different and are $CR^9$ (wherein $R^9$ is a hydrogen atom, a halogen atom, an optionally substituted $C_{1-6}$ alkyl group, an optionally substituted $C_{2-6}$ alkenyl group, an optionally substituted $C_{3-8}$ cycloalkyl group, an optionally substituted $C_{4-8}$ cycloalkenyl group, an optionally substituted $C_{3-8}$ cycloalkyl-$C_{1-6}$ alkyl group or an optionally substituted aryl group) or a nitrogen atom;

$X^2$ is $CR^{10}$ (wherein $R^{10}$ is a hydrogen atom, an optionally protected carboxyl group, an optionally substituted carbamoyl group, an optionally substituted $C_{1-6}$ alkyl group or an optionally substituted aryl group) or a nitrogen atom;

$X^3$ is $CR^{11}$ (wherein $R^{11}$ is a hydrogen atom, an optionally substituted $C_{1-6}$ alkyl group, an optionally substituted $C_{3-8}$ cycloalkyl group, an optionally substituted aryl group, an optionally substituted ar-$C_{1-6}$ alkyl group or an optionally substituted acyl group) or a nitrogen atom;

$X^{4a}$ is $CH_2$, $CH_2$—$CH_2$ or C=O;

$X^5$ is $CH_2$ or C=O;

$X^6$ is $CH_2$, $CH_2$—$CH_2$, C=O, $NR^{12}$ (wherein $R^{12}$ is a hydrogen atom, an imino protecting group, an optionally substituted $C_{1-6}$ alkyl group, an optionally substituted $C_{3-8}$ cycloalkyl group or an optionally substituted $C_{3-8}$ cycloalkyl-$C_{1-6}$ alkyl group), an oxygen atom or a sulfur atom; and $R^8$ is a hydrogen atom, an optionally substituted $C_{1-6}$ alkyl group, an optionally substituted $C_{3-8}$ cycloalkyl group, an optionally substituted $C_{3-8}$ cycloalkyl-$C_{1-6}$ alkyl group, an optionally substituted aryl group, an optionally substituted ar-$C_{1-6}$ alkyl group, an optionally substituted acyl group, an optionally substituted heterocyclic group or an optionally substituted heterocyclic $C_{1-6}$ alkyl group,
provided that when $G^1$ is CH, $G^2$ is CH, $G^3$ is CH, $R^1$ is a chlorine atom, a bromine atom, an iodine atom, a $C_{1-4}$ alkyl group, a trifluoromethyl group, a dibutylamino group, a methoxy group or a substituted phenyloxy group, $R^2$ is —COOH and $R^3$ is a hydrogen atom, then $R^4$ is a group as represented by the general formulas (3-1a) to (3-3a):

[Formula 6]

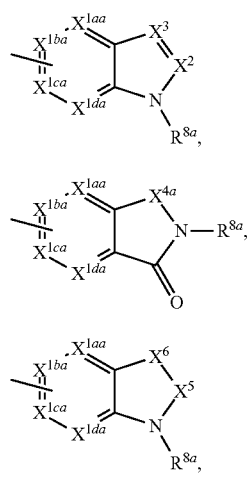

(wherein
$X^{1aa}$, $X^{1ba}$, $X^{1ca}$ and $X^{1da}$ are identical or different and are $CR^{9a}$ (wherein $R^{9a}$ is a hydrogen atom, a halogen atom, an optionally substituted $C_{1-6}$ alkyl group, an optionally substituted $C_{3-8}$ cycloalkyl group or an optionally substituted aryl group) or a nitrogen atom;
$X^2$ is $CR^{10}$ (wherein $R^{10}$ is a hydrogen atom, an optionally protected carboxyl group, an optionally substituted carbamoyl group, an optionally substituted $C_{1-6}$ alkyl group or an optionally substituted aryl group) or a nitrogen atom;
$X^3$ is $CR^{11}$ (wherein $R^{11}$ is a hydrogen atom, an optionally substituted $C_{1-6}$ alkyl group, an optionally substituted $C_{3-8}$ cycloalkyl group, an optionally substituted aryl group, an optionally substituted ar-$C_{1-6}$ alkyl group or an optionally substituted acyl group) or a nitrogen atom;
$X^5$ is $CH_2$ or C=O;
$X^6$ is $CH_2$, $CH_2$—$CH_2$, C=O, $NR^{12}$ (wherein $R^{12}$ is a hydrogen atom, an imino protecting group, an optionally substituted $C_{1-6}$ alkyl group, an optionally substituted $C_{3-8}$ cycloalkyl group or an optionally substituted $C_{3-8}$ cycloalkyl-$C_{1-6}$ alkyl group), an oxygen atom or a sulfur atom;
$R^{8a}$ is an optionally substituted $C_{3-6}$ alkyl group, an optionally substituted $C_{3-8}$ cycloalkyl group, an optionally substituted $C_{3-8}$ cycloalkyl-$C_{1-6}$ alkyl group, an optionally substituted aryl group, an optionally substituted ar-$C_{1-6}$ alkyl group, an optionally substituted acyl group, an optionally substituted heterocyclic group or an optionally substituted heterocyclic $C_{1-6}$ alkyl group; and
$X^{4a}$ is as defined above)).
[9] The compound or the salt thereof according to any of [1] to [8], wherein $R^4$ is a group as represented by the general formula (4-1) or (4-2):

[Formula 7]

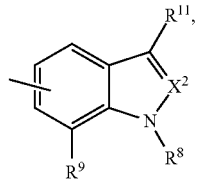

(4-1)

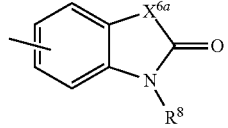

(4-2)

(wherein
$X^2$ is $CR^{10}$ (wherein $R^{10}$ is a hydrogen atom, an optionally protected carboxyl group, an optionally substituted carbamoyl group, an optionally substituted $C_{1-6}$ alkyl group or an optionally substituted aryl group) or a nitrogen atom;
$X^{6a}$ is $CH_2$, $NR^{12}$ (wherein $R^{12}$ is a hydrogen atom, an imino protecting group, an optionally substituted $C_{1-6}$ alkyl group, an optionally substituted $C_{3-8}$ cycloalkyl group or an optionally substituted $C_{3-8}$ cycloalkyl-$C_{1-6}$ alkyl group), an oxygen atom or a sulfur atom;
$R^8$ is a hydrogen atom, an optionally substituted $C_{1-6}$ alkyl group, an optionally substituted $C_{3-8}$ cycloalkyl group, an optionally substituted $C_{3-8}$ cycloalkyl-$C_{1-6}$ alkyl group, an optionally substituted aryl group, an optionally substituted ar-$C_{1-6}$ alkyl group, an optionally substituted acyl group, an optionally substituted heterocyclic group or an optionally substituted heterocyclic $C_{1-6}$ alkyl group;
$R^9$ is a hydrogen atom, a halogen atom, an optionally substituted $C_{1-6}$ alkyl group, an optionally substituted $C_{2-6}$ alkenyl group, an optionally substituted $C_{3-8}$ cycloalkyl group, an optionally substituted $C_{4-8}$ cycloalkenyl group, an optionally substituted $C_{3-8}$ cycloalkyl-$C_{1-6}$ alkyl group or an optionally substituted aryl group; and
$R^{11}$ is a hydrogen atom, an optionally substituted $C_{1-6}$ alkyl group, an optionally substituted $C_{3-8}$ cycloalkyl group, an optionally substituted aryl group, an optionally substituted ar-$C_{1-6}$ alkyl group or an optionally substituted acyl group,
provided that when $G^1$ is CH, $G^2$ is CH, $G^3$ is CH, $R^1$ is a chlorine atom, a bromine atom, an iodine atom, a $C_{1-4}$ alkyl group, a trifluoromethyl group, a dibutylamino group, a methoxy group or a substituted phenyloxy group, $R^2$ is —COOH and $R^3$ is a hydrogen atom, then $R^4$ is a group as represented by the general formula (4-1a) or (4-2a):

[Formula 8]

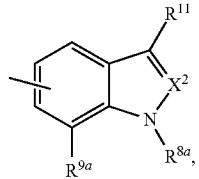

(4-1a)

-continued

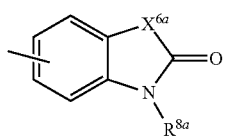
(4-2a)

(wherein $R^{8a}$ is an optionally substituted $C_{3-6}$ alkyl group, an optionally substituted $C_{3-8}$ cycloalkyl group, an optionally substituted $C_{3-8}$ cycloalkyl-$C_{1-6}$ alkyl group, an optionally substituted aryl group, an optionally substituted ar-$C_{1-6}$ alkyl group, an optionally substituted acyl group, an optionally substituted heterocyclic group or an optionally substituted heterocyclic $C_{1-6}$ alkyl group;

$R^{9a}$ is a hydrogen atom, a halogen atom, an optionally substituted $C_{1-6}$ alkyl group, an optionally substituted $C_{3-8}$ cycloalkyl group or an optionally substituted aryl group; and $R^{11}$, $X^2$, $X^{4a}$ and $X^{6a}$ are as defined above)).

[10] The compound or the salt thereof according to any of [1] to [9], wherein $G^1$ and $G^2$ are CH; $G^3$ is a nitrogen atom; and $R^4$ is a group as represented by the general formula (5-1):

[Formula 9]

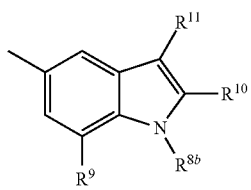
(5-1)

(wherein $R^{8b}$ is an optionally substituted $C_{1-6}$ alkyl group, an optionally substituted $C_{3-8}$ cycloalkyl group, an optionally substituted $C_{3-8}$ cycloalkyl-$C_{1-6}$ alkyl group, an optionally substituted aryl group or an optionally substituted ar-$C_{1-6}$ alkyl group;

$R^9$ is a hydrogen atom, a halogen atom, an optionally substituted $C_{1-6}$ alkyl group, an optionally substituted $C_{2-6}$ alkenyl group, an optionally substituted $C_{3-8}$ cycloalkyl group, an optionally substituted $C_{4-8}$ cycloalkenyl group, an optionally substituted $C_{3-8}$ cycloalkyl-$C_{1-6}$ alkyl group or an optionally substituted aryl group;

$R^{10}$ is a hydrogen atom, an optionally protected carboxyl group, an optionally substituted carbamoyl group, an optionally substituted $C_{1-6}$ alkyl group or an optionally substituted aryl group; and $R^{11}$ is a hydrogen atom, an optionally substituted $C_{1-6}$ alkyl group, an optionally substituted $C_{3-8}$ cycloalkyl group, an optionally substituted aryl group, an optionally substituted ar-$C_{1-6}$ alkyl group or an optionally substituted acyl group).

[11] The compound or the salt thereof according to any of [1] to [10], wherein $G^1$ and $G^2$ are CH; $G^3$ is a nitrogen atom; and $R^4$ is a group as represented by the general formula (5-1a):

[Formula 10]

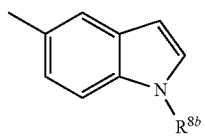
(5-1a)

(wherein $R^{8b}$ is an optionally substituted $C_{1-6}$ alkyl group, an optionally substituted $C_{3-8}$ cycloalkyl group, an optionally substituted $C_{3-8}$ cycloalkyl-$C_{1-6}$ alkyl group, an optionally substituted ar-$C_{1-6}$ alkyl group or an optionally substituted aryl group).

[12] The compound or the salt thereof according to any of [1] to [10], wherein $G^1$ and $G^2$ are CH; $G^3$ is a nitrogen atom; and $R^4$ is a group as represented by the general formula (5-1b):

[Formula 11]

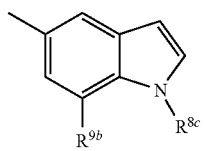
(5-1b)

(wherein $R^{8c}$ is an optionally substituted $C_{1-6}$ alkyl group; and $R^{9b}$ is an optionally substituted $C_{1-6}$ alkyl group, an optionally substituted $C_{3-8}$ cycloalkyl group, an optionally substituted $C_{3-8}$ cycloalkyl-$C_{1-6}$ alkyl group or an optionally substituted aryl group).

[13] The compound or the salt thereof according to any of [1] to [10], wherein $G^1$ and $G^2$ are CH; $G^3$ is a nitrogen atom; and $R^4$ is a group as represented by the general formula (5-1c):

[Formula 12]

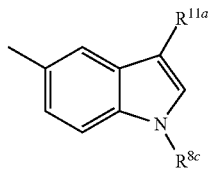
(5-1c)

(wherein $R^{8c}$ is an optionally substituted $C_{1-6}$ alkyl group; and $R^{11a}$ is an optionally substituted aryl group).

[14] The compound or the salt thereof according to [1], wherein the compound is at least one selected from the group consisting of 5-cyclopropyl-2-((1-(3-fluorobenzyl)-1H-indol-5-yl)amino)nicotinic acid, 5-cyclopropyl-2-((1-(2-fluorobenzyl)-1H-indol-5-yl)amino)nicotinic acid, 5-cyclopropyl-2-(1-methyl-3-phenyl-1H-indol-5-yl)amino) nicotinic acid, 5-cyclopropyl-2-((1-methyl-7-phenyl-1H-indol-5-yl)amino)nicotinic acid, 2-((7-(2-cyanophenyl)-1-methyl-1H-indol-5-yl)amino)-5-cyclopropylnicotinic acid, 2-((1-benzyl-1H-indol-5-yl)amino)-5-cyclopropylnicotinic acid, 5-cyclopropyl-2-((1-ethyl-2-phenyl-1H-indol-5-yl)

amino)nicotinic acid, 5-cyclopropyl-2-(1-isopentyl-1H-indol-5-ylamino)nicotinic acid, 2-((1-(cyclohexylmethyl)-1H-indol-5-yl)amino)-5-cyclopropylnicotinic acid, 2-((1-(cyclobutylmethyl)-1H-indol-5-yl)amino)-5-cyclopropylnicotinic acid, 2-((7-(4-cyanophenyl)-1-methyl-1H-indol-5-yl)amino)-5-cyclopropylnicotinic acid, 5-cyclopropyl-2-((7-(2-methoxyphenyl)-1-methyl-1H-indol-5-yl)amino)nicotinic acid, 5-cyclopropyl-2-((1-phenyl-1H-indol-5-yl)amino)nicotinic acid, 2-((1-(cyclopentylmethyl)-1H-indol-5-yl)amino)-5-cyclopropylnicotinic acid, 5-cyclopropyl-2-((1-(4-fluorobenzyl)-1H-indol-5-yl)amino) nicotinic acid, 5-cyclopropyl-2-((1-(3-(trifluoromethyl)benzyl)-1H-indol-5-yl)amino)nicotinic acid, 2-((1-(cyclohexylmethyl)-1H-indazol-5-yl)amino)-5-cyclopropylnicotinic acid, 5-cyclopropyl-2-((1-(4-fluorophenyl)-1H-indol-5-yl) amino)nicotinic acid, 2-((1-benzyl-1H-indol-5-yl)amino)-5-cyclopropylbenzoic acid, 3-((1-benzyl-1H-indol-5-yl)amino)-6-cyclopropylpyrazine-2-carboxylic acid, 5-cyclopropyl-2-((3-(2-fluorophenyl)-1-methyl-1H-indol-5-yl)amino)nicotinic acid, 5-cyclopropyl-2-((7-(4-fluorophenyl)-1-methyl-1H-indol-5-yl)amino)nicotinic acid, 2-((1-isobutyl-1H-indol-5-yl)amino)-5-cyclopropylnicotinic acid, 5-cyclopropyl-2-((7-(2-fluorophenyl)-1-methyl-1H-indol-5-yl)amino)nicotinic acid, 5-cyclopropyl-2-((7-(3-methoxypropyl)-1-methyl-1H-indol-5-yl)amino)nicotinic acid, 5-cyclopropyl-2-((7-(2-cyclopropylethyl)-1-methyl-1H-indol-5-yl)amino)nicotinic acid, 5-cyclopropyl-2-((7-isopropyl-1-methyl-1H-indol-5-yl)amino)nicotinic acid, 2-((1-benzyl-1H-indol-5-yl)amino)-5-cyclopropyl-N-(methylsulfonyl) nicotinamide, 2-((3-benzyl-2-oxo-2,3-dihydrobenzo[d] thiazol-6-yl)amino)-5-cyclopropylnicotinic acid and 2-((1-(cyclobutylmethyl)-1H-indol-4-yl)amino)-5-cyclopropylnicotinic acid.

[14'] The compound or the salt thereof according to [1], wherein the compound is at least one selected from the group consisting of 5-cyclopropyl-2-((1-(3-methoxybenzyl)-1H-indol-5-yl)amino)nicotinic acid, 2-((1-(3-cyanobenzyl)-1H-indol-5-yl)amino)-5-cyclopropylnicotinic acid, 5-cyclopropyl-2-((1-(2-methylbenzyl)-1H-indol-5-yl) amino)nicotinic acid, 5-cyclopropyl-2-((1-(3-methylbenzyl)-1H-indol-5-yl)amino)nicotinic acid, 5-cyclopropyl-2-((1-(4-methylbenzyl)-1H-indol-5-yl)amino)nicotinic acid, 2-((1-(3-chlorobenzyl)-1H-indol-5-yl)amino)-5-cyclopropylnicotinic acid, 2-((1-benzyl-6-methyl-1H-indol-5-yl) amino)-5-cyclopropylnicotinic acid, 5-cyclopropyl-2-((1-(2-phenylethyl)-1H-indol-5-yl)amino)nicotinic acid, 5-cyclopropyl-2-((1-(3-fluorobenzyl)-7-methyl-1H-indol-5-yl)amino)nicotinic acid, 2-((1-benzyl-7-methyl-1H-indol-5-yl)amino)-5-cyclopropylnicotinic acid, 5-cyclopropyl-2-((1-(2-ethylbutyl)-1H-indol-5-yl)amino)nicotinic acid, 5-cyclopropyl-2-((1-(3,4-difluorobenzyl)-1H-indol-5-yl) amino)nicotinic acid, 2-((1-butyl-1H-indol-5-yl)amino)-5-cyclopropylnicotinic acid, 5-cyclopropyl-2-((1-(2,5-difluorobenzyl)-1H-indol-5-yl)amino)nicotinic acid and 5-cyclopropyl-2-((1-(2,3-difluorobenzyl)-1H-indol-5-yl) amino)nicotinic acid.

[15] A pharmaceutical composition comprising the compound or the salt thereof according to any of [1] to [14].
[16] A keratinocyte proliferation inhibitor comprising the compound or the salt thereof according to any of [1] to [14].
[17] An agent for treating the disease involved in the overproliferation of keratinocytes, comprising the compound or the salt thereof according to any of [1] to [14].
[18] A TNFα production inhibitor comprising the compound or the salt thereof according to any of [1] to [14].
[19] An agent for treating the disease involved in the overproduction of TNFα, comprising the compound or the salt thereof according to any of [1] to [14].
[20] A medicament comprising the compound or the salt thereof according to any of [1] to [14].
[21] A method for inhibiting the proliferation of keratinocytes, comprising the step of administering to a subject the compound or the salt thereof according to any of [1] to [14].
[22] A method for treating the disease involved in the overproliferation of keratinocytes, comprising the step of administering to a subject the compound or the salt thereof according to any of [1] to [14].
[23] A method for inhibiting the production of TNFα, comprising the step of administering to a subject the compound or the salt thereof according to any of [1] to [14].
[24] A method for treating the disease involved in the overproduction of TNFα, comprising the step of administering to a subject the compound or the salt thereof according to any of [1] to [14].
[25] The compound or the salt thereof according to any of [1] to [14] for use in a method for inhibiting the proliferation of keratinocytes.
[26] The compound or the salt thereof according to any of [1] to [14] for use in a method for treating the disease involved in the overproliferation of keratinocytes.
[27] The compound or the salt thereof according to any of [1] to [14] for use in a method for inhibiting the production of TNFα.
[28] The compound or the salt thereof according to any of [1] to [14] for use in a method for treating the disease involved in the overproduction of TNFα.
[29] Use of the compound or the salt thereof according to any of [1] to [14] in the manufacture of a keratinocyte proliferation inhibitor.
[30] Use of the compound or the salt thereof according to any of [1] to [14] in the manufacture of a medicament for treating the disease involved in the overproliferation of keratinocytes.
[31] Use of the compound or the salt thereof according to any of [1] to [14] in the manufacture of a TNFα production inhibitor.
[32] Use of the compound or the salt thereof according to any of [1] to [14] in the manufacture of a medicament for treating the disease involved in the overproduction of TNFα.

Advantageous Effects of Invention

The novel amine derivatives or the salts thereof according to the present invention, which have the excellent effect of inhibiting the proliferation of keratinocytes and are superior in safety and pharmacokinetics, are useful for treatment such as prevention or therapy of the diseases involved in the overproliferation of keratinocytes, for example, skin diseases such as skin cancer, psoriasis, immunologic/allergic skin diseases and chronic wound.

Further, the novel amine derivatives or the salts thereof according to the present invention, which have the excellent effect of inhibiting the production of TNFα, are also useful for treatment such as prevention or therapy of the diseases involved in the overproduction of TNFα.

DESCRIPTION OF EMBODIMENTS

The present invention will be described in more detail below.

In the present specification, the following terms have the following meanings unless otherwise indicated.

The halogen atom refers to a fluorine atom, a chlorine atom, a bromine atom or an iodine atom.

The $C_{1-3}$ alkyl group refers to a methyl group, an ethyl group, a propyl group or an isopropyl group.

The $C_{1-4}$ alkyl group refers to a methyl group, an ethyl group, a propyl group, an isopropyl group, a butyl group, a sec-butyl group, an isobutyl group or a tert-butyl group.

The $C_{1-6}$ alkyl group refers to linear or branched $C_{1-6}$ alkyl groups such as a methyl group, an ethyl group, a propyl group, an isopropyl group, a butyl group, a sec-butyl group, an isobutyl group, a tert-butyl group, a pentyl group, an isopentyl group and a hexyl group.

The $C_{1-12}$ alkyl group refers to linear or branched $C_{1-12}$ alkyl groups such as a methyl group, an ethyl group, a propyl group, an isopropyl group, a butyl group, a sec-butyl group, an isobutyl group, a tert-butyl group, a pentyl group, an isopentyl group, a hexyl group, a heptyl group and an octyl group.

The $C_{3-6}$ alkyl group refers to linear or branched $C_{3-6}$ alkyl groups such as a propyl group, an isopropyl group, a butyl group, a sec-butyl group, an isobutyl group, a ten-butyl group, a pentyl group, an isopentyl group and a hexyl group.

The $C_{2-6}$ alkenyl group refers to linear or branched $C_{2-6}$ alkenyl groups such as a vinyl group, an allyl group, a propenyl group, an isopropenyl group, a butenyl group, an isobutenyl group, a 1,3-butadienyl group, a pentenyl group and a hexenyl group.

The $C_{3-6}$ cycloalkyl group refers to a cyclopropyl group, a cyclobutyl group, a cyclopentyl group or a cyclohexyl group.

The $C_{3-8}$ cycloalkyl group refers to $C_{3-8}$ cycloalkyl groups such as a cyclopropyl group, a cyclobutyl group, a cyclopentyl group and a cyclohexyl group.

The $C_{3-8}$ cycloalkyl-$C_{1-6}$ alkyl group refers to $C_{3-8}$ cycloalkyl-$C_{1-6}$ alkyl groups such as a cyclopropylmethyl group, a 2-(cyclopropyl)ethyl group, a cyclobutylmethyl group, a 2-(cyclobutyl)ethyl group, a cyclopentylmethyl group and a cyclohexylmethyl group.

The $C_{4-8}$ cycloalkenyl group refers to $C_{4-8}$ cycloalkenyl groups such as a cyclobutenyl group, a cyclopentenyl group, a cyclohexenyl group and a cyclohexanedienyl group.

The fused bicyclic hydrocarbon ring group refers to fused bicyclic hydrocarbon rings which may be partially hydrogenated, such as a pentalenyl group, an indanyl group, an indenyl group and a naphthyl group.

The fused tricyclic hydrocarbon ring group refers to fused tricyclic hydrocarbon rings which may be partially hydrogenated, such as a biphenylenyl group, an acenaphthenyl group, an acenaphthylenyl group, a fluorenyl group, a phenalenyl group, a phenanthrenyl group and an anthracenyl group.

The aryl group refers to a phenyl group, a fused bicyclic hydrocarbon ring group or a fused tricyclic hydrocarbon ring group.

The ar-$C_{1-6}$ alkyl group refers to aryl-$C_{1-6}$ alkyl groups such as a benzyl group, a diphenylmethyl group, a trityl group, a phenethyl group and a naphthylmethyl group.

The $C_{1-3}$ alkoxy group refers to a methoxy group, an ethoxy group, a propoxy group or an isopropoxy group.

The $C_{1-6}$ alkoxy group refers to linear or branched $C_{1-6}$ alkyloxy groups such as a methoxy group, an ethoxy group, a propoxy group, an isopropoxy group, a butoxy group, an isobutoxy group, a sec-butoxy group, a tert-butoxy group, a pentyloxy group and a hexyloxy group.

The $C_{1-6}$ alkoxy-$C_{1-6}$ alkyl group refers to $C_{1-6}$ alkyloxy-$C_{1-6}$ alkyl groups such as a methoxymethyl group and a 1-ethoxyethyl group.

The ar-$C_{1-6}$ alkoxy-$C_{1-6}$ alkyl group refers to ar-$C_{1-6}$ alkyloxy-$C_{1-6}$ alkyl groups such as a benzyloxymethyl group and a phenethyloxymethyl group.

The aryloxy group refers to aryloxy groups such as a phenoxy group and a naphthyloxy group.

The $C_{1-3}$ alkylthio group refers to a methylthio group, an ethylthio group, a propylthio group or an isopropylthio group.

The $C_{1-6}$ alkylthio group refers to $C_{1-6}$ alkylthio groups such as a methylthio group, an ethylthio group, a propylthio group and a butylthio group.

The arylthio group refers to arylthio groups such as a phenylthio group and a naphthylthio group.

The $C_{1-6}$ alkylsulfonyl group refers to $C_1$ alkylsulfonyl groups such as a methylsulfonyl group, an ethylsulfonyl group and a propylsulfonyl group.

The arylsulfonyl group refers to arylsulfonyl groups such as a benzenesulfonyl group, a p-toluenesulfonyl group and a naphthalenesulfonyl group.

The $C_{1-3}$ alkylamino group refers to a methylamino group, an ethylamino group, a propylamino group or an isopropylamino group.

The $C_{1-6}$ alkylamino group refers to linear or branched $C_{1-6}$ alkylamino groups such as a methylamino group, an ethylamino group, a propylamino group, an isopropylamino group, a butylamino group, a sec-butylamino group, a tert-butylamino group, a pentylamino group and a hexylamino group.

The di($C_{1-3}$ alkyl)amino group refers to linear or branched di($C_{1-3}$ alkyl)amino groups such as a dimethylamino group, a diethylamino group, a dipropylamino group, a diisopropylamino group, an (ethyl)(methyl)amino group and a (methyl)(propyl)amino group.

The di($C_{1-6}$ alkyl)amino group refers to linear or branched di($C_{1-6}$ alkyl)amino groups such as a dimethylamino group, a diethylamino group, a dipropylamino group, a diisopropylamino group, a dibutylamino group, a di(tert-butyl)amino group, a dipentylamino group, a dihexylamino group, an (ethyl)(methyl)amino group and a (methyl)(propyl)amino group.

The $C_{2-12}$ alkanoyl group refers to linear or branched $C_{2-12}$ alkanoyl groups such as an acetyl group, a propionyl group, a valeryl group, an isovaleryl group and a pivaloyl group.

The aroyl group refers to a benzoyl group or a naphthoyl group.

The heterocyclic carbonyl group refers to a nicotinoyl group, a thenoyl group, a pyrrolidinocarbonyl group or a furoyl group.

The (α-substituted) aminoacetyl group refers to (α-substituted) aminoacetyl groups having an optionally protected N-terminal, which are derived from amino acids (including amino acids such as glycine, alanine, valine, leucine, isoleucine, serine, threonine, cysteine, methionine, aspartic acid, glutamic acid, asparagine, glutamine, arginine, lysine, histidine, hydroxylysine, phenylalanine, tyrosine, tryptophan, proline and hydroxyproline).

The acyl group refers to a formyl group, a succinyl group, a glutaryl group, a maleoyl group, a phthaloyl group, a $C_{2-12}$ alkanoyl group, an aroyl group, a heterocyclic carbonyl group or an (α-substituted) aminoacetyl group.

The acyl-$C_{1-6}$ alkyl group refers to an acetylmethyl group, a benzoylmethyl group, a 1-benzoylethyl group or the like.

The acyloxy-$C_{1-6}$ alkyl group refers to an acetoxymethyl group, a propionyloxymethyl group, a pivaloyloxymethyl group, a benzoyloxymethyl group, a 1-(benzoyloxy)ethyl group or the like.

The $C_{1-6}$ alkoxycarbonyl group refers to linear or branched $C_{1-6}$ alkyloxycarbonyl groups such as a methoxycarbonyl group, an ethoxycarbonyl group, an isopropoxycarbonyl group, a tert-butoxycarbonyl group and a 1,1-dimethylpropoxycarbonyl group.

The ar-$C_{1-6}$ alkoxycarbonyl group refers to aryl-$C_{1-6}$ alkoxycarbonyl groups such as a benzyloxycarbonyl group and a phenethyloxycarbonyl group.

The aryloxycarbonyl group refers to aryloxycarbonyl groups such as a phenyloxycarbonyl group and a naphthyloxycarbonyl group.

The monocyclic nitrogen-containing heterocyclic group refers to monocyclic nitrogen-containing heterocyclic groups containing only a nitrogen atom(s) as the heteroatom(s) forming the ring, such as an azetidinyl group, a pyrrolidinyl group, a pyrrolinyl group, a pyrrolyl group, a piperidyl group, a tetrahydropyridyl group, a pyridyl group, a homopiperidinyl group, an octahydroazocinyl group, an imidazolidinyl group, an imidazolinyl group, an imidazolyl group, a pyrazolidinyl group, a pyrazolinyl group, a pyrazolyl group, a piperazinyl group, a pyrazinyl group, a pyridazinyl group, a pyrimidinyl group, a homopiperazinyl group, a triazolyl group and a tetrazolyl group.

The monocyclic oxygen-containing heterocyclic group refers to a tetrahydrofuranyl group, a furanyl group, a tetrahydropyranyl group, a dihydropyranyl group or a pyranyl group.

The monocyclic sulfur-containing heterocyclic group refers to a thienyl group.

The monocyclic nitrogen- and oxygen-containing heterocyclic group refers to monocyclic nitrogen- and oxygen-containing heterocyclic groups containing only nitrogen and oxygen atoms as the heteroatoms forming the ring, such as an oxazolyl group, an isoxazolyl group, an oxadiazolyl group and a morpholinyl group.

The monocyclic nitrogen- and sulfur-containing heterocyclic group refers to monocyclic nitrogen- and sulfur-containing heterocyclic groups containing only nitrogen and sulfur atoms as the heteroatoms forming the ring, such as a thiazolyl group, an isothiazolyl group, a thiadiazolyl group, a thiomorpholinyl group, a 1-oxidothiomorpholinyl group and a 1,1-dioxidothiomorpholinyl group.

The monocyclic heterocyclic group refers to a monocyclic nitrogen-containing heterocyclic group, a monocyclic oxygen-containing heterocyclic group, a monocyclic sulfur-containing heterocyclic group, a monocyclic nitrogen- and oxygen-containing heterocyclic group or a monocyclic nitrogen- and sulfur-containing heterocyclic group.

The bicyclic nitrogen-containing heterocyclic group refers to bicyclic nitrogen-containing heterocyclic groups containing only a nitrogen atom(s) as the heteroatom(s) forming the ring, such as an indolinyl group, an indolyl group, an isoindolinyl group, an isoindolyl group, a pyrrolopyridinyl group, an indazolyl group, a benzimidazolyl group, a benzotriazolyl group, a tetrahydroquinolinyl group, a dihydroquinolinyl group, a quinolinyl group, a tetrahydroquinolinyl group, a tetrahydroisoquinolinyl group, an isoquinolinyl group, a dihydroquinazolinyl group, a cinnolinyl group, a phthalazinyl group, a quinazolinyl group, a dihydroquinoxalinyl group, a quinoxalinyl group, a naphthyridinyl group, a purinyl group, a pteridinyl group and a quinuclidinyl group.

The bicyclic oxygen-containing heterocyclic group refers to bicyclic oxygen-containing heterocyclic groups containing only an oxygen atom(s) as the heteroatom(s) forming the ring, such as a 2,3-dihydrobenzofuranyl group, a benzofuranyl group, an isobenzofuranyl group, a chromanyl group, a chromenyl group, an isochromanyl group, a 1,3-benzodioxolyl group, a 1,3-benzodioxanyl group and a 1,4-benzodioxanyl group.

The bicyclic sulfur-containing heterocyclic group refers to bicyclic sulfur-containing heterocyclic groups containing only a sulfur atom(s) as the heteroatom(s) forming the ring, such as a 2,3-dihydrobenzothienyl group and a benzothienyl group.

The bicyclic nitrogen- and oxygen-containing heterocyclic group refers to bicyclic nitrogen- and oxygen-containing heterocyclic groups containing only nitrogen and oxygen atoms as the heteroatoms forming the ring, such as a dihydrobenzoxazolyl group, a benzoxazolyl group, a benzisoxazolyl group, a benzoxadiazolyl group, a benzomorpholinyl group, a dihydropyranopyridyl group, a dihydrodioxinopyridyl group and a dihydropyridoxazinyl group.

The bicyclic nitrogen- and sulfur-containing heterocyclic group refers to bicyclic nitrogen- and sulfur-containing heterocyclic groups containing nitrogen and sulfur atoms as the heteroatoms forming the ring, such as a dihydrobenzothiazolyl group, a benzothiazolyl group, a benzisothiazolyl group and a benzothiadiazolyl group.

The bicyclic heterocyclic group refers to a bicyclic nitrogen-containing heterocyclic group, a bicyclic oxygen-containing heterocyclic group, a bicyclic sulfur-containing heterocyclic group, a bicyclic nitrogen- and oxygen-containing heterocyclic group or a bicyclic nitrogen- and sulfur-containing heterocyclic group.

The tricyclic nitrogen-containing heterocyclic group refers to tricyclic nitrogen-containing heterocyclic groups containing a nitrogen atom(s) as the heteroatom(s) forming the ring, such as a tetrahydrocarbazolyl group, a carbazolyl group, an acridinyl group and a phenanthridinyl group.

The tricyclic oxygen-containing heterocyclic group refers to tricyclic oxygen-containing heterocyclic groups containing an oxygen atom(s) as the heteroatom(s) forming the ring, such as a xanthenyl group.

The tricyclic sulfur-containing heterocyclic group refers to tricyclic sulfur-containing heterocyclic groups containing a sulfur atom(s) as the heteroatom(s) forming the ring, such as a thianthrenyl group.

The tricyclic nitrogen- and oxygen-containing heterocyclic group refers to tricyclic nitrogen- and oxygen-containing heterocyclic groups containing nitrogen and oxygen atoms as the heteroatoms forming the ring, such as a phenoxazinyl group.

The tricyclic nitrogen- and sulfur-containing heterocyclic group refers to tricyclic nitrogen- and sulfur-containing heterocyclic groups containing nitrogen and sulfur atoms as the heteroatoms forming the ring, such as a phenothiazinyl group.

The tricyclic heterocyclic group refers to a tricyclic nitrogen-containing heterocyclic group, a tricyclic oxygen-containing heterocyclic group, a tricyclic sulfur-containing heterocyclic group, a tricyclic nitrogen- and oxygen-containing heterocyclic group or a tricyclic nitrogen- and sulfur-containing heterocyclic group.

The heterocyclic group refers to a monocyclic heterocyclic group, a bicyclic heterocyclic group or a tricyclic heterocyclic group.

The heterocyclic $C_{1-6}$ alkyl group refers to monocyclic nitrogen-containing heterocyclic $C_{1-6}$ alkyl groups such as an azetidinylmethyl group, an azetidinylethyl group, a pyrrolidinylmethyl group, a pyrrolidinylethyl group, a piperidylmethyl group, a piperidylethyl group, a pyridylmethyl group, a pyridylethyl group, an imidazolylmethyl group, an imidazolylethyl group, a piperazinylmethyl group and a piperazinylethyl group; monocyclic oxygen-containing heterocyclic $C_{1-6}$ alkyl groups such as a tetrahydrofuranylmethyl group and a tetrahydropyranylmethyl group; monocyclic sulfur-containing heterocyclic $C_{1-6}$ alkyl groups such as a thienylmethyl group; monocyclic nitrogen- and oxygen-containing heterocyclic $C_{1-6}$ alkyl groups such as an oxazolylmethyl group, an oxazolylethyl group, an isoxazolylmethyl group, an isoxazolylethyl group, a morpholinylmethyl group and a morpholinylethyl group; monocyclic nitrogen- and sulfur-containing heterocyclic $C_{1-6}$ alkyl groups such as a thiazolylmethyl group, a thiazolylethyl group, an isothiazolylmethyl group and an isothiazolylethyl group; bicyclic nitrogen-containing heterocyclic $C_{1-6}$ alkyl groups such as an indolylmethyl group, an indolylethyl group, a benzimidazolylmethyl group, a benzimidazolylethyl group, a quinolylmethyl group and a quinolylethyl group; bicyclic oxygen-containing heterocyclic $C_{1-6}$ alkyl groups such as a benzofuranylmethyl group, an isobenzofuranylmethyl group and a chromanylmethyl group; bicyclic sulfur-containing heterocyclic $C_{1-6}$ alkyl groups such as a benzothienylmethyl group; bicyclic nitrogen- and oxygen-containing heterocyclic $C_{1-6}$ alkyl groups such as a benzoxazolylmethyl group and a benzisoxazolylmethyl group; bicyclic nitrogen- and sulfur-containing heterocyclic $C_{1-6}$ alkyl groups such as a benzothiazolylmethyl group and a benzisothiazolylmethyl group; tricyclic nitrogen-containing heterocyclic $C_{1-6}$ alkyl groups such as a carbazolylmethyl group; tricyclic oxygen-containing heterocyclic $C_{1-6}$ alkyl groups such as a xanthenylmethyl group; and tricyclic sulfur-containing heterocyclic $C_{1-6}$ alkyl groups such as a thianthrenylmethyl group.

The silyl group refers to a trimethylsilyl group, a triethylsilyl group, a tributylsilyl group, a tert-butyldimethylsilyl group or the like.

Amino protecting groups include all groups that can be used as common protecting groups for amino groups, examples of which include those described in W. Greene et al., Protective Groups in Organic Synthesis, 4th ed., pp. 696-926, 2007, John Wiley & Sons, Inc. Specific examples include an ar-$C_{1-6}$ alkyl group, a $C_{1-6}$ alkoxy-$C_{1-6}$ alkyl group, an acyl group, a $C_{1-6}$ alkoxycarbonyl group, an ar-$C_{1-6}$ alkoxycarbonyl group, an aryloxycarbonyl group, a $C_{1-6}$ alkylsulfonyl group, an arylsulfonyl group or a silyl group.

Imino protecting groups include all groups that can be used as common protecting groups for imino groups, examples of which include those described in W. Greene et al., Protective Groups in Organic Synthesis, 4th ed., pp. 696-926, 2007, John Wiley & Sons, Inc. Specific examples include an ar-$C_{1-6}$ alkyl group, a $C_{1-6}$ alkoxy-$C_{1-6}$ alkyl group, an acyl group, a $C_{1-6}$ alkoxycarbonyl group, an ar-$C_{1-6}$ alkoxycarbonyl group, an aryloxycarbonyl group, a $C_{1-6}$ alkylsulfonyl group, an arylsulfonyl group or a silyl group.

Hydroxyl protecting groups include all groups that can be used as common protecting groups for hydroxyl groups, examples of which include those described in W. Greene et al., Protective Groups in Organic Synthesis, 4th ed., pp. 16-366, 2007, John Wiley & Sons, Inc. Specific examples include a $C_{1-6}$ alkyl group, a $C_{2-6}$ alkenyl group, an ar-$C_{1-6}$ alkyl group, a $C_{1-6}$ alkoxy-$C_{1-6}$ alkyl group, an ar-$C_{1-6}$ alkoxy-$C_{1-6}$ alkyl group, an acyl group, a $C_{1-6}$ alkoxycarbonyl group, an ar-$C_{1-6}$ alkoxycarbonyl group, a $C_{1-6}$ alkylsulfonyl group, an arylsulfonyl group, a silyl group, a tetrahydrofuranyl group or a tetrahydropyranyl group.

Carboxyl protecting groups include all groups that can be used as common protecting groups for carboxyl groups, examples of which include those described in W. Greene et al., Protective Groups in Organic Synthesis, 4th ed., pp. 533-646, 2007, John Wiley & Sons, Inc. Specific examples include a $C_{1-6}$ alkyl group, a $C_{2-6}$ alkenyl group, an aryl group, an ar-$C_{1-6}$ alkyl group, a $C_{1-6}$ alkoxy-$C_{1-6}$ alkyl group, an ar-$C_{1-6}$ alkoxy-$C_{1-6}$ alkyl group, an acyl-$C_{1-6}$ alkyl group, an acyloxy-$C_{1-6}$ alkyl group or a silyl group.

Leaving groups include a halogen atom, a $C_{1-6}$ alkylsulfonyloxy group or an arylsulfonyloxy group. The $C_{1-6}$ alkylsulfonyloxy group and the arylsulfonyloxy group may be substituted.

Aliphatic hydrocarbons include pentane, hexane or cyclohexane.

Halogenated hydrocarbons include methylene chloride, chloroform or dichloroethane.

Alcohols include methanol, ethanol, propanol, 2-propanol, butanol or 2-methyl-2-propanol.

Glycols include ethylene glycol, propylene glycol or diethylene glycol.

Ethers include diethyl ether, diisopropyl ether, dioxane, tetrahydrofuran, anisole, ethylene glycol dimethyl ether, diethylene glycol dimethyl ether or diethylene glycol diethyl ether.

Ketones include acetone, 2-butanone or 4-methyl-2-pentanone.

Esters include methyl acetate, ethyl acetate, propyl acetate or butyl acetate.

Amides include N,N-dimethylformamide, N,N-dimethylacetamide or 1-methyl-2-pyrolidone.

Nitriles include acetonitrile or propionitrile.

Sulfoxides include dimethyl sulfoxide.

Aromatic hydrocarbons include benzene, toluene or xylene.

Inorganic acids include hydrochloric acid, nitric acid, phosphoric acid, sulfuric acid, boric acid and hydrofluoric acid.

Organic acids include formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid or p-toluenesulfonic acid.

The acid refers to an inorganic acid or an organic acid.

Inorganic bases include sodium hydroxide, potassium hydroxide, sodium bicarbonate, sodium carbonate, potassium carbonate, cesium carbonate, tripotassium phosphate, tert-butoxy potassium or sodium hydride.

Organic bases include triethylamine, diisopropylethylamine, pyridine, 4-dimethylaminopyridine or N-methylmorpholine.

The base refers to an inorganic base or an organic base.

Palladium catalysts include metallic palladium such as palladium on carbon and palladium black; inorganic palladium salts such as palladium chloride; organic palladium salts such as palladium acetate; organopalladium complexes such as tetrakis(triphenylphosphine)palladium(0), bis(triphenylphosphine)palladium(II) dichloride, bis(di-tert-butyl(4-dimethylaminophenyl)phosphine)dichloropalladium(II), 1,1'-bis(diphenylphosphino)ferrocenepalladium(II) dichloride, (E)-di(μ-acetato)bis(o-(di-o-tolylphosphino)benzyl)dipalladium(II) and tris(dibenzylideneacetone)dipalladium(0); and polymer-supported organopalladium complexes such as polymer-supported bis(acetato)triphenylphosphinepalladium(II) and polymer-supported di(acetato)dicyclohexylphenylphosphinepalladium(II).

Copper catalysts include copper(I) bromide, copper(I) iodide and copper(II) acetate.

Metal catalysts include metallic palladium such as palladium on carbon and palladium black; palladium salts such as palladium oxide and palladium hydroxide; metallic nickel such as Raney nickel; and platinum salts such as platinum oxide.

Ligands include trialkylphosphines such as trimethylphosphine and tri-tert-butylphosphine; alkylbiscycloalkylphosphines such as butylbis(1-adamanthyl)phosphine; tricycloalkylphosphines such as tricyclohexylphosphine; triarylphosphines such as triphenylphosphine and tritolylphosphine; trialkyl phosphites such as trimethyl phosphite, triethyl phosphite and tributyl phosphite; tricycloalkyl phosphites such as tricyclohexyl phosphite; triaryl phosphites such as triphenyl phosphite; imidazolium salts such as 1,3-bis(2,4,6-trimethylphenyl)imidazolium chloride; diketones such as acetylacetone and octafluoroacetylacetone; amines such as trimethylamine, triethylamine, tripropylamine and triisopropylamine; 1,1'-bis(diphenylphosphino)ferrocene, 2,2'-bis(diphenylphosphino)-1,1'-binaphthyl, 2-dicyclohexylphosphino-2',6'-dimethoxybiphenyl, 2-dicyclohexylphosphino-2',4',6'-triisopropylbiphenyl, 2-(dicyclohexylphosphino)-3,6-dimethoxy-2',4',6'-triisopropyl-1,1'-biphenyl, 2-(di-tert-butylphosphino)-2'4',6'-triisopropylbiphenyl, 4,5'-bis(diphenylphosphino)-9,9'-dimethylxanthene and 2-(di-tert-butylphosphino)biphenyl.

Condensing agents include BOP (1H-1,2,3-benzotriazol-1-yloxy(tri(dimethylamino))phosphonium hexafluorophosphate), WSC (1-ethyl-3-(3-dimethylaminopropyl)carbodiimide hydrochloride), DCC (N,N-dicyclohexylcarbodiimide), HATU (O-(7-azabenzotriazol-1-yl)-1,1,3,3-tetramethyluronium hexafluorophosphate) and CDI (1,1'-carbonyldiimidazole).

Salts of the compounds of the general formula (1) include commonly known salts at basic groups such as an amino group or acidic groups such as a phenolic hydroxyl group or a carboxyl group.

Examples of the salts at basic groups include salts with mineral acids such as hydrochloric acid, hydrobromic acid, nitric acid and sulfuric acid; salts with organic carboxylic acids such as formic acid, acetic acid, citric acid, oxalic acid, fumaric acid, maleic acid, succinic acid, malic acid, tartaric acid, aspartic acid, trichloroacetic acid and trifluoroacetic acid; and salts with sulfonic acids such as methanesulfonic acid, benzenesulfonic acid, p-toluenesulfonic acid, mesitylenesulfonic acid and naphthalenesulfonic acid.

Examples of the salts at acidic groups include salts with alkali metals such as sodium and potassium; salts with alkaline earth metals such as calcium and magnesium; ammonium salts; and salts with nitrogen-containing organic bases such as trimethylamine, triethylamine, tributylamine, pyridine, N,N-dimethylaniline, N-methylpiperidine, N-methylmorpholine, diethylamine, dicyclohexylamine, procaine, dibenzylamine, N-benzyl-β-phenethylamine, 1-ephenamine and N,N'-dibenzylethylenediamine.

Examples of the diseases involved in the overproliferation of keratinocytes include skin diseases such as skin cancer, psoriasis, immunologic and allergic skin diseases, and chronic wound. Skin cancer or psoriasis is preferred, and psoriasis is more preferred.

Examples of the diseases involved in the overproduction of TNFα include septic shock, systemic lupus erythematosus, rheumatoid arthritis, psoriasis, inflammatory bowel disease, multiple sclerosis, ankylosing spondylitis, allergic disease, arteriosclerosis, insulin-resistant diabetes, graft-versus-host disease, viral hepatitis or infections such as HIV infection.

Rheumatoid arthritis, psoriasis, inflammatory bowel disease and multiple sclerosis are preferred, and psoriasis is more preferred.

Examples of the diseases involved in the cell proliferation include cancer, atherosclerosis, vascular restenosis, angiogenesis, diabetic retinopathy, psoriasis and endometriosis. Cancer and psoriasis are preferred, and psoriasis is more preferred.

A medicament as referred to herein includes a medicament for humans and a medicament for non-human animals (an animal medicament). Treatment includes prevention or therapy. Prevention includes inhibition of the onset, reduction in the risk of onset, and delay of the onset. Therapy includes amelioration, or inhibition of the progress (maintenance or delay), of the disease or condition of interest. Subjects for treatment include humans or non-human animals in need of such treatment. "Medicament", "agent" or "pharmaceutical composition" as referred to in the present invention can be provided as compositions in which the compounds or the salts thereof according to the present invention as active ingredients are appropriately mixed with formulation aids used for formulation such as excipients, carriers and diluents. "Medicament", "agent" or "pharmaceutical composition" may contain other active ingredients, and may be used together with a medicament containing other active ingredients.

The compounds of the present invention are preferably as described below.

$R^1$ is preferably a chlorine atom, a bromine atom, an optionally substituted $C_{1-6}$ alkyl group, an optionally substituted $C_{3-8}$ cycloalkyl group, an optionally substituted aryl group, an optionally substituted aryloxy group, an optionally substituted $C_{1-6}$ alkylthio group or an optionally substituted heterocyclic group, more preferably a chlorine atom, a bromine atom, a $C_1$-6 alkyl group, a $C_{3-8}$ cycloalkyl group, an aryl group, an aryloxy group optionally substituted with a methylsulfonyl group, a $C_{1-6}$ alkylthio group or a heterocyclic group, still more preferably a chlorine atom or a $C_{3-8}$ cycloalkyl group.

Substituents for the $C_{1-6}$ alkyl group, $C_{3-8}$ cycloalkyl group, aryl group, $C_{1-6}$ alkoxy group, aryloxy group, $C_{1-6}$ alkylthio group, arylthio group, $C_{1-6}$ alkylamino group, di($C_{1-6}$ alkyl)amino group and heterocyclic group of $R^1$ include at least one group selected from Substituent Group α.

The $C_{1-6}$ alkyl group of $R^1$ is preferably a $C_{1-4}$ alkyl group, more preferably a methyl group, an ethyl group or an isopropyl group.

The $C_{3-8}$ cycloalkyl group of $R^1$ is preferably a $C_{3-6}$ cycloalkyl group, more preferably a cyclopropyl group.

The aryl group of $R^1$ is preferably a phenyl group.

The $C_{1-6}$ alkoxy group of $R^1$ is preferably a $C_{1-3}$ alkoxy group, more preferably a methoxy group.

The aryloxy group of $R^1$ is preferably a phenyloxy group.

The $C_{1-6}$ alkylthio group of $R^1$ is preferably a $C_{1-3}$ alkylthio group, more preferably a methylthio group.

The arylthio group of $R^1$ is preferably a phenylthio group.

The $C_{1-6}$ alkylamino group of $R^1$ is preferably a $C_{1-3}$ alkylamino group, more preferably a methylamino group.

The di($C_{1-6}$ alkyl)amino group of $R^1$ is preferably a di($C_{1-3}$ alkyl)amino group, more preferably a dimethylamino group.

The heterocyclic group of $R^1$ is preferably a monocyclic heterocyclic group, more preferably a monocyclic nitrogen-containing heterocyclic group.

$R^2$ is preferably —$COOR^5$.

$R^5$ is preferably a hydrogen atom.

$R^6$ is preferably a hydrogen atom.

$R^7$ is preferably an optionally substituted $C_{1-3}$ alkyl group or an optionally substituted $C_{3-6}$ cycloalkyl group, more preferably a $C_{1-3}$ alkyl group optionally substituted with a halogen atom, or a $C_{3-6}$ cycloalkyl group, still more preferably a methyl group, a trifluoromethyl group or a cyclopropyl group.

Substituents for the $C_{1-6}$ alkyl group and $C_{3-8}$ cycloalkyl group of $R^7$ include at least one group selected from Substituent Group α.

$R^3$ is preferably a hydrogen atom.

$R^4$ is preferably an optionally substituted fused bicyclic hydrocarbon ring group or an optionally substituted bicyclic heterocyclic group.

However, when $R^4$ is an optionally substituted fused bicyclic hydrocarbon ring group, then $G^3$ is a nitrogen atom.

When $G^1$ is CH, $G^2$ is CH, $G^3$ is CH, $R^1$ is a chlorine atom, a bromine atom, an iodine atom, a $C_{1-4}$ alkyl group, a trifluoromethyl group, a dibutylamino group, a methoxy group or a substituted phenyloxy group, $R^2$ is —COOH and $R^3$ is a hydrogen atom, then $R^4$ is a group as represented by the general formulas (2-1) to (2-4):

[Formula 13]

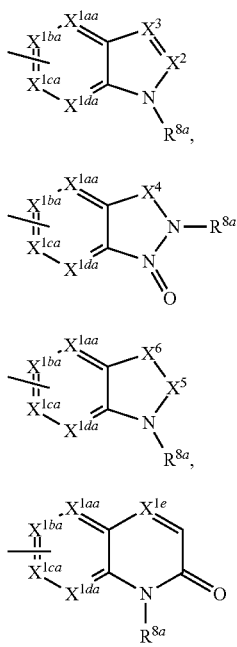

(2-1)

(2-2)

(2-3)

(2-4)

(wherein $X^{1aa}$, $X^{1ba}$, $X^{1ca}$, $X^{1da}$, $X^{1e}$, $X^2$, $X^3$, $X^4$, $X^5$, $X^6$ and $R^{8a}$ are as defined above).

$R^4$ is more preferably an optionally substituted bicyclic heterocyclic group, still more preferably a group as represented by the general formulas (3-1) to (3-3):

[Formula 14]

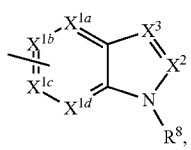

(3-1)

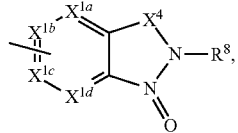

(3-2)

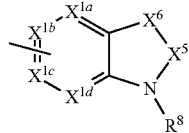

(3-3)

(wherein $X^{1a}$, $X^{1b}$, $X^{1c}$, $X^{1d}$, $X^2$, $X^3$, $X^{4a}$, $X^5$, $X^6$ and $R^8$ are as defined above), even more preferably a group as represented by the general formula (4-1) or (4-2):

[Formula 15]

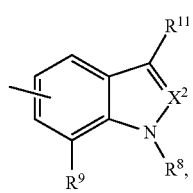

(4-1)

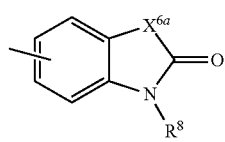

(4-2)

(wherein $X^2$, $X^{6a}$, $R^8$, $R^9$ and $R^{11}$ are as defined above).

$X^{1a}$, $X^{1b}$, $X^{1c}$ and $X^{1d}$ are preferably $CR^9$.

$R^9$ is preferably a hydrogen atom, an optionally substituted $C_{1-6}$ alkyl group, an optionally substituted $C_{3-8}$ cycloalkyl group, an optionally substituted $C_{3-8}$ cycloalkyl-$C_{1-6}$ alkyl group or an optionally substituted aryl group, more preferably a hydrogen atom, an optionally substituted $C_{1-6}$ alkyl group, an optionally substituted $C_{3-8}$ cycloalkyl-$C_{1-6}$ alkyl group or an optionally substituted aryl group, still more preferably a hydrogen atom or an optionally substituted aryl group.

Substituents for the $C_{1-6}$ alkyl group, $C_{2-6}$ alkenyl group, $C_{3-8}$ cycloalkyl group, $C_{4-8}$ cycloalkenyl group, $C_{3-8}$ cycloalkyl-$C_{1-6}$ alkyl group and aryl group of $R^9$ include at least one group selected from Substituent Group α.

When $R^4$ is a group as represented by the general formula (3-1), then $X^{1a}$, $X^{1b}$ and $X^{1c}$ are preferably CH and $X^{1d}$ is preferably $CR^9$.

When $R^4$ is a group as represented by the general formula (3-1), then $X^2$ is preferably $CR^{10}$.

$R^{10}$ is preferably a hydrogen atom or an optionally substituted $C_{1-6}$ alkyl group, more preferably a hydrogen atom.

Substituents for the carbamoyl group, $C_{1-6}$ alkyl group and aryl group of $R^{10}$ include at least one group selected from Substituent Group α.

When $R^4$ is a group as represented by the general formula (3-1), then $X^3$ is preferably $CR^{11}$.

$R^{11}$ is preferably a hydrogen atom or an optionally substituted aryl group, more preferably a hydrogen atom.

Substituents for the $C_{1-6}$ alkyl group, $C_{3-8}$ cycloalkyl group, aryl group, ar-$C_{1-6}$ alkyl group and acyl group of $R^{11}$ include at least one group selected from Substituent Group α.

When $R^4$ is a group as represented by the general formula (3-2), then $X^{1a}$, $X^{1b}$, $X^{1c}$ and $X^{1d}$ are preferably CH.

When $R^4$ is a group as represented by the general formula (3-2), then $X^{4a}$ is preferably $CH_2$.

When $R^4$ is a group as represented by the general formula (3-3), then $X^{1a}$, $X^{1b}$, $X^{1c}$ and $X^{1d}$ are preferably CH.

When $R^4$ is a group as represented by the general formula (3-3), then $X^5$ is preferably C=O.

When $R^4$ is a group as represented by the general formula (3-3), then $X^6$ is preferably $CH_2$, C=O, an oxygen atom, a sulfur atom or $NR^{12}$.

$R^{12}$ is preferably an optionally substituted $C_{1-6}$ alkyl group or an optionally substituted $C_{3-8}$ cycloalkyl group.

Substituents for the $C_{1-6}$ alkyl group, $C_{3-8}$ cycloalkyl group and $C_{3-8}$ cycloalkyl-$C_{1-6}$ alkyl group of $R^{12}$ include at least one group selected from Substituent Group α.

$R^{8'}$ is preferably a hydrogen atom, an optionally substituted $C_{1-6}$ alkyl group, an optionally substituted $C_{3-8}$ cycloalkyl group, an optionally substituted $C_{3-8}$ cycloalkyl-$C_{1-6}$ alkyl group, an optionally substituted aryl group, an optionally substituted ar-$C_{1-6}$ alkyl group, an optionally substituted acyl group, an optionally substituted heterocyclic group or an optionally substituted heterocyclic $C_{1-6}$ alkyl group.

Substituents for the $C_{1-12}$ alkyl group, $C_{3-8}$ cycloalkyl group, $C_{3-8}$ cycloalkyl-$C_{1-6}$ alkyl group, aryl group, ar-$C_{1-6}$ alkyl group, acyl group, heterocyclic group and heterocyclic $C_{1-6}$ alkyl group of $R^{8'}$ include at least one group selected from Substituent Group α.

$R^8$ is preferably an optionally substituted $C_{1-6}$ alkyl group, an optionally substituted $C_{3-8}$ cycloalkyl group, an optionally substituted $C_{3-8}$ cycloalkyl-$C_{1-6}$ alkyl group, an optionally substituted aryl group or an optionally substituted ar-$C_{1-6}$ alkyl group.

Substituents for the $C_{1-6}$ alkyl group, $C_{3-8}$ cycloalkyl group, $C_{3-8}$ cycloalkyl-$C_{1-6}$ alkyl group, aryl group, ar-$C_{1-6}$ alkyl group, acyl group, heterocyclic group and heterocyclic $C_{1-6}$ alkyl group of $R^8$ include at least one group selected from Substituent Group α.

$R^{11}$ is preferably a hydrogen atom or an optionally substituted aryl group.

Substituents for the $C_{1-6}$ alkyl group, $C_{3-8}$ cycloalkyl group, aryl group, ar-$C_{1-6}$ alkyl group and acyl group of $R^{11}$ include at least one group selected from Substituent Group α.

Still more preferably, $G^1$ and $G^2$ are CH, $G^3$ is a nitrogen atom and $R^4$ is a group as represented by the general formula (5-1):

[Formula 16]

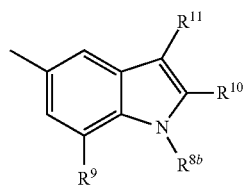

(5-1)

(wherein $R^{8b}$, $R^9$, $R^{10}$ and $R^{11}$ are as defined above).

$R^{8b}$ is preferably an optionally substituted aryl group or an optionally substituted ar-$C_{1-6}$ alkyl group.

Substituents for the $C_{1-6}$ alkyl group, $C_{3-8}$ cycloalkyl group, $C_{3-8}$ cycloalkyl-$C_{1-6}$ alkyl group, aryl group and ar-$C_{1-6}$ alkyl group of $R^{8b}$ include at least one group selected from Substituent Group α.

$R^{9'}$ is preferably a hydrogen atom, a halogen atom, an optionally substituted $C_{1-6}$ alkyl group, an optionally substituted $C_{2-6}$ alkenyl group, an optionally substituted $C_{3-8}$ cycloalkyl group, an optionally substituted $C_{4-8}$ cycloalkenyl group, an optionally substituted $C_{3-8}$ cycloalkyl-$C_{1-6}$ alkyl group or an optionally substituted aryl group.

Substituents for the $C_{1-6}$ alkyl group, $C_{2-6}$ alkenyl group, $C_{3-8}$ cycloalkyl group, $C_{4-8}$ cycloalkenyl group, $C_{3-8}$ cycloalkyl-$C_{1-6}$ alkyl group, aryl group and heterocyclic group of $R^{9'}$ include at least one group selected from Substituent Group α.

$R^9$ is preferably a hydrogen atom, an optionally substituted $C_{3-6}$ alkyl group, an optionally substituted $C_{3-8}$ cycloalkyl group, an optionally substituted $C_{3-8}$ cycloalkyl-$C_{1-6}$ alkyl group or an optionally substituted aryl group, more preferably a hydrogen atom or an optionally substituted aryl group.

Substituents for the $C_{1-6}$ alkyl group, $C_{2-6}$ alkenyl group, $C_{3-8}$ cycloalkyl group, $C_{4-8}$ cycloalkenyl group, $C_{3-8}$ cycloalkyl-$C_{1-6}$ alkyl group and aryl group of $R^9$ include at least one group selected from Substituent Group α.

$R^{10}$ is preferably a hydrogen atom or an optionally substituted $C_{1-6}$ alkyl group, more preferably a hydrogen atom.

Substituents for the carbamoyl group, $C_{1-6}$ alkyl group and aryl group of $R^{10}$ include at least one group selected from Substituent Group α.

$R^{11}$ is preferably a hydrogen atom or an optionally substituted aryl group.

Substituents for the $C_{1-6}$ alkyl group, $C_{3-8}$ cycloalkyl group, aryl group, ar-$C_{1-6}$ alkyl group and acyl group of $R^{11}$ include at least one group selected from Substituent Group α.

Particularly preferably, $G^1$ and $G^2$ are CH, $G^3$ is a nitrogen atom and $R^4$ is a group as represented by the general formula (5-1a):

[Formula 17]

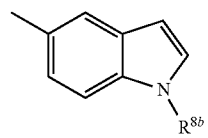

(5-1a)

(wherein $R^{8b}$ is as defined above).

$R^{8b}$ is preferably an optionally substituted $C_{1-6}$ alkyl group, an optionally substituted $C_{3-8}$ cycloalkyl-$C_{1-6}$ alkyl group or an optionally substituted ar-$C_{1-6}$ alkyl group.

Substituents for the $C_{1-6}$ alkyl group, $C_{3-8}$ cycloalkyl group, $C_{3-8}$ cycloalkyl-$C_{1-6}$ alkyl group, aryl group and ar-$C_{1-6}$ alkyl group of $R^{8b}$ include at least one group selected from Substituent Group α.

Particularly preferably, $G^1$ and $G^2$ are CH, $G^3$ is a nitrogen atom and $R^4$ is a group as represented by the general formula (5-1b):

[Formula 18]

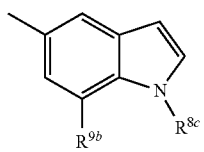

(5-1b)

(wherein $R^{8c}$ and $R^{9b}$ are as defined above).

$R^{8c}$ is preferably an optionally substituted $C_{1-6}$ alkyl group.

Substituents for the $C_{1-3}$ alkyl group of $R^{8c}$ include at least one group selected from Substituent Group α.

$R^{9b}$ is preferably an optionally substituted $C_{1-6}$ alkyl group, an optionally substituted $C_{3-8}$ cycloalkyl-$C_{1-6}$ alkyl group or an optionally substituted aryl group.

Substituents for the $C_{1-6}$ alkyl group, $C_{3-8}$ cycloalkyl group, $C_{3-8}$ cycloalkyl-$C_{1-6}$ alkyl group and aryl group of $R^{9b}$ include at least one group selected from Substituent Group α.

Particularly preferably, $G^1$ and $G^2$ are CH, $G^3$ is a nitrogen atom and $R^4$ is a group as represented by the general formula (5-1c):

[Formula 19]

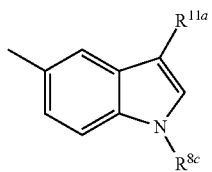

(5-1c)

(wherein $R^{8c}$ and $R^{11a}$ are as defined above).

$R^{8c}$ K is preferably an optionally substituted $C_{1-6}$ alkyl group.

Substituents for the $C_{1-6}$ alkyl group of $R^{8c}$ include at least one group selected from Substituent Group α.

$R^{11a}$ is preferably an optionally substituted aryl group.

Substituents for the aryl group of $R^{11a}$ include at least one group selected from Substituent Group α.

The novel amine derivative or the salt thereof according to the present invention is most preferably at least one compound selected from 5-cyclopropyl-2-((1-(3-fluorobenzyl)-1H-indol-5-yl)amino)nicotinic acid, 5-cyclopropyl-2-((1-(2-fluorobenzyl)-1H-indol-5-yl)amino)nicotinic acid, 5-cyclopropyl-2-(1-methyl-3-phenyl-1H-indol-5-yl)amino)nicotinic acid, 5-cyclopropyl-2-((1-methyl-7-phenyl-1H-indol-5-yl)amino)nicotinic acid, 2-((7-(2-cyanophenyl)-1-methyl-1H-indol-5-yl)amino)-5-cyclopropylnicotinic acid, 2-((1-benzyl-1H-indol-5-yl)amino)-5-cyclopropylnicotinic acid, 5-cyclopropyl-2-((1-ethyl-2-phenyl-1H-indol-5-yl)amino)nicotinic acid, 5-cyclopropyl-2-(1-isopentyl-1H-indol-5-ylamino)nicotinic acid, 2-((1-(cyclohexylmethyl)-1H-indol-5-yl)amino)-5-cyclopropylnicotinic acid, 2-((1-(cyclobutylmethyl)-1H-indol-5-yl)amino)-5-cyclopropylnicotinic acid, 2-((7-(4-cyanophenyl)-1-methyl-1H-indol-5-yl)amino)-5-cyclopropylnicotinic acid, 5-cyclopropyl-2-((7-(2-methoxyphenyl)-1-methyl-1H-indol-5-yl)amino)nicotinic acid, 5-cyclopropyl-2-((1-phenyl-1H-indol-5-yl)amino)nicotinic acid, 2-((1-(cyclopentylmethyl)-1H-indol-5-yl)amino)-5-cyclopropylnicotinic acid, 5-cyclopropyl-2-((1-(4-fluorobenzyl)-1H-indol-5-yl)amino)nicotinic acid, 5-cyclopropyl-2-((1-(3-(trifluoromethyl)benzyl)-1H-indol-5-yl)amino)nicotinic acid, 2-((1-(cyclohexylmethyl)-1H-indazol-5-yl)amino)-5-cyclopropylnicotinic acid, 5-cyclopropyl-2-((1-(4-fluorophenyl)-1H-indol-5-yl)amino)nicotinic acid, 2-((1-benzyl-1H-indol-5-yl)amino)-5-cyclopropylbenzoic acid, 3-((1-benzyl-1H-indol-5-yl)amino)-6-cyclopropylpyrazine-2-carboxylic acid, 5-cyclopropyl-2-((3-(2-fluorophenyl)-1-methyl-1H-indol-5-yl)amino)nicotinic acid, 5-cyclopropyl-2-((7-(4-fluorophenyl)-1-methyl-1H-indol-5-yl)amino)nicotinic acid, 2-((1-isobutyl-1H-indol-5-yl)amino)-5-cyclopropylnicotinic acid, 5-cyclopropyl-2-((7-(2-fluorophenyl)-1-methyl-1H-indol-5-yl)amino)nicotinic acid, 5-cyclopropyl-2-((7-(3-methoxypropyl)-1-methyl-1H-indol-5-yl)amino)nicotinic acid, 5-cyclopropyl-2-((7-(2-cyclopropylethyl)-1-methyl-1H-indol-5-yl)amino)nicotinic acid, 5-cyclopropyl-2-((7-isopropyl-1-methyl-1H-indol-5-yl)amino)nicotinic acid, 2-((1-benzyl-1H-indol-5-yl)amino)-5-cyclopropyl-N-(methylsulfonyl)nicotinamide, 2-((3-benzyl-2-oxo-2,3-dihydrobenzo[d]thiazol-6-yl)amino)-5-cyclopropylnicotinic acid and 2-((1-(cyclobutylmethyl)-1H-indol-4-yl)amino)-5-cyclopropylnicotinic acid, or a salt thereof.

In another embodiment, the novel amine derivative or the salt thereof according to the present invention is preferably at least one compound selected from 5-cyclopropyl-2-((1-(3-methoxybenzyl)-1H-indol-5-yl)amino)nicotinic acid, 2-((1-(3-cyanobenzyl)-1H-indol-5-yl)amino)-5-cyclopropylnicotinic acid, 5-cyclopropyl-2-((1-(2-methylbenzyl)-1H-indol-5-yl)amino)nicotinic acid, 5-cyclopropyl-2-((1-(3-methylbenzyl)-1H-indol-5-yl)amino)nicotinic acid, 5-cyclopropyl-2-((1-(4-methylbenzyl)-1H-indol-5-yl)amino)nicotinic acid, 2-((1-(3-chlorobenzyl)-1H-indol-5-yl)amino)-5-cyclopropylnicotinic acid, 2-((1-benzyl-6-methyl-1H-indol-5-yl)amino)-5-cyclopropylnicotinic acid, 5-cyclopropyl-2-((1-(2-phenylethyl)-1H-indol-5-yl)amino)nicotinic acid, 5-cyclopropyl-2-((1-(3-fluorobenzyl)-7-methyl-1H-indol-5-yl)amino)nicotinic acid, 2-((1-benzyl-7-methyl-1H-indol-5-yl)amino)-5-cyclopropylnicotinic acid, 5-cyclopropyl-2-((1-(2-ethylbutyl)-1H-indol-5-yl)amino)nicotinic acid, 5-cyclopropyl-2-((1-(3,4-difluorobenzyl)-1H-indol-5-yl)amino)nicotinic acid, 2-((1-butyl-1H-indol-5-yl)amino)-5-cyclopropylnicotinic acid, 5-cyclopropyl-2-((1-(2,5-difluorobenzyl)-1H-indol-5-yl)amino)nicotinic acid and 5-cyclopropyl-2-((1-(2,3-difluorobenzyl)-1H-indol-5-yl)amino)nicotinic acid, or a salt thereof.

Substituent Group α: a halogen atom, an optionally protected hydroxyl group, an optionally protected carboxyl group, an optionally protected amino group, a nitro group, a cyano group, a carbamoyl group optionally substituted with at least one group selected from Substituent Group β, a $C_{1-6}$ alkyl group optionally substituted with at least one group selected from Substituent Group β, a $C_{2-6}$ alkenyl group optionally substituted with at least one group selected from Substituent Group β, a $C_{3-8}$ cycloalkyl group optionally substituted with at least one group selected from Substituent Group β, a $C_{1-6}$ alkoxy group optionally substituted with at least one group selected from Substituent Group β, an acyl group optionally substituted with at least one group selected from Substituent Group β, an alkoxycarbonyl group optionally substituted with at least one group selected from Substituent Group β, a $C_{1-6}$ alkylamino group optionally substituted with at least one group selected from Substituent Group β, a di($C_{1-6}$ alkyl)amino group optionally substituted with at least one group selected from Substituent Group β, a $C_{1-6}$ alkylthio group optionally substituted with at least one group selected from Substituent Group β, a $C_{1-6}$ alkylsulfonyl group optionally substituted with at least one group selected from Substituent Group β, an aryl group optionally substituted with at least one group selected from Substituent Group β, a heterocyclic group optionally substituted with at least one group selected from Substituent Group β, and an oxo group.

Substituent Group β: a halogen atom, an optionally protected hydroxyl group, an optionally protected carboxyl group, an optionally protected amino group, a carbamoyl group, a $C_{1-6}$ alkyl group optionally substituted with a halogen atom, a $C_{1-6}$ alkoxy group optionally substituted with a halogen atom, a $C_{1-6}$ alkylamino group, a di($C_{1-6}$ alkyl)amino group, a heterocyclic group and an oxo group.

The novel amine derivatives or the salts thereof according to the present invention are preferably used for treatment such as prevention or therapy of skin cancer and psoriasis, and are more preferably used for treatment such as prevention or therapy of psoriasis.

When isomers (such as optical isomers, geometric isomers and tautomers) exist for the compounds represented by the general formula (1) or the salts thereof according to the present invention, the present invention encompasses such isomers. When solvates, hydrates and various forms of crystals exist for the compounds or salts, the present invention encompasses such solvates, hydrates and various forms of crystals.

Next, the processes for producing the compounds of the present invention will be described.

The compounds of the present invention are produced by combining methods known per se, and can be produced according to the production processes illustrated below, for example.

[Production Process 1]

[Formula 20]

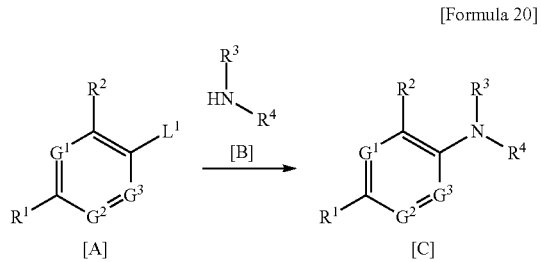

(In the formulas, $L^1$ is a leaving group; and $G^1$, $G^2$, $G^3$, $R^1$, $R^2$, $R^3$ and $R^4$ are as defined above.)

Methyl 2-bromo-5-chlorobenzoate, methyl 2-bromo-5-(trifluoromethyl)benzoate, methyl 2-chloro-5-cyclopropylnicotinate and the like are known as compounds of the general formula [A], for example.

1-Benzyl-1H-indol-5-amine, 1-benzyl-1H-indazol-5-amine and the like are known as compounds of the general formula [B], for example.

A compound of the general formula [C] or a salt thereof can be produced by reacting a compound of the general formula [A] or a salt thereof with a compound of the general formula [B] or a salt thereof in the presence or absence of a base, in the presence of a palladium catalyst and in the presence or absence of a ligand.

The solvent used in this reaction is not particularly limited insofar as it does not adversely affect the reaction. Examples of the solvent include aliphatic hydrocarbons, halogenated hydrocarbons, alcohols, glycols, ethers, ketones, esters, amides, nitriles, sulfoxides, aromatic hydrocarbons and water. Mixtures of such solvents may also be used.

Preferred solvents include ethers, esters and aromatic hydrocarbons.

The amount of the solvent used is not particularly limited, but is preferably 1 to 100 times (v/w), more preferably 1 to 10 times (v/w), still more preferably 1 to 5 times (v/w), that of the compound of the general formula [A] or a salt thereof.

Examples of the base used in this reaction include inorganic bases and organic bases.

Preferred bases include inorganic bases such as sodium bicarbonate, sodium carbonate, potassium carbonate, cesium carbonate and tripotassium phosphate; and organic bases such as pyridine, 4-(dimethylamino)pyridine, triethylamine and diisopropylethylamine.

The base is used in an amount of preferably 1 to 10 moles, more preferably 1 to 5 moles, still more preferably 1 to 2 moles, per mole of the compound of the general formula [A] or a salt thereof.

Preferred palladium catalysts used in this reaction include palladium acetate, tetrakis(triphenylphosphine)palladium(0) and tris(dibenzylideneacetone)dipalladium(0).

Combinations of such catalysts may also be used.

The palladium catalyst is used in an amount of preferably 0.00001 to 1 mole, more preferably 0.001 to 0.2 mole, per mole of the compound of the general formula [A] or a salt thereof.

Preferred ligands used in this reaction include triphenylphosphine, tritolylphosphine, tri-tert-butylphosphine, tricyclohexylphosphine, 2,2'-bis(diphenylphosphino)-1,1'-binaphthyl, 2-dicyclohexylphosphino-2',6'-dimethoxybiphenyl, 2-dicyclohexylphosphino-2',4',6'-triisopropylbiphenyl, 2-(di-tert-butylphosphino)-2',4',6'-triisopropylbiphenyl, 2-(di-tert-butylphosphino)biphenyl, 4,5'-bis(diphenylphosphino)-9,9'-dimethylxanthene and 2-(dicyclohexylphosphino)-3,6-dimethoxy-2',4',6'-triisopropyl-1,1'-biphenyl. Combinations of such ligands may also be used.

The ligand is used in an amount of preferably 0.00001 to 1 mole, more preferably 0.001 to 0.4 mole, per mole of the compound of the general formula [A] or a salt thereof.

The compound of the general formula [B] or a salt thereof is used in an amount of preferably 1 to 50 moles, more preferably 1 to 2 moles, per mole of the compound of the general formula [A] or a salt thereof.

This reaction can be preferably carried out at 40 to 170° C. for 1 minute to 24 hours under an inert gas (such as nitrogen or argon) atmosphere.

This reaction may be carried out under microwave irradiation.

[Production Process 2]

[Formula 21]

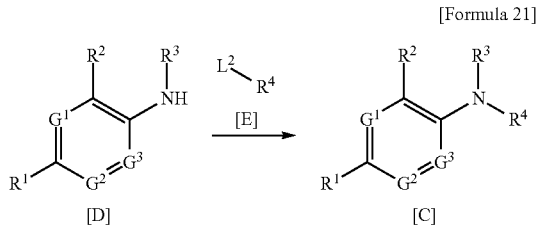

(In the formulas, $L^2$ is a leaving group; and $G^1$, $G^2$, $G^3$, $R^1$, $R^2$, $R^3$ and $R^4$ are as defined above.)

Methyl 2-amino-5-chlorobenzoate, methyl 2-amino-5-cyclopropylbenzoate and the like are known as compounds of the general formula [D], for example.

1-Benzyl-5-bromo-1H-indole, 1-benzyl-4-bromo-1H-indole and the like are known as compounds of the general formula [E], for example.

A compound of the general formula [C] or a salt thereof can be produced by reacting a compound of the general formula [D] or a salt thereof with a compound of the general formula [E] or a salt thereof in the presence or absence of a base, in the presence of a palladium catalyst and in the presence or absence of a ligand.

This process can be carried out in accordance with Production Process [1].

[Production Process 3]

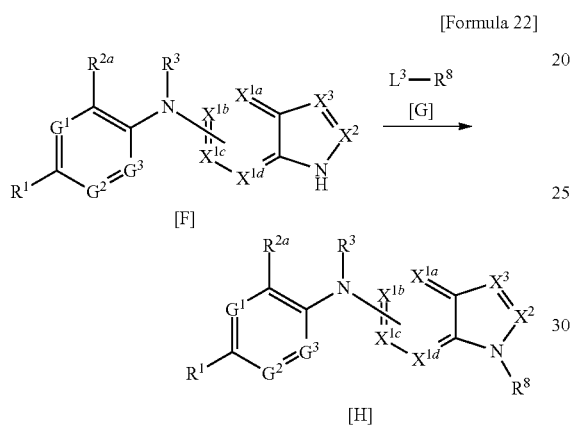

[Formula 22]

(In the formulas, $L^3$ is a leaving group; $R^{2a}$ is $-COOR^{5a}$ (wherein $R^{5a}$ is a carboxyl protecting group) or $-C(O)N(R^{6a})SO_2R^7$ (wherein $R^{6a}$ is an imino protecting group; and $R^7$ is as defined above); and $G^1$, $G^2$, $G^3$, $R^1$, $R^3$, $R^8$, $X^{1a}$, $X^{1b}$, $X^{1c}$, $X^{1d}$, $X^2$ and $X^3$ are as defined above.)

Benzyl bromide, 1-bromobutane, 1-(bromomethyl)-3-(2,2,2-trifluoroethoxy)benzene and the like are known as compounds of the general formula [G], for example.

A compound of the general formula [H] or a salt thereof can be produced by reacting a compound of the general formula [F] or a salt thereof with a compound of the general formula [G] or a salt thereof in the presence of a base.

The solvent used in this reaction is not particularly limited insofar as it does not adversely affect the reaction. Examples of the solvent include aliphatic hydrocarbons, halogenated hydrocarbons, alcohols, glycols, ethers, ketones, esters, amides, nitriles, sulfoxides, aromatic hydrocarbons and water. Mixtures of such solvents may also be used.

The amount of the solvent used is not particularly limited, but is preferably 1 to 100 times (v/w), more preferably 1 to 10 times (v/w), still more preferably 1 to 5 times (v/w), that of the compound of the general formula [F] or a salt thereof.

Examples of the base used in this reaction include inorganic bases and organic bases.

Preferred bases include inorganic bases such as sodium bicarbonate, sodium carbonate, potassium carbonate, sodium hydride and potassium tert-butoxide; and organic bases such as 1,8-diazabicyclo(5,4,0)undec-7-ene.

The base is used in an amount of preferably 1 to 5 moles, more preferably 1 to 2 moles, per mole of the compound of the general formula [F] or a salt thereof.

When $R^8$ is an optionally substituted acyl group, the reaction may be carried out in the presence of an additive.

Examples of the additive used in this reaction include 4-(dimethylamino)pyridine.

The additive is used in an amount of preferably 0.01 to 1 mole, more preferably 0.1 to 0.5 mole, per mole of the compound of the general formula [F] or a salt thereof.

The compound of the general formula [G] or a salt thereof is used in this reaction in an amount of preferably 1 to 5 moles, more preferably 1 to 1.5 moles, per mole of the compound of the general formula [F] or a salt thereof.

This reaction can be carried out usually at 0 to 200° C., preferably at 0 to 100° C., for 10 minutes to 24 hours.

[Production Process 4]

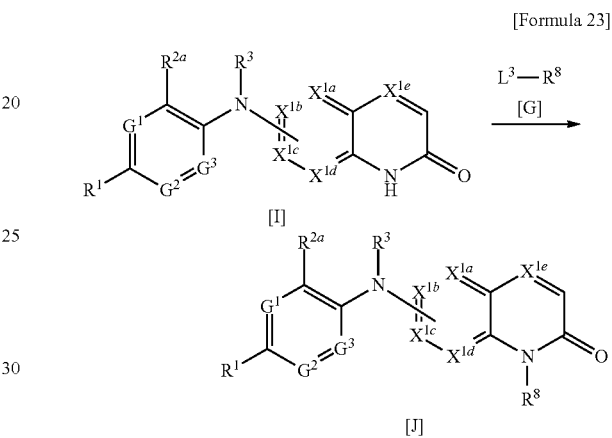

[Formula 23]

(In the formulas, $G^1$, $G^2$, $G^3$, $L^3$, $R^1$, $R^{2a}$, $R^3$, $R^8$, $X^{1a}$, $X^{1b}$, $X^{1c}$, $X^{1d}$ and $X^{1e}$ are as defined above.)

A compound of the general formula [J] or a salt thereof can be produced by reacting a compound of the general formula [I] or a salt thereof with a compound of the general formula [G] or a salt thereof in the presence of a base.

This process can be carried out in accordance with Production Process [3].

[Production Process 5]

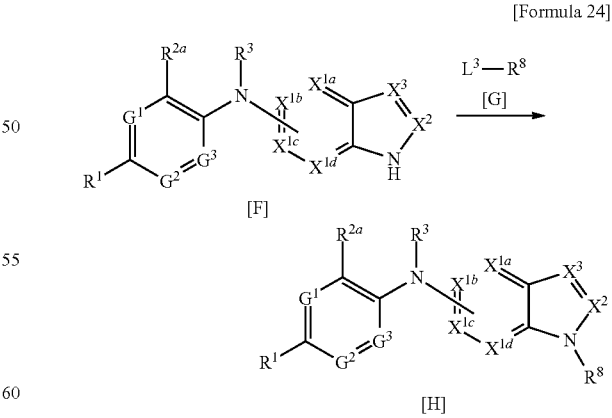

[Formula 24]

(In the formulas, $G^1$, $G^2$, $G^3$, $L^3$, $R^1$, $R^{2a}$, $R^3$, $R^8$, $X^{1a}$, $X^{1b}$, $X^{1c}$, $X^{1d}$, $X^2$ and $X^3$ are as defined above.)

A compound of the general formula [H] or a salt thereof can be produced by reacting a compound of the general formula [F] or a salt thereof with a compound of the general formula [G] or a salt thereof in the presence or absence of a base, in the presence of a palladium catalyst or a copper catalyst and in the presence or absence of a ligand.

The solvent used in this reaction is not particularly limited insofar as it does not adversely affect the reaction. Examples of the solvent include aliphatic hydrocarbons, halogenated hydrocarbons, alcohols, glycols, ethers, ketones, esters, amides, nitriles, sulfoxides, aromatic hydrocarbons and water. Mixtures of such solvents may also be used.

Preferred solvents include ethers, esters, aromatic hydrocarbons and amides.

The amount of the solvent used is not particularly limited, but is preferably 1 to 100 times (v/w), more preferably 1 to 10 times (v/w), still more preferably 1 to 5 times (v/w), that of the compound of the general formula [F] or a salt thereof.

Examples of the base used in this reaction include inorganic bases and organic bases.

Preferred bases include inorganic bases such as sodium bicarbonate, sodium carbonate, potassium carbonate, cesium carbonate and tripotassium phosphate; and organic bases such as pyridine, 4-(dimethylamino)pyridine, triethylamine and diisopropylethylamine.

The base is used in an amount of preferably 1 to 10 moles, more preferably 1 to 5 moles, still more preferably 1 to 1.5 moles, per mole of the compound of the formula [F] or a salt thereof.

Preferred palladium catalysts used in this reaction include palladium acetate, tetrakis(triphenylphosphine)palladium(0) and tris(dibenzylideneacetone)dipalladium(0). Combinations of such catalysts may also be used.

The palladium catalyst is used in an amount of preferably 0.00001 to 1 mole, more preferably 0.001 to 0.2 mole, per mole of the compound of the general formula [F] or a salt thereof.

Preferred ligands used in this reaction when the palladium catalyst is used include 2-dicyclohexylphosphino-2',4',6'-triisopropylbiphenyl, 2-(di-tert-butylphosphino)-2',4',6'-triisopropylbiphenyl, 2-(di-tert-butylphosphino)biphenyl, 4,5'-bis(diphenylphosphino)-9,9'-dimethylxanthene and 2-(dicyclohexylphosphino)-3,6-dimethoxy-2',4',6'-triisopropyl-1,1'-biphenyl. Combinations of such ligands may also be used.

The ligand is used in an amount of preferably 0.00001 to 1 mole, more preferably 0.001 to 0.4 mole, per mole of the compound of the general formula [F] or a salt thereof.

Examples of the copper catalyst used in this reaction include copper powder and copper iodide. Combinations of such catalysts may also be used.

The copper catalyst is used in an amount of preferably 0.00001 to 1 mole, more preferably 0.01 to 0.5 mole, per mole of the compound of the general formula [F] or a salt thereof.

Preferred ligands used in this reaction when the copper catalyst is used include 1,10-phenanthroline, trans-1,2-cyclohexanediamine and trans-N,N'-dimethylcyclohexane-1,2-diamine. Combinations of such ligands may also be used.

The ligand is used in an amount of preferably 0.00001 to 1 mole, more preferably 0.001 to 0.4 mole, per mole of the compound of the general formula [F] or a salt thereof.

The compound of the general formula [G] or a salt thereof is used in an amount of preferably 1 to 50 moles, more preferably 1 to 2 moles, per mole of the compound of the general formula [F] or a salt thereof.

This reaction can be preferably carried out at 40 to 170° C. for 1 minute to 24 hours under an inert gas (such as nitrogen or argon) atmosphere.

This reaction may be carried out under microwave irradiation.

[Production Process 6]

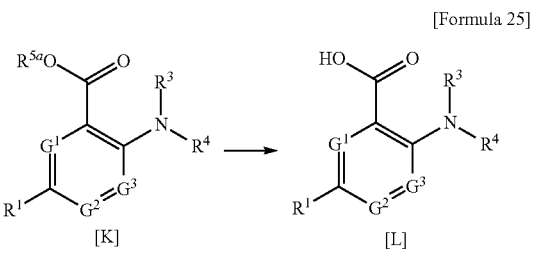

[Formula 25]

(In the formulas, $G^1$, $G^2$, $G^3$, $R^1$, $R^3$, $R^4$ and $R^{5a}$ are as defined above.)

A compound of the general formula [L] or a salt thereof can be produced by deprotecting a compound of the general formula [K] or a salt thereof.

This reaction can be carried out by a method described in W. Greene et al., Protective Groups in Organic Synthesis, 4th ed., pp. 533-646, 2007, John Wiley & Sons, Inc., or by a method equivalent to that method, for example.

Examples of the deprotection reaction include hydrolysis reaction using an acid or a base, dealkylation reaction using a salt, and reductive dealkylation reaction including metal catalyst hydrogenation reaction.

The solvent used in such a reaction is not particularly limited insofar as it does not adversely affect the reaction. Examples of the solvent include aliphatic hydrocarbons, halogenated hydrocarbons, alcohols, glycols, ethers, ketones, esters, amides, nitriles, sulfoxides, aromatic hydrocarbons and water. Mixtures of such solvents may also be used.

The amount of the solvent used is not particularly limited, but is preferably 1 to 100 times (v/w), more preferably 1 to 10 times (v/w), still more preferably 1 to 5 times (v/w), that of the compound of the general formula [K] or a salt thereof.

Examples of the acid used in the hydrolysis reaction using an acid include formic acid, hydrochloric acid, sulfuric acid, hydrobromic acid, trifluoroacetic acid, aluminum chloride and iodotrimethylsilane.

The acid is used in an amount of preferably 1 to 100000 moles, more preferably 1 to 1000 moles, per mole of the compound of the general formula [K] or a salt thereof.

Examples of the base used in the hydrolysis reaction using a base include inorganic bases such as sodium hydroxide, potassium hydroxide and lithium hydroxide; organic bases such as sodium methoxide, sodium ethoxide and potassium tert-butoxide; carbonates such as potassium carbonate and sodium carbonate; and tetrabutylammonium fluoride.

The base is used in an amount of preferably 1 to 1000 moles, more preferably 1 to 50 moles, per mole of the compound of the general formula [K] or a salt thereof.

Examples of the salt used in the dealkylation reaction using a salt include lithium iodide and sodium chloride.

The salt is used in an amount of preferably 1 to 100 moles, more preferably 1 to 10 moles, per mole of the compound of the general formula [K] or a salt thereof.

Examples of the metal catalyst used in the reductive dealkylation reaction including metal catalyst hydrogenation reaction include metallic palladium such as palladium on carbon and palladium black; palladium salts such as palladium oxide and palladium hydroxide; metallic nickel such as Raney nickel; and platinum salts such as platinum oxide.

The amount of the metal catalyst used is preferably 0.001 to 5 times (W/W), more preferably 0.01 to 1 time (W/W), that of the compound of the general formula [K] or a salt thereof.

Examples of the reducing agent include hydrogen; formic acid; formates such as sodium formate, ammonium formate and triethylammonium formate; cyclohexene and cyclohexadiene.

The reducing agent is used in an amount of preferably 2 to 100 moles, more preferably 2 to 10 moles, per mole of the compound of the general formula [K] or a salt thereof.

This reaction can be carried out at 0 to 200° C., preferably at 0 to 100° C., for 1 minute to 24 hours.

[Production Process 7]

[Formula 26]

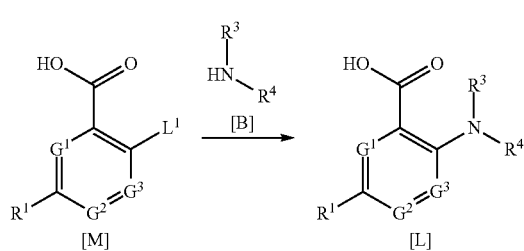

(In the formulas, $G^1$, $G^2$, $G^3$, $R^1$, $R^3$, $R^4$ and $L^1$ are as defined above.)

5-Bromo-2-chloronicotinic acid and the like are known as compounds of the general formula [M], for example.

1-Benzyl-1H-indol-5-amine and the like are known as compounds of the general formula [B], for example.

A compound of the general formula [L] or a salt thereof can be produced by reacting a compound of the general formula [M] or a salt thereof with a compound of the general formula [B] or a salt thereof in the presence of an acid or base.

The solvent used in this reaction is not particularly limited insofar as it does not adversely affect the reaction. Examples of the solvent include aliphatic hydrocarbons, halogenated hydrocarbons, alcohols, glycols, ethers, ketones, esters, amides, nitriles, sulfoxides, aromatic hydrocarbons, water and acetic acid. Mixtures of such solvents may also be used.

The amount of the solvent used is not particularly limited, but is preferably 1 to 100 times (v/w), more preferably 1 to 10 times (v/w), still more preferably 1 to 5 times (v/w), that of the compound of the general formula [M] or a salt thereof.

Examples of the base used in this reaction include inorganic bases and organic bases.

Preferred bases include inorganic bases such as sodium bicarbonate, sodium carbonate, potassium carbonate, cesium carbonate and tripotassium phosphate; and organic bases such as pyridine, 4-(dimethylamino)pyridine, triethylamine, diisopropylethylamine and 1,8-diazabicyclo(5,4,0)undec-7-ene.

The base is used in an amount of preferably 1 to 20 moles, more preferably 1 to 5 moles, per mole of the compound of the general formula [M] or a salt thereof.

Examples of the acid used in this reaction include hydrochloric acid, sulfuric acid, hydrobromic acid, acetic acid and p-toluenesulfonic acid.

The acid is used in an amount of preferably 1 to 100000 moles, more preferably 1 to 1000 moles, per mole of the compound of the general formula [M] or a salt thereof.

The acid is used in an amount of preferably 1 to 20 moles, more preferably 1 to 5 moles, per mole of the compound of the general formula [M] or a salt thereof.

The compound of the general formula [B] or a salt thereof is used in this reaction in an amount of preferably 1 to 20 moles, more preferably 1 to 5 moles, per mole of the compound of the general formula [M] or a salt thereof. This reaction can be carried out usually at 0 to 200° C., preferably at 100 to 170° C., for 10 minutes to 24 hours.

This reaction may be carried out under microwave irradiation.

[Production Process 8]

[Formula 27]

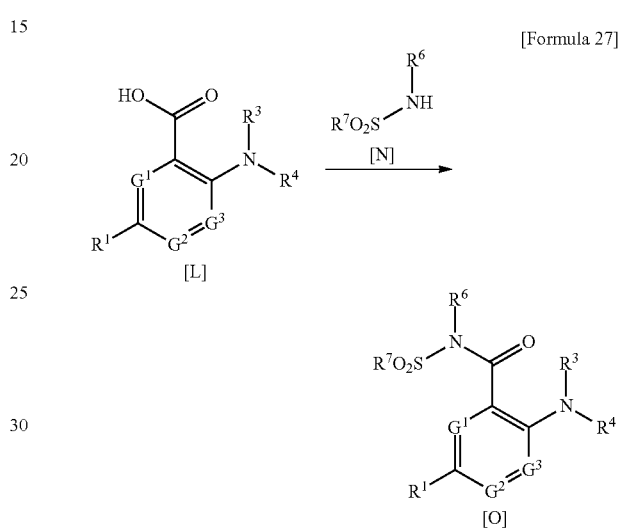

(In the formulas, $G^1$, $G^2$, $G^3$, $R^1$, $R^3$, $R^4$, $R^6$ and $R^7$ are as defined above.)

Methanesulfonamide and the like are known as compounds of the general formula [N], for example.

A compound of the general formula [O] or a salt thereof can be produced by reacting a compound of the general formula [L] or a salt thereof with a compound of the general formula [N] in the presence of a condensation agent and in the presence of a base.

The solvent used in this reaction is not particularly limited insofar as it does not adversely affect the reaction. Examples of the solvent include aliphatic hydrocarbons, halogenated hydrocarbons, alcohols, glycols, ethers, ketones, esters, amides, nitriles, sulfoxides, aromatic hydrocarbons and water. Mixtures of such solvents may also be used.

Preferred solvents include ethers and amides.

The amount of the solvent used is not particularly limited, but is preferably 1 to 100 times (v/w), more preferably 1 to 10 times (v/w), still more preferably 1 to 5 times (v/w), that of the compound of the general formula [L] or a salt thereof.

Examples of the condensation agent used in this reaction include carbodiimides such as N,N-dicyclohexylcarbodiimide and N-ethyl-N'-(3-dimethylaminopropyl)carbodiimide; carbonyls such as carbonyldiimidazole; acid azides such as diphenylphosphoryl azide; acid cyanides such as diethylphosphoryl cyanide; 2-ethoxy-1-ethoxycarbonyl-1,2-dihydroquinoline; O-benzotriazol-1-yl-1,1,3,3-tetramethyluronium hexafluorophosphate; and O-(7-azabenzotriazol-1-yl)-1,1,3,3-tetramethyluronium hexafluorophosphate.

Examples of the base used in this reaction include inorganic bases and organic bases.

Preferred bases include inorganic bases such as sodium bicarbonate, sodium carbonate, potassium carbonate, cesium carbonate and tripotassium phosphate; and organic bases such as pyridine, 4-(dimethylamino)pyridine, triethylamine, diisopropylethylamine and 1,8-diazabicyclo(5,4,0)undec-7-ene.

The base is used in an amount of preferably 1 to 20 moles, more preferably 1 to 5 moles, per mole of the compound of the general formula [L] or a salt thereof.

The condensation agent or the base is used in an amount of preferably one or more moles, more preferably 1 to 5 moles, per mole of the compound of the general formula [L] or a salt thereof.

This reaction can be carried out at −20 to 150° C., preferably at 0 to 100° C., for 1 minute to 24 hours.

[Production Process 9]

[Formula 28]

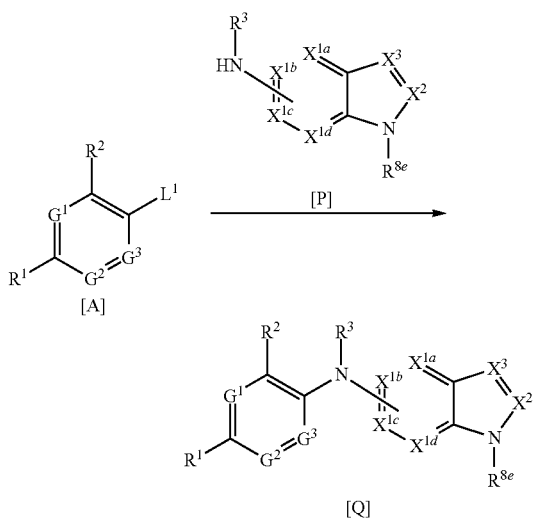

(In the formulas, $R^{8e}$ is a hydrogen atom or an imino protecting group; and $G^1$, $G^2$, $G^3$, $L^1$, $R^1$, $R^2$, $R^3$, $X^{1a}$, $X^{1b}$, $X^{1c}$, $X^{1d}$, $X^2$ and $X^3$ are as defined above.)

A compound of the general formula [Q] or a salt thereof can be produced by reacting a compound of the general formula [A] or a salt thereof with a compound of the general formula [P] or a salt thereof in the presence or absence of a base, in the presence of a palladium catalyst and in the presence or absence of a ligand.

This process can be carried out in accordance with Production Process [1].

[Production Process 10]

[Formula 29]

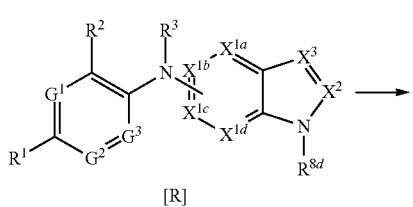

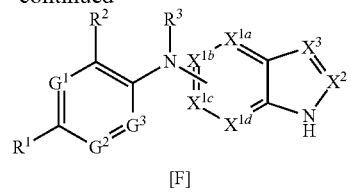

(In the formulas, $R^{8d}$ is an imino protecting group; and $G^1$, $G^2$, $G^3$, $R^1$, $R^2$, $R^3$, $X^{1a}$, $X^{1b}$, $X^{1c}$, $X^{1d}$, $X^2$ and $X^3$ are as defined above.)

A compound of the general formula [F] or a salt thereof can be produced by deprotecting a compound of the general formula [R] or a salt thereof.

This reaction can be carried out by a method described in M. Wuts, W. Greene, Protective Groups in Organic Synthesis, 4th ed., John Wiley & Sons, Inc., 2006, pp. 696-926 and the like, or by a method equivalent to that method, for example.

Compounds of the general formulas [C], [F], [H], [J], [L], [O] and [Q] or salts thereof thus obtained can be converted to other compounds of the general formula [1] or salts thereof by subjecting to reactions known per se such as condensation, addition, oxidation, reduction, rearrangement, substitution, halogenation, dehydration or hydrolysis or by appropriately combining such reactions, for example.

When isomers (such as optical isomers, geometric isomers and tautomers) exist for compounds in the production processes described above, such isomers can also be used. Solvates, hydrates and various forms of crystals of such compounds can also be used.

Next, there will be described the processes for producing compounds as raw materials for production of the compounds of the present invention.

[Production Process A]

[Formula 30]

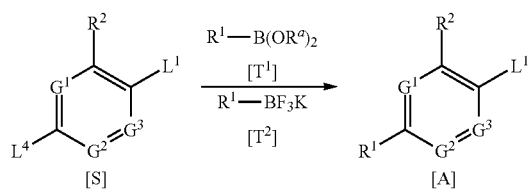

(In the formulas, $L^4$ is a leaving group; $R^a$ is a hydrogen atom or an optionally substituted $C_{1-6}$ alkyl group; and $G^1$, $G^2$, $G^3$, $L^1$, $R^1$ and $R^2$ are as defined above.)

Methyl 5-bromo-2-chloronicotinate and the like are known as compounds of the general formula [S], for example.

Examples of compounds of the general formula [T¹] include cyclopropylboronic acid.

Examples of compounds of the general formula [T²] include potassium cyclobutyltrifluoroborate.

A compound of the general formula [A] or a salt thereof can be produced by reacting a compound of the general formula [S] or a salt thereof with a compound of the general formula [T] or a salt thereof in the presence or absence of a base, in the presence of a palladium catalyst and in the presence or absence of a ligand.

The solvent used in this reaction is not particularly limited insofar as it does not adversely affect the reaction. Examples of the solvent include aliphatic hydrocarbons, halogenated hydrocarbons, alcohols, glycols, ethers, ketones, esters, amides, nitriles, sulfoxides, aromatic hydrocarbons and water. Mixtures of such solvents may also be used.

Preferred solvents include ethers, aromatic hydrocarbons and water.

The amount of the solvent used is not particularly limited, but is preferably 1 to 100 times (v/w), more preferably 1 to 10 times (v/w), still more preferably 1 to 5 times (v/w), that of the compound of the general formula [S] or a salt thereof.

Examples of the base used in this reaction include inorganic bases and organic bases.

Preferred bases include inorganic bases such as sodium bicarbonate, sodium carbonate, potassium carbonate, cesium carbonate and tripotassium phosphate.

The base is used in an amount of preferably 1 to 10 moles, more preferably 1 to 5 moles, still more preferably 1 to 1.5 moles, per mole of the compound of the general formula [S] or a salt thereof.

Preferred palladium catalysts used in this reaction include palladium acetate, tetrakis(triphenylphosphine)palladium (0), tris(dibenzylideneacetone)dipalladium(0) and bis(di-tert-butyl(4-dimethylaminophenyl)phosphine)dichloropalladium(II). Combinations of such catalysts may also be used.

The palladium catalyst is used in an amount of preferably 0.00001 to 1 mole, more preferably 0.001 to 0.2 mole, per mole of the compound of the general formula [S] or a salt thereof.

Preferred ligands used in this reaction include triphenylphosphine, tritolylphosphine, tri-tert-butylphosphine, tricyclohexylphosphine, 2,2'-bis(diphenylphosphino)-1,1'-binaphthyl, 2-dicyclohexylphosphino-2',6'-dimethoxybiphenyl, 2-dicyclohexylphosphino-2',4',6'-triisopropylbiphenyl, 2-(di-tert-butylphosphino)-2',4',6'-triisopropylbiphenyl, 2-(di-tert-butylphosphino)biphenyl, 4,5'-bis(diphenylphosphino)-9,9'-dimethylxanthene and 2-(dicyclohexylphosphino)-3,6-dimethoxy-2',4',6'-triisopropyl-1,1'-biphenyl. Combinations of such ligands may also be used.

The ligand is used in an amount of preferably 0.00001 to 1 mole, more preferably 0.001 to 0.4 mole, per mole of the compound of the general formula [S] or a salt thereof.

The compound of the general formula [T] or a salt thereof is used in an amount of preferably 1 to 50 moles, more preferably 1 to 2 moles, per mole of the compound of the general formula [S] or a salt thereof.

This reaction can be preferably carried out at 40 to 170° C. for 1 minute to 24 hours under an inert gas (such as nitrogen or argon) atmosphere.

This reaction may be carried out under microwave irradiation.

[Production Process B]

[Formula 31]

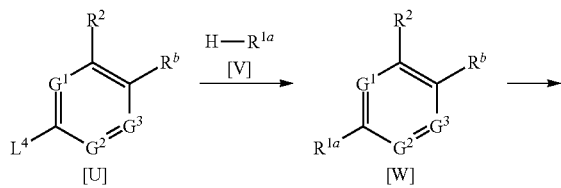

-continued

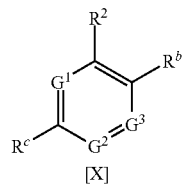

(In the formulas, $R^{1a}$ is an optionally substituted $C_{3-8}$ cycloalkenyl group; $R^b$ is a halogen atom or an optionally protected amino group; $R^e$ is an optionally substituted $C_{3-8}$ cycloalkyl group; and $G^1$, $G^2$, $G^3$, $L^4$ and $R^2$ are as defined above.)

(B-1)

Methyl 5-bromo-2-chloronicotinate and the like are known as compounds of the general formula [U], for example.

Cyclopentene, cyclohexene and the like are known as compounds of the general formula [V], for example.

A compound of the general formula [W] or a salt thereof can be produced by reacting a compound of the general formula [U] or a salt thereof with a compound of the general formula [V] in the presence or absence of a base, in the presence of a palladium catalyst and in the presence or absence of a ligand.

The solvent used in this reaction is not particularly limited insofar as it does not adversely affect the reaction. Examples of the solvent include aliphatic hydrocarbons, halogenated hydrocarbons, alcohols, glycols, ethers, ketones, esters, amides, nitriles, sulfoxides, aromatic hydrocarbons and water. Mixtures of such solvents may also be used.

Preferred solvents include ethers, aromatic hydrocarbons and amides.

The amount of the solvent used is not particularly limited, but is preferably 1 to 100 times (v/w), more preferably 1 to 10 times (v/w), still more preferably 1 to 5 times (v/w), that of the compound of the general formula [U] or a salt thereof.

Examples of the base used in this reaction include inorganic bases and organic bases.

Preferred bases include inorganic bases such as sodium bicarbonate, sodium carbonate, potassium carbonate, cesium carbonate and tripotassium phosphate; and organic bases such as pyridine, 4-(dimethylamino)pyridine, triethylamine and diisopropylethylamine.

The base is used in an amount of preferably 1 to 10 moles, more preferably 1 to 5 moles, still more preferably 1 to 1.5 moles, per mole of the compound of the general formula [U] or a salt thereof.

Preferred palladium catalysts used in this reaction include palladium acetate, tetrakis(triphenylphosphine)palladium(0) and tris(dibenzylideneacetone)dipalladium(0). Combinations of such catalysts may also be used.

The palladium catalyst is used in an amount of preferably 0.00001 to 1 mole, more preferably 0.001 to 0.2 mole, per mole of the compound of the general formula [U] or a salt thereof.

Preferred ligands used in this reaction include triphenylphosphine, tritolylphosphine, tri-tert-butylphosphine, tricyclohexylphosphine, 2,2'-bis(diphenylphosphino)-1,1'-binaphthyl, 2-dicyclohexylphosphino-2',6'-dimethoxybiphenyl, 2-dicyclohexylphosphino-2',4',6'-triisopropylbiphenyl, 2-(di-tert-butylphosphino)-2',4',6'-triisopropylbiphenyl, 2-(di-tert-butyl phosphino)biphenyl, 4,5'-bis(diphenylphosphino)-9,9'-dimethylxanthene and 2-(dicyclohexylphosphino)-3,6-dimethoxy-2',4',6'-triisopropyl-1,1'-biphenyl. Combinations of such ligands may also be used.

The ligand is used in an amount of preferably 0.00001 to 1 mole, more preferably 0.001 to 0.4 mole, per mole of the compound of the general formula [U] or a salt thereof.

The compound of the general formula [V] or a salt thereof is used in an amount of preferably 1 to 50 moles, more preferably 1 to 2 moles, per mole of the compound of the general formula [U] or a salt thereof.

This reaction can be preferably carried out at 40 to 170° C. for 1 minute to 24 hours under an inert gas (such as nitrogen or argon) atmosphere.

This reaction may be carried out under microwave irradiation.

(B-2)

A compound of the general formula [X] or a salt thereof can be produced by reducing a compound of the general formula [W].

Examples of the reduction reaction include catalytic hydrogenation reaction using a metal catalyst.

The solvent used in this reaction is not particularly limited insofar as it does not adversely affect the reaction. Examples of the solvent include aliphatic hydrocarbons, halogenated hydrocarbons, alcohols, glycols, ethers, ketones, esters, amides, nitriles, sulfoxides, aromatic hydrocarbons and water. Mixtures of such solvents may also be used.

Preferred solvents include ethers, esters, alcohols and amides.

The amount of the solvent used is not particularly limited, but is preferably 1 to 100 times (v/w), more preferably 1 to 10 times (v/w), still more preferably 1 to 5 times (v/w), that of the compound of the general formula [W] or a salt thereof.

Examples of the metal catalyst used in this reaction include metallic palladium such as palladium on carbon and palladium black; palladium salts such as palladium oxide and palladium hydroxide; metallic nickel such as Raney nickel; and platinum salts such as platinum oxide.

The amount of the metal catalyst used is preferably 0.001 to 5 times (W/W), more preferably 0.01 to 1 time (W/W), that of the compound of the general formula [W] or a salt thereof.

Examples of the reducing agent include hydrogen; formic acid; formates such as sodium formate, ammonium formate and triethylammonium formate; cyclohexene and cyclohexadiene.

The reducing agent is used in an amount of preferably 2 to 100 moles, more preferably 2 to 10 moles, per mole of the compound of the general formula [W] or a salt thereof.

This reaction can be carried out at 0 to 200° C., preferably at 0 to 100° C., for 1 minute to 24 hours.

[Production Process C]

[Formula 32]

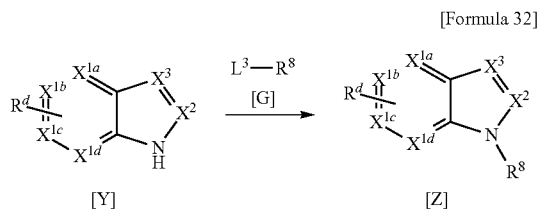

(In the formulas, $R^d$ is a halogen atom, a nitro group, or an optionally protected amino group; and $L^3$, $R^8$, $X^{1a}$, $X^{1b}$, $X^{1c}$, $X^{1d}$, $X^2$ and $X^3$ are as defined above.)

A compound of the general formula [Z] or a salt thereof can be produced by reacting a compound of the general formula [Y] or a salt thereof with a compound of the general formula [G] or a salt thereof in the presence of a base.

This process can be carried out in accordance with Production Process [3].

[Production Process D]

[Formula 33]

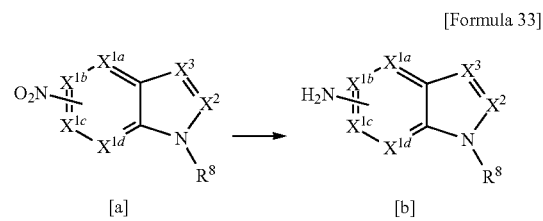

(In the formulas, $R^8$, $X^{1a}$, $X^{1b}$, $X^{1c}$, $X^{1d}$, $X^2$ and $X^3$ are as defined above.)

A compound of the general formula [b] or a salt thereof can be produced by reducing a compound of the general formula [a] or a salt thereof.

This reaction can be carried out by a method described in Richard C. Larock et al., Comprehensive Organic Transformations, 2nd ed., pp. 823-827, 1999, John Wiley & Sons, Inc., or by a method equivalent to that method.

Specific examples of the reaction include catalytic hydrogenation reaction using a metal catalyst, and reduction reaction using a metal such as iron or zinc in the presence or absence of an acid and in the presence or absence of a salt.

Catalytic hydrogenation reaction of the compound of the general formula [a] or a salt thereof can be carried out in accordance with Production Process (B-2).

The solvent used for reduction of the compound of the general formula [a] or a salt thereof using a metal is not particularly limited insofar as it does not adversely affect the reaction. Examples of the solvent include aliphatic hydrocarbons, halogenated hydrocarbons, alcohols, glycols, ethers, ketones, esters, amides, nitriles, sulfoxides, aromatic hydrocarbons and water. Mixtures of such solvents may also be used.

Preferred solvents include alcohols and water.

The amount of the solvent used is not particularly limited, but is preferably 1 to 100 times (v/w), more preferably 1 to 10 times (v/w), still more preferably 1 to 5 times (v/w), that of the compound of the general formula [a] or a salt thereof.

Examples of the metal used in this reaction include iron, zinc, tin and tin(II) chloride.

The metal is used in an amount of preferably 1 to 50 moles, more preferably 1 to 10 moles, per mole of the compound of the general formula [a] or a salt thereof.

Examples of the acid used in this reaction include hydrogen chloride, hydrogen bromide and acetic acid.

The amount of the acid used is preferably 0.001 to 100 times (W/V), more preferably 0.01 to 20 times (W/V), that of the compound of the general formula [a] or a salt thereof.

Examples of the salt used in this reaction include ammonium chloride.

The salt is used in an amount of preferably 0.01 to 10 moles, more preferably 0.1 to 5 moles, per mole of the compound of the general formula [a] or a salt thereof.

This reaction can be carried out at 0 to 200° C., preferably at 0 to 100° C., for 1 minute to 24 hours.

[Production Process E]

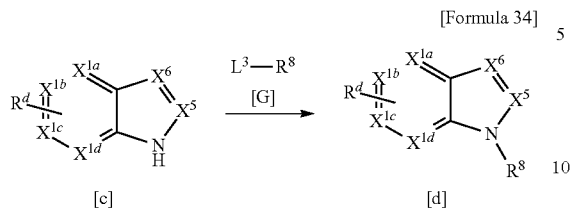

(In the formulas, $L^3$, $R^8$, $R^d$, $X^{1a}$, $X^{1b}$, $X^{1c}$, $X^{1d}$, $X^5$ and $X^6$ are as defined above.)

A compound of the general formula [d] or a salt thereof can be produced by reacting a compound of the general formula [c] or a salt thereof with a compound of the general formula [G] or a salt thereof in the presence of a base.

This process can be carried out in accordance with Production Process [3].

[Production Process F]

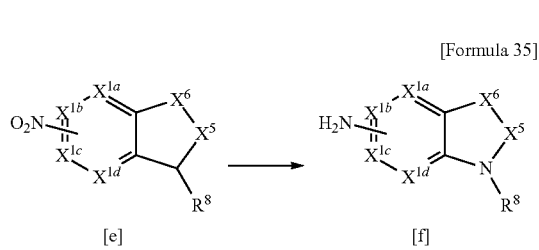

(In the formulas, Its, $X^{1a}$, $X^{1b}$, $X^{1c}$, $X^{1d}$, $X^5$ and $X^6$ are as defined above.)

A compound of the general formula [f] or a salt thereof can be produced by reducing a compound of the general formula [e] or a salt thereof.

This process can be carried out in accordance with Production Process [D].

[Production Process G]

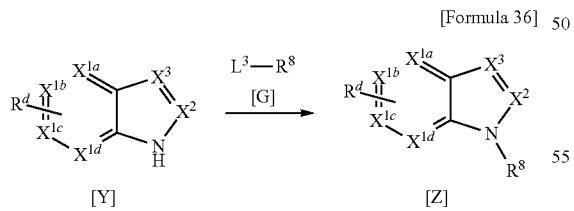

(In the formulas, $L^3$, $R^8$, $R^d$, $X^{1a}$, $X^{1b}$, $X^{1c}$, $X^{1d}$, $X^2$ and $X^3$ are as defined above.)

A compound of the general formula [Z] or a salt thereof can be produced by reacting a compound of the general formula [Y] or a salt thereof with a compound of the general formula [G] or a salt thereof in the presence or absence of a base, in the presence of a palladium catalyst or a copper catalyst and in the presence or absence of a ligand.

[Production Process H]

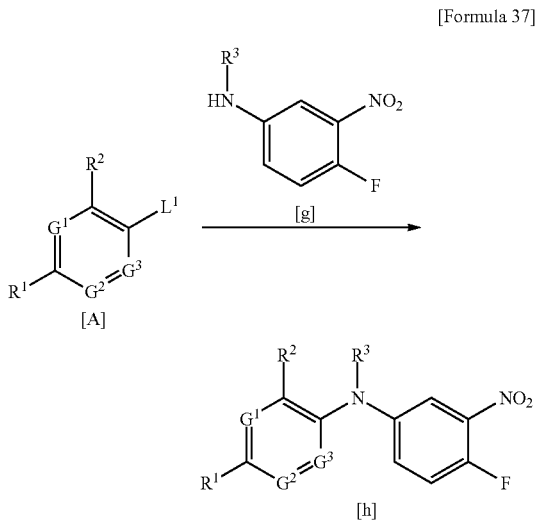

(In the formulas, $G^1$, $G^2$, $G^3$, $L^1$, $R^1$, $R^2$ and $R^3$ are as defined above.)

A compound of the general formula [h] or a salt thereof can be produced by reacting a compound of the general formula [A] or a salt thereof with a compound of the general formula [g] or a salt thereof in the presence or absence of a base, in the presence of a palladium catalyst and in the presence or absence of a ligand.

This process can be carried out in accordance with Production Process [I].

[Production Process I]

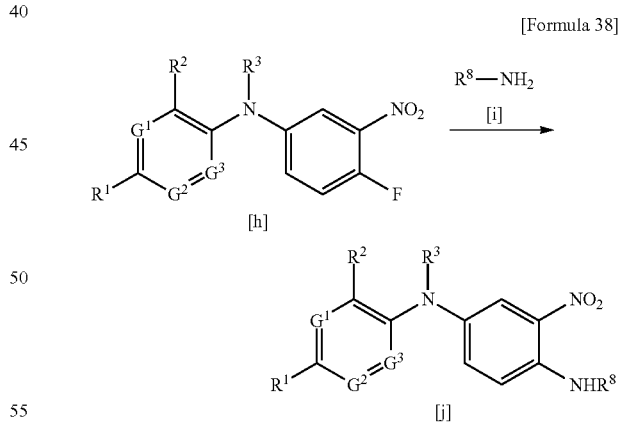

(In the formulas, $G^1$, $G^2$, $G^3$, $R^1$, $R^2$, $R^3$ and $R^8$ are as defined above.)

A compound of the general formula [j] or a salt thereof can be produced by reacting a compound of the general formula [h] or a salt thereof with a compound of the general formula [i] or a salt thereof in the presence of a base.

This process can be carried out in accordance with Production Process [3].

[Production Process J]

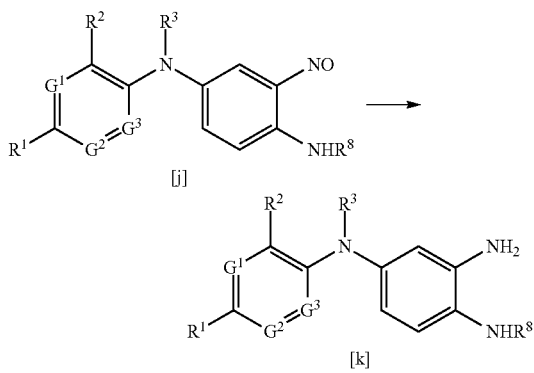

(In the formulas, $G^1$, $G^2$, $G^3$, $R^1$, $R^2$, $R^3$ and $R^8$ are as defined above.)

A compound of the general formula [k] or a salt thereof can be produced by reducing a compound of the general formula [j] or a salt thereof.

This process can be carried out in accordance with Production Process [D].

[Production Process K]

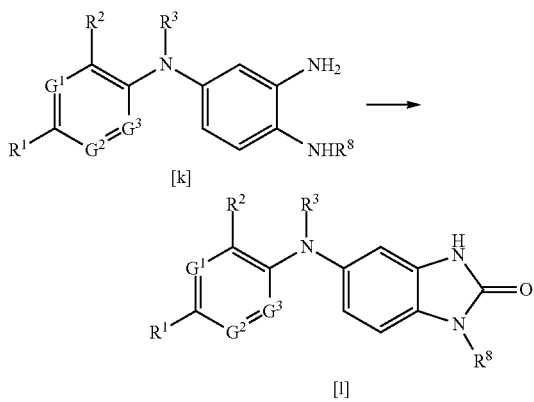

(In the formulas, $G^1$, $G^2$, $G^3$, $R^1$, $R^2$, $R^3$ and $R^8$ are as defined above.)

A compound of the general formula [l] or a salt thereof can be produced by reacting a compound of the general formula [k] or a salt thereof with carbonyldiimidazole in the presence or absence of a base.

The solvent used in this reaction is not particularly limited insofar as it does not adversely affect the reaction. Examples of the solvent include aliphatic hydrocarbons, halogenated hydrocarbons, alcohols, glycols, ethers, ketones, esters, amides, nitriles, sulfoxides, aromatic hydrocarbons and water. Mixtures of such solvents may also be used.

Preferred solvents include ethers and amides.

The amount of the solvent used is not particularly limited, but is preferably 1 to 100 times (v/w), more preferably 1 to 10 times (v/w), still more preferably 1 to 5 times (v/w), that of the compound of the general formula [k] or a salt thereof.

Examples of the base used in this reaction include inorganic bases and organic bases.

Preferred bases include inorganic bases such as sodium bicarbonate, sodium carbonate, potassium carbonate, cesium carbonate and tripotassium phosphate; and organic bases such as pyridine, 4-(dimethylamino)pyridine, triethylamine, diisopropylethylamine and 1,8-diazabicyclo(5,4,0)undec-7-ene.

The base is used in an amount of preferably 1 to 20 moles, more preferably 1 to 5 moles, per mole of the compound of the general formula [k] or a salt thereof.

Carbonyldiimidazole is used in an amount of preferably one or more moles, more preferably 1 to 2 moles, per mole of the compound of the general formula [k] or a salt thereof.

This reaction can be carried out at −20 to 150° C., preferably at 0 to 100° C., for 1 minute to 24 hours.

[Production Process L]

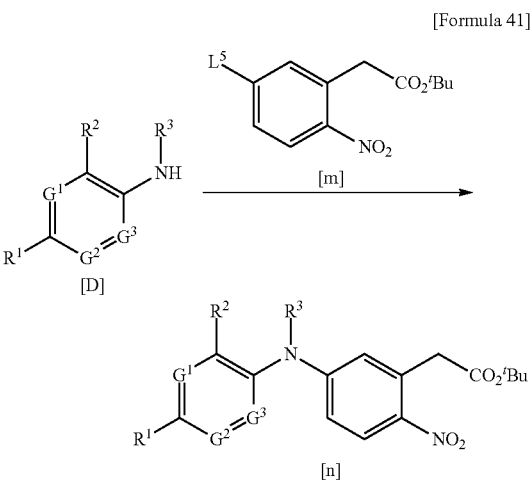

(In the formulas, $L^5$ is a leaving group; and $G^1$, $G^2$, $G^3$, $R^1$, $R^2$ and $R^3$ are as defined above.)

A compound of the general formula [n] or a salt thereof can be produced by reacting a compound of the general formula [D] or a salt thereof with a compound of the general formula [m] in the presence or absence of a base, in the presence of a palladium catalyst and in the presence or absence of a ligand.

This process can be carried out in accordance with Production Process [1].

[Production Process M]

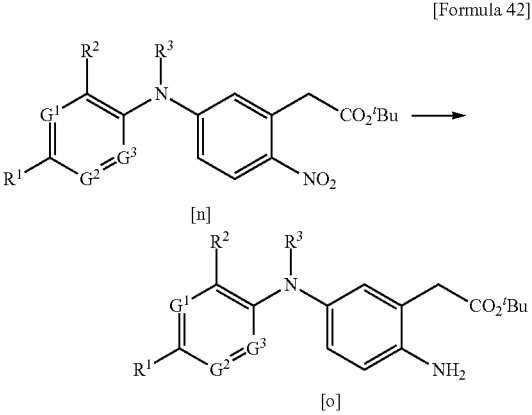

(In the formulas, $G^1$, $G^2$, $G^3$, $R^1$, $R^2$ and $R^3$ are as defined above.)

A compound of the general formula [o] or a salt thereof can be produced by reducing a compound of the general formula [n] or a salt thereof.

This process can be carried out in accordance with Production Process [D].

[Production Process N]

[Formula 43]

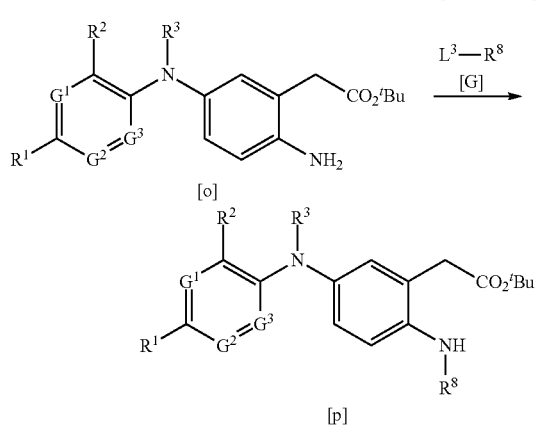

(In the formulas, $G^1$, $G^2$, $G^3$, $R^1$, $R^2$, $R^3$, $L^3$ and $R^8$ are as defined above.)

A compound of the general formula [p] or a salt thereof can be produced by reacting a compound of the general formula [o] or a salt thereof with a compound of the general formula [G] or a salt thereof in the presence of a base.

This process can be carried out in accordance with Production Process [3].

[Production Process O]

[Formula 44]

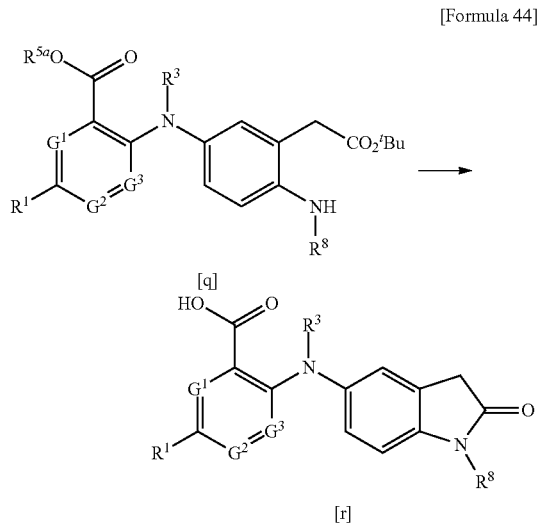

(In the formulas, $G^1$, $G^2$, $G^3$, $R^1$, $R^3$, $R^{5a}$ and $R^8$ are as defined above.)

A compound of the general formula [r] or a salt thereof can be produced by deprotecting a compound of the general formula [q] or a salt thereof and then subjecting it to ring closure reaction.

Examples of the deprotection reaction include hydrolysis reaction using an acid or base, dealkylation reaction using a salt, and reductive dealkylation reaction including metal catalyst hydrogenation reaction.

Examples of the ring closure reaction include ring closure reaction using an acid, examples of which include hydrochloric acid and trifluoroacetic acid.

This process can be carried out in accordance with Production Process [6].

Microwave synthesizers can be used in the production processes described above.

Compounds obtained in the production processes described above can be converted to other compounds by subjecting to reactions known per se such as condensation, addition, oxidation, reduction, rearrangement, substitution, halogenation, dehydration or hydrolysis or by appropriately combining such reactions, for example.

When amino, hydroxyl or carboxyl groups exist in compounds and intermediates thereof obtained in the production processes described above, the reactions can be carried out by appropriately changing the protecting groups for such groups. When two or more protecting groups exist in such a compound or intermediate, they can be selectively deprotected by subjecting to a reaction known per se.

Compounds used in the production processes described above, the compounds that may optionally be in the form of salts, can also be used as salts. Examples of such salts include those similar to salts of the above-mentioned compounds represented by the general formula (1) that are the compounds of the present invention.

When isomers (such as optical isomers, geometric isomers and tautomers) exist for compounds used in the production processes described above, such isomers can also be used.

When solvates, hydrates and various forms of crystals exist for the compounds, such solvates, hydrates and various forms of crystals can also be used.

The compounds represented by the general formula (1) or the salts thereof according to the present invention when used as a medicament may usually be mixed with formulation aids used for formulation such as excipients, carriers and diluents as appropriate.

Examples of additives include excipients, disintegrants, binders, lubricants, taste masking agents, colorants, flavoring agents, surfactants, coating agents and plasticizers.

Examples of excipients include sugar alcohols such as erythritol, mannitol, xylitol and sorbitol; saccharides such as white soft sugar, powdered sugar, lactose and glucose; cyclodextrins such as α-cyclodextrin, β-cyclodextrin, γ-cyclodextrin, hydroxypropyl-β-cyclodextrin and sulfobutyl ether-β-cyclodextrin sodium salt; celluloses such as crystalline cellulose and microcrystalline cellulose; and starches such as corn starch, potato starch and pregelatinized starch.

Examples of disintegrants include carmellose, carmellose calcium, croscarmellose sodium, sodium carboxymethyl starch, crospovidone, low-substituted hydroxypropylcellulose and partially pregelatinized starch.

Examples of binders include hydroxypropylcellulose, carmellose sodium and methylcellulose.

Examples of lubricants include stearic acid, magnesium stearate, calcium stearate, talc, hydrous silicon dioxide, light anhydrous silicic acid and sucrose fatty acid ester.

Examples of taste masking agents include aspartame, saccharin, stevia, thaumatin and acesulfame potassium.

Examples of colorants include titanium dioxide, iron sesquioxide, yellow iron sesquioxide, black iron oxide, Food Red No. 102, Food Yellow No. 4 and Food Yellow No. 5.

Examples of flavoring agents include essential oils such as orange oil, lemon oil, mentha oil and pine oil; essences such as orange essence and peppermint essence; flavors such as cherry flavor, vanilla flavor and fruit flavor; powdered flavors such as apple micron, banana micron, peach micron, strawberry micron and orange micron; vanillin; and ethylvanillin.

Examples of surfactants include sodium lauryl sulfate, dioctyl sodium sulfosuccinate, polysorbate and polyoxyethylene hydrogenated castor oil.

Examples of coating agents include hydroxypropylmethylcellulose, aminoalkyl methacrylate copolymer E, aminoalkyl methacrylate copolymer RS, ethylcellulose, cellulose acetate phthalate, hydroxypropylmethylcellulose phthalate, methacrylic acid copolymer L, methacrylic acid copolymer LD and methacrylic acid copolymer S.

Examples of plasticizers include triethyl citrate, macrogol, triacetin and propylene glycol.

These additives may be used singly or in combinations of two or more.

The amount of each additive is not particularly limited, and the additive can be added as appropriate to make it sufficiently effective depending on the intended application.

Such compounds or salts can be orally or parenterally administered according to conventional methods in the form of tablets, capsules, powders, syrups, granules, pills, suspensions, emulsions, liquids, powder formulations, suppositories, eye drops, nasal drops, ear drops, patches, ointments, injections or the like. The administration method, the dosage and the administration frequency can be selected as appropriate depending on the age, weight and symptom of the patient. Typically, the compound or a salt can be orally or parenterally administered to an adult at 0.01 to 1000 mg/kg in one or several doses per day.

EXAMPLES

The present invention will be described with reference to Reference Examples, Examples and Test Examples; however, the present invention is not limited thereto.

An automated purification system ISOLERA (manufactured by Biotage AB) or a medium pressure liquid chromatograph YFLC-Wprep2XY.N (Yamazen Corporation) was used for purification by column chromatography unless otherwise noted.

SNAP KP-Sil Cartridge (manufactured by Biotage AB) or Hi-Flash columns W001, W002, W003, W004 or W005 (Yamazen Corporation) was used as the carrier in silica gel column chromatography and SNAP KP-NH Cartridge (manufactured by Biotage AB) was used as the carrier in basic silica gel column chromatography unless otherwise noted.

PLC glass plate silica gel $F_{60}$ (manufactured by Merck KGaA) was used for preparative thin-layer chromatography.

The mixing ratio in the eluent is a ratio by volume. For example, the "gradient elution with hexane:ethyl acetate=100:0-50:50" refers to the fact that a 100% hexane/0% ethyl acetate eluent is finally changed to a 50% hexane/50% ethyl acetate eluent.

Initiator Sixty (manufactured by Biotage AB) was used as the microwave synthesizer.

H-Cube (manufactured by ThalesNano, Inc.) was used as the flow hydrogenation reactor.

MS spectra were measured using ACQUITY SQD LC/MS System (manufactured by Waters Corporation, ionization method: ESI (electrospray ionization)), M-8000 (manufactured by Hitachi Ltd., ionization method: ESI), LCMS-2010EV (manufactured by Shimadzu Corporation, ionization method: ESI performed simultaneously with APCI (atmospheric pressure chemical ionization)) or JMS-T100LP (DART) (manufactured by JEOL Ltd., ionization method: DART (direct analysis in real time)).

NMR spectra were measured with tetramethylsilane as internal standard using Bruker AV300 (manufactured by Bruker Corporation) or JNM-AL400 (manufactured by JEOL Ltd.) and all δ values were expressed as ppm.

Abbreviations in the NMR measurements have the following meanings.

s: Singlet
brs: Broad singlet
d: Doublet
dd: Double doublet
t: Triplet
q: Quartet
quin: Quintet
sext: Sextet
sep: Septet
m: Multiplet
DMSO-$d_6$: Deuterated dimethyl sulfoxide Abbreviations in Reference Examples and Examples have the following meanings.

Boc: tert-Butoxycarbonyl
Bu: Butyl
Et: Ethyl
Me: Methyl
Tf: Trifluoromethylsulfonyl
TBS: tert-Butyldimethylsilyl
tBu: tert-Butyl
Ph: Phenyl Reference Example 1

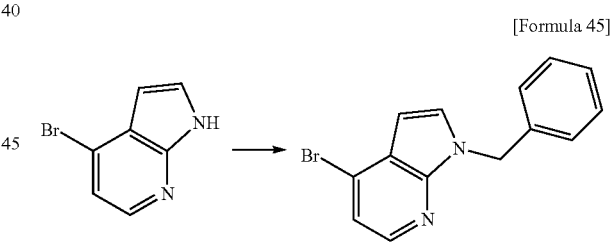

[Formula 45]

To the solution of 0.50 g of 4-bromo-1H-pyrrolo(2,3-b)pyridine in 3 mL of N,N-dimethylacetamide, 0.31 g of potassium tert-butoxide was added under ice-cooling, and the resultant was stirred for 15 minutes. To the reaction mixture, 0.33 mL of benzyl bromide was added dropwise under ice-cooling, and the resultant was stirred at room temperature for 30 minutes. To the reaction mixture, ethyl acetate and water were added, and the resultant was adjusted to pH 3.0 with 2 mol/L hydrochloric acid. The organic layer was separated, sequentially washed with water and a saturated aqueous sodium chloride solution and dried over anhydrous magnesium sulfate, and the solvent was distilled off under reduced pressure. The obtained residue was purified by silica gel column chromatography (gradient elution with hexane:ethyl acetate=100:0-50:50) to give 0.64 g of 1-benzyl-4-bromo-1H-pyrrolo(2,3-b)pyridine as a pale brown oil.

$^1$H-NMR (DMSO-d$_6$) δ: 5.50 (2H, s), 6.50 (1H, d, J=3.3 Hz), 7.20-7.37 (5H, m), 7.40 (1H, d, J=5.3 Hz), 7.79 (1H, d, J=3.3 Hz), 8.15 (1H, d, J=5.3 Hz).

Reference Example 2

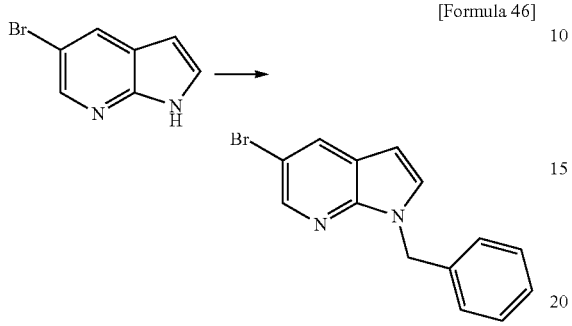

[Formula 46]

To the solution of 0.50 g of 5-bromo-1H-pyrrolo(2,3-b)pyridine in 3 mL of N,N-dimethylacetamide, 0.31 g of potassium tert-butoxide was added under ice-cooling, and the resultant was stirred for 15 minutes. To the reaction mixture, 0.33 mL of benzyl bromide was added dropwise under ice-cooling, and the resultant was stirred at room temperature for one hour. Ethyl acetate and water were added to the reaction mixture, and the resultant was adjusted to pH 2.0 with 2 mol/L hydrochloric acid. The organic layer was separated, sequentially washed with water and a saturated aqueous sodium chloride solution and dried over anhydrous magnesium sulfate, and the solvent was distilled off under reduced pressure. The obtained residue was purified by silica gel column chromatography (gradient elution with hexane:ethyl acetate=100:0-80:20) to give 0.45 g of 1-benzyl-5-bromo-1H-pyrrolo(2,3-b)pyridine as a white solid.

$^1$H-NMR (DMSO-d$_6$) δ: 5.48 (2H, s), 6.52 (1H, d, J=3.3 Hz), 7.19-7.34 (5H, m), 7.71 (1H, d, J=3.3 Hz), 8.24 (1H, d, J=2.6 Hz), 8.33 (1H, d, J=2.0 Hz).

Reference Example 3

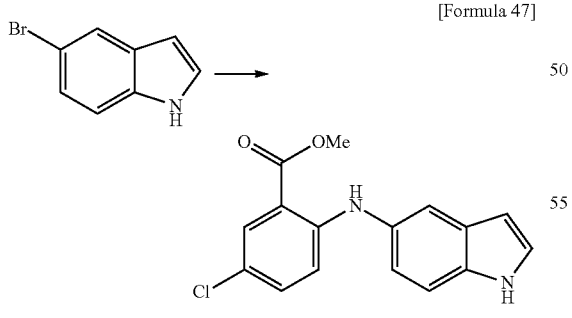

[Formula 47]

The mixture of 1.06 g of 1H-indol-5-amine, 2.0 g of methyl 2-bromo-5-chlorobenzoate, 0.37 g of tris(dibenzylideneacetone)dipalladium(0), 0.46 g of 4,5'-bis(diphenylphosphino)-9,9'-dimethylxanthene, 5.23 g of cesium carbonate, and 20 mL of toluene, was heated at reflux for four hours under a nitrogen atmosphere. The reaction mixture was cooled to room temperature, and ethyl acetate and water were then added thereto. The organic layer was separated, washed with a saturated aqueous sodium chloride solution and dried over anhydrous magnesium sulfate, and the solvent was distilled off under reduced pressure. The obtained residue was purified by silica gel column chromatography (gradient elution with hexane:ethyl acetate=100:0-80:20) to give 0.77 g of methyl 2-((1H-indol-5-yl)amino)-5-chlorobenzoate as a yellow oil.

$^1$H-NMR (DMSO-d$_6$) δ: 3.88 (3H, s), 6.40-6.44 (1H, m), 6.89 (1H, d, J=9.2 Hz), 6.97 (1H, dd, J=8.6, 2.0 Hz), 7.33 (1H, dd, J=9.2, 2.6 Hz), 7.37-7.47 (3H, m), 7.80 (1H, d, J=2.6 Hz), 9.24 (1H, s), 11.17 (1H, s).

Reference Example 4

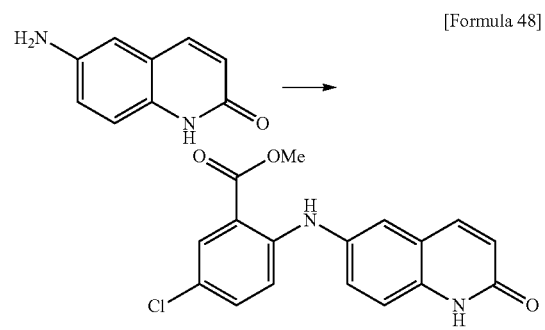

[Formula 48]

The mixture of 192 mg of 6-aminoquinolin-2(1H)-one, 300 mg of methyl 2-bromo-5-chlorobenzoate, 54.9 mg of tris(dibenzylideneacetone)dipalladium(0), 69.4 mg of 4,5'-bis(diphenylphosphino)-9,9'-dimethylxanthene, 0.78 g of cesium carbonate, and 3 mL of toluene, was heated at reflux for four hours under a nitrogen atmosphere. The reaction mixture was cooled to room temperature, and ethyl acetate and water were then added thereto. The solid was collected by filtration and washed with water, ethyl acetate and acetone to give 40 mg of methyl 5-chloro-2-((2-oxo-1,2-dihydroquinolin-6-yl)amino)benzoate.

$^1$H-NMR (DMSO-d$_6$) δ: 3.87 (3H, s), 6.51 (1H, dd, J=9.2, 1.3 Hz), 7.06 (1H, d, J=9.2 Hz), 7.33 (1H, d, J=8.6 Hz), 7.38-7.45 (2H, m), 7.58 (1H, d, J=2.0 Hz), 7.83 (1H, d, J=2.6 Hz), 7.87 (1H, d, J=9.9 Hz), 9.24 (1H, s), 11.77 (1H, s).

Reference Example 5

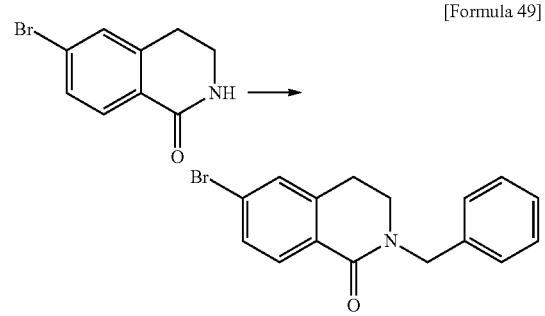

[Formula 49]

To the solution of 150 mg of 6-bromo-3,4-dihydroisoquinolin-1(2H)-one in 3 mL of N,N-dimethylacetamide, 90 mg of potassium tert-butoxide was added under ice-cooling, and the resultant was stirred for 10 minutes. To the reaction mixture, 87 µL of benzyl bromide was added under ice-cooling, and the resultant was stirred at room temperature for 30 minutes. Ethyl acetate and water were added to the reaction mixture, and the resultant was adjusted to pH 2.0 with 2 mol/L hydrochloric acid. The organic layer was separated, sequentially washed with water and a saturated aqueous sodium chloride solution and dried over anhydrous magnesium sulfate, and the solvent was distilled off under reduced pressure. The obtained residue was purified by silica gel column chromatography (gradient elution with hexane:ethyl acetate=90:10-70:30) to give 190 mg of 2-benzyl-6-bromo-3,4-dihydroisoquinolin-1(2H)-one as a colorless oil.

MS (ESI, m/z): 316 (M+H)$^+$.

Reference Example 6

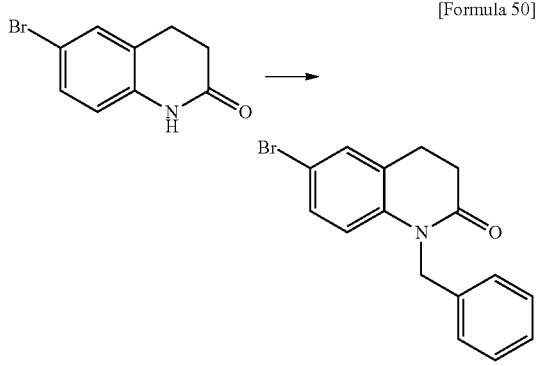

[Formula 50]

To the solution of 120 mg of 6-bromo-3,4-dihydroquinolin-2(1H)-one in 3 mL of N,N-dimethylacetamide, 71.4 mg of potassium tert-butoxide was added under ice-cooling, and the resultant was stirred for 10 minutes. To the reaction mixture, 69 µL of benzyl bromide was added under ice-cooling, and the resultant was stirred at room temperature for 30 minutes. Ethyl acetate and water were added to the reaction mixture, and the resultant was adjusted to pH 2.0 with 2 mol/L hydrochloric acid. The organic layer was separated, sequentially washed with water and a saturated aqueous sodium chloride solution and dried over anhydrous magnesium sulfate, and the solvent was distilled off under reduced pressure. The obtained residue was purified by silica gel column chromatography (gradient elution with hexane:ethyl acetate=90:10-70:30) to give 140 mg of 1-benzyl-6-bromo-3,4-dihydroquinolin-2(1H)-one as a white solid.

$^1$H-NMR (DMSO-d$_6$) δ: 2.66-2.75 (2H, m), 2.91-3.00 (2H, m), 5.13 (2H, s), 6.84 (1H, d, J=8.6 Hz), 7.16-7.25 (3H, m), 7.26-7.35 (3H, m), 7.45 (1H, d, J=2.0 Hz).

Reference Example 7

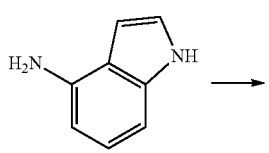

[Formula 51]

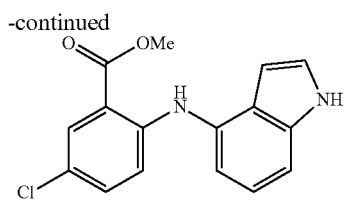

The mixture of 1.06 g of 1H-indol-4-amine, 2.0 g of methyl 2-bromo-5-chlorobenzoate, 220 mg of tris(dibenzylideneacetone)dipalladium (0), 54 mg of palladium acetate, 0.56 g of 4,5'-bis(diphenylphosphino)-9,9'-dimethylxanthene, 5.2 g of cesium carbonate, and 15 mL of toluene, was heated at reflux for one hour under a nitrogen atmosphere. The reaction mixture was cooled to room temperature, and ethyl acetate and water were then added thereto. The organic layer was separated, sequentially washed with water and a saturated aqueous sodium chloride solution and dried over anhydrous magnesium sulfate, and the solvent was distilled off under reduced pressure. The obtained residue was purified by silica gel column chromatography (gradient elution with hexane:ethyl acetate=90:10-70:30), and hexane and cyclohexane were added to the thus obtained residue, and the solid was collected by filtration to give 1.05 g of methyl 2-((1H-indol-4-yl)amino)-5-chlorobenzoate as a yellow solid.

$^1$H-NMR (DMSO-d$_6$) δ: 3.90 (3H, s), 6.24-6.29 (1H, m), 6.98 (1H, d, J=7.3 Hz), 7.06-7.15 (2H, m), 7.25 (1H, d, J=7.9 Hz), 7.34 (1H, t, J=2.6 Hz), 7.41 (1H, dd, J=8.9, 3.0 Hz), 7.86 (1H, d, J=2.6 Hz), 9.59 (1H, s), 11.28 (1H, s).

Reference Example 8

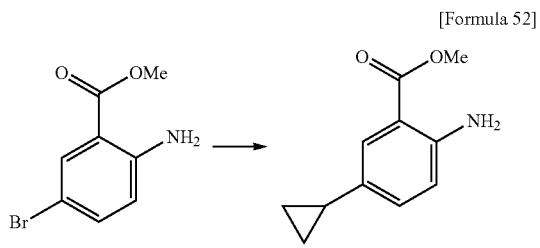 [SMILES: COC(=O)c1cc(Br)ccc1N ; COC(=O)c1cc(C2CC2)ccc1N]

[Formula 52]

The mixture of 6.0 g of methyl 2-amino-5-bromobenzoate, 4.05 g of cyclopropylboronic acid monohydrate, 0.29 g of palladium acetate, 0.73 g of tricyclohexylphosphine, 11 g of tripotassium phosphate, 48 mL of toluene, and 12 mL of water, was heated at reflux for five hours under a nitrogen atmosphere. After cooling the reaction mixture to room temperature, 0.9 g of cyclopropylboronic acid monohydrate, 0.15 g of palladium acetate and 0.37 g of tricyclohexylphosphine were added thereto, and the resultant was heated at reflux for four hours under a nitrogen atmosphere. The reaction mixture was cooled to room temperature, and ethyl acetate and water were then added. The organic layer was separated, washed with a saturated aqueous sodium chloride solution and dried over anhydrous magnesium sulfate, and the solvent was distilled off under reduced pressure. The obtained residue was purified by silica gel column chromatography (gradient elution with hexane:ethyl acetate=90:10-80:20) to give 3.5 g of methyl 2-amino-5-cyclopropylbenzoate as a pale brown oil.

¹H-NMR (CDCl₃) δ: 0.54-0.62 (2H, m), 0.81-0.90 (2H, m), 1.75-1.86 (1H, m), 3.86 (3H, s), 5.55 (2H, brs), 6.59 (1H, d, J=8.6 Hz), 7.03 (1H, dd, J=8.6, 2.6 Hz), 7.59 (1H, d, J=2.0 Hz).

Reference Example 9

[Formula 53]

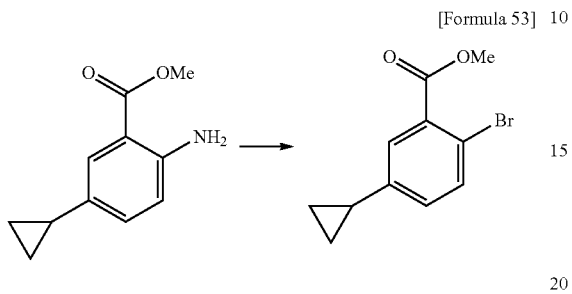

To the solution of 1.46 g of methyl 2-amino-5-cyclopropylbenzoate in 10 mL of dioxane, 10 mL of 47% hydrobromic acid was added. 5 mL of the solution of 0.58 g of sodium nitrite in water was added thereto under ice-cooling, and the resultant was stirred for 10 minutes. 5 mL of the solution of 2.74 g of copper bromide in 47% hydrobromic acid was added thereto under ice-cooling, and the resultant was stirred for 10 minutes. The reaction mixture was warmed to room temperature, stirred for three hours and then allowed to stand overnight. Ethyl acetate and water were added to the reaction mixture. The organic layer was separated, sequentially washed with water and a saturated aqueous sodium chloride solution and dried over anhydrous magnesium sulfate, and the solvent was distilled off under reduced pressure. The obtained residue was purified by silica gel column chromatography (gradient elution with hexane:ethyl acetate=90:10-70:30) to give 1.12 g of methyl 2-bromo-5-cyclopropylbenzoate as a colorless oil.

¹H-NMR (CDCl₃) δ: 0.66-0.74 (2H, m), 0.96-1.05 (2H, m), 1.82-1.95 (1H, m), 3.92 (3H, s), 7.02 (1H, dd, J=8.3, 2.3 Hz), 7.48 (1H, d, J=2.6 Hz), 7.51 (1H, d, J=7.9 Hz).

Reference Example 10

[Formula 54]

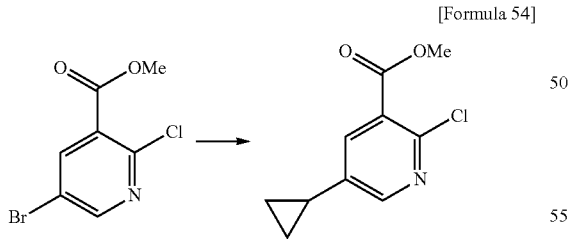

The mixture of 0.58 g of methyl 5-bromo-2-chloronicotinate, 0.36 g of cyclopropylboronic acid monohydrate, 26 mg of palladium acetate, 65 mg of tricyclohexylphosphine, 1.48 g of tripotassium phosphate, 5 mL of toluene, and 0.5 mL of water, was heated at reflux for two hours under a nitrogen atmosphere. The reaction mixture was cooled to room temperature, and ethyl acetate and water were added thereto. The organic layer was separated, sequentially washed with water and a saturated aqueous sodium chloride solution and dried over anhydrous magnesium sulfate, and the solvent was distilled off under reduced pressure. The obtained residue was purified by silica gel column chromatography (gradient elution with hexane:ethyl acetate=90:10-50:50) to give 0.28 g of methyl 2-chloro-5-cyclopropylnicotinate as a pale yellow oil.

¹H-NMR (CDCl₃) δ: 0.72-0.80 (2H, m), 1.05-1.15 (2H, m), 1.87-1.99 (1H, m), 3.95 (3H, s), 7.75 (1H, d, J=2.6 Hz), 8.31 (1H, d, J=2.6 Hz).

Reference Example 11

[Formula 55]

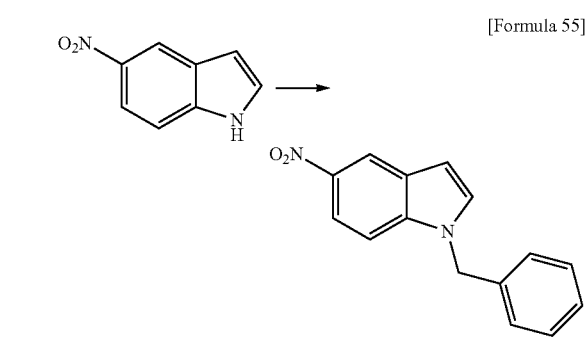

To the solution of 30 g of 5-nitro-1H-indole in 150 mL of N,N-dimethylacetamide, 22.9 g of potassium tert-butoxide was added in portions under ice-cooling, and the resultant was stirred for 10 minutes. To the reaction mixture, 24.3 mL of benzyl bromide was added dropwise under ice-cooling, and the resultant was stirred at room temperature for one hour. Water was added to the reaction mixture under ice-cooling, and the solid was collected by filtration and washed with water and diisopropyl ether to give 45.5 g of 1-benzyl-5-nitro-1H-indole as a pale brown solid.

¹H-NMR (DMSO-d₆) δ: 5.54 (2H, s), 6.81 (1H, d, J=3.3 Hz), 7.18-7.35 (5H, m), 7.69 (1H, d, J=9.2 Hz), 7.78 (1H, d, J=3.3 Hz), 8.00 (1H, dd, J=9.2, 2.0 Hz), 8.59 (1H, d, J=2.0 Hz).

Reference Example 12

[Formula 56]

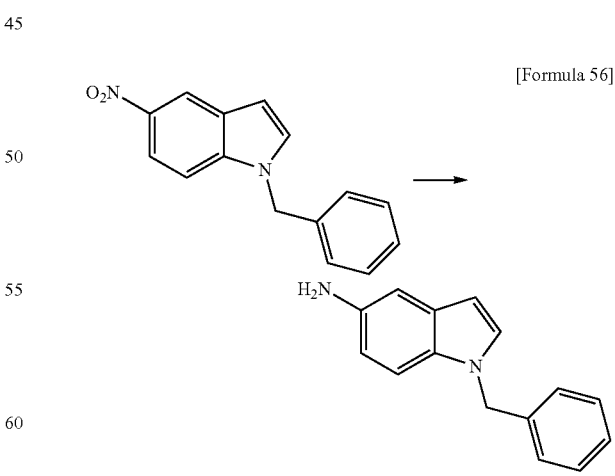

To the mixture of 45.5 g of 1-benzyl-5-nitro-1H-indole, 6.15 g of ammonium chloride, 360 mL of ethanol and 90 mL of water, 35.2 g of iron powder was added in portions at an external temperature of 70 to 75° C., and the resultant was heated at reflux for three hours and 30 minutes. After cooling the reaction mixture to room temperature, water and ethyl acetate were added thereto, and the insoluble matter was filtered off. The filter cake was washed with water and ethyl acetate. The filtrate and the washings were combined, the organic layer was separated, sequentially washed with water and a saturated aqueous sodium chloride solution and then dried over anhydrous magnesium sulfate, and the solvent was distilled off under reduced pressure. Diisopropyl ether and ethyl acetate were added to the obtained residue and the solid was collected by filtration. The obtained solid was purified by silica gel column chromatography (gradient elution with hexane:ethyl acetate=90:10-50:50), and hexane was added to the thus obtained residue, and the solid was collected by filtration to give 22.4 g of 1-benzyl-1H-indol-5-amine as a pale brown solid.

$^1$H-NMR (DMSO-d$_6$) δ: 4.47 (2H, s), 5.27 (2H, s), 6.17 (1H, d, J=2.6 Hz), 6.47 (1H, dd, J=8.6, 2.0 Hz), 6.68 (1H, d, J=2.0 Hz), 7.08 (1H, d, J=8.6 Hz), 7.12-7.17 (2H, m), 7.21-7.32 (4H, m).

Reference Example 13

[Formula 57]

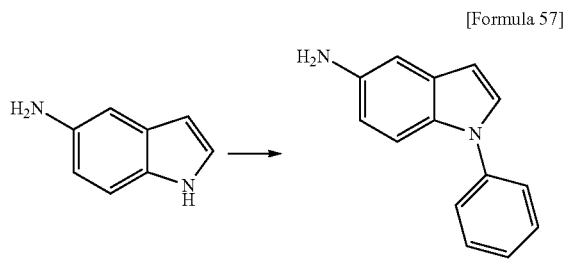 [SMILES: Nc1ccc2[nH]ccc2c1 ; Nc1ccc2c(ccn2-c2ccccc2)c1]

The mixture of 0.50 g of 1H-indol-5-amine, 0.42 mL of iodobenzene, 36 mg of copper(I) iodide, 91 μL of trans-cyclohexane-1,2-diamine, 1.6 g of tripotassium phosphate, and 5 mL of dioxane, was heated at reflux for four hours under a nitrogen atmosphere. After cooling the reaction mixture to room temperature, water and ethyl acetate were added thereto, and the insoluble matter was filtered off. The organic layer was separated, sequentially washed with water and a saturated aqueous sodium chloride solution and then dried over anhydrous magnesium sulfate, and the solvent was distilled off under reduced pressure. The obtained residue was purified by silica gel column chromatography (gradient elution with hexane:ethyl acetate=90:10-70:30) to give 0.61 g of 1-phenyl-1H-indol-5-amine as a pale brown oil.

$^1$H-NMR (CDCl$_3$) δ: 3.55 (2H, brs), 6.50 (1H, d, J=3.3 Hz), 6.68 (1H, dd, J=8.9, 2.3 Hz), 6.97 (1H, d, J=2.6 Hz), 7.24-7.36 (2H, m), 7.39 (1H, d, J=8.6 Hz), 7.45-7.53 (4H, m).

Reference Example 14

[Formula 58]

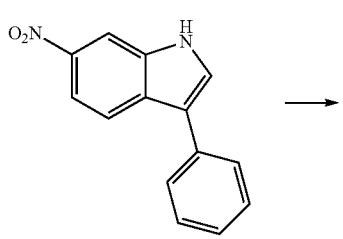

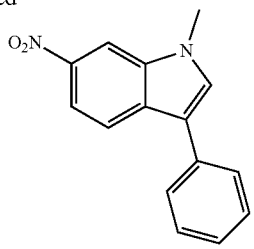

To the solution of 0.30 g of 6-nitro-3-phenyl-1H-indole in 3 mL of N,N-dimethylacetamide, 56 mg of 60% sodium hydride was added under ice-cooling, and the resultant was stirred for five minutes. To the reaction mixture, 94 μL of methyl iodide was added dropwise under ice-cooling, and the resultant was stirred at room temperature for one hour. Ethyl acetate and water were added to the reaction mixture, and it was adjusted to pH 2.0 with 2 mol/L hydrochloric acid. The organic layer was separated, sequentially washed with water and a saturated aqueous sodium chloride solution and dried over anhydrous magnesium sulfate, and the solvent was distilled off under reduced pressure. Diisopropyl ether and hexane were added to the obtained residue, and the solid was collected by filtration to give 235 mg of 1-methyl-6-nitro-3-phenyl-1H-indole as a brown solid.

$^1$H-NMR (CDCl$_3$) δ: 3.96 (3H, s), 7.30-7.38 (1H, m), 7.43-7.53 (3H, m), 7.58-7.65 (2H, m), 7.95 (1H, d, J=9.2 Hz), 8.08 (1H, dd, J=8.6, 2.0 Hz), 8.36 (1H, d, J=2.0 Hz).

Reference Example 15

[Formula 59]

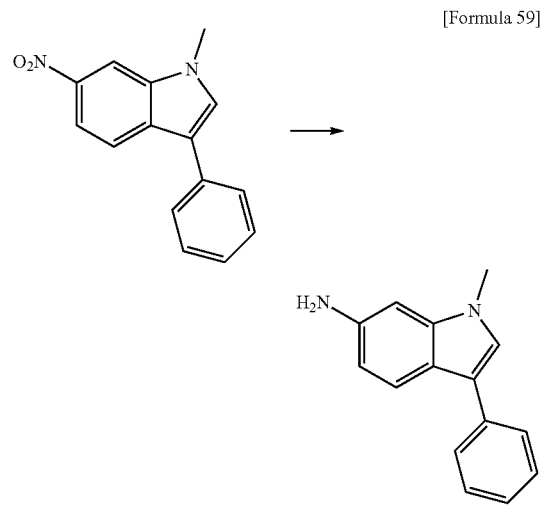

The mixture of 235 mg of 1-methyl-6-nitro-3-phenyl-1H-indole, 32 mg of ammonium chloride, 180 mg of iron powder, 5 mL of ethanol, and 1 mL of water, was heated at reflux for one hour under a nitrogen atmosphere. After cooling the reaction mixture to room temperature, water and ethyl acetate were added thereto, and the insoluble matter was filtered off. The filter cake was washed with ethyl acetate and water. The filtrate and the washings were combined, the organic layer was separated, washed with a saturated aqueous sodium chloride solution and then dried over anhydrous magnesium sulfate, and the solvent was distilled off under reduced pressure to give 0.19 g of 1-methyl-3-phenyl-1H-indol-6-amine as a brown solid.

$^1$H-NMR (DMSO-$d_6$) δ: 3.65 (3H, s), 4.90 (2H, s), 6.48-6.56 (2H, m), 7.13-7.21 (1H, m), 7.32 (1H, s), 7.33-7.42 (2H, m), 7.53 (1H, d, J=8.6 Hz), 7.56-7.62 (2H, m).

Reference Example 16

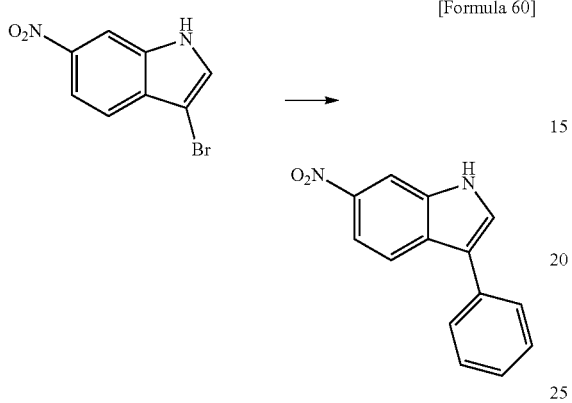

[Formula 60]

The mixture of 1.05 g of 3-bromo-6-nitro-1H-indole, 0.64 g of phenylboronic acid, 1.39 g of sodium carbonate, 93 mg of bis(di-tert-butyl(4-dimethylaminophenyl)phosphine)dichloropalladium(II), 10 mL of ethylene glycol dimethyl ether, and 1.0 mL of water, was heated at reflux for three hours under a nitrogen atmosphere. The reaction mixture was cooled to room temperature, and ethyl acetate and water were then added thereto. The organic layer was separated, sequentially washed with water and a saturated aqueous sodium chloride solution and dried over anhydrous magnesium sulfate, and the solvent was distilled off under reduced pressure. Diisopropyl ether and hexane were added to the obtained residue, and the solid was collected by filtration to give 0.95 g of 6-nitro-3-phenyl-1H-indole as a brown solid.

$^1$H-NMR (DMSO-$d_6$) δ: 7.27-7.35 (1H, m), 7.44-7.52 (2H, m), 7.69-7.75 (2H, m), 7.97 (1H, dd, J=8.6, 2.0 Hz), 8.03 (1H, d, J=9.2 Hz), 8.15 (1H, d, J=2.6 Hz), 8.40 (1H, d, J=2.0 Hz), 12.14 (1H, brs).

Reference Example 17

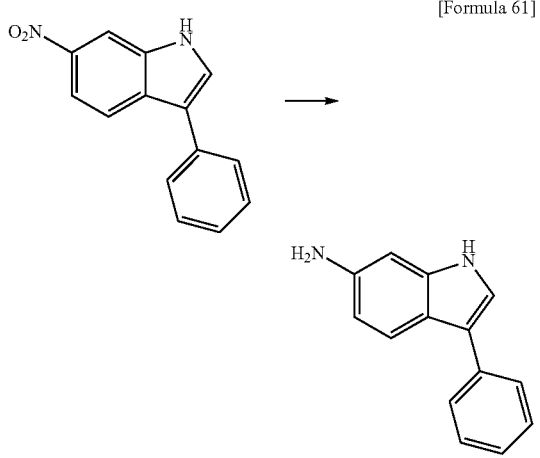

[Formula 61]

The mixture of 0.50 g of 6-nitro-3-phenyl-1H-indole, 72 mg of ammonium chloride, 0.41 g of iron powder, 5 mL of ethanol, and 1 mL of water, was heated at reflux for one hour under a nitrogen atmosphere. After cooling the reaction mixture to room temperature, water and ethyl acetate were added thereto, and the insoluble matter was filtered off. The filter cake was washed with ethyl acetate. The filtrate and the washings were combined, the organic layer was separated, washed with a saturated aqueous sodium chloride solution and then dried over anhydrous magnesium sulfate, and the solvent was distilled off under reduced pressure to give 0.41 g of 3-phenyl-1H-indol-6-amine as a brown foam.

$^1$H-NMR (DMSO-$d_6$) δ: 4.80 (2H, s), 6.47 (1H, dd, J=8.6, 2.0 Hz), 6.59 (1H, d, J=2.0 Hz), 7.12-7.20 (1H, m), 7.30-7.42 (3H, m), 7.52 (1H, d, J=8.6 Hz), 7.58-7.66 (2H, m), 10.72 (1H, s).

Reference Example 18

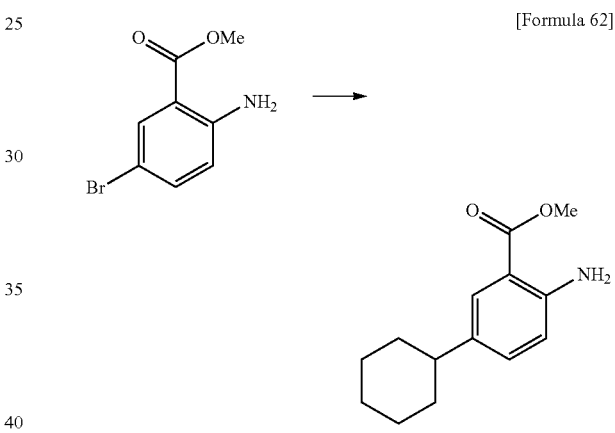

[Formula 62]

The reaction mixture of 0.30 g of methyl 2-amino-5-bromobenzoate, 0.264 mL of cyclohexene, 14.6 mg of palladium acetate, 39.6 mg of tri(o-tolyl)phosphine, 0.544 mL of triethylamine, and 1.5 mL of N,N-dimethylformamide, was stirred at an external temperature of 80° C. for three hours under a nitrogen atmosphere. 14.6 mg of palladium acetate and 39.6 mg of tri(o-tolyl)phosphine were then added thereto, and the resultant was stirred at 80° C. for one hour. The reaction mixture was cooled to room temperature, and water and ethyl acetate were added thereto. The organic layer was separated and dried over anhydrous sodium sulfate, and the solvent was distilled off under reduced pressure. The obtained residue was purified by silica gel column chromatography (hexane:ethyl acetate) to give 0.181 g of an oil. The solution of 0.170 g of the obtained oil in 10 mL of methanol was subjected to hydrogenation reaction (room temperature, normal pressure, flow rate: 1.5 mL/min, 10% Pd/C) using the flow hydrogenation reactor. The solvent of the obtained reaction solution was distilled off under reduced pressure to give 0.125 g of methyl 2-amino-5-cyclohexylbenzoate as a white solid.

$^1$H-NMR (CDCl$_3$) δ: 1.11-1.94 (10H, m), 2.31-2.48 (1H, m), 3.87 (3H, s), 5.56 (2H, s), 6.62 (1H, d, J=7.9 Hz), 7.15 (1H, dd, J=8.3, 2.3 Hz), 7.68 (1H, d, J=2.0 Hz).

Reference Example 19

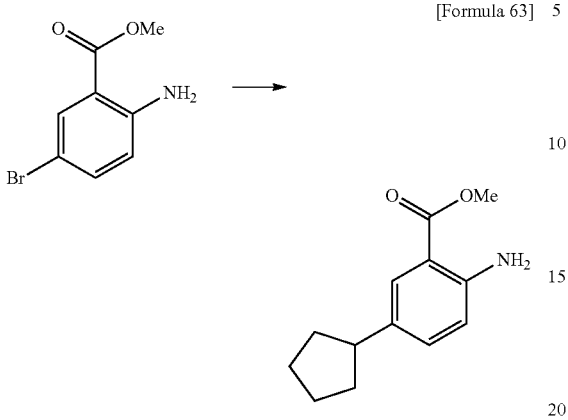

The mixture of 0.50 g of methyl 2-amino-5-bromobenzoate, 0.766 mL of cyclopentene, 48.7 mg of palladium acetate, 0.132 g of tri(o-tolyl)phosphine, 0.907 mL of triethylamine, and 2.5 mL of N,N-dimethylformamide, was stirred at an external temperature of 100° C. for four hours under a nitrogen atmosphere. The reaction mixture was cooled to room temperature, and water and ethyl acetate were added thereto. The organic layer was separated and dried over anhydrous sodium sulfate, and the solvent was distilled off under reduced pressure. The obtained residue was purified by silica gel column chromatography (hexane:ethyl acetate) to give 0.379 g of an oil. The solution of 0.370 g of the obtained oil in 20 mL of methanol was subjected to hydrogenation reaction (room temperature, normal pressure, flow rate: 1.5 mL/min, 10% Pd/C) using the flow hydrogenation reactor. The solvent of the obtained reaction solution was distilled off under reduced pressure to give 0.349 g of methyl 2-amino-5-cyclopentylbenzoate as a white solid.

$^1$H-NMR (CDCl$_3$) δ: 1.42-1.88 (6H, m), 1.94-2.09 (2H, m), 2.78-2.96 (1H, m), 3.87 (3H, s), 6.62 (1H, d, J=7.9 Hz), 7.18 (1H, dd, J=8.3, 2.3 Hz), 7.71 (1H, d, J=2.0 Hz).

Reference Example 20

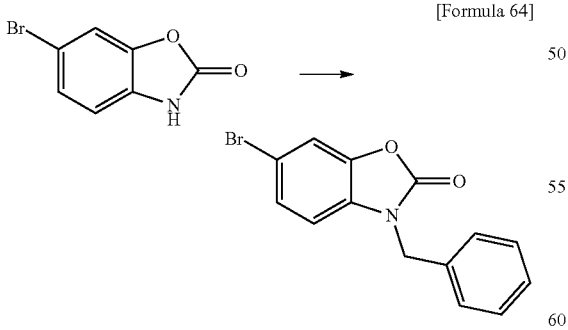

To the solution of 100 mg of 6-bromobenzo[d]oxazol-2(3H)-one in 1.0 mL of tetrahydrofuran, 57.7 mg of potassium tert-butoxide was added under ice-cooling, and the resultant was stirred under ice-cooling for 10 minutes, followed by addition of 61.1 μL of benzyl bromide. The reaction mixture was stirred at room temperature for 20 minutes and at an external temperature of 50° C. for two hours, then cooled to room temperature and allowed to stand overnight. Water and ethyl acetate were added to the reaction mixture. The organic layer was separated and dried over anhydrous sodium sulfate, and the solvent was distilled off under reduced pressure. The obtained residue was purified by silica gel column chromatography (hexane:ethyl acetate) to give 133 mg of 3-benzyl-6-bromobenzo[d]oxazol-2(3H)-one as a white solid.

$^1$H-NMR (CDCl$_3$) δ: 4.99 (2H, s), 6.55-6.92 (1H, m), 6.98-7.98 (7H, m).

Reference Example 21

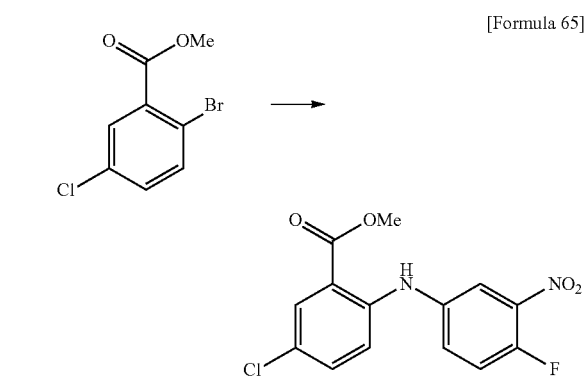

The mixture of 0.20 g of methyl 2-bromo-5-chlorobenzoate, 0.125 g of 4-fluoro-3-nitroaniline, 36.7 mg of tris(dibenzylideneacetone)dipalladium(0), 46.4 mg of 4,5'-bis(diphenylphosphino)-9,9'-dimethylxanthene, 0.521 g of cesium carbonate, and 2.0 mL of toluene, was stirred at an external temperature of 80° C. for 30 minutes under a nitrogen atmosphere. The reaction mixture was cooled to room temperature, and water and ethyl acetate were then added thereto. The organic layer was separated and dried over anhydrous sodium sulfate, and the solvent was distilled off under reduced pressure. The obtained solid was recrystallized from 2-propanol to give 0.20 g of methyl 5-chloro-2-((4-fluoro-3-nitrophenyl)amino)benzoate as a green solid.

$^1$H-NMR (DMSO-d$_6$) δ: 3.86 (3H, s), 7.28 (1H, d, J=8.6 Hz), 7.46-7.61 (2H, m), 7.62-7.71 (1H, m), 7.86 (1H, d, J=2.6 Hz), 7.96 (1H, dd, J=6.6, 3.3 Hz), 9.22 (1H, s).

Reference Example 22

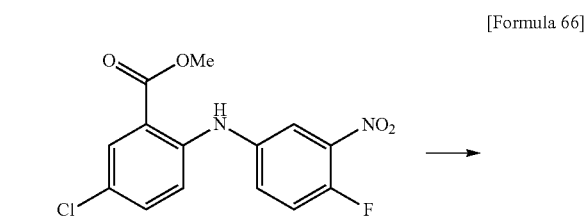

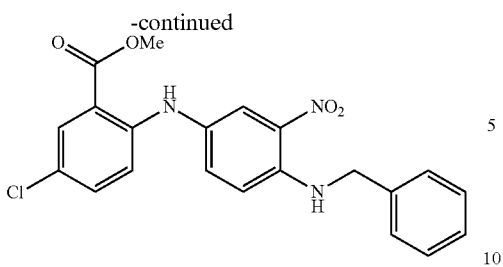

To the solution of 100 mg of methyl 5-chloro-2-((4-fluoro-3-nitrophenyl)amino)benzoate in 1.0 mL of N,N-dimethylformamide, 79.6 μL of diisopropylethylamine and 50.5 μL of benzylamine were added at room temperature under a nitrogen atmosphere, and the resultant was stirred at an external temperature of 50° C. for 30 minutes and at 70° C. for 25 minutes. The reaction mixture was allowed to stand at room temperature overnight, and ethyl acetate and water were then added thereto. The organic layer was separated and dried over anhydrous sodium sulfate, and the solvent was distilled off under reduced pressure. The obtained residue was purified by silica gel column chromatography (hexane:ethyl acetate) to give 130 mg of methyl 2-((4-(benzylamino)-3-nitrophenyl)amino)-5-chlorobenzoate as an oil.

$^1$H-NMR (DMSO-d$_6$) δ: 3.85 (3H, s), 4.66 (2H, d, J=5.9 Hz), 6.89 (1H, d, J=9.2 Hz), 6.98 (1H, d, J=9.2 Hz), 7.20-7.50 (7H, m), 7.80 (1H, d, J=2.6 Hz), 7.94 (1H, d, J=2.6 Hz), 8.71 (1H, t, J=6.3 Hz), 9.03 (1H, s).

Reference Example 23

[Formula 67]

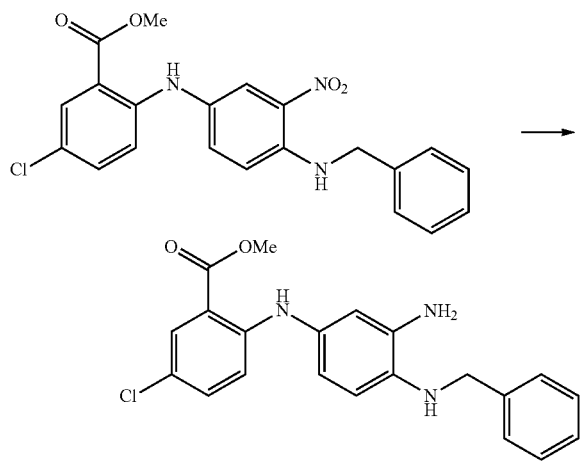

To the mixed solution of 125 mg of methyl 2-((4-(benzylamino)-3-nitrophenyl)amino)-5-chlorobenzoate, 1.9 mL of ethanol and 0.6 mL of water, 119 mg of reduced iron was added at room temperature under a nitrogen atmosphere, and the resultant was stirred at an external temperature of 50° C. for 30 minutes and then cooled to room temperature, followed by addition of water. The solid was removed by filtration through Celite and ethanol was distilled off under reduced pressure, followed by addition of ethyl acetate. The organic layer was separated and dried over anhydrous sodium sulfate, and the solvent was distilled off under reduced pressure. The obtained residue was purified by silica gel column chromatography (hexane:ethyl acetate) to give 31.3 mg of methyl 2-((3-amino-4-(benzylamino)phenyl)amino)-5-chlorobenzoate as an oil.

$^1$H-NMR (CDCl$_3$) δ: 3.89 (3H, s), 4.32 (2H, s), 5.47 (1H, s), 6.60-6.70 (3H, m), 6.93 (1H, d, J=9.2 Hz), 7.04-7.54 (7H, m), 7.66-7.76 (1H, m), 7.87 (1H, d, J=2.0 Hz), 9.12 (1H, s).

Reference Example 24

[Formula 68]

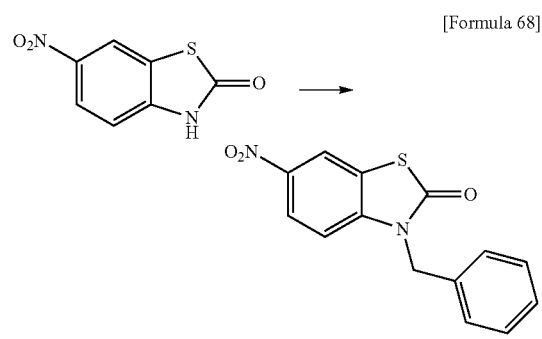

To the solution of 0.50 g of 6-nitrobenzo[d]thiazol-2(3H)-one in 2.5 mL of N,N-dimethylformamide, 0.334 mL of benzyl bromide and 0.705 g of potassium carbonate were added at room temperature, and the resultant was stirred at room temperature for 25 minutes. Water and ethyl acetate were added to the reaction mixture. The organic layer was separated and dried over anhydrous sodium sulfate, and the solvent was distilled off under reduced pressure. The obtained residue was washed with ethyl acetate and water to give 0.609 g of 3-benzyl-6-nitrobenzo[d]thiazol-2(3H)-one as a yellow solid.

$^1$H-NMR (CDCl$_3$) δ: 5.21 (2H, s), 7.06 (1H, d, J=8.6 Hz), 7.24-7.41 (5H, m), 8.15 (1H, dd, J=8.9, 2.3 Hz), 8.37 (1H, d, J=2.6 Hz).

Reference Example 25

[Formula 69]

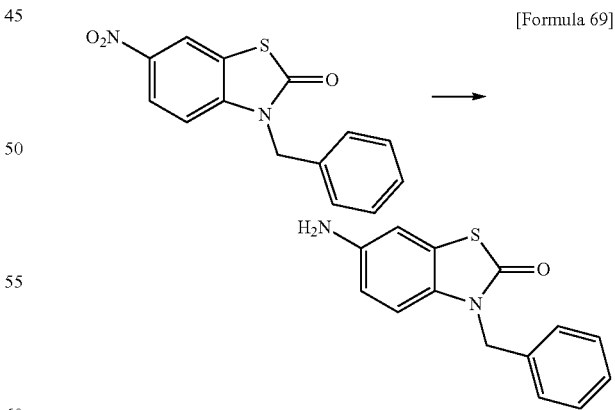

To the mixed solution of 0.20 g of 3-benzyl-6-nitrobenzo[d]thiazol-2(3H)-one, 2.0 mL of ethanol, 0.68 mL of water and 336 mg of ammonium chloride, 273 mg of reduced iron was added at room temperature under a nitrogen atmosphere, and the resultant was stirred at an external temperature of 80° C. for 30 minutes. After cooling the reaction mixture to room temperature, the solid was removed by filtration through Celite and the solvent was distilled off under reduced pressure. Ethyl acetate and water were added to the obtained residue. The organic layer was separated and dried over anhydrous sodium sulfate, and the solvent was distilled off under reduced pressure to give 0.173 g of 6-amino-3-benzylbenzo[d]thiazol-2(3H)-one as a yellow solid.

¹H-NMR (DMSO-d₆) δ: 5.00-5.10 (4H, m), 6.52 (1H, dd, J=8.6, 2.0 Hz), 6.79 (1H, d, J=2.6 Hz), 6.93 (1H, d, J=8.6 Hz), 7.21-7.39 (5H, m).

Reference Example 26

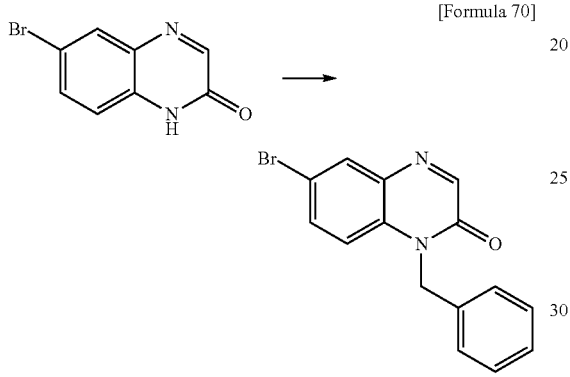

[Formula 70]

To the solution of 50 mg of 6-bromoquinoxalin-2(1H)-one in 0.5 mL of N,N-dimethylacetamide, 26.4 μL of benzyl bromide and 61.4 mg of potassium carbonate were added at room temperature, and the resultant was stirred at room temperature for 30 minutes and at an external temperature of 50° C. for 30 minutes. The reaction mixture was cooled to room temperature, and water and ethyl acetate were then added thereto. The organic layer was separated and dried over anhydrous sodium sulfate, and the solvent was distilled off under reduced pressure. The obtained residue was purified by silica gel column chromatography (hexane:ethyl acetate) to give 50 mg of 1-benzyl-6-bromoquinoxalin-2(1H)-one as a yellow solid.

¹H-NMR (DMSO-d₆) δ: 5.47 (2H, s), 7.20-7.38 (5H, m), 7.41 (1H, d, J=9.2 Hz), 7.73 (1H, dd, J=8.9, 2.3 Hz), 8.06 (1H, d, J=2.6 Hz), 8.39 (1H, s).

Reference Example 27

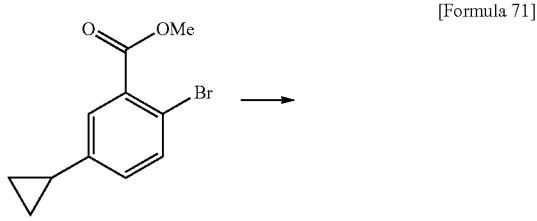

[Formula 71]

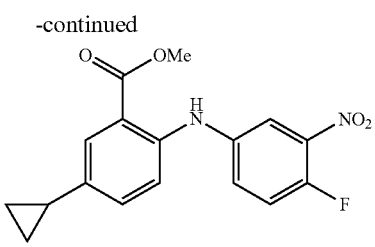

By the method similar to that of Reference Example 21, methyl 5-cyclopropyl-2-((4-fluoro-3-nitrophenyl)amino)benzoate was obtained from methyl 2-bromo-5-cyclopropylbenzoate and 4-fluoro-3-nitroaniline.

¹H-NMR (CDCl₃) δ: 0.60-0.71 (2H, m), 0.85-1.01 (2H, m), 1.80-1.93 (1H, m), 3.91 (3H, s), 7.02-7.84 (5H, m), 7.88 (1H, dd, J=6.6, 2.6 Hz), 9.41 (1H, s).

Reference Example 28

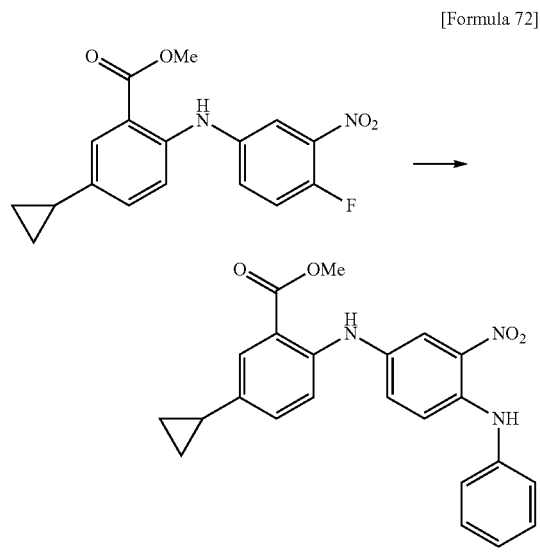

[Formula 72]

To the solution of 0.385 g of methyl 5-cyclopropyl-2-((4-fluoro-3-nitrophenyl)amino)benzoate in 3.4 mL of N,N-dimethylformamide, 0.597 mL of diisopropylethylamine and 0.213 mL of aniline were added at room temperature under a nitrogen atmosphere, and the resultant was stirred at an external temperature of 80° C. for 19 hours. The reaction mixture was cooled to room temperature, and ethyl acetate and water were then added thereto. The organic layer was separated and dried over anhydrous sodium sulfate, and the solvent was distilled off under reduced pressure. The obtained residue was purified by silica gel column chromatography (hexane:ethyl acetate) to give 0.175 g of methyl 5-cyclopropyl-2-((3-nitro-4-(phenylamino)phenyl)amino)benzoate as an oil.

¹H-NMR (CDCl₃) δ: 0.58-0.68 (2H, m), 0.83-0.97 (2H, m), 1.78-1.91 (1H, m), 3.90 (3H, s), 7.00 (1H, d, J=8.6 Hz), 7.09 (1H, dd, J=8.6, 2.6 Hz), 7.13-7.47 (7H, m), 7.70 (1H, d, J=2.0 Hz), 8.08 (1H, s), 9.21 (1H, s), 9.40 (1H, s).

Reference Example 29

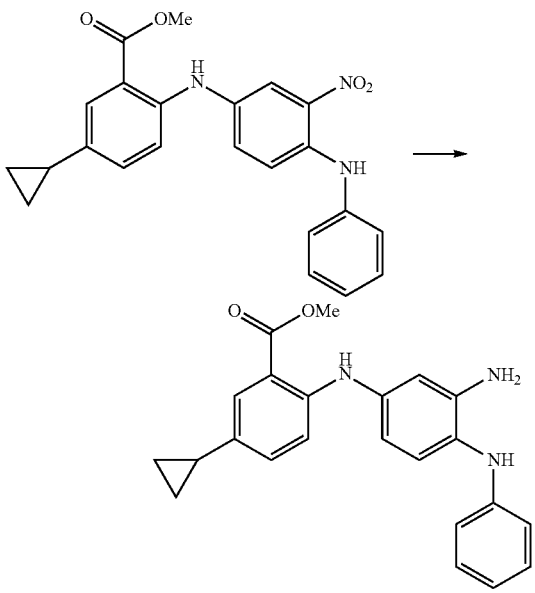
[Formula 73]

The solution of 0.170 g of methyl 5-cyclopropyl-2-((3-nitro-4-(phenylamino)phenyl)amino)benzoate in 4.2 mL of tetrahydrofuran was subjected to hydrogenation reaction (room temperature, normal pressure, flow rate: 1.5 mL/min, 10% Pd/C) using the flow hydrogenation reactor. The obtained reaction solution was added to the solution of 0.137 g of 1,1'-carbonyldiimidazole in 4.2 mL of tetrahydrofuran, and the resultant was stirred at room temperature for 30 minutes. Water and ethyl acetate were added to the reaction mixture. The organic layer was separated and dried over anhydrous sodium sulfate, and the solvent was distilled off under reduced pressure. The reaction with 1,1'-carbonyldiimidazole did not proceed and methyl 2-((3-amino-4-(phenylamino)phenyl)amino)-5-cyclopropylbenzoate was obtained as an oil.

MS (ESI, m/z): 374 (M+H)$^+$.

Reference Example 30

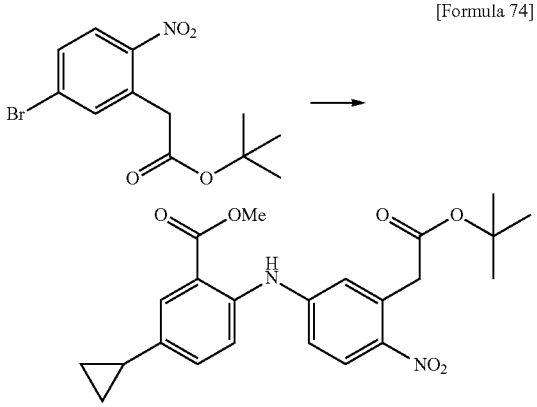
[Formula 74]

The mixture of 0.89 g of methyl 2-amino-5-cyclopropylbenzoate, 1.47 g of tert-butyl 2-(5-bromo-2-nitrophenyl)acetate, 52 mg of palladium acetate, 270 mg of 4,5'-bis(diphenylphosphino)-9,9'-dimethylxanthene, 3.03 g of cesium carbonate, and 10 mL of toluene, was heated at reflux for six hours and 30 minutes under a nitrogen atmosphere. After cooling the reaction mixture to room temperature, the insoluble matter was filtered off, and ethyl acetate and water were added to the filtrate. The organic layer was separated, washed with a saturated aqueous sodium chloride solution and dried over anhydrous magnesium sulfate, and the solvent was distilled off under reduced pressure. The obtained residue was purified by silica gel column chromatography (gradient elution with hexane:ethyl acetate=100:0-30:70). Hexane was added to the thus obtained residue, and the solid was collected by filtration to give 1.12 g of methyl 2-((3-(2-(tert-butoxy)-2-oxoethyl)-4-nitrophenyl)amino)-5-cyclopropylbenzoate as a yellow solid.

$^1$H-NMR (CDCl$_3$) δ: 0.65-0.71 (2H, m), 0.94-1.00 (2H, m), 1.46 (9H, s), 1.85-1.94 (1H, m), 3.89 (2H, s), 3.91 (3H, s), 6.96 (1H, d, J=2.0 Hz), 7.15 (1H, dd, J=9.2, 2.6 Hz), 7.20 (1H, dd, J=8.6, 2.0 Hz), 7.42 (1H, d, J=8.6 Hz), 7.74 (1H, d, J=2.6 Hz), 8.15 (1H, d, J=9.2 Hz), 9.59 (1H, s).

MS (ESI, m/z): 425 (M−H)$^-$.

Reference Example 31

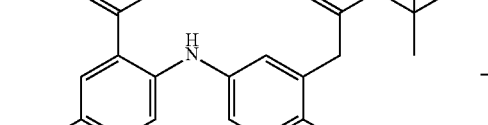
[Formula 75]

The mixture of 820 mg of methyl 2-((3-(2-(tert-butoxy)-2-oxoethyl)-4-nitrophenyl)amino)-5-cyclopropylbenzoate, 537 mg of iron powder, 72 mg of ammonium chloride, 15 mL of ethanol, and 3 mL of water, was heated at reflux for two hours and 20 minutes. After cooling the reaction mixture to room temperature, the insoluble matter was filtered off and the solvent was distilled off under reduced pressure. The obtained residue was purified by silica gel column chromatography (gradient elution with hexane:ethyl acetate=100:0-50:50). Hexane was added to the thus obtained residue, and the solid was collected by filtration to give 497 mg of methyl 2-((4-amino-3-(2-(tert-butoxy)-2-oxoethyl)phenyl)amino)-5-cyclopropylbenzoate as a white solid.

MS (ESI, m/z): 397 (M+H)$^+$.

Reference Example 32

[Formula 76]

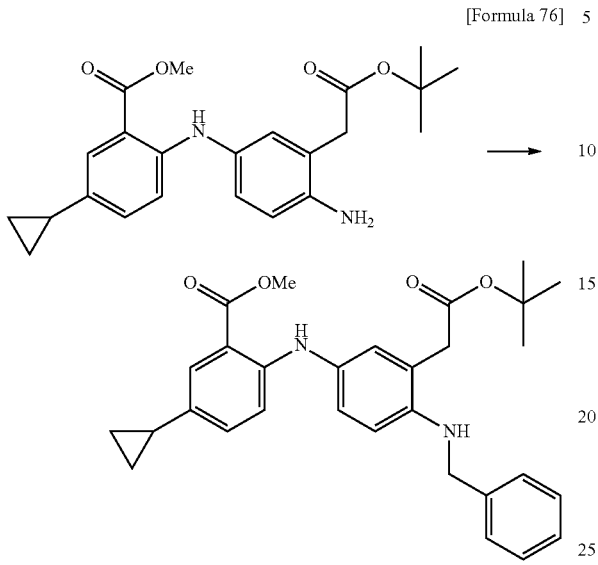

To the solution of 200 mg of methyl 2-((4-amino-3-(2-(tert-butoxy)-2-oxoethyl)phenyl)amino)-5-cyclopropylbenzoate in 1 mL of N,N-dimethylformamide, 77 mg of potassium carbonate and 66 μL of benzyl bromide were added, and the resultant was stirred at room temperature for one hour. The reaction mixture was allowed to stand overnight, and ethyl acetate and water were then added thereto. The organic layer was separated, washed with a saturated aqueous sodium chloride solution and dried over anhydrous sodium sulfate, and the solvent was distilled off under reduced pressure to give 237 mg of methyl 2-((4-benzylamino-3-(2-(tert-butoxy)-2-oxoethyl)phenyl)amino)-5-cyclopropylbenzoate as a yellow oil.

MS (ESI, m/z): 488 (M+H)$^+$.

Reference Example 33

[Formula 77]

To the solution of 100 mg of methyl 2-((4-amino-3-(2-(tert-butoxy)-2-oxoethyl)phenyl)amino)-5-cyclopropylbenzoate in 1 mL of N,N-dimethylformamide, 37 mg of potassium carbonate and 26 μL of bromomethylcyclopropane were added, and the resultant was stirred at room temperature for 14 hours and 55 minutes and then stirred at an external temperature of 60° C. for one hour and 55 minutes. After adding thereto 37 mg of potassium carbonate, the resultant was stirred at an external temperature of 80° C. for two hours and 50 minutes. After the reaction mixture was allowed to stand overnight, 37 mg of potassium carbonate and 26 μL of bromomethylcyclopropane were added thereto, and the resultant was stirred at an external temperature of 110° C. for seven hours and 20 minutes. The insoluble matter was filtered off and the solvent was then distilled off under reduced pressure. The obtained residue was purified by silica gel column chromatography (gradient elution with hexane:ethyl acetate=100:0-60:40) to give 65 mg of methyl 2-((3-(2-(tert-butoxy)-2-oxoethyl)-4-((cyclopropylmethyl)amino)phenyl)amino)-5-cyclopropylbenzoate as a yellow oil.

MS (ESI, m/z): 451 (M+H)$^+$.

Reference Example 34

[Formula 78]

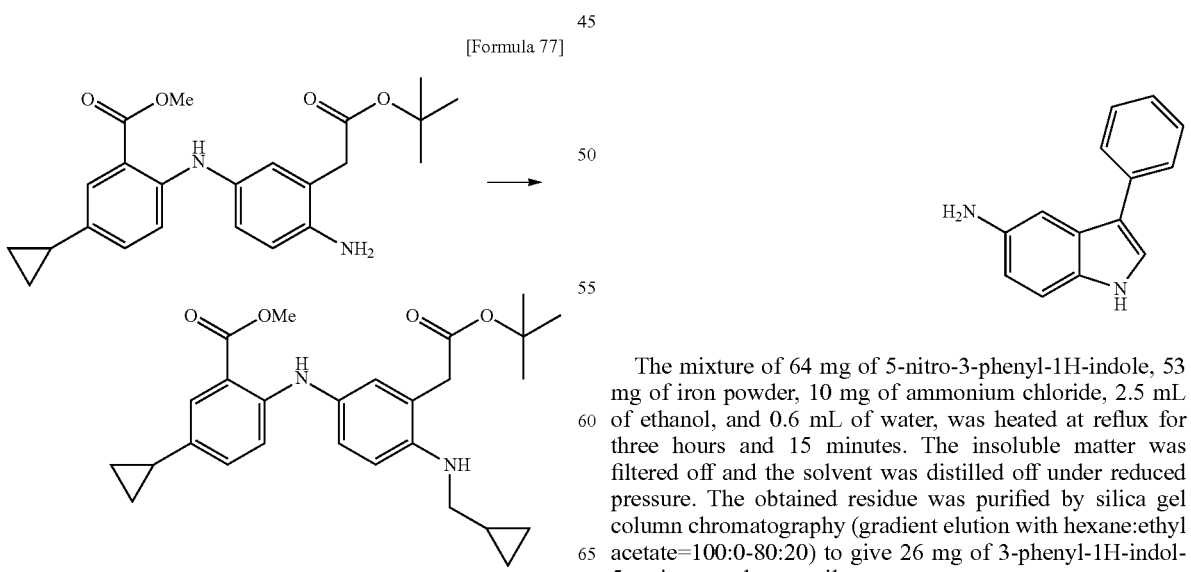

The mixture of 64 mg of 5-nitro-3-phenyl-1H-indole, 53 mg of iron powder, 10 mg of ammonium chloride, 2.5 mL of ethanol, and 0.6 mL of water, was heated at reflux for three hours and 15 minutes. The insoluble matter was filtered off and the solvent was distilled off under reduced pressure. The obtained residue was purified by silica gel column chromatography (gradient elution with hexane:ethyl acetate=100:0-80:20) to give 26 mg of 3-phenyl-1H-indol-5-amine as a brown oil.

MS (ESI, m/z): 209 (M+H)$^+$.

Reference Example 35

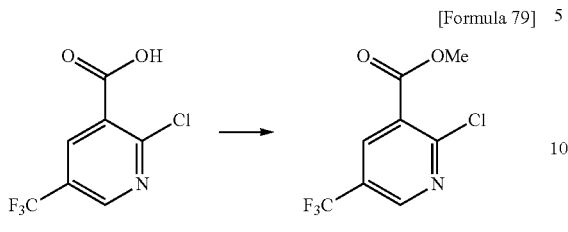

[Formula 79]

To the solution of 500 mg of 2-chloro-5-(trifluoromethyl) nicotinic acid in 2 mL of tetrahydrofuran, 197 μL of oxalyl chloride and 10 μL of N,N-dimethylformamide were added under ice-cooling, and the resultant was stirred for one hour. The reaction mixture was added dropwise to the solution of 462 μL of triethylamine in 5 mL of methanol under ice-cooling, followed by addition of ethyl acetate and water. The organic layer was separated, washed with a saturated aqueous sodium chloride solution and dried over anhydrous sodium sulfate, and the solvent was distilled off under reduced pressure. The obtained residue was purified by silica gel column chromatography (gradient elution with hexane:ethyl acetate=100:0-80:20) to give 400 mg of methyl 2-chloro-5-(trifluoromethyl)nicotinate as a colorless oil.

MS (ESI, m/z): 240 (M+H)$^+$.

Reference Example 36

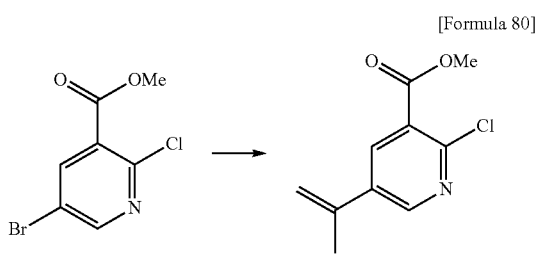

[Formula 80]

A mixture of 1.0 g of methyl 5-bromo-2-chloronicotinate, 820 μL of isopropenylboronic acid pinacol ester, 44 mg of palladium acetate, 112 mg of tricyclohexylphosphine, 2.12 g of tripotassium phosphate, 10 mL of toluene and 1 mL of water was heated at reflux for three hours and 15 minutes under a nitrogen atmosphere. The reaction mixture was cooled to room temperature, and ethyl acetate and water were then added thereto. The organic layer was separated, washed with a saturated aqueous sodium chloride solution and dried over magnesium sulfate, and the solvent was distilled off under reduced pressure. The obtained residue was purified by silica gel column chromatography (gradient elution with hexane:ethyl acetate=100:0-70:30) to give 700 mg of methyl 2-chloro-5-(prop-1-en-2-yl)nicotinate as a colorless oil.

$^1$H-NMR (DMSO-d$_6$) δ: 2.15 (3H, s), 3.90 (3H, s), 5.32 (1H, s), 5.67 (1H, s), 8.30 (1H, d, J=2.0 Hz), 8.74 (1H, d, J=2.0 Hz).

Reference Example 37

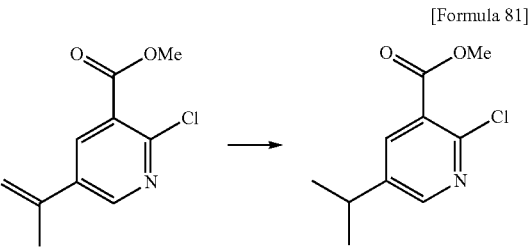

[Formula 81]

30 mL of the solution of 700 mg of methyl 2-chloro-5-(prop-1-en-2-yl)nicotinate in methanol was subjected to hydrogenation reaction (45 to 50° C., 1 bar, flow rate: 1 mL/min, 5% Pd/C) using the flow hydrogenation reactor. The solvent was distilled off under reduced pressure, and the obtained residue was then purified by silica gel column chromatography (gradient elution with hexane:ethyl acetate=100:0-50:50) to give 530 mg of methyl 2-chloro-5-isopropylnicotinate as a colorless oil.

$^1$H-NMR (DMSO-d$_6$) δ: 1.23 (6H, d, J=7.3 Hz), 3.03 (1H, sep, J=6.6 Hz), 3.89 (3H, s), 8.12 (1H, d, J=2.6 Hz), 8.51 (1H, d, J=2.6 Hz).

MS (ESI, m/z): 214 (M+H)$^+$.

Reference Example 38

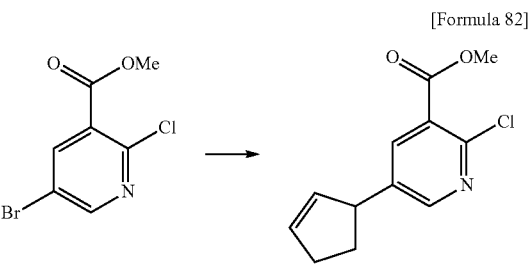 [SMILES: COC(=O)c1cc(Br)cnc1Cl ; COC(=O)c1cc(C2C=CCC2)cnc1Cl]

[Formula 82]

The mixture of 500 mg of methyl 5-bromo-2-chloronicotinate, 736 μL of cyclopentene, 45 mg of palladium acetate, 122 mg of tri(o-tolyl)phosphine, 836 μL of triethylamine, and 2 mL of N,N-dimethylacetamide, was stirred at an external temperature of 100° C. for two hours and 40 minutes under a nitrogen atmosphere. The reaction mixture was cooled to room temperature, and ethyl acetate and water were then added thereto. The organic layer was separated, washed with a saturated aqueous sodium chloride solution and dried over anhydrous sodium sulfate, and the solvent was distilled off under reduced pressure. The obtained residue was purified by silica gel column chromatography (gradient elution with hexane:ethyl acetate=100:0-50:50) to give 288 mg of methyl 2-chloro-5-(cyclopent-2-en-1-yl)nicotinate as a yellow oil.

$^1$H-NMR (DMSO-d$_6$) δ: 1.60-1.70 (1H, m), 2.34-2.48 (3H, m), 3.88 (3H, s), 3.98-4.03 (1H, m), 5.77-5.82 (1H, m), 6.01-6.06 (1H, m), 7.98 (1H, d, J=2.6 Hz), 8.43 (1H, d, J=2.6 Hz).

MS (ESI, m/z): 238 (M+H)$^+$.

Reference Example 39

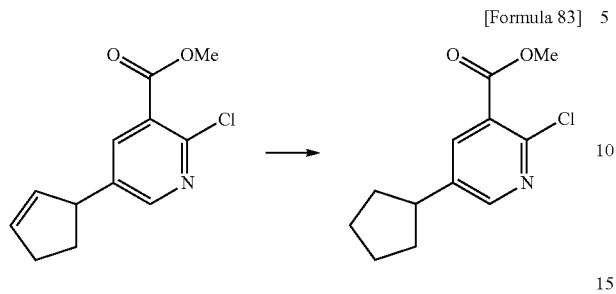

[Formula 83]

20 mL of the solution of 288 mg of methyl 2-chloro-5-(cyclopent-2-en-1-yl)nicotinate in methanol was subjected to hydrogenation reaction (room temperature, 1 bar, flow rate: 2 mL/min, 10% Pd/C) using the flow hydrogenation reactor. The solvent was distilled off under reduced pressure. The obtained residue was purified by silica gel column chromatography (gradient elution with hexane:ethyl acetate=100:0-70:30) to give 257 mg of methyl 2-chloro-5-cyclopentylnicotinate as a colorless oil.

$^1$H-NMR (DMSO-$d_6$) δ: 1.48-1.82 (6H, m), 2.01-2.10 (2H, m), 3.02-3.14 (1H, m), 3.88 (3H, s), 8.10 (1H, d, J=2.6 Hz), 8.50 (1H, d, J=2.6 Hz).

MS (ESI, m/z): 240 (M+H)$^+$.

Reference Example 40

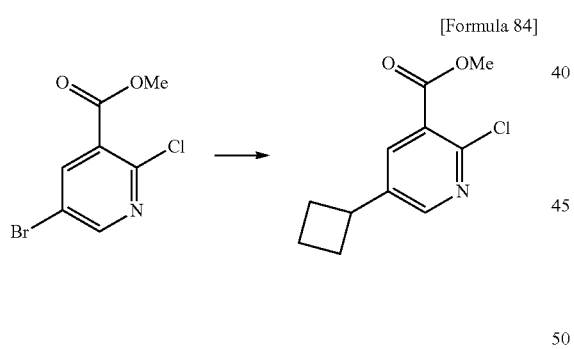

[Formula 84]

The mixture of 126 mg of methyl 5-bromo-2-chloronicotinate, 163 mg of potassium cyclobutyltrifluoroborate, 5.4 mg of butylbis(1-adamanthyl)phosphine, 2.2 mg of palladium acetate, 492 mg of cesium carbonate, 4.5 mL of toluene, and 0.5 mL of water, was stirred at an external temperature of 100° C. for 19 hours and 15 minutes under a nitrogen atmosphere. The reaction mixture was cooled to room temperature, and ethyl acetate and water were then added thereto. The organic layer was separated, washed with a saturated aqueous sodium chloride solution and dried over anhydrous sodium sulfate, and the solvent was distilled off under reduced pressure. The obtained residue was purified by silica gel column chromatography (gradient elution with hexane:ethyl acetate=100:0-80:20) to give 26 mg of methyl 2-chloro-5-cyclobutylnicotinate as a colorless oil.

MS (ESI, m/z): 226 (M+H)$^+$.

Reference Example 41

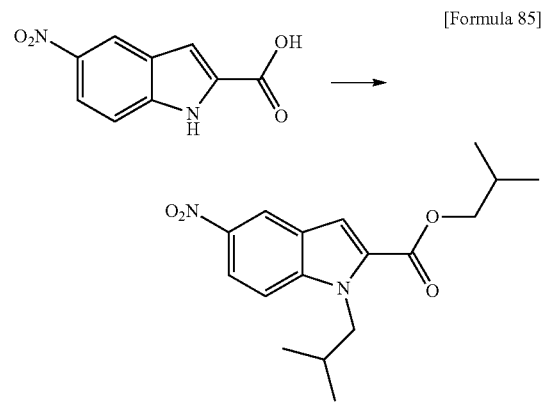

[Formula 85]

To the solution of 1.0 g of 5-nitro-1H-indole-2-carboxylic acid in 10 mL of N,N-dimethylacetamide 2.68 g of potassium carbonate and 2.11 mL of 1-bromo-2-methylpropane were added, and the resultant was stirred at an external temperature of 60° C. for one hour and 20 minutes. 2.1 mL of 1-bromo-2-methylpropane was added thereto, and the resultant was stirred at an external temperature of 80° C. for five hours. The reaction mixture was cooled to room temperature, and ethyl acetate and water were then added thereto. The organic layer was separated, sequentially washed with water and a saturated aqueous sodium chloride solution and dried over anhydrous magnesium sulfate, and the solvent was distilled off under reduced pressure to give isobutyl 1-isobutyl-5-nitro-1H-indole-2-carboxylate as an oil.

MS (ESI, m/z): 319 (M+H)$^+$.

Reference Example 42

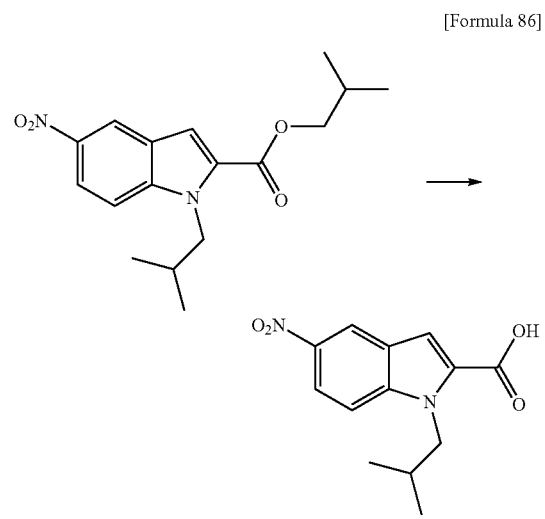

[Formula 86]

The mixture of isobutyl 1-isobutyl-5-nitro-1H-indole-2-carboxylate obtained in Reference Example 41, 5 mL of a 5 mol/L aqueous sodium hydroxide solution, 20 mL of tetrahydrofuran, and 10 mL of methanol, was heated at reflux for two hours and 10 minutes. After cooling the reaction mixture to room temperature, 5 mL of 5 mol/L hydrochloric acid was added thereto, and the solvent was distilled off under reduced pressure. Water and methanol were added to the obtained residue, and the solid was collected by filtration to give 1.21 g of 1-isobutyl-5-nitro-1H-indole-2-carboxylic acid as a pale brown solid.

¹H-NMR (DMSO-d₆) δ: 0.81 (6H, d, J=6.6 Hz), 2.03-2.17 (1H, m), 4.50 (2H, d, J=7.3 Hz), 7.54 (1H, s), 7.87 (1H, d, J=9.2 Hz), 8.14 (1H, dd, J=9.2, 2.6 Hz), 8.74 (1H, d, J=2.0 Hz).

MS (ESI, m/z): 263 (M+H)⁺, 261 (M−H)⁻.

Reference Example 43

[Formula 87]

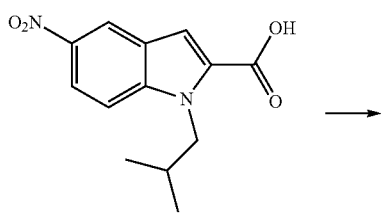

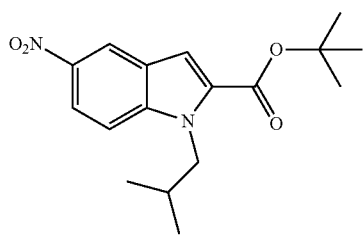

To the solution of 600 mg of 1-isobutyl-5-nitro-1H-indole-2-carboxylic acid in 30 mL of tetrahydrofuran, 477 µL of triethylamine, 56 mg of 4-(dimethylamino)pyridine and 1.05 mL of di-tert-butyl dicarbonate were added under ice-cooling, and the resultant was stirred at an external temperature of 60° C. for four hours and 10 minutes. 477 µL of triethylamine and 1.05 mL of di-tert-butyl dicarbonate were added thereto, and the resultant was stirred at an external temperature of 60° C. for one hour and 20 minutes. 0.5 mL of di-tert-butyl dicarbonate was added thereto, and the resultant was stirred at an external temperature of 60° C. for three hours and five minutes, and 0.5 mL of di-tert-butyl dicarbonate and 477 µL of triethylamine were then added thereto, and the resultant was stirred at an external temperature of 60° C. for one hour and five minutes. The reaction mixture was cooled to room temperature, and ethyl acetate and water were then added thereto. The organic layer was separated, sequentially washed with water and a saturated aqueous sodium chloride solution and dried over anhydrous magnesium sulfate, and the solvent was distilled off under reduced pressure to give tert-butyl 1-isobutyl-5-nitro-1H-indole-2-carboxylate as a brown oil.

MS (ESI, m/z): 319 (M+H)⁺.

Reference Example 44

[Formula 88]

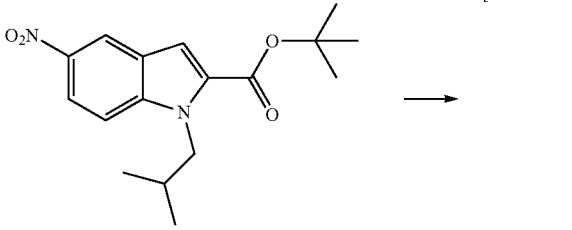

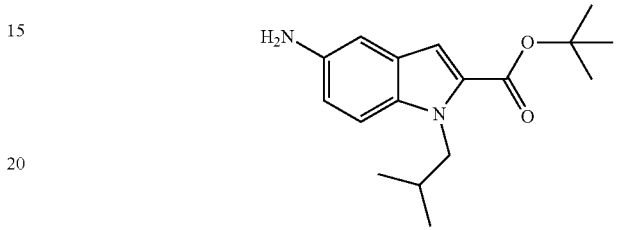

The mixture of tert-butyl 1-isobutyl-5-nitro-1H-indole-2-carboxylate obtained in Reference Example 43, 86 mg of ammonium chloride, 0.38 g of iron powder, 60 mL of ethanol, and 15 mL of water, was heated at reflux for two hours and 20 minutes. After cooling the reaction mixture to room temperature, the insoluble matter was filtered off. The filter cake was washed with ethyl acetate. The filtrate and the washings were combined, water was added thereto, the organic layer was separated, washed with a saturated aqueous sodium chloride solution and then dried over anhydrous magnesium sulfate, and the solvent was distilled off under reduced pressure. The obtained residue was purified by silica gel column chromatography (hexane:ethyl acetate) to give 0.52 g of tert-butyl 5-amino-1-isobutyl-1H-indole-2-carboxylate as a brown oil.

MS (ESI, m/z): 289 (M+H)⁺.

Reference Example 45

[Formula 89]

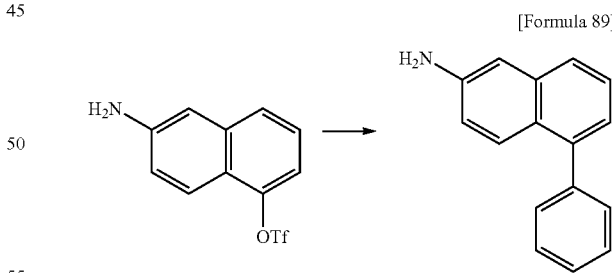

The mixture of 600 mg of (6-aminonaphthalen-1-yl) trifluoromethanesulfonate, 252 mg of phenylboronic acid, 798 mg of tripotassium phosphate, 133 mg of bis(di-tert-butyl(4-dimethylaminophenyl)phosphine)dichloropalladium(II), 20 mL of dioxane, and 5 mL of water, was heated at reflux for 3.5 hours. 69 mg of phenylboronic acid was added to the reaction mixture, and the resultant was heated at reflux for 55 minutes. After cooling the reaction mixture to room temperature, the organic layer was separated. The organic layer was washed with water and the aqueous layers were combined and extracted with ethyl acetate. The organic layer and the extract were combined and dried over anhydrous sodium sulfate, and the solvent was distilled off under reduced pressure. The obtained residue was purified by silica gel column chromatography (gradient elution with hexane:ethyl acetate=95:5-70:30) to give 265 mg of 5-phenylnaphthalen-2-amine as a yellow solid.

MS (ESI, m/z): 220 (M+H)⁺.

Reference Example 46

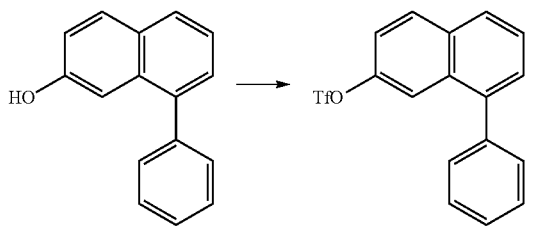

[Formula 90]

To the solution of 1.0 g of 8-phenylnaphthalen-2-ol in 15 mL of tetrahydrofuran, 352 mg of sodium tert-butoxide was added under ice-cooling, and 1.3 g of N-phenylbis(trifluoromethanesulfonimide) was further added thereto, and the resultant was stirred for 1.5 hours. Water and ethyl acetate were added to the reaction mixture, and the organic layer was separated and the aqueous layer was extracted with ethyl acetate. The organic layer and the extract were combined and dried over anhydrous sodium sulfate, and the solvent was distilled off under reduced pressure. The obtained residue was purified by silica gel column chromatography (gradient elution with hexane:ethyl acetate=100:0-85:15) to give 1.28 g of (8-phenylnaphthalen-2-yl)trifluoromethanesulfonate as a white solid.

MS (ESI, m/z): 351 (M−H)⁻.

Reference Example 47

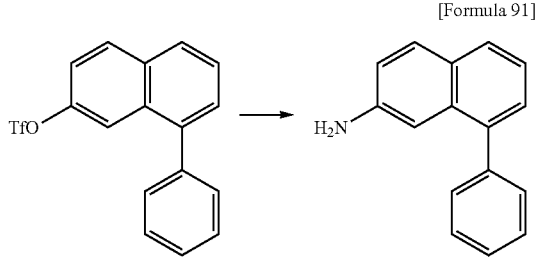 [SMILES: O=S(=O)(Oc1ccc2cccc(-c3ccccc3)c2c1)C(F)(F)F ; Nc1ccc2cccc(-c3ccccc3)c2c1]

[Formula 91]

The mixture of 500 mg of (8-phenylnaphthalen-2-yl)trifluoromethanesulfonate, 200 mg of tert-butyl carbamate, 65 mg of tris(dibenzylideneacetone)dipalladium(0), 82 mg of 4,5'-bis(diphenylphosphino)-9,9'-dimethylxanthene, 925 mg of cesium carbonate, and 5 mL of toluene, was stirred at 190° C. for one hour using microwave equipment. After cooling the reaction mixture to room temperature, the insoluble matter was filtered off and the solvent was distilled off under reduced pressure. The obtained residue was purified by silica gel column chromatography (gradient elution with hexane:ethyl acetate=100:0-70:30) to give 130 mg of 8-phenylnaphthalen-2-amine as a yellow oil.

MS (ESI, m/z): 220 (M+H)⁺.

Reference Example 48

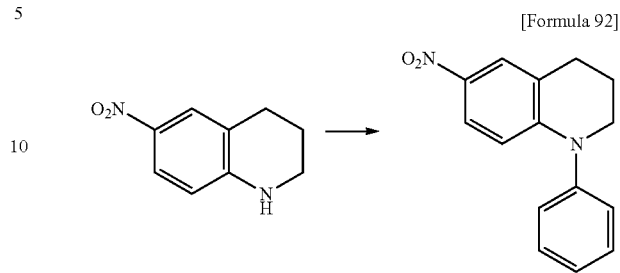

[Formula 92]

The mixture of 50 mg of 6-nitro-1,2,3,4-tetrahydroquinoline, 32 μL of bromobenzene, 13 mg of tris(dibenzylideneacetone)dipalladium (0), 16 mg of 4,5'-bis(diphenylphosphino)-9,9'-dimethylxanthene, 183 mg of cesium carbonate, and 1.5 mL of toluene, was stirred at 150° C. for one hour and then at 190° C. for one hour using microwave equipment. After cooling the reaction mixture to room temperature, the insoluble matter was filtered off and the solvent was distilled off under reduced pressure. The obtained residue was purified by silica gel column chromatography (gradient elution with hexane:ethyl acetate=100:0-80:20) to give 40 mg of 6-nitro-1-phenyl-1,2,3,4-tetrahydroquinoline as a yellow oil.

MS (ESI, m/z): 255 (M+H)⁺.

Reference Example 49

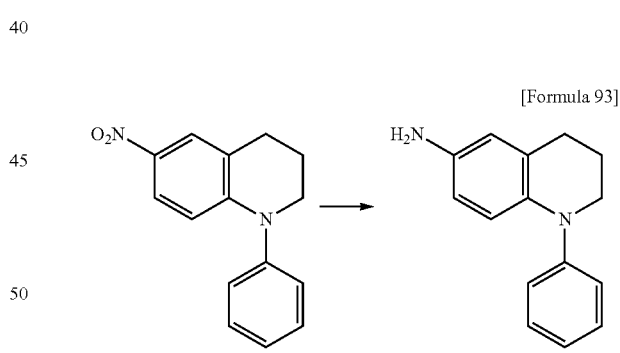

[Formula 93]

The solution of 40 mg of 6-nitro-1-phenyl-1,2,3,4-tetrahydroquinoline in 8 mL of methanol was subjected to hydrogenation reaction (room temperature, 1 bar, flow rate: 1 mL/min, 10% Pd/C) using the flow hydrogenation reactor. The solvent was distilled off under reduced pressure to give 36 mg of 1-phenyl-1,2,3,4-tetrahydroquinolin-6-amine as a yellow oil.

MS (ESI, m/z): 225 (M+H)⁺.

Reference Example 50

[Formula 94]

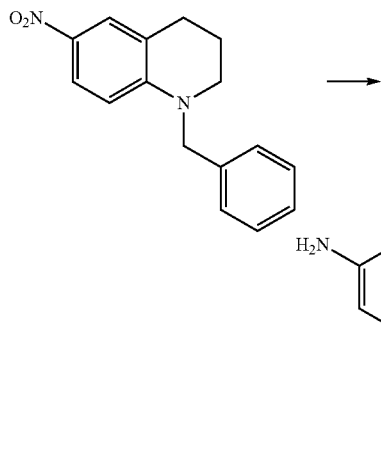

The mixture of 130 mg of 1-benzyl-6-nitro-1,2,3,4-tetrahydroquinoline, 24 mg of ammonium chloride, 75 mg of iron powder, 2 mL of ethanol and 0.5 mL of water was heated at reflux for one hour and 20 minutes. After cooling the reaction mixture to room temperature, 113 mg of iron powder was added thereto, and the resultant was heated at reflux for one hour. After cooling the reaction mixture to room temperature, the insoluble matter was filtered off. The filter cake was washed with methanol, the washings and the filtrate were combined and the solvent was distilled off under reduced pressure. Ethyl acetate, water and a saturated aqueous sodium bicarbonate solution were added thereto, the organic layer was separated and the aqueous layer was extracted with ethyl acetate. The organic layer and the extract were combined and dried over anhydrous sodium sulfate, and the solvent was distilled off under reduced pressure. The obtained residue was purified by silica gel column chromatography (gradient elution with hexane:ethyl acetate=100:0-60:40) to give 84 mg of 1-benzyl-1,2,3,4-tetrahydroquinolin-6-amine as a yellow oil.
MS (ESI, m/z): 239 (M+H)$^+$.

Reference Example 51

[Formula 95]

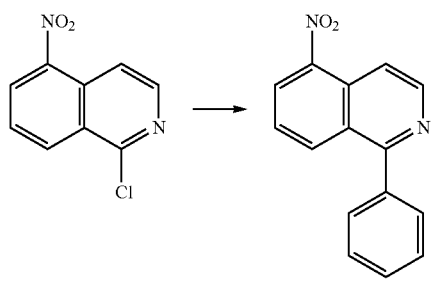

The mixture of 237 mg of 1-chloro-5-nitroisoquinoline, 153 mg of phenylboronic acid, 484 mg of tripotassium phosphate, 40 mg of bis(di-tert-butyl(4-dimethylaminophenyl)phosphine)dichloropalladium(II), 8 mL of dioxane, and 2 mL of water, was stirred at 100° C. for 1.5 hours. 28 mg of phenylboronic acid was added to the reaction mixture, and the resultant was heated at reflux for 30 minutes. The reaction mixture was cooled to room temperature, and ethyl acetate and water were then added thereto. The organic layer was separated and the aqueous layer was extracted with ethyl acetate. The organic layer and the extract were combined and the solvent was distilled off under reduced pressure. The obtained residue was purified by silica gel column chromatography (gradient elution with hexane:ethyl acetate=100:0-80:20) to give 233 mg of 5-nitro-1-phenylisoquinoline as a yellow solid.
MS (ESI, m/z): 251 (M+H)$^+$.

Reference Example 52

[Formula 96]

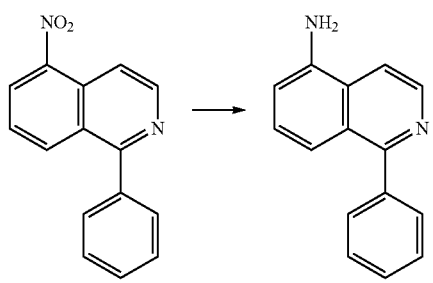

The mixed solution of 233 mg of 5-nitro-1-phenylisoquinoline, 10 mL of methanol and 2 mL of tetrahydrofuran was subjected to hydrogenation reaction (room temperature, 1 bar, flow rate: 1.5 mL/min, 10% Pd/C) using the flow hydrogenation reactor. The solvent was distilled off under reduced pressure to give 1-phenylisoquinolin-5-amine as a yellow solid.
MS (ESI, m/z): 221 (M+H)$^+$.

Reference Example 53

[Formula 97]

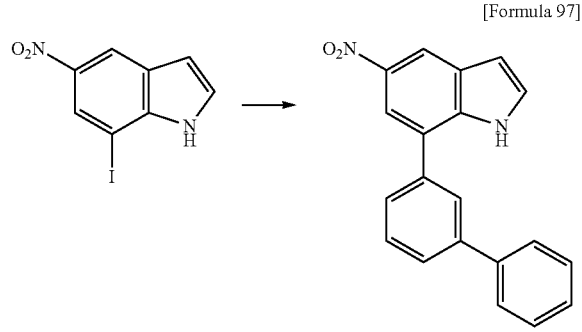 [SMILES: O=[N+]([O-])c1cc(I)c2[nH]ccc2c1 ; O=[N+]([O-])c1cc(-c2cccc(-c3ccccc3)c2)c2[nH]ccc2c1]

The mixture of 100 mg of 7-iodo-5-nitro-1H-indole, 76 mg of 3-biphenylboronic acid, 147 mg of tripotassium phosphate, 25 mg of bis(di-tert-butyl(4-dimethylaminophenyl)phosphine)dichloropalladium(II), 10 mL of dioxane, and 2 mL of water, was stirred at 100° C. for one hour. The reaction mixture was cooled to room temperature, and ethyl acetate and water were then added thereto. The organic layer was separated and the aqueous layer was extracted with ethyl acetate. The organic layer and the extract were combined and the solvent was distilled off under reduced pressure. The obtained residue was purified by silica gel column chromatography (gradient elution with hexane:ethyl acetate=100:0-70:30) to give 137 mg of 7-([1,1'-biphenyl]-3-yl)-5-nitro-1H-indole as a brown solid.

MS (ESI, m/z): 315 (M+H)$^+$.

Reference Example 54

[Formula 98]

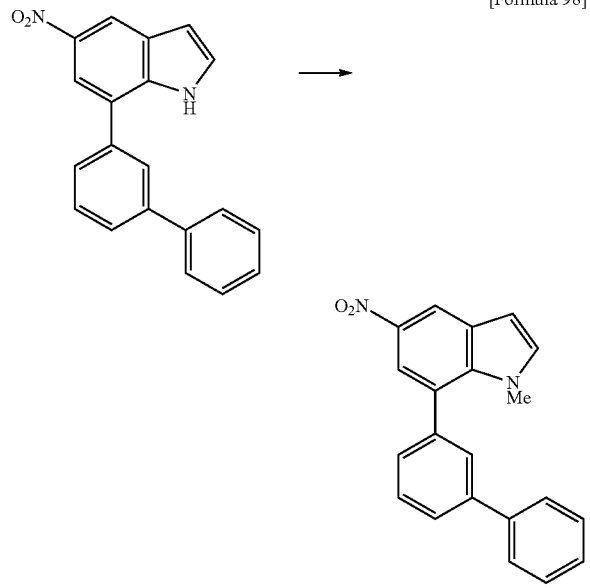

To the solution of 137 mg of 7-([1,1'-biphenyl]-3-yl)-5-nitro-1H-indole and 35 µL of methyl iodide in 4 mL of N,N-dimethylformamide, 19 mg of 60% sodium hydride was added under ice-cooling, and the resultant was stirred at room temperature for 30 minutes. Water and ethyl acetate were added to the reaction mixture, and the organic layer was separated and the aqueous layer was extracted with ethyl acetate. The organic layer and the extract were combined and the solvent was distilled off under reduced pressure. The obtained residue was purified by silica gel column chromatography (gradient elution with hexane:ethyl acetate=100:0-70:30) to give 132 mg of 7-([1,1'-biphenyl]-3-yl)-1-methyl-5-nitro-1H-indole as a brown oil.

MS (ESI, m/z): 329 (M+H)$^+$.

Reference Example 55

[Formula 99]

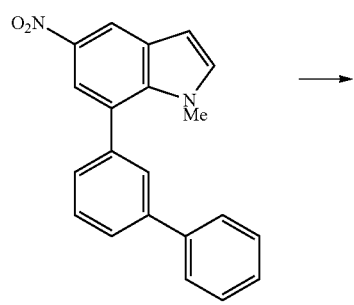

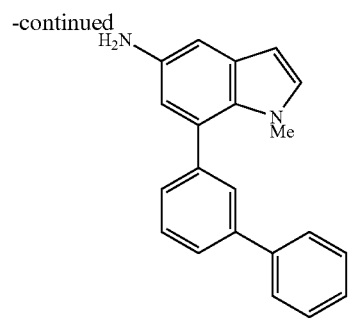

The mixture of 132 mg of 7-([1,1'-biphenyl]-3-yl)-1-methyl-5-nitro-1H-indole, 11 mg of ammonium chloride, 67 mg of iron powder, 2 mL of ethanol, and 0.5 mL of water, was stirred at 60° C. for 40 minutes. 33 mg of ammonium chloride and 112 mg of iron powder were added thereto, and the resultant was stirred at 60° C. for one hour. After cooling the reaction mixture to room temperature, the insoluble matter was filtered off. Ethyl acetate, water and a saturated aqueous sodium bicarbonate solution were added thereto. The organic layer was separated and the aqueous layer was extracted with ethyl acetate. The organic layer and the extract were combined and dried over anhydrous sodium sulfate, and the solvent was distilled off under reduced pressure. The obtained residue was purified by silica gel column chromatography (gradient elution with hexane:ethyl acetate=100:0-60:40) to give 90 mg of 7-([1,1'-biphenyl]-3-yl)-1-methyl-1H-indol-5-amine as a yellow foam.

MS (ESI, m/z): 299 (M+H)$^+$.

Reference Example 56

[Formula 100]

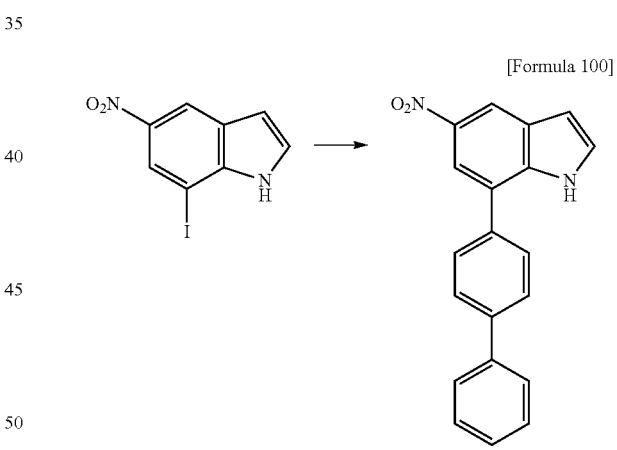

The mixture of 100 mg of 7-iodo-5-nitro-1H-indole, 76 mg of 4-biphenylboronic acid, 147 mg of tripotassium phosphate, 25 mg of bis(di-tert-butyl(4-dimethylaminophenyl)phosphine)dichloropalladium(II), 10 mL of dioxane, and 2 mL of water, was stirred at 100° C. for one hour. The reaction mixture was cooled to room temperature, and ethyl acetate and water were then added thereto. The organic layer was separated and the aqueous layer was extracted with ethyl acetate. The organic layer and the extract were combined and the solvent was distilled off under reduced pressure. The obtained residue was purified by silica gel column chromatography (gradient elution with hexane:ethyl acetate=100:0-70:30) to give 145 mg of 7-([1,1'-biphenyl]-4-yl)-5-nitro-1H-indole as a brown solid.

MS (ESI, m/z): 313 (M−H)$^-$.

Reference Example 57

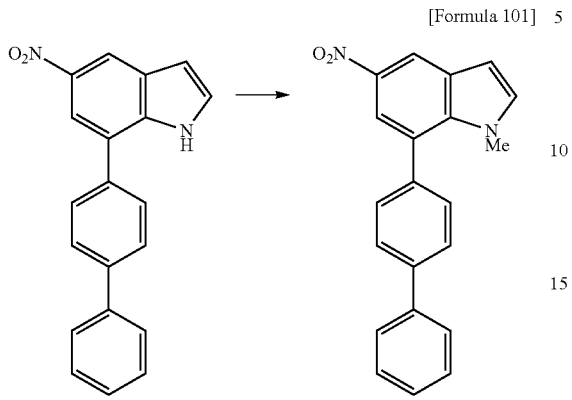

[Formula 101]

To the solution of 137 mg of 7-([1,1'-biphenyl]-4-yl)-5-nitro-1H-indole and 35 μL of methyl iodide in 4 mL of N,N-dimethylformamide, 19 mg of 60% sodium hydride was added under ice-cooling, and the resultant was stirred at room temperature for 30 minutes. Water and ethyl acetate were added to the reaction mixture, and the organic layer was separated and the aqueous layer was extracted with ethyl acetate. The organic layer and the extract were combined and the solvent was distilled off under reduced pressure. The obtained residue was purified by silica gel column chromatography (gradient elution with hexane:ethyl acetate=100:0-70:30) to give 32 mg of 7-([1,1'-biphenyl]-4-yl)-1-methyl-5-nitro-1H-indole as a black solid.

MS (ESI, m/z): 329 (M+H)$^+$.

Reference Example 58

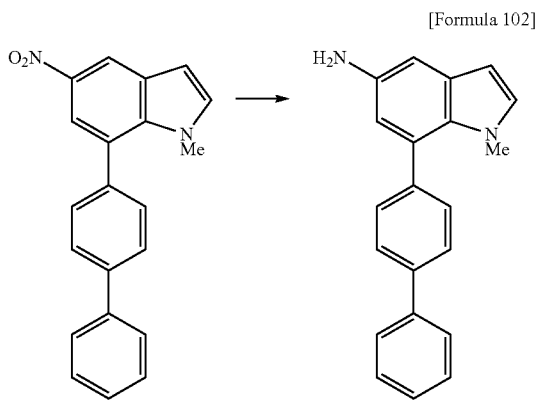 [SMILES: O=[N+]([O-])c1cc(-c2ccc(-c3ccccc3)cc2)c2[nH]ccc2c1 ; Cn1ccc2cc([N+](=O)[O-])cc(-c3ccc(-c4ccccc4)cc3)c21]

[Formula 102]

The mixture of 32 mg of 7-([1,1'-biphenyl]-4-yl)-1-methyl-5-nitro-1H-indole, 2.9 mg of ammonium chloride, 18 mg of iron powder, 2 mL of ethanol, and 0.5 mL of water, was stirred at 60° C. for 40 minutes. 8.7 mg of ammonium chloride and 30 mg of iron powder were added thereto, and the resultant was stirred at 60° C. for four hours and 20 minutes. After cooling the reaction mixture to room temperature, and the insoluble matter was filtered off, and ethyl acetate, water and a saturated aqueous sodium bicarbonate solution were added to the solvent. The organic layer was separated and the aqueous layer was extracted with ethyl acetate. The organic layer and the extract were combined and dried over anhydrous sodium sulfate, and the solvent was distilled off under reduced pressure. The obtained residue was purified by silica gel column chromatography (gradient elution with hexane:ethyl acetate=100:0-60:40) to give 8.7 mg of 7-([1,1'-biphenyl]-4-yl)-1-methyl-1H-indol-5-amine as a brown oil.

MS (ESI, m/z): 299 (M+H)$^+$.

Reference Example 59

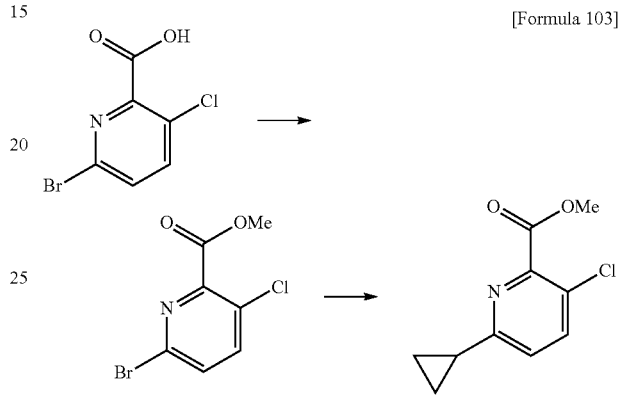

[Formula 103]

To the solution of 300 mg of 6-bromo-3-chloropicolinic acid in 7 mL of methanol, 0.3 mL of concentrated sulfuric acid was added, and the resultant was heated at reflux for two hours. After cooling the reaction mixture to room temperature, the solvent was distilled off under reduced pressure. Ethyl acetate and a saturated aqueous sodium bicarbonate solution were added to the obtained residue. The organic layer was separated and dried over anhydrous magnesium sulfate, and the solvent was distilled off under reduced pressure to give 225 mg of methyl 6-bromo-3-chloropicolinate as a white solid.

The mixture of 225 mg of methyl 6-bromo-3-chloropicolinate, 140 mg of cyclopropylboronic acid monohydrate, 10 mg of palladium acetate, 25 mg of tricyclohexylphosphine, 401 mg of tripotassium phosphate, 10 mL of toluene, and 1 mL of water, was heated at reflux for seven hours under a nitrogen atmosphere. The reaction mixture was cooled to room temperature, and ethyl acetate and water were then added thereto. The organic layer was separated and dried over anhydrous magnesium sulfate, and the solvent was then distilled off under reduced pressure. The obtained residue was purified by silica gel column chromatography (gradient elution with hexane:ethyl acetate=95:5-80:20) to give 221 mg of methyl 3-chloro-6-cyclopropylpicolinate as a colorless oil.

MS (ESI, m/z): 212 (M+H)$^+$.

Reference Example 60

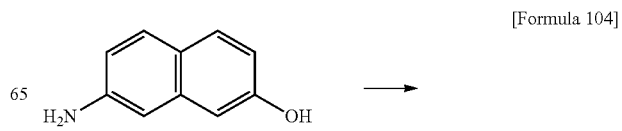

[Formula 104]

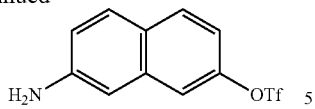

To the solution of 239 mg of 7-aminonaphthalen-2-ol in 10 mL of tetrahydrofuran, 144 mg of sodium tert-butoxide was added under ice-cooling, and the resultant was stirred for 10 minutes, and 535 mg of N-phenyl-bis(trifluoromethanesulfonimide) was then added thereto, and the further resultant was stirred for 30 minutes. The solvent was distilled off under reduced pressure. Chloroform was added to the obtained residue, and the insoluble matter was filtered off, and the solvent was distilled off under reduced pressure. The thus obtained residue was purified by silica gel column chromatography (gradient elution with hexane:ethyl acetate=95:5-67:33) to give (7-aminonaphthalen-2-yl)trifluoromethanesulfonate.

MS (ESI, m/z): 292 (M+H)$^+$.

Reference Example 61

[Formula 105]

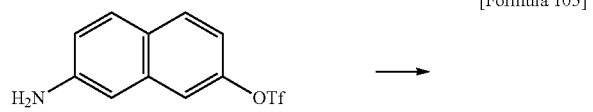

The mixture of (7-aminonaphthalen-2-yl)trifluoromethanesulfonate obtained in Reference Example 60, 183 mg of phenylboronic acid, 543 mg of tripotassium phosphate, 53 mg of bis(di-tert-butyl(4-dimethylaminophenyl)phosphine)dichloropalladium(II), 3 mL of dioxane, and 1 mL of water, was stirred at 150° C. for 20 minutes using microwave equipment. The reaction mixture was cooled to room temperature, and ethyl acetate and water were then added thereto. The organic layer was separated and dried over anhydrous magnesium sulfate, and the solvent was then distilled off under reduced pressure. The obtained residue was purified by silica gel column chromatography (gradient elution with hexane:ethyl acetate=91:9-67:33), and hexane was added to the thus obtained residue, and the solid was collected by filtration to give 61 mg of 7-phenyl-naphthalen-2-amine as a brown solid.

MS (ESI, m/z): 220 (M+H)$^+$.

Reference Example 62

[Formula 106]

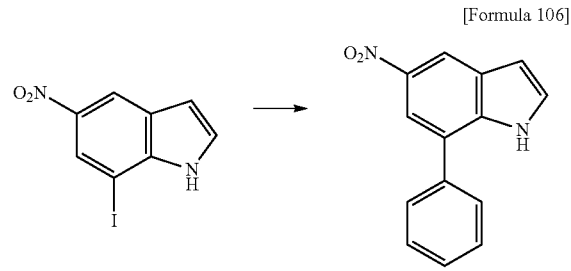 [SMILES: O=[N+]([O-])c1cc(I)c2[nH]ccc2c1 ; O=[N+]([O-])c1cc(-c2ccccc2)c2[nH]ccc2c1]

The mixture of 720 mg of 7-iodo-5-nitro-1H-indole, 365 mg of phenylboronic acid, 815 mg of tripotassium phosphate, 88 mg of bis(di-tert-butyl(4-dimethylaminophenyl)phosphine)dichloropalladium (II), 9 mL of dioxane, and 3 mL of water, was stirred at 150° C. for 20 minutes using microwave equipment. The reaction mixture was cooled to room temperature, and ethyl acetate and water were then added thereto. The organic layer was separated and dried over anhydrous magnesium sulfate, and the solvent was then distilled off under reduced pressure. The obtained residue was purified by silica gel column chromatography (gradient elution with chloroform:ethyl acetate=100:0-75:25), and ethyl acetate and hexane were added to the thus obtained residue, and the solid was collected by filtration to give 376 mg of 5-nitro-7-phenyl-1H-indole as a yellow solid.

MS (ESI, m/z): 237 (M−H)$^-$.

Reference Example 63

[Formula 107]

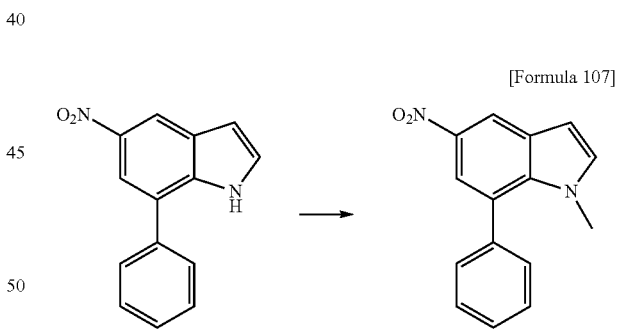

To the solution of 119 mg of 5-nitro-7-phenyl-1-indole in 2 mL of N,N-dimethylformamide, 22 mg of 60% sodium hydride was added under ice-cooling, and the resultant was stirred for 30 minutes. To the reaction mixture, 34 μL of methyl iodide was added under ice-cooling, and the resultant was stirred for 30 minutes. Ethyl acetate and water were added to the reaction mixture. The organic layer was separated and dried over anhydrous magnesium sulfate, and the solvent was then distilled off under reduced pressure. The obtained residue was purified by silica gel column chromatography (gradient elution with hexane:ethyl acetate=95:5-75:25) to give 1-methyl-5-nitro-7-phenyl-1H-indole.

MS (ESI, m/z): 253 (M+H)$^+$.

Reference Example 64

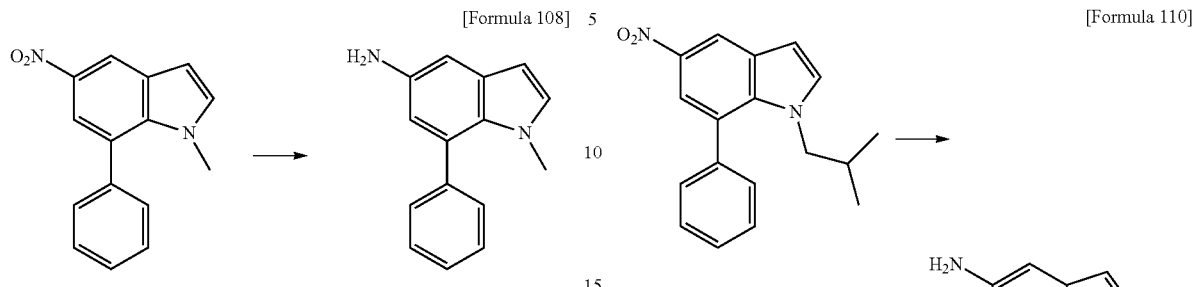

[Formula 108]

The solution of 1-methyl-5-nitro-7-phenyl-1H-indole obtained in Reference Example 63 in methanol was subjected to hydrogenation reaction (room temperature, flow rate: 1 mL/min, 10% Pd/C) using the flow hydrogenation reactor, and the solvent was then distilled off under reduced pressure. The obtained residue was purified by silica gel column chromatography (gradient elution with hexane:ethyl acetate=91:9-33:67) to give 1-methyl-7-phenyl-1H-indol-5-amine.

MS (ESI, m/z): 223 (M+H)$^+$.

Reference Example 65

[Formula 109]

To the solution of 119 mg of 5-nitro-7-phenyl-1H-indole in 2 mL of N,N-dimethylformamide, 22 mg of 60% sodium hydride was added under ice-cooling, and the resultant was stirred for 30 minutes. 60 µL of 1-bromo-2-methylpropane was added to the reaction mixture, and stirred for one hour. Ethyl acetate and water were added to the reaction mixture. The organic layer was separated and dried over anhydrous magnesium sulfate, and the solvent was then distilled off under reduced pressure. The obtained residue was purified by silica gel column chromatography (gradient elution with hexane:ethyl acetate=95:5-75:25) to give 1-isobutyl-5-nitro-7-phenyl-1H-indole.

MS (ESI, m/z): 295 (M+H)$^+$.

Reference Example 66

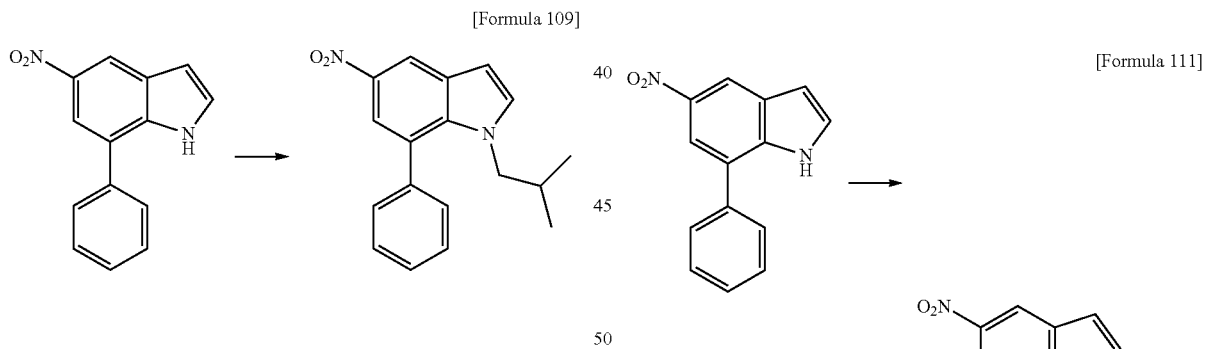

[Formula 110]

The solution of 1-isobutyl-5-nitro-7-phenyl-1H-indole obtained in Reference Example 65 in methanol was subjected to hydrogenation reaction (room temperature, flow rate: 1 mL/min, 10% Pd/C) using the flow hydrogenation reactor. The solvent was then distilled of under reduced pressure. The obtained residue was purified by silica gel column chromatography (gradient elution with hexane:ethyl acetate=91:9-33:67) to give 1-isobutyl-7-phenyl-1H-indol-5-amine.

MS (ESI, m/z): 265 (M+H)$^+$.

Reference Example 67

[Formula 111]

The mixture of 131 mg of 5-nitro-7-phenyl-1H-indole, 133 mg of di-tert-butyl dicarbonate, 7.0 mg of 4-(dimethylamino)pyridine, 0.4 mL of triethylamine, and 4 mL of dichloromethane, was stirred for one hour. The solvent was distilled off under reduced pressure. The obtained residue was purified by silica gel column chromatography (gradient elution with hexane:ethyl acetate=95:5-75:25) to give tert-butyl 5-nitro-7-phenyl-1H-indole-1-carboxylate.

MS (ESI, m/z): 339 (M+H)$^+$.

Reference Example 68

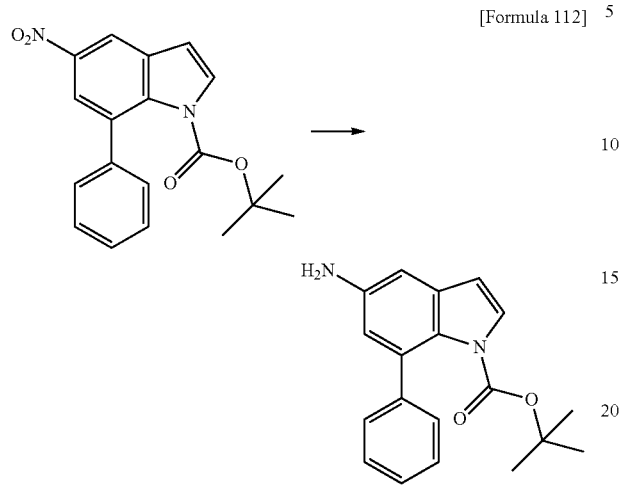

The solution of tert-butyl 5-nitro-7-phenyl-1H-indole-1-carboxylate obtained in Reference Example 67 in methanol was subjected to hydrogenation reaction (room temperature, flow rate: 1 mL/min, 10% Pd/C) using the flow hydrogenation reactor. The solvent was then distilled off under reduced pressure. The obtained residue was purified by silica gel column chromatography (gradient elution with hexane:ethyl acetate=91:9-33:67) to give tert-butyl 5-amino-7-phenyl-1H-indole-1-carboxylate.

MS (ESI, m/z): 309 (M+H)$^+$.

Reference Example 69

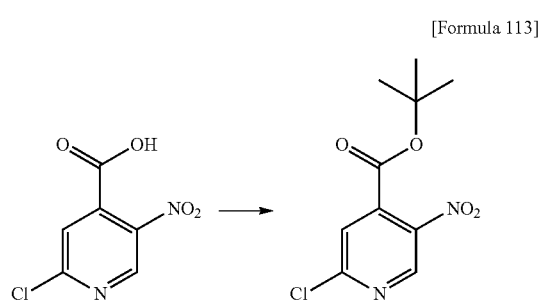 [SMILES: O=C(O)c1cc(Cl)ncc1[N+](=O)[O-] ; CC(C)(C)OC(=O)c1cc(Cl)ncc1[N+](=O)[O-]]

The mixture of 405 mg of 2-chloro-5-nitroisonicotinic acid, 873 mg of di-tert-butyl dicarbonate, 80.6 mg of 4-(dimethylamino)pyridine, 5 mL of tert-butanol, and 5 mL of dichloromethane, was stirred for one hour. The reaction mixture was allowed to stand overnight and then heated at reflux for three hours. After cooling the reaction mixture to room temperature, the solvent was distilled off under reduced pressure. The obtained residue was purified by silica gel column chromatography (gradient elution with hexane: ethyl acetate=95:5-67:33), methanol and water were added to the thus obtained residue, and the solid was collected by filtration to give 244 mg of tert-butyl 2-chloro-5-nitroisonicotinate as a white solid.

Reference Example 70

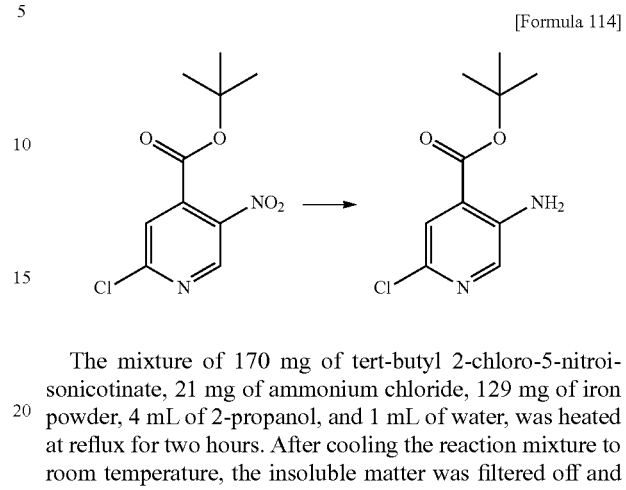

The mixture of 170 mg of tert-butyl 2-chloro-5-nitroisonicotinate, 21 mg of ammonium chloride, 129 mg of iron powder, 4 mL of 2-propanol, and 1 mL of water, was heated at reflux for two hours. After cooling the reaction mixture to room temperature, the insoluble matter was filtered off and the solvent was distilled off under reduced pressure. A saturated aqueous sodium bicarbonate solution and ethyl acetate were added to the obtained residue. The organic layer was separated and dried over anhydrous magnesium sulfate, and the solvent was then distilled off under reduced pressure. The thus obtained residue was purified by silica gel column chromatography (gradient elution with hexane:ethyl acetate=95:5-50:50) to give 114 mg of tert-butyl 5-amino-2-chloroisonicotinate as a green solid.

MS (ESI, m/z): 229 (M+H)$^+$

Reference Example 71

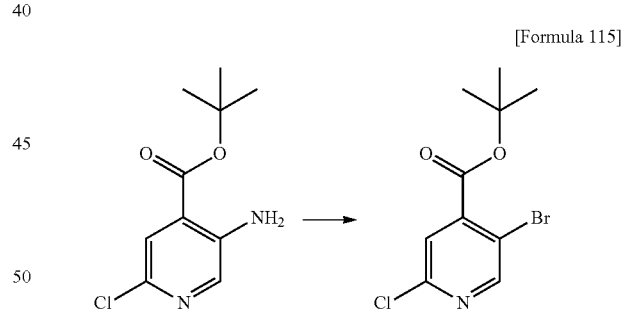

The mixture of 114 mg of tert-butyl 5-amino-2-chloroisonicotinate, 135 µL of isoamyl nitrite, 193 µL of trimethylsilyl bromide, and 5 mL of dichloromethane, was stirred at room temperature for three hours. Ethyl acetate and a saturated aqueous sodium bicarbonate solution were added to the reaction mixture. The organic layer was separated and dried over anhydrous magnesium sulfate, and the solvent was then distilled off under reduced pressure.

The obtained residue was purified by silica gel column chromatography (gradient elution with hexane:ethyl acetate=100:0-83:17) to give tert-butyl 5-bromo-2-chloroisonicotinate.

MS (ESI, m/z): 294 (M+H)$^+$.

Reference Example 72

[Formula 116]

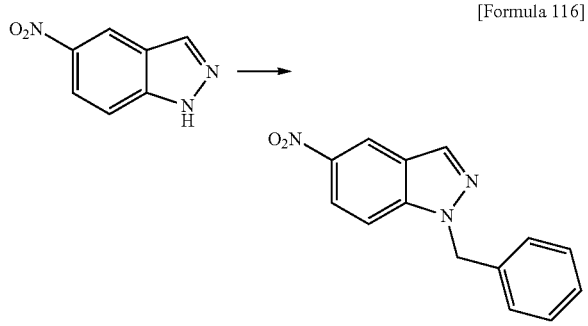

By the method similar to that of Reference Example 11, 1-benzyl-5-nitro-1H-indazole was obtained from 5-nitro-1H-indazole and benzyl bromide.

$^1$H-NMR (DMSO-d$_6$) δ: 5.77 (2H, s), 7.22-7.39 (5H, m), 7.96 (1H, d, J=9.2 Hz), 8.23 (1H, dd, J=9.2, 2.0 Hz), 8.45 (1H, s), 8.85 (1H, d, J=2.0 Hz).

Reference Example 73

[Formula 117]

By the method similar to that of Reference Example 12, 1-benzyl-1H-indazol-5-amine was obtained from 1-benzyl-5-nitro-1H-indazole.

$^1$H-NMR (DMSO-d$_6$) δ: 4.80 (2H, s), 5.51 (2H, s), 6.72-6.81 (2H, m), 7.13-7.38 (6H, m), 7.74 (1H, s).

Reference Example 74

[Formula 118]

To the solution of 0.77 g of ethyl 1-benzyl-5-nitro-1H-indole-2-carboxylate in 3.0 mL of ethanol and 5 mL of tetrahydrofuran, 0.95 mL of a 5 mol/L aqueous sodium hydroxide solution was added at room temperature, and the resultant was stirred at an external temperature of 50 to 60° C. for 2 hours. After cooling the reaction mixture to room temperature, water was added thereto. The reaction mixture was adjusted to pH 2.0 by adding 2 mol/L hydrochloric acid. The obtained solid was collected by filtration to give 0.68 g of 1-benzyl-5-nitro-1H-indole-2-carboxylic acid as a pale brown solid.

$^1$H-NMR (DMSO-d$_6$) δ: 5.96 (2H, s), 7.00-7.07 (2H, m), 7.18-7.33 (3H, m), 7.62 (1H, s), 7.79 (1H, d, J=9.2 Hz), 8.14 (1H, dd, J=9.2, 2.0 Hz), 8.77 (1H, d, J=2.0 Hz).

Reference Example 75

[Formula 119]

The mixture of 0.66 g of 1-benzyl-5-nitro-1H-indole-2-carboxylic acid, 82 mg of 4-(dimethylamino)pyridine, 0.97 g of di-tert-butyl dicarbonate, and 6 mL of tert-butanol, was stirred at an external temperature of 50 to 60° C. for 15 minutes. 6 mL of tetrahydrofuran was added thereto, and the resultant was stirred at an external temperature of 50 to 70° C. for four hours. The reaction mixture was cooled to room temperature, and ethyl acetate and water were then added thereto. The reaction mixture was adjusted to pH 2.0 by adding thereto 2 mol/L hydrochloric acid. The organic layer was separated, sequentially washed with water, a saturated aqueous sodium bicarbonate solution and a saturated aqueous sodium chloride solution and dried over anhydrous magnesium sulfate, and the solvent was distilled off under reduced pressure. Chloroform was added to the obtained residue, the insoluble matter was filtered off and the filter cake was washed with chloroform. The filtrate and the washings were combined and the solvent was distilled off under reduced pressure. The obtained residue was purified by silica gel column chromatography (gradient elution with hexane:ethyl acetate=80:20-50:50) to give 0.51 g of tert-butyl 1-benzyl-5-nitro-1H-indole-2-carboxylate as a pale yellow solid.

¹H-NMR (DMSO-d₆) δ: 1.50 (9H, s), 5.91 (2H, s), 6.97-7.04 (2H, m), 7.18-7.33 (3H, m), 7.57 (1H, s), 7.81 (1H, d, J=9.2 Hz), 8.15 (1H, dd, J=9.2, 2.6 Hz), 8.76 (1H, d, J=2.6 Hz).

Reference Example 76

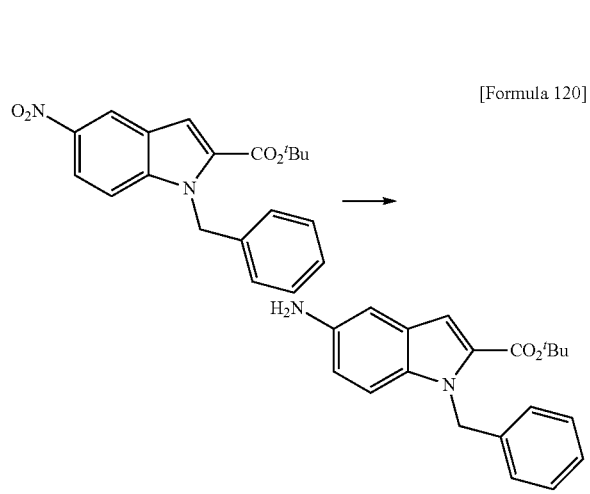

[Formula 120]

By the method similar to that of Reference Example 12, tert-butyl 5-amino-1-benzyl-1H-indole-2-carboxylate was obtained from tert-butyl 1-benzyl-5-nitro-1H-indole-2-carboxylate.

¹H-NMR (DMSO-d₆) δ: 1.47 (9H, s), 4.73 (2H, s), 5.70 (2H, s), 6.65-6.76 (2H, m), 6.92-7.02 (3H, m), 7.13-7.31 (4H, m).

Reference Example 77

[Formula 121]

By the method similar to that of Reference Example 12, tert-butyl 4-((5-amino-1H-indol-1-yl)methyl)piperidine-1-carboxylate was obtained from tert-butyl 4-((5-nitro-1H-indol-1-yl)methyl)piperidine-1-carboxylate.

¹H-NMR (CDCl₃) δ: 1.09-1.30 (2H, m), 1.44 (9H, s), 1.48-1.60 (2H, m), 1.89-2.04 (1H, m), 2.52-2.68 (2H, m), 3.92 (2H, d, J=7.3 Hz), 4.00-4.20 (2H, m), 6.29 (1H, d, J=2.6 Hz), 6.68 (1H, dd, J=8.6, 2.0 Hz), 6.93 (1H, d, J=2.0 Hz), 6.96 (1H, d, J=3.3 Hz), 7.12 (1H, d, J=8.6 Hz).

Reference Example 78

[Formula 122]

By the method similar to that of Reference Example 30, 5-nitro-1-phenylindoline was obtained from 5-nitroindoline and bromobenzene.

¹H-NMR (CDCl₃) δ: 3.22 (2H, t, J=8.3 Hz), 4.15 (2H, t, J=8.6 Hz), 6.93 (1H, d, J=8.6 Hz), 7.11-7.19 (1H, m), 7.24-7.32 (2H, m), 7.37-7.46 (2H, m), 7.98-8.07 (2H, m).

Reference Example 79

[Formula 123]

By the method similar to that of Reference Example 12, 1-phenylindolin-5-amine was obtained from 5-nitro-1-phenylindoline.

¹H-NMR (CDCl₃) δ: 3.05 (2H, t, J=8.3 Hz), 3.38 (2H, brs), 3.89 (2H, t, J=8.3 Hz), 6.46 (1H, d, J=8.6 Hz), 6.60-6.65 (1H, m), 6.88 (1H, t, J=7.3 Hz), 7.01 (1H, d, J=8.6 Hz), 7.12-7.18 (2H, d, J=7.9 Hz), 7.27-7.35 (2H, m).

Reference Example 80

[Formula 124]

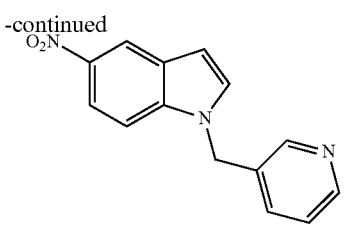
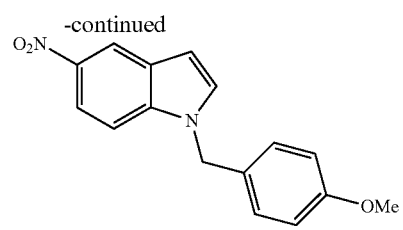

In accordance with the method of Reference Example 11 except for using N,N-dimethylformamide as a solvent, 5-nitro-1-(pyridin-3-ylmethyl)-1H-indole was obtained from 5-nitro-1H-indole and 3-(chloromethyl)pyridine.

$^1$H-NMR (DMSO-$d_6$) δ: 5.59 (2H, s), 6.83 (1H, d, J=2.6 Hz), 7.34 (1H, dd, J=7.3, 4.6 Hz), 7.57-7.64 (1H, m), 7.76 (1H, d, J=9.2 Hz), 7.83 (1H, d, J=3.3 Hz), 8.02 (1H, dd, J=8.9, 2.3 Hz), 8.48 (1H, dd, J=5.0, 1.7 Hz), 8.57 (1H, d, J=2.0 Hz), 8.59 (1H, d, J=2.0 Hz).

In accordance with the method of Reference Example 11 except for using N,N-dimethylformamide as a solvent, 1-(4-methoxybenzyl)-5-nitro-1H-indole was obtained from 5-nitro-1H-indole and 1-(chloromethyl)-4-methoxybenzene.

$^1$H-NMR (DMSO-$d_6$) δ: 3.70 (3H, s), 5.44 (2H, s), 6.78 (1H, d, J=3.3 Hz), 6.84-6.91 (2H, m), 7.18-7.25 (2H, m), 7.71 (1H, d, J=9.2 Hz), 7.76 (1H, d, J=3.3 Hz), 8.00 (1H, dd, J=9.2, 2.0 Hz), 8.57 (1H, d, J=2.6 Hz).

Reference Example 81

Reference Example 83

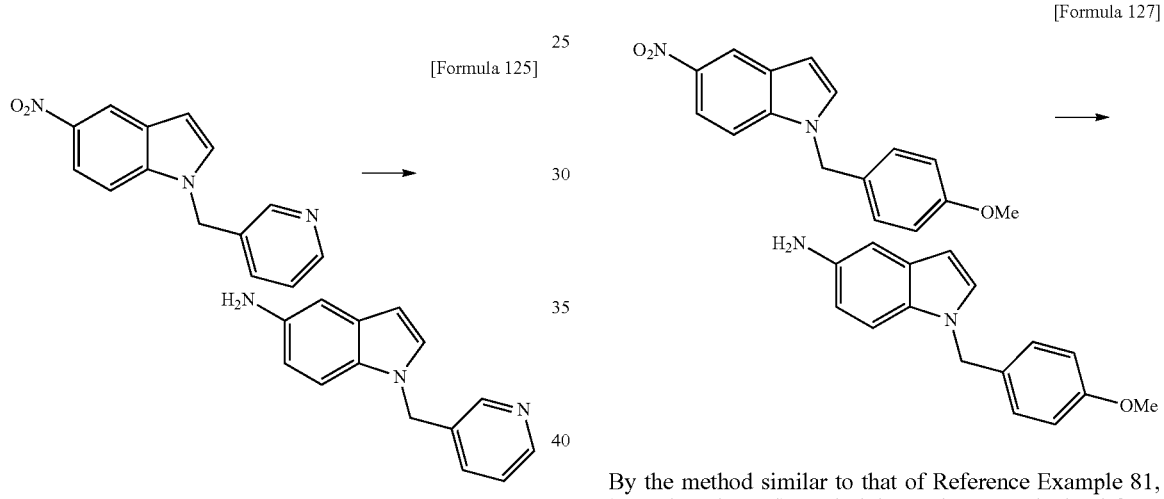

[Formula 125]

[Formula 127]

To the solution of 330 mg of 5-nitro-1-(pyridin-3-ylmethyl)-1H-indole in 16.5 mL of ethanol and 16.5 mL of ethyl acetate, 66 mg of 10% palladium on carbon was added, and the resultant was stirred at room temperature for three hours and 30 minutes under a hydrogen atmosphere. The insoluble matter was filtered off and the solvent was distilled off under reduced pressure to give 280 mg of 1-(pyridin-3-ylmethyl)-1H-indol-5-amine.

$^1$H-NMR (DMSO-$d_6$) δ: 4.49 (2H, s), 5.32 (2H, s), 6.18 (1H, d, J=4.0 Hz), 6.49 (1H, dd, J=8.6, 2.0 Hz), 6.68 (1H, d, J=2.0 Hz), 7.14 (1H, d, J=8.6 Hz), 7.27-7.34 (2H, m), 7.48-4-7.55 (1H, m), 8.41-8.47 (2H, m).

By the method similar to that of Reference Example 81, 1-(4-methoxybenzyl)-1H-indol-5-amine was obtained from 1-(4-methoxybenzyl)-5-nitro-1H-indole.

$^1$H-NMR (DMSO-$d_6$) δ: 3.69 (3H, s), 4.45 (2H, s), 5.18 (2H, s), 6.14 (1H, d, J=2.6 Hz), 6.47 (1H, dd, J=8.6, 2.0 Hz), 6.67 (1H, d, J=2.0 Hz), 6.80-6.86 (2H, m), 7.07-7.16 (3H, m), 7.24 (1H, d, J=3.3 Hz).

Reference Example 82

Reference Example 84

[Formula 126]

[Formula 128]

The suspension of 0.86 mL of benzoyl chloride and 0.99 g of aluminum chloride in 10 mL of dichloromethane was added to 20 mL of dichloromethane at 0° C., and the resultant was stirred at 0° C. for 15 minutes. The suspension of 0.75 g of 5-nitro-1H-indole in 10 mL of dichloromethane was added thereto, and the resultant was stirred at room temperature for one hour and then at 45° C. for three hours and 20 minutes. Ethyl acetate and water were added to the reaction mixture. The organic layer was separated and dried over anhydrous magnesium sulfate, and the solvent was distilled off under reduced pressure. Hexane was added to the obtained residue. The solid was collected by filtration to give 0.2 g of (5-nitro-1H-indol-3-yl)(phenyl)methanone as a solid.

$^1$H-NMR (DMSO-$d_6$) δ: 7.49-8.02 (6H, m), 8.18 (1H, dd, J=8.9, 2.3 Hz), 8.27 (1H, d, J=3.3 Hz), 9.14 (1H, d, J=2.0 Hz), 12.68 (1H, brs).

Reference Example 85

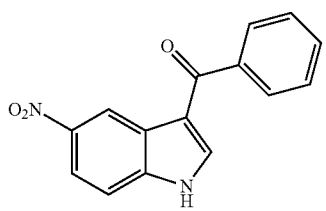

[Formula 129]

In accordance with the method of Reference Example 11 except for using N,N-dimethylformamide as a solvent, (1-benzyl-5-nitro-1H-indol-3-yl)(phenyl)methanone was obtained from (5-nitro-1H-indol-3-yl)(phenyl)methanone and benzyl bromide.

$^1$H-NMR (DMSO-$d_6$) δ: 5.66 (2H, s), 7.20-7.40 (5H, m), 7.53-7.73 (3H, m), 7.80 (1H, d, J=8.6 Hz), 7.84-7.94 (2H, m), 8.12-8.20 (1H, m), 8.58 (1H, s), 9.15 (1H, s).

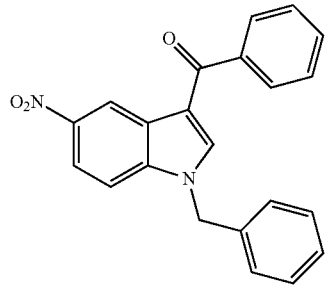

Reference Example 86

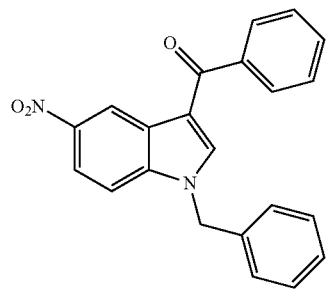

[Formula 130]

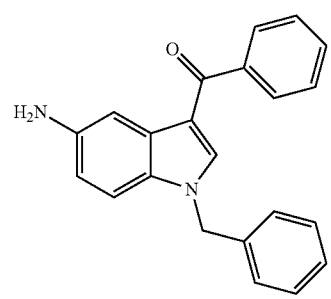

By the method similar to that of Reference Example 12, (5-amino-1-benzyl-1H-indol-3-yl)(phenyl)methanone was obtained from (1-benzyl-5-nitro-1H-indol-3-yl)(phenyl) methanone.

$^1$H-NMR (DMSO-$d_6$) δ: 4.89 (2H, s), 5.41 (2H, s), 6.54-6.6 (1H, m), 7.17 (1H, d, J=8.6 Hz), 7.21-7.36 (5H, m), 7.48-7.62 (4H, m), 7.71-7.78 (2H, m), 7.97 (1H, s).

Reference Example 87

[Formula 131]

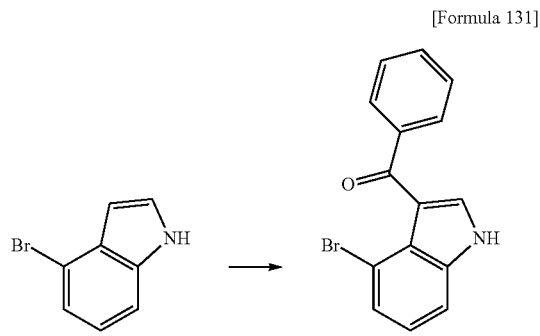 [SMILES: Brc1cccc2[nH]ccc12 ; O=C(c1ccccc1)c1c[nH]c2cccc(Br)c12]

By the method similar to that of Reference Example 84, (4-Bromo-1H-indol-3-yl)(phenyl)methanone was obtained from 4-bromo-1H-indole and benzoyl chloride.

$^1$H-NMR (DMSO-$d_6$) δ: 7.17 (1H, t, J=7.9 Hz), 7.38 (1H, d, J=6.6 Hz), 7.49-7.68 (4H, m), 7.79-7.87 (3H, m), 12.17 (1H, brs).

Reference Example 88

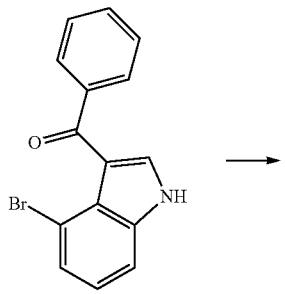

[Formula 132]

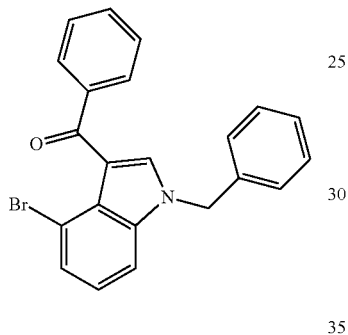

In accordance with the method of Reference Example 11 except for using N,N-dimethylformamide as a solvent, (1-benzyl-4-bromo-1H-indol-3-yl)(phenyl)methanone was obtained from (4-bromo-1H-indol-3-yl)(phenyl)methanone and benzyl bromide.

$^1$H-NMR (DMSO-$d_6$) δ: 5.54 (2H, s), 7.17 (1H, t, J=7.9 Hz), 7.22-7.44 (6H, m), 7.50-7.71 (4H, m), 7.81-7.90 (2H, m), 8.13 (1H, s).

Reference Example 89

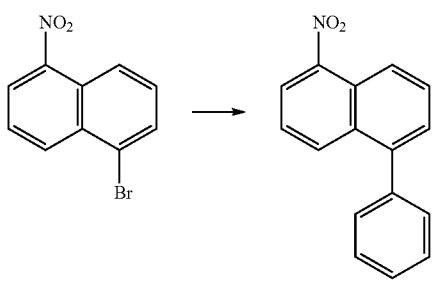

[Formula 133]

By the method similar to that of Reference Example 45, 1-nitro-5-phenylnaphthalene was obtained from 1-bromo-5-nitronaphthalene and phenylboronic acid.

MS (ESI, m/z): 250 (M+H)$^+$.

Reference Example 90

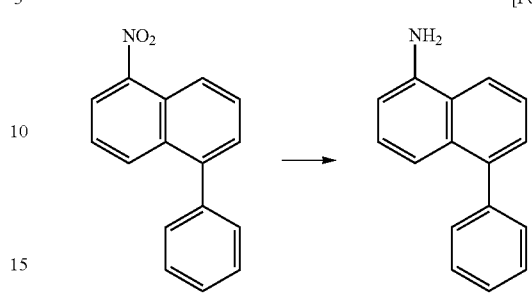

[Formula 134]

By the method similar to that of Reference Example 49, 5-phenylnaphthalen-1-amine was obtained from 1-nitro-5-phenylnaphthalene.

MS (ESI, m/z): 220 (M+H)$^+$.

Reference Example 91

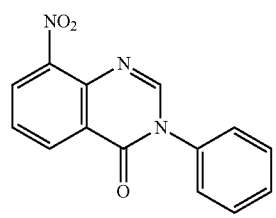

[Formula 135]

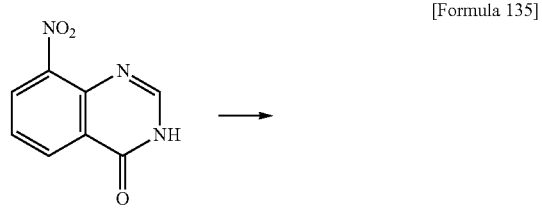

The mixture of 50 mg of 8-nitroquinazolin-4(3H)-one, 96 mg of phenylboronic acid, 143 mg of copper(II) acetate, 0.30 mL of pyridine, and 1.2 mL of dichloromethane, was stirred at 100° C. for one hour using microwave equipment. The reaction mixture was stirred again at 120° C. for one hour using microwave equipment. The reaction mixture was cooled to room temperature and then allowed to stand overnight. Water and ethyl acetate were added thereto, and the aqueous layer was extracted with ethyl acetate. The organic layer and the extract were combined and the solvent was distilled off under reduced pressure. The obtained residue was purified by silica gel column chromatography (gradient elution with hexane:ethyl acetate=90:10-60:40) to give 23 mg of 8-nitro-3-phenylquinazolin-4(3H)-one as a yellow oil.

MS (ESI, m/z): 268 (M+H)$^+$.

Reference Example 92

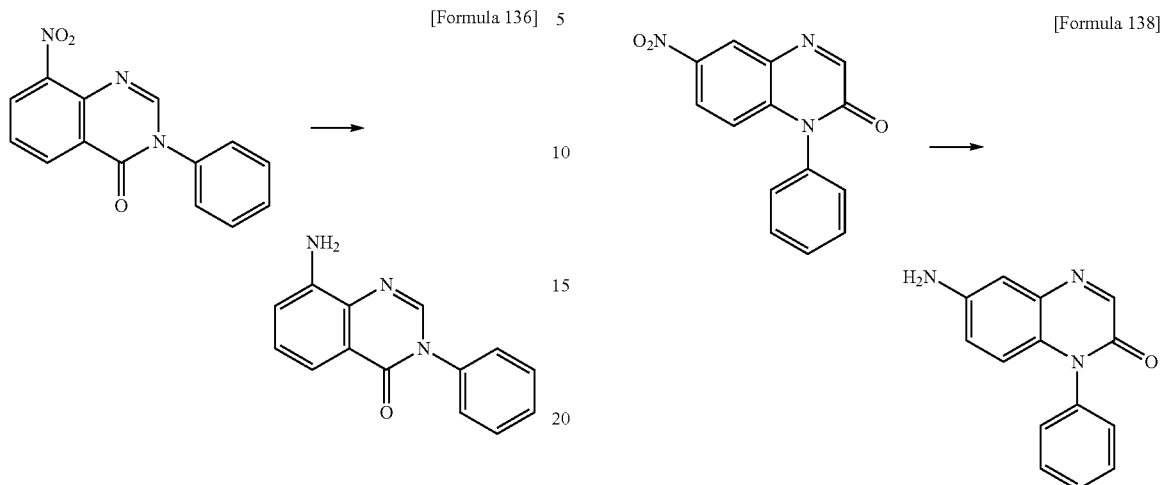

[Formula 136]

By the method similar to that of Reference Example 49, 8-amino-3-phenylquinazolin-4(3H)-one was obtained from 8-nitro-3-phenylquinazolin-4(3H)-one.

MS (ESI, m/z): 238 (M+H)$^+$.

Reference Example 93

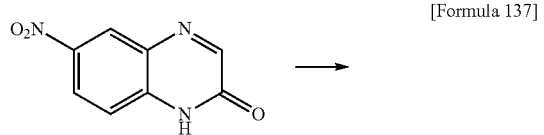

[Formula 137]

The mixture of 191 mg of 6-nitroquinoxalin-2(1H)-one, 244 mg of phenylboronic acid, 36 mg of copper(11) acetate, 0.3 g of molecular sieves 4 A, 178 µL of pyridine, and 10 mL of dichloromethane, was stirred for four days, and the insoluble matter was then filtered off, and the solvent was distilled off under reduced pressure. The obtained residue was purified by silica gel column chromatography (gradient elution with chloroform:ethyl acetate=100:0-91:9) to give 6-nitro-1-phenylquinoxalin-2(1H)-one as a yellow solid.

MS (ESI, m/z): 268 (M+H)$^+$.

Reference Example 94

[Formula 138]

The mixture of 6-nitro-1-phenylquinoxalin-2(1H)-one obtained in Reference Example 93, 32 mg of ammonium chloride, 168 mg of iron powder, 16 mL of 2-propanol, and 4 mL of water, was heated at reflux for one hour. After cooling the reaction mixture to room temperature, the insoluble matter was filtered off and the solvent was distilled off under reduced pressure. A saturated aqueous sodium bicarbonate solution and ethyl acetate were added to the residue. The organic layer was separated and dried over anhydrous magnesium sulfate, and the solvent was then distilled off under reduced pressure. Ethyl acetate and hexane were added to the obtained residue, and the solid was collected by filtration to give 162 mg of 6-amino-1-phenylquinoxalin-2(1H)-one as a yellow solid.

MS (ESI, m/z): 238 (M+H)$^+$.

Reference Example 95

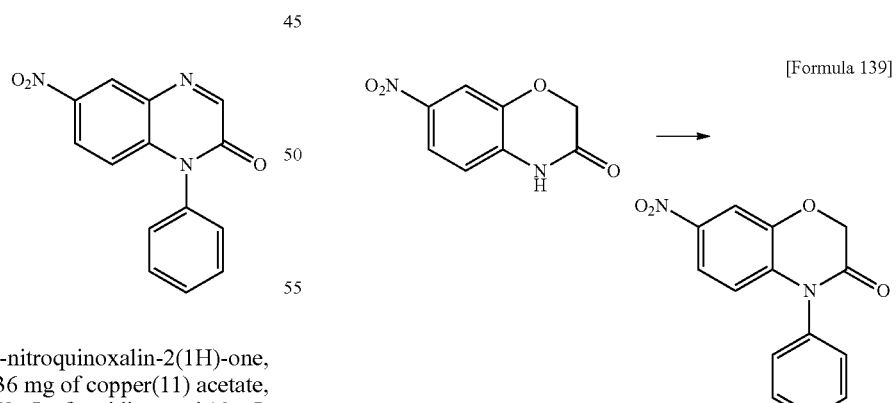

[Formula 139]

By the method similar to that of Reference Example 93, 7-nitro-4-phenyl-2H-benzo[b][1,4]oxazin-3(4H)-one was obtained from 7-nitro-2H-benzo[b][1,4]oxazin-3(4H)-one and phenylboronic acid.

MS (ESI, m/z): 271 (M+H)$^+$.

Reference Example 96

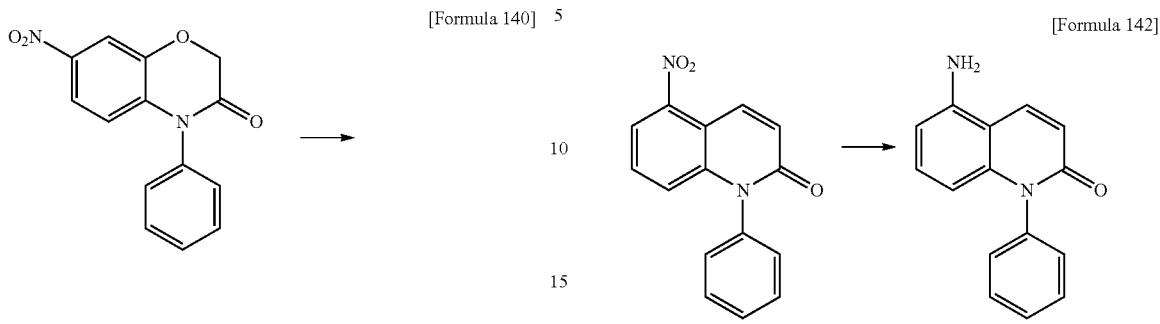
[Formula 140]

By the method similar to that of Reference Example 64, 7-amino-4-phenyl-2H-benzo[b][1,4]oxazin-3(4H)-one was obtained from 7-nitro-4-phenyl-2H-benzo[b][1,4]oxazin-3(4H)-one.

MS (ESI, m/z): 241 (M+H)$^+$.

Reference Example 97

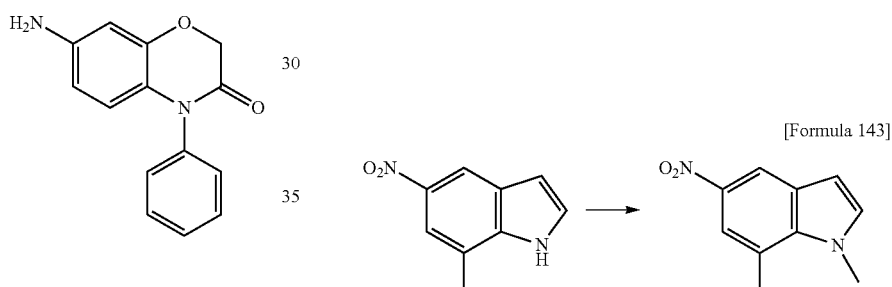
[Formula 141]

By the method similar to that of Reference Example 93, 5-nitro-1-phenylquinolin-2(1H)-one was obtained from 5-nitroquinolin-2(1H)-one and phenylboronic acid.

MS (ESI, m/z): 267 (M+H)$^+$.

Reference Example 98

[Formula 142]

By the method similar to that of Reference Example 70, 5-amino-1-phenylquinolin-2(1H)-one was obtained from 5-nitro-1-phenylquinolin-2(1H)-one.

MS (ESI, m/z): 237 (M+H)$^+$.

Reference Example 99

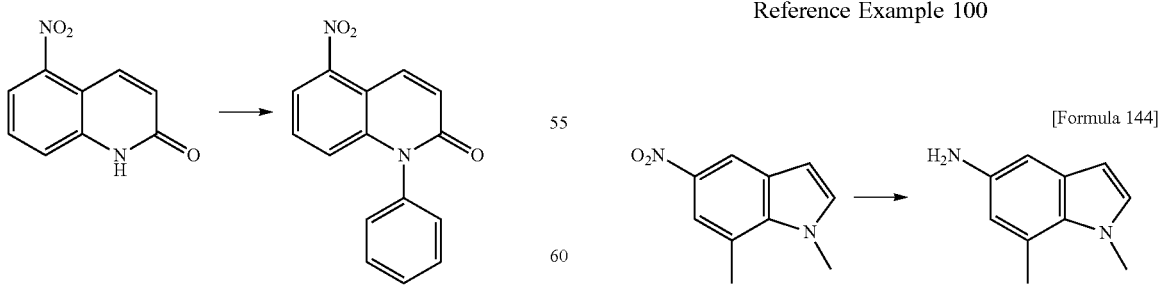
[Formula 143]

By the method similar to that of Reference Example 63, 1,7-dimethyl-5-nitro-1H-indole was obtained from 7-methyl-5-nitro-1H-indole.

MS (ESI, m/z): 191 (M+H)$^+$.

Reference Example 100

[Formula 144]

By the method similar to that of Reference Example 64, 1,7-dimethyl-1H-indol-5-amine was obtained from 1,7-dimethyl-5-nitro-1H-indole.

MS (ESI, m/z): 161 (M+H)$^+$.

Reference Example 101

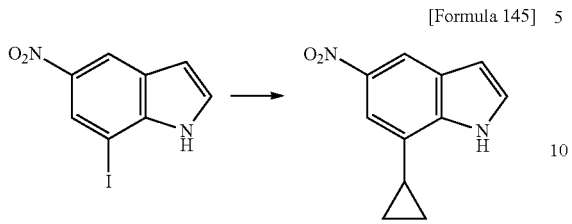

[Formula 145]

By the method similar to that of Reference Example 62, 7-cyclopropyl-5-nitro-1H-indole was obtained from 7-iodo-5-nitro-1H-indole and cyclopropylboronic acid.

MS (ESI, m/z): 201 (M−H)⁻.

Reference Example 102

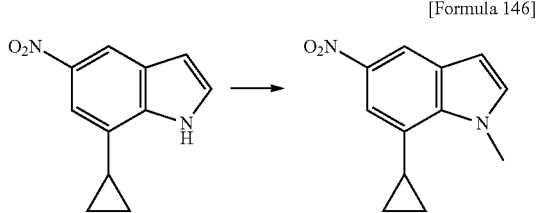 [SMILES: O=[N+]([O-])c1cc(C2CC2)c2[nH]ccc2c1 ; Cn1ccc2cc([N+](=O)[O-])cc(C3CC3)c21]

[Formula 146]

By the method similar to that of Reference Example 63, 7-cyclopropyl-1-methyl-5-nitro-1H-indole was obtained from 7-cyclopropyl-5-nitro-1H-indole.

MS (ESI, m/z): 217 (M+H)⁺.

Reference Example 103

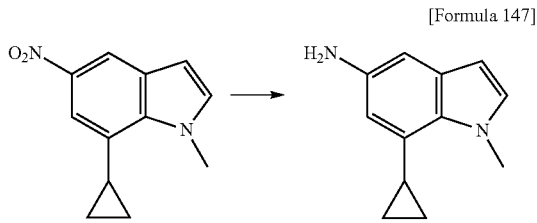 [SMILES: Cn1ccc2cc([N+](=O)[O-])cc(C3CC3)c21 ; Cn1ccc2cc(N)cc(C3CC3)c21]

[Formula 147]

By the method similar to that of Reference Example 64, 7-cyclopropyl-1-methyl-1H-indol-5-amine was obtained from 7-cyclopropyl-1-methyl-5-nitro-1H-indole.

MS (ESI, m/z): 187 (M+H)⁺.

Reference Example 104

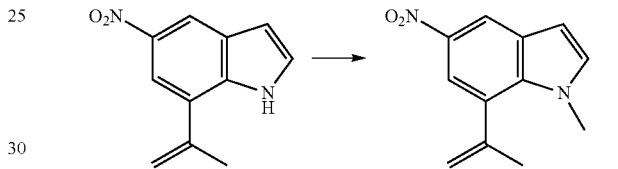

[Formula 148]

By the method similar to that of Reference Example 62, 5-nitro-7-(prop-1-en-2-yl)-1H-indole was obtained from 7-iodo-5-nitro-1H-indole and isopropenylboronic acid pinacol ester.

MS (ESI, m/z): 201 (M−H)⁻.

Reference Example 105

[Formula 149]

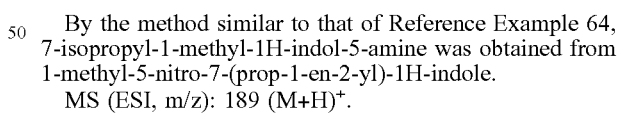

By the method similar to that of Reference Example 63, 1-methyl-5-nitro-7-(prop-1-en-2-yl)-1H-indole was obtained from 5-nitro-7-(prop-1-en-2-yl)-1H-indole.

Reference Example 106

[Formula 150]

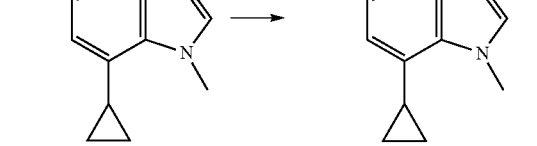

By the method similar to that of Reference Example 64, 7-isopropyl-1-methyl-1H-indol-5-amine was obtained from 1-methyl-5-nitro-7-(prop-1-en-2-yl)-1H-indole.

MS (ESI, m/z): 189 (M+H)⁺.

Reference Example 107

[Formula 151]

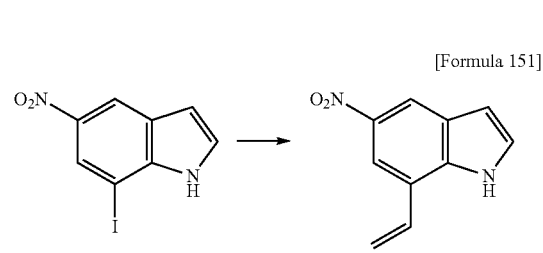

By the method similar to that of Reference Example 62, 5-nitro-7-vinyl-1H-indole was obtained from 7-iodo-5-nitro-1H-indole and vinylboronic acid pinacol ester.

MS (ESI, m/z): 187 (M−H)⁻.

Reference Example 108

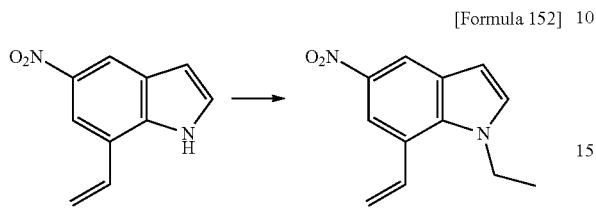

[Formula 152]

By the method similar to that of Reference Example 63, 1-ethyl-5-nitro-7-vinyl-1H-indole was obtained from 5-nitro-7-vinyl-1H-indole and ethyl iodide.

Reference Example 109

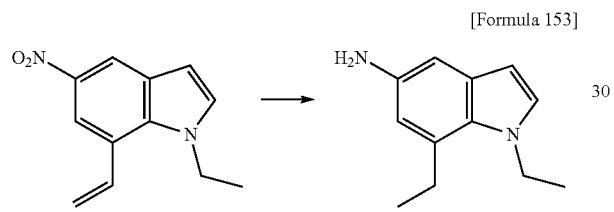

[Formula 153]

By the method similar to that of Reference Example 64, 1,7-Diethyl-1H-indol-5-amine was obtained from 1-ethyl-5-nitro-7-vinyl-1H-indole.

MS (ESI, m/z): 189 (M+H)⁺.

Reference Example 110

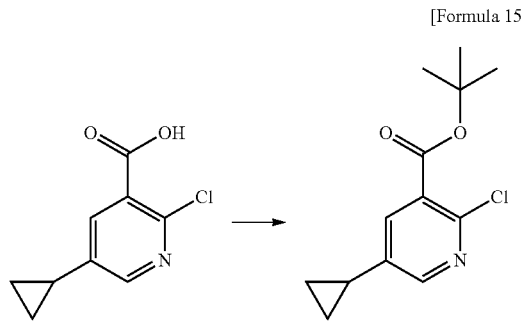

[Formula 154]

The mixture of 1.51 g of 2-chloro-5-cyclopropylnicotinic acid, 3.62 g of di-tert-butyl dicarbonate, 335 mg of 4-(dimethylamino)pyridine, 30 mL of tert-butanol, and 30 mL of dichloromethane, was heated at reflux for two hours. After cooling the reaction mixture to room temperature, the solvent was distilled off under reduced pressure. Ethyl acetate and a saturated aqueous sodium bicarbonate solution were added to the obtained residue. The organic layer was separated and dried over anhydrous magnesium sulfate, and the solvent was then distilled off under reduced pressure. The thus obtained residue was purified by silica gel column chromatography (gradient elution with hexane:ethyl acetate=100:0-20:80) to give 2.04 g of tert-butyl 2-chloro-5-cyclopropylnicotinate as a colorless oil.

MS (ESI, m/z): 254 (M+H)⁺.

Reference Example 111

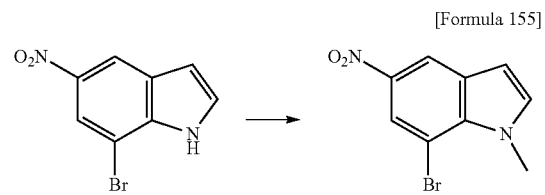

[Formula 155]

To the solution of 10.0 g of 7-bromo-5-nitro-1H-indole in 100 mL of N,N-dimethylformamide, 4.89 g of potassium tert-butoxide was added under ice-cooling, and the resultant was stirred for 10 minutes. 3.36 mL of methyl iodide was added thereto, and the resultant was stirred at room temperature for one hour. Water was added thereto under ice-cooling, followed by stirring. The solid was collected by filtration and washed with water to give 10.2 g of 7-bromo-1-methyl-5-nitro-1H-indole as a yellow solid.

MS (ESI, m/z): 257 (M+H)⁺.

Reference Example 112

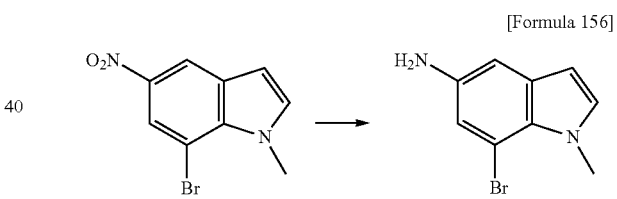

[Formula 156]

The mixture of 3.0 g of 7-bromo-1-methyl-5-nitro-1H-indole, 7.63 g of ammonium chloride, 13.1 g of iron powder, 160 ml of 2-propanol, and 40 mL of water, was heated at reflux for 45 minutes. After cooling the reaction mixture to 65° C., 3.5 g of 7-bromo-1-methyl-5-nitro-1H-indole was added thereto, and the resultant was heated at reflux for 15 minutes. After cooling the reaction mixture to 65° C., 3.5 g of 7-bromo-1-methyl-5-nitro-1H-indole was added thereto, and the resultant was heated at reflux for three hours. After cooling the reaction mixture to room temperature, the insoluble matter was filtered off. Ethyl acetate was added thereto, and the organic layer was separated and the aqueous layer was extracted with ethyl acetate. The organic layer and the extract were combined and dried over anhydrous sodium sulfate, and the solvent was then distilled off under reduced pressure. The obtained residue was purified by silica gel column chromatography (gradient elution with hexane:ethyl acetate=100:0-60:40) and recrystallization was carried out by adding ethyl acetate and hexane to the thus obtained residue to give 4.21 g of 7-bromo-1-methyl-1H-indol-5-amine as pale brown needle crystals.

MS (ESI, m/z): 225, 227 (M+H)⁺.

Reference Example 113

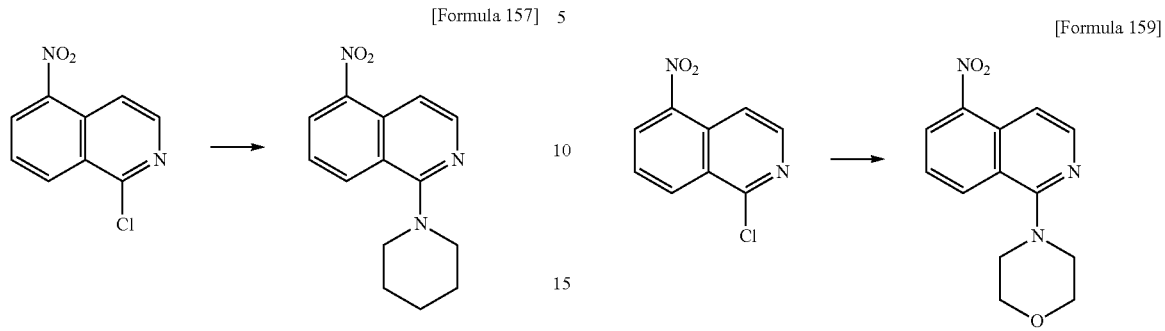

[Formula 157]

The mixture of 100 mg of 1-chloro-5-nitroisoquinoline and 150 μL of piperidine in 2.0 mL of N,N-dimethylformamide was stirred at 60° C. for 5 hours. Water and ethyl acetate were added thereto, and the organic layer was separated and washed with water twice. The solvent was distilled off from the organic layer under reduced pressure to give 111 mg of 5-nitro-1-(piperidin-1-yl)isoquinoline as an orange solid.

MS (ESI, m/z): 258 (M+H)$^+$.

Reference Example 114

[Formula 158]

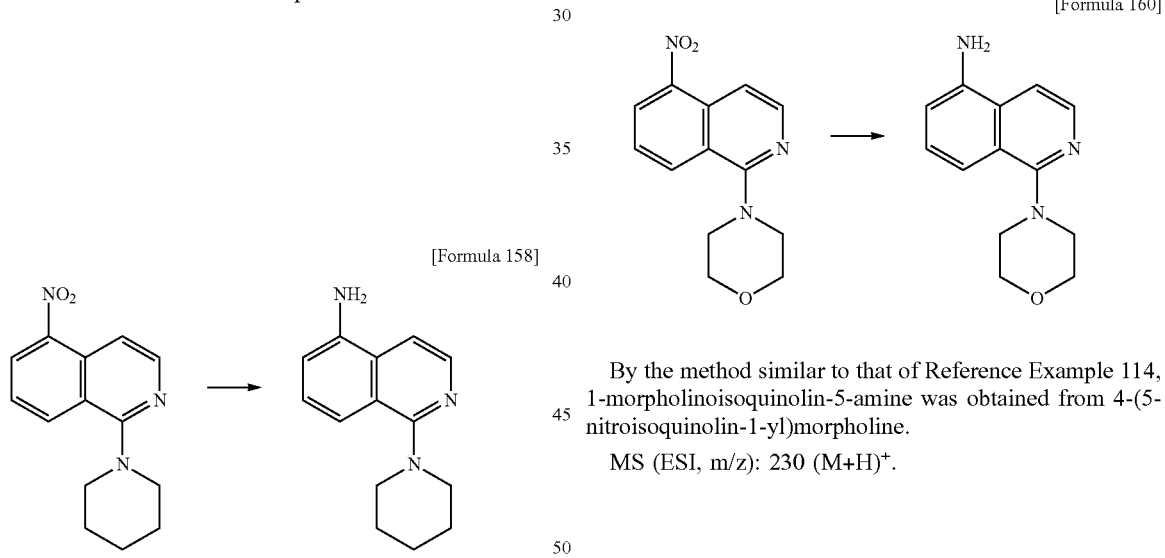

The solution of 100 mg of 5-nitro-1-(piperidin-1-yl)isoquinoline in 16 mL of methanol and 4 ml of tetrahydrofuran was subjected to hydrogenation reaction (room temperature, 1 bar, flow rate: 1 mL/min, 10% Pd/C) using the flow hydrogenation reactor. The solvent was distilled off under reduced pressure to give 105 mg of 1-(piperidin-1-yl)isoquinolin-5-amine as a yellow solid.

MS (ESI, m/z): 228 (M+H)$^+$.

Reference Example 115

[Formula 159]

By the method similar to that of Reference Example 113, 4-(5-nitroisoquinolin-1-yl)morpholine was obtained from 1-chloro-5-nitroisoquinoline and morpholine.

MS (ESI, m/z): 260 (M+H)$^+$.

Reference Example 116

[Formula 160]

By the method similar to that of Reference Example 114, 1-morpholinoisoquinolin-5-amine was obtained from 4-(5-nitroisoquinolin-1-yl)morpholine.

MS (ESI, m/z): 230 (M+H)$^+$.

Reference Example 117

[Formula 161]

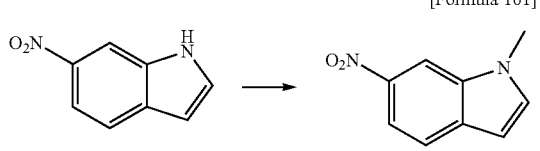

By the method similar to that of Reference Example 63, 1-methyl-6-nitro-1H-indole was obtained from 6-nitro-1H-indole.

Reference Example 118

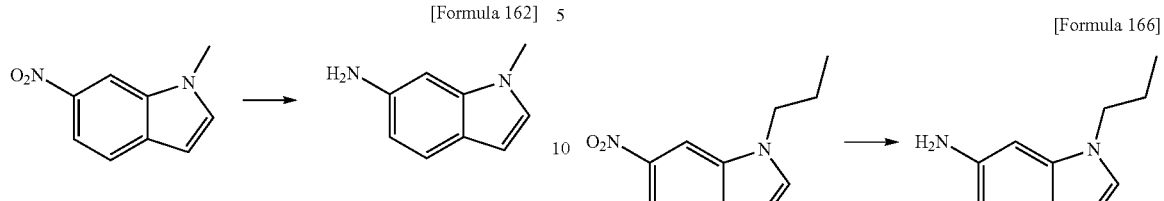

By the method similar to that of Reference Example 64, 1-methyl-1H-indol-6-amine was obtained from 1-methyl-6-nitro-1H-indole.

Reference Example 119

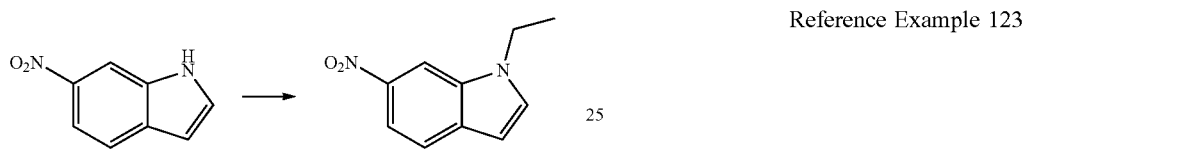

By the method similar to that of Reference Example 63, 1-ethyl-6-nitro-1H-indole was obtained from 6-nitro-1H-indole.
MS (ESI, m/z): 191 (M+H)$^+$.

Reference Example 120

[Formula 164]

By the method similar to that of Reference Example 64, 1-ethyl-1H-indol-6-amine was obtained from 1-ethyl-6-nitro-1H-indole.
MS (ESI, m/z): 161 (M+H)$^+$.

Reference Example 121

[Formula 165]

By the method similar to that of Reference Example 63, 6-nitro-1-propyl-1H-indole was obtained from 6-nitro-1H-indole.
MS (ESI, m/z): 205 (M+H)$^+$.

Reference Example 122

[Formula 166]

By the method similar to that of Reference Example 64, 1-propyl-1H-indol-6-amine was obtained from 6-nitro-1-propyl-1H-indole.
MS (ESI, m/z): 175 (M±H)$^+$.

Reference Example 123

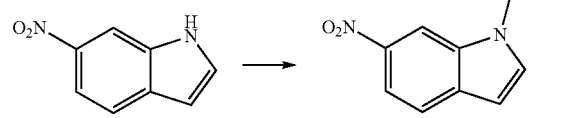

[Formula 167]

By the method similar to that of Reference Example 63, 1-isopropyl-6-nitro-1H-indole was obtained from 6-nitro-1H-indole.
MS (ESI, m/z): 205 (M+H)$^+$.

Reference Example 124

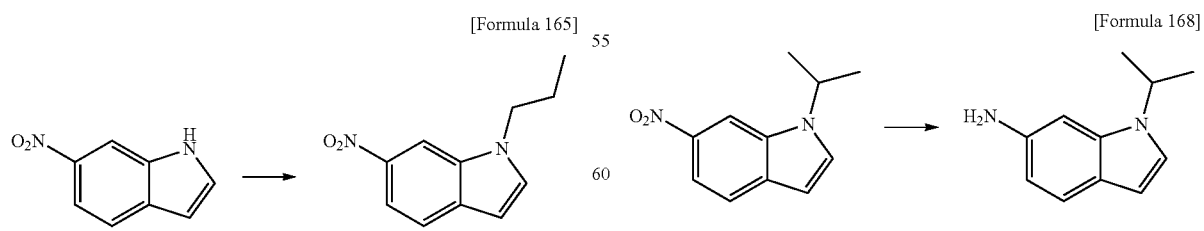

[Formula 168]

By the method similar to that of Reference Example 64, 1-isopropyl-1H-indol-6-amine was obtained from 1-isopropyl-6-nitro-1H-indole.
MS (ESI, m/z): 175 (M+H)$^+$.

Reference Example 125

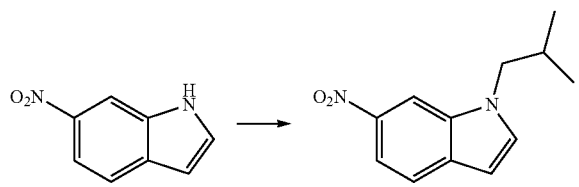

[Formula 169]

By the method similar to that of Reference Example 63, 1-isobutyl-6-nitro-1H-indole was obtained from 6-nitro-1H-indole.

MS (ESI, m/z): 219 (M+H)$^+$.

Reference Example 126

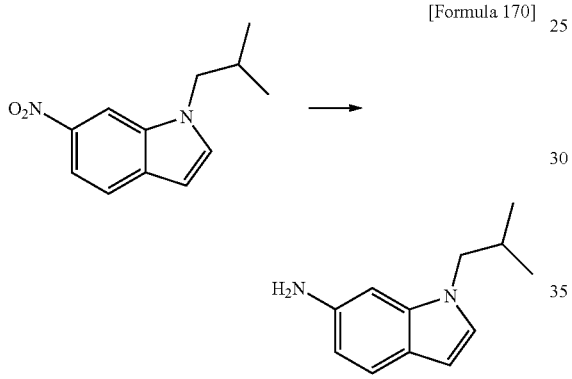

[Formula 170]

By the method similar to that of Reference Example 64, 1-isobutyl-1H-indol-6-amine was obtained from 1-isobutyl-6-nitro-1H-indole.

MS (ESI, m/z): 189 (M+H)$^+$.

Reference Example 128

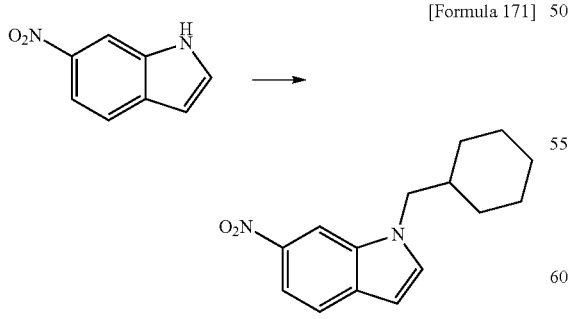

[Formula 171]

By the method similar to that of Reference Example 63, 1-(cyclohexylmethyl)-6-nitro-1H-indole was obtained from 6-nitro-1H-indole.

MS (ESI, m/z): 259 (M+H)$^+$.

Reference Example 128

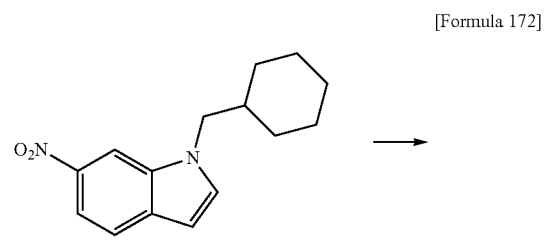

[Formula 172]

By the method similar to that of Reference Example 64, 1-(cyclohexylmethyl)-1H-indol-6-amine was obtained from 1-(cyclohexylmethyl)-6-nitro-1H-indole.

MS (ESI, m/z): 229 (M+H)$^+$.

Reference Example 129

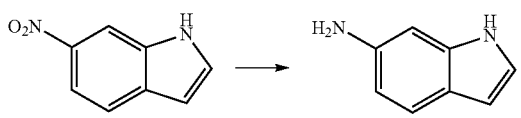

[Formula 173]

By the method similar to that of Reference Example 64, 1H-indol-6-amine was obtained from 6-nitro-1H-indole.

Reference Example 130

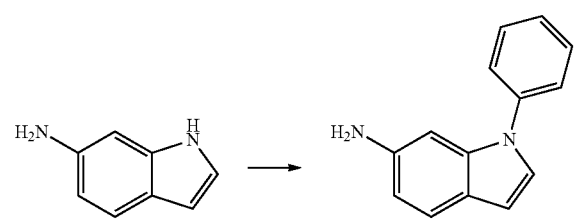

[Formula 174]

By the method similar to that of Example 230, 1-phenyl-1H-indol-6-amine was obtained from 1H-indol-6-amine.

MS (ESI, m/z): 209 (M+H)$^+$.

Reference Example 131

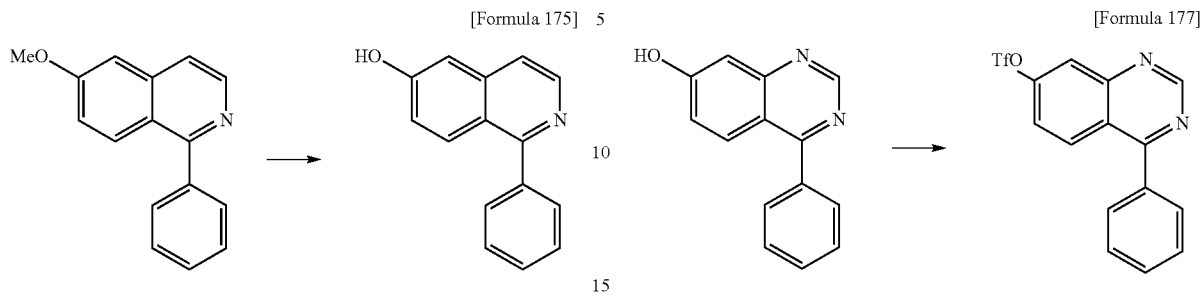

[Formula 175]

To 321 mg of 6-methoxy-1-phenylisoquinoline, 4 mL of 48% hydrobromic acid was added, and the resultant was heated at reflux for seven hours. After cooling the reaction mixture to room temperature, ethyl acetate and a saturated aqueous sodium bicarbonate solution were added to the reaction mixture and the solid was filtered off. The organic layer of the filtrate was separated and dried over anhydrous magnesium sulfate, and the solvent was then distilled off under reduced pressure. Ethyl acetate, hexane and the solid previously obtained were added to the obtained residue, and the solid was collected by filtration to give 329 mg of 1-phenylisoquinolin-6-ol as a white solid.

MS (ESI, m/z): 222 (M+H)$^+$.

Reference Example 132

[Formula 176]

To the mixed solution of 329 mg of 1-phenylisoquinolin-6-ol in 5 mL of dichloromethane and 0.5 mL of triethylamine, 276 pt of trifluoromethanesulfonic anhydride was added under ice-cooling, and the resultant was stirred for one hour. The reaction mixture was purified by silica gel column chromatography (gradient elution with hexane:ethyl acetate=80:20-40:60) to give 382 mg of 1-phenylisoquinolin-6-yl trifluoromethanesulfonate as a brown oil.

MS (ESI, m/z): 354 (M+H)$^+$.

Reference Example 133

[Formula 177]

By the method similar to that of Reference Example 132, 4-phenylquinazolin-7-yl trifluoromethanesulfonate was obtained from 4-phenylquinazolin-7-ol.

MS (ESI, m/z): 355 (M+H)$^+$.

Reference Example 134

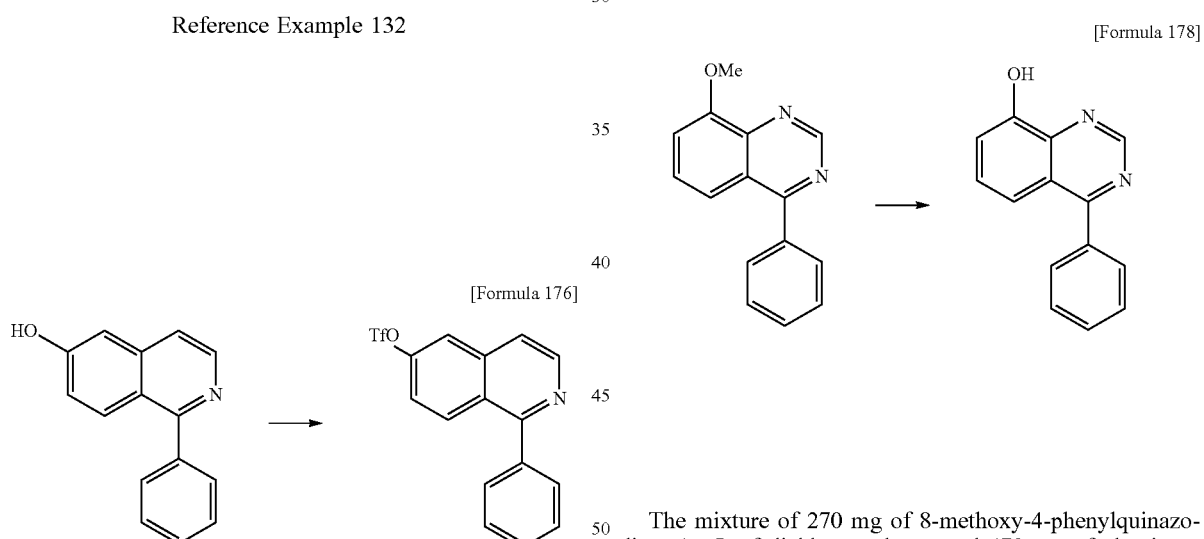

[Formula 178]

The mixture of 270 mg of 8-methoxy-4-phenylquinazoline, 4 mL of dichloromethane, and 472 mg of aluminum chloride, was stirred at 100° C. for 20 minutes using microwave equipment. After the reaction mixture was cooled to room temperature, ice, a saturated aqueous sodium bicarbonate solution and ethyl acetate were added thereto. After the solid was removed by filtration through Celite, the organic layer was separated and the aqueous layer was extracted with ethyl acetate. The organic layer and the extract were combined and dried over anhydrous magnesium sulfate, and the solvent was distilled off under reduced pressure. The obtained residue was purified by silica gel column chromatography (gradient elution with hexane:ethyl acetate=80:20-50:50), and ethyl acetate and hexane were added to the thus obtained residue, and the solid was collected by filtration to give 92 mg of 4-phenylquinazolin-8-ol as a white solid.

MS (ESI, m/z): 221 (M−H)$^−$.

Reference Example 135

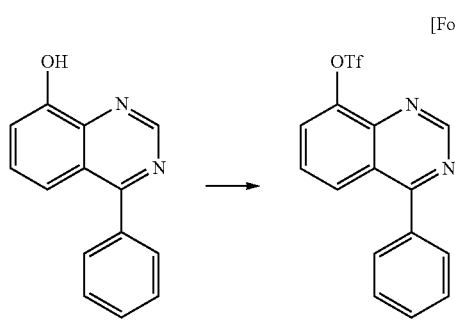

[Formula 179]

By the method similar to that of Reference Example 132, 4-phenylquinazolin-8-yl trifluoromethanesulfonate was obtained from 4-phenylquinazolin-8-ol.

MS (ESI, m/z): 355 (M+H)$^+$.

Reference Example 136

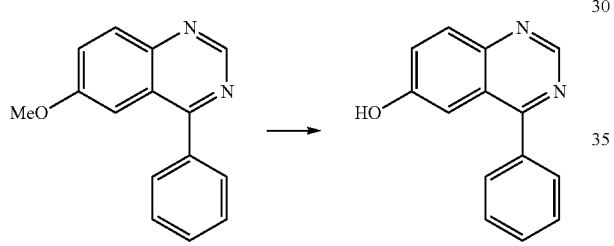

[Formula 180]

By the method similar to that of Reference Example 134, 4-phenylquinazolin-6-ol was obtained from 6-methoxy-4-phenylquinazoline.

MS (ESI, m/z): 223 (M+H)$^+$.

Reference Example 137

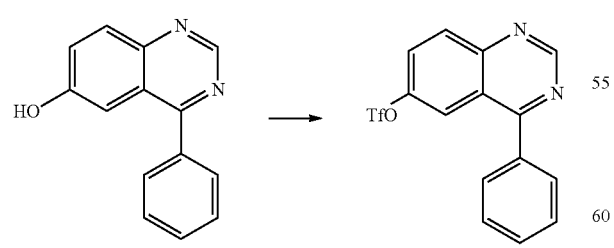

[Formula 181]

By the method similar to that of Reference Example 132, 4-phenylquinazolin-6-yl trifluoromethanesulfonate was obtained from 4-phenylquinazolin-6-ol.

MS (ESI, m/z): 355 (M+H)$^+$.

Reference Example 138

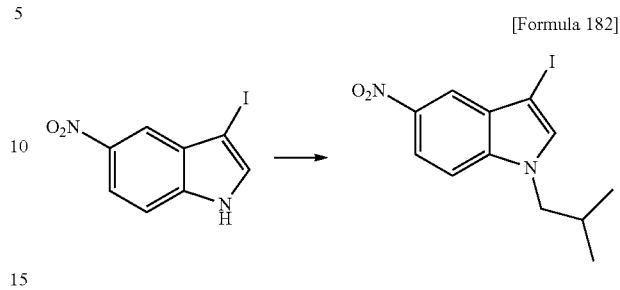

[Formula 182]

By the method similar to that of Reference Example 63, 3-iodo-1-isobutyl-5-nitro-1H-indole was obtained from 3-iodo-5-nitro-1H-indole.

MS (ESI, m/z): 344 (M+H)$^+$.

Reference Example 139

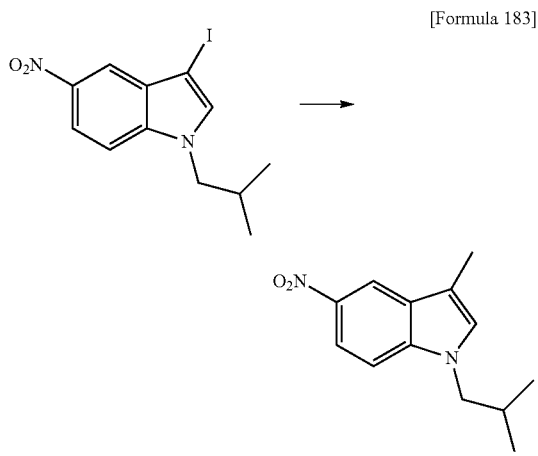

[Formula 183]

By the method similar to that of Reference Example 62, 1-isobutyl-3-methyl-5-nitro-1H-indole was obtained from 3-iodo-1-isobutyl-5-nitro-1H-indole.

MS (ESI, m/z): 233 (M+H)$^+$.

Reference Example 140

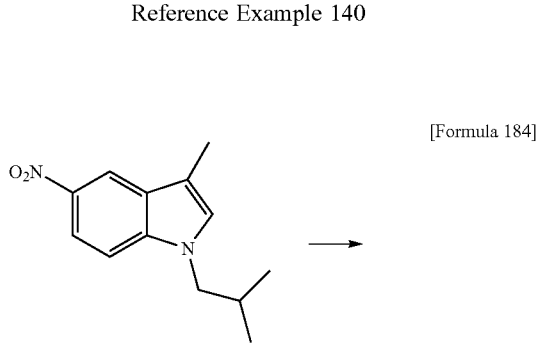

[Formula 184]

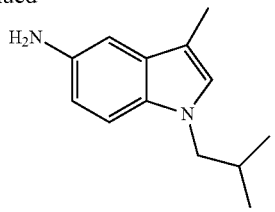

By the method similar to that of Reference Example 64, 1-isobutyl-3-methyl-1H-indol-5-amine was obtained from 1-isobutyl-3-methyl-5-nitro-1H-indole.

MS (ESI, m/z): 203 (M+H)$^+$.

Reference Example 141

[Formula 185]

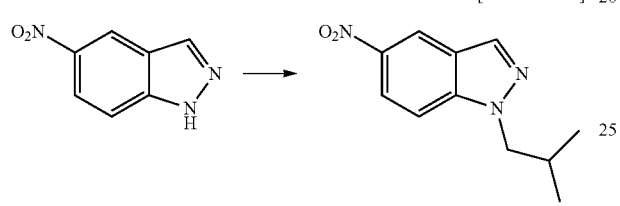

To the solution of 700 mg of 5-nitro-1H-indazole in 10 mL of N,N-dimethylacetamide, 578 mg of potassium tert-butoxide was added under ice-cooling, and the resultant was stirred for five minutes. To the reaction mixture, 0.93 mL of 1-bromo-2-methylpropane was added under ice-cooling, and the resultant was stirred for three hours and 20 minutes and then stirred at 50 to 60° C. for three hours and 50 minutes. The reaction mixture was allowed to stand overnight, and 240 mg of potassium tert-butoxide and 310 μL of 1-bromo-2-methylpropane were then added thereto, and the resultant was stirred at 50° C. for one hour and 40 minutes. After ethyl acetate and water were added to the reaction mixture, the organic layer was separated, sequentially washed with water and a saturated aqueous sodium chloride solution and dried over anhydrous sodium sulfate, and the solvent was distilled off under reduced pressure. The obtained residue was purified by silica gel column chromatography (gradient elution with hexane:ethyl acetate=100:0-80:20) to give 495 mg of 1-isobutyl-5-nitro-1H-indazole as an orange solid.

$^1$H-NMR (DMSO-d$_6$) δ: 0.86 (6H, d, J=6.6 Hz), 2.24 (1H, sep, J=6.6 Hz), 4.32 (2H, d, J=7.3 Hz), 7.93 (1H, d, J=9.9 Hz), 8.22 (1H, dd, J=9.2, 2.6 Hz), 8.42 (1H, s), 8.84 (1H, d, J=2.0 Hz).

MS (ESI, m/z): 220 (M+H)$^+$.

Reference Example 142

[Formula 186]

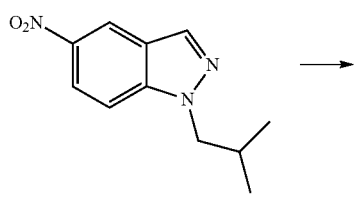

The mixture of 485 mg of 1-isobutyl-5-nitro-1H-indazole, 83 mg of ammonium chloride, 432 mg of iron powder, 35 mL of ethanol, and 10 mL of water, was heated at reflux for four hours and 20 minutes. After cooling the reaction mixture to room temperature, the insoluble matter was filtered off. The filter cake was washed with methanol, the washings and the filtrate were combined and the solvent was distilled off under reduced pressure. Water was added to the obtained residue, and the solid was collected by filtration to give 332 mg of 1-isobutyl-1H-indazol-5-amine as a pale red solid.

MS (ESI, m/z): 190 (M+H)$^+$.

Reference Example 143

[Formula 187]

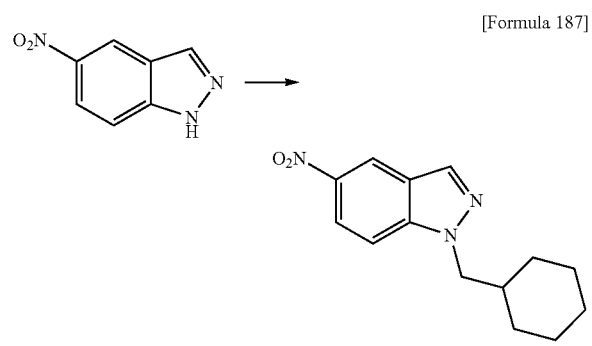

By the method similar to that of Reference Example 141, 1-(cyclohexylmethyl)-5-nitro-1H-indazole was obtained from 5-nitro-1H-indazole.

$^1$H-NMR (DMSO-d$_6$) δ: 0.94-1.22 (5H, m), 1.42-1.51 (2H, m), 1.55-1.70 (3H, m), 1.83-1.99 (1H, m), 4.34 (2H, d, J=7.3 Hz), 7.92 (1H, d, J=9.9 Hz), 8.21 (1H, dd, J=9.2, 2.0 Hz), 8.41 (1H, s), 8.83 (1H, d, J=2.0 Hz).

MS (ESI, m/z): 260 (M+H)$^+$.

Reference Example 144

[Formula 188]

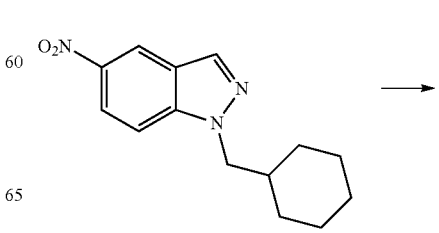

-continued

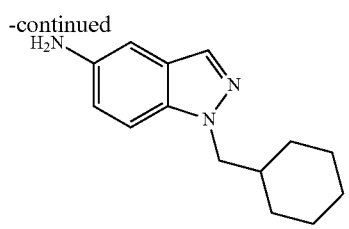

By the method similar to that of Reference Example 142, 1-(cyclohexylmethyl)-1H-indazol-5-amine was obtained from 1-(cyclohexylmethyl)-5-nitro-1H-indazole.
MS (ESI, m/z): 230 (M+H)$^+$.

Reference Example 145

[Formula 189]

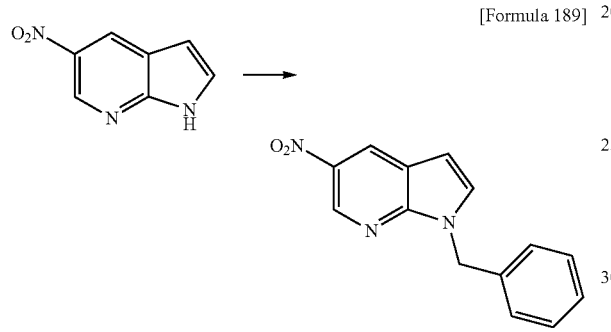

By the method similar to that of Reference Example 141, 1-benzyl-5-nitro-1H-pyrrolo(2,3-b)pyridine was obtained from 5-nitro-1H-pyrrolo(2,3-b)pyridine.
MS (ESI, m/z): 254 (M+H)$^+$.

Reference Example 146

[Formula 190]

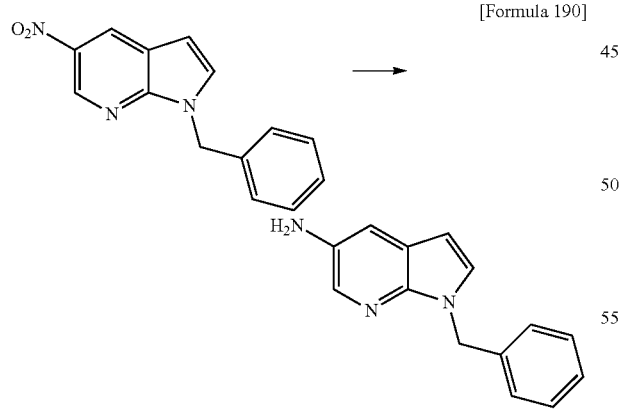

By the method similar to that of Reference Example 142, 1-benzyl-1H-pyrrolo(2,3-b)pyridin-5-amine was obtained from 1-benzyl-5-nitro-1H-pyrrolo(2,3-b)pyridine.
$^1$H-NMR (DMSO-d$_6$) δ: 4.72 (2H, s), 5.35 (2H, s), 6.21 (1H, d, J=3.3 Hz), 7.10 (1H, d, J=2.6 Hz), 7.15-7.32 (5H, m), 7.39 (1H, d, J=3.3 Hz), 7.74 (1H, d, J=2.6 Hz).
MS (ESI, m/z): 224 (M+H)$^+$.

Reference Example 147

[Formula 191]

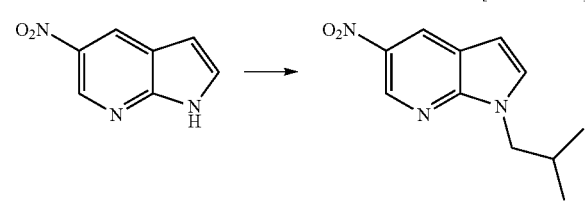

By the method similar to that of Reference Example 141, 1-isobutyl-5-nitro-1H-pyrrolo(2,3-b)pyridine was obtained from 5-nitro-1H-pyrrolo(2,3-b)pyridine.
MS (ESI, m/z): 220 (M+H)$^+$.

Reference Example 148

[Formula 192]

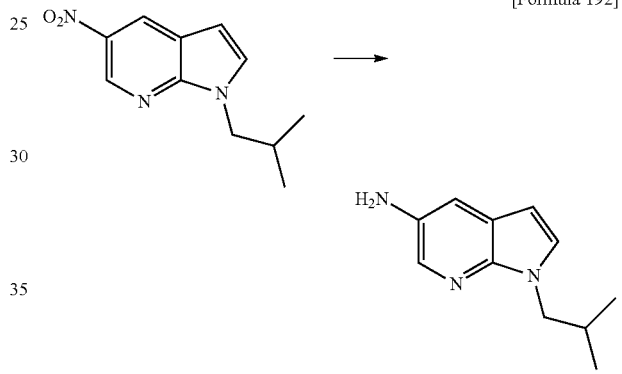

By the method similar to that of Reference Example 142, 1-isobutyl-1H-pyrrolo(2,3-b)pyridin-5-amine was obtained from 1-isobutyl-5-nitro-1H-pyrrolo(2,3-b)pyridine.
MS (ESI, m/z): 190 (M+H)$^+$.

Reference Example 149

[Formula 193]

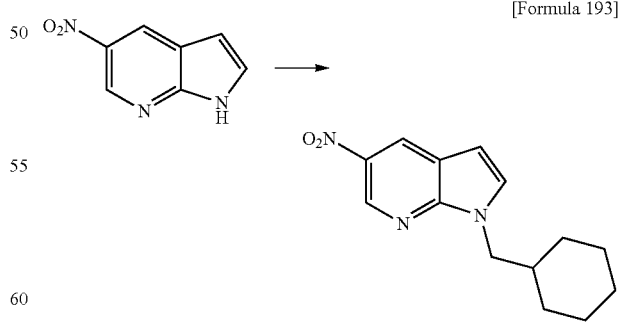

By the method similar to that of Reference Example 141, 1-(cyclohexylmethyl)-5-nitro-1H-pyrrolo(2,3-b)pyridine was obtained from 5-nitro-1H-pyrrolo(2,3-b)pyridine and (bromomethyl)cyclohexane.
MS (ESI, m/z): 260 (M+H)$^+$.

Reference Example 150

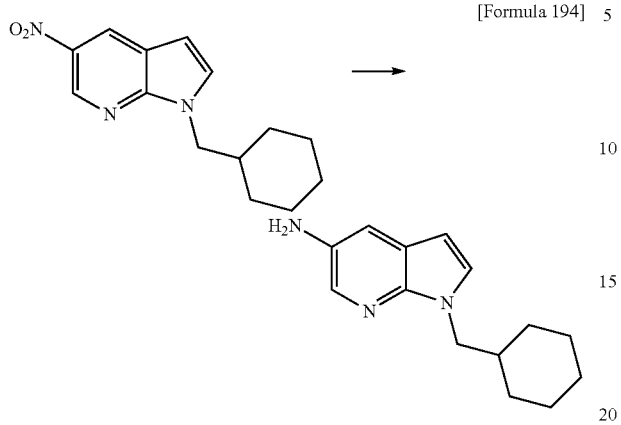

[Formula 194]

By the method similar to that of Reference Example 142, 1-(cyclohexylmethyl)-1H-pyrrolo(2,3-b)pyridin-5-amine was obtained from 1-(cyclohexylmethyl)-5-nitro-1H-pyrrolo(2,3-b)pyridine.

MS (ESI, m/z): 230 (M+H)$^+$.

Reference Example 151

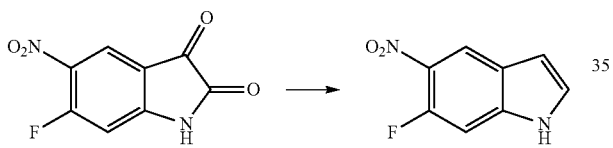

[Formula 195]

To the solution of 200 mg of 6-fluoro-5-nitro-1H-indole-2,3-dione in 4 mL of tetrahydrofuran, 2.2 mL of a 1.1 mol/L borane-tetrahydrofuran solution was added dropwise under ice-cooling and a nitrogen atmosphere, and the resultant was stirred at room temperature for one hour and 30 minutes and then stirred at 50° C. for 15 minutes. After cooling the reaction mixture to room temperature, water and 1 mL of 1 mol/L hydrochloric acid were added thereto dropwise, and the solvent was distilled off under reduced pressure. After adding ethyl acetate and water, the organic layer was separated, washed with a saturated aqueous sodium chloride solution and dried over anhydrous sodium sulfate, and the solvent was distilled off under reduced pressure to give 172 mg of 6-fluoro-5-nitro-1H-indole as a yellow brown solid.

$^1$H-NMR (DMSO-d$_6$) δ: 6.71 (1H, s), 7.47 (1H, d, J=11.9 Hz), 7.60 (1H, s), 8.48 (1H, d, J=7.3 Hz), 11.82 (1H, s).

MS (ESI, m/z): 179 (M−H)$^−$.

Reference Example 152

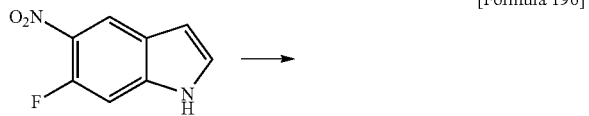

[Formula 196]

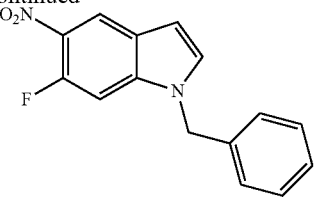

By the method similar to that of Reference Example 141, 1-benzyl-6-fluoro-5-nitro-1H-indole was obtained from 6-fluoro-5-nitro-1H-indole.

$^1$H-NMR (DMSO-d$_6$) δ: 5.49 (2H, s), 6.78 (1H, d, J=3.3 Hz), 7.23-7.38 (5H, m), 7.73-7.80 (2H, m), 8.49 (1H, d, J=7.9 Hz)

MS (ESI, m/z): 271 (M+H)$^+$.

Reference Example 153

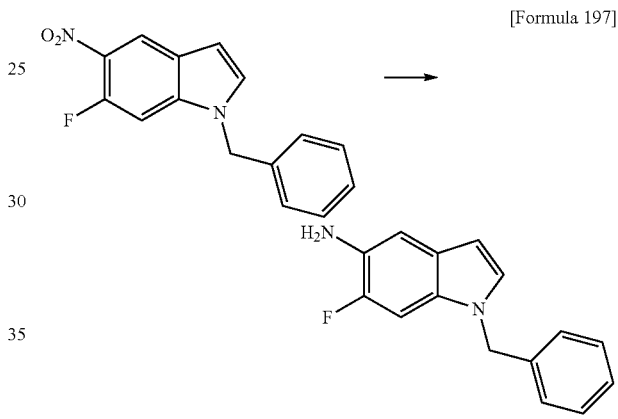

[Formula 197]

By the method similar to that of Reference Example 142, 1-benzyl-6-fluoro-1H-indol-5-amine was obtained from 1-benzyl-6-fluoro-5-nitro-1H-indole.

MS (ESI, m/z): 241 (M+H)$^+$.

Reference Example 154

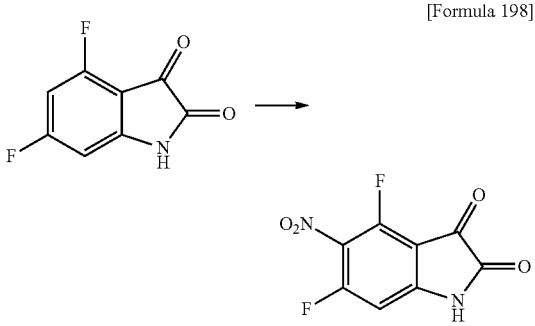

[Formula 198]

To the solution of 250 mg of 4,6-difluoro-1H-indole-2,3-dione in 3 mL of sulfuric acid, 109 μL of 60% nitric acid was added dropwise at −20° C., and the resultant was stirred for 15 minutes. Water was added dropwise to the reaction mixture, followed by addition of ethyl acetate. The organic layer was separated, sequentially washed with a saturated aqueous sodium bicarbonate solution and a saturated aqueous sodium chloride solution and dried over anhydrous sodium sulfate, and the solvent was distilled off under reduced pressure. The obtained residue was purified by silica gel column chromatography (gradient elution with hexane: ethyl acetate) to give 180 mg of 4,6-difluoro-5-nitro-1H-indole-2,3-dione as a yellow solid.

$^1$H-NMR (DMSO-$d_6$) δ: 6.95 (1H, d, J=10.6 Hz), 11.95 (1H, s)

MS (ESI, m/z): 227 (M−H)$^-$.

Reference Example 155

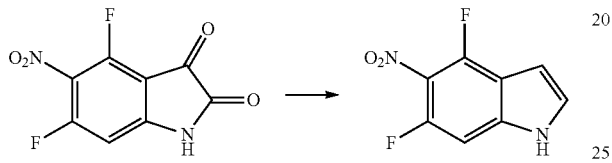

[Formula 199]

By the method similar to that of Reference Example 151, 4,6-difluoro-5-nitro-1H-indole was obtained from 4,6-difluoro-5-nitro-1H-indole-2,3-dione.

$^1$H-NMR (DMSO-$d_6$) δ: 6.74-6.78 (1H, m), 7.42 (1H, d, J=11.1 Hz), 7.61-7.64 (1H, m), 12.08 (1H, brs)

MS (ESI, m/z): 197 (M−H)$^-$.

Reference Example 156

[Formula 200]

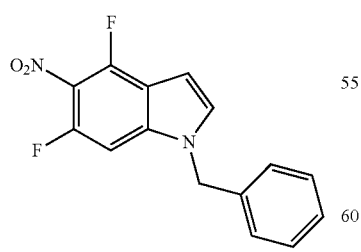

By the method similar to that of Reference Example 141, 1-benzyl-4,6-difluoro-5-nitro-1H-indole was obtained from 4,6-difluoro-5-nitro-1H-indole and benzyl bromide.

MS (ESI, m/z): 291 (M+H)$^+$.

Reference Example 157

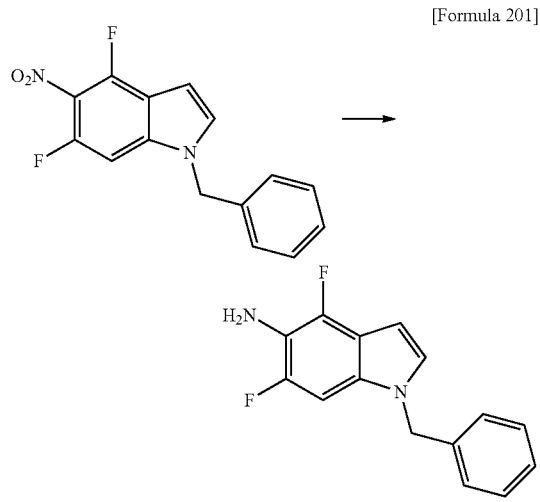

[Formula 201]

By the method similar to that of Reference Example 142, 1-benzyl-4,6-difluoro-1H-indol-5-amine was obtained from 1-benzyl-4,6-difluoro-5-nitro-1H-indole.

MS (ESI, m/z): 259 (M+H)$^+$.

Reference Example 158

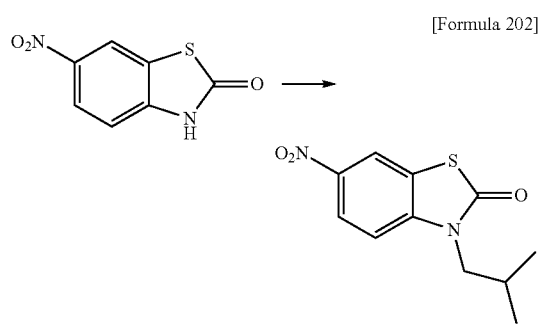

[Formula 202]

By the method similar to that of Reference Example 141, 3-isobutyl-6-nitro-1,3-benzothiazol-2(3H)-one was obtained from 6-nitro-1,3-benzothiazol-2(3H)-one and 1-bromo-2-methylpropane.

MS (ESI, m/z): 253 (M+H)$^+$.

Reference Example 159

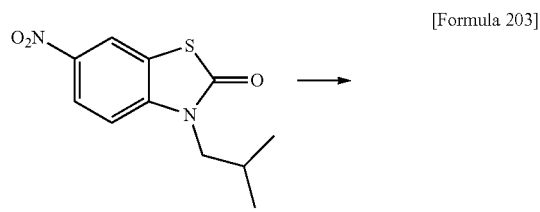

[Formula 203]

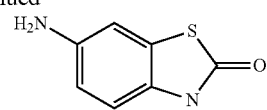

By the method similar to that of Reference Example 142, 6-amino-3-isobutyl-1,3-benzothiazol-2(3H)-one was obtained from 3-isobutyl-6-nitro-1,3-benzothiazol-2(3H)-one.

Reference Example 160

[Formula 204]

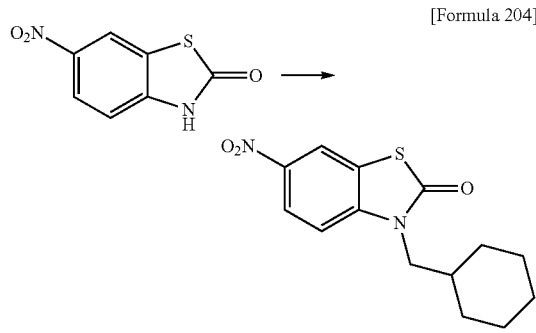

By the method similar to that of Reference Example 141, 3-(cyclohexylmethyl)-6-nitro-1,3-benzothiazol-2(3H)-one was obtained from 6-nitro-1,3-benzothiazol-2(3H)-one.

MS (ESI, m/z): 293 (M+H)$^+$.

Reference Example 161

[Formula 205]

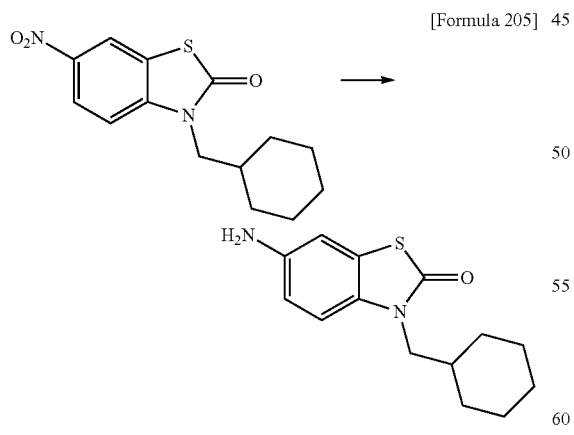

By the method similar to that of Reference Example 142, 6-amino-3-(cyclohexylmethyl)-1,3-benzothiazol-2(3H)-one was obtained from 3-(cyclohexylmethyl)-6-nitro-1,3-benzothiazol-2(3H)-one.

MS (ESI, m/z): 263 (M+H)$^+$.

Reference Example 162

[Formula 206]

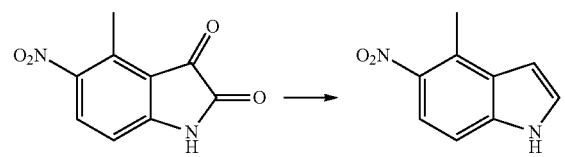

By the method similar to that of Reference Example 154, 4-methyl-5-nitro-1H-indole-2,3-dione was obtained from 4-methyl-1H-indole-2,3-dione.

$^1$H-NMR (DMSO-d$_6$) δ: 2.72 (3H, s), 6.91 (1H, d, J=8.6 Hz), 8.25 (1H, d, J=8.6 Hz), 11.55 (1H, brs).

Reference Example 163

[Formula 207]

By the method similar to that of Reference Example 151, 4-methyl-5-nitro-1H-indole was obtained from 4-methyl-5-nitro-1H-indole-2,3-dione.

$^1$H-NMR (DMSO-d$_6$) δ: 2.76 (3H, s), 6.78-6.82 (1H, m), 7.39 (1H, d, J=9.2 Hz), 7.54-7.59 (1H, m), 7.81 (1H, d, J=8.6 Hz), 11.73 (1H, brs).

MS (ESI, m/z): 175 (M−H)$^-$.

Reference Example 164

[Formula 208]

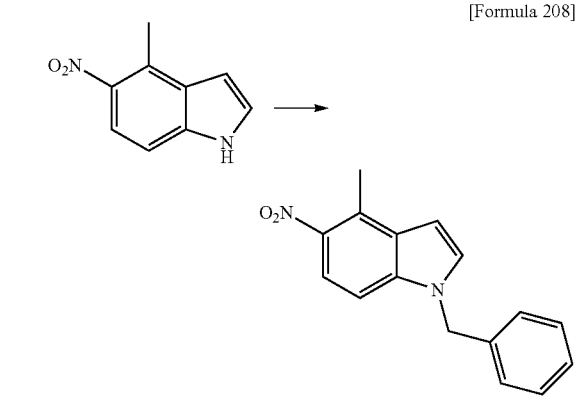

By the method similar to that of Reference Example 141, 1-benzyl-4-methyl-5-nitro-1H-indole was obtained from 4-methyl-5-nitro-1H-indole.

MS (ESI, m/z): 267 (M+H)$^+$.

Reference Example 165

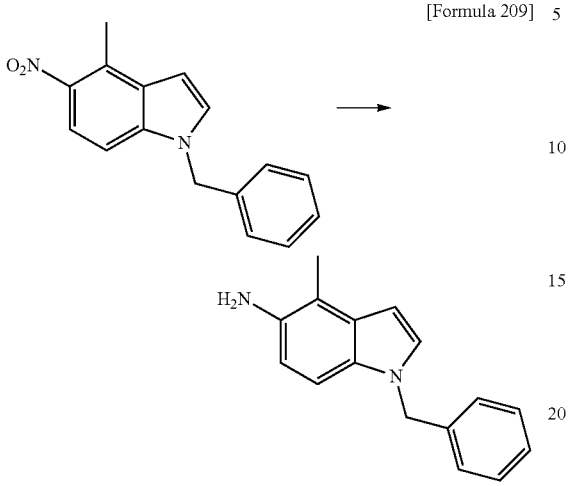

[Formula 209]

By the method similar to that of Reference Example 142, 1-benzyl-4-methyl-1H-indol-5-amine was obtained from 1-benzyl-4-methyl-5-nitro-1H-indole.
MS (ESI, m/z): 237 (M+H)$^+$.

Reference Example 166

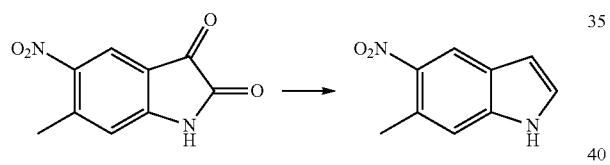

[Formula 210]

By the method similar to that of Reference Example 151, 6-methyl-5-nitro-1H-indole was obtained from 6-methyl-5-nitro-1H-indole-2,3-dione.
$^1$H-NMR (DMSO-d$_6$) δ: 2.62 (3H, s), 6.61-6.65 (1H, m), 7.39 (1H, s), 7.50-7.54 (1H, m), 8.37 (1H, s), 11.59 (1H, brs).
MS (ESI, m/z): 175 (M−H)$^−$.

Reference Example 167

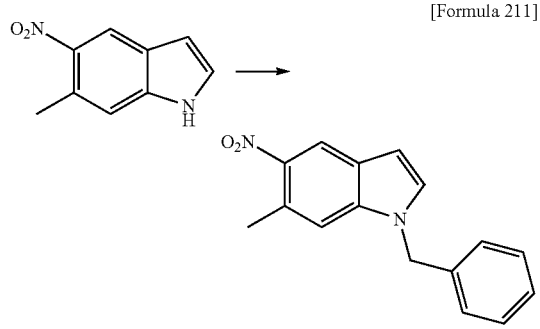

[Formula 211]

By the method similar to that of Reference Example 141, 1-benzyl-6-methyl-5-nitro-1H-indole was obtained from 6-methyl-5-nitro-1H-indole.
MS (ESI, m/z): 267 (M+H)$^+$.

Reference Example 168

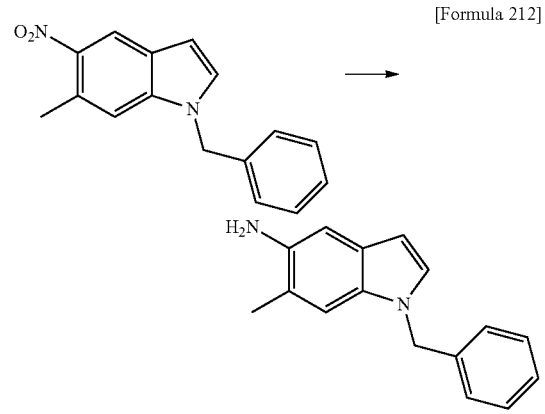

[Formula 212]

By the method similar to that of Reference Example 142, 1-benzyl-6-methyl-1H-indol-5-amine was obtained from 1-benzyl-6-methyl-5-nitro-1H-indole.
MS (ESI, m/z): 237 (M+H)$^+$.

Reference Example 169

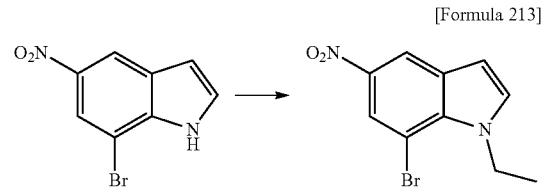

[Formula 213]

To the solution of 1.0 g of 7-bromo-5-nitro-1H-indole in 10 mL of N,N-dimethylformamide, 0.48 g of potassium tert-butoxide was added under ice-cooling, and the resultant was stirred for five minutes. 0.43 mL of ethyl iodide was added thereto, and the resultant was stirred at room temperature for one hour and five minutes. 0.046 g of potassium tert-butoxide and 0.066 mL of ethyl iodide were added thereto under ice-cooling, and the resultant was stirred at room temperature for 20 minutes. Water and ethyl acetate were added thereto under ice-cooling, and the organic layer was separated and the aqueous layer was extracted with ethyl acetate. The organic layer and the extract were combined, washed with a saturated aqueous sodium chloride solution and dried over anhydrous sodium sulfate, and the solvent was distilled off under reduced pressure. The obtained residue was purified by silica gel column chromatography (gradient elution with hexane:ethyl acetate=100:0-85:15) to give 0.52 g of 7-bromo-1-ethyl-5-nitro-1H-indole as a yellow solid.
$^1$H-NMR (CDCl$_3$) δ: 1.51 (3H, t, J=7.2 Hz), 4.65 (2H, q, J=7.2 Hz), 6.71 (1H, d, J=3.4 Hz), 7.25 (1H, d, J=3.2 Hz), 8.30 (1H, d, J=2.2 Hz), 8.50 (1H, d, J=2.2 Hz).

Reference Example 170

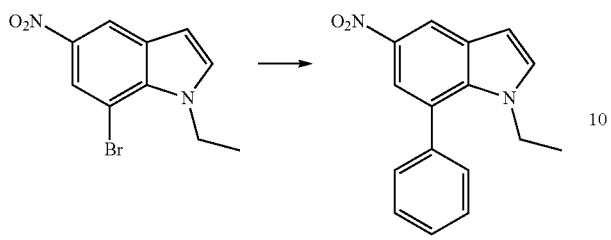

[Formula 214]

The mixture of 0.26 g of 7-bromo-1-ethyl-5-nitro-1H-indole, 0.18 g of phenylboronic acid, 0.41 g of tripotassium phosphate, 0.068 g of bis(di-tert-butyl(4-dimethylaminophenyl)phosphine)dichloropalladium(II), 7.5 mL of dioxane, and 2 mL of water, was heated at reflux for one hour and 10 minutes under a nitrogen atmosphere. After cooling the reaction mixture to room temperature, the insoluble matter was filtered off, and ethyl acetate and water were added to the filtrate. The organic layer was separated and the aqueous layer was extracted with ethyl acetate. The organic layer and the extract were combined, washed with a saturated aqueous sodium chloride solution and dried over anhydrous sodium sulfate, and the solvent was distilled off under reduced pressure. The obtained residue was purified by silica gel column chromatography (gradient elution with hexane:ethyl acetate=100:0-90:10) to give 0.24 g of 1-ethyl-5-nitro-7-phenyl-1H-indole as a yellow solid.

$^1$H-NMR (DMSO-$d_6$) δ: 0.91 (3H, t, J=7.1 Hz), 3.76 (2H, q, J=7.1 Hz), 6.89 (1H, d, J=3.4 Hz), 7.50-7.55 (5H, m), 7.66 (1H, d, J=3.2 Hz), 7.72 (1H, d, J=2.4 Hz), 8.61 (1H, d, J=2.4 Hz).

Reference Example 171

[Formula 215]

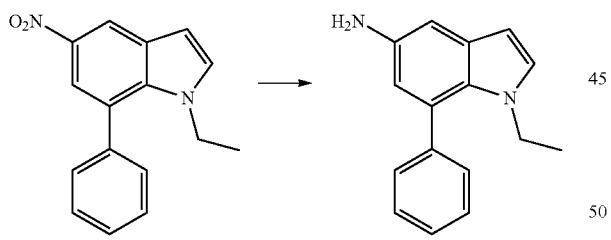

To the solution of 0.23 g of 1-ethyl-5-nitro-7-phenyl-1H-indole in 15 mL of methanol, 0.05 g of 10% palladium on carbon was added, and the resultant was stirred at room temperature for one hour and 15 minutes under a hydrogen atmosphere. The insoluble matter was filtered off and the solvent was distilled off under reduced pressure. 15 mL of methanol and 0.05 g of 10% palladium on carbon were added to the obtained residue, and the resultant was stirred at room temperature for one hour under a hydrogen atmosphere. The insoluble matter was filtered off and the solvent was distilled off under reduced pressure. The thus obtained residue was purified by silica gel column chromatography (gradient elution with hexane:ethyl acetate=90:10-60:40) to give 0.12 g of 1-ethyl-7-phenyl-1H-indol-5-amine as a yellow solid.

$^1$H-NMR (DMSO-$d_6$) δ: 0.79 (3H, t, J=7.1 Hz), 3.58 (2H, q, J=7.1 Hz), 4.55 (2H, s), 6.22 (1H, d, J=3.2 Hz), 6.30 (1H, d, J=2.2 Hz), 6.69 (1H, d, J=2.2 Hz), 7.12 (1H, d, J=2.9 Hz), 7.36-7.48 (5H, m).

MS (ESI, m/z): 237 (M+H)$^+$.

Reference Example 172

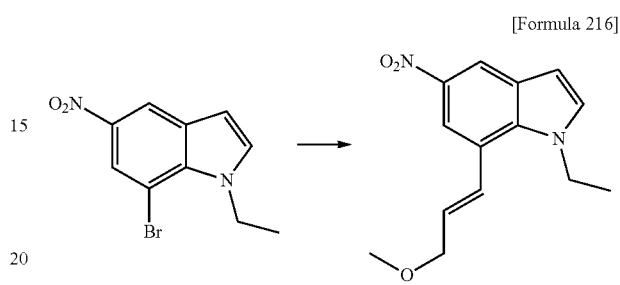

[Formula 216]

By the method similar to that of Reference Example 170, 1-ethyl-7-((1E)-3-methoxyprop-1-en-1-yl)-5-nitro-1H-indole was obtained from 7-bromo-1-ethyl-5-nitro-1H-indole and (E)-2-(3-methoxyprop-1-enyl)-4,4,5,5-tetramethyl-1,3,2-dioxaborolane.

$^1$H-NMR (DMSO-$d_6$) δ: 1.37 (3H, t, J=7.1 Hz), 3.36 (3H, s), 4.16 (2H, dd, J=5.4, 1.7 Hz), 4.42 (2H, q, J=7.3 Hz), 6.31 (1H, dt, J=15.4, 5.4 Hz), 6.78 (1H, d, J=3.2 Hz), 7.31 (1H, d, J=15.6 Hz), 7.63 (1H, d, J=3.2 Hz), 7.90 (1H, d, J=2.2 Hz), 8.49 (1H, d, J=2.4 Hz).

Reference Example 173

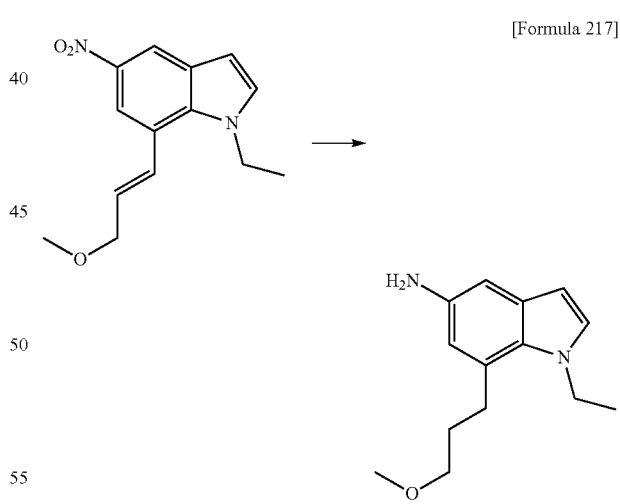

[Formula 217]

By the method similar to that of Reference Example 171, 1-ethyl-7-(3-methoxypropyl)-1H-indol-5-amine was obtained from 1-ethyl-7-((1E)-3-methoxyprop-1-en-1-yl)-5-nitro-1H-indole.

$^1$H-NMR (DMSO-$d_6$) δ: 1.25 (3H, t, J=7.1 Hz), 1.75-1.86 (2H, m), 2.80-2.88 (2H, m), 3.26 (3H, s), 3.36-3.42 (2H, m), 4.19 (2H, q, J=7.1 Hz), 4.41 (2H, s), 6.11 (1H, d, J=2.9 Hz), 6.30 (1H, d, J=2.2 Hz), 6.51 (1H, d, J=2.2 Hz), 7.08 (1H, d, J=3.2 Hz).

MS (ESI, m/z): 233 (M+H)$^+$.

Reference Example 174

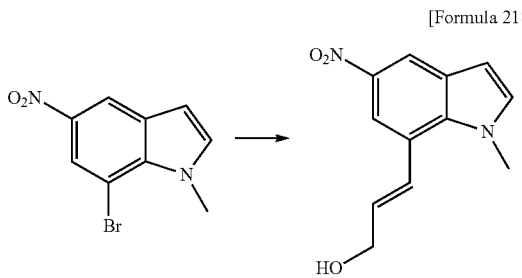

[Formula 218]

The mixture of 0.5 g of 7-bromo-1-methyl-5-nitro-1H-indole, 0.77 mL of ((1E)-3-((tert-butyl(dimethyl)silyl)oxy)prop-1-en-1-yl)boronic acid, 0.83 g of tripotassium phosphate, 0.14 g of bis(di-tert-butyl(4-dimethylaminophenyl)phosphine)dichloropalladium(II), 15 mL of dioxane, and 4 mL of water, was heated at reflux for one hour and 15 minutes under a nitrogen atmosphere. 0.1 mL of ((1E)-3-((tert-butyl(dimethyl)silyl)oxy)prop-1-en-1-yl)boronic acid was further added thereto, and the resultant was heated at reflux for one hour and 20 minutes. After cooling the reaction mixture to room temperature, the insoluble matter was filtered off, and water and ethyl acetate were added to the filtrate. The organic layer was separated and the aqueous layer was extracted with ethyl acetate. The organic layer and the extract were combined, washed with a saturated aqueous sodium chloride solution and dried over anhydrous sodium sulfate, and the solvent was distilled off under reduced pressure. The obtained residue was purified by silica gel column chromatography (gradient elution with hexane:ethyl acetate=100:0-90:10). 15 mL of methanol and 2 mL of 6 mol/L hydrochloric acid were added to the thus obtained residue and the resultant was stirred at room temperature for 10 minutes. The reaction mixture was adjusted to pH 6.5 by adding thereto a 2 mol/L aqueous sodium hydroxide solution. Ethyl acetate was added, the organic layer was separated and the aqueous layer was extracted with ethyl acetate. The organic layer and the extract were combined, washed with a saturated aqueous sodium chloride solution and dried over anhydrous sodium sulfate, and the solvent was distilled off under reduced pressure to give 0.45 g of (2E)-3-(1-methyl-5-nitro-1H-indol-7-yl)prop-2-en-1-ol as a yellow solid.

$^1$H-NMR (DMSO-$d_6$) δ: 4.06 (3H, s), 4.17-4.24 (2H, m), 5.01 (1H, t, J=5.6 Hz), 6.32 (1H, dt, J=15.4, 4.6 Hz), 6.73 (1H, d, J=3.2 Hz), 7.39 (1H, d, J=15.6 Hz), 7.53 (1H, d, J=3.4 Hz), 7.90 (1H, d, J=2.3 Hz), 8.46 (1H, d, J=2.2 Hz).

Reference Example 175

To the solution of 0.15 g of (2E)-3-(1-methyl-5-nitro-1H-indol-7-yl)prop-2-en-1-ol in 1.5 mL of N,N-dimethylformamide, 0.039 g of 60% sodium hydride was added under ice-cooling, and the resultant was stirred for 30 minutes under a nitrogen atmosphere. 0.11 mL of ethyl iodide was added thereto, and the resultant was stirred at room temperature for 35 minutes. 0.053 mL of ethyl iodide was added thereto under ice-cooling, and the resultant was stirred at room temperature for 15 minutes. Ice and water were added thereto under ice-cooling, and the solid was collected by filtration to give 0.15 g of 7-((1E)-3-ethoxyprop-1-en-1-yl)-1-methyl-5-nitro-1H-indole as a yellow solid.

$^1$H-NMR (DMSO-$d_6$) δ: 1.18 (3H, t, J=7.1 Hz), 3.54 (2H, q, J=6.8 Hz), 4.05 (3H, s), 4.18 (2H, dd, J=5.6, 1.7 Hz), 6.29 (1H, dt, J=15.6, 5.4 Hz), 6.74 (1H, d, J=3.2 Hz), 7.45 (1H, d, J=15.6 Hz), 7.54 (1H, d, J=3.4 Hz), 7.92 (1H, d, J=2.2 Hz), 8.47 (1H, d, J=2.2 Hz).

Reference Example 176

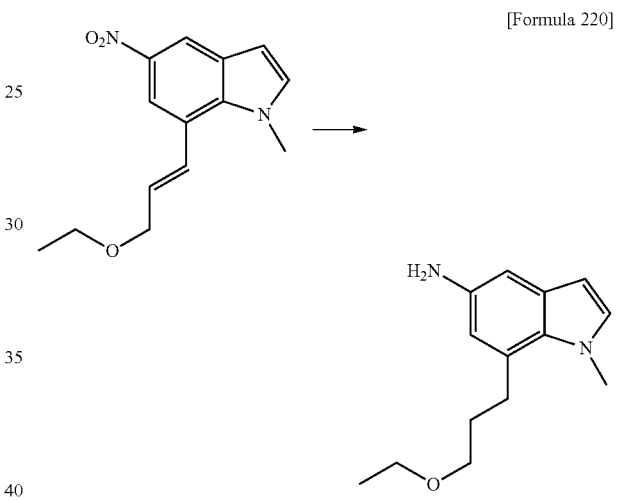

[Formula 220]

By the method similar to that of Reference Example 171, 7-(3-ethoxypropyl)-1-methyl-1H-indol-5-amine was obtained from 7-((1E)-3-ethoxyprop-1-en-1-yl)-1-methyl-5-nitro-1H-indole.

$^1$H-NMR (DMSO-$d_6$) δ: 1.13 (3H, t, J=7.1 Hz), 1.80-1.92 (2H, m), 2.94-3.01 (2H, m), 3.36-3.53 (4H, m), 3.87 (3H, s), 4.45-4.50 (2H, m), 6.05 (1H, d, J=3.2 Hz), 6.29 (1H, d, J=2.0 Hz), 6.49 (1H, d, J=2.2 Hz), 6.98 (1H, d, J=3.2 Hz).

MS (ESI, m/z): 233 (M+H)$^+$.

Reference Example 177

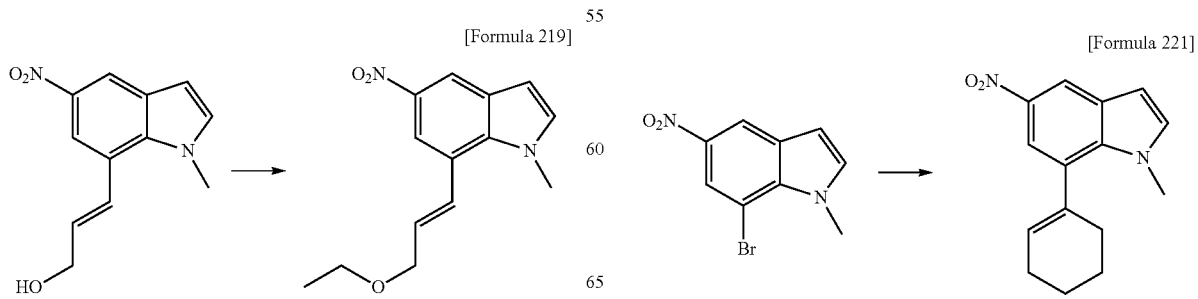

[Formula 219]

[Formula 221]

By the method similar to that of Reference Example 170, 7-(cyclohex-1-en-1-yl)-1-methyl-5-nitro-1H-indole was obtained from 7-bromo-1-methyl-5-nitro-1H-indole and 2-(cyclohex-1-en-1-yl)-4,4,5,5-tetramethyl-1,3,2-dioxaborolane.

$^1$H-NMR (DMSO-d$_6$) δ: 1.65-1.84 (4H, m), 2.16-2.26 (2H, m), 2.29-2.37 (2H, m), 3.88 (3H, s), 5.73-5.78 (1H, m), 6.76 (1H, d, J=3.2 Hz), 7.55 (1H, d, J=3.2 Hz), 7.64 (1H, d, J=2.2 Hz), 8.46 (1H, d, J=2.4 Hz).

Reference Example 178

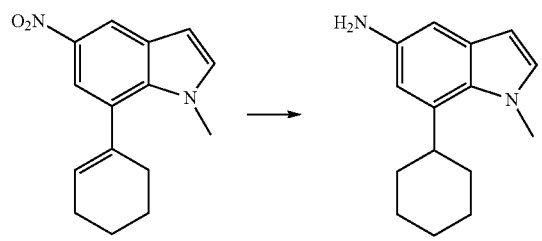

[Formula 222]

To the mixture of 0.343 g of 7-(cyclohex-1-en-1-yl)-1-methyl-5-nitro-1H-indole, 1.5 mL of acetic acid and 15 mL of methanol, 0.17 g of 10% palladium hydroxide on carbon was added, and the resultant was stirred at 55° C. for seven hours under a hydrogen atmosphere. After cooling the reaction mixture to room temperature, the insoluble matter was filtered off and the solvent was distilled off under reduced pressure. 1.5 mL of acetic acid, 10 mL of methanol and 0.17 g of 10% palladium hydroxide on carbon were added to the obtained residue, and the resultant was stirred at 55° C. for three hours under a hydrogen atmosphere. After cooling the reaction mixture to room temperature, the insoluble matter was filtered off and the solvent was distilled off under reduced pressure. 2.0 mL of acetic acid, 10 mL of methanol and 0.17 g of 10% palladium hydroxide on carbon were added to the thus obtained residue, and the resultant was stirred at 55° C. for four hours and 15 minutes under a hydrogen atmosphere. After cooling the reaction mixture to room temperature, the insoluble matter was filtered off and the solvent was distilled off under reduced pressure. A saturated aqueous sodium bicarbonate solution and ethyl acetate were added to the obtained residue, and the organic layer was separated and the aqueous layer was extracted with ethyl acetate. The organic layer and the extract were combined, washed with a saturated aqueous sodium chloride solution and dried over anhydrous sodium sulfate, and the solvent was distilled off under reduced pressure. The thus obtained residue was purified by silica gel column chromatography (gradient elution with hexane:ethyl acetate=90:10-60:40) to give 0.046 g of 7-cyclohexyl-1-methyl-1H-indol-5-amine as a yellow oil.

$^1$H-NMR (DMSO-d$_6$) δ: 1.38-1.53 (5H, m), 1.71-1.91 (6H, m), 3.88 (3H, s), 4.34-4.44 (2H, m), 6.05 (1H, d, J=2.9 Hz), 6.41 (1H, d, J=2.2 Hz), 6.47 (1H, d, J=2.0 Hz), 6.97 (1H, d, J=2.9 Hz).

MS (ESI, m/z): 229 (M+H)$^+$.

Reference Example 179

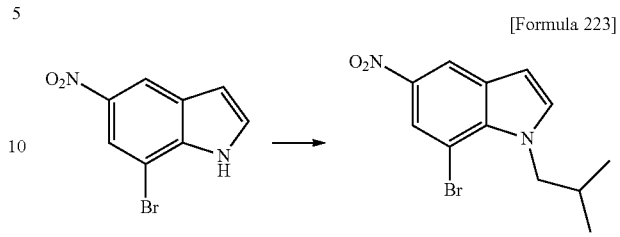

[Formula 223]

To the solution of 0.30 g of 7-bromo-5-nitro-1H-indole in 3 mL of N,N-dimethylformamide, 0.18 g of potassium tert-butoxide was added under ice-cooling, and the resultant was stirred for five minutes. 0.16 mL of 1-iodo-2-methylpropane was added thereto, and the resultant was stirred at room temperature for one hour. 0.18 g of potassium tert-butoxide and 0.16 mL of 1-iodo-2-methylpropane were added thereto, and the resultant was stirred at room temperature for one hour and 10 minutes. 0.18 g of potassium tert-butoxide and 0.16 mL of 1-iodo-2-methylpropane were added thereto, and the resultant was stirred at 60° C. for one hour and 20 minutes. 0.36 g of potassium tert-butoxide and 0.31 mL of 1-iodo-2-methylpropane were added thereto, and the resultant was stirred at 60° C. for two hours. 0.18 g of potassium tert-butoxide and 0.16 mL of 1-iodo-2-methylpropane were added thereto, and the resultant was stirred at 90° C. for one hour. 0.18 g of potassium tert-butoxide and 0.16 mL of 1-iodo-2-methylpropane were added thereto, and the resultant was stirred at 90° C. for one hour. 0.18 g of potassium tert-butoxide and 0.16 mL of 1-iodo-2-methylpropane were added thereto, and the resultant was stirred at 90° C. for four hours. Water, ethyl acetate and 2 mol/L hydrochloric acid were added to the reaction mixture under ice-cooling, the organic layer was separated, washed with a saturated aqueous sodium chloride solution and dried over anhydrous sodium sulfate, and the solvent was distilled off under reduced pressure. The obtained residue was purified by silica gel column chromatography (gradient elution with hexane:ethyl acetate=100:0-85:15) to give 0.24 g of 7-bromo-1-(2-methylpropyl)-5-nitro-1H-indole as a yellow solid.

$^1$H-NMR (DMSO-d$_6$) δ: 0.86 (6H, d, J=6.8 Hz), 2.14 (1H, sep, J=6.8 Hz), 4.39 (2H, d, J=7.6 Hz), 6.86 (1H, d, J=3.2 Hz), 7.71 (1H, d, J=3.2 Hz), 8.17 (1H, d, J=2.2 Hz), 8.61 (1H, d, J=2.2 Hz).

Reference Example 180

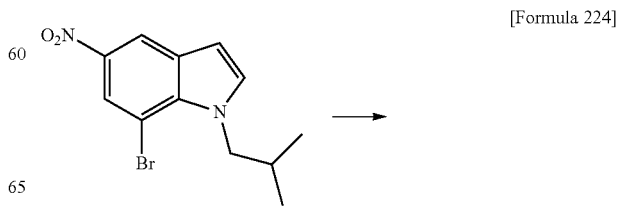

[Formula 224]

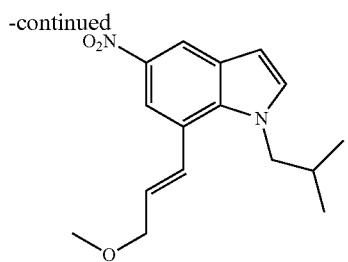

The mixture of 0.24 g of 7-bromo-1-(2-methylpropyl)-5-nitro-1H-indole, 0.34 mL of (E)-2-(3-methoxyprop-1-enyl)-4,4,5,5-tetramethyl-1,3,2-dioxaborolane, 0.35 g of tripotassium phosphate, 0.057 g of bis(di-tert-butyl(4-dimethylaminophenyl)phosphine)dichloropalladium (II), 2 mL of dioxane, and 0.5 mL of water, was heated at reflux for three hours and 10 minutes under a nitrogen atmosphere. The reaction mixture was cooled to room temperature, and ethyl acetate and water were then added thereto. The organic layer was separated and the aqueous layer was extracted with ethyl acetate. The organic layer and the extract were combined, washed with a saturated aqueous sodium chloride solution and dried over anhydrous sodium sulfate, and the solvent was distilled off under reduced pressure. The obtained residue was purified by silica gel column chromatography (gradient elution with hexane:ethyl acetate=100:0-85:15) to give 0.17 g of 7-((1E)-3-methoxyprop-1-en-1-yl)-1-(2-methylpropyl)-5-nitro-1H-indole as a brown oil.

$^1$H-NMR (DMSO-$d_6$) δ: 0.84 (6H, d, J=6.6 Hz), 1.94-2.06 (1H, m), 3.36 (3H, s), 4.15 (2H, dd, J=5.1, 1.4 Hz), 4.18 (2H, d, J=7.3 Hz), 6.31 (1H, dt, J=15.6, 5.1 Hz), 6.76 (1H, d, J=3.2 Hz), 7.29 (1H, d, J=15.4 Hz), 7.58 (1H, d, J=3.4 Hz), 7.91 (1H, d, J=2.2 Hz), 8.49 (1H, d, J=2.2 Hz).

Reference Example 181

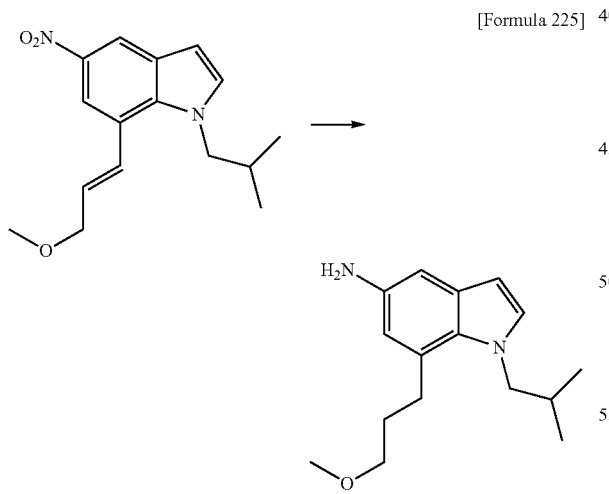

[Formula 225]

To the solution of 0.17 g of 7-((1E)-3-methoxyprop-1-en-1-yl)-1-(2-methylpropyl)-5-nitro-1H-indole in 10 mL of methanol, 0.085 g of 10% palladium on carbon was added, and the resultant was stirred at 50° C. for three hours under a hydrogen atmosphere. The insoluble matter was filtered off and the solvent was distilled off under reduced pressure to give 0.14 g of 7-(3-methoxypropyl)-1-(2-methylpropyl)-1H-indol-5-amine as a brown oil.

$^1$H-NMR (DMSO-$d_6$) δ: 0.80 (6H, d, J=6.6 Hz), 1.72-1.82 (2H, m), 1.89 (1H, sep, J=6.6 Hz), 2.77-2.85 (2H, m), 3.27 (3H, s), 3.37-3.42 (2H, m), 3.92 (2H, d, J=7.3 Hz), 4.40 (2H, s), 6.07 (1H, d, J=2.9 Hz), 6.30 (1H, d, J=2.2 Hz), 6.51 (1H, d, J=1.9 Hz), 7.04 (1H, d, J=3.2 Hz).

MS (ESI, m/z): 261 (M+H)$^+$.

Reference Example 182

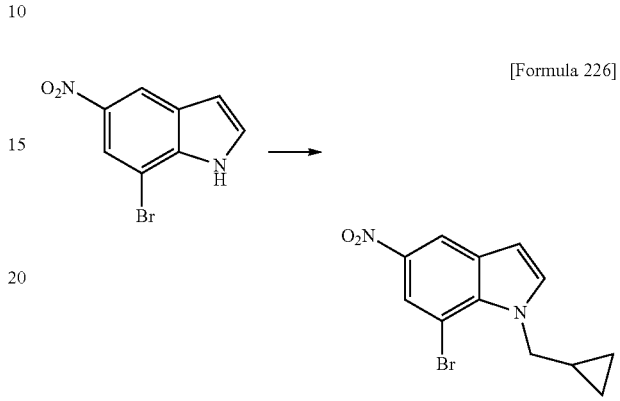

[Formula 226]

By the method similar to that of Reference Example 179, 7-bromo-1-(cyclopropylmethyl)-5-nitro-1H-indole was obtained from 7-bromo-5-nitro-1H-indole and (bromomethyl)cyclopropane.

$^1$H-NMR (DMSO-$d_6$) δ: 0.40-0.54 (4H, m), 1.28-1.40 (1H, m), 4.49 (2H, d, J=7.1 Hz), 6.87 (1H, d, J=3.2 Hz), 7.77 (1H, d, J=3.2 Hz), 8.17 (1H, d, J=2.2 Hz), 8.60 (1H, d, J=2.2 Hz).

Reference Example 183

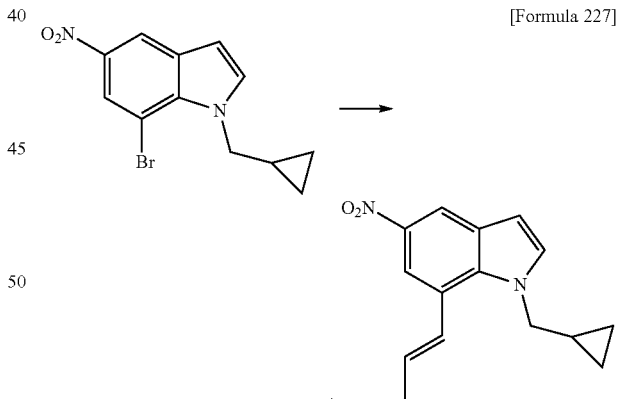

[Formula 227]

By the method similar to that of Reference Example 180, 1-(cyclopropylmethyl)-7-((1E)-3-methoxyprop-1-en-1-yl)-5-nitro-1H-indole was obtained from 7-bromo-1-(cyclopropylmethyl)-5-nitro-1H-indole.

$^1$H-NMR (DMSO-$d_6$) δ: 0.35-0.41 (2H, m), 0.48-0.54 (2H, m), 1.18-1.28 (1H, m), 3.36 (3H, s), 4.16 (2H, dd, J=5.4, 1.7 Hz), 4.27 (2H, d, J=6.8 Hz), 6.31 (1H, dt, J=15.4, 5.4 Hz), 6.78 (1H, d, J=3.2 Hz), 7.38 (1H, d, J=15.6 Hz), 7.66 (1H, d, J=3.4 Hz), 7.91 (1H, d, J=2.2 Hz), 8.50 (1H, d, J=2.2 Hz).

Reference Example 184

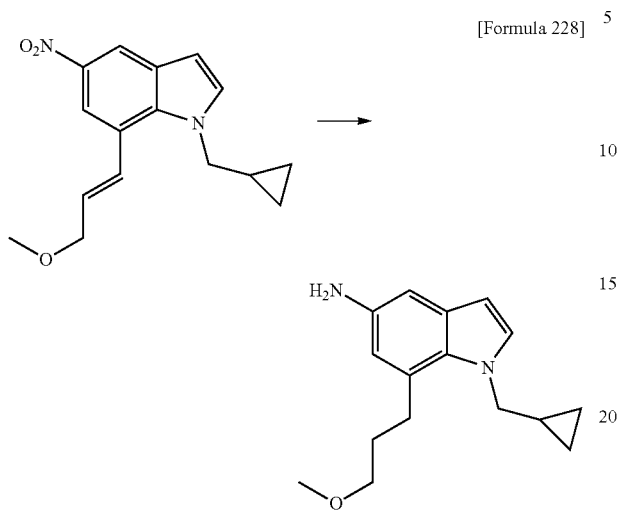

[Formula 228]

By the method similar to that of Reference Example 181, 1-(cyclopropylmethyl)-7-(3-methoxypropyl)-1H-indol-5-amine was obtained from 1-(cyclopropylmethyl)-7-((1E)-3-methoxyprop-1-en-1-yl)-5-nitro-1H-indole.

$^1$H-NMR (DMSO-d$_6$) δ: 0.25-0.32 (2H, m), 0.41-0.50 (2H, m), 1.09-1.18 (1H, m), 1.76-1.86 (2H, m), 2.86-2.94 (2H, m), 3.27 (3H, s), 3.36-3.42 (2H, m), 4.05 (2H, d, J=6.6 Hz), 4.43 (2H, s), 6.10 (1H, d, J=3.2 Hz), 6.30 (1H, d, J=2.0 Hz), 6.51 (1H, d, J=2.0 Hz), 7.13 (1H, d, J=2.9 Hz).

MS (ESI, m/z): 259 (M+H)$^+$.

Reference Example 185

[Formula 229]

By the method similar to that of Reference Example 179, 7-bromo-5-nitro-1-pentyl-1H-indole was obtained from 7-bromo-5-nitro-1H-indole and 1-bromopentane.

$^1$H-NMR (DMSO-d$_6$) δ: 0.82-0.89 (3H, m), 1.20-1.37 (4H, m), 1.73-1.85 (2H, m), 4.53-4.61 (2H, m), 6.85 (1H, d, J=3.2 Hz), 7.73 (1H, d, J=3.2 Hz), 8.16 (1H, d, J=2.2 Hz), 8.60 (1H, d, J=2.2 Hz).

Reference Example 186

By the method similar to that of Reference Example 180, 7-((1E)-3-methoxyprop-1-en-1-yl)-5-nitro-1-pentyl-1H-indole was obtained from 7-bromo-5-nitro-1-pentyl-1H-indole.

$^1$H-NMR (DMSO-d$_6$) δ: 0.82-0.88 (3H, m), 1.21-1.34 (4H, m), 1.68-1.78 (2H, m), 3.36 (3H, s), 4.15 (2H, dd, J=5.4, 1.7 Hz), 4.35 (2H, t, J=7.3 Hz), 6.31 (1H, dt, J=15.6, 5.1 Hz), 6.76 (1H, d, J=3.4 Hz), 7.29 (1H, d, J=15.6 Hz), 7.61 (1H, d, J=3.2 Hz), 7.90 (1H, d, J=2.2 Hz), 8.48 (1H, d, J=2.4 Hz).

Reference Example 187

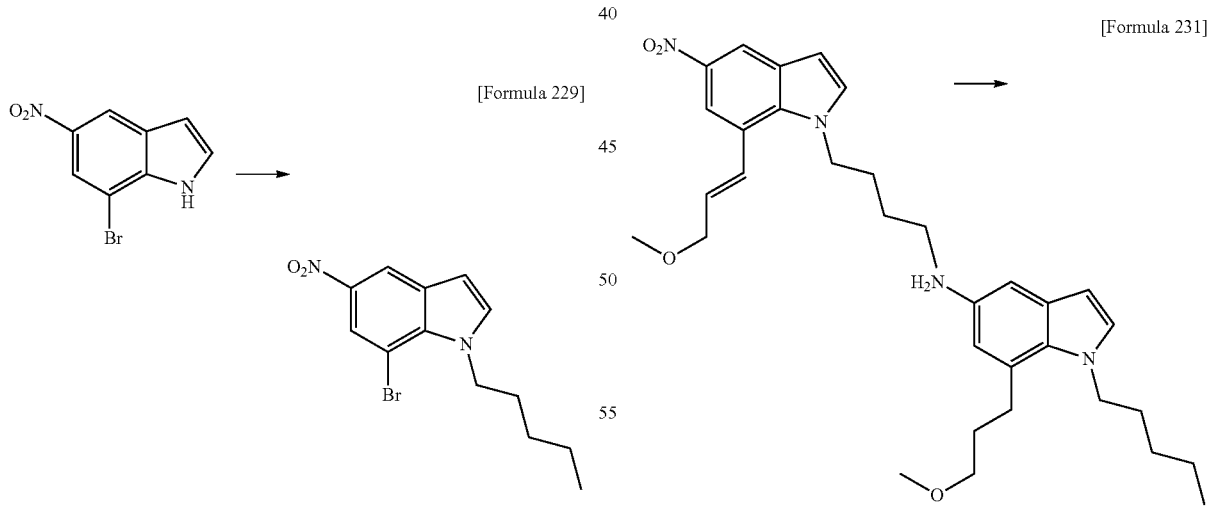

[Formula 230]

[Formula 231]

By the method similar to that of Reference Example 181, 7-(3-methoxypropyl)-1-pentyl-1H-indol-5-amine was obtained from 7-((1E)-3-methoxyprop-1-en-1-yl)-5-nitro-1-pentyl-1H-indole.

$^1$H-NMR (DMSO-d$_6$) δ: 0.85 (3H, t, J=6.8 Hz), 1.16-1.33 (4H, m), 1.57-1.66 (2H, m), 1.74-1.84 (2H, m), 2.78-2.87 (2H, m), 3.27 (3H, s), 3.39 (2H, t, J=6.4 Hz), 4.12 (2H, t,

J=7.1 Hz), 4.33-4.44 (2H, m), 6.08 (1H, d, J=3.2 Hz), 6.29 (1H, d, J=2.2 Hz), 6.50 (1H, d, J=2.2 Hz), 7.06 (1H, d, J=3.2 Hz).
MS (ESI, m/z): 275 (M+H)$^+$.

Reference Example 188

[Formula 232]

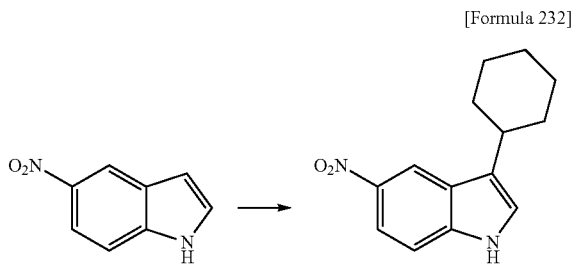 [SMILES: O=[N+]([O-])c1ccc2[nH]ccc2c1 ; O=[N+]([O-])c1ccc2[nH]cc(C3CCCCC3)c2c1]

The mixture of 5.9 mL of triethylsilane, 3.0 g of trichloroacetic acid, and 10 mL of toluene, was stirred at 75° C. for 35 minutes. The mixture of 2.0 g of 5-nitro-1H-indole, 1.4 mL of cyclohexanone, and 10 mL of toluene, was added dropwise to the reaction mixture, and the resultant was stirred at 75° C. for four hours and 20 minutes. The reaction mixture was cooled to room temperature, and a saturated aqueous sodium bicarbonate solution and ethyl acetate were then added thereto under ice-cooling. The organic layer was separated and the aqueous layer was extracted with ethyl acetate. The organic layer and the extract were combined, washed with a saturated aqueous sodium chloride solution and dried over anhydrous sodium sulfate, and the solvent was distilled off under reduced pressure. The obtained residue was purified by silica gel column chromatography (gradient elution with hexane:ethyl acetate=100:0-80:20) to give 0.87 g of 3-cyclohexyl-5-nitro-1H-indole as a yellow solid.
$^1$H-NMR (DMSO-d$_6$) δ: 1.20-1.34 (1H, m), 1.38-1.54 (4H, m), 1.70-1.86 (3H, m), 1.94-2.03 (2H, m), 2.82-2.93 (1H, m), 7.36 (1H, d, J=2.2 Hz), 7.50 (1H, d, J=9.0 Hz), 7.97 (1H, dd, J=8.9, 2.3 Hz), 8.52 (1H, d, J=2.2 Hz), 11.56 (1H, brs).
MS (ESI, m/z): 243 (M−H)$^-$.

Reference Example 189

[Formula 233]

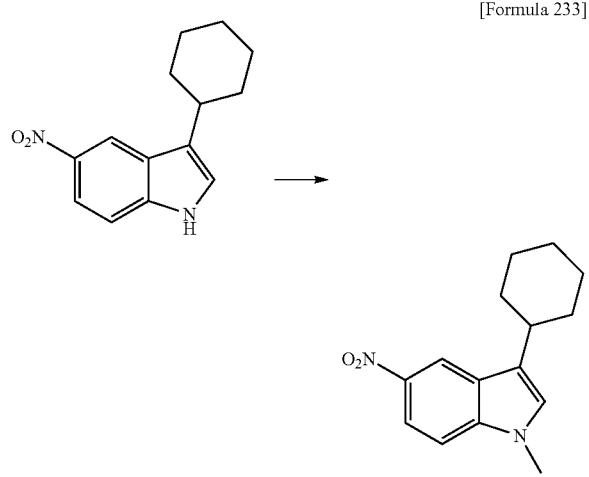

To the solution of 0.91 g of 3-cyclohexyl-5-nitro-1H-indole in 4.6 mL of N,N-dimethylformamide, 0.50 g of potassium tert-butoxide was added under ice-cooling, and the resultant was stirred for two minutes. 0.28 mL of methyl iodide was added thereto, and the resultant was stirred at room temperature for one hour. 0.503 g of potassium tert-butoxide and 0.28 mL of methyl iodide were added thereto, and the resultant was stirred at room temperature for 50 minutes. 0.101 g of potassium tert-butoxide and 0.06 mL of methyl iodide were added thereto, and the resultant was stirred at room temperature for two hours. Water was added to the reaction mixture and the solid was collected by filtration to give 0.93 g of 3-cyclohexyl-1-methyl-5-nitro-1H-indole as a yellow solid.
$^1$H-NMR (DMSO-d$_6$) δ: 1.20-1.32 (1H, m), 1.35-1.54 (4H, m), 1.69-1.85 (3H, m), 1.93-2.04 (2H, m), 2.82-2.94 (1H, m), 3.82 (3H, s), 7.35 (1H, s), 7.58 (1H, d, J=9.0 Hz), 8.02 (1H, dd, J=9.0, 2.2 Hz), 8.53 (1H, d, J=2.2 Hz).

Reference Example 190

[Formula 234]

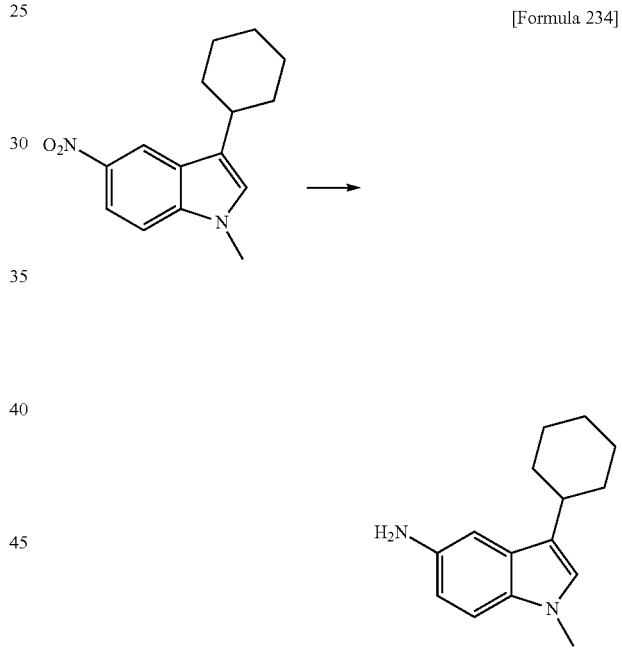

To the solution of 0.93 g of 3-cyclohexyl-1-methyl-5-nitro-1H-indole in 30 mL of methanol, 0.45 g of 10% palladium on carbon was added, and the resultant was stirred at room temperature for two hours and 15 minutes under a hydrogen atmosphere. The insoluble matter was filtered off and the solvent was distilled off under reduced pressure. The obtained residue was purified by silica gel column chromatography (gradient elution with hexane:ethyl acetate=90:10-60:40) to give 0.75 g of 3-cyclohexyl-1-methyl-1H-indol-5-amine as a brown oil.
$^1$H-NMR (DMSO-d$_6$) δ: 1.20-1.29 (1H, m), 1.30-1.46 (4H, m), 1.67-1.83 (3H, m), 1.91-1.98 (2H, m), 2.55-2.65 (1H, m), 3.56 (3H, s), 4.45 (2H, s), 6.50 (1H, dd, J=8.6, 2.0 Hz), 6.70 (1H, d, J=2.2 Hz), 6.81 (1H, s), 7.03 (1H, d, J=8.5 Hz).
MS (ESI, m/z): 229 (M+H)$^+$.

Reference Example 191

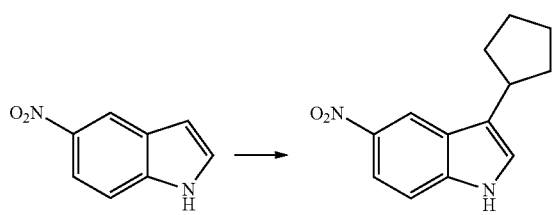

[Formula 235]

By the method similar to that of Reference Example 188, 3-cyclopentyl-5-nitro-1H-indole was obtained from 5-nitro-1H-indole and cyclopentanone.

$^1$H-NMR (DMSO-d$_6$) δ: 1.57-1.83 (6H, m), 2.04-2.19 (2H, m), 3.20-3.40 (1H, m), 7.36-7.42 (1H, m), 7.50 (1H, d, J=8.8 Hz), 7.98 (1H, dd, J=9.0, 2.4 Hz), 8.51 (1H, d, J=2.2 Hz), 11.55 (1H, brs).

MS (ESI, m/z): 229 (M−H)$^-$.

Reference Example 192

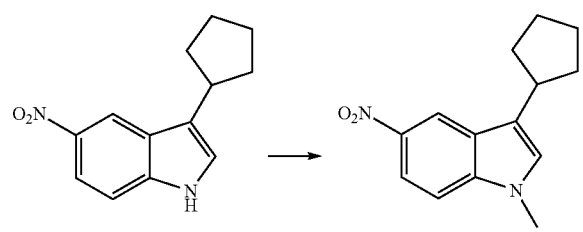

[Formula 236]

By the method similar to that of Reference Example 189, 3-cyclopentyl-1-methyl-5-nitro-1H-indole was obtained from 3-cyclopentyl-5-nitro-1H-indole.

$^1$H-NMR (DMSO-d$_6$) δ: 1.53-1.83 (6H, m), 2.06-2.18 (2H, m), 3.25-3.30 (1H, m), 3.81 (3H, s), 7.40 (1H, s), 7.59 (1H, d, J=9.0 Hz), 8.03 (1H, dd, J=9.0, 2.2 Hz), 8.51 (1H, d, J=2.2 Hz).

Reference Example 193

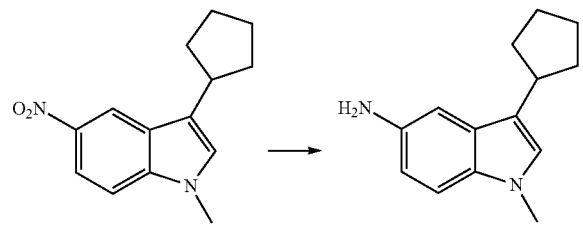

[Formula 237]

By the method similar to that of Reference Example 190, 3-cyclopentyl-1-methyl-1H-indol-5-amine was obtained from 3-cyclopentyl-1-methyl-5-nitro-1H-indole.

$^1$H-NMR (DMSO-d$_6$) δ: 1.51-1.79 (6H, m), 1.95-2.15 (2H, m), 2.99-3.10 (1H, m), 3.59 (3H, s), 4.45 (2H, s), 6.51 (1H, dd, J=8.5, 2.2 Hz), 6.70 (1H, d, J=1.7 Hz), 6.85 (1H, s), 7.03 (1H, d, J=8.5 Hz).

MS (ESI, m/z): 215 (M+H)$^+$.

Reference Example 194

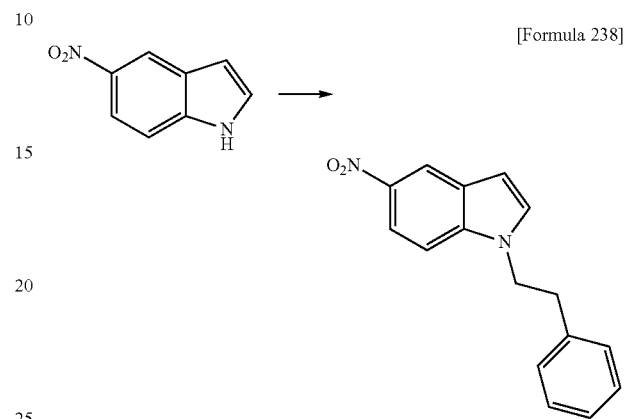

[Formula 238]

To the solution of 2.0 g of 5-nitro-1H-indole in 10 mL of N,N-dimethylformamide, 5.5 g of potassium tert-butoxide was added under ice-cooling, and the resultant was stirred for nine minutes. 6.6 mL of (2-bromoethyl)benzene was added thereto, and the resultant was stirred at room temperature for one hour. 3 mL of (2-bromoethyl)benzene was added to the reaction mixture, and the resultant was stirred at room temperature for 30 minutes. 2.8 g of potassium tert-butoxide was then added thereto, and the resultant was stirred at room temperature for 30 minutes. Water and ethyl acetate were added to the reaction mixture under ice-cooling. The organic layer was separated, sequentially washed with 2 mol/L hydrochloric acid, a saturated aqueous sodium bicarbonate solution and a saturated aqueous sodium chloride solution and dried over anhydrous sodium sulfate, and the solvent was distilled off under reduced pressure. The obtained residue was purified by silica gel column chromatography (gradient elution with hexane:ethyl acetate=100:0-80:20) to give 1.44 g of 5-nitro-1-(2-phenylethyl)-1H-indole as an orange solid.

$^1$H-NMR (DMSO-d$_6$) δ: 3.09 (2H, t, J=7.2 Hz), 4.52 (2H, t, J=7.2 Hz), 6.71 (1H, d, J=3.2 Hz), 7.14-7.27 (5H, m), 7.57 (1H, d, J=3.2 Hz), 7.65 (1H, d, J=9.0 Hz), 7.97 (1H, dd, J=9.0, 2.4 Hz), 8.54 (1H, d, J=2.2 Hz).

Reference Example 195

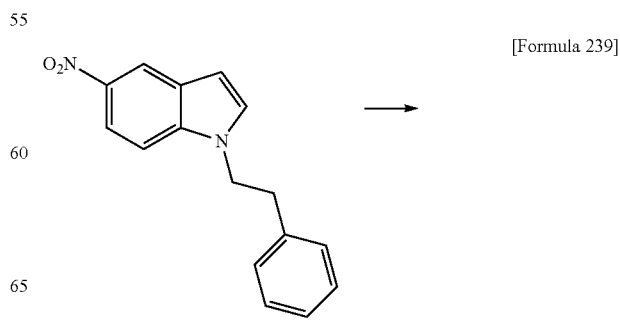

[Formula 239]

-continued

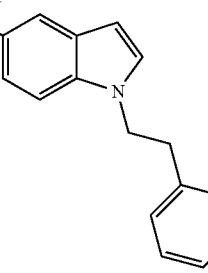

To the solution of 1.44 g of 5-nitro-1-(2-phenylethyl)-1H-indole in 15 mL of tetrahydrofuran, 0.3 g of 10% palladium on carbon was added, and the resultant was stirred at room temperature for two hours and 10 minutes under a hydrogen atmosphere. 0.4 g of 10% palladium on carbon was added to the reaction mixture, and the resultant was stirred at 45° C. for one hour and 10 minutes. After cooling the reaction mixture to room temperature, the insoluble matter was filtered off and the solvent was distilled off under reduced pressure. The obtained residue was purified by silica gel column chromatography (gradient elution with hexane:ethyl acetate=90:10-50:50) to give 1.14 g of 1-(2-phenylethyl)-1H-indol-5-amine as a brown oil.

$^1$H-NMR (DMSO-$d_6$) δ: 3.00 (2H, t, J=7.6 Hz), 4.26 (2H, t, J=7.3 Hz), 4.45 (2H, s), 6.06 (1H, d, J=2.9 Hz), 6.52 (1H, dd, J=8.6, 2.2 Hz), 6.66 (1H, d, J=2.0 Hz), 7.05 (1H, d, J=3.0 Hz), 7.15-7.29 (6H, m).

MS (ESI, m/z): 237 (M+H)$^+$.

Reference Example 196

[Formula 240]

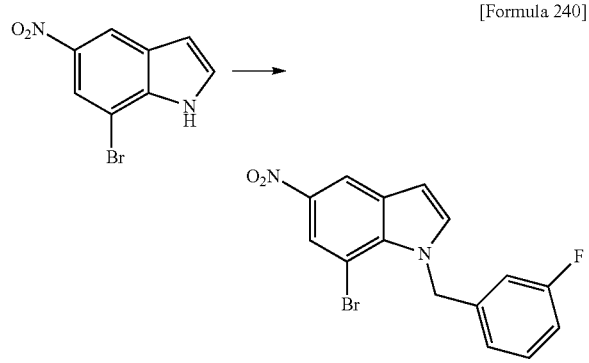

To the solution of 1.0 g of 7-bromo-5-nitro-1H-indole in 5 mL of N,N-dimethylformamide, 0.56 g of potassium tert-butoxide was added under ice-cooling, and the resultant was stirred for four minutes. 0.62 mL of 3-fluorobenzyl bromide was added thereto, and the resultant was stirred for 10 minutes. Water, ethyl acetate and hexane were added to the reaction mixture, and the organic layer was separated, washed with a saturated aqueous sodium chloride solution and dried over anhydrous sodium sulfate, and the solvent was distilled off under reduced pressure. The obtained residue was purified by silica gel column chromatography (gradient elution with hexane:ethyl acetate=100:0-80:20) to give 1.4 g of 7-bromo-1-(3-fluorobenzyl)-5-nitro-1H-indole as a yellow solid.

$^1$H-NMR (DMSO-$d_6$) δ: 5.93 (2H, s), 6.74 (1H, d, J=7.8 Hz), 6.82 (1H, d, J=10.2 Hz), 6.98 (1H, d, J=3.2 Hz), 7.06-7.14 (1H, m), 7.31-7.40 (1H, m), 7.86 (1H, d, J=3.2 Hz), 8.15 (1H, d, J=2.2 Hz), 8.66 (1H, d, J=2.2 Hz).

Reference Example 197

[Formula 241]

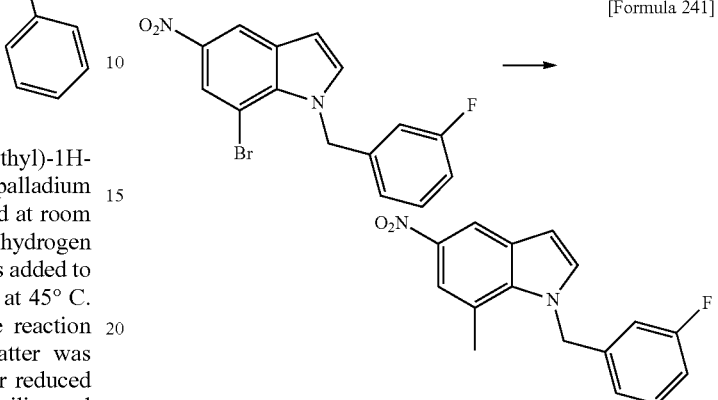

The mixture of 1.4 g of 7-bromo-1-(3-fluorobenzyl)-5-nitro-1H-indole, 0.72 g of methylboronic acid, 1.7 g of tripotassium phosphate, 0.28 g of bis(di-tert-butyl(4-dimethylaminophenyl)phosphine)dichloropalladium(II), 14 mL of dioxane, and 3.5 mL of water, was heated at reflux for one hour and 30 minutes. After cooling the reaction mixture to room temperature, the insoluble matter was filtered off and ethyl acetate and water were added to the filtrate. The organic layer was separated, washed with a saturated aqueous sodium chloride solution and dried over anhydrous sodium sulfate, and the solvent was then distilled off under reduced pressure. The obtained residue was purified by silica gel column chromatography (gradient elution with hexane:ethyl acetate=95:5-75:25) to give 1.16 g of 1-(3-fluorobenzyl)-7-methyl-5-nitro-1H-indole as an orange oil.

$^1$H-NMR (DMSO-$d_6$) δ: 2.53 (3H, s), 5.76 (2H, s), 6.65-6.76 (2H, m), 6.86 (1H, d, J=3.2 Hz), 7.06-7.15 (1H, m), 7.33-7.41 (1H, m), 7.70 (1H, d, J=3.2 Hz), 7.76 (1H, d, J=1.5 Hz), 8.46 (1H, d, J=2.4 Hz).

Reference Example 198

[Formula 242]

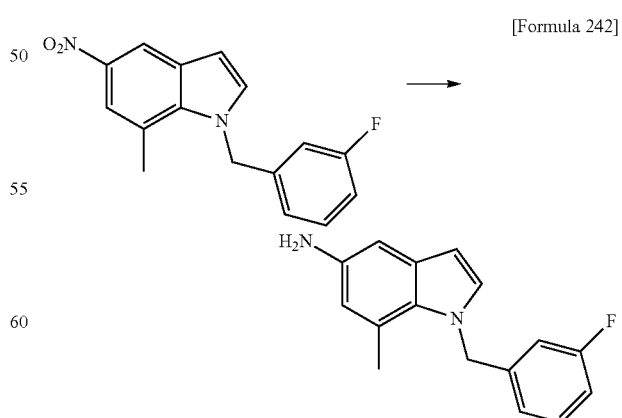

The mixture of 0.92 g of 1-(3-fluorobenzyl)-7-methyl-5-nitro-1H-indole, 0.12 g of ammonium chloride, 0.54 g of iron powder, 15 mL of ethanol, and 4.5 mL of water, was heated at reflux for one hour and 40 minutes. After cooling the reaction mixture to room temperature, the insoluble matter was filtered off and the filter cake was washed with ethyl acetate. The filtrate and the washings were combined, and water was added thereto, and the organic layer was separated, washed with a saturated aqueous sodium chloride solution and then dried over anhydrous sodium sulfate, and the solvent was distilled off under reduced pressure. The obtained residue was purified by silica gel column chromatography (gradient elution with hexane:ethyl acetate=90:10-50:50) to give 0.62 g of 1-(3-fluorobenzyl)-7-methyl-1H-indol-5-amine as an orange oil.

$^1$H-NMR (DMSO-$d_6$) δ: 2.27 (3H, s), 4.42 (2H, s), 5.52 (2H, s), 6.18-6.23 (2H, m), 6.51-6.61 (2H, m), 6.66-6.72 (1H, m), 7.00-7.08 (1H, m), 7.18-7.23 (1H, m), 7.28-7.37 (1H, m).

MS (ESI, m/z): 255 (M+H)$^+$.

Reference Example 199

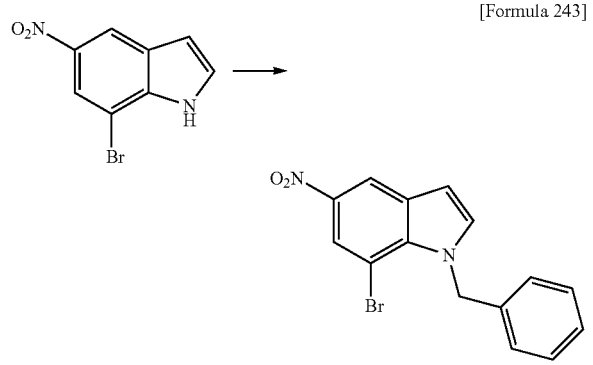

[Formula 243]

To the solution of 1.0 g of 7-bromo-5-nitro-1H-indole in 5 mL of N,N-dimethylformamide, 0.51 g of potassium tert-butoxide was added under ice-cooling, and the resultant was stirred for five minutes. 0.54 mL of (bromomethyl)benzene was added thereto, and the resultant was stirred at room temperature for two hours and 15 minutes. 0.093 g of potassium tert-butoxide and 0.098 mL of (bromomethyl)benzene were added to the reaction mixture under ice-cooling, and the resultant was stirred at room temperature for 25 minutes. Water was added to the reaction mixture and the solid was collected by filtration to give 1.4 g of 1-benzyl-7-bromo-5-nitro-1H-indole as a brown solid.

$^1$H-NMR (DMSO-$d_6$) δ: 5.91 (2H, s), 6.93-7.01 (3H, m), 7.21-7.36 (3H, m), 7.84 (1H, d, J=3.2 Hz), 8.14 (1H, d, J=2.2 Hz), 8.65 (1H, d, J=2.2 Hz).

Reference Example 200

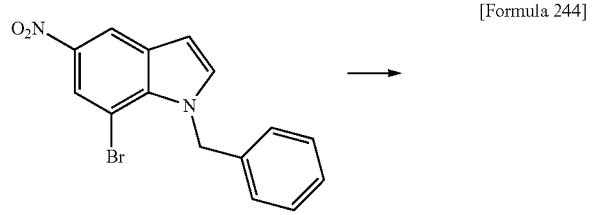

[Formula 244]

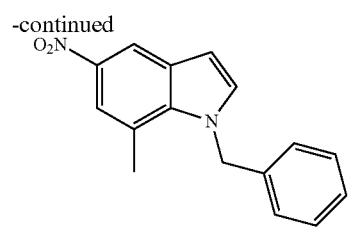

The mixture of 1.4 g of 1-benzyl-7-bromo-5-nitro-1H-indole, 0.50 g of methylboronic acid, 1.8 g of tripotassium phosphate, 0.29 g of bis(di-tert-butyl(4-dimethylaminophenyl)phosphine)dichloropalladium(II), 14 mL of dioxane, and 3.5 mL of water, was stirred at 100° C. for one hour and 40 minutes. The reaction mixture was cooled to room temperature, and ethyl acetate and water were then added thereto. The organic layer was separated and the aqueous layer was extracted with ethyl acetate. The organic layer and the extract were combined, washed with a saturated aqueous sodium chloride solution and dried over anhydrous sodium sulfate, and the solvent was then distilled off under reduced pressure. The obtained residue was purified by silica gel column chromatography (gradient elution with hexane:ethyl acetate=100:0-85:15) to give 0.91 g of 1-benzyl-7-methyl-5-nitro-1H-indole as an orange oil.

$^1$H-NMR (DMSO-$d_6$) δ: 2.53 (3H, s), 5.74 (2H, s), 6.85 (1H, d, J=3.2 Hz), 6.86-6.92 (2H, m), 7.20-7.36 (3H, m), 7.69 (1H, d, J=3.2 Hz), 7.72-7.76 (1H, m), 8.46 (1H, d, J=2.2 Hz).

Reference Example 201

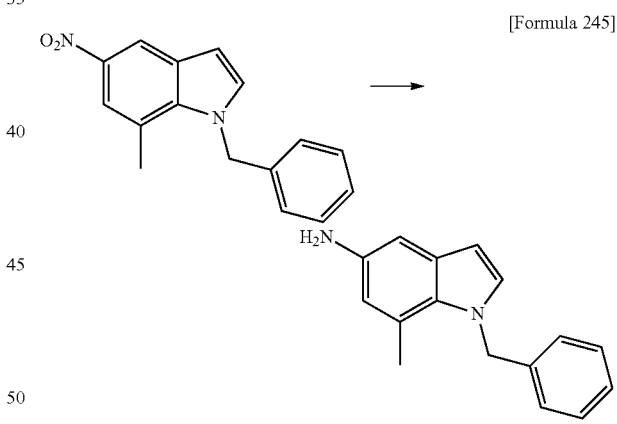

[Formula 245]

The mixture of 0.91 g of 1-benzyl-7-methyl-5-nitro-1H-indole, 0.13 g of ammonium chloride, 0.57 g of iron powder, 7.5 mL of ethanol, and 0.9 mL of water, was heated at reflux for two hours and 30 minutes. 0.19 g of iron powder was added to the reaction mixture, and the resultant was heated at reflux for 30 minutes. After cooling the reaction mixture to room temperature, the insoluble matter was filtered off and the filter cake was washed with ethyl acetate and water. The filtrate and the washings were combined, the organic layer was separated and the aqueous layer was extracted with ethyl acetate. The organic layer and the extract were combined, washed with a saturated aqueous sodium chloride solution and dried over anhydrous sodium sulfate, and the solvent was then distilled off under reduced pressure. The obtained residue was purified by silica gel column chromatography (gradient elution with hexane:ethyl acetate=90:10-60:40) to give 0.55 g of 1-benzyl-7-methyl-1H-indol-5-amine as a brown oil.

¹H-NMR (DMSO-d₆) δ: 2.28 (3H, s), 4.40 (2H, s), 5.49 (2H, s), 6.16-6.20 (2H, m), 6.51-6.55 (1H, m), 6.81-6.87 (2H, m), 7.17-7.23 (2H, m), 7.23-7.30 (2H, m).

MS (ESI, m/z): 237 (M+H)⁺.

Reference Example 202

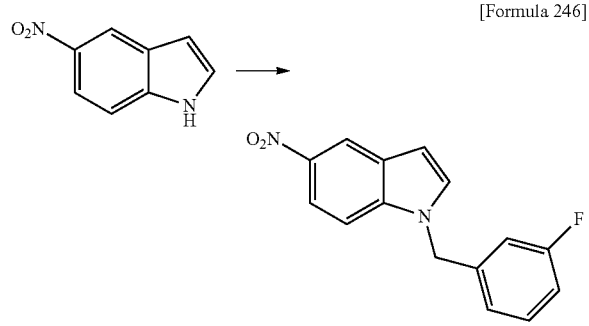

[Formula 246]

To the solution of 20 g of 5-nitro-1H-indole in 100 mL of N,N-dimethylformamide, 15.3 g of potassium tert-butoxide was added at 7° C., and the resultant was stirred for 10 minutes. 16.9 mL of 3-fluorobenzyl bromide was added thereto at 10° C., and the resultant was stirred at room temperature for four hours. 400 mL of water was added to the reaction mixture under ice-cooling and the solid was collected by filtration and washed with water and diisopropyl ether to give 32.3 g of 1-(3-fluorobenzyl)-5-nitro-1H-indole as a brown solid.

¹H-NMR (DMSO-D₆) δ: 5.56 (2H, s), 6.83 (1H, dd, J=3.2, 0.7 Hz), 7.01-7.14 (3H, m), 7.33-7.41 (1H, m), 7.71 (1H, d, J=9.3 Hz), 7.81 (1H, d, J=3.2 Hz), 8.02 (1H, dd, J=9.0, 2.4 Hz), 8.60 (1H, d, J=2.4 Hz).

Reference Example 203

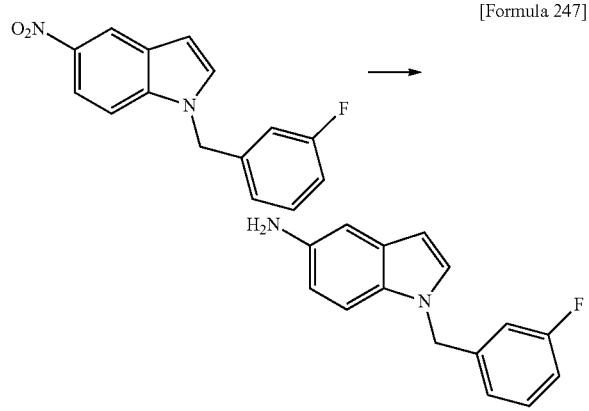

[Formula 247]

The mixture of 32.2 g of 1-(3-fluorobenzyl)-5-nitro-1H-indole, 260 mL of ethanol, 30 mL of water, 4.11 g of ammonium chloride, and 11.8 g of iron powder, was heated at reflux for 30 minutes under a nitrogen atmosphere. 11.8 g of iron powder was added to the reaction mixture, and the resultant was heated at reflux for five hours. After cooling the reaction mixture to room temperature, ethyl acetate and water were added thereto, the insoluble matter was filtered off and the filter cake was washed with ethyl acetate and water. The filtrate and the washings were combined, the organic layer was separated, sequentially washed with water and a saturated aqueous sodium chloride solution and dried over anhydrous magnesium sulfate, and the solvent was distilled off under reduced pressure. Diisopropyl ether, ethyl acetate and cyclohexane were added to the obtained residue and the solid was filtered off to give 20.1 g of 1-(3-fluorobenzyl)-1H-indol-5-amine as a brown solid.

¹H-NMR (CDCl₃) δ: 3.48 (2H, brs), 5.24 (2H, s), 6.37 (1H, dd, J=3.0, 0.9 Hz), 6.63 (1H, dd, J=8.5, 2.2 Hz), 6.73-6.79 (1H, m), 6.84-6.89 (1H, m), 6.90-6.97 (2H, m), 7.02 (1H, d, J=8.5 Hz), 7.04 (1H, d, J=3.2 Hz), 7.20-7.28 (1H, m).

Example 1

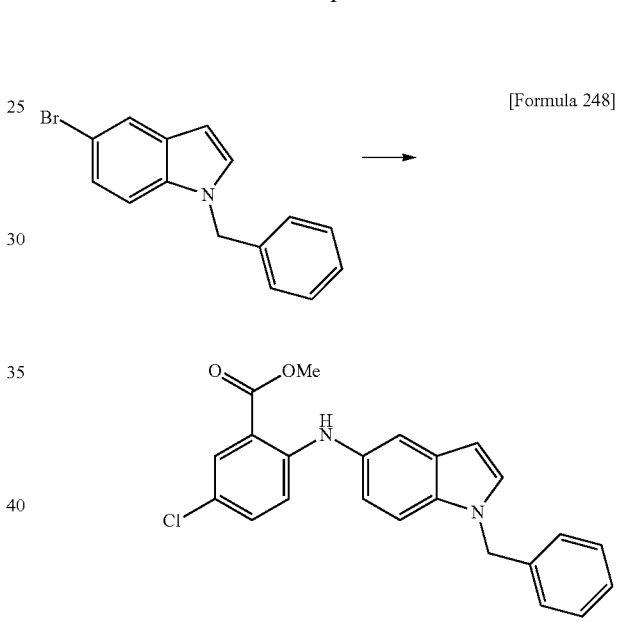

[Formula 248]

The mixture of 1.0 g of 1-benzyl-5-bromo-1H-indole, 0.65 g of methyl 2-amino-5-chlorobenzoate, 39.2 mg of palladium acetate, 202 mg of 4,5'-bis(diphenylphosphino)-9,9'-dimethylxanthene, 2.27 g of cesium carbonate, and 10 mL of toluene, was heated at reflux for four hours under a nitrogen atmosphere. The reaction mixture was cooled to room temperature, and ethyl acetate and water were then added thereto. The organic layer was separated, sequentially washed with water and a saturated aqueous sodium chloride solution and dried over anhydrous magnesium sulfate, and the solvent was distilled off under reduced pressure. The obtained residue was purified by silica gel column chromatography (gradient elution with hexane:ethyl acetate=100:0-80:20) to give 380 mg of methyl 2-((1-benzyl-1H-indol-5-yl)amino)-5-chlorobenzoate as a yellow oil.

¹H-NMR (DMSO-d₆) δ: 3.87 (3H, s), 5.43 (2H, s), 6.47 (1H, d, J=3.3 Hz), 6.90 (1H, d, J=9.2 Hz), 6.99 (1H, dd, J=8.6, 2.0 Hz), 7.19-7.36 (6H, m), 7.44 (1H, d, J=2.0 Hz), 7.49 (1H, d, J=9.2 Hz), 7.56 (1H, d, J=3.3 Hz), 7.80 (1H, d, J=2.6 Hz), 9.22 (1H, s).

Example 2

[Formula 249]

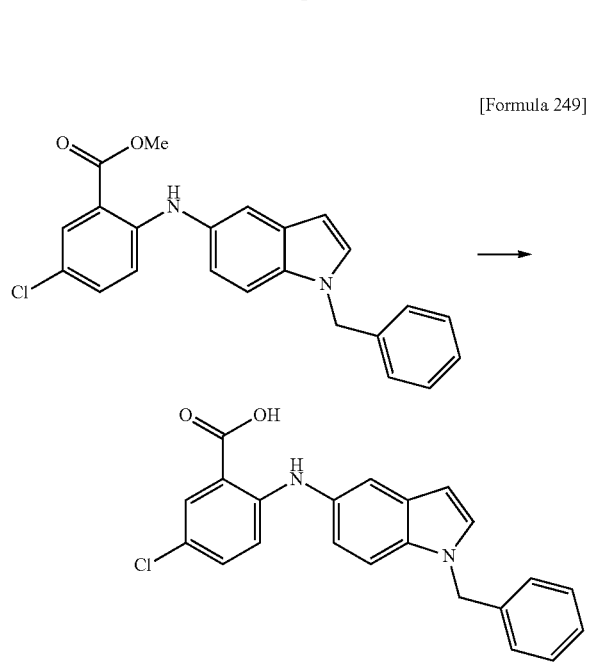

To the solution of 0.38 g of methyl 2-((1-benzyl-1H-indol-5-yl)amino)-5-chlorobenzoate in 2.0 mL of ethanol and 1.0 mL of tetrahydrofuran, 0.39 mL of a 5 mol/L aqueous sodium hydroxide solution was added at room temperature, and the resultant was stirred at room temperature for four hours. Water was added to the reaction mixture, and the resultant was adjusted to pH 2.0 with 2 mol/L hydrochloric acid. The solid was collected by filtration and washed with water and cyclohexane. The obtained solid was purified by silica gel column chromatography (hexane:ethyl acetate=0:100), and cyclohexane was added to the obtained residue, and the solid was collected by filtration to give 0.24 g of 2-((1-benzyl-1H-indol-5-yl)amino)-5-chlorobenzoic acid as a yellow solid.

$^1$H-NMR (DMSO-$d_6$) δ: 5.43 (2H, s), 6.47 (1H, d, J=3.3 Hz), 6.90 (1H, d, J=8.6 Hz), 6.98 (1H, dd, J=8.6, 2.0 Hz), 7.18-7.36 (6H, m), 7.43 (1H, d, J=2.0 Hz), 7.48 (1H, d, J=8.6 Hz), 7.55 (1H, d, J=2.6 Hz), 7.78 (1H, d, J=2.6 Hz), 9.51 (1H, brs).

MS (ESI, m/z): 377 (M+H)$^+$, 375 (M−H)$^-$.

Example 3

[Formula 250]

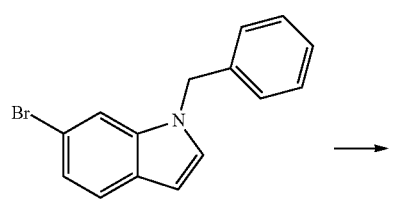

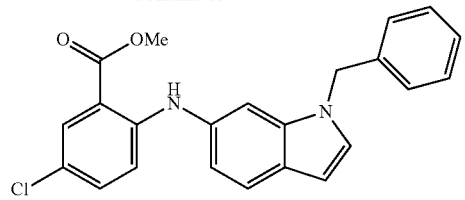

The mixture of 0.3 g of 1-benzyl-6-bromo-1H-indole, 0.2 g of methyl 2-amino-5-chlorobenzoate, 7 mg of palladium acetate, 30.4 mg of 4,5'-bis(diphenylphosphino)-9,9'-dimethylxanthene, 0.68 g of cesium carbonate, and 5 mL of toluene, was heated at reflux for one hour under a nitrogen atmosphere. The reaction mixture was cooled to room temperature and then allowed to stand at room temperature overnight. 7 mg of palladium acetate was added to the reaction mixture, and the resultant was heated at reflux for three hours under a nitrogen atmosphere. The reaction mixture was cooled to room temperature, and ethyl acetate and water were then added thereto. The organic layer was separated and the aqueous layer was extracted with ethyl acetate. The organic layer and the extract were combined, sequentially washed with water and a saturated aqueous sodium chloride solution and dried over anhydrous magnesium sulfate, and the solvent was distilled off under reduced pressure. The obtained residue was purified by silica gel column chromatography (gradient elution with hexane:ethyl acetate=100:0-90:10) to give 0.12 g of methyl 2-((1-benzyl-1H-indol-6-yl)amino)-5-chlorobenzoate as a yellow oil.

$^1$H-NMR (DMSO-$d_6$) δ: 3.86 (3H, s), 5.40 (2H, s), 6.49 (1H, d, J=2.6 Hz), 6.91 (1H, dd, J=8.3, 1.7 Hz), 6.95 (1H, d, J=8.6 Hz), 7.16-7.37 (7H, m), 7.50 (1H, d, J=3.3 Hz), 7.57 (1H, d, J=7.9 Hz), 7.81 (1H, d, J=2.6 Hz), 9.30 (1H, s).

Example 4

[Formula 251]

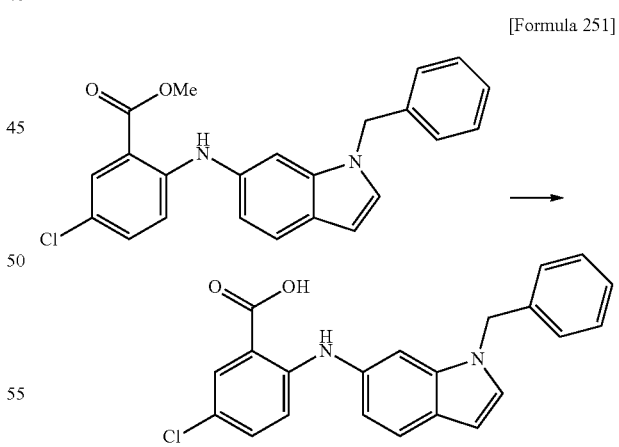

To the solution of 0.11 g of methyl 2-((1-benzyl-1H-indol-6-yl)amino)-5-chlorobenzoate in 2.0 mL of ethanol and 2.0 mL of tetrahydrofuran, 0.11 mL of a 5 mol/L aqueous sodium hydroxide solution was added at room temperature, and the resultant was stirred for one hour. 0.11 mL of a 5 mol/L aqueous sodium hydroxide solution was added thereto, and the resultant was stirred at an external temperature of 40° C. for one hour. After cooling the reaction mixture to room temperature, water was added thereto. The reaction mixture was adjusted to pH 2.0 with 3 mol/L hydrochloric acid. The solid was collected by filtration to give 80 mg of 2-((1-benzyl-1H-indol-6-yl)amino)-5-chlorobenzoic acid as a yellow solid.

¹H-NMR (DMSO-d₆) δ: 5.40 (2H, s), 6.48 (1H, d, J=2.6 Hz), 6.91 (1H, dd, J=8.3, 1.7 Hz), 6.95 (1H, d, J=9.2 Hz), 7.16-7.37 (7H, m), 7.49 (1H, d, J=3.3 Hz), 7.56 (1H, d, J=8.6 Hz), 7.80 (1H, d, J=2.6 Hz), 9.58 (1H, s).

MS (ESI, m/z): 377 (M+H)⁺, 375 (M–H)⁻.

Example 5

[Formula 252]

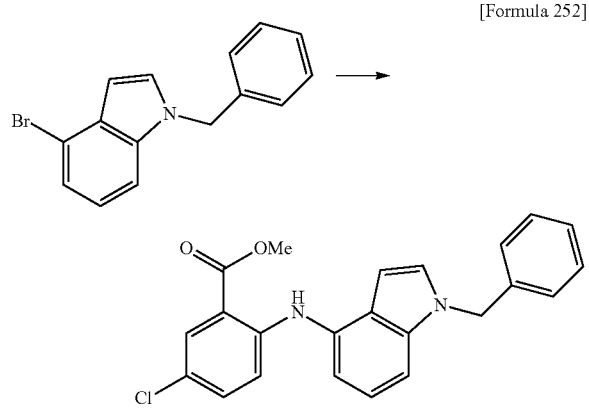

The mixture of 0.2 g of 1-benzyl-4-bromo-1H-indole, 0.13 g of methyl 2-amino-5-chlorobenzoate, 7.9 mg of palladium acetate, 41 mg of 4,5'-bis(diphenylphosphino)-9,9'-dimethylxanthene, 0.46 g of cesium carbonate, and 3 mL of toluene, was heated at reflux for three hours under a nitrogen atmosphere. The reaction mixture was cooled to room temperature, and ethyl acetate and water were then added thereto. The organic layer was separated, sequentially washed with water and a saturated aqueous sodium chloride solution and dried over anhydrous magnesium sulfate, and the solvent was distilled off under reduced pressure. The obtained residue was purified by silica gel column chromatography (gradient elution with hexane:ethyl acetate=100:0-80:20) to give 0.16 g of methyl 2-((1-benzyl-1H-indol-4-yl)amino)-5-chlorobenzoate as a yellow oil.

¹H-NMR (DMSO-d₆) δ: 3.90 (3H, s), 5.44 (2H, s), 6.35 (1H, d, J=2.6 Hz), 7.01 (1H, d, J=7.3 Hz), 7.10 (1H, d, J=7.9 Hz), 7.16 (1H, d, J=9.2 Hz), 7.19-7.36 (6H, m), 7.42 (1H, dd, J=9.2, 2.6 Hz), 7.52 (1H, d, J=3.3 Hz), 7.87 (1H, d, J=2.6 Hz), 9.60 (1H, s).

Example 6

[Formula 253]

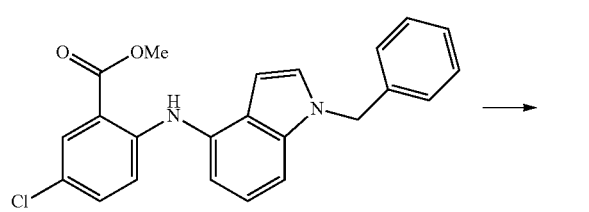

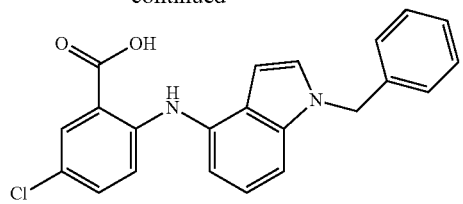

To the solution of 0.15 g of methyl 2-((1-benzyl-1H-indol-4-yl)amino)-5-chlorobenzoate in 2.0 mL of ethanol and 1.0 mL of tetrahydrofuran, 154 μL of a 5 mol/L aqueous sodium hydroxide solution was added at room temperature, and the resultant was stirred at an external temperature of 40 to 50° C. for two hours and 10 minutes. After cooling the reaction mixture to room temperature, water was added thereto. The reaction mixture was adjusted to pH 2.0 with 3 mol/L hydrochloric acid. The solid was collected by filtration to give 0.13 g of 2-((1-benzyl-1H-indol-4-yl)amino)-5-chlorobenzoic acid as a yellow solid.

¹H-NMR (DMSO-d₆) δ: 5.44 (2H, s), 6.35 (1H, d, J=3.3 Hz), 7.02 (1H, d, J=7.3 Hz), 7.06-7.36 (8H, m), 7.40 (1H, dd, J=9.2, 2.6 Hz), 7.51 (1H, d, J=3.3 Hz), 7.86 (1H, d, J=2.6 Hz), 9.93 (1H, s).

MS (ESI, m/z): 377 (M+H)⁺.

Example 7

[Formula 254]

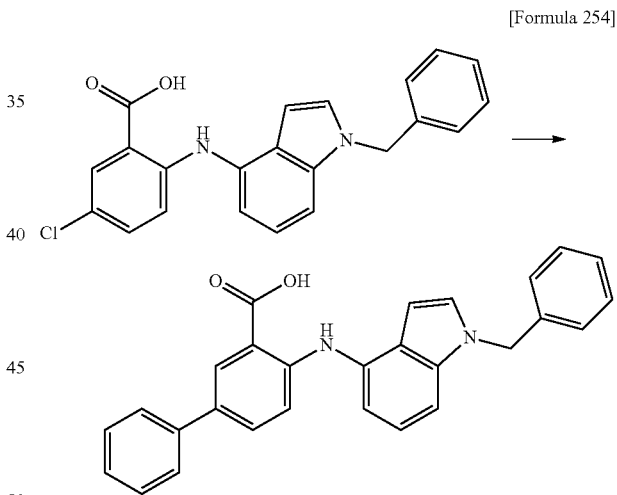

The mixture of 80 mg of 2-((1-benzyl-1H-indol-4-yl)amino)-5-chlorobenzoic acid, 31 mg of phenylboronic acid, 45 mg of sodium carbonate, 4.5 mg of bis(di-tert-butyl(4-dimethylaminophenyl)phosphine)dichloropalladium(II), 1.2 mL of ethylene glycol dimethyl ether, and 0.3 mL of water, was heated at reflux for two hours under a nitrogen atmosphere. 4.5 mg of bis(di-tert-butyl(4-dimethylaminophenyl)phosphine)dichloropalladium(II) was added to the reaction mixture, and the resultant was heated at reflux for five hours under a nitrogen atmosphere. The reaction mixture was cooled to room temperature, and ethyl acetate and water were then added thereto, and the resultant was adjusted to pH 2.0 with 2 mol/L hydrochloric acid. The organic layer was separated, sequentially washed with water and a saturated aqueous sodium chloride solution and dried over anhydrous magnesium sulfate, and the solvent was distilled off under reduced pressure. The obtained residue was purified by silica gel column chromatography (hexane:ethyl acetate=80:20), and cyclohexane was added to the thus obtained residue, and the solid was collected by filtration to give 50 mg of 4-((1-benzyl-1H-indol-4-yl)amino)-[1,1'-biphenyl]-3-carboxylic acid as a yellow solid.

$^1$H-NMR (DMSO-$d_6$) δ: 5.45 (2H, s), 6.42 (1H, d, J=3.3 Hz), 7.04-7.38 (10H, m), 7.39-7.47 (2H, m), 7.52 (1H, d, J=3.3 Hz), 7.58-7.65 (2H, m), 7.73 (1H, dd, J=8.9, 2.3 Hz), 8.21 (1H, d, J=2.6 Hz), 10.06 (1H, s).

MS (ESI/APCI, m/z): 419 (M+H)$^+$, 417 (M−H)$^−$.

Example 8

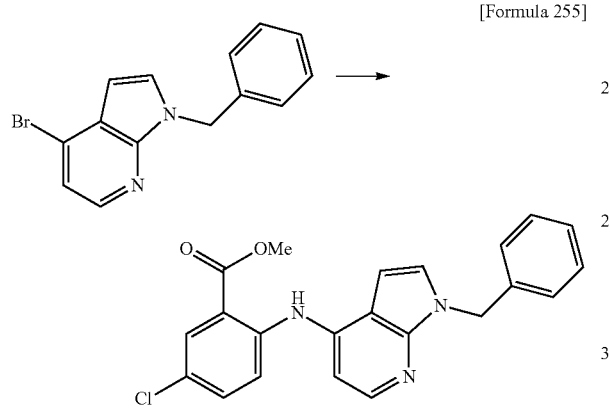

[Formula 255]

The mixture of 0.3 g of 1-benzyl-4-bromo-1H-pyrrolo(2,3-b)pyridine, 0.19 g of methyl 2-amino-5-chlorobenzoate, 11.7 mg of palladium acetate, 60 mg of 4,5'-bis(diphenylphosphino)-9,9'-dimethylxanthene, 0.68 g of cesium carbonate, and 3 mL of toluene, was heated at reflux for four hours under a nitrogen atmosphere. The reaction mixture was cooled to room temperature, and ethyl acetate and water were then added thereto. The organic layer was separated, washed with a saturated aqueous sodium chloride solution and dried over anhydrous magnesium sulfate, and the solvent was distilled off under reduced pressure. The obtained residue was purified by silica gel column chromatography (gradient elution with hexane:ethyl acetate=90:10-50:50) to give 0.33 g of methyl 2-((1-benzyl-1H-pyrrolo(2,3-b)pyridin-4-yl)amino)-5-chlorobenzoate as a pale yellow solid.

$^1$H-NMR (DMSO-$d_6$) δ: 3.87 (3H, s), 5.46 (2H, s), 6.48 (1H, d, J=3.3 Hz), 6.98 (1H, d, J=5.9 Hz), 7.20-7.35 (5H, m), 7.51 (1H, d, J=3.3 Hz), 7.58-7.64 (2H, m), 7.90-7.94 (1H, m), 8.11 (1H, d, J=5.9 Hz), 9.71 (1H, s).

Example 9

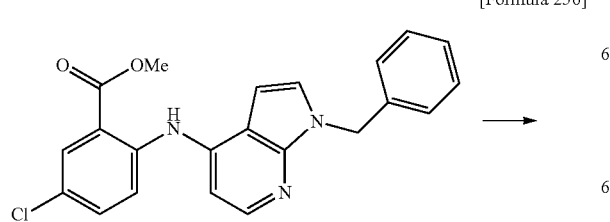

[Formula 256]

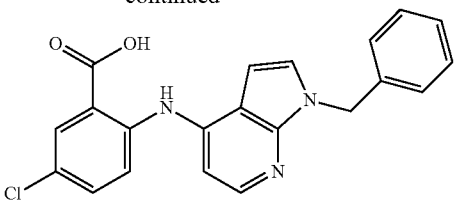

To the solution of 200 mg of methyl 2-((1-benzyl-1H-pyrrolo(2,3-b)pyridin-4-yl)amino)-5-chlorobenzoate in 2.0 mL of ethanol and 1.0 mL of tetrahydrofuran, 204 μL of a 5 mol/L aqueous sodium hydroxide solution was added at room temperature, and the resultant was stirred at room temperature for two hours. Water was added to the reaction mixture, and the resultant was adjusted to pH 2.5 with 2 mol/L hydrochloric acid. The solid was collected by filtration to give 0.14 g of 2-((1-benzyl-1H-pyrrolo(2,3-b)pyridin-4-yl)amino)-5-chlorobenzoic acid as a white solid.

$^1$H-NMR (DMSO-$d_6$) δ: 5.47 (2H, s), 6.47 (1H, d, J=3.3 Hz), 7.04 (1H, d, J=5.3 Hz), 7.20-7.35 (5H, m), 7.52 (1H, d, J=4.0 Hz), 7.55-7.66 (2H, m), 7.93 (1H, d, J=2.0 Hz), 8.12 (1H, d, J=5.9 Hz), 10.24 (1H, s).

MS (ESI/APCI, m/z): 378 (M+H)$^+$, 376 (M−H)$^−$.

Example 10

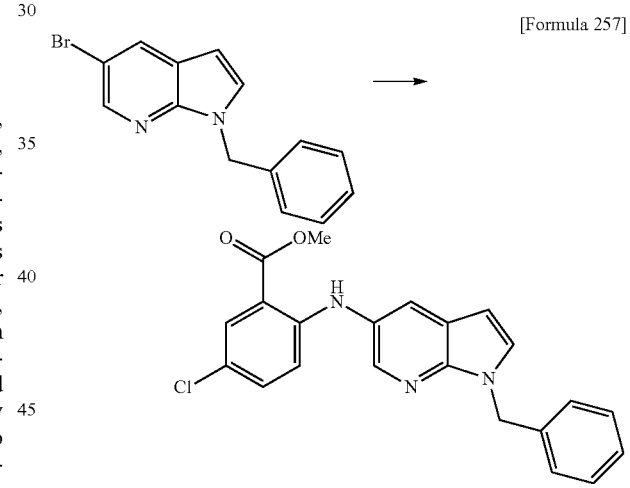

[Formula 257]

The mixture of 0.2 g of 1-benzyl-5-bromo-1H-pyrrolo(2,3-b)pyridine, 0.13 g of methyl 2-amino-5-chlorobenzoate, 7.8 mg of palladium acetate, 40 mg of 4,5'-bis(diphenylphosphino)-9,9'-dimethylxanthene, 0.45 g of cesium carbonate, and 2 mL of toluene, was heated at reflux for five hours under a nitrogen atmosphere. The reaction mixture was cooled to room temperature, and ethyl acetate and water were then added thereto. The organic layer was separated, sequentially washed with water and a saturated aqueous sodium chloride solution and dried over anhydrous magnesium sulfate, and the solvent was distilled off under reduced pressure. The obtained residue was purified by basic silica gel column chromatography (gradient elution with hexane:ethyl acetate=100:0-80:20), and ethanol was added to the thus obtained residue, and the solid was collected by filtration to give 35 mg of methyl 2-((1-benzyl-1H-pyrrolo(2,3-b)pyridin-5-yl)amino)-5-chlorobenzoate as a pale yellow solid.

¹H-NMR (DMSO-d₆) δ: 3.88 (3H, s), 5.49 (2H, s), 6.51 (1H, d, J=3.3 Hz), 6.81 (1H, d, J=9.2 Hz), 7.21-7.38 (6H, m), 7.69 (1H, d, J=4.0 Hz), 7.82 (1H, d, J=2.6 Hz), 7.92 (1H, d, J=2.6 Hz), 8.18 (1H, d, J=2.6 Hz), 9.21 (1H, s).

Example 11

[Formula 258]

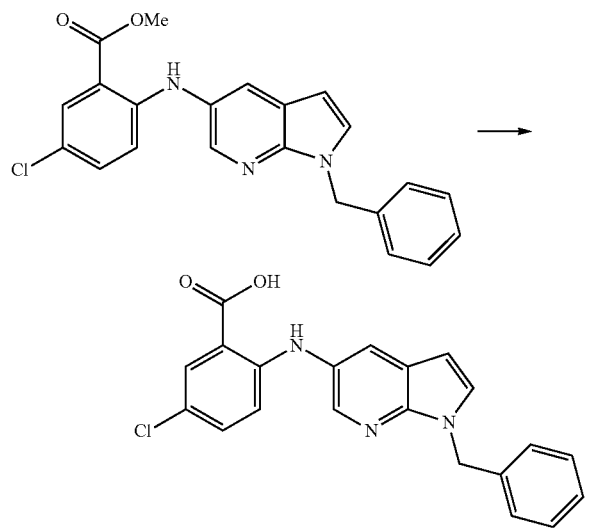

To the solution of 35 mg of methyl 2-((1-benzyl-1H-pyrrolo(2,3-b)pyridin-5-yl)amino)-5-chlorobenzoate in 1.0 mL of ethanol and 1.0 mL of tetrahydrofuran, 36 μL of a 5 mol/L aqueous sodium hydroxide solution was added at room temperature, and the resultant was stirred at room temperature for one hour. 36 μL of a 5 mol/L aqueous sodium hydroxide solution was added thereto at room temperature, and the resultant was stirred at an external temperature of 40° C. for one hour. The reaction mixture was cooled to room temperature, and water was added thereto, and the resultant was adjusted to pH 3.0 with 2 mol/L hydrochloric acid. The solid was collected by filtration to give 25 mg of 2-((1-benzyl-1H-pyrrolo(2,3-b)pyridin-5-yl)amino)-5-chlorobenzoic acid as a pale yellow solid.

¹H-NMR (DMSO-d₆) δ: 5.49 (2H, s), 6.51 (1H, d, J=3.3 Hz), 6.82 (1H, d, J=8.6 Hz), 7.22-7.40 (6H, m), 7.68 (1H, d, J=3.3 Hz), 7.82 (1H, d, J=2.6 Hz), 7.92 (1H, d, J=2.6 Hz), 8.18 (1H, d, J=2.6 Hz), 9.48 (1H, s).

MS (ESI/APCI, m/z): 378 (M+H)⁺, 376 (M−H)⁻.

Example 12

[Formula 259]

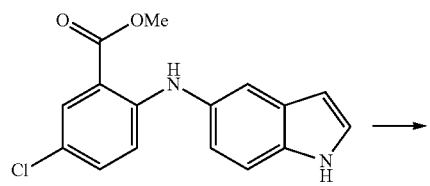

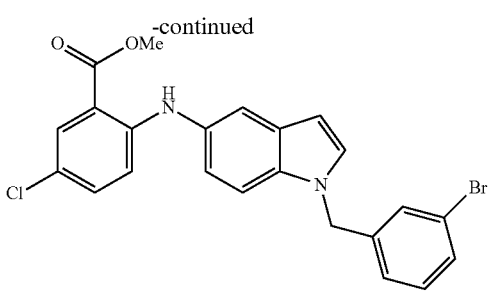

To the solution of 100 mg of methyl 2-((1H-indol-5-yl)amino)-5-chlorobenzoate in 1 mL of N,N-dimethylacetamide, 41 mg of potassium tert-butoxide was added under ice-cooling, and the resultant was stirred for 15 minutes. 92 mg of 1-bromo-3-(bromomethyl)benzene was added to the reaction mixture under ice-cooling, and the resultant was stirred under ice-cooling for one hour. Ethyl acetate and water were added to the reaction mixture, and the resultant was adjusted to pH 2.0 with 2 mol/L hydrochloric acid. The organic layer was separated, sequentially washed with water and a saturated aqueous sodium chloride solution and dried over anhydrous magnesium sulfate, and the solvent was distilled off under reduced pressure. The obtained residue was purified by silica gel column chromatography (gradient elution with hexane:ethyl acetate=90:10-80:20) to give 0.12 g of methyl 2-((1-(3-bromobenzyl)-1H-indol-5-yl)amino)-5-chlorobenzoate as a yellow oil.

¹H-NMR (DMSO-d₆) δ: 3.87 (3H, s), 5.45 (2H, s), 6.49 (1H, d, J=3.3 Hz), 6.91 (1H, d, J=9.2 Hz), 7.00 (1H, dd, J=9.2, 2.0 Hz), 7.18-7.36 (3H, m), 7.42-7.53 (4H, m), 7.58 (1H, d, J=3.3 Hz), 7.80 (1H, d, J=2.6 Hz), 9.23 (1H, s).

Example 13

[Formula 260]

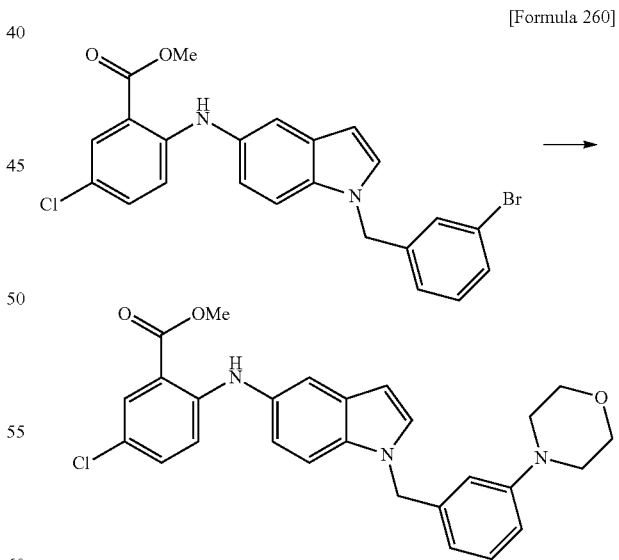

To the solution of 0.12 g of methyl 2-((1-(3-bromobenzyl)-1H-indol-5-yl)amino)-5-chlorobenzoate in 2 mL of toluene, 22.3 μL of morpholine, 2.9 mg of palladium acetate, 14.8 mg of 4,5'-bis(diphenylphosphino)-9,9'-dimethylxanthene and 166 mg of cesium carbonate were added, and the resultant was heated at reflux for four hours under a nitrogen atmosphere. 11.2 μL of morpholine, 11.7 mg of tris(dibenzylideneacetone)dipalladium(0), 12.2 mg of 2-dicyclohexylphosphino-2',4',6'-triisopropylbiphenyl and 83 mg of cesium carbonate were added to the reaction mixture, and the resultant was heated at reflux for three hours under a nitrogen atmosphere. The reaction mixture was cooled to room temperature, and ethyl acetate and water were then added thereto. The organic layer was separated, sequentially washed with water and a saturated aqueous sodium chloride solution and dried over anhydrous magnesium sulfate, and the solvent was distilled off under reduced pressure. The obtained residue was purified by silica gel column chromatography (gradient elution with hexane:ethyl acetate=100:0-80:20) to give 10 mg of methyl 5-chloro-2-((1-(3-morpholinobenzyl)-1H-indol-5-yl)amino)benzoate as a yellow oil.

$^1$H-NMR (CDCl$_3$) δ: 3.06-3.13 (4H, m), 3.79-3.86 (4H, m), 3.90 (3H, s), 5.28 (2H, s), 6.50 (1H, d, J=2.6 Hz), 6.61-6.70 (2H, m), 6.82 (1H, dd, J=8.3, 2.3 Hz), 6.91 (1H, d, J=9.2 Hz), 7.02 (1H, dd, J=8.6, 2.0 Hz), 7.11-7.30 (4H, m), 7.48 (1H, d, J=2.0 Hz), 7.90 (1H, d, J=2.6 Hz), 9.32 (1H, s).

Example 14

[Formula 261]

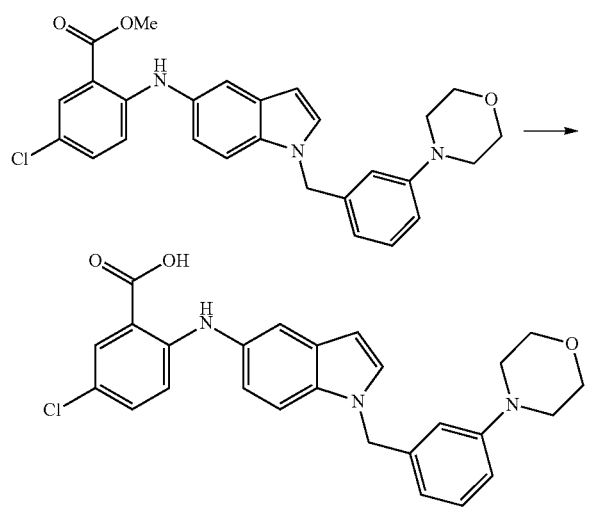

To the solution of 10 mg of methyl 5-chloro-2-((1-(3-morpholinobenzyl)-1H-indol-5-yl)amino)benzoate in 0.5 mL of ethanol and 0.5 mL of tetrahydrofuran, 16.8 μL of a 5 mol/L aqueous sodium hydroxide solution was added at room temperature, and the resultant was stirred at room temperature for four hours. Water was added to the reaction mixture, and the resultant was adjusted to pH 3.0 with 2 mol/L hydrochloric acid. The solid was collected by filtration to give 7.0 mg of 5-chloro-2-((1-(3-morpholinobenzyl)-1H-indol-5-yl)amino)benzoic acid as a pale brown solid.

$^1$H-NMR (DMSO-d$_6$) δ: 3.02-3.10 (4H, m), 3.67-3.76 (4H, m), 5.34 (2H, s), 6.45 (1H, d, J=2.6 Hz), 6.62 (1H, d, J=7.3 Hz), 6.82 (1H, dd, J=8.3, 2.3 Hz), 6.86-6.95 (2H, m), 6.98 (1H, dd, J=8.9, 2.3 Hz), 7.15 (1H, t, J=7.9 Hz), 7.28 (1H, dd, J=9.2, 2.6 Hz), 7.42 (1H, d, J=2.0 Hz), 7.49 (1H, d, J=9.2 Hz), 7.54 (1H, d, J=2.6 Hz), 7.78 (1H, d, J=2.6 Hz)

MS (ESI/APCI, m/z): 460 (M–H)$^-$.

Example 15

[Formula 262]

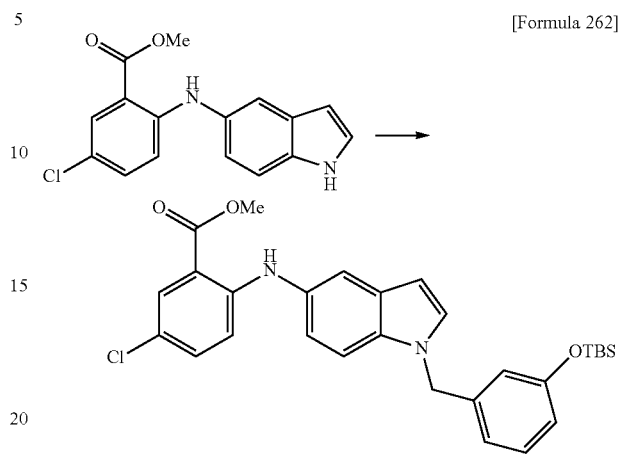

To the solution of 0.4 g of methyl 2-((1H-indol-5-yl)amino)-5-chlorobenzoate in 3 mL of N,N-dimethylacetamide, 164 mg of potassium tert-butoxide was added under ice-cooling, and the resultant was stirred for 10 minutes. The solution of 0.4 g of (3-(bromomethyl)phenoxy)(tert-butyl)dimethylsilane in 1 mL of N,N-dimethylacetamide was added to the reaction mixture under ice-cooling, and the resultant was stirred under ice-cooling for 35 minutes. Ice water and ethyl acetate were added to the reaction mixture, and the resultant was adjusted to pH 2.5 with 2 mol/L hydrochloric acid. The organic layer was separated, sequentially washed with water and a saturated aqueous sodium chloride solution and dried over anhydrous magnesium sulfate, and the solvent was distilled off under reduced pressure. The obtained residue was purified by silica gel column chromatography (gradient elution with hexane:ethyl acetate=100:0-80:20) to give 0.27 g of methyl 2-((1-(3-((tert-butyldimethylsilyl)oxy)benzyl)-1H-indol-5-yl)amino)-5-chlorobenzoate as a yellow oil.

$^1$H-NMR (DMSO-d$_6$) δ: 0.07 (6H, s), 0.87 (9H, s), 3.87 (3H, s), 5.40 (2H, s), 6.48 (1H, d, J=3.3 Hz), 6.53-6.57 (1H, m), 6.71 (1H, dd, J=7.9, 2.0 Hz), 6.82-6.91 (2H, m), 6.98 (1H, dd, J=8.6, 2.0 Hz), 7.19 (1H, t, J=7.9 Hz), 7.31 (1H, dd, J=9.2, 2.6 Hz), 7.42-7.48 (2H, m), 7.54 (1H, d, J=2.6 Hz), 7.80 (1H, d, J=2.6 Hz), 9.23 (1H, s).

Example 16

[Formula 263]

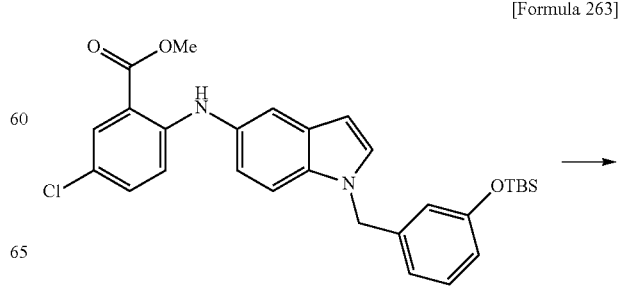

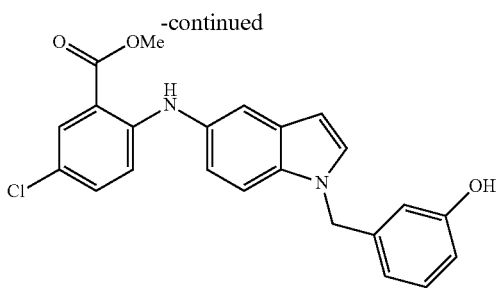

To the solution of 25 mg of methyl 2-((1-(3-((tert-butyldimethylsilyl)oxy)benzyl)-1H-indol-5-yl)amino)-5-chlorobenzoate in 0.5 mL of tetrahydrofuran, 48 pt of a 1.0 mol/L tetrabutylammonium fluoride/tetrahydrofuran solution was added at room temperature, and the resultant was stirred at room temperature for 30 minutes. Water and ethyl acetate were added to the reaction mixture. The organic layer was separated, sequentially washed with water and a saturated aqueous sodium chloride solution and dried over anhydrous magnesium sulfate, and the solvent was distilled off under reduced pressure to give 20 mg of methyl 5-chloro-2-((1-(3-hydroxybenzyl)-1H-indol-5-yl)amino)benzoate as a yellow oil.

$^1$H-NMR (CDCl$_3$) δ: 3.90 (3H, s), 5.25 (2H, s), 6.49 (1H, d, J=2.6 Hz), 6.53-6.57 (1H, m), 6.68-6.78 (2H, m), 6.92 (1H, d, J=9.2 Hz), 7.01 (1H, dd, J=8.6, 2.0 Hz), 7.10-7.24 (4H, m), 7.47 (1H, d, J=2.0 Hz), 7.89 (1H, d, J=2.6 Hz), 9.31 (1H, s).

Example 17

[Formula 264]

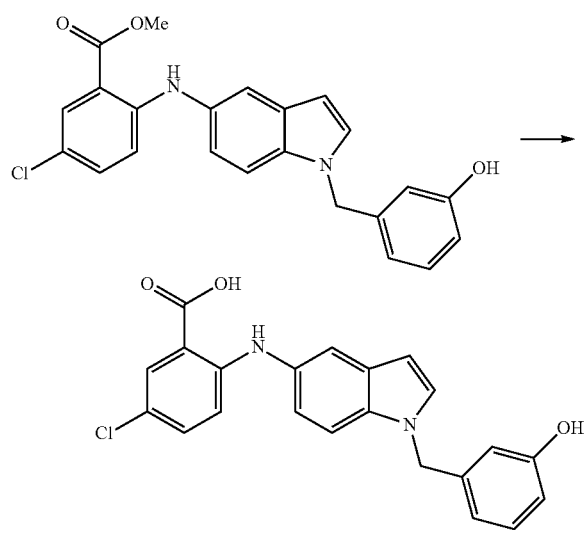

To the solution of 20 mg of methyl 5-chloro-2-((1-(3-hydroxybenzyl)-1H-indol-5-yl)amino)benzoate in 1.0 mL of ethanol, 39 μL of a 5 mol/L aqueous sodium hydroxide solution was added at room temperature, and the resultant was stirred at an external temperature of 40° C. for 15 minutes. 39 μL of a 5 mol/L aqueous sodium hydroxide solution was added thereto, and the resultant was stirred at an external temperature of 50° C. for one hour. The reaction mixture was cooled to room temperature, and water was added thereto, and the resultant was adjusted to pH 2.0 with 2 mol/L hydrochloric acid. The solid was collected by filtration and washed with water and diisopropyl ether to give 10 mg of 5-chloro-2-((1-(3-hydroxybenzyl)-1H-indol-5-yl)amino)benzoic acid as a pale brown solid.

$^1$H-NMR (DMSO-d$_6$) δ: 5.34 (2H, s), 6.46 (1H, d, J=3.3 Hz), 6.52-6.57 (1H, m), 6.60-6.70 (2H, m), 6.91 (1H, d, J=9.2 Hz), 6.99 (1H, dd, J=8.6, 2.0 Hz), 7.11 (1H, t, J=7.6 Hz), 7.30 (1H, dd, J=8.6, 2.6 Hz), 7.40-7.47 (2H, m), 7.51 (1H, d, J=3.3 Hz), 7.79 (1H, d, J=2.6 Hz), 9.38 (1H, s), 9.51 (1H, brs)

MS (ESI/APCI, m/z): 393 (M+H)$^+$, 391 (M−H)$^−$.

Example 18

[Formula 265]

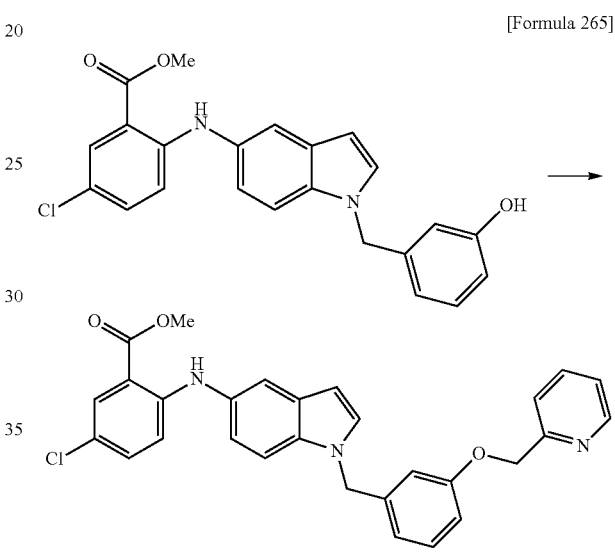

To the solution of 100 mg of methyl 5-chloro-2-((1-(3-hydroxybenzyl)-1H-indol-5-yl)amino)benzoate in 1 mL of N,N-dimethylacetamide, 85 mg of potassium carbonate and 48.4 mg of 2-(chloromethyl)pyridine hydrochloride were added, and the resultant was stirred at an external temperature of 60 to 80° C. for one hour and then stirred at an external temperature of 100 to 110° C. for three hours. The reaction mixture was cooled to room temperature, and ethyl acetate and water were then added thereto. The organic layer was separated and the aqueous layer was extracted with ethyl acetate. The organic layer and the extract were combined, sequentially washed with water and a saturated aqueous sodium chloride solution and dried over anhydrous magnesium sulfate, and the solvent was distilled off under reduced pressure. The obtained residue was purified by silica gel column chromatography (gradient elution with hexane: ethyl acetate=90:10-70:30) to give 90 mg of methyl 5-chloro-2-((1-(3-(pyridin-2-ylmethoxy)benzyl)-1H-indol-5-yl)amino)benzoate as a pale brown oil.

$^1$H-NMR (DMSO-d$_6$) δ: 3.87 (3H, s), 5.12 (2H, s), 5.39 (2H, s), 6.47 (1H, d, J=2.6 Hz), 6.81 (1H, d, J=7.9 Hz), 6.87-6.95 (3H, m), 6.98 (1H, dd, J=8.6, 2.0 Hz), 7.19-7.28 (1H, m), 7.29-7.36 (2H, m), 7.41-7.50 (3H, m), 7.55 (1H, d, J=3.3 Hz), 7.76-7.84 (2H, m), 8.53-8.58 (1H, m), 9.22 (1H, s).

Example 19

[Formula 266]

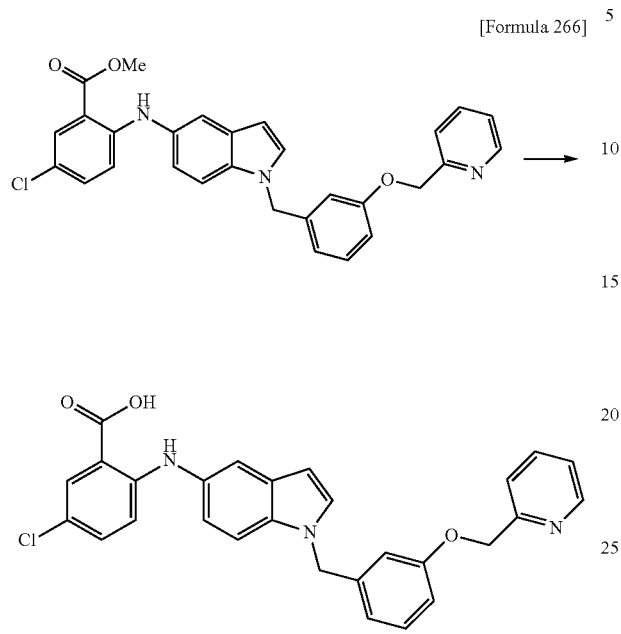

To the solution of 80 mg of methyl 5-chloro-2-((1-(3-(pyridin-2-ylmethoxy)benzyl)-1H-indol-5-yl)amino)benzoate in 2.0 mL of ethanol and 0.5 mL of tetrahydrofuran, 64 µL of a 5 mol/L aqueous sodium hydroxide solution was added at room temperature, and the resultant was stirred at room temperature for one hour. 64 µL of a 5 mol/L aqueous sodium hydroxide solution was added thereto, and the resultant was stirred at an external temperature of 45 to 50° C. for four hours. The reaction mixture was cooled to room temperature, and water was added thereto, and the resultant was adjusted to pH 2.8 with 2 mol/L hydrochloric acid. The solid was collected by filtration to give 70 mg of 5-chloro-2-((1-(3-(pyridin-2-ylmethoxy)benzyl)-1H-indol-5-yl)amino)benzoic acid as a yellow solid.

$^1$H-NMR (DMSO-$d_6$) δ: 5.12 (2H, s), 5.39 (2H, s), 6.46 (1H, d, J=3.3 Hz), 6.81 (1H, d, J=7.3 Hz), 6.87-6.95 (3H, m), 6.97 (1H, dd, J=8.6, 2.0 Hz), 7.18-7.36 (3H, m), 7.41-7.49 (3H, m), 7.53 (1H, d, J=3.3 Hz), 7.75-7.85 (2H, m), 8.55 (1H, d, J=4.0 Hz), 9.48 (1H, s).

MS (ESI/APCI, m/z): 484 (M+H)$^+$, 482 (M–H)$^-$.

Example 20

[Formula 267]

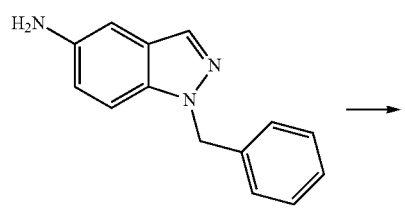

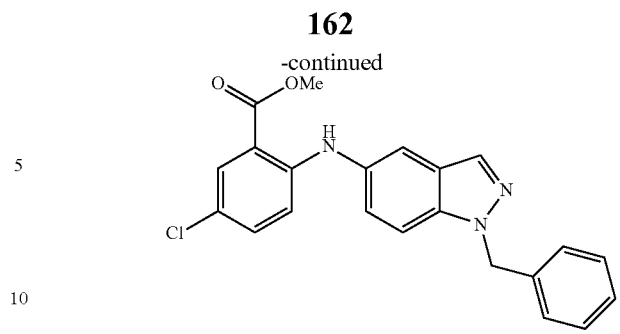

The mixture of 179 mg of 1-benzyl-1H-indazol-5-amine, 200 mg of methyl 2-bromo-5-chlorobenzoate, 36.6 mg of tris(dibenzylideneacetone)dipalladium(0), 46.3 mg of 4,5'-bis(diphenylphosphino)-9,9'-dimethylxanthene, 0.52 g of cesium carbonate, and 2 mL of toluene, was stirred at an external temperature of 110 to 120° C. for three hours and 30 minutes under a nitrogen atmosphere. The reaction mixture was cooled to room temperature, and ethyl acetate and water were then added thereto. The organic layer was separated, washed with a saturated aqueous sodium chloride solution and dried over anhydrous magnesium sulfate, and the solvent was distilled off under reduced pressure. The obtained residue was purified by silica gel column chromatography (gradient elution with hexane:ethyl acetate=100:0-70:30) to give 156 mg of methyl 2-((1-benzyl-1H-indazol-5-yl)amino)-5-chlorobenzoate as a yellow solid.

$^1$H-NMR (DMSO-$d_6$) δ: 3.87 (3H, s), 5.67 (2H, s), 6.96 (1H, d, J=9.2 Hz), 7.22-7.40 (7H, m), 7.65 (1H, d, J=2.0 Hz), 7.74 (1H, d, J=9.2 Hz), 7.82 (1H, d, J=2.6 Hz), 8.07 (1H, s), 9.26 (1H, s).

Example 21

[Formula 268]

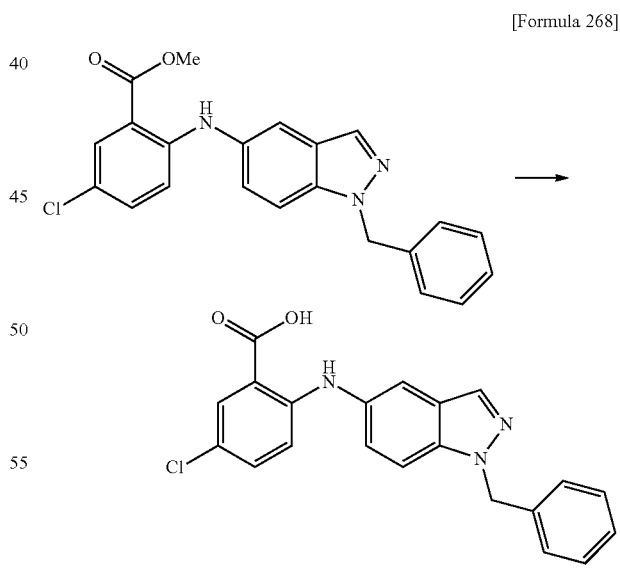

To the solution of 124 mg of methyl 2-((1-benzyl-1H-indazol-5-yl)amino)-5-chlorobenzoate in 1 mL of ethanol and 1 mL of tetrahydrofuran, 127 µL of a 5 mol/L aqueous sodium hydroxide solution was added at room temperature, and the resultant was stirred at room temperature for seven hours. Water was added to the reaction mixture, and the resultant was adjusted to pH 2.0 with 2 mol/L hydrochloric acid. The solid was collected by filtration and washed with water and methyl tert-butyl ether to give 85 mg of 2-((1-benzyl-1H-indazol-5-yl)amino)-5-chlorobenzoic acid as a pale yellow solid.

$^1$H-NMR (DMSO-$d_6$) δ: 5.66 (2H, s), 6.97 (1H, d, J=9.2 Hz), 7.21-7.38 (7H, m), 7.64 (1H, d, J=1.3 Hz), 7.73 (1H, d, J=9.2 Hz), 7.81 (1H, d, J=2.6 Hz), 8.06 (1H, s), 9.55 (1H, s).

MS (ESI/APCI, m/z): 378 (M+H)$^+$, 376 (M−H)$^−$.

Example 22

[Formula 269]

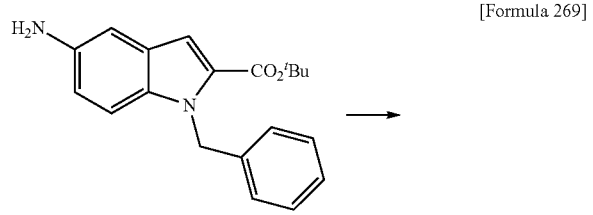

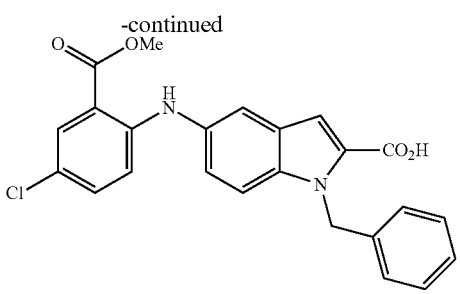

By the method similar to that of Example 20, tert-butyl 1-benzyl-5-((4-chloro-2-(methoxycarbonyl)phenyl)amino)-1H-indole-2-carboxylate was obtained from tert-butyl 5-amino-1-benzyl-1H-indole-2-carboxylate and methyl 2-bromo-5-chlorobenzoate.

$^1$H-NMR (DMSO-$d_6$) δ: 1.50 (9H, s), 3.87 (3H, s), 5.84 (2H, s), 6.97 (1H, d, J=9.2 Hz), 7.01-7.07 (2H, m), 7.17-7.33 (5H, m), 7.36 (1H, dd, J=9.2, 2.6 Hz), 7.57-7.63 (2H, m), 7.82 (1H, d, J=2.6 Hz), 9.27 (1H, s).

Example 23

[Formula 270]

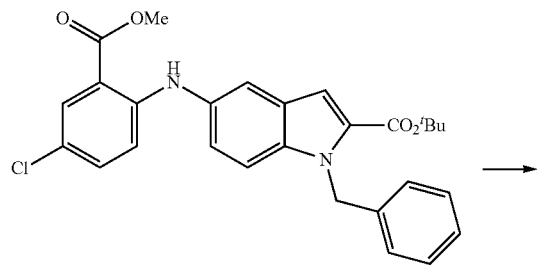

To the solution of 0.51 g of tert-butyl 1-benzyl-5-((4-chloro-2-(methoxycarbonyl)phenyl)amino)-1H-indole-2-carboxylate in 2 mL of methylene chloride, 2 mL of trifluoroacetic acid was added at room temperature, and the resultant was stirred at room temperature for two hours. The solvent was distilled off under reduced pressure, and ethyl acetate and cyclohexane were added to the obtained residue. The solid was collected by filtration to give 0.39 g of 1-benzyl-5-((4-chloro-2-(methoxycarbonyl)phenyl)amino)-1H-indole-2-carboxylic acid as a yellow solid.

$^1$H-NMR (DMSO-$d_6$) δ: 3.87 (3H, s), 5.89 (2H, s), 6.97 (1H, d, J=9.2 Hz), 7.03-7.09 (2H, m), 7.15-7.32 (5H, m), 7.37 (1H, dd, J=9.2, 2.6 Hz), 7.55-7.62 (2H, m), 7.81 (1H, d, J=2.6 Hz), 9.25 (1H, s).

MS (ESI/APCI, m/z): 435 (M+H)$^+$, 433 (M−H)$^−$.

Example 24

[Formula 271]

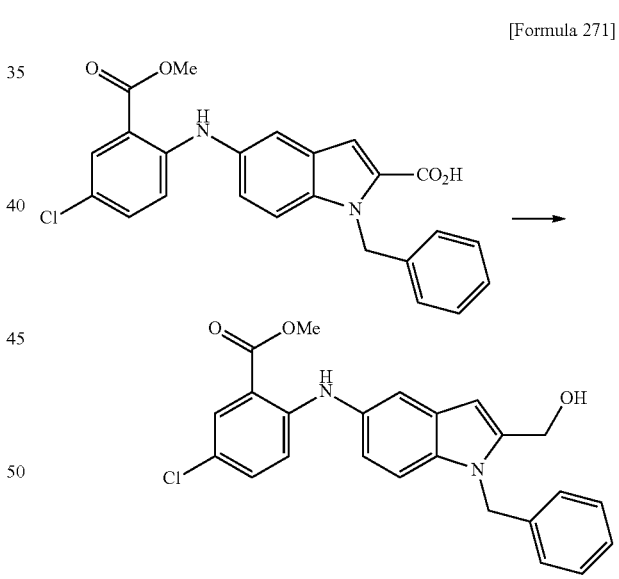

To the solution of 60 mg of 1-benzyl-5-((4-chloro-2-(methoxycarbonyl)phenyl)amino)-1H-indole-2-carboxylic acid in 2 mL of tetrahydrofuran, 21 μL of triethylamine and 20 μL of isobutyl chloroformate were added under ice-cooling, and the resultant was stirred for 30 minutes. 5.2 mg of sodium borohydride was added to the reaction mixture under ice-cooling, and the resultant was stirred for 30 minutes. 10.4 mg of sodium borohydride and several drops of water were added to the reaction mixture under ice-cooling and the resultant was stirred for 30 minutes. 10.4 mg of sodium borohydride was added to the reaction mixture under ice-cooling, and the resultant was stirred for 30 minutes. Ethyl acetate and water were added to the reaction mixture. The organic layer was separated and the aqueous layer was extracted with ethyl acetate. The organic layer and the extract were combined, sequentially washed with water and a saturated aqueous sodium chloride solution and dried over anhydrous magnesium sulfate, and the solvent was distilled off under reduced pressure. The obtained residue was purified by silica gel column chromatography (gradient elution with hexane:ethyl acetate=90:10-60:40) to give 41 mg of methyl 2-((1-benzyl-2-(hydroxymethyl)-1H-indol-5-yl)amino)-5-chlorobenzoate as a pale yellow solid.

$^1$H-NMR (DMSO-d$_6$) δ: 3.87 (3H, s), 4.60 (2H, d, J=5.3 Hz), 5.36 (1H, t, J=5.3 Hz), 5.49 (2H, s), 6.45 (1H, s), 6.90 (1H, d, J=9.2 Hz), 6.95 dd, J=8.6, 2.0 Hz), 7.05-7.11 (2H, m), 7.19-7.39 (5H, m), 7.41 (1H, d, J=1.3 Hz), 7.80 (1H, d, J=2.6 Hz), 9.22 (1H, s).

Example 25

[Formula 272]

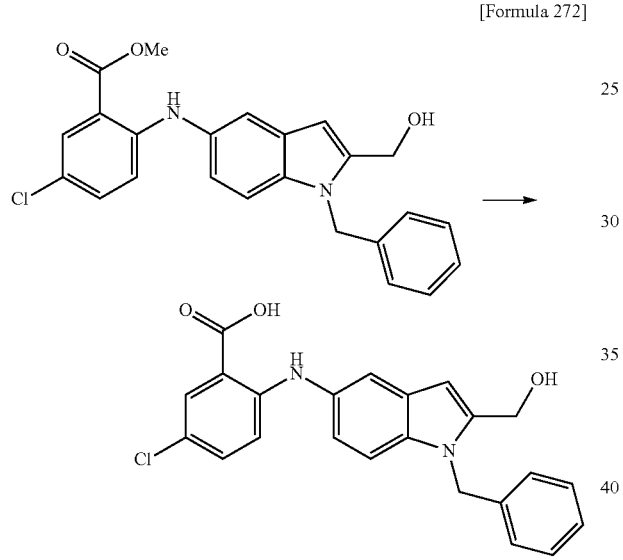

By the method similar to that of Example 6, 2-((1-benzyl-2-(hydroxymethyl)-1H-indol-5-yl)amino)-5-chlorobenzoic acid was obtained from methyl 2-((1-benzyl-2-(hydroxymethyl)-1H-indol-5-yl)amino)-5-chlorobenzoate.

$^1$H-NMR (DMSO-d$_6$) δ: 4.60 (2H, d, J=5.3 Hz), 5.36 (1H, t, J=5.6 Hz), 5.48 (2H, s), 6.44 (1H, s), 6.91 (1H, d, J=9.2 Hz), 6.95 (1H, dd, J=8.6, 2.0 Hz), 7.04-7.11 (2H, m), 7.19-7.38 (5H, m), 7.41 (1H, d, J=1.3 Hz), 7.78 (1H, d, J=2.6 Hz), 9.49 (1H, s).

Example 26

[Formula 273]

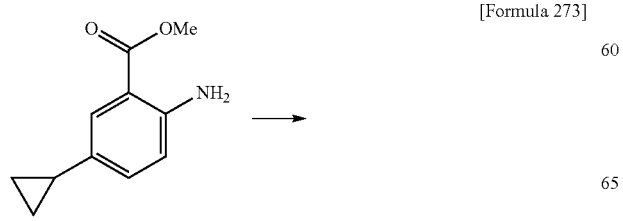

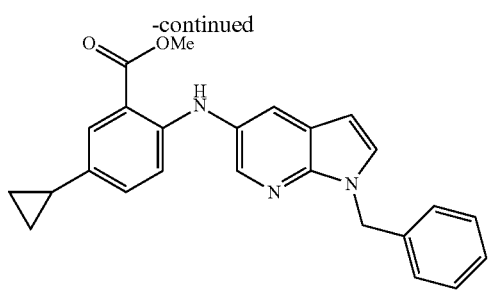

The mixture of 126 mg of methyl 2-amino-5-cyclopropylbenzoate, 157 mg of 1-benzyl-5-bromo-1H-pyrrolo(2,3-b)pyridine, 25.1 mg of tris(dibenzylideneacetone)dipalladium(0), 31.7 mg of 4,5'-bis(diphenylphosphino)-9,9'-dimethylxanthene, 0.36 g of cesium carbonate, and 2 mL of toluene, was heated at reflux in a sealed tube for five hours under a nitrogen atmosphere. The reaction mixture was cooled to room temperature, and ethyl acetate and water were then added thereto. The organic layer was separated, sequentially washed with water and a saturated aqueous sodium chloride solution and dried over anhydrous magnesium sulfate, and the solvent was distilled off under reduced pressure. The obtained residue was purified by silica gel column chromatography (gradient elution with hexane:ethyl acetate=100:0-70:30) to give 38 mg of methyl 2-((1-benzyl-1H-pyrrolo(2,3-b)pyridin-5-yl)amino)-5-cyclopropylbenzoate as a pale brown oil.

$^1$H-NMR (DMSO-d$_6$) δ: 0.50-0.58 (2H, m), 0.82-0.90 (2H, m), 1.80-1.91 (1H, m), 3.86 (3H, s), 5.48 (2H, s), 6.49 (1H, d, J=4.0 Hz), 6.78 (1H, d, J=8.6 Hz), 7.07 (1H, dd, J=8.9, 2.3 Hz), 7.21-7.36 (5H, m), 7.62 (1H, d, J=2.6 Hz), 7.66 (1H, d, J=3.3 Hz), 7.87 (1H, d, J=2.0 Hz), 8.15 (1H, d, J=2.0 Hz), 9.07 (1H, s).

Example 27

[Formula 274]

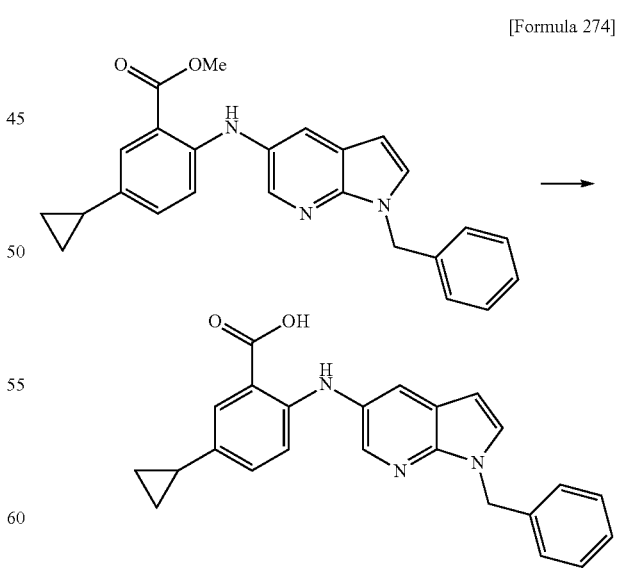

To the solution of 34 mg of methyl 2-((1-benzyl-1H-pyrrolo(2,3-b)pyridin-5-yl)amino)-5-cyclopropylbenzoate in 0.5 mL of ethanol and 0.5 mL of tetrahydrofuran, 34 µL of a 5 mol/L aqueous sodium hydroxide solution was added at room temperature, and the resultant was stirred at an external temperature of 40 to 50° C. for four hours. After cooling the reaction mixture to room temperature, and water was added thereto, and the resultant was adjusted to pH 3.0 with 2 mol/L hydrochloric acid, and ethyl acetate was added thereto. The organic layer was separated, sequentially washed with water and a saturated aqueous sodium chloride solution and dried over anhydrous magnesium sulfate, and the solvent was distilled off under reduced pressure. Cyclohexane was added to the obtained residue. The solid was collected by filtration to give 20 mg of 2-((1-benzyl-1H-pyrrolo(2,3-b)pyridin-5-yl)amino)-5-cyclopropylbenzoic acid as a pale brown solid.

$^1$H-NMR (DMSO-d$_6$) δ: 0.50-0.58 (2H, m), 0.81-0.90 (2H, m), 1.79-1.90 (1H, m), 5.48 (2H, s), 6.48 (1H, d, J=3.3 Hz), 6.78 (1H, d, J=8.6 Hz), 7.05 (1H, dd, J=8.9, 2.3 Hz), 7.21-7.36 (5H, m), 7.62 (1H, d, J=2.0 Hz), 7.65 (1H, d, J=3.3 Hz), 7.87 (1H, d, J=2.6 Hz), 8.15 (1H, d, J=2.0 Hz), 9.33 (1H, s), 12.96 (1H, brs).

Example 28

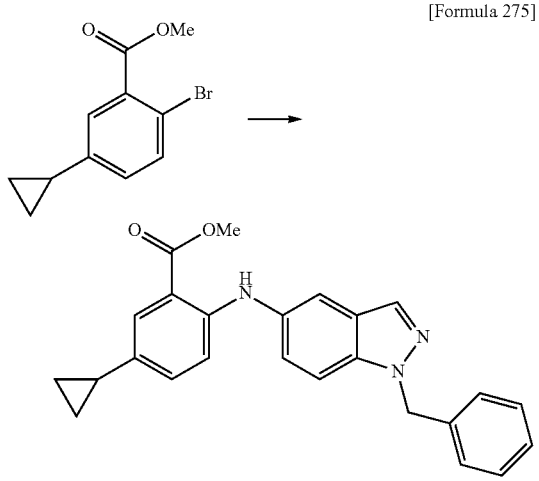

[Formula 275]

The mixture of 200 mg of methyl 2-bromo-5-cyclopropylbenzoate, 175 mg of 1-benzyl-1H-indazol-5-amine, 35.9 mg of tris(dibenzylideneacetone)dipalladium(0), 45.3 mg of 4,5'-bis(diphenylphosphino)-9,9'-dimethylxanthene, 0.51 g of cesium carbonate, and 2 mL of toluene, was heated at reflux in a sealed tube for two hours and 30 minutes under a nitrogen atmosphere. The reaction mixture was cooled to room temperature, and ethyl acetate and water were then added thereto. The organic layer was separated, sequentially washed with water and a saturated aqueous sodium chloride solution and dried over anhydrous magnesium sulfate, and the solvent was distilled off under reduced pressure. The obtained residue was purified by silica gel column chromatography (gradient elution with hexane:ethyl acetate=90:10-70:30) to give 230 mg of methyl 2-((1-benzyl-1H-indazol-5-yl)amino)-5-cyclopropylbenzoate as a pale brown oil.

$^1$H-NMR (CDCl$_3$) δ: 0.56-0.64 (2H, m), 0.83-0.92 (2H, m), 1.76-1.88 (1H, m), 3.90 (3H, s), 5.59 (2H, s), 6.94-7.06 (2H, m), 7.18-7.36 (7H, m), 7.54-7.57 (1H, m), 7.70 (1H, d, J=2.0 Hz), 7.97 (1H, s), 9.25 (1H, s).

Example 29

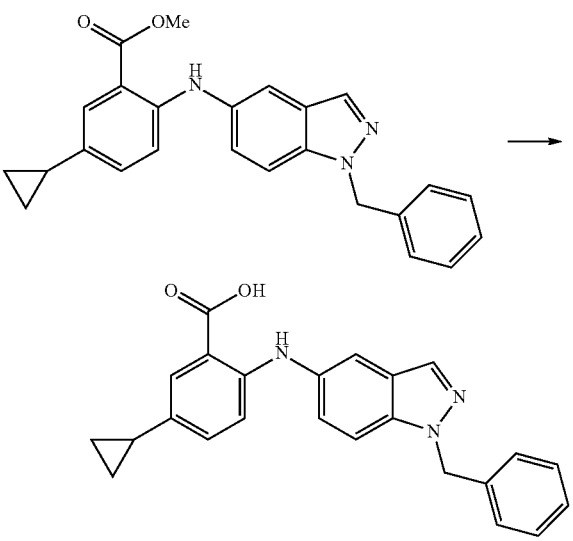

[Formula 276]

To the solution of 220 mg of methyl 2-((1-benzyl-1H-indazol-5-yl)amino)-5-cyclopropylbenzoate in 1 mL of ethanol and 1 mL of tetrahydrofuran, 222 μL of a 5 mol/L aqueous sodium hydroxide solution was added at room temperature, and the resultant was stirred at an external temperature of 40 to 50° C. for four hours. After cooling the reaction mixture to room temperature, and water was added thereto, the resultant was adjusted to pH 2.0 with 2 mol/L hydrochloric acid, and ethyl acetate was added thereto. The organic layer was separated, sequentially washed with water and a saturated aqueous sodium chloride solution and dried over anhydrous magnesium sulfate, and the solvent was distilled off under reduced pressure. Ethyl acetate and cyclohexane were added to the obtained residue and the solid was collected by filtration. Methanol was added to the thus obtained solid. The solid was collected by filtration to give 80 mg of 2-((1-benzyl-1H-indazol-5-yl)amino)-5-cyclopropylbenzoic acid as a pale yellow solid.

$^1$H-NMR (DMSO-d$_6$) δ: 0.50-0.59 (2H, m), 0.81-0.91 (2H, m), 1.79-1.91 (1H, m), 5.65 (2H, s), 6.96 (1H, d, J=8.6 Hz), 7.07 (1H, dd, J=8.6, 2.0 Hz), 7.20-7.36 (6H, m), 7.58 (1H, d, J=1.3 Hz), 7.62 (1H, d, J=2.0 Hz), 7.69 (1H, d, J=9.2 Hz), 8.03 (1H, s), 9.40 (1H, s), 12.97 (1H, brs).

Example 30

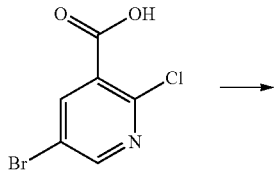

[Formula 277]

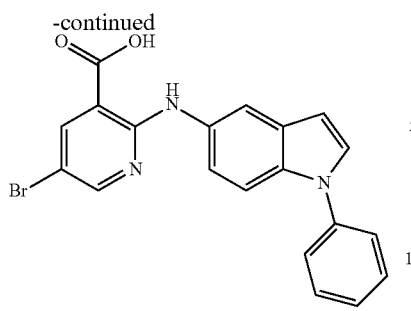

To the solution of 200 mg of 5-bromo-2-chloronicotinic acid in 2 mL of acetic acid, 176 mg of 1-phenyl-1H-indol-5-amine was added, and the resultant was stirred in a sealed tube at an external temperature of 140 to 150° C. for four hours. The reaction mixture was cooled to room temperature, and ethyl acetate and cyclohexane were then added thereto. The insoluble matter was filtered off, and ethyl acetate and water were added to the filtrate. The organic layer was separated, sequentially washed with water and a saturated aqueous sodium chloride solution and dried over anhydrous magnesium sulfate, and the solvent was distilled off under reduced pressure. The obtained residue was purified by silica gel column chromatography (gradient elution with hexane:ethyl acetate=50:50-0:100), and cyclohexane was added to the thus obtained residue, and the solid was collected by filtration to give 15 mg of 5-bromo-2-((1-phenyl-1H-indol-5-yl)amino)nicotinic acid as a pale brown solid.

$^1$H-NMR (DMSO-d$_6$) δ: 6.68 (1H, d, J=3.3 Hz), 7.28 (1H, dd, J=8.6, 2.0 Hz), 7.36-7.44 (1H, m), 7.51-7.64 (5H, m), 7.66 (1H, d, J=3.3 Hz), 8.06 (1H, d, J=2.0 Hz), 8.28 (1H, d, J=2.6 Hz), 8.45 (1H, d, J=2.6 Hz), 10.35 (1H, s).

Example 31

[Formula 278]

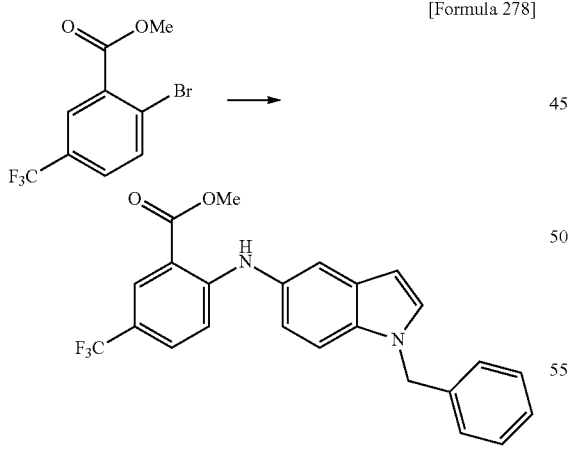

The mixture of 19 mg of methyl 2-bromo-5-(trifluoromethyl)benzoate, 15 mg of 1-benzyl-1H-indol-5-amine, 6.2 mg of tris(dibenzylideneacetone)dipalladium(0), 7.8 mg of 4,5'-bis(diphenylphosphino)-9,9'-dimethylxanthene, 44 mg of cesium carbonate, and 2.5 mL of toluene, was stirred at 150° C. for 30 minutes under a nitrogen atmosphere using microwave equipment. The reaction mixture was cooled to room temperature, and ethyl acetate and water were then added thereto. The organic layer was separated, sequentially washed with water and a saturated aqueous sodium chloride solution and dried over anhydrous magnesium sulfate, and the solvent was distilled off under reduced pressure. The obtained residue was purified by silica gel column chromatography (gradient elution with hexane:ethyl acetate=100:0-80:20) to give 26 mg of methyl 2-((1-benzyl-1H-indol-5-yl)amino)-5-(trifluoromethyl)benzoate as a pale brown oil.

$^1$H-NMR (DMSO-d$_6$) δ: 3.90 (3H, s), 5.45 (2H, s), 6.50 (1H, d, J=2.6 Hz), 6.96 (1H, d, J=8.6 Hz), 7.03 (1H, dd, J=8.6, 2.0 Hz), 7.20-7.37 (5H, m), 7.47-7.62 (4H, m), 8.08-8.13 (1H, m), 9.60 (1H, s).

Example 32

[Formula 279]

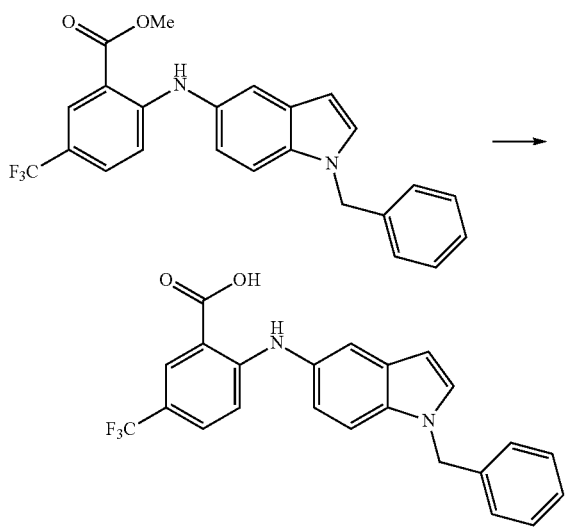

To the solution of 25 mg of methyl 2-((1-benzyl-1H-indol-5-yl)amino)-5-(trifluoromethyl)benzoate in 0.5 mL of ethanol and 0.5 mL of tetrahydrofuran, 24 μL of a 5 mol/L aqueous sodium hydroxide solution was added at room temperature, and the resultant was stirred at an external temperature of 40 to 50° C. for two hours. Water was added to the reaction mixture, and the resultant was adjusted to pH 2.0 with 2 mol/L hydrochloric acid. The solid was collected by filtration to give 20 mg of 2-((1-benzyl-1H-indol-5-yl)amino)-5-(trifluoromethyl)benzoic acid as a pale yellow solid.

$^1$H-NMR (DMSO-d$_6$) δ: 5.45 (2H, s), 6.49 (1H, d, J=3.3 Hz), 6.96 (1H, d, J=8.6 Hz), 7.03 (1H, dd, J=8.9, 2.3 Hz), 7.21-7.37 (5H, m), 7.47-7.60 (4H, m), 8.10 (1H, d, J=2.0 Hz), 9.88 (1H, s).

Example 33

[Formula 280]

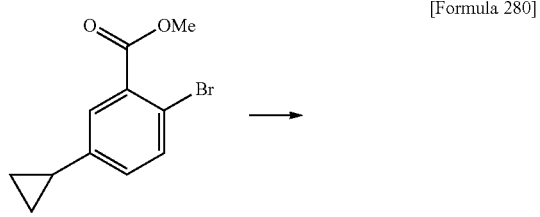

-continued

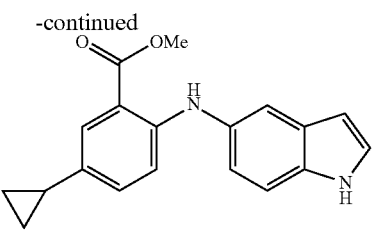

The mixture of 1.45 g of 1H-indol-5-amine, 2.8 g of methyl 2-bromo-5-cyclopropylbenzoate, 123 mg of palladium acetate, 0.64 g of 4,5'-bis(diphenylphosphino)-9,9'-dimethylxanthene, 7.19 g of cesium carbonate, and 25 mL of toluene, was heated at reflux for five hours under a nitrogen atmosphere. 504 mg of tris(dibenzylideneacetone)dipalladium(0) was added to the reaction mixture, and the resultant was heated at reflux for two hours under a nitrogen atmosphere. The reaction mixture was cooled to room temperature, and ethyl acetate and water were then added thereto. The insoluble matter was filtered off and the filter cake was washed with ethyl acetate and water. The filtrate and the washings were combined, the organic layer was separated, sequentially washed with water and a saturated aqueous sodium chloride solution and dried over anhydrous magnesium sulfate, and the solvent was distilled off under reduced pressure. The obtained residue was purified by silica gel column chromatography (gradient elution with hexane:ethyl acetate=100:0-80:20) to give 1.6 g of methyl 2-((1H-indol-5-yl)amino)-5-cyclopropylbenzoate as a pale brown oil.

$^1$H-NMR (DMSO-$d_6$) δ: 0.50-0.57 (2H, m), 0.80-0.89 (2H, m), 1.78-1.90 (1H, m), 3.85 (3H, s), 6.37-6.41 (1H, m), 6.87 (1H, d, J=8.6 Hz), 6.94 (1H, dd, J=8.6, 2.0 Hz), 7.05 (1H, dd, J=8.9, 2.3 Hz), 7.33-7.43 (3H, m), 7.61 (1H, d, J=2.6 Hz), 9.09 (1H, s), 11.11 (1H, s).

Example 34

[Formula 281]

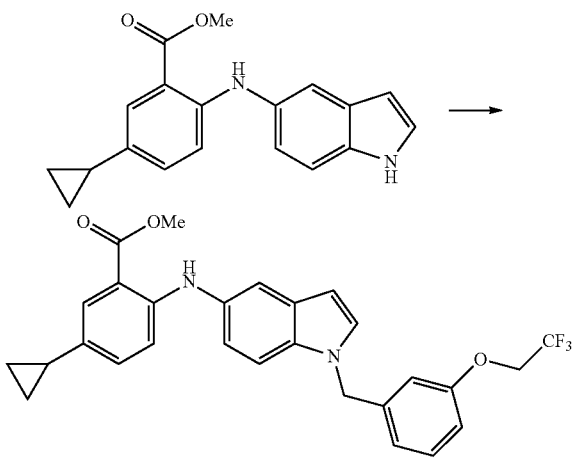

To the solution of 100 mg of methyl 2-((1H-indol-5-yl)amino)-5-cyclopropylbenzoate in 2 mL of N,N-dimethylacetamide, 40 mg of potassium tert-butoxide was added under ice-cooling, and the resultant was stirred for 10 minutes. 97 mg of 1-(bromomethyl)-3-(2,2,2-trifluoroethoxyl)benzene was added to the reaction mixture under ice-cooling, and the resultant was stirred at room temperature for one hour. Ethyl acetate and water were added to the reaction mixture, and the resultant was adjusted to pH 2.0 with 2 mol/L hydrochloric acid. The organic layer was separated, sequentially washed with water and a saturated aqueous sodium chloride solution and dried over anhydrous magnesium sulfate, and the solvent was distilled off under reduced pressure. The obtained residue was purified by silica gel column chromatography (gradient elution with hexane:ethyl acetate=90:10-80:20) to give 110 mg of methyl 5-cyclopropyl-2-((1-(3-(2,2,2-trifluoroethoxyl)benzyl)-1H-indol-5-yl)amino)benzoate as a pale yellow oil.

$^1$H-NMR (CDCl$_3$) δ: 0.55-0.63 (2H, m), 0.81-0.90 (2H, m), 1.75-1.82 (1H, m), 3.90 (3H, s), 4.28 (2H, q, J=8.1 Hz), 5.29 (2H, s), 6.50 (1H, d, J=3.3 Hz), 6.69-6.74 (1H, m), 6.79-6.87 (2H, m), 6.92-7.07 (3H, m), 7.13 (1H, d, J=3.3 Hz), 7.18-7.31 (2H, m), 7.50 (1H, d, J=2.0 Hz), 7.68 (1H, d, J=2.0 Hz), 9.20 (1H, s).

Example 35

[Formula 282]

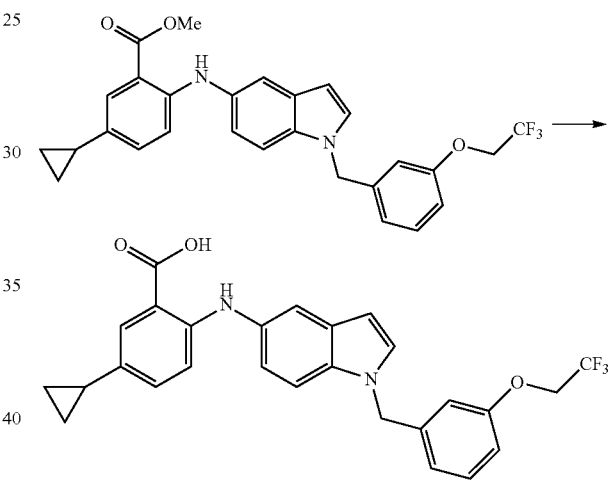

To the solution of 100 mg of methyl 5-cyclopropyl-2-((1-(3-(2,2,2-trifluoroethoxyl)benzyl)-1H-indol-5-yl)amino)benzoate in 1 mL of ethanol and 1 mL of tetrahydrofuran, 81 μL of a 5 mol/L aqueous sodium hydroxide solution was added at room temperature, and the resultant was stirred at an external temperature of 40 to 50° C. for two hours. 162 μL of a 5 mol/L aqueous sodium hydroxide solution was added to the reaction mixture, and the resultant was stirred at an external temperature of 40 to 50° C. for three hours. The reaction mixture was cooled to room temperature, and ethyl acetate and water were then added thereto, and the resultant was adjusted to pH 2.0 with 2 mol/L hydrochloric acid. The organic layer was separated, sequentially washed with water and a saturated aqueous sodium chloride solution and dried over anhydrous magnesium sulfate, and the solvent was distilled off under reduced pressure. The obtained residue was purified by silica gel column chromatography (gradient elution with hexane:ethyl acetate=90:10-50:50), and cyclohexane and diisopropyl ether were added to the thus obtained residue, and the solid was collected by filtration to give 43 mg of 5-cyclopropyl-2-((1-(3-(2,2,2-trifluoroethoxyl)benzyl)-1H-indol-5-yl)amino)benzoic acid as a pale brown solid.

¹H-NMR (DMSO-d₆) δ: 0.48-0.56 (2H, m), 0.79-0.88 (2H, m), 1.76-1.88 (1H, m), 4.73 (2H, q, J=8.8 Hz), 5.38 (2H, s), 6.43 (1H, d, J=2.6 Hz), 6.82-7.03 (6H, m), 7.23-7.32 (1H, m), 7.38 (1H, d, J=2.0 Hz), 7.44 (1H, d, J=9.2 Hz), 7.52 (1H, d, J=3.3 Hz), 7.60 (1H, d, J=2.6 Hz).

Example 36

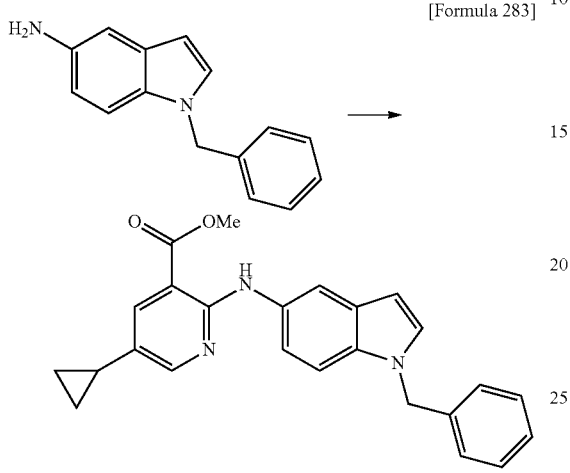

[Formula 283]

The mixture of 105 mg of 1-benzyl-1H-indol-5-amine, 100 mg of methyl 2-chloro-5-cyclopropylnicotinate, 21.7 mg of tris(dibenzylideneacetone)dipalladium(0), 27.3 mg of 4,5'-bis(diphenylphosphino)-9,9'-dimethylxanthene, 308 mg of cesium carbonate, and 2 mL of toluene, was stirred in a sealed tube at an external temperature of 120 to 130° C. for three hours under a nitrogen atmosphere. The reaction mixture was cooled to room temperature, and ethyl acetate and water were then added thereto. The organic layer was separated, sequentially washed with water and a saturated aqueous sodium chloride solution and dried over anhydrous magnesium sulfate, and the solvent was distilled off under reduced pressure. The obtained residue was purified by silica gel column chromatography (gradient elution with hexane: ethyl acetate=90:10-70:30) to give 126 mg of methyl 2-((1-benzyl-1H-indol-5-yl)amino)-5-cyclopropylnicotinate as a yellow solid.

¹H-NMR (CDCl₃) δ: 0.58-0.66 (2H, m), 0.87-0.95 (2H, m), 1.75-1.87 (1H, m), 3.92 (3H, s), 5.31 (2H, s), 6.51 (1H, d, J=3.3 Hz), 7.07-7.14 (3H, m), 7.19-7.33 (5H, m), 7.89 (1H, d, J=2.0 Hz), 7.91 (1H, d, J=2.6 Hz), 8.19 (1H, d, J=2.6 Hz), 9.83 (1H, s).

Example 37

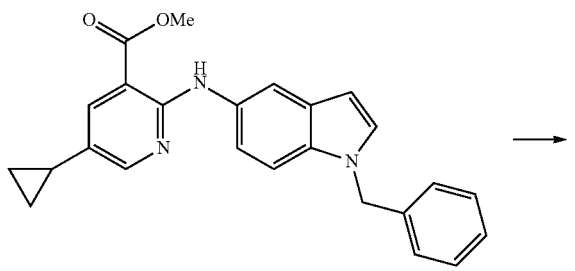

[Formula 284]

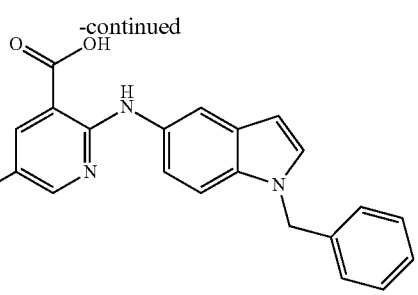

-continued

To the solution of 120 mg of methyl 2-((1-benzyl-1H-indol-5-yl)amino)-5-cyclopropylnicotinate in 1.0 mL of ethanol and 1.0 mL of tetrahydrofuran, 120 μL of a 5 mol/L aqueous sodium hydroxide solution was added at room temperature, and the resultant was stirred at an external temperature of 50 to 60° C. for two hours. After cooling the reaction mixture to room temperature, water was added thereto, and the resultant was adjusted to pH 3.0 with 2 mol/L hydrochloric acid, and ethyl acetate and water were added thereto. The organic layer was separated, sequentially washed with water and a saturated aqueous sodium chloride solution and dried over anhydrous magnesium sulfate, and the solvent was distilled off under reduced pressure. Diisopropyl ether, ethyl acetate and cyclohexane were added to the obtained residue, and the solid was collected by filtration to give 70 mg of 2-((1-benzyl-1H-indol-5-yl)amino)-5-cyclopropylnicotinic acid as a yellow solid.

¹H-NMR (DMSO-d₆) δ: 0.58-0.68 (2H, m), 0.85-0.96 (2H, m), 1.82-1.95 (1H, m), 5.40 (2H, s), 6.43 (1H, d, J=2.6 Hz), 7.11-7.40 (7H, m), 7.47 (1H, d, J=2.6 Hz), 7.86 (1H, d, J=2.0 Hz), 7.93-7.99 (1H, m), 8.18 (1H, d, J=2.0 Hz), 10.11 (1H, s).

MS (ESI, m/z): 384 (M+H)⁺, 382 (M−H)⁻.

Example 38

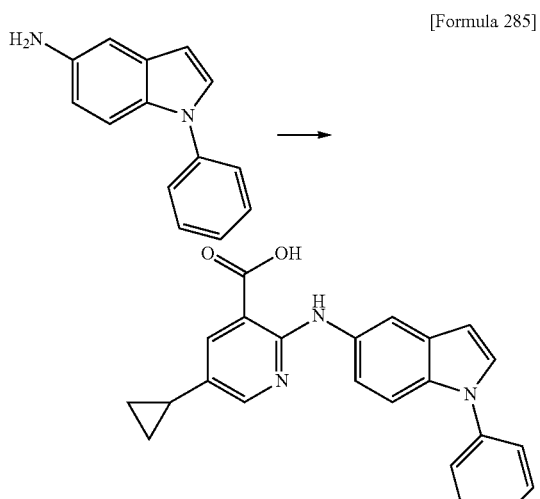

[Formula 285]

The mixture of 99 mg of 1-phenyl-1H-indol-5-amine, 100 mg of methyl 2-chloro-5-cyclopropylnicotinate, 21.7 mg of tris(dibenzylideneacetone)dipalladium(0), 27.3 mg of 4,5'-bis(diphenylphosphino)-9,9'-dimethylxanthene, 308 mg of cesium carbonate, and 2 mL of toluene, was stirred in a sealed tube at an external temperature of 120 to 130° C. for three hours under a nitrogen atmosphere. The reaction mixture was cooled to room temperature, and ethyl acetate and water were then added thereto. The organic layer was separated, sequentially washed with water and a saturated aqueous sodium chloride solution and dried over anhydrous magnesium sulfate, and the solvent was distilled off under reduced pressure. The obtained residue was purified by silica gel column chromatography (gradient elution with hexane: ethyl acetate=90:10-70:30), and cyclohexane was added to the thus obtained residue, and the solid was collected by filtration to give 120 mg of methyl 5-cyclopropyl-2-((1-phenyl-1H-indol-5-yl)amino)nicotinate as a yellow solid.

$^1$H-NMR (DMSO-d$_6$) δ: 0.62-0.71 (2H, m), 0.88-0.97 (2H, m), 1.87-2.00 (1H, m), 3.90 (3H, s), 6.67 (1H, d, J=3.3 Hz), 7.28 (1H, dd, J=8.6, 2.0 Hz), 7.35-7.43 (1H, m), 7.49-7.63 (5H, m), 7.65 (1H, d, J=3.3 Hz), 7.91 (1H, d, J=2.6 Hz), 8.12 (1H, d, J=2.0 Hz), 8.26 (1H, d, J=2.6 Hz), 9.93 (1H, s).

Example 39

[Formula 286]

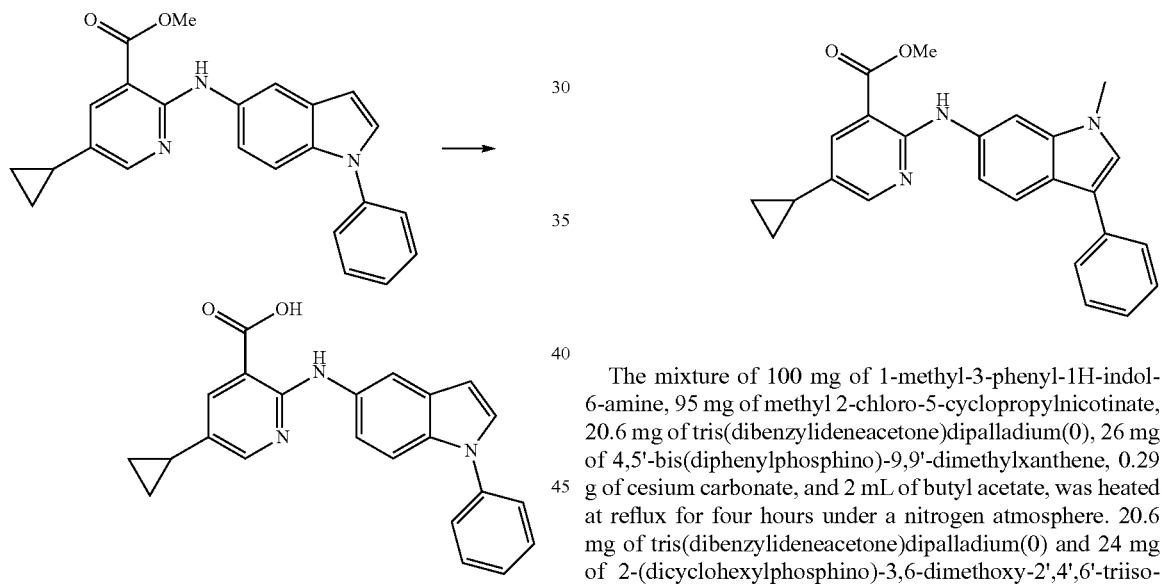

To the suspension of 112 mg of methyl 5-cyclopropyl-2-((1-phenyl-1H-indol-5-yl)amino)nicotinate in 1.0 mL of ethanol and 1.0 mL of tetrahydrofuran, 117 μL of a 5 mol/L aqueous sodium hydroxide solution was added at room temperature, and the resultant was stirred at an external temperature of 40 to 50° C. for one hour and 30 minutes. The reaction mixture was cooled to room temperature, and water was then added thereto, and the resultant was adjusted to pH 3.0 with 2 mol/L hydrochloric acid. The solid was collected by filtration to give 60 mg of 5-cyclopropyl-2-((1-phenyl-1H-indol-5-yl)amino)nicotinic acid as a yellow solid.

$^1$H-NMR (DMSO-d$_6$) δ: 0.62-0.71 (2H, m), 0.87-0.97 (2H, m), 1.86-1.98 (1H, m), 6.67 (1H, d, J=3.3 Hz), 7.27 (1H, dd, J=8.6, 2.0 Hz), 7.35-7.44 (1H, m), 7.49-7.63 (5H, m), 7.65 (1H, d, J=3.3 Hz), 7.91 (1H, d, J=2.6 Hz), 8.13 (1H, d, J=2.0 Hz), 8.21 (1H, d, J=2.0 Hz), 10.25 (1H, s).

Example 40

[Formula 287]

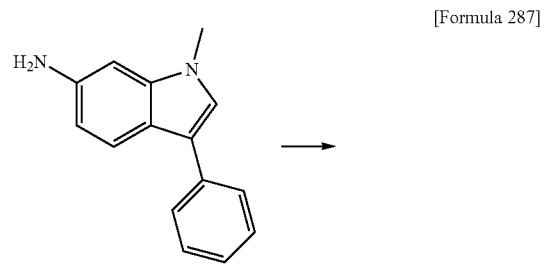

The mixture of 100 mg of 1-methyl-3-phenyl-1H-indol-6-amine, 95 mg of methyl 2-chloro-5-cyclopropylnicotinate, 20.6 mg of tris(dibenzylideneacetone)dipalladium(0), 26 mg of 4,5'-bis(diphenylphosphino)-9,9'-dimethylxanthene, 0.29 g of cesium carbonate, and 2 mL of butyl acetate, was heated at reflux for four hours under a nitrogen atmosphere. 20.6 mg of tris(dibenzylideneacetone)dipalladium(0) and 24 mg of 2-(dicyclohexylphosphino)-3,6-dimethoxy-2',4',6'-triisopropyl-1,1'-biphenyl were added to the reaction mixture, and the resultant was heated at reflux for one hour. The reaction mixture was cooled to room temperature, and ethyl acetate and water were then added thereto. The organic layer was separated, sequentially washed with water and a saturated aqueous sodium chloride solution and dried over anhydrous magnesium sulfate, and the solvent was distilled off under reduced pressure. The obtained residue was purified by silica gel column chromatography (gradient elution with hexane: ethyl acetate=90:10-70:30) to give 120 mg of methyl 5-cyclopropyl-2-((1-methyl-3-phenyl-1H-indol-6-yl)amino) nicotinate as a yellow solid.

$^1$H-NMR (DMSO-d$_6$) δ: 0.65-0.72 (2H, m), 0.89-0.98 (2H, m), 1.89-2.00 (1H, m), 3.81 (3H, s), 3.92 (3H, s), 7.21 (1H, d, J=7.3 Hz), 7.26 (1H, dd, J=8.9, 1.7 Hz), 7.38-7.47 (2H, m), 7.61 (1H, s), 7.67 (2H, d, J=7.9 Hz), 7.80 (1H, d, J=8.6 Hz), 7.93 (1H, d, J=2.6 Hz), 8.05 (1H, d, J=2.0 Hz), 8.30 (1H, d, J=2.6 Hz), 10.09 (1H, s).

Example 41

[Formula 288]

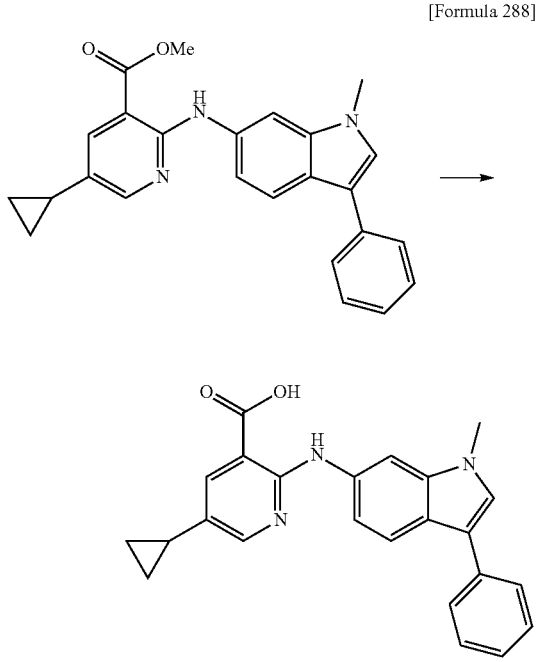 [SMILES: COC(=O)c1cc(C2CC2)cnc1Nc1ccc2c(-c3ccccc3)cn(C)c2c1 ; Cn1cc(-c2ccccc2)c2ccc(Nc3ncc(C4CC4)cc3C(=O)O)cc21]

To the solution of 120 mg of methyl 5-cyclopropyl-2-((1-methyl-3-phenyl-1H-indol-6-yl)amino)nicotinate in 1.0 mL of ethanol and 1.0 mL of tetrahydrofuran, 121 pt of a 5 mol/L aqueous sodium hydroxide solution was added at room temperature, and the resultant was stirred at an external temperature of 50 to 60° C. for one hour. The reaction mixture was cooled to room temperature, and water was then added thereto, and the resultant was adjusted to pH 2.7 with 2 mol/L hydrochloric acid. The obtained solid was collected by filtration to give 95 mg of 5-cyclopropyl-2-((1-methyl-3-phenyl-1H-indol-6-yl)amino)nicotinic acid as a pale brown solid.

$^1$H-NMR (DMSO-$d_6$) δ: 0.64-0.72 (2H, m), 0.88-0.98 (2H, m), 1.87-2.00 (1H, m), 3.81 (3H, s), 7.17-7.27 (2H, m), 7.37-7.47 (2H, m), 7.61 (1H, s), 7.63-7.69 (2H, m), 7.79 (1H, d, J=8.6 Hz), 7.92 (1H, d, J=2.6 Hz), 8.08 (1H, d, J=1.3 Hz), 8.27 (1H, d, J=2.6 Hz), 10.38 (1H, s).

MS (ESI, m/z): 384 (M+H)$^+$, 382 (M−H)$^-$.

Example 42

[Formula 289]

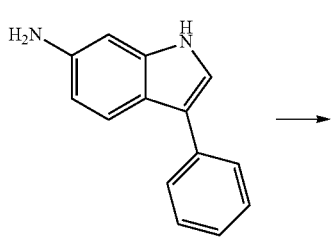

The mixture of 0.41 g of 3-phenyl-1H-indol-6-amine, 0.41 g of methyl 2-chloro-5-cyclopropylnicotinate, 88.7 mg of tris(dibenzylideneacetone)dipalladium(0), 112 mg of 4,5'-bis(diphenylphosphino)-9,9'-dimethylxanthene, 1.26 g of cesium carbonate, and 4 mL of butyl acetate, was stirred in a sealed tube at an external temperature of 110 to 130° C. for two hours under a nitrogen atmosphere. The reaction mixture was cooled to room temperature, and ethyl acetate and water were then added thereto. The organic layer was separated, sequentially washed with water and a saturated aqueous sodium chloride solution and dried over anhydrous magnesium sulfate, and the solvent was distilled off under reduced pressure. The obtained residue was purified by silica gel column chromatography (gradient elution with hexane: ethyl acetate=90:10-70:30) to give 0.17 g of butyl 5-cyclopropyl-2-((3-phenyl-1H-indol-6-yl)amino)nicotinate as a pale brown solid.

$^1$H-NMR (CDCl$_3$) δ: 0.60-0.69 (2H, m), 0.85-1.05 (5H, m), 1.50 (2H, sext, J=7.6 Hz), 1.73-191 (3H, m), 4.35 (2H, t, J=6.6 Hz), 7.14 (1H, dd, J=8.6, 2.0 Hz), 7.22-7.31 (3H, m), 7.38-7.47 (2H, m), 7.67 (1H, d, J=6.6 Hz), 7.84 (1H, d, J=8.6 Hz), 7.94 (1H, d, J=2.0 Hz), 8.15-8.28 (2H, m), 10.14 (1H, s).

Example 43

[Formula 290]

To the solution of 30 mg of butyl 5-cyclopropyl-2-((3-phenyl-1H-indol-6-yl)amino)nicotinate in 1.0 mL of ethanol and 1.0 mL of tetrahydrofuran, 28 μL of a 5 mol/L aqueous sodium hydroxide solution was added at room temperature, and the resultant was stirred at an external temperature of 40 to 50° C. for two hours. The reaction mixture was cooled to room temperature, and water was then added thereto, and the resultant was adjusted to pH 3.0 with 2 mol/L hydrochloric acid. The solid was collected by filtration and purified by silica gel column chromatography (gradient elution with hexane:ethyl acetate=20:80-0:100), and hexane and ethyl acetate were added to the obtained residue, and the solid was collected by filtration to give 7 mg of 5-cyclopropyl-2-((3-phenyl-1H-indol-6-yl)amino)nicotinic acid as a yellow solid.

$^1$H-NMR (DMSO-$d_6$) δ: 0.63-0.70 (2H, m), 0.89-0.97 (2H, m), 1.88-2.00 (1H, m), 7.03 (1H, dd, J=8.9, 1.7 Hz), 7.21 (1H, t, J=7.6 Hz), 7.38-7.46 (2H, m), 7.59 (1H, d, J=2.6 Hz), 7.65-7.71 (2H, m), 7.77 (1H, d, J=8.6 Hz), 7.90 (1H, d, J=2.6 Hz), 8.22-8.28 (2H, m), 10.56 (1H, brs), 11.23 (1H, s).

MS (ESI, m/z): 370 (M+H)$^+$, 368 (M−H)$^−$.

Example 44

[Formula 291]

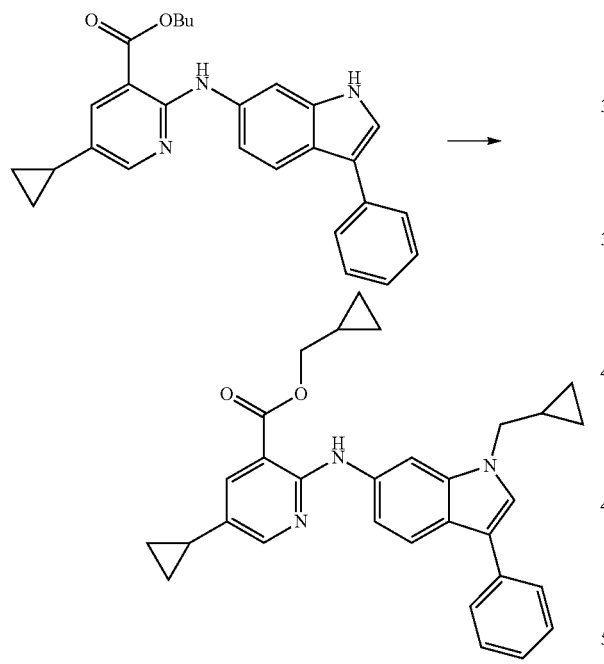

To the solution of 82 mf of butyl 5-cyclopropyl-2-((3-phenyl-1H-indol-6-yl)amino)nicotinate in 2 mL of N,N-dimethylacetamide, 8.5 mg of 60% sodium hydride was added under ice-cooling, and the resultant was stirred for 10 minutes. To the reaction mixture, 21 μl of (bromomethyl)cyclopropane was added dropwise under ice-cooling, and the resultant was stirred at room temperature for one hour. To the reaction mixture, 8.5 mL of 60% sodium hydride and 63 μL of (bromomethyl)cyclopropane were added dropwise, and the resultant was stirred at room temperature for 30 minutes and then stirred at an external temperature of 30 to 50° C. for two hours. Ethyl acetate and water were added to the reaction mixture, and the resultant was adjusted to pH 2.0 with 2 mol/L hydrochloric acid. The organic layer was separated, sequentially washed with water and a saturated aqueous sodium chloride solution and dried over anhydrous magnesium sulfate, and the solvent was distilled off under reduced pressure. The obtained residue was purified by silica gel column chromatography (gradient elution with hexane:ethyl acetate=90:10-70:30) to give 53.3 mg of cyclopropylmethyl 5-cyclopropyl-2-((1-(cyclopropylmethyl)-3-phenyl-1H-indol-6-yl)amino)nicotinate as a yellow oil.

$^1$H-NMR (CDCl$_3$) δ: 0.36-0.48 (4H, m), 0.62-0.72 (6H, m), 0.89-1.00 (2H, m), 1.24-1.39 (2H, m), 1.81-1.93 (1H, m), 4.01 (2H, d, J=6.6 Hz), 4.18 (2H, d, J=7.3 Hz), 7.21 (1H, dd, J=8.6, 2.0 Hz), 7.24-7.29 (1H, m), 7.34 (1H, s), 7.38-7.47 (2H, m), 7.64-7.71 (2H, m), 7.85 (1H, d, J=8.6 Hz), 7.99 (1H, d, J=2.6 Hz), 8.05 (1H, d, J=2.0 Hz), 8.25 (1H, d, J=2.6 Hz), 10.12 (1H, s).

Example 45

[Formula 292]

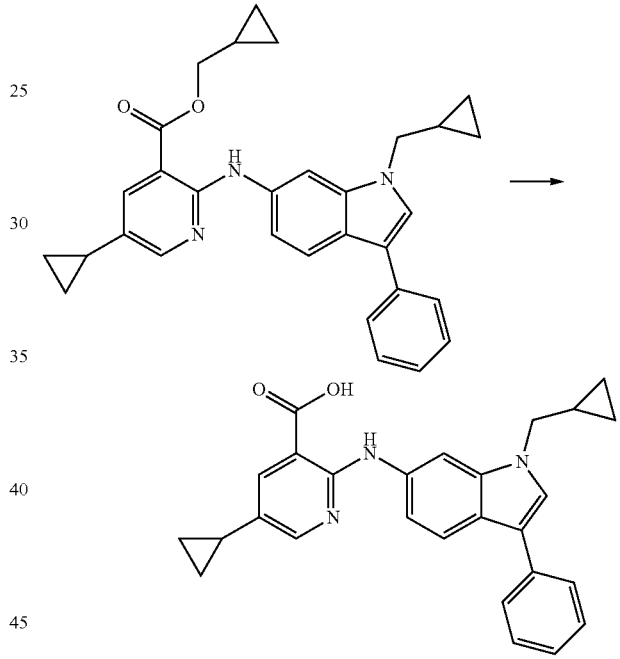

To the solution of 53 mg of cyclopropylmethyl 5-cyclopropyl-2-((1-(cyclopropylmethyl)-3-phenyl-1H-indol-6-yl)amino)nicotinate in 1.0 mL of ethanol and 1.0 mL of tetrahydrofuran, 44 μL of a 5 mol/L aqueous sodium hydroxide solution was added at room temperature, and the resultant was stirred at an external temperature of 40 to 50° C. for two hours. The reaction mixture was cooled to room temperature, and water was then added thereto, and the resultant was adjusted to pH 2.7 with 2 mol/L hydrochloric acid. The solid was collected by filtration to give 40 mg of 5-cyclopropyl-2-((1-(cyclopropylmethyl)-3-phenyl-1H-indol-6-yl)amino)nicotinic acid as a pale brown solid.

$^1$H-NMR (DMSO-$d_6$) δ: 0.43-0.61 (4H, m), 0.63-0.72 (2H, m), 0.88-0.99 (2H, m), 1.22-1.39 (1H, m), 1.88-2.00 (1H, m), 4.05 (2H, d, J=7.3 Hz), 7.17-7.27 (2H, m), 7.39-7.47 (2H, m), 7.63-7.72 (3H, m), 7.79 (1H, d, J=8.6 Hz), 7.91 (1H, d, J=2.0 Hz), 8.17 (1H, d, J=1.3 Hz), 8.27 (1H, d, J=2.0 Hz), 10.35 (1H, s).

MS (ESI, m/z): 424 (M+H)$^+$.

Example 46

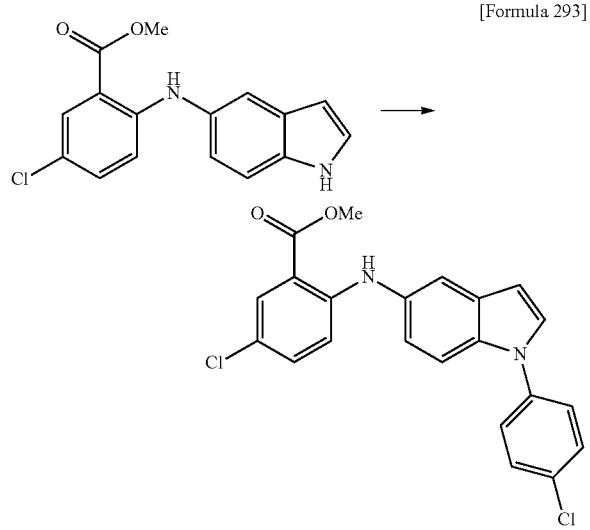

[Formula 293]

The reaction mixture of 50 mg of methyl 2-((1H-indol-5-yl)amino)-5-chlorobenzoate, 38.1 mg of 4-bromochlorobenzene, 1.9 mg of palladium acetate, 9.6 mg of 4,5'-bis(diphenylphosphino)-9,9'-dimethylxanthene, 108 mg of cesium carbonate, and 0.58 mL of toluene, was heated at reflux for three hours under a nitrogen atmosphere. The reaction mixture was cooled to room temperature, and water and ethyl acetate were then added thereto. The organic layer was separated and dried over anhydrous sodium sulfate, and the solvent was distilled off under reduced pressure. The obtained residue was purified by silica gel column chromatography (hexane:ethyl acetate) to give 49 mg of methyl 5-chloro-2-((1-(4-chlorophenyl)-1H-indol-5-yl)amino)benzoate as an oil.

$^1$H-NMR (CDCl$_3$) δ: 3.92 (3H, s), 6.65 (1H, d, J=3.3 Hz), 6.96 (1H, d, J=9.2 Hz), 7.09 (1H, dd, J=8.6, 2.0 Hz), 7.17 (1H, dd, J=8.9, 2.3 Hz), 7.32 (1H, d, J=3.3 Hz), 7.40-7.56 (6H, m), 7.92 (1H, d, J=2.6 Hz), 9.37 (1H, brs).

Example 47

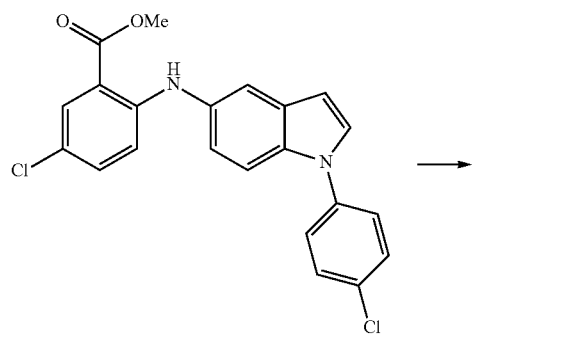

[Formula 294]

To the solution of 40.5 mg of methyl 5-chloro-2-((1-(4-chlorophenyl)-1H-indol-5-yl)amino)benzoate in 0.5 mL of ethanol, 78.8 μL of a 5 mol/L aqueous sodium hydroxide solution was added at room temperature, and the resultant was stirred at an external temperature of 80° C. for 10 minutes. The reaction mixture was cooled to room temperature, and water and 3 mol/L hydrochloric acid were then added thereto. The solid was collected by filtration to give 35.5 mg of 5-chloro-2-((1-(4-chlorophenyl)-1H-indol-5-yl)amino)benzoic acid as a yellow solid.

$^1$H-NMR (DMSO-d$_6$) δ: 6.68 (1H, d, J=3.3 Hz), 7.02 (1H, d, J=9.2 Hz), 7.06 (1H, dd, J=8.9, 2.3 Hz), 7.24 (1H, dd, J=9.2, 2.6 Hz), 7.50 (1H, d, J=2.0 Hz), 7.56 (1H, d, J=8.6 Hz), 7.59-7.66 (4H, m), 7.67 (1H, d, J=3.3 Hz), 7.82 (1H, d, J=2.6 Hz).

MS (ESI, m/z): 395 (M−H)$^-$.

Example 48

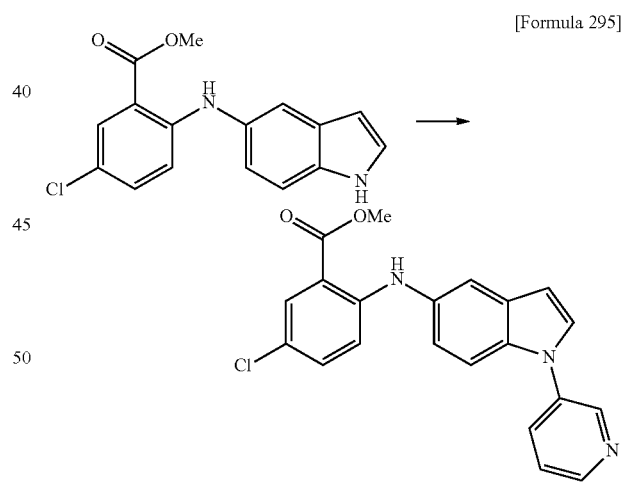

[Formula 295]

The reaction mixture of 50 mg of methyl 2-((1H-indol-5-yl)amino)-5-chlorobenzoate, 19.4 μL of 3-bromopyridine, 1.6 mg of copper(I) iodide, 70.5 mg of tripotassium phosphate, 5.2 pt of trans-N,N'-dimethylcyclohexane-1,2-diamine, and 0.58 mL of toluene, was stirred at 100° C. for two hours under a nitrogen atmosphere. The reaction mixture was cooled to room temperature, and water and ethyl acetate were added thereto. The organic layer was separated and dried over anhydrous sodium sulfate, and the solvent was distilled off under reduced pressure. The obtained residue was purified by silica gel column chromatography (hexane:

ethyl acetate) to give 16 mg of methyl 5-chloro-2-((1-(pyridin-3-yl)-1H-indol-5-yl)amino)benzoate as an oil.

Example 49

[Formula 296]

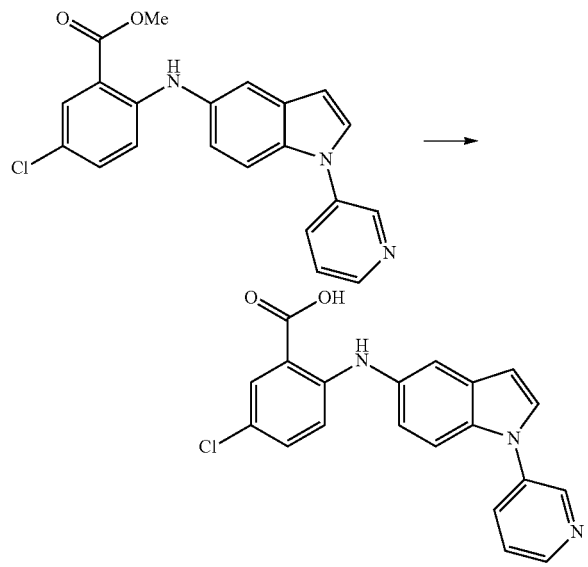

To the solution of 16 mg of methyl 5-chloro-2-((1-(pyridin-3-yl)-1H-indol-5-yl)amino)benzoate in 0.2 mL of ethanol, 16.9 µL of a 5 mol/L aqueous sodium hydroxide solution was added at room temperature, and the resultant was stirred at an external temperature of 80° C. for 10 minutes. The reaction mixture was cooled to room temperature, and water and 3 mol/L hydrochloric acid were then added thereto, and the solid was collected by filtration to give 14.9 mg of 5-chloro-2-((1-(pyridin-3-yl)-1H-indol-5-yl)amino)benzoic acid as a yellow solid.

$^1$H-NMR (DMSO-$d_6$) δ: 6.74 (1H, d, J=3.3 Hz), 7.01 (1H, d, J=9.2 Hz), 7.12 (1H, dd, J=8.6, 2.0 Hz), 7.30-7.39 (1H, m), 7.53-7.67 (3H, m), 7.75-7.84 (2H, m), 8.06-8.15 (1H, m), 8.62 (1H, d, J=4.6 Hz), 8.88 (1H, d, J=2.6 Hz), 9.50-9.76 (1H, m).

MS (ESI, m/z): 362 (M−H)$^-$.

Example 50

[Formula 297]

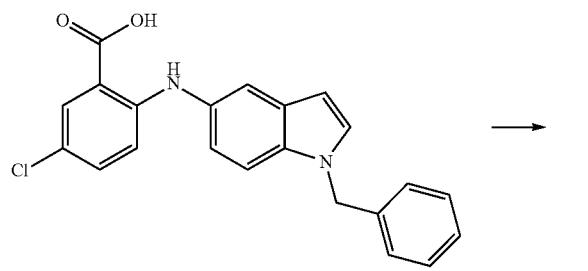

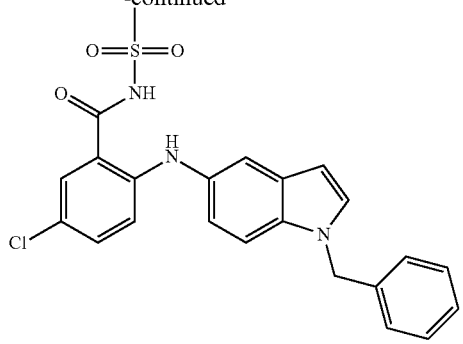

To the solution of 50 mg of 2-((1-benzyl-1H-indol-5-yl)amino)-5-chlorobenzoic acid in 0.5 mL of tetrahydrofuran, 50.4 mg of 1,1'-carbonyldiimidazole was added under ice-cooling, and the resultant was stirred at room temperature for 30 minutes. To the reaction mixture, 46.6 µL of 1,8-diazabicyclo[5,4,0]undec-7-ene and 29.6 mg of methanesulfonamide were added under ice-cooling, and the resultant was stirred at room temperature for 2.5 hours. Water and ethyl acetate were added to the reaction mixture. The organic layer was separated and dried over anhydrous sodium sulfate, and the solvent was distilled off under reduced pressure. The obtained residue was purified by silica gel column chromatography (chloroform:methanol) to give 14.3 mg of 2-((1-benzyl-1H-indol-5-yl)amino)-5-chloro-N-(methylsulfonyl)benzamide as a yellow solid.

$^1$H-NMR (DMSO-$d_6$) δ: 2.90 (3H, s), 5.40 (2H, s), 6.43 (1H, d, J=3.3 Hz), 6.88-6.95 (2H, m), 7.09 (1H, dd, J=9.2, 2.6 Hz), 7.19-7.36 (6H, m), 7.42 (1H, d, J=8.6 Hz), 7.49 (1H, d, J=3.3 Hz), 7.92 (1H, d, J=3.3 Hz), 10.85 (1H, brs).

MS (ESI, m/z): 454 (M+H)$^+$, 452 (M−H)$^-$.

Example 51

[Formula 298]

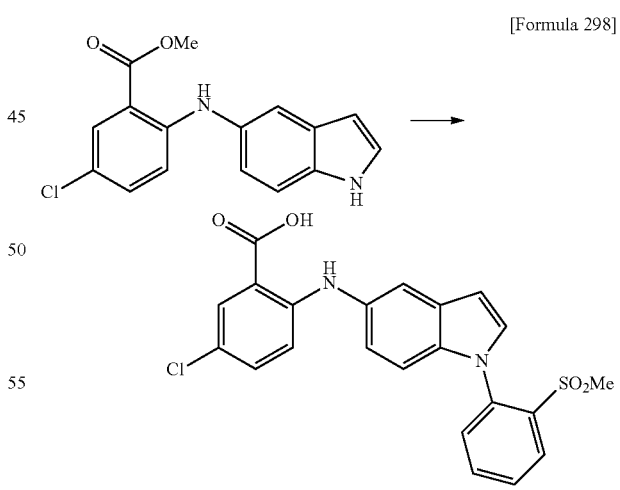

The mixture of 46.2 mg of methyl 2-((1H-indol-5-yl)amino)-5-chlorobenzoate, 26.8 mg of 2-fluorophenyl (methyl)sulfone, 100 mg of cesium carbonate, and 0.5 mL of N,N-dimethylacetamide, was stirred at an external temperature of 80° C. for 2.5 hours. The reaction mixture was cooled to room temperature and allowed to stand overnight. The reaction mixture was stirred at 80° C. for two hours, followed by addition of water, 2 mol/L hydrochloric acid and ethyl acetate. The organic layer was separated and dried over anhydrous sodium sulfate, and the solvent was distilled off under reduced pressure. The obtained residue was purified by silica gel column chromatography (chloroform:methanol) to give 4.9 mg of 5-chloro-2-((1-(2-(methylsulfonyl)phenyl)-1H-indol-5-yl)amino)benzoic acid as a yellow solid.

$^1$H-NMR (DMSO-$d_6$) δ: 2.74 (3H, s), 6.67 (1H, d, J=3.3 Hz), 6.95-7.01 (2H, m), 7.04 (1H, d, J=9.2 Hz), 7.15-7.25 (1H, m), 7.44-7.54 (2H, m), 7.58 (1H, dd, J=7.9, 1.3 Hz), 7.78-7.95 (3H, m), 8.21 (1H, dd, J=7.9, 2.0 Hz).

MS (ESI, m/z): 441 (M+H)$^+$, 439 (M−H)$^−$.

Example 52

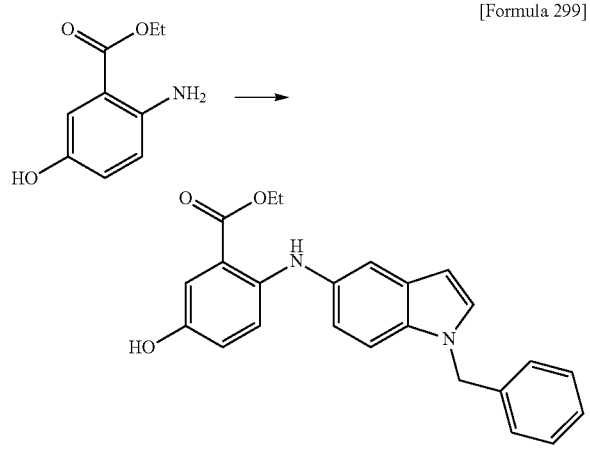

[Formula 299]

The mixture of 0.500 g of ethyl 2-amino-5-hydroxybenzoate, 0.856 g of 1-benzyl-5-bromo-1H-indole, 0.137 g of palladium acetate, 0.174 g of 4,5'-bis(diphenylphosphino)-9,9'-dimethylxanthene, 1.95 g of cesium carbonate, and 5.0 mL of toluene, was heated at reflux for one hour under a nitrogen atmosphere. The reaction mixture was cooled to room temperature, and water and ethyl acetate were then added thereto. The organic layer was separated and dried over anhydrous sodium sulfate, and the solvent was distilled off under reduced pressure. The obtained residue was purified by silica gel column chromatography (hexane:ethyl acetate) to give 84 mg of ethyl 2-((1-benzyl-1H-indol-5-yl)amino)-5-hydroxybenzoate as an oil.

Example 53

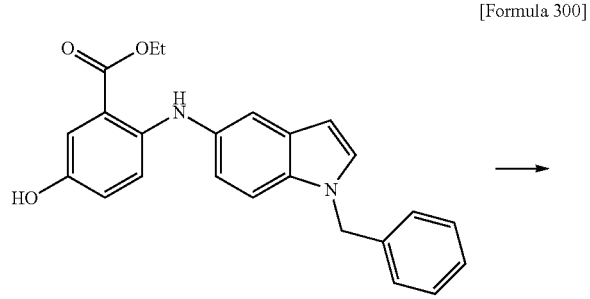

[Formula 300]

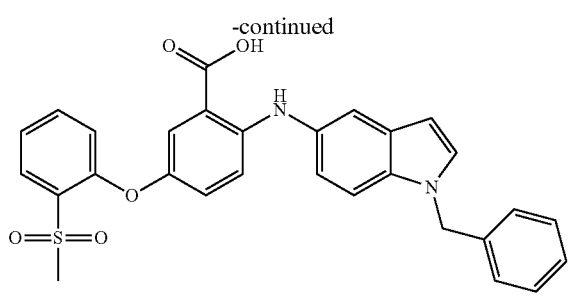

-continued

To the solution of 44.3 mg of ethyl 2-((1-benzyl-1H-indol-5-yl)amino)-5-hydroxybenzoate in 0.5 mL of N,N-dimethylacetamide, 14.3 mg of potassium tert-butoxide was added under ice-cooling. After such resultant was stirred for 10 minutes under ice-cooling, 22.1 mg of 2-fluorophenyl (methyl)sulfone was added thereto, and the resultant was stirred at an external temperature of 80° C. for four hours. The reaction mixture was cooled to room temperature and allowed to stand overnight, and 74.9 mg of cesium carbonate was then added thereto, and the resultant was stirred at 80° C. for 1.5 hours. The reaction mixture was cooled to room temperature, and water and ethyl acetate were then added thereto. The organic layer was separated and dried over anhydrous sodium sulfate, and the solvent was distilled off under reduced pressure. The obtained residue was purified by silica gel column chromatography (chloroform:methanol). The obtained solid was purified by preparative thin-layer chromatography (chloroform:methanol) to give 8.4 mg of 2-((1-benzyl-1H-indol-5-yl)amino)-5-(2-(methylsulfonyl)phenoxy)benzoic acid as a yellow solid.

$^1$H-NMR (DMSO-$d_6$) δ: 3.36 (3H, s), 5.43 (2H, s), 6.47 (1H, d, J=2.6 Hz), 6.90-7.06 (3H, m), 7.15-7.37 (7H, m), 7.43-7.52 (2H, m), 7.54 (1H, d, J=2.6 Hz), 7.57-7.69 (2H, m), 7.89 (1H, dd, J=7.6, 1.7 Hz), 9.49 (1H, s).

MS (ESI, m/z): 513 (M+H)$^+$, 511 (M−H)$^−$.

Example 54

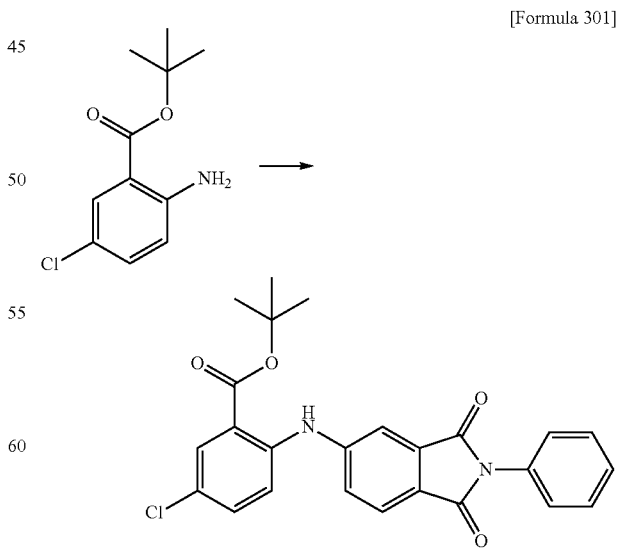

[Formula 301]

The mixture of 0.226 g of tert-butyl 2-amino-5-chlorobenzoate, 0.300 g of 5-bromo-2-phenylisoindoline-1,3- dione, 54.6 mg of tris(dibenzylideneacetone)dipalladium(0), 68.9 mg of 4,5'-bis(diphenylphosphino)-9,9'-dimethylxanthene, 0.648 g of cesium carbonate, and 2.3 mL of toluene, was stirred at an external temperature of 80° C. for three hours under a nitrogen atmosphere. The reaction mixture was cooled to room temperature and allowed to stand for 64.5 hours, and water and ethyl acetate were then added thereto. The organic layer was separated and dried over anhydrous sodium sulfate, and the solvent was distilled off under reduced pressure. The obtained residue was purified by silica gel column chromatography (hexane:ethyl acetate). The obtained solid was washed with methanol to give 0.199 g of ten-butyl 5-chloro-2-((1,3-dioxo-2-phenylisoindolin-5-yl)amino)benzoate as a yellow solid.

Example 55

[Formula 302]

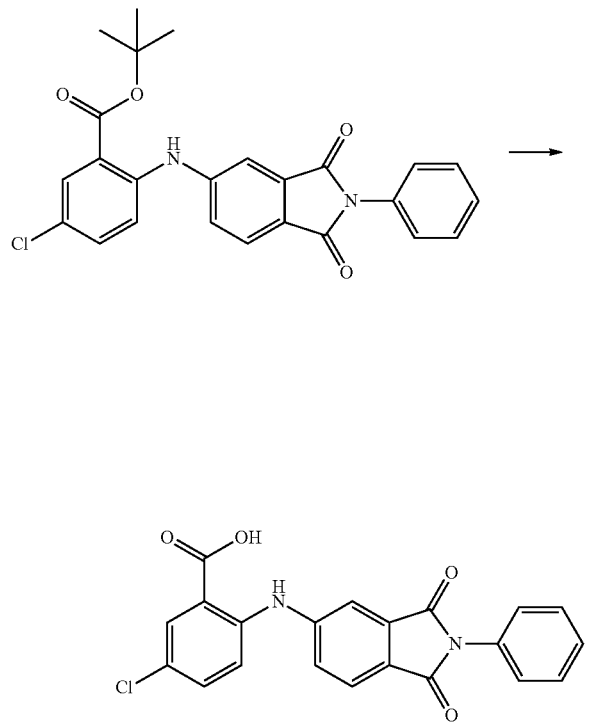

To 0.100 g of tert-butyl 5-chloro-2-((1,3-dioxo-2-phenylisoindolin-5-yl)amino)benzoate, 0.5 mL of trifluoroacetic acid was added at room temperature, and the resultant was stirred at an external temperature of 60° C. for 10 minutes. After cooling the reaction mixture to room temperature, trifluoroacetic acid was distilled off under reduced pressure. Ethyl acetate was added to the obtained residue, and the insoluble matter was filtered off and the solvent was distilled off under reduced pressure to give 45 mg of 5-chloro-2-((1,3-dioxo-2-phenylisoindolin-5-yl)amino)benzoic acid as a yellow solid.

$^1$H-NMR (DMSO-$d_6$) δ: 7.39-7.47 (3H, m), 7.48-7.65 (6H, m), 7.85 (1H, d, J=8.6 Hz), 7.91 (1H, d, J=2.6 Hz), 9.80 (1H, s).

MS (ESI, m/z): 393 (M+H)$^+$, 391 (M−H)$^-$.

Example 56

[Formula 303]

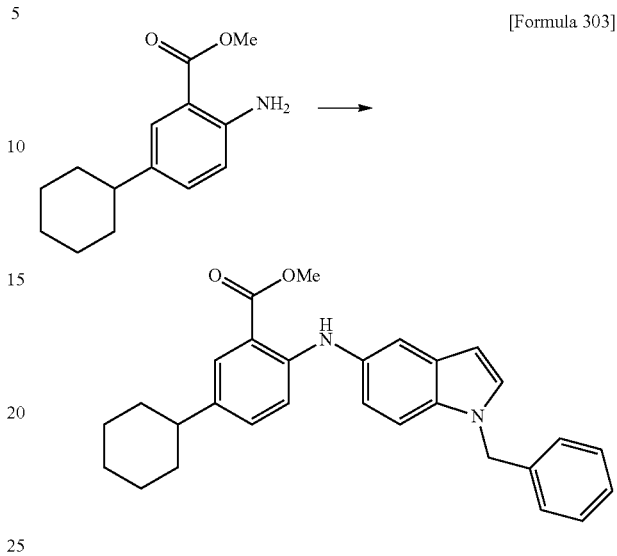

The mixture of 0.100 g of methyl 2-amino-5-cyclohexylbenzoate, 0.123 g of 1-benzyl-5-bromo-1H-indole, 19.7 mg of tris(dibenzylideneacetone)dipalladium(0), 24.8 mg of 4,5'-bis(diphenylphosphino)-9,9'-dimethylxanthene, 0.280 g of cesium carbonate, and 1.0 mL of toluene, was stirred at an external temperature of 100° C. for two hours under a nitrogen atmosphere. The reaction mixture was cooled to room temperature, and water and ethyl acetate were then added thereto. The organic layer was separated and dried over anhydrous sodium sulfate, and the solvent was distilled off under reduced pressure. The obtained residue was sequentially purified by silica gel column chromatography (hexane:ethyl acetate) and preparative thin-layer chromatography (hexane:ethyl acetate) to give 3.5 mg of methyl 2-((1-benzyl-1H-indol-5-yl)amino)-5-cyclohexylbenzoate as a yellow oil.

$^1$H-NMR (CDCl$_3$) δ: 1.13-2.11 (10H, m), 2.28-2.60 (1H, m), 3.91 (3H, s), 5.33 (2H, s), 6.43-6.66 (1H, m), 6.88-7.67 (11H, m), 7.70-7.95 (1H, m), 9.23 (1H, s).

Example 57

[Formula 304]

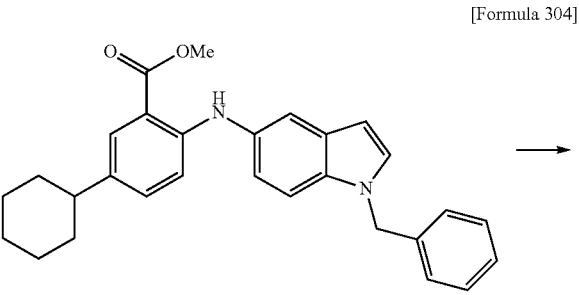

-continued

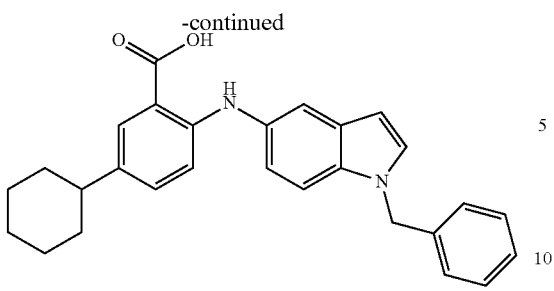

To the solution of 3.5 mg of methyl 2-((1-benzyl-1H-indol-5-yl)amino)-5-cyclohexylbenzoate in 0.5 mL of ethanol, 0.1 mL of a 5 mol/L aqueous sodium hydroxide solution was added at room temperature, and the resultant was stirred at an external temperature of 80° C. for 20 minutes. The reaction mixture was cooled to room temperature and 2 mol/L hydrochloric acid, and ethyl acetate were then added thereto. The organic layer was separated and dried over anhydrous sodium sulfate, and the solvent was distilled off under reduced pressure. The obtained residue was purified by silica gel column chromatography (chloroform:methanol) to give 3 mg of 2-((1-benzyl-1H-indol-5-yl)amino)-5-cyclohexylbenzoic acid as a yellow solid.

$^1$H-NMR (DMSO-$d_6$) δ: 1.13-1.44 (5H, m), 1.61-1.86 (5H, m), 2.30-2.45 (1H, m), 5.41 (2H, s), 6.44 (1H, d, J=3.3 Hz), 6.89 (1H, d, J=8.6 Hz), 6.95 (1H, dd, J=8.6, 2.0 Hz), 7.08-7.47 (8H, m), 7.51 (1H, d, J=2.6 Hz), 7.69 (1H, d, J=2.0 Hz).

MS (ESI/APCI, m/z): 425 (M+H)$^+$, 423 (M−H)$^−$.

Example 58

[Formula 305]

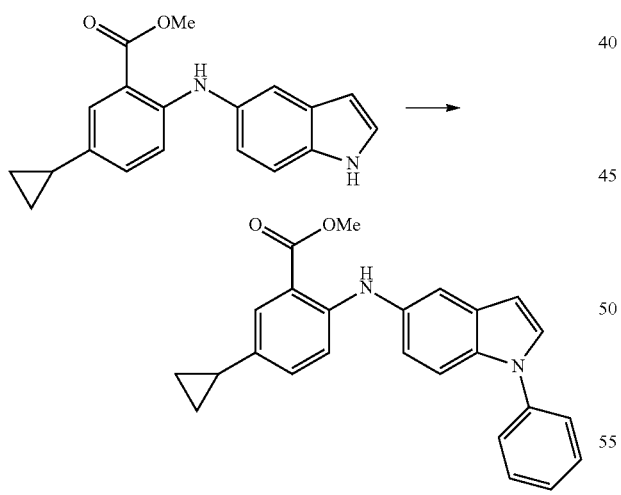

The mixture of 40 mg of methyl 2-((1H-indol-5-yl)amino)-5-cyclopropylbenzoate, 14.7 μL of iodobenzene, 12 mg of tris(dibenzylideneacetone)dipalladium(0), 25 mg of 2-dicyclohexylphosphino-2',4',6'-triisopropylbiphenyl, 55.6 mg of tripotassium phosphate, and 0.4 mL of toluene, was stirred at an external temperature of 100° C. for 16 hours under a nitrogen atmosphere. The reaction mixture was cooled to room temperature, and water and ethyl acetate were then added thereto. The organic layer was separated and dried over anhydrous sodium sulfate, and the solvent was distilled off under reduced pressure and the obtained residue was then purified by silica gel column chromatography (hexane:ethyl acetate) to give 18.1 mg of methyl 5-cyclopropyl-2-((1-phenyl-1H-indol-5-yl)amino)benzoate as a yellow oil.

$^1$H-NMR (CDCl$_3$) δ: 0.54-0.72 (2H, m), 0.79-1.02 (2H, m), 1.75-1.89 (1H, m), 3.91 (3H, s), 6.58-6.73 (1H, m), 6.94-7.18 (3H, m), 7.30-7.44 (2H, m), 7.46-7.65 (6H, m), 7.66-7.76 (1H, m), 9.25 (1H, s).

Example 59

[Formula 306]

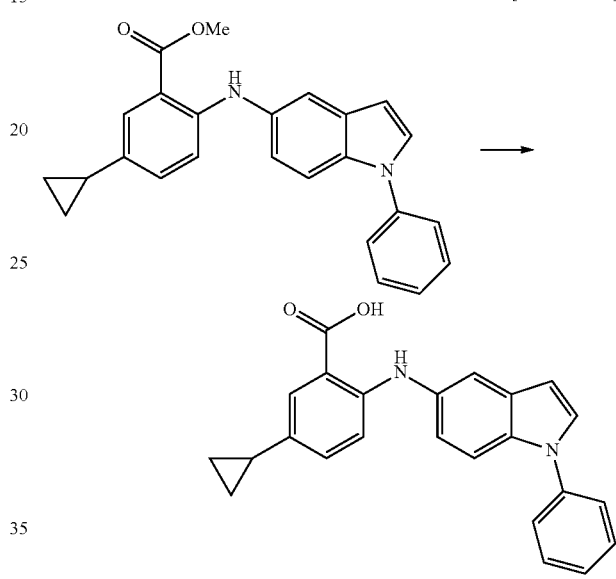

To the solution of 18.1 mg of methyl 5-cyclopropyl-2-((1-phenyl-1H-indol-5-yl)amino)benzoate in 0.18 mL of ethanol, 37.8 μL of a 5 mol/L aqueous sodium hydroxide solution was added at room temperature, and the resultant was stirred at an external temperature of 70° C. for 15 minutes. The reaction mixture was cooled to room temperature, and water and 2 mol/L hydrochloric acid were then added thereto. The solid was collected by filtration and recrystallized from ethanol to give 5.4 mg of 5-cyclopropyl-2-((1-phenyl-1H-indol-5-yl)amino)benzoic acid as a green solid.

$^1$H-NMR (DMSO-$d_6$) δ: 0.49-0.61 (2H, m), 0.79-0.92 (2H, m), 1.77-1.91 (1H, m), 6.66 (1H, d, J=2.6 Hz), 6.92-7.13 (3H, m), 7.33-7.73 (9H, m), 9.41 (1H, brs), 12.92 (1H, brs).

MS (ESI, m/z): 369 (M+H)$^+$, 367 (M−H)$^−$.

Example 60

[Formula 307]

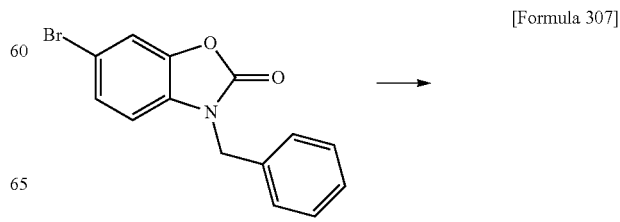

-continued

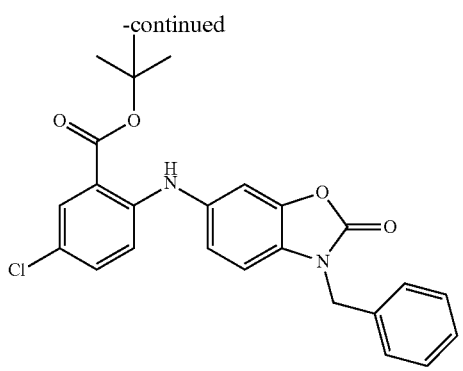

The mixture of 50 mg of 3-benzyl-6-bromobenzo[d]oxazol-2(3H)-one, 37.3 mg of tert-butyl 2-amino-5-chlorobenzoate, 7.5 mg of tris(dibenzylideneacetone)dipalladium(0), 9.5 mg of 4,5'-bis(diphenylphosphino)-9,9'-dimethylxanthene, 107 mg of cesium carbonate, and 0.3 mL of toluene, was stirred at an external temperature of 80° C. for 2.5 hours under a nitrogen atmosphere. The reaction mixture was cooled to room temperature and allowed to stand overnight, and water and ethyl acetate were then added thereto. The organic layer was separated and dried over anhydrous sodium sulfate, and the solvent was distilled off under reduced pressure. The obtained residue was purified by silica gel column chromatography (hexane:ethyl acetate) to give 47.5 mg of tert-butyl 2-((3-benzyl-2-oxo-2,3-dihydrobenzo[d]oxazol-6-yl)amino)-5-chlorobenzoate as an oil.

$^1$H-NMR (CDCl$_3$) δ: 1.60 (9H, s), 5.00 (2H, s), 6.77 (1H, d, J=8.6 Hz), 6.90-7.00 (2H, m), 7.13 (1H, d, J=2.0 Hz), 7.19 (1H, dd, J=9.2, 2.6 Hz), 7.28-7.41 (5H, m), 7.84 (1H, d, J=2.6 Hz), 9.45 (1H, s).

Example 61

[Formula 308]

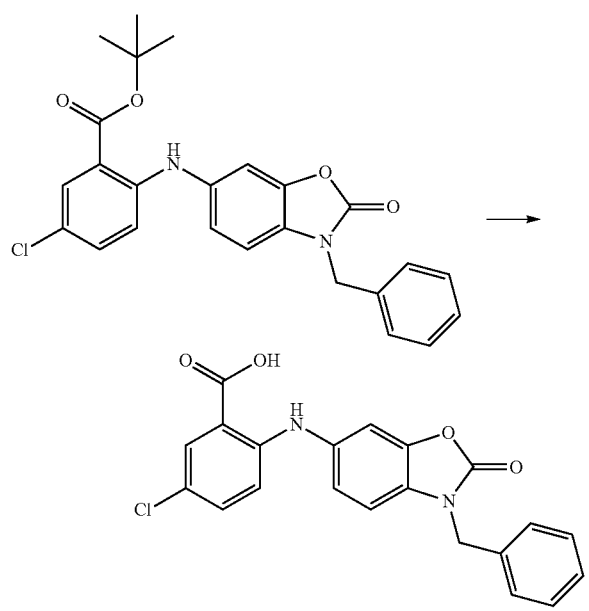

To the solution of 20 mg of tert-butyl 2-((3-benzyl-2-oxo-2,3-dihydrobenzo[d]oxazol-6-yl)amino)-5-chlorobenzoate in 0.2 mL of dichloromethane, 0.1 mL of trifluoroacetic acid was added under ice-cooling, and the resultant was stirred at room temperature for three hours and 20 minutes. Trifluoroacetic acid was distilled off under reduced pressure. The obtained solid was washed with ethyl acetate to give 8.9 mg of 2-((3-benzyl-2-oxo-2,3-dihydrobenzo[d]oxazol-6-yl)amino)-5-chlorobenzoic acid as a white solid.

$^1$H-NMR (DMSO-d$_6$) δ: 5.05 (2H, s), 7.03 (1H, d, J=9.2 Hz), 7.08 (1H, dd, J=8.6, 2.0 Hz), 7.20 (1H, d, J=8.6 Hz), 7.27-7.46 (7H, m), 7.80 (1H, s), 9.50 (1H, s).

MS (ESI/APCI, m/z): 395 (M+H)$^+$, 393 (M−H)$^-$.

Example 62

[Formula 309]

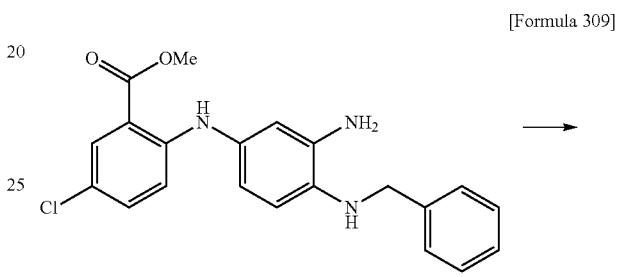

To the solution of 31.3 mg of methyl 2-((3-amino-4-(benzylamino)phenyl)amino)-5-chlorobenzoate in 0.6 mL of tetrahydrofuran, 19.9 mg of 1,1'-carbonyldiimidazole was added at room temperature, and the resultant was stirred at room temperature for one hour and 10 minutes. 19.9 mg of 1,1'-carbonyldiimidazole was added thereto, and the resultant was stirred at room temperature for 55 minutes. Water and ethyl acetate were added to the reaction mixture. The organic layer was separated and dried over anhydrous sodium sulfate, and the solvent was distilled off under reduced pressure. The obtained residue was purified by silica gel column chromatography (hexane:ethyl acetate) to give 22.3 mg of methyl 2-((1-benzyl-2-oxo-2,3-dihydro-1H-benzo[d]imidazol-5-yl)amino)-5-chlorobenzoate as a white solid.

$^1$H-NMR (CDCl$_3$) δ: 3.90 (3H, s), 5.07 (2H, s), 6.78-6.98 (4H, m), 7.18 (1H, dd, J=8.9, 2.3 Hz), 7.23-7.39 (5H, m), 7.90 (1H, d, J=2.6 Hz), 8.32 (1H, s), 9.29 (1H, s).

Example 63

[Formula 310]

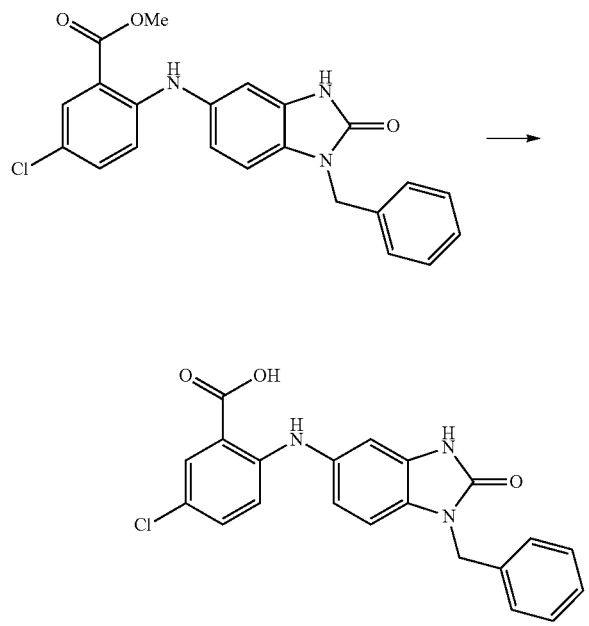

To the solution of 3.0 mg of methyl 2-((1-benzyl-2-oxo-2,3-dihydro-1H-benzo[d]imidazol-5-yl)amino)-5-chlorobenzoate in 0.1 mL of ethanol, 50 μL of a 5 mol/L aqueous sodium hydroxide solution was added at room temperature, and the resultant was stirred at an external temperature of 50° C. for 20 minutes. The reaction mixture was cooled to room temperature, and water and 2 mol/L hydrochloric acid were then added thereto, and the solid was collected by filtration to give 2.0 mg of 2-((1-benzyl-2-oxo-2,3-dihydro-1H-benzo[d]imidazol-5-yl)amino)-5-chlorobenzoic acid as a yellow solid.

$^1$H-NMR (DMSO-$d_6$) δ: 5.00 (2H, s), 6.81-6.92 (2H, m), 6.95 (1H, d, J=8.6 Hz), 7.03 (1H, d, J=7.9 Hz), 7.22-7.39 (6H, m), 7.78 (1H, d, J=2.6 Hz), 9.44 (1H, brs), 11.01 (1H, s).

MS (ESI/APCI, m/z): 394 (M+H)$^+$, 392 (M−H)$^-$.

Example 64

[Formula 311]

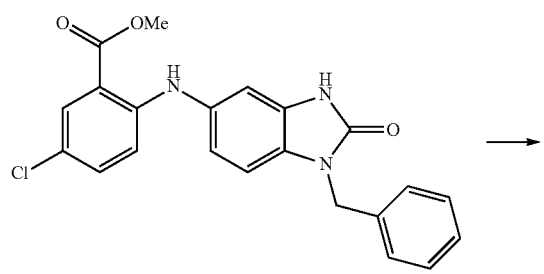

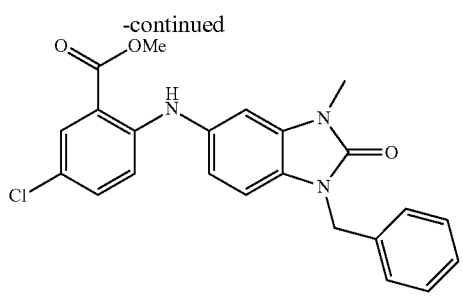

To the solution of 18 mg of methyl 2-((1-benzyl-2-oxo-2,3-dihydro-1H-benzo[d]imidazol-5-yl)amino)-5-chlorobenzoate in 0.4 mL of tetrahydrofuran, 5.5 μL of iodomethane and 12.2 mg of potassium carbonate were added at room temperature, and the resultant was stirred at 40° C. for 30 minutes. 5.5 μL of iodomethane was added thereto, and the resultant was stirred at an external temperature of 40° C. for 15 minutes. The reaction mixture was cooled to room temperature, and water and ethyl acetate were added thereto. The organic layer was separated and dried over anhydrous sodium sulfate, and the solvent was distilled off under reduced pressure to give 19 mg of methyl 2-((1-benzyl-3-methyl-2-oxo-2,3-dihydro-1H-benzo[d]imidazol-5-yl)amino)-5-chlorobenzoate as an oil.

Example 65

[Formula 312]

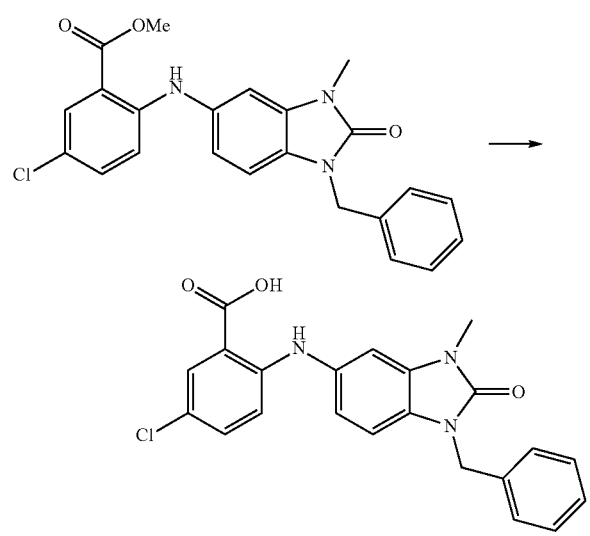

By the method similar to that of Example 63, 2-((1-benzyl-3-methyl-2-oxo-2,3-dihydro-1H-benzo[d]imidazol-5-yl)amino)-5-chlorobenzoic acid was obtained from methyl 2-((1-benzyl-3-methyl-2-oxo-2,3-dihydro-1H-benzo[d]imidazol-5-yl)amino)-5-chlorobenzoate.

$^1$H-NMR (DMSO-$d_6$) δ: 3.36 (3H, s), 5.06 (2H, s), 6.91 (1H, dd, J=8.6, 2.0 Hz), 6.98 (1H, d, J=9.2 Hz), 7.06-7.17 (2H, m), 7.22-7.41 (6H, m), 7.80 (1H, d, J=2.6 Hz), 9.51 (1H, s).

MS (ESI/APCI, m/z): 406 (M−H)$^-$.

Example 66

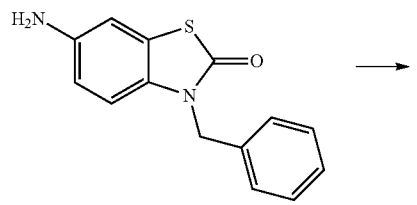

[Formula 313]

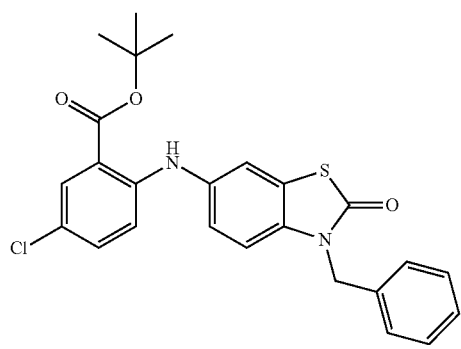

The mixture of 50 mg of 6-amino-3-benzylbenzo[d]thiazol-2(3H)-one, 56.4 mg of tert-butyl 2-bromo-5-chlorobenzoate, 10.1 mg of tris(dibenzylideneacetone)dipalladium(0), 12.7 mg of 4,5'-bis(diphenylphosphino)-9,9'-dimethylxanthene, 143 mg of cesium carbonate, and 1.0 mL of toluene, was stirred at an external temperature of 80° C. for one hour under a nitrogen atmosphere. The reaction mixture was cooled to room temperature, and water and ethyl acetate were then added thereto. The organic layer was separated and dried over anhydrous sodium sulfate, and the solvent was distilled off under reduced pressure. The obtained residue was purified by silica gel column chromatography (chloroform:methanol) to give 83.2 mg of tert-butyl 2-((3-benzyl-2-oxo-2,3-dihydrobenzo[d]thiazol-6-yl)amino)-5-chlorobenzoate as an oil.

Example 67

[Formula 314]

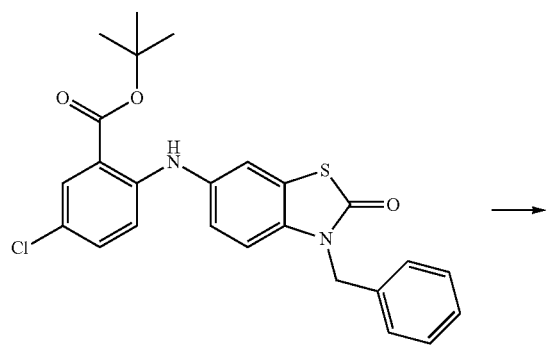

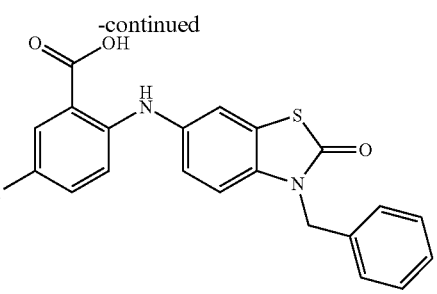

To 83.2 mg of tert-butyl 2-((3-benzyl-2-oxo-2,3-dihydrobenzo[d]thiazol-6-yl)amino)-5-chlorobenzoate, 0.2 mL of trifluoroacetic acid was added at room temperature, and the resultant was stirred at an external temperature of 50° C. for 30 minutes. After cooling the reaction mixture to room temperature, trifluoroacetic acid was distilled off under reduced pressure. Ethyl acetate was added to the obtained solid and the solid was collected by filtration to give 15.2 mg of 2-((3-benzyl-2-oxo-2,3-dihydrobenzo[d]thiazol-6-yl)amino)-5-chlorobenzoic acid as a white solid.

$^1$H-NMR (DMSO-$d_6$) δ: 5.19 (2H, s), 7.04 (1H, d, J=8.6 Hz), 7.16-7.42 (8H, m), 7.66 (1H, d, J=2.0 Hz), 7.81 (1H, d, J=2.6 Hz), 9.54 (1H, s).

MS (ESI/APCI, m/z): 409 (M−H)⁻.

Example 68

[Formula 315]

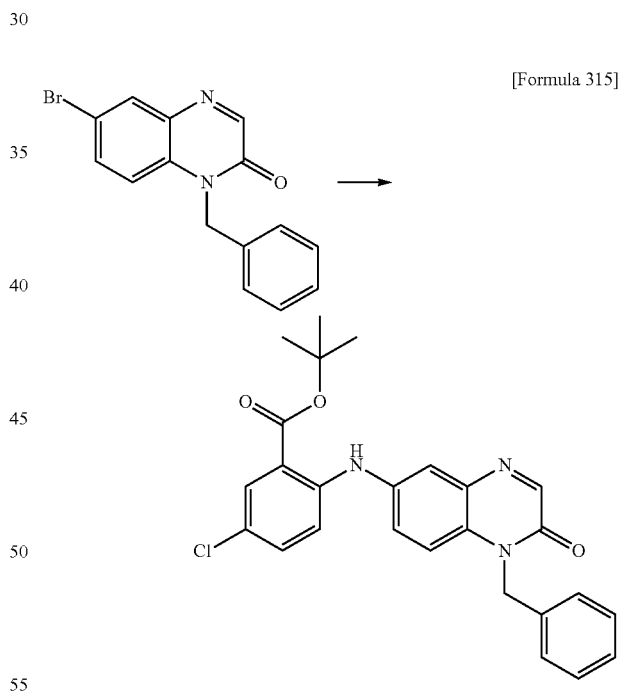

The mixture of 21.7 mg of 1-benzyl-6-bromoquinoxalin-2(1H)-one, 30 mg of tert-butyl 2-amino-5-chlorobenzoate, 4.4 mg of tris(dibenzylideneacetone)dipalladium(0), 5.5 mg of 4,5'-bis(diphenylphosphino)-9,9'-dimethylxanthene, 61.9 mg of cesium carbonate, and 0.3 mL of toluene, was heated at reflux for 30 minutes under a nitrogen atmosphere, and 4.4 mg of tris(dibenzylideneacetone)dipalladium(0) and 5.5 mg of 4,5'-bis(diphenylphosphino)-9,9'-dimethylxanthene were then added thereto, and the resultant was heated at reflux for 30 minutes. 4.4 mg of tris(dibenzylideneacetone)dipalladium(0) and 5.5 mg of 4,5'-bis(diphenylphosphino)-9,9'- dimethylxanthene were further added thereto, and the resultant was heated at reflux for 30 minutes. The reaction mixture was cooled to room temperature, and water and ethyl acetate were then added thereto. The organic layer was separated and dried over anhydrous sodium sulfate, and the solvent was distilled off under reduced pressure. The obtained residue was purified by silica gel column chromatography (hexane:ethyl acetate) to give 6.4 mg of tert-butyl 2-((1-benzyl-2-oxo-1,2-dihydroquinoxalin-6-yl)amino)-5-chlorobenzoate as an oil.

$^1$H-NMR (CDCl$_3$) δ: 1.60 (9H, s), 5.49 (2H, s), 7.07-7.41 (9H, m), 7.75 (1H, d, J=2.6 Hz), 7.87 (1H, d, J=2.6 Hz), 8.41 (1H, s), 9.61 (1H, s).

Example 69

[Formula 316]

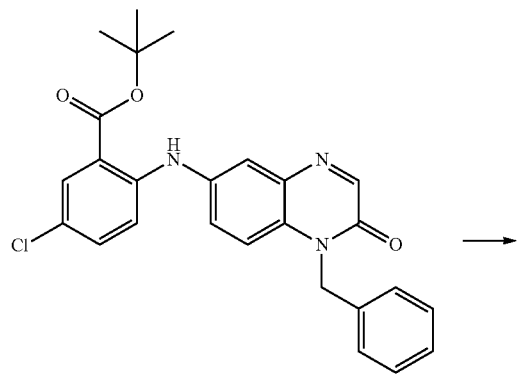

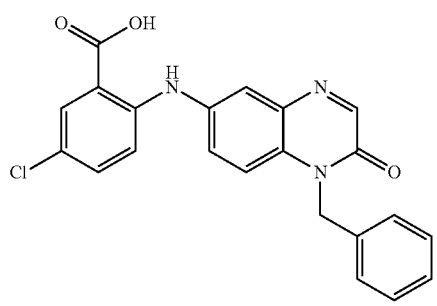

To 6.3 mg of tert-butyl 2-((1-benzyl-2-oxo-1,2-dihydroquinoxalin-6-yl)amino)-5-chlorobenzoate, 0.2 mL of trifluoroacetic acid was added at room temperature, and the resultant was stirred at room temperature for one hour. Trifluoroacetic acid was distilled off under reduced pressure. The obtained residue was sequentially purified by silica gel column chromatography (chloroform:methanol) and preparative thin-layer chromatography (chloroform:methanol) to give 1.3 mg of 2-((1-benzyl-2-oxo-1,2-dihydroquinoxalin-6-yl)amino)-5-chlorobenzoic acid as a yellow solid.

$^1$H-NMR (DMSO-d$_6$) δ: 5.49 (2H, s), 7.18 (1H, d, J=9.2 Hz), 7.23-7.42 (6H, m), 7.43-7.50 (2H, m), 7.69 (1H, s), 7.84 (1H, d, J=2.6 Hz), 8.36 (1H, s).

MS (ESI/APCI, m/z): 404 (M–H)$^-$.

Example 70

[Formula 317]

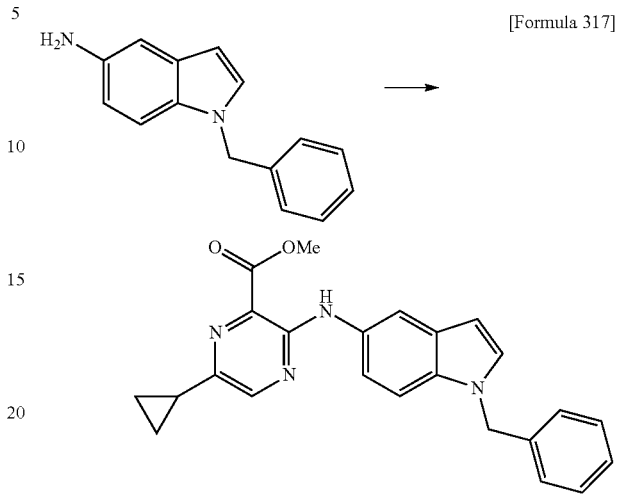

The mixture of 260 mg of 1-benzyl-1H-indol-5-amine, 0.3 g of methyl 3-bromo-6-cyclopropylpyrazine-2-carboxylate, 54 mg of tris(dibenzylideneacetone)dipalladium(0), 68 mg of 4,5'-bis(diphenylphosphino)-9,9'-dimethylxanthene, 0.76 g of cesium carbonate, and 3 mL of toluene, was stirred at 150° C. for 50 minutes under a nitrogen atmosphere using microwave equipment. The reaction mixture was cooled to room temperature, and ethyl acetate and water were then added thereto. The organic layer was separated, sequentially washed with water and a saturated aqueous sodium chloride solution and dried over anhydrous magnesium sulfate, and the solvent was distilled off under reduced pressure. The obtained residue was purified by silica gel column chromatography (gradient elution with hexane:ethyl acetate=90:10-50:50), and hexane was added to the thus obtained residue, and the solid was collected by filtration to give 80 mg of methyl 3-((1-benzyl-1H-indol-5-yl)amino)-6-cyclopropylpyrazine-2-carboxylate as a yellow solid.

$^1$H-NMR (DMSO-d$_6$) δ: 0.80-0.99 (4H, m), 2.05-2.17 (1H, m), 3.90 (3H, s), 5.41 (2H, s), 6.45 (1H, d, J=3.3 Hz), 7.14 (1H, dd, J=8.6, 2.0 Hz), 7.17-7.35 (5H, m), 7.39 (1H, d, J=8.6 Hz), 7.50 (1H, d, J=3.3 Hz), 7.87 (1H, d, J=2.0 Hz), 8.33 (1H, s), 9.71 (1H, s).

Example 71

[Formula 318]

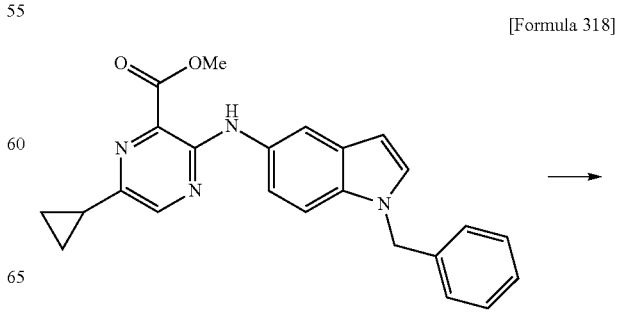

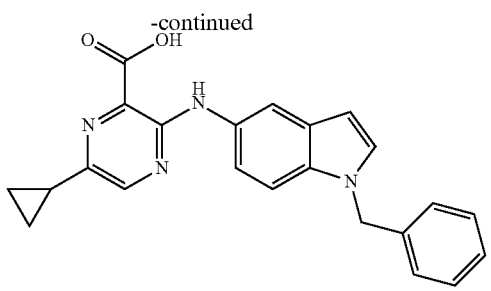

To the solution of 0.15 g of methyl 3-((1-benzyl-1H-indol-5-yl)amino)-6-cyclopropylpyrazine-2-carboxylate in 1.0 mL of ethanol and 1.0 mL of tetrahydrofuran, 0.15 mL of a 5 mol/L aqueous sodium hydroxide solution was added at room temperature, and the resultant was warmed to an external temperature of 40 to 50° C. 5.0 mL of ethanol and 5.0 mL of water were added to the reaction mixture, and the resultant was stirred at an external temperature of 40 to 50° C. for one hour. The reaction mixture was cooled to room temperature, and water was added thereto, and the resultant was adjusted to pH 2.8 with 2 mol/L hydrochloric acid. The solid was collected by filtration and purified by silica gel column chromatography (gradient elution with chloroform:methanol=100:0-90:10), and diisopropyl ether was added to the obtained residue, and the solid was collected by filtration to give 80 mg of 3-((1-benzyl-1H-indol-5-yl)amino)-6-cyclopropylpyrazine-2-carboxylic acid as an orange solid.

$^1$H-NMR (DMSO-$d_6$) δ: 0.86-0.96 (4H, m), 2.03-2.16 (1H, m), 5.41 (2H, s), 6.45 (1H, d, J=2.6 Hz), 7.14 (1H, dd, J=8.6, 2.0 Hz), 7.17-7.35 (5H, m), 7.39 (1H, d, J=9.2 Hz), 7.49 (1H, d, J=3.3 Hz), 7.90 (1H, d, J=2.0 Hz), 8.31 (1H, s), 10.11 (1H, s).

MS (ESI, m/z): 385 (M+H)$^+$, 383 (M−H)$^-$.

Example 72

[Formula 319]

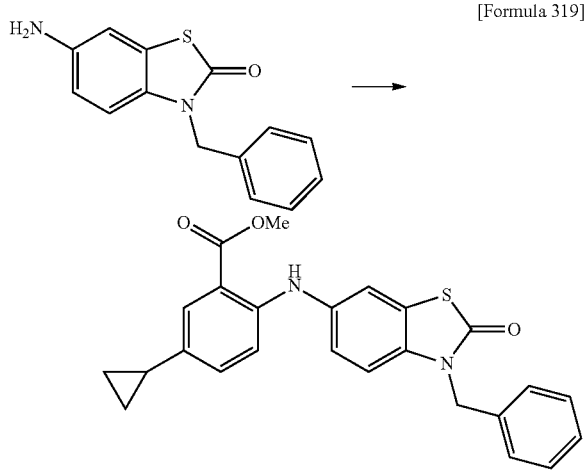

The mixture of 50 mg of 6-amino-3-benzylbenzo[d]thiazol-2(3H)-one, 50 mg of methyl 2-bromo-5-cyclopropylbenzoate, 8.9 mg of tris(dibenzylideneacetone)dipalladium (0), 11.3 mg of 4,5'-bis(diphenylphosphino)-9,9'-dimethylxanthene, 128 mg of cesium carbonate, and 0.5 mL of toluene, was stirred at an external temperature of 80° C. for two hours. The reaction mixture was cooled to room temperature, and water and ethyl acetate were then added thereto. The organic layer was separated and dried over anhydrous sodium sulfate, and the solvent was distilled off under reduced pressure. The obtained residue was purified by silica gel column chromatography (hexane:ethyl acetate) to give 12.2 mg of methyl 2-((3-benzyl-2-oxo-2,3-dihydrobenzo[d]thiazol-6-yl)amino)-5-cyclopropylbenzoate as an oil.

$^1$H-NMR (CDCl$_3$) δ: 0.56-0.66 (2H, m), 0.81-0.95 (2H, m), 1.77-1.89 (1H, m), 3.89 (3H, s), 5.14 (2H, s), 6.90 (1H, d, J=8.6 Hz), 6.97-7.14 (3H, m), 7.23-7.45 (6H, m), 7.68 (1H, d, J=2.0 Hz), 9.22 (1H, s).

Example 73

[Formula 320]

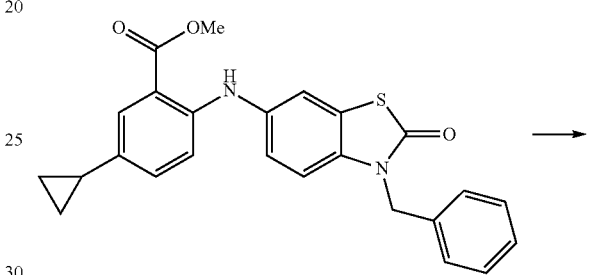

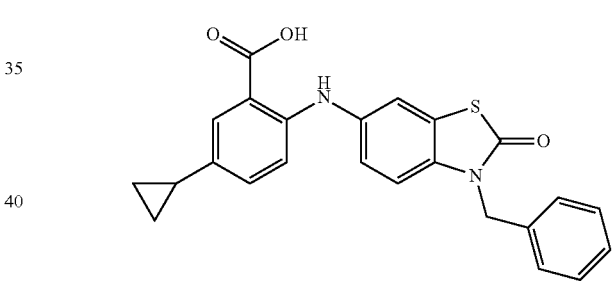

To the solution of 12.2 mg of methyl 2-((3-benzyl-2-oxo-2,3-dihydrobenzo[d]thiazol-6-yl)amino)-5-cyclopropylbenzoate in 0.12 mL of ethanol, 11.3 μL of a 5 mol/L aqueous sodium hydroxide solution was added at room temperature, and the resultant was stirred at an external temperature of 50° C. for one hour and stirred at 70° C. for 30 minutes. The reaction mixture was cooled to room temperature, and water, 1 mol/L hydrochloric acid and ethyl acetate were then added thereto. The organic layer was separated and dried over anhydrous sodium sulfate, and the solvent was distilled off under reduced pressure. The obtained residue was purified by preparative thin-layer chromatography (chloroform:methanol) to give 3.3 mg of 2-((3-benzyl-2-oxo-2,3-dihydrobenzo[d]thiazol-6-yl)amino)-5-cyclopropylbenzoic acid as a yellow solid.

$^1$H-NMR (DMSO-$d_6$) δ: 0.51-0.59 (2H, m), 0.82-0.91 (2H, m), 1.80-1.92 (1H, m), 5.17 (2H, s), 7.02 (1H, d, J=8.6 Hz), 7.08 (1H, dd, J=8.6, 2.0 Hz), 7.15 (1H, dd, J=8.9, 2.3 Hz), 7.19-7.41 (6H, m), 7.56-7.64 (2H, m), 9.42 (1H, brs), 13.04 (1H, brs).

MS (ESI/APCI, m/z): 415 (M−H)$^-$.

Example 74

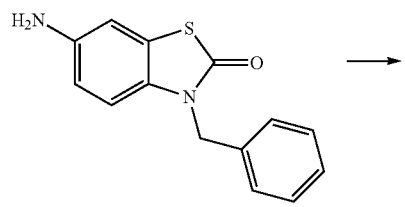

[Formula 321]

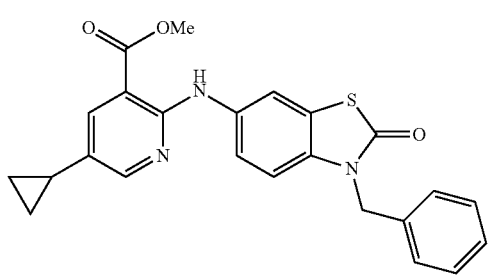

The mixture of 41.5 mg of 6-amino-3-benzylbenzo[d]thiazol-2(3H)-one, 50.2 mg of methyl 2-chloro-5-cyclopropylnicotinate, 8.9 mg of tris(dibenzylideneacetone)dipalladium(0), 11.3 mg of 4,5'-bis(diphenylphosphino)-9,9'-dimethylxanthene, 128 mg of cesium carbonate, and 0.5 mL of toluene, was stirred at an external temperature of 80° C. for two hours. The reaction mixture was cooled to room temperature, and water and ethyl acetate were then added thereto.

The organic layer was separated and dried over anhydrous sodium sulfate, and the solvent was distilled off under reduced pressure. The obtained residue was purified by silica gel chromatography (hexane:ethyl acetate) to give 23.4 mg of methyl 2-((3-benzyl-2-oxo-2,3-dihydrobenzo[d]thiazol-6-yl)amino)-5-cyclopropylnicotinate as an oil.

$^1$H-NMR (CDCl$_3$) δ: 0.59-0.68 (2H, m), 0.90-0.99 (2H, m), 1.77-1.89 (1H, m), 3.92 (3H, s), 5.14 (2H, s), 6.89 (1H, d, J=9.3 Hz), 7.19-7.38 (6H, m), 7.90 (1H, d, J=2.6 Hz), 8.04 (1H, d, J=2.0 Hz), 8.19 (1H, d, J=2.6 Hz), 9.97 (1H, s).

Example 75

[Formula 322]

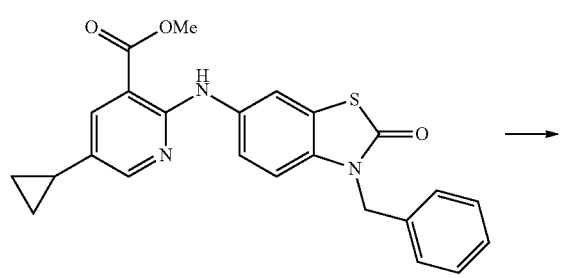

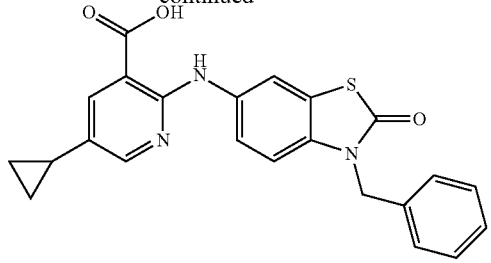

To the solution of 23.4 mg of methyl 2-((3-benzyl-2-oxo-2,3-dihydrobenzo[d]thiazol-6-yl)amino)-5-cyclopropylnicotinate in 0.23 mL of ethanol, 21.6 μL of a 5 mol/L aqueous sodium hydroxide solution was added at room temperature, and the resultant was stirred at an external temperature of 50° C. for one hour. The reaction mixture was cooled to room temperature, and water, 1 mol/L hydrochloric acid and ethyl acetate were then added thereto. The organic layer was separated and dried over anhydrous sodium sulfate, and the solvent was distilled off under reduced pressure. The obtained solid was washed with methanol to give 4.8 mg of 2-((3-benzyl-2-oxo-2,3-dihydrobenzo[d]thiazol-6-yl)amino)-5-cyclopropylnicotinic acid as a yellow solid.

$^1$H-NMR (DMSO-d$_6$) δ: 0.60-0.70 (2H, m), 0.88-0.97 (2H, m), 1.84-1.97 (1H, m), 5.17 (2H, s), 7.21 (1H, d, J=9.2 Hz), 7.24-7.40 (5H, m), 7.47 (1H, dd, J=8.6, 2.0 Hz), 7.89 (1H, d, J=2.0 Hz), 8.15 (1H, d, J=2.0 Hz), 8.21 (1H, d, J=2.6 Hz), 10.22 (1H, s), 13.57 (1H, s).

MS (ESI/APCI, m/z): 418 (M+H)$^+$, 416 (INA-H)$^-$.

Example 76

[Formula 323]

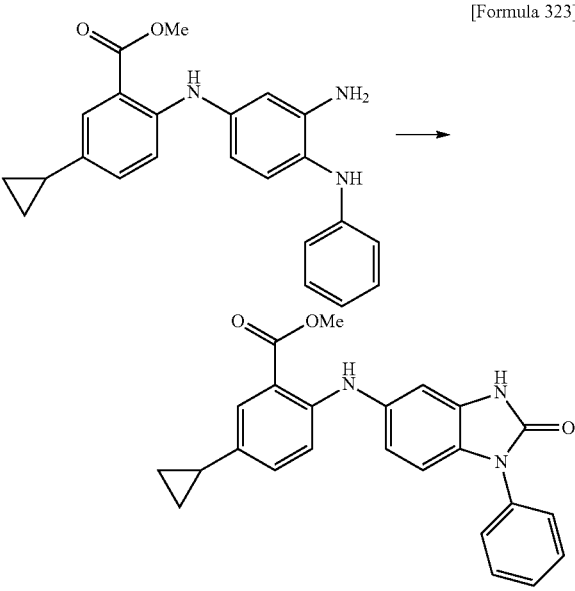

To the solution of methyl 2-((3-amino-4-(phenylamino)phenyl)amino)-5-cyclopropylbenzoate obtained in Reference Example 29 in 1.7 mL of N,N-dimethylformamide, 137 mg of 1,1'-carbonyldiimidazole was added at room temperature, and the resultant was stirred at room temperature for 30 minutes. Water and ethyl acetate were added to the reaction mixture. The organic layer was separated and dried over anhydrous sodium sulfate, and the solvent was distilled off under reduced pressure. The obtained residue was purified by silica gel column chromatography (hexane:ethyl acetate) to give 82.3 mg of methyl 5-cyclopropyl-2-((2-oxo-1-phenyl-2,3-dihydro-1H-benzo[d]imidazol-5-yl)amino)benzoate as a yellow solid.

$^1$H-NMR (DMSO-$d_6$) δ: 0.52-0.61 (2H, m), 0.83-0.92 (2H, m), 1.81-1.93 (1H, m), 3.85 (3H, d, J=2.6 Hz), 6.86 (1H, dd, J=8.6, 2.0 Hz), 6.91-7.06 (3H, m), 7.12 (1H, dd, J=8.6, 2.0 Hz), 7.37-7.48 (1H, m), 7.51-7.65 (5H, m), 9.06 (1H, s), 11.14 (1H, s).

Example 77

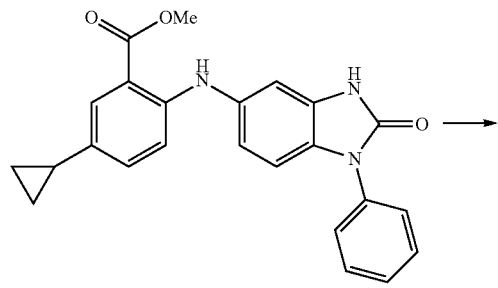

[Formula 324]

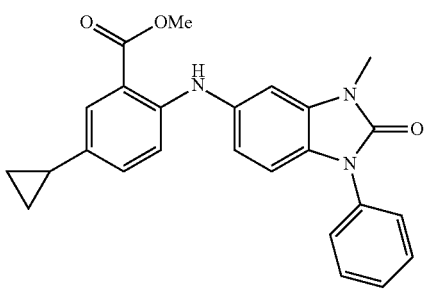

To the solution of 10 mg of methyl 5-cyclopropyl-2-((2-oxo-1-phenyl-2,3-dihydro-1H-benzo[d]imidazol-5-yl)amino)benzoate in 0.2 mL of N,N-dimethylformamide, 7.8 µL of iodomethane and 16.4 mg of cesium carbonate were added at room temperature, and the resultant was stirred at room temperature for 30 minutes. Water and ethyl acetate were added to the reaction mixture. The organic layer was separated and dried over anhydrous sodium sulfate, and the solvent was distilled off under reduced pressure. The obtained residue was purified by silica gel column chromatography (hexane:ethyl acetate) to give 11.3 mg of methyl 5-cyclopropyl-2-((3-methyl-2-oxo-1-phenyl-2,3-dihydro-1H-benzo[d]imidazol-5-yl)amino)benzoate as an oil.

$^1$H-NMR (CDCl$_3$) δ: 0.58-0.67 (2H, m), 0.81-0.98 (2H, m), 1.77-1.90 (1H, m), 3.46 (3H, s), 3.92 (3H, s), 6.89-6.99 (2H, m), 7.00-7.12 (3H, m), 7.35-7.45 (1H, m), 7.46-7.60 (4H, m), 7.71 (1H, s), 9.27 (1H, s).

Example 78

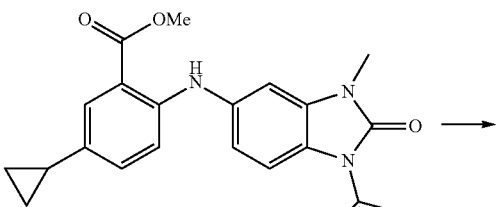

[Formula 325]

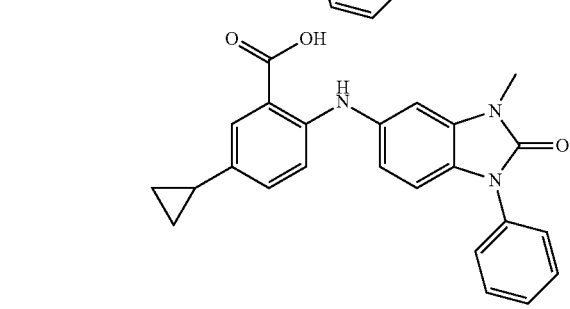

To the solution of 11.3 mg of methyl 5-cyclopropyl-2-((3-methyl-2-oxo-1-phenyl-2,3-dihydro-1H-benzo[d]imidazol-5-yl)amino)benzoate in 0.2 mL of ethanol, 21.8 µL of a 5 mol/L aqueous sodium hydroxide solution was added at room temperature, and the resultant was stirred at room temperature for 13 hours and 10 minutes and stirred at 50° C. for 10 minutes. The reaction mixture was cooled to room temperature, and water and 2 mol/L hydrochloric acid were then added thereto. The obtained solid was collected by filtration to give 10.3 mg of 5-cyclopropyl-2-((3-methyl-2-oxo-1-phenyl-2,3-dihydro-1H-benzo[d]imidazol-5-yl)amino)benzoic acid as a yellow solid.

$^1$H-NMR (DMSO-$d_6$) δ: 0.52-0.61 (2H, m), 0.81-0.92 (2H, m), 1.81-1.92 (1H, m), 3.39 (3H, s), 6.92 (1H, dd, J=8.6, 2.0 Hz), 6.98-7.14 (3H, m), 7.18 (1H, d, J=2.0 Hz), 7.39-7.50 (1H, m), 7.51-7.66 (5H, m), 9.44 (1H, brs), 12.99 (1H, brs).

MS (ESI/APCI, m/z): 400 (M+H)$^+$, 398 (M−H)$^−$.

Example 79

[Formula 326]

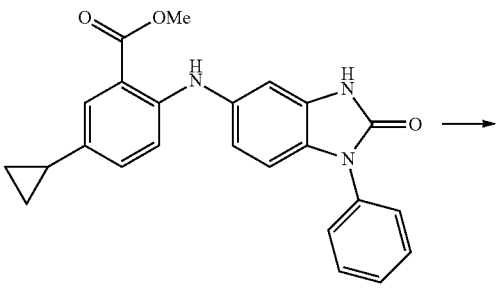

-continued

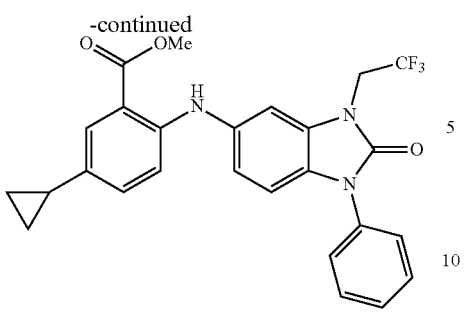

By the method similar to that of Example 77, methyl 5-cyclopropyl-2-((2-oxo-1-phenyl-3-(2,2,2-trifluoroethyl)-2,3-dihydro-1H-benzo[d]imidazol-5-yl)amino)benzoate was obtained from methyl 5-cyclopropyl-2-((2-oxo-1-phenyl-2,3-dihydro-1H-benzo[d]imidazol-5-yl)amino)benzoate and 2,2,2-trifluoroethyl trifluoromethanesulfonate.

$^1$H-NMR (CDCl$_3$) δ: 0.58-0.67 (2H, m), 0.82-0.96 (2H, m), 1.78-1.90 (1H, m), 3.92 (3H, s), 4.50 (2H, q, J=8.6 Hz), 6.97 (1H, dd, J=8.6, 2.0 Hz), 7.01-7.12 (4H, m), 7.37-7.48 (1H, m), 7.50-7.60 (4H, m), 7.71 (1H, s), 9.31 (1H, s).

Example 80

[Formula 327]

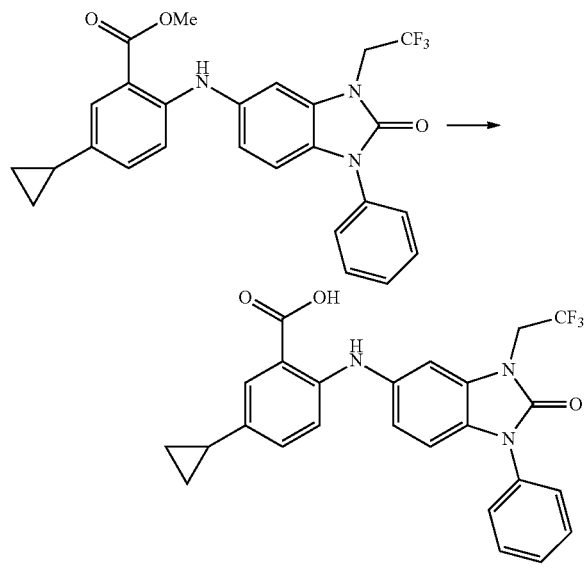

To the solution of 11.3 mg of methyl 5-cyclopropyl-2-((2-oxo-1-phenyl-3-(2,2,2-trifluoroethyl)-2,3-dihydro-1H-benzo[d]imidazol-5-yl)amino)benzoate in 0.2 mL of ethanol, 18.8 pt of a 5 mol/L aqueous sodium hydroxide solution was added at room temperature, and the resultant was stirred at room temperature for 15 hours. Water and 2 mol/L hydrochloric acid were added to the reaction mixture and the solid was collected by filtration to give 9.0 mg of 5-cyclopropyl-2-((2-oxo-1-phenyl-3-(2,2,2-trifluoroethyl)-2,3-dihydro-1H-benzo[d]imidazol-5-yl)amino)benzoic acid as a yellow solid.

$^1$H-NMR (DMSO-d$_6$) δ: 0.53-0.61 (2H, m), 0.83-0.92 (2H, m), 1.80-1.93 (1H, m), 4.88 (2H, q, J=9.5 Hz), 6.94-7.13 (4H, m), 7.34-7.53 (2H, m), 7.55-7.65 (5H, m), 9.51 (1H, s).

MS (ESI/APCI, m/z): 468 (M+H)$^+$, 466 (M-H)$^-$.

Example 81

[Formula 328]

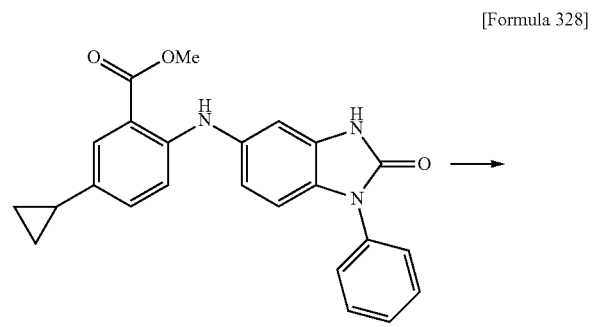

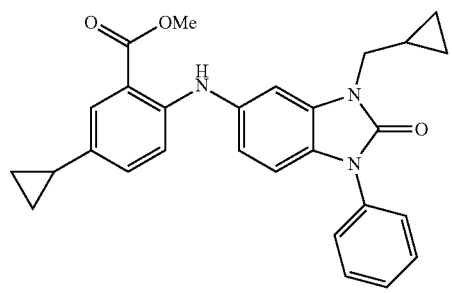

By the method similar to that of Example 77, methyl 5-cyclopropyl-2-((3-(cyclopropylmethyl)-2-oxo-1-phenyl-2,3-dihydro-1H-benzo[d]imidazol-5-yl)amino)benzoate was obtained from methyl 5-cyclopropyl-2-((2-oxo-1-phenyl-2,3-dihydro-1H-benzo[d]imidazol-5-yl)amino)benzoate and (bromomethyl)cyclopropane.

$^1$H-NMR (CDCl$_3$) δ: 0.42-0.50 (2H, m), 0.54-0.66 (4H, m), 0.83-0.95 (2H, m), 1.20-1.33 (1H, m), 1.78-1.89 (1H, m), 3.79 (2H, d, J=6.6 Hz), 3.92 (3H, d, J=2.0 Hz), 6.92 (1H, dd, J=8.6, 2.0 Hz), 6.99-7.10 (4H, m), 7.35-7.43 (1H, m), 7.49-7.61 (4H, m), 7.71 (1H, s), 9.28 (1H, s).

Example 82

[Formula 329]

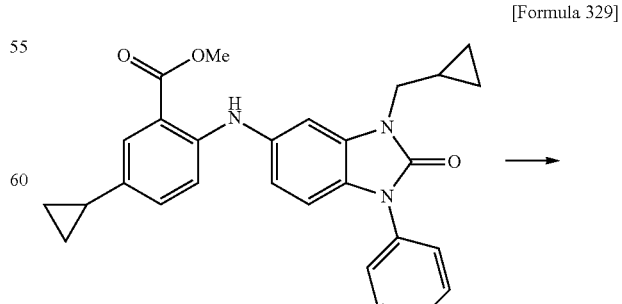

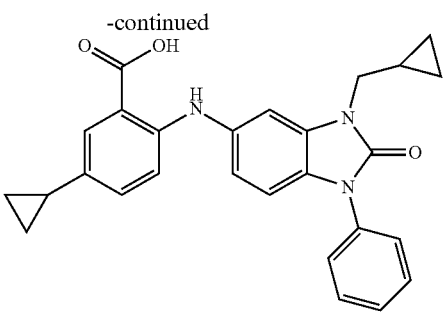

By the method similar to that of Example 63, 5-cyclopropyl-2-((3-(cyclopropylmethyl)-2-oxo-1-phenyl-2,3-dihydro-1H-benzo[d]imidazol-5-yl)amino)benzoic acid was obtained from methyl 5-cyclopropyl-2-((3-(cyclopropylmethyl)-2-oxo-1-phenyl-2,3-dihydro-1H-benzo[d]imidazol-5-yl)amino)benzoate.

$^1$H-NMR (DMSO-d$_6$) δ: 0.36-0.61 (6H, m), 0.82-0.93 (2H, m), 1.18-1.32 (1H, m), 1.81-1.92 (1H, m), 3.80 (2H, d, J=6.6 Hz), 6.92 (1H, dd, J=8.3, 1.7 Hz), 6.99-7.14 (3H, m), 7.29 (1H, d, J=2.0 Hz), 7.40-7.50 (1H, m), 7.52-7.65 (5H, m), 9.42 (1H, s).

MS (ESI/APCI, m/z): 440 (M+H)$^+$, 438 (M−H)$^-$.

Example 83

[Formula 330]

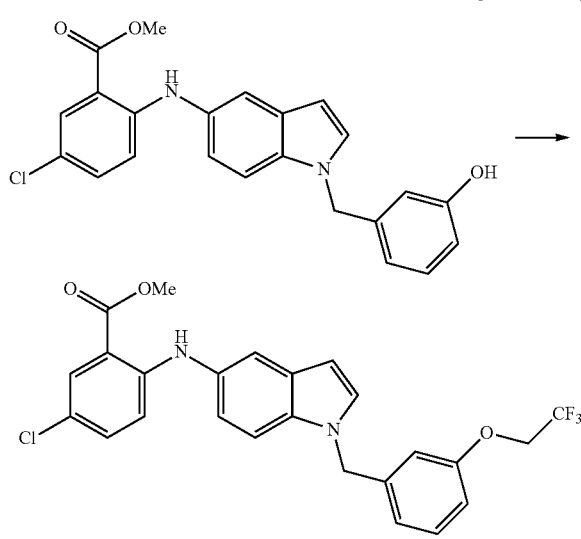

To the solution of 80 mg of methyl 5-chloro-2-((1-(3-hydroxybenzyl)-1H-indol-5-yl)amino)benzoate in 0.8 mL of N,N-dimethylformamide, 30 mg of potassium carbonate was added at room temperature, and the resultant was stirred in a sealed tube for 10 minutes. 214 of 1,1,1-trifluoro-2-iodoethane was added to the reaction mixture, and the resultant was stirred at an external temperature of 50° C. for one hour and 55 minutes. 21 μL of 1,1,1-trifluoro-2-iodoethane was added to the reaction mixture, and the resultant was stirred at an external temperature of 80° C. for three hours and 50 minutes. 21 μL of 1,1,1-trifluoro-2-iodoethane was added to the reaction mixture, and the resultant was stirred at an external temperature of 100° C. for three hours. Ethyl acetate and water were added to the reaction mixture, and the resultant was adjusted to pH 2.0 with 2 mol/L hydrochloric acid. The organic layer was separated and dried over anhydrous magnesium sulfate, and the solvent was then distilled off under reduced pressure. The obtained residue was purified by silica gel column chromatography to give 30 mg of methyl 5-chloro-2-((1-(3-(2,2,2-trifluoroethoxy)benzyl)-1H-indol-5-yl)amino)benzoate as a yellow oil.

$^1$H-NMR (CDCl$_3$) δ: 3.90 (3H, s), 4.28 (2H, q, J=8.1 Hz), 5.29 (2H, s), 6.52 (1H, d, J=2.6 Hz), 6.69-6.74 (1H, m), 6.78-6.86 (2H, m), 6.92 (1H, d, J=9.2 Hz), 7.02 (1H, dd, J=8.6, 2.0 Hz), 7.10-7.17 (2H, m), 7.20-7.31 (2H, m), 7.49 (1H, d, J=2.0 Hz), 7.90 (1H, d, J=2.6 Hz), 9.33 (1H, s).

Example 84

[Formula 331]

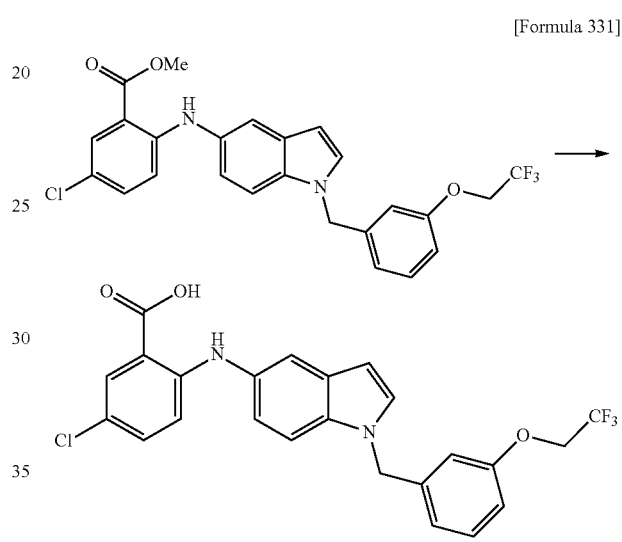

By the method similar to that of Example 63, 5-chloro-2-((1-(3-(2,2,2-trifluoroethoxy)benzyl)-1H-indol-5-yl)amino)benzoic acid was obtained from methyl 5-chloro-2-((1-(3-(2,2,2-trifluoroethoxy)benzyl)-1H-indol-5-yl)amino)benzoate.

$^1$H-NMR (DMSO-d$_6$) δ: 4.73 (2H, q, J=9.0 Hz), 5.40 (2H, s), 6.47 (1H, d, J=3.3 Hz), 6.84-7.02 (5H, m), 7.23-7.34 (2H, m), 7.43 (1H, d, J=2.0 Hz), 7.49 (1H, d, J=8.6 Hz), 7.56 (1H, d, J=3.3 Hz), 7.78 (1H, d, J=2.6 Hz), 9.50 (1H, brs).

MS (ESI/APCI, m/z): 473 (M−H)$^-$.

Example 85

[Formula 332]

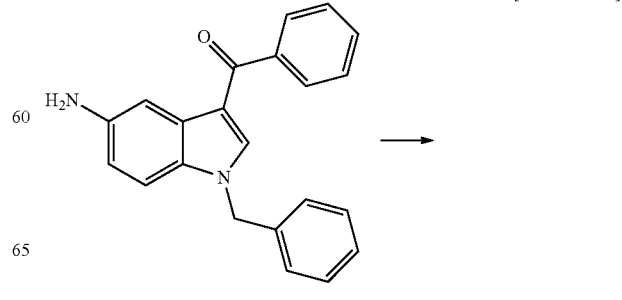

-continued

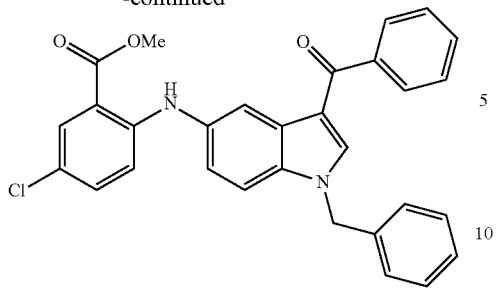

By the method similar to that of Example 20, methyl 2-((3-benzoyl-1-benzyl-1H-indol-5-yl)amino)-5-chlorobenzoate was obtained from (5-amino-1-benzyl-1H-indol-3-yl)(phenyl)methanone and methyl 2-bromo-5-chlorobenzoate.

$^1$H-NMR (DMSO-$d_6$) δ: 3.88 (3H, s), 5.56 (2H, s), 7.04 (1H, d, J=8.6 Hz), 7.14-7.20 (1H, m), 7.23-7.86 (13H, m), 8.12-8.17 (1H, m), 8.30 (1H, s), 9.31 (1H, s).

Example 86

[Formula 333]

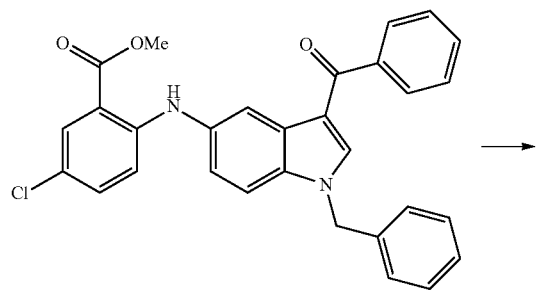

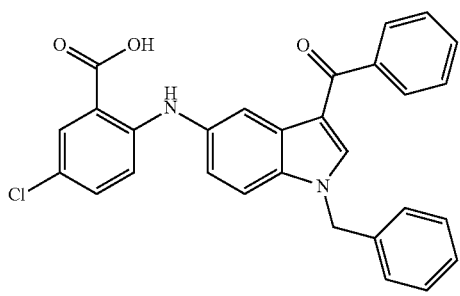

By the method similar to that of Example 37, 2-((3-benzoyl-1-benzyl-1H-indol-5-yl)amino)-5-chlorobenzoic acid was obtained from methyl 2-((3-benzoyl-1-benzyl-1H-indol-5-yl)amino)-5-chlorobenzoate.

$^1$H-NMR (DMSO-$d_6$) δ: 5.56 (2H, s), 7.05 (1H, d, J=9.2 Hz), 7.17 (1H, dd, J=8.6, 2.0 Hz), 7.24-7.41 (6H, m), 7.52-7.66 (4H, m), 7.77-7.86 (3H, m), 8.14 (1H, d, J=2.0 Hz), 8.29 (1H, s), 9.63 (1H, brs).

MS (ESI/APCI, m/z): 479 (M−H)$^-$.

Example 87

[Formula 334]

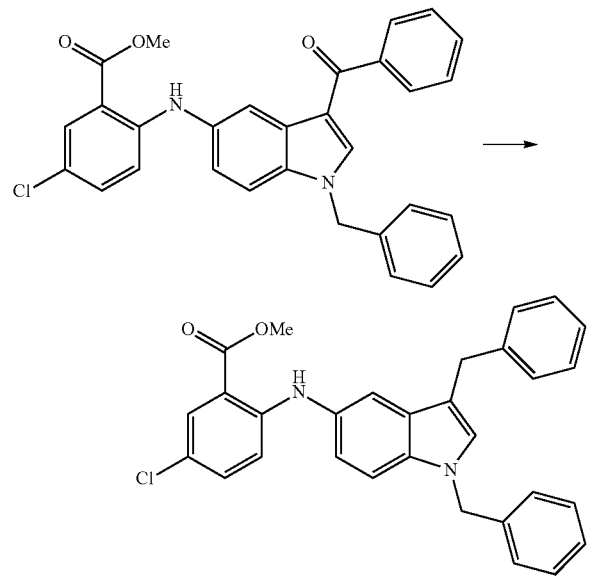

To the solution of 30 mg of methyl 2-((3-benzoyl-1-benzyl-1H-indol-5-yl)amino)-5-chlorobenzoate in 0.6 mL of tetrahydrofuran, 0.2 mL of a 1 mol/L solution of borane-tetrahydrofuran complex in tetrahydrofuran was added at 0° C., and the resultant was stirred at room temperature for five hours and 50 minutes. 0.2 mL of a 1 mol/L solution of borane-tetrahydrofuran complex in tetrahydrofuran was added to the reaction mixture, and the resultant was stirred for three hours and 30 minutes and then allowed to stand for two days. Ethyl acetate and water were added to the reaction mixture. The organic layer was separated and dried over anhydrous magnesium sulfate, and the solvent was then distilled off under reduced pressure. The obtained residue was purified by silica gel column chromatography to give 22 mg of methyl 5-chloro-2-((1,3-dibenzyl-1H-indol-5-yl)amino)benzoate.

$^1$H-NMR (CDCl$_3$) δ: 3.89 (3H, s), 4.07 (2H, s), 5.26 (2H, s), 6.82-7.37 (16H, m), 7.88 (1H, d, J=2.6 Hz), 9.30 (1H, s).

Example 88

[Formula 335]

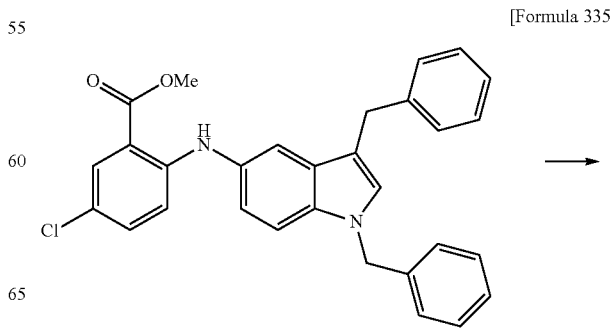

-continued

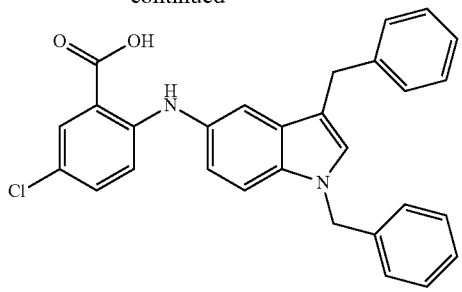

By the method similar to that of Example 63, 5-chloro-2-((1,3-dibenzyl-1H-indol-5-yl)amino)benzoic acid was obtained from methyl 5-chloro-2-((1,3-dibenzyl-1H-indol-5-yl)amino)benzoate.

$^1$H-NMR (DMSO-$d_6$) δ: 4.03 (2H, s), 5.37 (2H, s), 6.81 (1H, d, J=9.2 Hz), 6.93-6.99 (1H, m), 7.11-7.38 (13H, m), 7.43 (1H, d, J=8.6 Hz), 7.77 (1H, d, J=2.6 Hz), 9.48 (1H, brs).

MS (ESI/APCI, m/z): 465 (M−H)$^−$.

Example 89

[Formula 336]

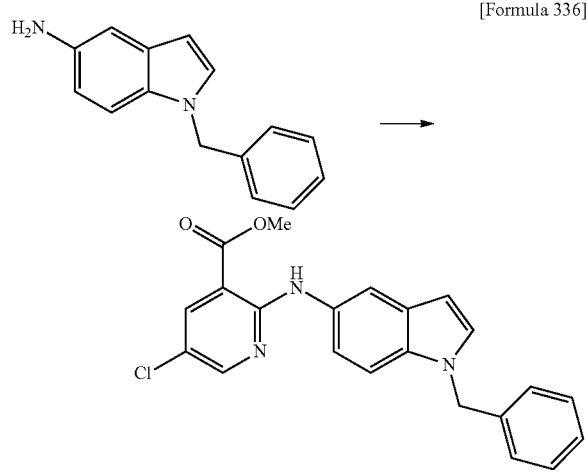

The mixture of 216 mg of 1-benzyl-1H-indol-5-amine, 200 mg of methyl 2,5-dichloronicotinate, 89 mg of tris(dibenzylideneacetone)dipalladium(0), 112 mg of 4,5'-bis(diphenylphosphino)-9,9'-dimethylxanthene, 0.63 g of cesium carbonate, and 3 mL of toluene, was heated at reflux for three hours under a nitrogen atmosphere. The reaction mixture was cooled to room temperature, and ethyl acetate and water were then added thereto. The organic layer was separated, washed with a saturated aqueous sodium chloride solution and dried over anhydrous magnesium sulfate, and the solvent was distilled off under reduced pressure. The obtained residue was purified by silica gel column chromatography (gradient elution with hexane:ethyl acetate=90:10-70:30) to give 45 mg of methyl 2-((1-benzyl-1H-indol-5-yl)amino)-5-chloronicotinate as a pale brown solid.

$^1$H-NMR (DMSO-$d_6$) δ: 3.90 (3H, s), 5.41 (2H, s), 6.46 (1H, d, J=2.6 Hz), 7.12-7.55 (8H, m), 7.87 (1H, d, J=2.0 Hz), 8.18 (1H, d, J=3.3 Hz), 8.37 (1H, d, J=2.6 Hz), 9.89 (1H, s).

MS (ESI, m/z): 392 (M+H)$^+$.

Example 90

[Formula 337]

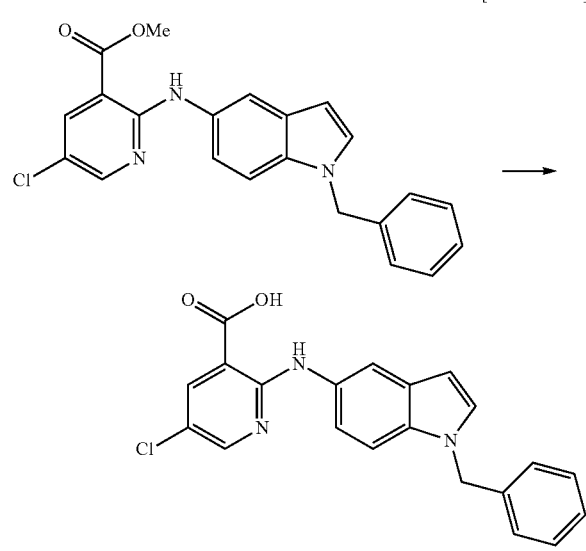

To the solution of 45 mg of methyl 2-((1-benzyl-1H-indol-5-yl)amino)-5-chloronicotinate in 1.0 mL of ethanol, 46 μL of a 5 mol/L aqueous sodium hydroxide solution was added and 2.0 mL of tetrahydrofuran at room temperature, and the resultant was stirred at an external temperature of 40 to 60° C. for two hours. The reaction mixture was cooled to room temperature, and water was then added thereto, and the resultant was adjusted to pH 2.0 with 2 mol/L hydrochloric acid. The solid was collected by filtration and washed with water and diisopropyl ether to give 30 mg of 2-((1-benzyl-1H-indol-5-yl)amino)-5-chloronicotinic acid as a yellow solid.

$^1$H-NMR (DMSO-$d_6$) δ: 5.41 (2H, s), 6.45 (1H, d, J=2.6 Hz), 7.12-7.35 (6H, m), 7.39 (1H, d, J=8.6 Hz), 7.50 (1H, d, J=2.6 Hz), 7.89 (1H, d, J=2.0 Hz), 8.15 (1H, d, J=2.6 Hz), 8.34 (1H, d, J=2.6 Hz), 10.20 (1H, s).

MS (ESI, m/z): 378 (M+H)$^+$, 376 (M−H)$^−$.

Example 91

[Formula 338]

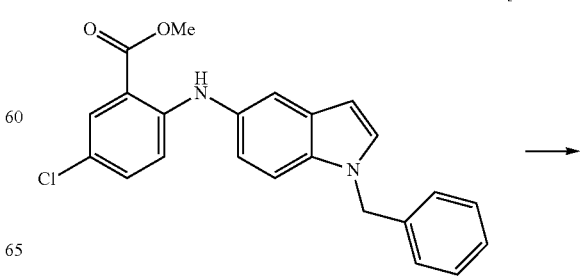

-continued

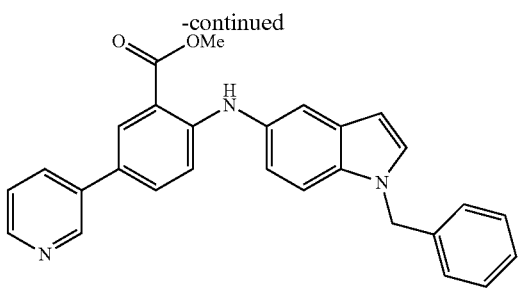

The mixture of 100 mg of methyl 2-((1-benzyl-1H-indol-5-yl)amino)-5-chlorobenzoate, 127 mg of potassium (3-pyridine)cyclic-triolborate, 18 mg of bis(di-tert-butyl(4-dimethylaminophenyl)phosphine)dichloropalladium(II), and 2.0 mL of toluene, was stirred in a sealed tube at an external temperature of 110° C. for seven hours under a nitrogen atmosphere. After cooling the reaction mixture to room temperature, the insoluble matter was filtered off and the solvent was distilled off under reduced pressure. The obtained residue was purified by silica gel column chromatography to give 23 mg of methyl 2-((1-benzyl-1H-indol-5-yl)amino)-5-(pyridin-3-yl)benzoate.

$^1$H-NMR (DMSO-$d_6$) δ: 3.90 (3H, s), 5.45 (2H, s), 6.49 (1H, d, J=3.3 Hz), 6.99-7.08 (2H, m), 7.20-7.60 (9H, m), 7.72 (1H, dd, J=9.2, 2.0 Hz), 7.94-8.02 (1H, m), 8.18 (1H, d, J=2.0 Hz), 8.46-8.52 (1H, m), 8.77-8.83 (1H, m), 9.37 (1H, s).

MS (ESI, m/z): 434 (M+H)$^+$.

Example 92

[Formula 339]

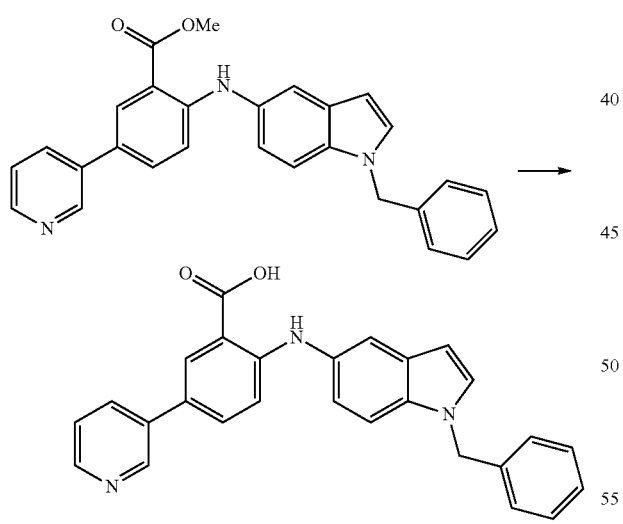

By the method similar to that of Example 37, 2-((1-benzyl-1H-indol-5-yl)amino)-5-(pyridin-3-yl)benzoic acid was obtained from methyl 2-((1-benzyl-1H-indol-5-yl)amino)-5-(pyridin-3-yl)benzoate.

$^1$H-NMR (DMSO-$d_6$) δ: 5.44 (2H, s), 6.48 (1H, d, J=2.6 Hz), 7.03 (2H, d, J=9.2 Hz), 7.20-7.37 (5H, m), 7.39-7.53 (3H, m), 7.56 (1H, d, J=3.3 Hz), 7.70 (1H, dd, J=8.9, 2.3 Hz), 7.95-8.02 (1H, m), 8.17 (1H, d, J=2.6 Hz), 8.49 (1H, d, J=4.0 Hz), 8.78-8.83 (1H, s), 9.63 (1H, s), 13.15 (1H, brs).

MS (ESI, m/z): 420 (M+H)$^+$, 418 (M−H)$^-$.

Example 93

[Formula 340]

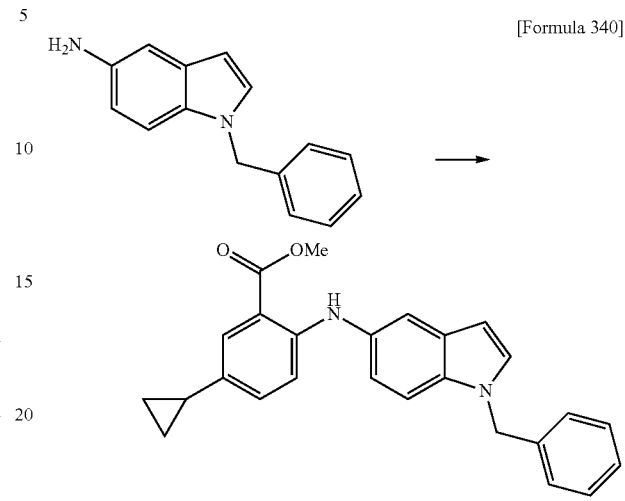

The mixture of 245 mg of 1-benzyl-1H-indol-5-amine, 0.28 g of methyl 2-bromo-5-cyclopropylbenzoate, 50 mg of tris(dibenzylideneacetone)dipalladium(0), 64 mg of 4,5'-bis(diphenylphosphino)-9,9'-dimethylxanthene, 0.72 g of cesium carbonate, and 3 mL of toluene, was heated at reflux in a sealed tube for three hours under a nitrogen atmosphere. The reaction mixture was cooled to room temperature, and ethyl acetate and water were then added thereto. The organic layer was separated, sequentially washed with water and a saturated aqueous sodium chloride solution and dried over anhydrous magnesium sulfate, and the solvent was distilled off under reduced pressure. The obtained residue was purified by silica gel column chromatography (gradient elution with hexane:ethyl acetate=90:10-80:20) to give 0.3 g of methyl 2-((1-benzyl-1H-indol-5-yl)amino)-5-cyclopropylbenzoate as a yellow oil.

$^1$H-NMR (CDCl$_3$) δ: 0.55-0.63 (2H, m), 0.81-0.90 (2H, m), 1.75-1.86 (1H, m), 3.90 (3H, s), 5.32 (2H, s), 6.49 (1H, d, J=3.3 Hz), 6.92-7.07 (3H, m), 7.10-7.17 (3H, m), 7.21-7.36 (4H, m), 7.49 (1H, d, J=2.0 Hz), 7.68 (1H, d, J=2.0 Hz), 9.20 (1H, s).

Example 94

[Formula 341]

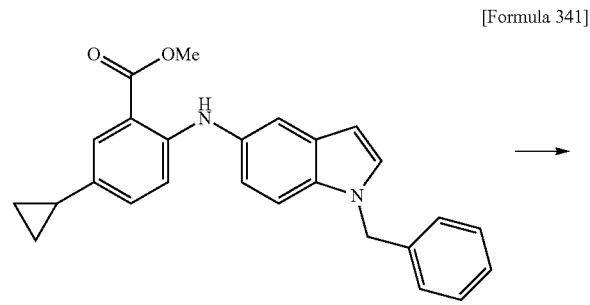

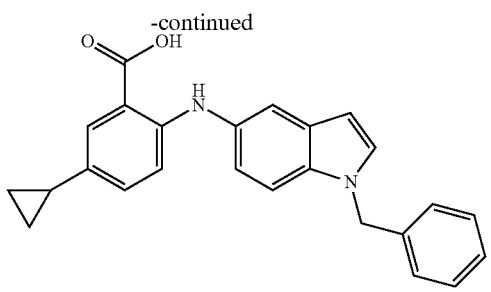

To the solution of 0.3 g of methyl 2-((1-benzyl-1H-indol-5-yl)amino)-5-cyclopropylbenzoate in 2.0 mL of ethanol and 2.0 mL of tetrahydrofuran, 0.3 mL of a 5 mol/L aqueous sodium hydroxide solution was added at room temperature, and the resultant was stirred at an external temperature of 50 to 60° C. for two hours. After cooling the reaction mixture to room temperature, water was added thereto, and the resultant was adjusted to pH 2.0 with 2 mol/L hydrochloric acid, and ethyl acetate was added thereto. The organic layer was separated, sequentially washed with water and a saturated aqueous sodium chloride solution and dried over anhydrous magnesium sulfate, and the solvent was distilled off under reduced pressure. Diisopropyl ether was added to the obtained residue, and the solid was collected by filtration to give 0.18 g of 2-((1-benzyl-1H-indol-5-yl)amino)-5-cyclopropylbenzoic acid as a pale yellow solid.

$^1$H-NMR (DMSO-$d_6$) δ: 0.49-0.56 (2H, m), 0.79-0.89 (2H, m), 1.77-1.88 (1H, m), 5.41 (2H, s), 6.44 (1H, d, J=3.3 Hz), 6.88 (1H, d, J=8.6 Hz), 6.95 (1H, dd, J=8.6, 2.0 Hz), 7.02 (1H, dd, J=8.6, 2.0 Hz), 7.19-7.36 (5H, m), 7.39 (1H, d, J=2.0 Hz), 7.44 (1H, d, J=8.6 Hz), 7.52 (1H, d, J=3.3 Hz), 7.60 (1H, d, J=2.0 Hz), 9.33 (1H, brs), 12.86 (1H, brs).

MS (ESI, m/z): 383 (M+H)$^+$.

Example 95

[Formula 342]

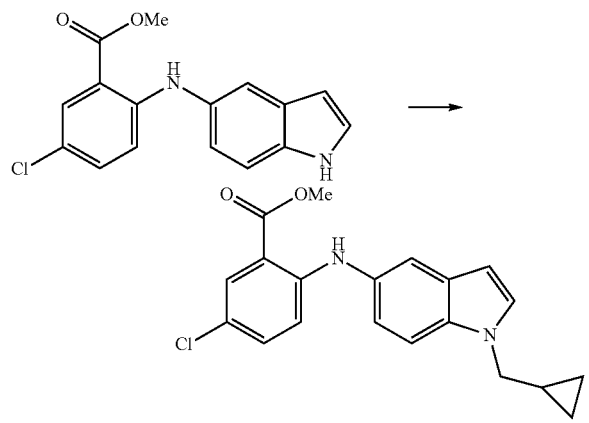

To the solution of 100 mg of methyl 2-((1H-indol-5-yl)amino)-5-chlorobenzoate in 2 mL of N,N-dimethylacetamide, 42 mg of potassium tert-butoxide was added under ice-cooling, and the resultant was stirred for five minutes. 36 μL of (bromomethyl)cyclopropane was added to the reaction mixture under ice-cooling, and the resultant was stirred at the same temperature for 45 minutes and then stirred at room temperature for one hour and 20 minutes. Water and ethyl acetate were added to the reaction mixture. The organic layer was separated and the aqueous layer was extracted with ethyl acetate. The organic layer and the extract were combined, washed with a saturated aqueous sodium chloride solution and dried over anhydrous magnesium sulfate, and the solvent was distilled off under reduced pressure. The obtained residue was purified by silica gel column chromatography (gradient elution with hexane:ethyl acetate=100:0-50:50) to give 80 mg of methyl 5-chloro-2-((1-(cyclopropylmethyl)-1H-indol-5-yl)amino)benzoate as a yellow oil.

$^1$H-NMR (CDCl$_3$) δ: 0.34-0.40 (2H, m), 0.61-0.67 (2H, m) 1.23-1.32 (1H, m), 3.90 (3H, s), 3.97 (2H, d, J=6.6 Hz), 6.46 (1H, d, J=3.3 Hz), 6.91 (1H, d, J=9.2 Hz), 7.05 (1H, dd, J=8.6, 2.0 Hz), 7.13 (1H, dd, J=9.2, 2.6 Hz), 7.24 (1H, d, J=2.6 Hz), 7.34 (1H, d, J=8.6 Hz), 7.47 (1H, d, J=2.0 Hz), 7.90 (1H, d, J=2.6 Hz), 9.33 (1H, s).

Example 96

[Formula 343]

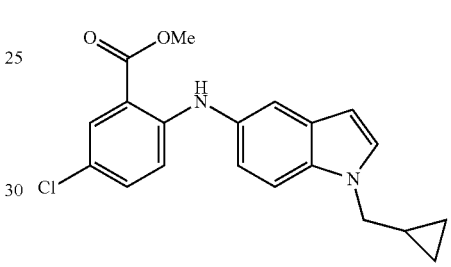

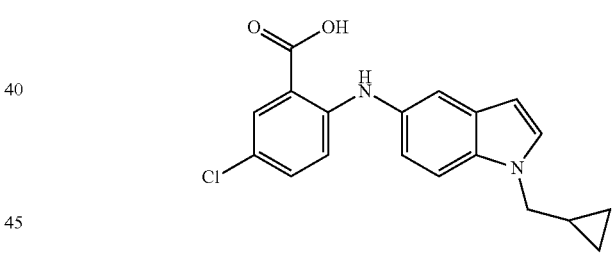

To the mixed solution of 79 mg of methyl 5-chloro-2-((1-(cyclopropylmethyl)-1H-indol-5-yl)amino)benzoate in 0.8 mL of ethanol and 0.4 mL of tetrahydrofuran, 90 μL of a 5 mol/L aqueous sodium hydroxide solution was added at room temperature, and the resultant was heated at reflux for 30 minutes. After cooling the reaction mixture to room temperature, the solvent was distilled off under reduced pressure. 6 mol/L hydrochloric acid and water were added to the obtained residue, and the solid was collected by filtration to give 62 mg of 5-chloro-2-((1-(cyclopropylmethyl)-1H-indol-5-yl)amino)benzoic acid as a yellow solid.

$^1$H-NMR (CDCl$_3$) δ: 0.36-0.42 (2H, m), 0.63-0.69 (2H, m), 1.27-1.36 (1H, m), 4.00 (2H, d, J=6.6 Hz), 6.48 (1H, d, J=3.3 Hz), 6.91 (1H, d, J=9.2 Hz), 7.07 (1H, dd, J=8.6, 2.0 Hz), 7.18 (1H, dd, J=8.9, 2.3 Hz), 7.27 (1H, d, J=2.6 Hz), 7.38 (1H, d, J=8.6 Hz), 7.49 (1H, d, J=2.0 Hz), 7.95 (1H, d, J=2.6 Hz), 9.23 (1H, brs)

MS (ESI, m/z): 341 (M+H)$^+$, 339 (M−H)$^−$.

Example 97

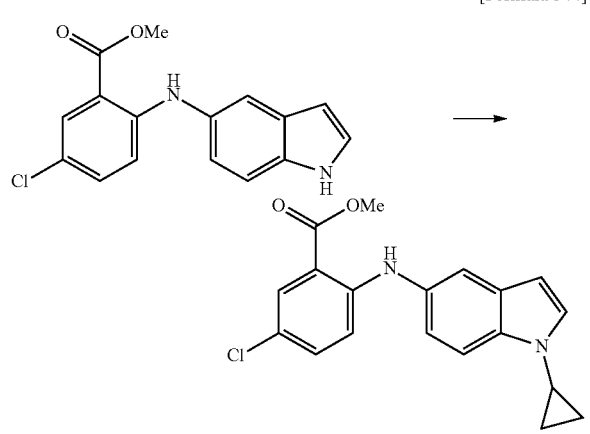

[Formula 344]

To the solution of 90 mg of methyl 2-((1H-indol-5-yl)amino)-5-chlorobenzoate in 3 mL of 1,2-dichloroethane, 52 mg of cyclopropylboronic acid, 64 mg of sodium carbonate, 24 μL of pyridine and 60 mg of copper(II) acetate were added, and the resultant was heated at reflux for three hours and 10 minutes under a nitrogen atmosphere. The reaction mixture was allowed to stand overnight and then heated at reflux for eight hours and 10 minutes. 52 mg of cyclopropylboronic acid, 64 mg of sodium carbonate, 24 μL of pyridine and 60 mg of copper(II) acetate were added thereto, and the resultant was heated at reflux for one hour and 15 minutes. After cooling the reaction mixture to room temperature, ethyl acetate and an aqueous ammonium chloride solution were added thereto, and the insoluble matter was filtered off. Water and ethyl acetate were added to the filtrate, the organic layer was separated and the aqueous layer was extracted with ethyl acetate. The organic layer and the extract were combined, washed with a saturated aqueous sodium chloride solution and dried over anhydrous magnesium sulfate, and the solvent was distilled off under reduced pressure. The obtained residue was purified by silica gel column chromatography (gradient elution with chloroform:methanol=100:0-80:20) to give 55 mg of methyl 5-chloro-2-((1-(cyclopropyl)-1H-indol-5-yl)amino)benzoate as a brown oil.

$^1$H-NMR (CDCl$_3$) δ: 1.02-1.08 (4H, m), 3.30-3.38 (1H, m), 3.89 (3H, s), 6.39 (1H, d, J=3.3 Hz), 6.90 (1H, d, J=9.2 Hz), 7.07 (1H, dd, J=8.6, 2.0 Hz), 7.11-7.15 (2H, m), 7.44 (1H, d, J=2.0 Hz), 7.54 (1H, d, J=8.6 Hz), 7.90 (1H, d, J=2.6 Hz), 9.33 (1H, s).

Example 98

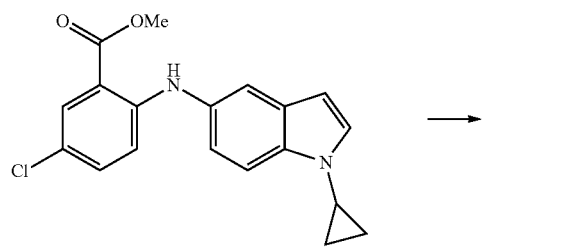

[Formula 345]

-continued

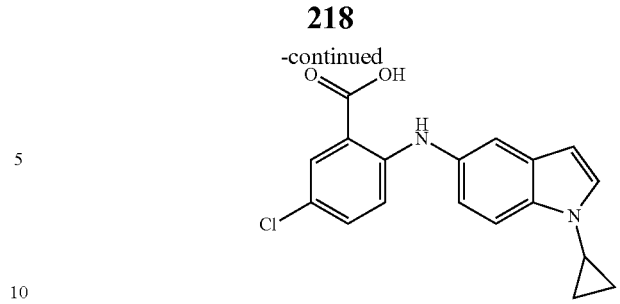

By the method similar to that of Example 96, 5-chloro-2-((1-(cyclopropyl)-1H-indol-5-yl)amino)benzoic acid was obtained from methyl 5-chloro-2-((1-(cyclopropyl)-1H-indol-5-yl)amino)benzoate.

$^1$H-NMR (CDCl$_3$) δ: 1.02-1.11 (4H, m), 3.32-3.41 (1H, m), 6.41 (1H, d, J=2.6 Hz), 6.90 (1H, d, J=9.2 Hz), 7.08 (1H, dd, J=8.6, 2.0 Hz), 7.16-7.20 (2H, m), 7.46 (1H, d, J=2.0 Hz), 7.57 (1H, d, J=8.6 Hz), 7.95 (1H, d, J=2.6 Hz), 9.24 (1H, brs).

MS (ESI, m/z): 327 (M+H)$^+$, 325 (M−H)$^−$.

Example 99

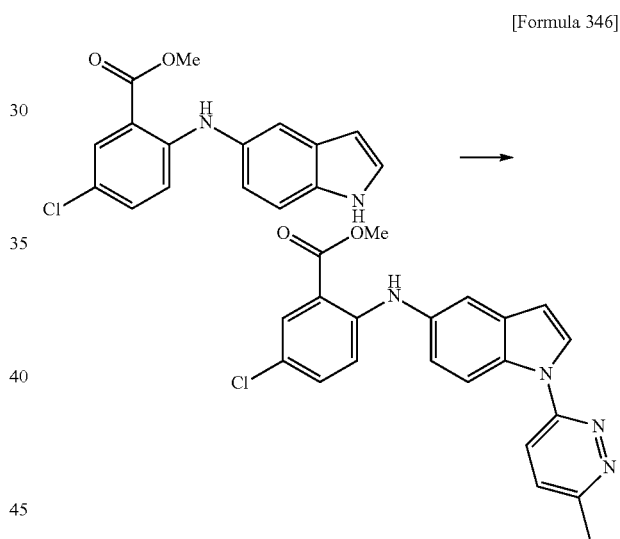

[Formula 346]

The mixture of 34 mg of methyl 2-((1H-indol-5-yl)amino)-5-chlorobenzoate, 27 mg of 3-iodo-6-methylpyridazine, 2 mg of copper(I) iodide, 70 mg of tripotassium phosphate, 4 μL of trans-N,N'-dimethylcyclohexane-1,2-diamine, and 3 mL of toluene, was stirred at 135 to 145° C. for 30 minutes under a nitrogen atmosphere using microwave equipment. The reaction mixture was allowed to stand overnight, and 2 mg of copper iodide and 4 μL of trans-N,N'-dimethylcyclohexane-1,2-diamine were then added thereto, and the resultant was stirred at 160° C. for 30 minutes under a nitrogen atmosphere using microwave equipment. The reaction mixture was cooled to room temperature and then filtered through a membrane filter, and the solvent was distilled off under reduced pressure. The obtained residue was purified by silica gel column chromatography (gradient elution with hexane:ethyl acetate=100:0-30:70) to give 27 mg of methyl 5-chloro-2-((1-(6-methylpyridazin-3-yl)-1H-indol-5-yl)amino)benzoate as a yellow oil.

MS (ESI, m/z): 393 (M+H)$^+$.

Example 100

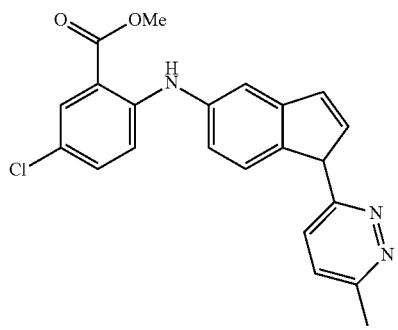

[Formula 347]

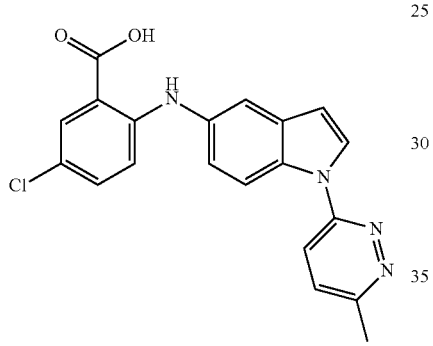

By the method similar to that of Example 96, 5-chloro-2-((1-(6-methylpyridazin-3-yl)-1H-indol-5-yl)amino)benzoic acid was obtained from methyl 5-chloro-2-((1-(6-methylpyridazin-3-yl)-1H-indol-5-yl)amino)benzoate.

$^1$H-NMR (DMSO-d$_6$) δ: 2.67 (3H, s), 6.82 (1H, d, J=3.3 Hz), 7.09 (1H, d, J=8.6 Hz), 7.20 (1H, dd, J=8.6, 2.0 Hz), 7.38 (1H, dd, J=9.2, 2.6 Hz), 7.57 (1H, d, J=2.0 Hz), 7.78 (1H, d, J=9.2 Hz), 7.83 (1H, d, J=2.6 Hz), 8.08 (1H, d, J=7.9 Hz), 8.10 (1H, d, J=2.0 Hz), 8.47 (1H, d, J=8.6 Hz), 9.66 (1H, brs).

MS (ESI, m/z): 379 (M+H)$^+$, 377 (M–H)$^-$.

Example 101

[Formula 348]

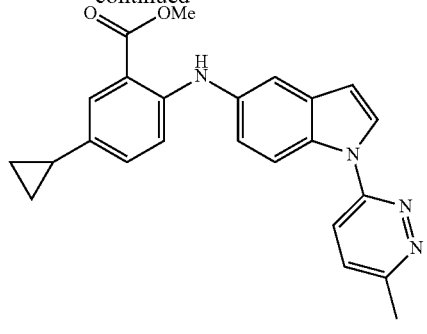

The mixture of 100 mg of methyl 2-((1H-indol-5-yl)amino)-5-cyclopropylbenzoate, 92 mg of 3-iodo-6-methylpyridazine, 6 mg of copper(I) iodide, 210 mg of tripotassium phosphate, 13 μL of trans-N,N'-dimethylcyclohexane-1,2-diamine, and 3 mL of toluene, was heated at reflux for six hours and 45 minutes under a nitrogen atmosphere. The reaction mixture was allowed to stand overnight and then heated at reflux for 12 hours and 20 minutes. The reaction mixture was filtered through a membrane filter and the solvent was then distilled off under reduced pressure. The obtained residue was purified by silica gel column chromatography (gradient elution with hexane:ethyl acetate=100:0-70:30) to give 112 mg of methyl 5-cyclopropyl-2-((1-(6-methylpyridazin-3-yl)-1H-indol-5-yl)amino)benzoate as a yellow oil.

MS (ESI, m/z): 399 (M+H)$^+$.

Example 102

[Formula 349]

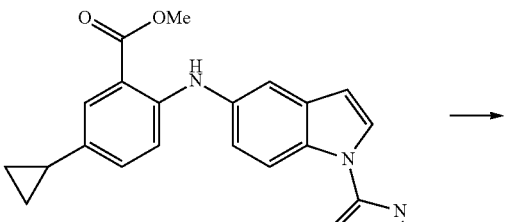

By the method similar to that of Example 96, 5-cyclopropyl-2-((1-(6-methylpyridazin-3-yl)-1H-indol-5-yl)amino)benzoic acid was obtained from methyl 5-cyclopropyl-2-((1-(6-methylpyridazin-3-yl)-1H-indol-5-yl)amino)benzoate.

$^1$H-NMR (DMSO-$d_6$) δ: 0.54-0.59 (2H, m), 0.83-0.90 (2H, m), 1.82-1.91 (1H, m), 2.67 (3H, s), 6.79 (1H, d, J=3.3 Hz), 7.08-7.10 (2H, m), 7.17 (1H, dd, J=9.2, 2.0 Hz), 7.51 (1H, d, J=2.0 Hz), 7.64 (1H, s), 7.77 (1H, d, J=9.2 Hz), 8.07 (1H, d, J=3.3 Hz), 8.09 (1H, d, J=2.0 Hz), 8.44 (1H, d, J=8.6 Hz), 9.47 (1H, s).

MS (ESI, m/z): 385 (M+H)$^+$, 383 (M−H)$^−$.

Example 103

[Formula 350]

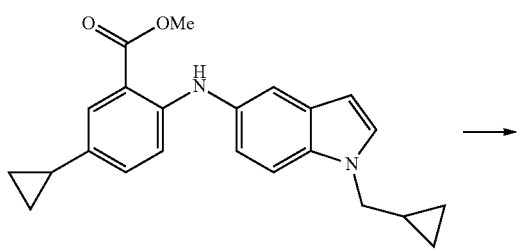

To the solution of 100 mg of methyl 2-((1H-indol-5-yl)amino)-5-cyclopropylbenzoate in 1 mL of N,N-dimethylformamide, 40 mg of potassium tert-butoxide was added under ice-cooling, and the resultant was stirred for five minutes. 35 μL of 1-(bromomethyl)cyclopropane was added thereto under the ice-cooling, and the resultant was warmed to room temperature and stirred for 30 minutes. Water and ethyl acetate were added to the reaction mixture. The organic layer was separated, washed with water and dried over anhydrous magnesium sulfate, and the solvent was distilled off under reduced pressure. The obtained residue was purified by silica gel column chromatography (gradient elution with hexane:ethyl acetate=100:0-30:70) to give 135 mg of methyl 5-cyclopropyl-2-((1-(cyclopropylmethyl)-1H-indol-5-yl)amino)benzoate as a yellow brown oil.

MS (ESI, m/z): 361 (M+H)$^+$.

Example 104

[Formula 351]

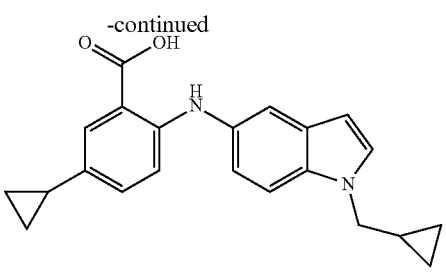

The mixture of 135 mg of methyl 5-cyclopropyl-2-((1-(cyclopropylmethyl)-1H-indol-5-yl)amino)benzoate, 0.5 mL of a 5 mol/L aqueous sodium hydroxide solution, 2 mL of ethanol, and 2 mL of tetrahydrofuran, was heated at reflux for three hours. After cooling the reaction mixture to room temperature, 6 mol/L hydrochloric acid and water were added thereto, and the solvent was distilled off under reduced pressure. Water and methanol were added to the obtained residue, and the solid was collected by filtration to give 60 mg of 5-cyclopropyl-2-((1-(cyclopropylmethyl)-1H-indol-5-yl)amino)benzoic acid as a yellow solid.

$^1$H-NMR (DMSO-$d_6$) δ: 0.36-0.41 (2H, m), 0.49-0.56 (4H, m), 0.81-0.88 (2H, m), 1.20-1.30 (1H, m), 1.79-1.88 (1H, m), 4.03 (2H, d, J=7.3 Hz), 6.38 (1H, d, J=3.3 Hz), 6.88 (1H, d, J=8.6 Hz), 6.98 (1H, dd, J=8.6, 2.0 Hz), 7.03 (1H, dd, J=8.9, 2.3 Hz), 7.37 (1H, d, J=2.0 Hz), 7.44 (1H, d, J=3.3 Hz), 7.51 (1H, d, J=8.6 Hz), 7.60 (1H, d, J=2.0 Hz), 9.34 (1H, brs).

MS (ESI, m/z): 347 (M+H)$^+$, 345 (M−H)$^−$.

Example 105

[Formula 352]

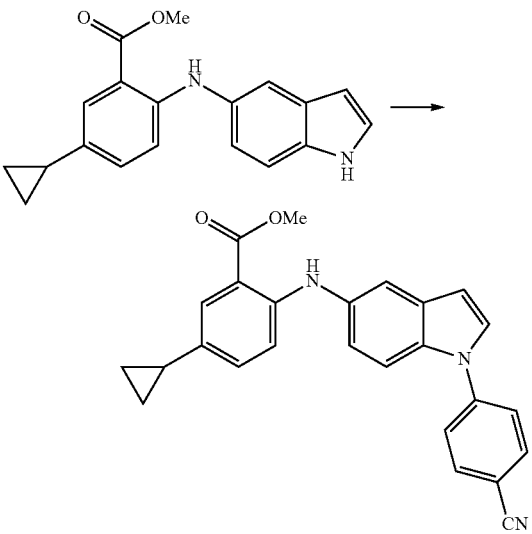

To the solution of 50 mg of methyl 2-((1H-indol-5-yl)amino)-5-cyclopropylbenzoate in 2 mL of toluene, 37 mg of 4-iodobenzonitrile, 7 mg of tris(dibenzylideneacetone)dipalladium(0), 8 mg of 2-dicyclohexylphosphino-2',4',6'-triisopropylbiphenyl and 68 mg of tripotassium phosphate were added, and the resultant was heated at reflux for one hour and 20 minutes under a nitrogen atmosphere. The reaction mixture was allowed to stand overnight, and 14 mg of tris(dibenzylideneacetone)dipalladium(0) and 16 mg of 2-dicyclohexylphosphino-2',4',6'-triisopropylbiphenyl were added thereto, and the resultant was heated at reflux for eight hours and 10 minutes under a nitrogen atmosphere. 37 mg of 4-iodobenzonitrile were added to the reaction mixture, and the resultant was heated at reflux for two hours and 30 minutes under a nitrogen atmosphere. The reaction mixture was allowed to stand overnight, and 14 mg of tris(dibenzylideneacetone)dipalladium(0) and 16 mg of 2-dicyclohexylphosphino-2',4',6'-triisopropylbiphenyl were then added thereto, and the resultant was heated at reflux for nine hours and 50 minutes under a nitrogen atmosphere. The reaction mixture was allowed to stand overnight and then filtered through a membrane filter, and the solvent was then distilled off under reduced pressure. The obtained residue was purified by silica gel column chromatography (gradient elution with hexane:ethyl acetate=100:0-50:50). Hexane and methanol were added to the thus obtained residue, and the solid was collected by filtration to give 20 mg of methyl 2-((1-(4-cyanophenyl)-1H-indol-5-yl)amino)-5-cyclopropylbenzoate as a yellow solid.

MS (ESI, m/z): 408 (M+H)$^+$.

Example 106

[Formula 353]

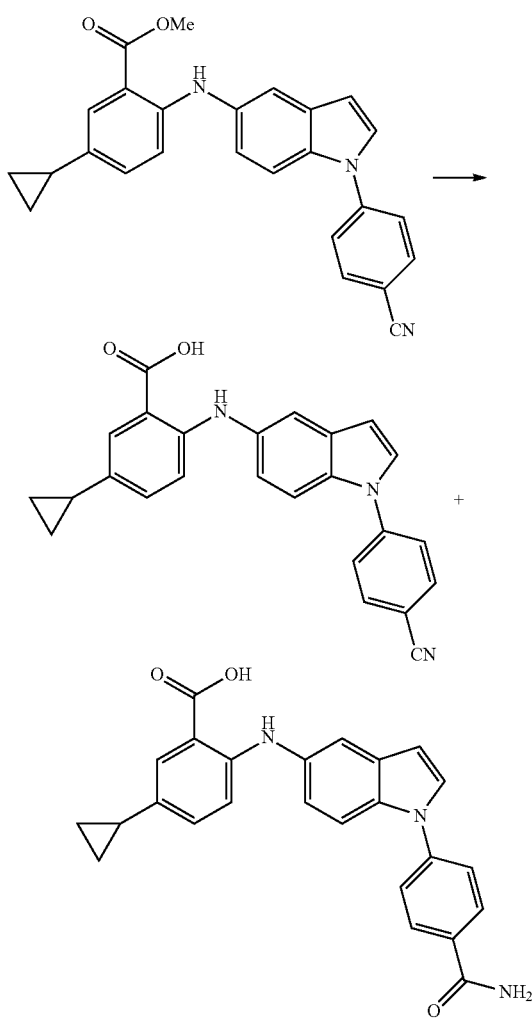

The mixture of 20 mg of methyl 2-((1-(4-cyanophenyl)-1H-indol-5-yl)amino)-5-cyclopropylbenzoate, 150 μL of a 5 mol/L aqueous sodium hydroxide solution, 2 mL of tetrahydrofuran, and 2 mL of ethanol, was heated at reflux for one hour and 45 minutes. 6 mol/L hydrochloric acid and water were added to the reaction mixture. The solid was collected by filtration and purified by preparative thin-layer chromatography to give 6.2 mg of 2-((1-(4-cyanophenyl)-1H-indol-5-yl)amino)-5-cyclopropylbenzoic acid and 2.3 mg of 2-((1-(4-carbamoylphenyl)-1H-indol-5-yl)amino)-5-cyclopropylbenzoic acid.

Example 106-1

2-((1-(4-Cyanophenyl)-1H-indol-5-yl)amino)-5-cyclopropylbenzoic acid $^1$H-NMR (DMSO-d$_6$) δ: 0.51-0.62 (2H, m), 0.95-1.80 (2H, m), 1.80-1.95 (1H, m), 6.75 (1H, s), 7.02-7.14 (3H, m), 7.51-7.90 (6H, m), 8.04 (2H, d, J=6.6 Hz), 9.47 (1H, brs).

MS (ESI, m/z): 394 (M+H)$^+$, 392 (M−H)$^-$.

Example 106-2

2-((1-(4-Carbamoylphenyl)-1H-indol-5-yl)amino)-5-cyclopropylbenzoic acid $^1$H-NMR (DMSO-d$_6$) δ: 0.54-0.59 (2H, m), 0.84-0.90 (2H, m), 1.82-1.91 (1H, m), 6.72 (1H, d, J=3.3 Hz), 7.01 (1H, d, J=8.6 Hz), 7.07-7.13 (2H, m), 7.46 (1H, s), 7.52 (1H, d, J=2.0 Hz), 7.63-7.77 (5H, m), 8.07-8.11 (3H, m), 9.44 (1H, s).

MS (ESI, m/z): 412 (M+H)$^+$, 410 (M−H)$^-$.

Example 107

[Formula 354]

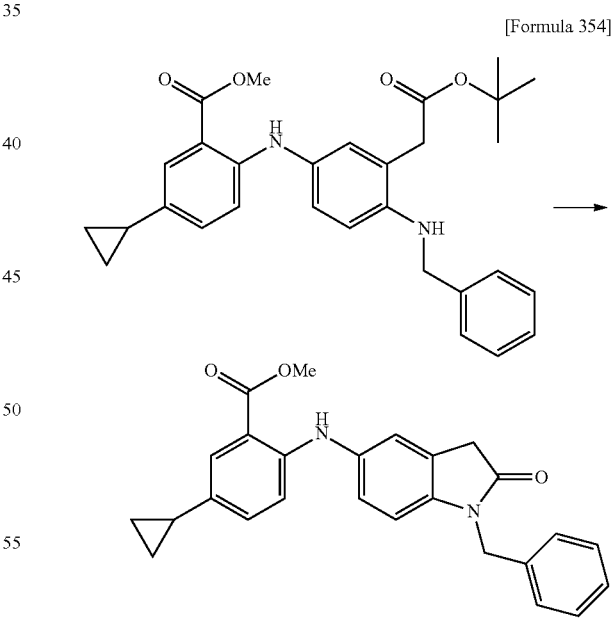

The mixture of 138 mg of methyl 2-((4-benzylamino-3-(2-(tert-butoxy)-2-oxoethyl)phenyl)amino)-5-cyclopropylbenzoate, 139 mg of lithium hydroxide monohydrate, 2 mL of tetrahydrofuran, 2 mL of methanol, and 0.5 mL of water, was stirred at an external temperature of 55° C. for two hours and 15 minutes. The reaction mixture was allowed to stand overnight and then concentrated, and 5 mL trifluoroacetic acid and molecular sieves 4 A were added to the obtained residue, and the resultant was stirred at room temperature for one hour and 40 minutes. A saturated aqueous sodium bicarbonate solution and ethyl acetate were added to the reaction mixture. The organic layer was separated and sequentially washed with water and a saturated aqueous sodium chloride solution, and the solvent was distilled off under reduced pressure. The obtained residue was purified by silica gel column chromatography (gradient elution with hexane:ethyl acetate=100:0-0:100). Methanol was added to the thus obtained residue, and the solid was collected by filtration to give 20 mg of 2-((1-benzyl-2-oxoindolin-5-yl)amino)-5-cyclopropylbenzoic acid as a yellow solid.

$^1$H-NMR (DMSO-d$_6$) δ: 0.51-0.58 (2H, m), 0.82-0.88 (2H, m), 1.79-1.90 (1H, m), 3.68 (2H, s), 4.88 (2H, s), 6.84 (1H, d, J=7.9 Hz), 6.92 (1H, d, J=8.6 Hz), 7.00-7.08 (2H, m), 7.16 (1H, s), 7.26-7.36 (5H, m), 7.60 (1H, d, J=2.0 Hz).

MS (ESI, m/z): 399 (M+H)$^+$, 397 (M−H)$^-$.

Example 108

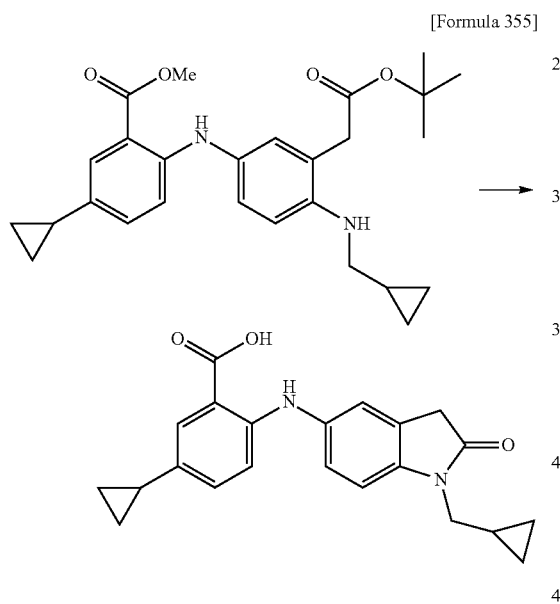

[Formula 355]

The mixture of 65 mg of methyl 2-((3-(2-(tert-butoxy)-2-oxoethyl)-4-((cyclopropylmethyl)amino)phenyl)amino)-5-cyclopropylbenzoate, 61 mg of lithium hydroxide monohydrate, 2 mL of tetrahydrofuran, 2 mL of methanol, and 1 mL of water, was stirred at an external temperature of 55° C. for three hours and 30 minutes. The solvent was distilled off under reduced pressure, and 3 mL trifluoroacetic acid and molecular sieves 4 A were added to the obtained residue, and the resultant was stirred at room temperature for two hours and 10 minutes. A saturated aqueous sodium bicarbonate solution and ethyl acetate were added to the reaction mixture. The organic layer was separated and sequentially washed with water and a saturated aqueous sodium chloride solution, and the solvent was distilled off under reduced pressure. The obtained residue was purified by silica gel column chromatography (gradient elution with hexane:ethyl acetate=100:0-0:100). Methanol was added to the thus obtained residue, and the solid was collected by filtration to give 5 mg of 5-cyclopropyl-2-((1-(cyclopropylmethyl)-2-oxoindolin-5-yl)amino)benzoic acid as an orange solid.

$^1$H-NMR (DMSO-d$_6$) δ: 0.31-0.36 (2H, m), 0.43-0.50 (2H, m), 0.52-0.58 (2H, m), 0.82-0.90 (2H, m), 1.08-1.20 (1H, m), 1.80-1.90 (1H, m), 3.18-3.66 (4H, m), 6.94 (1H, d, J=8.6 Hz), 7.04-7.17 (4H, m), 7.61 (1H, s), 9.31 (1H, brs).

MS (ESI, m/z): 363 (M+H)$^+$, 361 (M−H)$^-$.

Example 109

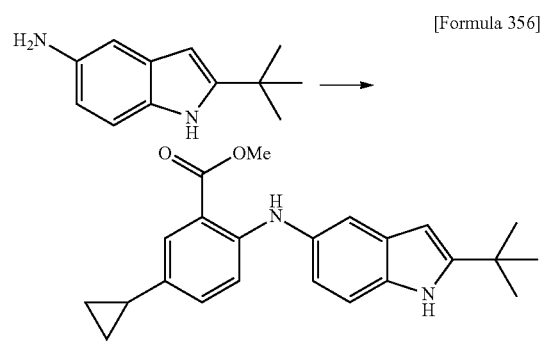

[Formula 356]

The mixture of 100 mg of 2-(tert-butyl)-1H-indol-5-amine, 142 mg of methyl 2-bromo-5-cyclopropylbenzoate, 24 mg of tris(dibenzylideneacetone)dipalladium(0), 31 mg of 4,5'-bis(diphenylphosphino)-9,9'-dimethylxanthene, 346 mg of cesium carbonate, and 2 mL of toluene, was heated at reflux for 15 hours and 30 minutes under a nitrogen atmosphere. The insoluble matter was filtered off and the solvent was distilled off under reduced pressure. The obtained residue was purified by silica gel column chromatography (gradient elution with hexane:ethyl acetate=100:0-80:20) to give 178 mg of methyl 2-((2-(tert-butyl)-1H-indol-5-yl)amino)-5-cyclopropylbenzoate as a yellow oil.

MS (ESI, m/z): 363 (M+H)$^+$.

Example 110

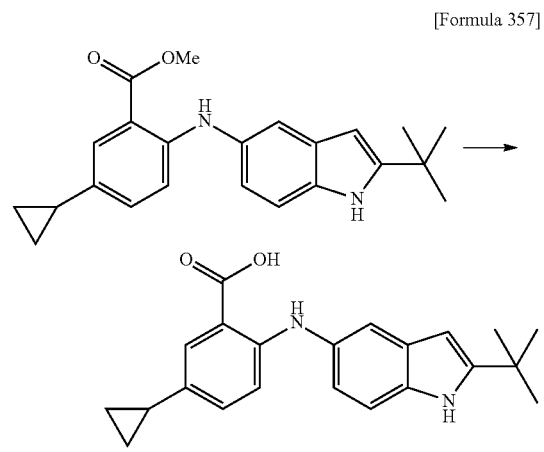

[Formula 357]

By the method similar to that of Example 96, 2-((2-(tert-butyl)-1H-indol-5-yl)amino)-5-cyclopropylbenzoic acid was obtained from methyl 2-((2-(tert-butyl)-1H-indol-5-yl)amino)-5-cyclopropylbenzoate.

$^1$H-NMR (DMSO-d$_6$) δ: 0.50-0.56 (2H, m), 0.81-0.87 (2H, m), 1.35 (9H, s), 1.78-1.87 (1H, m), 6.09 (1H, d, J=2.0 Hz), 6.80-6.87 (2H, m), 7.01 (1H, dd, J=8.6, 2.0 Hz), 7.25 (1H, d, J=2.0 Hz), 7.29 (1H, d, J=7.9 Hz), 7.59 (1H, d, J=2.0 Hz), 9.29 (1H, brs), 10.90 (1H, s), 12.82 (1H, brs).

MS (ESI, m/z): 349 (M+H)$^+$, 347 (M−H)$^-$.

Example 111

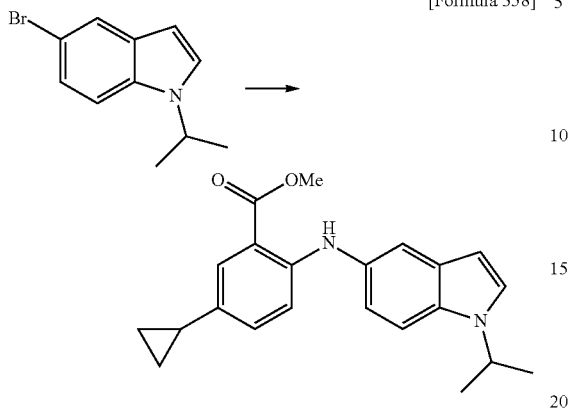

[Formula 358]

The mixture of 100 mg of 5-bromo-1-isopropyl-1H-indole, 84 mg of methyl 2-amino-5-cyclopropylbenzoate, 19 mg of tris(dibenzylideneacetone)dipalladium(0), 20 mg of 2-dicyclohexylphosphino-2',4',6'-triisopropylbiphenyl, 178 mg of tripotassium phosphate, and 2 mL of toluene, was heated at reflux for 15 hours and 30 minutes under a nitrogen atmosphere. The insoluble matter was filtered off and the solvent was distilled off under reduced pressure. The obtained residue was purified by silica gel column chromatography (gradient elution with hexane:ethyl acetate=100:0-60:40) to give 16 mg of methyl 5-cyclopropyl-2-((1-isopropyl-1H-indol-5-yl)amino)benzoate as a yellow oil.

MS (ESI, m/z): 349 (M+H)$^+$.

Example 112

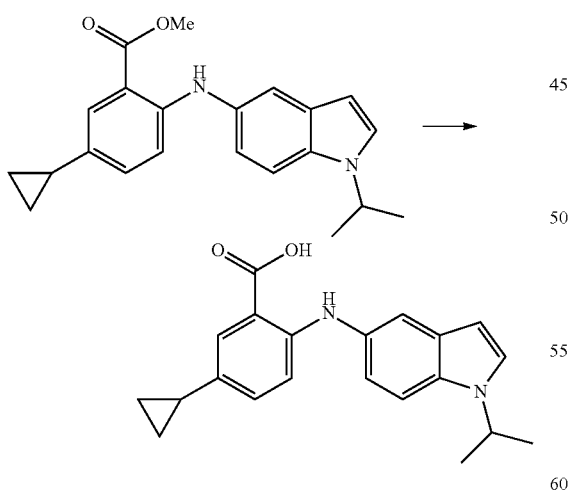

[Formula 359]

By the method similar to that of Example 96, 5-cyclopropyl-2-((1-isopropyl-1H-indol-5-yl)amino)benzoic acid was obtained from methyl 5-cyclopropyl-2-((1-isopropyl-1H-indol-5-yl)amino)benzoate.

$^1$H-NMR (DMSO-$d_6$) δ: 0.50-0.56 (2H, m), 0.82-0.88 (2H, m), 1.46 (6H, d, J=6.6 Hz), 1.78-1.88 (1H, m), 4.73 (1H, sep, J=6.6 Hz), 6.40 (1H, d, J=3.3 Hz), 6.89 (1H, d, J=8.6 Hz), 6.98 (1H, dd, J=8.6, 2.0 Hz), 7.03 (1H, dd, J=8.9, 2.3 Hz), 7.37 (1H, d, J=1.3 Hz), 7.47-7.52 (2H, m), 7.60 (1H, d, J=2.0 Hz), 9.34 (1H, brs), 12.86 (1H, brs).

MS (ESI, m/z): 335 (M+H)$^+$, 333 (M−H)$^-$.

Example 113

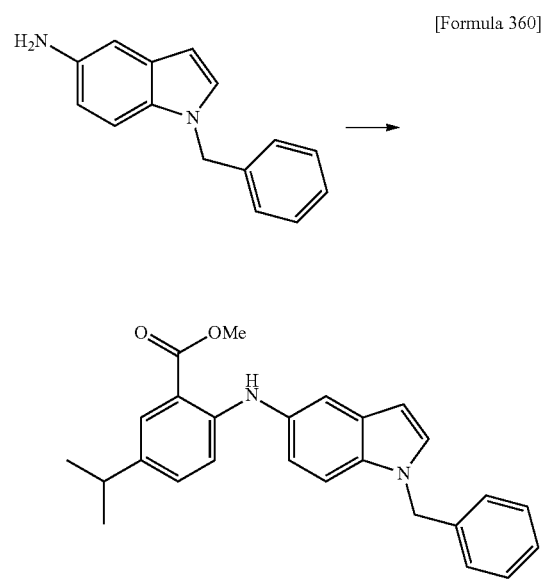

[Formula 360]

The mixture of 80 mg of 1-benzyl-1H-indol-5-amine, 100 mg of methyl 2-iodo-5-isopropylbenzoate, 15 mg of tris(dibenzylideneacetone)dipalladium(0), 19 mg of 4,5'-bis(diphenylphosphino)-9,9'-dimethylxanthene, 214 mg of cesium carbonate, and 2 mL of toluene, was heated at reflux for three hours and 10 minutes under a nitrogen atmosphere. The insoluble matter was filtered off and the solvent was distilled off under reduced pressure. The obtained residue was purified by silica gel column chromatography (gradient elution with hexane:ethyl acetate=100:0-80:20) to give 122 mg of methyl 2-((1-benzyl-1H-indol-5-yl)amino)-5-isopropylbenzoate as a yellow oil.

MS (ESI, m/z): 399 (M+H)$^+$.

Example 114

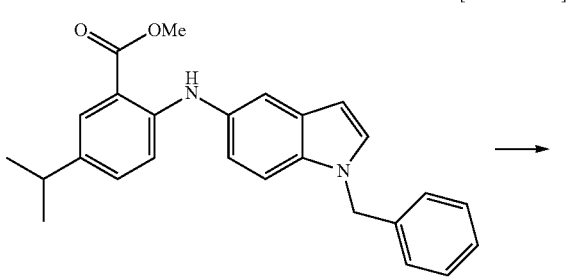

[Formula 361]

-continued

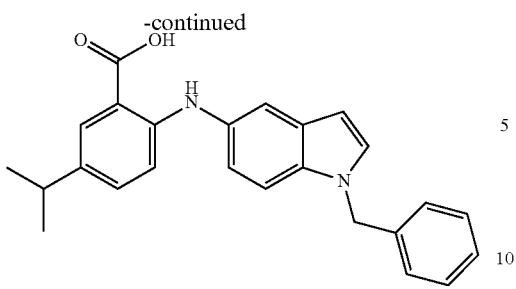

By the method similar to that of Example 96, 2-((1-benzyl-1H-indol-5-yl)amino)-5-isopropylbenzoic acid was obtained from methyl 2-((1-benzyl-1H-indol-5-yl)amino)-5-isopropylbenzoate.

$^1$H-NMR (DMSO-$d_6$) δ: 1.15 (6H, d, J=6.6 Hz), 2.73 (1H, sep, J=6.6 Hz), 5.37 (2H, s), 6.36 (1H, d, =2.6 Hz), 6.85 (1H, dd, J=8.6, 2.0 Hz), 6.90 (1H, dd, J=8.6, 2.0 Hz), 6.96 (1H, d, J=8.6 Hz), 7.18-7.35 (7H, m), 7.41 (1H, d, J=3.3 Hz), 7.75 (1H, d, J=2.6 Hz), 11.50 (1H, s).

MS (ESI, m/z): 385 (M+H)$^+$, 383 (M−H)$^−$.

Example 115

[Formula 362]

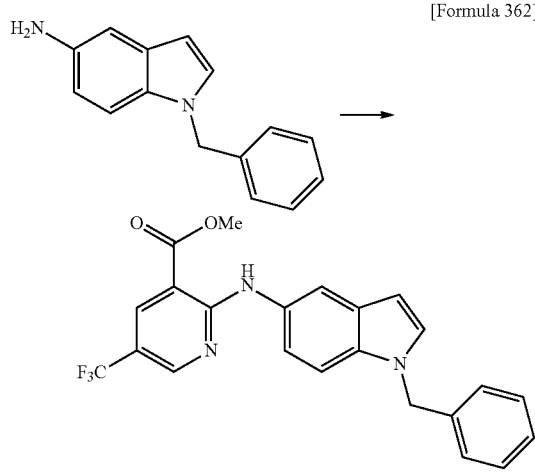

The mixture of 97 mg of 1-benzyl-1H-indol-5-amine, 100 mg of methyl 2-chloro-5-(trifluoromethyl)nicotinate, 19 mg of tris(dibenzylideneacetone)dipalladium(0), 24 mg of 4,5′-bis(diphenylphosphino)-9,9′-dimethylxanthene, 272 mg of cesium carbonate, and 1 mL of butyl acetate, was heated at reflux for 2 hours and 20 minutes. The reaction mixture was cooled to room temperature, and ethyl acetate and water were then added thereto. The organic layer was separated, washed with a saturated aqueous sodium chloride solution and dried over anhydrous sodium sulfate, and the solvent was distilled off under reduced pressure. The obtained residue was purified by silica gel column chromatography (gradient elution with hexane:ethyl acetate=100:0-50:50). Water and methanol were added to the thus obtained residue, and the solid was collected by filtration to give 91 mg of methyl 2-((1-benzyl-1H-indol-5-yl)amino)-5-(trifluoromethyl)nicotinate as a yellow solid.

$^1$H-NMR (DMSO-$d_6$) δ: 3.93 (3H, s), 5.43 (2H, s), 6.48 (1H, d, J=2.6 Hz), 7.18-7.34 (6H, m), 7.43 (1H, d, J=8.6 Hz), 7.54 (1H, d, J=3.3 Hz), 7.88 (1H, d, J=2.0 Hz), 8.38 (1H, d, J=2.6 Hz), 8.66 (1H, d, J=2.0 Hz), 10.20 (1H, s).

MS (ESI, m/z): 426 (M+H)$^+$.

Example 116

[Formula 363]

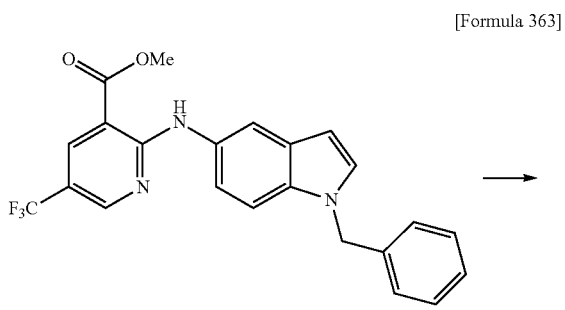

The mixture of 91 mg of methyl 2-((1-benzyl-1H-indol-5-yl)amino)-5-(trifluoromethyl)nicotinate, 85 μL of a 5 mol/L aqueous sodium hydroxide solution, 2 mL of tetrahydrofuran, and 2 mL of methanol, was stirred at an external temperature of 40° C. for two hours and 15 minutes. The reaction mixture was cooled to room temperature and then adjusted to pH 3 by adding thereto 71 μL of 6 mol/L hydrochloric acid and water, and the solvent was distilled off under reduced pressure. Water and methanol were added to the residue and the solid was collected by filtration to give 80 mg of 2-((1-benzyl-1H-indol-5-yl)amino)-5-(trifluoromethyl)nicotinic acid as a yellow solid.

$^1$H-NMR (DMSO-$d_6$) δ: 5.43 (2H, s), 6.48 (1H, d, J=3.3 Hz), 7.18-7.34 (6H, m), 7.43 (1H, d, J=8.6 Hz), 7.53 (1H, d, J=2.6 Hz), 7.90 (1H, d, J=2.0 Hz), 8.35 (1H, d, J=2.6 Hz), 8.64 (1H, d, J=2.0 Hz), 10.55 (1H, s).

MS (ESI, m/z): 412 (M+H)$^+$, 410 (M−H)$^−$.

Example 117

[Formula 364]

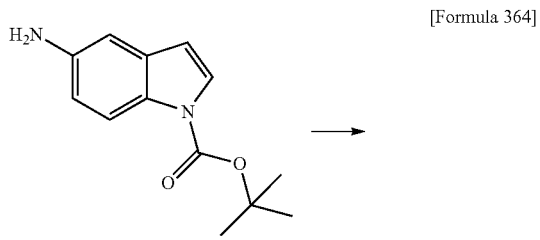

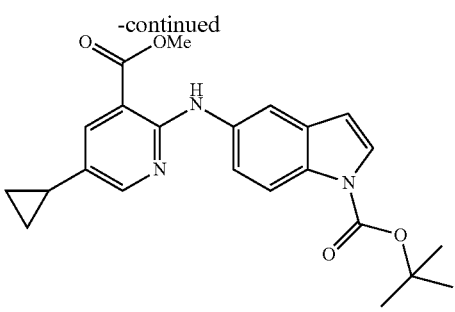

The mixture of 3.96 g of tert-butyl 5-amino-1H-indole-1-carboxylate, 3.50 g of methyl 2-chloro-5-cyclopropylnicotinate, 0.76 g of tris(dibenzylideneacetone)dipalladium (0), 0.95 g of 4,5'-bis(diphenylphosphino)-9,9'-dimethylxanthene, 13.5 g of cesium carbonate, and 50 mL of butyl acetate, was heated at reflux for two hours under a nitrogen atmosphere and then allowed to stand overnight. The reaction mixture was heated under reflux for five hours and 55 minutes, and 100 mg of methyl 2-chloro-5-cyclopropylnicotinate was then added thereto, and the resultant was heated under reflux for four hours and 5 minutes. The reaction mixture was cooled to room temperature, and ethyl acetate and water were then added thereto. The organic layer was separated, washed with a saturated aqueous sodium chloride solution and dried over anhydrous magnesium sulfate, and the solvent was distilled off under reduced pressure. The obtained residue was purified by silica gel column chromatography (gradient elution with hexane:ethyl acetate=100:0-30:70) to give 4.35 g of tert-butyl 5-((5-cyclopropyl-3-(methoxycarbonyl)pyridin-2-yl)amino)-1H-indole-1-carboxylate as a yellow oil.

MS (ESI, m/z): 408 (M+H)$^+$.

Example 118

[Formula 365]

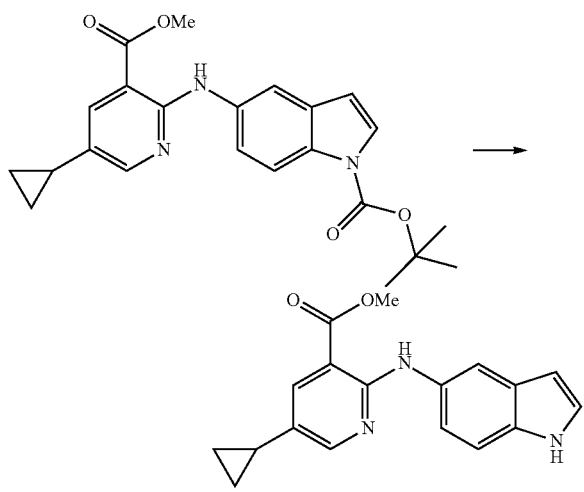

The solution of 4.35 g of tert-butyl 5-((5-cyclopropyl-3-(methoxycarbonyl)pyridin-2-yl)amino)-1H-indole-1-carboxylate in 15 mL of N,N-dimethylacetamide was stirred at 150° C. for six hours. The solvent was distilled off under reduced pressure and the obtained residue was then purified by silica gel column chromatography (gradient elution with hexane:ethyl acetate=100:0-80:20). Hexane and ethyl acetate were added to the thus obtained residue, and the solid was collected by filtration to give 2.59 g of methyl 2-((1H-indol-5-yl)amino)-5-cyclopropylnicotinate as a pale brown solid.

$^1$H-NMR (DMSO-d$_6$) δ: 0.61-0.68 (2H, m), 0.87-0.95 (2H, m), 1.85-1.96 (1H, m), 3.89 (3H, s), 6.37 (1H, s), 7.15 (1H, dd, J=8.6, 2.0 Hz), 7.29-7.35 (2H, m), 7.88 (1H, d, J=2.7 Hz), 7.93 (1H, d, J=2.1 Hz), 8.21 (1H, d, J=2.0 Hz), 9.82 (1H, s), 10.99 (1H, s).

MS (ESI, m/z): 308 (M+H)$^+$.

Example 119

[Formula 366]

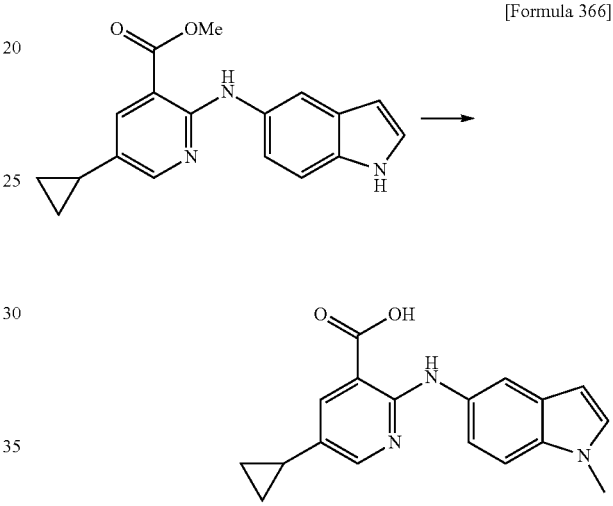

To the solution of 150 mg of methyl 2-((1H-indol-5-yl)amino)-5-cyclopropylnicotinate in 1.5 mL of N,N-dimethylacetamide, 60 mg of potassium tert-butoxide and 33 μL of iodomethane were added under ice-cooling, and the resultant was stirred for three hours and 15 minutes and then stirred at an external temperature of 40° C. for one hour and 50 minutes. 27 mg of potassium tert-butoxide and 15 μL of iodomethane were added thereto, and the resultant was stirred at an external temperature of 40° C. for three hours and 10 minutes, and 2 mL of water was then added thereto, and the resultant was stirred at the same temperature for 45 minutes. The reaction mixture was allowed to stand overnight, and 195 pt of a 5 mol/L aqueous sodium hydroxide solution was then added thereto, and the resultant was stirred at room temperature for one hour and 5 minutes. The reaction mixture was adjusted to pH 2 by adding thereto 5 mol/L hydrochloric acid and water. The solid was collected by filtration and washed with water and methanol to give 28 mg of 5-cyclopropyl-2-((1-methyl-1H-indol-5-yl)amino)nicotinic acid as a yellow solid.

$^1$H-NMR (DMSO-d$_6$) δ: 0.61-0.67 (2H, m), 0.87-0.94 (2H, m), 1.85-1.95 (1H, m), 3.77 (3H, s), 6.36 (1H, d, J=2.6 Hz), 7.21 (1H, dd, J=8.6, 2.0 Hz), 7.28 (1H, d, J=3.3 Hz), 7.36 (1H, d, J=9.2 Hz), 7.87 (1H, d, J=2.6 Hz), 7.98 (1H, d, J=2.0 Hz), 8.19 (1H, d, J=2.0 Hz), 10.15 (1H, s), 13.41 (1H, brs).

MS (ESI, m/z): 308 (M+H)$^+$, 306 (M-H)$^-$.

Example 120

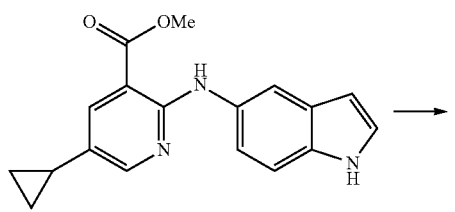

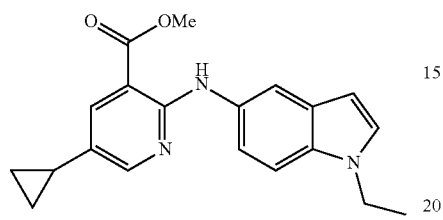

To the solution of 150 mg of methyl 2-((1H-indol-5-yl)amino)-5-cyclopropylnicotinate in 1 mL of N,N-dimethylacetamide, 60 mg of potassium tert-butoxide and 43 µL of iodoethane were added under ice-cooling, and the resultant was stirred for three hours and 15 minutes and then stirred at an external temperature of 40° C. for one hour and 50 minutes. 27 mg of potassium tert-butoxide and 18 µL of iodoethane were added thereto, and the resultant was stirred at an external temperature of 40° C. for three hours and 10 minutes, and 2 mL of water was then added thereto, and the resultant was stirred at the same temperature for 45 minutes. The reaction mixture was allowed to stand overnight, and ethyl acetate and water were then added thereto. The organic layer was separated, washed with a saturated aqueous sodium chloride solution and dried over anhydrous sodium sulfate, and the solvent was distilled off under reduced pressure. The obtained residue was purified by silica gel column chromatography (gradient elution with hexane:ethyl acetate=100:0-70:30) to give 115 mg of methyl 5-cyclopropyl-2-((1-ethyl-1H-indol-5-yl)amino)nicotinate as a yellow oil.

MS (ESI, m/z): 336 (M+H)$^+$.

Example 121

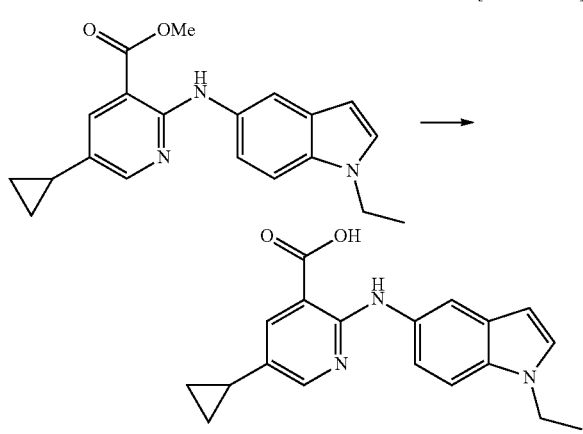

By the method similar to that of Example 116, 5-cyclopropyl-2-((1-ethyl-1H-indol-5-yl)amino)nicotinic acid was obtained from methyl 5-cyclopropyl-2-((1-ethyl-1H-indol-5-yl)amino)nicotinate.

$^1$H-NMR (DMSO-d$_6$) δ: 0.61-0.67 (2H, m), 0.87-0.94 (2H, m), 1.36 (3H, t, J=6.9 Hz), 1.85-1.95 (1H, m), 4.18 (2H, q, J=7.0 Hz), 6.37 (1H, d, J=2.6 Hz), 7.20 (1H, dd, J=8.9, 1.7 Hz), 7.35 (1H, d, J=2.6 Hz), 7.40 (1H, d, J=8.6 Hz), 7.88 (1H, d, J=2.0 Hz), 7.95 (1H, d, J=1.3 Hz), 8.18 (1H, d, J=2.6 Hz), 10.14 (1H, s), 13.41 (1H, brs).

MS (ESI, m/z): 322 (M+H)$^+$, 320 (M−H)$^-$.

Example 122

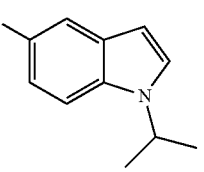

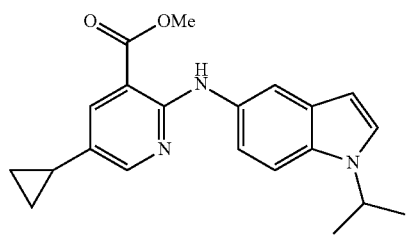

The mixture of 91 mg of 1-isopropyl-1H-indol-5-amine, 100 mg of methyl 2-chloro-5-cyclopropyl-nicotinate, 22 mg of tris(dibenzylideneacetone)dipalladium(0), 27 mg of 4,5'-bis(diphenylphosphino)-9,9'-dimethylxanthene, 308 mg of cesium carbonate, and 1 mL of butyl acetate, was heated at reflux for three hours under a nitrogen atmosphere. The reaction mixture was cooled to room temperature and then allowed to stand overnight, and ethyl acetate and water were added thereto. The organic layer was separated, washed with a saturated aqueous sodium chloride solution and dried over anhydrous sodium sulfate, and the solvent was distilled off under reduced pressure. The obtained residue was purified by silica gel column chromatography (gradient elution with hexane:ethyl acetate=100:0-80:20) to give 150 mg of methyl 5-cyclopropyl-2-((1-isopropyl-1H-indol-5-yl)amino)nicotinate as a brown oil.

$^1$H-NMR (DMSO-d$_6$) δ: 0.62-0.67 (2H, m), 0.85-0.95 (2H, m), 1.45 (6H, d, J=6.6 Hz), 1.88-1.93 (1H, m), 3.84 (3H, s), 4.71 (1H, sep, J=6.9 Hz), 6.40 (1H, d, J=2.6 Hz), 7.19 (1H, dd, J=8.6, 2.0 Hz), 7.42-7.47 (2H, m), 7.88 (1H, d, J=2.6 Hz), 7.93 (1H, d, J=2.0 Hz), 8.21 (1H, d, J=2.0 Hz), 9.83 (1H, s).

MS (ESI, m/z): 350 (M+H)$^+$.

Example 123


[Formula 370]

By the method similar to that of Example 116, 5-cyclopropyl-2-((1-isopropyl-1H-indol-5-yl)amino)nicotinic acid was obtained from methyl 5-cyclopropyl-2-((1-isopropyl-1H-indol-5-yl)amino)nicotinate.

$^1$H-NMR (DMSO-$d_6$) δ: 0.61-0.67 (2H, m), 0.87-0.94 (2H, m), 1.45 (6H, d, J=6.6 Hz), 1.86-1.93 (1H, m), 4.71 (1H, sep, J=6.6 Hz), 6.39 (1H, d, J=3.3 Hz), 7.19 (1H, dd, J=8.6, 2.0 Hz), 7.41-7.45 (2H, m), 7.87 (1H, d, J=2.6 Hz), 7.94 (1H, d, J=2.0 Hz), 8.19 (1H, d, J=2.0 Hz), 10.12 (1H, s), 13.40 (1H, brs).
MS (ESI, m/z): 336 (M+H)$^+$.

Example 124

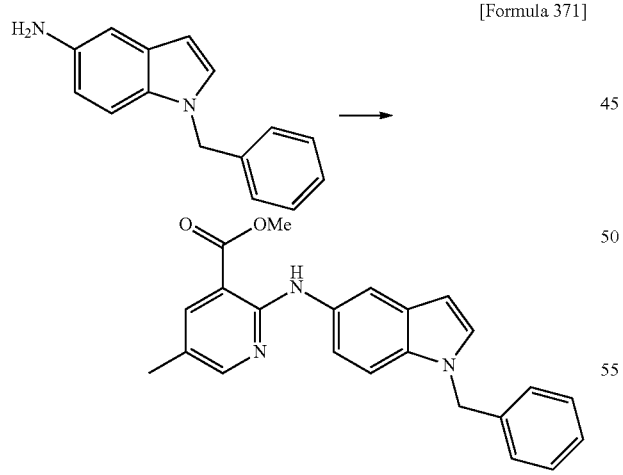

[Formula 371]

The mixture of 118 mg of 1-benzyl-1H-indol-5-amine, 100 mg of methyl 2-chloro-5-methylnicotinate, 25 mg of tris(dibenzylideneacetone)dipalladium(0), 31 mg of 4,5'-bis(diphenylphosphino)-9,9'-dimethylxanthene, 352 mg of cesium carbonate, and 5 mL of toluene, was heated at reflux for five hours and 30 minutes under a nitrogen atmosphere. The reaction mixture was cooled to room temperature, and ethyl acetate and water were then added thereto. The organic layer was separated, washed with a saturated aqueous sodium chloride solution and dried over anhydrous sodium sulfate, and the solvent was distilled off under reduced pressure. The obtained residue was purified by silica gel column chromatography (gradient elution with hexane:ethyl acetate=100:0-70:30). Water and methanol were added to the thus obtained residue, and the solid was collected by filtration to give 60 mg of methyl 2-((1-benzyl-1H-indol-5-yl)amino)-5-methylnicotinate as a yellow solid.

$^1$H-NMR (DMSO-$d_6$) δ: 2.27 (3H, s), 3.88 (3H, s), 5.40 (2H, s), 6.44 (1H, d, J=2.6 Hz), 7.14-7.39 (7H, m), 7.48 (1H, d, J=2.6 Hz), 7.95 (1H, d, J=1.3 Hz), 8.05 (1H, d, J=2.0 Hz), 8.21 (1H, d, J=2.0 Hz), 9.82 (1H, s).
MS (ESI, m/z): 372 (M+H)$^+$.

Example 125

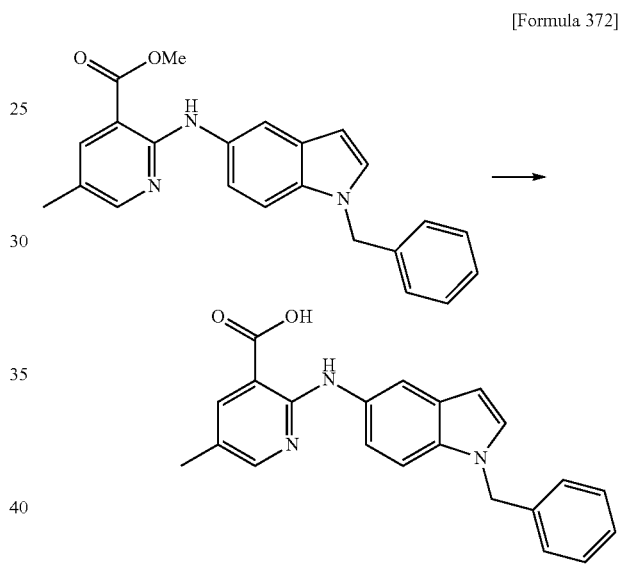

[Formula 372]

By the method similar to that of Example 116, 2-((1-benzyl-1H-indol-5-yl)amino)-5-methylnicotinic acid was obtained from methyl 2-((1-benzyl-1H-indol-5-yl)amino)-5-methylnicotinate.

$^1$H-NMR (DMSO-$d_6$) δ: 2.21 (3H, s), 5.41 (2H, s), 6.46 (1H, d, J=2.6 Hz), 7.13-7.34 (6H, m), 7.41 (1H, d, J=9.2 Hz), 7.51 (1H, d, J=3.3 Hz), 7.90 (1H, s), 8.10-8.15 (2H, m), 10.19 (1H, s).
MS (ESI, m/z): 358 (M+H)$^+$, 356 (M−H)$^−$.

Example 126

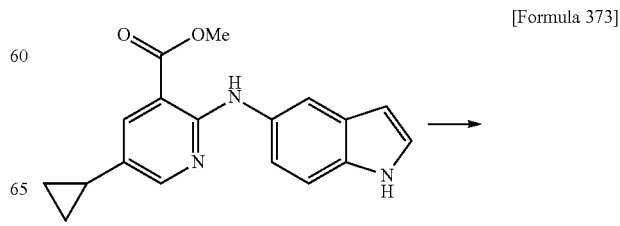

[Formula 373]

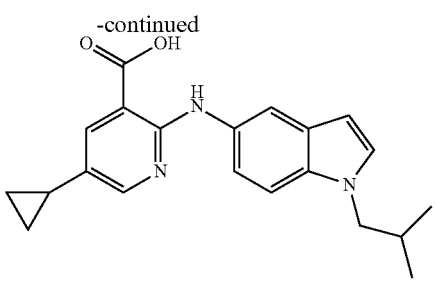

To the solution of 120 mg of methyl 2-((1H-indol-5-yl)amino)-5-cyclopropylnicotinate in 2 mL of N,N-dimethylacetamide, 120 mg of potassium tert-butoxide, 85 μL of 1-bromo-2-methylpropane and molecular sieves 4 A were added under ice-cooling, and the resultant was stirred for two hours and 15 minutes. 53 mg of potassium tert-butoxide and 85 of 1-bromo-2-methylpropane were added thereto under water-cooling, and the resultant was stirred for one hour and 25 minutes. The reaction mixture was allowed to stand overnight, and 53 mg of potassium tert-butoxide and 85 μL of 1-bromo-2-methylpropane were then added thereto under water-cooling, and the resultant was stirred for two hours and 20 minutes. The reaction mixture was adjusted to pH 3 by adding thereto 260 pt of 6 mol/L hydrochloric acid and water, followed by addition of ethyl acetate and water. The organic layer was separated, washed with a saturated aqueous sodium chloride solution and dried over anhydrous sodium sulfate, and the solvent was distilled off under reduced pressure. The obtained residue was purified by silica gel column chromatography (gradient elution with hexane:ethyl acetate=100:0-0:100) to give 67 mg of 2-((1-isobutyl-1H-indol-5-yl)amino)-5-cyclopropylnicotinic acid as a yellow solid.

$^1$H-NMR (DMSO-d$_6$) δ: 0.61-0.67 (2H, m), 0.85 (6H, d, J=6.6 Hz), 0.89-0.94 (2H, m), 1.86-1.94 (1H, m), 2.06-2.12 (1H, m), 3.95 (2H, d, J=7.3 Hz), 6.36 (1H, d, J=3.3 Hz), 7.18 (1H, dd, J=8.6, 1.3 Hz), 7.30 (1H, d, J=3.3 Hz), 7.40 (1H, d, J=8.6 Hz), 7.87 (1H, d, J=2.6 Hz), 7.95 (1H, d, J=1.3 Hz), 8.19 (1H, d, J=2.6 Hz), 10.11 (1H, s), 13.39 (1H, brs).

MS (ESI, m/z): 350 (M+H)$^+$, 348 (M−H)$^−$.

Example 127

[Formula 374]

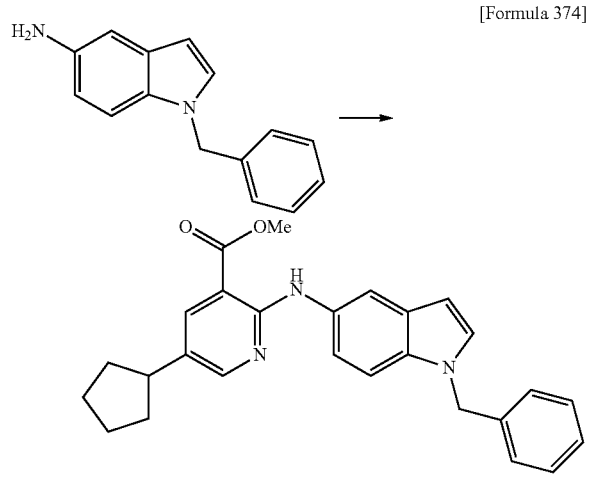

The mixture of 100 mg of 1-benzyl-1H-indol-5-amine, 103 mg of methyl 2-chloro-5-cyclopentylnicotinate, 20 mg of tris(dibenzylideneacetone)dipalladium(0), 25 mg of 4,5'-bis(diphenylphosphino)-9,9'-dimethylxanthene, 280 mg of cesium carbonate, and 1 mL of butyl acetate, was heated at reflux for four hours and five minutes under a nitrogen atmosphere. The reaction mixture was cooled to room temperature, and ethyl acetate and water were then added thereto. The organic layer was separated, washed with a saturated aqueous sodium chloride solution and dried over anhydrous sodium sulfate, and the solvent was distilled off under reduced pressure. The obtained residue was purified by silica gel column chromatography (gradient elution with hexane:ethyl acetate=100:0-30:70). Diisopropyl ether was added to the thus obtained residue, and the solid was collected by filtration to give 132 mg of methyl 2-((1-benzyl-1H-indol-5-yl)amino)-5-cyclopentylnicotinate as a yellow solid.

$^1$H-NMR (DMSO-d$_6$) δ: 1.41-1.82 (6H, m), 1.95-2.05 (2H, m), 2.86-2.99 (1H, m), 3.89 (3H, s), 5.40 (2H, s), 6.44 (1H, d, J=2.6 Hz), 7.15-7.39 (7H, m), 7.48 (1H, d, J=3.3 Hz), 7.96 (1H, d, J=2.0 Hz), 8.06 (1H, d, J=2.6 Hz), 8.28 (1H, d, J=2.6 Hz), 9.84 (1H, s).

MS (ESI, m/z): 426 (M+H)$^+$, 424 (M−H)$^−$.

Example 128

[Formula 375]

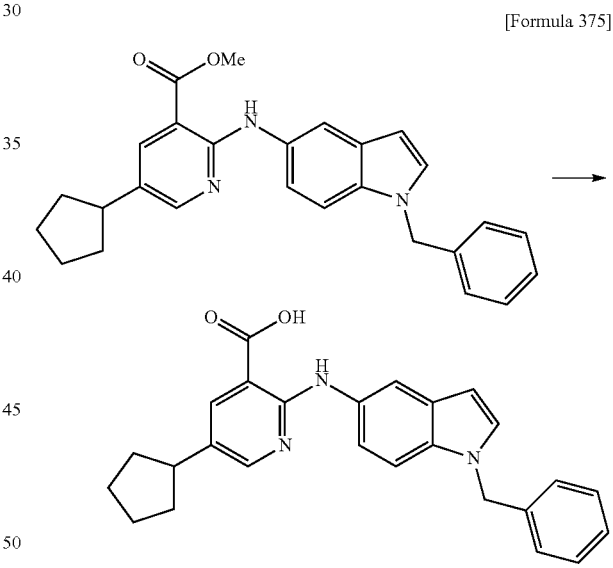

The mixture of 132 mg of methyl 2-((1-benzyl-1H-indol-5-yl)amino)-5-cyclopentylnicotinate, 124 pt of a 5 mol/L aqueous sodium hydroxide solution, 2 mL of tetrahydrofuran, and 1 mL of methanol, was stirred at an external temperature of 40° C. for three hours and 20 minutes. After cooling the reaction mixture to room temperature, 103 μL of 6 mol/L hydrochloric acid was added thereto, and ethyl acetate and water were added thereto. The organic layer was separated and the aqueous layer was extracted with ethyl acetate. The organic layer and the extract layer were combined, washed with a saturated aqueous sodium chloride solution and dried over anhydrous sodium sulfate, and the solvent was distilled off under reduced pressure. The obtained residue was purified by silica gel column chromatography (gradient elution with chloroform:methanol=100:

0-90:10). Hexane and ethyl acetate were added to the thus obtained residue, and the solid was collected by filtration to give 65 mg of 2-((1-benzyl-1H-indol-5-yl)amino)-5-cyclopentylnicotinic acid as a yellow solid.

¹H-NMR (DMSO-d₆) δ: 1.42-1.55 (2H, m), 1.56-1.80 (4H, m), 1.95-2.05 (2H, m), 2.86-2.98 (1H, m), 5.40 (2H, s), 6.43 (1H, d, J=3.3 Hz), 7.15-7.38 (7H, m), 7.47 (1H, d, J=2.6 Hz), 7.97 (1H, d, J=2.0 Hz), 8.05 (1H, d, J=2.6 Hz), 8.24 (1H, d, J=2.0 Hz), 10.15 (1H, s).

MS (ESI, m/z): 412 (M+H)⁺, 410 (M−H)⁻.

Example 129

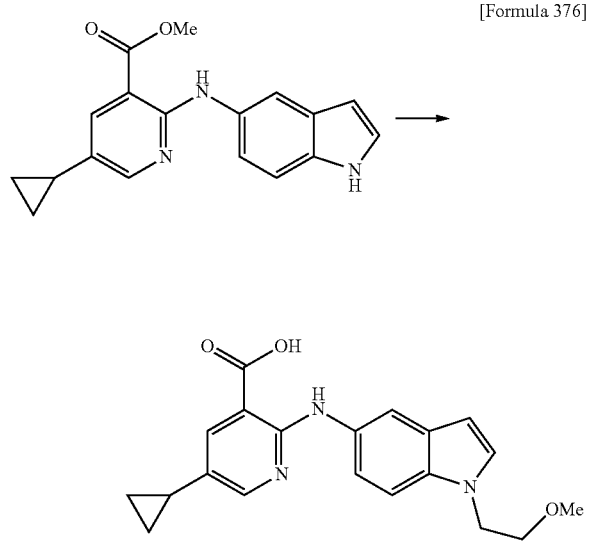

[Formula 376]

To the solution of 120 mg of methyl 2-((1H-indol-5-yl)amino)-5-cyclopropylnicotinate in 1 mL of N,N-dimethylacetamide, 53 mg of potassium tert-butoxide, 74 of 2-bromoethyl methyl ether and molecular sieves 4 A were added under ice-cooling, and the resultant was stirred for two hours and 15 minutes. 53 mg of potassium tert-butoxide and 74 μL of 2-bromoethyl methyl ether were added thereto under ice-cooling, and the resultant was stirred for one hour and 25 minutes and then allowed to stand overnight. The reaction mixture was adjusted to pH 2 by adding thereto 167 μL of 6 mol/L hydrochloric acid and water, followed by addition of ethyl acetate and water. The organic layer was separated, washed with a saturated aqueous sodium chloride solution and dried over anhydrous sodium sulfate, and the solvent was distilled off under reduced pressure. The obtained residue was purified by silica gel column chromatography (gradient elution with hexane:ethyl acetate containing 2% acetic acid=100:0-50:50) to give 7 mg of 5-cyclopropyl-2-((1-(2-methoxyethyl)-1H-indol-5-yl)amino)nicotinic acid as a yellow solid.

¹H-NMR (DMSO-d₆) δ: 0.61-0.65 (2H, m), 0.85-0.95 (2H, m), 1.85-1.94 (1H, m), 3.22 (3H, s), 3.65 (2H, t, J=5.3 Hz), 4.30 (2H, t, J=5.3 Hz), 6.36 (1H, d, J=3.3 Hz), 7.19 (1H, d, J=8.6, 2.0 Hz), 7.31 (1H, d, J=2.6 Hz), 7.41 (1H, d, J=9.2 Hz), 7.87 (1H, d, J=2.6 Hz), 7.95 (1H, s), 8.19 (1H, d, J=2.6 Hz), 10.14 (1H, s), 13.41 (1H, brs).

MS (ESI, m/z): 352 (M+H)⁺, 350 (M−H)⁻.

Example 130

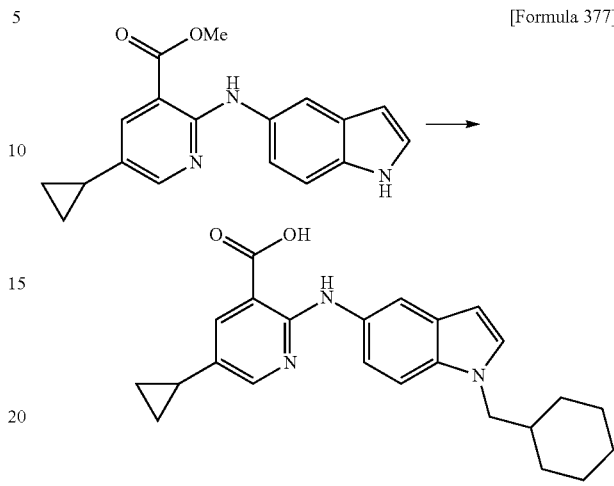

[Formula 377]

To the solution of 100 mg of methyl 2-((1H-indol-5-yl)amino)-5-cyclopropylnicotinate in 1.5 mL of N,N-dimethylacetamide, 135 mg of potassium tert-butoxide and 136 μL of (bromomethyl)cyclohexane were added, and the resultant was stirred for one hour and 30 minutes. 90 mg of potassium tert-butoxide and 91 μL of (bromomethyl)cyclohexane were added thereto, and the resultant was stirred for two hours and 50 minutes. The reaction mixture was allowed to stand overnight and then adjusted to pH 3 by adding thereto 1 mol/L hydrochloric acid and water, followed by addition of ethyl acetate and water. The organic layer was separated, washed with a saturated aqueous sodium chloride solution and dried over anhydrous sodium sulfate, and the solvent was distilled off under reduced pressure. The obtained residue was purified by silica gel column chromatography (gradient elution with hexane:ethyl acetate=50:50-0:100). Diisopropyl ether and hexane were added to the thus obtained residue, and the solid was collected by filtration to give 60 mg of 2-((1-(cyclohexylmethyl)-1H-indol-5-yl)amino)-5-cyclopropylnicotinic acid as a yellow solid.

¹H-NMR (DMSO-d₆) δ: 0.60-0.67 (2H, m), 0.80-1.22 (7H, m), 1.45-1.70 (5H, m), 1.73-1.83 (1H, m), 1.85-1.95 (1H, m), 3.98 (2H, d, J=7.3 Hz), 6.35 (1H, d, J=3.3 Hz), 7.17 (1H, dd, J=8.9, 1.7 Hz), 7.28 (1H, d, J=2.6 Hz), 7.39 (1H, d, J=8.6 Hz), 7.86 (1H, d, J=2.6 Hz), 7.93 (1H, d, J=1.3 Hz), 8.17-8.20 (1H, m), 10.12 (1H, s), 13.40 (1H, brs).

MS (ESI, m/z): 390 (M+H)⁺, 388 (M−H)⁻.

Example 131

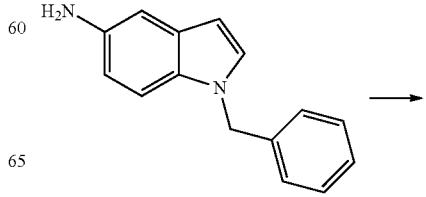

[Formula 378]

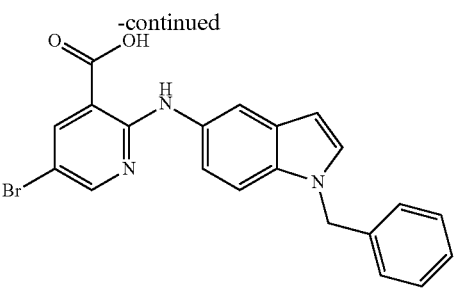

The mixture of 745 mg of 1-benzyl-1H-indol-5-amine, 700 mg of methyl 5-bromo-2-chloronicotinate, 1.82 g of cesium carbonate, and 5 mL of N,N-dimethylacetamide, was stirred at 170° C. for 30 minutes under a nitrogen atmosphere using microwave equipment. The reaction mixture was cooled to room temperature and then adjusted to be acidic by adding thereto 1 mol/L hydrochloric acid and water. Ethyl acetate and water were added thereto. The organic layer was separated, washed with a saturated aqueous sodium chloride solution and dried over anhydrous magnesium sulfate, and the solvent was distilled off under reduced pressure. The obtained residue was purified by silica gel column chromatography (gradient elution with chloroform:methanol=100:0-90:10). Ethyl acetate and methanol were added to the thus obtained residue, and the solid was collected by filtration to give 280 mg of 2-((1-benzyl-1H-indol-5-yl)amino)-5-bromonicotinic acid as a yellow solid.

$^1$H-NMR (DMSO-$d_6$) δ: 5.41 (2H, s), 6.45 (1H, d, J=3.3 Hz), 7.14-7.33 (6H, m), 7.39 (1H, d, J=8.6 Hz), 7.50 (1H, d, J=2.6 Hz), 7.88 (1H, d, J=2.0 Hz), 8.25 (1H, d, J=2.6 Hz), 8.39 (1H, d, J=2.6 Hz), 10.21 (1H, s).

MS (ESI, m/z): 424 (M+H)$^+$, 422 (M−H)$^-$.

Example 132

[Formula 379]

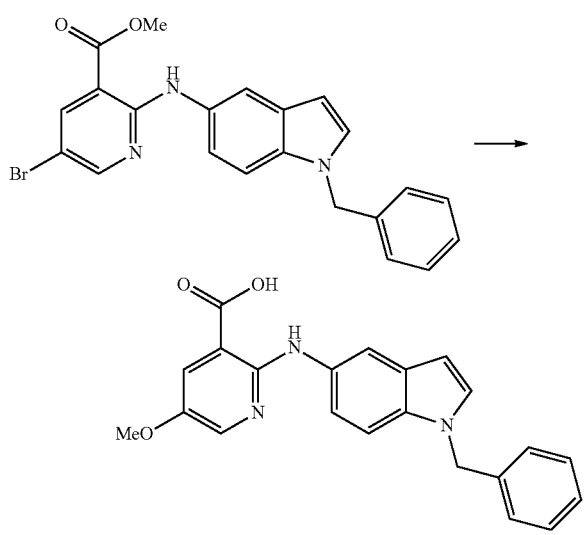

The mixture of 80 mg of 2-((1-benzyl-1H-indol-5-yl)amino)-5-bromonicotinic acid, 35 mg of copper(I) bromide, 760 μL of a 5 mol/L sodium methoxide-methanol solution, and 760 μL of N,N-dimethylacetamide, was stirred at an external temperature of 140° C. for 20 minutes under a nitrogen atmosphere. The reaction mixture was cooled to room temperature and then made acidic by adding thereto 760 μL of 5 mol/L hydrochloric acid and water. Ethyl acetate and water were added thereto. The organic layer was separated, washed with a saturated aqueous sodium chloride solution and dried over anhydrous sodium sulfate, and the solvent was distilled off under reduced pressure. The obtained residue was purified by silica gel column chromatography (gradient elution with hexane:ethyl acetate containing 1% acetic acid=100:0-50:50). Water and methanol were added to the thus obtained residue, and the solid was collected by filtration to give 15 mg of 2-((1-benzyl-1H-indol-5-yl)amino)-5-methoxynicotinic acid as a yellow solid.

$^1$H-NMR (DMSO-$d_6$) δ: 3.78 (3H, s), 5.39 (2H, s), 6.42 (1H, d, J=3.3 Hz), 7.10-7.38 (7H, m), 7.46 (1H, d, J=3.3 Hz), 7.79 (1H, d, J=3.3 Hz), 7.96 (1H, d, J=2.0 Hz), 8.16 (1H, d, J=3.3 Hz), 9.97 (1H, s), 13.54 (1H, brs).

MS (ESI, m/z): 374 (M+H)$^+$, 372 (M−H)$^-$.

Example 133

[Formula 380]

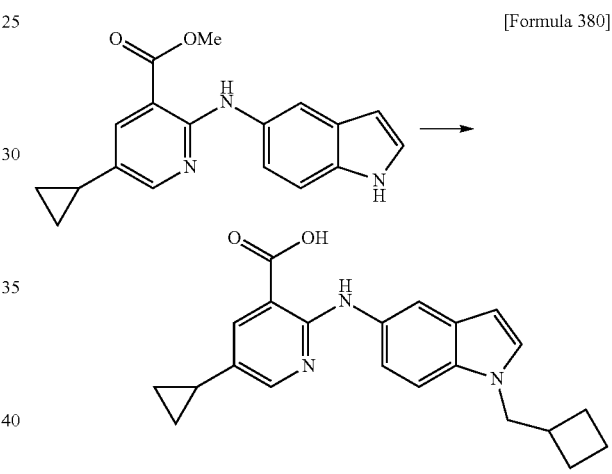

To the solution of 100 mg of methyl 2-((1H-indol-5-yl)amino)-5-cyclopropylnicotinate in 2 mL of N,N-dimethylacetamide, 135 mg of potassium tert-butoxide and 109 μL of (bromomethyl)cyclobutane were added under ice-cooling, and the resultant was stirred for three hours and 35 minutes. 90 mg of potassium tert-butoxide and 73 μL of (bromomethyl)cyclobutane were added thereto under ice-cooling, and the resultant was stirred for one hour and 25 minutes. 23 mg of potassium tert-butoxide and 18 μL of (bromomethyl)cyclobutane were added thereto under ice-cooling, and the resultant was stirred for 20 minutes. The reaction mixture was adjusted to pH 2 by adding thereto 1 mol/L hydrochloric acid and water, followed by addition of ethyl acetate and water. The organic layer was separated, washed with a saturated aqueous sodium chloride solution and dried over anhydrous sodium sulfate, and the solvent was distilled off under reduced pressure. The obtained residue was purified by silica gel column chromatography (gradient elution with ethyl acetate:methanol=100:0-95:5) to give 50 mg of 2-((1-(cyclobutylmethyl)-1H-indol-5-yl)amino)-5-cyclopropylnicotinic acid as a yellow solid.

$^1$H-NMR (DMSO-$d_6$) δ: 0.61-0.66 (2H, m), 0.87-0.93 (2H, m), 1.73-1.99 (7H, m), 2.71-2.82 (1H, m), 4.15 (2H, d, J=7.3 Hz), 6.35 (1H, d, J=2.6 Hz), 7.18 (1H, dd, J=8.6, 2.0

Hz), 7.32 (1H, d, J=2.6 Hz), 7.40 (1H, d, J=8.6 Hz), 7.86 (1H, d, J=2.6 Hz), 7.95 (1H, d, J=2.0 Hz), 8.17 (1H, d, J=2.6 Hz), 10.25 (1H, brs), 13.42 (1H, brs).

MS (ESI, m/z): 362 (M+H)+, 360 (M−H)−.

Example 134

[Formula 381]

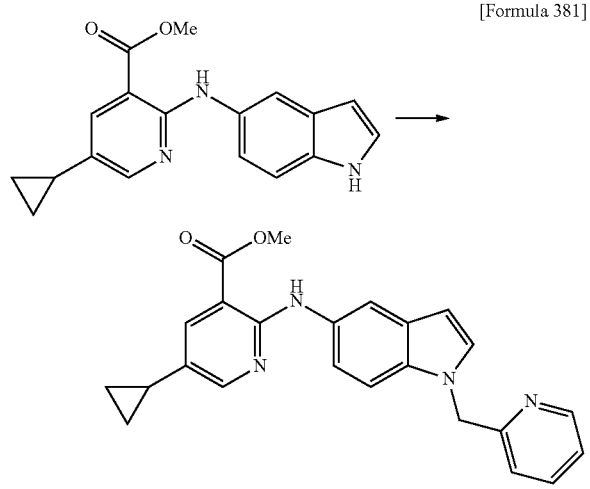

The mixture of 90 mg of methyl 2-((1H-indol-5-yl)amino)-5-cyclopropylnicotinate, 89 mg of potassium tert-butoxide, 89 mg of 2-(bromomethyl)pyridine hydrobromide, and 1 mL of N,N-dimethylacetamide, was stirred for three hours and 30 minutes under ice-cooling. Ethyl acetate and water were added to the reaction mixture, and the organic layer was separated, washed with a saturated aqueous sodium chloride solution and dried over anhydrous sodium sulfate, and the solvent was distilled off under reduced pressure. The obtained residue was purified by silica gel column chromatography (gradient elution with ethyl acetate:methanol=100:0-95:5) to give 77 mg of methyl 5-cyclopropyl-2-((1-(pyridin-2-ylmethyl)-1H-indol-5-yl)amino)nicotinate as a white solid.

MS (ESI, m/z): 399 (M+H)+.

Example 135

[Formula 382]

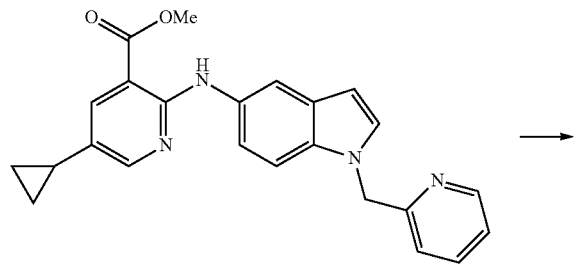

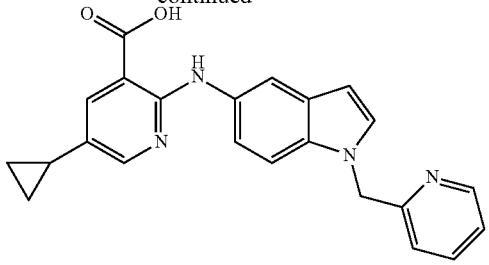

By the method similar to that of Example 116, 5-cyclopropyl-2-((1-(pyridin-2-ylmethyl)-1H-indol-5-yl)amino)nicotinic acid was obtained from methyl 5-cyclopropyl-2-((1-(pyridin-2-ylmethyl)-1H-indol-5-yl)amino)nicotinate.

1H-NMR (DMSO-d6) δ: 0.61-0.68 (2H, m), 0.88-0.93 (2H, m), 1.85-1.94 (1H, m), 5.48 (2H, s), 6.45 (1H, d, J=2.6 Hz), 6.94 (1H, d, J=7.9 Hz), 7.15 (1H, dd, J=8.6, 2.0 Hz), 7.24-7.29 (1H, m), 7.33 (1H, d, J=9.2 Hz), 7.47 (1H, d, J=3.3 Hz), 7.71 (1H, td, J=7.8, 1.8), 7.86 (1H, d, J=2.6 Hz), 7.98 (1H, d, J=2.0 Hz), 8.18 (1H, d, J=2.6 Hz), 8.54 (1H, dd, J=4.0, 2.0 Hz), 10.11 (1H, s), 13.42 (1H, brs).

MS (ESI, m/z): 385 (M+H)+, 383 (M−H)−.

Example 136

[Formula 383]

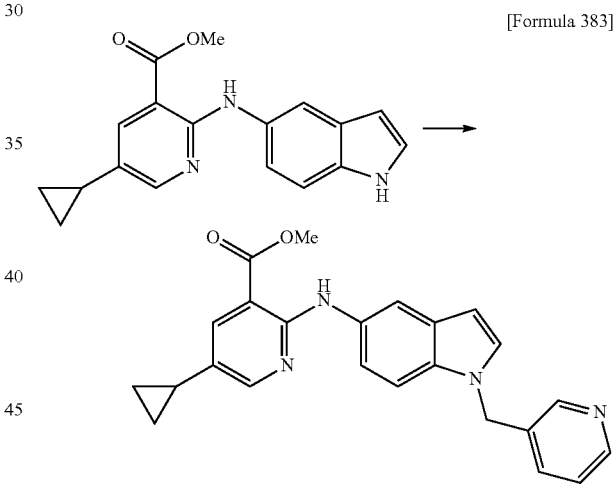

The mixture of 60 mg of methyl 2-((1H-indol-5-yl)amino)-5-cyclopropylnicotinate, 59 mg of potassium tert-butoxide, 59 mg of 3-(bromomethyl)pyridine hydrobromide, and 1 mL of N,N-dimethylacetamide, was stirred for two hours and 15 minutes under ice-cooling. Ethyl acetate and water were added to the reaction mixture. The organic layer was separated, washed with a saturated aqueous sodium chloride solution and dried over anhydrous sodium sulfate, and the solvent was distilled off under reduced pressure. The obtained residue was purified by silica gel column chromatography (gradient elution with hexane:ethyl acetate=50:50-0:100) to give 46 mg of methyl 5-cyclopropyl-2-((1-(pyridin-3-ylmethyl)-1H-indol-5-yl)amino)nicotinate as a gray solid.

1H-NMR (DMSO-d6) δ: 0.61-0.67 (2H, m), 0.87-0.95 (2H, m), 1.86-1.94 (1H, m), 3.89 (3H, s), 5.45 (2H, s), 6.45 (1H, d, J=2.6 Hz), 7.17 (1H, dd, J=8.9, 2.3 Hz), 7.33 (1H, dd, J=7.9, 4.6 Hz), 7.43 (1H, d, J=9.2 Hz), 7.51 (1H, d, J=2.6

Hz), 7.54-7.59 (1H, m), 7.88 (1H, d, J=2.6 Hz), 7.97 (1H, d, J=2.0 Hz), 8.20 (1H, d, J=2.6 Hz), 8.46 (1H, dd, J=4.6, 2.0 Hz), 8.52 (1H, d, J=2.0 Hz), 9.82 (1H, s).
MS (ESI, m/z): 399 (M+H)⁺.

Example 137

[Formula 384]

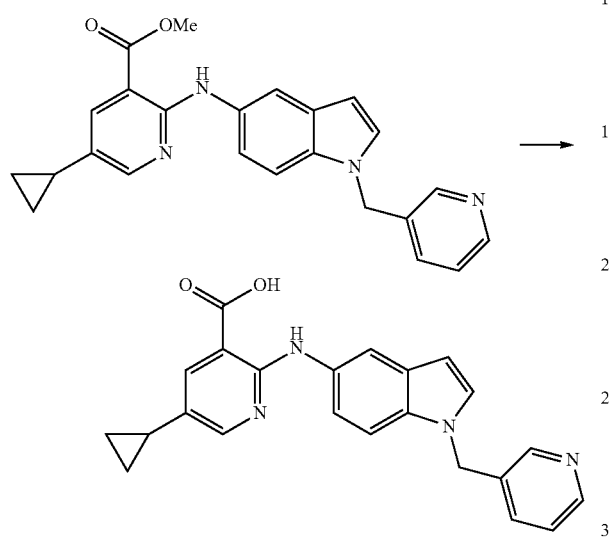

By the method similar to that of Example 116, 5-cyclopropyl-2-((1-(pyridin-3-ylmethyl)-1H-indol-5-yl)amino)nicotinic acid was obtained from methyl 5-cyclopropyl-2-((1-(pyridin-3-ylmethyl)-1H-indol-5-yl)amino)nicotinate.
¹H-NMR (DMSO-d₆) δ: 0.61-0.68 (2H, m), 0.86-0.94 (2H, m), 1.85-1.94 (1H, m), 5.45 (2H, s), 6.45 (1H, d, J=3.3 Hz), 7.18 (1H, dd, J=8.6, 2.0 Hz), 7.33 (1H, dd, J=7.9, 4.6 Hz), 7.42 (1H, d, J=8.6 Hz), 7.51 (1H, d, J=2.6 Hz), 7.54-7.59 (1H, m), 7.86 (1H, d, J=2.6 Hz), 7.97 (1H, d, J=2.0 Hz), 8.18 (1H, d, J=2.6 Hz), 8.46 (1H, dd, J=4.6, 1.3 Hz), 8.52 (1H, d, J=1.3 Hz), 10.11 (1H, s), 13.40 (1H, brs).
MS (ESI, m/z): 385 (M+H)⁺, 383 (M−H)⁻.

Example 138

[Formula 385]

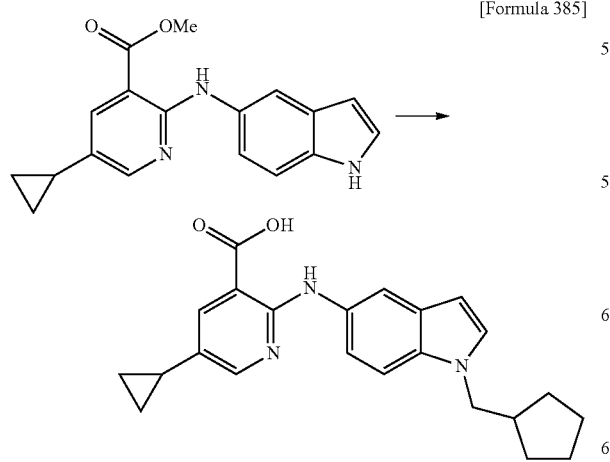

To the solution of 100 mg of methyl 2-((1H-indol-5-yl)amino)-5-cyclopropylnicotinate in 1 mL of N,N-dimethylacetamide, 89 mg of potassium tert-butoxide and 50 mg of (bromomethyl)cyclopentane were added under ice-cooling, and the resultant was stirred for two hours. The reaction mixture was allowed to stand overnight, and 45 mg of potassium tert-butoxide and 50 mg of (bromomethyl)cyclopentane were then added thereto under ice-cooling, and the resultant was stirred for 12 hours. The reaction mixture was allowed to stand overnight and then adjusted to pH 2 by adding thereto 1 mol/L hydrochloric acid and water, followed by addition of ethyl acetate and water. The organic layer was separated, washed with a saturated aqueous sodium chloride solution and dried over anhydrous sodium sulfate, and the solvent was distilled off under reduced pressure. The obtained residue was purified by silica gel column chromatography (gradient elution with chloroform:methanol=100:0-90:10). Diisopropyl ether was added to the thus obtained residue, and the solid was collected by filtration to give 2-((1-(cyclopentylmethyl)-1H-indol-5-yl)amino)-5-cyclopropylnicotinic acid as a yellow solid.
¹H-NMR (DMSO-d₆) δ: 0.59-0.64 (2H, m), 0.86-0.92 (2H, m), 1.19-1.30 (2H, m), 1.46-1.67 (6H, m), 1.83-1.92 (1H, m), 2.38 (1H, sep, J=7.3 Hz), 4.04 (2H, d, J=7.3 Hz), 6.34 (1H, d, J=2.6 Hz), 7.17 (1H, dd, J=8.6, 2.0 Hz), 7.32 (1H, d, J=2.6 Hz), 7.38 (1H, d, J=9.2 Hz), 7.86 (1H, d, J=2.0 Hz), 8.00 (1H, d, J=2.0 Hz), 8.11 (1H, d, J=2.6 Hz), 10.82 (1H, brs).
MS (ESI, m/z): 376 (M+H)⁺, 374 (M−H)⁻.

Example 139

[Formula 386]

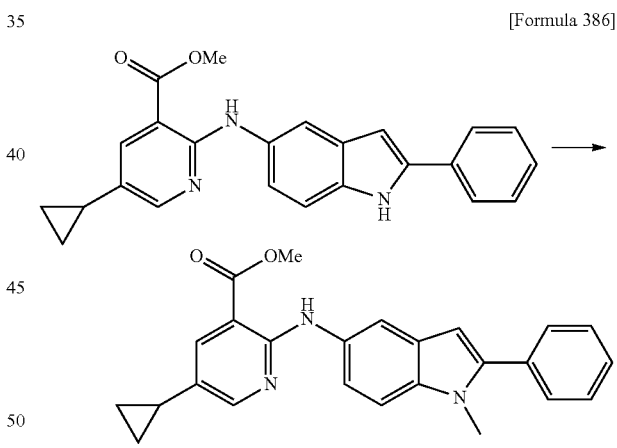

To the solution of 70 mg of methyl 5-cyclopropyl-2-((2-phenyl-1H-indol-5-yl)amino)nicotinate in 750 μL of N,N-dimethylacetamide, 30 mg of potassium tert-butoxide and 13 μL of iodomethane were added under ice-cooling, and the resultant was stirred for three hours. 4 μL of iodomethane was added thereto under ice-cooling, and the resultant was stirred for 20 minutes. Ethyl acetate and water were added to the reaction mixture. The organic layer was separated, washed with a saturated aqueous sodium chloride solution and dried over anhydrous sodium sulfate, and the solvent was distilled off under reduced pressure. The obtained residue was purified by silica gel column chromatography (gradient elution with hexane:ethyl acetate=100:0-50:50) to give 53 mg of methyl 5-cyclopropyl-2-((1-methyl-2-phenyl-1H-indol-5-yl)amino)nicotinate as a yellow oil.

¹H-NMR (DMSO-d₆) δ: 0.63-0.69 (2H, m), 0.88-0.96 (2H, m), 1.87-1.97 (1H, m), 3.74 (3H, s), 3.91 (3H, s), 6.54 (1H, s), 7.27 (1H, dd, J=8.6, 2.0 Hz), 7.41-7.47 (2H, m), 7.49-7.55 (2H, m), 7.59-7.62 (2H, m), 7.90 (1H, d, J=2.6 Hz), 8.03 (1H, d, J=2.0 Hz), 8.25 (1H, d, J=2.6 Hz), 9.91 (1H, s).
MS (ESI, m/z): 398 (M+H)⁺.

Example 140

[Formula 387]

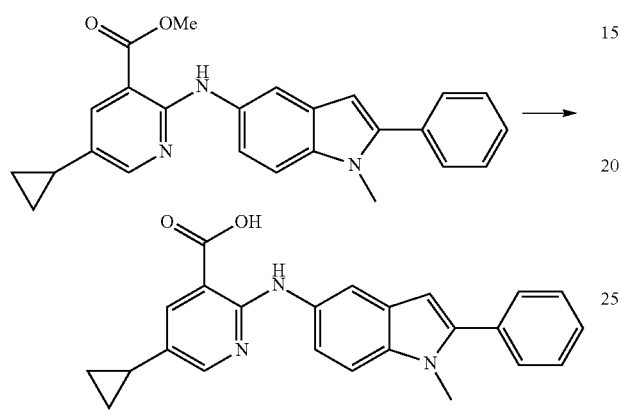

By the method similar to that of Example 116, 5-cyclopropyl-2-((1-methyl-2-phenyl-1H-indol-5-yl)amino)nicotinic acid was obtained from methyl 5-cyclopropyl-2-((1-methyl-2-phenyl-1H-indol-5-yl)amino)nicotinate.
¹H-NMR (DMSO-d₆) δ: 0.63-0.68 (2H, m), 0.88-0.95 (2H, m), 1.87-1.96 (1H, m), 3.74 (3H, s), 6.54 (1H, s), 7.27 (1H, dd, J=9.2, 2.0 Hz), 7.41-7.47 (2H, m), 7.49-7.56 (2H, m), 7.59-7.63 (2H, m), 7.90 (1H, d, J=2.6 Hz), 8.04 (1H, d, J=2.0 Hz), 8.21 (1H, d, J=2.6 Hz), 10.22 (1H, s), 13.47 (1H, brs).
MS (ESI, m/z): 384 (M+H)⁺, 382 (M−H)⁻.

Example 141

[Formula 388]

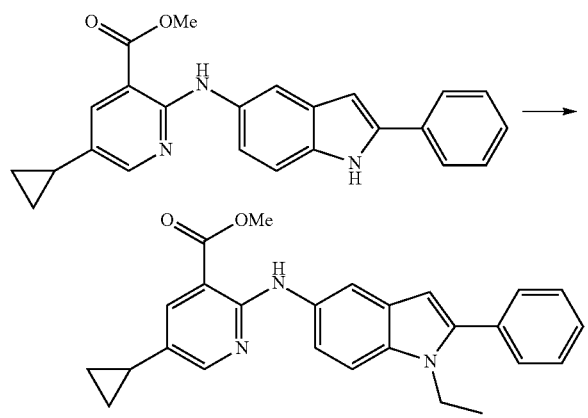

The mixture of 103 mg of methyl 5-cyclopropyl-2-((2-phenyl-1H-indol-5-yl)amino)nicotinate, 38 mg of potassium tert-butoxide, 32 µL of iodoethane, and 2 mL of N,N-dimethylacetamide, was stirred for three hours and 50 minutes under ice-cooling. Ethyl acetate and water were added to the reaction mixture. The organic layer was separated, washed with a saturated aqueous sodium chloride solution and dried over anhydrous sodium sulfate, and the solvent was distilled off under reduced pressure. Ethyl acetate and methanol were added to the obtained residue, and the solid was collected by filtration to give 70 mg of methyl 5-cyclopropyl-2-((1-ethyl-2-phenyl-1H-indol-5-yl)amino)nicotinate as a yellow solid.
¹H-NMR (DMSO-d₆) δ: 0.63-0.69 (2H, m), 0.88-0.96 (2H, m), 1.21 (3H, t, J=6.9 Hz), 1.87-1.97 (1H, m), 3.91 (3H, s), 4.20 (2H, q, J=7.3 Hz), 6.49 (1H, s), 7.26 (1H, dd, J=9.2, 2.0 Hz), 7.45-7.58 (6H, m), 7.90 (1H, d, J=2.6 Hz), 8.00 (1H, d, J=2.0 Hz), 8.25 (1H, d, J=2.0 Hz), 9.90 (1H, s).
MS (ESI, m/z): 412 (M+H)⁺.

Example 142

[Formula 389]

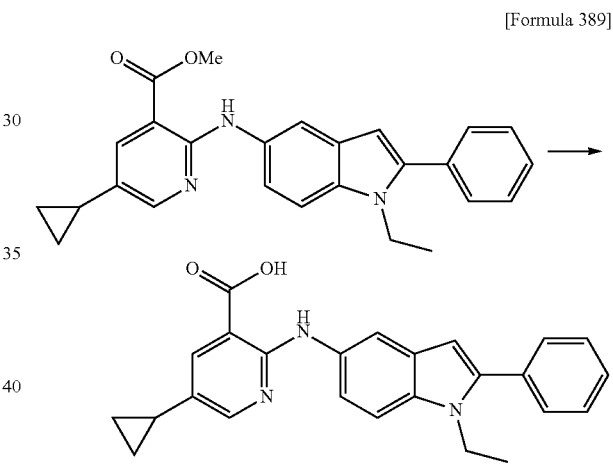

The mixture of 69 mg of methyl 5-cyclopropyl-2-((1-ethyl-2-phenyl-1H-indol-5-yl)amino)nicotinate, 100 µL of a 5 mol/L aqueous sodium hydroxide solution, 4 mL of tetrahydrofuran, and 1 mL of methanol, was stirred at an external temperature of 50° C. for five hours and 45 minutes. After cooling the reaction mixture to room temperature, 100 µL of 5 mol/L hydrochloric acid was added thereto, and ethyl acetate and water were added thereto. The organic layer was separated, washed with a saturated aqueous sodium chloride solution and dried over anhydrous sodium sulfate, and the solvent was distilled off under reduced pressure. Hexane and ethyl acetate were added to the obtained residue, and the solid was collected by filtration to give 50 mg of 5-cyclopropyl-2-((1-ethyl-2-phenyl-1H-indol-5-yl)amino)nicotinic acid as a yellow solid.
¹H-NMR (DMSO-d₆) δ: 0.62-0.68 (2H, m), 0.88-0.95 (2H, m), 1.21 (3H, t, J=6.6 Hz), 1.86-1.96 (1H, m), 4.20 (2H, q, J=7.3 Hz), 6.49 (1H, s), 7.27 (1H, dd, J=9.2, 2.0 Hz), 7.45-7.57 (6H, m), 7.89 (1H, d, J=2.6 Hz), 8.00-8.03 (1H, m), 8.22 (1H, d, J=2.0 Hz), 10.18 (1H, s), 13.43 (1H, brs).
MS (ESI, m/z): 398 (M+H)⁺, 396 (M−H)⁻.

Example 143

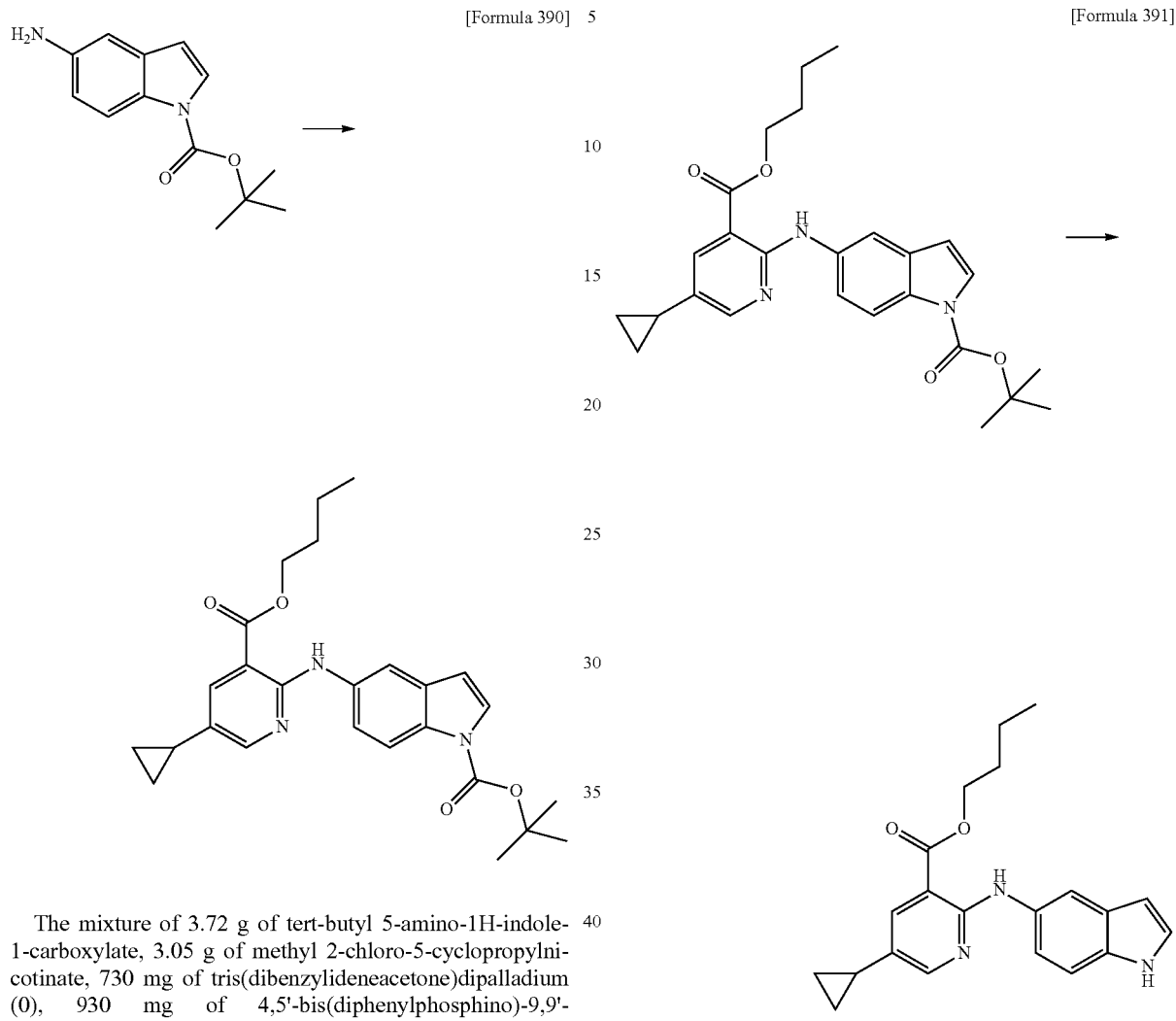

The mixture of 3.72 g of tert-butyl 5-amino-1H-indole-1-carboxylate, 3.05 g of methyl 2-chloro-5-cyclopropylnicotinate, 730 mg of tris(dibenzylideneacetone)dipalladium (0), 930 mg of 4,5'-bis(diphenylphosphino)-9,9'-dimethylxanthene, 13.1 g of cesium carbonate, and 50 mL of butyl acetate, was stirred at an external temperature of 90° C. for three hours under a nitrogen atmosphere and then heated at reflux for four hours and 20 minutes. The reaction mixture was cooled to room temperature, and ethyl acetate and water were then added thereto. The organic layer was separated, washed with a saturated aqueous sodium chloride solution and dried over anhydrous magnesium sulfate, and the solvent was distilled off under reduced pressure. The obtained residue was purified by silica gel column chromatography (gradient elution with hexane:ethyl acetate=100: 0-50:50) to give 2.10 g of tert-butyl 5-((3-(butoxycarbonyl)-5-cyclopropylpyridin-2-yl)amino)-1H-indole-1-carboxylate as a yellow oil.

$^1$H-NMR (DMSO-$d_6$) δ: 0.63-0.70 (2H, m), 0.89-0.99 (5H, m), 1.39-1.48 (2H, m), 1.63 (9H, s), 1.74 (2H, quin, J=7.9 Hz), 1.90-1.99 (1H, m), 4.33 (2H, t, J=6.6 Hz), 6.68 (1H, d, J=3.3 Hz), 7.43 (1H, dd, J=8.6, 2.0 Hz), 7.64 (1H, d, J=4.0 Hz), 7.93 (1H, d, J=2.6 Hz), 7.96 (1H, d, J=9.2 Hz), 8.11 (1H, d, J=2.0 Hz), 8.26 (1H, d, J=2.6 Hz), 10.01 (1H, s).

MS (ESI, m/z): 450 (M+H)$^+$.

Example 144

The solution of 1.50 g of tert-butyl 5-((3-(butoxycarbonyl)-5-cyclopropylpyridin-2-yl)amino)-1H-indole-1-carboxylate in 5 mL of N,N-dimethylacetamide was stirred at an external temperature of 150° C. for nine hours and 20 minutes. The reaction mixture was allowed to stand overnight and then stirred at an external temperature of 150° C. for two hours and 30 minutes. The solvent was distilled off under reduced pressure and the obtained residue was then purified by silica gel column chromatography (gradient elution with hexane:ethyl acetate=100:0-60:40). Hexane and ethyl acetate were added to the thus obtained residue, and the solid was collected by filtration to give 930 mg of butyl 2-((1H-indol-5-yl)amino)-5-cyclopropylnicotinate as a white solid.

$^1$H-NMR (DMSO-$d_6$) δ: 0.61-0.67 (2H, m), 0.88-0.95 (2H, m), 0.96 (3H, t, J=7.3 Hz), 1.44 (2H, sext, J=7.9 Hz), 1.73 (2H, quin, J=7.9 Hz), 1.86-1.95 (1H, m), 4.32 (2H, t, J=6.6 Hz), 6.37 (1H, s), 7.15 (1H, dd, J=8.6, 2.0 Hz), 7.29-7.35 (2H, m), 7.89 (1H, d, J=1.3 Hz), 7.93 (1H, d, J=1.3 Hz), 8.20 (1H, d, J=2.0 Hz), 9.84 (1H, s), 10.99 (1H, s).

MS (ESI, m/z): 350 (M+H)$^+$.

Example 145

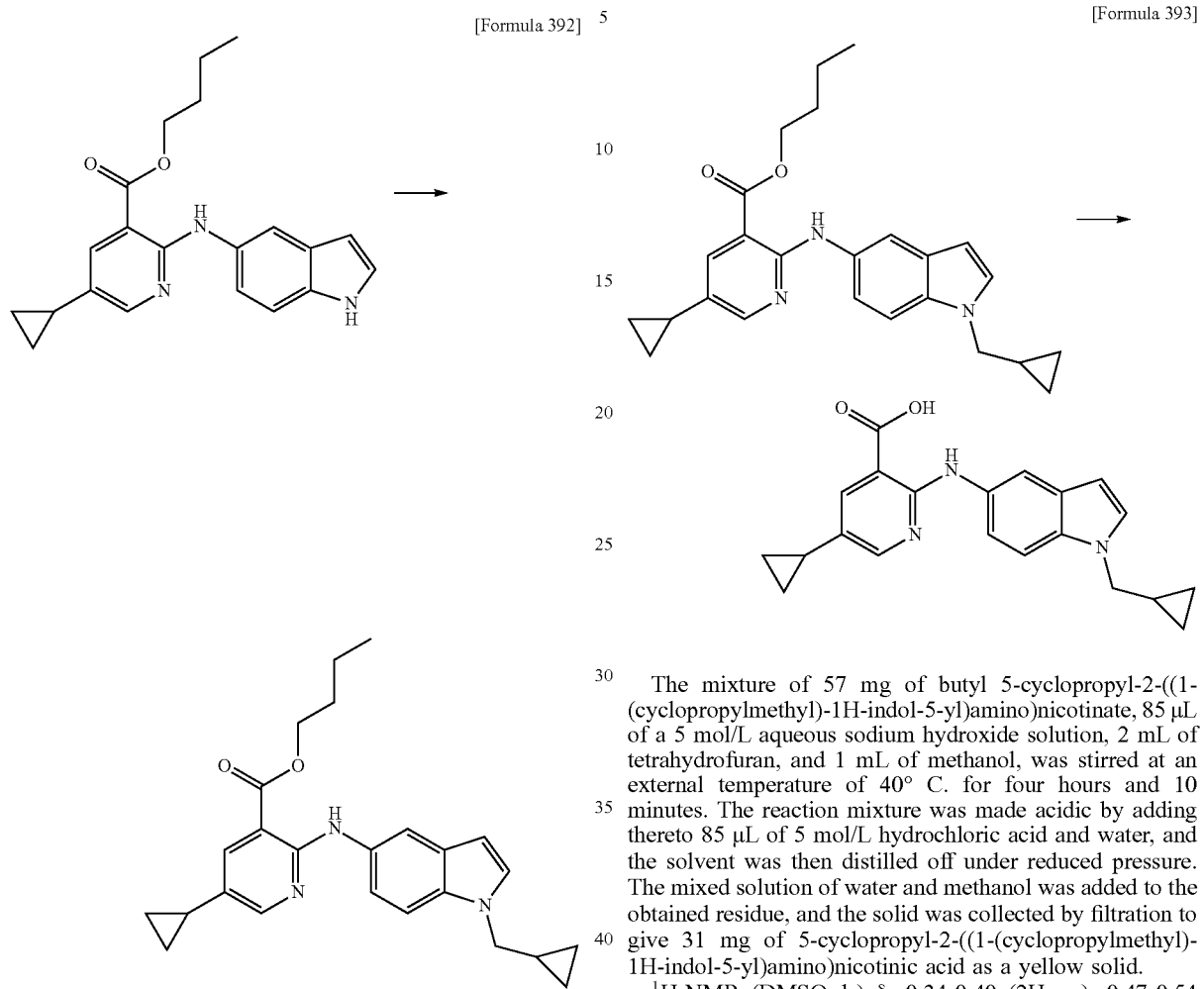

[Formula 392]

The mixture of 60 mg of butyl 2-((1H-indol-5-yl)amino)-5-cyclopropylnicotinate, 29 mg of potassium tert-butoxide, 50 μL of (bromomethyl)cyclopropane, and 1 mL of N,N-dimethylacetamide, was stirred for one hour and 20 minutes under ice-cooling. Ethyl acetate and water were added to the reaction mixture. The organic layer was separated, washed with a saturated aqueous sodium chloride solution and dried over anhydrous sodium sulfate, and the solvent was distilled off under reduced pressure. The obtained residue was purified by silica gel column chromatography (gradient elution with hexane:ethyl acetate=100:0-80:20) to give 58 mg of butyl 5-cyclopropyl-2-((1-(cyclopropylmethyl)-1H-indol-5-yl)amino)nicotinate as a yellow oil.

¹H-NMR (DMSO-d₆) δ: 0.35-0.42 (2H, m), 0.46-0.57 (2H, m), 0.61-0.67 (2H, m), 0.88-0.95 (2H, m), 0.96 (3H, t, J=7.3 Hz), 1.19-1.30 (1H, m), 1.40-1.51 (2H, m), 1.74 (2H, quin, J=7.3 Hz), 1.88-1.96 (1H, m), 4.01 (2H, d, J=7.3 Hz), 4.32 (2H, t, J=6.6 Hz), 6.37 (1H, d, J=3.3 Hz), 7.19 (1H, dd, J=8.6, 2.0 Hz), 7.39 (1H, d, J=2.6 Hz), 7.44 (1H, d, J=8.6 Hz), 7.90 (1H, d, J=2.6 Hz), 7.93 (1H, d, J=2.0 Hz), 8.20 (1H, d, J=2.6 Hz), 9.84 (1H, s).

MS (ESI, m/z): 404 (M+H)⁺.

Example 146

[Formula 393]

The mixture of 57 mg of butyl 5-cyclopropyl-2-((1-(cyclopropylmethyl)-1H-indol-5-yl)amino)nicotinate, 85 μL of a 5 mol/L aqueous sodium hydroxide solution, 2 mL of tetrahydrofuran, and 1 mL of methanol, was stirred at an external temperature of 40° C. for four hours and 10 minutes. The reaction mixture was made acidic by adding thereto 85 μL of 5 mol/L hydrochloric acid and water, and the solvent was then distilled off under reduced pressure. The mixed solution of water and methanol was added to the obtained residue, and the solid was collected by filtration to give 31 mg of 5-cyclopropyl-2-((1-(cyclopropylmethyl)-1H-indol-5-yl)amino)nicotinic acid as a yellow solid.

¹H-NMR (DMSO-d₆) δ: 0.34-0.40 (2H, m), 0.47-0.54 (2H, m), 0.57-0.63 (2H, m), 0.84-0.92 (2H, m), 1.20-1.28 (1H, m), 1.81-1.91 (1H, m), 4.00 (2H, d, J=7.3 Hz), 6.34 (1H, d, J=2.6 Hz), 7.18 (1H, dd, J=8.6, 2.0 Hz), 7.35 (1H, d, J=3.3 Hz), 7.39 (1H, d, J=8.6 Hz), 7.83 (1H, d, J=2.6 Hz), 8.03-8.07 (2H, m), 11.32 (1H, brs).

MS (ESI, m/z): 348 (M+H)⁺, 346 (M−H)⁻.

Example 147

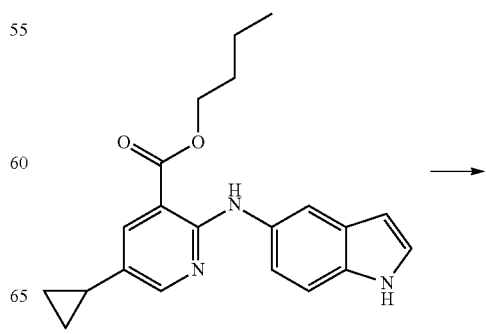

[Formula 394]

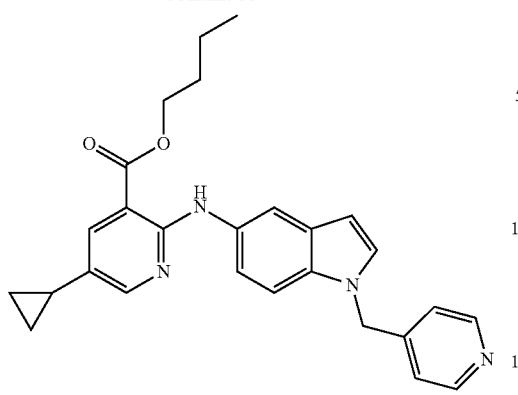

The mixture of 60 mg of butyl 2-((1H-indol-5-yl)amino)-5-cyclopropylnicotinate, 52 mg of potassium tert-butoxide, 52 mg of (4-bromomethyl)pyridine hydrobromide, and 1 mL of N,N-dimethylacetamide, was stirred for one hour and 40 minutes under ice-cooling. Ethyl acetate and water were added to the reaction mixture. The organic layer was separated, washed with a saturated aqueous sodium chloride solution and dried over anhydrous sodium sulfate, and the solvent was distilled off under reduced pressure. The obtained residue was purified by silica gel column chromatography (gradient elution with ethyl acetate:methanol=100:0-95:5) to give 48 mg of butyl 5-cyclopropyl-2-((1-(pyridin-4-ylmethyl)-1H-indol-5-yl)amino)nicotinate as a yellow oil.

$^1$H-NMR (DMSO-$d_6$) δ: 0.60-0.67 (2H, m), 0.88-0.94 (2H, m), 0.95 (3H, t, J=7.3 Hz), 1.43 (2H, sext, J=7.3 Hz), 1.72 (2H, quin, 6.6 Hz), 1.88-1.96 (1H, m), 4.31 (2H, t, J=6.6 Hz), 5.48 (2H, s), 6.48 (1H, d, J=3.3 Hz), 7.07 (2H, d, J=5.9 Hz), 7.16 (1H, dd, J=8.9, 1.7 Hz), 7.31 (1H, d, J=8.6 Hz), 7.50 (1H, d, J=3.3 Hz), 7.89 (1H, d, J=2.6 Hz), 7.99 (1H, d, J=2.0 Hz), 8.19 (1H, d, J=2.6 Hz), 8.46-8.50 (2H, m), 9.84 (1H, s).

MS (ESI, m/z): 441 (M+H)$^+$.

Example 148

[Formula 395]

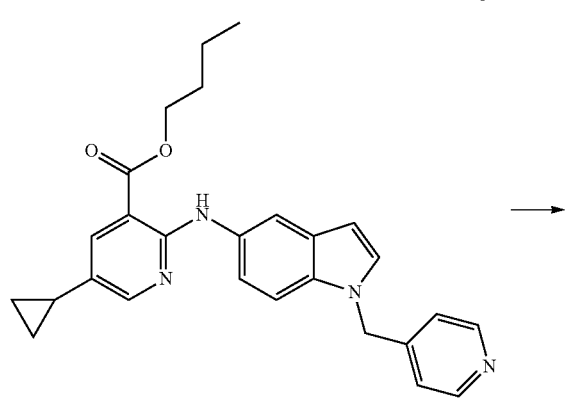

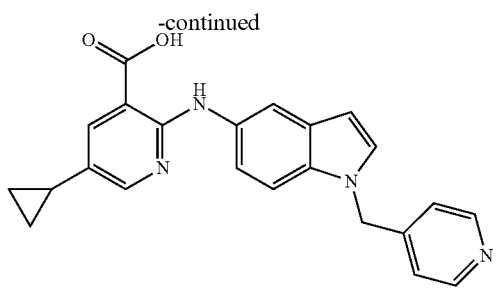

By the method similar to that of Example 116, 5-cyclopropyl-2-((1-(pyridin-4-ylmethyl)-1H-indol-5-yl)amino)nicotinic acid was obtained from butyl 5-cyclopropyl-2-((1-(pyridin-4-ylmethyl)-1H-indol-5-yl)amino)nicotinate.

$^1$H-NMR (DMSO-$d_6$) δ: 0.61-0.67 (2H, m), 0.85-0.94 (2H, m), 1.85-1.95 (1H, m), 5.48 (2H, s), 6.48 (1H, d, J=3.3 Hz), 7.07 (2H, d, J=5.9 Hz), 7.16 (1H, dd, J=8.9, 1.7 Hz), 7.30 (1H, d, J=8.6 Hz), 7.49 (1H, d, J=3.3 Hz), 7.86 (1H, d, J=2.6 Hz), 8.00 (1H, d, J=2.0 Hz), 8.18 (1H, d, J=2.6 Hz), 8.48 (2H, d, J=5.9 Hz), 10.11 (1H, s).

MS (ESI, m/z): 385 (M+H)$^+$, 383 (M−H)$^−$.

Example 149

[Formula 396]

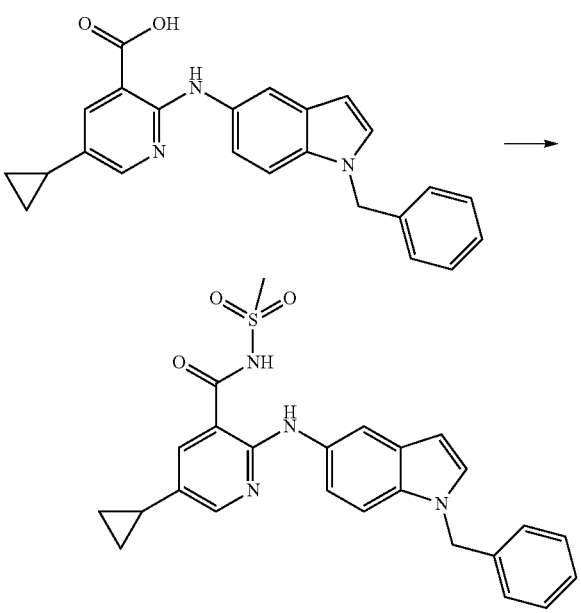

To 5 mL of the solution of 300 mg of 2-((1-benzyl-1H-indol-5-yl)amino)-5-cyclopropylnicotinic acid in tetrahydrofuran, 165 mg of 1,1'-carbonyldiimidazole was added under ice-cooling, and the resultant was stirred for one hour and 10 minutes. 224 mg of methanesulfonamide and 350 μL of 1,8-diazabicyclo[5.4.0]undec-7-ene were added thereto, and the resultant was then heated at reflux for four hours and 30 minutes. The reaction mixture was cooled to room temperature, and ethyl acetate and water were then added thereto, and the resultant was adjusted to pH 2 with 5 mol/L hydrochloric acid. The organic layer was separated, washed with a saturated aqueous sodium chloride solution and dried over anhydrous sodium sulfate, and the solvent was distilled off under reduced pressure. Ethyl acetate was added to the obtained residue, and the solid was collected by filtration to give 107 mg of 2-((1-benzyl-1H-indol-5-yl)amino)-5-cyclopropyl-N-(methylsulfonyl)nicotinamide as a yellow solid.

$^1$H-NMR (DMSO-d$_6$) δ: 0.67-0.73 (2H, m), 0.91-0.98 (2H, m), 1.87-1.98 (1H, m), 3.22 (3H, s), 5.41 (2H, s), 6.51 (1H, d, J=3.3 Hz), 7.14 (1H, dd, J=8.6, 2.0 Hz), 7.22-7.36 (5H, m), 7.46 (1H, d, J=8.6 Hz), 7.53 (1H, d, J=2.6 Hz), 7.81 (1H, d, J=2.0 Hz), 7.98 (2H, s).

MS (ESI, m/z): 459 (M−H)$^−$.

Example 150

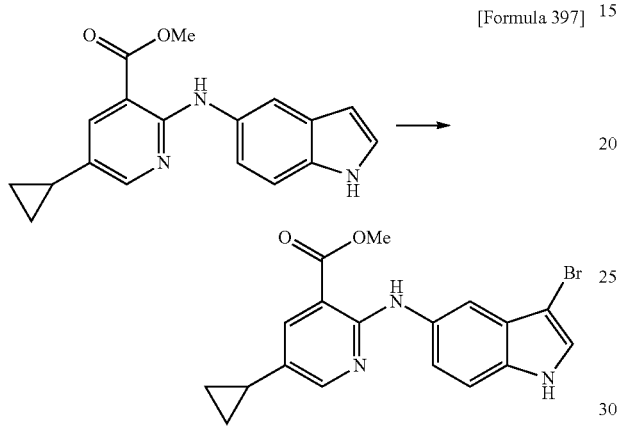

[Formula 397]

To 3 mL of the solution of 100 mg of methyl 2-((1H-indol-5-yl)amino)-5-cyclopropylnicotinate in tetrahydrofuran, 64 mg of N-bromosuccinimide was added under ice-cooling, and the resultant was stirred for 25 minutes. Ethyl acetate and water were added to the reaction mixture. The organic layer was separated, washed with a saturated aqueous sodium chloride solution and dried over anhydrous sodium sulfate, and the solvent was distilled off under reduced pressure. Hexane and diisopropyl ether were added to the obtained residue, and the solid was collected by filtration to give 87 mg of methyl 2-((3-bromo-1H-indol-5-yl)amino)-5-cyclopropylnicotinate as an orange solid.

MS (ESI, m/z): 386 (M+H)$^+$, 384 (M−H)$^−$.

Example 151

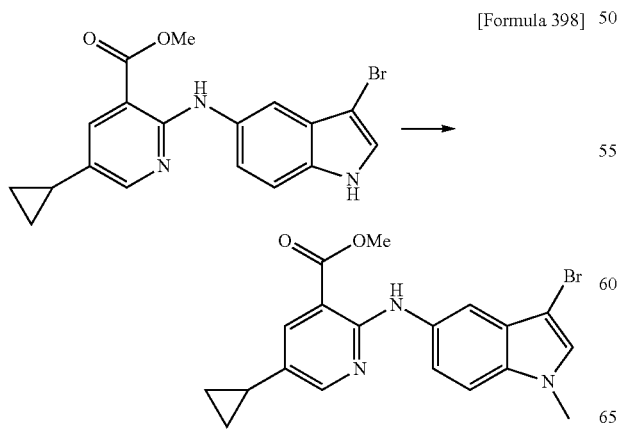

[Formula 398]

To the solution of 600 mg of methyl 2-((3-bromo-1H-indol-5-yl)amino)-5-cyclopropylnicotinate in 7 mL of N,N-dimethylacetamide, 236 mg of potassium tert-butoxide and 290 μL of iodomethane were added under ice-cooling, and the resultant was stirred for one hour. 96 mg of potassium tert-butoxide was added thereto under ice-cooling, and the resultant was stirred for one hour and 35 minutes. 96 mg of potassium tert-butoxide was added thereto under ice-cooling, and the resultant was stirred for one hour and 25 minutes. Ethyl acetate and water were added to the reaction mixture. The organic layer was separated, washed with a saturated aqueous sodium chloride solution and dried over anhydrous sodium sulfate, and the solvent was distilled off under reduced pressure. Methanol was added to the obtained residue, and the solid was collected by filtration to give 432 mg of methyl 2-((3-bromo-1-methyl-1H-indol-5-yl)amino)-5-cyclopropylnicotinate as a yellow solid.

$^1$H-NMR (DMSO-d$_6$) δ: 0.65-0.71 (2H, m), 0.89-0.95 (2H, m), 1.88-1.98 (1H, m), 3.78 (3H, s), 3.90 (3H, s), 7.29 (1H, dd, J=9.2, 2.0 Hz), 7.45 (1H, d, J=9.2 Hz), 7.52 (1H, s), 7.90-7.93 (2H, m), 8.26 (1H, d, J=2.6 Hz), 9.95 (1H, s).

MS (ESI, m/z): 400 (M+H)$^+$.

Example 152

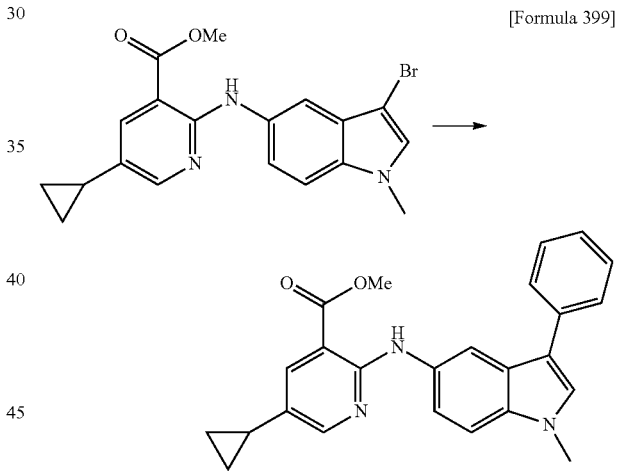

[Formula 399]

The mixture of 80 mg of methyl 2-((3-bromo-1-methyl-1H-indol-5-yl)amino)-5-cyclopropylnicotinate, 49 mg of phenylboronic acid, 7 mg of bis(di-tert-butyl(4-dimethylaminophenyl)phosphine)dichloropalladium(II), 55 mg of potassium carbonate, 1 mL of toluene, and 100 μL of water, was stirred at an external temperature of 110° C. for two hours under a nitrogen atmosphere. Ethyl acetate and water were added to the reaction mixture. The organic layer was separated, washed with a saturated aqueous sodium chloride solution and dried over anhydrous sodium sulfate, and the solvent was distilled off under reduced pressure. The obtained residue was purified by silica gel column chromatography (gradient elution with hexane:ethyl acetate=100:0-70:30). Methanol was added to the thus obtained residue, and the solid was collected by filtration to give 50 mg of methyl 5-cyclopropyl-2-((1-methyl-3-phenyl-1H-indol-5-yl)amino)nicotinate as a yellow solid.

MS (ESI, m/z): 398 (M+H)$^+$.

Example 153

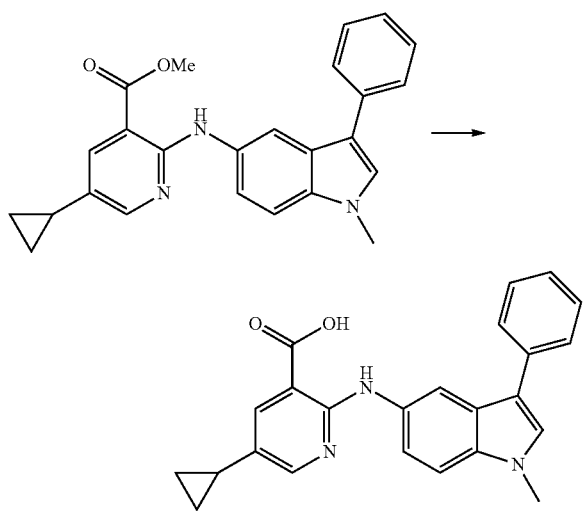

[Formula 400]

The mixture of 50 mg of methyl 5-cyclopropyl-2-(1-methyl-3-phenyl-1H-indol-5-yl)amino)nicotinate, 60 μL of a 5 mol/L aqueous sodium hydroxide solution, 2 mL of tetrahydrofuran, and 1 mL of methanol, was stirred at an external temperature of 50° C. for four hours and 30 minutes. The solvent was distilled off under reduced pressure, and 60 μL of 5 mol/L hydrochloric acid, water and methanol were added to the obtained residue, and the solid was collected by filtration to give 50 mg of 5-cyclopropyl-2-(1-methyl-3-phenyl-1H-indol-5-yl)amino)nicotinic acid as a yellow solid.

$^1$H-NMR (DMSO-$d_6$) δ: 0.62-0.68 (2H, m), 0.88-0.94 (2H, m), 1.88-1.96 (1H, m), 3.81 (3H, s), 7.20-7.26 (1H, m), 7.33 (1H, dd, J=8.6, 2.0 Hz), 7.40-7.48 (3H, m), 7.64-7.68 (3H, m), 7.92 (1H, d, J=2.6 Hz), 8.14 (1H, d, J=2.6 Hz), 8.24 (1H, d, J=1.3 Hz), 10.21 (1H, s).

MS (ESI, m/z): 384 (M+H)$^+$, 382 (M−H)$^-$.

Example 154

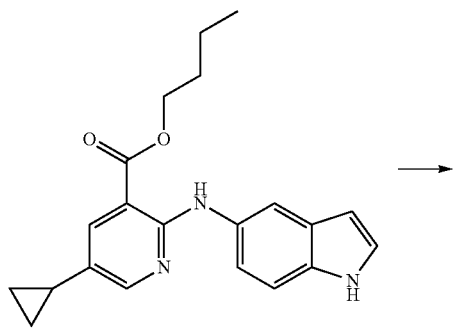

[Formula 401]

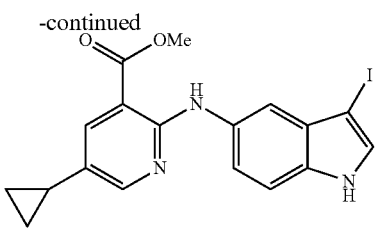

The mixture of 200 mg of butyl 2-((1H-indol-5-yl)amino)-5-cyclopropylnicotinate, 160 mg of iodine, 46 mg of sodium hydroxide, and 5 mL of methanol, was stirred for two hours and 20 minutes under ice-cooling. The solvent was distilled off under reduced pressure, and the reaction mixture was then adjusted to be neutral by adding thereto 1 mol/L hydrochloric acid and water, followed by addition of ethyl acetate and water. The organic layer was separated, sequentially washed with a saturated aqueous sodium bisulfite solution, water and a saturated aqueous sodium chloride solution and dried over anhydrous sodium sulfate, and the solvent was distilled off under reduced pressure. Ethyl acetate and methanol were added to the obtained residue, and the solid was collected by filtration to give 55 mg of methyl 5-cyclopropyl-2-((3-iodo-1H-indol-5-yl)amino)nicotinate as a brown solid.

$^1$H-NMR (DMSO-$d_6$) δ: 0.64-0.70 (2H, m), 0.88-0.98 (2H, m), 1.88-1.97 (1H, m), 3.90 (3H, s), 7.26 (1H, dd, J=8.6, 2.0 Hz), 7.37 (1H, d, J=8.6 Hz), 7.52 (1H, d, J=2.6 Hz), 7.70 (1H, d, J=2.6 Hz), 7.90 (1H, d, J=2.6 Hz), 8.24 (1H, d, J=2.6 Hz), 9.90 (1H, s), 11.45 (1H, s).

MS (ESI, m/z): 434 (M+H)$^+$.

Example 155

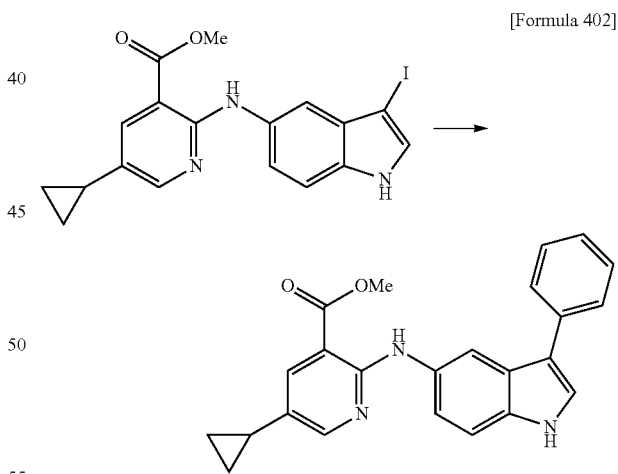

[Formula 402]

The mixture of 50 mg of methyl 5-cyclopropyl-2-((3-iodo-1H-indol-5-yl)amino)nicotinate, 28 mg of phenylboronic acid, 4 mg of bis(di-tert-butyl(4-dimethylaminophenyl)phosphine)dichloropalladium(II), 32 mg of potassium carbonate, 1 mL of toluene, and 100 μL of water, was stirred at 90° C. for two hours and 45 minutes. The reaction mixture was cooled to room temperature, and ethyl acetate and water were then added thereto. The organic layer was separated, washed with a saturated aqueous sodium chloride solution and dried over anhydrous sodium sulfate, and the solvent was distilled off under reduced pressure. The obtained residue was purified by silica gel column chromatography (gradient elution with hexane:ethyl acetate=100:0-50:50) to give 45 mg of methyl 5-cyclopropyl-2-((3-phenyl-1H-indol-5-yl)amino)nicotinate as a colorless oil.

MS (ESI, m/z): 384 (M+H)⁺.

Example 156

[Formula 403]

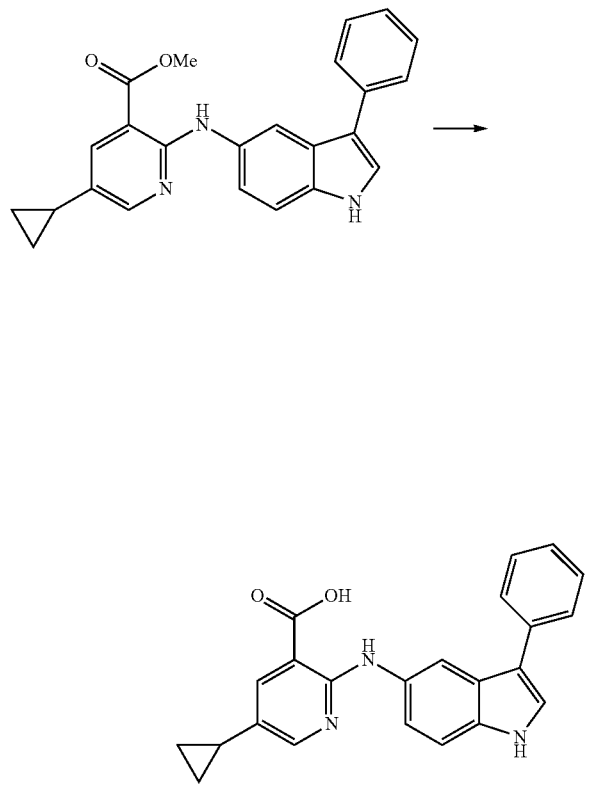

The mixture of 45 mg of methyl 5-cyclopropyl-2-((3-phenyl-1H-indol-5-yl)amino)nicotinate, 70 µL of a 5 mol/L aqueous sodium hydroxide solution, 2 mL of tetrahydrofuran, and 1 mL of methanol, was stirred at an external temperature of 40° C. for three hours and then allowed to stand overnight. The reaction mixture was adjusted to pH 2 by adding thereto 5 mol/L hydrochloric acid and water. The solvent was distilled off under reduced pressure and ethyl acetate and tetrahydrofuran were added to the obtained residue. The solid was collected by filtration and purified by preparative thin-layer chromatography (hexane:ethyl acetate containing 1% acetic acid=25:75), and hexane and ethyl acetate were added to the thus obtained residue, and the solid was collected by filtration to give 6 mg of 5-cyclopropyl-2-((3-phenyl-1H-indol-5-yl)amino)nicotinic acid.

¹H-NMR (DMSO-d₆) δ: 0.54-0.60 (2H, m), 0.82-0.89 (2H, m), 1.78-1.88 (1H, m), 7.18-7.25 (1H, m), 7.28-7.37 (2H, m), 7.40-7.47 (2H, m), 7.58 (1H, d, J=2.6 Hz), 7.68 (2H, d, J=7.3 Hz), 7.80 (1H, d, J=2.0 Hz), 7.94 (1H, d, J=2.6 Hz), 8.33 (1H, s), 11.13 (1H, s), 12.31 (1H, brs).

MS (ESI, m/z): 370 (M+H)⁺, 368 (M−H)⁻.

Example 157

[Formula 404]

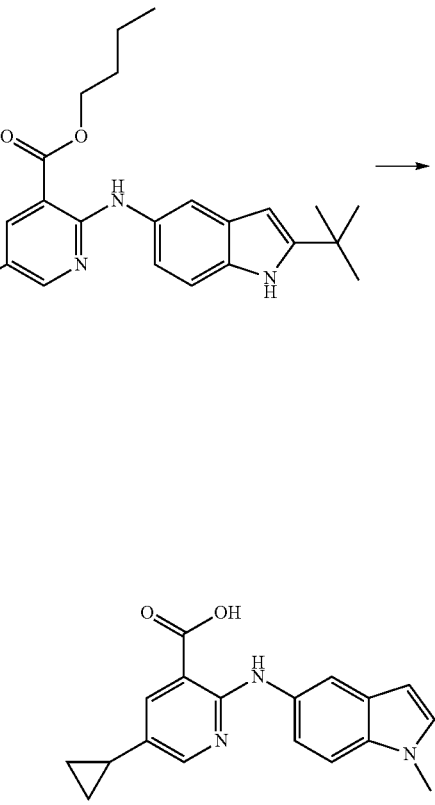

To the solution of 89 mg of butyl 2-((2-(tert-butyl)-1H-indol-5-yl)amino)-5-cyclopropylnicotinate in 1 mL of N,N-dimethylacetamide, 33 mg of potassium tert-butoxide and 14 µL of iodomethane were added under ice-cooling, and the resultant was stirred for two hours and 35 minutes. 66 mg of potassium tert-butoxide, 5 µL of iodomethane and 1 mL of N,N-dimethylacetamide were added thereto under ice-cooling, and the resultant was stirred for 30 minutes and then allowed to stand overnight. 33 mg of potassium tert-butoxide and 5 µL of iodomethane were added thereto under ice-cooling, and the resultant was stirred for 20 minutes, and ethyl acetate, water and 5 mol/L hydrochloric acid were then added to the reaction mixture. The organic layer was separated, washed with a saturated aqueous sodium chloride solution and dried over anhydrous sodium sulfate, and the solvent was distilled off under reduced pressure. The obtained residue was purified by silica gel column chromatography (hexane:ethyl acetate), and hexane and ethyl acetate were added to the thus obtained residue, and the solid was collected by filtration to give 42 mg of 2-((2-(tert-butyl)-1-methyl-1H-indol-5-yl)amino)-5-cyclopropylnicotinic acid as a yellow solid.

¹H-NMR (DMSO-d₆) δ: 0.60-0.68 (2H, m), 0.86-0.94 (2H, m), 1.42 (9H, s), 1.84-1.95 (1H, m), 3.85 (3H, s), 6.19 (1H, s), 7.17 (1H, dd, J=8.6, 2.0 Hz), 7.31 (1H, d, J=8.6 Hz), 7.84 (1H, d, J=1.8 Hz), 7.86 (1H, d, J=2.1 Hz), 8.17 (1H, d, J=2.6 Hz), 10.14 (1H, s).

MS (ESI, m/z): 364 (M+H)⁺, 362 (M−H)⁻.

Example 158

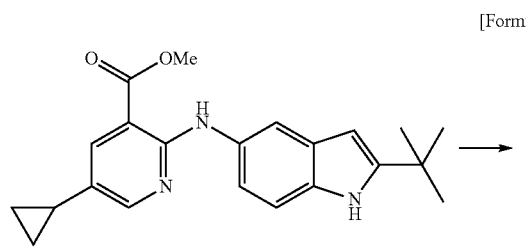

[Formula 405]

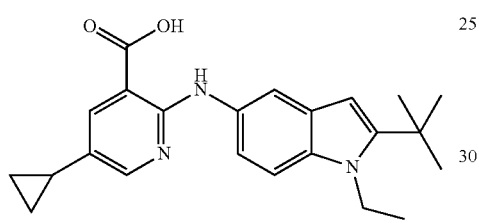

To the solution of 90 mg of methyl 2-((2-(tert-butyl)-1H-indol-5-yl)amino)-5-cyclopropylnicotinate in 1 mL of N,N-dimethylacetamide, 31 mg of potassium tert-butoxide and 22 µL of iodoethane were added under ice-cooling, and the resultant was stirred for two hours and 20 minutes. 62 mg of potassium tert-butoxide was added thereto, and the resultant was stirred for four hours and 40 minutes and then allowed to stand overnight. 31 mg of potassium tert-butoxide and 5 µL of iodoethane were added thereto under ice-cooling, and the resultant was stirred for three hours and 40 minutes. 31 mg of potassium tert-butoxide and 10 µL of iodoethane were added thereto under ice-cooling, and the resultant was stirred for three hours and 30 minutes and allowed to stand overnight. The reaction mixture was adjusted to pH 2 by adding thereto ethyl acetate, water and 5 mol/L hydrochloric acid. The organic layer was separated, washed with a saturated aqueous sodium chloride solution and dried over anhydrous sodium sulfate, and the solvent was distilled off under reduced pressure. The obtained residue was purified by silica gel column chromatography (gradient elution with hexane: ethyl acetate=100:0-50:50), and hexane and ethyl acetate were added to the thus obtained residue, and the solid was collected by filtration to give 25 mg of 2-((2-(tert-butyl)-1-ethyl-1H-indol-5-yl)amino)-5-cyclopropylnicotinic acid as a yellow solid.

$^1$H-NMR (DMSO-d$_6$) δ: 0.61-0.66 (2H, m), 0.85-0.96 (2H, m), 1.32 (3H, t, J=6.9 Hz), 1.48 (9H, s), 1.85-1.95 (1H, m), 4.35 (2H, q, J=6.8 Hz), 6.14 (1H, s), 7.17 (1H, dd, J=8.6, 2.0 Hz), 7.28 (1H, d, J=8.4 Hz), 7.82 (1H, d, J=2.1 Hz), 7.86 (1H, d, J=2.7 Hz), 8.17 (1H, d, J=2.6 Hz), 10.10 (1H, s).

MS (ESI, m/z): 378 (M+H)$^+$, 376 (M−H)$^−$.

Example 159

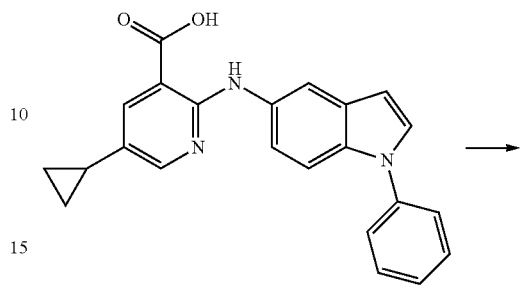

[Formula 406]

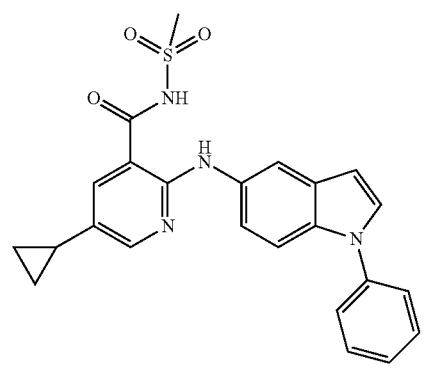

To 1 mL of the solution of 150 mg of 5-cyclopropyl-2-((1-phenyl-1H-indol-5-yl)amino)nicotinic acid in tetrahydrofuran, 132 mg of 1,1'-carbonyldiimidazole was added under ice-cooling, and the resultant was stirred at the same temperature for one hour and 40 minutes. 193 mg of methanesulfonamide and 303 µL of 1,8-diazabicyclo[5.4.0]undec-7-ene were added thereto, and the resultant was heated at reflux for one hour and 30 minutes. The reaction mixture was allowed to stand overnight, and ethyl acetate and water were added thereto, followed by addition of 800 µL of 5 mol/L hydrochloric acid. The organic layer was separated, washed with a saturated aqueous sodium chloride solution and dried over anhydrous sodium sulfate, and the solvent was distilled off under reduced pressure. The obtained residue was purified by silica gel column chromatography (gradient elution with ethyl acetate:methanol=100:0-90:10). Water and methanol were added to the thus obtained residue, and the solid was collected by filtration to give 29 mg of 5-cyclopropyl-N-(methylsulfonyl)-2-((1-phenyl-1H-indol-5-yl)amino)nicotinamide as a yellow solid.

$^1$H-NMR (DMSO-d$_6$) δ: 0.63-0.70 (2H, m), 0.87-0.95 (2H, m), 1.83-1.94 (1H, m), 3.12 (3H, s), 6.65 (1H, d, J=3.3 Hz), 7.26 (1H, dd, J=8.6, 2.0 Hz), 7.35-7.42 (1H, m), 7.49-7.63 (6H, m), 7.93 (1H, d, J=2.0 Hz), 8.13 (1H, d, J=2.0 Hz), 8.18 (1H, d, J=2.0 Hz).

MS (ESI, m/z): 447 (M+H)$^+$, 445 (M−H)$^−$.

Example 160

[Formula 407]

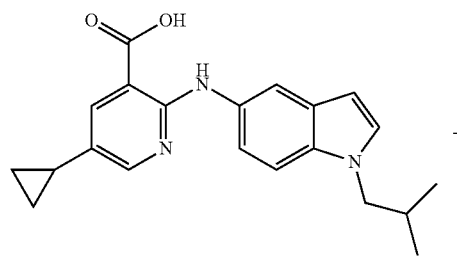

→

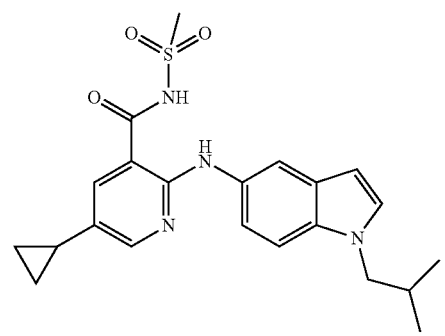

By the method similar to that of Example 149, 5-cyclopropyl-2-((1-isobutyl-1H-indol-5-yl)amino)-N-(methylsulfonyl)nicotinamide was obtained from 5-cyclopropyl-2-((1-isobutyl-1H-indol-5-yl)amino)nicotinic acid.

$^1$H-NMR (DMSO-d$_6$) δ: 0.71-0.78 (2H, m), 0.85 (6H, d, J=6.6 Hz), 0.88-0.95 (2H, m), 1.84-1.95 (1H, m), 2.05-2.22 (1H, m), 3.96 (2H, d, J=7.3 Hz), 6.39 (1H, d, J=2.6 Hz), 7.16 (1H, dd, J=9.2, 2.0 Hz), 7.34 (1H, d, J=2.6 Hz), 7.44 (1H, d, J=8.6 Hz), 7.83-7.92 (2H, m), 8.09-8.21 (1H, m).

MS (ESI, m/z): 427 (M+H)$^+$, 425 (M−H)$^-$.

Example 161

-continued

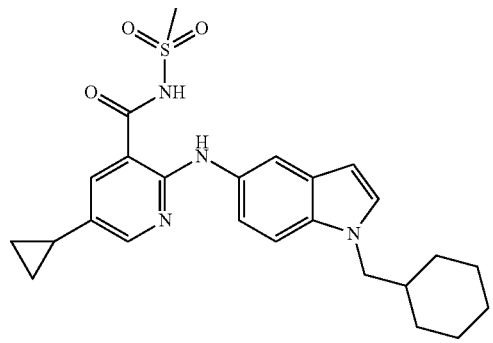

To 5 mL of the solution of 205 mg of 2-((1-cyclohexylmethyl)-1H-indol-5-yl)amino)-5-cyclopropylnicotinic acid in tetrahydrofuran, 256 mg of 1, 1'-carbonyldiimidazole was added under ice-cooling, and the resultant was stirred for 50 minutes and then stirred at room temperature for two hours and 30 minutes. 301 mg of methanesulfonamide and 469 μL of 1,8-diazabicyclo[5.4.0]undec-7-ene were added thereto, and the resultant was stirred at room temperature for 30 minutes and then allowed to stand overnight. The reaction mixture was adjusted to pH 2 by adding thereto 5 mol/L hydrochloric acid and water, followed by addition of ethyl acetate and water. The organic layer was separated, washed with a saturated aqueous sodium chloride solution and dried over anhydrous sodium sulfate, and the solvent was distilled off under reduced pressure. Water and methanol were added to the obtained residue, and the solid was collected by filtration to give 211 mg of 2-((1-(cyclohexylmethyl)-1H-indol-5-yl)amino)-5-cyclopropyl-N-(methylsulfonyl)nicotinamide as a yellow solid.

$^1$H-NMR (DMSO-d$_6$) δ: 0.67-0.74 (2H, m), 0.92-1.19 (7H, m), 1.45-1.73 (5H, m), 1.73-1.84 (1H, m), 1.89-1.99 (1H, m), 3.17 (3H, s), 4.02 (2H, d, J=6.6 Hz), 6.47 (1H, d, J=3.3 Hz), 7.14 (1H, dd, J=8.6, 2.0 Hz), 7.36 (1H, d, J=3.3 Hz), 7.52 (1H, d, J=8.6 Hz), 7.73 (1H, s), 7.89 (1H, s), 8.09 (1H, s).

MS (ESI, m/z): 467 (M+H)$^+$, 465 (M−H)$^-$.

Example 162

[Formula 408]

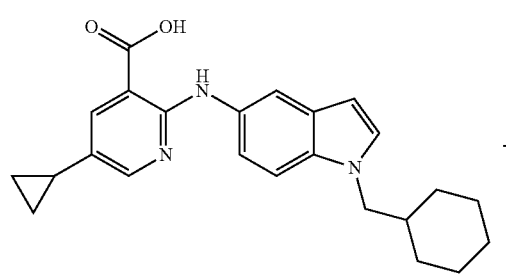

→

[Formula 409]

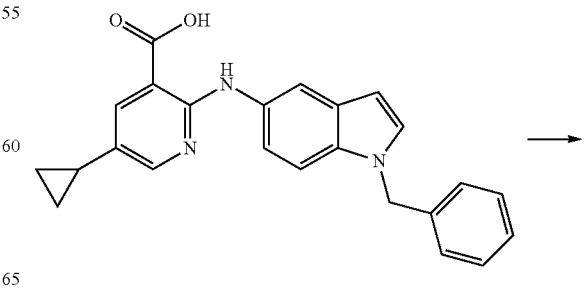

→

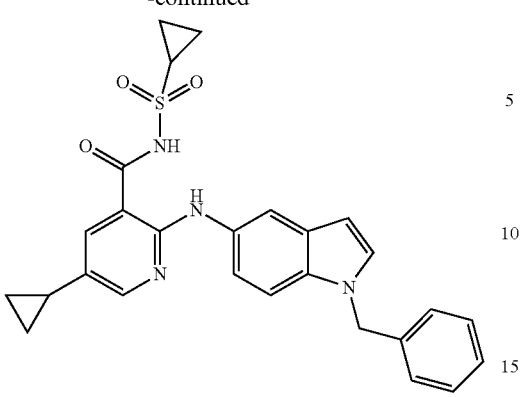

To the solution of 80 mg of 2-((1-benzyl-1H-indol-5-yl)amino)-5-cyclopropylnicotinic acid in 3 mL of tetrahydrofuran, 68 mg of 1,1'-carbonyldiimidazole was added, and the resultant was stirred at room temperature for three hours and 35 minutes. 101 mg of cyclopropanesulfonamide and 125 μL of 1,8-diazabicyclo[5.4.0]undec-7-ene were added thereto, and the resultant was stirred for five minutes and then allowed to stand overnight. The reaction mixture was adjusted to pH 3 by adding 5 mol/L hydrochloric acid and water, followed by addition of ethyl acetate and water. The organic layer was separated, washed with a saturated aqueous sodium chloride solution and dried over anhydrous sodium sulfate, and the solvent was distilled off under reduced pressure. The obtained residue was purified by silica gel column chromatography (gradient elution with hexane:ethyl acetate=100:0-20:80). Water and methanol were added to the thus obtained residue, and the solid was collected by filtration to give 51 mg of 2-((1-benzyl-1H-indol-5-yl)amino)-5-cyclopropyl-N-(cyclopropylsulfonyl)nicotinamide.

$^1$H-NMR (DMSO-$d_6$) δ: 0.67-0.76 (2H, m), 0.90 (2H, m), 0.95-1.19 (4H, m), 1.83-1.94 (1H, m), 3.10-3.20 (1H, m), 5.40 (2H, s), 6.44 (1H, d, J=2.6 Hz), 7.14 (1H, dd, J=8.9, 1.7 Hz), 7.17-7.42 (6H, m), 7.48 (1H, d, J=2.6 Hz), 7.80-7.94 (2H, m), 8.16 (1H, s).

MS (ESI, m/z): 487 (M+H)$^+$, 485 (M−H)$^-$.

Example 163

[Formula 410]

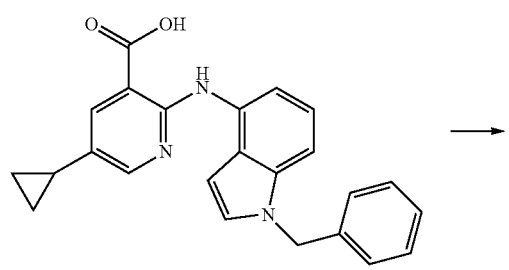

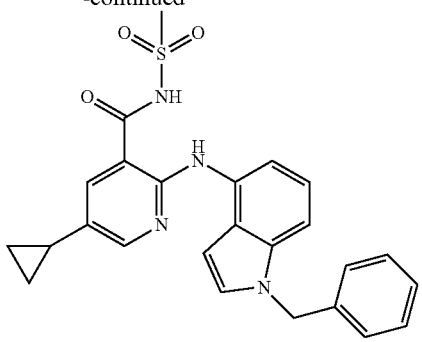

By the method similar to that of Example 149, 2-((1-benzyl-1H-indol-4-yl)amino)-5-cyclopropyl-N-(methylsulfonyl)nicotinamide was obtained from 2-((1-benzyl-1H-indol-4-yl)amino)-5-cyclopropylnicotinic acid.

$^1$H-NMR (DMSO-$d_6$) δ: 0.71-0.77 (2H, m), 0.89-0.97 (2H, m), 1.87-1.96 (1H, m), 3.28 (3H, s), 5.42 (2H, s), 6.75 (1H, m), 7.01-7.08 (2H, m), 7.16-7.33 (5H, m), 7.47 (1H, d, J=3.3 Hz), 7.93 (1H, d, J=2.6 Hz), 8.14 (1H, d, J=6.6 Hz), 8.26 (1H, s)

MS (ESI, m/z): 461 (M+H)$^+$, 459 (M−H)$^-$.

Example 164

[Formula 411]

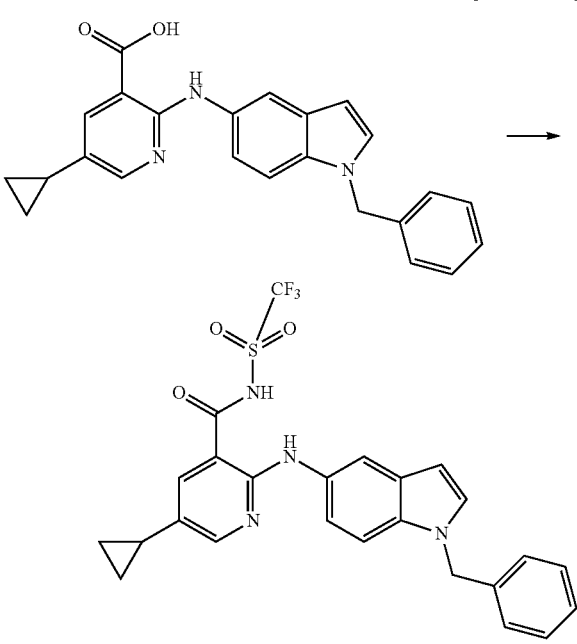

To the solution of 80 mg of 2-((1-benzyl-1H-indol-5-yl)amino)-5-cyclopropylnicotinic acid in 3 mL of tetrahydrofuran, 85 mg of 1,1'-carbonyldiimidazole was added, and the resultant was stirred at room temperature for three hours and 30 minutes. 93 mg of trifluoromethanesulfonamide and 94 μL of 1,8-diazabicyclo[5.4.0]undec-7-ene were added thereto, and the resultant was stirred at room temperature for four hours and 10 minutes and then heated at reflux for two hours and 40 minutes. The reaction mixture was cooled to room temperature and then adjusted to pH 2 by adding

Example 165

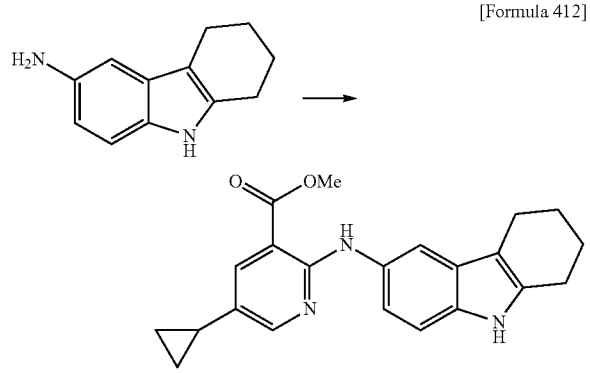

[Formula 412]

The mixture of 500 mg of 2,3,4,9-tetrahydro-1H-carbazol-6-amine, 567 mg of methyl 2-chloro-5-cyclopropylnicotinate, 123 mg of tris(dibenzylideneacetone)dipalladium (0), 155 mg of 4,5'-bis(diphenylphosphino)-9,9'-dimethylxanthene, 2.0 g of cesium carbonate, and 10 mL of amyl acetate, was stirred at an external temperature of 135° C. for three hours under a nitrogen atmosphere. The reaction mixture was cooled to room temperature, and ethyl acetate and water were then added thereto. The organic layer was separated, sequentially washed with water and a saturated aqueous sodium chloride solution and dried over anhydrous sodium sulfate, and the solvent was distilled off under reduced pressure. The obtained residue was purified by silica gel column chromatography (gradient elution with hexane:ethyl acetate=100:0-80:20). Methanol was added to the thus obtained residue, and the solid was collected by filtration to give 550 mg of methyl 5-cyclopropyl-2-((2,3,4,9-tetrahydro-1H-carbazol-6-yl)amino)nicotinate as a yellow solid.

$^1$H-NMR (DMSO-d$_6$) δ: 0.61-0.67 (2H, m), 0.86-0.93 (2H, m), 1.75-1.85 (4H, m), 1.85-1.95 (1H, m), 2.55-2.62 (2H, m), 2.65-2.72 (2H, m), 3.89 (3H, s), 7.13 (1H, dd, J=8.6, 1.3 Hz), 7.18 (1H, d, J=8.6 Hz), 7.60 (1H, d, J=1.3 Hz), 7.87 (1H, d, J=2.6 Hz), 8.19 (1H, d, J=2.0 Hz), 9.79 (1H, s), 10.54 (1H, s).

MS (ESI, m/z): 362 (M+H)$^+$.

thereto 5 mol/L hydrochloric acid and water, followed by addition of ethyl acetate and water. The organic layer was separated, washed with a saturated aqueous sodium chloride solution and dried over anhydrous sodium sulfate, and the solvent was distilled off under reduced pressure. The obtained residue was purified by silica gel column chromatography (gradient elution with hexane:ethyl acetate=100:0-0:100) to give 66 mg of 2-((1-benzyl-1H-indol-5-yl)amino)-5-cyclopropyl-N-((trifluoromethyl)sulfonyl)nicotinamide as a yellow oil.

$^1$H-NMR (DMSO-d$_6$) δ: 0.55-0.61 (2H, m), 0.85-0.93 (2H, m), 1.82-1.90 (1H, m), 5.38 (2H, s), 6.41 (1H, d, J=2.6 Hz), 7.11 (1H, dd, J=8.6, 2.0 Hz), 7.17-7.37 (6H, m), 7.44 (1H, d, J=2.6 Hz), 7.98 (1H, d, J=2.0 Hz), 8.04 (2H, m), 11.02 (1H, s)

MS (ESI, m/z): 515 (M+H)$^+$, 513 (M–H)$^−$.

Example 166

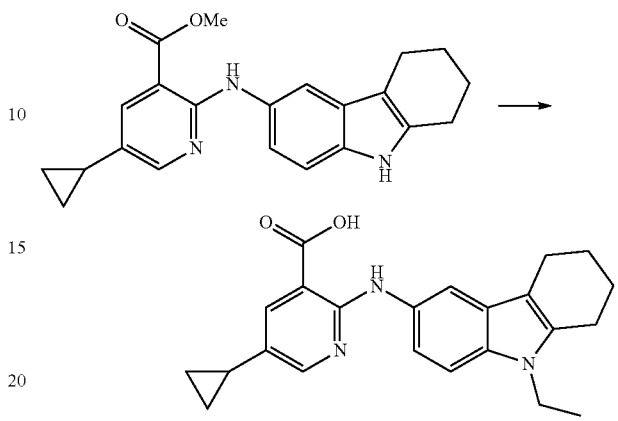

[Formula 413]

By the method similar to that of Example 141, 5-cyclopropyl-2-((9-ethyl-2,3,4,9-tetrahydro-1H-carbazol-6-yl)amino)nicotinic acid was obtained from methyl 5-cyclopropyl-2-((2,3,4,9-tetrahydro-1H-carbazol-6-yl)amino)nicotinate and iodoethane.

$^1$H-NMR (DMSO-d$_6$) δ: 0.61-0.66 (2H, m), 0.86-0.93 (2H, m), 1.21 (3H, t, J=6.9 Hz), 1.73-1.93 (5H, m), 2.56-2.63 (2H, m), 2.67-2.74 (2H, m), 4.06 (2H, q, J=7.0 Hz), 7.19 (1H, dd, J=8.6, 2.0 Hz), 7.29 (1H, d, J=8.6 Hz), 7.64 (1H, d, J=2.0 Hz), 7.86 (1H, d, J=2.6 Hz), 8.16 (1H, d, J=2.0 Hz), 10.11 (1H, s), 13.39 (1H, brs).

MS (ESI, m/z): 376 (M+H)$^+$, 374 (M–H)$^−$.

Example 167

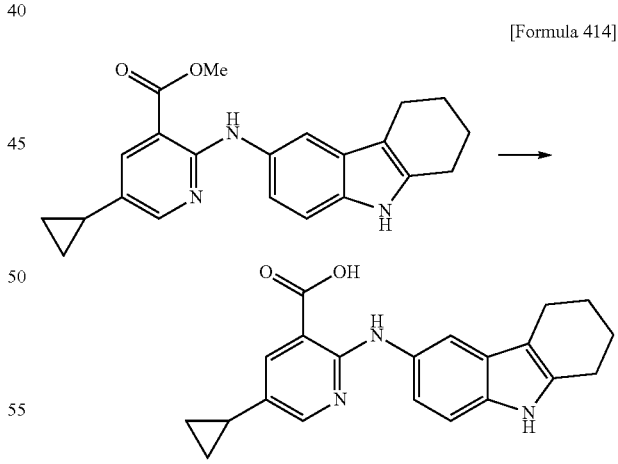

[Formula 414]

By the method similar to that of Example 116, 5-cyclopropyl-2-((2,3,4,9-tetrahydro-1H-carbazol-6-yl)amino)nicotinic acid was obtained from methyl 5-cyclopropyl-2-((2,3,4,9-tetrahydro-1H-carbazol-6-yl)amino)nicotinate.

$^1$H-NMR (DMSO-d$_6$) δ: 0.61-0.67 (2H, m), 0.86-0.93 (2H, m), 1.76-1.93 (5H, m), 2.55-2.63 (2H, m), 2.65-2.72 (2H, m), 7.11-7.18 (2H, m), 7.61 (1H, s), 7.85 (1H, d, J=2.6 Hz), 8.16 (1H, d, J=2.0 Hz), 10.10 (1H, s), 10.51 (1H, s).

MS (ESI, m/z): 348 (M+H)$^+$, 346 (M–H)$^−$.

Example 168

[Formula 415]

By the method similar to that of Example 150, methyl 2-((3-bromo-1-ethyl-1H-indol-5-yl)amino)-5-cyclopropyl-nicotinate was obtained from methyl 5-cyclopropyl-2-((1-ethyl-1H-indol-5-yl)amino)nicotinate.

$^1$H-NMR (DMSO-d$_6$) δ: 0.64-0.71 (2H, m), 0.88-0.95 (2H, m), 1.36 (3H, t, J=7.3 Hz), 1.87-1.97 (1H, m), 3.90 (3H, s), 4.19 (2H, q, J=7.0 Hz), 7.28 (1H, dd, J=8.6, 2.0 Hz), 7.50 (1H, d, J=9.2 Hz), 7.59 (1H, s), 7.92-7.89 (2H, m), 8.26 (1H, d, J=2.6 Hz), 9.94 (1H, s).

MS (ESI, m/z): 414 (M+H)$^+$.

Example 169

[Formula 416]

The mixture of 60 mg of methyl 2-((3-bromo-1-ethyl-1H-indol-5-yl)amino)-5-cyclopropylnicotinate, 25 mg of phenylboronic acid, 4.7 mg of bis(di-tert-butyl(4-dimethylaminophenyl)phosphine)dichloropalladium(II), 46 mg of potassium carbonate, 1 mL of toluene, and 100 μL of water, was heated at reflux for one hour and 50 minutes under a nitrogen atmosphere. Ethyl acetate and water were added to the reaction mixture. The organic layer was separated, washed with a saturated aqueous sodium chloride solution and dried over anhydrous sodium sulfate, and the solvent was distilled off under reduced pressure. The obtained residue was purified by silica gel column chromatography (gradient elution with hexane:ethyl acetate=100:0-80:20) to give 46 mg of methyl 5-cyclopropyl-2-((1-ethyl-3-phenyl-1H-indol-5-yl)amino)nicotinate as a yellow oil.

$^1$H-NMR (DMSO-d$_6$) δ: 0.62-0.68 (2H, m), 0.87-0.94 (2H, m), 1.42 (3H, t, J=6.9 Hz), 1.86-1.96 (1H, m), 3.90 (3H, s), 4.24 (2H, q, J=7.3 Hz), 7.26-7.20 (1H, m), 7.35 (1H, dd, J=8.6, 2.0 Hz), 7.41-7.52 (3H, m), 7.66 (2H, d, J=7.3 Hz), 7.73 (1H, s), 7.89 (1H, d, J=2.6 Hz), 8.21-8.19 (2H, m), 9.87 (1H, s).

MS (ESI, m/z): 412 (M+H)$^+$.

Example 170

[Formula 417]

The mixture of 45 mg of methyl 5-cyclopropyl-2-((1-ethyl-3-phenyl-1H-indol-5-yl)amino)nicotinate, 66 μL of a 5 mol/L aqueous sodium hydroxide solution, and 1 mL of a tetrahydrofuran-methanol mixed solution, was stirred at an external temperature of 50° C. for three hours. The reaction mixture was allowed to stand overnight, and 60 μL of 5 mol/L hydrochloric acid was then added thereto, and the solvent was distilled off under reduced pressure. Water and methanol were added to the obtained residue, and the solid was collected by filtration to give 38 mg of 5-cyclopropyl-2-((1-ethyl-3-phenyl-1H-indol-5-yl)amino)nicotinic acid as a yellow solid.

$^1$H-NMR (DMSO-d$_6$) δ: 0.63-0.69 (2H, m), 0.88-0.95 (2H, m), 1.42 (3H, t, J=6.9 Hz), 1.88-1.98 (1H, m), 4.25 (2H, q, J=7.3 Hz), 7.23 (1H, t, J=7.3 Hz), 7.31 (1H, dd, J=8.6, 2.0 Hz), 7.44 (2H, t, J=7.6 Hz), 7.52 (1H, d, J=8.6 Hz), 7.66 (2H, d, J=7.3 Hz), 7.75 (1H, s), 7.94 (1H, d, J=2.6 Hz), 8.12 (1H, d, J=2.6 Hz), 8.20 (1H, d, J=1.3 Hz), 10.21 (1H, s).

MS (ESI, m/z): 398 (M+H)$^+$, 396 (M−H)$^−$.

Example 171

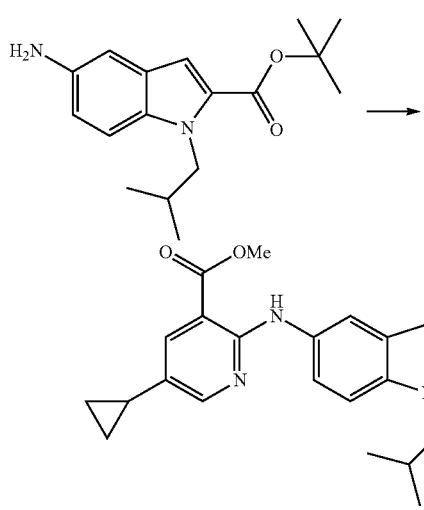

[Formula 418]

By the method similar to that of Example 165, tert-butyl 5-((5-cyclopropyl-3-(methoxycarbonyl)pyridin-2-yl)amino)-1-isobutyl-1H-indole-2-carboxylate was obtained from tert-butyl 5-amino-1-isobutyl-1H-indole-2-carboxylate and methyl 2-chloro-5-cyclopropylnicotinate.

MS (ESI, m/z): 465 (M+H)$^+$.

Example 172

[Formula 419]

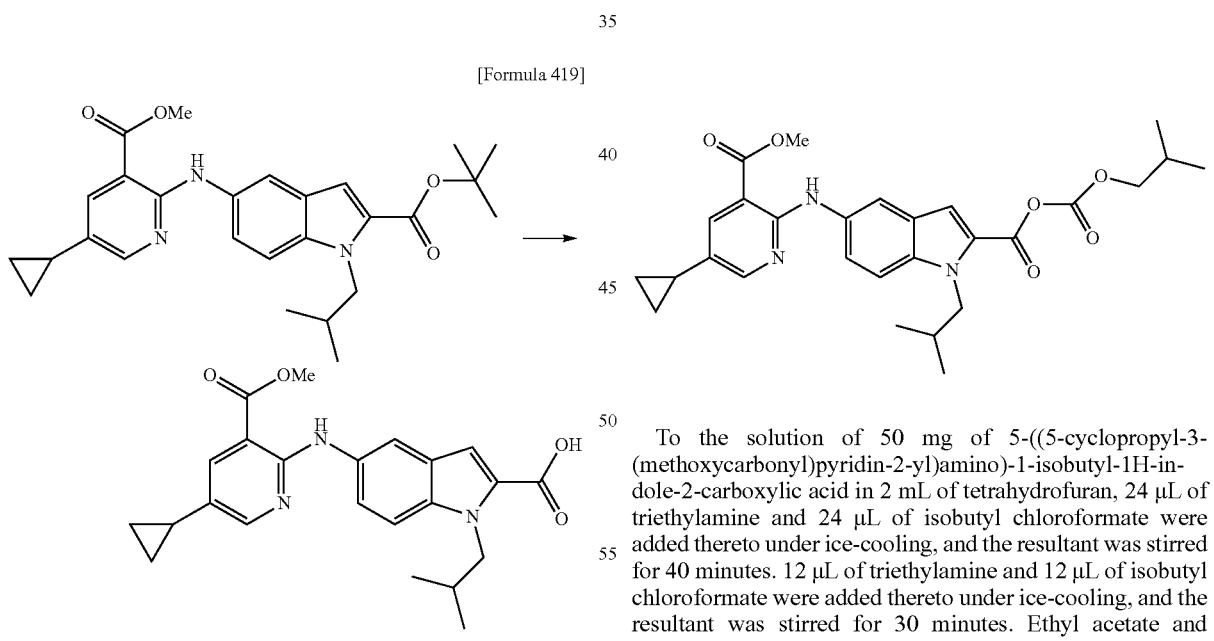

To 20 mL of the solution of 650 mg of tert-butyl 5-((5-cyclopropyl-3-(methoxycarbonyl)pyridin-2-yl)amino)-1-isobutyl-1H-indole-2-carboxylate in 1,2-dichloromethane, 2.08 mL of trifluoroacetic acid was added, and the resultant was heated at reflux for two hours and 30 minutes. The solvent was distilled off from the reaction mixture under reduced pressure. Water and methanol were added to the obtained residue, and the solid was collected by filtration to give 760 mg of 5-((5-cyclopropyl-3-(methoxycarbonyl)pyridin-2-yl)amino)-1-isobutyl-1H-indole-2-carboxylic acid as a yellow solid.

$^1$H-NMR (DMSO-d$_6$) δ: 0.62-0.70 (2H, m), 0.81 (6H, d, J=6.6 Hz), 0.89-0.95 (2H, m), 1.89-1.98 (1H, m), 2.05-2.15 (1H, m), 3.56-4.22 (3H, m), 4.40 (2H, d, J=7.3 Hz), 7.19 (1H, s), 7.38 (1H, dd, J=9.2, 2.0 Hz), 7.56 (1H, d, J=9.2 Hz), 7.93 (1H, d, J=2.6 Hz), 8.07 (1H, d, J=2.0 Hz), 8.22 (1H, d, J=2.6 Hz), 9.91 (1H, s).

MS (ESI, m/z): 408 (M+H)$^+$, 406 (M−H)$^−$.

Example 173

[Formula 420]

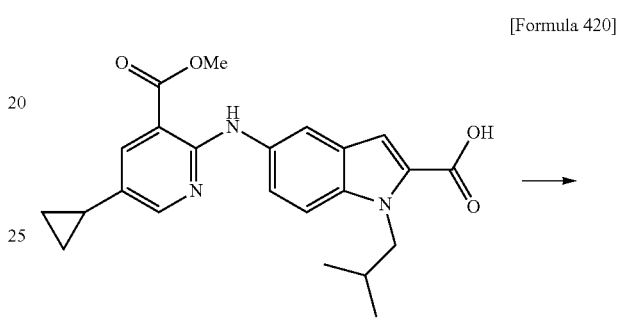

To the solution of 50 mg of 5-((5-cyclopropyl-3-(methoxycarbonyl)pyridin-2-yl)amino)-1-isobutyl-1H-indole-2-carboxylic acid in 2 mL of tetrahydrofuran, 24 μL of triethylamine and 24 μL of isobutyl chloroformate were added thereto under ice-cooling, and the resultant was stirred for 40 minutes. 12 μL of triethylamine and 12 μL of isobutyl chloroformate were added thereto under ice-cooling, and the resultant was stirred for 30 minutes. Ethyl acetate and ice-cold 0.5 mol/L hydrochloric acid were added to the reaction mixture. The organic layer was separated, sequentially washed with water and a saturated aqueous sodium chloride solution and dried over anhydrous sodium sulfate, and the solvent was distilled off under reduced pressure to give (5-((5-cyclopropyl-3-(methoxycarbonyl)pyridin-2-yl)amino)-1-isobutyl-1H-indole-2-carboxylic acid)(isobutoxycarboxylic acid) anhydride as a yellow oil.

MS (ESI, m/z): 509 (M+H)$^+$.

Example 174

[Formula 421]

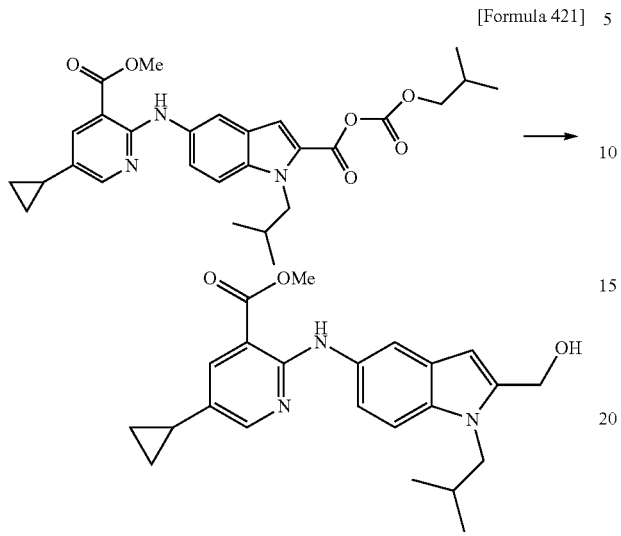

To the solution of (5-((5-cyclopropyl-3-(methoxycarbonyl)pyridin-2-yl)amino)-1-isobutyl-1H-indole-2-carboxylic acid)(isobutoxycarboxylic acid) anhydride obtained in Example 173 in 2 mL of tetrahydrofuran, the solution of 19 mg of sodium borohydride in 200 μL of water was added under ice-cooling, and the resultant was stirred for 55 minutes. The reaction mixture was allowed to stand overnight, and 1 mol/L hydrochloric acid and ethyl acetate were then added thereto. The organic layer was separated, sequentially washed with water and a saturated aqueous sodium chloride solution and dried over anhydrous sodium sulfate, and the solvent was distilled off under reduced pressure. The obtained residue was purified by silica gel column chromatography (gradient elution with hexane:ethyl acetate=100:0-50:50) to give 23 mg of methyl 5-cyclopropyl-2-((2-hydroxymethyl)-1-isobutyl-1H-indol-5-yl)amino)nicotinate as a yellow oil.

$^1$H-NMR (DMSO-$d_6$) δ: 0.61-0.68 (2H, m), 0.86 (6H, d, J=6.6 Hz), 0.88-0.95 (2H, m), 1.86-1.96 (1H, m), 2.14-2.25 (1H, m), 3.89 (3H, s), 3.99 (2H, d, J=7.9 Hz), 4.62 (2H, d, J=5.3 Hz), 5.22 (1H, t, J=5.6 Hz), 6.32 (1H, s), 7.17 (1H, dd, J=8.6, 2.0 Hz), 7.36 (1H, d, J=8.6 Hz), 7.87 (1H, d, J=2.0 Hz), 7.88 (1H, d, J=2.6 Hz), 8.22 (1H, d, J=2.6 Hz), 9.82 (1H, s).

MS (ESI, m/z): 394 (M+H)$^+$.

Example 175

[Formula 422]

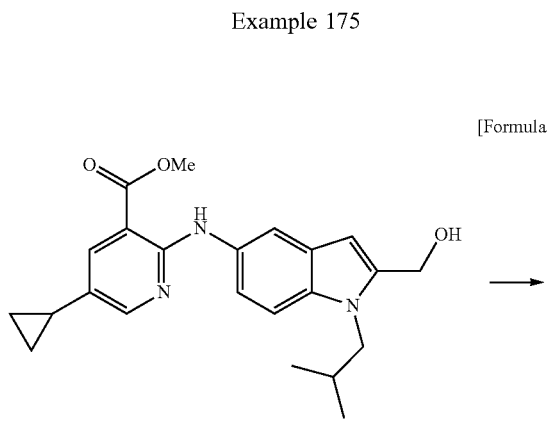

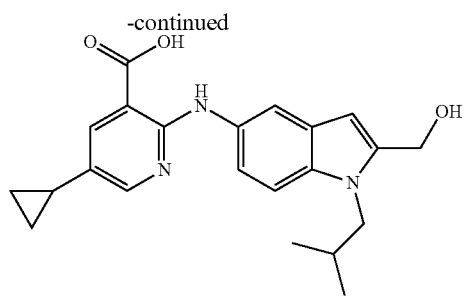

By the method similar to that of Example 116, 5-cyclopropyl-2-((2-(hydroxymethyl)-1-isobutyl-1H-indol-5-yl)amino)nicotinic acid was obtained from methyl 5-cyclopropyl-2-((2-(hydroxymethyl)-1-isobutyl-1H-indol-5-yl)amino)nicotinate.

$^1$H-NMR (DMSO-$d_6$) δ: 0.62-0.68 (2H, m), 0.86 (6H, d, J=6.6 Hz), 0.88-0.94 (2H, m), 1.86-1.96 (1H, m), 2.14-2.25 (1H, m), 3.99 (2H, d, J=7.3 Hz), 4.62 (2H, s), 6.32 (1H, s), 7.17 (1H, dd, J=8.6, 2.0 Hz), 7.37 (1H, d, J=8.6 Hz), 7.86 (1H, d, J=2.0 Hz), 7.89 (1H, d, J=2.0 Hz), 8.17 (1H, d, J=2.6 Hz), 10.12 (1H, s).

MS (ESI, m/z): 380 (M+H)$^+$, 378 (M−H)$^−$.

Example 176

[Formula 423]

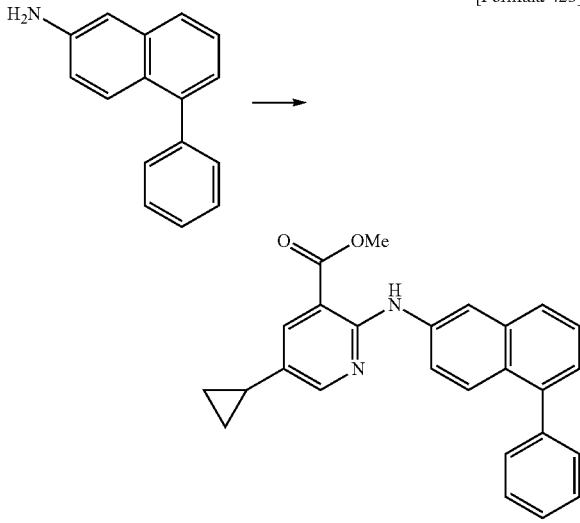

The mixture of 265 mg of 5-phenylnaphthalen-2-amine, 282 mg of methyl 2-chloro-5-cyclopropylnicotinate, 55 mg of tris(dibenzylideneacetone)dipalladium(0), 70 mg of 4,5'-bis(diphenylphosphino)-9,9'-dimethylxanthene, 788 mg of cesium carbonate, and 4 mL of toluene, was stirred at 190° C. for one hour using microwave equipment. After cooling the reaction mixture to room temperature, the insoluble matter was filtered off and the solvent was distilled off under reduced pressure. The obtained residue was purified by silica gel column chromatography (gradient elution with hexane:chloroform=80:20-40:60) to give 360 mg of methyl 5-cyclopropyl-2-((5-phenylnaphthalen-2-yl)amino)nicotinate as a yellow oil.

MS (ESI, m/z): 395 (M+H)$^+$.

Example 177

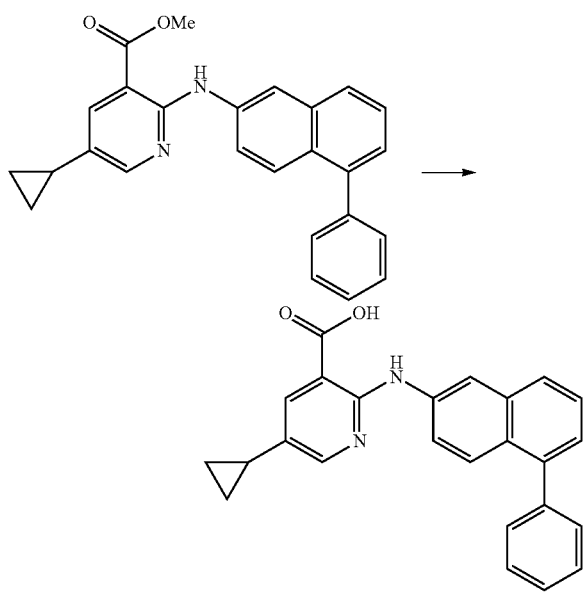

[Formula 424]

To the mixed solution of 360 mg of methyl 5-cyclopropyl-2-((5-phenylnaphthalen-2-yl)amino)nicotinate in 2 mL of methanol and 4 mL of tetrahydrofuran, 1 mL of a 1 mol/L aqueous sodium hydroxide solution was added at room temperature, and the resultant was stirred at an external temperature of 70 to 80° C. for five hours. The reaction mixture was allowed to stand at room temperature overnight. 1 mL of a 5 mol/L aqueous sodium hydroxide solution was added thereto, and the resultant was stirred at an external temperature of 70 to 80° C. for two hours. After cooling the reaction mixture to room temperature, the solvent was distilled off under reduced pressure. Water and methanol were added to the obtained residue and the resultant was adjusted to pH 2.7 with 1 mol/L hydrochloric acid. The solid was collected by filtration to give 340 mg of 5-cyclopropyl-2-((5-phenylnaphthalen-2-yl)amino)nicotinic acid as a yellow solid.

$^1$H-NMR (DMSO-$d_6$) δ: 0.63-0.65 (2H, m), 0.88-0.95 (2H, m), 1.85-1.94 (1H, m), 7.18 (1H, d, J=6.6 Hz), 7.43-7.56 (7H, m), 7.68 (1H, d, J=8.6 Hz), 7.77 (1H, d, J=8.6 Hz), 7.88 (1H, d, J=2.6 Hz), 8.13 (1H, d, J=2.0 Hz), 8.64 (1H, d, J=2.0 Hz), 12.65 (1H, s).

MS (ESI, m/z): 381 (M+H)$^+$, 379 (M−H)$^−$.

Example 178

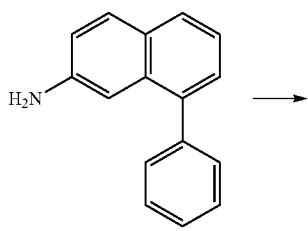

[Formula 425]

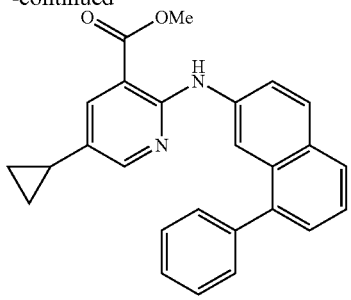

The mixture of 130 mg of 8-phenylnaphthalen-2-amine, 138 mg of methyl 2-chloro-5-cyclopropylnicotinate, 27 mg of tris(dibenzylideneacetone)dipalladium(0), 34 mg of 4,5'-bis(diphenylphosphino)-9,9'-dimethylxanthene, 386 mg of cesium carbonate, and 5 mL of toluene, was stirred at 190° C. for one hour using microwave equipment. After cooling the reaction mixture to room temperature, the insoluble matter was filtered off and the solvent was distilled off under reduced pressure. The obtained residue was purified by silica gel column chromatography (gradient elution with hexane:chloroform=70:30-40:60) to give 150 mg of methyl 5-cyclopropyl-2-((8-phenylnaphthalen-2-yl)amino)nicotinate as a yellow oil.

MS (ESI, m/z): 395 (M+H)$^+$.

Example 179

[Formula 426]

To the mixed solution of 150 mg of methyl 5-cyclopropyl-2-((8-phenylnaphthalen-2-yl)amino)nicotinate in 2 mL of methanol and 4 mL of tetrahydrofuran, 1 mL of a 1 mol/L aqueous sodium hydroxide solution was added at room temperature, and the resultant was stirred at an external temperature of 70 to 80° C. for 50 minutes. After cooling the reaction mixture to room temperature, the solvent was distilled off under reduced pressure. Water was added to the reaction mixture, and the resultant was adjusted to pH 2.8 with 1 mol/L hydrochloric acid. The solid was collected by filtration to give 125 mg of 5-cyclopropyl-2-((8-phenyl-naphthalen-2-yl)amino)nicotinic acid as a yellow solid.

$^1$H-NMR (DMSO-d$_6$) δ: 0.63-0.68 (2H, m), 0.90-0.96 (2H, m), 1.90-1.99 (1H, m), 7.38-7.51 (3H, m), 7.54-7.61 (4H, m), 7.69 (1H, dd, J=9.2, 2.0 Hz), 7.85-7.87 (2H, m), 7.93 (1H, d, J=8.6 Hz), 8.13 (1H, d, J=2.6 Hz), 8.48 (1H, d, J=2.0 Hz), 10.43 (1H, s), 13.62 (1H, s).

MS (ESI, m/z): 381 (M+H)$^+$, 379 (M−H)$^−$.

Example 180

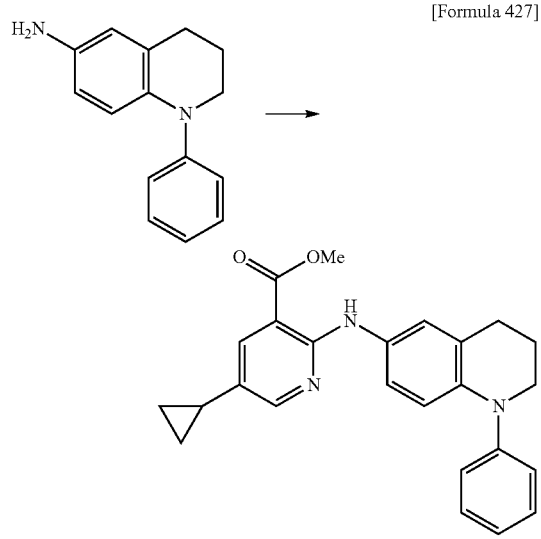

[Formula 427]

The mixture of 36 mg of 1-phenyl-1,2,3,4-tetrahydroquinolin-6-amine, 37 mg of methyl 2-chloro-5-cyclopropylnicotinate, 7.3 mg of tris(dibenzylideneacetone)dipalladium (0), 9.3 mg of 4,5'-bis(diphenylphosphino)-9,9'-dimethylxanthene, 104 mg of cesium carbonate, and 2 mL of toluene, was stirred at 190° C. for one hour using microwave equipment. After cooling the reaction mixture to room temperature, the insoluble matter was filtered off and the solvent was distilled off under reduced pressure. The obtained residue was purified by silica gel column chromatography (gradient elution with hexane:ethyl acetate=100:0-80:20) to give 20 mg of methyl 5-cyclopropyl-2-((1-phenyl-1,2,3,4-tetrahydroquinolin-6-yl)amino)nicotinate as a yellow oil.

MS (ESI, m/z): 400 (M+H)$^+$.

Example 181

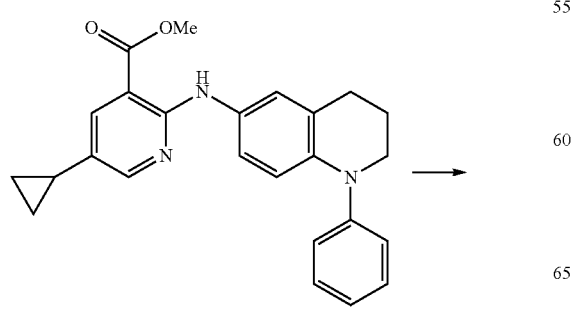

[Formula 428]

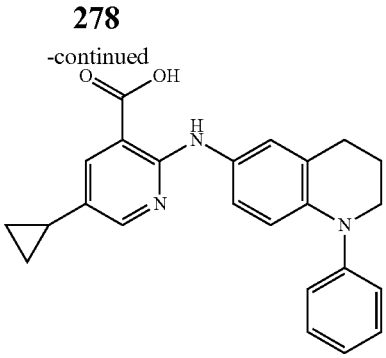

To the mixed solution of 20 mg of methyl 5-cyclopropyl-2-((1-phenyl-1,2,3,4-tetrahydroquinolin-6-yl)amino)nicotinate in 2 mL of methanol and 4 mL of tetrahydrofuran, 1 mL of a 1 mol/L aqueous sodium hydroxide solution was added at room temperature, and the resultant was stirred at an external temperature of 70 to 80° C. for one hour. After cooling the reaction mixture to room temperature, the solvent was distilled off under reduced pressure. Methanol and water were added to the obtained residue and the resultant was adjusted to pH 2.8 with 1 mol/L hydrochloric acid, and ethyl acetate was then added thereto, and the organic layer was separated and the solvent was distilled off under reduced pressure. The obtained residue was purified by preparative thin-layer chromatography (gradient elution with hexane:ethyl acetate=60:40), and hexane was added to the thus obtained residue, and the solid was collected by filtration to give 3.2 mg of 5-cyclopropyl-2-((1-phenyl-1,2,3,4-tetrahydroquinolin-6-yl)amino)nicotinic acid as a yellow solid.

$^1$H-NMR (DMSO-d$_6$) δ: 0.60-0.67 (2H, m), 0.80-0.94 (2H, m), 1.85-1.97 (3H, m), 2.76 (2H, t, J=6.6 Hz), 3.57 (2H, t, J=5.6 Hz), 6.69 (1H, d, J=8.6 Hz), 7.01 (1H, t, J=7.3 Hz), 7.17-7.23 (3H, m), 7.29-7.34 (3H, m), 7.85 (1H, d, J=2.0 Hz), 8.17 (1H, d, J=2.0 Hz), 9.99 (1H, s).

MS (ESI, m/z): 386 (M+H)$^+$, 384 (M−H)$^−$.

Example 182

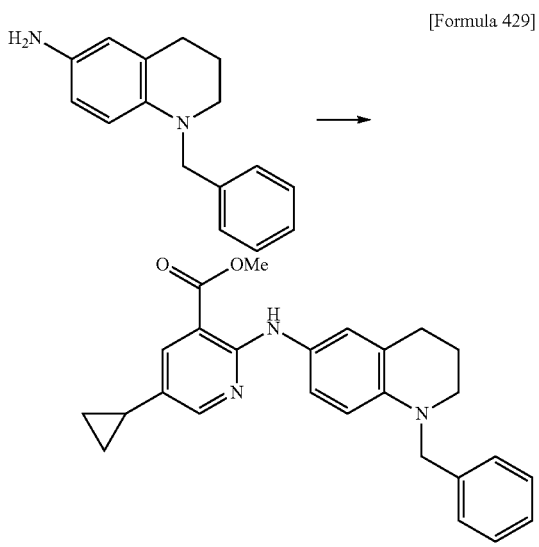

[Formula 429]

The mixture of 80 mg of 1-benzyl-1,2,3,4-tetrahydroquinolin-6-amine, 85 mg of methyl 2-chloro-5-cyclopropylnicotinate, 15.5 mg of tris(dibenzylideneacetone)dipalladium (0), 19.4 mg of 4,5'-bis(diphenylphosphino)-9,9'-dimethylxanthene, 219 mg of cesium carbonate, and 4 mL of toluene, was stirred at 190° C. for one hour using microwave equipment. After cooling the reaction mixture to room temperature, the insoluble matter was filtered off and the solvent was distilled off under reduced pressure. The obtained residue was purified by silica gel column chromatography (gradient elution with hexane:ethyl acetate=100:0-80:20) to give 170 mg of methyl 2-((1-benzyl-1,2,3,4-tetrahydroquinolin-6-yl)amino)-5-cyclopropylnicotinate as a yellow oil.

MS (ESI, m/z): 414 (M+H)+.

Example 183

[Formula 430]

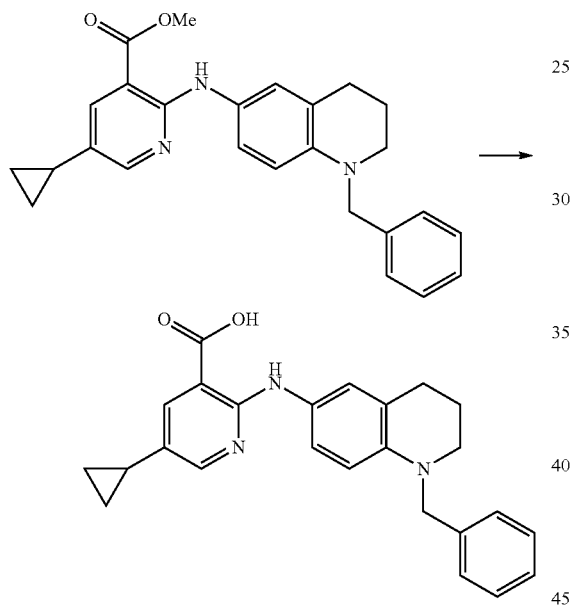

To the mixed solution of 170 mg of methyl 2-((1-benzyl-1,2,3,4-tetrahydroquinolin-6-yl)amino)-5-cyclopropylnicotinate in 1 mL of methanol and 2 mL of tetrahydrofuran, 0.5 mL of a 1 mol/L aqueous sodium hydroxide solution was added at room temperature, and the resultant was heated at reflux for 45 minutes. After cooling the reaction mixture to room temperature, the solvent was distilled off under reduced pressure. Methanol and water were added to the obtained residue and the resultant was adjusted to pH 2.8 with 1 mol/L hydrochloric acid. The solid was collected by filtration to give 120 mg of 2-((1-benzyl-1,2,3,4-tetrahydroquinolin-6-yl)amino)-5-cyclopropylnicotinic acid as a yellow solid.

1H-NMR (DMSO-d6) δ: 0.58-0.64 (2H, m), 0.85-0.91 (2H, m), 1.82-1.98 (3H, m), 2.69-2.77 (2H, m), 3.35-3.47 (2H, m), 4.46 (2H, s), 6.43 (1H, d, J=9.2 Hz), 7.11-7.14 (2H, m), 7.20-7.35 (5H, m), 7.82 (1H, s), 8.11 (1H, s), 9.81 (1H, s).

MS (ESI, m/z): 400 (M+H)+, 398 (M−H)−.

Example 184

[Formula 431]

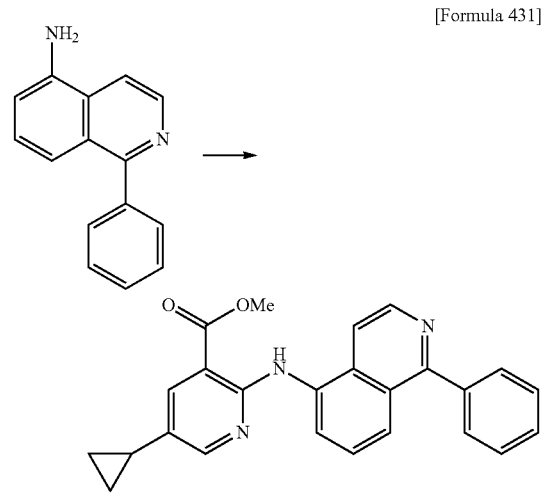

The mixture of 110 mg of 1-phenylisoquinolin-5-amine, 116 mg of methyl 2-chloro-5-cyclopropylnicotinate, 46 mg of tris(dibenzylideneacetone)dipalladium(0), 58 mg of 4,5'-bis(diphenylphosphino)-9,9'-dimethylxanthene, 326 mg of cesium carbonate, and 5 mL of toluene, was stirred at 190° C. for one hour using microwave equipment. After cooling the reaction mixture to room temperature, the insoluble matter was filtered off and the solvent was distilled off under reduced pressure. The obtained residue was purified by silica gel column chromatography (gradient elution with hexane:ethyl acetate=100:0-75:25) to give 119 mg of methyl 5-cyclopropyl-2-((1-phenylisoquinolin-5-yl)amino)nicotinate as a yellow oil.

MS (ESI, m/z): 396 (M+H)+.

Example 185

[Formula 432]

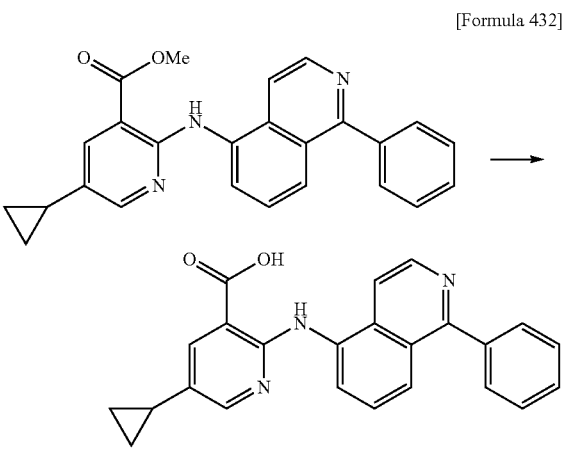

To the mixed solution of 119 mg of methyl 5-cyclopropyl-2-((1-phenylisoquinolin-5-yl)amino)nicotinate in 1 mL of methanol and 4 mL of tetrahydrofuran, 1 mL of a 1 mol/L aqueous sodium hydroxide solution was added at room temperature, and the resultant was stirred at 60° C. for two hours and 30 minutes. After cooling the reaction mixture to room temperature, the solvent was distilled off under reduced pressure. Methanol and water were added to the obtained residue and the resultant was adjusted to pH 2.8 with 1 mol/L hydrochloric acid. The solid was collected by filtration to give a yellow solid. The obtained solid was dissolved in 3 mL of water and the reaction solution was adjusted to pH 12 by adding thereto a 1 mol/L aqueous sodium hydroxide solution at room temperature and then adjusted to pH 4.0 with 1 mol/L hydrochloric acid. The solid was collected by filtration to give 50 mg of 5-cyclopropyl-2-((1-phenylisoquinolin-5-yl)amino)nicotinic acid as a yellow solid.

$^1$H-NMR (DMSO-$d_6$) δ: 0.69-0.71 (2H, m), 0.92-0.98 (2H, m), 1.92-2.01 (1H, m), 7.52-7.70 (7H, m), 7.91 (1H, d, J=5.9 Hz), 8.00 (1H, d, J=2.6 Hz), 8.26 (1H, d, J=2.6 Hz), 8.64-8.67 (2H, m), 11.04 (1H, s).

MS (ESI, m/z): 382 (M+H)$^+$, 380 (M−H)$^−$.

Example 186

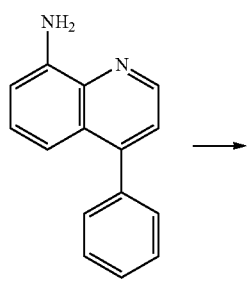

[Formula 433]

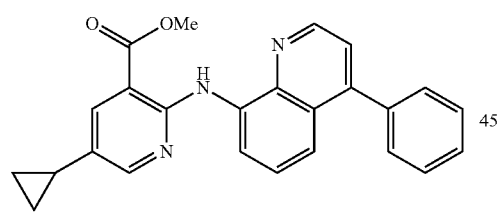

The mixture of 80 mg of 4-phenylquinolin-8-amine, 115 mg of methyl 2-chloro-5-cyclopropylnicotinate, 66 mg of tris(dibenzylideneacetone)dipalladium(0), 78 mg of 2-(dicyclohexylphosphino)-3,6-dimethoxy-2',4',6'-triisopropyl-1,1'biphenyl, 237 mg of cesium carbonate, and 5 mL of toluene, was stirred at 190° C. for five hours using microwave equipment and then stirred at 190° C. for two hours using microwave equipment. The reaction mixture was cooled to room temperature and then allowed to stand overnight. The insoluble matter was filtered off and the solvent was distilled off under reduced pressure. The obtained residue was purified by silica gel column chromatography (gradient elution with hexane:ethyl acetate=100:0-85:15) to give 110 mg of methyl 5-cyclopropyl-2-((4-phenylquinolin-8-yl)amino)nicotinate as a brown oil.

MS (ESI, m/z): 396 (M+H)$^+$.

Example 187

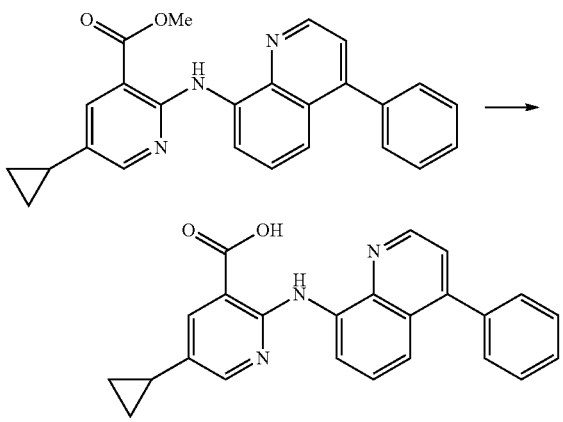

[Formula 434]

To the mixed solution of 110 mg of methyl 5-cyclopropyl-2-((4-phenylquinolin-8-yl)amino)nicotinate in 2 mL of methanol and 4 mL of tetrahydrofuran, 1 mL of a 1 mol/L aqueous sodium hydroxide solution was added at room temperature, and the resultant was stirred at 60° C. for 30 minutes. After cooling the reaction mixture to room temperature, the solvent was distilled off under reduced pressure. Methanol and water were added to the reaction mixture, and the resultant was adjusted to pH 4.0 with 1 mol/L hydrochloric acid. Ethyl acetate was added thereto, and the organic layer was separated and the solvent was distilled off under reduced pressure. The obtained residue was purified by silica gel column chromatography (hexane:ethyl acetate=50:50). Hexane was added to the thus obtained residue, and the solid was collected by filtration to give 32 mg of 5-cyclopropyl-2-((4-phenylquinolin-8-yl)amino)nicotinic acid as a yellow solid.

$^1$H-NMR (DMSO-$d_6$) δ: 0.72-0.73 (2H, m), 0.94-1.00 (2H, m), 1.95-2.04 (1H, m), 7.37 (1H, dd, J=8.6, 1.3 Hz), 7.51-7.61 (7H, m), 8.00 (1H, d, J=2.6 Hz), 8.39 (1H, d, J=2.6 Hz), 8.94 (1H, d, J=4.0 Hz), 9.13 (1H, dd, J=7.9, 1.3 Hz), 12.30 (1H, s).

MS (ESI, m/z): 382 (M+H)$^+$, 380 (M−H)$^−$.

Example 188

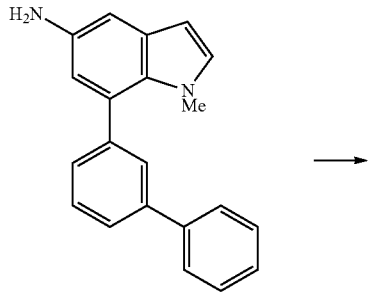

[Formula 435]

-continued

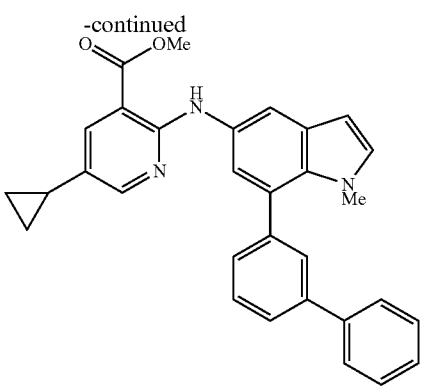

The mixture of 90 mg of 7-([1,1'-biphenyl]-3-yl)-1-methyl-1H-indol-5-amine, 70 mg of methyl 2-chloro-5-cyclopropylnicotinate, 28 mg of tris(dibenzylideneacetone)dipalladium(0), 35 mg of 4,5'-bis(diphenylphosphino)-9,9'-dimethylxanthene, 197 mg of cesium carbonate, and 4 mL of toluene, was stirred at 190° C. for one hour using microwave equipment.

After cooling the reaction mixture to room temperature, the insoluble matter was filtered off and the solvent was distilled off under reduced pressure. The obtained residue was purified by silica gel column chromatography (gradient elution with hexane:ethyl acetate=100:0-80:20) to give 112 mg of methyl 2-((7-([1,1'-biphenyl]-3-yl)-1-methyl-1H-indol-5-yl)amino)-5-cyclopropylnicotinate as a yellow oil.

MS (ESI, m/z): 474 (M+H)$^+$.

Example 189

[Formula 436]

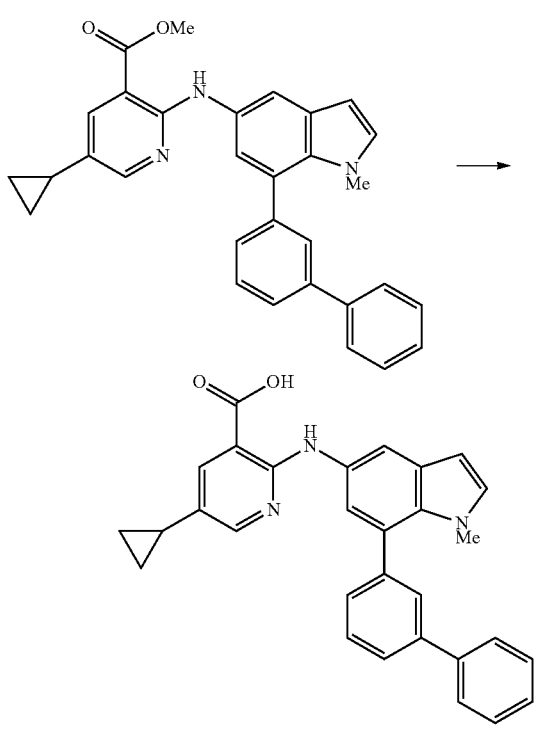

To the mixed solution of 112 mg of methyl 2-((7-([1,1'-biphenyl]-3-yl)-1-methyl-1H-indol-5-yl)amino)-5-cyclo-propylnicotinate in 2 mL of methanol and 4 mL of tetrahydrofuran, 1 mL of a 1 mol/L aqueous sodium hydroxide solution was added at room temperature, and the resultant was stirred at 60° C. for one hour. After cooling the reaction mixture to room temperature, the solvent was distilled off under reduced pressure. Methanol and water were added to the obtained residue and the resultant was adjusted to pH 3.0 with 1 mol/L hydrochloric acid. The solid was collected by filtration to give 58 mg of 2-((7-([1,1'-biphenyl]-3-yl)-1-methyl-1H-indol-5-yl)amino)-5-cyclopropylnicotinic acid as a yellow solid.

$^1$H-NMR (DMSO-d$_6$) δ: 0.64-0.65 (2H, m), 0.87-0.93 (2H, m), 1.85-1.94 (1H, m), 3.31 (3H, s), 6.47 (1H, d, J=3.3 Hz), 7.09 (1H, d, J=2.0 Hz), 7.25 (1H, d, J=2.6 Hz), 7.38 (1H, t, J=7.3 Hz), 7.47 (3H, t, J=7.6 Hz), 7.57 (1H, t, J=7.6 Hz), 7.76 (4H, t, J=6.9 Hz), 7.88 (1H, d, J=2.6 Hz), 8.07 (1H, d, J=2.6 Hz), 8.21 (1H, d, J=2.6 Hz), 10.23 (1H, s).

MS (ESI, m/z): 460 (M+H)$^+$.

Example 190

[Formula 437]

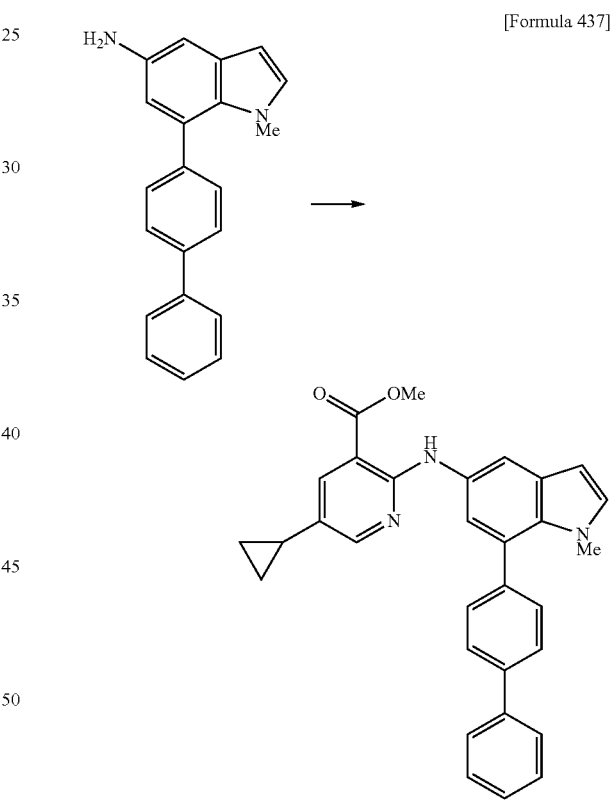

The mixture of 8.7 mg of 7-([1,1'-biphenyl]-4-yl)-1-methyl-1H-indol-5-amine, 6.8 mg of methyl 2-chloro-5-cyclopropylnicotinate, 2.7 mg of tris(dibenzylideneacetone)dipalladium(0), 3.4 mg of 4,5'-bis(diphenylphosphino)-9,9'-dimethylxanthene, 19 mg of cesium carbonate, and 1.5 mL of toluene, was stirred at 190° C. for one hour using microwave equipment and then stirred at 190° C. for one hour using microwave equipment. After cooling the reaction mixture to room temperature, the insoluble matter was filtered off and the solvent was distilled off under reduced pressure. The obtained residue was purified by silica gel column chromatography (gradient elution with hexane:ethyl

Example 191

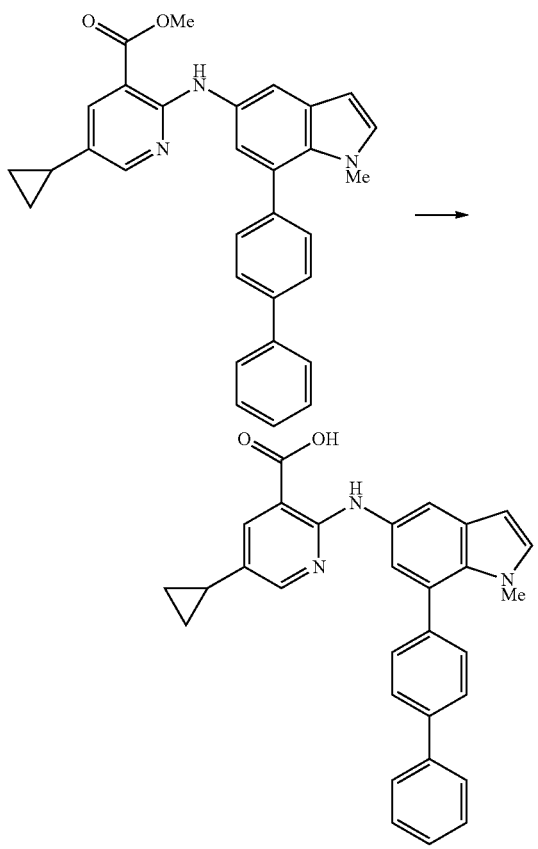

[Formula 438]

To the mixed solution of 7.5 mg of methyl 2-((7-([1,1'-biphenyl]-4-yl)-1-methyl-1H-indol-5-yl)amino)-5-cyclopropylnicotinate in 0.5 mL of methanol and 1 mL of tetrahydrofuran, 0.5 mL of a 1 mol/L aqueous sodium hydroxide solution was added at room temperature, and the resultant was stirred at 60° C. for one hour. After cooling the reaction mixture to room temperature, the solvent was distilled off under reduced pressure. Methanol and water were added to the obtained residue and the resultant was adjusted to pH 2.5 with 1 mol/L hydrochloric acid, and ethyl acetate was then added thereto, and the organic layer was separated and the solvent was distilled off under reduced pressure. The thus obtained residue was purified by preparative thin-layer chromatography (hexane:ethyl acetate=70:30) to give 1.9 mg of 2-((7-([1,1'-biphenyl]-4-yl)-1-methyl-1H-indol-5-yl)amino)-5-cyclopropylnicotinic acid as a yellow solid.

$^{1}$H-NMR (DMSO-d$_{6}$) δ: 0.63-0.65 (2H, m), 0.81-0.96 (2H, m), 1.86-1.89 (1H, m), 3.36 (3H, s), 6.46 (1H, d, J=2.6 Hz), 7.06 (1H, d, J=2.0 Hz), 7.25 (1H, d, J=2.6 Hz), 7.40 (1H, t, J=7.3 Hz), 7.49-7.58 (4H, m), 7.76-7.80 (4H, m), 7.87 (1H, d, J=2.6 Hz), 8.07 (1H, d, J=2.0 Hz), 8.18 (1H, d, J=2.6 Hz).

MS (ESI, m/z): 460 (M+H)$^{+}$.

Example 192

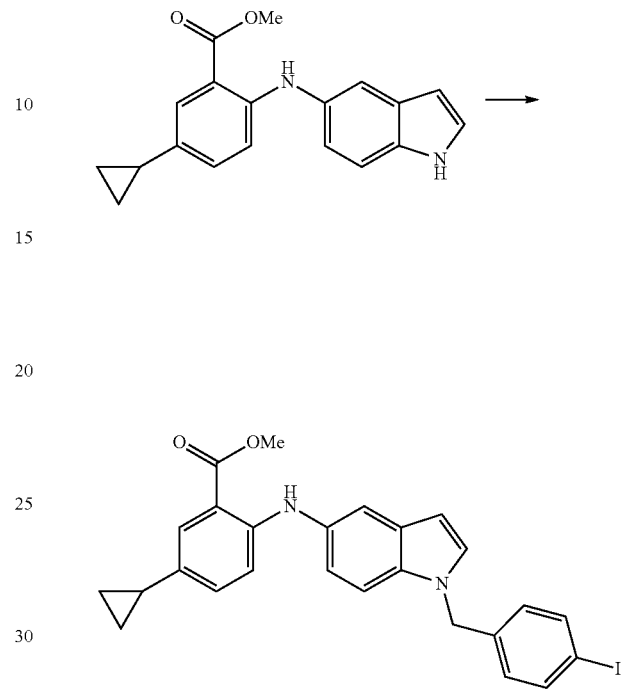

[Formula 439]

To the solution of 400 mg of methyl 2-((1H-indol-5-yl)amino)-5-cyclopropylbenzoate in 4 mL of N,N-dimethylacetamide, 161 mg of potassium tert-butoxide was added under ice-cooling, and the resultant was stirred for 10 minutes. To the reaction mixture, 426 mg of 4-iodobenzyl bromide was added under ice-cooling, and the resultant was stirred at room temperature for four hours. Ethyl acetate and water were added to the reaction mixture. The organic layer was separated and dried over anhydrous magnesium sulfate, and the solvent was then distilled off under reduced pressure. The obtained residue was purified by silica gel column chromatography (gradient elution with hexane:ethyl acetate=91:9-50:50) to give 641 mg of methyl 5-cyclopropyl-2-((1-(4-iodobenzyl)-1H-indol-5-yl)amino)benzoate as a yellow oil.

Example 193

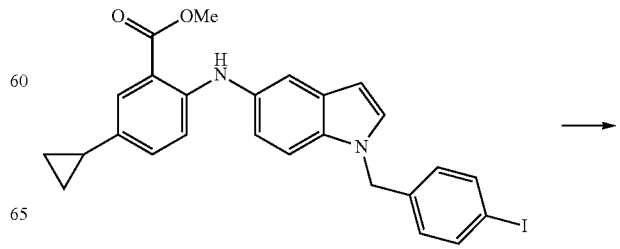

[Formula 440]

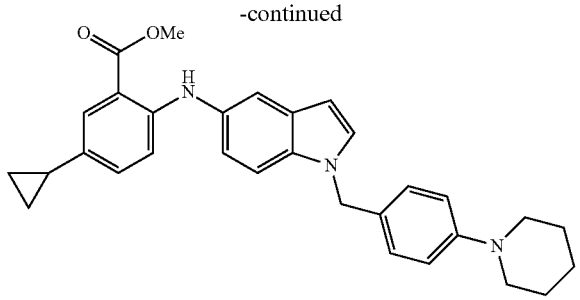

The mixture of 160 mg of methyl 5-cyclopropyl-2-((1-(4-iodobenzyl)-1H-indol-5-yl)amino)benzoate, 0.1 mL of piperidine, 6 mg of tris(dibenzylideneacetone)dipalladium (0), 11 mg of 4,5'-bis(diphenylphosphino)-9,9'-dimethylxanthene, 319 mg of cesium carbonate, and 2 mL of dioxane, was stirred in a sealed tube at an external temperature 130° C. for four hours under a nitrogen atmosphere. After cooling the reaction mixture to room temperature, the insoluble matter was filtered off and the solvent was distilled off under reduced pressure. The obtained residue was purified by silica gel column chromatography (gradient elution with hexane:ethyl acetate=91:9-67:33) to give methyl 5-cyclopropyl-2-((1-(4-(piperidin-1-yl)benzyl)-1H-indol-5-yl)amino)benzoate as a yellow oil.

Example 194

[Formula 441]

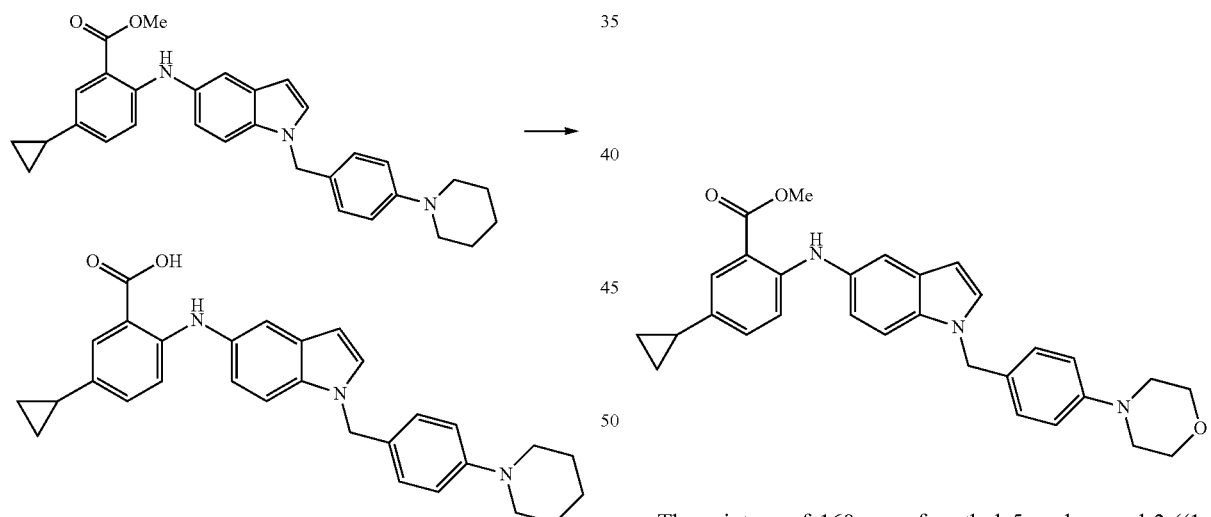

To the mixed solution of methyl 5-cyclopropyl-2-((1-(4-(piperidin-1-yl)benzyl)-1H-indol-5-yl)amino)benzoate obtained in Example 193 in 2 mL of methanol and 4 mL of tetrahydrofuran, 1 mL of a 1 mol/L aqueous sodium hydroxide solution was added, and the resultant was stirred at an external temperature of 40 to 50° C. for 10 hours. The reaction mixture was cooled to room temperature and 1 mL of 1 mol/L hydrochloric acid, and ethyl acetate and a saturated aqueous dipotassium hydrogenphosphate solution were then added thereto. The organic layer was separated and dried over anhydrous magnesium sulfate, and the solvent was then distilled off under reduced pressure. The obtained residue was purified by silica gel column chromatography (gradient elution with hexane:ethyl acetate=83:17-50:50), and ethyl acetate was added to the thus obtained residue, and the solid was collected by filtration and washed with methanol to give 47 mg of 5-cyclopropyl-2-((1-(4-(piperidin-1-yl)benzyl)-1H-indol-5-yl)amino)benzoic acid as a yellow solid.

$^1$H-NMR (DMSO-$d_6$) δ: 0.49-0.57 (2H, m), 0.80-0.90 (2H, m), 1.44-1.63 (6H, m), 1.76-1.89 (1H, m), 3.03-3.11 (4H, m), 5.26 (2H, s), 6.40 (1H, d, J=2.6 Hz), 6.83-6.90 (3H, m), 6.92-7.05 (2H, m), 7.12 (2H, d, J=8.6 Hz), 7.37 (1H, d, J=2.0 Hz), 7.44-7.50 (2H, m), 7.59 (1H, d, J=2.0 Hz), 9.32 (1H, brs).

MS (ESI, m/z): 466 (M+H)$^+$.

Example 195

[Formula 442]

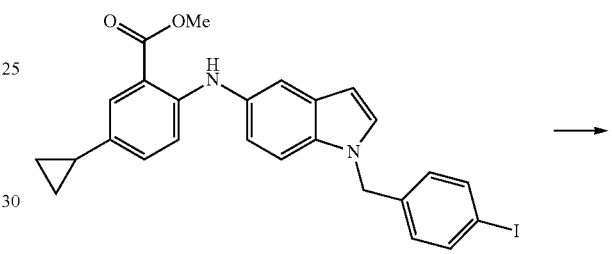

The mixture of 160 mg of methyl 5-cyclopropyl-2-((1-(4-iodobenzyl)-1H-indol-5-yl)amino)benzoate, 0.1 mL of morpholine, 6 mg of tris(dibenzylideneacetone)dipalladium (0), 11 mg of 4,5'-bis(diphenylphosphino)-9,9'-dimethylxanthene, 319 mg of cesium carbonate, and 2 mL of dioxane, was stirred in a sealed tube at an external temperature 130° C. for four hours under a nitrogen atmosphere. After cooling the reaction mixture to room temperature, the insoluble matter was filtered off and the solvent was distilled off under reduced pressure. The obtained residue was purified by silica gel column chromatography (gradient elution with hexane:ethyl acetate=83:17-0:100) to give methyl 5-cyclopropyl-2-((1-(4-morpholinobenzyl)-1H-indol-5-yl)amino)benzoate as a yellow oil.

Example 196

[Formula 443]

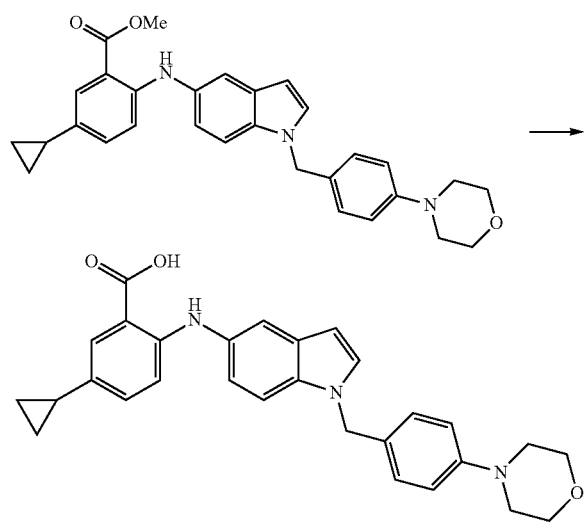

To the mixed solution of methyl 5-cyclopropyl-2-((1-(4-morpholinobenzyl)-1H-indol-5-yl)amino)benzoate obtained in Example 195 in 2 mL of methanol and 4 mL of tetrahydrofuran, 1 mL of a 1 mol/L aqueous sodium hydroxide solution was added, and the resultant was stirred at an external temperature of 40 to 50° C. for eight hours. The reaction mixture was cooled to room temperature, and 1 mL of 1 mol/L hydrochloric acid, ethyl acetate and a saturated aqueous dipotassium hydrogenphosphate solution were then added thereto. The organic layer was separated and dried over anhydrous magnesium sulfate, and the solvent was then distilled off under reduced pressure. The obtained residue is purified by silica gel column chromatography (gradient elution with chloroform:methanol=100:0-91:9), and chloroform was added to the thus obtained residue, and the solid was collected by filtration and washed with methanol to give 33 mg of 5-cyclopropyl-2-((1-(4-morpholinobenzyl)-1H-indol-5-yl)amino)benzoic acid as a yellow solid.

$^1$H-NMR (DMSO-$d_6$) δ: 0.49-0.57 (2H, m), 0.80-0.90 (2H, m), 1.77-1.87 (1H, m), 3.02-3.08 (4H, m), 3.67-3.74 (4H, m), 5.28 (2H, s), 6.40 (1H, d, J=2.6 Hz), 6.84-6.91 (3H, m), 6.91-7.04 (2H, m), 7.15 (2H, d, J=8.6 Hz), 7.37 (1H, d, J=1.3 Hz), 7.44-7.50 (2H, m), 7.59 (1H, d, J=2.0 Hz), 9.32 (1H, brs).

MS (ESI, m/z): 468 (M+H)$^+$.

Example 197

[Formula 444]

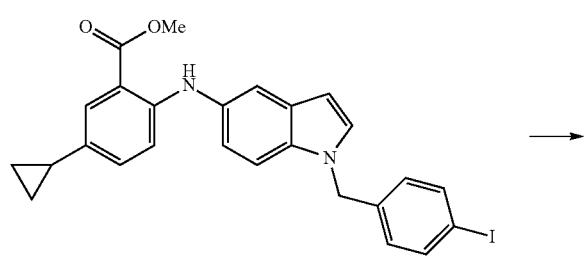

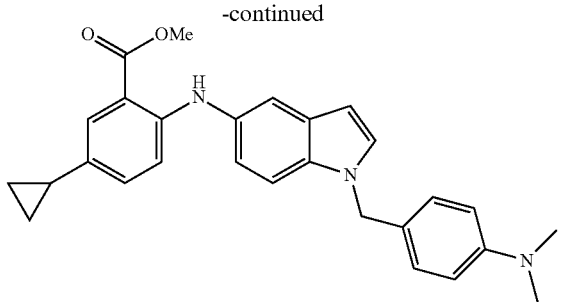

The mixture of 160 mg of methyl 5-cyclopropyl-2-((1-(4-iodobenzyl)-1H-indol-5-yl)amino)benzoate, 0.4 mL of a 2 mol/L solution of dimethylamine in tetrahydrofuran, 6 mg of tris(dibenzylideneacetone)dipalladium(0), 11 mg of 4,5'-bis(diphenylphosphino)-9,9'-dimethylxanthene, 319 mg of cesium carbonate, and 3 mL of dioxane, was stirred at 130° C. for 1.5 hours using microwave equipment. After cooling the reaction mixture to room temperature, the insoluble matter was filtered off and the solvent was distilled off under reduced pressure. The obtained residue was purified by silica gel column chromatography (gradient elution with hexane:ethyl acetate=91:9-50:50) to give methyl 5-cyclopropyl-2-((1-(4-(dimethylamino)benzyl)-1H-indol-5-yl)amino)benzoate as a yellow oil.

Example 198

[Formula 445]

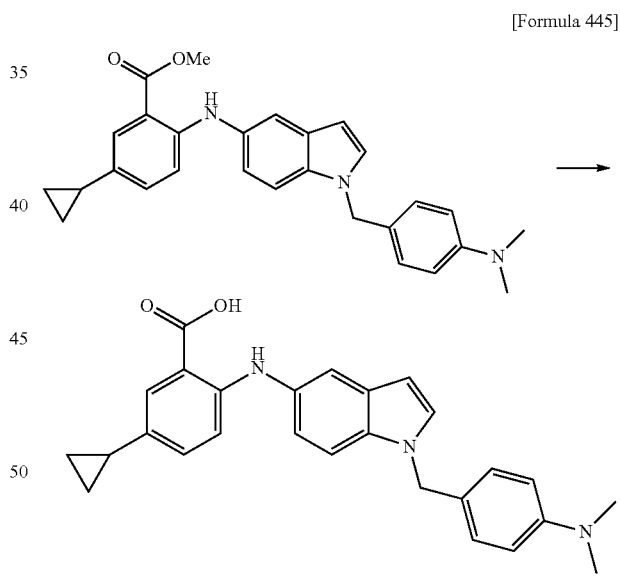

To the mixed solution of methyl 5-cyclopropyl-2-((1-(4-(dimethylamino)benzyl)-1H-indol-5-yl)amino)benzoate obtained in Example 197 in 2 mL of methanol and 4 mL of tetrahydrofuran, 1 mL of a 1 mol/L aqueous sodium hydroxide solution was added, and the resultant was stirred at an external temperature of 40 to 50° C. for eight hours. The reaction mixture was cooled to room temperature, and 1 mL of 1 mol/L hydrochloric acid, ethyl acetate and a saturated aqueous dipotassium hydrogenphosphate solution were then added thereto. The organic layer was separated and dried over anhydrous magnesium sulfate, and the solvent was then distilled off under reduced pressure. The obtained residue was purified by silica gel column chromatography (gradient elution with hexane:ethyl acetate=83:17-33:67), and chloroform was added to the thus obtained residue, and the solid was collected by filtration and washed with methanol to give 20 mg of 5-cyclopropyl-2-((1-(4-(dimethylamino)benzyl)-1H-indol-5-yl)amino)benzoic acid as a yellow solid.

$^1$H-NMR (DMSO-$d_6$) δ: 0.49-0.57 (2H, m), 0.80-0.90 (2H, m), 1.77-1.87 (1H, m), 2.84 (6H, s), 5.24 (2H, s), 6.39 (1H, d, J=2.6 Hz), 6.66 (2H, d, J=9.2 Hz), 6.86 (1H, d, J=8.6 Hz), 6.91-7.04 (2H, m), 7.13 (2H, d, J=8.6 Hz), 7.34-7.38 (1H, m), 7.44-7.50 (2H, m), 7.59 (1H, d, J=2.6 Hz), 9.32 (1H, brs).

MS (ESI, m/z): 426 (M+H)$^+$.

Example 199

[Formula 446]

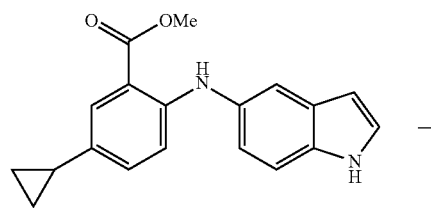

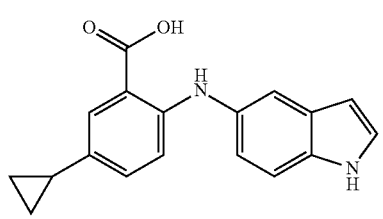

To the mixed solution of 306 mg of methyl 2-((1H-indol-5-yl)amino)-5-cyclopropylbenzoate in 4 mL of methanol and 8 mL of tetrahydrofuran, 2 mL of a 2 mol/L aqueous sodium hydroxide solution was added, and the resultant was stirred at an external temperature of 60 to 70° C. for four hours. The reaction mixture was cooled to room temperature, and 1 mol/L hydrochloric acid and ethyl acetate were then added thereto. The organic layer was separated, washed with a saturated aqueous sodium chloride solution and then dried over anhydrous magnesium sulfate, and the solvent was distilled off under reduced pressure. The obtained residue was purified by silica gel column chromatography (gradient elution with hexane:ethyl acetate=83:17-67:33), and diisopropyl ether and hexane were added to the thus obtained residue, and the solid was collected by filtration and washed with hexane to give 264 mg of 2-((1H-indol-5-yl)amino)-5-cyclopropylbenzoic acid.

$^1$H-NMR (DMSO-$d_6$) δ: 0.49-0.57 (2H, m), 0.80-0.90 (2H, m), 1.78-1.88 (1H, m), 6.35-6.42 (1H, m), 6.85-7.05 (3H, m), 7.33-7.41 (3H, m), 7.60 (1H, d, J=2.0 Hz), 9.33 (1H, brs), 11.09 (1H, s), 12.85 (1H, brs).

Example 200

[Formula 447]

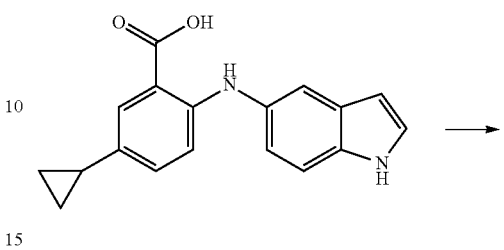

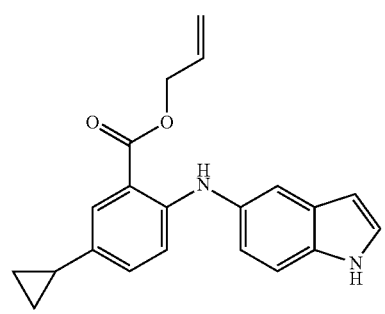

To the solution of 260 mg of 2-((1H-indol-5-yl)amino)-5-cyclopropylbenzoic acid in 5 mL of N,N-dimethylformamide, 374 mg of sodium bicarbonate was added, and the resultant was stirred for 10 minutes. 184 µL of allyl bromide was added to the reaction mixture, and the resultant was stirred at room temperature for one hour. The reaction mixture was allowed to stand overnight and then stirred at room temperature for three hours. Ethyl acetate and a saturated aqueous sodium bicarbonate solution were added to the reaction mixture. The organic layer was separated and dried over anhydrous magnesium sulfate, and the solvent was distilled off under reduced pressure to give allyl 2-((1H-indol-5-yl)amino)-5-cyclopropylbenzoate as a yellow oil.

The obtained allyl 2-((1H-indol-5-yl)amino)-5-cyclopropylbenzoate was dissolved in dichloromethane to a total volume of 6 mL.

Example 201

[Formula 448]

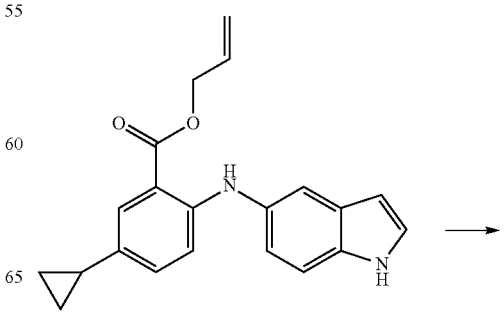

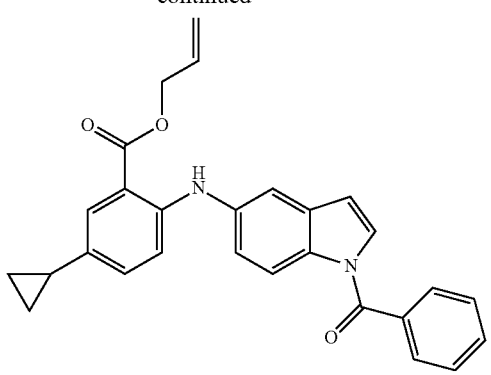

To the solution of allyl 2-((1H-indol-5-yl)amino)-5-cyclopropylbenzoate obtained in Example 200 in 3 mL of dichloromethane, 186 μL of triethylamine, 56 μL of benzoyl chloride and 5 mg of 4-(dimethylamino)pyridine were added, and the resultant was stirred at room temperature for one hour and then allowed to stand overnight. Ethyl acetate and a saturated aqueous sodium bicarbonate solution were added to the reaction mixture. The organic layer was separated, washed with water and dried over anhydrous magnesium sulfate, and the solvent was distilled off under reduced pressure. The obtained residue was purified by silica gel column chromatography (gradient elution with hexane:ethyl acetate=90:10-67:33). Ethyl acetate and hexane were added to the thus obtained residue, and the solid was collected by filtration and washed with hexane to give 114 mg of allyl 2-(1-benzoyl-1H-indol-5-yl)amino)-5-cyclopropylbenzoate as a yellow solid.

$^1$H-NMR (DMSO-d$_6$) δ: 0.55-0.63 (2H, m), 0.84-0.93 (2H, m), 1.86-1.95 (1H, m), 4.83 (2H, d, J=5.9 Hz), 5.26-5.47 (2H, m), 6.00-6.15 (1H, m), 6.71 (1H, d, J=3.3 Hz), 7.14 (2H, s), 7.24 (1H, dd, J=8.9, 2.3 Hz), 7.39 (1H, d, J=4.0 Hz), 7.50-7.80 (7H, m), 8.25 (1H, d, J=8.6 Hz), 9.22 (1H, s).

Example 202

[Formula 449]

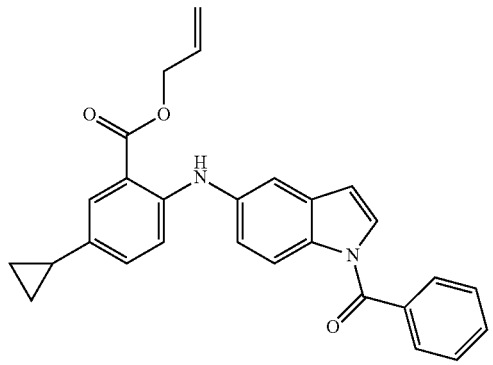

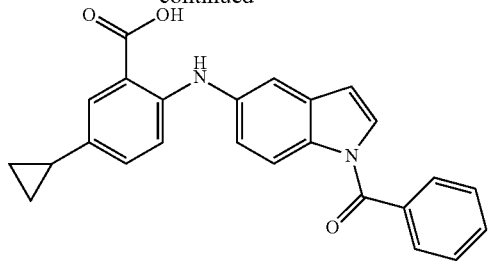

To the solution of 44 mg of allyl 2-((1-benzoyl-1H-indol-5-yl)amino)-5-cyclopropylbenzoate in 2 mL of acetonitrile, 18 μL of pyrrolidine and 6 mg of tetrakistriphenylphosphinepalladium(0) were added, and the resultant was stirred at room temperature for two hours. Ethyl acetate and 1 mol/L hydrochloric acid were added to the reaction mixture. The organic layer was separated, washed with a saturated aqueous sodium chloride solution and dried over anhydrous magnesium sulfate, and the solvent was distilled off under reduced pressure. Diisopropyl ether was added to the obtained residue, and the solid was collected by filtration and washed with hexane to give 30 mg of 2-((1-benzoyl-1H-indol-5-yl)amino)-5-cyclopropylbenzoic acid as a yellow solid.

$^1$H-NMR (DMSO-d$_6$) δ: 0.55-0.63 (2H, m), 0.84-0.93 (2H, m), 1.83-1.92 (1H, m), 6.71 (1H, d, J=3.3 Hz), 7.08-7.17 (2H, m), 7.23 (1H, dd, J=8.6, 2.0 Hz), 7.38 (1H, d, J=4.0 Hz), 7.52-7.80 (7H, m), 8.25 (1H, d, J=8.6 Hz), 9.54 (1H, brs).

MS (ESI, m/z): 397 (M+H)$^+$.

Example 203

[Formula 450]

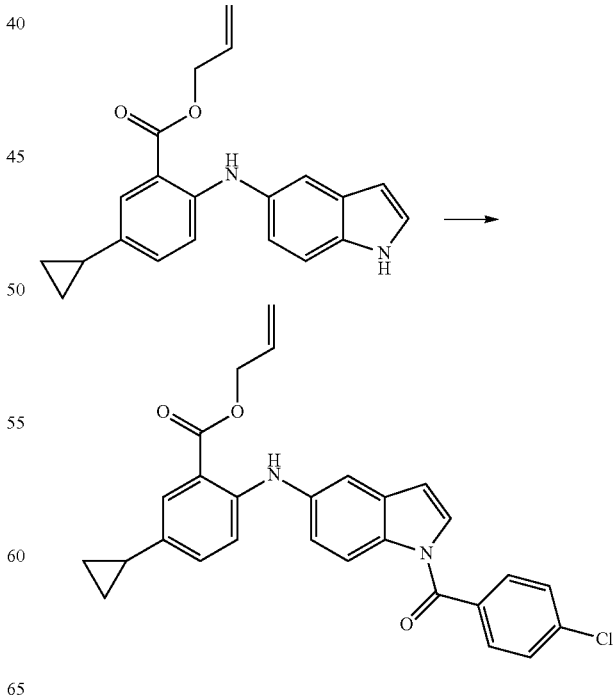

To the solution of allyl 2-((1H-indol-5-yl)amino)-5-cyclopropylbenzoate obtained in Example 200 in 3 mL of dichloromethane, 186 μL of triethylamine, 63 μL of 4-chlorobenzoyl chloride and 5 mg of 4-(dimethylamino)pyridine were added, and the resultant was stirred at room temperature for one hour and then allowed to stand overnight. Ethyl acetate and a saturated aqueous sodium bicarbonate solution were added to the reaction mixture. The organic layer was separated, washed with water and dried over anhydrous magnesium sulfate, and the solvent was distilled off under reduced pressure. The obtained residue was purified by silica gel column chromatography (gradient elution with hexane:ethyl acetate=90:10-67:33). Ethyl acetate and hexane were added to the thus obtained residue, and the solid was collected by filtration and washed with hexane to give 108 mg of allyl 2-((1-(4-chlorobenzoyl)-1H-indol-5-yl)amino)-5-cyclopropylbenzoate as a yellow solid.

$^1$H-NMR (DMSO-d$_6$) δ: 0.55-0.63 (2H, m), 0.84-0.93 (2H, m), 1.84-1.96 (1H, m), 4.80-4.86 (2H, m), 5.27-5.46 (2H, m), 6.05-6.16 (1H, m), 6.72 (1H, d, J=3.3 Hz), 7.14 (2H, d, J=1.3 Hz), 7.24 (1H, dd, J=9.2, 2.0 Hz), 7.41 (1H, d, J=3.3 Hz), 7.52 (1H, d, J=2.0 Hz), 7.65-7.72 (3H, m), 7.78-7.83 (2H, m), 8.25 (1H, d, J=9.2 Hz), 9.22 (1H, s).

Example 204

$^1$H-NMR (DMSO-d$_6$) δ: 0.52-0.62 (2H, m), 0.82-0.91 (2H, m), 1.83-1.94 (1H, m), 6.71 (1H, d, J=4.0 Hz), 7.08-7.17 (2H, m), 7.23 (1H, dd, J=8.9, 2.3 Hz), 7.41 (1H, d, J=4.0 Hz), 7.52 (1H, d, J=2.0 Hz), 7.64-7.70 (3H, m), 7.77-7.83 (2H, m), 8.25 (1H, d, J=8.6 Hz), 9.52 (1H, brs).

MS (ESI, m/z): 431 (M+H)$^+$.

Example 205

[Formula 452]

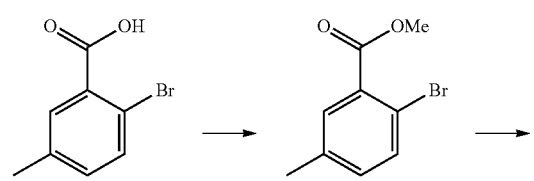

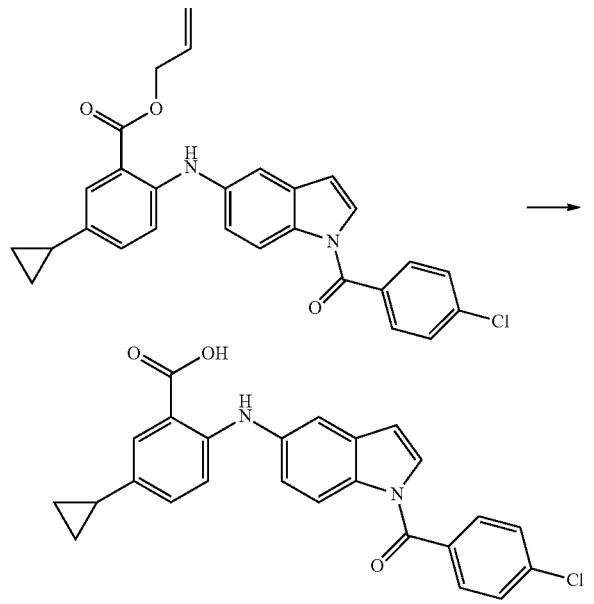

To the solution of 47 mg of allyl 2-((1-(4-chlorobenzoyl)-1H-indol-5-yl)amino)-5-cyclopropylbenzoate in 2 mL of acetonitrile, 18 μL of pyrrolidine and 6 mg of tetrakistriphenylphosphinepalladium(0) were added, and the resultant was stirred at room temperature for two hours. Ethyl acetate and 1 mol/L hydrochloric acid were added to the reaction mixture. The organic layer was separated, washed with a saturated aqueous sodium chloride solution and dried over anhydrous magnesium sulfate, and the solvent was distilled off under reduced pressure. Diisopropyl ether was added to the obtained residue, and the solid was collected by filtration and washed with hexane to give 16 mg of 2-((1-(4-chlorobenzoyl)-1H-indol-5-yl)amino)-5-cyclopropylbenzoic acid as a yellow solid.

To the solution of 108 mg of 2-bromo-5-methylbenzoic acid in 10 mL of methanol, 0.5 mL of concentrated sulfuric acid was added, and the resultant was heated at reflux for three hours. The reaction mixture was cooled to room temperature, and a saturated aqueous sodium bicarbonate solution and ethyl acetate were then added thereto. The organic layer was separated and dried over anhydrous magnesium sulfate, and the solvent was distilled off under reduced pressure to give methyl 2-bromo-5-methylbenzoate.

To the obtained methyl 2-bromo-5-methylbenzoate, 110 mg of 1-benzyl-1H-indol-5-amine, 10 mg of tris(dibenzylideneacetone)dipalladium(0), 18 mg of 4,5'-bis(diphenylphosphino)-9,9'-dimethylxanthene, 342 mg of cesium carbonate and 4 mL of toluene were added, and the resultant was stirred at 190° C. for one hour and 30 minutes using microwave equipment. After cooling the reaction mixture to room temperature, the insoluble matter was filtered off and the solvent was distilled off under reduced pressure. The obtained residue was purified by silica gel column chromatography (gradient elution with hexane:ethyl acetate=100:0-75:25) to give methyl 2-((1-benzyl-1H-indol-5-yl)amino)-5-methylbenzoate as a yellow oil.

MS (ESI, m/z): 371 (M+H)$^+$.

Example 206

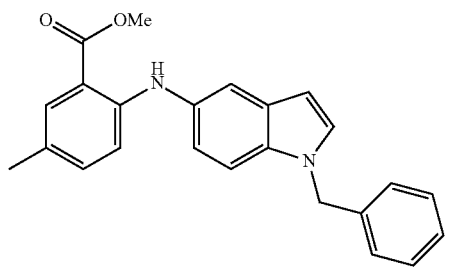

[Formula 453]

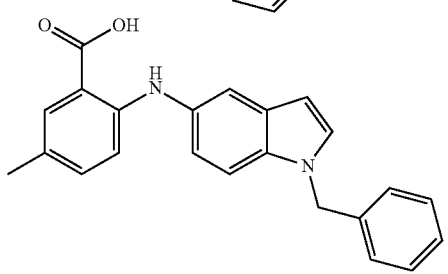

To the mixed solution of methyl 2-((1-benzyl-1H-indol-5-yl)amino)-5-methylbenzoate obtained in Example 205 in 2 mL of methanol and 4 mL of tetrahydrofuran, 1 mL of a 1 mol/L aqueous sodium hydroxide solution was added, and the resultant was stirred at an external temperature of 60 to 70° C. for five hours. After cooling the reaction mixture to room temperature, the solvent was distilled off under reduced pressure. 1.5 mL of 1 mol/L hydrochloric acid, 1 mL of methanol and 5 mL of water were added to the obtained residue, and the solid was collected by filtration to give 10 mg of 2-((1-benzyl-1H-indol-5-yl)amino)-5-methylbenzoic acid as a yellow solid.

$^1$H-NMR (DMSO-$d_6$) δ: 2.18 (3H, s), 5.42 (2H, s), 6.44 (1H, d, J=2.6 Hz), 6.89 (1H, d, J=8.6 Hz), 6.96 (1H, dd, J=8.6, 2.0 Hz), 7.08-7.68 (10H, m), 9.34 (1H, brs).

MS (ESI, m/z): 357 (M+H)$^+$.

Example 207

[Formula 454]

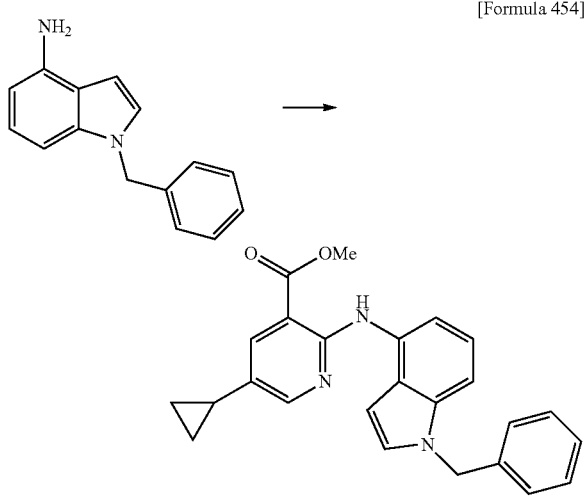

The mixture of 184 mg of 1-benzyl-1H-indol-4-amine, 172 mg of methyl 2-chloro-5-cyclopropylnicotinate, 16 mg of tris(dibenzylideneacetone)dipalladium(0), 28 mg of 4,5'-bis(diphenylphosphino)-9,9'-dimethylxanthene, 624 mg of cesium carbonate, and 14 mL of toluene, was stirred at 190° C. for one hour and 30 minutes using microwave equipment. After cooling the reaction mixture to room temperature, the insoluble matter was filtered off and the solvent was distilled off under reduced pressure. The obtained residue was purified by silica gel column chromatography (gradient elution with hexane:ethyl acetate=91:9-50:50) to give methyl 2-((1-benzyl-1H-indol-4-yl)amino)-5-cyclopropylnicotinate.

MS (ESI, m/z): 398 (M+H)$^+$.

Example 208

[Formula 455]

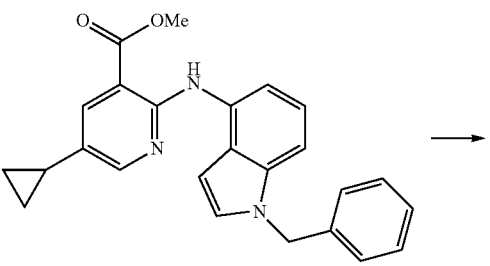

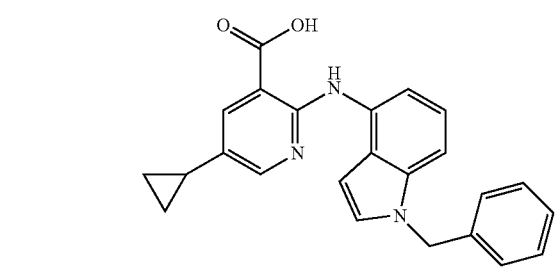

To the mixed solution of methyl 2-((1-benzyl-1H-indol-4-yl)amino)-5-cyclopropylnicotinate obtained in Example 207 in 2 mL of methanol and 4 mL of tetrahydrofuran, 1 mL of a 1 mol/L aqueous sodium hydroxide solution was added, and the resultant was heated at reflux for two hours. After cooling the reaction mixture to room temperature, the solvent was distilled off under reduced pressure. Water was added to the obtained residue and the resultant was adjusted to pH 2.5 to 3.0 with 1 mol/L hydrochloric acid, followed by addition of methanol. The solid was collected by filtration to give 220 mg of 2-((1-benzyl-1H-indol-4-yl)amino)-5-cyclopropylnicotinic acid as a yellow solid.

$^1$H-NMR (DMSO-$d_6$) δ: 0.64-0.72 (2H, m), 0.90-0.98 (2H, m), 1.88-2.00 (1H, m), 5.42 (2H, s), 6.54 (1H, d, J=3.3 Hz), 7.02-7.12 (2H, m), 7.16-7.34 (5H, m), 7.51 (1H, d, J=3.3 Hz), 7.94 (1H, d, J=2.6 Hz), 8.17 (1H, dd, J=6.9, 1.7 Hz), 8.30 (1H, d, J=2.0 Hz), 10.82 (1H, brs).

MS (ESI, m/z): 384 (M+H)$^+$.

Example 209

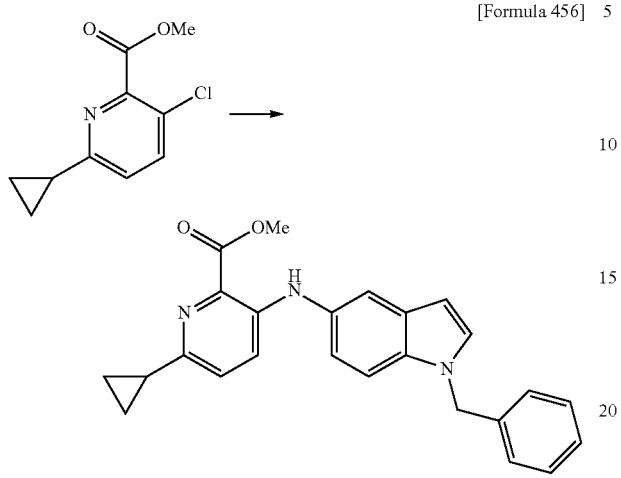

[Formula 456]

The mixture of 221 mg of methyl 3-chloro-6-cyclopropylpicolinate, 253 mg of 1-benzyl-1H-indol-5-amine, 19 mg of tris(dibenzylideneacetone)dipalladium(0), 36 mg of 4,5'-bis(diphenylphosphino)-9,9'-dimethylxanthene, 710 mg of cesium carbonate, and 15 mL of dioxane, was stirred at 180° C. for one hour using microwave equipment. After cooling the reaction mixture to room temperature, the insoluble matter was filtered off and the solvent was distilled off under reduced pressure. The obtained residue was purified by silica gel column chromatography (gradient elution with hexane:ethyl acetate=95:5-67:33) to give methyl 3-((1-benzyl-1H-indol-5-yl)amino)-6-cyclopropylpicolinate.

MS (ESI, m/z): 398 (M+H)$^+$.

Example 210

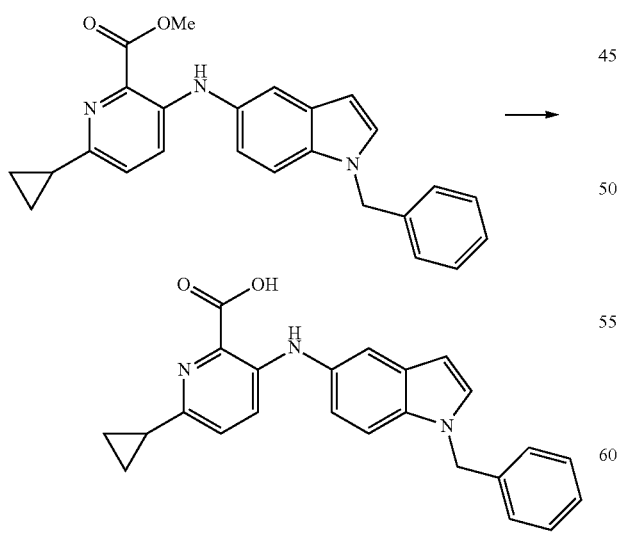

[Formula 457]

To the mixed solution of methyl 3-((1-benzyl-1H-indol-5-yl)amino)-6-cyclopropylpicolinate obtained in Example 209 in 4 mL of methanol and 8 mL of tetrahydrofuran, 2 mL of a 1 mol/L aqueous sodium hydroxide solution was added, and the resultant was stirred at an external temperature of 40 to 50° C. for three hours. After cooling the reaction mixture to room temperature, the solvent was distilled off under reduced pressure. Water was added to the obtained residue and the resultant was adjusted to pH 2.5 to 3.0 with 1 mol/L hydrochloric acid. The solid was collected by filtration to give 70 mg of 3-((1-benzyl-1H-indol-5-yl)amino)-6-cyclopropylpicolinic acid as a yellow solid.

$^1$H-NMR (DMSO-d$_6$) δ: 0.80-0.87 (4H, m), 1.96-2.07 (1H, m), 5.40 (2H, s), 6.41 (1H, d, J=2.6 Hz), 6.90 (1H, dd, J=8.6, 2.0 Hz), 7.01 (1H, d, J=8.6 Hz), 7.18-7.35 (7H, m), 7.41 (1H, d, J=8.6 Hz), 7.49 (1H, d, J=3.3 Hz).

MS (ESI, m/z): 384 (M+H)$^+$.

Example 2111

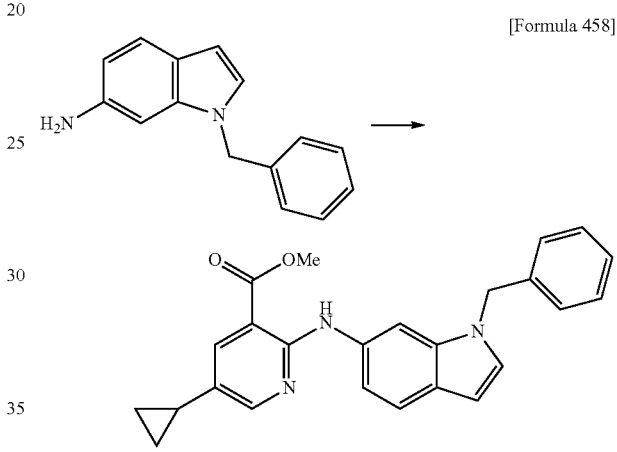

[Formula 458]

The mixture of 92 mg of 1-benzyl-1H-indol-6-amine, 86 mg of methyl 2-chloro-5-cyclopropylnicotinate, 8 mg of tris(dibenzylideneacetone)dipalladium(0), 14 mg of 4,5'-bis(diphenylphosphino)-9,9'-dimethylxanthene, 312 mg of cesium carbonate, and 4 mL of toluene, was stirred at 190° C. for one hour and 30 minutes using microwave equipment. After cooling the reaction mixture to room temperature, the insoluble matter was filtered off and the solvent was distilled off under reduced pressure. The obtained residue was purified by silica gel column chromatography (gradient elution with hexane:ethyl acetate=91:9-50:50) to give methyl 2-((1-benzyl-1H-indol-6-yl)amino)-5-cyclopropylnicotinate.

MS (ESI, m/z): 398 (M+H)$^+$.

Example 212

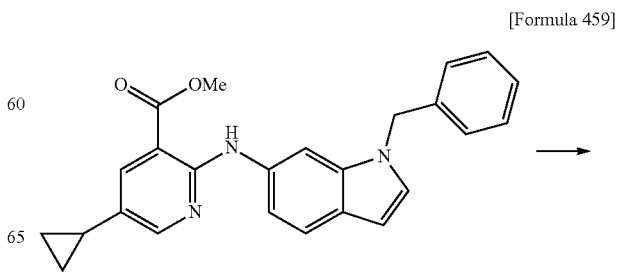

[Formula 459]

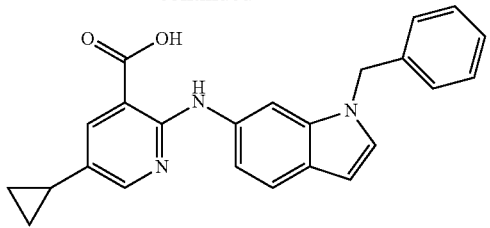

To the mixed solution of methyl 2-((1-benzyl-1H-indol-6-yl)amino)-5-cyclopropylnicotinate obtained in Example 211 in 2 mL of methanol and 4 mL of tetrahydrofuran, 1 mL of a 1 mol/L aqueous sodium hydroxide solution was added, and the resultant was heated at reflux for three hours. After cooling the reaction mixture to room temperature, the solvent was distilled off under reduced pressure. Methanol and water were added to the obtained residue and the resultant was adjusted to pH 2.5 to 3.0 with 1 mol/L hydrochloric acid. The solid was collected by filtration to give 136 mg of 2-((1-benzyl-1H-indol-6-yl)amino)-5-cyclopropylnicotinic acid as a yellow solid.

$^1$H-NMR (DMSO-$d_6$) δ: 0.62-0.68 (2H, m), 0.88-0.97 (2H, m), 1.86-1.98 (1H, m), 5.36 (2H, s), 6.41 (1H, d, J=2.6 Hz), 7.11 (1H, dd, J=8.6, 1.3 Hz), 7.20-7.48 (7H, m), 7.86 (1H, d, J=2.6 Hz), 8.02 (1H, s), 8.19 (1H, d, J=2.6 Hz), 10.38 (1H, brs).

MS (ESI, m/z): 384 (M+H)$^+$.

Example 213

[Formula 460]

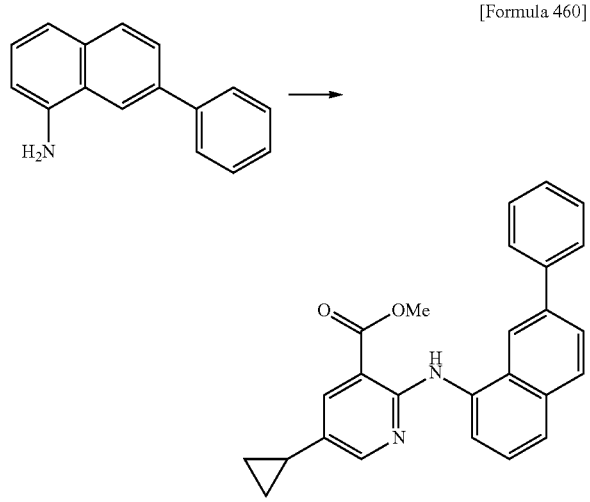

The mixture of 96 mg of 7-phenylnaphthalen-1-amine, 85 mg of methyl 2-chloro-5-cyclopropylnicotinate, 7 mg of tris(dibenzylideneacetone)dipalladium(0), 14 mg of 4,5'-bis(diphenylphosphino)-9,9'-dimethylxanthene, 274 mg of cesium carbonate, and 4 mL of toluene, was stirred at 190° C. for one hour using microwave equipment. After cooling the reaction mixture to room temperature, the insoluble matter was filtered off and the solvent was distilled off under reduced pressure. The obtained residue was purified by silica gel column chromatography (gradient elution with hexane:ethyl acetate=95:5-75:25) to give methyl 5-cyclopropyl-2-((7-phenylnaphthalen-1-yl)amino)nicotinate as a yellow solid.

MS (ESI, m/z): 395 (M+H)$^+$.

Example 214

[Formula 461]

To the mixed solution of methyl 5-cyclopropyl-2-((7-phenylnaphthalen-1-yl)amino)nicotinate obtained in Example 213 in 2 mL of methanol and 4 mL of tetrahydrofuran, 1 mL of a 1 mol/L aqueous sodium hydroxide solution was added, and the resultant was heated at reflux for one hour. After cooling the reaction mixture to room temperature, the solvent was distilled off under reduced pressure. Methanol and water were added to the obtained residue and the resultant was adjusted to pH 2.5 to 3.0 with 1 mol/L hydrochloric acid. The solid was collected by filtration to give 79 mg of 5-cyclopropyl-2-((7-phenylnaphthalen-1-yl)amino)nicotinic acid as a yellow solid.

$^1$H-NMR (DMSO-$d_6$) δ: 0.66-0.74 (2H, m), 0.91-0.99 (2H, m), 1.91-2.02 (1H, m), 7.38-7.58 (4H, m), 7.64 (1H, d, J=7.9 Hz), 7.78-7.83 (2H, m), 7.88 (1H, dd, J=8.6, 1.3 Hz), 7.97-8.08 (2H, m), 8.29 (1H, d, J=2.6 Hz), 8.40 (1H, s), 8.60 (1H, d, J=7.9 Hz), 11.23 (1H, brs).

MS (ESI, m/z): 381 (M+H)$^+$.

Example 215

[Formula 462]

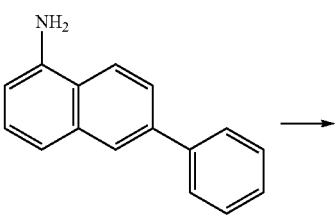

-continued

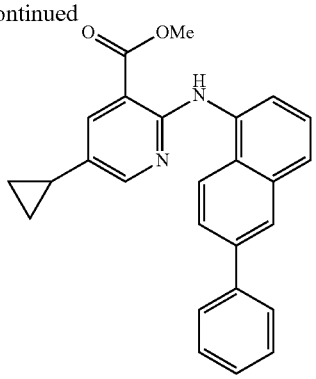

The mixture of 96 mg of 6-phenylnaphthalen-1-amine, 85 mg of methyl 2-chloro-5-cyclopropylnicotinate, 7 mg of tris(dibenzylideneacetone)dipalladium(0), 14 mg of 4,5'-bis(diphenylphosphino)-9,9'-dimethylxanthene, 274 mg of cesium carbonate, and 4 mL of toluene, was stirred at 190° C. for one hour using microwave equipment. After cooling the reaction mixture to room temperature, the insoluble matter was filtered off and the solvent was distilled off under reduced pressure. The obtained residue was purified by silica gel column chromatography (gradient elution with hexane:ethyl acetate=95:5-75:25) to give methyl 5-cyclopropyl-2-((6-phenylnaphthalen-1-yl)amino)nicotinate as a yellow solid.

MS (ESI, m/z): 395 (M+H)+.

Example 216

[Formula 463]

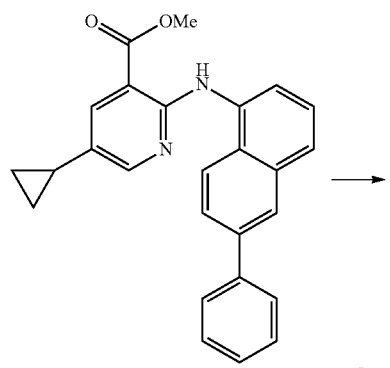

To the mixed solution of methyl 5-cyclopropyl-2-((6-phenylnaphthalen-1-yl)amino)nicotinate obtained in Example 215 in 2 mL of methanol and 4 mL of tetrahydrofuran, 1 mL of a 1 mol/L aqueous sodium hydroxide solution was added, and the resultant was heated at reflux for one hour. After cooling the reaction mixture to room temperature, the solvent was distilled of under reduced pressure. Methanol and water were added to the obtained residue and the resultant was adjusted to pH 2.5 to 3.0 with 1 mol/L hydrochloric acid. The solid was collected by filtration to give 30 mg of 5-cyclopropyl-2-((6-phenylnaphthalen-1-yl)amino)nicotinic acid as a yellow solid.

1H-NMR (DMSO-d6) δ: 0.64-0.72 (2H, m), 0.90-0.98 (2H, m), 1.90-1.99 (1H, m), 7.41 (1H, t, J=7.3 Hz), 7.49-7.56 (3H, m), 7.69 (1H, d, J=7.9 Hz), 7.82-7.98 (4H, m), 8.18-8.26 (3H, m), 8.46 (1H, d, J=7.9 Hz).

MS (ESI, m/z): 381 (M+H)+.

Example 217

[Formula 464]

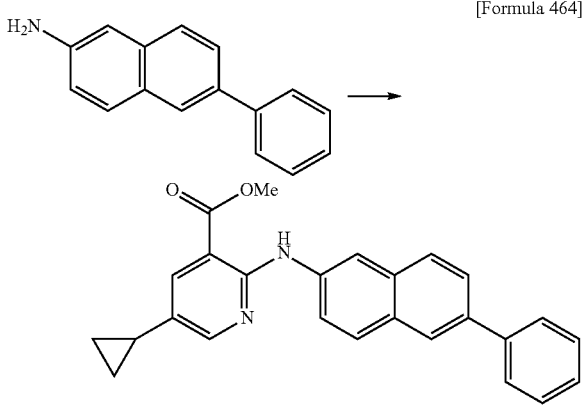

By the method similar to that of Example 215, methyl 5-cyclopropyl-2-((6-phenylnaphthalen-2-yl)amino)nicotinate was obtained from 6-phenylnaphthalen-2-amine and methyl 2-chloro-5-cyclopropylnicotinate.

MS (ESI, m/z): 395 (M+H)+.

Example 218

[Formula 465]

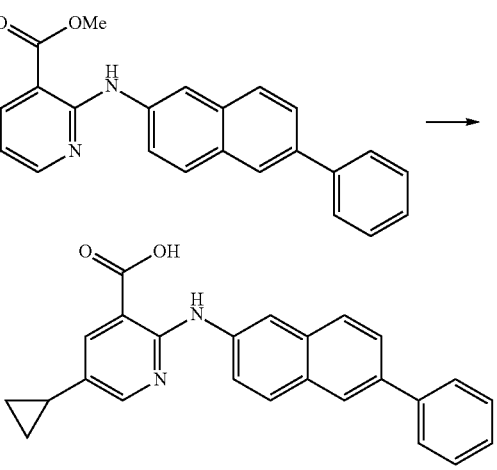

By the method similar to that of Example 216, 5-cyclopropyl-2-((6-phenylnaphthalen-2-yl)amino)nicotinic acid was obtained from methyl 5-cyclopropyl-2-((6-phenylnaphthalen-2-yl)amino)nicotinate.

$^1$H-NMR (DMSO-$d_6$) δ: 0.68-0.75 (2H, m), 0.92-1.01 (2H, m), 1.92-2.03 (1H, m), 7.38 (1H, t, J=7.3 Hz), 7.51 (2H, t, J=7.6 Hz), 7.66-7.98 (7H, m), 8.14 (1H, s), 8.35 (1H, d, J=2.6 Hz), 8.49 (1H, s), 10.59 (1H, s).

MS (ESI, m/z): 381 (M+H)$^+$.

Example 219

[Formula 466]

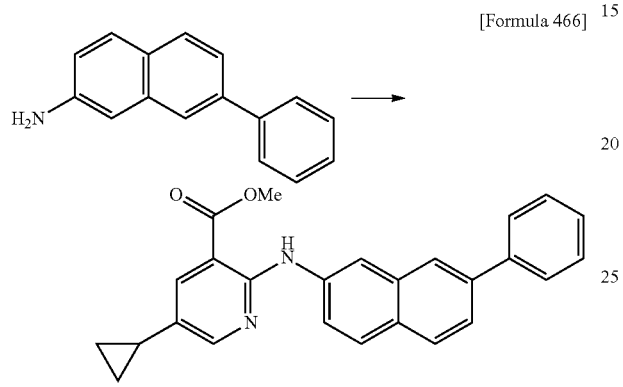

The mixture of 61 mg of 7-phenylnaphthalen-2-amine, 65 mg of methyl 2-chloro-5-cyclopropylnicotinate, 5 mg of tris(dibenzylideneacetone)dipalladium(0), 10 mg of 4,5'-bis(diphenylphosphino)-9,9'-dimethylxanthene, 128 mg of cesium carbonate, and 4 mL of toluene, was stirred at 190° C. for one hour using microwave equipment. After cooling the reaction mixture to room temperature, the insoluble matter was filtered off and the solvent was distilled off under reduced pressure. The obtained residue was purified by silica gel column chromatography (gradient elution with hexane:ethyl acetate=100:0-75:25) to give methyl 5-cyclopropyl-2-((7-phenylnaphthalen-2-yl)amino)nicotinate.

MS (ESI, m/z): 395 (M+H)$^+$.

Example 220

[Formula 467]

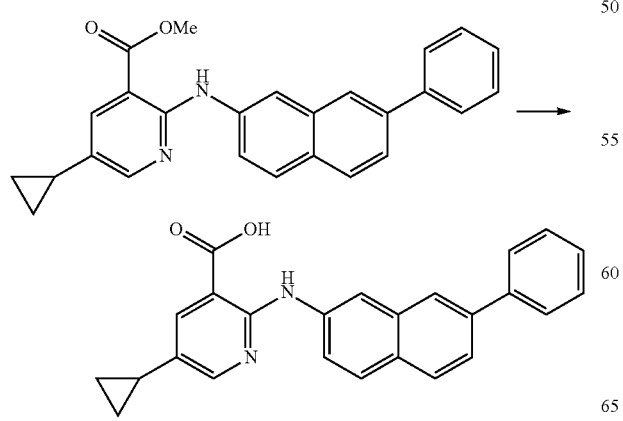

To the mixed solution of methyl 5-cyclopropyl-2-((7-phenylnaphthalen-2-yl)amino)nicotinate obtained in Example 219 in 2 mL of methanol and 4 mL of tetrahydrofuran, 1 mL of a 1 mol/L aqueous sodium hydroxide solution was added, and the resultant was heated at reflux for two hours. After cooling the reaction mixture to room temperature, the solvent was distilled off under reduced pressure. Methanol and water were added to the obtained residue and the resultant was adjusted to pH 2.5 to 3.0 with 1 mol/L hydrochloric acid. The solid was collected by filtration and washed with water to give 23 mg of 5-cyclopropyl-2-((7-phenylnaphthalen-2-yl)amino)nicotinic acid as a yellow solid.

$^1$H-NMR (DMSO-$d_6$) δ: 0.67-0.74 (2H, m), 0.92-0.99 (2H, m), 1.91-2.03 (1H, m), 7.40 (1H, t, J=7.3 Hz), 7.52 (2H, t, J=7.3 Hz), 7.65-7.71 (2H, m), 7.79-7.97 (5H, m), 8.08 (1H, s), 8.33 (1H, d, J=2.6 Hz), 8.53 (1H, d, J=1.3 Hz), 10.64 (1H, brs).

MS (ESI, m/z): 381 (M+H)$^+$.

Example 221

[Formula 468]

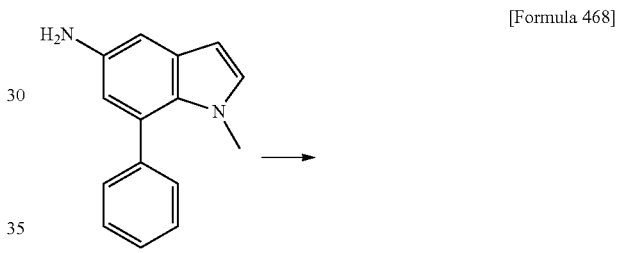

The mixture of 1-methyl-7-phenyl-1H-indol-5-amine obtained in Reference Example 64, 106 mg of methyl 2-chloro-5-cyclopropylnicotinate, 9 mg of tris(dibenzylideneacetone)dipalladium(0), 17 mg of 4,5'-bis(diphenylphosphino)-9,9'-dimethylxanthene, 228 mg of cesium carbonate, and 4 mL of toluene, was stirred at 190° C. for one hour using microwave equipment. After cooling the reaction mixture to room temperature, the insoluble matter was filtered off and the solvent was distilled off under reduced pressure. The obtained residue was purified by silica gel column chromatography (gradient elution with hexane:ethyl acetate=95:5-75:25) to give methyl 5-cyclopropyl-2-((1-methyl-7-phenyl-1H-indol-5-yl)amino)nicotinate.

MS (ESI, m/z): 398 (M+H)$^+$.

Example 222

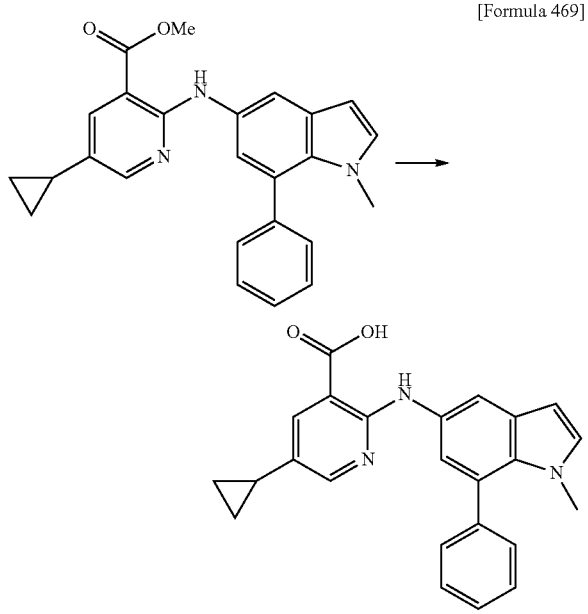

To the mixed solution of methyl 5-cyclopropyl-2-((1-methyl-7-phenyl-1H-indol-5-yl)amino)nicotinate obtained in Example 221 in 2 mL of methanol and 4 mL of tetrahydrofuran, 1 mL of a 1 mol/L aqueous sodium hydroxide solution was added, and the resultant was heated at reflux for one hour. After cooling the reaction mixture to room temperature, the solvent was distilled off under reduced pressure. Methanol and water were added to the obtained residue and the resultant was adjusted to pH 2.5 to 3.0 with 1 mol/L hydrochloric acid. The solid was collected by filtration to give 171 mg of 5-cyclopropyl-2-((1-methyl-7-phenyl-1H-indol-5-yl)amino)nicotinic acid as a yellow solid.

$^1$H-NMR (DMSO-$d_6$) δ: 0.61-0.67 (2H, m), 0.85-0.94 (2H, m), 1.84-1.95 (1H, m), 3.25 (3H, s), 6.45 (1H, d, J=3.3 Hz), 7.00 (1H, d, J 2.0 Hz), 7.23 (1H, d, J=3.3 Hz), 7.43-7.49 (5H, m), 7.87 (1H, d, J=2.6 Hz), 8.05 (1H, d, J=2.0 Hz), 8.19 (1H, d, J=2.6 Hz), 10.35 (1H, brs).

MS (ESI, m/z): 384 (M+H)$^+$.

Example 223

[Formula 470]

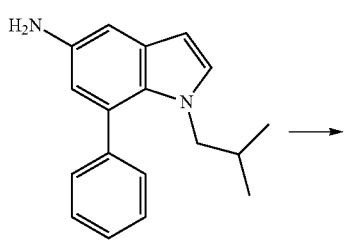

[Formula 469]

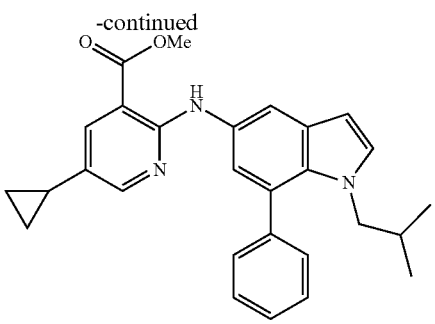

The mixture of 1-isobutyl-7-phenyl-1H-indol-5-amine obtained in Reference Example 66, 106 mg of methyl 2-chloro-5-cyclopropylnicotinate, 9 mg of tris(dibenzylideneacetone)dipalladium(0), 17 mg of 4,5'-bis(diphenylphosphino)-9,9'-dimethylxanthene, 228 mg of cesium carbonate, and 4 mL of toluene, was stirred at 190° C. for one hour using microwave equipment. After cooling the reaction mixture to room temperature, the insoluble matter was filtered off and the solvent was distilled off under reduced pressure. The obtained residue was purified by silica gel column chromatography (gradient elution with hexane:ethyl acetate=95:5-75:25) to give methyl 5-cyclopropyl-2-((1-isobutyl-7-phenyl-1H-indol-5-yl)amino)nicotinate.

MS (ESI, m/z): 440 (M+H)$^+$.

Example 224

[Formula 471]

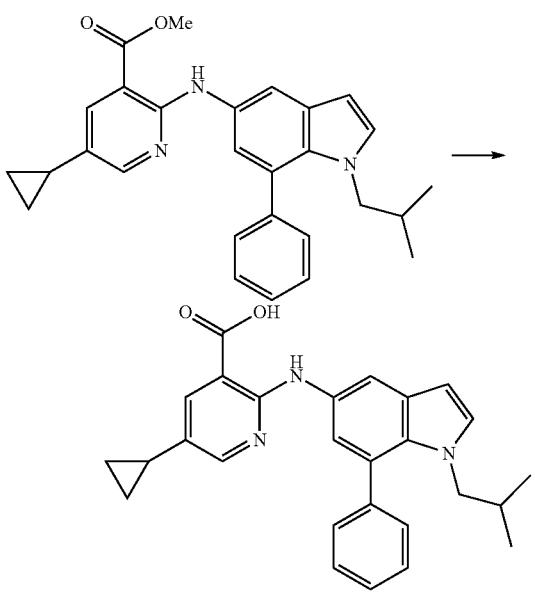

To the mixed solution of methyl 5-cyclopropyl-2-((1-isobutyl-7-phenyl-1H-indol-5-yl)amino)nicotinate obtained in Example 223 in 2 mL of methanol and 4 mL of tetrahydrofuran, 1 mL of a 1 mol/L aqueous sodium hydroxide solution was added, and the resultant was heated at reflux for one hour. After cooling the reaction mixture to room temperature, the solvent was distilled off under reduced pressure. Methanol and water were added to the obtained residue and the resultant was adjusted to pH 2.5 to 3.0 with 1 mol/L hydrochloric acid. The solid was collected by filtration to give 17 mg of 5-cyclopropyl-2-((1-isobutyl-7-phenyl-1H-indol-5-0)amino)nicotinic acid as a yellow solid.

$^1$H-NMR (DMSO-d$_6$) δ: 0.35 (6H, d, J=6.6 Hz), 0.62-0.69 (2H, m), 0.80-0.93 (2H, m), 1.31-1.42 (1H, m), 1.84-1.95 (1H, m), 3.52 (2H, d, J=6.6 Hz), 6.45 (1H, d, J=3.3 Hz), 6.98 (1H, d, J=2.0 Hz), 7.27 (1H, d, J=2.6 Hz), 7.43-7.51 (5H, m), 7.87 (1H, d, J=2.6 Hz), 8.04 (1H, d, J=2.0 Hz), 8.20 (1H, d, J=2.0 Hz), 10.24 (1H, s).

MS (ESI, m/z): 426 (M+H)$^+$.

Example 225

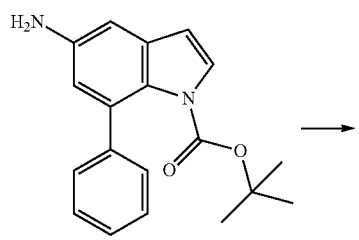

[Formula 472]

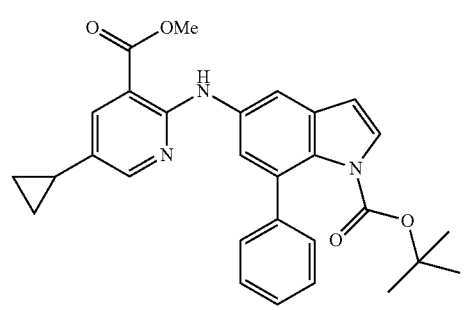

The mixture of tert-butyl 5-amino-7-phenyl-1H-indole-1-carboxylate obtained in Reference Example 68, 116 mg of methyl 2-chloro-5-cyclopropylnicotinate, 23 mg of tris(dibenzylideneacetone)dipalladium(0), 43 mg of 4,5'-bis(diphenylphosphino)-9,9'-dimethylxanthene, 407 mg of cesium carbonate, and 10 mL of butyl acetate, was heated at reflux for seven hours under a nitrogen atmosphere. After cooling the reaction mixture to room temperature, the insoluble matter was filtered off and the solvent was distilled off under reduced pressure. The obtained residue was purified by silica gel column chromatography (gradient elution with hexane:ethyl acetate=95:5-75:25) to give tert-butyl 5-((5-cyclopropyl-3-(methoxycarbonyl)pyridin-2-yl)amino)-7-phenyl-1H-indole-1-carboxylate.

MS (ESI, m/z): 484 (M+H)$^+$.

Example 226

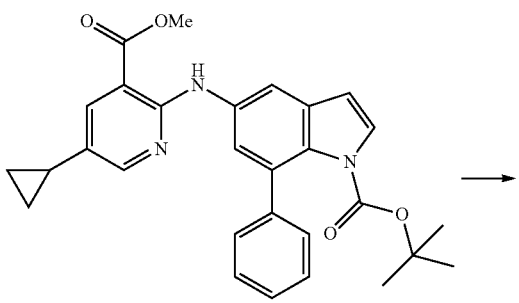

[Formula 473]

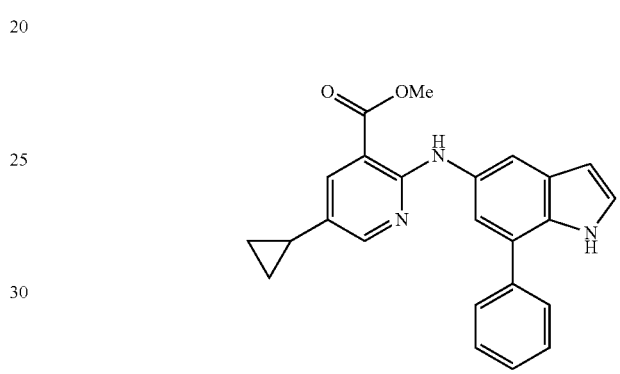

The solution of tert-butyl 5-((5-cyclopropyl-3-(methoxycarbonyl)pyridin-2-yl)amino)-7-phenyl-1H-indole-1-carboxylate obtained in Example 225 in 10 mL of N,N-dimethylacetamide was stirred at 150 to 160° C. for six hours. After cooling the reaction mixture to room temperature, the solvent was distilled off under reduced pressure. The obtained residue was purified by silica gel column chromatography (gradient elution with hexane:ethyl acetate=95:5-67:33) to give methyl 5-cyclopropyl-2-((7-phenyl-1H-indol-5-yl)amino)nicotinate as a yellow oil.

MS (ESI, m/z): 384 (M+H)$^+$.

Example 227

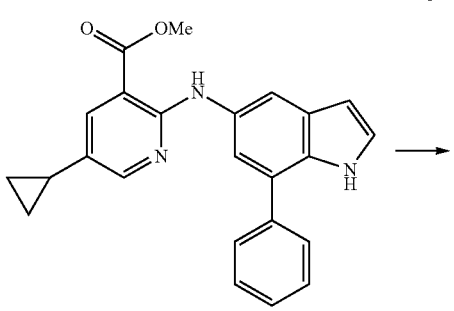

[Formula 474]

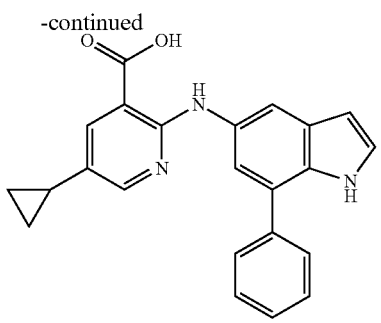

To the mixed solution of methyl 5-cyclopropyl-2-((7-phenyl-1H-indol-5-yl)amino)nicotinate obtained in Example 226 in 2 mL of methanol and 4 mL of tetrahydrofuran, 1 mL of a 1 mol/L aqueous sodium hydroxide solution was added, and the resultant was heated at reflux for one hour. After cooling the reaction mixture to room temperature, the solvent was distilled off under reduced pressure. Methanol and water were added to the obtained residue and the resultant was adjusted to pH 2.5 to 3.0 with 1 mol/L hydrochloric acid. The solid was collected by filtration to give 5 mg of 5-cyclopropyl-2-((7-phenyl-1H-indol-5-yl)amino)nicotinic acid as a yellow solid.

$^1$H-NMR (DMSO-$d_6$) δ: 0.61-0.69 (2H, m), 0.87-0.97 (2H, m), 1.84-1.95 (1H, m), 6.44-6.50 (1H, m), 7.22 (1H, d, J=2.0 Hz), 7.29 (1H, t, J=2.6 Hz), 7.42 (1H, t, J=7.3 Hz), 7.53 (2H, t, J=7.3 Hz), 7.67 (2H, d, J=7.3 Hz), 7.88 (1H, d, J=2.6 Hz), 7.96 (1H, d, J=1.3 Hz), 8.20 (1H, d, J=2.6 Hz), 10.18 (1H, s), 10.89 (1H, s).

MS (ESI, m/z): 370 (M+H)$^+$.

Example 228

[Formula 475]

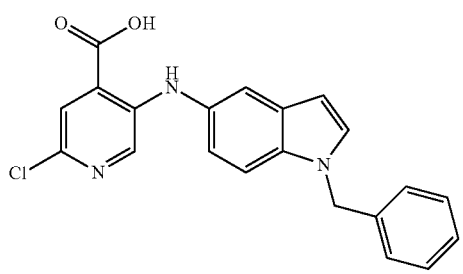

To tert-butyl 5-bromo-2-chloroisonicotinate obtained in Reference Example 71, 111 mg of 1-benzyl-1H-indol-5-amine, 10 mg of tris(dibenzylideneacetone)dipalladium(0), 18 mg of 4,5'-bis(diphenylphosphino)-9,9'-dimethylxanthene, 342 mg of cesium carbonate and 4 mL of toluene were added, and the resultant was stirred at 190° C. for one hour using microwave equipment. After cooling the reaction mixture to room temperature, the insoluble matter was filtered off and the solvent was distilled off under reduced pressure. The obtained residue was purified by silica gel column chromatography (gradient elution with hexane:ethyl acetate=100:0-80:20) to give tert-butyl 5-((1-benzyl-1H-indol-5-yl)amino)-2-chloroisonicotinate.

MS (ESI, m/z): 434 (M+H)$^+$.

Example 229

[Formula 476]

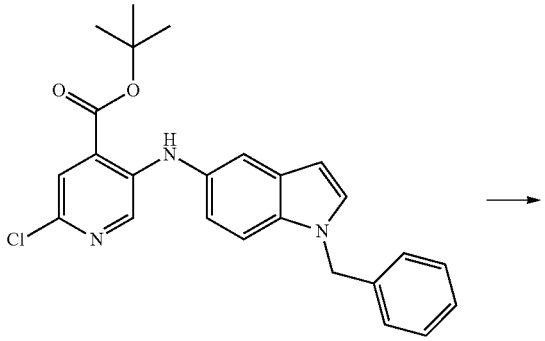

To the mixed solution of tert-butyl 5-((1-benzyl-1H-indol-5-yl)amino)-2-chloroisonicotinate obtained in Example 228 in 2 mL of methanol and 4 mL of tetrahydrofuran, 1 mL of a 1 mol/L aqueous sodium hydroxide solution was added, and the resultant was stirred for three hours. The solvent was distilled off from the reaction mixture under reduced pressure. Water was added to the obtained residue and the resultant was adjusted to pH 2.5 to 3.0 with 1 mol/L hydrochloric acid, followed by addition of ethyl acetate. The organic layer was separated and dried over anhydrous magnesium sulfate, and the solvent was then distilled off under reduced pressure. Ethyl acetate and hexane were added to the thus obtained residue, and the solid was collected by filtration to give 3 mg of 5-((1-benzyl-1H-indol-5-yl)amino)-2-chloroisonicotinic acid as a yellow solid.

$^1$H-NMR (DMSO-$d_6$) δ: 5.44 (2H, s), 6.48 (1H, d, J=3.3 Hz), 7.05 (1H, dd, J=8.6, 2.0 Hz), 7.19-7.38 (5H, m), 7.47-7.53 (2H, m), 7.56 (1H, d, J=2.6 Hz), 7.65 (1H, s), 8.08 (1H, s), 9.09 (1H, s).

MS (ESI, m/z): 378 (M+H)$^+$.

Example 230

[Formula 477]

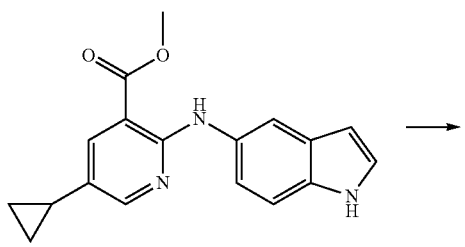

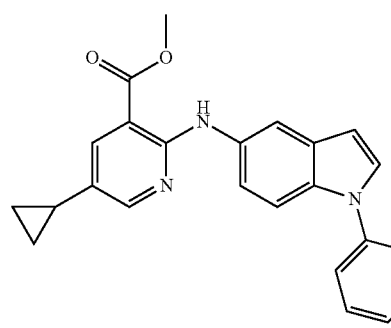

The mixture of 50 mg of methyl 2-((1H-indol-5-yl)amino)-5-cyclopropylnicotinate, 19 μL of 1-fluoro-3-iodobenzene, 2 mg of copper(I) iodide, 4 μL of trans-cyclohexane-1,2-diamine, 70 mg of tripotassium phosphate, and 2 mL of dioxane, was stirred at 180° C. for three hours using microwave equipment. After cooling the reaction mixture to room temperature, the insoluble matter was filtered off and the solvent was distilled off under reduced pressure. The obtained residue was purified by silica gel column chromatography (gradient elution with hexane:ethyl acetate=100:0-75:25) to give methyl 5-cyclopropyl-2-((1-(3-fluorophenyl)-1H-indol-5-yl)amino)nicotinate.

MS (ESI, m/z): 402 (M+H)$^+$.

Example 231

[Formula 478]

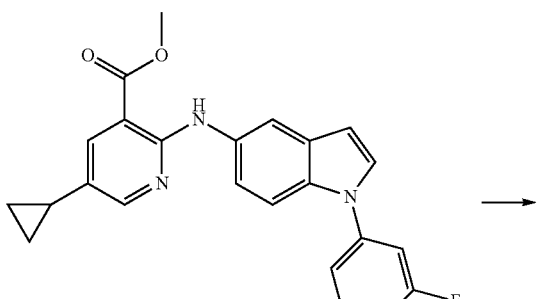

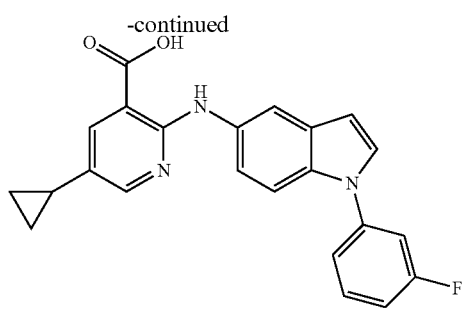

To the mixed solution of methyl 5-cyclopropyl-2-((1-(3-fluorophenyl)-1H-indol-5-yl)amino)nicotinate obtained in Example 230 in 2 mL of methanol and 4 mL of tetrahydrofuran, 1 mL of a 1 mol/L aqueous sodium hydroxide solution was added, and the resultant was heated at reflux for one hour. After cooling the reaction mixture to room temperature, the solvent was distilled off under reduced pressure. Methanol and water were added to the obtained residue and the resultant was adjusted to pH 2.5 to 3.0 with 1 mol/L hydrochloric acid. The solid was collected by filtration to give 12 mg of 5-cyclopropyl-2-((1-(3-fluorophenyl)-1H-indol-5-yl)amino)nicotinic acid as a yellow solid.

$^1$H-NMR (DMSO-d$_6$) δ: 0.63-0.71 (2H, m), 0.89-0.96 (2H, m), 1.87-1.98 (1H, m), 6.69 (1H, d, J=3.3 Hz), 7.18-7.34 (2H, m), 7.46-7.71 (5H, m), 7.90 (1H, d, J=2.6 Hz), 8.15 (1H, d, J=2.0 Hz), 8.23 (1H, d, J=2.6 Hz), 10.26 (1H, s).

MS (ESI, m/z): 388 (M+H)$^+$.

Example 232

[Formula 479]

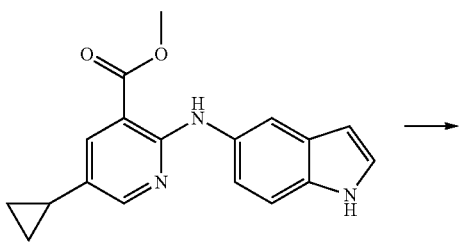

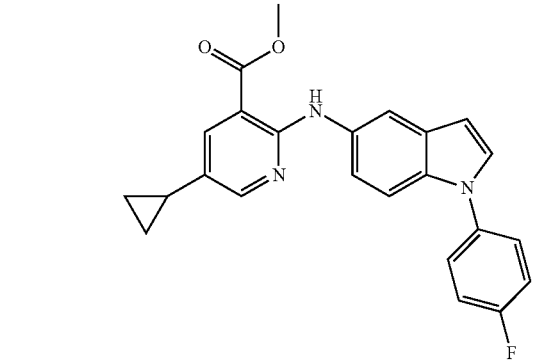

The mixture of 50 mg of methyl 2-((1H-indol-5-yl)amino)-5-cyclopropylnicotinate, 190, of 1-fluoro-4-iodobenzene, 2 mg of copper(I) iodide, 4 μL of trans-cyclohexane-1,2-diamine, 70 mg of tripotassium phosphate, and 2 mL of dioxane, was stirred at 180° C. for three hours using

Example 233

[Formula 480]

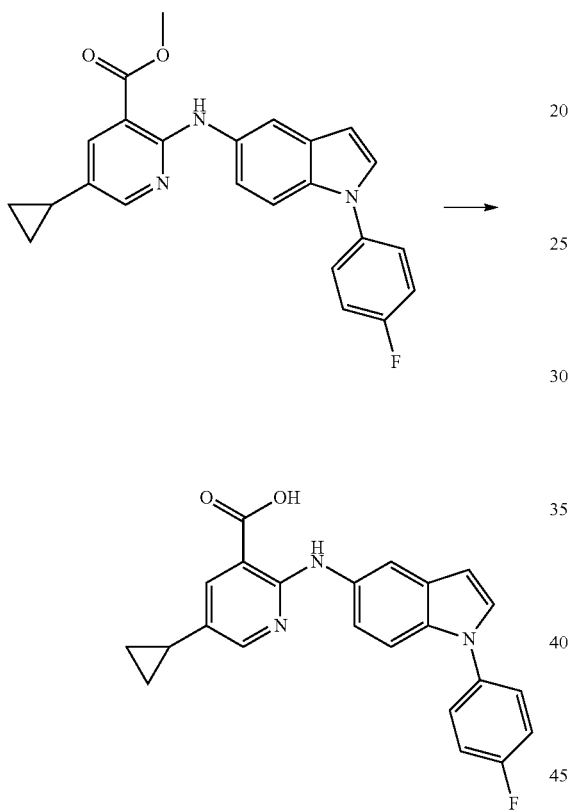

To the mixed solution of methyl 5-cyclopropyl-2-((1-(4-fluorophenyl)-1H-indol-5-yl)amino)nicotinate obtained in Example 232 in 2 mL of methanol and 4 mL of tetrahydrofuran, 1 mL of a 1 mol/L aqueous sodium hydroxide solution was added, and the resultant was heated at reflux for one hour. After cooling the reaction mixture to room temperature, the solvent was distilled off under reduced pressure. Methanol and water were added to the obtained residue and the resultant was adjusted to pH 2.5 to 3.0 with 1 mol/L hydrochloric acid. The solid was collected by filtration to give 14 mg of 5-cyclopropyl-2-((1-(4-fluorophenyl)-1H-indol-5-yl)amino)nicotinic acid as a yellow solid.

$^1$H-NMR (DMSO-$d_6$) δ: 0.62-0.69 (2H, m), 0.89-0.95 (2H, m), 1.87-1.97 (1H, m), 6.66 (1H, d, J=3.3 Hz), 7.27 (1H, dd, J=9.2, 2.0 Hz), 7.37-7.48 (3H, m), 7.59-7.66 (3H, m), 7.89 (1H, d, J=2.6 Hz), 8.14 (1H, d, J 2.0 Hz), 8.22 (1H, d, J 2.6 Hz), 10.23 (1H, s).

MS (ESI, m/z): 388 (M+H)$^+$.

Example 234

[Formula 481]

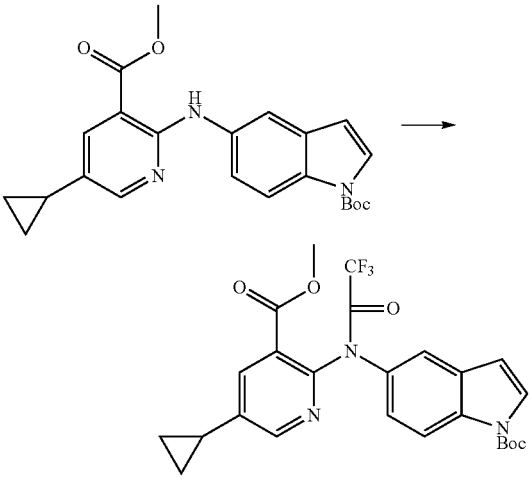

The mixture of 407 mg of tert-butyl 5-((5-cyclopropyl-3-(methoxycarbonyl)pyridin-2-yl)amino)-1H-indole-1-carboxylate, 167 µL of trifluoroacetic anhydride, 0.5 mL of triethylamine, and 10 mL of dichloromethane, was stirred for 30 minutes.

The solvent was distilled off from the reaction mixture under reduced pressure. The obtained residue was purified by silica gel column chromatography (gradient elution with hexane:ethyl acetate=100:0-75:25) to give tert-butyl 5-(N-(5-cyclopropyl-3-(methoxycarbonyl)pyridin-2-yl)-2,2,2-trifluoroacetamido)-1H-indole-1-carboxylate.

MS (ESI, m/z): 504 (M+H)$^+$.

Example 235

[Formula 482]

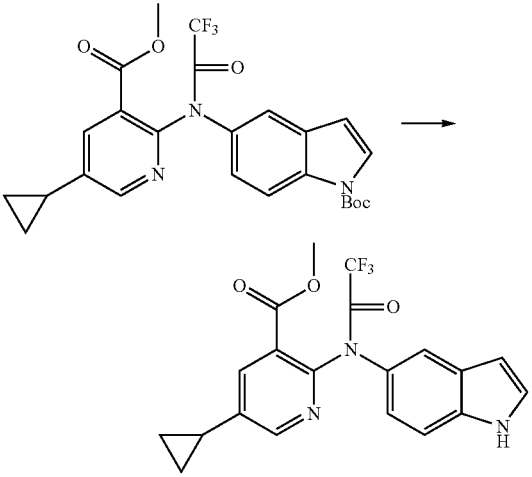

The solution of tert-butyl 5-(N-(5-cyclopropyl-3-(methoxycarbonyl)pyridin-2-yl)-2,2,2-trifluoroacetamido)-1H-indole-1-carboxylate obtained in Example 234 in 20 mL of N,N-dimethylacetamide was stirred at 150 to 160° C. for four hours. After cooling the reaction mixture to room temperature, the solvent was distilled off under reduced pressure. The obtained residue was purified by silica gel column chromatography (gradient elution with hexane:ethyl acetate=91:9-67:33) to give methyl 5-cyclopropyl-2-(2,2,2-trifluoro-N-(1H-indol-5-yl)acetamido)nicotinate.

The obtained methyl 5-cyclopropyl-2-(2,2,2-trifluoro-N-(1H-indol-5-yl)acetamido)nicotinate was dissolved in N,N-dimethylformamide to a total volume of 8 mL.

MS (ESI, m/z): 404 (M+H)+.

Example 236

[Formula 483]

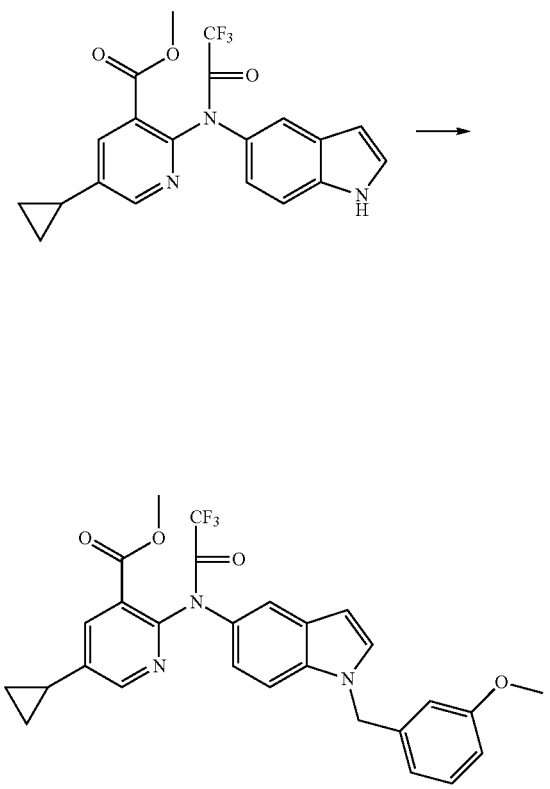

To 2 mL of the solution of methyl 5-cyclopropyl-2-(2,2,2-trifluoro-N-(1H-indol-5-yl)acetamido)nicotinate obtained in Example 235 in N,N-dimethylformamide, 12 mg of 60% sodium hydride was added under ice-cooling, and the resultant was stirred for 15 minutes. To the reaction mixture, 45 μL of 3-methoxybenzyl bromide was added under ice-cooling, and the resultant was stirred at room temperature for 30 minutes. Ethyl acetate and a saturated aqueous sodium chloride solution were added to the reaction mixture. The organic layer was separated and dried over anhydrous magnesium sulfate, and the solvent was then distilled off under reduced pressure. The obtained residue was purified by silica gel column chromatography (gradient elution with hexane:ethyl acetate=100:0-75:25) to give methyl 5-cyclopropyl-2-(2,2,2-trifluoro-N-(1-(3-methoxybenzyl)-1H-indol-5-yl)acetamido)nicotinate.

MS (ESI, m/z): 524 (M+H)+.

Example 237

[Formula 484]

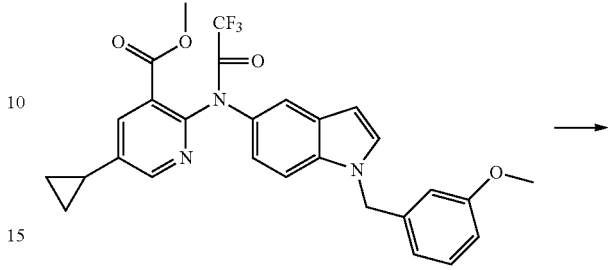

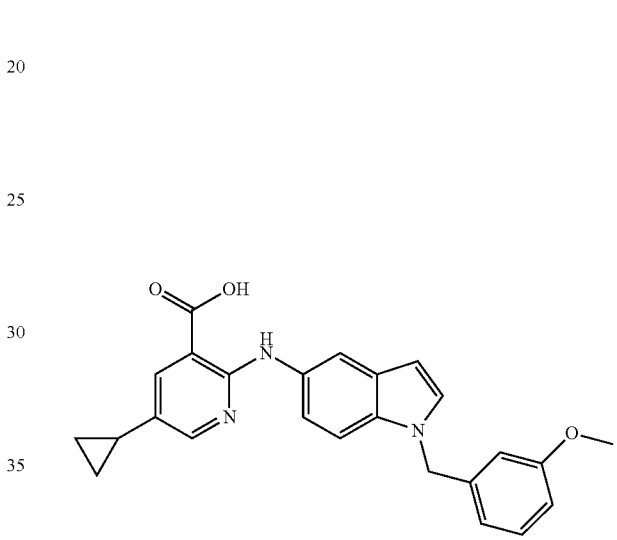

To the mixed solution of methyl 5-cyclopropyl-2-(2,2,2-trifluoro-N-(1-(3-methoxybenzyl)-1H-indol-5-yl)acetamido)nicotinate obtained in Example 236 in 2 mL of methanol and 4 mL of tetrahydrofuran, 1 mL of a 1 mol/L aqueous sodium hydroxide solution was added, and the resultant was heated at reflux for one hour. After cooling the reaction mixture to room temperature, the solvent was distilled off under reduced pressure. Ethyl acetate and water were added to the obtained residue and the resultant was adjusted to pH 2.5 to 3.0 with 1 mol/L hydrochloric acid. The organic layer was separated and dried over anhydrous magnesium sulfate, and the solvent was then distilled off under reduced pressure. The obtained residue was purified by silica gel column chromatography (gradient elution with hexane:ethyl acetate=50:50-0:100), and ethyl acetate and hexane were added to the thus obtained residue, and the solid was collected by filtration to give 5 mg of 5-cyclopropyl-2-((1-(3-methoxybenzyl)-1H-indol-5-yl)amino)nicotinic acid as a yellow solid.

$^1$H-NMR (DMSO-$d_6$) δ: 0.61-0.66 (2H, m), 0.87-0.93 (2H, m), 1.84-1.95 (1H, m), 3.69 (3H, s), 5.36 (2H, s), 6.43 (1H, d, J=2.6 Hz), 6.70-6.84 (3H, m), 7.13-7.24 (2H, m), 7.36 (1H, d, J=9.2 Hz), 7.47 (1H, d, J=3.3 Hz), 7.86 (1H, d, J=2.6 Hz), 7.96 (1H, d, J=2.0 Hz), 8.17 (1H, d, J=2.6 Hz), 10.10 (1H, s).

MS (ESI, m/z): 414 (M+H)+.

Example 238

[Formula 485]

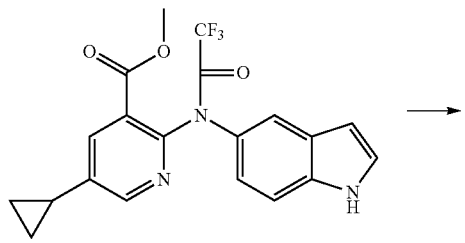

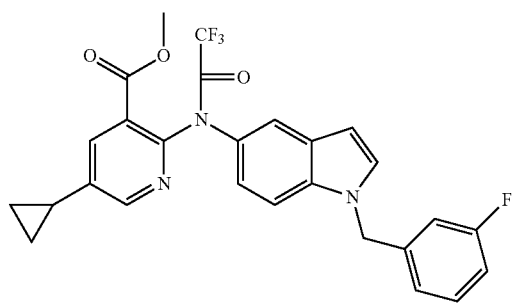

To the solution of 65 mg of methyl 5-cyclopropyl-2-(2,2,2-trifluoro-N-(1H-indol-5-yl)acetamido)nicotinate in 2 mL of N,N-dimethylformamide, 8 mg of 60% sodium hydride and 25 µL of 3-fluorobenzyl bromide were added under ice-cooling, and the resultant was stirred at room temperature for 30 minutes. Ethyl acetate and water were added to the reaction mixture. The organic layer was separated and dried over anhydrous magnesium sulfate, and the solvent was then distilled off under reduced pressure. The obtained residue was purified by silica gel column chromatography (gradient elution with hexane:ethyl acetate=100:0-67:33) to give methyl 5-cyclopropyl-2-(2,2,2-trifluoro-N-(1-(3-fluorobenzyl)-1H-indol-5-yl)acetamido)nicotinate.

MS (ESI, m/z): 512 (M+H)$^+$.

Example 239

[Formula 486]

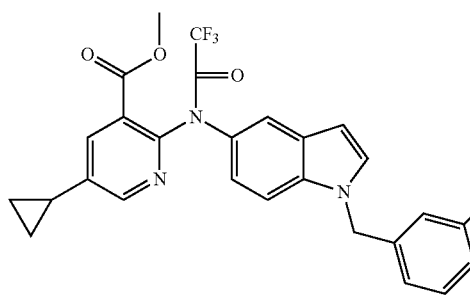

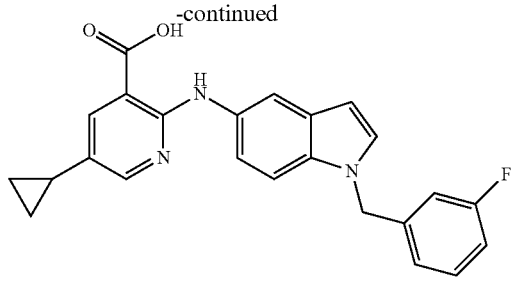

To the mixed solution of methyl 5-cyclopropyl-2-(2,2,2-trifluoro-N-(1-(3-fluorobenzyl)-1H-indol-5-yl)acetamido)nicotinate obtained in Example 238 in 2 mL of methanol and 4 mL of tetrahydrofuran, 1 mL of a 1 mol/L aqueous sodium hydroxide solution was added, and the resultant was heated at reflux for one hour. After cooling the reaction mixture to room temperature, the solvent was distilled off under reduced pressure. Ethyl acetate and water were added to the obtained residue and the resultant was adjusted to pH 2.5 to 3.0 with 1 mol/L hydrochloric acid. The organic layer was separated and dried over anhydrous magnesium sulfate, and the solvent was then distilled off under reduced pressure. The thus obtained residue was purified by silica gel column chromatography (gradient elution with hexane:ethyl acetate=50:50-0:100), and ethyl acetate and hexane were added thereto, and the solid was collected by filtration to give 22 mg of 5-cyclopropyl-2-((1-(3-fluorobenzyl)-1H-indol-5-yl)amino)nicotinic acid as a yellow solid.

$^1$H-NMR (DMSO-d$_6$) δ: 0.61-0.68 (2H, m), 0.86-0.96 (2H, m), 1.85-1.96 (1H, m), 5.43 (2H, s), 6.45 (1H, d, J=3.3 Hz), 6.95-7.20 (4H, m), 7.32-7.40 (2H, m), 7.50 (1H, d, J=3.3 Hz), 7.87 (1H, d, J=2.6 Hz), 7.97 (1H, d, J=2.0 Hz), 8.18 (1H, d, J=2.6 Hz), 10.10 (1H, s).

MS (ESI, m/z): 402 (M+H)$^+$

Example 240

[Formula 487]

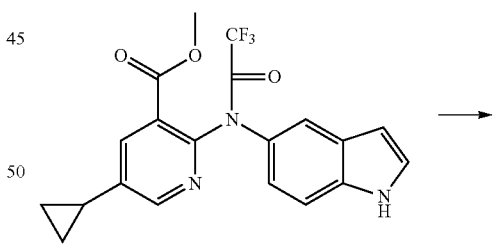

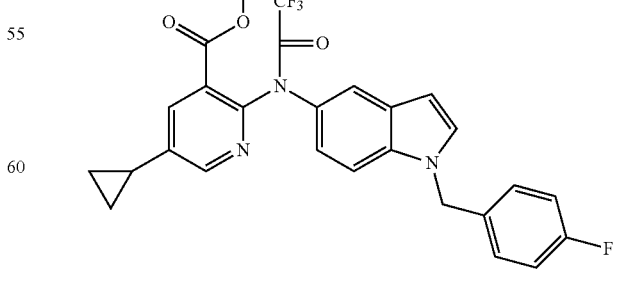

To the solution of 65 mg of methyl 5-cyclopropyl-2-(2,2,2-trifluoro-N-(1H-indol-5-yl)acetamido)nicotinate in 2 mL of N,N-dimethylformamide, 8 mg of 60% sodium hydride and 25 µL of 4-fluorobenzyl bromide were added under ice-cooling, and the resultant was stirred at room temperature for 30 minutes. Ethyl acetate and water were added to the reaction mixture. The organic layer was separated and dried over anhydrous magnesium sulfate, and the solvent was then distilled off under reduced pressure. The obtained residue was purified by silica gel column chromatography (gradient elution with hexane:ethyl acetate=100:0-67:33) to give methyl 5-cyclopropyl-2-(2,2,2-trifluoro-N-(1-(4-fluorobenzyl)-1H-indol-5-yl)acetamido)nicotinate.

MS (ESI, m/z): 512 (M+H)$^+$.

Example 241

[Formula 488]

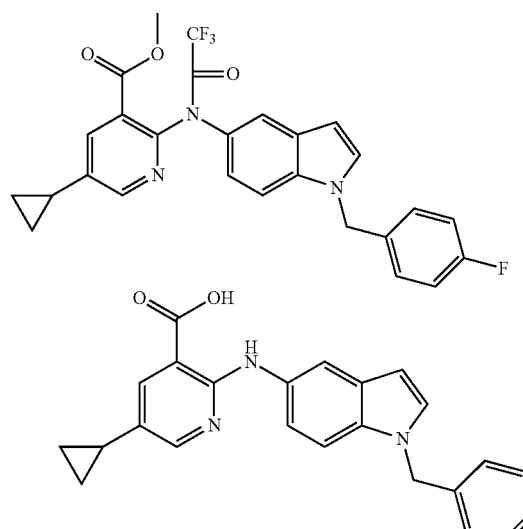

To the mixed solution of methyl 5-cyclopropyl-2-(2,2,2-trifluoro-N-(1-(4-fluorobenzyl)-1H-indol-5-yl)acetamido)nicotinate obtained in Example 240 in 2 mL of methanol and 4 mL of tetrahydrofuran, 1 mL of a 1 mol/L aqueous sodium hydroxide solution was added, and the resultant was heated at reflux for one hour. After cooling the reaction mixture to room temperature, the solvent was distilled off under reduced pressure. Ethyl acetate and water were added to the obtained residue and the resultant was adjusted to pH 2.5 to 3.0 with 1 mol/L hydrochloric acid. The organic layer was separated and dried over anhydrous magnesium sulfate, and the solvent was then distilled off under reduced pressure. The obtained residue was purified by silica gel column chromatography (gradient elution with hexane:ethyl acetate=50:50-0:100), and ethyl acetate and hexane were added to the thus obtained residue, and the solid was collected by filtration to give 21 mg of 5-cyclopropyl-2-((1-(4-fluorobenzyl)-1H-indol-5-yl)amino)nicotinic acid as a yellow solid.

$^1$H-NMR (DMSO-d$_6$) δ: 0.60-0.68 (2H, m), 0.85-0.95 (2H, m), 1.84-1.95 (1H, m), 5.38 (2H, s), 6.43 (1H, d, J=3.3 Hz), 7.09-7.30 (5H, m), 7.38 (1H, d, J=8.6 Hz), 7.48 (1H, d, J=3.3 Hz), 7.86 (1H, d, J=2.6 Hz), 7.96 (1H, d, J=1.3 Hz), 8.17 (1H, d, J=2.6 Hz), 10.10 (1H, s).

MS (ESI, m/z): 402 (M+H)$^+$.

Example 242

[Formula 489]

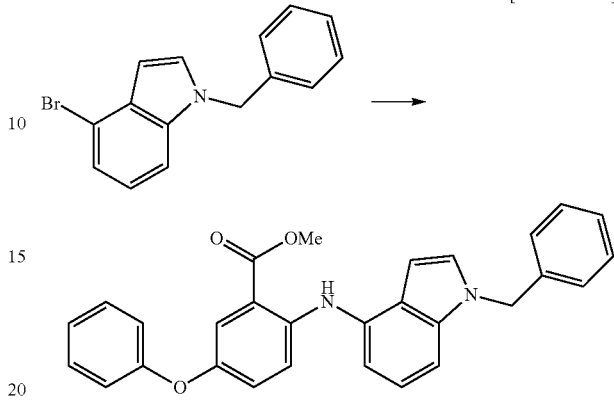

By the method similar to that of Example 5, methyl 2-((1-benzyl-1H-indol-4-yl)amino)-5-phenoxybenzoate was obtained from 1-benzyl-4-bromo-1H-indole and methyl 2-amino-5-phenoxybenzoate.

$^1$H-NMR (DMSO-d$_6$) δ: 3.85 (3H, s), 5.44 (2H, s), 6.42 (1H, d, J=3.3 Hz), 6.93-7.13 (5H, m), 7.18-7.41 (10H, m), 7.51 (1H, d, J=2.6), 7.54 (1H, d, J=3.3 Hz), 9.53 (1H, s).

Example 243

[Formula 490]

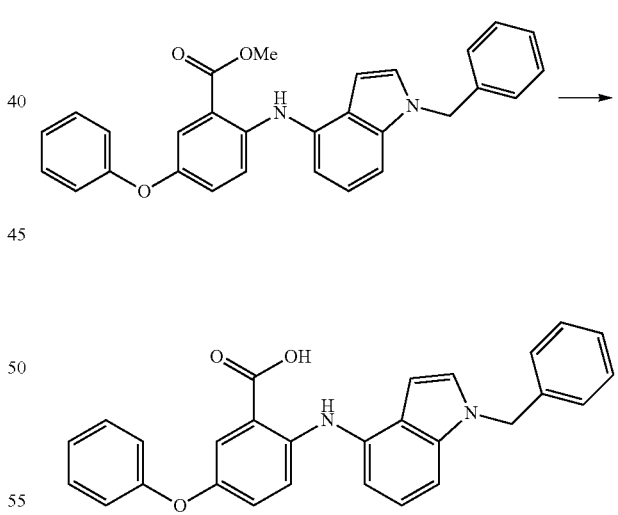

By the method similar to that of Example 37, 2-((1-benzyl-1H-indol-4-yl)amino)-5-phenoxybenzoic acid was obtained from methyl 2-((1-benzyl-1H-indol-4-yl)amino)-5-phenoxybenzoate.

$^1$H-NMR (DMSO-d$_6$) δ: 5.43 (2H, s), 6.42 (1H, d, J=3.3 Hz), 6.93-7.13 (5H, m), 7.15-7.41 (10H, m), 7.50 (1H, d, J=3.3 Hz), 7.53 (1H, d, J=2.6 Hz), 9.83 (1H, s), 13.30 (1H, brs).

MS (ESI/APCI, m/z): 435 (M+H)$^+$, 433 (M−H)$^-$.

Example 244

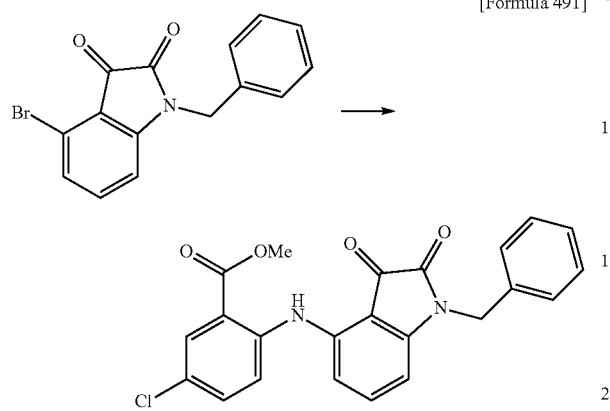

By the method similar to that of Example 5, methyl 2-((1-benzyl-2,3-dioxoindolin-4-yl)amino)-5-chlorobenzoate was obtained from 1-benzyl-4-bromoindoline-2,3-dione and methyl 2-amino-5-chlorobenzoate.

$^1$H-NMR (DMSO-$d_6$) δ: 3.90 (3H, s), 4.90 (2H, s), 6.45 (1H, d, J=7.9 Hz), 7.00 (1H, d, J=8.6 Hz), 7.24-7.46 (6H, m), 7.63-7.67 (2H, m), 7.92-7.95 (1H, m), 10.43 (1H, s).

Example 245

Example 246

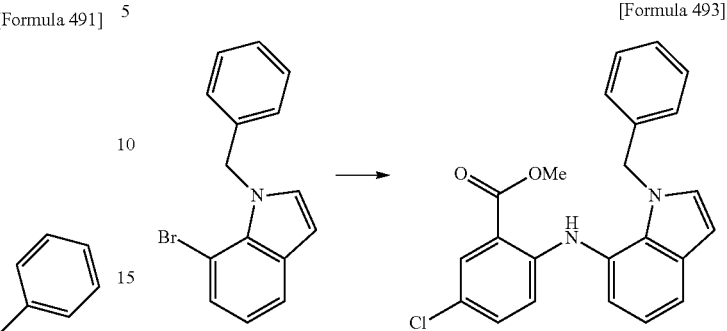

By the method similar to that of Example 5, methyl 2-((1-benzyl-1H-indol-7-yl)amino)-5-chlorobenzoate was obtained from 1-benzyl-7-bromo-1H-indole and methyl 2-amino-5-chlorobenzoate.

$^1$H-NMR (DMSO-$d_6$) δ: 3.85 (3H, s), 5.38 (2H, s), 6.19 (1H, d, J=8.6 Hz), 6.61 (1H, d, J=3.3 Hz), 6.63-6.69 (2H, m), 6.93 (1H, d, J=7.3 Hz), 7.03-7.11 (4H, m), 7.13 (1H, dd, J=9.2, 2.6 Hz), 7.47 (1H, d, J=3.3 Hz), 7.57 (1H, d, J=7.9 Hz), 7.72 (1H, d, J=2.6 Hz), 8.94 (1H, s).

Example 247

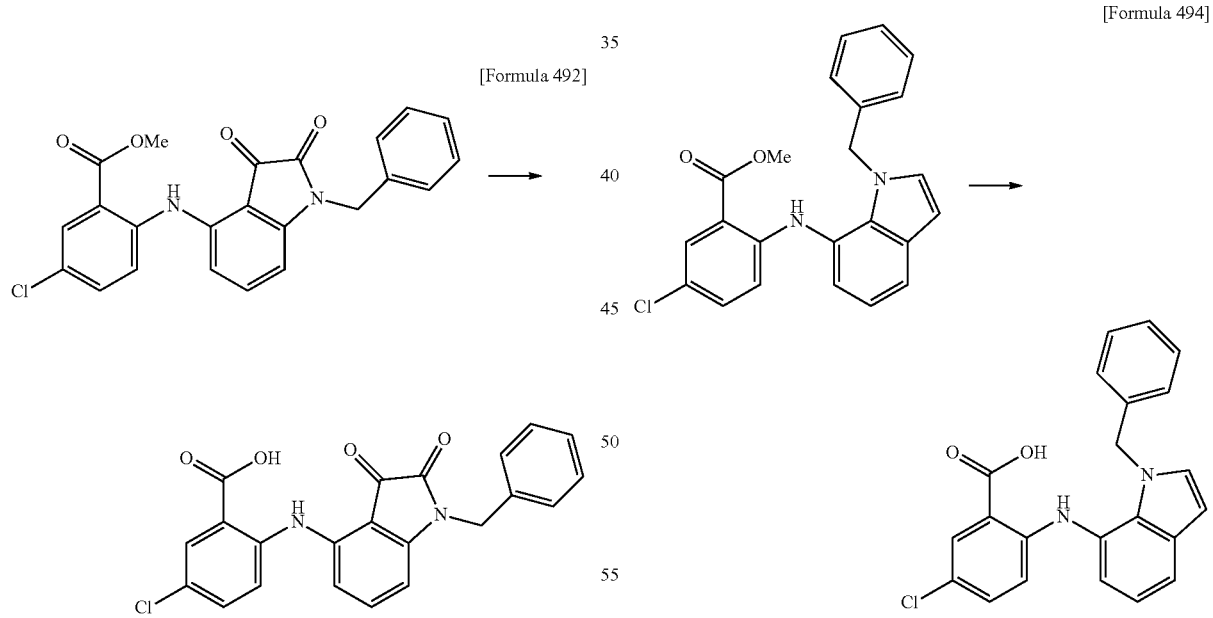

By the method similar to that of Example 37, 2-((1-benzyl-2,3-dioxoindolin-4-yl)amino)-5-chlorobenzoic acid was obtained from methyl 2-((1-benzyl-2,3-dioxoindolin-4-yl)amino)-5-chlorobenzoate.

$^1$H-NMR (DMSO-$d_6$) δ: 4.90 (2H, s), 6.44 (1H, d, J=7.9 Hz), 7.03 (1H, d, J=8.6 Hz), 7.24-7.45 (6H, m), 7.57-7.66 (2H, m), 7.90-7.94 (1H, m), 10.74 (1H, s).

MS (ESI/APCI, m/z): 407 (M+H)$^+$, 405 (M−H)$^-$.

By the method similar to that of Example 37, 2-((1-benzyl-1H-indol-7-yl)amino)-5-chlorobenzoic acid was obtained from methyl 2-((1-benzyl-1H-indol-7-yl)amino)-5-chlorobenzoate.

$^1$H-NMR (DMSO-$d_6$) δ: 5.39 (2H, s), 6.21 (1H, d, J=8.6 Hz), 6.60 (1H, d, J=3.3 Hz), 6.67-6.73 (2H, m), 6.94 (1H, d, J=7.3 Hz), 7.03-7.10 (4H, m), 7.14 (1H, dd, J=9.2, 2.6 Hz), 7.47 (1H, d, J=2.6 Hz), 7.55 (1H, d, J=7.9 Hz), 7.74 (1H, d, J=2.6 Hz), 9.30 (1H, s), 13.31 (1H, brs).

Example 248

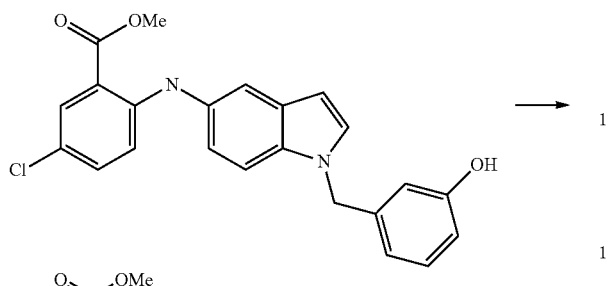

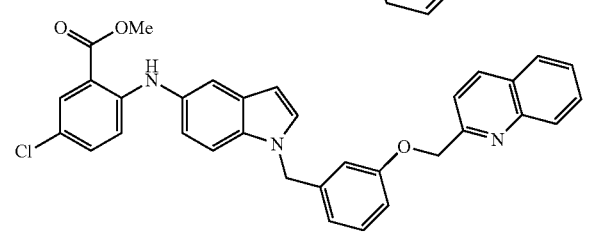

By the method similar to that of Example 18, methyl 5-chloro-2-((1-(3-(quinolin-2-ylmethoxy)benzyl)-1H-indol-5-yl)amino)benzoate was obtained from methyl 5-chloro-2-((1-(3-hydroxybenzyl)-1H-indol-5-yl)amino)benzoate and 2-(bromomethyl)quinoline.

$^1$H-NMR (DMSO-d$_6$) δ: 3.87 (3H, s), 5.32 (2H, s), 5.39 (2H, s), 6.42 (1H, d, J=2.6 Hz), 6.82 (1H, d, J=7.3 Hz), 6.85-6.92 (2H, m), 6.93-7.00 (2H, m), 7.20-7.28 (1H, m), 7.32 (1H, dd, J=8.6, 2.6 Hz), 7.38-7.46 (2H, m), 7.53 (1H, d, J=2.6 Hz), 7.56-7.64 (2H, m), 7.74-7.82 (2H, m), 7.94-8.04 (2H, m), 8.38 (1H, d, J=8.6 Hz), 9.21 (1H, s).

Example 249

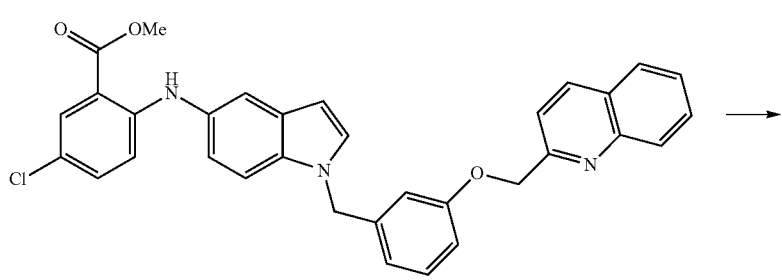

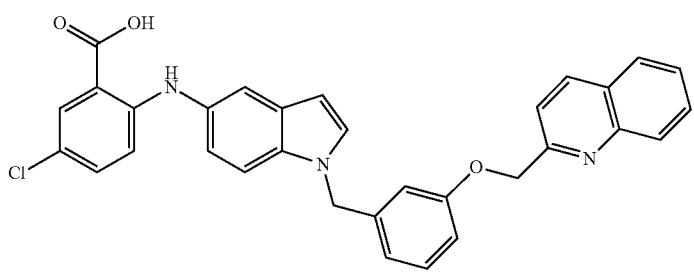

By the method similar to that of Example 37, 5-chloro-2-((1-(3-(quinolin-2-ylmethoxy)benzyl)-1H-indol-5-yl)amino)benzoic acid was obtained from methyl 5-chloro-2-((1-(3-(quinolin-2-ylmethoxy)benzyl)-1H-indol-5-yl)amino)benzoate.

$^1$H-NMR (DMSO-d$_6$) δ: 5.32 (2H, s), 5.38 (2H, s), 6.41 (1H, d, J=2.6 Hz), 6.79-7.00 (5H, m), 7.20-7.33 (2H, m), 7.36-7.45 (2H, m), 7.52 (1H, d, J=3.3 Hz), 7.56-7.65 (2H, m), 7.73-7.83 (2H, m), 7.93-8.05 (2H, m), 8.37 (1H, d, J=7.9 Hz), 9.47 (1H, s).

MS (ESI/APCI, m/z): 534 (M+H)$^+$.

Example 250

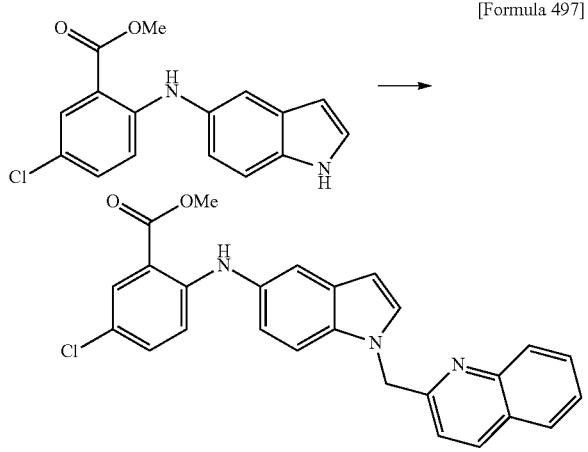

By the method similar to that of Example 12, methyl 5-chloro-2-((1-(quinolin-2-ylmethyl)-1H-indol-5-yl)amino)benzoate was obtained from methyl 2-((1H-indol-5-yl)amino)-5-chlorobenzoate and 2-(bromomethyl)quinoline.

¹H-NMR (DMSO-d₆) δ: 3.86 (3H, s), 5.72 (2H, s), 6.54 (1H, d, J=2.6 Hz), 6.90 (1H, d, J=9.2 Hz), 6.97 (1H, dd, J=8.9, 1.7 Hz), 7.10 (1H, d, J=8.6 Hz), 7.32 (1H, dd, J=8.9, 3.0 Hz), 7.44-7.50 (2H, m), 7.56-7.63 (1H, m), 7.64 (1H, d, J=3.3 Hz), 7.74-7.82 (2H, m), 7.91-7.96 (1H, m), 8.02 (1H, d, J=8.6 Hz), 8.30 (1H, d, J=8.6 Hz), 9.22 (1H, s).

Example 251

[Formula 498]

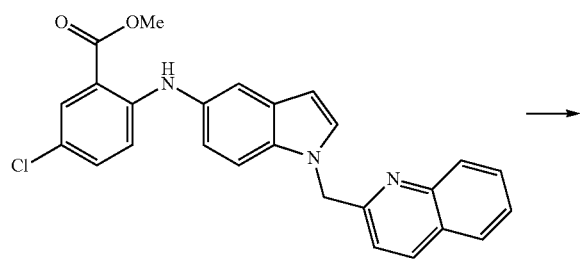

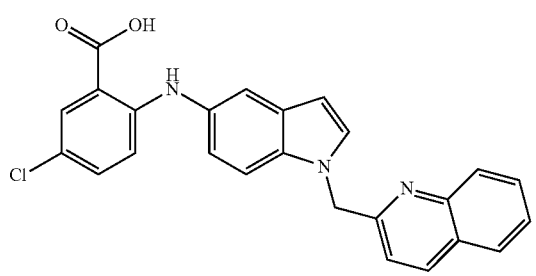

By the method similar to that of Example 37, 5-chloro-2-((1-(quinolin-2-ylmethyl)-1H-indol-5-yl)amino)benzoic acid was obtained from methyl 5-chloro-2-((1-(quinolin-2-ylmethyl)-1H-indol-5-yl)amino)benzoate.

¹H-NMR (DMSO-d₆) δ: 5.72 (2H, s), 6.53 (1H, d, J=3.3 Hz), 6.91 (1H, d, J=9.2 Hz), 6.97 (1H, dd, J=8.6, 2.0 Hz), 7.10 (1H, d, J=8.6 Hz), 7.30 (1H, dd, J=9.2, 2.6 Hz), 7.43-7.50 (2H, m), 7.55-7.66 (2H, m), 7.74-7.82 (2H, m), 7.94 (1H, d, J=8.6 Hz), 8.02 (1H, d, J=7.9 Hz), 8.30 (1H, d, J=7.9 Hz), 9.49 (1H, s).

MS (ESI/APCI, m/z): 428 (M+H)⁺, 426 (M−H)⁻.

Example 252

[Formula 499]

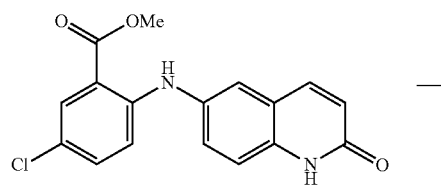

-continued

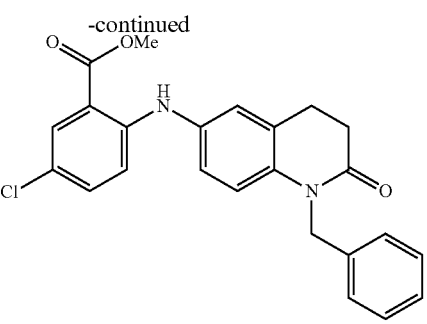

To the suspension of 40 mg of methyl 5-chloro-2-((2-oxo-1,2-dihydroquinolin-6-yl)amino)benzoate in 1 mL of N,N-dimethylacetamide, 25.3 mg of potassium carbonate and 17.4 μL of benzyl bromide were added, and the resultant was stirred at an external temperature of 70 to 80° C. for three hours. The reaction mixture was cooled to room temperature, and ethyl acetate and water were then added thereto, and the resultant was adjusted to pH 3.0 with 2 mol/L hydrochloric acid. The organic layer was separated and the aqueous layer was extracted with ethyl acetate. The organic layer and the extract were combined, sequentially washed with water and a saturated aqueous sodium chloride solution and dried over anhydrous magnesium sulfate, and the solvent was distilled off under reduced pressure. The obtained residue was purified by silica gel column chromatography (gradient elution with hexane:ethyl acetate=90:10-70:30) to give 23 mg of methyl 2-((1-benzyl-2-oxo-1,2-dihydroquinolin-6-yl)amino)-5-chlorobenzoate as a yellow solid.

¹H-NMR (CDCl₃) δ: 3.91 (3H, s), 5.56 (2H, s), 6.82 (1H, d, J=9.2 Hz), 7.02 (1H, d, J=8.6 Hz), 7.19-7.36 (8H, m), 7.40 (1H, d, J=2.6 Hz), 7.67 (1H, d, J=9.2 Hz), 7.93 (1H, d, J=2.6 Hz), 9.39 (1H, s).

Example 253

[Formula 500]

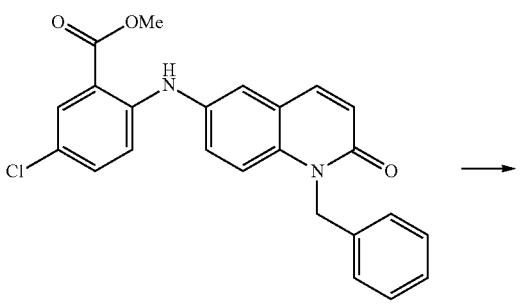

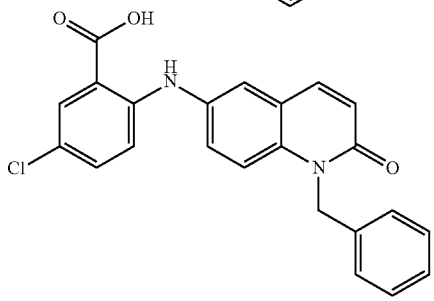

By the method similar to that of Example 37, 2-((1-benzyl-2-oxo-1,2-dihydroquinolin-6-yl)amino)-5-chlorobenzoic acid was obtained from methyl 2-((1-benzyl-2-oxo-1,2-dihydroquinolin-6-yl)amino)-5-chlorobenzoate.

$^1$H-NMR (DMSO-d$_6$) δ: 5.52 (2H, s), 6.74 (1H, d, J=9.9 Hz), 7.11 (1H, d, J=9.2 Hz), 7.18-7.46 (8H, m), 7.67 (1H, d, J=2.0 Hz), 7.82 (1H, d, J=3.3 Hz), 7.96 (1H, d, J=9.2 Hz), 9.57 (1H, s).

MS (ESI/APCI, m/z): 405 (M+H)$^+$, 403 (M−H)$^−$.

Example 254

[Formula 501]

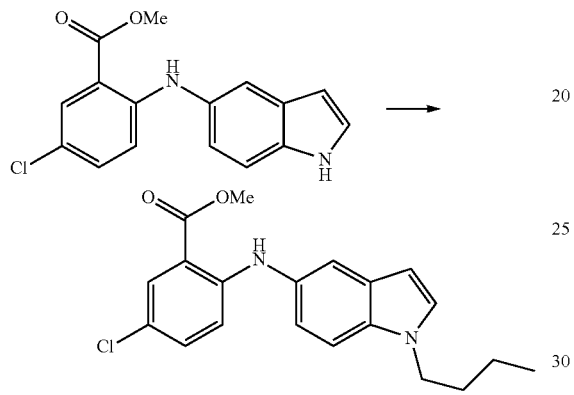

By the method similar to that of Example 12, methyl 2-((1-butyl-1H-indol-5-yl)amino)-5-chlorobenzoate was obtained from methyl 2-((1H-indol-5-yl)amino)-5-chlorobenzoate and 1-bromobutane.

$^1$H-NMR (DMSO-d$_6$) δ: 0.89 (3H, t, J=7.6 Hz), 1.26 (2H, sext, J=7.6 Hz), 1.74 (2H, quin, J=7.6 Hz), 3.87 (3H, s), 4.18 (2H, t, J=7.3 Hz), 6.40 (1H, d, J=2.6 Hz), 6.90 (1H, d, J=9.2 Hz), 7.01 (1H, dd, J=8.6, 2.0 Hz), 7.34 (1H, dd, J=9.2, 2.6 Hz), 7.39-7.44 (2H, m), 7.51 (1H, d, J=8.6 Hz), 7.80 (1H, d, J=2.6 Hz), 9.24 (1H, s).

Example 255

[Formula 502]

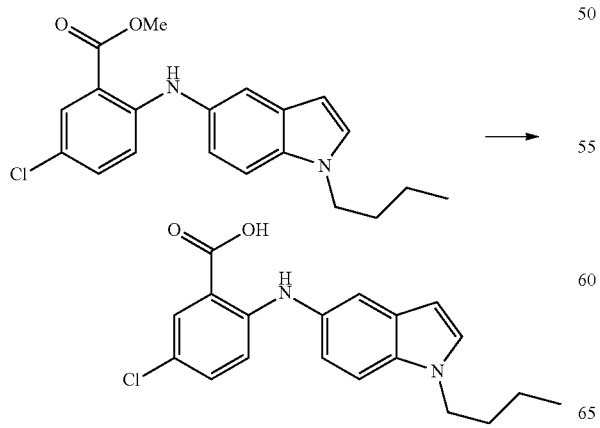

By the method similar to that of Example 37, 2-((1-butyl-1H-indol-5-yl)amino)-5-chlorobenzoic acid was obtained from methyl 2-((1-butyl-1H-indol-5-yl)amino)-5-chlorobenzoate.

$^1$H-NMR (DMSO-d$_6$) δ: 0.90 (3H, t, J=7.3 Hz), 1.26 (2H, sext, J=7.6 Hz), 1.74 (2H, quin, J=7.6 Hz), 4.17 (2H, t, J=7.3 Hz), 6.40 (1H, d, J=2.6 Hz), 6.91 (1H, d, J=8.6 Hz), 7.01 (1H, dd, J=8.9, 2.3 Hz), 7.32 (1H, dd, J=8.6, 2.6 Hz), 7.38-7.43 (2H, m), 7.51 (1H, d, J=8.6 Hz), 7.79 (1H, d, J=2.6 Hz), 9.49 (1H, s), 13.26 (1H, brs).

MS (ESI/APCI, m/z): 343 (M+H)$^+$, 341 (M−H)$^−$.

Example 256

[Formula 503]

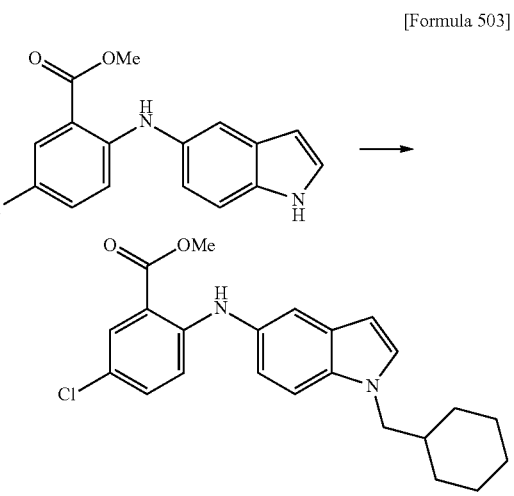

By the method similar to that of Example 12, methyl 5-chloro-2-((1-(cyclohexylmethyl)-1H-indol-5-yl)amino)benzoate was obtained from methyl 2-((1H-indol-5-yl)amino)-5-chlorobenzoate and (bromomethyl)cyclohexane.

$^1$H-NMR (DMSO-d$_6$) δ: 0.90-1.30 (5H, m), 1.45-1.85 (6H, m), 3.87 (3H, s), 4.01 (2H, d, J=7.3 Hz), 6.40 (1H, d, J=3.3 Hz), 6.91 (1H, d, J=9.2 Hz), 7.00 (1H, dd, J=8.6, 2.0 Hz), 7.31-7.38 (2H, m), 7.42 (1H, d, J=2.0 Hz), 7.52 (1H, d, J=9.2 Hz), 7.80 (1H, d, J=2.6 Hz), 9.23 (1H, s).

Example 257

[Formula 504]

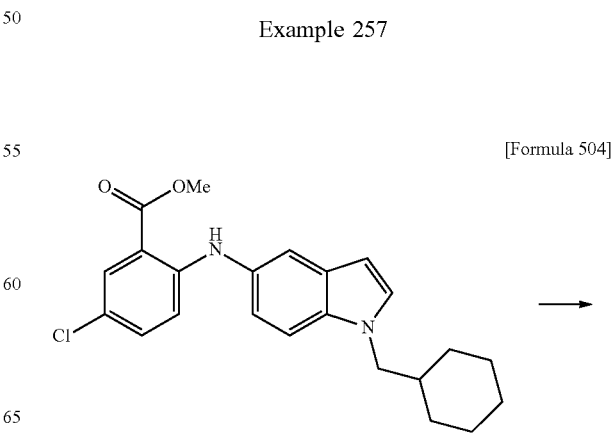

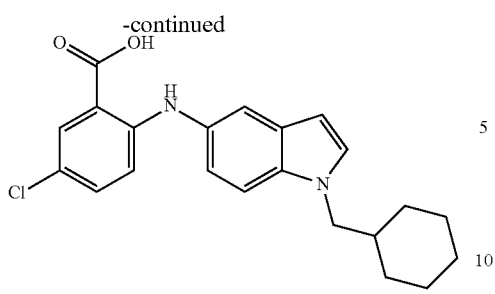

By the method similar to that of Example 37, 5-chloro-2-((1-(cyclohexylmethyl)-1H-indol-5-yl)amino)benzoic acid was obtained from methyl 5-chloro-2-((1-(cyclohexylmethyl)-1H-indol-5-yl)amino)benzoate.

¹H-NMR (DMSO-d₆) δ: 0.90-1.25 (5H, m), 1.45-1.90 (6H, m), 4.01 (2H, d, J=7.3 Hz), 6.39 (1H, d, J=3.3 Hz), 6.92 (1H, d, J=8.6 Hz), 7.00 (1H, dd, J=8.6, 2.0 Hz), 7.32 (1H, dd, J=9.2, 2.6 Hz), 7.36 (1H, d, J=3.3 Hz), 7.38-7.43 (1H, m), 7.50 (1H, d, J=8.6 Hz), 7.79 (1H, d, J=2.6 Hz), 9.50 (1H, s).

MS (ESI/APCI, m/z): 383 (M+H)⁺, 381 (M−H)⁻.

Example 258

[Formula 505]

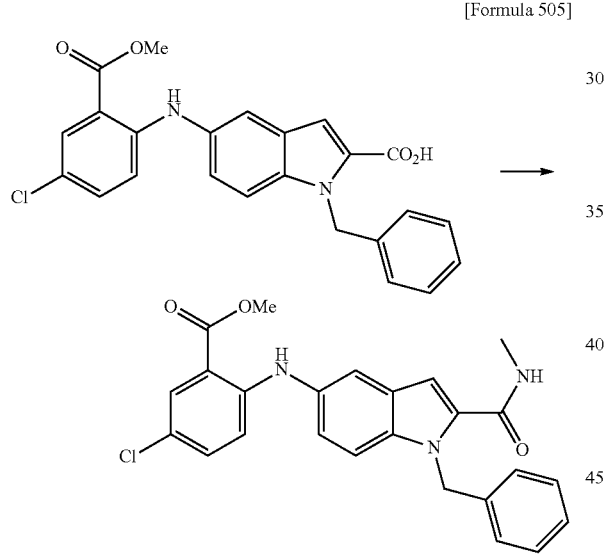

To the solution of 120 mg of 1-benzyl-5-((4-chloro-2-(methoxycarbonyl)phenyl)amino)-1H-indole-2-carboxylic acid in 2 mL of N,N-dimethylacetamide, 56 mg of methylamine hydrochloride, 157 mg of O-(7-azabenzotriazol-1-yl)-1,1,3,3-tetramethyluronium hexafluorophosphate and 231 μL of triethylamine were added, and the resultant was stirred at room temperature for one hour and then allowed to stand overnight. Ethyl acetate and water were added to the reaction mixture, and the resultant was adjusted to pH 2 with 2 mol/L hydrochloric acid. The organic layer was separated, sequentially washed with water and a saturated aqueous sodium chloride solution and dried over anhydrous magnesium sulfate, and the solvent was distilled off under reduced pressure. The obtained residue was purified by silica gel column chromatography (gradient elution with hexane:ethyl acetate=90:10-20:80) to give 103 mg of methyl 2-((1-benzyl-2-(methylcarbamoyl)-1H-indol-5-yl)amino)-5-chlorobenzoate as a yellow solid.

¹H-NMR (DMSO-d₆) δ: 2.77 (3H, d, J=4.6 Hz), 3.87 (3H, s), 5.88 (2H, s), 6.94 (1H, d, J=9.2 Hz), 7.06-7.15 (4H, m), 7.16-7.31 (3H, m), 7.35 (1H, dd, J=9.2, 2.6 Hz), 7.49-7.57 (2H, m), 7.81 (1H, d, J=2.6 Hz), 8.52-8.60 (1H, m), 9.24 (1H, s).

Example 259

[Formula 506]

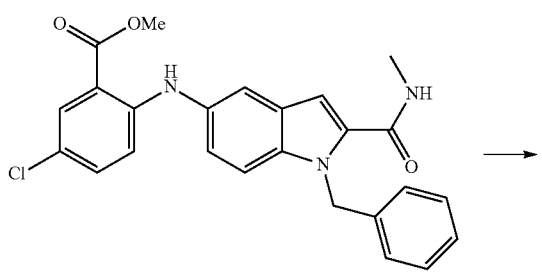

By the method similar to that of Example 37, 2-((1-benzyl-2-(methylcarbamoyl)-1H-indol-5-yl)amino)-5-chlorobenzoic acid was obtained from methyl 2-((1-benzyl-2-(methylcarbamoyl)-1H-indol-5-yl)amino)-5-chlorobenzoate.

¹H-NMR (DMSO-d₆) δ: 2.77 (3H, d, J=4.6 Hz), 5.87 (2H, s), 6.94 (1H, d, J=9.2 Hz), 7.06-7.14 (4H, m), 7.16-7.30 (3H, m), 7.33 (1H, dd, J=9.2, 2.6 Hz), 7.48-7.56 (2H, m), 7.80 (1H, d, J=2.6 Hz), 8.51-8.60 (1H, m), 9.51 (1H, s).

MS (ESI/APCI, m/z): 434 (M+H)⁺, 432 (M−H)⁻.

Example 260

[Formula 507]

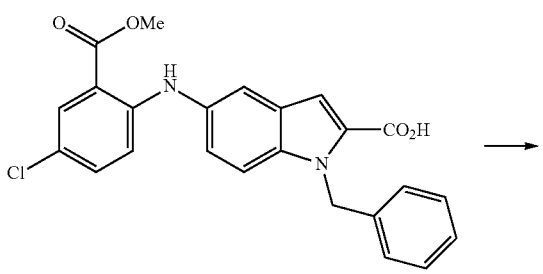

Example 262

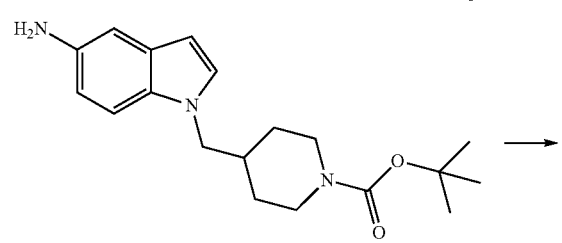

[Formula 509]

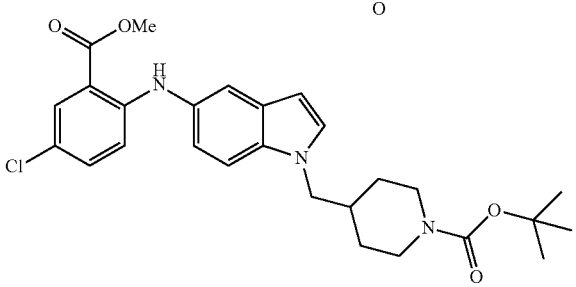

By the method similar to that of Example 20, tert-butyl 4-((5-((4-chloro-2-(methoxycarbonyl)phenyl)amino)-1H-indol-1-yl)methyl)piperidine-1-carboxylate was obtained from tert-butyl 4-((5-amino-1H-indol-1-yl)methyl)piperidine-1-carboxylate and methyl 2-bromo-5-chlorobenzoate.

$^1$H-NMR (DMSO-d$_6$) δ: 1.03-1.22 (2H, m), 1.35-1.52 (2H, m), 1.38 (9H, s), 1.90-2.08 (1H, m), 2.54-2.75 (2H, m), 3.85-3.98 (2H, m), 3.88 (3H, s), 4.08 (2H, d, J=7.9 Hz), 6.41 (1H, d, J=2.6 Hz), 6.92 (1H, d, J=9.2 Hz), 7.01 (1H, dd, J=8.6, 2.0 Hz), 7.35 (1H, dd, J=9.2, 2.6 Hz), 7.39 (1H, d, J=2.6 Hz), 7.42 (1H, d, J=1.3 Hz), 7.56 (1H, d, J=8.6 Hz), 7.81 (1H, d, J=2.6 Hz), 9.24 (1H, s).

Example 263

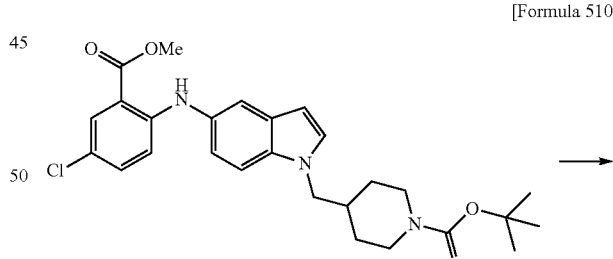

[Formula 510]

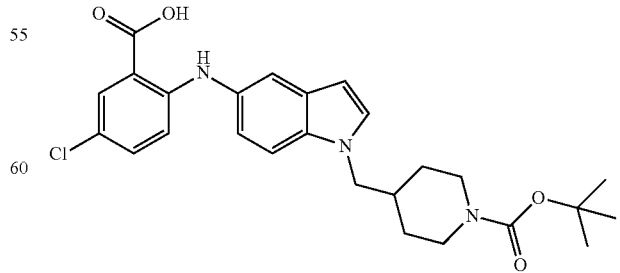

By the method similar to that of Example 37, 2-((1-((1-(tert-butoxycarbonyl)piperidin-4-yl)methyl)-1H-indol-5-yl)

---

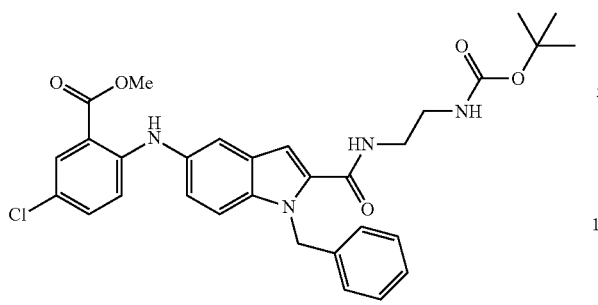

By the method similar to that of Example 258, methyl 2-((1-benzyl-2-((2-((tert-butoxycarbonyl)amino)ethyl)carbamoyl)-1H-indol-5-yl)amino)-5-chlorobenzoate was obtained from 1-benzyl-5-((4-chloro-2-(methoxycarbonyl)phenyl)amino)-1H-indole-2-carboxylic acid and tert-butyl (2-aminoethyl)carbamate.

$^1$H-NMR (DMSO-d$_6$) δ: 1.38 (9H, s), 3.02-3.15 (2H, m), 3.23-3.40 (2H, m), 3.87 (3H, s), 5.85 (2H, s), 6.86-6.97 (2H, m), 7.08-7.31 (7H, m), 7.35 (1H, dd, J=9.2, 2.6 Hz), 7.50-7.58 (2H, m), 7.81 (1H, d, J=2.6 Hz), 8.53-8.62 (1H, m), 9.24 (1H, s).

Example 261

[Formula 508]

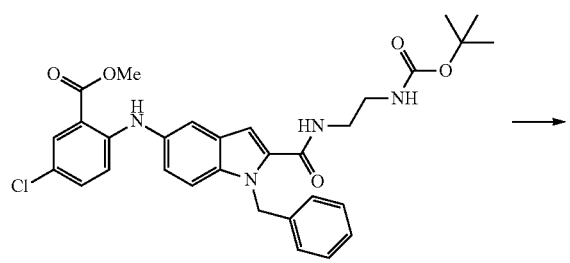

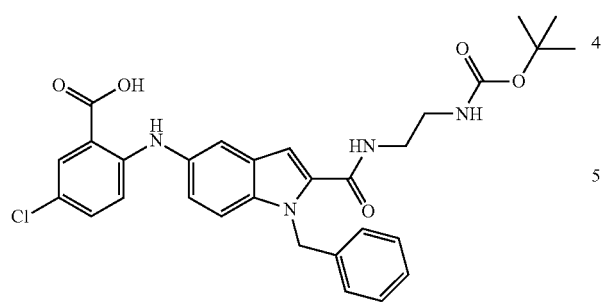

By the method similar to that of Example 37, 2-((1-benzyl-2-((2-((tert-butoxycarbonyl)amino)ethyl)carbamoyl)-1H-indol-5-yl)amino)-5-chlorobenzoic acid was obtained from methyl 2-((1-benzyl-2-((2-((tert-butoxycarbonyl)amino)ethyl)carbamoyl)-1H-indol-5-yl)amino)-5-chlorobenzoate.

$^1$H-NMR (DMSO-d$_6$) δ: 1.38 (9H, s), 3.02-3.50 (4H, m), 5.84 (2H, s), 6.86-6.99 (2H, m), 7.05-7.15 (4H, m), 7.16-7.31 (4H, m), 7.45-7.53 (2H, m), 7.80 (1H, d, J=2.6 Hz), 8.51-8.60 (1H, m).

amino)-5-chlorobenzoic acid was obtained from tert-butyl 4-((5-((4-chloro-2-(methoxycarbonyl)phenyl)amino)-1H-indol-1-yl)methyl)piperidine-1-carboxylate.

$^1$H-NMR (DMSO-d$_6$) δ: 1.02-1.21 (2H, m), 1.35-1.52 (2H, m), 1.38 (9H, s), 1.88-2.09 (1H, m), 2.55-2.75 (2H, m), 3.86-3.99 (2H, m), 4.08 (2H, d, J=6.6 Hz), 6.40 (1H, d, J=2.6 Hz), 6.93 (1H, d, J=9.2 Hz), 7.01 (1H, dd, J=8.6, 2.0 Hz), 7.30 (1H, dd, J=9.2, 2.6 Hz), 7.38 (1H, d, J=2.6 Hz), 7.41 (1H, d, J=2.0 Hz), 7.55 (1H, d, J 8.6 Hz), 7.80 (1H, d, J 2.6 Hz).

MS (ESI/APCI, m/z): 482 (M−H)$^−$.

Example 264

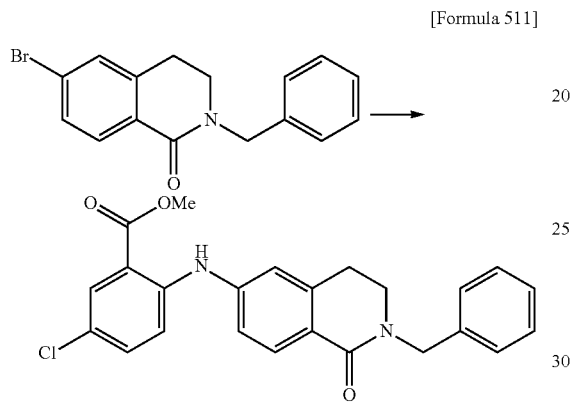

[Formula 511]

By the method similar to that of Example 5, methyl 2-((2-benzyl-1-oxo-1,2,3,4-tetrahydroisoquinolin-6-yl)amino)-5-chlorobenzoate was obtained from 2-benzyl-6-bromo-3,4-dihydroisoquinolin-1-(2H)-one and methyl 2-amino-5-chlorobenzoate.

$^1$H-NMR (DMSO-d$_6$) δ: 2.91 (2H, t, J=6.6 Hz), 3.46 (2H, t, J=6.6 Hz), 3.86 (3H, s), 4.69 (2H, s), 7.09 (1H, d, J=2.0 Hz), 7.17 (1H, dd, J=8.3, 2.3 Hz), 7.23-7.39 (5H, m), 7.45 (1H, d, J=9.2 Hz), 7.53 (1H, dd, J=8.9, 2.3 Hz), 7.83-7.89 (2H, m), 9.32 (1H, s).

Example 265

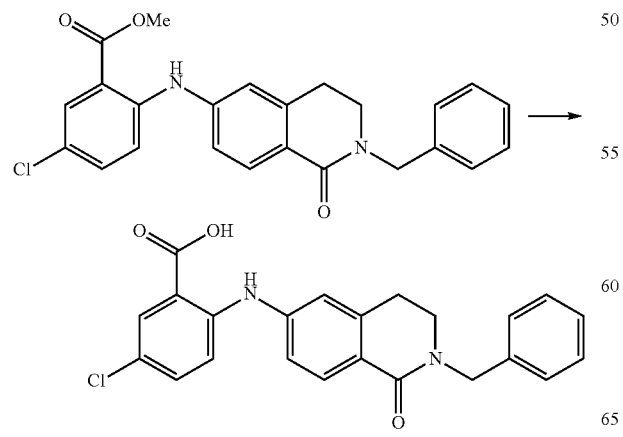

[Formula 512]

By the method similar to that of Example 37, 2-((2-benzyl-1-oxo-1,2,3,4-tetrahydroisoquinolin-6-yl)amino)-5-chlorobenzoic acid was obtained from methyl 2-((2-benzyl-1-oxo-1,2,3,4-tetrahydroisoquinolin-6-yl)amino)-5-chlorobenzoate.

$^1$H-NMR (DMSO-d$_6$) δ: 2.92 (2H, t, J=6.6 Hz), 3.46 (2H, t, J=6.6 Hz), 4.70 (2H, s), 7.11 (1H, d, J=2.0 Hz), 7.19 (1H, dd, J=8.6, 2.0 Hz), 7.23-7.39 (5H, m), 7.45 (1H, d, J=9.2 Hz), 7.51 (1H, dd, J=9.2, 2.6 Hz), 7.84-7.90 (2H, m), 9.71 (1H, s).

MS (ESI/APCI, m/z): 405 (M−H)$^−$.

Example 266

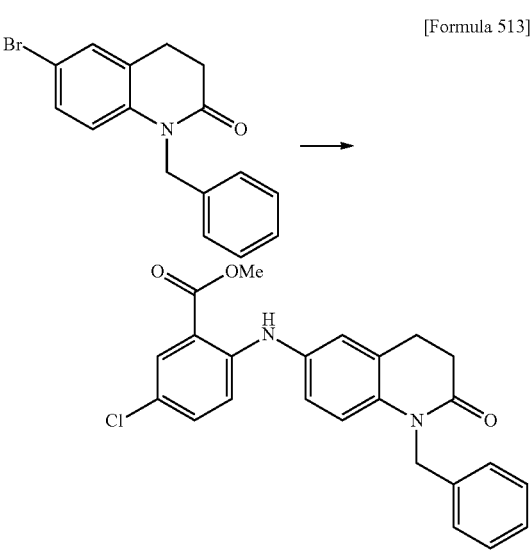

[Formula 513]

By the method similar to that of Example 5, methyl 2-((1-benzyl-2-oxo-1,2,3,4-tetrahydroquinolin-6-yl)amino)-5-chlorobenzoate was obtained from 1-benzyl-6-bromo-3,4-dihydroquinolin-2-(1H)-one and methyl 2-amino-5-chlorobenzoate.

$^1$H-NMR (DMSO-d$_6$) δ: 2.66-2.75 (2H, m), 2.90-3.00 (2H, m), 3.85 (3H, s), 5.14 (2H, s), 6.91 (1H, d, J=8.6 Hz), 6.99-7.09 (2H, m), 7.16 (1H, d, J=2.0 Hz), 7.19-7.27 (3H, m), 7.28-7.36 (2H, m), 7.40 (1H, dd, J=8.6, 2.6 Hz), 7.80 (1H, d, J=2.6 Hz), 9.14 (1H, s).

Example 267

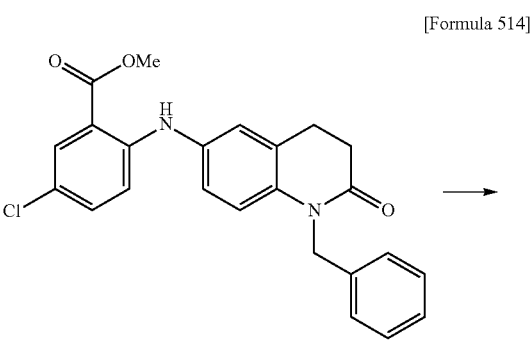

[Formula 514]

-continued

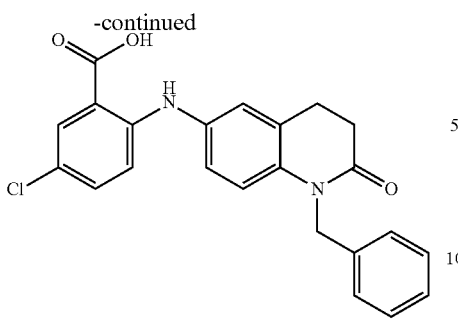

By a method similar to that of Example 37, 2-((1-benzyl-2-oxo-1,2,3,4-tetrahydroquinolin-6-yl)amino)-5-chlorobenzoic acid was obtained from methyl 2-((1-benzyl-2-oxo-1,2,3,4-tetrahydroquinolin-6-yl)amino)-5-chlorobenzoate.

$^1$H-NMR (DMSO-d$_6$) δ: 2.66-2.75 (2H, m), 2.90-2.99 (2H, m), 5.14 (2H, s), 6.90 (1H, d, J=8.6 Hz), 7.02 (1H, dd, J=8.6, 2.0 Hz), 7.06 (1H, d, J=9.2 Hz), 7.16 (1H, d, J=2.6 Hz), 7.19-7.26 (3H, m), 7.28-7.34 (2H, m), 7.37 (1H, dd, J=8.6, 2.6 Hz), 7.80 (1H, d, J=2.6 Hz), 9.46 (1H, s).

MS (ESI/APCI, m/z): 405 (M−H)$^-$.

Example 268

[Formula 515]

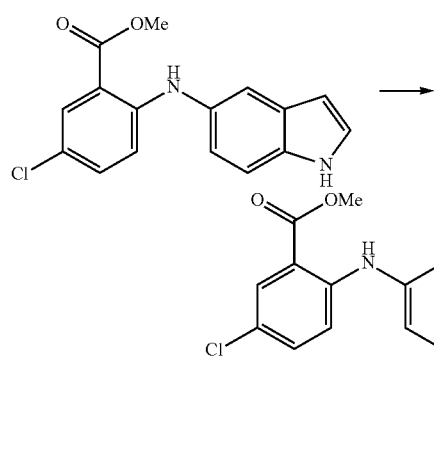

The mixture of 80 mg of methyl 2-((1H-indol-5-yl)amino)-5-chlorobenzoate, 60 μL of iodobenzene, 24.7 mg of tris(dibenzylideneacetone)dipalladium(0), 50.5 mg of 2-dicyclohexylphosphino-2',4',6'-triisopropylbiphenyl, 113 mg of tripotassium phosphate, and 2 mL of toluene, was heated at reflux for three hours under a nitrogen atmosphere. The reaction mixture was cooled to room temperature, and ethyl acetate and water were then added thereto. The organic layer was separated, washed with a saturated aqueous sodium chloride solution and dried over anhydrous magnesium sulfate, and the solvent was distilled off under reduced pressure. The obtained residue was purified by silica gel column chromatography (gradient elution with hexane:ethyl acetate=90:10-70:30) to give 42 mg of methyl 5-chloro-2-((1-phenyl-1H-indol-5-yl)amino)benzoate as a pale brown oil.

$^1$H-NMR (CDCl$_3$) δ: 3.91 (3H, s), 6.64 (1H, d, J=2.6 Hz), 6.97 (1H, d, J=9.2 Hz), 7.07 (1H, dd, J=8.9, 2.3 Hz), 7.16 (1H, dd, J=8.9, 2.3 Hz), 7.30-7.40 (2H, m), 7.48-7.57 (6H, m), 7.91 (1H, d, J=2.6 Hz), 9.37 (1H, s).

Example 269

[Formula 516]

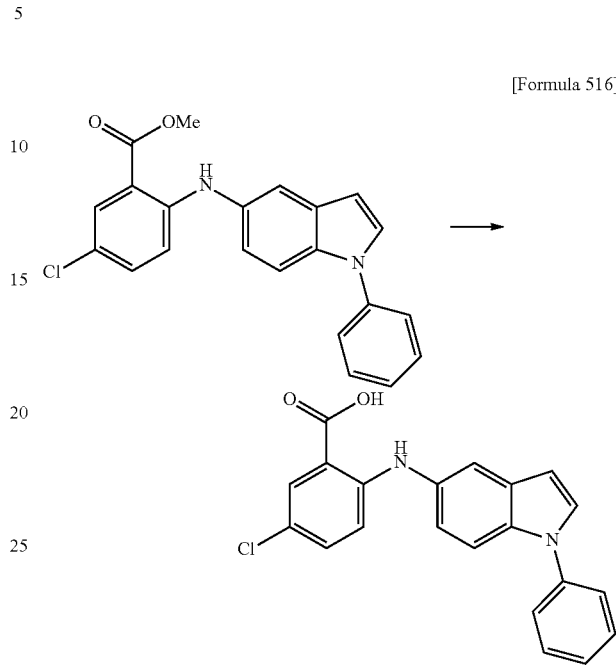

By the method similar to that of Example 37, 5-chloro-2-((1-phenyl-1H-indol-5-yl)amino)benzoic acid was obtained from methyl 5-chloro-2-((1-phenyl-1H-indol-5-yl)amino)benzoate.

$^1$H-NMR (DMSO-d$_6$) δ: 6.69 (1H, d, J=3.3 Hz), 7.00 (1H, d, J=9.2 Hz), 7.09 (1H, dd, J=8.6, 2.0 Hz), 7.35 (1H, dd, J=8.6, 2.6 Hz), 7.38-7.45 (1H, m), 7.53-7.65 (6H, m), 7.70 (1H, d, J=3.3 Hz), 7.81 (1H, d, J=2.6 Hz), 9.56 (1H, s).

Example 270

[Formula 517]

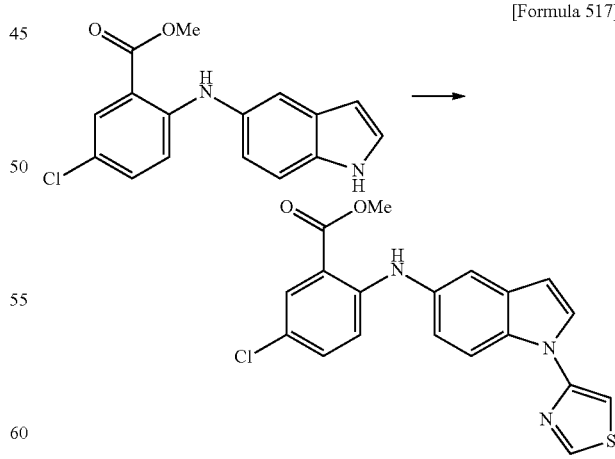

By the method similar to that of Example 268, methyl 5-chloro-2-((1-(thiazol-4-yl)-1H-indol-5-yl)amino)benzoate was obtained from methyl 2-((1H-indol-5-yl)amino)-5-chlorobenzoate and 4-bromothiazole.

MS (ESI, m/z): 384 (M+H)$^+$.

Example 271

[Formula 518]

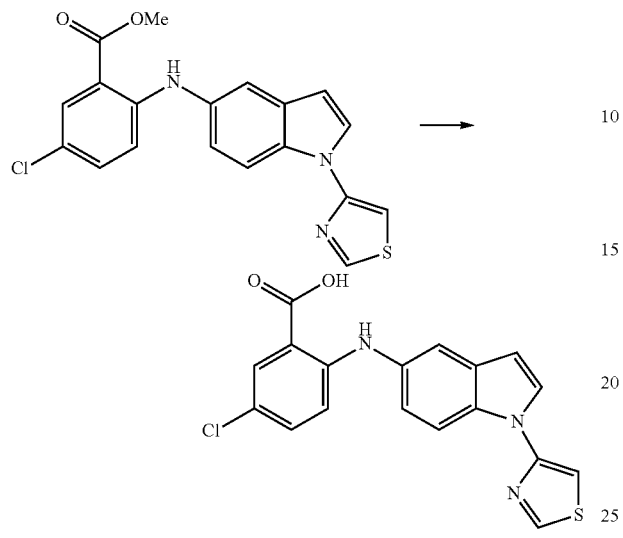

By the method similar to that of Example 37, 5-chloro-2-((1-(thiazol-4-yl)-1H-indol-5-yl)amino)benzoic acid was obtained from methyl 5-chloro-2-((1-(thiazol-4-yl)-1H-indol-5-yl)amino)benzoate.

$^1$H-NMR (DMSO-$d_6$) δ: 6.71 (1H, d, J=3.3 Hz), 7.03 (1H, d, J=9.2 Hz), 7.16 (1H, dd, J=8.9, 2.3 Hz), 7.36 (1H, dd, J=9.2, 2.6 Hz), 7.54 (1H, d, J=2.0 Hz), 7.80-7.84 (2H, m), 7.94 (1H, d, J=3.3 Hz), 8.09 (1H, d, J=8.6 Hz), 9.26 (1H, d, J=2.0 Hz), 9.60 (1H, brs).

MS (ESI, m/z): 368 (M−H)$^-$.

Example 272

[Formula 519]

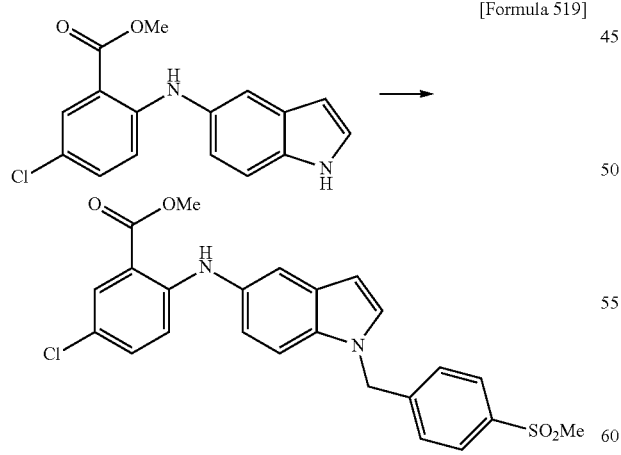

By the method similar to that of Example 12, methyl 5-chloro-2-((1-(4-(methylsulfonyl)benzyl)-1H-indol-5-yl)amino)benzoate was obtained from methyl 2-((1H-indol-5-yl)amino)-5-chlorobenzoate and 1-(bromomethyl)-4-(methylsulfonyl)benzene.

$^1$H-NMR (CDCl$_3$) δ: 3.03 (3H, s), 3.91 (3H, s), 5.43 (2H, s), 6.57 (1H, d, J=3.3 Hz), 6.90-6.96 (1H, m), 7.04 (1H, dd, J=8.6, 2.0 Hz), 7.13-7.20 (3H, m), 7.24-7.31 (2H, m), 7.51 (1H, d, J=2.0 Hz), 7.86-7.93 (3H, m), 9.34 (1H, s).

Example 273

[Formula 520]

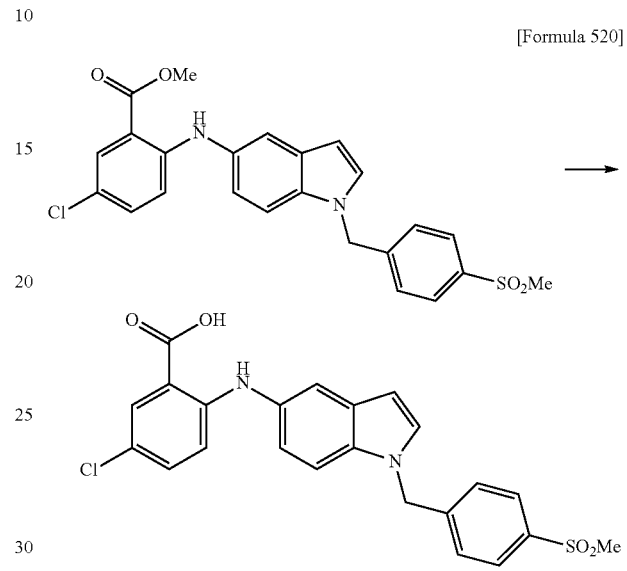

By the method similar to that of Example 37, 5-chloro-2-((1-(4-(methylsulfonyl)benzyl)-1H-indol-5-yl)amino)benzoic acid was obtained from methyl 5-chloro-2-((1-(4-(methylsulfonyl)benzyl)-1H-indol-5-yl)amino)benzoate.

$^1$H-NMR (DMSO-$d_6$) δ: 3.17 (3H, s), 5.57 (2H, s), 6.51 (1H, d, J=3.3 Hz), 6.92 (1H, d, J=9.2 Hz), 7.00 (1H, dd, J=8.6, 2.0 Hz), 7.31 (1H, dd, J=9.2, 2.6 Hz), 7.40-7.50 (4H, m), 7.59 (1H, d, J=2.6 Hz), 7.79 (1H, d, J=2.6 Hz), 7.88 (2H, d, J=7.9 Hz), 9.50 (1H, s).

Example 274

[Formula 521]

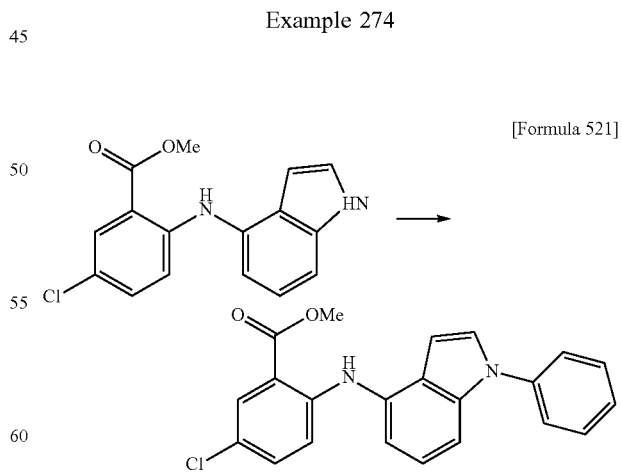

By the method similar to that of Example 268, methyl 5-chloro-2-((1-phenyl-1H-indol-4-yl)amino)benzoate was obtained from methyl 2-((1H-indol-4-yl)amino)-5-chlorobenzoate and iodobenzene.

Example 275

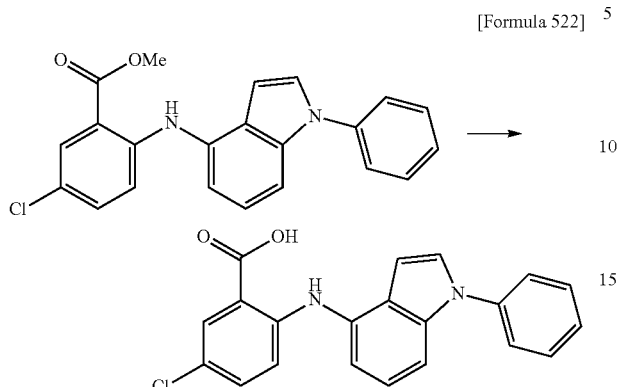

By the method similar to that of Example 37, 5-chloro-2-((1-phenyl-1H-indol-4-yl)amino)benzoic acid was obtained from methyl 5-chloro-2-((1-phenyl-1H-indol-4-yl)amino)benzoate.

$^1$H-NMR (DMSO-d$_6$) δ: 6.56 (1H, d, J=3.3 Hz), 7.13 (1H, d, J=7.3 Hz), 7.18-7.25 (2H, m), 7.35 (1H, d, J=7.9 Hz), 7.39-7.47 (2H, m), 7.56-7.64 (4H, m), 7.66 (1H, d, J=3.3 Hz), 7.88 (1H, d, J=2.6 Hz), 10.00 (1H, s).

Example 276

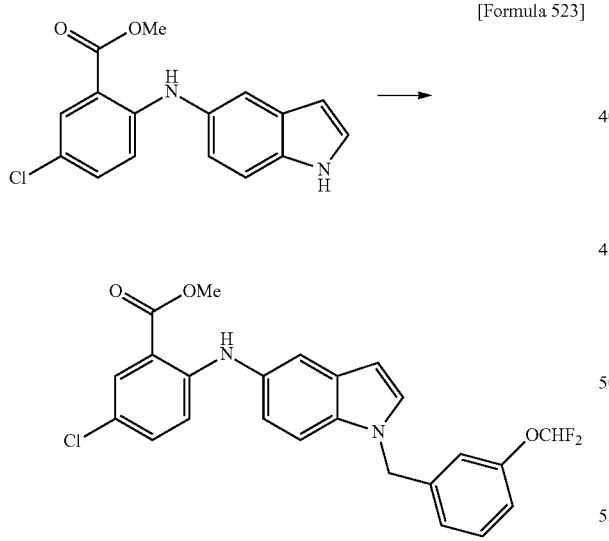

By the method similar to that of Example 12, methyl 5-chloro-2-((1-(3-(difluoromethoxy)benzyl)-1H-indol-5-yl)amino)benzoate was obtained from methyl 2-((1H-indol-5-yl)amino)-5-chlorobenzoate and 1-(bromomethyl)-3-(difluoromethoxy)benzene.

$^1$H-NMR (CDCl$_3$) δ: 3.91 (3H, s), 5.32 (2H, s), 6.47 (1H, t, J=73.7 Hz), 6.53 (1H, d, J=3.3 Hz), 6.88-6.98 (3H, m), 7.00-7.07 (2H, m), 7.11-7.18 (2H, m), 7.20-7.34 (2H, m), 7.50 (1H, d, J=2.0 Hz), 7.90 (1H, d, J=2.6 Hz), 9.33 (1H, s).

Example 277

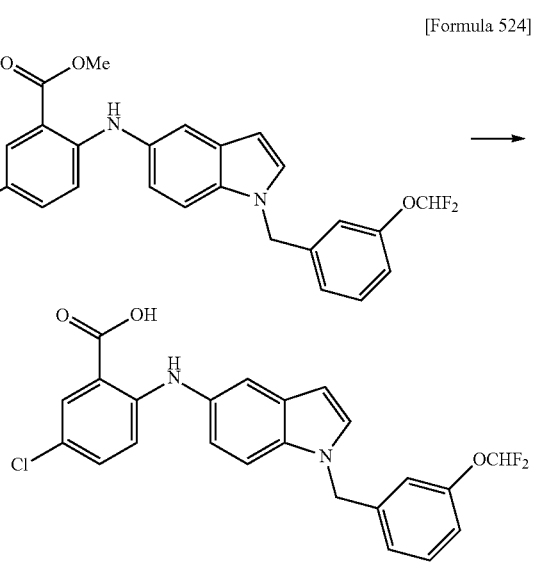

By the method similar to that of Example 37, 5-chloro-2-((1-(3-(difluoromethoxy)benzyl)-1H-indol-5-yl)amino)benzoic acid was obtained from methyl 5-chloro-2-((1-(3-(difluoromethoxy)benzyl)-1H-indol-5-yl)amino)benzoate.

$^1$H-NMR (DMSO-d$_6$) δ: 5.45 (2H, s), 6.48 (1H, d, J=3.3 Hz), 6.91 (1H, d, J=9.2 Hz), 7.00 (1H, dd, J=8.6, 2.0 Hz), 7.03-7.10 (3H, m), 7.20 (1H, t, J=74.0 Hz), 7.31 (1H, dd, J=9.2, 2.6 Hz), 7.33-7.46 (2H, m), 7.49 (1H, d, J=8.6 Hz), 7.56 (1H, d, J=2.6 Hz), 7.79 (1H, d, J=2.6 Hz), 9.49 (1H, s).

Example 278

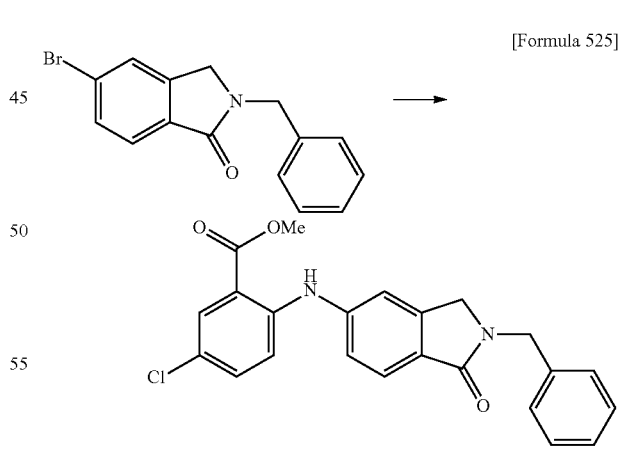

By the method similar to that of Example 5, methyl 2-((2-benzyl-1-oxoisoindolin-5-yl)amino)-5-chlorobenzoate was obtained from 2-benzyl-5-bromoisoindolin-1-one and methyl 2-amino-5-chlorobenzoate.

$^1$H-NMR (CDCl$_3$) δ: 3.91 (3H, s), 4.23 (2H, s), 4.79 (2H, s), 7.19 (1H, s), 7.24-7.38 (8H, m), 7.83 (1H, d, J=8.6 Hz), 7.95 (1H, t, J=1.3 Hz), 9.59 (1H, s).

Example 279

[Formula 526]

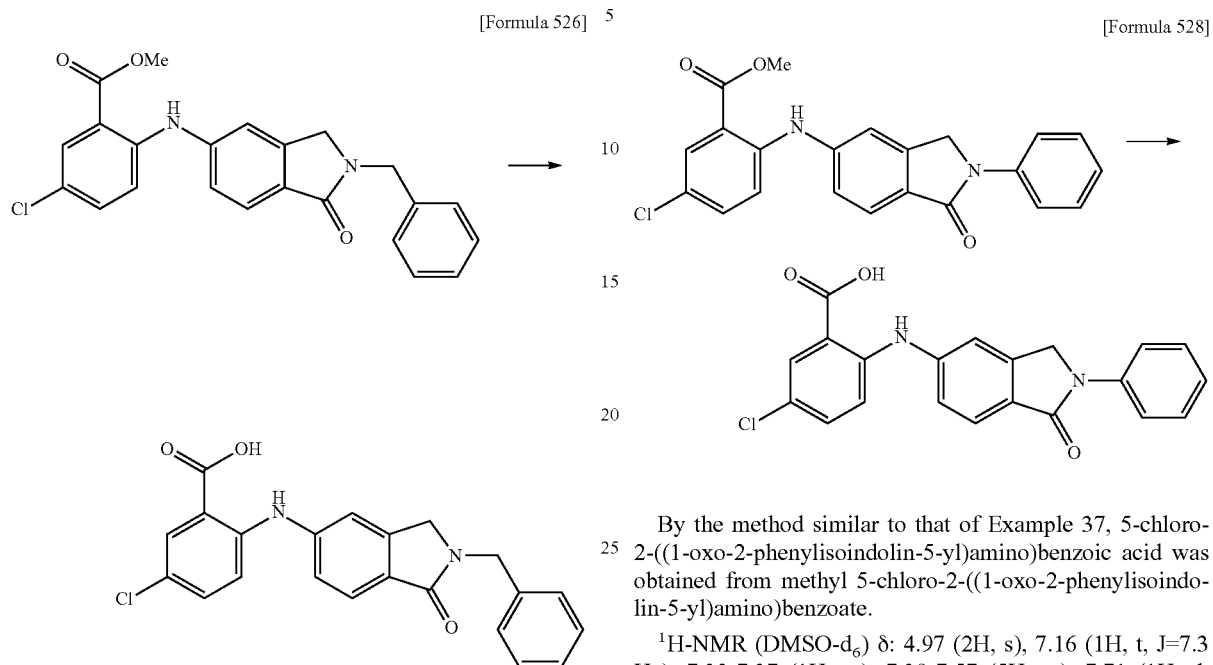

By the method similar to that of Example 37, 2-((2-benzyl-1-oxoisoindolin-5-yl)amino)-5-chlorobenzoic acid was obtained from methyl 2-((2-benzyl-1-oxoisoindolin-5-yl)amino)-5-chlorobenzoate.

$^1$H-NMR (DMSO-d$_6$) δ: 4.31 (2H, s), 4.70 (2H, s), 7.23-7.50 (9H, m), 7.66 (1H, d, J=7.9 Hz), 7.86 (1H, d, J=2.6 Hz), 9.76 (1H, s).

Example 280

[Formula 527]

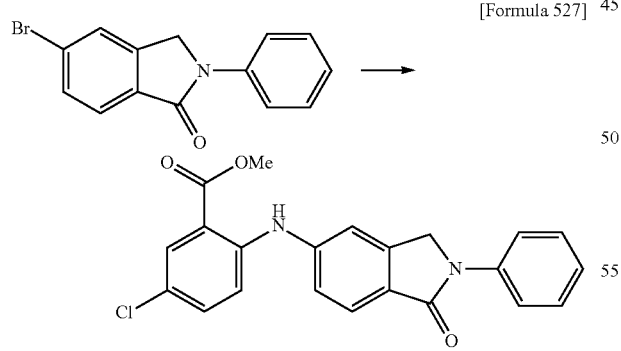

By the method similar to that of Example 5, methyl 5-chloro-2-((1-oxo-2-phenylisoindolin-5-yl)amino)benzoate was obtained from 5-bromo-2-phenylisoindolin-1-one and methyl 2-amino-5-chlorobenzoate.

$^1$H-NMR (CDCl$_3$) δ: 3.94 (3H, s), 4.83 (2H, s), 7.14-7.21 (1H, m), 7.28-7.48 (6H, m), 7.82-7.89 (3H, m), 7.98 (1H, d, J=2.0 Hz), 9.67 (1H, s).

Example 281

[Formula 528]

By the method similar to that of Example 37, 5-chloro-2-((1-oxo-2-phenylisoindolin-5-yl)amino)benzoic acid was obtained from methyl 5-chloro-2-((1-oxo-2-phenylisoindolin-5-yl)amino)benzoate.

$^1$H-NMR (DMSO-d$_6$) δ: 4.97 (2H, s), 7.16 (1H, t, J=7.3 Hz), 7.32-7.37 (1H, m), 7.39-7.57 (5H, m), 7.71 (1H, d, J=8.6 Hz), 7.86-7.93 (3H, m), 9.81 (1H, s).

Example 282

[Formula 529]

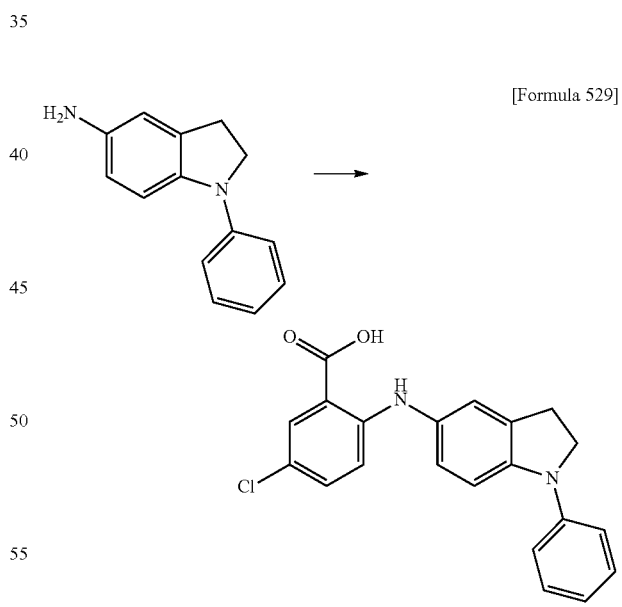

By the method similar to that of Example 5, methyl 5-chloro-2-((1-phenylindolin-5-yl)amino)benzoate was obtained from 1-phenylindolin-5-amine and methyl 2-bromo-5-chlorobenzoate.

$^1$H-NMR (CDCl$_3$) δ: 3.13 (2H, t, J=8.3 Hz), 3.90 (3H, s), 3.99 (2H, t, J=8.3 Hz), 6.87-7.05 (4H, m), 7.12 (1H, d, J=7.9 Hz), 7.15-7.26 (3H, m), 7.30-7.40 (2H, m), 7.89 (1H, d, J=2.6 Hz), 9.16 (1H, s).

Example 283

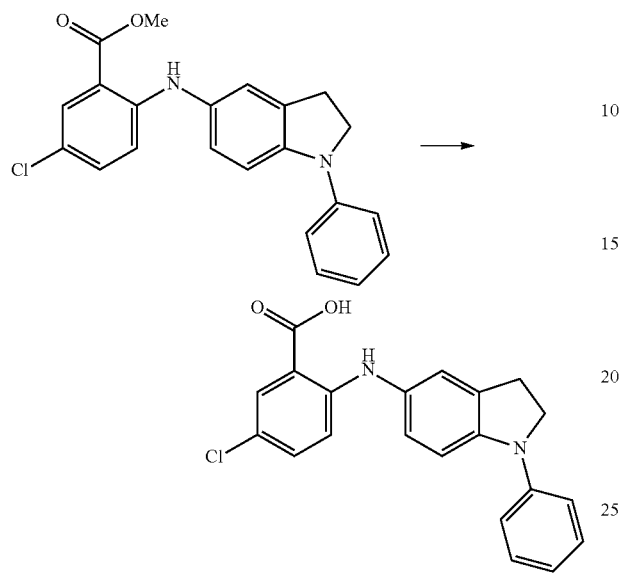

By the method similar to that of Example 37, 5-chloro-2-((1-phenylindolin-5-yl)amino)benzoic acid was obtained from methyl 5-chloro-2-((1-phenylindolin-5-yl)amino)benzoate.

¹H-NMR (DMSO-d₆) δ: 3.10 (2H, t, J=8.3 Hz), 3.96 (2H, t, J=8.6 Hz), 6.90-6.99 (3H, m), 7.07-7.15 (2H, m), 7.20-7.27 (2H, m), 7.31-7.40 (3H, m), 7.78 (1H, d, J=2.6 Hz), 9.37 (1H, s).

Example 284

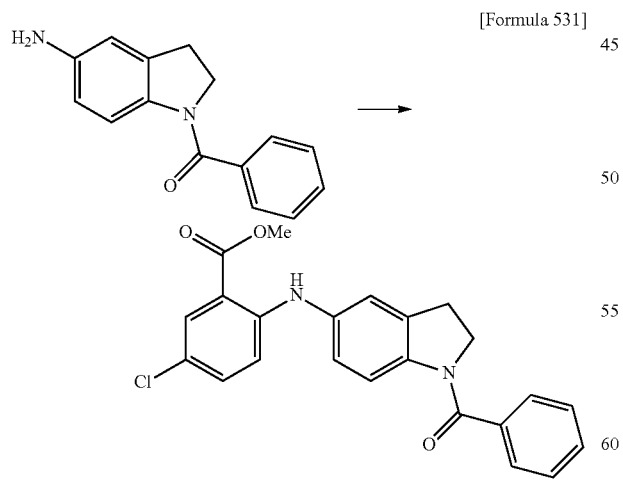

By the method similar to that of Example 5, methyl 2-((1-benzoylindolin-5-yl)amino)-5-chlorobenzoate was obtained from (5-aminoindolin-1-yl)(phenyl)methanone and methyl 2-bromo-5-chlorobenzoate.

¹H-NMR (CDCl₃) δ: 3.11 (2H, t, J=8.3 Hz), 3.91 (3H, s), 4.00-4.22 (2H, m), 6.97-7.11 (3H, m), 7.22 (1H, dd, J=9.2, 2.6 Hz), 7.40-7.62 (5H, m), 7.91 (1H, d, J=2.6 Hz), 8.18 (1H, brs), 9.31 (1H, s).

Example 285

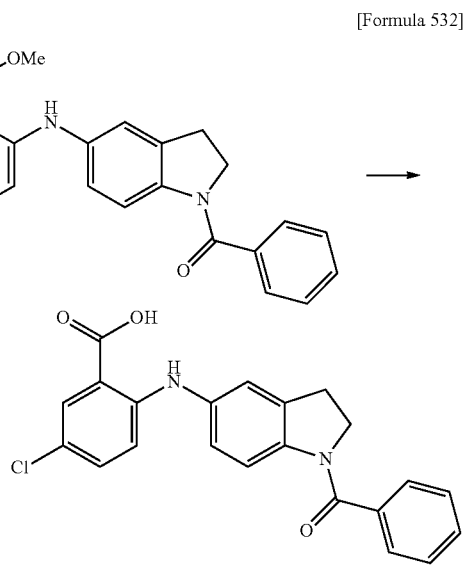

By the method similar to that of Example 37, 2-((1-Benzoylindolin-5-yl)amino)-5-chlorobenzoic acid was obtained from methyl 2-((1-benzoylindolin-5-yl)amino)-5-chlorobenzoate.

¹H-NMR (DMSO-d₆) δ: 3.09 (2H, t, J=8.3 Hz), 4.02 (2H, t, J=8.3 Hz), 7.09 (2H, d, J=9.2 Hz), 7.19 (1H, s), 7.40 (1H, dd, J=9.2, 2.6 Hz), 7.45-7.64 (5H, m), 7.82 (1H, d, J=2.6 Hz), 8.06 (1H, brs), 9.55 (1H, s).

Example 286

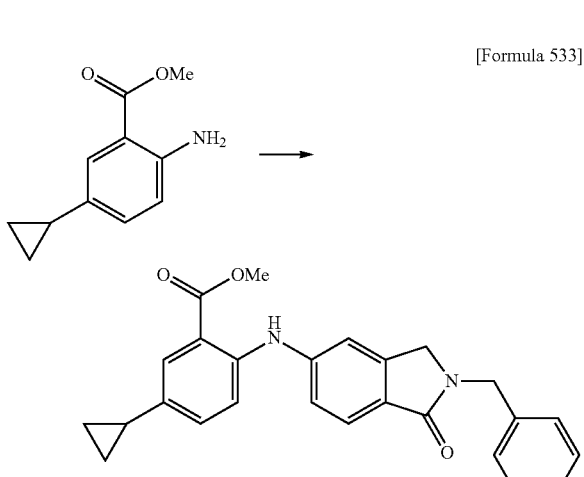

The mixture of 46 mg of methyl 2-amino-5-cyclopropylbenzoate, 60 mg of 2-benzyl-5-bromoisoindolin-1-one, 9.2 mg of tris(dibenzylideneacetone)dipalladium(0), 12 mg of 4,5'-bis(diphenylphosphino)-9,9'-dimethylxanthene, 0.13 g of cesium carbonate, and 2.5 mL of toluene, was stirred at 150° C. for 20 minutes under a nitrogen atmosphere using microwave equipment. The reaction mixture was cooled to room temperature, and 2.2 mg of palladium acetate was added thereto, and the resultant was stirred at 150° C. for 20 minutes under a nitrogen atmosphere using microwave equipment. The reaction mixture was cooled to room temperature, and ethyl acetate and water were then added thereto. The organic layer was separated, sequentially washed with water and a saturated aqueous sodium chloride solution and dried over anhydrous magnesium sulfate, and the solvent was distilled off under reduced pressure. The obtained residue was purified by silica gel column chromatography (gradient elution with hexane:ethyl acetate=90:10-70:30) to give 60 mg of methyl 2-((2-benzyl-1-oxoisoindolin-5-yl)amino)-5-cyclopropylbenzoate as a pale brown oil.

$^1$H-NMR (CDCl$_3$) δ: 0.60-0.67 (2H, m), 0.88-0.96 (2H, m), 1.80-1.90 (1H, m), 3.89 (3H, s), 4.20 (2H, s), 4.78 (2H, s), 7.11 (1H, dd, J=8.6, 2.0 Hz), 7.14-7.17 (1H, m), 7.20-7.38 (7H, m), 7.71 (1H, d, J=2.0 Hz), 7.79 (1H, d, J=8.6 Hz), 9.46 (1H, s).

Example 287

[Formula 534]

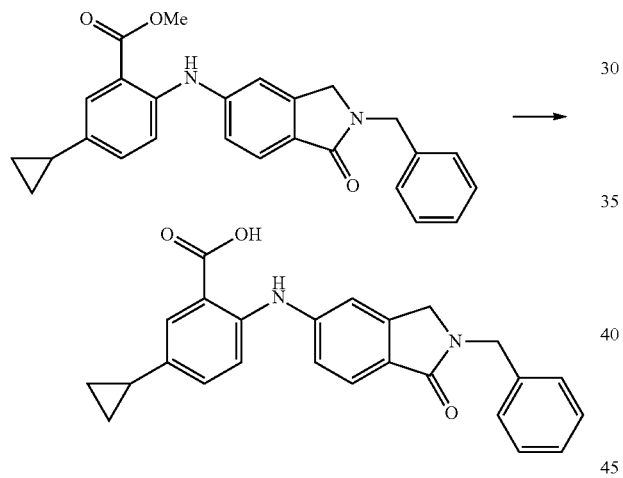

By the method similar to that of Example 37, 2-((2-benzyl-1-oxoisoindolin-5-yl)amino)-5-cyclopropylbenzoic acid was obtained from methyl 2-((2-benzyl-1-oxoisoindolin-5-yl)amino)-5-cyclopropylbenzoate.

$^1$H-NMR (DMSO-d$_6$) δ: 0.56-0.65 (2H, m), 0.86-0.96 (2H, m), 1.85-1.97 (1H, m), 4.28 (2H, s), 4.69 (2H, s), 7.13-7.41 (9H, m), 7.61 (1H, d, J=7.9 Hz), 7.66 (1H, d, J=2.0 Hz), 9.58 (1H, s), 13.19 (1H, brs).

Example 288

[Formula 535]

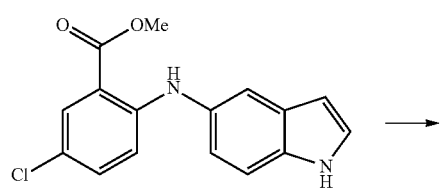

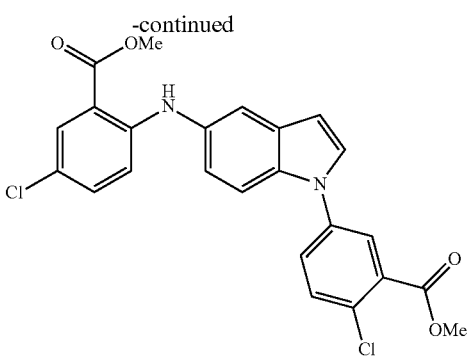

By the method similar to that of Example 5, methyl 2-chloro-5-(5-((4-chloro-2-(methoxycarbonyl)phenyl)amino)-1H-indol-1-yl)benzoate was obtained from methyl 2-((1H-indol-5-yl)amino)-5-chlorobenzoate and methyl 5-bromo-2-chlorobenzoate.

$^1$H-NMR (CDCl$_3$) δ: 3.92 (3H, s), 3.98 (3H, s), 6.67 (1H, d, J=2.6 Hz), 6.97 (1H, d, J=9.2 Hz), 7.11 (1H, dd, J=8.6, 2.0 Hz), 7.18 (1H, dd, J=9.2, 2.6 Hz), 7.34 (1H, d, J=3.3 Hz), 7.44-7.68 (4H, m), 7.92 (1H, d, J=2.6 Hz), 7.99 (1H, d, J=2.0 Hz), 9.38 (1H, brs).

Example 289

[Formula 536]

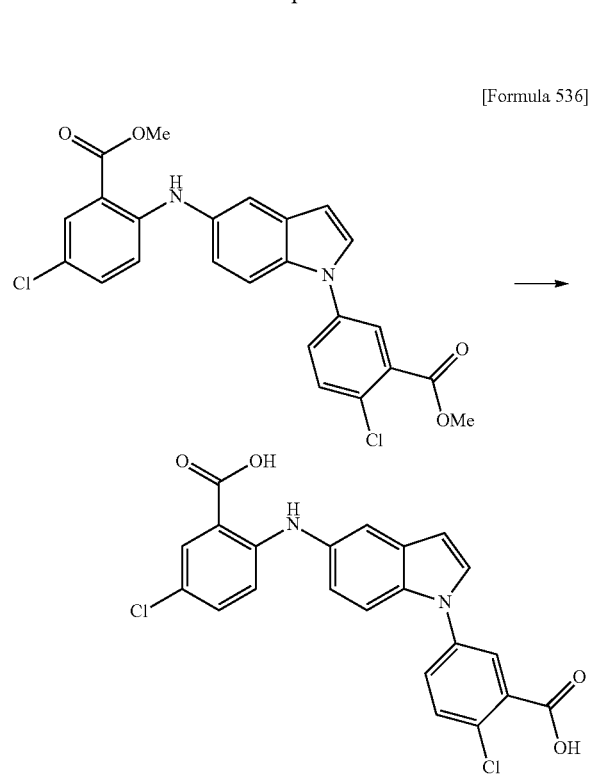

By the method similar to that of Example 47, 2-((1-(3-carboxy-4-chlorophenyl)-1H-indol-5-yl)amino)-5-chlorobenzoic acid was obtained from methyl 2-chloro-5-(5-((4-chloro-2-(methoxycarbonyl)phenyl)amino)-1H-indol-1-yl)benzoate.

$^1$H-NMR (DMSO-d$_6$) δ: 6.72 (1H, d, J=3.3 Hz), 7.01 (1H, d, J=9.2 Hz), 7.13 (1H, dd, J=8.6, 2.0 Hz), 7.36 (1H, dd, J=9.2, 2.6 Hz), 7.56 (1H, d, J=2.0 Hz), 7.61 (1H, d, J=8.6 Hz), 7.70-7.85 (4H, m), 7.97 (1H, d, J=2.6 Hz), 9.57 (1H, brs).

MS (ESI/APCI, m/z): 439 (M−H)$^-$.

Example 290

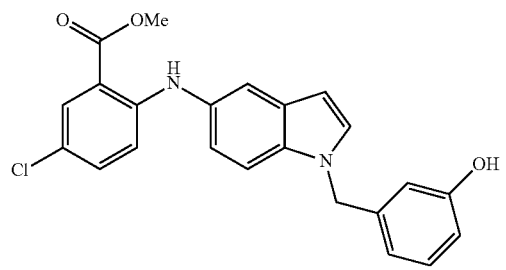
[Formula 537]

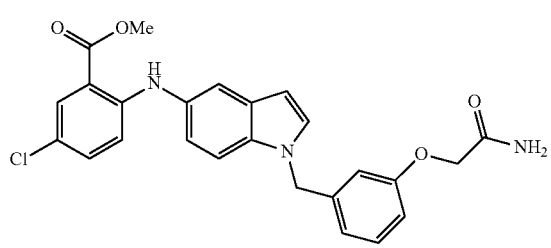

To the solution of 50 mg of methyl 5-chloro-2-((1-(3-hydroxybenzyl)-1H-indol-5-yl)amino)benzoate and 19.3 mg of 2-bromoacetamide in 0.26 mL of N,N-dimethylformamide, 70.2 mg of potassium carbonate was added at room temperature, and the resultant was stirred at room temperature for four hours. Water and ethyl acetate were added to the reaction mixture. The organic layer was separated and dried over anhydrous sodium sulfate and the solvent was distilled off under reduced pressure. The obtained residue was purified by silica gel column chromatography (hexane:ethyl acetate) to give 26 mg of methyl 2-((1-(3-(2-amino-2-oxoethoxy)benzyl)-1H-indol-5-yl)amino)-5-chlorobenzoate as an oil.

$^1$H-NMR (CDCl$_3$) δ: 3.91 (3H, s), 4.43 (2H, s), 5.31 (2H, s), 5.46-5.69 (1H, m), 6.32-6.57 (2H, m), 6.64-6.70 (1H, m), 6.78-6.87 (2H, m), 6.93 (1H, d, J=9.2 Hz), 7.02 (1H, dd, J=8.9, 2.3 Hz), 7.11-7.19 (2H, m), 7.20-7.33 (2H, m), 7.50 (1H, d, J=2.0 Hz), 7.90 (1H, d, J=2.6 Hz), 9.33 (1H, brs).

Example 291

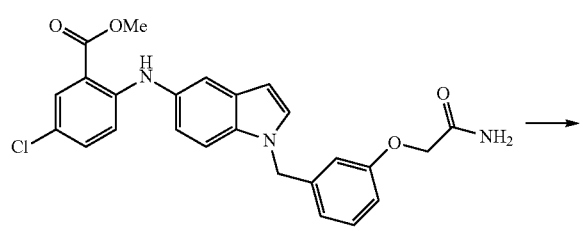
[Formula 538]

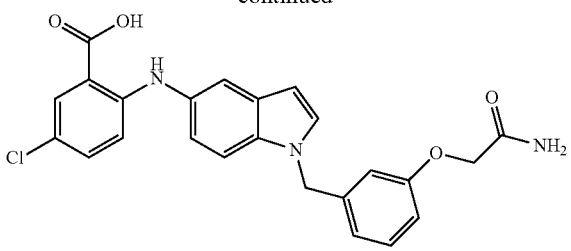

By the method similar to that of Example 47, 2-((1-(3-(2-amino-2-oxoethoxy)benzyl)-1H-indol-5-yl)amino)-5-chlorobenzoic acid was obtained from methyl 2-((1-(3-(2-amino-2-oxoethoxy)benzyl)-1H-indol-5-yl)amino)-5-chlorobenzoate.

$^1$H-NMR (DMSO-d$_6$) δ: 4.62 (2H, s), 5.39 (2H, s), 6.46 (1H, d, J=3.3 Hz), 6.73-6.84 (3H, m), 6.91 (1H, d, J=9.2 Hz), 6.99 (1H, dd, J=8.6, 2.0 Hz), 7.16-7.35 (2H, m), 7.43 (1H, d, J=2.0 Hz), 7.49 (1H, d, J=8.6 Hz), 7.55 (1H, d, J=3.3 Hz), 7.78 (1H, d, J=2.6 Hz), 9.49 (1H, brs).

MS (ESI/APCI, m/z): 448 (M–H)$^-$.

Example 292

[Formula 539]

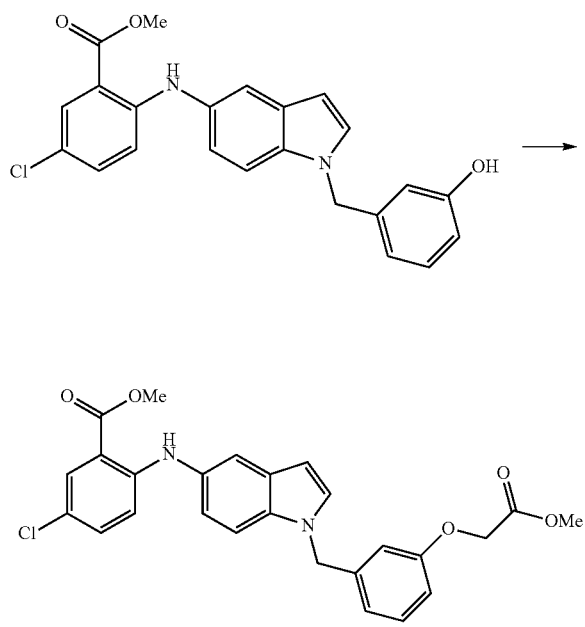

By the method similar to that of Example 290, methyl 5-chloro-2-((1-(3-(2-methoxy-2-oxoethoxy)benzyl)-1H-indol-5-yl)amino)benzoate was obtained from methyl 5-chloro-2-((1-(3-hydroxybenzyl)-1H-indol-5-yl)amino)benzoate and methyl 2-bromoacetate.

$^1$H-NMR (CDCl$_3$) δ: 3.76 (3H, s), 3.91 (3H, s), 4.56 (2H, s), 5.29 (2H, s), 6.51 (1H, d, J=2.6 Hz), 6.63-6.70 (1H, m), 6.75-6.83 (2H, m), 6.93 (1H, d, J=9.2 Hz), 7.02 (1H, dd, J=8.6, 2.0 Hz), 7.10-7.19 (2H, m), 7.20-7.29 (2H, m), 7.48 (1H, d, J=2.0 Hz), 7.90 (1H, d, J=2.6 Hz), 9.32 (1H, brs).

Example 293

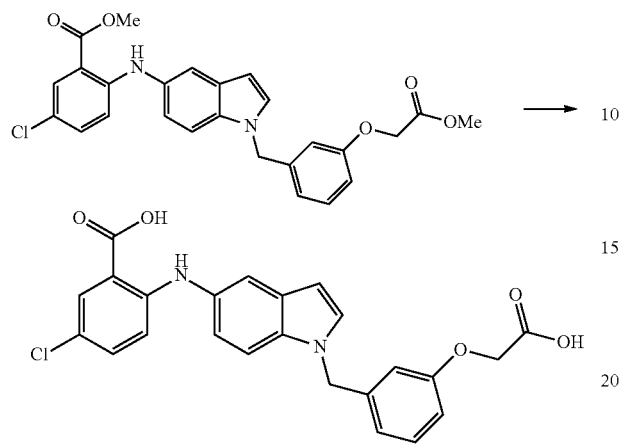
[Formula 540]

By the method similar to that of Example 47, 2-((1-(3-(carboxymethoxy)benzyl)-1H-indol-5-yl)amino)-5-chlorobenzoic acid was obtained from methyl 5-chloro-2-((1-(3-(2-methoxy-2-oxoethoxy)benzyl)-1H-indol-5-yl)amino)benzoate.

$^1$H-NMR (DMSO-d$_6$) δ: 4.62 (2H, s), 5.39 (2H, s), 6.46 (1H, d, J=2.6 Hz), 6.74-6.84 (3H, m), 6.91 (1H, d, J=9.2 Hz), 6.99 (1H, dd, J=8.6, 2.0 Hz), 7.18-7.26 (1H, m), 7.30 (1H, dd, J=9.2, 2.6 Hz), 7.43 (1H, d, J=2.0 Hz), 7.49 (1H, d, J=8.6 Hz), 7.54 (1H, d, J=2.6 Hz), 7.78 (1H, d, J=2.6 Hz), 9.50 (1H, brs).

MS (ESI/APCI, m/z): 451 (M+H)$^+$, 449 (M−H)$^−$.

Example 294

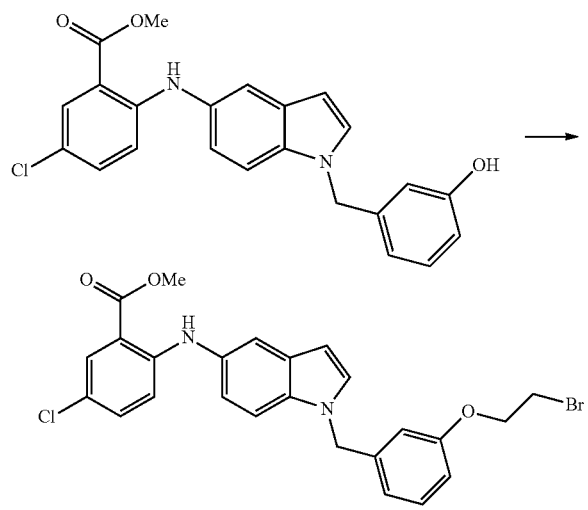
[Formula 541]

To the solution of 89.4 mg of methyl 5-chloro-2-((1-(3-hydroxybenzyl)-1H-indol-5-yl)amino)benzoate and 190 µL of 1,2-dibromoethane in 0.47 mL of N,N-dimethylformamide, 91.2 mg of potassium carbonate was added at room temperature, and the resultant was stirred for 6.5 hours. The reaction mixture was allowed to stand overnight, and water and ethyl acetate were then added thereto. The organic layer was separated and dried over anhydrous sodium sulfate, and the solvent was distilled off under reduced pressure. The obtained residue was purified by silica gel column chromatography (hexane:ethyl acetate) to give 20 mg of methyl 2-((1-(3-(2-bromoethoxy)benzyl)-1H-indol-5-yl)amino)-5-chlorobenzoate as an oil.

$^1$H-NMR (CDCl$_3$) δ: 3.59 (2H, t, J=6.3 Hz), 3.91 (3H, s), 4.22 (2H, t, J=6.3 Hz), 5.29 (2H, s), 6.51 (1H, d, J=3.3 Hz), 6.66-6.70 (1H, m), 6.76 (1H, d, J=7.9 Hz), 6.82 (1H, dd, J=8.3, 2.3 Hz), 6.92 (1H, d, J=9.2 Hz), 7.02 (1H, dd, J=8.6, 2.0 Hz), 7.10-7.19 (2H, m), 7.20-7.29 (2H, m), 7.49 (1H, d, J=2.0 Hz), 7.90 (1H, d, J=2.6 Hz), 9.32 (1H, brs).

Example 295

[Formula 542]

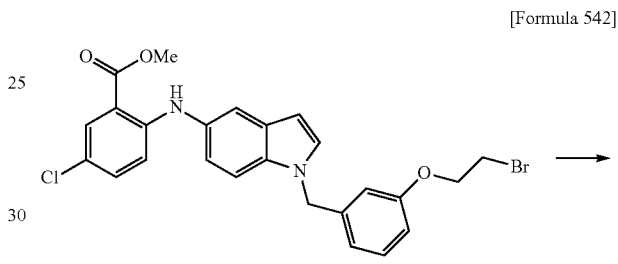

The mixture of 19 mg of methyl 2-((1-(3-(2-bromoethoxyl)benzyl)-1H-indol-5-yl)amino)-5-chlorobenzoate, 9.7 µL of morpholine, 15.3 mg of potassium carbonate, and 0.2 mL of N,N-dimethylformamide, was stirred at an external temperature of 80° C. for 30 minutes. The reaction mixture was cooled to room temperature, and water and ethyl acetate were then added thereto. The organic layer was separated and dried over anhydrous sodium sulfate, and the solvent was distilled off under reduced pressure. The obtained residue was purified by silica gel column chromatography (hexane:ethyl acetate) to give 20.1 mg of methyl 5-chloro-2-((1-(3-(2-morpholinoethoxyl)benzyl)-1H-indol-5-yl)amino)benzoate as an oil.

$^1$H-NMR (CDCl$_3$) δ: 2.45-2.67 (4H, m), 2.68-2.88 (2H, m), 3.64-3.82 (4H, m), 3.91 (3H, s), 3.99-4.21 (2H, m), 5.28 (2H, s), 6.45-6.60 (1H, s), 6.65-7.10 (5H, m), 7.10-7.36 (4H, m), 7.43-7.58 (1H, m), 7.85-7.98 (1H, m), 9.24-9.44 (1H, m).

Example 296

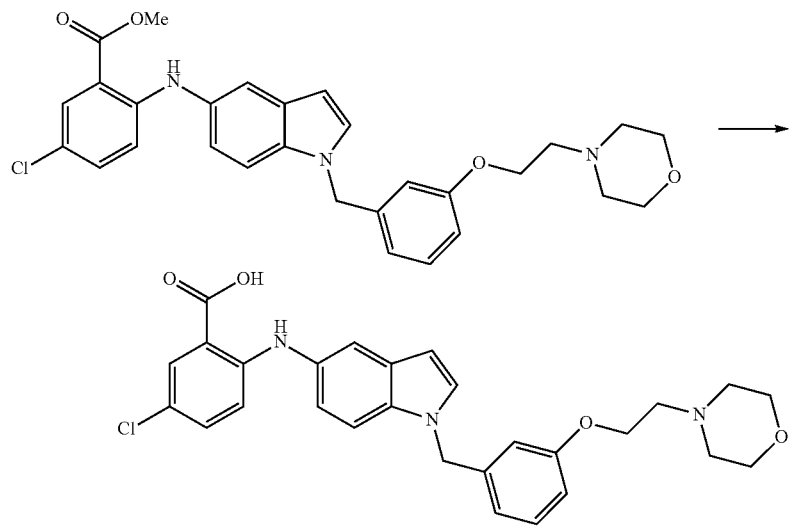
[Formula 543]

By the method similar to that of Example 47, 5-chloro-2-((1-(3-(2-morpholinoethoxyl)benzyl)-1H-indol-5-yl)amino)benzoic acid was obtained from methyl 5-chloro-2-((1-(3-(2-morpholinoethoxyl)benzyl)-1H-indol-5-yl)amino)benzoate.

$^1$H-NMR (CD$_3$OD) δ: 3.25-3.34 (8H, m), 3.51-3.61 (2H, m), 4.25-4.35 (2H, m), 5.39 (2H, s), 6.49 (1H, d, J=3.3 Hz), 6.67-6.75 (1H, m), 6.85-7.02 (4H, m), 7.12-7.22 (1H, m), 7.23-7.36 (3H, m), 7.38-7.46 (1H, m), 7.86 (1H, d, J=2.6 Hz).

MS (ESI/APCI, m/z): 506 (M+H)$^+$, 504 (M−H)$^-$.

Example 297

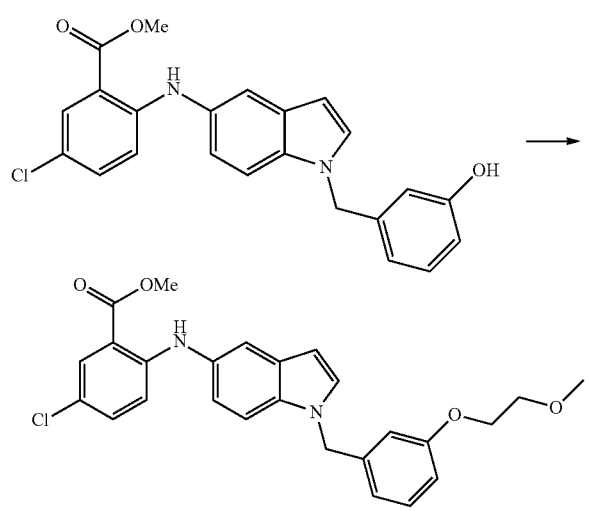
[Formula 544]

By the method similar to that of Example 290, methyl 5-chloro-2-((1-(3-(2-methoxyethoxyl)benzyl)-1H-indol-5-yl)amino)benzoate was obtained from methyl 5-chloro-2-((1-(3-hydroxybenzyl)-1H-indol-5-yl)amino)benzoate and 1-bromo-2-methoxyethane.

$^1$H-NMR (CDCl$_3$) δ: 3.42 (3H, s), 3.59-3.86 (2H, m), 3.91 (3H, s), 3.99-4.20 (2H, m), 5.28 (2H, s), 6.46-6.59 (1H, m), 6.63-7.08 (5H, m), 7.10-7.36 (4H, m), 7.41-7.61 (1H, m), 7.83-8.02 (1H, m), 9.31 (1H, brs).

Example 298

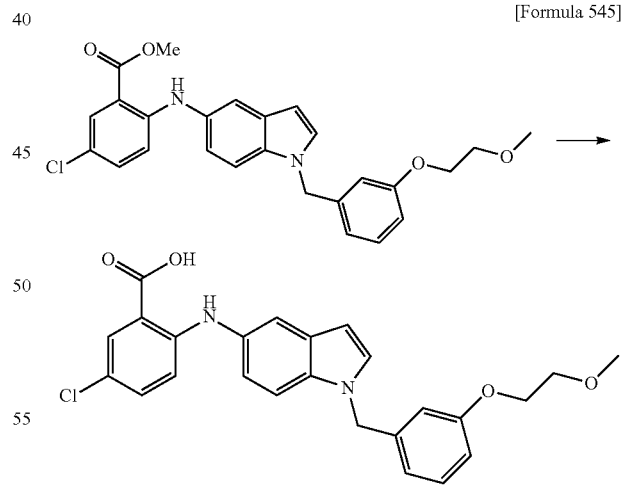
[Formula 545]

By the method similar to that of Example 47, 5-chloro-2-((1-(3-(2-methoxyethoxyl)benzyl)-1H-indol-5-yl)amino)benzoic acid was obtained from methyl 5-chloro-2-((1-(3-(2-methoxyethoxyl)benzyl)-1H-indol-5-yl)amino)benzoate.

$^1$H-NMR (DMSO-d$_6$) δ: 3.27 (3H, s), 3.55-3.67 (2H, m), 3.94-4.08 (2H, m), 5.39 (2H, s), 6.46 (1H, d, J=2.6 Hz), 6.73-6.87 (3H, m), 6.91 (1H, d, J=8.6 Hz), 6.99 (1H, dd, J=8.6, 2.0 Hz), 7.17-7.27 (1H, m), 7.30 (1H, dd, J=9.2, 2.6

Hz), 7.43 (1H, d, J=1.3 Hz), 7.48 (1H, d, J=8.6 Hz), 7.55 (1H, d, J=3.3 Hz), 7.78 (1H, d, J=2.6 Hz), 9.48 (1H, brs), 13.26 (1H, brs).

MS (ESI, m/z): 451 (M+H)$^+$, 449 (M−H)$^−$.

Example 299

[Formula 546]

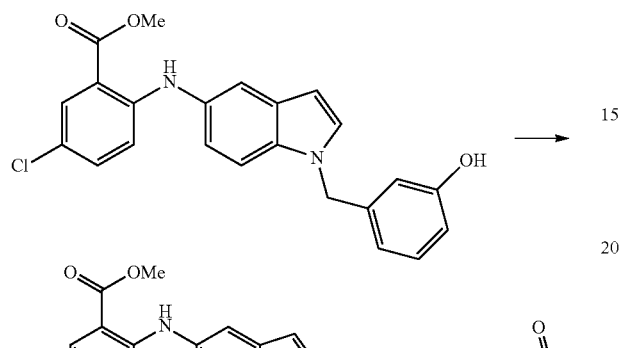

By the method similar to that of Example 290, methyl 2-((1-(3-(2-acetoxyethoxyl)benzyl)-1H-indol-5-yl)amino)-5-chlorobenzoate was obtained from methyl 5-chloro-2-((1-(3-hydroxybenzyl)-1H-indol-5-yl)amino)benzoate and 2-bromoethyl acetate.

Example 300

[Formula 547]

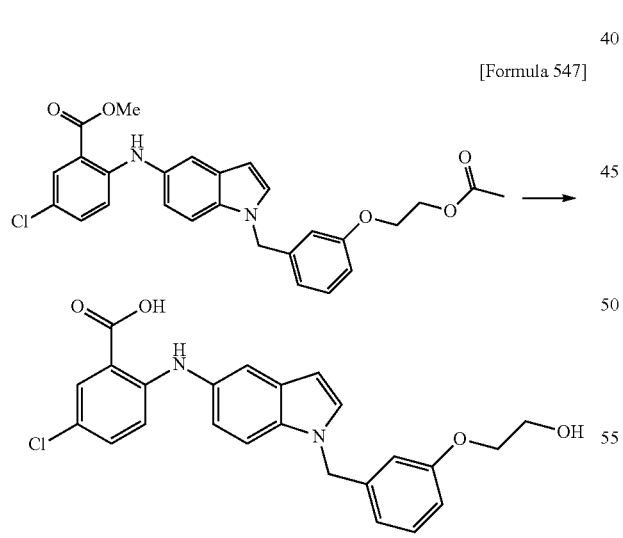

To the solution of 24.1 mg of methyl 2-((1-(3-(2-acetoxyethoxy)benzyl)-1H-indol-5-yl)amino)-5-chlorobenzoate in 0.3 mL of ethanol, 39.2 μL of a 5 mol/L aqueous sodium hydroxide solution was added at room temperature, and the resultant was stirred at an external temperature of 80° C. for 10 minutes. The reaction mixture was cooled to room temperature, and water and 3 mol/L hydrochloric acid were then added thereto. The solid was collected by filtration and purified by silica gel column chromatography (chloroform:methanol) to give 12.1 mg of 5-chloro-2-((1-(3-(2-hydroxyethoxy)benzyl)-1H-indol-5-yl)amino)benzoic acid as a yellow solid.

$^1$H-NMR (DMSO-d$_6$) δ: 3.61-3.72 (2H, m), 3.86-3.96 (2H, m), 4.82 (1H, t, J=5.6 Hz), 5.39 (2H, s), 6.47 (1H, d, J=3.3 Hz), 6.71-6.86 (3H, m), 6.91 (1H, d, J=9.2 Hz), 6.99 (1H, dd, J=8.6, 2.0 Hz), 7.17-7.27 (1H, m), 7.30 (1H, dd, J=9.2, 2.6 Hz), 7.43 (1H, d, J=2.0 Hz), 7.48 (1H, d, J=9.2 Hz), 7.55 (1H, d, J=3.3 Hz), 7.78 (1H, d, J=2.6 Hz), 9.50 (1H, brs).

MS (ESI, m/z): 437 (M+H)$^+$, 435 (M−H)$^−$.

Example 301

[Formula 548]

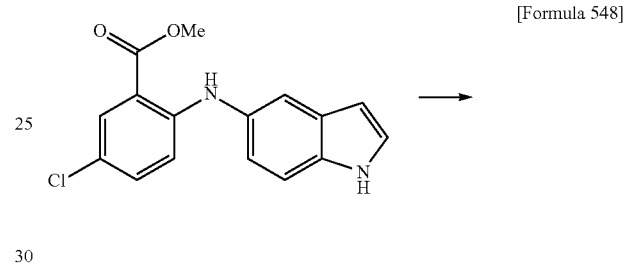

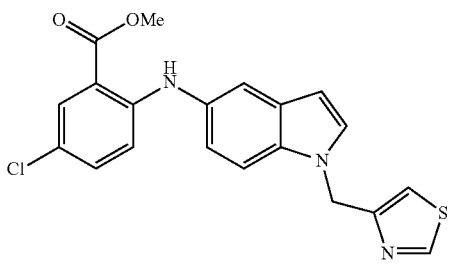

To the solution of 50 mg of methyl 2-((1H-indol-5-yl)amino)-5-chlorobenzoate and 33.8 mg of 4-(chloromethyl)thiazole hydrochloride in 0.5 mL of N,N-dimethylacetamide, 46.6 mg of potassium tert-butoxide was added under ice-cooling, and the resultant was stirred under ice-cooling for five minutes and then stirred at room temperature for 25 minutes. Water and ethyl acetate were added to the reaction mixture. The organic layer was separated and dried over anhydrous sodium sulfate and the solvent was distilled off under reduced pressure. The obtained residue was purified by silica gel column chromatography (hexane:ethyl acetate) to give 27.4 mg of methyl 5-chloro-2-((1-(thiazol-4-ylmethyl)-1H-indol-5-yl)amino)benzoate as an oil.

$^1$H-NMR (CDCl$_3$) δ: 3.91 (3H, s), 5.52 (2H, s), 6.53 (1H, d, J=3.3 Hz), 6.88 (1H, d, J=1.3 Hz), 6.92 (1H, d, J=9.2 Hz), 7.05 (1H, dd, J=8.9, 2.3 Hz), 7.14 (1H, dd, J=9.2, 2.6 Hz), 7.25 (1H, d, J=3.3 Hz), 7.33 (1H, d, J=8.6 Hz), 7.49 (1H, d, J=2.0 Hz), 7.90 (1H, d, J=2.6 Hz), 8.81 (1H, d, J=2.0 Hz), 9.33 (1H, brs).

Example 302

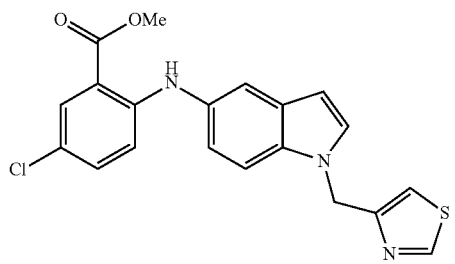

[Formula 549]

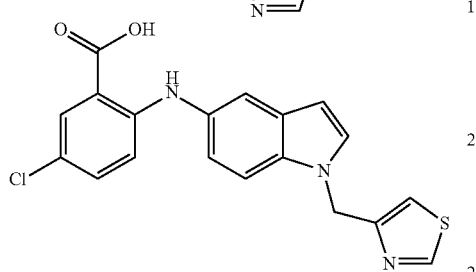

By the method similar to that of Example 47, 5-chloro-2-((1-(thiazol-4-ylmethyl)-1H-indol-5-yl)amino)benzoic acid was obtained from methyl 5-chloro-2-((1-(thiazol-4-ylmethyl)-1H-indol-5-yl)amino)benzoate.

$^1$H-NMR (DMSO-$d_6$) δ: 5.54 (2H, s), 6.44 (1H, d, J=3.3 Hz), 6.90 (1H, d, J=9.2 Hz), 7.01 (1H, dd, J=8.6, 2.0 Hz), 7.31 (1H, dd, J=9.2, 2.6 Hz), 7.42 (1H, d, J=2.0 Hz), 7.50 (1H, d, J=3.3 Hz), 7.55 (1H, d, J=2.0 Hz), 7.59 (1H, d, J=8.6 Hz), 7.79 (1H, d, J=2.6 Hz), 9.06 (1H, d, J=2.0 Hz), 9.49 (1H, brs), 13.28 (1H, brs).

MS (ESI/APCI, m/z): 382 (M−H)⁻.

Example 303

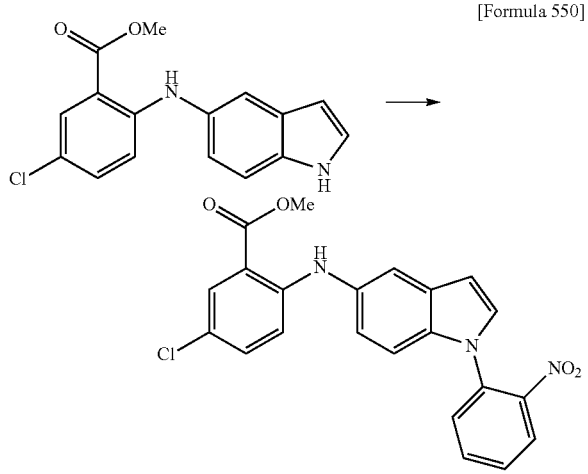

[Formula 550]

To the solution of 30 mg of methyl 2-((1H-indol-5-yl)amino)-5-chlorobenzoate and 65.2 mg of cesium carbonate in 0.3 mL of dimethyl sulfoxide, 10.5 μL of 2-fluoronitrobenzene was added at room temperature. After stirring at an external temperature of 50° C. for one hour, 5 μL of 2-fluoronitrobenzene was added thereto, and the resultant was further stirred at 50° C. for 75 minutes. The reaction mixture was cooled to room temperature, and water and ethyl acetate were then added thereto. The organic layer was separated and dried over anhydrous sodium sulfate, and the solvent was distilled off under reduced pressure. The obtained residue was purified by silica gel column chromatography (hexane:ethyl acetate) to give 39 mg of methyl 5-chloro-2-((1-(2-nitrophenyl)-1H-indol-5-yl)amino)benzoate as an oil.

$^1$H-NMR (CDCl$_3$) δ: 3.91 (3H, s), 6.70 (1H, d, J=3.3 Hz), 6.98 (1H, d, J=9.2 Hz), 7.05 (1H, dd, J=8.9, 2.3 Hz), 7.12 (1H, d, J=8.6 Hz), 7.15-7.21 (2H, m), 7.49-7.66 (3H, m), 7.72-7.82 (1H, m), 7.91 (1H, d, J=2.6 Hz), 8.06 (1H, d, J=8.6 Hz), 9.35 (1H, brs).

Example 304

[Formula 551]

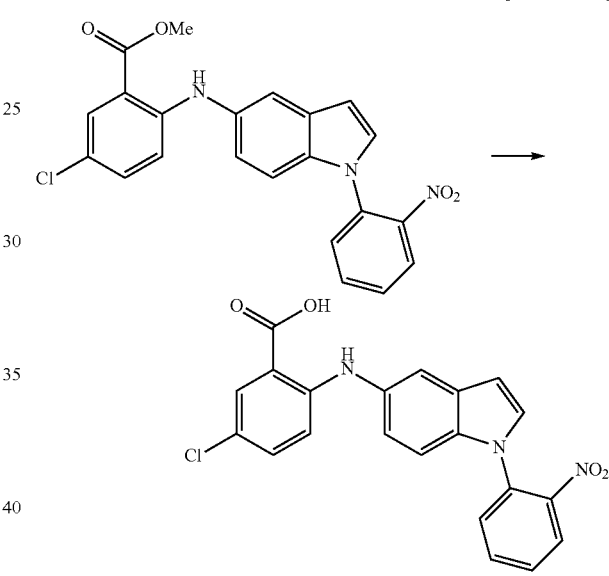

By the method similar to that of Example 47, 5-chloro-2-((1-(2-nitrophenyl)-1H-indol-5-yl)amino)benzoic acid was obtained from methyl 5-chloro-2-((1-(2-nitrophenyl)-1H-indol-5-yl)amino)benzoate.

$^1$H-NMR (DMSO-$d_6$) δ: 6.71 (1H, d, J=3.3 Hz), 7.00 (1H, d, J=9.2 Hz), 7.05 (1H, dd, J=8.6, 2.0 Hz), 7.12 (1H, d, J=8.6 Hz), 7.35 (1H, dd, J=9.2, 2.6 Hz), 7.51-7.58 (2H, m), 7.71-7.84 (3H, m), 7.89-7.99 (1H, m), 8.22 (1H, dd, J=8.3, 1.7 Hz), 9.58 (1H, s).

MS (ESI, m/z): 408 (M+H)⁺, 406 (M−H)⁻.

Example 305

[Formula 552]

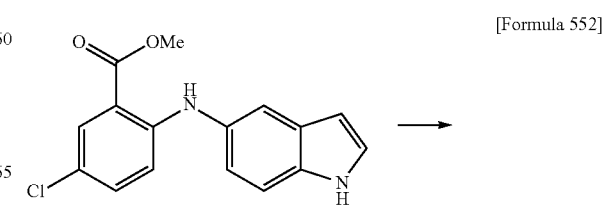

-continued

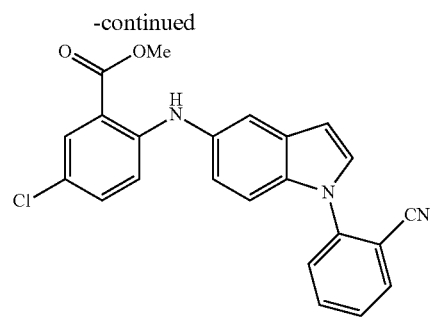

By the method similar to that of Example 303, methyl 5-chloro-2-((1-(2-cyanophenyl)-1H-indol-5-yl)amino)benzoate was obtained from methyl 2-((1H-indol-5-yl)amino)-5-chlorobenzoate and 2-fluorobenzonitrile.

$^1$H-NMR (CDCl$_3$) δ: 3.92 (3H, s), 6.65-6.85 (1H, m), 6.91-8.04 (11H, m), 9.38 (1H, brs).

Example 306

[Formula 553]

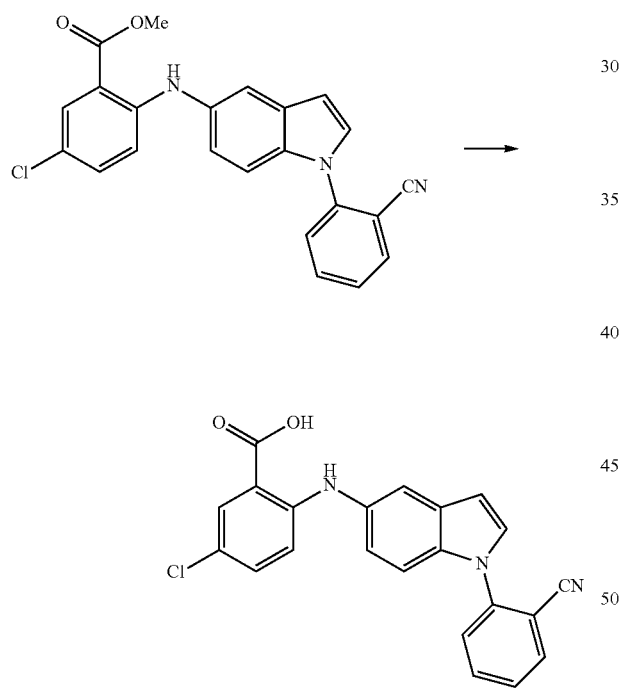

By the method similar to that of Example 47, 5-chloro-2-((1-(2-cyanophenyl)-1H-indol-5-yl)amino)benzoic acid was obtained from methyl 5-chloro-2-((1-(2-cyanophenyl)-1H-indol-5-yl)amino)benzoate.

$^1$H-NMR (DMSO-d$_6$) δ: 6.76 (1H, d, J=3.3 Hz), 7.02 (1H, d, J=9.2 Hz), 7.11 (1H, dd, J=8.6, 2.0 Hz), 7.28-7.39 (2H, m), 7.58 (1H, d, J=1.3 Hz), 7.65-7.72 (1H, m), 7.74 (1H, d, J=3.3 Hz), 7.77 (1H, d, J=7.3 Hz), 7.82 (1H, d, J=2.6 Hz), 7.89-7.97 (1H, m), 8.11 (1H, dd, J=7.6, 1.7 Hz), 9.58 (1H, brs), 13.33 (1H, brs).

MS (ESI, m/z): 388 (M+H)$^+$, 386 (M−H)$^−$.

Example 307

[Formula 554]

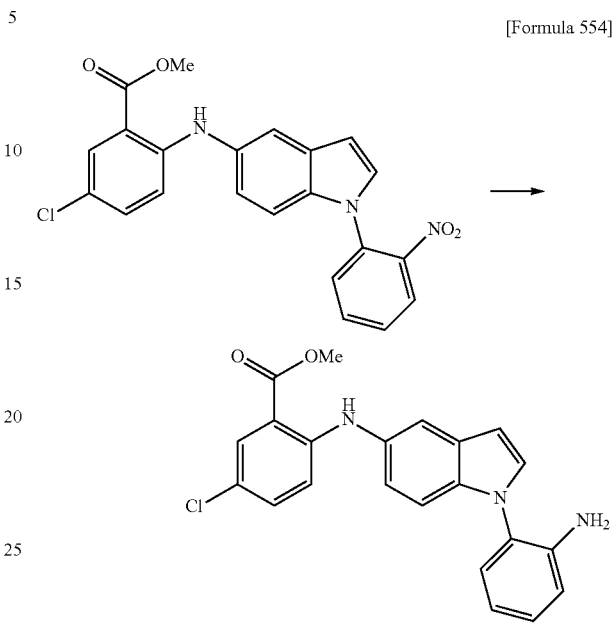

To the mixture of 140 mg of 5-chloro-2-((1-(2-nitrophenyl)-1H-indol-5-yl)amino)benzoic acid, 160 mg of ammonium chloride, 1.8 mL of ethanol and 0.42 mL of water, 130 mg of reduced iron was added, and the resultant was heated at reflux for 1.5 hours. After cooling the reaction mixture to room temperature, the insoluble matter was filtered off and the solvent was distilled off under reduced pressure. The obtained residue was purified by silica gel column chromatography (hexane:ethyl acetate) to give 133 mg of methyl 2-((1-(2-aminophenyl)-1H-indol-5-yl)amino)-5-chlorobenzoate as an oil.

$^1$H-NMR (CDCl$_3$) δ: 3.63 (2H, s), 3.91 (3H, s), 6.66 (1H, d, J=3.3 Hz), 6.82-6.92 (2H, m), 6.97 (1H, d, J=9.2 Hz), 7.05 (1H, dd, J=8.6, 2.0 Hz), 7.10-7.19 (2H, m), 7.19-7.31 (3H, m), 7.53 (1H, d, J=2.0 Hz), 7.91 (1H, d, J=2.6 Hz), 9.36 (1H, s).

Example 308

[Formula 555]

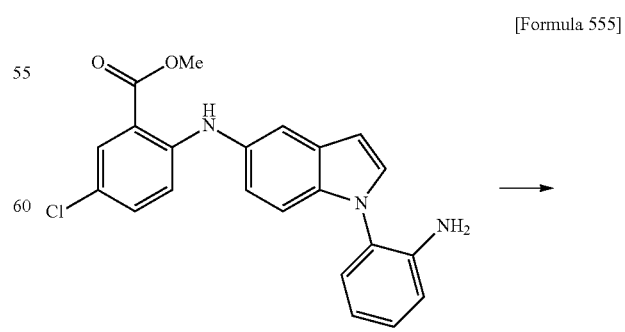

-continued

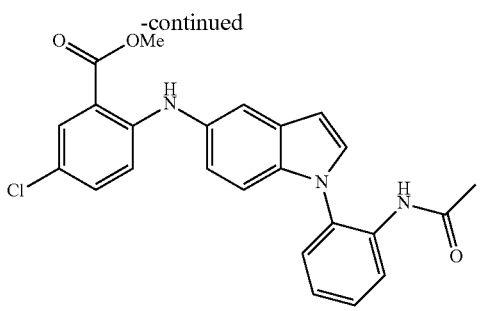

To the solution of 30 mg of methyl 2-((1-(2-aminophenyl)-1H-indol-5-yl)amino)-5-chlorobenzoate and 12.3 µL of pyridine in 0.23 mL of dichloromethane, 8.2 µL of acetyl chloride was added under ice-cooling, and the resultant was stirred for 10 minutes. A saturated aqueous sodium bicarbonate solution was added to the reaction mixture, and the resultant was then warmed to room temperature, and ethyl acetate was added thereto. The organic layer was separated and dried over anhydrous sodium sulfate and the solvent was distilled off under reduced pressure. The obtained residue was purified by silica gel column chromatography (hexane: ethyl acetate) to give 30 mg of methyl 2-((1-(2-acetamidophenyl)-1H-indol-5-yl)amino)-5-chlorobenzoate as an oil.

$^1$H-NMR (CDCl$_3$) δ: 1.95 (3H, s), 3.92 (3H, s), 6.67-6.92 (2H, m), 6.93-7.41 (7H, m), 7.42-7.65 (2H, m), 7.85-8.03 (1H, m), 8.33-8.54 (1H, m), 9.40 (1H, brs).

Example 309

[Formula 556]

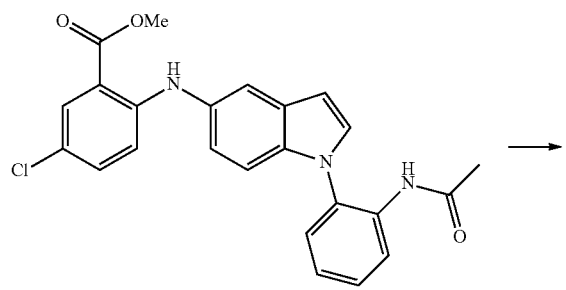

By the method similar to that of Example 300, 2-((1-(2-acetamidophenyl)-1H-indol-5-yl)amino)-5-chlorobenzoic acid was obtained from methyl 2-((1-(2-acetamidophenyl)-1H-indol-5-yl)amino)-5-chlorobenzoate.

$^1$H-NMR (DMSO-d$_6$) δ: 1.82 (3H, s), 6.66 (1H, d, J=3.3 Hz), 6.91-7.12 (3H, m), 7.25-7.55 (6H, m), 7.72 (1H, d, J=8.6 Hz), 7.81 (1H, d, J=2.6 Hz), 9.33 (1H, s).

Example 310

[Formula 557]

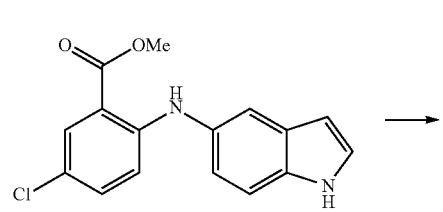

The reaction mixture of 50 mg of methyl 2-((1H-indol-5-yl)amino)-5-chlorobenzoate, 19.3 µL of 2-bromopyridine, 1.6 mg of copper(I) iodide, 70.5 mg of tripotassium phosphate, 5.2 µL of trans-N,N'-dimethylcyclohexane-1,2-diamine, and 0.58 mL of toluene, was heated at reflux for two hours under a nitrogen atmosphere. The reaction mixture was cooled to room temperature, and water and ethyl acetate were added thereto. The organic layer was separated and dried over anhydrous sodium sulfate, and the solvent was distilled off under reduced pressure. The obtained residue was purified by silica gel column chromatography (hexane: ethyl acetate) to give 14.4 mg of methyl 5-chloro-2-((1-(pyridin-2-yl)-1H-indol-5-yl)amino)benzoate as an oil.

$^1$H-NMR (CDCl$_3$) δ: 3.92 (3H, s), 6.68 (1H, d, J=4.0 Hz), 7.00 (1H, d, J=9.2 Hz), 7.12-7.23 (3H, m), 7.44-7.52 (2H, m), 7.73 (1H, d, J=4.0 Hz), 7.79-7.89 (1H, m), 7.92 (1H, d, J=2.0 Hz), 8.26 (1H, d, J=9.2 Hz), 8.54-8.60 (1H, m), 9.39 (1H, brs).

Example 311

[Formula 558]

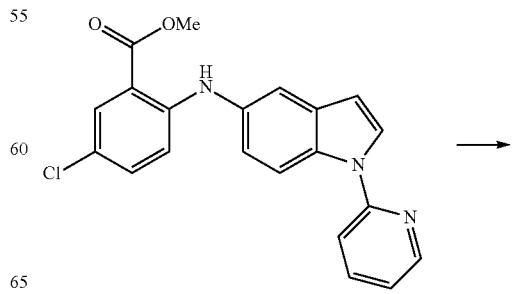

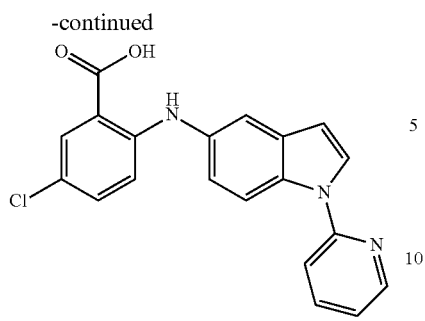

By the method similar to that of Example 47, 5-chloro-2-((1-(pyridin-2-yl)-1H-indol-5-yl)amino)benzoic acid was obtained from methyl 5-chloro-2-((1-(pyridin-2-yl)-1H-indol-5-yl)amino)benzoate.

$^1$H-NMR (DMSO-d$_6$) δ: 6.75 (1H, d, J=4.0 Hz), 7.06 (1H, d, J=9.2 Hz), 7.16 (1H, dd, J=9.2, 2.0 Hz), 7.27-7.41 (2H, m), 7.54 (1H, d, J=2.0 Hz), 7.74-7.86 (2H, m), 7.94-8.05 (1H, m), 8.09 (1H, d, J=3.3 Hz), 8.46 (1H, d, J=8.6 Hz), 8.58 (1H, d, J=4.0 Hz), 9.60 (1H, brs).

MS (ESI/APCI, m/z): 364 (M+H)$^+$, 362 (M−H)$^−$.

Example 312

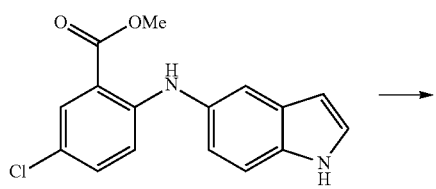

[Formula 559]

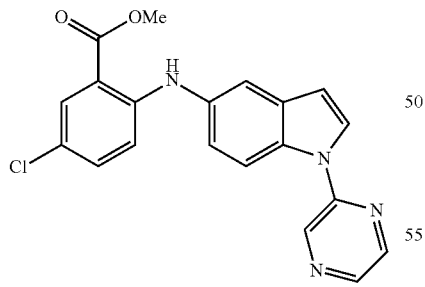

By the method similar to that of Example 310, methyl 5-chloro-2-((1-(pyrazin-2-yl)-1H-indol-5-yl)amino)benzoate was obtained from methyl 2-((1H-indol-5-yl)amino)-5-chlorobenzoate and 2-bromopyrazine.

$^1$H-NMR (CDCl$_3$) δ: 3.93 (3H, s), 6.69-6.86 (1H, m), 6.98-7.14 (1H, m), 7.15-7.38 (2H, m), 7.46-7.60 (1H, m), 7.70-7.86 (1H, m), 7.89-8.03 (1H, m), 8.25-8.65 (3H, m), 8.78-9.07 (1H, m), 9.34-9.53 (1H, m).

Example 313

[Formula 560]

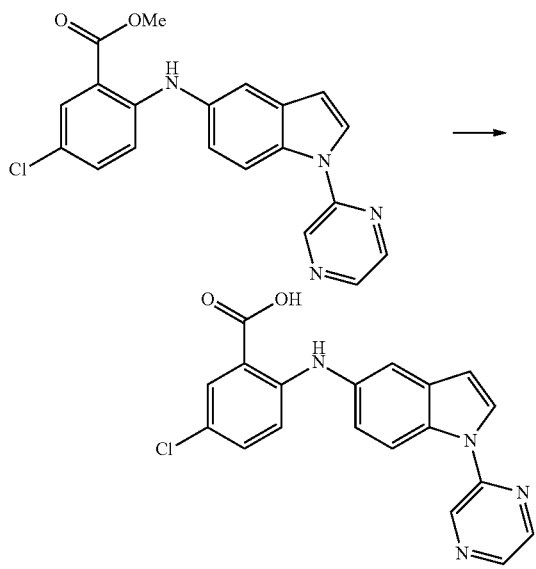

By the method similar to that of Example 47, 5-chloro-2-((1-(pyrazin-2-yl)-1H-indol-5-yl)amino)benzoic acid was obtained from methyl 5-chloro-2-((1-(pyrazin-2-yl)-1H-indol-5-yl)amino)benzoate.

$^1$H-NMR (DMSO-d$_6$) δ: 6.83 (1H, d, J 3.3 Hz), 7.08 (1H, d, J=9.2 Hz), 7.20 (1H, dd, J=8.9, 2.3 Hz), 7.38 (1H, dd, J=9.2, 2.6 Hz), 7.57 (1H, d, J=2.6 Hz), 7.83 (1H, d, J=2.6 Hz), 8.24 (1H, d, J=3.3 Hz), 8.49 (1H, d, J=8.6 Hz), 8.53 (1H, d, J=2.6 Hz), 8.57-8.64 (1H, m), 9.20 (1H, d, J=1.3 Hz), 9.61 (1H, s).

MS (ESI/APCI, m/z): 363 (M−H)$^−$.

Example 314

[Formula 561]

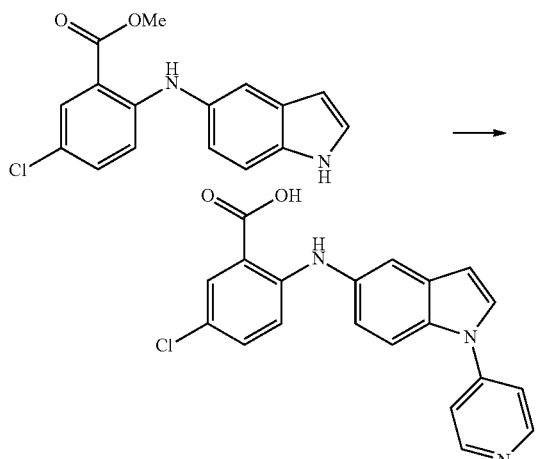

By the method similar to that of Example 48, methyl 5-chloro-2-((1-(pyridin-4-yl)-1H-indol-5-yl)amino)benzoate was obtained from methyl 2-((1H-indol-5-yl)amino)-5-chlorobenzoate and 4-iodopyridine.

¹H-NMR (CDCl₃) δ: 3.92 (3H, s), 6.65-6.83 (1H, m), 6.91-7.36 (5H, m), 7.38-7.83 (5H, m), 7.87-8.05 (1H, m), 9.41 (1H, brs).

Example 315

[Formula 562]

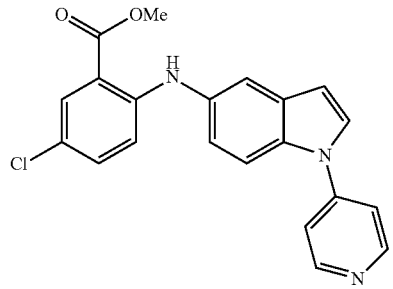

→

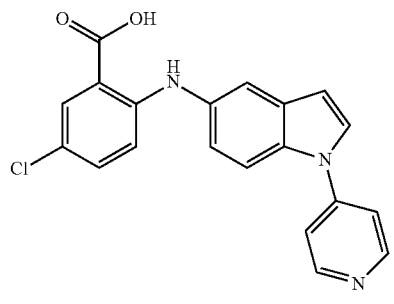

By the method similar to that of Example 49, 5-chloro-2-((1-(pyridin-4-yl)-1H-indol-5-yl)amino)benzoic acid was obtained from methyl 5-chloro-2-((1-(pyridin-4-yl)-1H-indol-5-yl)amino)benzoate.

¹H-NMR (DMSO-d₆) δ: 6.79 (1H, d, J=4.0 Hz), 7.05 (1H, d, J=9.2 Hz), 7.17 (1H, dd, J=8.6, 2.0 Hz), 7.37 (1H, dd, J=8.6, 2.6 Hz), 7.58 (1H, d, J=2.0 Hz), 7.70-7.79 (2H, m), 7.80-7.94 (3H, m), 8.72 (2H, d, J=5.3 Hz), 9.59 (1H, brs).

MS (ESI/APCI, m/z): 362 (M−H)⁻.

Example 316

[Formula 563]

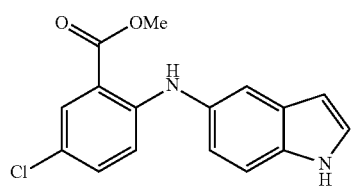

→

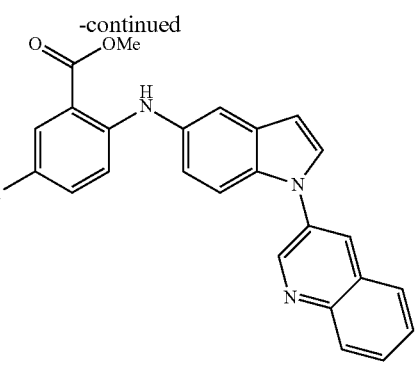

By the method similar to that of Example 48, methyl 5-chloro-2-((1-(quinolin-3-yl)-1H-indol-5-yl)amino)benzoate was obtained from methyl 2-((1H-indol-5-yl)amino)-5-chlorobenzoate and 3-bromoquinoline.

¹H-NMR (CDCl₃) δ: 3.93 (3H, s), 6.75 (1H, d, J=3.3 Hz), 7.00 (1H, d, J=9.2 Hz), 7.10-7.23 (2H, m), 7.47 (1H, d, J=3.3 Hz), 7.54-7.71 (3H, m), 7.74-7.84 (1H, m), 7.87-7.96 (2H, m), 8.21 (1H, d, J=9.2 Hz), 8.26 (1H, d, J=2.6 Hz), 9.16 (1H, d, J=2.6 Hz), 9.40 (1H, s).

Example 317

[Formula 564]

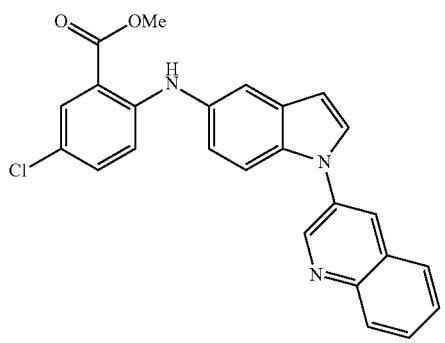

→

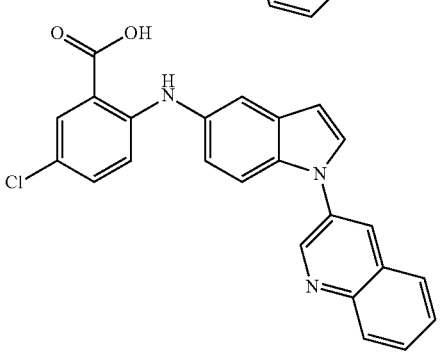

By the method similar to that of Example 49, 5-chloro-2-((1-(quinolin-3-yl)-1H-indol-5-yl)amino)benzoic acid was obtained from methyl 5-chloro-2-((1-(quinolin-3-yl)-1H-indol-5-yl)amino)benzoate.

¹H-NMR (DMSO-d₆) δ: 6.80 (1H, d, J=3.3 Hz), 7.03 (1H, d, J=9.2 Hz), 7.16 (1H, dd, J=8.6, 2.0 Hz), 7.37 (1H, dd, J=8.9, 3.0 Hz), 7.60 (1H, d, J=2.0 Hz), 7.68-7.78 (2H, m), 7.78-7.87 (2H, m), 7.93 (1H, d, J=3.3 Hz), 8.13 (2H, d, J=8.6 Hz), 8.67 (1H, d, J=2.6 Hz), 9.21 (1H, d, J=2.6 Hz), 9.59 (1H, s).

MS (ESI/APCI, m/z): 414 (M+H)⁺, 412 (M−H)⁻.

Example 318

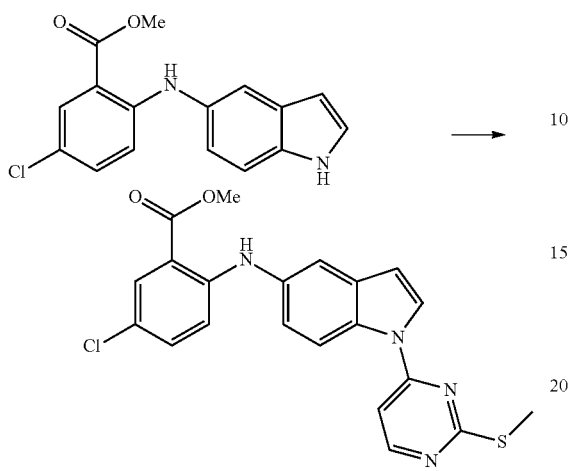

[Formula 565]

By the method similar to that of Example 5, methyl 5-chloro-2-((1-(2-(methylthio)pyrimidin-4-yl)-1H-indol-5-yl)amino)benzoate was obtained from methyl 2-((1H-indol-5-yl)amino)-5-chlorobenzoate and 4-chloro-2-(methylthio)pyrimidine.

$^{1}$H-NMR (DMSO-$d_6$) δ: 2.64 (3H, s), 3.88 (3H, s), 6.85 (1H, d, J=3.3 Hz), 7.12 (1H, d, J=9.2 Hz), 7.25 (1H, dd, J=8.6, 2.0 Hz), 7.41 (1H, dd, J=9.2, 2.6 Hz), 7.55 (1H, d, J=2.0 Hz), 7.60 (1H, d, J=5.9 Hz), 7.84 (1H, d, J=2.6 Hz), 8.21 (1H, d, J=4.0 Hz), 8.60-8.67 (2H, m), 9.33 (1H, s).

Example 319

[Formula 566]

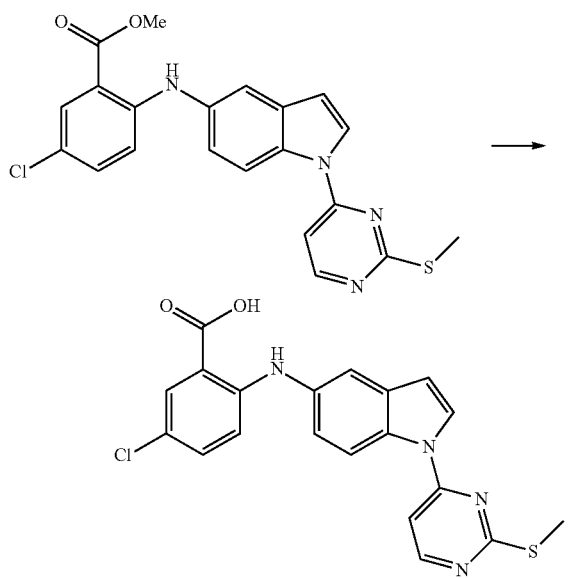

By the method similar to that of Example 49, 5-chloro-2-((1-(2-(methylthio)pyrimidin-4-yl)-1H-indol-5-yl)amino)benzoic acid was obtained from methyl 5-chloro-2-((1-(2-(methylthio)pyrimidin-4-yl)-1H-indol-5-yl)amino)benzoate.

$^{1}$H-NMR (DMSO-$d_6$) δ: 2.64 (3H, s), 6.80 (1H, d, J=3.3 Hz), 7.06-7.21 (3H, m), 7.42 (1H, d, J=2.0 Hz), 7.55 (1H, d, J=5.9 Hz), 7.84 (1H, d, J=2.0 Hz), 8.13 (1H, d, J=4.0 Hz), 8.53 (1H, d, J=8.6 Hz), 8.58 (1H, d, J=5.9 Hz).

MS (ESI/APCI, m/z): 409 (M−H)$^{-}$.

Example 320

[Formula 567]

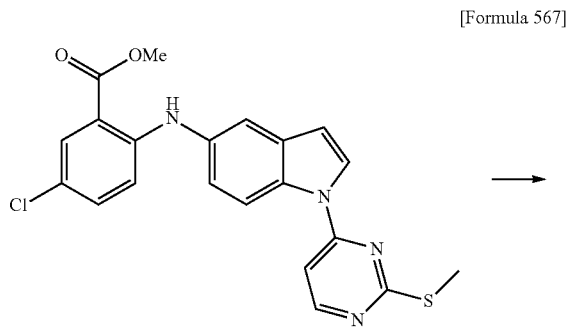

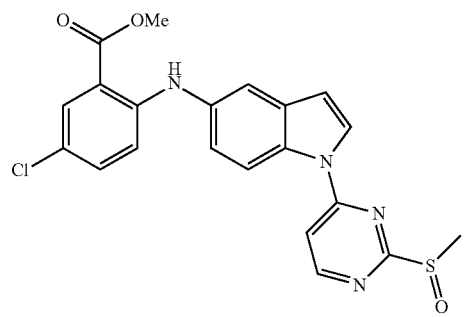

To the solution of 100 mg of methyl 5-chloro-2-((1-(2-(methylthio)pyrimidin-4-yl)-1H-indol-5-yl)amino)benzoate in 1.0 mL of dichloromethane, 69.1 mg of 3-chloroperbenzoic acid (77%) was added under ice-cooling. The resultant was stirred at room temperature for 15 minutes. A saturated aqueous sodium bicarbonate solution and a saturated aqueous sodium sulfite solution were added to the reaction mixture. The organic layer was separated, sequentially washed with water and a saturated aqueous sodium chloride solution and then dried over anhydrous sodium sulfate, and the solvent was distilled off under reduced pressure to give 108 mg of methyl 5-chloro-2-((1-(2-(methylsulfinyl)pyrimidin-4-yl)-1H-indol-5-yl)amino)benzoate as an oil.

$^{1}$H-NMR (CDCl$_3$) δ: 3.04 (3H, s), 3.93 (3H, s), 6.78 (1H, d, J=4.0 Hz), 7.09 (1H, d, J=9.2 Hz), 7.18-7.32 (2H, m), 7.39 (1H, d, J=5.9 Hz), 7.46 (1H, d, J=2.0 Hz), 7.74 (1H, d, J=4.0 Hz), 7.94 (1H, d, J=2.6 Hz), 8.69 (1H, d, J=9.2 Hz), 8.78 (1H, d, J=5.9 Hz), 9.46 (1H, s).

Example 321

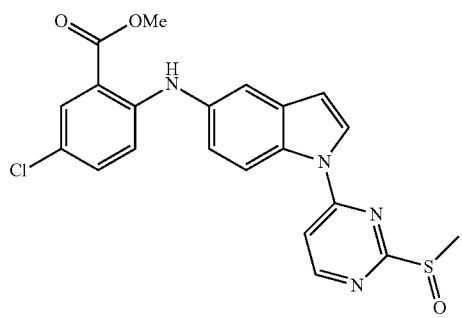

[Formula 568]

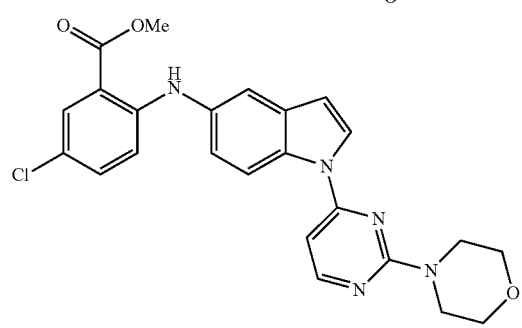

The mixture of 30 mg of methyl 5-chloro-2-((1-(2-(methylsulfinyl)pyrimidin-4-yl)-1H-indol-5-yl)amino)benzoate, 18.9 µL of triethylamine, 8.9 µL of morpholine, and 0.3 mL of tetrahydrofuran, was stirred at room temperature for 14.5 hours and then stirred at an external temperature of 70° C. for two hours. 8.9 µL of morpholine was added thereto, and the resultant was stirred at 70° C. for five hours, and the reaction solution was then cooled to room temperature, allowed to stand overnight and then stirred at 70° C. for one hour. The reaction mixture was cooled to room temperature and the solvent was distilled off under reduced pressure. The obtained residue was purified by silica gel column chromatography (hexane:ethyl acetate) to give 30 mg of methyl 5-chloro-2-((1-(2-morpholinopyrimidin-4-yl)-1H-indol-5-yl)amino)benzoate as an oil.

Example 322

[Formula 569]

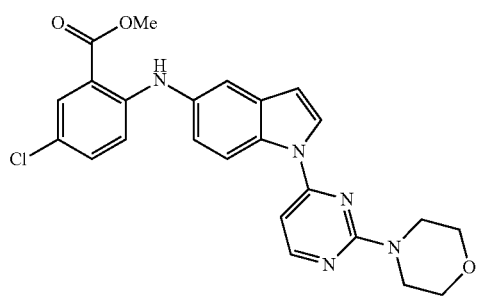

-continued

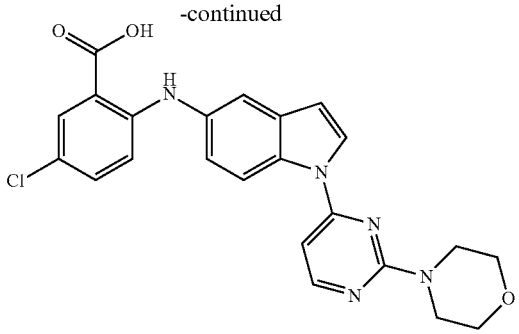

To the solution of 29 mg of methyl 5-chloro-2-((1-(2-morpholinopyrimidin-4-yl)-1H-indol-5-yl)amino)benzoate in 0.37 mL of ethanol, 25.8 µL of a 5 mol/L aqueous sodium hydroxide solution was added at room temperature, and the resultant was stirred at 70° C. for 20 minutes. The reaction mixture was cooled to room temperature, and water and 3 mol/L hydrochloric acid were added thereto. The solid was collected by filtration to give 27.3 mg of 5-chloro-2-((1-(2-morpholinopyrimidin-4-yl)-1H-indol-5-yl)amino)benzoic acid as a yellow solid.

$^1$H-NMR (DMSO-$d_6$) δ: 3.65-3.89 (8H, m), 6.78 (1H, d, J=3.3 Hz), 7.04-7.15 (2H, m), 7.21 (1H, dd, J=8.9, 2.3 Hz), 7.39 (1H, dd, J=9.2, 2.6 Hz), 7.53 (1H, d, J=2.0 Hz), 7.83 (1H, d, J=2.6 Hz), 8.14 (1H, d, J=3.3 Hz), 8.43 (1H, d, J=5.3 Hz), 8.50 (1H, d, J=9.2 Hz), 9.61 (1H, brs).

MS (ESI, m/z): 450 (M+H)$^+$, 448 (M−H)$^−$.

Example 323

[Formula 570]

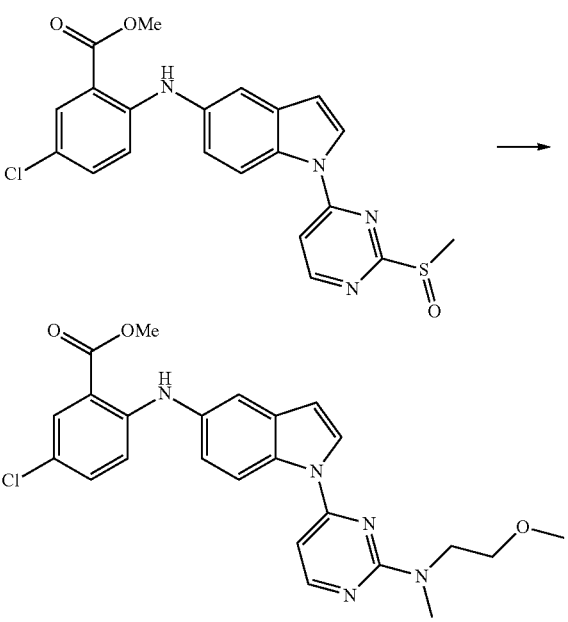

By the method similar to that of Example 321, methyl 5-chloro-2-((1-(2-((2-methoxyethyl)(methyl)amino)pyrimidin-4-yl)-1H-indol-5-yl)amino)benzoate was obtained from methyl 5-chloro-2-((1-(2-(methylsulfinyl)pyrimidin-4-yl)-1H-indol-5-yl)amino)benzoate and N-(2-methoxyethyl)-N-methylamine.

Example 324

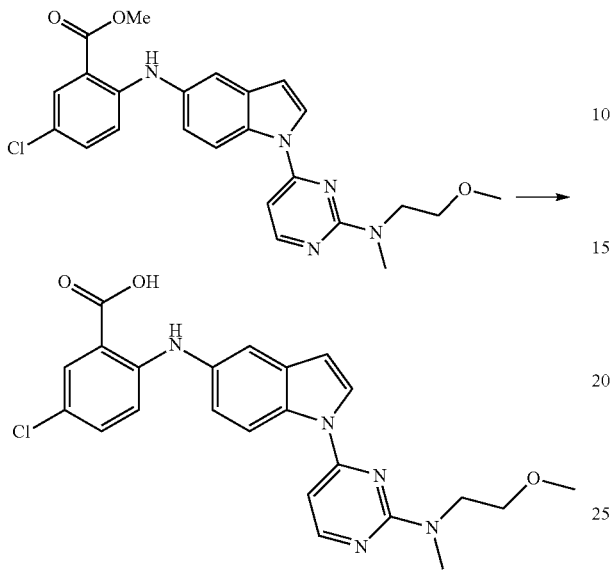

[Formula 571]

By the method similar to that of Example 322, 5-chloro-2-((1-(2-((2-methoxyethyl)(methyl)amino)pyrimidin-4-yl)-1H-indol-5-yl)amino)benzoic acid was obtained from methyl 5-chloro-2-((1-(2-((2-methoxyethyl)(methyl)amino)pyrimidin-4-yl)-1H-indol-5-yl)amino)benzoate.

$^1$H-NMR (DMSO-d$_6$) δ: 3.19-3.36 (6H, m), 3.53-3.74 (2H, m), 3.80-3.98 (2H, m), 6.84 (1H, d, J=4.0 Hz), 7.02-7.27 (3H, m), 7.40 (1H, dd, J=9.2, 2.6 Hz), 7.55 (1H, d, J=2.0 Hz), 7.83 (1H, d, J=2.6 Hz), 8.19 (1H, d, J=3.3 Hz), 8.38 (1H, d, J=5.9 Hz), 8.59 (1H, d, J=7.3 Hz), 9.63 (1H, s).

MS (ESI, m/z): 452 (M+H)$^+$, 450 (M−H)$^−$.

Example 325

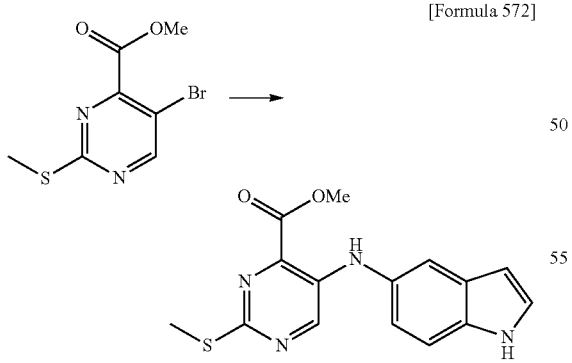

[Formula 572]

The mixture of 0.7 g of methyl 5-bromo-2-(methylthio)pyrimidine-4-carboxylate, 0.352 g of 5-aminoindole, 73.1 mg of tris(dibenzylideneacetone)dipalladium(0), 17.9 mg of palladium acetate, 0.185 g of 4,5'-bis(diphenylphosphino)-9,9'-dimethylxanthene, 1.73 g of cesium carbonate, and 7.0 mL of toluene, was stirred at an external temperature of 80° C. for two hours under a nitrogen atmosphere. The reaction mixture was cooled to room temperature, and water and ethyl acetate were then added thereto. The organic layer was separated and dried over anhydrous sodium sulfate, and the solvent was distilled off under reduced pressure. The obtained residue was purified by silica gel column chromatography (hexane:ethyl acetate) to give 0.34 g of methyl 5-((1H-indol-5-yl)amino)-2-(methylthio)pyrimidine-4-carboxylate as a yellow solid.

Example 326

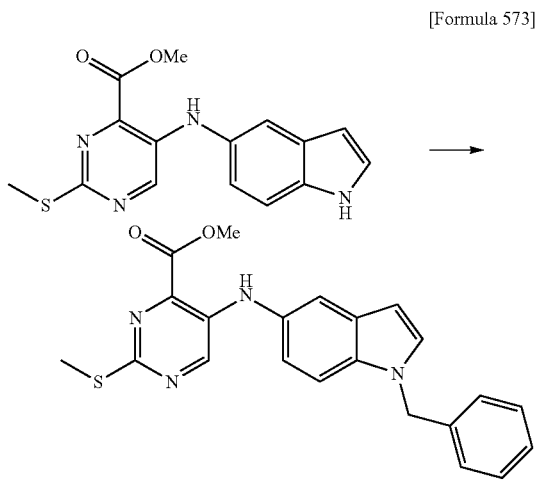

[Formula 573]

To the solution of 0.264 g of methyl 5-((1H-indol-5-yl)amino)-2-(methylthio)pyrimidine-4-carboxylate in 3.0 mL of N,N-dimethylacetamide, 94.3 mg of potassium tert-butoxide was added under ice-cooling, and the resultant was stirred for 10 minutes under ice-cooling. 100 µL of benzyl bromide was added to the reaction mixture, and the resultant was stirred for 10 minutes under ice-cooling and then stirred at room temperature for 30 minutes. A saturated aqueous ammonium chloride solution and ethyl acetate were added to the reaction mixture. The organic layer was separated, sequentially washed with water and a saturated aqueous sodium chloride solution and dried over anhydrous sodium sulfate, and the solvent was distilled off under reduced pressure. The obtained residue was purified by silica gel column chromatography (hexane:ethyl acetate) to give 97 mg of methyl 5-((1-benzyl-1H-indol-5-yl)amino)-2-(methylthio)pyrimidine-4-carboxylate as a yellow oil.

Example 327

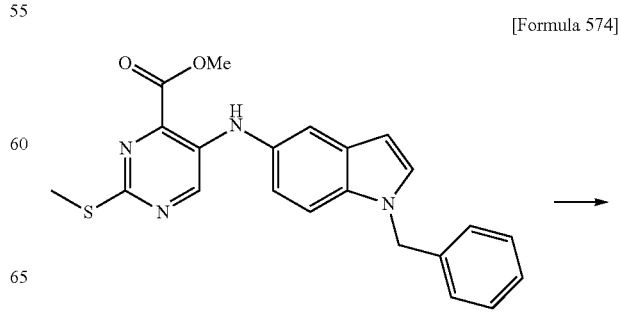

[Formula 574]

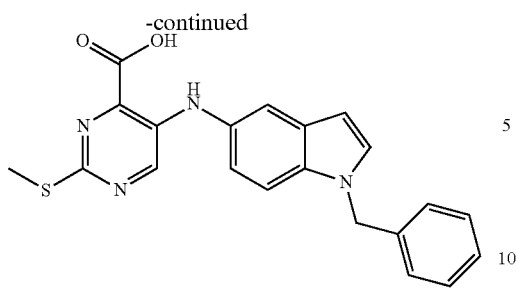

By the method similar to that of Example 49, 5-((1-benzyl-1H-indol-5-yl)amino)-2-(methylthio)pyrimidine-4-carboxylic acid was obtained from methyl 5-((1-benzyl-1H-indol-5-yl)amino)-2-(methylthio)pyrimidine-4-carboxylate.

$^1$H-NMR (DMSO-$d_6$) δ: 2.45-2.56 (3H, m), 5.43 (2H, s), 6.46 (1H, d, J=2.6 Hz), 7.03 (1H, dd, J=8.6, 2.0 Hz), 7.18-7.37 (5H, m), 7.45-7.51 (2H, m), 7.54 (1H, d, J=2.6 Hz), 8.53 (1H, s), 8.83 (1H, s).

MS (ESI, m/z): 391 (M+H)$^+$, 389 (M−H)$^−$.

Example 328

[Formula 575]

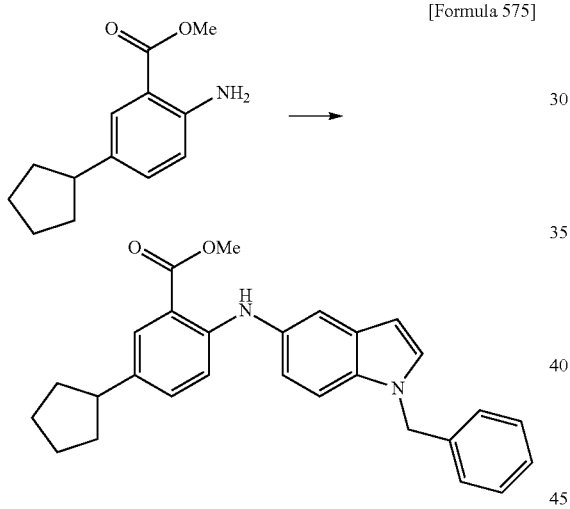

The reaction mixture of 0.150 g of methyl 2-amino-5-cyclopentylbenzoate, 0.196 g of 1-benzyl-5-bromo-1H-indole, 31.3 mg of tris(dibenzylideneacetone)dipalladium(0), 39.6 mg of 4,5'-bis(diphenylphosphino)-9,9'-dimethylxanthene, 0.446 g of cesium carbonate, and 1.5 mL of toluene, was stirred at an external temperature of 80° C. for two hours and then stirred at 100° C. further for two hours under a nitrogen atmosphere. The reaction mixture was cooled to room temperature, and water and ethyl acetate were then added thereto. The organic layer was separated and dried over anhydrous sodium sulfate, and the solvent was distilled off under reduced pressure. The obtained residue was purified by silica gel column chromatography (hexane:ethyl acetate) to give 12.8 mg of methyl 2-((1-benzyl-1H-indol-5-yl)amino)-5-cyclopentylbenzoate as an oil.

$^1$H-NMR (CDCl$_3$) δ: 1.43-1.88 (6H, m), 1.93-2.10 (2H, m), 2.81-2.96 (1H, m), 3.90 (3H, s), 5.32 (2H, s), 6.52 (1H, dd, J=12.9, 3.0 Hz), 6.62 (1H, d, J=8.6 Hz), 6.98 (1H, dd, J=8.6, 2.6 Hz), 7.05 (1H, dd, J=8.6, 2.0 Hz), 7.09-7.38 (7H, m), 7.50 (1H, d, J=2.0 Hz), 7.80 (1H, d, J=2.6 Hz), 9.22 (1H, s).

Example 329

[Formula 576]

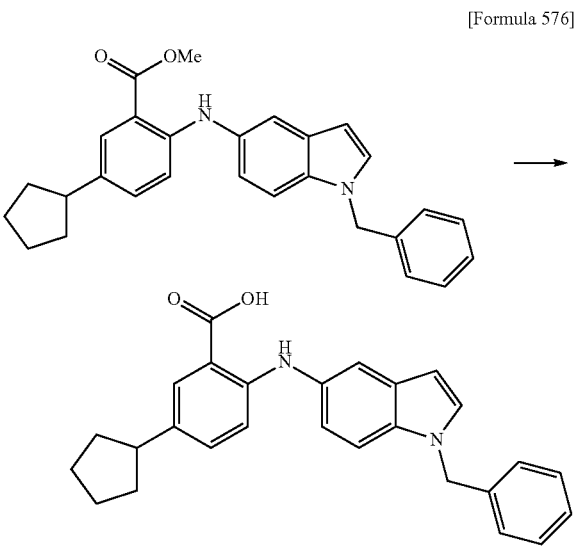

By the method similar to that of Example 57, 2-((1-benzyl-1H-indol-5-yl)amino)-5-cyclopentylbenzoic acid was obtained from methyl 2-((1-benzyl-1H-indol-5-yl)amino)-5-cyclopentylbenzoate.

$^1$H-NMR (DMSO-$d_6$) δ: 1.33-1.85 (6H, m), 1.87-2.06 (2H, m), 2.74-2.99 (1H, m), 5.42 (2H, s), 6.44 (1H, d, J=2.6 Hz), 6.86-7.03 (2H, m), 7.15-7.50 (8H, m), 7.52 (1H, d, J=3.3 Hz), 7.71 (1H, d, J=2.0 Hz), 9.36 (1H, s), 12.83 (1H, s).

MS (ESI/APCI, m/z): 409 (M−H)$^−$.

Example 330

[Formula 577]

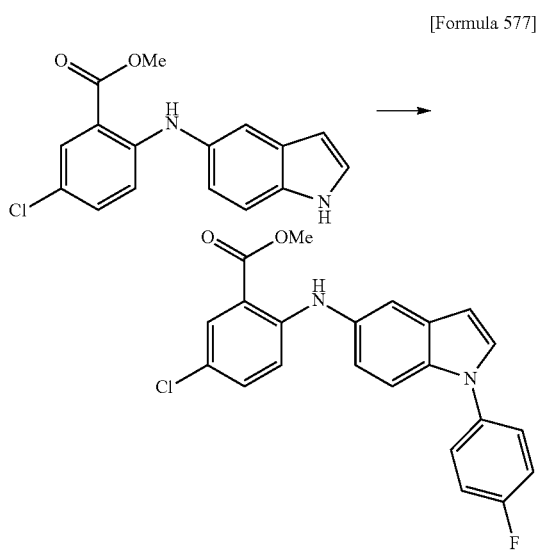

The mixture of 30 mg of methyl 2-((1H-indol-5-yl)amino)-5-chlorobenzoate, 13.8 pa, of 1-fluoro-4-iodobenzene, 9.1 mg of tris(dibenzylideneacetone)dipalladium(0), 11.6 mg of 4,5'-bis(diphenylphosphino)-9,9'-dimethylxanthene, 65 mg of cesium carbonate, and 0.3 mL of toluene, was stirred at an external temperature of 100° C. for 15 hours and 50 minutes under a nitrogen atmosphere. The reaction mixture was cooled to room temperature, and water and ethyl acetate were then added thereto. The organic layer was separated and dried over anhydrous sodium sulfate, and the solvent was distilled off under reduced pressure. The obtained residue was purified by silica gel column chromatography (hexane:ethyl acetate) to give 31 mg of methyl 5-chloro-2-((1-(4-fluorophenyl)-1H-indol-5-yl)amino)benzoate as a yellow oil.

$^1$H-NMR (DMSO-d$_6$) δ: 3.88 (3H, s), 6.65-6.76 (1H, m), 6.98 (1H, dd, J=9.2, 3.3 Hz), 7.09 (1H, dd, J=9.2, 2.0 Hz), 7.31-7.77 (8H, m), 7.82 (1H, d, J=2.6 Hz), 9.29 (1H, s).

Example 331

[Formula 578]

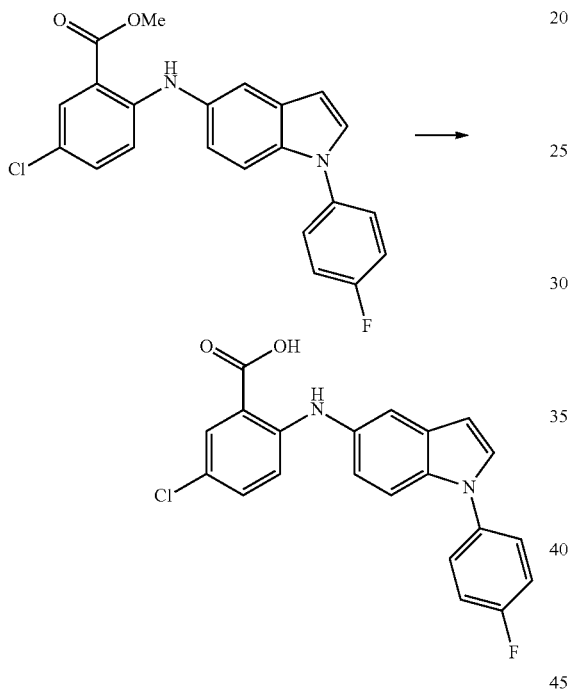

By the method similar to that of Example 47, 5-chloro-2-((1-(4-fluorophenyl)-1H-indol-5-yl)amino)benzoic acid was obtained from methyl 5-chloro-2-((1-(4-fluorophenyl)-1H-indol-5-yl)amino)benzoate.

$^1$H-NMR (DMSO-d$_6$) δ: 6.65-6.73 (1H, m), 6.99 (1H, dd, J=9.2, 3.3 Hz), 7.09 (1H, dd, J=8.9, 2.3 Hz), 7.30-7.74 (8H, m), 7.81 (1H, d, J=2.6 Hz), 9.58 (1H, s).

MS (ESI/APCI, m/z): 379 (M−H)$^-$.

Example 332

[Formula 579]

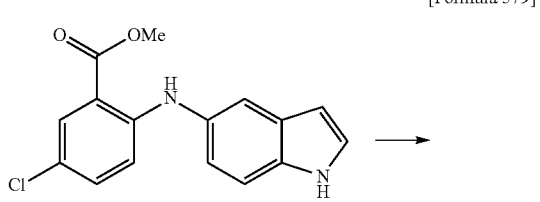

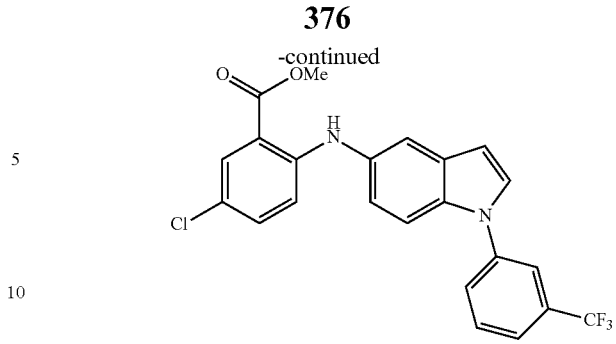

By the method similar to that of Example 330, methyl 5-chloro-2-((1-(3-(trifluoromethyl)phenyl)-1H-indol-5-yl)amino)benzoate was obtained from methyl 2-((1H-indol-5-yl)amino)-5-chlorobenzoate and 1-iodo-3-(trifluoromethyl)benzene.

$^1$H-NMR (DMSO-d$_6$) δ: 3.88 (3H, s), 6.74 (1H, d, J=3.3 Hz), 7.01 (1H, d, J=9.2 Hz), 7.14 (1H, dd, J=8.6, 2.0 Hz), 7.39 (1H, dd, J=9.2, 2.6 Hz), 7.53-7.66 (2H, m), 7.74-7.88 (4H, m), 7.91-8.02 (2H, m), 9.30 (1H, s).

Example 333

[Formula 580]

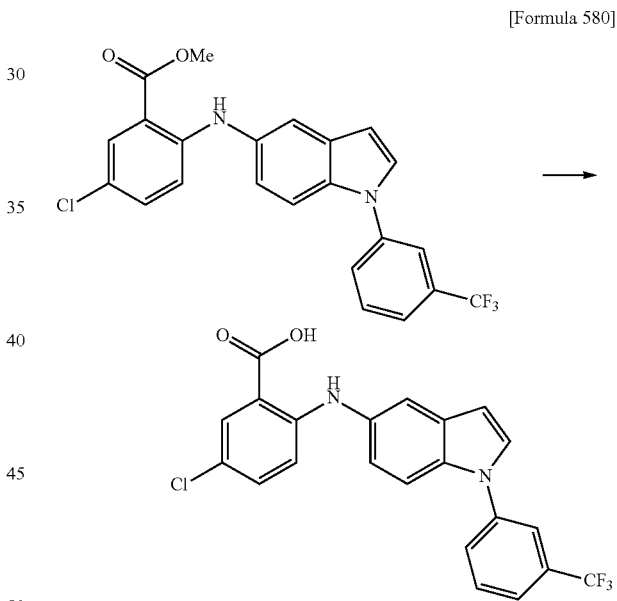

To the solution of 14.6 mg of methyl 5-chloro-2-((1-(3-(trifluoromethyl)phenyl)-1H-indol-5-yl)amino)benzoate in 0.2 mL of ethanol, 26.2 µL of a 5 mol/L aqueous sodium hydroxide solution was added at room temperature, and the resultant was stirred at an external temperature of 80° C. for 15 minutes. The reaction mixture was cooled to room temperature, and water, 2 mol/L hydrochloric acid and ethyl acetate were then added thereto. The organic layer was separated and dried over anhydrous sodium sulfate, and the solvent was distilled off under reduced pressure. The obtained residue was purified by silica gel column chromatography (chloroform:methanol) to give 5 mg of 5-chloro-2-((1-(3-(trifluoromethyl)phenyl)-1H-indol-5-yl)amino) benzoic acid as a yellow solid.

$^1$H-NMR (DMSO-d$_6$) δ: 6.74 (1H, d, J=3.3 Hz), 7.02 (1H, d, J=9.2 Hz), 7.14 (1H, dd, J=8.6, 2.0 Hz), 7.36 (1H, dd,

J=9.2, 2.6 Hz), 7.54-7.65 (2H, m), 7.73-7.88 (4H, m), 7.91-8.01 (2H, m), 9.60 (1H, s).
MS (ESI/APCI, m/z): 429 (M–H)⁻.

Example 334

[Formula 581]

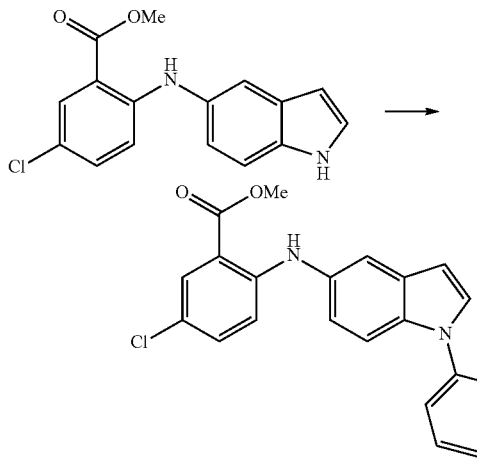

The mixture of 30 mg of methyl 2-((1H-indol-5-yl)amino)-5-chlorobenzoate, 13.1 μL of 1-bromo-2-fluorobenzene, 9.1 mg of tris(dibenzylideneacetone)dipalladium(0), 19.1 mg of 2-dicyclohexylphosphino-2',4',6'-triisopropylbiphenyl, 42.5 mg of tripotassium phosphate, and 0.3 mL of toluene, was stirred at an external temperature of 100° C. for three hours under a nitrogen atmosphere. The reaction mixture was cooled to room temperature, and water and ethyl acetate were then added thereto. The organic layer was separated and dried over anhydrous sodium sulfate, and the solvent was distilled off under reduced pressure, and the residue was then purified by silica gel column chromatography (hexane:ethyl acetate), and the obtained solid was washed with ethanol to give 20.3 mg of methyl 5-chloro-2-((1-(2-fluorophenyl)-1H-indol-5-yl)amino)benzoate as a yellow solid.

¹H-NMR (DMSO-d₆) δ: 3.88 (3H, s), 6.72 (1H, d, J=3.3 Hz), 6.98 (1H, d, J=9.2 Hz), 7.09 (1H, dd, J=8.6, 2.0 Hz), 7.26 (1H, dd, J=8.6, 2.0 Hz), 7.33-7.72 (7H, m), 7.82 (1H, d, J=2.6 Hz), 9.29 (1H, s).

Example 335

[Formula 582]

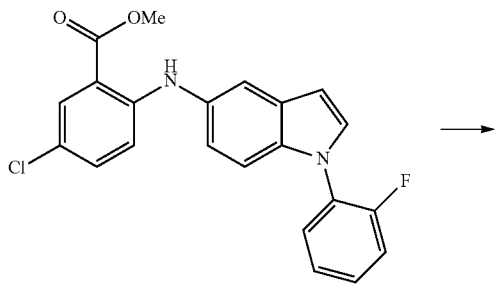

-continued

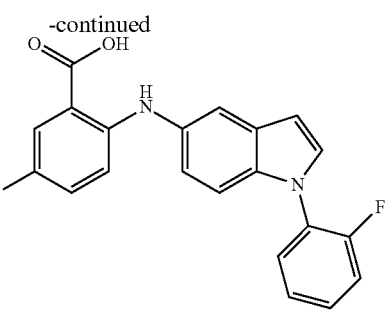

By the method similar to that of Example 57, 5-chloro-2-((1-(2-fluorophenyl)-1H-indol-5-yl)amino)benzoic acid was obtained from methyl 5-chloro-2-((1-(2-fluorophenyl)-1H-indol-5-yl)amino)benzoate.

¹H-NMR (DMSO-d₆) δ: 6.71 (1H, d, J=3.3 Hz), 6.99 (1H, d, J=8.6 Hz), 7.08 (1H, dd, J=8.6, 2.0 Hz), 7.25 (1H, dd, J=8.6, 2.0 Hz), 7.35 (1H, dd, J=8.6, 2.6 Hz), 7.38-7.48 (1H, m), 7.49-7.71 (5H, m), 7.81 (1H, d, J=2.6 Hz), 9.56 (1H, s), 13.34 (1H, s).

MS (ESI/APCI, m/z): 381 (M+H)⁺, 379 (M–H)⁻.

Example 336

[Formula 583]

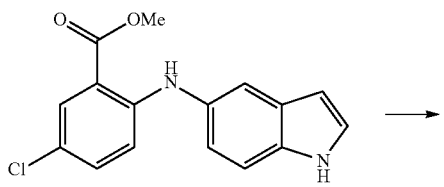

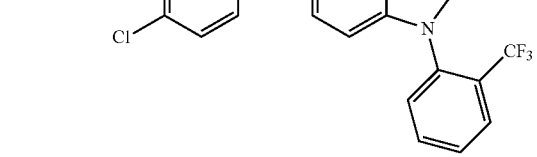

By the method similar to that of Example 334, methyl 5-chloro-2-((1-(2-trifluoromethyl)phenyl)-1H-indol-5-yl)amino)benzoate was obtained from methyl 2-((1H-indol-5-yl)amino)-5-chlorobenzoate and 1-iodo-2-(trifluoromethyl)benzene.

¹H-NMR (DMSO-d₆) δ: 3.88 (3H, s), 6.74 (1H, d, J=3.3 Hz), 7.01 (1H, d, J=9.2 Hz), 7.14 (1H, dd, J=8.6, 2.0 Hz), 7.39 (1H, dd, J=9.2, 2.6 Hz), 7.54-7.66 (2H, m), 7.73-7.89 (4H, m), 7.91-8.02 (2H, m), 9.30 (1H, s).

Example 337

[Formula 584]

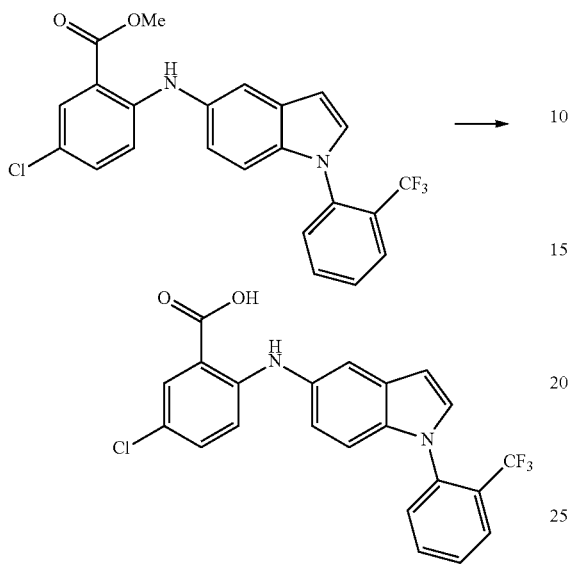

By the method similar to that of Example 57, 5-chloro-2-((1-(2-(trifluoromethyl)phenyl)-1H-indol-5-yl)amino)benzoic acid was obtained from methyl 5-chloro-2-((1-(2-(trifluoromethyl)phenyl)-1H-indol-5-yl)amino)benzoate.

$^1$H-NMR (DMSO-$d_6$) δ: 6.74 (1H, d, J=3.3 Hz), 7.02 (1H, d, J=8.6 Hz), 7.14 (1H, dd, J=8.6, 2.0 Hz), 7.36 (1H, dd, J=9.2, 2.6 Hz), 7.54-7.65 (2H, m), 7.73-7.88 (4H, m), 7.91-8.02 (2H, m), 9.58 (1H, s), 13.35 (1H, s).

MS (ESI/APCI, adz): 431 (M+H)$^+$, 429 (M−H)$^−$.

Example 338

[Formula 585]

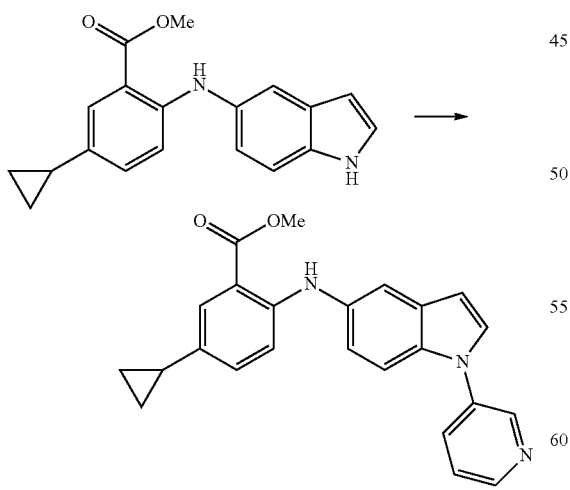

By the method similar to that of Example 58, methyl 5-cyclopropyl-2-((1-(pyridin-3-yl)-1H-indol-5-yl)amino)benzoate was obtained from methyl 2-((1H-indol-5-yl)amino)-5-cyclopropylbenzoate and 3-iodopyridine.

$^1$H-NMR (CDCl$_3$) δ: 0.56-0.65 (2H, m), 0.80-0.97 (2H, m), 1.75-1.89 (1H, m), 3.92 (3H, d, J=2.0 Hz), 6.68 (1H, d, J=4.0 Hz), 6.99-7.07 (2H, m), 7.13 (1H, dd, J=8.6, 2.0 Hz), 7.34 (1H, d, J=3.3 Hz), 7.43-7.59 (3H, m), 7.67-7.73 (1H, m), 7.82-7.90 (1H, m), 8.62 (1H, dd, J=4.6, 1.3 Hz), 8.85 (1H, d, J=2.0 Hz), 9.27 (1H, s).

Example 339

[Formula 586]

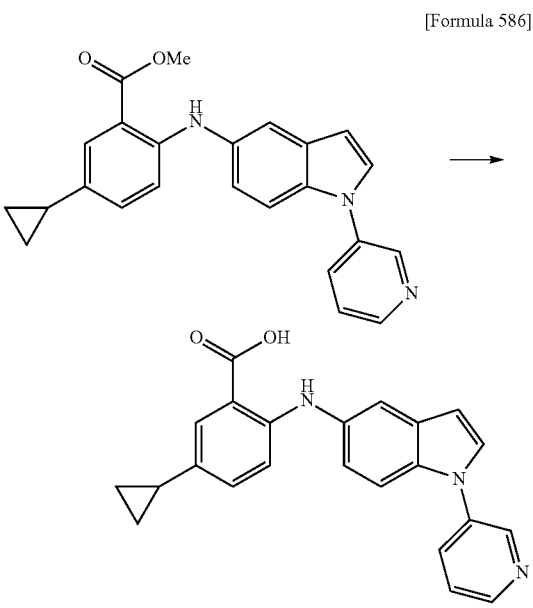

To the solution of 34.8 mg of methyl 5-cyclopropyl-2-((1-(pyridin-3-yl)-1H-indol-5-yl)amino)benzoate in 0.35 mL of ethanol, 72.6 μL of a 5 mol/L aqueous sodium hydroxide solution was added at room temperature, and the resultant was stirred at an external temperature of 70° C. for 15 minutes. The reaction mixture was cooled to room temperature, and water and 2 mol/L hydrochloric acid were then added thereto. The solid was collected by filtration and washed with water. The obtained solid was recrystallized from the mixed solution of ethanol and ethyl acetate to give 11.2 mg of 5-cyclopropyl-2-((1-(pyridin-3-yl)-1H-indol-5-yl)amino)benzoic acid as a yellow solid.

$^1$H-NMR (DMSO-$d_6$) δ: 0.47-0.64 (2H, m), 0.77-0.96 (2H, m), 1.77-1.94 (1H, m), 6.72 (1H, d, J=2.6 Hz), 6.92-7.18 (3H, m), 7.45-7.70 (4H, m), 7.76 (1H, d, J=3.3 Hz), 8.10 (1H, d, J=7.9 Hz), 8.61 (1H, d, J=4.0 Hz), 8.88 (1H, d, J=2.0 Hz), 9.42 (1H, brs), 12.93 (1H, brs).

MS (ESI, m/z): 370 (M+H)$^+$, 368 (M−H)$^−$.

Example 340

[Formula 587]

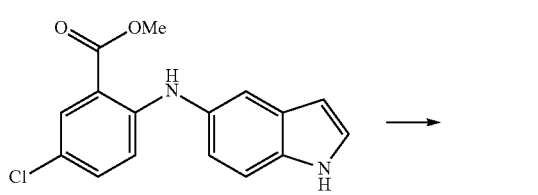

-continued

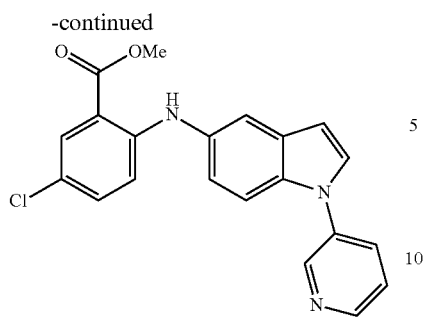

In accordance with the method of Example 12 except for using N,N-dimethylformamide as a solvent and potassium carbonate as a base, methyl 5-chloro-2-((1-(pyridin-2-ylmethyl)-1H-indol-5-yl)amino)benzoate was obtained from methyl 2-((1H-indol-5-yl)amino)-5-chlorobenzoate and 2-(chloromethyl)pyridine.

$^1$H-NMR (DMSO-d$_6$) δ: 3.87 (3H, s), 5.52 (2H, s), 6.49 (1H, d, J=2.6 Hz), 6.90 (1H, d, J=9.2 Hz), 6.95-7.06 (2H, m), 7.25-7.37 (2H, m), 7.42-4-7.50 (2H, m), 7.55 (1H, d, J=2.6 Hz), 7.73 (1H, td, J=7.8, 1.8 Hz), 7.80 (1H, d, J=2.6 Hz), 8.52-8.57 (1H, m), 9.23 (1H, s).

Example 341

[Formula 588]

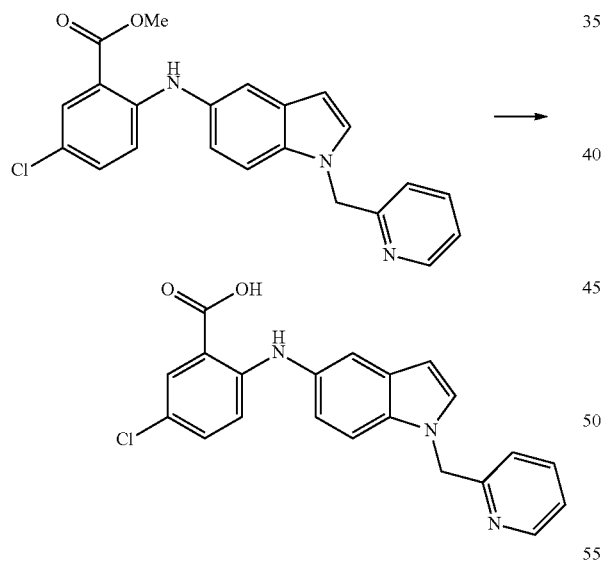

By the method similar to that of Example 63, 5-chloro-2-((1-(pyridin-2-ylmethyl)-1H-indol-5-yl)amino)benzoic acid was obtained from methyl 5-chloro-2-((1-(pyridin-2-ylmethyl)-1H-indol-5-yl)amino)benzoate.

$^1$H-NMR (DMSO-d$_6$) δ: 5.51 (2H, s), 6.48 (1H, d, J=3.3 Hz), 6.91 (1H, d, J=9.2 Hz), 6.95-7.05 (2H, m), 7.25-7.34 (2H, m), 7.42-7.48 (2H, m), 7.54 (1H, d, J=3.3 Hz), 7.73 (1H, td, J=7.6, 2.0 Hz), 7.78 (1H, d, J=2.6 Hz), 8.51-8.57 (1H, m), 9.48 (1H, s).

MS (ESI/APCI, m/z): 376 (M–H)$^-$.

Example 342

[Formula 589]

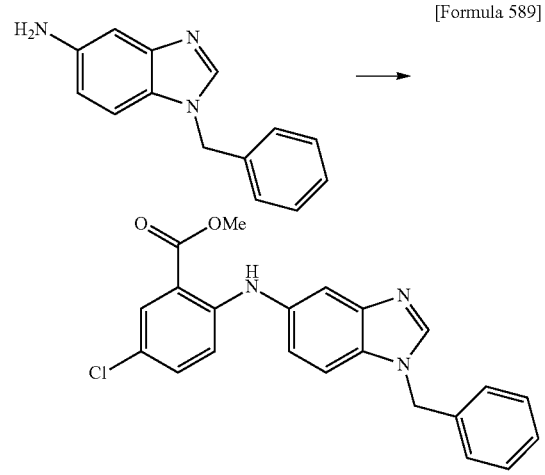

By the method similar to that of Example 20, methyl 2-((1-benzyl-1H-benzo[d]imidazol-5-yl)amino)-5-chlorobenzoate was obtained from 1-benzyl-1H-benzo[d]imidazol-5-amine and methyl 2-bromo-5-chlorobenzoate.

$^1$H-NMR (DMSO-d$_6$) δ: 3.87 (3H, s), 5.51 (2H, s), 6.96 (1H, d, J=8.6 Hz), 7.08-7.15 (1H, m), 7.25-7.40 (6H, m), 7.50-7.58 (2H, m), 7.81 (1H, d, J=2.6 Hz), 8.45 (1H, s), 9.26 (1H, s).

Example 343

[Formula 590]

By the method similar to that of Example 63, 2-((1-benzyl-1H-benzo[d]imidazol-5-yl)amino)-5-chlorobenzoic acid was obtained from methyl 2-((1-benzyl-1H-benzo[d]imidazol-5-yl)amino)-5-chlorobenzoate.

$^1$H-NMR (DMSO-d$_6$) δ: 5.55 (2H, s), 7.02 (1H, d, J=8.6 Hz), 7.18 (1H, dd, J=8.6, 2.0 Hz), 7.29-7.40 (6H, m), 7.56 (1H, d, J=1.3 Hz), 7.59 (1H, d, J=8.6 Hz), 7.81 (1H, d, J=2.6 Hz), 8.68 (1H, s), 9.55 (1H, s).

MS (ESI/APCI, m/z): 376 (M–H)⁻.

Example 344

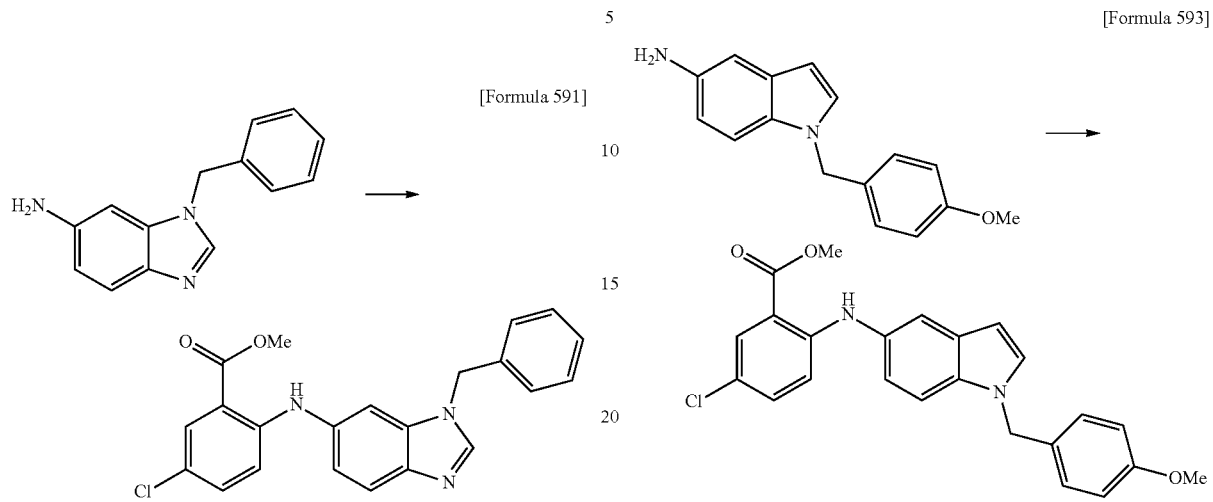

[Formula 591]

By the method similar to that of Example 20, methyl 2-((1-benzyl-1H-benzo[d]imidazol-6-yl)amino)-5-chlorobenzoate was obtained from 1-benzyl-1H-benzo[d]imidazol-6-amine and methyl 2-bromo-5-chlorobenzoate.

¹H-NMR (DMSO-d₆) δ: 3.86 (3H, s), 5.47 (2H, s), 6.97 (1H, d, J=9.2 Hz), 7.05-7.12 (1H, m), 7.25-7.50 (7H, m), 7.66 (1H, d, J=8.6 Hz), 7.82 (1H, d, J=2.6 Hz), 8.40 (1H, s), 9.32 (1H, s).

Example 345

[Formula 592]

By the method similar to that of Example 63, 2-((1-benzyl-1H-benzo[d]imidazol-6-yl)amino)-5-chlorobenzoic acid was obtained from methyl 2-((1-benzyl-1H-benzo[d]imidazol-6-yl)amino)-5-chlorobenzoate.

¹H-NMR (DMSO-d₆) δ: 5.64 (2H, s), 7.05 (1H, d, J=8.6 Hz), 7.31-7.47 (7H, m), 7.66 (1H, d, J=2.0 Hz), 7.77 (1H, d, J=8.6 Hz), 7.85 (1H, d, J=2.6 Hz), 9.30 (1H, s), 9.69 (1H, s).

MS (ESI/APCI, m/z): 376 (M–H)⁻.

Example 346

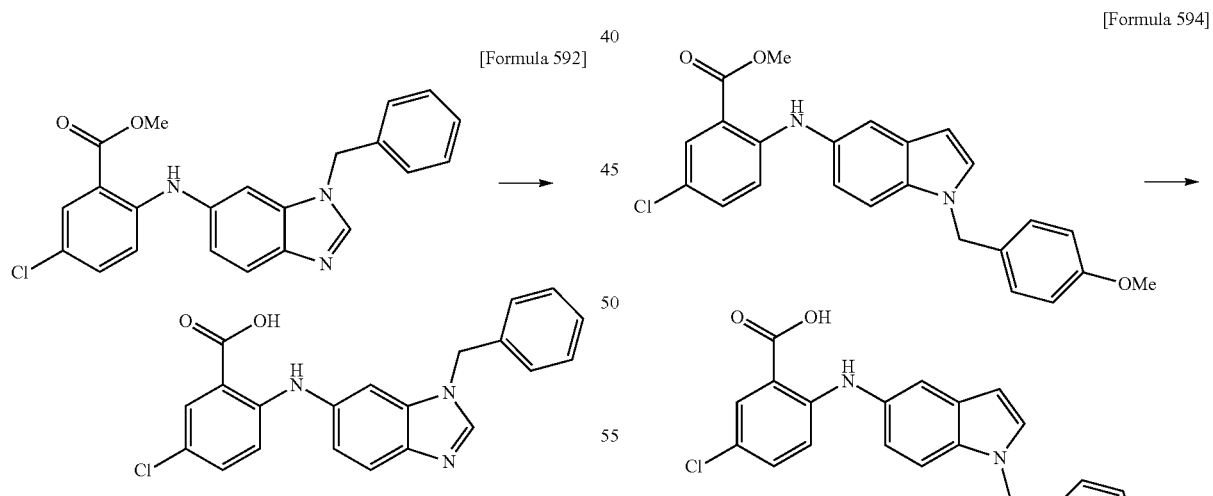

[Formula 593]

By the method similar to that of Example 20, methyl 5-chloro-2-((1-(4-methoxybenzyl)-1H-indol-5-yl)amino)benzoate was obtained from 1-(4-methoxybenzyl)-1H-indol-5-amine and methyl 2-bromo-5-chlorobenzoate.

¹H-NMR (DMSO-d₆) δ: 3.71 (3H, s), 3.87 (3H, s), 5.34 (2H, s), 6.45 (1H, d, J=3.3 Hz), 6.84-6.92 (3H, m), 6.98 (1H, dd, J=8.6, 2.0 Hz), 7.17-7.25 (2H, m), 7.32 (1H, dd, J=9.2, 2.6 Hz), 7.38-7.55 (3H, m), 7.80 (1H, d, J=2.6 Hz), 9.22 (1H, s).

Example 347

[Formula 594]

By the method similar to that of Example 37, 5-chloro-2-((1-(4-methoxybenzyl)-1H-indol-5-yl)amino)benzoic acid was obtained from methyl 5-chloro-2-((1-(4-methoxybenzyl)-1H-indol-5-yl)amino)benzoate.

¹H-NMR (DMSO-d₆) δ: 3.71 (3H, s), 5.34 (2H, s), 6.44 (1H, d, J=3.3 Hz), 6.84-6.92 (3H, m), 6.98 (1H, dd, J=8.6, 2.0 Hz), 7.17-7.25 (2H, m), 7.30 (1H, dd, J=9.2, 2.6 Hz), 7.42 (1H, d, J=2.0 Hz), 7.47-7.55 (2H, m), 7.78 (1H, d, J=2.6 Hz), 9.48 (1H, brs).

MS (ESI/APCI, m/z): 405 (M−H)⁻.

Example 348

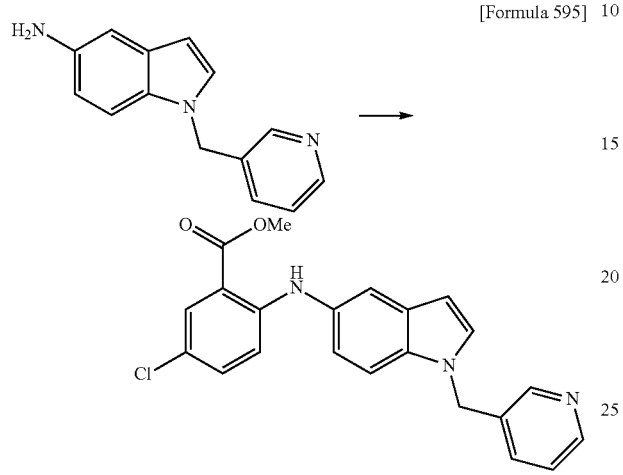

[Formula 595]

By the method similar to that of Example 20, methyl 5-chloro-2-((1-(pyridin-3-ylmethyl)-1H-indol-5-yl)amino) benzoate was obtained from 1-(pyridin-3-ylmethyl)-1H-indol-5-amine and methyl 2-bromo-5-chlorobenzoate.

¹H-NMR (DMSO-d₆) δ: 3.87 (3H, s), 5.49 (2H, s), 6.49 (1H, d, J=3.3 Hz), 6.90 (1H, d, J=8.6 Hz), 7.01 (1H, dd, J=8.6, 2.0 Hz), 7.29-7.38 (2H, m), 7.45 (1H, d, J=2.0 Hz), 7.52-7.65 (3H, m), 7.80 (1H, d, J=2.6 Hz), 8.44-8.50 (1H, m), 8.52-8.57 (1H, m), 9.23 (1H, s).

Example 349

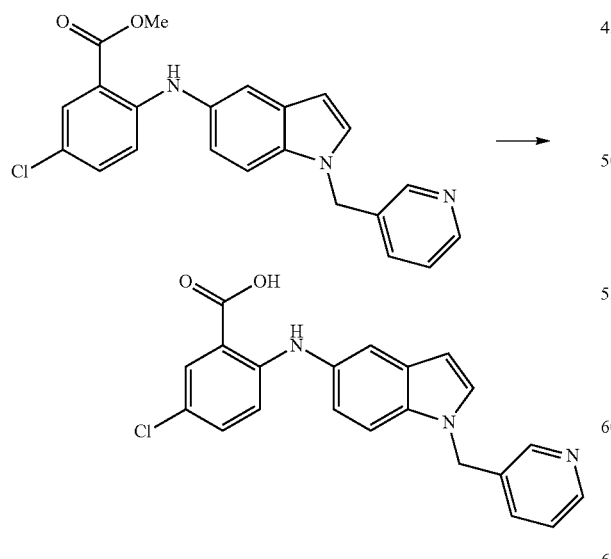

[Formula 596]

By the method similar to that of Example 37, 5-chloro-2-((1-(pyridin-3-ylmethyl)-1H-indol-5-yl)amino)benzoic acid was obtained from methyl 5-chloro-2-((1-(pyridin-3-ylmethyl)-1H-indol-5-yl)amino)benzoate.

¹H-NMR (DMSO-d₆) δ: 5.48 (2H, s), 6.48 (1H, d, J=3.3 Hz), 6.91 (1H, d, J=9.2 Hz), 7.01 (1H, dd, J=8.6, 2.0 Hz), 7.27-7.38 (2H, m), 7.44 (1H, d, J=2.0 Hz), 7.51-7.64 (3H, m), 7.79 (1H, d, J=2.6 Hz), 8.47 (1H, dd, J=4.6, 1.3 Hz), 8.54 (1H, d, J=2.0 Hz), 9.50 (1H, brs).

MS (ESI/APCI, m/z): 376 (M−H)⁻.

Example 350

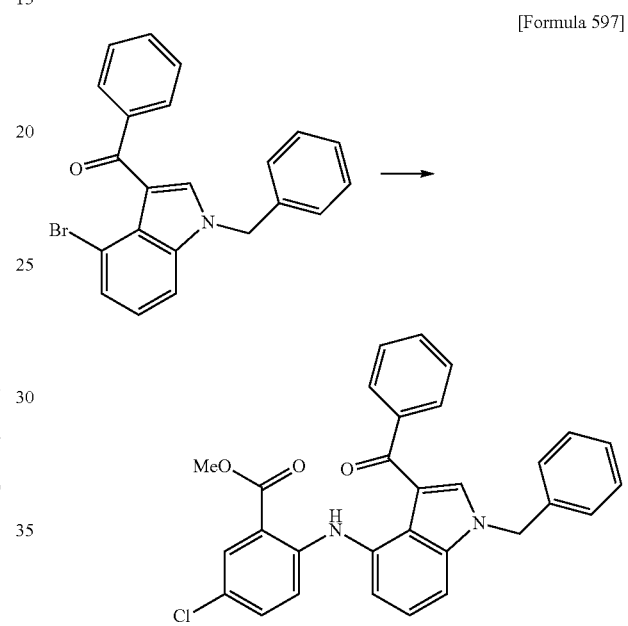

[Formula 597]

By the method similar to that of Example 5, methyl 2-((3-benzoyl-1-benzyl-1H-indol-4-yl)amino)-5-chlorobenzoate was obtained from (1-benzyl-4-bromo-1H-indol-3-yl)(phenyl)methanone and methyl 2-amino-5-chlorobenzoate.

¹H-NMR (DMSO-d₆) δ: 3.90 (3H, s), 5.53 (2H, s), 7.07-7.44 (10H, m), 7.50-7.68 (3H, m), 7.76-7.86 (3H, m), 8.14 (1H, s), 10.18 (1H, s).

Example 351

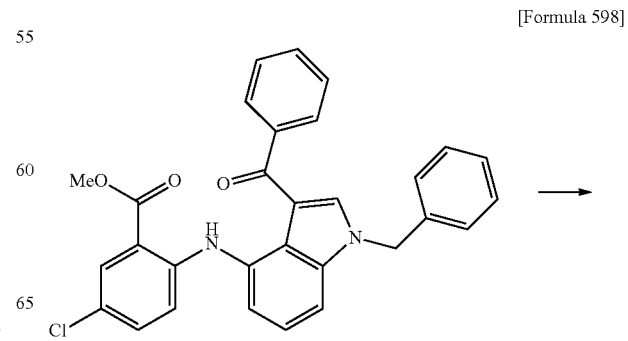

[Formula 598]

-continued

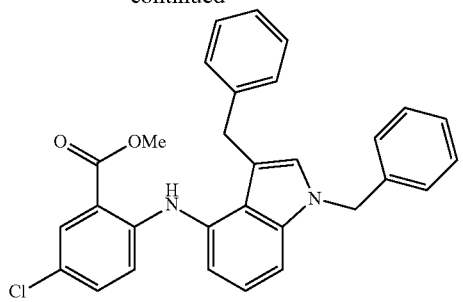

By the method similar to that of Example 87, methyl 5-chloro-2-((1,3-dibenzyl-1H-indol-4-yl)amino)benzoate was obtained from methyl 2-((3-benzoyl-1-benzyl-1H-indol-4-yl)amino)-5-chlorobenzoate. $^1$H-NMR (DMSO-$d_6$) δ: 3.84 (3H, s), 3.99 (2H, s), 5.40 (2H, s), 6.64 (1H, d, J=9.2 Hz), 6.84-7.16 (7H, m), 7.18-7.39 (8H, m), 7.73 (1H, d, J=2.6 Hz), 9.19 (1H, s).

Example 352

[Formula 599]

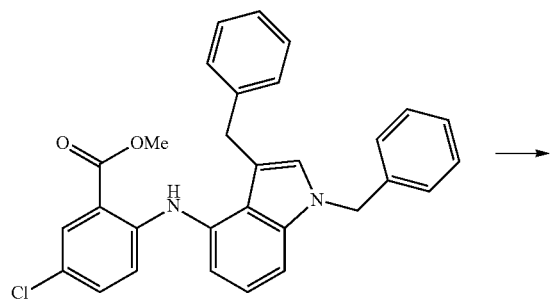

By the method similar to that of Example 37, 5-chloro-2-((1,3-dibenzyl-1H-indol-4-yl)amino)benzoic acid was obtained from methyl 5-chloro-2-(0,3-dibenzyl-1H-indol-4-yl)amino)benzoate.

$^1$H-NMR (DMSO-$d_6$) δ: 4.03 (2H, s), 5.39 (2H, s), 6.72 (1H, d, J=9.2 Hz), 6.89 (1H, d, J=7.3 Hz), 6.93-7.13 (6H, m), 7.16-7.36 (8H, m), 7.74 (1H, d, J=2.6 Hz), 9.63 (1H, s).

MS (ESI/APCI, m/z): 465 (M–H)$^-$.

Example 353

[Formula 600]

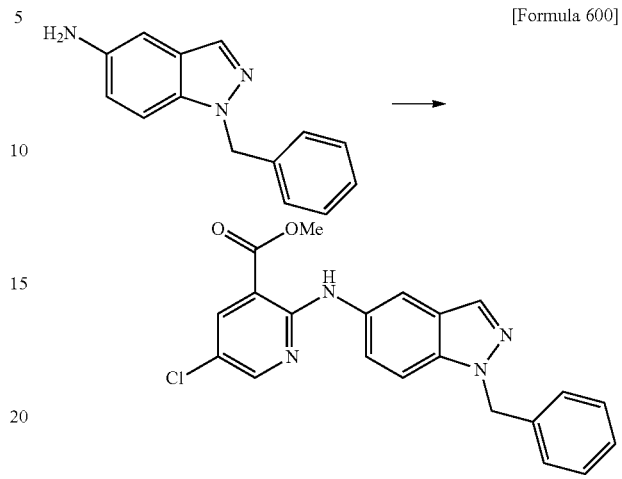

By the method similar to that of Example 20, methyl 2-((1-benzyl-1H-indazol-5-yl)amino)-5-chloronicotinate was obtained from 1-benzyl-1H-indazol-5-amine and methyl 2,5-dichloronicotinate.

$^1$H-NMR (DMSO-$d_6$) δ: 3.92 (3H, s), 5.65 (2H, s), 7.18-7.50 (6H, m), 7.67 (1H, d, J=9.2 Hz), 8.08 (1H, s), 8.14 (1H, d, J=2.0 Hz), 8.22 (1H, d, J=2.6 Hz), 8.42 (1H, d, J=2.6 Hz), 9.97 (1H, s).

Example 354

[Formula 601]

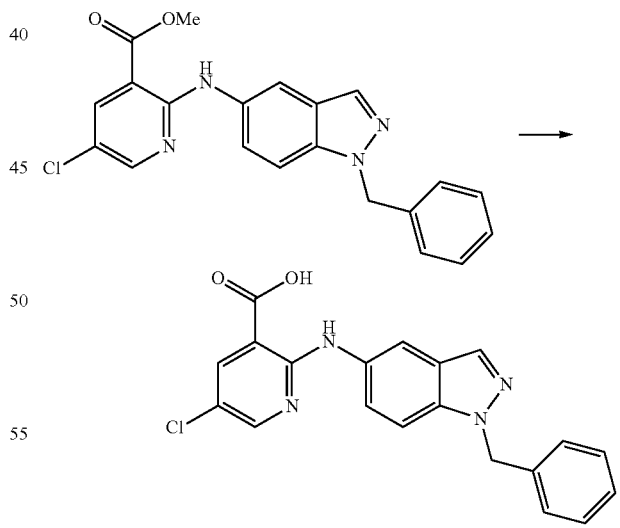

By the method similar to that of Example 63, 2-((1-benzyl-1H-indazol-5-yl)amino)-5-chloronicotinic acid was obtained from methyl 2-((1-benzyl-1H-indazol-5-yl)amino)-5-chloronicotinate.

$^1$H-NMR (DMSO-$d_6$) δ: 5.64 (2H, s), 7.13-7.52 (6H, m), 7.64 (1H, d, J=9.2 Hz), 8.05 (1H, s), 8.12-8.24 (2H, m), 8.30-8.36 (1H, m), 10.80 (1H, brs).

Example 355

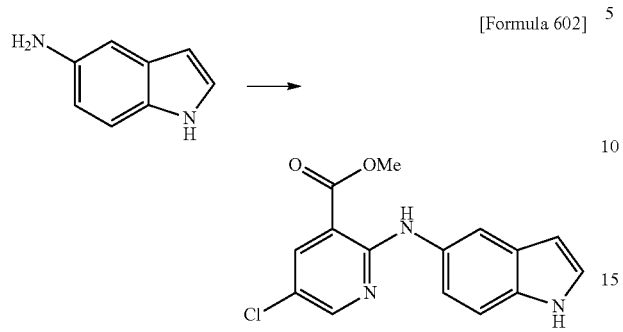

By the method similar to that of Reference Example 7, methyl 2-((1H-indol-5-yl)amino)-5-chloronicotinate was obtained from 1H-indol-5-amine and methyl 2,5-dichloronicotinate.

$^{1}$H-NMR (DMSO-d$_{6}$) δ: 3.91 (3H, s), 6.36-6.42 (1H, m), 7.11-7.20 (1H, m), 7.30-7.39 (2H, m), 7.86 (1H, s), 8.19 (1H, d, J=2.6 Hz), 8.38 (1H, d, J=2.6 Hz), 9.90 (1H, s), 11.04 (1H, brs).

MS (ESI, m/z): 302 (M+H)$^{+}$, 300 (M−H)$^{-}$.

Example 356

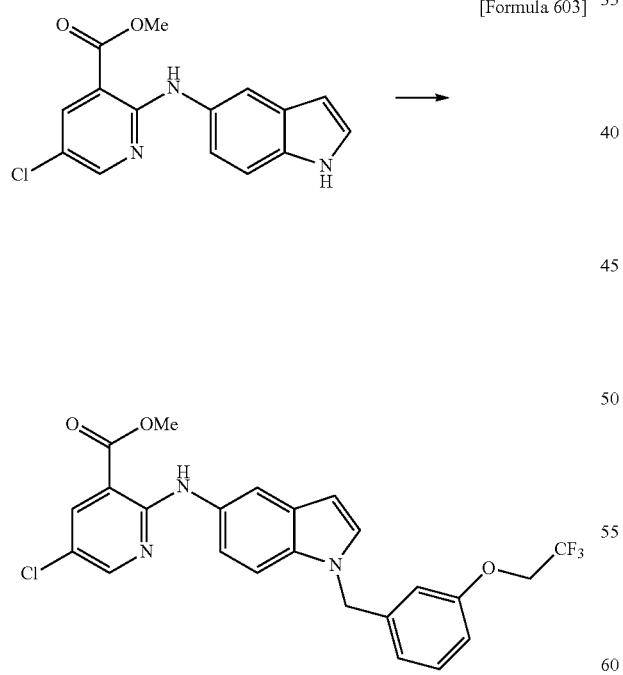

By the method similar to that of Example 12, methyl 5-chloro-2-((1-(3-(2,2,2-trifluoroethoxy)benzyl)-1H-indol-5-yl)amino)nicotinate was obtained from methyl 2-((1H-indol-5-yl)amino)-5-chloronicotinate and 1-(bromomethyl)-3-(2,2,2-trifluoroethoxy)benzene.

Example 357

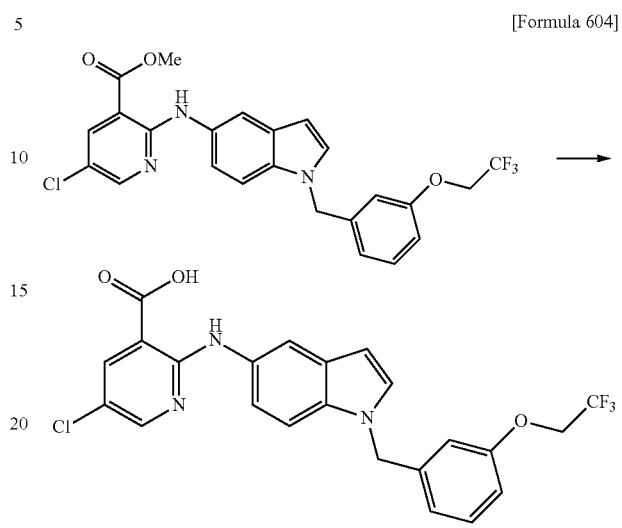

By the method similar to that of Example 63, 5-chloro-2-((1-(3-(2,2,2-trifluoroethoxyl)benzyl)-1H-indol-5-yl)amino)nicotinic acid was obtained from methyl 5-chloro-2-((1-(3-(2,2,2-trifluoroethoxy)benzyl)-1H-indol-5-yl)amino)nicotinate.

$^{1}$H-NMR (DMSO-d$_{6}$) δ: 4.72 (2H, q, J=8.8 Hz), 5.38 (2H, s), 6.46 (1H, d, J=2.6 Hz), 6.84 (1H, d, J=7.3 Hz), 6.91-6.98 (2H, m), 7.17 (1H, dd, J=8.6, 2.0 Hz), 7.23-7.31 (1H, m), 7.41 (1H, d, J=9.2 Hz), 7.51 (1H, d, J=2.6 Hz), 7.90 (1H, d, J=2.0 Hz), 8.15 (1H, d, J=2.6 Hz), 8.34 (1H, d, J=2.6 Hz), 10.22 (1H, brs).

Example 358

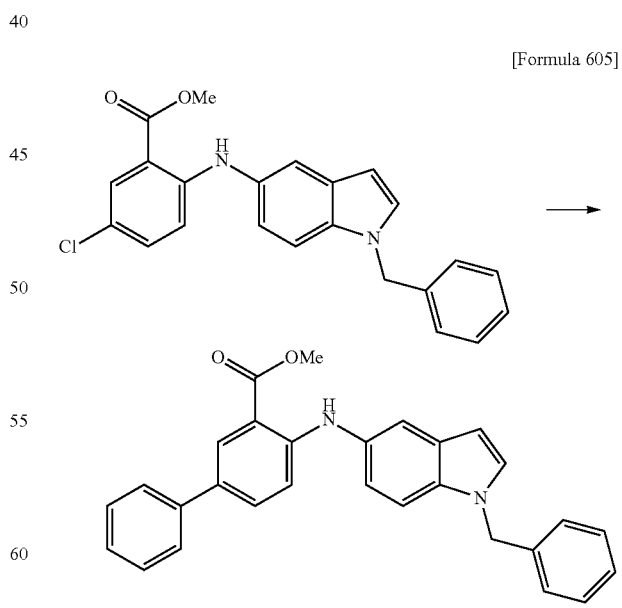

By the method similar to that of Example 7, methyl 4-((1-benzyl-1H-indol-5-yl)amino)-[1,1'-biphenyl]-3-carboxylate was obtained from methyl 2-((1-benzyl-1H-indol-5-yl)amino)-5-chlorobenzoate and phenylboronic acid.

¹H-NMR (DMSO-d₆) δ: 3.90 (3H, s), 5.44 (2H, s), 6.49 (1H, d, J=3.3 Hz), 6.98-7.06 (2H, m), 7.20-7.70 (14H, m), 8.14 (1H, d, J=2.6 Hz), 9.32 (1H, s).
MS (ESI, m/z): 433 (M+H)⁺.

Example 359

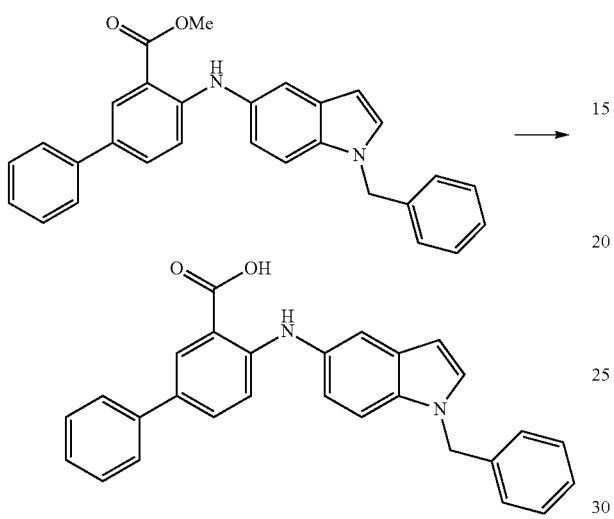

By the method similar to that of Example 37, 4-((1-Benzyl-1H-indol-5-yl)amino)-[1,1'-biphenyl]-3-carboxylic acid was obtained from methyl 4-((1-benzyl-1H-indol-5-yl)amino)-[1,1'-biphenyl]-3-carboxylate.

¹H-NMR (DMSO-d₆) δ: 5.44 (2H, s), 6.48 (1H, d, J=2.6 Hz), 6.99-7.06 (2H, m), 7.20-7.60 (13H, m), 7.64 (1H, dd, J=8.6, 2.6 Hz), 8.14 (1H, d, J=2.6 Hz), 9.58 (1H, s).
MS (ESI, m/z): 419 (M+H)⁺.

Example 360

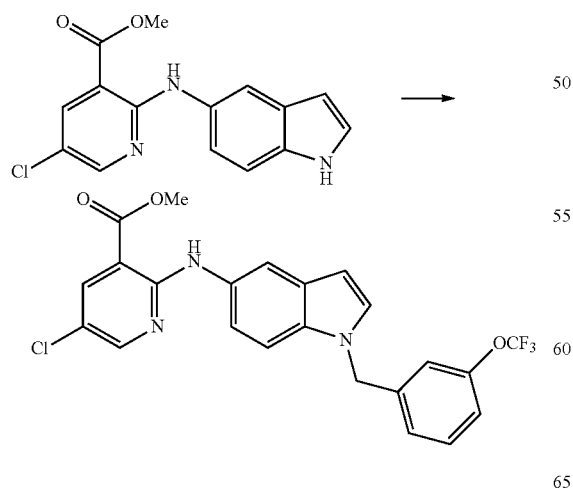

By the method similar to that of Example 12, methyl 5-chloro-2-((1-(3-(trifluoromethoxy)benzyl)-1H-indol-5-yl)amino)nicotinate was obtained from methyl 2-((1H-indol-5-yl)amino)-5-chloronicotinate and 1-(bromomethyl)-3-(trifluoromethoxy)benzene.

¹H-NMR (DMSO-d₆) δ: 3.90 (3H, s), 5.48 (2H, s), 6.48 (1H, d, J=2.6 Hz), 7.10-7.60 (7H, m), 7.86-7.93 (1H, m), 8.18 (1H, d, J=2.6 Hz), 8.37 (1H, d, J=2.0 Hz), 9.89 (1H, s).
MS (ESI, m/z): 476, 478 (M+H)⁺.

Example 361

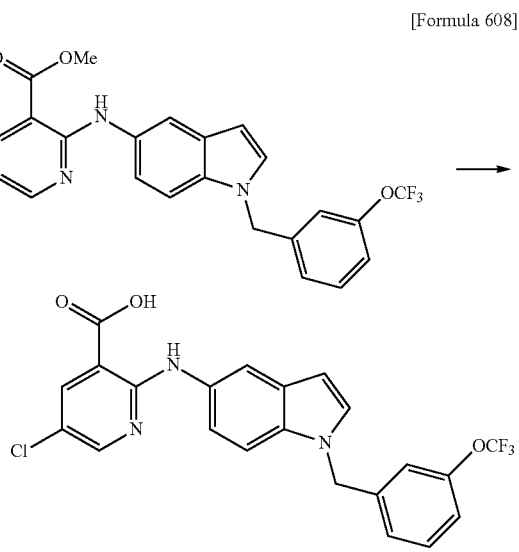

By the method similar to that of Example 37, 5-chloro-2-((1-(3-(trifluoromethoxy)benzyl)-1H-indol-5-yl)amino) nicotinic acid was obtained from methyl 5-chloro-2-((1-(3-(trifluoromethoxy)benzyl)-1H-indol-5-yl)amino)nicotinate.

¹H-NMR (DMSO-d₆) δ: 5.48 (2H, s), 6.48 (1H, d, J=3.3 Hz), 7.13-7.29 (4H, m), 7.38-7.48 (2H, m), 7.53 (1H, d, J=2.6 Hz), 7.92 (1H, d, J=2.0 Hz), 8.16 (1H, d, J=2.6 Hz), 8.35 (1H, d, J=2.6 Hz), 10.24 (1H, s).
MS (ESI, m/z): 462, 464 (M+H)⁺, 460 (M−H)⁻.

Example 362

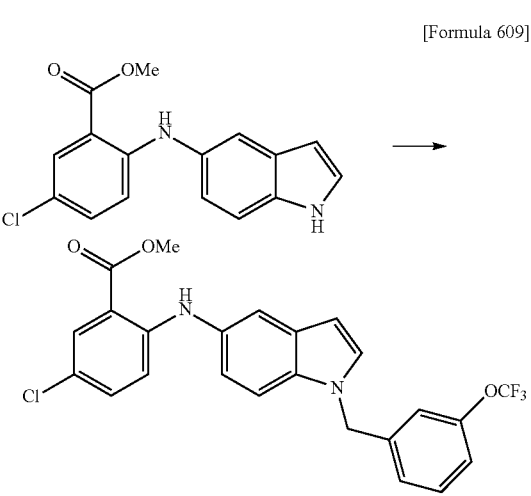

By the method similar to that of Example 12, methyl 5-chloro-2-((1-(3-(trifluoromethoxy)benzyl)-1H-indol-5-yl)amino)benzoate was obtained from methyl 2-((1H-indol-5-yl)amino)-5-chlorobenzoate and 1-(bromomethyl)-3-(trifluoromethoxy)benzene.

$^1$H-NMR (DMSO-$d_6$) δ: 3.87 (3H, s), 5.51 (2H, s), 6.50 (1H, d, J=2.6 Hz), 6.90 (1H, d, J=9.2 Hz), 7.00 (1H, dd, J=9.2, 2.0 Hz), 7.18-7.29 (3H, m), 7.33 (1H, dd, J=9.2, 2.6 Hz), 7.42-7.54 (3H, m), 7.59 (1H, d, J=3.3 Hz), 7.80 (1H, d, J=2.6 Hz), 9.23 (1H, s).

MS (ESI, m/z): 475 (M+H)$^+$.

Example 363

[Formula 610]

By the method similar to that of Example 63, 5-chloro-2-((1-(3-(trifluoromethoxy)benzyl)-1H-indol-5-yl)amino)benzoic acid was obtained from methyl 5-chloro-2-((1-(3-(trifluoromethoxy)benzyl)-1H-indol-5-yl)amino)benzoate.

$^1$H-NMR (DMSO-$d_6$) δ: 5.50 (2H, s), 6.49 (1H, d, J=2.6 Hz), 6.91 (1H, d, J=8.6 Hz), 7.00 (1H, dd, J=8.6, 2.0 Hz), 7.17-7.34 (4H, m), 7.42-7.53 (3H, m), 7.58 (1H, d, J=2.6 Hz), 7.79 (1H, d, J=2.6 Hz), 9.50 (1H, brs).

MS (ESI, m/z): 461 (M+H)$^+$, 459 (M–H)$^-$.

Example 364

[Formula 611]

By the method similar to that of Example 12, methyl 5-chloro-2-((1-(3-(difluoromethoxy)benzyl)-1H-indol-5-yl)amino)nicotinate was obtained from methyl 2-((1H-indol-5-yl)amino)-5-chloronicotinate and 1-(bromomethyl)-3-(difluoromethoxy)benzene.

$^1$H-NMR (DMSO-$d_6$) δ: 3.90 (3H, s), 5.44 (2H, s), 6.47 (1H, d, J=3.3 Hz), 7.00-7.09 (3H, m), 7.14-7.20 (2H, m), 7.32-7.45 (2H, m), 7.52 (1H, d, J=2.6 Hz), 7.88 (1H, d, J=1.3 Hz), 8.18 (1H, d, J=2.6 Hz), 8.37 (1H, d, J=2.6 Hz), 9.89 (1H, s).

MS (ESI, m/z): 458 (M+H)$^+$.

Example 365

[Formula 612]

By the method similar to that of Example 63, 5-chloro-2-((1-(3-(difluoromethoxy)benzyl)-1H-indol-5-yl)amino)nicotinic acid was obtained from methyl 5-chloro-2-((1-(3-(difluoromethoxy)benzyl)-1H-indol-5-yl)amino)nicotinate.

$^1$H-NMR (DMSO-$d_6$) δ: 5.43 (2H, s), 6.47 (1H, d, J=2.6 Hz), 6.99-7.10 (3H, m), 7.14-7.20 (2H, m), 7.32-7.45 (2H, m), 7.52 (1H, d, J=2.6 Hz), 7.91 (1H, d, J=2.0 Hz), 8.16 (1H, d, J=2.6 Hz), 8.34 (1H, d, J=2.6 Hz), 10.24 (1H, brs).

MS (ESI, m/z): 444 (M+H)$^+$, 442 (M–H)$^-$.

Example 366

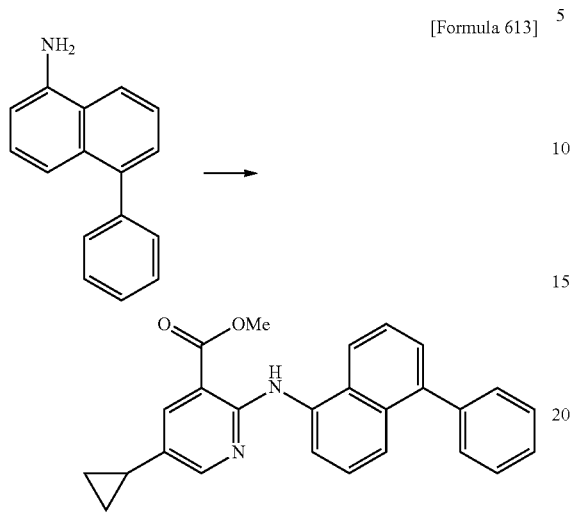

[Formula 613]

By the method similar to that of Example 176, methyl 5-cyclopropyl-2-((5-phenylnaphthalen-1-yl)amino)nicotinate was obtained from 5-phenylnaphthalen-1-amine and methyl 2-chloro-5-cyclopropylnicotinate.

MS (ESI, m/z): 395 (M+H)+.

Example 367

[Formula 614]

By the method similar to that of Example 116, 5-cyclopropyl-2-((5-phenylnaphthalen-1-yl)amino)nicotinic acid was obtained from methyl 5-cyclopropyl-2-((5-phenylnaphthalen-1-yl)amino)nicotinate.

$^1$H-NMR (DMSO-d$_6$) δ: 0.67-0.69 (2H, m), 0.92-0.95 (2H, m), 1.90-1.99 (1H, m), 7.47-7.55 (8H, m), 7.64 (1H, dd, J=8.6, 7.3 Hz), 7.97 (1H, d, J=2.6 Hz), 8.12 (1H, d, J=8.6 Hz), 8.22 (1H, d, J=2.6 Hz), 8.32 (1H, dd, J=7.3, 1.3 Hz), 10.84 (1H, s), 13.72 (1H, s).

MS (ESI, m/z): 381 (M+H)+, 379 (M−H)−.

Example 368

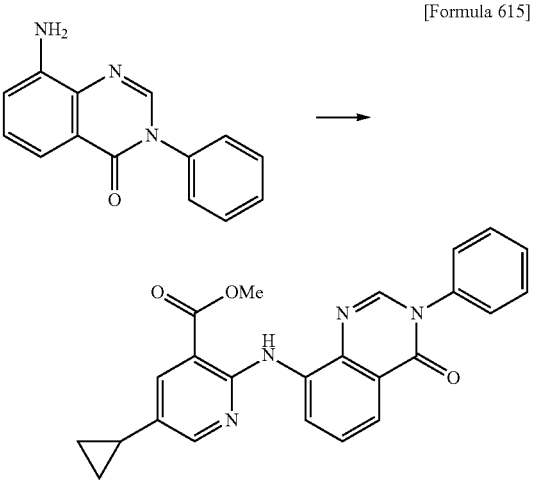

[Formula 615]

By the method similar to that of Example 176, methyl 5-cyclopropyl-2-((4-oxo-3-phenyl-3,4-dihydroquinazolin-8-yl)amino)nicotinate was obtained from 8-amino-3-phenylquinazolin-4(3H)-one and methyl 2-chloro-5-cyclopropylnicotinate.

MS (ESI, m/z): 413 (M+H)+.

Example 369

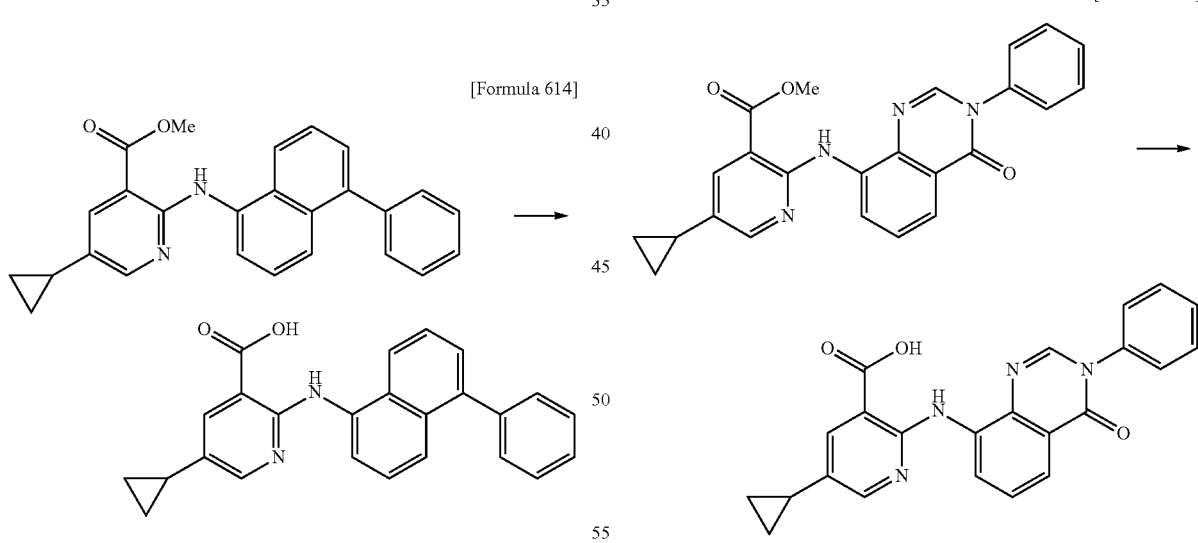

[Formula 616]

By the method similar to that of Example 116, 5-cyclopropyl-2-((4-oxo-3-phenyl-3,4-dihydroquinazolin-8-yl)amino)nicotinic acid was obtained from methyl 5-cyclopropyl-2-((4-oxo-3-phenyl-3,4-dihydroquinazolin-8-yl)amino)nicotinate.

$^1$H-NMR (DMSO-d$_6$) δ: 0.71-0.73 (2H, m), 0.94-1.00 (2H, m), 1.94-2.03 (1H, m), 7.50-7.59 (6H, m), 7.73 (1H, dd, J=7.9, 1.3 Hz), 7.98 (1H, d, J=2.6 Hz), 8.37 (1H, d, J=2.6 Hz), 8.42 (1H, s), 9.21 (1H, dd, J=7.9, 1.3 Hz), 11.74 (1H, s).

MS (ESI, m/z): 399 (M+H)+, 397 (M−H)−.

Example 370

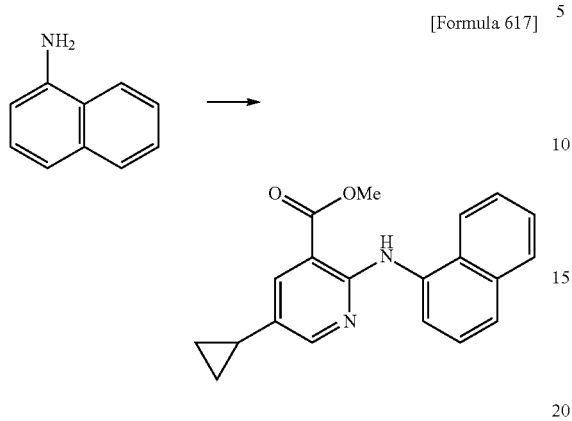

[Formula 617]

By the method similar to that of Example 176, methyl 5-cyclopropyl-2-(naphthalen-1-ylamino)nicotinate was obtained from naphthalen-1-amine and methyl 2-chloro-5-cyclopropylnicotinate.

MS (ESI, m/z): 319 (M+H)$^+$.

Example 371

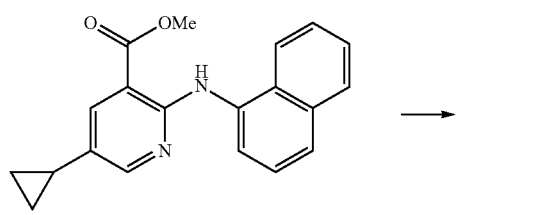

[Formula 618]

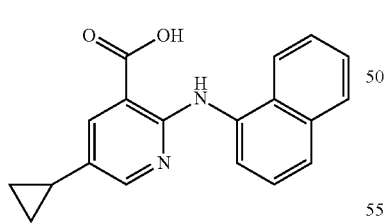

By the method similar to that of Example 116, 5-cyclopropyl-2-(naphthalen-1-ylamino)nicotinic acid was obtained from methyl 5-cyclopropyl-2-(naphthalen-1-ylamino)nicotinate.

$^1$H-NMR (DMSO-d$_6$) δ: 0.66-0.71 (2H, m), 0.91-0.97 (2H, m), 1.90-1.99 (1H, m), 7.48-7.66 (4H, m), 7.96 (2H, dd, J=8.3, 2.3 Hz), 8.08 (1H, d, J=7.9 Hz), 8.24 (1H, d, J=2.6 Hz), 8.39 (1H, d, J=6.6 Hz), 10.85 (1H, s).

MS (ESI, m/z): 305 (M+H)$^+$, 303 (M−H)$^−$.

Example 372

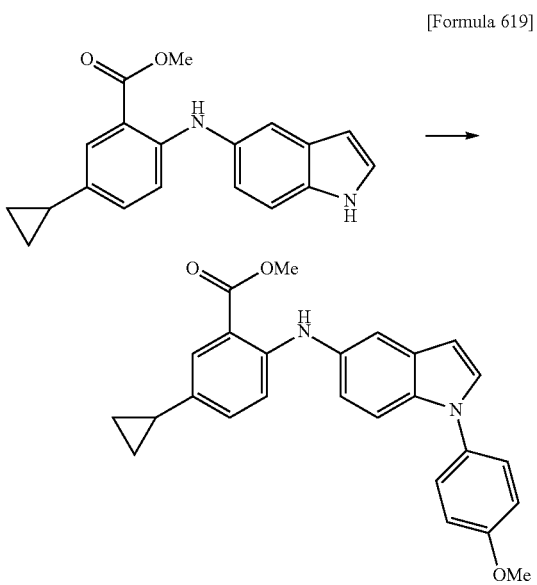

[Formula 619]

The mixture of 50 mg of methyl 2-((1H-indol-5-yl)amino)-5-cyclopropylbenzoate, 56 mg of 1-iodo-4-methoxybenzene, 30 mg of copper(I) iodide, 102 mg of tripotassium phosphate, 6 μL of trans-N,N'-dimethylcyclohexane-1,2-diamine, and 2 mL of toluene, was heated at reflux for nine hours under a nitrogen atmosphere. The reaction mixture was allowed to stand overnight, and the insoluble matter was then filtered off through a membrane filter and the solvent was distilled off under reduced pressure. The obtained residue was purified by silica gel column chromatography (gradient elution with hexane:ethyl acetate=100:0-50:50) to give 45 mg of methyl 5-cyclopropyl-2-((1-(4-methoxyphenyl)-1H-indol-5-yl)amino)benzoate as a yellow oil.

MS (ESI, m/z): 413 (M+H)$^+$.

Example 373

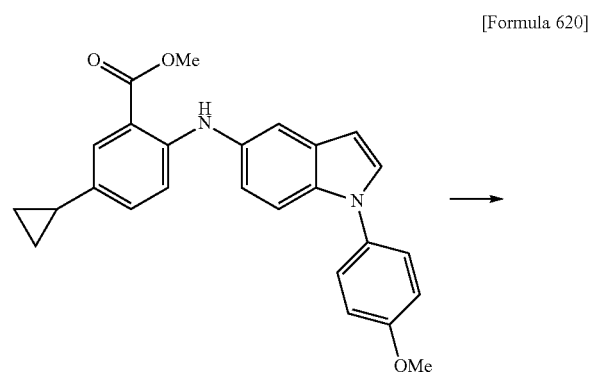

[Formula 620]

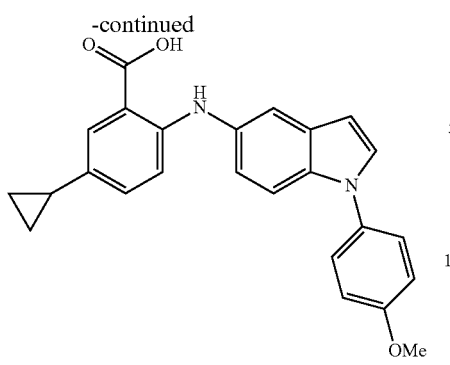

By the method similar to that of Example 96, 5-cyclopropyl-2-((1-(4-methoxyphenyl)-1H-indol-5-yl)amino)benzoic acid was obtained from methyl 5-cyclopropyl-2-((1-(4-methoxyphenyl)-1H-indol-5-yl)amino)benzoate.

$^1$H-NMR (DMSO-$d_6$) δ: 0.52-0.58 (2H, m), 0.82-0.87 (2H, m), 1.80-1.89 (1H, m), 3.83 (3H, s), 6.62 (1H, d, J=3.3 Hz), 6.96 (1H, d, J=8.6 Hz), 7.08-7.11 (2H, m), 7.13 (2H, d, J=8.6 Hz), 7.42-7.53 (4H, m), 7.58 (1H, d, J=2.6 Hz), 7.62 (1H, d, J=2.0 Hz), 9.39 (1H, s).

MS (ESI, m/z): 399 (M+H)$^+$, 397 (M−H)$^−$.

Example 374

[Formula 621]

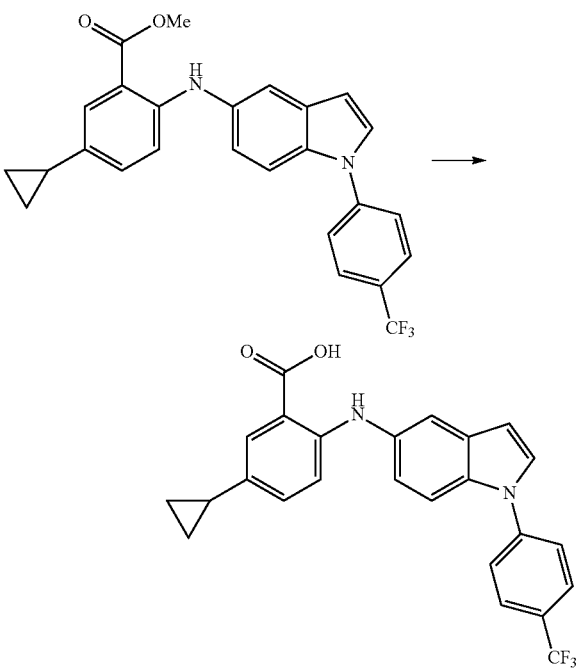

The mixture of 50 mg of methyl 2-((1H-indol-5-yl)amino)-5-cyclopropylbenzoate, 35 μL of 1-iodo-4-(trifluoromethyl)benzene, 30 mg of copper(I) iodide, 169 mg of cesium carbonate, and 2 mL of N,N-dimethylformamide, was stirred at 130° C. for three hours under a nitrogen atmosphere. The reaction mixture was allowed to stand overnight, and the insoluble matter was then filtered off through a membrane filter and the solvent was distilled off under reduced pressure. The obtained residue was purified by silica gel column chromatography (gradient elution with hexane:ethyl acetate=100:0-70:30) to give 45 mg of methyl 5-cyclopropyl-2-((1-(4-(trifluoromethyl)phenyl)-1H-indol-5-yl)amino)benzoate as a yellow oil.

MS (ESI, m/z): 451 (M+H)$^+$.

Example 375

[Formula 622]

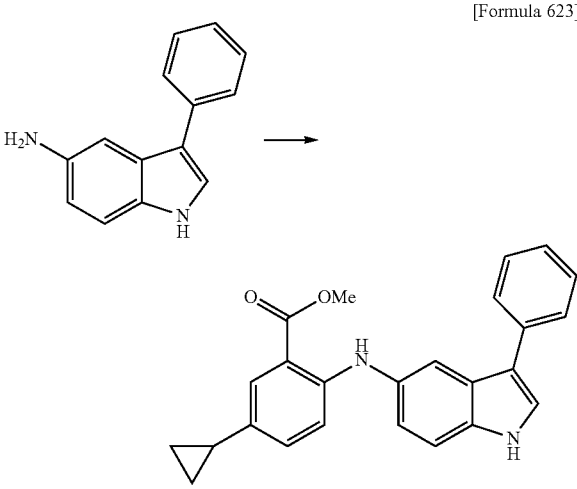

By the method similar to that of Example 96, 5-cyclopropyl-2-((1-(4-(trifluoromethyl)phenyl)-1H-indol-5-yl)amino)benzoic acid was obtained from methyl 5-cyclopropyl-2-((1-(4-(trifluoromethyl)phenyl)-1H-indol-5-yl)amino)benzoate.

$^1$H-NMR (DMSO-$d_6$) δ: 0.53-0.58 (2H, m), 0.83-0.89 (2H, m), 1.80-1.90 (1H, m), 6.72 (1H, d, J=3.3 Hz), 7.03 (2H, s), 7.09 (1H, dd, J=9.2, 2.0 Hz), 7.50 (1H, d, J=2.0 Hz), 7.63 (1H, s), 7.67 (1H, d, J=9.2 Hz), 7.78 (1H, d, J=3.3 Hz), 7.87 (2H, d, J=9.2 Hz), 7.94 (2H, d, J=9.2 Hz).

MS (ESI, m/z): 437 (M+H)$^+$, 435 (M−H)$^−$.

Example 376

[Formula 623]

By the method similar to that of Example 20, methyl 5-cyclopropyl-2-((3-phenyl-1H-indol-5-yl)amino)benzoate was obtained from 3-phenyl-1H-indol-5-amine and methyl 2-bromo-5-cyclopropylbenzoate.

MS (ESI, m/z): 383 (M+H)⁺.

Example 377

[Formula 624]

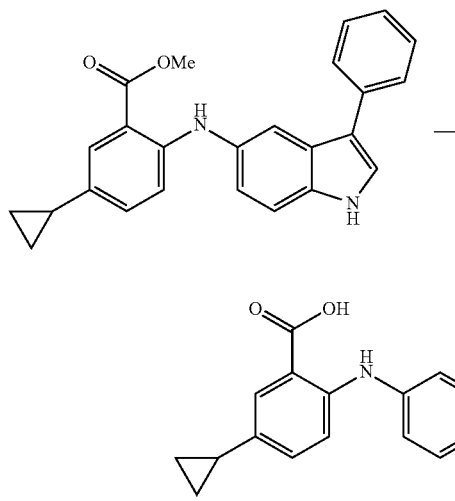

By the method similar to that of Example 96, 5-cyclopropyl-2-((3-phenyl-1H-indol-5-yl)amino)benzoic acid was obtained from methyl 5-cyclopropyl-2-((3-phenyl-1H-indol-5-yl)amino)benzoate.

$^1$H-NMR (DMSO-d$_6$) δ: 0.50-0.56 (2H, m), 0.80-0.88 (2H, m), 1.77-1.87 (1H, m), 6.88 (1H, d, J=8.6 Hz), 7.03 (2H, d, J=8.6 Hz), 7.18-7.23 (1H, m), 7.38-7.48 (3H, m), 7.60-7.75 (5H, m), 9.38 (1H, brs), 11.40 (1H, s), 12.88 (1H, brs).

MS (ESI, m/z): 369 (M+H)⁺, 367 (M−H)⁻.

Example 378

[Formula 625]

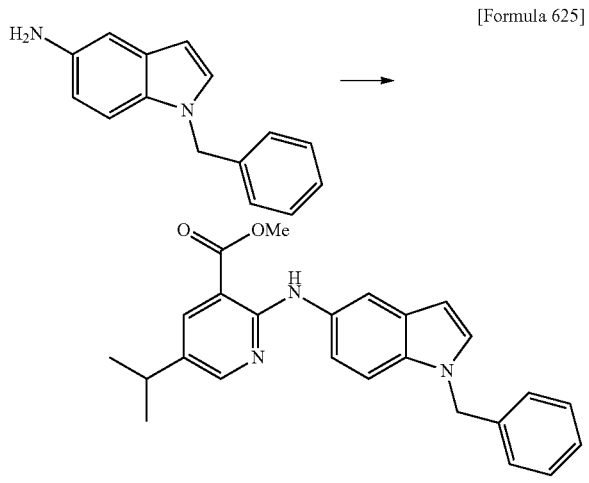

By the method similar to that of Example 115, methyl 2-((1-benzyl-1H-indol-5-yl)amino)-5-isopropylnicotinate was obtained from 1-benzyl-1H-indol-5-amine and methyl 2-chloro-5-isopropylnicotinate.

$^1$H-NMR (DMSO-d$_6$) δ: 1.20 (6H, d, J=6.6 Hz), 2.88 (1H, sep, J=6.6 Hz), 3.90 (3H, s), 5.40 (2H, s), 6.44 (1H, d, J=3.3 Hz), 7.15-7.39 (7H, m), 7.48 (1H, d, J=3.3 Hz), 7.96 (1H, d, J=2.0 Hz), 8.07 (1H, d, J=2.6 Hz), 8.29 (1H, d, J=2.6 Hz), 9.84 (1H, s).

MS (ESI, m/z): 400 (M+H)⁺.

Example 379

[Formula 626]

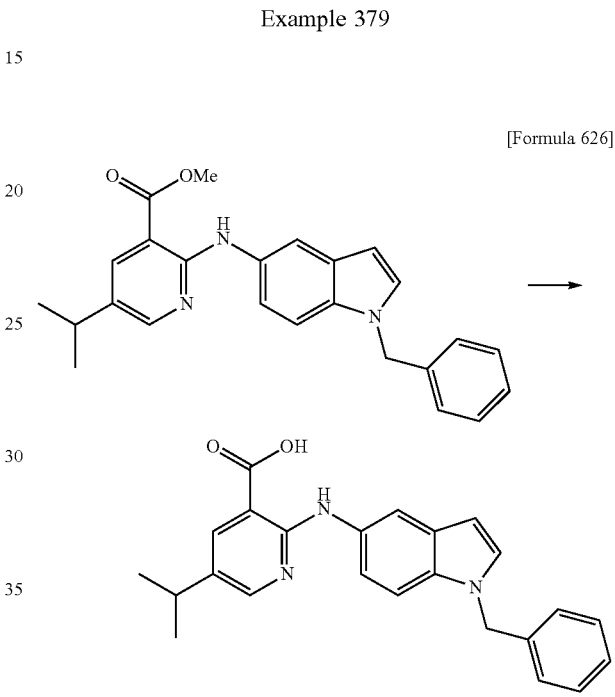

By the method similar to that of Example 116, 2-((1-benzyl-1H-indol-5-yl)amino)-5-isopropylnicotinic acid was obtained from methyl 2-((1-benzyl-1H-indol-5-yl)amino)-5-isopropylnicotinate.

$^1$H-NMR (DMSO-d$_6$) δ: 1.20 (6H, d, J=6.6 Hz), 2.87 (1H, sep, J=6.6 Hz), 5.40 (2H, s), 6.44 (1H, d, J=3.3 Hz), 7.14-7.38 (7H, m), 7.48 (1H, d, J=3.3 Hz), 7.97 (1H, d, J=2.0 Hz), 8.07 (1H, d, J=2.6 Hz), 8.25 (1H, d, J=2.6 Hz), 10.13 (1H, s), 13.40 (1H, brs).

MS (ESI, m/z): 386 (M+H)⁺, 384 (M−H)⁻.

Example 380

[Formula 627]

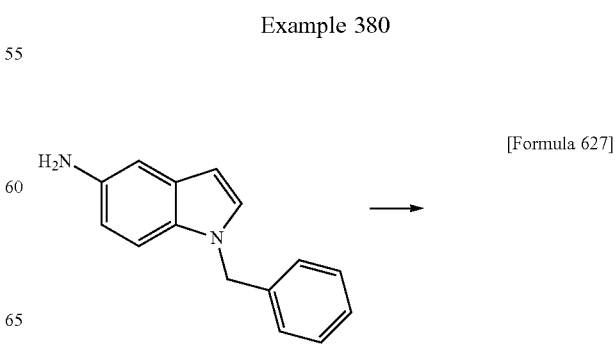

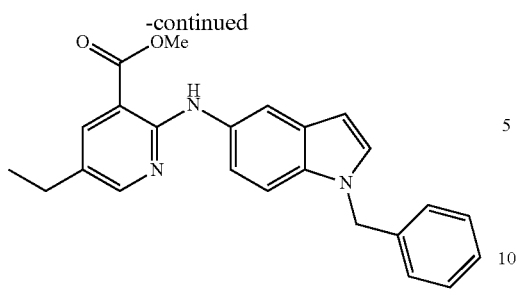

By the method similar to that of Example 115, methyl 2-((1-benzyl-1H-indol-5-yl)amino)-5-ethylnicotinate was obtained from 1-benzyl-1H-indol-5-amine and methyl 2-chloro-5-ethylnicotinate.

$^1$H-NMR (DMSO-d$_6$) δ: 1.16 (3H, t, J=7.6 Hz), 2.54 (2H, q, J=7.9 Hz), 3.89 (3H, s), 5.40 (2H, s), 6.44 (1H, d, J=3.3 Hz), 7.14-7.37 (7H, m), 7.48 (1H, d, J=3.3 Hz), 7.96 (1H, d, J=2.0 Hz), 8.07 (1H, d, J=2.6 Hz), 8.24 (1H, d, J=2.0 Hz), 9.84 (1H, s).

MS (ESI, m/z): 387 (M+H)$^+$.

Example 381

[Formula 628]

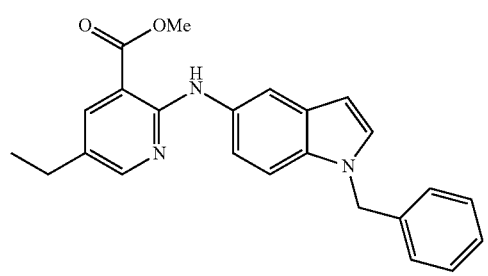

By the method similar to that of Example 116, 2-((1-benzyl-1H-indol-5-yl)amino)-5-ethylnicotinic acid was obtained from methyl 2-((1-benzyl-1H-indol-5-yl)amino)-5-ethylnicotinate.

$^1$H-NMR (DMSO-d$_6$) δ: 1.16 (3H, t, J=7.6 Hz), 2.53 (2H, q, J=7.6 Hz), 5.40 (2H, s), 6.44 (1H, d, J=2.6 Hz), 7.15-7.34 (6H, m), 7.36 (1H, d, J=3.6 Hz), 7.47 (1H, d, J=3.3 Hz), 7.97 (1H, d, J=2.0 Hz), 8.05 (1H, d, J=2.6 Hz), 8.21 (1H, d, J=2.0 Hz), 10.13 (1H, s).

MS (ESI, m/z): 372 (M+H)$^+$, 370 (M−H)$^−$.

Example 382

[Formula 629]

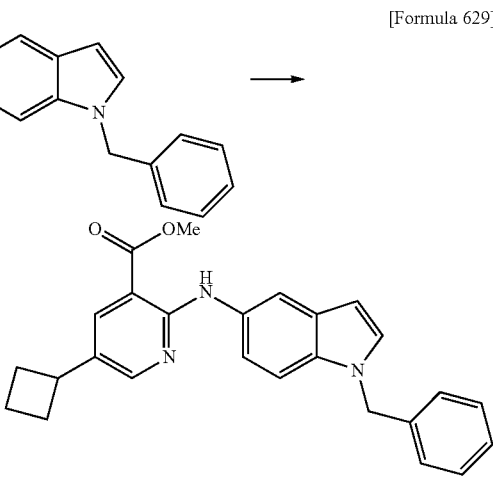

By the method similar to that of Example 115, methyl 2-((1-benzyl-1H-indol-5-yl)amino)-5-cyclobutylnicotinate was obtained from 1-benzyl-1H-indol-5-amine and methyl 2-chloro-5-cyclobutylnicotinate.

$^1$H-NMR (DMSO-d$_6$) δ: 1.78-1.87 (1H, m), 1.91-2.13 (3H, m), 2.22-2.32 (2H, m), 3.48 (1H, quin, J=8.6 Hz), 3.90 (3H, s), 5.40 (2H, s), 6.44 (1H, d, J=3.3 Hz), 7.13-7.34 (6H, m), 7.37 (1H, d, J=8.6 Hz), 7.48 (1H, d, J=3.3 Hz), 7.96 (1H, d, J=2.0 Hz), 8.08 (1H, d, J=2.6 Hz), 8.26 (1H, d, J=2.6 Hz), 9.85 (1H, s).

MS (ESI, m/z): 412 (M+H)$^+$.

Example 383

[Formula 630]

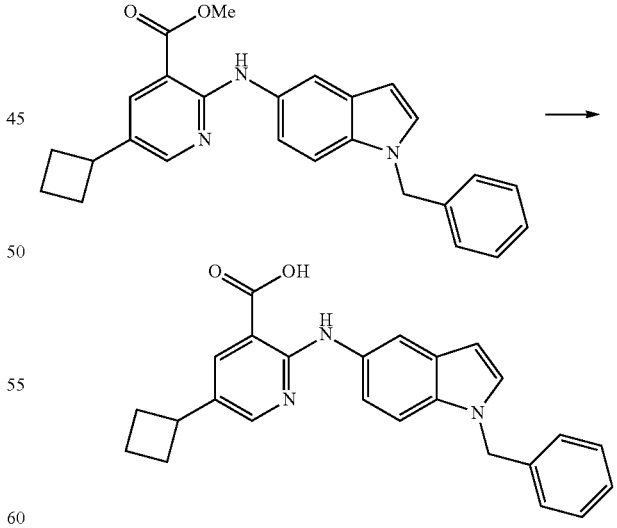

By the method similar to that of Example 116, 2-((1-benzyl-1H-indol-5-yl)amino)-5-cyclobutylnicotinic acid was obtained from methyl 2-((1-benzyl-1H-indol-5-yl)amino)-5-cyclobutylnicotinate.

$^1$H-NMR (DMSO-d$_6$) δ: 1.81-2.11 (4H, m), 2.24-2.31 (2H, m), 3.48 (1H, quin, J=8.6 Hz), 5.36 (2H, s), 6.43 (1H, d, J=3.3 Hz), 7.16-7.35 (7H, m), 7.42 (1H, d, J=3.3 Hz), 8.01-8.05 (2H, m), 8.11 (1H, d, J=2.6 Hz).
MS (ESI, m/z): 398 (M+H)⁺, 396 (M−H)⁻.

Example 384

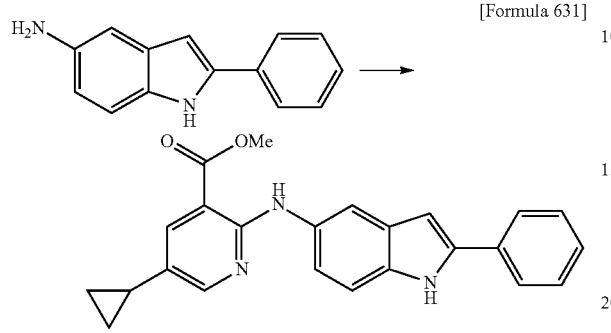

[Formula 631]

By the method similar to that of Example 115, methyl 5-cyclopropyl-2-((2-phenyl-1H-indol-5-yl)amino)nicotinate was obtained from 2-phenyl-1H-indol-5-amine and methyl 2-chloro-5-cyclopropylnicotinate.
$^1$H-NMR (DMSO-$d_6$) δ: 0.63-0.69 (2H, m), 0.88-0.96 (2H, m), 0.87-1.96 (1H, m), 3.90 (3H, s), 6.87 (1H, d, J=1.3 Hz), 7.18 (1H, dd, J=8.6, 2.0 Hz), 7.30-7.36 (2H, m), 7.43-7.49 (2H, m), 7.86 (2H, d, J=7.3 Hz), 7.89 (1H, d, J=2.6 Hz), 7.97 (1H, d, J=1.3 Hz), 8.24 (1H, d, J=2.6 Hz), 9.86 (1H, s), 11.45 (1H, s).
MS (ESI, m/z): 384 (M+H)⁺.

Example 385

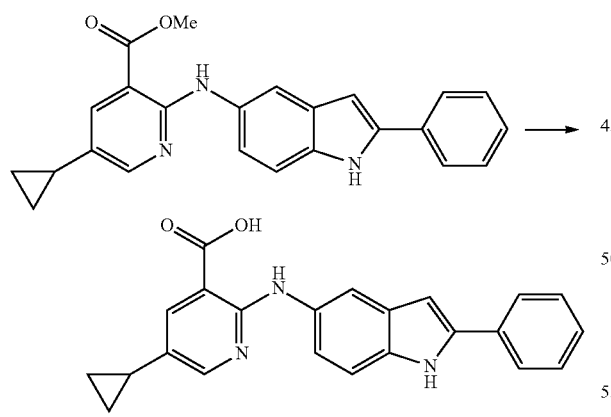

[Formula 632]

By the method similar to that of Example 116, 5-cyclopropyl-2-((2-phenyl-1H-indol-5-yl)amino)nicotinic acid was obtained from methyl 5-cyclopropyl-2-((2-phenyl-1H-indol-5-yl)amino)nicotinate.
$^1$H-NMR (DMSO-$d_6$) δ: 0.63-0.68 (2H, m), 0.88-0.95 (2H, m), 1.86-1.96 (1H, m), 6.86 (1H, d, J=1.3 Hz), 7.17 (1H, dd, J=8.6, 2.0 Hz), 7.27-7.35 (2H, m), 7.43-7.49 (2H, m), 7.83-7.88 (3H, m), 7.99 (1H, d, J=1.3 Hz), 8.21 (1H, d, J=2.6 Hz), 10.21 (1H, brs), 11.42 (1H, s), 13.42 (1H, brs).
MS (ESI, m/z): 370 (M+H)⁺, 368 (M−H)⁻.

Example 386

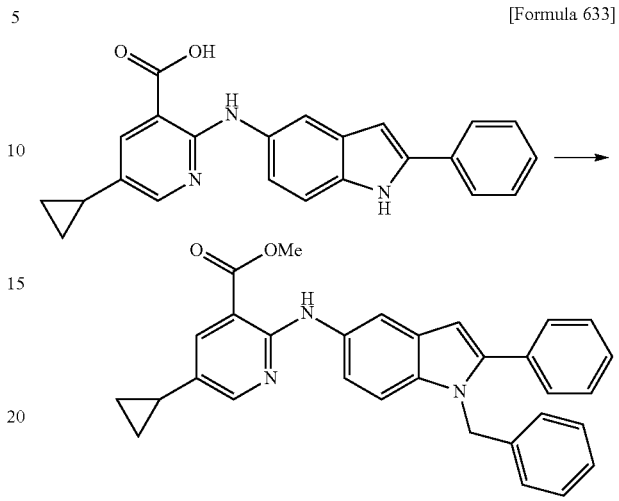

[Formula 633]

The mixture of 60 mg of methyl 5-cyclopropyl-2-((2-phenyl-1H-indol-5-yl)amino)nicotinate, 26 mg of potassium tert-butoxide, 22 μL of benzyl bromide, and 1 mL of N,N-dimethylacetamide, was stirred for one hour under ice-cooling. Ethyl acetate and water were added to the reaction mixture. The organic layer was separated, washed with a saturated aqueous sodium chloride solution and dried over anhydrous sodium sulfate, and the solvent was distilled off under reduced pressure. The obtained residue was purified by silica gel column chromatography (gradient elution with hexane:ethyl acetate=100:0-60:40) to give 30 mg of methyl 2-((1-benzyl-2-phenyl-1H-indol-5-yl)amino)-5-cyclopropylnicotinate as a yellow oil.
MS (ESI, m/z): 474 (M+H)⁺.

Example 387

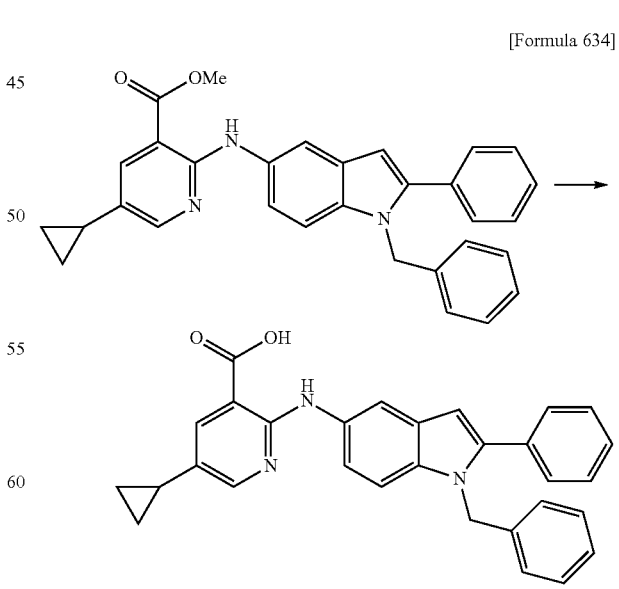

[Formula 634]

By the method similar to that of Example 116, 2-((1-benzyl-2-phenyl-1H-indol-5-yl)amino)-5-cyclopropylnicotinic acid was obtained from methyl 2-((1-benzyl-2-phenyl-1H-indol-5-yl)amino)-5-cyclopropylnicotinate.

$^1$H-NMR (DMSO-d$_6$) δ: 0.52-0.65 (2H, m), 0.82-0.92 (2H, m), 1.76-1.87 (1H, m), 5.42 (2H, s), 6.57 (1H, s), 6.92 (2H, d, J=6.6 Hz), 7.09-7.28 (5H, m), 7.35-7.53 (5H, m), 7.79 (1H, d, J=1.3 Hz), 7.93 (1H, d, J=2.0 Hz), 8.24 (1H, s), 12.73 (1H, s).

MS (ESI, m/z): 460 (M+H)$^+$, 458 (M−H)$^−$.

Example 388

[Formula 635]

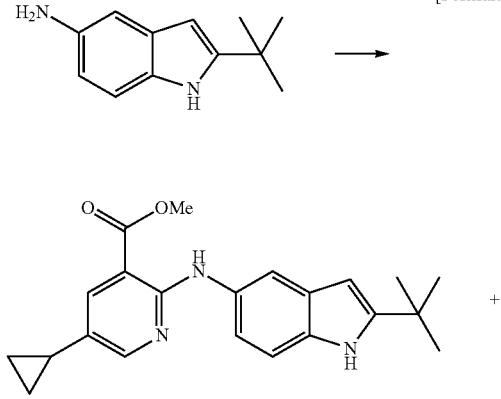

By the method similar to that of Example 115, methyl 2-((2-(tert-butyl)-1H-indol-5-yl)amino)-5-cyclopropylnicotinate and butyl 2-((2-(tert-butyl)-1H-indol-5-yl)amino)-5-cyclopropylnicotinate were obtained from 2-(tert-butyl)-1H-indol-5-amine and methyl 2-chloro-5-cyclopropylnicotinate.

Methyl 2-((2-(tert-butyl)-1H-indol-5-yl)amino)-5-cyclopropylnicotinate $^1$H-NMR (DMSO-d$_6$) δ: 0.61-0.67 (2H, m), 0.87-0.94 (2H, m), 1.34 (9H, s), 1.85-1.95 (1H, m), 3.84 (3H, s), 6.07 (1H, d, J=2.0 Hz), 7.10 (1H, dd, J=8.6, 2.0 Hz), 7.23 (1H, d, J=8.6 Hz), 7.75 (1H, d, J=2.0 Hz), 7.87 (1H, d, J=2.6 Hz), 8.19 (1H, d, J=2.0 Hz), 9.78 (1H, s), 10.78 (1H, s).

MS (ESI, m/z): 364 (M+H)$^+$

Butyl 2-((2-(tert-butyl)-1H-indol-5-yl)amino)-5-cyclopropylnicotinate

MS (ESI, m/z): 406 (M+H)$^+$.

Example 389

[Formula 636]

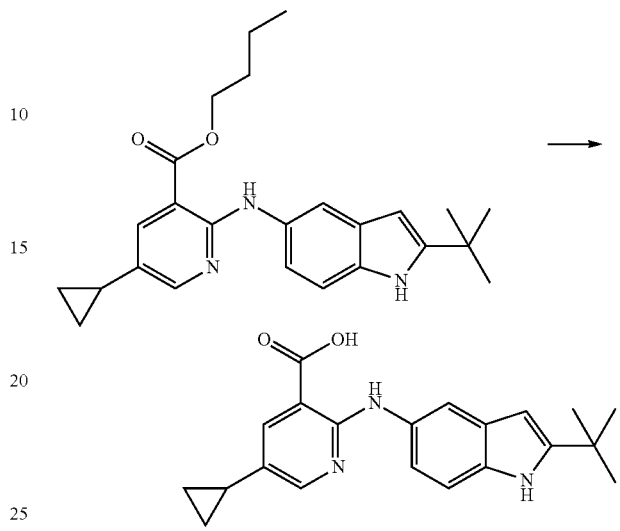

By the method similar to that of Example 116, 2-((2-(tert-butyl)-1H-indol-5-yl)amino)-5-cyclopropylnicotinic acid was obtained from butyl 2-((2-(tert-butyl)-1H-indol-5-yl)amino)-5-cyclopropylnicotinate.

$^1$H-NMR (DMSO-d$_6$) δ: 0.57-0.63 (2H, m), 0.85-0.92 (2H, m), 1.34 (9H, s), 1.81-1.92 (1H, m), 6.04 (1H, d, J=2.0 Hz), 7.11 (1H, dd, J=8.6, 2.0 Hz), 7.19 (1H, d, J=8.6 Hz), 7.83-7.86 (2H, m), 8.06 (1H, d, J=2.6 Hz), 10.69 (1H, s), 10.98 (1H, brs).

MS (ESI, m/z): 350 (M+H)$^+$, 348 (M−H)$^−$.

Example 390

[Formula 637]

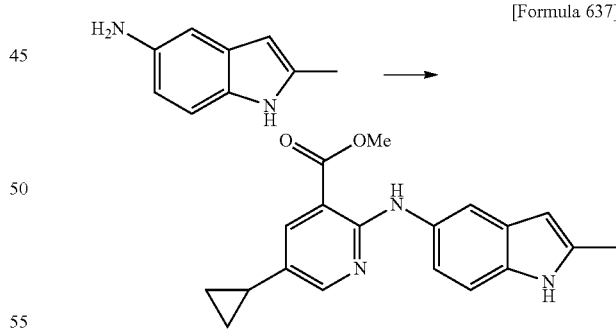

By the method similar to that of Example 115, methyl 5-cyclopropyl-2-((2-methyl-1H-indol-5-yl)amino)nicotinate was obtained from 2-methyl-1H-indol-5-amine and methyl 2-chloro-5-cyclopropylnicotinate.

$^1$H-NMR (DMSO-d$_6$) δ: 0.61-0.68 (2H, m), 0.87-0.95 (2H, m), 1.85-1.95 (1H, m), 2.36 (3H, s), 3.92 (3H, s), 6.06 (1H, s), 7.06 (1H, dd, J=8.6, 2.0 Hz), 7.20 (1H, d, J=8.7 Hz), 7.75-7.80 (1H, m), 7.87 (1H, d, J=2.7 Hz), 8.20 (1H, d, J=2.0 Hz), 9.79 (1H, s), 10.80 (1H, s).

MS (ESI, m/z): 322 (M+H)$^+$.

Example 391

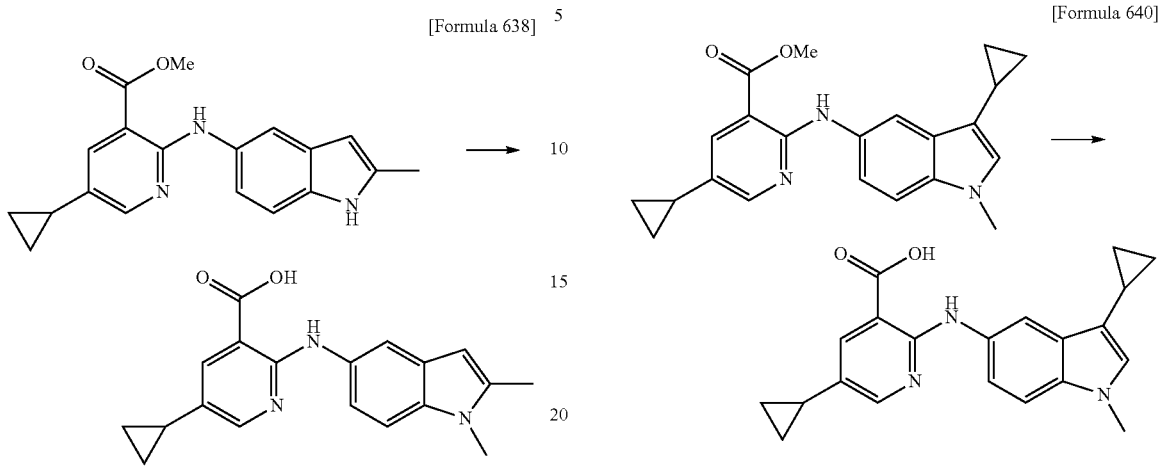

By the method similar to that of Example 157, 5-cyclopropyl-2-((1,2-dimethyl-1H-indol-5-yl)amino)nicotinic acid was obtained from methyl 5-cyclopropyl-2-((2-methyl-1H-indol-5-yl)amino)nicotinate.

$^1$H-NMR (DMSO-$d_6$) δ: 0.60-0.68 (2H, m), 0.86-0.95 (2H, m), 1.84-1.95 (1H, m), 2.38 (3H, s), 3.64 (3H, s), 6.15 (1H, s), 7.14 (1H, d, J=8.6 Hz), 7.29 (1H, d, J=8.6 Hz), 7.84 (1H, s), 7.87 (1H, d, J=1.8 Hz), 8.18 (1H, d, J=2.0 Hz), 10.11 (1H, s), 13.40 (1H, brs).

MS (ESI, m/z): 322 (M+H)$^+$, 320 (M–H)$^-$.

Example 392

[Formula 639]

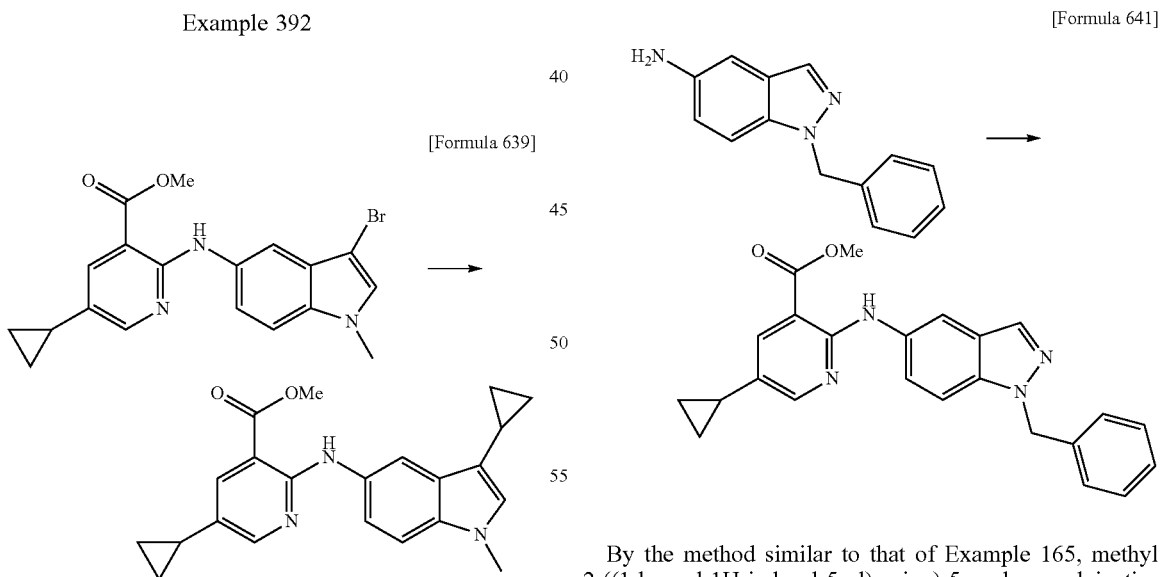

By the method similar to that of Example 152, methyl 5-cyclopropyl-2-((3-cyclopropyl-1-methyl-1H-indol-5-yl)amino)nicotinate was obtained from methyl 2-((3-bromo-1-methyl-1H-indol-5-yl)amino)-5-cyclopropylnicotinate and cyclopropylboronic acid.

MS (ESI, m/z): 362 (M+H)$^+$.

Example 393

[Formula 640]

By the method similar to that of Example 116, 5-cyclopropyl-2-((3-cyclopropyl-1-methyl-1H-indol-5-yl)amino) nicotinic acid was obtained from methyl 5-cyclopropyl-2-((3-cyclopropyl-1-methyl-1H-indol-5-yl)amino)nicotinate.

$^1$H-NMR (DMSO-$d_6$) δ: 0.52-0.59 (2H, m), 0.59-0.66 (2H, m), 0.81-0.94 (4H, m), 1.82-1.93 (2H, m), 3.67 (3H, s), 6.95 (1H, s), 7.27 (1H, d, J=8.6 Hz), 7.32 (1H, dd, J=8.6, 2.0 Hz), 7.85 (1H, d, J=2.6 Hz), 7.93 (1H, d, J=1.3 Hz), 8.10 (1H, d, J=2.6 Hz), 10.88 (1H, brs).

MS (ESI, m/z): 348 (M+H)$^+$, 346 (M–H)$^-$.

Example 394

[Formula 641]

By the method similar to that of Example 165, methyl 2-((1-benzyl-1H-indazol-5-yl)amino)-5-cyclopropylnicotinate was obtained from 1-benzyl-1H-indazol-5-amine and methyl 2-chloro-5-cyclopropylnicotinate.

$^1$H-NMR (DMSO-$d_6$) δ: 0.63-0.69 (2H, m), 0.88-0.94 (2H, m), 1.87-1.97 (1H, m), 3.90 (3H, s), 5.64 (2H, s), 7.20-7.35 (5H, m), 7.41 (1H, dd, J=9.2, 2.0 Hz), 7.63 (1H, d, J=9.2 Hz), 7.90 (1H, d, J=2.0 Hz), 8.04 (1H, s), 8.26-8.22 (2H, m), 9.92 (1H, s).

MS (ESI, m/z): 399 (M+H)$^+$.

Example 395

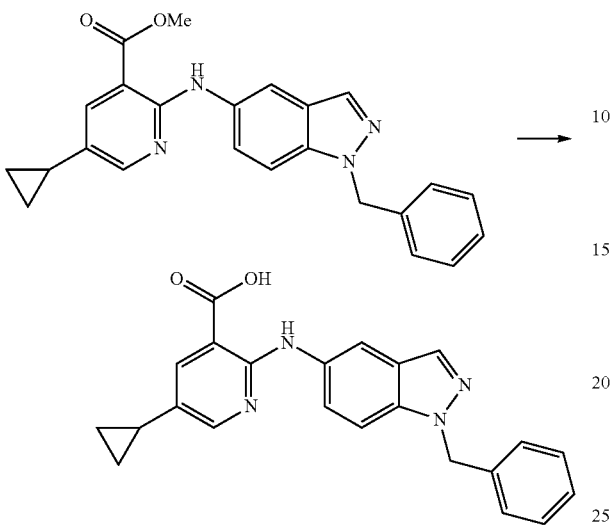

By the method similar to that of Example 116, 2-((1-benzyl-1H-indazol-5-yl)amino)-5-cyclopropylnicotinic acid was obtained from methyl 2-((1-benzyl-1H-indazol-5-yl)amino)-5-cyclopropylnicotinate.

¹H-NMR (DMSO-d₆) δ: 0.62-0.68 (2H, m), 0.88-0.96 (2H, m), 1.86-1.96 (1H, s), 5.64 (2H, s), 7.20-7.35 (5H, m), 7.40 (1H, dd, J=9.2, 2.0 Hz), 7.62 (1H, d, J=9.2 Hz), 7.89 (1H, d, J=2.6 Hz), 8.04 (1H, s), 8.22 (1H, d, J=2.6 Hz), 8.26 (1H, d, J=2.0 Hz), 10.24 (1H, s).

MS (ESI, m/z): 385 (M+H)⁺, 383 (M–H)⁻.

Example 396

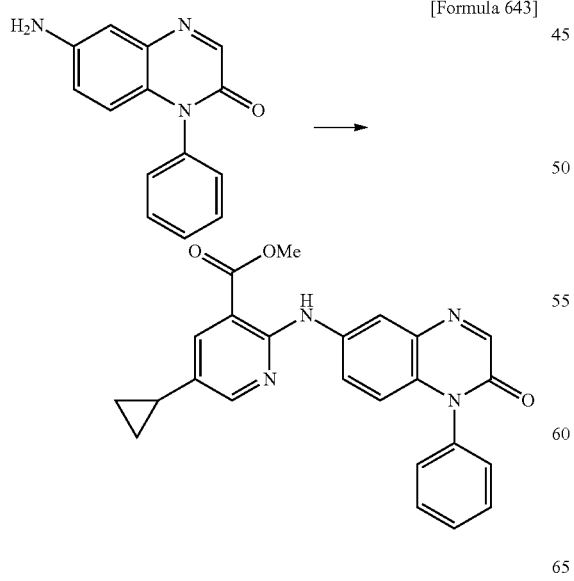

By the method similar to that of Example 223, methyl 5-cyclopropyl-2-((2-oxo-1-phenyl-1,2-dihydroquinoxalin-6-yl)amino)nicotinate was obtained from 6-amino-1-phenylquinoxalin-2(1H)-one and methyl 2-chloro-5-cyclopropylnicotinate.

MS (ESI, m/z): 413 (M+H)⁺.

Example 397

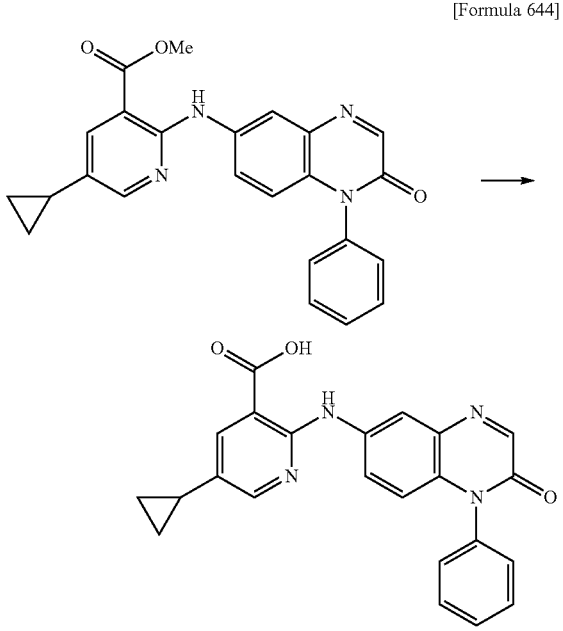

By the method similar to that of Example 224, 5-cyclopropyl-2-((2-oxo-1-phenyl-1,2-dihydroquinoxalin-6-yl)amino)nicotinic acid was obtained from methyl 5-cyclopropyl-2-((2-oxo-1-phenyl-1,2-dihydroquinoxalin-6-yl)amino)nicotinate.

¹H-NMR (DMSO-d₆) δ: 0.65-0.72 (2H, m), 0.90-0.98 (2H, m), 1.90-2.00 (1H, m), 6.55 (1H, d, J=9.2 Hz), 7.41-7.46 (2H, m), 7.51-7.70 (4H, m), 7.92 (1H, d, J=2.6 Hz), 8.28 (1H, d, J=2.6 Hz), 8.32 (1H, s), 8.55 (1H, d, J=2.6 Hz), 10.35 (1H, s).

MS (ESI, m/z): 399 (M+H)⁺.

Example 398

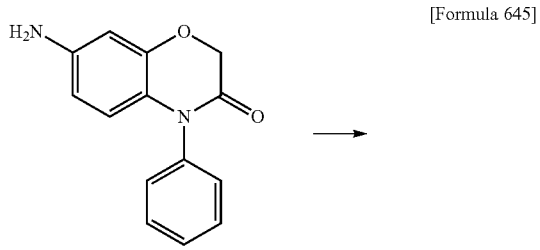

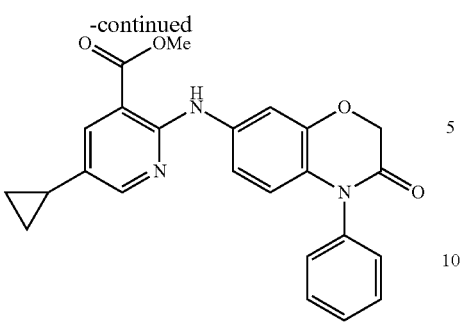

By the method similar to that of Example 223, methyl 5-cyclopropyl-2-((3-oxo-4-phenyl-3,4-dihydro-2H-benzo[b][1,4]oxazin-7-yl)amino)nicotinate was obtained from 7-amino-4-phenyl-2H-benzo[b][1,4]oxazin-3(4H)-one and methyl 2-chloro-5-cyclopropylnicotinate.

MS (ESI, m/z): 416 (M+H)+.

Example 399

[Formula 646]

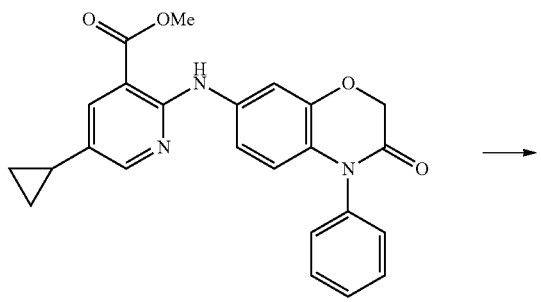

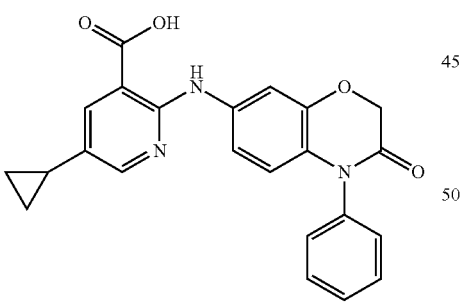

By the method similar to that of Example 224, 5-cyclopropyl-2-((3-oxo-4-phenyl-3,4-dihydro-2H-benzo[b][1,4]oxazin-7-yl)amino)nicotinic acid was obtained from methyl 5-cyclopropyl-2-((3-oxo-4-phenyl-3,4-dihydro-2H-benzo[b][1,4]oxazin-7-yl)amino)nicotinate.

$^1$H-NMR (DMSO-d$_6$) δ: 0.62-0.69 (2H, m), 0.88-0.97 (2H, m), 1.86-1.98 (1H, m), 4.80 (2H, s), 6.24 (1H, d, J=9.2 Hz), 6.95 (1H, dd, J=8.9, 2.3 Hz), 7.31-7.37 (2H, m), 7.46-7.61 (3H, m), 7.81 (1H, d, J=2.0 Hz), 7.88 (1H, d, J=2.6 Hz), 8.20-8.24 (1H, m), 10.38 (1H, brs).

MS (ESI, m/z): 402 (M+H)+.

Example 400

[Formula 647]

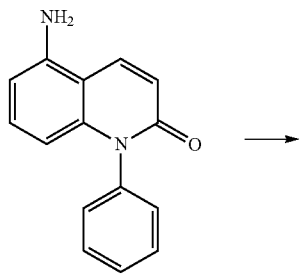

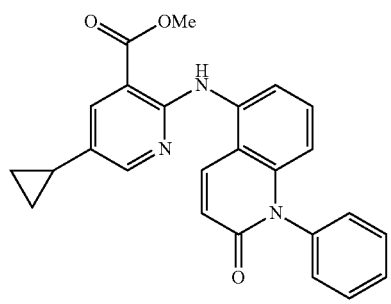

By the method similar to that of Example 223, methyl 5-cyclopropyl-2-((2-oxo-1-phenyl-1,2-dihydroquinolin-5-yl)amino)nicotinate was obtained from 5-amino-1-phenylquinolin-2(1H)-one and methyl 2-chloro-5-cyclopropylnicotinate.

MS (ESI, m/z): 412 (M+H)+.

Example 401

[Formula 648]

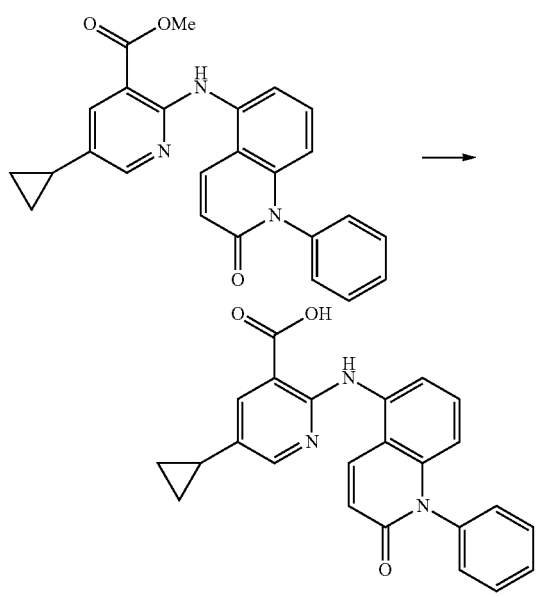

By the method similar to that of Example 224, 5-cyclopropyl-2-((2-oxo-1-phenyl-1,2-dihydroquinolin-5-yl)

amino)nicotinic acid was obtained from methyl 5-cyclopropyl-2-((2-oxo-1-phenyl-1,2-dihydroquinolin-5-yl)amino)nicotinate.

$^1$H-NMR (DMSO-d$_6$) δ: 0.64-0.71 (2H, m), 0.90-0.98 (2H, m), 1.88-2.00 (1H, m), 6.22 (1H, d, J=8.6 Hz), 6.72 (1H, d, J=9.9 Hz), 7.30-7.41 (3H, m), 7.52-7.67 (3H, m), 7.88 (1H, d, J=7.3 Hz), 7.95 (1H, d, J=2.6 Hz), 8.07 (1H, d, J=9.9 Hz), 8.20 (1H, d, J=2.6 Hz), 10.58 (1H, s).

MS (ESI, m/z): 398 (M+H)$^+$.

Example 402

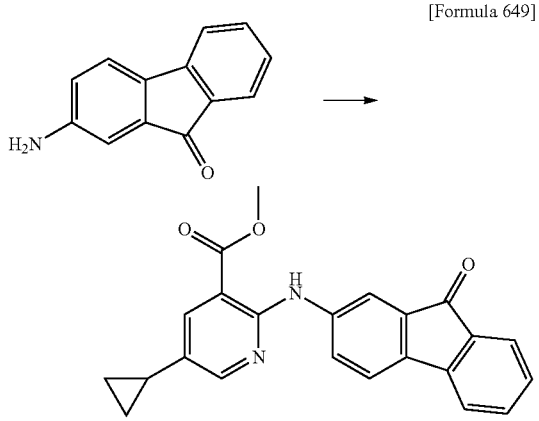

[Formula 649]

By the method similar to that of Example 223, methyl 5-cyclopropyl-2-((9-oxo-9H-fluoren-2-yl)amino)nicotinate was obtained from 2-amino-9H-fluoren-9-one and methyl 2-chloro-5-cyclopropylnicotinate.

MS (ESI, m/z): 371 (M+H)$^+$.

Example 403

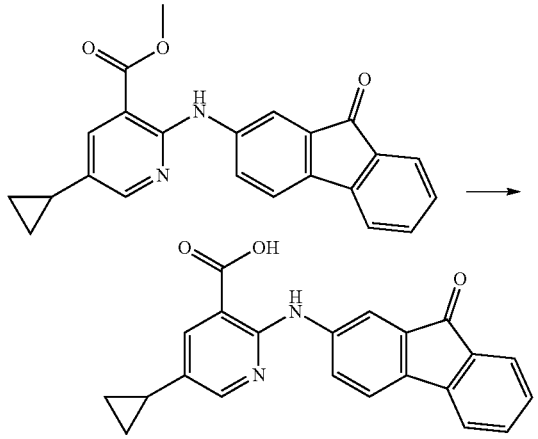

[Formula 650]

By the method similar to that of Example 224, 5-cyclopropyl-2-((9-oxo-9H-fluoren-2-yl)amino)nicotinic acid was obtained from methyl 5-cyclopropyl-2-((9-oxo-9H-fluoren-2-yl)amino)nicotinate.

$^1$H-NMR (DMSO-d$_6$) δ: 0.65-0.73 (2H, m), 0.90-0.97 (2H, m), 1.88-2.00 (1H, m), 7.27 (1H, t, J=6.9 Hz), 7.52-7.59 (2H, m), 7.65-7.70 (3H, m), 7.93 (1H, d, J=2.6 Hz), 8.22-8.28 (2H, m), 11.18 (1H, brs).

MS (ESI, m/z): 357 (M+H)$^+$.

Example 404

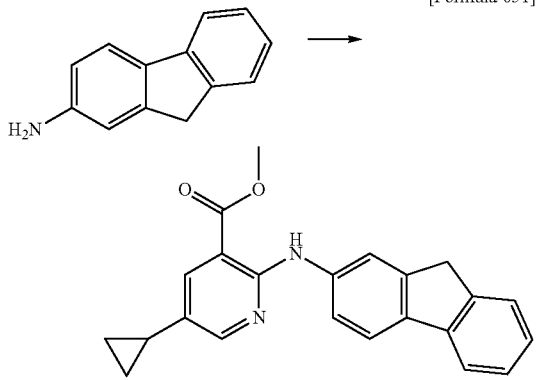

[Formula 651]

By the method similar to that of Example 223, methyl 2-((9H-fluoren-2-yl)amino)=5-cyclopropylnicotinate was obtained from 9H-fluoren-2-amine and methyl 2-chloro-5-cyclopropylnicotinate.

MS (ESI, m/z): 357 (M+H)$^+$.

Example 405

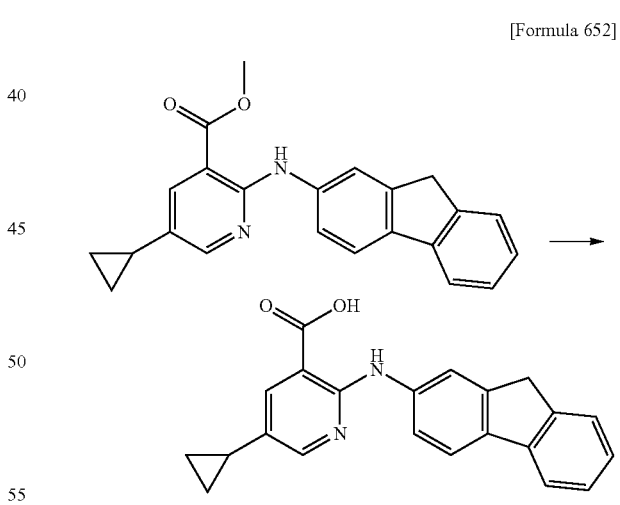

[Formula 652]

By the method similar to that of Example 224, 2-((9H-fluoren-2-yl)amino)-5-cyclopropylnicotinic acid was obtained from methyl 2-((9H-fluoren-2-yl)amino)-5-cyclopropylnicotinate.

$^1$H-NMR (DMSO-d$_6$) δ: 0.64-0.73 (2H, m), 0.90-0.97 (2H, m), 1.89-1.99 (1H, m), 3.91 (2H, s), 7.21-7.27 (1H, m), 7.35 (1H, t, J=7.3 Hz), 7.51-7.64 (2H, m), 7.76-7.83 (2H, m), 7.93 (1H, d, J=2.6 Hz), 8.06-8.10 (1H, m), 8.29 (1H, d, J=2.6 Hz), 10.46 (1H, s).

MS (ESI, m/z): 343 (M+H)$^+$.

Example 406

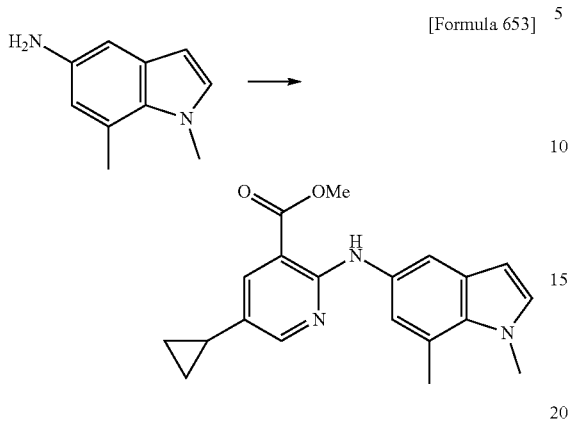

[Formula 653]

By the method similar to that of Example 223, methyl 5-cyclopropyl-2-((1,7-dimethyl-1H-indol-5-yl)amino)nicotinate was obtained from 1,7-dimethyl-1H-indol-5-amine and methyl 2-chloro-5-cyclopropylnicotinate.

MS (ESI, m/z): 336 (M+H)$^+$.

Example 407

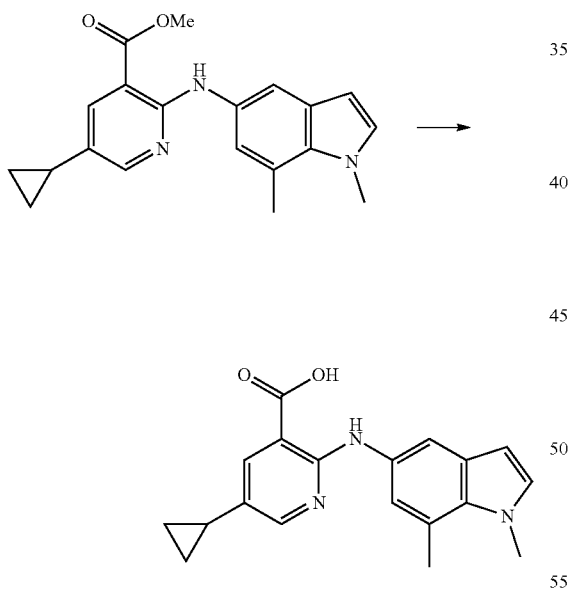

[Formula 654]

By the method similar to that of Example 224, 5-cyclopropyl-2-((1,7-dimethyl-1H-indol-5-yl)amino)nicotinic acid was obtained from methyl 5-cyclopropyl-2-((1,7-dimethyl-1H-indol-5-yl)amino)nicotinate.

$^1$H-NMR (DMSO-d$_6$) δ: 0.62-0.70 (2H, m), 0.86-0.95 (2H, m), 1.87-1.97 (1H, m), 2.71 (3H, s), 4.03 (3H, s), 6.31 (1H, d, J=2.6 Hz), 6.84 (1H, s), 7.19 (1H, d, J=2.6 Hz), 7.80 (1H, d, J=1.3 Hz), 7.94 (1H, d, J=2.0 Hz), 8.13 (1H, d, J=2.0 Hz), 10.16 (1H, s).

MS (ESI, m/z): 322 (M+H)$^+$.

Example 408

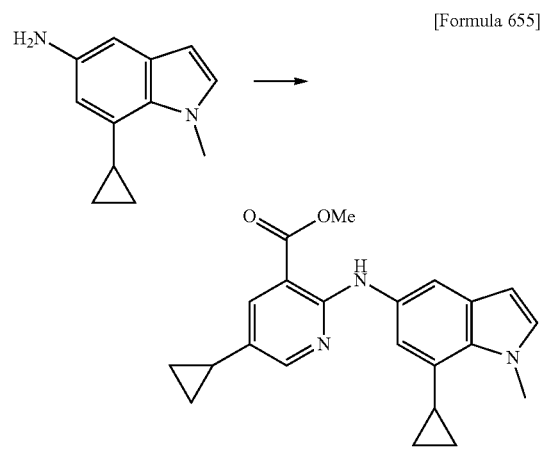

[Formula 655]

By the method similar to that of Example 223, methyl 5-cyclopropyl-2-((7-cyclopropyl-1-methyl-1H-indol-5-yl)amino)nicotinate was obtained from 7-cyclopropyl-1-methyl-1H-indol-5-amine and methyl 2-chloro-5-cyclopropylnicotinate.

MS (ESI, m/z): 362 (M+H)$^+$.

Example 409

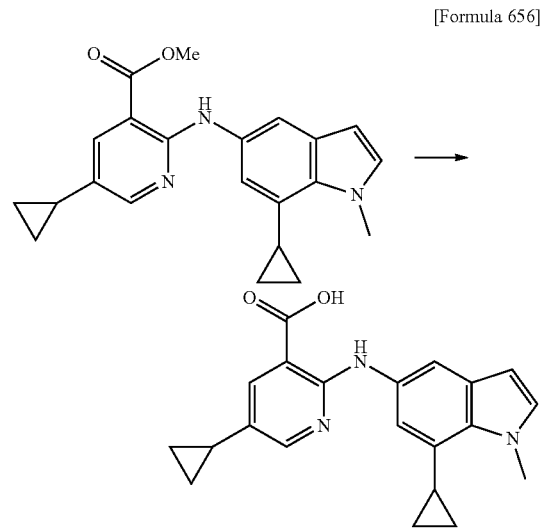

[Formula 656]

By the method similar to that of Example 224, 5-cyclopropyl-2-((7-cyclopropyl-1-methyl-1H-indol-5-yl)amino) nicotinic acid was obtained from methyl 5-cyclopropyl-2-((7-cyclopropyl-1-methyl-1H-indol-5-yl)amino)nicotinate.

$^1$H-NMR (DMSO-d$_6$) δ: 0.61-0.68 (2H, m), 0.76-1.02 (6H, m), 1.84-1.95 (1H, m), 3.10-3.50 (1H, m), 4.16 (3H, s), 6.31 (1H, d, J=2.6 Hz), 6.82 (1H, d, J=1.3 Hz), 7.19 (1H, d, J=2.6 Hz), 7.82-7.88 (2H, m), 8.19 (1H, d, J=2.6 Hz), 10.06 (1H, s).

MS (ESI, m/z): 348 (M+H)$^+$.

Example 410

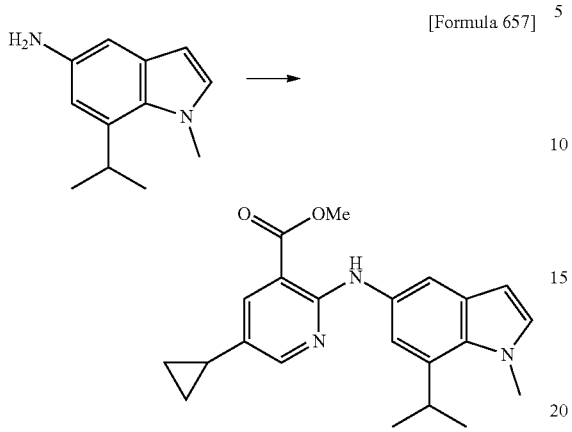

[Formula 657]

By the method similar to that of Example 223, methyl 5-cyclopropyl-2-((7-isopropyl-1-methyl-1H-indol-5-yl)amino)nicotinate was obtained from 7-isopropyl-1-methyl-1H-indol-5-amine and methyl 2-chloro-5-cyclopropylnicotinate.

MS (ESI, m/z): 364 (M+H)$^+$.

Example 411

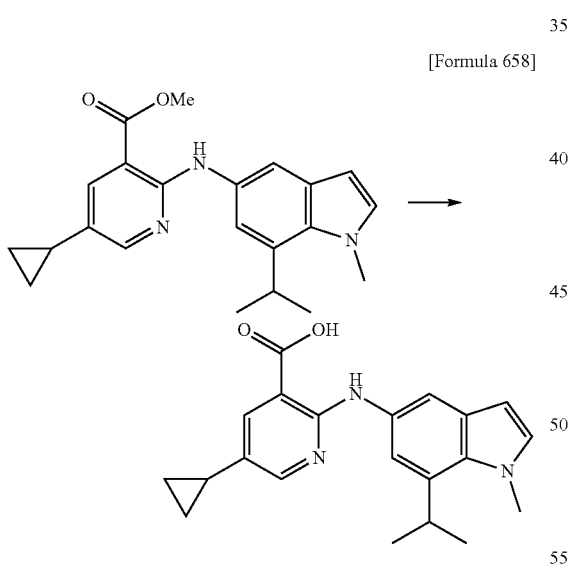

[Formula 658]

By the method similar to that of Example 224, 5-cyclopropyl-2-((7-isopropyl-1-methyl-1H-indol-5-yl)amino)nicotinic acid was obtained from methyl 5-cyclopropyl-2-((7-isopropyl-1-methyl-1H-indol-5-yl)amino)nicotinate.

$^1$H-NMR (DMSO-d$_6$) δ: 0.61-0.68 (2H, m), 0.86-0.95 (2H, m), 1.32 (6H, d, J=7.3 Hz), 1.84-1.95 (1H, m), 3.74-3.85 (1H, m), 3.99 (3H, s), 6.32 (1H, d, J=2.6 Hz), 6.97 (1H, d, J=2.0 Hz), 7.17 (1H, d, J=3.3 Hz), 7.84-7.93 (2H, m), 8.20 (1H, d, J=2.6 Hz), 10.13 (1H, s).

MS (ESI, m/z): 350 (M+H)$^+$.

Example 412

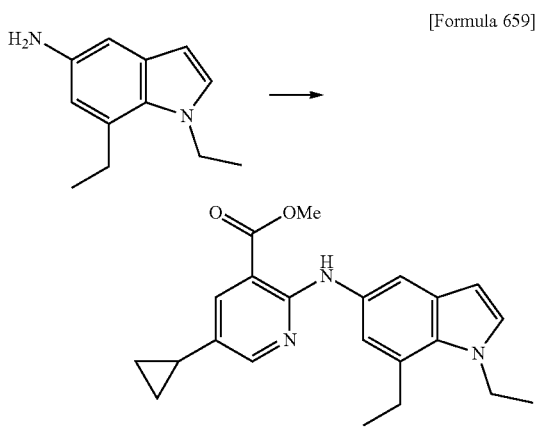

[Formula 659]

By the method similar to that of Example 223, methyl 5-cyclopropyl-2-((1,7-diethyl-1H-indol-5-yl)amino)nicotinate was obtained from 1,7-diethyl-1H-indol-5-amine and methyl 2-chloro-5-cyclopropylnicotinate.

MS (ESI, m/z): 364 (M+H)$^+$.

Example 413

[Formula 660]

By the method similar to that of Example 224, 5-cyclopropyl-2-((1,7-diethyl-1H-indol-5-yl)amino)nicotinic acid was obtained from methyl 5-cyclopropyl-2-((1,7-diethyl-1H-indol-5-yl)amino)nicotinate.

$^1$H-NMR (DMSO-d$_6$) δ: 0.61-0.68 (2H, m), 0.87-0.95 (2H, m), 1.25-1.37 (6H, m), 1.84-1.95 (1H, m), 2.98 (2H, q, J=7.5 Hz), 4.30 (2H, q, J=7.0 Hz), 6.37 (1H, d, J=2.6 Hz), 6.90 (1H, d, J=2.0 Hz), 7.27 (1H, d, J=3.3 Hz), 7.84-7.94 (2H, m), 8.20 (1H, d, J=2.6 Hz), 10.13 (1H, s).

MS (ESI, m/z): 350 (M+H)$^+$.

Example 414

[Formula 661]

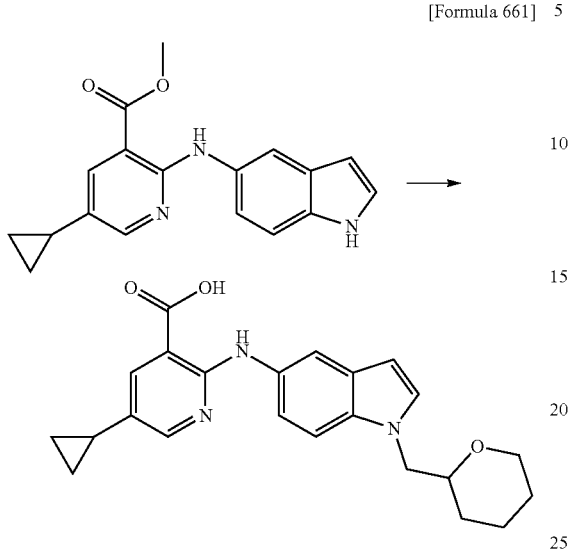

The mixture of 49 mg of methyl 2-((1H-indol-5-yl)amino)-5-cyclopropylnicotinate, 90 mg of potassium tert-butoxide, 143 mg of 2-(bromomethyl)tetrahydro-2H-pyran, and 2 mL of N,N-dimethylformamide, was stirred for three hours. The reaction mixture was adjusted to pH 2.5 to 3.0 by adding thereto ethyl acetate, water and concentrated hydrochloric acid. The organic layer was separated and dried over anhydrous magnesium sulfate, and the solvent was then distilled off under reduced pressure. The obtained residue was purified by silica gel column chromatography (gradient elution with hexane:ethyl acetate=75:25-0:100), and ethyl acetate and hexane were added to the thus obtained residue, and the solid was collected by filtration to give 8 mg of 5-cyclopropyl-2-((1-((tetrahydro-2H-pyran-2-yl)methyl)-1H-indol-5-yl)amino)nicotinic acid as a red solid.

$^1$H-NMR (DMSO-$d_6$) δ: 0.61-0.68 (2H, m), 0.87-0.95 (2H, m), 1.11-1.28 (1H, m), 1.35-1.60 (4H, m), 1.70-1.82 (1H, m), 1.84-1.96 (1H, m), 3.20-3.50 (1H, m), 3.54-3.65 (1H, m), 3.80-3.88 (1H, m), 4.10-4.18 (2H, m), 6.35 (1H, d, J=3.3 Hz), 7.17 (1H, dd, J=8.6, 2.0 Hz), 7.27 (1H, d, J=2.6 Hz), 7.40 (1H, d, J=8.6 Hz), 7.86 (1H, d, J=2.6 Hz), 7.93 (1H, d, J=2.0 Hz), 8.18 (1H, d, J=2.6 Hz), 10.17 (1H, s).

MS (ESI, m/z): 392 (M+H)$^+$.

Example 415

[Formula 662]

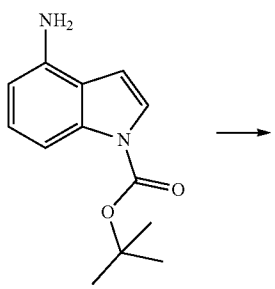

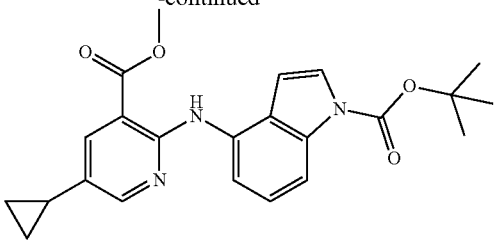

By the method similar to that of Example 225, tert-butyl 4-((5-cyclopropyl-3-(methoxycarbonyl)pyridin-2-yl)amino)-1H-indole-1-carboxylate was obtained from tert-butyl 4-amino-1H-indole-1-carboxylate and methyl 2-chloro-5-cyclopropylnicotinate.

MS (ESI, m/z): 408 (M+H)$^+$.

Example 416

[Formula 663]

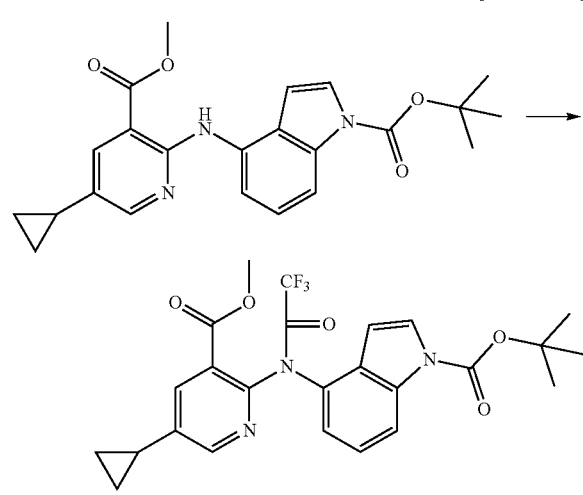

By the method similar to that of Example 234, tert-butyl 4-(N-(5-cyclopropyl-3-(methoxycarbonyl)pyridin-2-yl)-2,2,2-trifluoroacetamido)-1H-indole-1-carboxylate was obtained from tert-butyl 4-((5-cyclopropyl-3-(methoxycarbonyl)pyridin-2-yl)amino)-1H-indole-1-carboxylate.

MS (ESI, m/z): 504 (M+H)$^+$.

Example 417

[Formula 664]

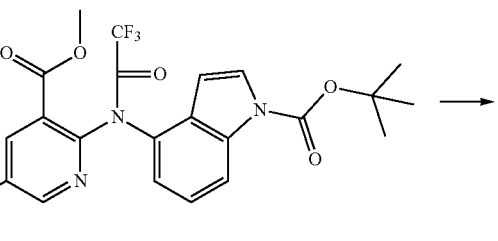

-continued

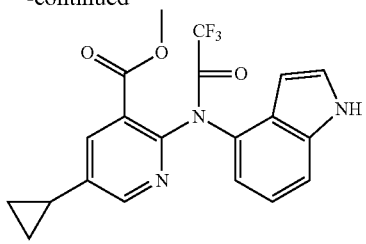

By the method similar to that of Example 235, methyl 5-cyclopropyl-2-(2,2,2-trifluoro-N-(1H-indol-4-yl)acetamido)nicotinate was obtained from tert-butyl 4-(N-(5-cyclopropyl-3-(methoxycarbonyl)pyridin-2-yl)-2,2,2-trifluoroacetamido)-1H-indole-1-carboxylate.

MS (ESI, m/z): 404 (M+H)$^+$.

Example 418

[Formula 665]

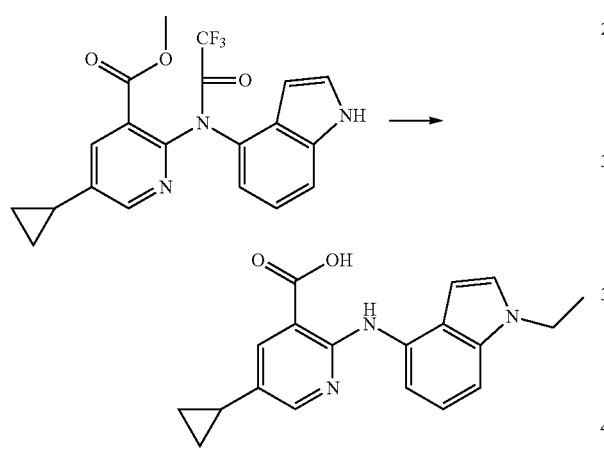

To the solution of 65 mg of methyl 5-cyclopropyl-2-(2,2,2-trifluoro-N-(1H-indol-4-yl)acetamido)nicotinate in 2 mL of N,N-dimethylformamide, 8 mg of 60% sodium hydride and 16 μL of ethyl iodide were added under ice-cooling, and the resultant was stirred for 30 minutes. To the reaction mixture, ethyl acetate and water were added. The organic layer was separated and dried over anhydrous magnesium sulfate, and the solvent was then distilled off under reduced pressure. After the obtained residue was purified by silica gel column chromatography (gradient elution with hexane:ethyl acetate=100:0-75:25), 2 mL of methanol, 4 mL of tetrahydrofuran and a 1 mL of 1 mol/L aqueous sodium hydroxide solution were added to the thus obtained residue and the resultant was heated at reflux for 30 minutes. After cooling the reaction mixture to room temperature, the solvent was distilled off under reduced pressure. Water was added to the obtained residue and the resultant was adjusted to pH 2.5 to 3.0 with 1 mol/L hydrochloric acid, followed by addition of ethyl acetate. The organic layer was separated and dried over anhydrous magnesium sulfate, and the solvent was then distilled off under reduced pressure. The obtained residue was purified by silica gel column chromatography (gradient elution with hexane:ethyl acetate=67:33-0:100), and ethyl acetate and hexane were added to the thus obtained residue, and the solid was collected by filtration to give 11 mg of 5-cyclopropyl-2-((1-ethyl-1H-indol-4-yl)amino)nicotinic acid as a yellow solid.

$^1$H-NMR (DMSO-d$_6$) δ: 0.65-0.73 (2H, m), 0.90-0.97 (2H, m), 1.36 (3H, t, J=7.3 Hz), 1.89-2.00 (1H, m), 4.20 (2H, q, J=7.3 Hz), 6.48 (1H, d, J=3.3 Hz), 7.05-7.15 (2H, m), 7.38 (1H, d, J=3.3 Hz), 7.94 (1H, d, J=2.6 Hz), 8.18 (1H, dd, J=6.6, 2.0 Hz), 8.30 (1H, d, J=2.0 Hz), 10.82 (1H, s).

MS (ESI, m/z): 322 (M+H)$^+$.

Example 419

[Formula 666]

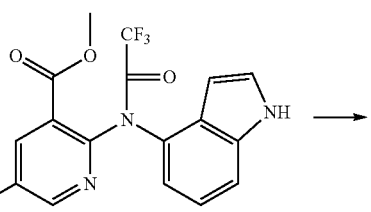

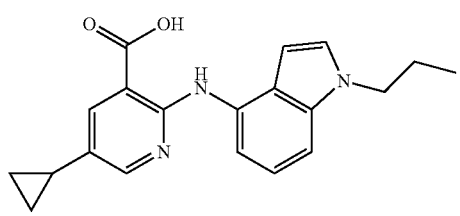

By the method similar to that of Example 418, 5-cyclopropyl-2-((1-propyl-1H-indol-4-yl)amino)nicotinic acid was obtained from methyl 5-cyclopropyl-2-(2,2,2-trifluoro-N-(1H-indol-4-yl)acetamido)nicotinate and 1-iodopropane.

$^1$H-NMR (DMSO-d$_6$) δ: 0.65-0.73 (2H, m), 0.84 (3H, t, J=7.6 Hz), 0.90-0.98 (2H, m), 1.71-1.85 (2H, m), 1.89-2.00 (1H, m), 4.13 (2H, t, J=6.9 Hz), 6.48 (1H, d, J=3.3 Hz), 7.05-7.15 (2H, m), 7.37 (1H, d, J=3.3 Hz), 7.94 (1H, d, J=2.6 Hz), 8.18 (1H, dd, J=6.9, 1.7 Hz), 8.30 (1H, d, J=2.6 Hz), 10.83 (1H, s).

MS (ESI, m/z): 336 (M+H)$^+$.

Example 420

[Formula 667]

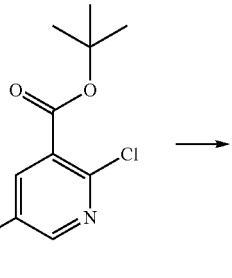

425

-continued

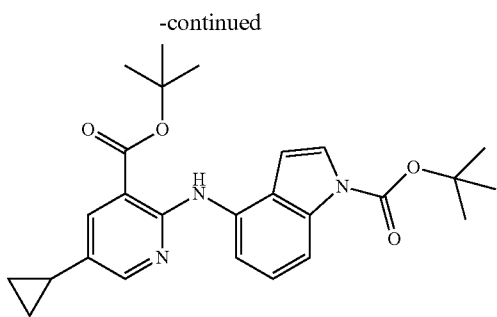

By the method similar to that of Example 225, tert-butyl 4-((3-tert-butoxycarbonyl)-5-cyclopropylpyridin-2-yl)amino)-1H-indole-1-carboxylate was obtained from tert-butyl 2-chloro-5-cyclopropylnicotinate and tert-butyl 4-amino-1H-indole-1-carboxylate.

MS (ESI, m/z): 450 (M+H)$^+$.

Example 421

[Formula 668]

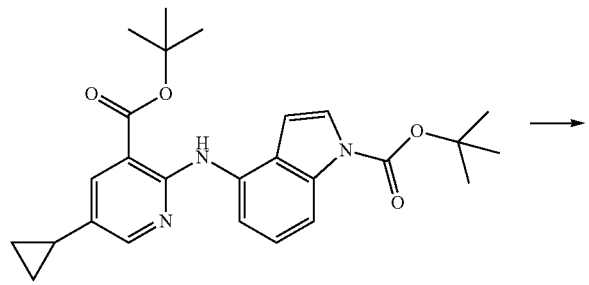

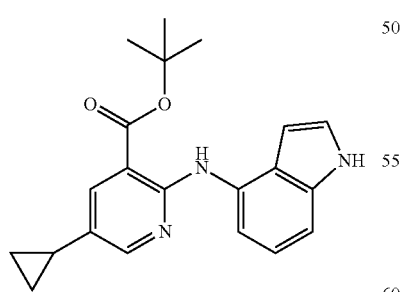

By the method similar to that of Example 235, tert-butyl 2-((1H-indol-4-yl)amino)-5-cyclopropylnicotinate was obtained from tert-butyl 4-((3-tert-butoxycarbonyl)-5-cyclopropylpyridin-2-yl)amino)-1H-indole-1-carboxylate.

MS (ESI, m/z): 350 (M+H)$^+$.

426

Example 422

[Formula 669]

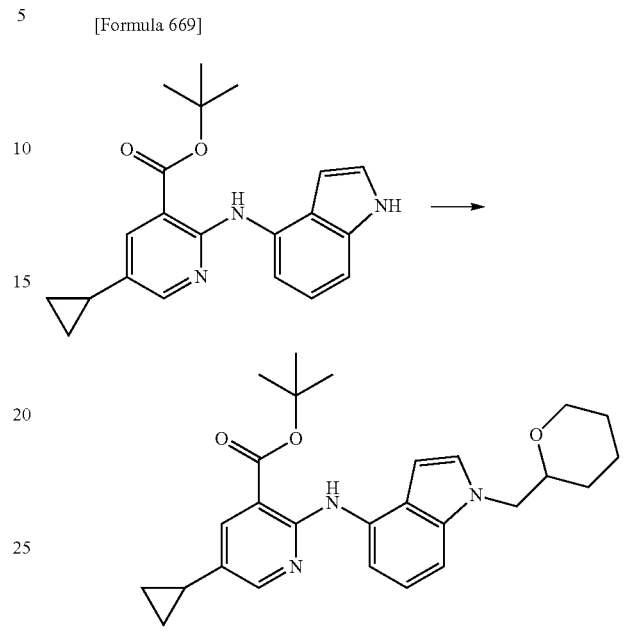

To the solution of 56 mg of tert-butyl 2-((1H-indol-4-yl)amino)-5-cyclopropylnicotinate in 2 mL of N,N-dimethylformamide, 22 mg of potassium tert-butoxide and 36 mg of 2-(bromomethyl)tetrahydro-2H-pyran were added, and the resultant was stirred for one hour and then allowed to stand overnight. Water and ethyl acetate were added to the reaction mixture. The organic layer was separated and dried over anhydrous magnesium sulfate, and the solvent was distilled off under reduced pressure. The obtained residue was purified by silica gel column chromatography (gradient elution with hexane:ethyl acetate=100:0-67:33) to give tert-butyl 5-cyclopropyl-2-((1-((tetrahydro-2H-pyran-2-yl)methyl)-1H-indol-4-yl)amino)nicotinate as a yellow oil.

MS (ESI, m/z): 448 (M+H)$^+$.

Example 423

[Formula 670]

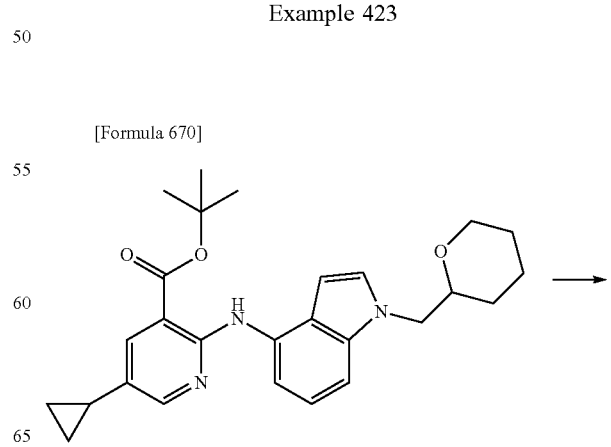

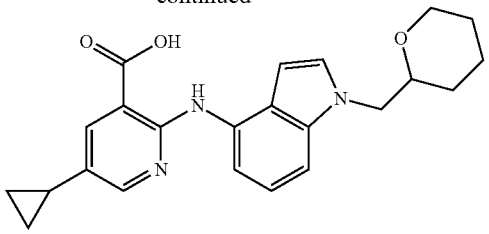

After the mixed solution of tert-butyl 5-cyclopropyl-2-((1-((tetrahydro-2H-pyran-2-yl)methyl)-1H-indol-4-yl)amino)nicotinate obtained in Example 422 in 3 mL of dichloromethane and 3 mL of trifluoroacetic acid was stirred for four hours, the solvent was distilled off under reduced pressure. Ethyl acetate and water were added to the obtained residue and the resultant was adjusted to pH 2.5 to 3.0 with a 1 mol/L aqueous sodium hydroxide solution. The organic layer was separated and dried over anhydrous magnesium sulfate, and the solvent was then distilled off under reduced pressure. The obtained residue was purified by silica gel column chromatography (gradient elution with hexane:ethyl acetate=75:25-0:100), and ethyl acetate and hexane were added to the thus obtained residue, and the solid was collected by filtration to give 13 mg of 5-cyclopropyl-2-((1-((tetrahydro-2H-pyran-2-yl)methyl)-1H-indol-4-yl)amino)nicotinic acid as a yellow solid.

$^1$H-NMR (DMSO-d$_6$) δ: 0.65-0.73 (2H, m), 0.90-0.98 (2H, m), 1.10-1.77 (6H, m), 1.90-2.00 (1H, m), 3.20-3.70 (2H, m), 3.80-3.88 (1H, m), 4.13-4.20 (2H, m), 6.46 (1H, d, J=3.3 Hz), 7.04-7.17 (2H, m), 7.31 (1H, d, J=3.3 Hz), 7.94 (1H, d, J=2.6 Hz), 8.14 (1H, d, J=7.3 Hz), 8.30 (1H, d, J=2.6 Hz), 10.76 (1H, s).

MS (ESI, m/z): 392 (M+H)$^+$.

Example 424

[Formula 671]

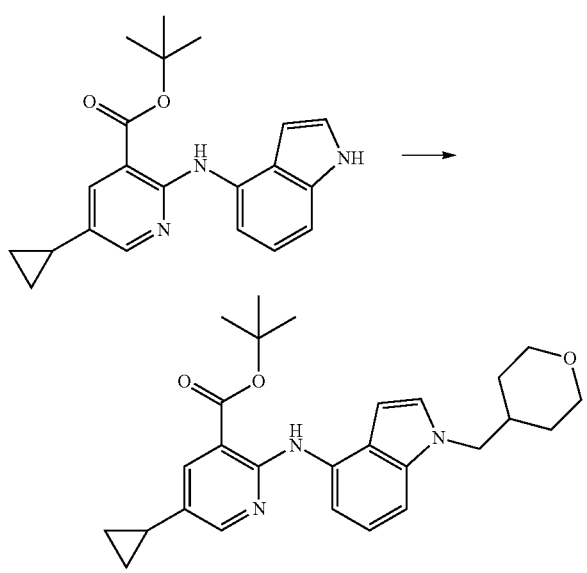

To the solution of 56 mg of tert-butyl 2-((1H-indol-4-yl)amino)-5-cyclopropylnicotinate in 2 mL of N,N-dimethylformamide, 22 mg of potassium tert-butoxide and 36 mg of 4-(bromomethyl)tetrahydro-2H-pyran were added, and the resultant was stirred for one hour and then allowed to stand overnight. Water and ethyl acetate were added to the reaction mixture. The organic layer was separated and dried over anhydrous magnesium sulfate, and the solvent was distilled off under reduced pressure. The obtained residue was purified by silica gel column chromatography (gradient elution with hexane:ethyl acetate=100:0-67:33) to give tert-butyl 5-cyclopropyl-2-((1-((tetrahydro-2H-pyran-4-yl)methyl)-1H-indol-4-yl)amino)nicotinate as a yellow oil.

MS (ESI, m/z): 448 (M+H)$^+$.

Example 425

[Formula 672]

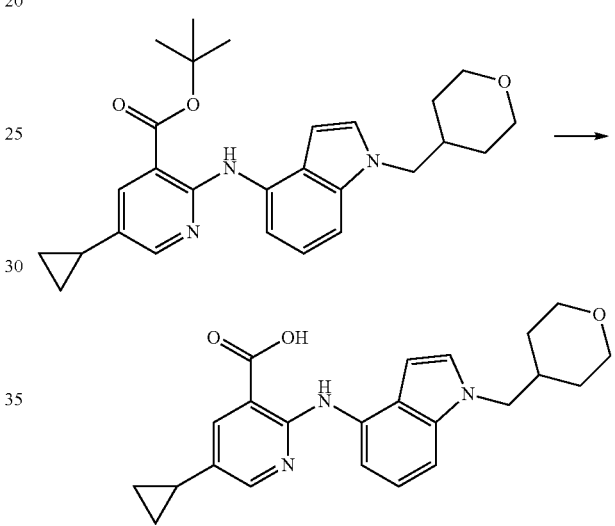

After the mixed solution of tert-butyl 5-cyclopropyl-2-((1-((tetrahydro-2H-pyran-4-yl)methyl)-1H-indol-4-yl)amino)nicotinate obtained in Example 424 in 3 mL of dichloromethane and 3 mL of trifluoroacetic acid was stirred for four hours, the solvent was distilled off under reduced pressure. Ethyl acetate and water were added to the obtained residue and the resultant was adjusted to pH 2.5 to 3.0 with a 1 mol/L aqueous sodium hydroxide solution. The organic layer was separated and dried over anhydrous magnesium sulfate, and the solvent was then distilled off under reduced pressure. The obtained residue was purified by silica gel column chromatography (gradient elution with hexane:ethyl acetate=75:25-0:100), and ethyl acetate and hexane were added to the thus obtained residue, and the solid was collected by filtration to give 11 mg of 5-cyclopropyl-2-((1-((tetrahydro-2H-pyran-4-yl)methyl)-1H-indol-4-yl)amino)nicotinic acid as a yellow solid.

$^1$H-NMR (DMSO-d$_6$) δ: 0.65-0.73 (2H, m), 0.90-0.97 (2H, m), 1.20-1.43 (4H, m), 1.88-2.14 (2H, m), 3.10-3.50 (2H, m), 3.76-3.86 (2H, m), 4.07 (2H, d, J=7.3 Hz), 6.48 (1H, d, J=3.3 Hz), 7.05-7.19 (2H, m), 7.35 (1H, d, J=3.3 Hz), 7.93 (1H, d, J=2.6 Hz), 8.18 (1H, d, J=7.3 Hz), 8.30 (1H, d, J=2.6 Hz), 10.83 (1H, s).

MS (ESI, m/z): 392 (M+H)$^+$.

Example 426

[Formula 673]

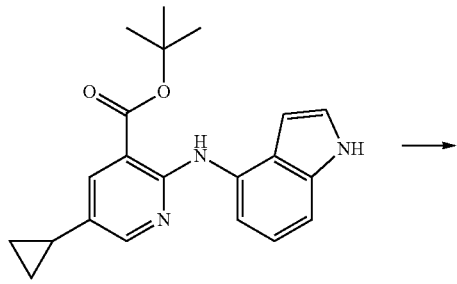

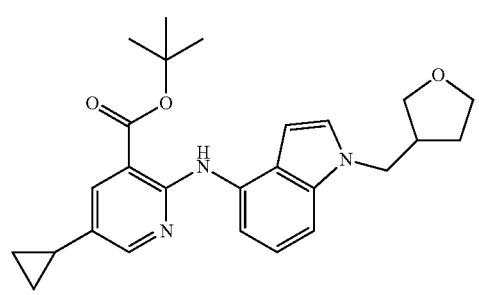

To the solution of 56 mg of tert-butyl 2-((1H-indol-4-yl)amino)-5-cyclopropylnicotinate in 2 mL of N,N-dimethylformamide, 22 mg of potassium tert-butoxide and 33 mg of 3-(bromomethyl)tetrahydrofuran were added, and the resultant was stirred for one hour and then allowed to stand overnight. Water and ethyl acetate were added to the reaction mixture. The organic layer was separated and dried over anhydrous magnesium sulfate, and the solvent was distilled off under reduced pressure. The obtained residue was purified by silica gel column chromatography (gradient elution with hexane:ethyl acetate=100:0-67:33) to give tert-butyl 5-cyclopropyl-2-((1-(((tetrahydrofuran-3-yl)methyl)-1H-indol-4-yl)amino)nicotinate as a yellow oil.

MS (ESI, m/z): 434 (M+H)+.

Example 427

[Formula 674]

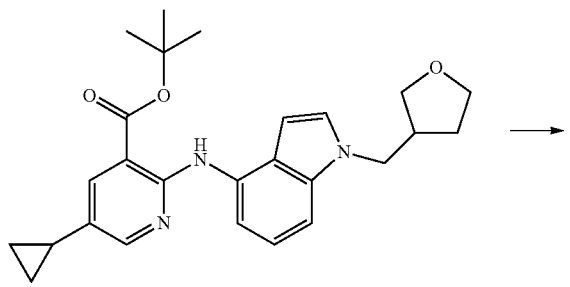

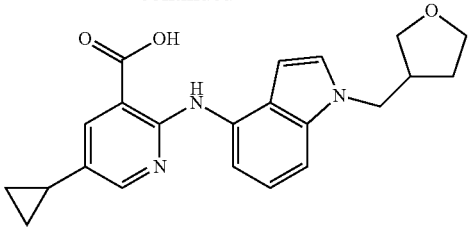

-continued

After the mixed solution of tert-butyl 5-cyclopropyl-2-((1-(((tetrahydrofuran-3-yl)methyl)-1H-indol-4-yl)amino)nicotinate obtained in Example 426 in 3 mL of dichloromethane and 3 mL of trifluoroacetic acid was stirred for four hours, the solvent was distilled off under reduced pressure. Ethyl acetate and water were added to the obtained residue and the resultant was adjusted to pH 2.5 to 3.0 with a 1 mol/L aqueous sodium hydroxide solution. The organic layer was separated and dried over anhydrous magnesium sulfate, and the solvent was distilled off under reduced pressure. The obtained residue was purified by silica gel column chromatography (gradient elution with hexane:ethyl acetate=75:25-0:100), and ethyl acetate and hexane were added to the thus obtained residue, and the solid was collected by filtration to give 5 mg of 5-cyclopropyl-2-((1-(((tetrahydrofuran-3-yl)methyl)-1H-indol-4-yl)amino)nicotinic acid as a yellow solid.

$^1$H-NMR (DMSO-$d_6$) δ: 0.65-0.73 (2H, m), 0.90-0.98 (2H, m), 1.54-1.68 (1H, m), 1.82-1.99 (2H, m), 2.69-2.83 (1H, m), 3.20-3.50 (1H, m), 3.58-3.68 (2H, m), 3.77-3.87 (1H, m), 4.18 (2H, d, J=7.3 Hz), 6.49 (1H, d, J=2.6 Hz), 7.06-7.19 (2H, m), 7.41 (1H, d, J=3.3 Hz), 7.94 (1H, d, J=2.6 Hz), 8.19 (1H, d, J=6.6 Hz), 8.30 (1H, d, J=2.6 Hz), 10.83 (1H, s).

MS (ESI, m/z): 378 (M+H)+.

Example 428

[Formula 675]

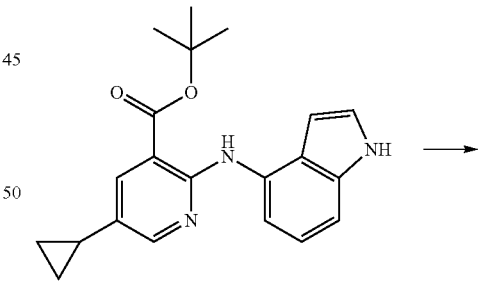

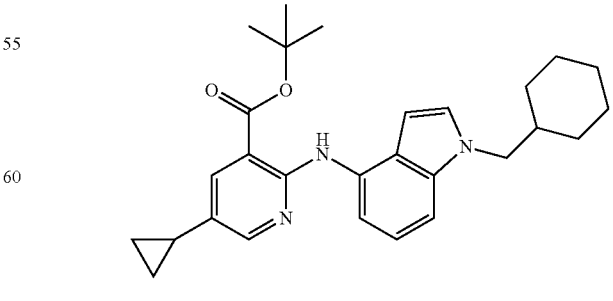

To the solution of 56 mg of tert-butyl 2-((1H-indol-4-yl)amino)-5-cyclopropylnicotinate in 2 mL of N,N-dimethylformamide, 22 mg of potassium tert-butoxide and 28 μL of (bromomethyl)cyclohexane were added, and the resultant was stirred for one hour and then allowed to stand overnight. Water and ethyl acetate were added to the reaction mixture. The organic layer was separated and dried over anhydrous magnesium sulfate, and the solvent was distilled off under reduced pressure. The obtained residue was purified by silica gel column chromatography (gradient elution with hexane: ethyl acetate=100:0-67:33) to give tert-butyl 2-((1-(cyclohexylmethyl)-1H-indol-4-yl)amino)-5-cyclopropylnicotinate as a yellow oil.

MS (ESI, m/z): 446 (M+H)$^+$.

Example 429

[Formula 676]

The mixed solution of tert-butyl 2-((1-(cyclohexylmethyl)-1H-indol-4-yl)amino)-5-cyclopropylnicotinate obtained in Example 428 in 3 mL of dichloromethane and 3 mL of trifluoroacetic acid was stirred for four hours and then the solvent was distilled off under reduced pressure. Ethyl acetate and water were added to the obtained residue and the resultant was adjusted to pH 2.5 to 3.0 with a 1 mol/L aqueous sodium hydroxide solution. The organic layer was separated and dried over anhydrous magnesium sulfate, and the solvent was then distilled off under reduced pressure. The obtained residue was purified by silica gel column chromatography (gradient elution with hexane:ethyl acetate=75:25-0:100), and ethyl acetate and hexane were added to the thus obtained residue, and the solid was collected by filtration to give 3 mg of 2-((1-(cyclohexylmethyl)-1H-indol-4-yl)amino)-5-cyclopropylnicotinic acid as a yellow solid.

$^1$H-NMR (DMSO-d$_6$) δ: 0.65-2.00 (16H, m), 4.00 (2H, d, J=7.3 Hz), 6.47 (1H, d, J=3.3 Hz), 7.04-7.15 (2H, m), 7.32 (1H, d, J=2.6 Hz), 7.94 (1H, d, J=2.6 Hz), 8.17 (1H, dd, J=6.9, 1.7 Hz), 8.30 (1H, d, J=2.6 Hz), 10.80 (1H, s).

MS (ESI, m/z): 390 (M+H)$^+$.

Example 430

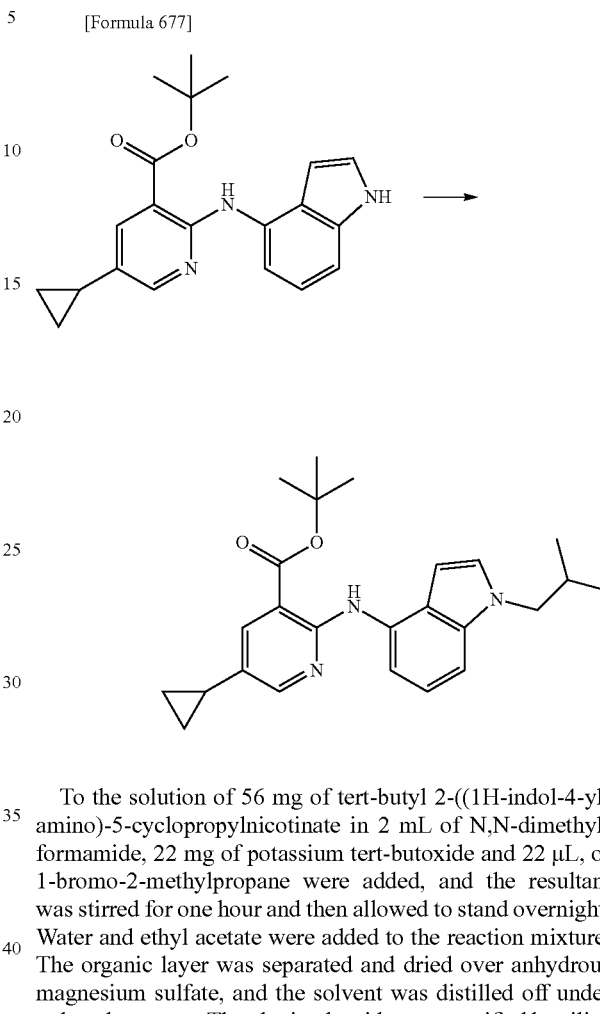

[Formula 677]

To the solution of 56 mg of tert-butyl 2-((1H-indol-4-yl)amino)-5-cyclopropylnicotinate in 2 mL of N,N-dimethylformamide, 22 mg of potassium tert-butoxide and 22 μL, of 1-bromo-2-methylpropane were added, and the resultant was stirred for one hour and then allowed to stand overnight. Water and ethyl acetate were added to the reaction mixture. The organic layer was separated and dried over anhydrous magnesium sulfate, and the solvent was distilled off under reduced pressure. The obtained residue was purified by silica gel column chromatography (gradient elution with hexane: ethyl acetate=100:0-67:33) to give tert-butyl 5-cyclopropyl-2-((1-isobutyl-1H-indol-4-yl)amino)nicotinate as a yellow oil.

MS (ESI, m/z): 406 (M+H)$^+$.

Example 431

[Formula 678]

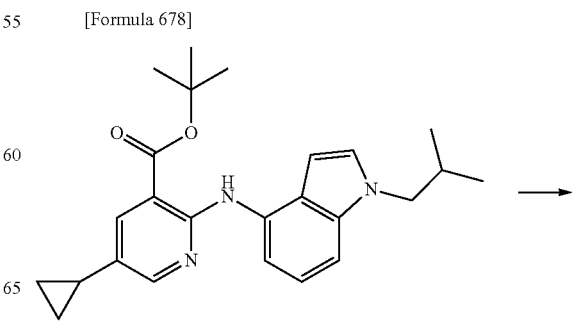

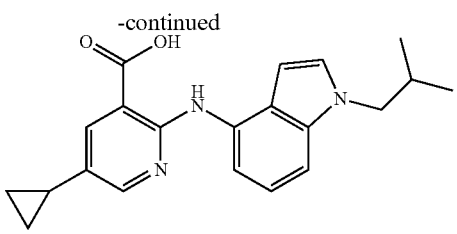

The mixed solution of tert-butyl 5-cyclopropyl-2-((1-isobutyl-1H-indol-4-yl)amino)nicotinate obtained in Example 430 in 3 mL of dichloromethane and 3 mL of trifluoroacetic acid was stirred for four hours and then the solvent was distilled off under reduced pressure. Ethyl acetate and water were added to the obtained residue and the resultant was adjusted to pH 2.5 to 3.0 with a 1 mol/L aqueous sodium hydroxide solution. The organic layer was separated and dried over anhydrous magnesium sulfate, and the solvent was then distilled off under reduced pressure. The obtained residue was purified by silica gel column chromatography (gradient elution with hexane:ethyl acetate=75:25-0:100), and ethyl acetate and hexane were added to the thus obtained residue, and the solid was collected by filtration to give 3 mg of 5-cyclopropyl-2-((1-isobutyl-1H-indol-4-yl)amino)nicotinic acid as a yellow solid.

$^1$H-NMR (DMSO-$d_6$) δ: 0.65-0.73 (2H, m), 0.82-0.98 (8H, m), 1.90-2.01 (1H, m), 2.05-2.20 (1H, m), 3.98 (2H, d, J=7.3 Hz), 6.48 (1H, d, J=3.3 Hz), 7.04-7.16 (2H, m), 7.35 (1H, d, J=3.3 Hz), 7.94 (1H, d, J=2.0 Hz), 8.17 (1H, d, J=7.3 Hz), 8.31 (1H, d, J=2.6 Hz), 10.78 (1H, s).

MS (ESI, m/z): 350 (M+H)$^+$.

Example 432

[Formula 679]

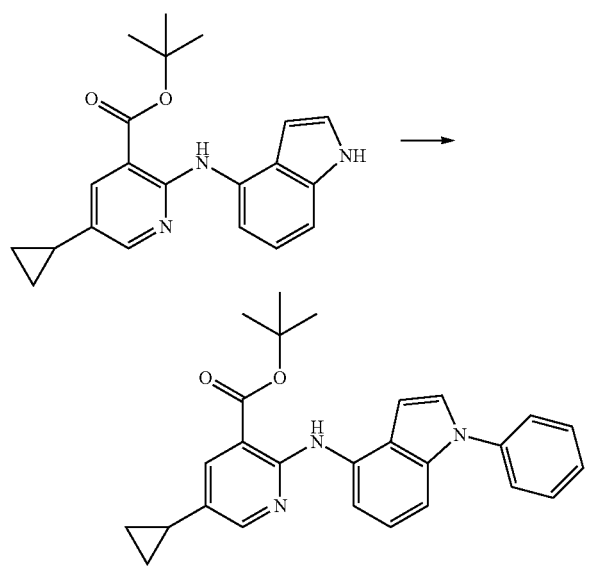

The mixture of 56 mg of tert-butyl 2-((1H-indol-4-yl)amino)-5-cyclopropylnicotinate, 18 μL of iodobenzene, 2 mg of copper(I) iodide, 4 μL of trans-cyclohexane-1,2-diamine, 70 mg of tripotassium phosphate, and 2 mL of dioxane, was stirred at 140° C. for two hours using microwave equipment. After cooling the reaction mixture to room temperature, ethyl acetate was added, the insoluble matter was filtered off and the solvent was distilled off under reduced pressure. The obtained residue was purified by silica gel column chromatography (gradient elution with hexane:ethyl acetate=100:0-67:33) to give tert-butyl 5-cyclopropyl-2-((1-phenyl-1H-indol-4-yl)amino)nicotinate as a yellow oil.

MS (ESI, m/z): 426 (M+H)$^+$.

Example 433

[Formula 680]

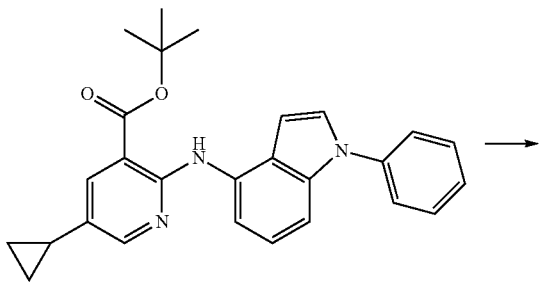

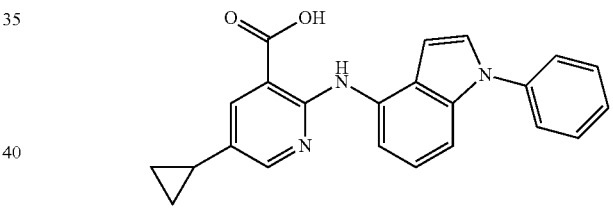

The mixed solution of tert-butyl 5-cyclopropyl-2-((1-phenyl-1H-indol-4-yl)amino)nicotinate obtained in Example 432 in 3 mL of dichloromethane and 3 mL of trifluoroacetic acid was stirred for four hours and then the solvent was distilled off under reduced pressure. Ethyl acetate and water were added to the obtained residue and the resultant was adjusted to pH 2.5 to 3.0 with a 1 mol/L aqueous sodium hydroxide solution. The organic layer was separated and dried over anhydrous magnesium sulfate, and the solvent was then distilled off under reduced pressure. The obtained residue was purified by silica gel column chromatography (gradient elution with hexane:ethyl acetate=75:25-0:100), and ethyl acetate and hexane were added to the thus obtained residue, and the solid was collected by filtration to give 8 mg of 5-cyclopropyl-2-((1-phenyl-1H-indol-4-yl)amino)nicotinic acid as a yellow solid.

$^1$H-NMR (DMSO-$d_6$) δ: 0.66-0.74 (2H, m), 0.91-0.99 (2H, m), 1.90-2.02 (1H, m), 6.74 (1H, d, J=3.3 Hz), 7.13-7.24 (2H, m), 7.37-7.49 (1H, m), 7.56-7.69 (5H, m), 7.97 (1H, d, J=2.6 Hz), 8.24-8.34 (2H, m), 10.93 (1H, s).

MS (ESI, m/z): 370 (M+H)$^+$.

Example 434

[Formula 681]

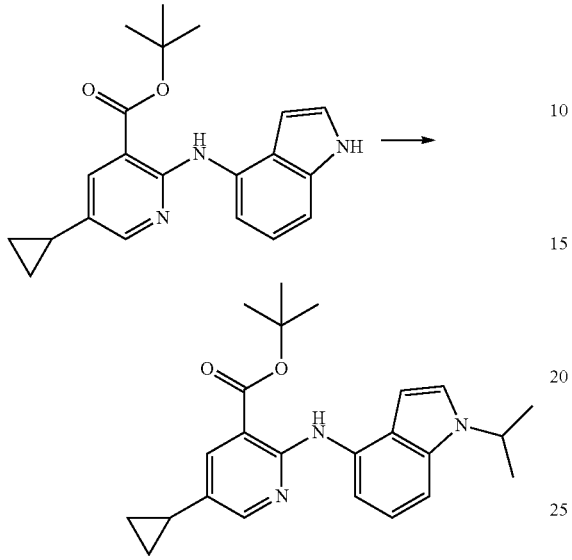

To the solution of 56 mg of tert-butyl 2-((1H-indol-4-yl)amino)-5-cyclopropylnicotinate in 2 mL of N,N-dimethylformamide, 22 mg of potassium tert-butoxide and 20 μL of 2-iodopropane were added, and the resultant was stirred for three hours. Water and ethyl acetate were added to the reaction mixture. The organic layer was separated and dried over anhydrous magnesium sulfate, and the solvent was distilled off under reduced pressure.

The obtained residue was purified by silica gel column chromatography (gradient elution with hexane:ethyl acetate=100:0-67:33) to give tert-butyl 5-cyclopropyl-2-((1-isopropyl-1H-indol-4-yl)amino)nicotinate as an oil.

MS (ESI, m/z): 392 (M+H)$^+$.

Example 435

[Formula 682]

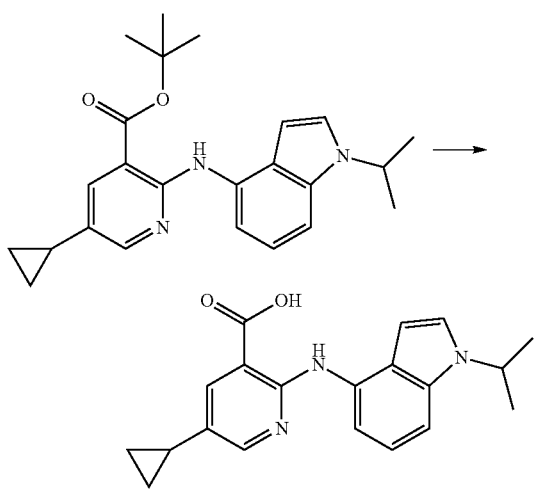

To the mixed solution of tert-butyl 5-cyclopropyl-2-((1-isopropyl-1H-indol-4-yl)amino)nicotinate obtained in Example 434 in 1 mL of methanol and 2 mL of tetrahydrofuran, 0.5 mL of a 1 mol/L aqueous sodium hydroxide solution was added, and the resultant was stirred at 150° C. for 15 minutes using microwave equipment. After cooling the reaction mixture to room temperature, the solvent was distilled off under reduced pressure. Methanol and water were added thereto, and the resultant was adjusted to pH 2.5 to 3.0 with 1 mol/L hydrochloric acid. The solid was collected by filtration to give 13 mg of 5-cyclopropyl-2-((1-isopropyl-1H-indol-4-yl)amino)nicotinic acid as a yellow solid.

$^1$H-NMR (DMSO-d$_6$) δ: 0.65-0.73 (2H, m), 0.91-0.98 (2H, m), 1.46 (6H, d, J=6.6 Hz), 1.89-2.00 (1H, m), 4.66-4.79 (1H, m), 6.51 (1H, d, J=3.3 Hz), 7.06-7.19 (2H, m), 7.48 (1H, d, J=3.3 Hz), 7.94 (1H, d, J=2.6 Hz), 8.17 (1H, d, J=7.3 Hz), 8.30 (1H, d, J=2.6 Hz), 10.79 (1H, s).

MS (ESI, m/z): 336 (M+H)$^+$.

Example 436

[Formula 683]

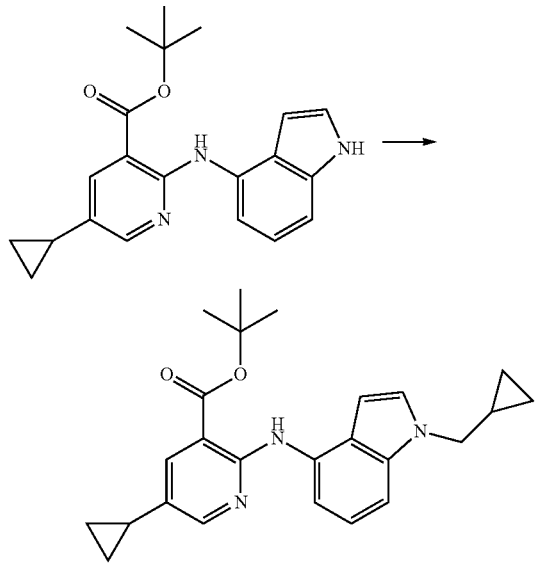

To the solution of 56 mg of tert-butyl 2-((1H-indol-4-yl)amino)-5-cyclopropylnicotinate in 2 mL of N,N-dimethylformamide, 22 mg of potassium tert-butoxide and 19 μL of (bromomethyl)cyclopropane were added, and the resultant was stirred for three hours.

Water and ethyl acetate were added to the reaction mixture. The organic layer was separated and dried over anhydrous magnesium sulfate, and the solvent was distilled off under reduced pressure. The obtained residue was purified by silica gel column chromatography (gradient elution with hexane:ethyl acetate=100:0-67:33) to give tert-butyl 5-cyclopropyl-2-((1-(cyclopropylmethyl)-1H-indol-4-yl)amino)nicotinate as an oil.

MS (ESI, m/z): 404 (M+H)$^+$.

Example 437

[Formula 684]

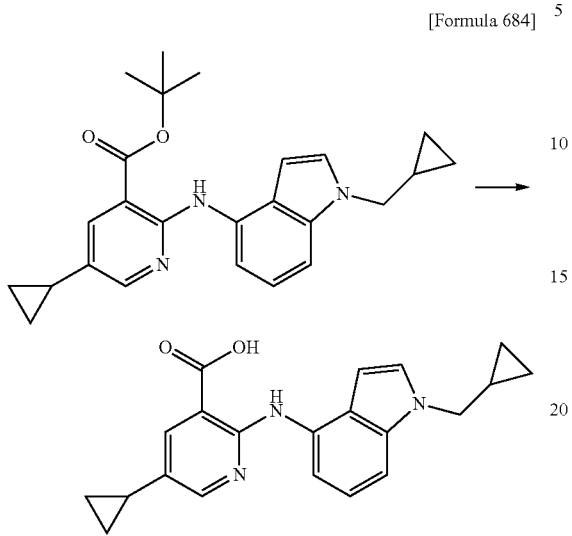

To the mixed solution of tert-butyl 5-cyclopropyl-2-((1-(cyclopropylmethyl)-1H-indol-4-yl)amino)nicotinate obtained in Example 436 in 1 mL of methanol and 2 mL of tetrahydrofuran, 0.5 mL of a 1 mol/L aqueous sodium hydroxide solution was added, and the resultant was stirred at 150° C. for 15 minutes using microwave equipment. After cooling the reaction mixture to room temperature, the solvent was distilled off under reduced pressure. Methanol and water were added to the obtained residue and the resultant was adjusted to pH 2.5 to 3.0 with 1 mol/L hydrochloric acid. The solid was collected by filtration to give 40 mg of 5-cyclopropyl-2-((1-(cyclopropylmethyl)-1H-indol-4-yl)amino)nicotinic acid as a yellow solid.

$^1$H-NMR (DMSO-d$_6$) δ: 0.36-0.55 (4H, m), 0.65-0.73 (2H, m), 0.90-0.98 (2H, m), 1.17-1.31 (1H, m), 1.89-2.01 (1H, m), 4.04 (2H, d, J=7.3 Hz), 6.48 (1H, d, J=3.3 Hz), 7.06-7.19 (2H, m), 7.43 (1H, d, J=3.3 Hz), 7.94 (1H, d, J=2.6 Hz), 8.17 (1H, d, J=7.3 Hz), 8.31 (1H, d, J=2.6 Hz), 10.78 (1H, s).

MS (ESI, m/z): 348 (M+H)$^+$.

Example 438

[Formula 685]

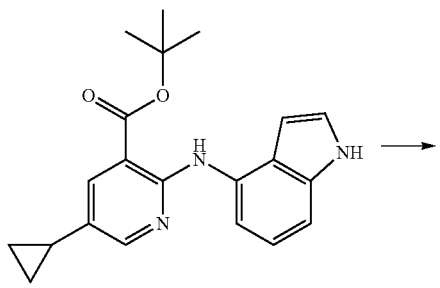

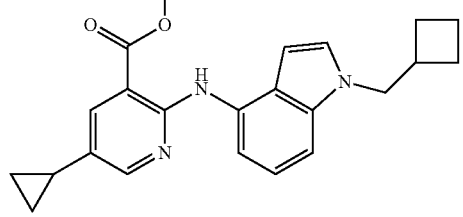

To the solution of 56 mg of tert-butyl 2-((1H-indol-4-yl)amino)-5-cyclopropylnicotinate in 2 mL of N,N-dimethylformamide, 22 mg of potassium tert-butoxide and 22 µL of (bromomethyl)cyclobutane were added and the resultant was stirred for three hours. Water and ethyl acetate were added to the reaction mixture. The organic layer was separated and dried over anhydrous magnesium sulfate, and the solvent was distilled off under reduced pressure. The obtained residue was purified by silica gel column chromatography (gradient elution with hexane:ethyl acetate=100:0-67:33) to give tert-butyl 2-((1-(cyclobutylmethyl)-1H-indol-4-yl)amino)-5-cyclopropylnicotinate as an oil.

MS (ESI, m/z): 418 (M+H)$^+$.

Example 439

[Formula 686]

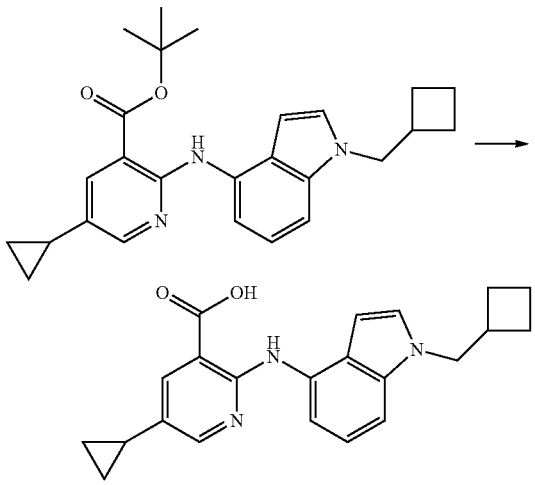

To the mixed solution of tert-butyl 2-((1-(cyclobutylmethyl)-1H-indol-4-yl)amino)-5-cyclopropylnicotinate obtained in Example 438 in 1 mL of methanol and 2 mL of tetrahydrofuran, 0.5 mL of a 1 mol/L aqueous sodium hydroxide solution was added, and the resultant was stirred at 150° C. for 15 minutes using microwave equipment. After cooling the reaction mixture to room temperature, the solvent was distilled off under reduced pressure. Methanol and water were added to the obtained residue and the resultant was adjusted to pH 2.5 to 3.0 with 1 mol/L hydrochloric acid. The solid was collected by filtration to give 36 mg of 2-((1-(cyclobutylmethyl)-1H-indol-4-yl)amino)-5-cyclopropylnicotinic acid as a yellow solid.

$^1$H-NMR (DMSO-d$_6$) δ: 0.64-0.72 (2H, m), 0.90-0.98 (2H, m), 1.70-2.01 (7H, m), 2.70-2.84 (1H, m), 4.18 (2H, d,

J=7.3 Hz), 6.47 (1H, d, J=2.6 Hz), 7.03-7.16 (2H, m), 7.36 (1H, d, J=3.3 Hz), 7.93 (1H, d, J=2.6 Hz), 8.17 (1H, d, J=6.6 Hz), 8.30 (1H, d, J=2.6 Hz), 10.79 (1H, s).

MS (ESI, m/z): 362 (M+H)⁺.

Example 440

[Formula 687]

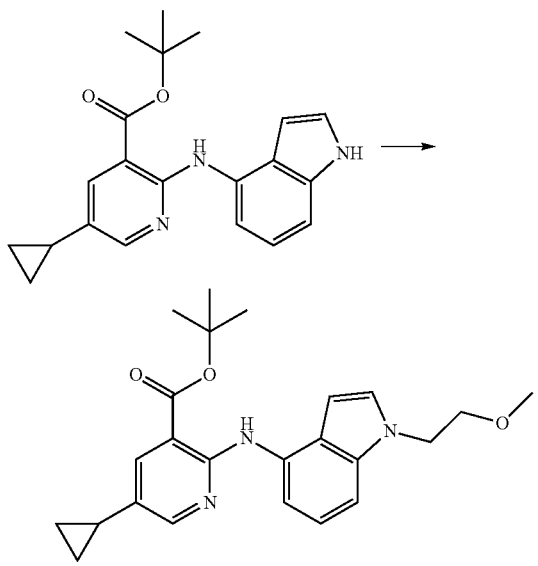

To the solution of 56 mg of tert-butyl 2-((1H-indol-4-yl)amino)-5-cyclopropylnicotinate in 2 mL of N,N-dimethylformamide, 22 mg of potassium tert-butoxide and 19 μL of 1-bromo-2-methoxyethane were added, and the resultant was stirred for three hours. Water and ethyl acetate were added to the reaction mixture. The organic layer was separated and dried over anhydrous magnesium sulfate, and the solvent was distilled off under reduced pressure. The obtained residue was purified by silica gel column chromatography (gradient elution with hexane:ethyl acetate=100: 0-67:33) to give tert-butyl 5-cyclopropyl-2-((1-(2-methoxyethyl)-1H-indol-4-yl)amino)nicotinate as an oil.

MS (ESI, m/z): 408 (M+H)⁺.

Example 441

[Formula 688]

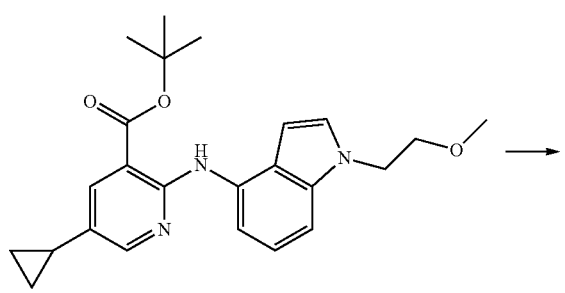

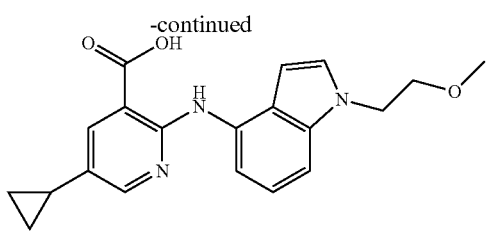

To the mixed solution of tert-butyl 5-cyclopropyl-2-((1-(2-methoxyethyl)-1H-indol-4-yl)amino)nicotinate obtained in Example 440 in 1 mL of methanol and 2 mL of tetrahydrofuran, 0.5 mL of a 1 mol/L aqueous sodium hydroxide solution was added, and the resultant was stirred at 150° C. for 15 minutes using microwave equipment. After cooling the reaction mixture to room temperature, the solvent was distilled off under reduced pressure. Methanol and water were added to the obtained residue and the resultant was adjusted to pH 2.5 to 3.0 with 1 mol/L hydrochloric acid. The solid was collected by filtration to give 20 mg of 5-cyclopropyl-2-((1-(2-methoxyethyl)-1H-indol-4-yl)amino)nicotinic acid as a yellow solid.

¹H-NMR (DMSO-d₆) δ: 0.65-0.73 (2H, m), 0.90-0.97 (2H, m), 1.89-2.04 (1H, m), 3.22 (3H, s), 3.66 (2H, t, J=5.3 Hz), 4.32 (2H, t, J=5.3 Hz), 6.48 (1H, d, J=3.3 Hz), 7.05-7.16 (2H, m), 7.34 (1H, d, J=3.3 Hz), 7.93 (1H, d, J=2.6 Hz), 8.17 (1H, d, J=7.3 Hz), 8.29 (1H, d, J=2.6 Hz), 10.91 (1H, brs).

MS (ESI, m/z): 352 (M+H)⁺.

Example 442

[Formula 689]

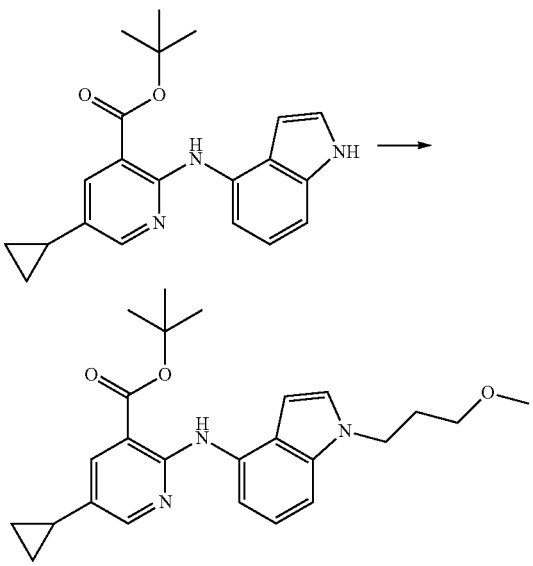

To the solution of 56 mg of tert-butyl 2-((1H-indol-4-yl)amino)-5-cyclopropylnicotinate in 2 mL of N,N-dimethylformamide, 22 mg of potassium tert-butoxide and 22 μL of 1-bromo-3-methoxypropane were added, and the resultant was stirred for three hours. Water and ethyl acetate were added to the reaction mixture. The organic layer was separated and dried over anhydrous magnesium sulfate, and the solvent was distilled off under reduced pressure. The obtained residue was purified by silica gel column chromatography (gradient elution with hexane:ethyl acetate=100:0-67:33) to give tert-butyl 5-cyclopropyl-2-((1-(3-methoxypropyl)-1H-indol-4-yl)amino)nicotinate as an oil.

MS (ESI, m/z): 422 (M+H)$^+$.

Example 443

[Formula 690]

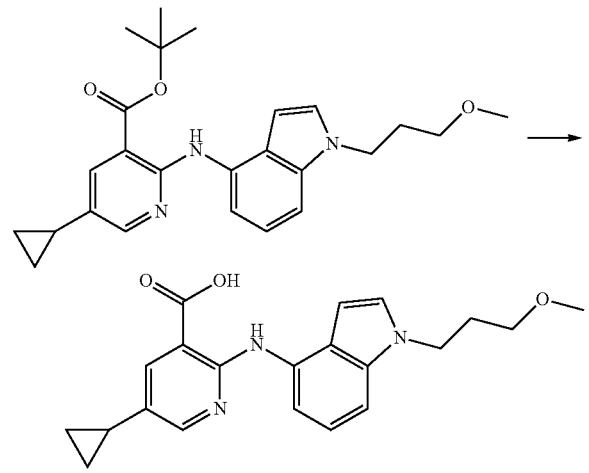

To the mixed solution of tert-butyl 5-cyclopropyl-2-((1-(3-methoxypropyl)-1H-indol-4-yl)amino)nicotinate obtained in Example 442 in 1 mL of methanol and 2 mL of tetrahydrofuran, 0.5 mL of a 1 mol/L aqueous sodium hydroxide solution was added, and the resultant was stirred at 150° C. for 15 minutes using microwave equipment. After cooling the reaction mixture to room temperature, the solvent was distilled off under reduced pressure. Methanol and water were added to the obtained residue and the resultant was adjusted to pH 2.5 to 3.0 with 1 mol/L hydrochloric acid. The solid was collected by filtration to give 23 mg of 5-cyclopropyl-2-((1-(3-methoxypropyl)-1H-indol-4-yl)amino)nicotinic acid as a yellow solid.

$^1$H-NMR (DMSO-d$_6$) δ: 0.65-0.73 (2H, m), 0.91-0.97 (2H, m), 1.89-2.04 (3H, m), 3.21-3.28 (5H, m), 4.22 (2H, t, J=6.9 Hz), 6.49 (1H, d, J=3.3 Hz), 7.11 (2H, d, J=4.6 Hz), 7.34 (1H, d, J=3.3 Hz), 7.94 (1H, d, J=2.6 Hz), 8.18 (1H, t, J=4.3 Hz), 8.31 (1H, d, J=2.6 Hz), 10.80 (1H, s).

MS (ESI, m/z): 366 (M+H)$^+$.

Example 444

[Formula 691]

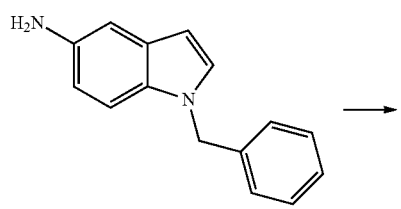

-continued

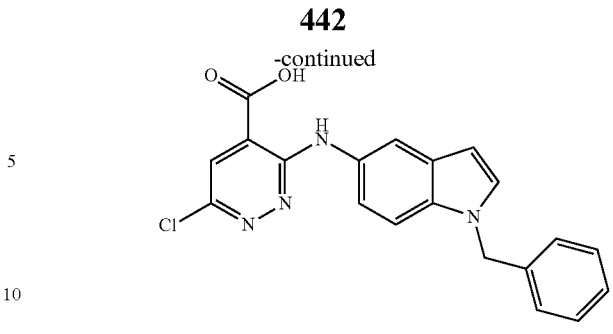

To the solution of 50 mg of 1-benzyl-1H-indol-5-amine and 74 mg of 3,6-dichloropyridazine-4-carboxylic acid in 2 mL of tetrahydrofuran, 100 μL of a 1.6 mol/L solution of lithium bis(trimethylsilyl)amide in tetrahydrofuran was added dropwise at an external temperature of −70° C. under a nitrogen atmosphere, and the resultant was stirred for 50 minutes. The reaction mixture was warmed to room temperature, stirred for eight hours and 10 minutes and allowed to stand for two days. Ethyl acetate and water were added to the reaction mixture, the organic layer was separated and the aqueous layer was extracted with ethyl acetate. The organic layer and the extract were combined, washed with a saturated aqueous sodium chloride solution and dried over anhydrous magnesium sulfate, and the solvent was distilled off under reduced pressure. The obtained residue was purified by silica gel column chromatography (gradient elution with chloroform:methanol=100:0-70:30). Methanol was added to the thus obtained residue, and the solid was collected by filtration to give 20 mg of 3-((1-benzyl-1H-indol-5-yl)amino)-6-chloropyridazine-4-carboxylic acid as an orange brown solid.

$^1$H-NMR (DMSO-d$_6$) δ: 5.40 (2H, s), 6.45 (1H, d, J=3.3 Hz), 7.17-7.34 (6H, m), 7.39 (1H, d, J=8.6 Hz), 7.46 (1H, d, J=2.6 Hz), 7.74 (1H, s), 8.18 (1H, d, J=2.0 Hz), 12.22 (1H, brs).

MS (ESI, m/z): 379 (M+H)$^+$, 377 (M−H)$^-$.

Example 445

[Formula 692]

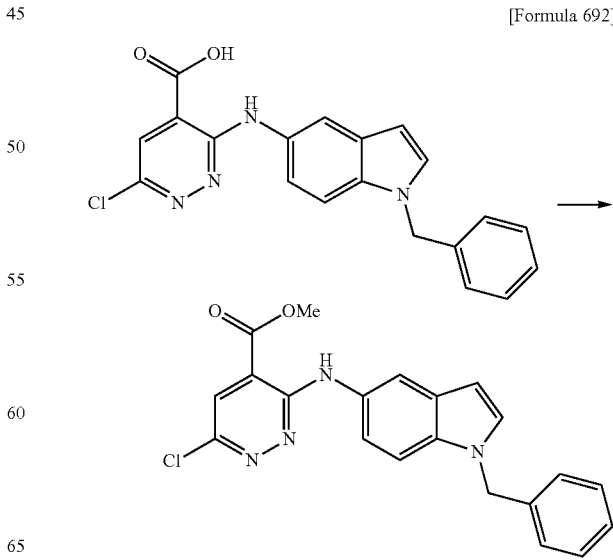

443

To the solution of 202 mg of 3-((1-benzyl-1H-indol-5-yl)amino)-6-chloropyridazine-4-carboxylic acid in 12 mL of N,N-dimethylacetamide, 221 mg of potassium carbonate and 50 μL of iodomethane were added under ice-cooling, and the resultant was stirred at an external temperature of 60° C. for three hours. The reaction mixture was cooled to room temperature, and hexane, ethyl acetate and water were added thereto. The organic layer was separated and washed with water and the solvent was then distilled off under reduced pressure. Hexane was added to the obtained residue, and the solid was collected by filtration to give 204 mg of methyl 3-((1-benzyl-1H-indol-5-yl)amino)-6-chloropyridazine-4-carboxylate as a red brown solid.

$^1$H-NMR (DMSO-$d_6$) δ: 3.94 (3H, s), 5.43 (2H, s), 6.49 (1H, d, J=2.6 Hz), 7.18-7.34 (6H, m), 7.44 (1H, d, J=8.6 Hz), 7.53 (1H, d, J=3.3 Hz), 7.94-7.97 (2H, m), 9.46 (1H, s).

MS (ESI, m/z): 393 (M+H)$^+$.

Example 446

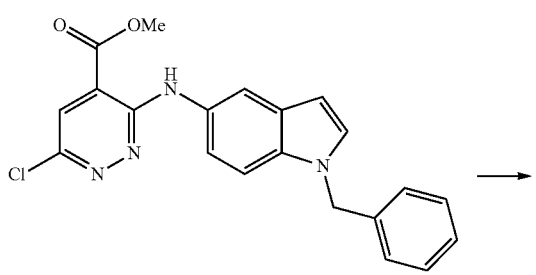

[Formula 693]

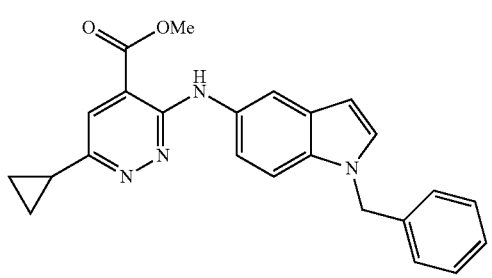

The mixture of 79 mg of methyl 3-((1-benzyl-1H-indol-5-yl)amino)-6-chloropyridazine-4-carboxylate, 31 mg of cyclopropylboronic acid monohydrate, 4.5 mg of palladium acetate, 8.3 mg of 2-dicyclohexylphosphino-2',6'-dimethoxybiphenyl, 128 mg of potassium phosphate, and 2 mL of toluene, was heated at reflux for nine hours under a nitrogen atmosphere. The reaction mixture was cooled to room temperature and allowed to stand overnight. The insoluble matter was filtered off and the solvent was distilled off under reduced pressure. The obtained residue was purified by silica gel column chromatography (gradient elution with hexane: ethyl acetate=100:0-80:20) to give 43 mg of methyl 3-((1-benzyl-1H-indol-5-yl)amino)-6-cyclopropylpyridazine-4-carboxylate as a brown oil.

MS (ESI, m/z): 399 (M+H)$^+$.

Example 447

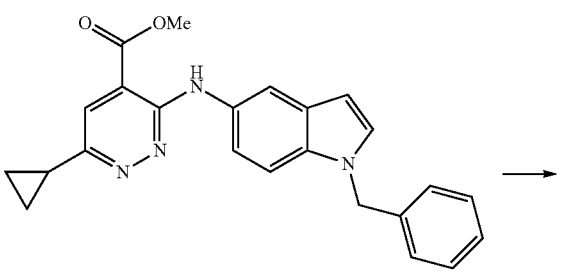

[Formula 694]

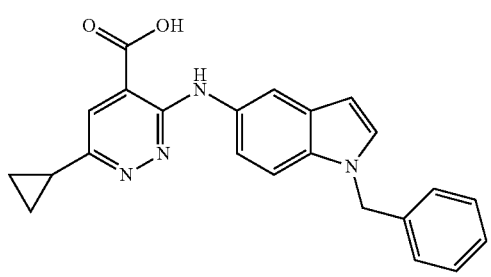

The mixture of 43 mg of methyl 3-((1-benzyl-1H-indol-5-yl)amino)-6-cyclopropylpyridazine-4-carboxylate, 110 μL of a 5 mol/L aqueous sodium hydroxide solution, 2 mL of tetrahydrofuran, and 2 mL of methanol, was stirred at an external temperature of 60° C. for two hours and 15 minutes. After cooling the reaction mixture to room temperature, 6 mol/L hydrochloric acid and water were added and the solvent was distilled off under reduced pressure. Water and methanol were added to the obtained residue, and the solid was collected by filtration to give 36 mg of 3-((1-benzyl-1H-indol-5-yl)amino)-6-cyclopropylpyridazine-4-carboxylic acid as an orange solid.

$^1$H-NMR (DMSO-$d_6$) δ: 0.94-1.04 (4H, m), 2.17-2.29 (1H, m), 5.42 (2H, s), 6.47 (1H, d, J=2.6 Hz), 7.18-7.34 (6H, m), 7.41 (1H, d, J=8.6 Hz), 7.50 (1H, d, J=3.3 Hz), 7.75 (1H, s), 8.08 (1H, s).

MS (ESI, m/z): 385 (M+H)$^+$, 383 (INA-H)$^-$.

Example 448

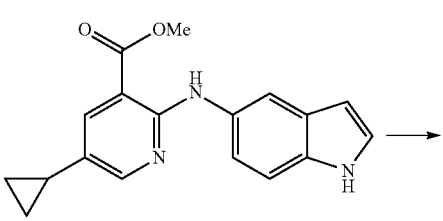

[Formula 695]

-continued

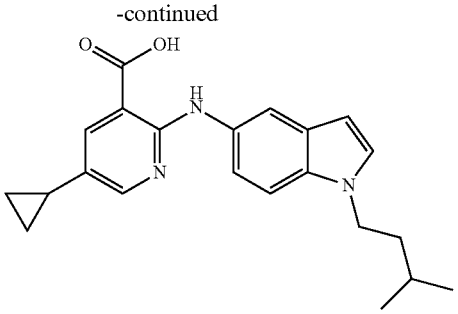

To the solution of 100 mg of methyl 2-((1H-indol-5-yl)amino)-5-cyclopropylnicotinate in 2 mL of N,N-dimethylformamide, 44 mg of potassium tert-butoxide and 59 μL of 1-bromo-3-methylbutane were added under ice-cooling, and the resultant was stirred at room temperature for two hours and 20 minutes. 44 mg of potassium tert-butoxide and 59 of 1-bromo-3-methylbutane were added thereto at room temperature, and the resultant was stirred for three hours and 30 minutes. The reaction mixture was allowed to stand overnight, and 44 mg of potassium tert-butoxide and 59 μL of 1-bromo-3-methylbutane were then added thereto, and the resultant was stirred for two hours. 44 mg of potassium tert-butoxide and 59 μL of 1-bromo-3-methylbutane were further added thereto, and the resultant was stirred for one hour and 30 minutes. Ethyl acetate and water were added to the reaction mixture and the resultant was made acidic by adding thereto 2 mol/L hydrochloric acid, and the organic layer was then separated. The organic layer was washed with a saturated aqueous sodium chloride solution and dried over anhydrous sodium sulfate, and the solvent was distilled off under reduced pressure. The obtained residue was purified by silica gel column chromatography (gradient elution with hexane:ethyl acetate=100:0-50:50). Water and methanol were added to the thus obtained residue, and the solid was collected by filtration to give 82 mg of 5-cyclopropyl-2-(1-isopentyl-1H-indol-5-ylamino)nicotinic acid as a yellow solid.

$^1$H-NMR (DMSO-$d_6$) δ: 0.61-0.67 (2H, m), 0.87-0.94 (8H, m), 1.44-1.55 (1H, m), 1.65 (2H, q, J=7.2 Hz), 1.85-1.93 (1H, m), 4.15 (2H, t, J=7.3 Hz), 6.36 (1H, d, J=2.4 Hz), 7.19 (1H, dd, J=8.8, 2.0 Hz), 7.33 (1H, d, J=2.9 Hz), 7.38 (1H, d, J=9.0 Hz), 7.87 (1H, d, J=2.4 Hz), 7.94 (1H, d, J=1.7 Hz), 8.18 (1H, d, J=2.7 Hz), 10.12 (1H, s), 13.38 (1H, brs).

Example 449

[Formula 696]

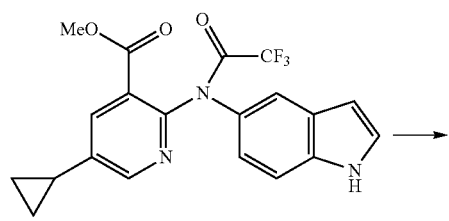

-continued

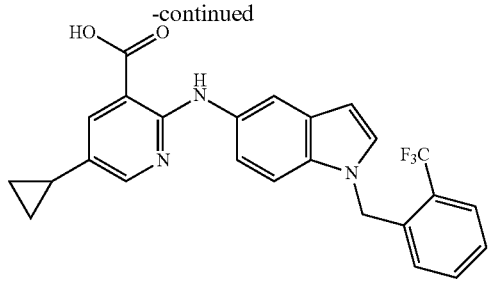

To the mixture of 50 mg of methyl 5-cyclopropyl-2-(2,2,2-trifluoro-N-(1H-indol-5-yl)acetamido)nicotinate, 33 mg of 1-(bromomethyl)-2-(trifluoromethyl)benzene and 1.5 mL of N,N-dimethylformamide, 6.4 mg of 60% sodium hydride was added under ice-cooling, and the resultant was stirred for 15 minutes. 6.4 mg of 60% sodium hydride was further added thereto, and the resultant was stirred for 40 minutes. 50 μL of a 5 mol/L aqueous sodium hydroxide solution was added thereto, and the resultant was stirred at room temperature for four hours. The reaction mixture was allowed to stand at room temperature overnight. Ethyl acetate and water were added to the reaction mixture, and the resultant was then adjusted to pH 2.5 by adding 1 mol/L hydrochloric acid thereto. The organic layer was separated and the aqueous layer was extracted with ethyl acetate twice. The organic layer and the extract were combined and the solvent was distilled off under reduced pressure. The obtained residue was purified by silica gel column chromatography (gradient elution with hexane:ethyl acetate=90:10-20:80), and ethyl acetate and hexane were added to the thus obtained residue, and the solid was collected by filtration to give 36 mg of 5-cyclopropyl-2-((1-(2-(trifluoromethyl)benzyl)-1H-indol-5-yl)amino)nicotinic acid as a yellow solid.

$^1$H-NMR (CDCl$_3$) δ: 0.61-0.67 (2H, m), 0.90-0.96 (2H, m), 1.77-1.86 (1H, m), 5.47 (2H, s), 6.53-6.58 (2H, m), 7.06-7.13 (2H, m), 7.20-7.35 (3H, m), 7.69 (1H, d, J=7.1 Hz), 7.89-7.97 (2H, m), 8.14 (1H, s), 9.96 (1H, brs).

MS (ESI, m/z): 452 (M+H)$^+$, 450 (M−H)$^-$.

Example 450

[Formula 697]

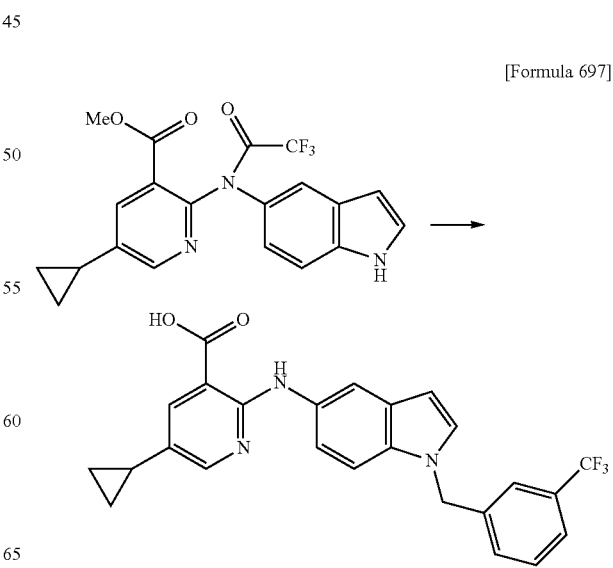

447

By the method similar to that of Example 449, 5-cyclopropyl-2-((1-(3-(trifluoromethyl)benzyl)-1H-indol-5-yl)amino)nicotinic acid was obtained from methyl 5-cyclopropyl-2-(2,2,2-trifluoro-N-(1H-indol-5-yl)acetamido)nicotinate and 1-(bromomethyl)-3-(trifluoromethyl)benzene.

¹H-NMR (DMSO-d₆) δ: 0.59-0.67 (2H, m), 0.84-0.94 (2H, m), 1.82-1.96 (1H, m), 5.52 (2H, s), 6.46 (1H, d, J=2.6 Hz), 7.12-7.20 (1H, m), 7.36-7.46 (2H, m), 7.50-7.65 (4H, m), 7.86 (1H, d, J=2.0 Hz), 7.99 (1H, d, J=1.3 Hz), 8.18 (1H, d, J=2.0 Hz), 10.15 (1H, s).

MS (ESI, m/z): 452 (M+H)⁺, 450 (M−H)⁻.

Example 451

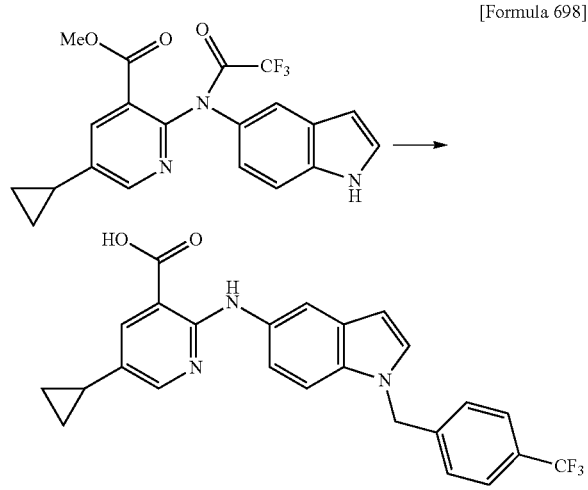

[Formula 698]

By the method similar to that of Example 449, 5-cyclopropyl-2-((1-(4-(trifluoromethyl)benzyl)-1H-indol-5-yl)amino)nicotinic acid was obtained from methyl 5-cyclopropyl-2-(2,2,2-trifluoro-N-(1H-indol-5-yl)acetamido)nicotinate and 1-(bromomethyl)-4-(trifluoromethyl)benzene.

¹H-NMR (DMSO-d₆) δ: 0.60-0.68 (2H, m), 0.84-0.94 (2H, m), 1.82-1.96 (1H, m), 5.53 (2H, s), 6.47 (1H, d, J=2.6 Hz), 7.16 (1H, dd, J=8.9, 1.7 Hz), 7.30-7.38 (3H, m), 7.50 (1H, d, J=3.3 Hz), 7.68 (2H, d, J=7.9 Hz), 7.86 (1H, d, J=2.6 Hz), 7.99 (1H, d, J=1.3 Hz), 8.18 (1H, d, J=2.0 Hz), 10.13 (1H, s).

MS (ESI, m/z): 452 (M+H)⁺, 450 (M−H)⁻.

Example 452

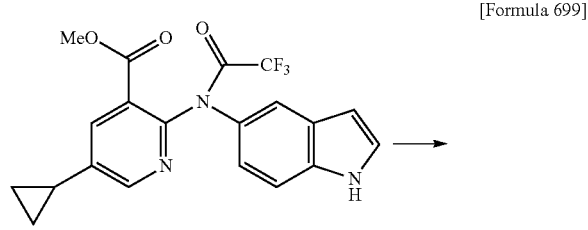

[Formula 699]

448

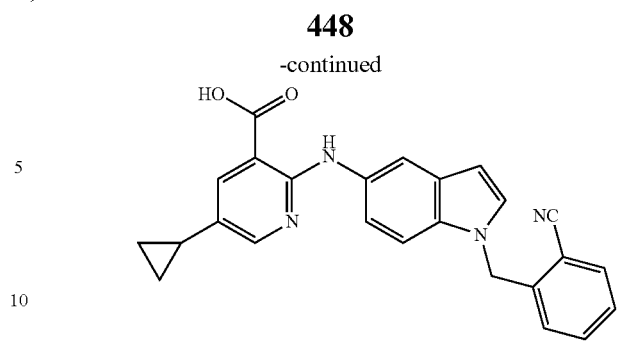

By the method similar to that of Example 449, 2-((1-(2-cyanobenzyl)-1H-indol-5-yl)amino)-5-cyclopropylnicotinic acid was obtained from methyl 5-cyclopropyl-2-(2,2,2-trifluoro-N-(1H-indol-5-yl)acetamido)nicotinate and 2-(bromomethyl)benzonitrile.

¹H-NMR (DMSO-d₆) δ: 0.60-0.68 (2H, m), 0.86-0.95 (2H, m), 1.83-1.96 (1H, m), 5.64 (2H, s), 6.49 (1H, d, J=2.6 Hz), 6.87 (1H, d, J=7.9 Hz), 7.19 (1H, dd, J=8.6, 2.0 Hz), 7.35 (1H, d, J=9.2 Hz), 7.42-7.52 (2H, m), 7.55-7.64 (1H, m), 7.84-7.94 (2H, m), 8.01 (1H, s), 8.19 (1H, d, J=2.6 Hz), 10.15 (1H, s).

MS (ESI, m/z): 409 (M+H)⁺, 407 (M−H)⁻.

Example 453

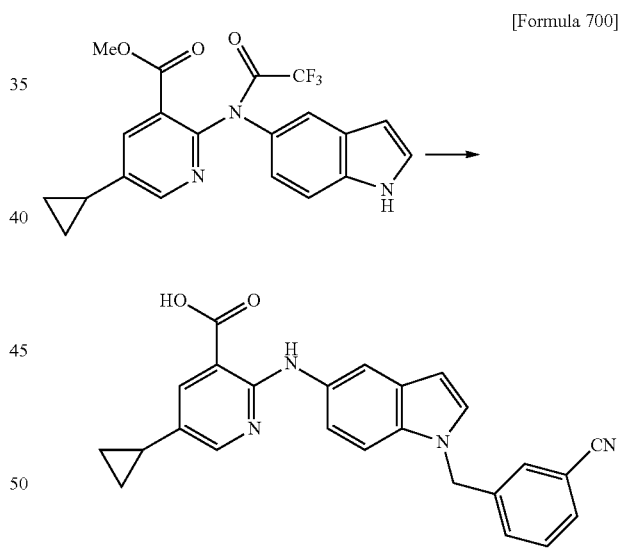

[Formula 700]

By the method similar to that of Example 449, 2-((1-(3-cyanobenzyl)-1H-indol-5-yl)amino)-5-cyclopropylnicotinic acid was obtained from methyl 5-cyclopropyl-2-(2,2,2-trifluoro-N-(1H-indol-5-yl)acetamido)nicotinate and 3-(bromomethyl)benzonitrile.

¹H-NMR (DMSO-d6) δ: 0.59-0.68 (2H, m), 0.84-0.95 (2H, m), 1.83-1.95 (1H, m), 5.47 (2H, s), 6.46 (1H, d, J=2.6 Hz), 7.18 (1H, dd, J=8.6, 2.0 Hz), 7.39 (1H, d, J=8.6 Hz), 7.45-7.57 (3H, m), 7.64-7.76 (2H, m), 7.86 (1H, d, J=2.6 Hz), 7.98 (1H, d, J=1.3 Hz), 8.18 (1H, d, J=2.6 Hz), 10.14 (1H, s).

MS (ESI, m/z): 409 (M+H)⁺.

Example 454

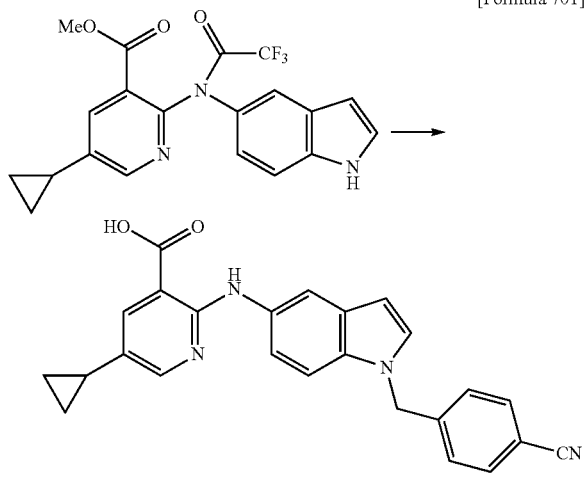

By the method similar to that of Example 449, 2-((1-(4-cyanobenzyl)-1H-indol-5-yl)amino)-5-cyclopropylnicotinic acid was obtained from methyl 5-cyclopropyl-2-(2,2,2-trifluoro-N-(1H-indol-5-yl)acetamido)nicotinate and 4-(bromomethyl)benzonitrile.

$^1$H-NMR (DMSO-$d_6$) δ: 0.59-0.68 (2H, m), 0.84-0.95 (2H, m), 1.83-1.96 (1H, m), 5.52 (2H, s), 6.47 (1H, d, J=2.6 Hz), 7.16 (1H, dd, J=8.9, 1.7 Hz), 7.26-7.35 (3H, m), 7.49 (1H, d, J=2.6 Hz), 7.79 (2H, d, 0.1=7.8 Hz), 7.86 (1H, d, J=2.6 Hz), 7.99 (1H, d, J=2.0 Hz), 8.17 (1H, d, J=2.0 Hz), 10.14 (1H, s).

MS (ESI, m/z): 409 (M+H)$^+$.

Example 455

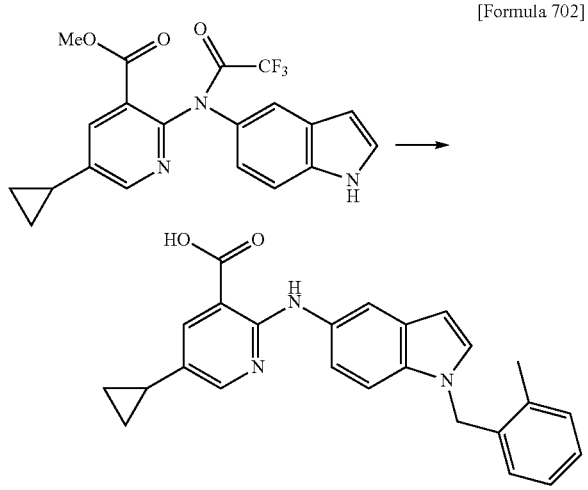

By the method similar to that of Example 449, 5-cyclopropyl-2-((1-(2-methylbenzyl)-1H-indol-5-yl)amino)nicotinic acid was obtained from methyl 5-cyclopropyl-2-(2,2,2-trifluoro-N-(1H-indol-5-yl)acetamido)nicotinate and 1-(bromomethyl)-2-methylbenzene.

$^1$H-NMR (DMSO-$d_6$) δ: 0.60-0.68 (2H, m), 0.84-0.96 (2H, m), 1.82-1.98 (1H, m), 2.32 (3H, s), 5.40 (2H, s), 6.46 (1H, d, J=3.3 Hz), 6.53 (1H, d, J=7.3 Hz), 7.00-7.10 (1H, m), 7.12-7.24 (3H, m), 7.26-7.34 (2H, m), 7.86 (1H, d, J=2.6 Hz), 8.01 (1H, d, J=2.0 Hz), 8.18 (1H, d, J=2.6 Hz), 10.15 (1H, s).

MS (ESI, m/z): 398 (M+H)$^+$, 396 (M−H)$^−$.

Example 456

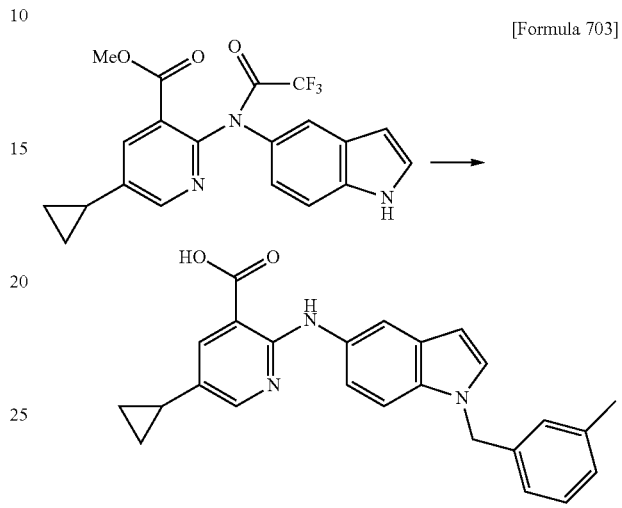

By the method similar to that of Example 449, 5-cyclopropyl-2-((1-(3-methylbenzyl)-1H-indol-5-yl)amino)nicotinic acid was obtained from methyl 5-cyclopropyl-2-(2,2,2-trifluoro-N-(1H-indol-5-yl)acetamido)nicotinate and 1-(bromomethyl)-3-methylbenzene.

$^1$H-NMR (DMSO-$d_6$) δ: 0.58-0.68 (2H, m), 0.84-0.94 (2H, m), 1.82-1.94 (1H, m), 2.24 (3H, s), 5.35 (2H, s), 6.42 (1H, d, J=2.6 Hz), 6.94-7.23 (5H, m), 7.35 (1H, d, J=8.6 Hz), 7.45 (1H, d, J=2.6 Hz), 7.86 (1H, d, J=2.6 Hz), 7.96 (1H, d, J=2.0 Hz), 8.17 (1H, d, J=2.6 Hz), 10.14 (1H, s).

MS (ESI, m/z): 398 (M+H)$^+$, 396 (M−H)$^−$.

Example 457

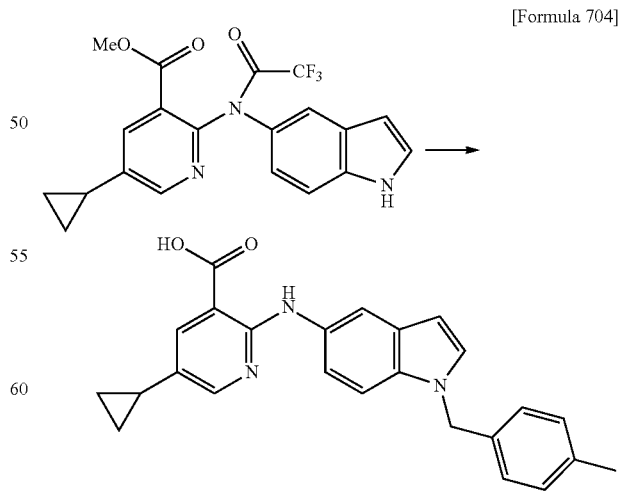

By the method similar to that of Example 449, 5-cyclopropyl-2-((1-(4-methylbenzyl)-1H-indol-5-yl)amino)nicotinic acid was obtained from methyl 5-cyclopropyl-2-(2,2,2-trifluoro-N-(1H-indol-5-yl)acetamido)nicotinate and 1-(bromomethyl)-4-methylbenzene.

¹H-NMR (DMSO-d₆) δ: 0.59-0.68 (2H, m), 0.84-0.96 (2H, m), 1.80-1.95 (1H, m), 2.24 (3H, s), 5.33 (2H, s), 6.41 (1H, d, J=3.3 Hz), 7.10 (4H, s), 7.14 (1H, dd, J=9.2, 2.0 Hz), 7.34 (1H, d, J=8.6 Hz), 7.44 (1H, d, J=3.3 Hz), 7.85 (1H, d, J=2.6 Hz), 7.95 (1H, d, J=1.3 Hz), 8.17 (1H, d, J=2.6 Hz), 10.12 (1H, s).

MS (ESI, m/z): 398 (M+H)⁺, 396 (M−H)⁻.

Example 458

[Formula 705]

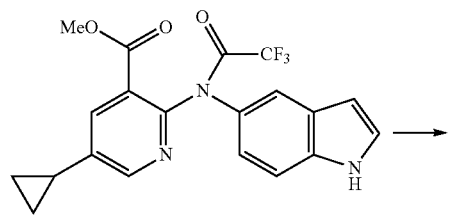

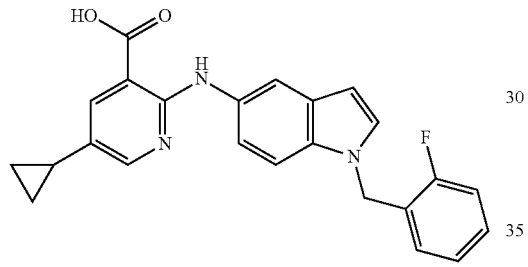

By the method similar to that of Example 449, 5-cyclopropyl-2-((1-(2-fluorobenzyl)-1H-indol-5-yl)amino)nicotinic acid was obtained from methyl 5-cyclopropyl-2-(2,2,2-trifluoro-N-(1H-indol-5-yl)acetamido)nicotinate and 1-(bromomethyl)-2-fluorobenzene.

¹H-NMR (DMSO-d₆) δ: 0.60-0.67 (2H, m), 0.86-0.94 (2H, m), 1.84-1.94 (1H, m), 5.45 (2H, s), 6.44 (1H, d, J=3.2 Hz), 6.98-7.05 (1H, m), 7.07-7.26 (3H, m), 7.28-7.36 (1H, m), 7.39 (1H, d, J=8.8 Hz), 7.42 (1H, d, J=2.9 Hz), 7.86 (1H, d, J=2.7 Hz), 7.97 (1H, d, J=2.0 Hz), 8.18 (1H, d, J=2.4 Hz), 10.13 (1H, s).

MS (ESI, m/z): 402 (M+H)⁺, 400 (M−H)⁻.

Example 459

[Formula 706]

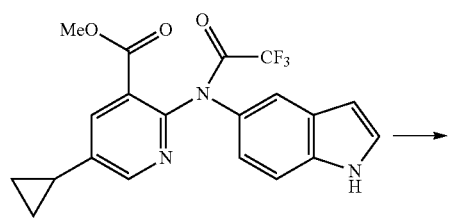

-continued

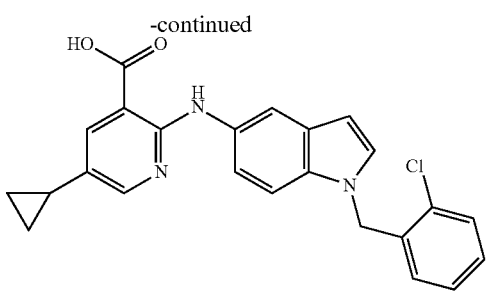

By the method similar to that of Example 449, 2-((1-(2-chlorobenzyl)-1H-indol-5-yl)amino)-5-cyclopropylnicotinic acid was obtained from methyl 5-cyclopropyl-2-(2,2,2-trifluoro-N-(1H-indol-5-yl)acetamido)nicotinate and 1-(bromomethyl)-2-chlorobenzene.

¹H-NMR (DMSO-d₆) δ: 0.60-0.68 (2H, m), 0.84-0.96 (2H, m), 1.83-1.96 (1H, m), 5.50 (2H, s), 6.48 (1H, d, J=3.3 Hz), 6.62-6.68 (1H, m), 7.12-7.36 (4H, m), 7.42 (1H, d, J=2.6 Hz), 7.48-7.54 (1H, m), 7.87 (1H, d, J=2.0 Hz), 8.01 (1H, d, J=2.0 Hz), 8.19 (1H, d, J=2.6 Hz), 10.14 (1H, s).

MS (ESI, m/z): 418 (M+H)⁺, 416 (M−H)⁻.

Example 460

[Formula 707]

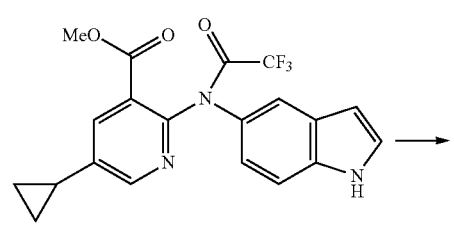

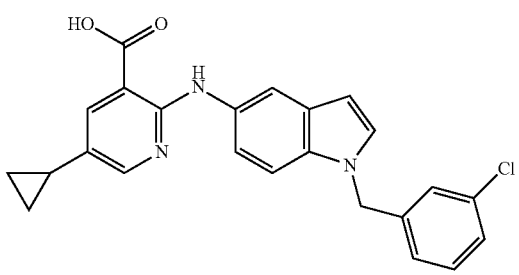

By the method similar to that of Example 449, 2-((1-(3-chlorobenzyl)-1H-indol-5-yl)amino)-5-cyclopropylnicotinic acid was obtained from methyl 5-cyclopropyl-2-(2,2,2-trifluoro-N-(1H-indol-5-yl)acetamido)nicotinate and 1-(bromomethyl)-3-chlorobenzene.

¹H-NMR (DMSO-d₆) δ: 0.59-0.68 (2H, m), 0.84-0.96 (2H, m), 1.82-1.96 (1H, m), 5.42 (2H, s), 6.45 (1H, d, J=3.3 Hz), 7.10-7.26 (3H, m), 7.28-7.41 (3H, m), 7.50 (1H, d, J=3.3 Hz), 7.86 (1H, d, J=2.6 Hz), 7.98 (1H, d, J=2.0 Hz), 8.17 (1H, d, J=2.6 Hz).

MS (ESI, m/z): 418 (M+H)⁺, 416 (M−H)⁻.

Example 461

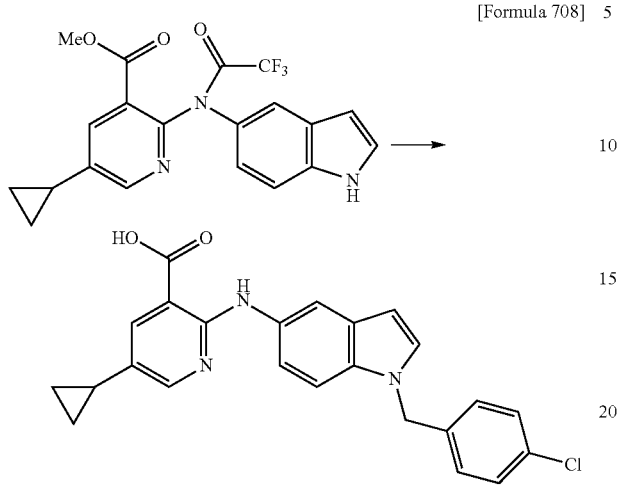
[Formula 708]

By the method similar to that of Example 449, 2-((1-(4-Chlorobenzyl)-1H-indol-5-yl)amino)-5-cyclopropylnicotinic acid was obtained from methyl 5-cyclopropyl-2-(2,2,2-trifluoro-N-(1H-indol-5-yl)acetamido)nicotinate.

$^1$H-NMR (DMSO-d$_6$) δ: 0.59-0.68 (2H, m), 0.84-0.96 (2H, m), 1.83-1.95 (1H, m), 5.40 (2H, s), 6.44 (1H, d, J=3.3 Hz), 7.12-7.24 (3H, m), 7.30-7.40 (3H, m), 7.47 (1H, d, J=2.6 Hz), 7.86 (1H, d, J=2.6 Hz), 7.97 (1H, d, J=2.0 Hz), 8.17 (1H, d, J=2.6 Hz), 10.12 (1H, s).

MS (ESI, m/z): 418 (M+H)$^+$, 416 (M−H)$^−$.

Example 462

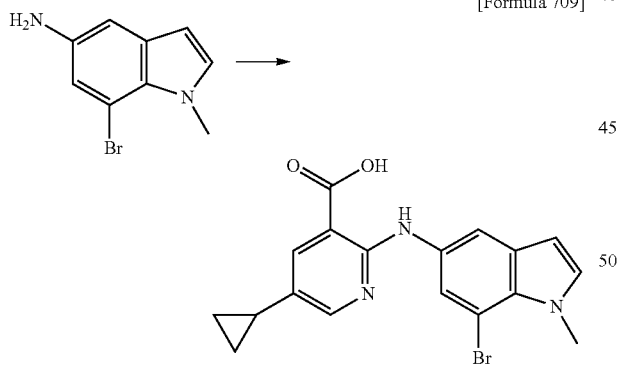
[Formula 709]

The mixed solution of 7.47 g of 7-bromo-1-methyl-1H-indol-5-amine, 6.56 g of 2-chloro-5-cyclopropylnicotinic acid and 3.16 g of p-toluenesulfonic acid monohydrate in 50 mL of ethanol and 25 mL of water was added to 25 mL of 5 mol/L hydrochloric acid under heating at reflux, and the resultant was stirred for 20 hours. 656 mg of 2-chloro-5-cyclopropylnicotinic acid and 20 mL of 5 mol/L hydrochloric acid were added thereto, and the resultant was heated at reflux for nine hours. The reaction mixture was adjusted to pH 3.0 by adding an aqueous sodium hydroxide solution at room temperature. Ethyl acetate was added thereto, and the organic layer was separated and the aqueous layer was extracted with ethyl acetate. The organic layer and the extract were combined and dried over anhydrous sodium sulfate, and the solvent was then distilled off under reduced pressure. The obtained residue was purified by silica gel column chromatography (gradient elution with hexane:ethyl acetate=90:10-0:100) to give 2.55 g of 2-((7-bromo-1-methyl-1H-indol-5-yl)amino)-5-cyclopropylnicotinic acid as a yellow solid.

MS (ESI, m/z): 386, 388 (M+H)$^+$.

Example 463

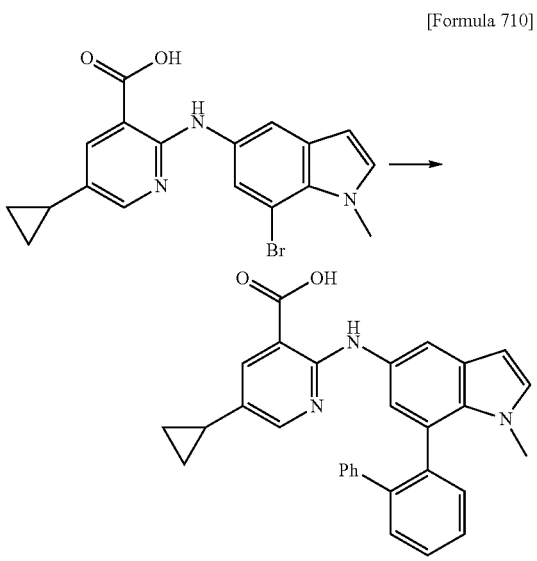
[Formula 710]

The mixture of 50 mg of 2-((7-bromo-1-methyl-1H-indol-5-yl)amino)-5-cyclopropylnicotinic acid, 28 mg of 2-biphenylboronic acid, 55 mg of tripotassium phosphate, 9.0 mg of bis(di-tert-butyl(4-dimethylaminophenyl)phosphine)dichloropalladium(II), 0.75 mL of dioxane, and 0.25 mL of water, was heated at reflux for four hours. 28 mg of 2-biphenylboronic acid was added to the reaction mixture, and the resultant was allowed to stand at room temperature overnight. Such a reaction mixture was heated at reflux for seven hours. The reaction mixture was cooled to room temperature and then adjusted to pH 2.0 by adding thereto water and hydrochloric acid. Ethyl acetate was added thereto, and the organic layer was separated and the aqueous layer was extracted with ethyl acetate twice. The organic layer and the extract were combined and the solvent was distilled off under reduced pressure. The obtained residue was purified by silica gel column chromatography (gradient elution with hexane:ethyl acetate=100:0-20:80), and ethyl acetate and hexane were added to the thus obtained residue, and the solid was collected by filtration to give 10.2 mg of 2-((7-([1,1'-biphenyl]-2-yl)-1-methyl-1H-indol-5-yl)amino)-5-cyclopropylnicotinic acid as a yellow solid.

$^1$H-NMR (CDCl$_3$) δ: 0.57-0.68 (2H, m), 0.82-0.96 (2H, m), 1.75-1.86 (1H, m), 3.22 (3H, s), 6.37 (1H, d, J=3.2 Hz), 6.79 (1H, d, J=2.9 Hz), 6.95-7.53 (10H, m), 7.84-8.14 (3H, m).

MS (ESI, m/z): 460 (M+H)$^+$, 458 (M−H)$^−$.

Example 464

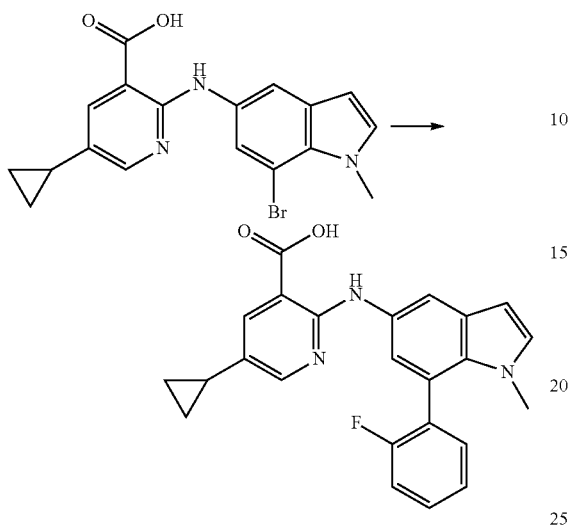

[Formula 711]

By the method similar to that of Example 463, 5-cyclopropyl-2-((7-(2-fluorophenyl)-1-methyl-1H-indol-5-yl)amino)nicotinic acid was obtained from 2-((7-bromo-1-methyl-1H-indol-5-yl)amino)-5-cyclopropylnicotinic acid.

¹H-NMR (DMSO-d₆) δ: 0.60-0.70 (2H, m), 0.84-0.96 (2H, m), 1.82-1.96 (1H, m), 3.28 (3H, s), 6.45 (1H, d, J=3.3 Hz), 7.06 (1H, d, J=2.0 Hz), 7.24 (1H, d, J=3.3 Hz), 7.28-7.40 (2H, m), 7.46-7.58 (2H, m), 7.88 (1H, d, J=2.6 Hz), 8.07 (1H, d, J=2.0 Hz), 8.20 (1H, d, J=2.6 Hz), 10.26 (1H, s).

MS (ESI, m/z): 402 (M+H)⁺, 400 (M−H)⁻.

Example 465

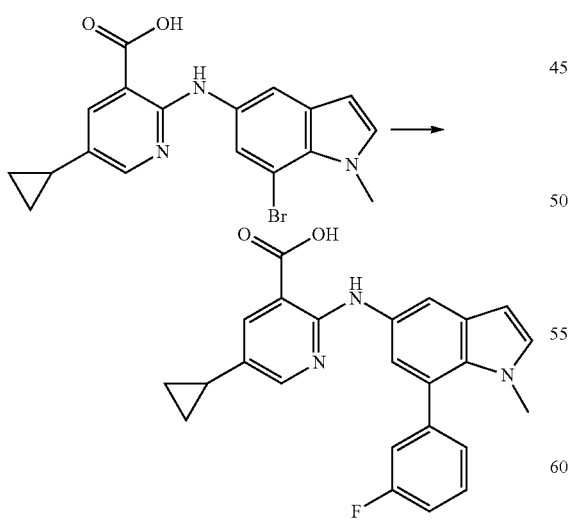

[Formula 712]

By the method similar to that of Example 463, 5-cyclopropyl-2-((7-(3-fluorophenyl)-1-methyl-1H-indol-5-yl)amino)nicotinic acid was obtained from 2-((7-bromo-1-methyl-1H-indol-5-yl)amino)-5-cyclopropylnicotinic acid.

¹H-NMR (CDCl₃) δ: 0.60-0.66 (2H, m), 0.82-0.95 (2H, m), 1.76-1.85 (1H, m), 3.29 (3H, s), 6.51 (1H, d, J=2.9 Hz), 6.95 (1H, d, J=2.9 Hz), 7.04-7.12 (2H, m), 7.15-7.29 (2H, m), 7.32-7.41 (1H, m), 7.90-7.98 (2H, m), 8.13-8.20 (1H, m), 9.89 (1H, brs).

MS (ESI, m/z): 402 (M+H)⁺, 400 (M−H)⁻.

Example 466

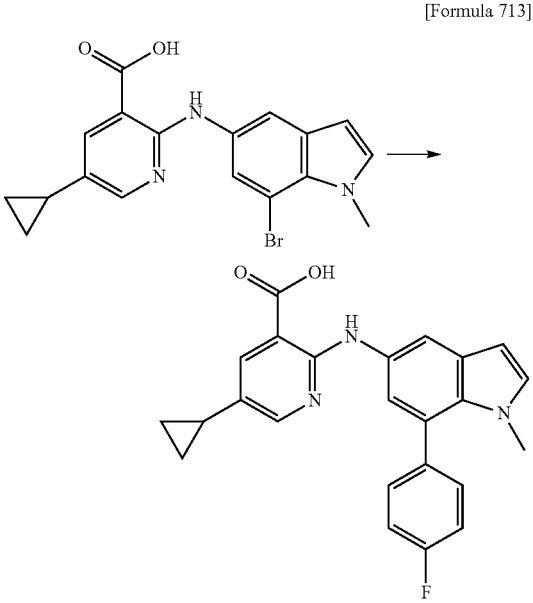

[Formula 713]

By the method similar to that of Example 463, 5-cyclopropyl-2-((7-(4-fluorophenyl)-1-methyl-1H-indol-5-yl)amino)nicotinic acid was obtained from 2-((7-bromo-1-methyl-1H-indol-5-yl)amino)-5-cyclopropylnicotinic acid.

¹H-NMR (DMSO-d6) δ: 0.60-0.69 (2H, m), 0.84-0.95 (2H, m), 1.83-1.95 (1H, m), 3.26 (3H, s), 6.45 (1H, d, J=2.6 Hz), 7.00 (1H, d, J=2.0 Hz), 7.24 (1H, d, J=2.6 Hz), 7.25-7.34 (2H, m), 7.46-7.55 (2H, m), 7.88 (1H, d, J=2.6 Hz), 8.05 (1H, d, J=2.0 Hz), 8.20 (1H, d, J=2.0 Hz), 10.25 (1H, s).

MS (ESI, m/z): 402 (M+H)⁺, 400 (M−H)⁻.

Example 467

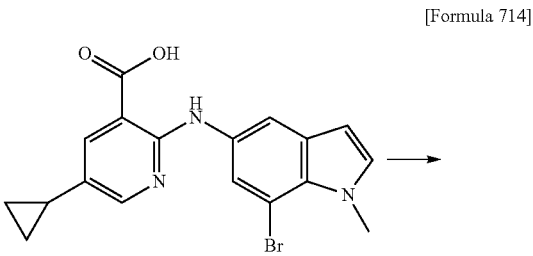

[Formula 714]

-continued

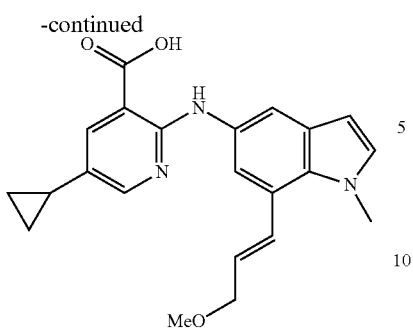

By the method similar to that of Example 463, (E)-5-cyclopropyl-2-((7-(3-methoxyprop-1-en-1-yl)-1-methyl-1H-indol-5-yl)amino)nicotinic acid was obtained from 2-((7-bromo-1-methyl-1H-indol-5-yl)amino)-5-cyclopropylnicotinic acid and (E)-3-methoxy-1-propenylboronic acid pinacol ester.

$^1$H-NMR (DMSO-d$_6$) δ: 0.60-0.70 (2H, m), 0.84-0.98 (2H, m), 1.80-2.00 (1H, m), 3.20-3.50 (3H, m), 3.96 (3H, s), 4.06-4.14 (2H, m), 6.13 (1H, dt, J=15.4, 5.8 Hz), 6.34 (1H, d, J=3.3 Hz), 7.17 (1H, d, J=2.0 Hz), 7.22 (1H, d, J=3.3 Hz), 7.43 (1H, d, J=15.9 Hz), 7.87 (1H, d, J=2.6 Hz), 7.95 (1H, d, J=1.3 Hz), 8.20 (1H, d, J=2.6 Hz), 10.14 (1H, s).

MS (ESI, m/z): 378 (M+H)$^+$, 376 (M−H)$^−$.

Example 468

[Formula 715]

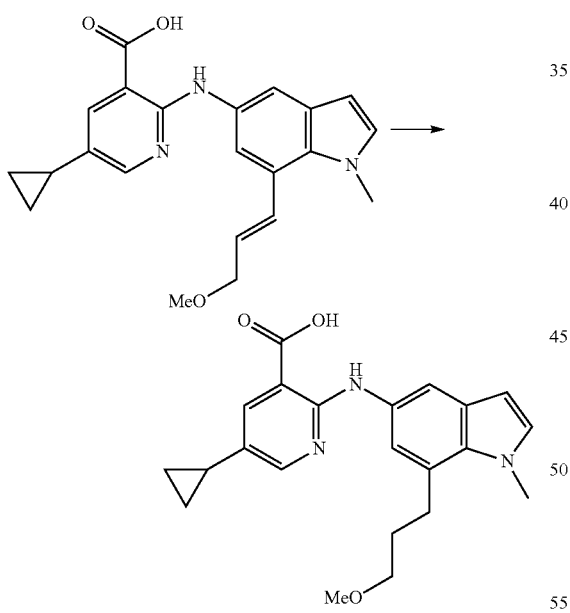

The solution of 40 mg of (E)-5-cyclopropyl-2-((7-(3-methoxyprop-1-en-1-yl)-1-methyl-1H-indol-5-yl)amino)nicotinic acid in 8 mL of methanol was subjected to hydrogenation reaction (room temperature, 1 bar, flow rate: 1.5 mL/min, 10% Pd/C) using the flow hydrogenation reactor. The solvent was distilled off under reduced pressure and the obtained residue was then purified by silica gel column chromatography (gradient elution with hexane:ethyl acetate=90:10-0:100) to give 2.0 mg of 5-cyclopropyl-2-((7-(3-methoxypropyl)-1-methyl-1H-indol-5-yl)amino)nicotinic acid as a yellow solid.

$^1$H-NMR (DMSO-d$_6$) δ: 0.60-0.68 (2H, m), 0.84-0.96 (2H, m), 1.80-1.96 (3H, m), 2.98-3.10 (2H, m), 3.27 (3H, s), 3.42 (2H, t, J=6.3 Hz), 3.97 (3H, s), 6.32 (1H, d, J=3.3 Hz), 6.86 (1H, d, J=2.0 Hz), 7.17 (1H, d, J=3.3 Hz), 7.87 (1H, d, J=2.6 Hz), 7.93 (1H, d, J=2.0 Hz), 8.20 (1H, d, J=2.6 Hz), 10.14 (1H, s).

MS (ESI, m/z): 380 (M+H)$^+$.

Example 469

[Formula 716]

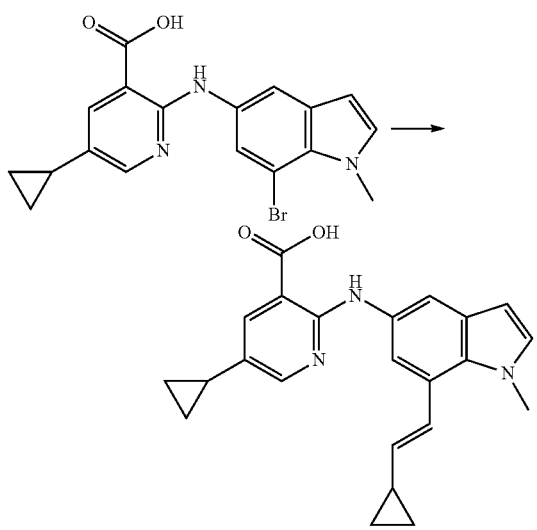

By the method similar to that of Example 463, (E)-5-cyclopropyl-2-((7-(2-cyclopropylvinyl)-1-methyl-1H-indol-5-yl)amino)nicotinic acid was obtained from 2-((7-bromo-1-methyl-1H-indol-5-yl)amino)-5-cyclopropylnicotinic acid and trans-2-cyclopropylvinylboronic acid pinacol ester.

$^1$H-NMR (DMSO-d$_6$) δ: 0.52-0.70 (4H, m), 0.75-0.96 (4H, m), 1.60-1.76 (1H, m), 1.82-1.96 (1H, m), 3.98 (3H, s), 5.63 (1H, dd, J=15.2, 9.2 Hz), 6.31 (1H, d, J=3.3 Hz), 7.03 (1H, d, J=2.0 Hz), 7.19 (1H, d, J=3.3 Hz), 7.26 (1H, d, J=15.9 Hz), 7.86 (1H, d, J=2.6 Hz), 7.91 (1H, d, J=2.0 Hz), 8.19 (1H, d, J=2.6 Hz), 10.10 (1H, brs).

MS (ESI, m/z): 374 (M+H)$^+$.

Example 470

[Formula 717]

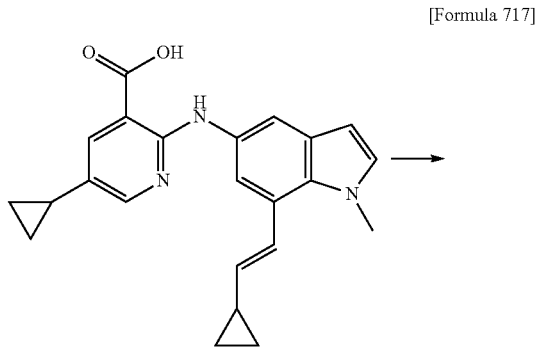

-continued

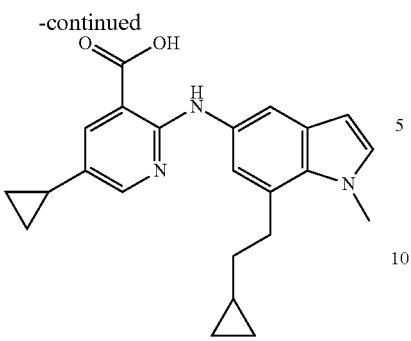

By the method similar to that of Example 468, 5-cyclopropyl-2-((7-(2-cyclopropylethyl)-1-methyl-1H-indol-5-yl)amino)nicotinic acid as a yellow solid was obtained from (E)-5-cyclopropyl-2-((7-(2-cyclopropylvinyl)-1-methyl-1H-indol-5-yl)amino)nicotinic acid.

$^1$H-NMR (DMSO-$d_6$) δ: 0.08-0.16 (2H, m), 0.38-0.50 (2H, m), 0.60-0.68 (2H, m), 0.76-0.96 (3H, m), 1.50-1.62 (2H, m), 1.82-1.96 (1H, m), 3.04-3.14 (2H, m), 3.98 (3H, s), 6.31 (1H, d, J=3.3 Hz), 6.87 (1H, d, J=2.0 Hz), 7.17 (1H, d, J=2.6 Hz), 7.86 (1H, d, J=2.6 Hz), 7.92 (1H, d, J=2.0 Hz), 8.20 (1H, d, J=2.6 Hz), 10.09 (1H, s).

MS (ESI, m/z): 376 (M+H)$^+$, 374 (M−H)$^-$.

Example 471

[Formula 718]

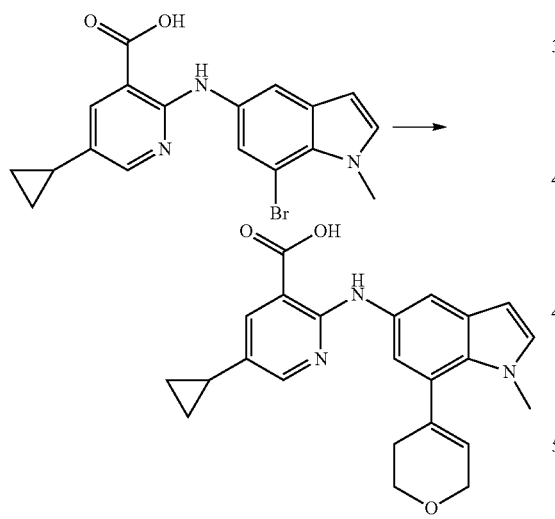

By the method similar to that of Example 463, 5-cyclopropyl-2-((7-(3,6-dihydro-2H-pyran-4-yl)-1-methyl-1H-indol-5-yl)amino)nicotinic acid was obtained from 2-((7-bromo-1-methyl-1H-indol-5-yl)amino)-5-cyclopropylnicotinic acid and 3,6-dihydro-2H-pyran-4-boronic acid pinacol ester.

$^1$H-NMR (DMSO-$d_6$) δ: 0.60-0.70 (2H, m), 0.84-0.96 (2H, m), 1.83-1.96 (1H, m), 2.36-2.48 (2H, m), 3.78 (3H, s), 3.88 (2H, t, J=5.3 Hz), 4.20-4.28 (2H, m), 5.74-5.80 (1H, m), 6.38 (1H, d, J=2.6 Hz), 6.86 (1H, d, J=2.0 Hz), 7.23 (1H, d, J=2.6 Hz), 7.87 (1H, d, J=2.6 Hz), 8.00 (1H, d, J=2.0 Hz), 8.20 (1H, d, J=2.6 Hz), 10.26 (1H, brs).

MS (ESI, m/z): 390 (M+H)$^+$, 388 (M−H)$^-$.

Example 472

[Formula 719]

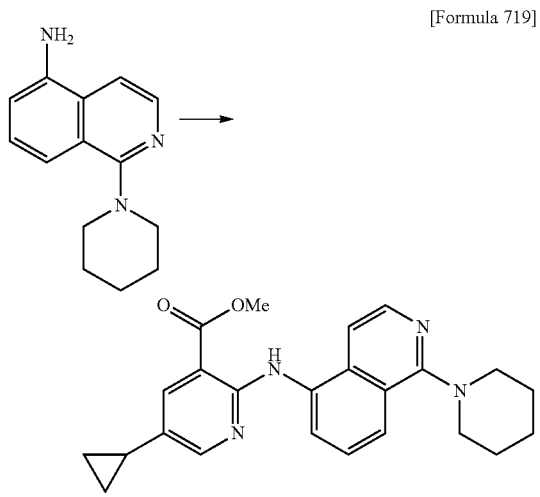

The mixture of 105 mg of 1-(piperidin-1-yl)isoquinolin-5-amine, 100 mg of methyl 2-chloro-5-cyclopropylnicotinate, 42 mg of tris(dibenzylideneacetone)dipalladium(0), 53 mg of 4,5'-bis(diphenylphosphino)-9,9'-dimethylxanthene, 301 mg of cesium carbonate, and 5 mL of toluene, was stirred at 190° C. for one hour using microwave equipment. After cooling the reaction mixture to room temperature, the insoluble matter was filtered off and the solvent was distilled off under reduced pressure. The obtained residue was purified by silica gel column chromatography (gradient elution with hexane:ethyl acetate=100:0-70:30) to give 86 mg of methyl 5-cyclopropyl-2-(1-(piperidin-1-yl)isoquinolin-5-ylamino)nicotinate as a brown oil.

MS (ESI, m/z): 403 (M+H)$^+$.

Example 473

[Formula 720]

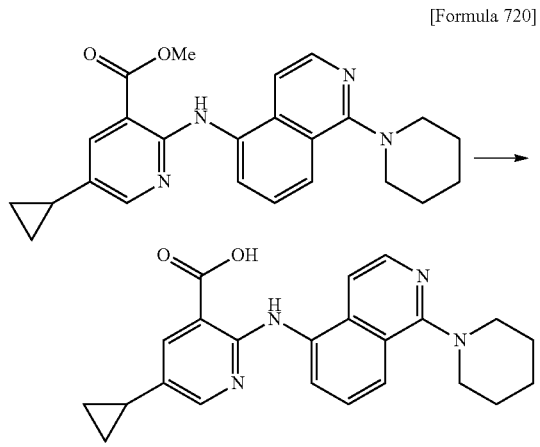

To the mixed solution of 86 mg of methyl 5-cyclopropyl-2-(1-(piperidin-1-yl)isoquinolin-5-ylamino)nicotinate in 1 mL of methanol and 2 mL of tetrahydrofuran, 86 μL of a 5 mol/L aqueous sodium hydroxide solution was added at room temperature, and the resultant was stirred at an external temperature of 60° C. for 30 minutes. After cooling the reaction mixture to room temperature, the solvent was distilled off under reduced pressure. The reaction mixture was adjusted to pH 4.0 by adding thereto hydrochloric acid. Ethyl acetate was added thereto, and the organic layer was separated and the aqueous layer was extracted with ethyl acetate. The organic layer and the extract were combined and the solvent was distilled off under reduced pressure. The obtained residue was purified by silica gel column chromatography (gradient elution with chloroform:methanol=100:0-95:5), and ethyl acetate and hexane were added to the thus obtained residue, and the solid was collected by filtration to give 12 mg of 5-cyclopropyl-2-(1-(piperidin-1-yl)isoquinolin-5-ylamino)nicotinic acid as a yellow solid.

$^1$H-NMR (DMSO-$d_6$) δ: 0.64-0.72 (2H, m), 0.89-0.99 (2H, m), 1.58-1.83 (6H, m), 1.88-2.00 (1H, m), 3.20-3.50 (4H, m), 7.45 (1H, d, J=5.9 Hz), 7.56 (1H, t, J=8.3 Hz), 7.73 (1H, d, J=8.6 Hz), 7.96 (1H, d, J=2.0 Hz), 8.15 (1H, d, J=5.9 Hz), 8.24 (1H, d, J=2.0 Hz), 8.60 (1H, d, J=7.9 Hz).

MS (ESI, m/z): 389 (M+H)$^+$.

Example 474

[Formula 721]

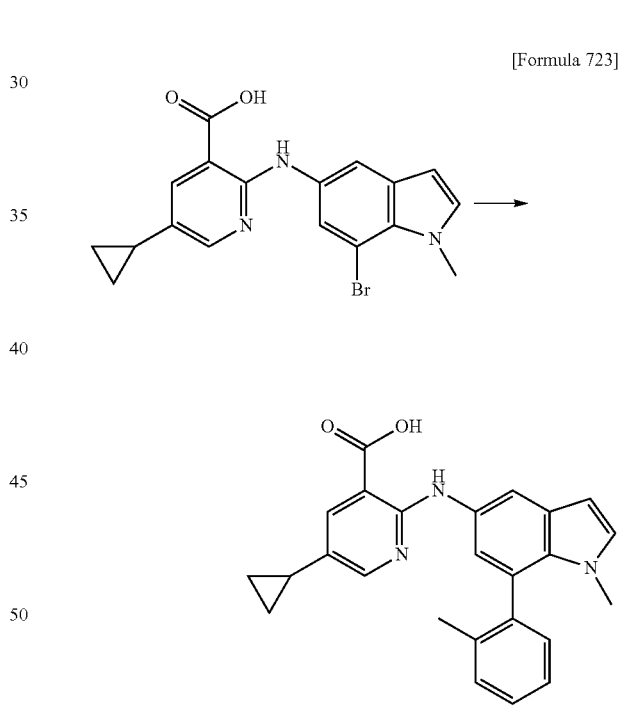

By the method similar to that of Example 472, methyl 5-cyclopropyl-2-(1-morpholinoisoquinolin-5-ylamino)nicotinate was obtained from 1-morpholinoisoquinolin-5-amine and methyl 2-chloro-5-cyclopropylnicotinate.

MS (ESI, m/z): 405 (M+H)$^+$.

Example 475

[Formula 722]

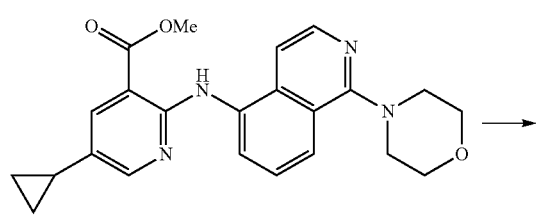

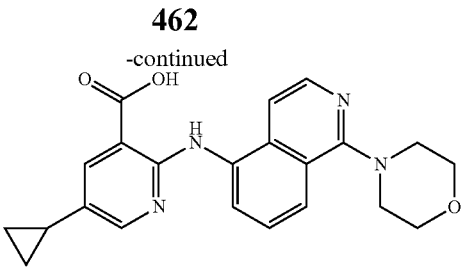

By the method similar to that of Example 473, 5-cyclopropyl-2-(1-morpholinoisoquinolin-5-ylamino)nicotinic acid was obtained from methyl 5-cyclopropyl-2-(1-morpholinoisoquinolin-5-ylamino)nicotinate.

$^1$H-NMR (DMSO-$d_6$) δ: 0.64-0.73 (2H, m), 0.90-0.99 (2H, m), 1.88-2.02 (1H, m), 3.20-3.50 (4H, m), 3.82-3.92 (4H, m), 7.50 (1H, d, J=5.9 Hz), 7.58 (1H, t, J=8.3 Hz), 7.81 (1H, d, J=7.9 Hz), 7.97 (1H, d, J=2.6 Hz), 8.19 (1H, d, J=5.9 Hz), 8.25 (1H, J=2.6 Hz), 8.60 (1H, d, J=7.9 Hz), 10.89 (1H, s), 13.78 (1H, brs).

MS (ESI, m/z): 391 (M+H)$^+$.

Example 476

[Formula 723]

By the method similar to that of Example 463, 5-cyclopropyl-2-((1-methyl-7-(o-tolyl)-1H-indol-5-yl)amino)nicotinic acid was obtained from 2-((7-bromo-1-methyl-1H-indol-5-yl)amino)-5-cyclopropylnicotinic acid and 2-methylphenylboronic acid.

$^1$H-NMR (CDCl$_3$) δ: 0.60-0.67 (2H, m), 0.84-0.96 (2H, m), 1.77-1.86 (1H, m), 2.11 (3H, s), 3.15 (3H, s), 6.49 (1H, d, J=2.9 Hz), 6.91 (1H, d, J=3.2 Hz), 6.97 (1H, d, J=2.0 Hz), 7.20-7.38 (4H, m), 7.94 (1H, d, J=2.4 Hz), 8.02-8.09 (1H, m), 8.22 (1H, s), 9.86 (1H, brs).

MS (ESI, m/z): 398 (M+H)$^+$.

Example 477

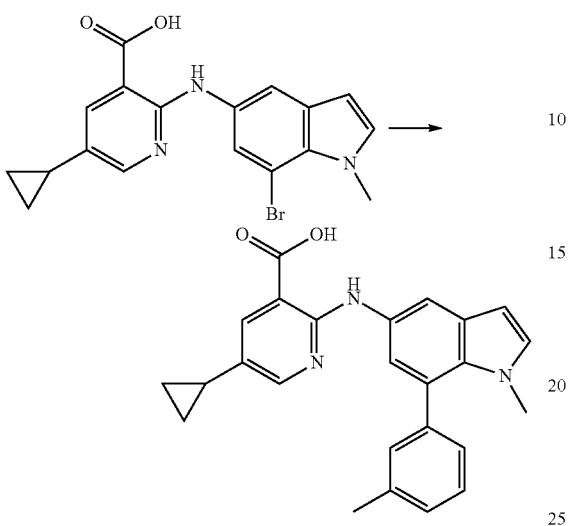

[Formula 724]

By the method similar to that of Example 463, 5-cyclopropyl-2-((1-methyl-7-(m-tolyl)-1H-indol-5-yl)amino)nicotinic acid was obtained from 2-((7-bromo-1-methyl-1H-indol-5-yl)amino)-5-cyclopropylnicotinic acid and 3-methylphenylboronic acid.

$^1$H-NMR (CDCl$_3$) δ: 0.60-0.66 (2H, m), 0.88-0.95 (2H, m), 1.76-1.86 (1H, m), 2.40 (3H, s), 3.27 (3H, s), 6.50 (1H, d, J=3.2 Hz), 6.93 (1H, d, J=2.9 Hz), 7.04 (1H, d, J=2.0 Hz), 7.16-7.32 (4H, m), 7.90-8.00 (2H, m), 8.18 (1H, s), 9.89 (1H, brs).

MS (ESI, m/z): 398 (M+H)$^+$, 396 (M−H)$^−$.

Example 478

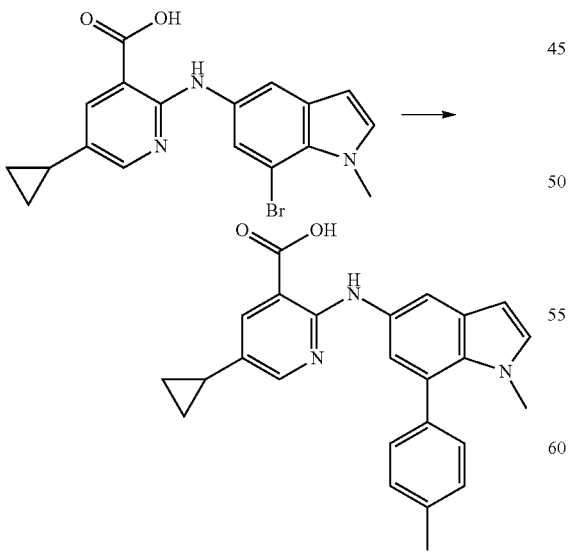

[Formula 725]

By the method similar to that of Example 463, 5-cyclopropyl-2-((1-methyl-7-(p-tolyl)-1H-indol-5-yl)amino)nicotinic acid was obtained from 2-((7-bromo-1-methyl-1H-indol-5-yl)amino)-5-cyclopropylnicotinic acid and 4-methylphenylboronic acid.

$^1$H-NMR (DMSO-d$_6$) δ: 0.61-0.67 (2H, m), 0.85-0.93 (2H, m), 1.84-1.93 (1H, m), 2.39 (3H, s), 3.26 (3H, s), 6.43 (1H, d, J=3.2 Hz), 6.97 (1H, d, J=2.0 Hz), 7.21 (1H, d, J=2.9 Hz), 7.27 (2H, d, J=7.8 Hz), 7.34 (2H, d, J=8.0 Hz), 7.87 (1H, d, J=2.7 Hz), 8.03 (1H, d, J=2.2 Hz), 8.18 (1H, d, =2.4 Hz).

MS (ESI, m/z): 398 (M+H)$^+$, 396 (M−H)$^−$.

Example 479

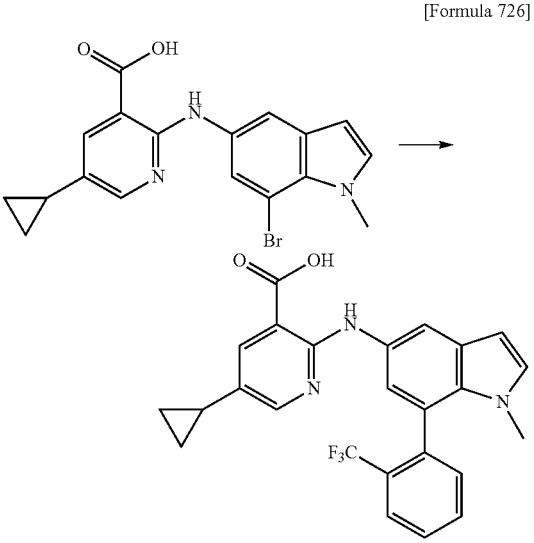

[Formula 726]

By the method similar to that of Example 463, 5-cyclopropyl-2-((1-methyl-7-(2-trifluoromethyl)phenyl)-1H-indol-5-yl)amino)nicotinic acid was obtained from 2-((7-bromo-1-methyl-1H-indol-5-yl)amino)-5-cyclopropylnicotinic acid and 2-(trifluoromethyl)phenylboronic acid.

$^1$H-NMR (CDCl$_3$) δ: 0.60-0.66 (2H, m), 0.86-0.95 (2H, m), 1.76-1.87 (1H, m), 3.11 (3H, s), 6.48 (1H, d, J=2.9 Hz), 6.90 (1H, d, J=3.2 Hz), 7.04 (1H, s), 7.47-7.59 (3H, m), 7.75-7.82 (1H, m), 7.91-7.96 (1H, m), 8.00-8.06 (1H, m), 8.14-8.22 (1H, m).

MS (ESI, m/z): 452 (M+H)$^+$, 450 (M−H)$^−$.

Example 480

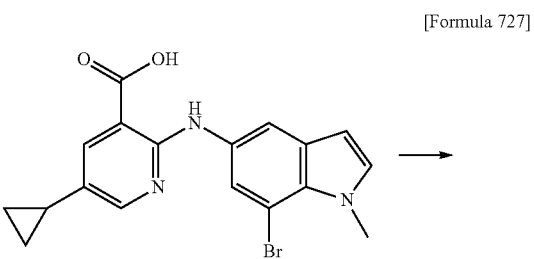

[Formula 727]

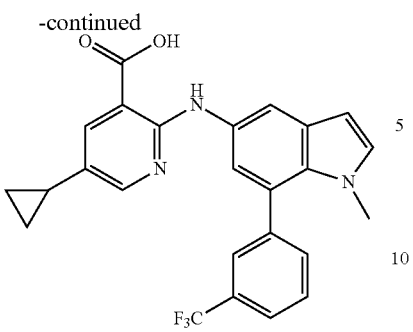

By the method similar to that of Example 463, 5-cyclopropyl-2-((1-methyl-7-(3-trifluoromethyl)phenyl)-1H-indol-5-yl)amino)nicotinic acid was obtained from 2-((7-bromo-1-methyl-1H-indol-5-yl)amino)-5-cyclopropylnicotinic acid and 3-(trifluoromethyl)phenylboronic acid.

$^1$H-NMR (DMSO-$d_6$) δ: 0.60-0.69 (2H, m), 0.84-0.96 (2H, m), 1.83-1.96 (1H, m), 3.24 (3H, s), 6.48 (1H, d, J=2.6 Hz), 7.06 (1H, d, J=2.6 Hz), 7.27 (1H, d, J=2.6 Hz), 7.66-7.86 (4H, m), 7.88 (1H, d, J=2.6 Hz), 8.10 (1H, d, J=2.0 Hz), 8.20 (1H, d, J=2.6 Hz), 10.27 (1H, brs).

MS (ESI, m/z): 452 (M+H)$^+$.

Example 481

[Formula 728]

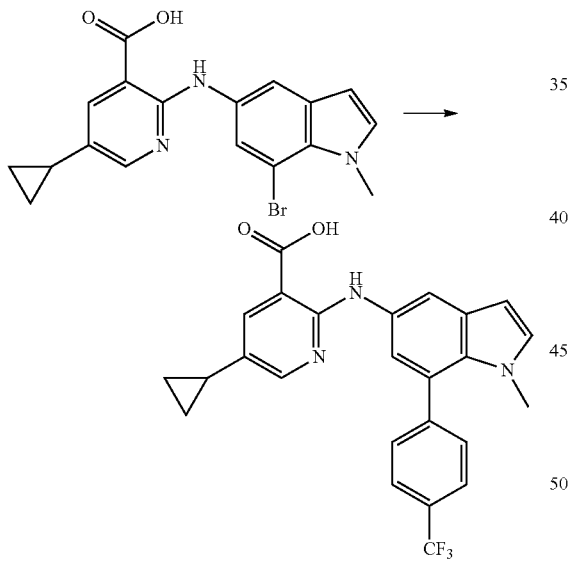

By the method similar to that of Example 463, 5-cyclopropyl-2-((1-methyl-7-(4-trifluoromethyl)phenyl)-1H-indol-5-yl)amino)nicotinic acid was obtained from 2-((7-bromo-1-methyl-1H-indol-5-yl)amino)-5-cyclopropylnicotinic acid and 4-(trifluoromethyl)phenylboronic acid.

$^1$H-NMR (DMSO-$d_6$) δ: 0.60-0.69 (2H, m), 0.84-0.96 (2H, m), 1.83-1.96 (1H, m), 3.27 (3H, s), 6.48 (1H, d, J=2.6 Hz), 7.08 (1H, d, J=2.0 Hz), 7.28 (1H, d, J=3.3 Hz), 7.72 (2H, d, J=7.9 Hz), 7.83 (2H, d, J=7.9 Hz), 7.88 (1H, d, J=2.6 Hz), 8.08 (1H, d, J=2.0 Hz), 8.20 (1H, d, J=2.6 Hz), 10.26 (1H, brs).

MS (ESI, m/z): 452 (M+H)$^+$, 450 (M−H)$^−$.

Example 482

[Formula 729]

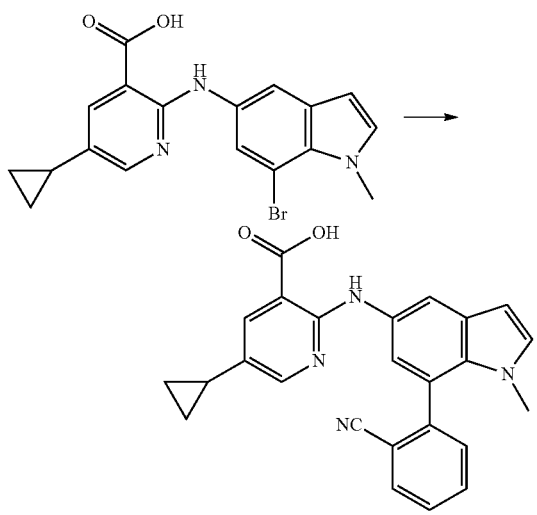

By the method similar to that of Example 463, 2-((7-(2-cyanophenyl)-1-methyl-1H-indol-5-yl)amino)-5-cyclopropylnicotinic acid was obtained from 2-((7-bromo-1-methyl-1H-indol-5-yl)amino)-5-cyclopropylnicotinic acid and 2-cyanophenylboronic acid.

$^1$H-NMR (DMSO-$d_6$) δ: 0.60-0.70 (2H, m), 0.84-0.95 (2H, m), 1.84-1.96 (1H, m), 3.20 (3H, s), 6.49 (1H, d, J=3.3 Hz), 7.12 (1H, d, J=2.0 Hz), 7.28 (1H, d, J=2.6 Hz), 7.65-7.72 (2H, m), 7.77-7.83 (1H, m), 7.89 (1H, d, J=2.6 Hz), 7.98 (1H, d, J=7.9 Hz), 8.15 (1H, d, J=2.0 Hz), 8.21 (1H, d, J=2.0 Hz), 10.30 (1H, brs).

MS (ESI, m/z): 409 (M+H)$^+$, 407 (M−H)$^−$.

Example 483

[Formula 730]

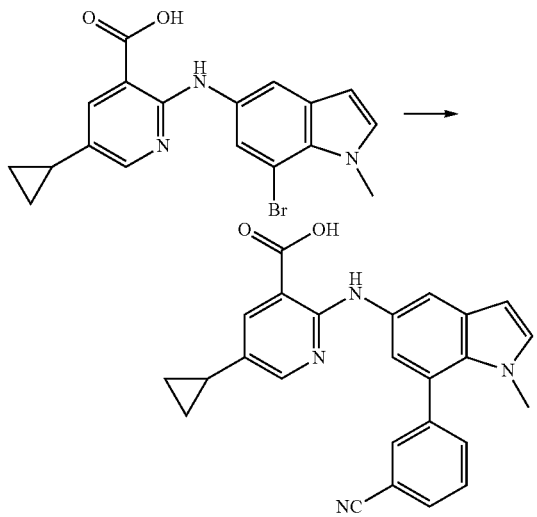

467

By the method similar to that of Example 463, 2-((7-(3-cyanophenyl)-1-methyl-1H-indol-5-yl)amino)-5-cyclopropylnicotinic acid was obtained from 2-((7-bromo-1-methyl-1H-indol-5-yl)amino)-5-cyclopropylnicotinic acid and 3-cyanophenylboronic acid.

$^1$H-NMR (DMSO-$d_6$) δ: 0.60-0.69 (2H, m), 0.85-0.95 (2H, m), 1.83-1.96 (1H, m), 3.26 (3H, s), 6.47 (1H, d, J=3.3 Hz), 7.04 (1H, d, J=2.0 Hz), 7.27 (1H, d, J=2.6 Hz), 7.67 (1H, t, J=7.9 Hz), 7.83 (1H, d, J=7.9 Hz), 7.88 (1H, d, J=2.7 Hz), 7.92 (1H, d, J=8.1 Hz), 7.98 (1H, s), 8.11 (1H, d, J=2.0 Hz), 8.20 (1H, d, =2.6 Hz), 10.23 (1H, brs).

MS (ESI, m/z): 409 (M+H)$^+$, 407 (M−H)$^-$.

Example 484

[Formula 731]

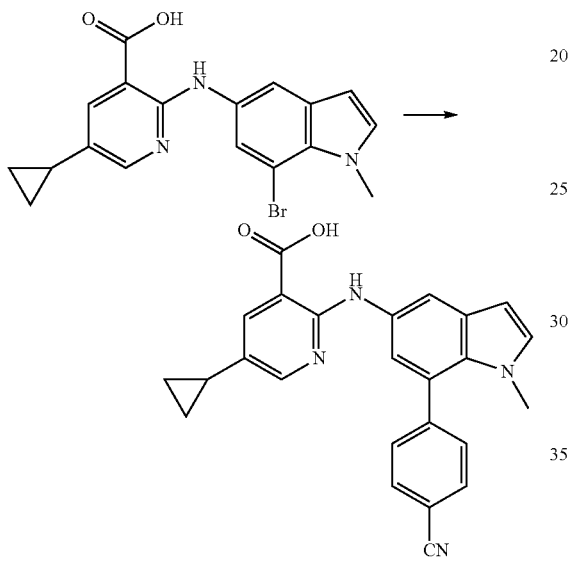

By the method similar to that of Example 463, 2-((7-(4-cyanophenyl)-1-methyl-1H-indol-5-yl)amino)-5-cyclopropylnicotinic acid was obtained from 2-((7-bromo-1-methyl-1H-indol-5-yl)amino)-5-cyclopropylnicotinic acid and 4-cyanophenylboronic acid.

$^1$H-NMR (DMSO-$d_6$) δ: 0.60-0.69 (2H, m), 0.84-0.96 (2H, m), 1.84-1.95 (1H, m), 3.27 (3H, s), 6.48 (1H, d, J=2.6 Hz), 7.06 (1H, d, J=2.6 Hz), 7.28 (1H, d, J=2.6 Hz), 7.69 (2H, d, J=7.9 Hz), 7.88 (1H, d, J=2.0 Hz), 7.94 (2H, d, J=7.9 Hz), 8.09 (1H, d, J=2.0 Hz), 8.20 (1H, d, J=2.6 Hz), 10.25 (1H, s).

MS (ESI, m/z): 409 (M+H)$^+$, 407 (M−H)$^-$.

Example 485

[Formula 732]

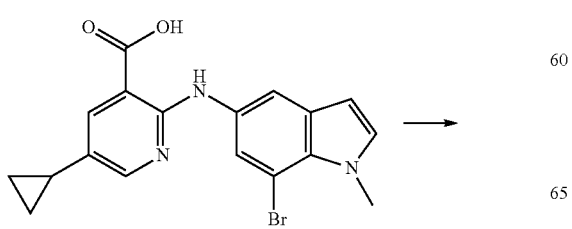

468

-continued

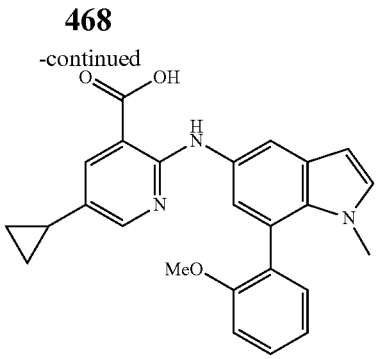

By the method similar to that of Example 463, 5-cyclopropyl-2-((7-(2-methoxyphenyl)-1-methyl-1H-indol-5-yl)amino)nicotinic acid was obtained from 2-((7-bromo-1-methyl-1H-indol-5-yl)amino)-5-cyclopropylnicotinic acid and 2-methoxyphenylboronic acid.

$^1$H-NMR (DMSO-$d_6$) δ: 0.60-0.69 (2H, m), 0.84-0.95 (2H, m), 1.80-2.00 (1H, m), 3.21 (3H, s), 3.70 (3H, s), 6.39 (1H, d, J=2.6 Hz), 6.90 (1H, d, J=2.0 Hz), 7.04 (1H, t, J=6.9 Hz), 7.12 (1H, d, J=7.9 Hz), 7.17 (1H, d, J=3.3 Hz), 7.28 (1H, dd, J=7.3, 1.3 Hz), 7.38-7.48 (1H, m), 7.87 (1H, d, J=2.6 Hz), 8.01 (1H, d, J=2.0 Hz), 8.20 (1H, d, J=2.6 Hz), 10.22 (1H, s).

MS (ESI, m/z): 414 (M+H)$^+$.

Example 486

[Formula 733]

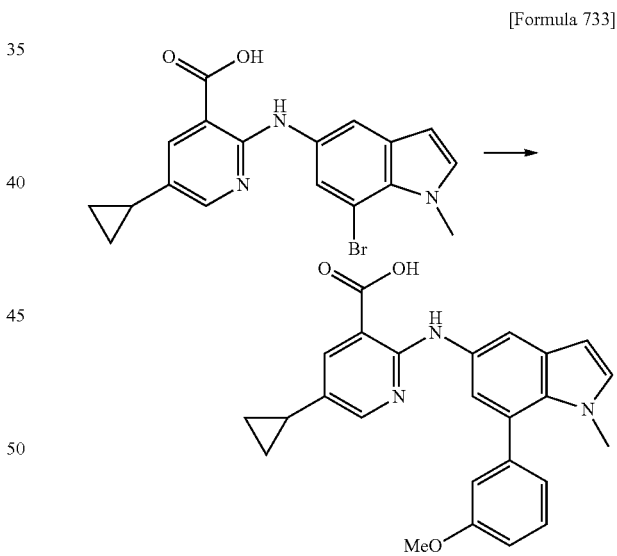

By the method similar to that of Example 463, 5-cyclopropyl-2-((7-(3-methoxyphenyl)-1-methyl-1H-indol-5-yl)amino)nicotinic acid was obtained from 2-((7-bromo-1-methyl-1H-indol-5-yl)amino)-5-cyclopropylnicotinic acid and 3-methoxyphenylboronic acid.

$^1$H-NMR (DMSO-$d_6$) δ: 0.60-0.69 (2H, m), 0.84-0.95 (2H, m), 1.82-1.95 (1H, m), 3.29 (3H, s), 3.81 (3H, s), 6.45 (1H, d, J=3.3 Hz), 6.96-7.06 (4H, m), 7.23 (1H, d, J=3.3 Hz), 7.32-7.42 (1H, m), 7.88 (1H, d, J=2.6 Hz), 8.04 (1H, d, J=2.0 Hz), 8.20 (1H, d, J=2.0 Hz), 10.25 (1H, brs).

MS (ESI, m/z): 414 (M+H)$^+$, 412 (M−H)$^-$.

Example 487

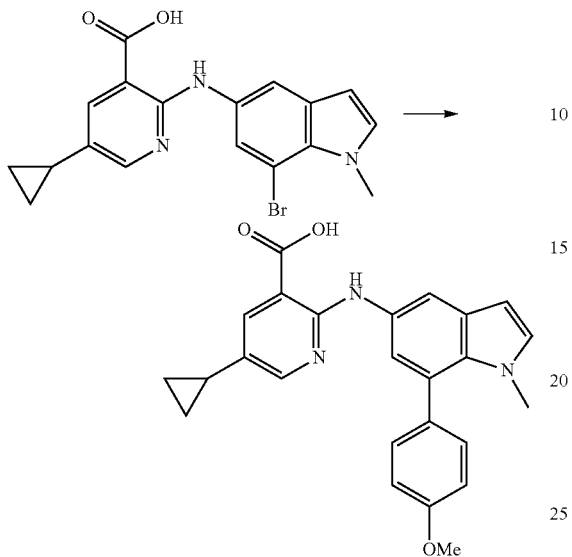

[Formula 734]

By the method similar to that of Example 463, 5-cyclopropyl-2-((7-(4-methoxyphenyl)-1-methyl-1H-indol-5-yl)amino)nicotinic acid was obtained from 2-((7-bromo-1-methyl-1H-indol-5-yl)amino)-5-cyclopropylnicotinic acid and 4-methoxyphenylboronic acid.

$^1$H-NMR (DMSO-$d_6$) δ: 0.60-0.69 (2H, m), 0.84-0.95 (2H, m), 1.82-1.96 (1H, m), 3.28 (3H, s), 3.83 (3H, s), 6.43 (1H, d, J=3.3 Hz), 6.96 (1H, d, J=2.0 Hz), 7.02 (2H, d, J=8.6 Hz), 7.22 (1H, d, J=3.3 Hz), 7.38 (2H, d, J=8.6 Hz), 7.87 (1H, d, J=2.6 Hz), 8.02 (1H, d, J=2.6 Hz), 8.20 (1H, d, J=2.0 Hz), 10.23 (1H, brs).

MS (ESI, m/z): 414 (M+H)$^+$, 412 (M-H)$^-$.

Example 488

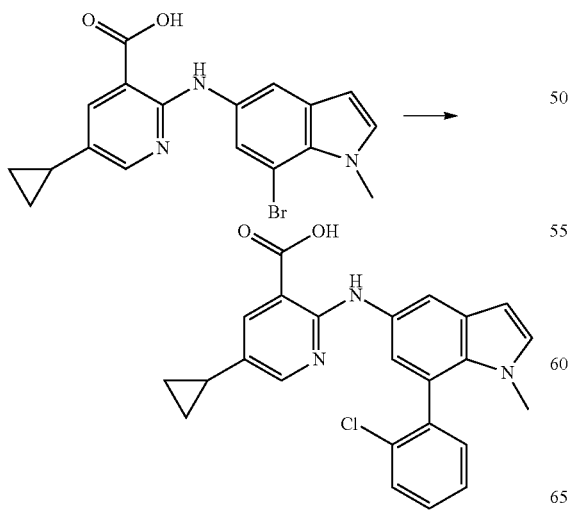

[Formula 735]

By the method similar to that of Example 463, 2-((7-(2-chlorophenyl)-1-methyl-1H-indol-5-yl)amino)-5-cyclopropylnicotinic acid was obtained from 2-((7-bromo-1-methyl-1H-indol-5-yl)amino)-5-cyclopropylnicotinic acid and 2-chlorophenylboronic acid.

$^1$H-NMR (DMSO-$d_6$) δ: 0.60-0.69 (2H, m), 0.84-0.95 (2H, m), 1.82-1.96 (1H, m), 3.20 (3H, s), 6.43 (1H, d, J=3.3 Hz), 6.99 (1H, d, J=2.0 Hz), 7.22 (1H, d, J=3.3 Hz), 7.40-7.64 (4H, m), 7.88 (1H, d, J=2.6 Hz), 8.09 (1H, d, J=2.0 Hz), 8.19 (1H, d, J=2.6 Hz), 10.43 (1H, brs).

MS (ESI, m/z): 418 (M+H)$^+$.

Example 489

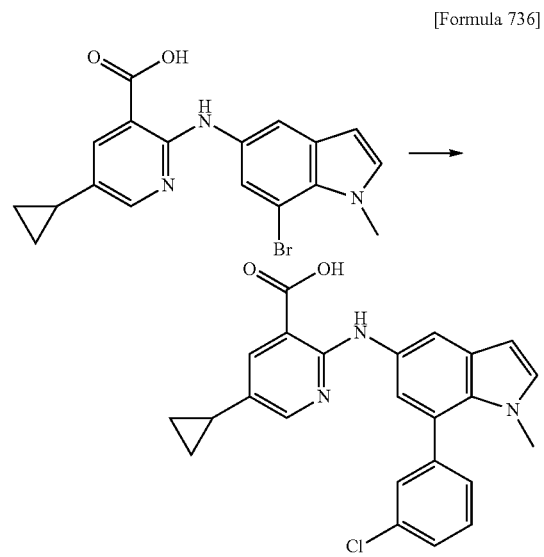

[Formula 736]

By the method similar to that of Example 463, 2-((7-(3-chlorophenyl)-1-methyl-1H-indol-5-yl)amino)-5-cyclopropylnicotinic acid was obtained from 2-((7-bromo-1-methyl-1H-indol-5-yl)amino)-5-cyclopropylnicotinic acid and 3-chlorophenylboronic acid.

$^1$H-NMR (DMSO-$d_6$) δ: 0.60-0.69 (2H, m), 0.84-0.95 (2H, m), 1.82-1.95 (1H, m), 3.28 (3H, s), 6.46 (1H, d, J=2.6 Hz), 7.04 (1H, d, J=2.0 Hz), 7.25 (1H, d, J=3.3 Hz), 7.41-7.57 (4H, m), 7.88 (1H, d, J=2.6 Hz), 8.07 (1H, d, J=2.0 Hz), 8.19 (1H, d, J=2.6 Hz), 10.34 (1H, brs).

MS (ESI, m/z): 418 (M+H)$^+$, 416 (M-H)$^-$.

Example 490

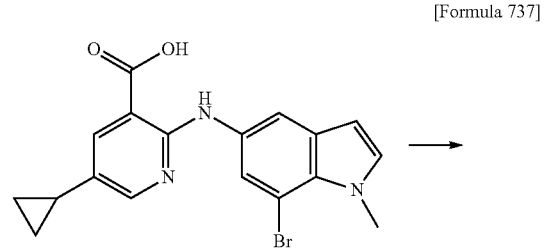

[Formula 737]

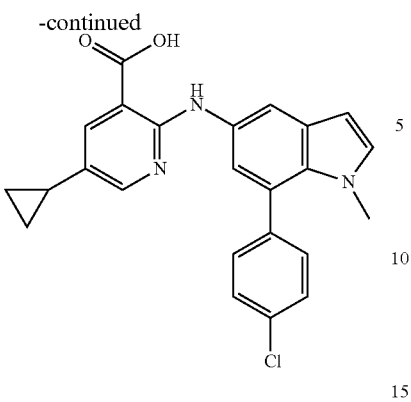

By the method similar to that of Example 463, 2-((7-(4-chlorophenyl)-1-methyl-1H-indol-5-yl)amino)-5-cyclopropylnicotinic acid was obtained from 2-((7-bromo-1-methyl-1H-indol-5-yl)amino)-5-cyclopropylnicotinic acid and 4-chlorophenylboronic acid.

$^1$H-NMR (DMSO-$d_6$) δ: 0.60-0.68 (2H, m), 0.85-0.95 (2H, m), 1.80-1.95 (1H, m), 3.28 (3H, s), 6.46 (1H, d, J=2.6 Hz), 7.01 (1H, d, J=2.0 Hz), 7.25 (1H, d, J=2.6 Hz), 7.46-7.60 (4H, m), 7.88 (1H, d, J=2.6 Hz), 8.06 (1H, d, J=2.0 Hz), 8.20 (1H, d, J=2.0 Hz), 10.25 (1H, brs).

MS (ESI, m/z): 418 (M+H)$^+$, 416 (M−H)$^-$.

Example 491

[Formula 738]

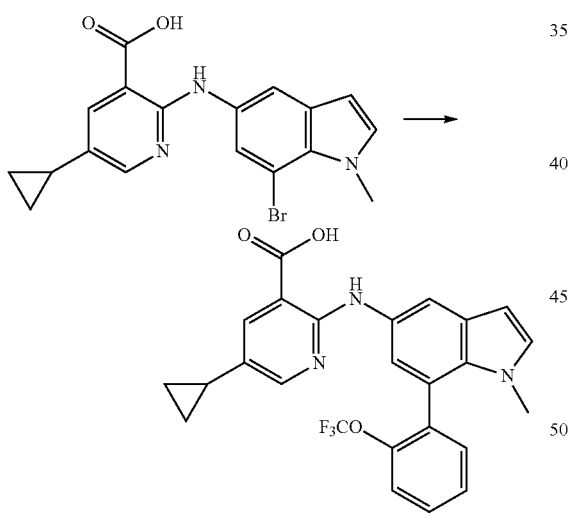

By the method similar to that of Example 463, 5-cyclopropyl-2-((1-methyl-7-(2-(trifluoromethoxy)phenyl)-1H-indol-5-yl)amino)nicotinic acid was obtained from 2-((7-bromo-1-methyl-1H-indol-5-yl)amino)-5-cyclopropylnicotinic acid and 2-(trifluoromethoxy)phenylboronic acid.

$^1$H-NMR (DMSO-$d_6$) δ: 0.60-0.69 (2H, m), 0.86-0.95 (2H, m), 1.82-1.96 (1H, m), 3.20 (3H, s), 6.44 (1H, d, J=3.3 Hz), 7.03 (1H, d, J=2.0 Hz), 7.23 (1H, d, J=3.3 Hz), 7.46-7.66 (4H, m), 7.88 (1H, d, J=2.6 Hz), 8.09 (1H, d, J=2.0 Hz), 8.20 (1H, d, J=2.6 Hz), 10.27 (1H, s).

MS (ESI, m/z): 468 (M+H)$^+$, 466 (M−H)$^-$.

Example 492

[Formula 739]

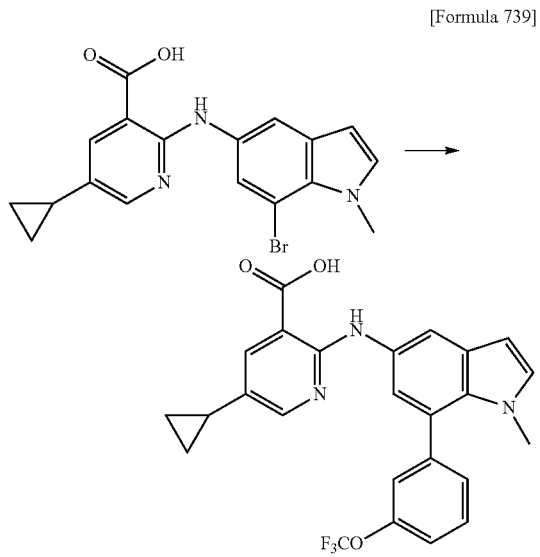

By the method similar to that of Example 463, 5-cyclopropyl-2-((1-methyl-7-(3-(trifluoromethoxy)phenyl)-1H-indol-5-yl)amino)nicotinic acid was obtained from 2-((7-bromo-1-methyl-1H-indol-5-yl)amino)-5-cyclopropylnicotinic acid and 3-(trifluoromethoxy)phenylboronic acid.

$^1$H-NMR (DMSO-$d_6$) δ: 0.60-0.69 (2H, m), 0.84-0.95 (2H, m), 1.84-1.95 (1H, m), 3.26 (3H, s), 6.47 (1H, d, J=3.3 Hz), 7.05 (1H, d, J=2.0 Hz), 7.26 (1H, d, J=3.3 Hz), 7.42-7.66 (4H, m), 7.88 (1H, d, J=2.6 Hz), 8.08 (1H, d, J=2.0 Hz), 8.20 (1H, d, J=2.6 Hz), 10.25 (1H, s).

MS (ESI, m/z): 468 (M+H)$^+$, 466 (M−H)$^-$.

Example 493

[Formula 740]

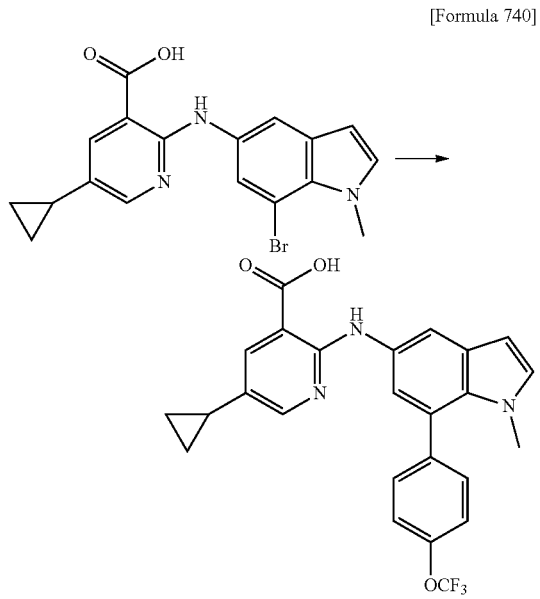

473

By the method similar to that of Example 463, 5-cyclopropyl-2-((1-methyl-7-(4-(trifluoromethoxy)phenyl)-1H-indol-5-yl)amino)nicotinic acid was obtained from 2-((7-bromo-1-methyl-1H-indol-5-yl)amino)-5-cyclopropylnicotinic acid and 4-(trifluoromethoxy)phenylboronic acid.

$^1$H-NMR (DMSO-d$_6$) δ: 0.60-0.69 (2H, m), 0.86-0.95 (2H, m), 1.83-1.96 (1H, m), 3.27 (3H, s), 6.46 (1H, d, J=2.6 Hz), 7.04 (1H, d, J=2.0 Hz), 7.26 (1H, d, J=3.3 Hz), 7.45 (2H, d, J=7.9 Hz), 7.61 (2H, d, J=8.6 Hz), 7.88 (1H, d, J=2.6 Hz), 8.07 (1H, d, J=2.0 Hz), 8.20 (1H, d, J=2.6 Hz), 10.25 (1H, s).

MS (ESI, m/z): 468 (M+H)$^+$, 466 (M−H)$^-$.

Example 494

[Formula 741]

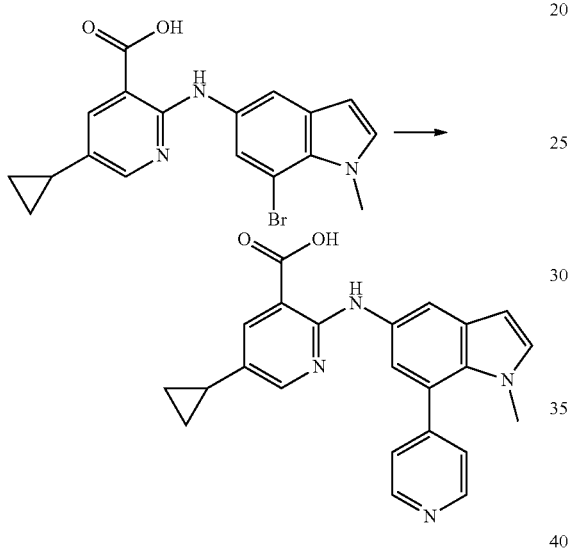

By the method similar to that of Example 463, 5-cyclopropyl-2-((1-methyl-7-(pyridin-4-yl)-1H-indol-5-yl)amino)nicotinic acid was obtained from 2-((7-bromo-1-methyl-1H-indol-5-yl)amino)-5-cyclopropylnicotinic acid and 4-pyridinylboronic acid.

$^1$H-NMR (DMSO-d$_6$) δ: 0.60-0.68 (2H, m), 0.84-0.94 (2H, m), 1.82-1.94 (1H, m), 3.20-3.40 (3H, m), 6.48 (1H, d, J=3.3 Hz), 7.06 (1H, d, J=2.0 Hz), 7.28 (1H, d, J=3.3 Hz), 7.49-7.56 (2H, m), 7.87 (1H, d, J=2.6 Hz), 8.11 (1H, d, J=2.0 Hz), 8.17 (1H, d, J=2.6 Hz), 8.62-8.69 (2H, m).

MS (ESI, m/z): 385 (M+H)$^+$, 383 (M−H)$^-$.

Example 495

[Formula 742]

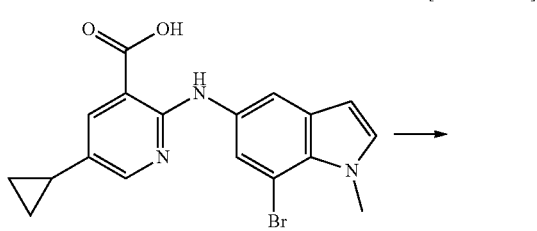

474

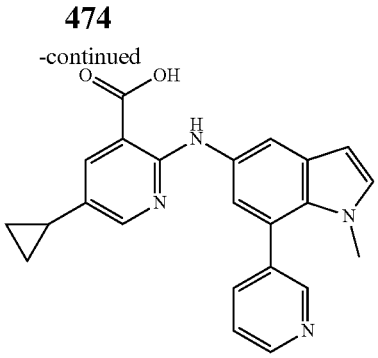

By the method similar to that of Example 463, 5-cyclopropyl-2-((1-methyl-7-(pyridin-3-yl)-1H-indol-5-yl)amino)nicotinic acid was obtained from 2-((7-bromo-1-methyl-1H-indol-5-yl)amino)-5-cyclopropylnicotinic acid and 3-pyridinylboronic acid.

$^1$H-NMR (DMSO-d$_6$) δ: 0.60-0.69 (2H, m), 0.84-0.96 (2H, m), 1.82-1.96 (1H, m), 3.28 (3H, s), 6.47 (1H, d, J=3.3 Hz), 7.06 (1H, d, J=2.0 Hz), 7.27 (1H, d, J=3.3 Hz), 7.50 (1H, dd, J=7.6, 5.0 Hz), 7.85-7.96 (2H, m), 8.10 (1H, d, J=2.0 Hz), 8.20 (1H, d, J=2.6 Hz), 8.65 (1H, dd, J=4.6, 1.3 Hz), 8.70 (1H, d, J=1.3 Hz), 10.30 (1H, brs).

MS (ESI, m/z): 385 (M+H)$^+$, 383 (M−H)$^-$.

Example 496

[Formula 743]

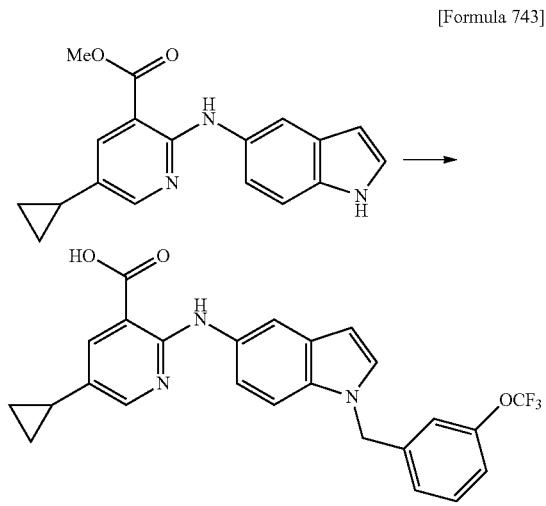

To the mixture of 50 mg of methyl 2-((1H-indol-5-yl)amino)-5-cyclopropylnicotinate, 40 μL of 1-(bromomethyl)-3-(trifluoromethoxy)benzene and 1.5 mL of N,N-dimethylformamide, 15 mg of 60% sodium hydride was added under ice-cooling, and the resultant was stirred at room temperature for 20 minutes. 100 μL of a 5 mol/L aqueous sodium hydroxide solution was added thereto, and the resultant was stirred at room temperature for two hours and 40 minutes. The reaction mixture was allowed to stand at room temperature overnight. The reaction mixture was adjusted to pH 2.5 by adding thereto hydrochloric acid. Ethyl acetate was added thereto, and the organic layer was separated and the aqueous layer was extracted with ethyl acetate twice. The organic layer and the extract were combined and the solvent was distilled of under reduced pressure. The obtained residue was purified by silica gel column chromatography (gradient elution with hexane:ethyl acetate=90:10-50:50) to give 58 mg of 5-cyclopropyl-2-((1-(3-(trifluoromethoxy)benzyl)-1H-indol-5-yl)amino)nicotinic acid as a yellow solid.

$^1$H-NMR (DMSO-d$_6$) δ: 0.59-0.67 (2H, m), 0.86-0.95 (2H, m), 1.82-1.95 (1H, m), 5.47 (2H, s), 6.46 (1H, d, J=3.3 Hz), 7.13-7.22 (3H, m), 7.24 (1H, d, J=8.6 Hz), 7.38 (1H, d, J=8.6 Hz), 7.44 (1H, t, =7.9 Hz), 7.50 (1H, d, J=2.6 Hz), 7.86 (1H, d, J=2.6 Hz), 7.99 (1H, d, J=2.0 Hz), 8.18 (1H, d, J=2.6 Hz), 10.14 (1H, s).

MS (ESI, m/z): 468 (M+H)$^+$, 466 (M−H)$^-$.

Example 497

[Formula 744]

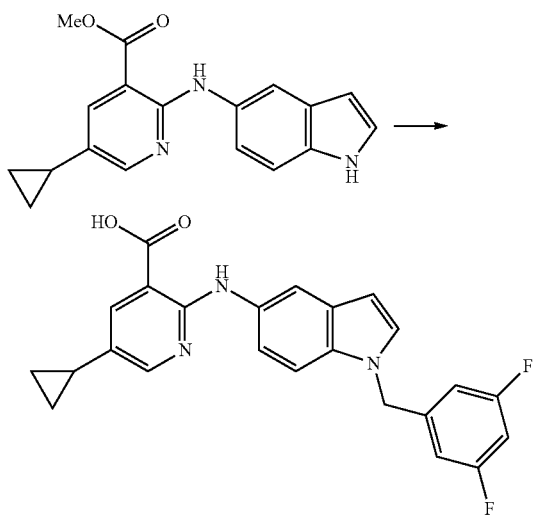

By the method similar to that of Example 496, 5-cyclopropyl-2-((1-(3,5-difluorobenzyl)-1H-indol-5-yl)amino)nicotinic acid was obtained from methyl 2-((1H-indol-5-yl)amino)-5-cyclopropylnicotinate and 1-(bromomethyl)-3,5-difluorobenzene.

$^1$H-NMR (DMSO-d$_6$) δ: 0.59-0.68 (2H, m), 0.85-0.95 (2H, m), 1.82-1.96 (1H, m), 5.44 (2H, s), 6.46 (1H, d, J=2.6 Hz), 6.82-6.92 (2H, m), 7.07-7.22 (2H, m), 7.38 (1H, d, J=8.6 Hz), 7.51 (1H, d, J=3.3 Hz), 7.86 (1H, d, J=2.0 Hz), 7.99 (1H, d, J=2.0 Hz), 8.18 (1H, d, J=2.6 Hz), 10.16 (1H, brs).

MS (ESI, m/z): 420 (M+H)$^+$, 418 (M−H)$^-$.

Example 498

[Formula 745]

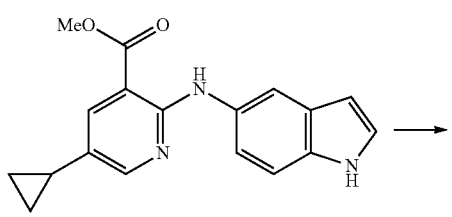

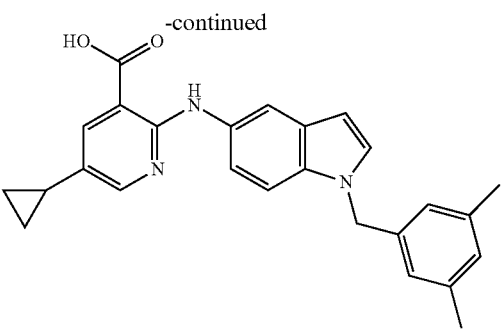

By the method similar to that of Example 496, 5-cyclopropyl-2-((1-(3,5-dimethylbenzyl)-1H-indol-5-yl)amino)nicotinic acid was obtained from methyl 2-((1H-indol-5-yl)amino)-5-cyclopropylnicotinate and 1-(bromomethyl)-3,5-dimethylbenzene.

$^1$H-NMR (DMSO-d$_6$) δ: 0.59-0.64 (2H, m), 0.87-1.00 (2H, m), 1.86-1.93 (1H, m), 2.20 (6H, s), 5.30 (2H, s), 6.42 (1H, d, J=3.3 Hz), 6.78-6.92 (3H, m), 7.16 (1H, dd, J=8.6, 2.0 Hz), 7.35 (1H, d, J=8.6 Hz), 7.44 (1H, d, J=2.6 Hz), 7.86 (1H, d, J=2.6 Hz), 7.95 (1H, d, J=2.0 Hz), 8.17 (1H, d, J=2.0 Hz), 10.10 (1H, s).

MS (ESI, m/z): 412 (M+H)$^+$, 410 (M−H)$^-$.

Example 499

[Formula 746]

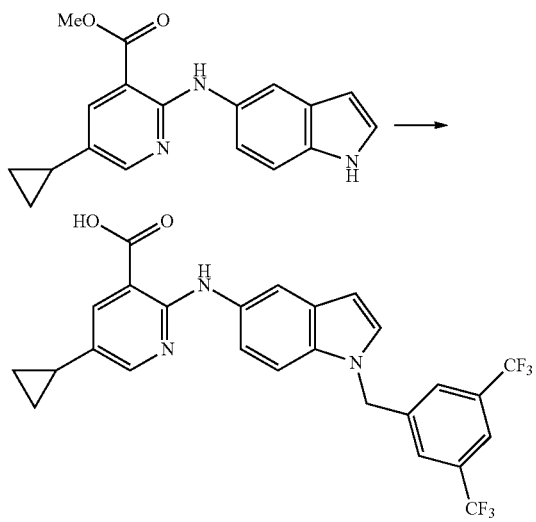

By the method similar to that of Example 496, 2-((1-(3,5-bis(trifluoromethyl)benzyl)-1H-indol-5-yl)amino)-5-cyclopropylnicotinic acid was obtained from methyl 2-((1H-indol-5-yl)amino)-5-cyclopropylnicotinate and 1-(bromomethyl)-3,5-bis(trifluoromethyl)benzene.

$^1$H-NMR (DMSO-d$_6$) δ: 0.59-0.68 (2H, m), 0.85-0.95 (2H, m), 1.82-1.96 (1H, m), 5.62 (2H, s), 6.49 (1H, d, J=2.6 Hz), 7.19 (1H, dd, J=8.6, 2.0 Hz), 7.45 (1H, d, J=9.2 Hz), 7.58 (1H, d, J=2.6 Hz), 7.83-7.90 (3H, m), 7.98-8.05 (2H, m), 8.18 (1H, d, J=2.0 Hz), 10.15 (1H, brs).

MS (ESI, m/z): 520 (M+H)$^+$, 518 (M−H)$^-$.

Example 500

[Formula 747]

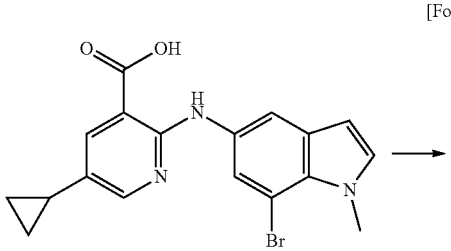

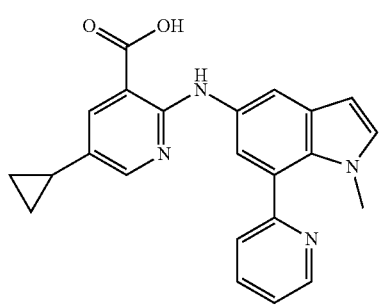

The reaction mixture of 100 mg of 2-((7-bromo-1-methyl-1H-indol-5-yl)amino)-5-cyclopropylnicotinic acid, 286 mg of 2-(tributylstannyl)pyridine, 47 mg of tris(dibenzylideneacetone)dipalladium(0), 32 mg of tri(o-tolyl)phosphine and 2.0 mL of N,N-dimethylformamide was heated at reflux at an external temperature of 120° C. for three hours under a nitrogen atmosphere. After the mixture was cooled to room temperature, a saturated aqueous potassium fluoride solution was added thereto, and the resultant was stirred for one hour. The insoluble matter was filtered off and the filtrate was adjusted to pH 4.0 by adding thereto hydrochloric acid. Ethyl acetate was added thereto, and the organic layer was separated and the aqueous layer was extracted with ethyl acetate. The organic layer and the extract were combined and the solvent was distilled off under reduced pressure. The obtained residue was purified by silica gel column chromatography (gradient elution with chloroform:methanol=100:0-95:5). The residue was purified again by silica gel column chromatography (gradient elution with hexane:ethyl acetate=80:20-0:100). 6.3 mg of 5-cyclopropyl-2-((1-methyl-7-(pyridin-2-yl)-1H-indol-5-yl)amino)nicotinic acid as a yellow solid was obtained.

$^1$H-NMR (DMSO-$d_6$) δ: 0.60-0.69 (2H, m), 0.85-0.95 (2H, m), 1.83-1.96 (1H, m), 3.20-3.50 (3H, m), 6.47 (1H, d, J=3.3 Hz), 7.15 (1H, d, J=2.0 Hz), 7.26 (1H, d, J=3.3 Hz), 7.38-7.48 (1H, m), 7.65 (1H, d, J=7.9 Hz), 7.85-7.96 (2H, m), 8.08 (1H, d, J=2.0 Hz), 8.19 (1H, d, J=2.0 Hz), 8.69 (1H, d, J=4.6 Hz).

MS (ESI, m/z): 385 (M+H)$^+$, 383 (M−H)$^−$.

Example 501

[Formula 748]

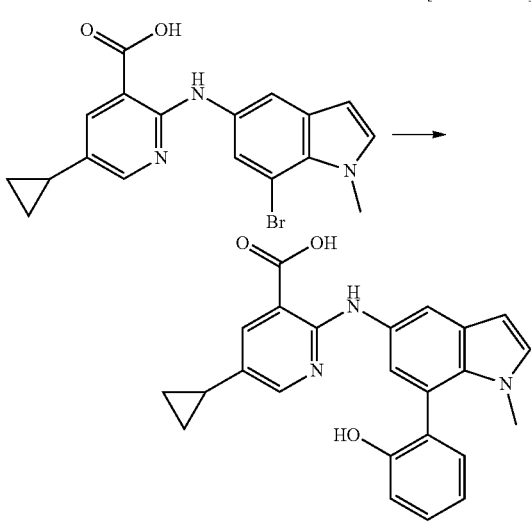

By the method similar to that of Example 463, 5-cyclopropyl-2-((7-(2-hydroxyphenyl)-1-methyl-1H-indol-5-yl)amino)nicotinic acid was obtained from 2-((7-bromo-1-methyl-1H-indol-5-yl)amino)-5-cyclopropylnicotinic acid and 2-hydroxyphenylboronic acid.

$^1$H-NMR (DMSO-$d_6$) δ: 0.60-0.69 (2H, m), 0.84-0.95 (2H, m), 1.83-1.95 (1H, m), 3.20-3.40 (3H, m), 6.39 (1H, d, J=3.3 Hz), 6.84-6.98 (3H, m), 7.14-7.30 (3H, m), 7.87 (1H, d, J=2.6 Hz), 8.01 (1H, d, J=2.0 Hz), 8.20 (1H, d, J=2.6 Hz), 9.45 (1H, s), 10.23 (1H, brs).

MS (ESI, m/z): 400 (M+H)$^+$, 398 (M−H)$^−$.

Example 502

[Formula 749]

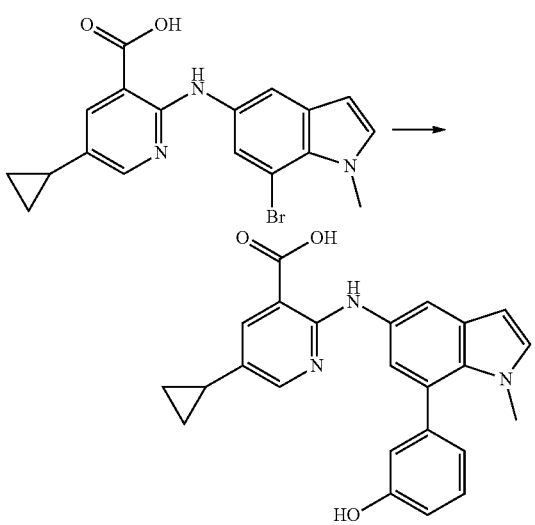

By the method similar to that of Example 463, 5-cyclopropyl-2-((7-(3-hydroxyphenyl)-1-methyl-1H-indol-5-yl)amino)nicotinic acid was obtained from 2-((7-bromo-1- methyl-1H-indol-5-yl)amino)-5-cyclopropylnicotinic acid and 3-hydroxyphenylboronic acid.

$^1$H-NMR (DMSO-d$_6$) δ: 0.60-0.69 (2H, m), 0.84-0.94 (2H, m), 1.83-1.95 (1H, m), 3.30 (3H, s), 6.44 (1H, d, J=3.3 Hz), 6.78-6.89 (3H, m), 6.99 (1H, d, J=2.0 Hz), 7.20-7.29 (2H, m), 7.88 (1H, d, J=2.6 Hz), 8.01 (1H, d, J=2.0 Hz), 8.20 (1H, d, J=2.6 Hz), 9.57 (1H, s), 10.25 (1H, brs).

MS (ESI, m/z): 400 (M+H)$^+$, 398 (M−H)$^−$.

Example 503

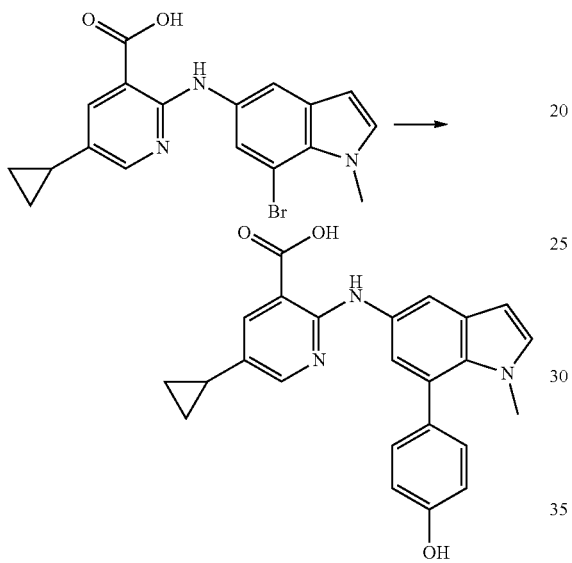

[Formula 750]

By the method similar to that of Example 463, 5-cyclopropyl-2-((7-(4-hydroxyphenyl)-1-methyl-1H-indol-5-yl) amino)nicotinic acid was obtained from 2-((7-bromo-1-methyl-1H-indol-5-yl)amino)-5-cyclopropylnicotinic acid and 4-hydroxyphenylboronic acid.

$^1$H-NMR (DMSO-d$_6$) δ: 0.60-0.69 (2H, m), 0.84-0.95 (2H, m), 1.82-1.95 (1H, m), 3.28 (3H, s), 6.42 (1H, d, J=3.3 Hz), 6.84 (2H, d, J=8.6 Hz), 6.93 (1H, d, J=2.0 Hz), 7.20 (1H, d, J=3.3 Hz), 7.24 (2H, d, J=8.7 Hz), 7.87 (1H, d, J=2.6 Hz), 8.00 (1H, d, J=2.0 Hz), 8.20 (1H, d, J=2.0 Hz), 9.55 (1H, s), 10.23 (1H, brs).

MS (ESI, m/z): 400 (M+H)$^+$, 398 (M−H)$^−$.

Example 504

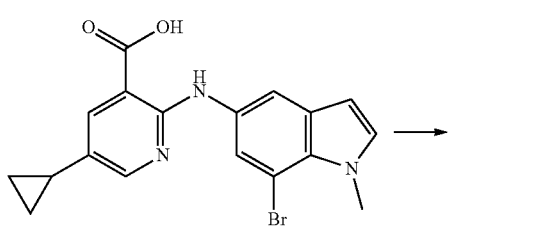

[Formula 751]

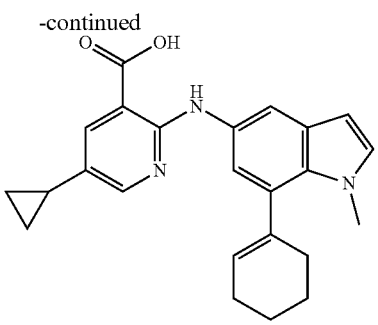

-continued

By the method similar to that of Example 463, 2-((7-cyclohex-1-en-1-yl)-1-methyl-1H-indol-5-yl)amino)-5-cyclopropylnicotinic acid was obtained from 2-((7-bromo-1-methyl-1H-indol-5-yl)amino)-5-cyclopropylnicotinic acid and (1-cyclohexen-1-yl)boronic acid pinacol ester.

$^1$H-NMR (DMSO-d$_6$) δ: 0.60-0.69 (2H, m), 0.84-0.95 (2H, m), 1.62-1.96 (5H, m), 2.14-2.36 (4H, m), 3.78 (3H, s), 5.63-5.72 (1H, m), 6.36 (1H, d, J=2.6 Hz), 6.76 (1H, d, J=2.0 Hz), 7.20 (1H, d, J=2.6 Hz), 7.87 (1H, d, J=2.6 Hz), 7.98 (1H, d, J=2.0 Hz), 8.20 (1H, d, J=2.6 Hz), 10.17 (1H, brs).

MS (ESI, m/z): 388 (M+H)$^+$.

Example 505

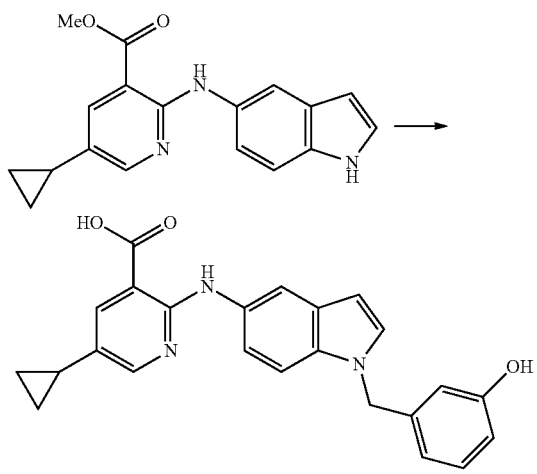

[Formula 752]

To the solution of 500 mg of methyl 2-((1H-indol-5-yl)amino)-5-cyclopropylnicotinate in 10 mL of N,N-dimethylformamide, 456 mg of potassium tert-butoxide was added under ice-cooling, and the resultant was stirred for five minutes. The solution of 516 mg of (3-(bromomethyl)phenoxy)(tert-butyl)dimethylsilane in 2 mL of N,N-dimethylformamide was added thereto under ice-cooling, and the resultant was stirred for 55 minutes. 2 mL of a 5 mol/L aqueous sodium hydroxide solution was added thereto, and the resultant was stirred at room temperature for five hours and 30 minutes. The reaction mixture was adjusted to pH 2.5 by adding thereto hydrochloric acid. Ethyl acetate was added thereto, and the organic layer was separated and the aqueous layer was extracted with ethyl acetate twice. The organic layer and the extract were combined and the solvent was distilled off under reduced pressure. The obtained residue was purified by silica gel column chromatography (gradient elution with hexane:ethyl acetate=70:30-20:80) to give 220 mg of 5-cyclopropyl-2-((1-(3-hydroxybenzyl)-1H-indol-5-yl)amino)nicotinic acid as a pale brown solid.

$^1$H-NMR (DMSO-d$_6$) δ: 0.58-0.68 (2H, m), 0.83-0.95 (2H, m), 1.82-1.94 (1H, m), 5.31 (2H, s), 6.42 (1H, d, J=2.6 Hz), 6.50 (1H, s), 6.58-6.68 (2H, m), 7.04-7.18 (2H, m), 7.32 (1H, d, J=9.2 Hz), 7.42 (1H, d, J=2.6 Hz), 7.85 (1H, d, J=2.6 Hz), 7.94-8.02 (1H, m), 8.12-8.18 (1H, m), 9.35 (1H, s).

MS (ESI, m/z): 400 (M+H)$^+$.

Example 506

[Formula 753]

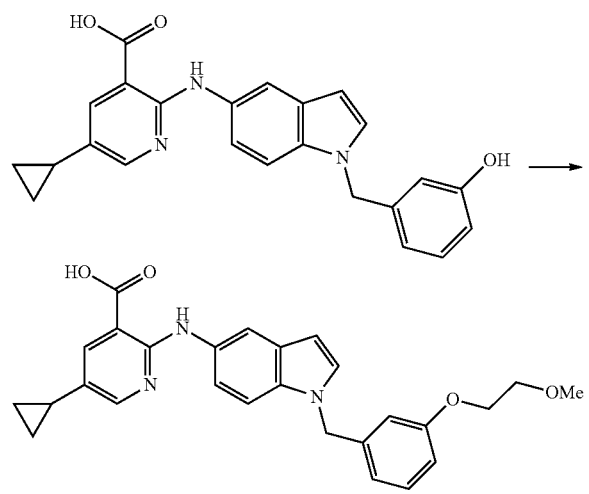

The reaction mixture of 50 mg of 5-cyclopropyl-2-((1-(3-hydroxybenzyl)-1H-indol-5-yl)amino)nicotinic acid, 24 μL of 1-bromo-2-methoxyethane, 51 mg of potassium carbonate and 1.0 mL of N,N-dimethylformamide was stirred at room temperature for 30 minutes. Such a reaction mixture was stirred at an external temperature of 60° C. for one hour and 30 minutes. After cooling it to room temperature, 24 μL of 1-bromo-2-methoxyethane and 20 mg of 60% sodium hydride were added thereto, and the resultant was stirred for 30 minutes. The reaction mixture was adjusted to pH 2.5 by adding thereto hydrochloric acid. Ethyl acetate was added thereto, and the organic layer was separated and the aqueous layer was extracted with ethyl acetate twice. The organic layer and the extract were combined and the solvent was distilled off under reduced pressure. The obtained residue was purified by silica gel column chromatography (gradient elution with hexane:ethyl acetate=90:10-20:80). The obtained solid was purified by preparative thin-layer chromatography (ethyl acetate) to give 18.8 mg of 5-cyclopropyl-2-((1-(3-(2-methoxyethoxy)benzyl)-1H-indol-5-yl)amino)nicotinic acid as a yellow solid.

$^1$H-NMR (DMSO-d$_6$) δ: 0.58-0.68 (2H, m), 0.80-0.95 (2H, m), 1.82-1.95 (1H, m), 3.27 (3H, s), 3.56-3.65 (2H, m), 3.96-4.04 (2H, m), 5.35 (2H, s), 6.43 (1H, d, J=2.6 Hz), 6.70-6.85 (3H, m), 7.12-7.25 (2H, m), 7.36 (1H, d, J=9.2 Hz), 7.47 (1H, d, J=2.6 Hz), 7.86 (1H, d, J=2.6 Hz), 7.97 (1H, d, J=1.3 Hz), 8.17 (1H, d, J=2.6 Hz), 10.14 (1H, brs).

MS (ESI, m/z): 458 (M+H)$^+$, 456 (M−H)$^−$.

Example 507

[Formula 754]

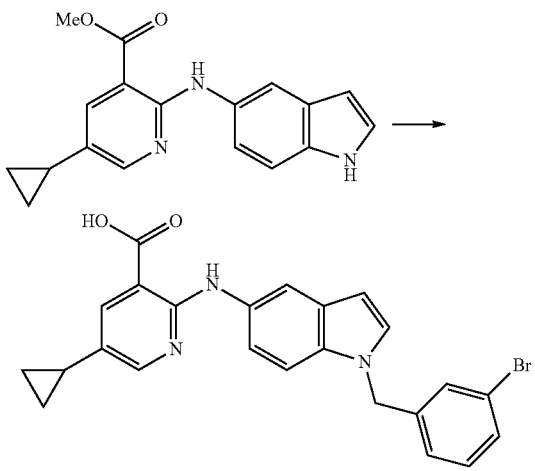

By the method similar to that of Example 496, 2-((1-(3-bromobenzyl)-1H-indol-5-yl)amino)-5-cyclopropylnicotinic acid was obtained from methyl 2-((1H-indol-5-yl)amino)-5-cyclopropylnicotinate and 1-(bromomethyl)-3-bromobenzene.

MS (ESI, m/z): 464 (M+H)$^+$.

Example 508

[Formula 755]

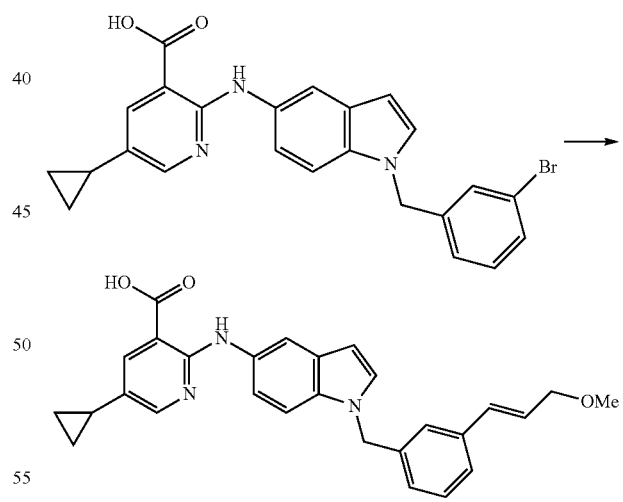

The mixture of 42 mg of 2-((1-(3-bromobenzyl)-1H-indol-5-yl)amino)-5-cyclopropylnicotinic acid, 23 μL of trans-3-methoxy-1-propenylboronic acid pinacol ester, 39 mg of tripotassium phosphate, 6.4 mg of bis(di-tert-butyl(4-dimethylaminophenyl)phosphine)dichloropalladium(II), 1.5 mL of dioxane and 0.4 mL of water was heated at reflux for two hours. The reaction mixture was cooled to room temperature and then adjusted to pH 2.5 by adding thereto hydrochloric acid. Ethyl acetate was added thereto, and the organic layer was separated and the aqueous layer was extracted with ethyl acetate twice. The organic layer and the extract were combined and the solvent was distilled off under reduced pressure. The obtained residue was purified by silica gel column chromatography (gradient elution with hexane:ethyl acetate=90:10-30:70) to give 25.5 mg of (E)-5-cyclopropyl-2-((1-(3-(3-methoxyprop-1-en-1-yl)benzyl)-1H-indol-5-yl)amino)nicotinic acid as a yellow solid.

¹H-NMR (DMSO-d₆) δ: 0.58-0.68 (2H, m), 0.85-0.94 (2H, m), 1.80-1.95 (1H, m), 3.26 (3H, s), 3.98-4.04 (2H, m), 5.38 (2H, s), 6.22-6.35 (1H, m), 6.43 (1H, d, J=2.6 Hz), 6.54 (1H, d, J=15.9 Hz), 7.05 (1H, d, J=7.3 Hz), 7.16 (1H, dd, J=8.6, 2.0 Hz), 7.26 (1H, t, J=7.9 Hz), 7.30-7.42 (3H, m), 7.49 (1H, d, J=3.3 Hz), 7.86 (1H, d, J=2.6 Hz), 7.90-8.00 (1H, m), 8.17 (1H, d, J=2.6 Hz), 10.12 (1H, brs).

MS (ESI, m/z): 454 (M+H)⁺, 452 (M−H)⁻.

Example 509

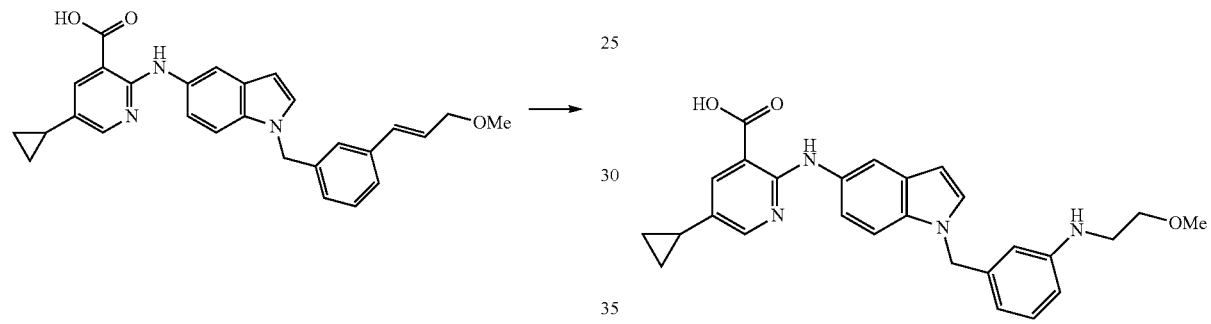

[Formula 756]

The solution of 23 mg of (E)-5-cyclopropyl-2-((1-(3-(3-methoxyprop-1-en-1-yl)benzyl)-1H-indol-5-yl)amino)nicotinic acid in 5 ml of methanol and 1 ml of tetrahydrofuran was subjected to hydrogenation reaction (room temperature, 1 bar, flow rate: 2 mL/min, 10% Pd/C) using the flow hydrogenation reactor. The solvent was distilled off under reduced pressure, and the obtained residue was then purified by preparative thin-layer chromatography (ethyl acetate) to give 1.1 mg of 5-cyclopropyl-2-((1-(3-(3-methoxypropyl)benzyl)-1H-indol-5-yl)amino)nicotinic acid as a yellow solid.

¹H-NMR (CDCl₃) δ: 0.58-0.65 (2H, m), 0.87-0.94 (2H, m), 1.76-1.88 (3H, m), 2.62 (2H, t, J=7.8 Hz), 3.30 (3H, s), 3.33 (2H, t, J=6.5 Hz), 5.25 (2H, s), 6.46-6.51 (1H, m), 6.89-6.98 (2H, m), 7.05-7.10 (2H, m), 7.16-7.32 (3H, m), 7.82-7.89 (1H, m), 7.92-7.99 (1H, m), 8.08-8.18 (1H, m).

MS (ESI, m/z): 456 (M+H)⁺, 454 (M−H)⁻.

Example 510

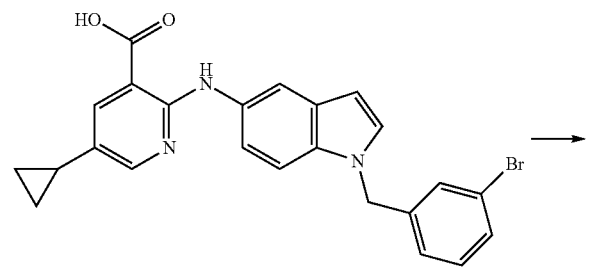

[Formula 757]

The mixture of 50 mg of 2-((1-(3-bromobenzyl)-1H-indol-5-yl)amino)-5-cyclopropylnicotinic acid, 188 μL of 2-methoxyethylamine, 9.9 mg of tris(dibenzylideneacetone)dipalladium(0), 11.6 mg of 2-(dicyclohexylphosphino)-3,6-dimethoxy-2',4',6'-triisopropyl-1,1'biphenyl, 106 mg of sodium tert-butoxide and 4 mL of dioxane was stirred at 160° C. for one hour using microwave equipment. After cooling the reaction mixture to room temperature, the insoluble matter was filtered off and the solvent was distilled off under reduced pressure. The reaction mixture was adjusted to pH 4.0 by adding thereto hydrochloric acid. Ethyl acetate was added thereto, and the organic layer was separated and the aqueous layer was extracted with ethyl acetate twice and further extracted with tetrahydrofuran twice. The organic layer and the extract were combined and the solvent was distilled off under reduced pressure. The obtained residue was purified by silica gel column chromatography (gradient elution with hexane:ethyl acetate=70:30-0:100→ethyl acetate:methanol=95:5) to give 7.5 mg of 5-cyclopropyl-2-((1-(3-((2-methoxyethyl)amino)benzyl)-1H-indol-5-yl)amino)nicotinic acid as a yellow solid.

¹H-NMR (DMSO-d₆) δ: 0.55-0.62 (2H, m), 0.83-0.91 (2H, m), 1.80-1.90 (1H, m), 3.06-3.15 (2H, m), 3.23 (3H, s), 3.41 (2H, t, J=5.9 Hz), 5.11-5.25 (2H, m), 5.56 (1H, brs), 6.32-6.47 (4H, m), 6.94-7.00 (1H, m), 7.13 (1H, dd, J=8.5, 2.0 Hz), 7.30 (1H, d, J=8.8 Hz), 7.37 (1H, d, J=3.2 Hz), 7.84 (1H, d, J=2.4 Hz), 8.02-8.08 (2H, m).

MS (ESI, m/z): 457 (M+H)⁺.

Example 511

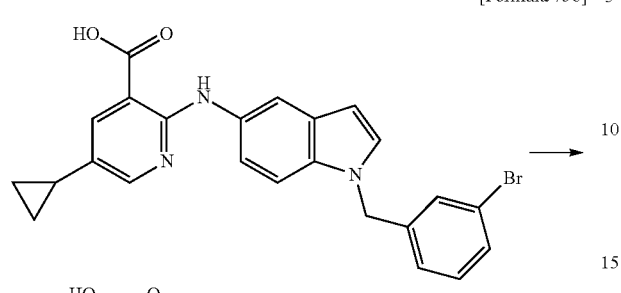

[Formula 758]

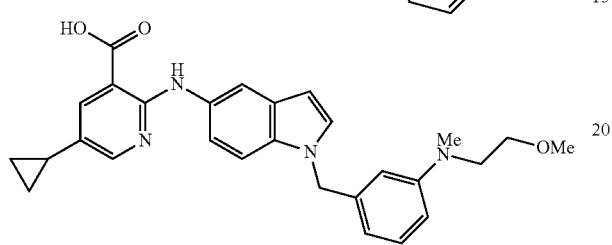

The mixture of 50 mg of 2-((1-(3-bromobenzyl)-1H-indol-5-yl)amino)-5-cyclopropylnicotinic acid, 235 μL of (2-methoxyethyl)methylamine, 9.9 mg of tris(dibenzylideneacetone)dipalladium(0), 11.6 mg of 2-(dicyclohexylphosphino)-3,6-dimethoxy-2',4',6'-triisopropyl-1,1'biphenyl, 106 mg of sodium tert-butoxide and 4 mL of dioxane was stirred at 160° C. for one hour using microwave equipment. After cooling the reaction mixture to room temperature, the insoluble matter was filtered off and the solvent was distilled off under reduced pressure. The reaction mixture was adjusted to pH 4.0 by adding thereto hydrochloric acid. Ethyl acetate was added thereto, and the organic layer was separated and the aqueous layer was extracted with ethyl acetate twice. The organic layer and the extract were combined and the solvent was distilled off under reduced pressure. The obtained residue was purified by silica gel column chromatography (gradient elution with chloroform:methanol=100:0-95:5) to give 26.5 mg of 5-cyclopropyl-2-((1-(3-((2-methoxyethyl)(methyl)amino)benzyl)-1H-indol-5-yl)amino)nicotinic acid as a yellow solid.

$^1$H-NMR (CDCl$_3$) δ: 0.60-0.67 (2H, m), 0.89-0.96 (2H, m), 1.76-1.85 (1H, m), 2.90 (3H, s), 3.30 (3H, s), 3.39-3.49 (4H, m), 5.18 (2H, s), 6.38-6.45 (2H, m), 6.48 (1H, d, J=2.9 Hz), 6.57-6.64 (1H, m), 7.05-7.15 (2H, m), 7.19-7.30 (2H, m), 7.85 (1H, s), 7.94-8.00 (1H, m), 8.09 (1H, s), 10.04 (1H, brs).

MS (ESI, m/z): 471 (M+H)$^+$, 469 (M−H)$^-$.

Example 512

[Formula 759]

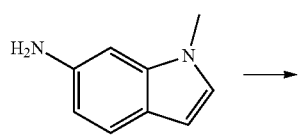 →

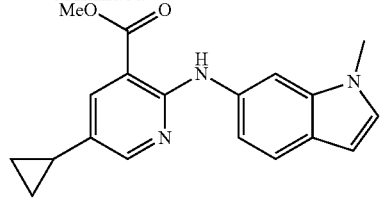

By the method similar to that of Example 221, methyl 5-cyclopropyl-2-((1-methyl-1H-indol-6-yl)amino)nicotinate was obtained from 1-methyl-1H-indol-6-amine and methyl 2-chloro-5-cyclopropylnicotinate.

MS (ESI, m/z): 322 (M+H)$^+$.

Example 513

[Formula 760]

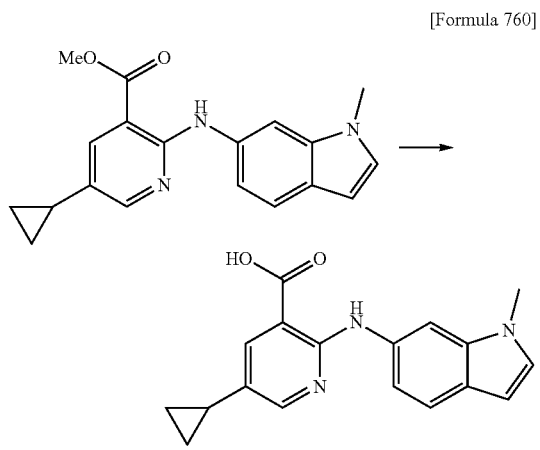

By the method similar to that of Example 222, 5-cyclopropyl-2-((1-methyl-1H-indol-6-yl)amino)nicotinic acid was obtained from methyl 5-cyclopropyl-2-((1-methyl-1H-indol-6-yl)amino)nicotinate.

$^1$H-NMR (DMSO-d$_6$) δ: 0.63-0.71 (2H, m), 0.88-0.97 (2H, m), 1.86-1.99 (1H, m), 3.75 (3H, s), 6.35 (1H, d, J=2.6 Hz), 7.13 (1H, dd, J=8.3, 1.7 Hz), 7.22 (1H, d, J=3.3 Hz), 7.45 (1H, d, J=8.6 Hz), 7.90 (1H, d, J=2.6 Hz), 7.96 (1H, s), 8.24 (1H, d, J=2.6 Hz), 10.32 (1H, s).

MS (ESI, m/z): 308 (M+H)$^+$.

Example 514

[Formula 761]

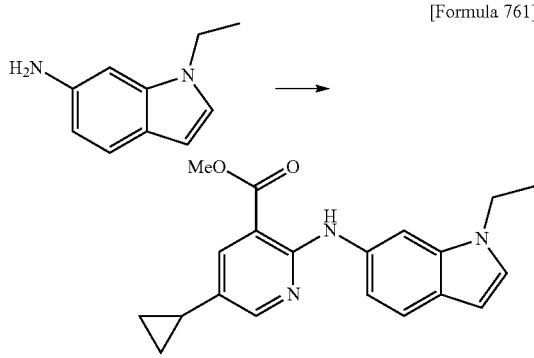

By the method similar to that of Example 221, methyl 5-cyclopropyl-2-((1-ethyl-1H-indol-6-yl)amino)nicotinate was obtained from 1-ethyl-1H-indol-6-amine and methyl 2-chloro-5-cyclopropylnicotinate.

MS (ESI, m/z): 336 (M+H)+.

Example 515

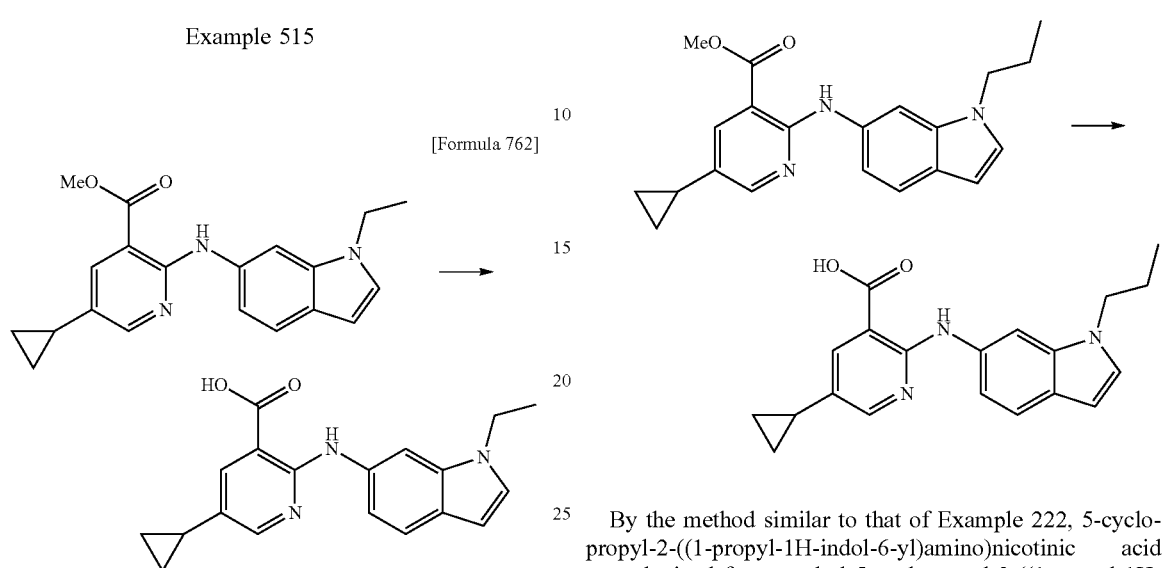

[Formula 762]

By the method similar to that of Example 222, 5-cyclopropyl-2-((1-ethyl-1H-indol-6-yl)amino)nicotinic acid was obtained from methyl 5-cyclopropyl-2-((1-ethyl-1H-indol-6-yl)amino)nicotinate.

$^1$H-NMR (DMSO-$d_6$) δ: 0.63-0.70 (2H, m), 0.88-0.96 (2H, m), 1.37 (3H, t, J=7.3 Hz), 1.86-1.98 (1H, m), 4.15 (2H, q, J=7.3 Hz), 6.36 (1H, d, J=2.6 Hz), 7.13 (1H, dd, J=8.3, 1.7 Hz), 7.28 (1H, d, J=3.3 Hz), 7.44 (1H, d, J=8.6 Hz), 7.89 (1H, d, J=2.6 Hz), 7.97 (1H, s), 8.23 (1H, d, J=2.0 Hz), 10.28 (1H, s).

MS (ESI, m/z): 322 (M+H)+.

Example 516

[Formula 763]

By the method similar to that of Example 221, methyl 5-cyclopropyl-2-((1-propyl-1H-indol-6-yl)amino)nicotinate was obtained from 1-propyl-1H-indol-6-amine and methyl 2-chloro-5-cyclopropylnicotinate.

MS (ESI, m/z): 350 (M+H)+.

Example 517

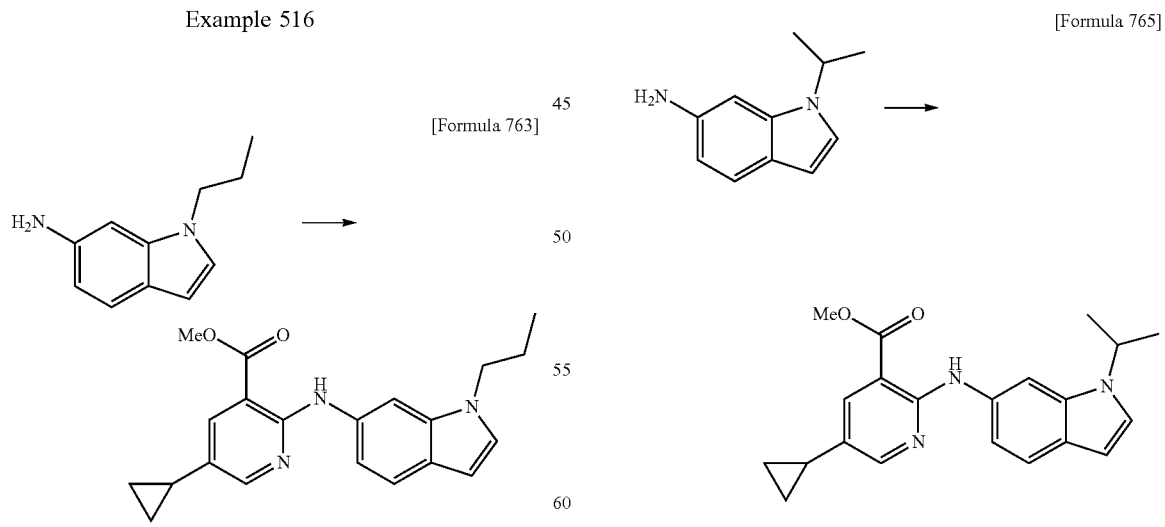

[Formula 764]

By the method similar to that of Example 222, 5-cyclopropyl-2-((1-propyl-1H-indol-6-yl)amino)nicotinic acid was obtained from methyl 5-cyclopropyl-2-((1-propyl-1H-indol-6-yl)amino)nicotinate.

$^1$H-NMR (DMSO-$d_6$) δ: 0.62-0.70 (2H, m), 0.82-0.96 (5H, m), 1.72-1.98 (3H, m), 4.08 (2H, t, 6.9 Hz), 6.35 (1H, d, J=2.6 Hz), 7.13 (1H, dd, J=8.6, 2.0 Hz), 7.27 (1H, d, J=3.3 Hz), 7.44 (1H, d, J=8.6 Hz), 7.89 (1H, d, J=2.6 Hz), 7.96 (1H, s), 8.22 (1H, d, J=2.6 Hz), 10.28 (1H, s).

MS (ESI, m/z): 336 (M+H)+.

Example 518

[Formula 765]

By the method similar to that of Example 221, methyl 5-cyclopropyl-2-((1-isopropyl-1H-indol-6-yl)amino)nicotinate was obtained from 1-isopropyl-1H-indol-6-amine and methyl 2-chloro-5-cyclopropylnicotinate.

MS (ESI, m/z): 350 (M+H)+.

Example 519

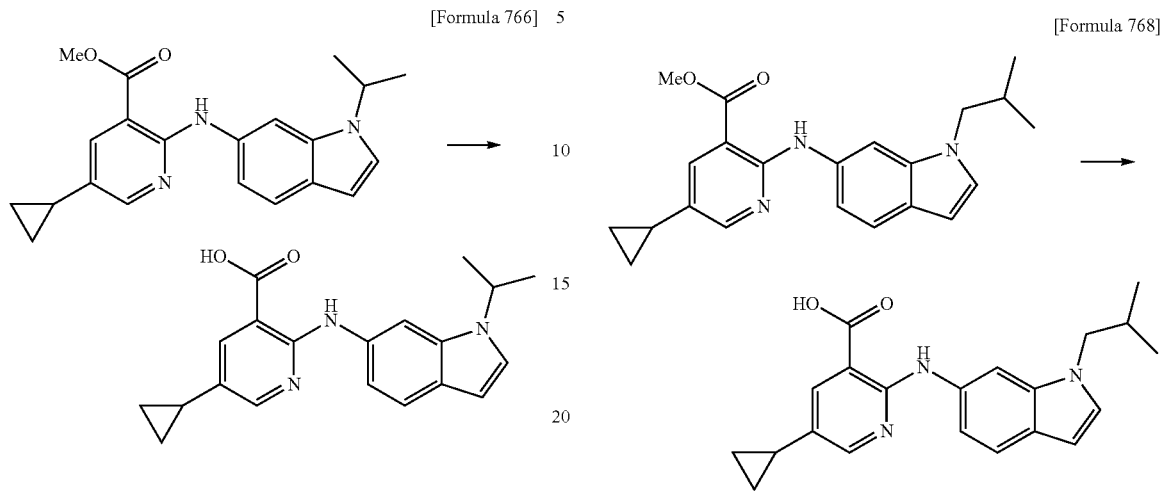

[Formula 766]

By the method similar to that of Example 222, 5-cyclopropyl-2-((1-isopropyl-1H-indol-6-yl)amino)nicotinic acid was obtained from methyl 5-cyclopropyl-2-((1-isopropyl-1H-indol-6-yl)amino)nicotinate.

$^1$H-NMR (DMSO-$d_6$) δ: 0.62-0.70 (2H, m), 0.87-0.96 (2H, m), 1.46 (6H, d, J=6.6 Hz), 1.86-1.97 (1H, m), 4.59-4.74 (1H, m), 6.38 (1H, d, J=2.6 Hz), 7.11 (1H, dd, J=8.6, 2.0 Hz), 7.38 (1H, d, J=3.3 Hz), 7.44 (1H, d, J=8.6 Hz), 7.89 (1H, d, J=2.6 Hz), 8.02 (1H, s), 8.23 (1H, d, J=2.6 Hz), 10.32 (1H, s).

MS (ESI, m/z): 336 (M+H)$^+$.

Example 520

[Formula 767]

By the method similar to that of Example 221, methyl 5-cyclopropyl-2-((1-isobutyl-1H-indol-6-yl)amino)nicotinate was obtained from 1-isobutyl-1H-indol-6-amine and methyl 2-chloro-5-cyclopropylnicotinate.

MS (ESI, m/z): 364 (M+H)$^+$.

Example 521

[Formula 768]

By the method similar to that of Example 222, 5-cyclopropyl-2-((1-isobutyl-1H-indol-6-yl)amino)nicotinic acid was obtained from methyl 5-cyclopropyl-2-((1-isobutyl-1H-indol-6-yl)amino)nicotinate.

$^1$H-NMR (DMSO-$d_6$) δ: 0.62-0.70 (2H, m), 0.85-0.95 (8H, m), 1.86-1.97 (1H, m), 2.06-2.22 (1H, m), 3.92 (2H, d, J=6.6 Hz), 6.35 (1H, d, J=2.6 Hz), 7.13 (1H, dd, J=8.6, 2.0 Hz), 7.24 (1H, d, J=3.3 Hz), 7.44 (1H, d, J=8.6 Hz), 7.88 (1H, d, J=2.6 Hz), 7.95 (1H, s), 8.21 (1H, d, J=2.6 Hz), 10.32 (1H, s).

MS (ESI, m/z): 350 (M+H)$^+$.

Example 522

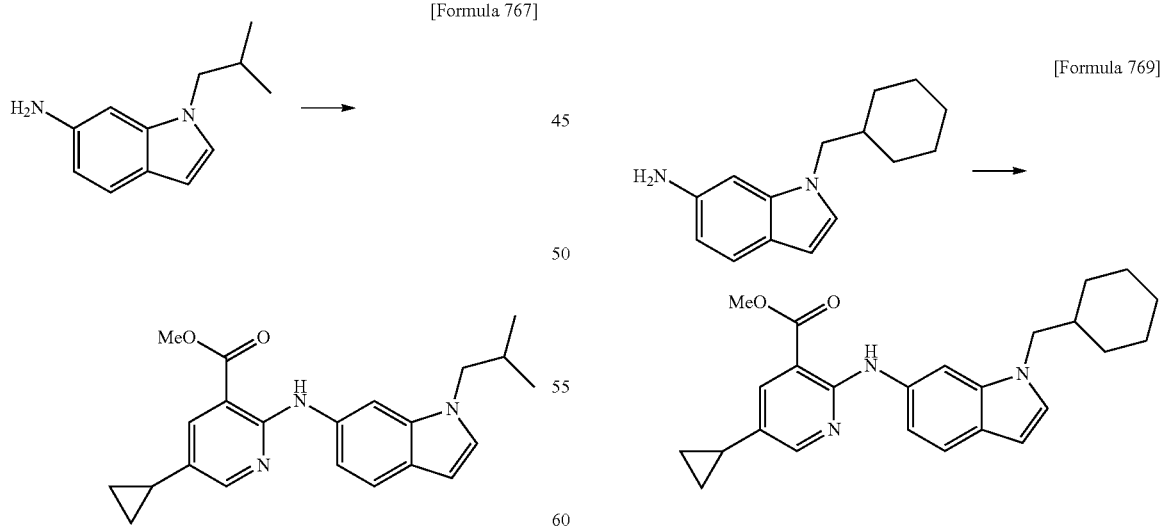

[Formula 769]

By the method similar to that of Example 221, methyl 2-((1-(cyclohexylmethyl)-1H-indol-6-yl)amino)-5-cyclopropylnicotinate was obtained from 1-(cyclohexylmethyl)-1H-indol-6-amine and methyl 2-chloro-5-cyclopropylnicotinate.

MS (ESI, m/z): 404 (M+H)$^+$.

Example 523

[Formula 770]

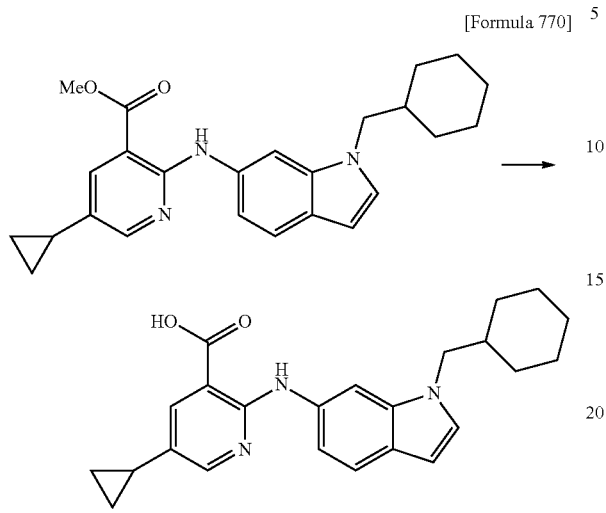

By the method similar to that of Example 222, 2-((1-(cyclohexylmethyl)-1H-indol-6-yl)amino)-5-cyclopropylnicotinic acid was obtained from methyl 2-((1-(cyclohexylmethyl)-1H-indol-6-yl)amino)-5-cyclopropylnicotinate.

$^1$H-NMR (DMSO-d$_6$) δ: 0.61-0.69 (2H, m), 0.83-1.26 (7H, m), 1.48-1.98 (7H, m), 3.95 (2H, d, J=7.3 Hz), 6.34 (1H, d, J=3.3 Hz), 7.14 (1H, dd, J=8.6, 2.0 Hz), 7.22 (1H, d, J=2.6 Hz), 7.43 (1H, d, J=7.9 Hz), 7.87 (1H, d, J=2.6 Hz), 7.91 (1H, s), 8.21 (1H, d, J=2.6 Hz), 10.28 (1H, s).

MS (ESI, m/z): 390 (M+H)$^+$.

Example 524

[Formula 771]

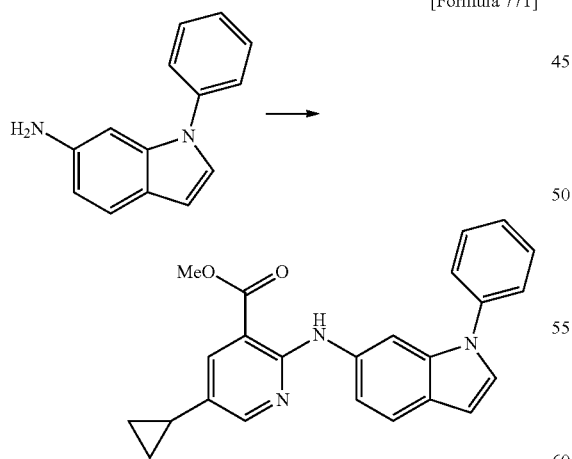

By the method similar to that of Example 221, methyl 5-cyclopropyl-2-((1-phenyl-1H-indol-6-yl)amino)nicotinate was obtained from 1-phenyl-1H-indol-6-amine and methyl 2-chloro-5-cyclopropylnicotinate.

MS (ESI, m/z): 384 (M+H)$^+$.

Example 525

[Formula 772]

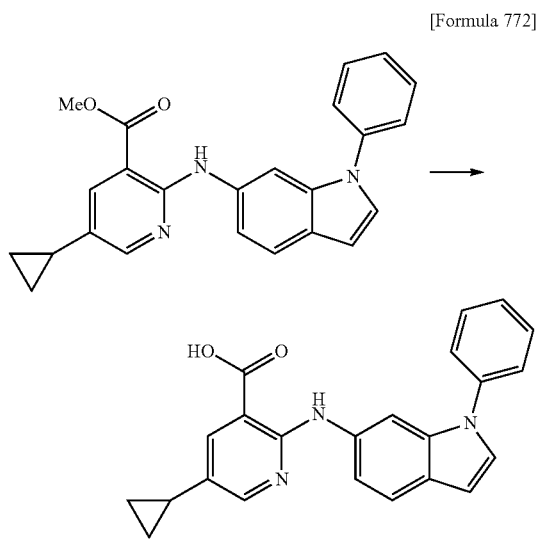

By the method similar to that of Example 222, 5-cyclopropyl-2-((1-phenyl-1H-indol-6-yl)amino)nicotinic acid was obtained from methyl 5-cyclopropyl-2-((1-phenyl-1H-indol-6-yl)amino)nicotinate.

$^1$H-NMR (DMSO-d$_6$) δ: 0.62-0.69 (2H, m), 0.85-0.95 (2H, m), 1.84-1.97 (1H, m), 6.64 (1H, d, J=2.6 Hz), 7.17 (1H, dd, J=8.6, 1.3 Hz), 7.35-7.46 (1H, m), 7.53-7.65 (6H, m), 7.88 (1H, d, J=2.6 Hz), 8.17 (1H, d, J=2.6 Hz), 8.30 (1H, s), 10.36 (1H, s).

MS (ESI, m/z): 370 (M+H)$^+$.

Example 526

[Formula 773]

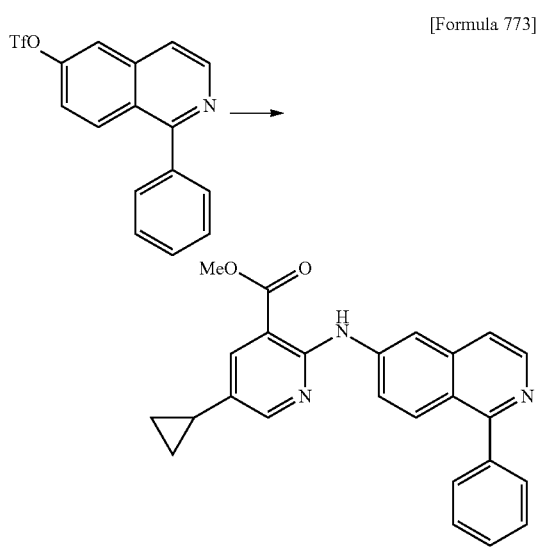

The mixture of 129 mg of 1-phenylisoquinolin-6-yl trifluoromethanesulfonate, 70 mg of methyl 2-amino-5-cyclopropylnicotinate, 8 mg of tris(dibenzylideneacetone)dipalladium(0), 14 mg of 4,5'-bis(diphenylphosphino)-9,9'- dimethylxanthene, 214 mg of cesium carbonate, and 4 mL of toluene, was stirred at 195° C. for one hour using microwave equipment.

After cooling the reaction mixture to room temperature, the insoluble matter was filtered off and the solvent was distilled off under reduced pressure. The obtained residue was purified by silica gel column chromatography (gradient elution with hexane:ethyl acetate=70:30-30:70) to give 94 mg of methyl 5-cyclopropyl-2-((1-phenylisoquinolin-6-yl)amino)nicotinate as a brown oil.

MS (ESI, m/z): 396 (M+H)⁺.

Example 527

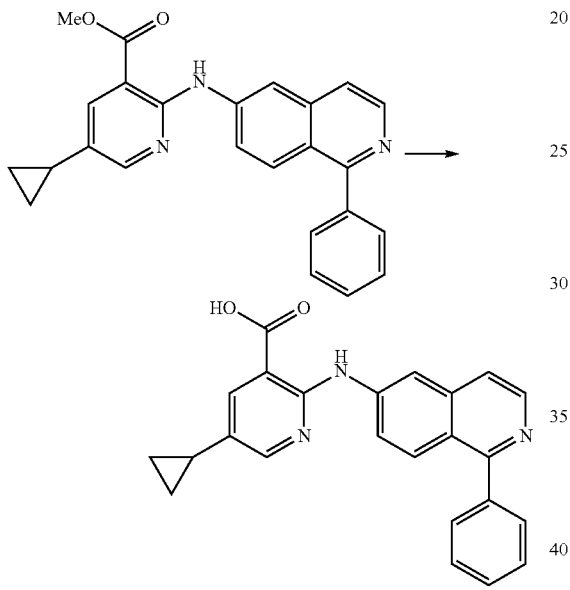

[Formula 774]

To the mixed solution of 94 mg of methyl 5-cyclopropyl-2-((1-phenylisoquinolin-6-yl)amino)nicotinate in 2 mL of methanol and 4 mL of tetrahydrofuran, 1 mL of a 1 mol/L aqueous sodium hydroxide solution was added, and the resultant was heated at reflux for one hour. After cooling the reaction mixture to room temperature, the solvent was distilled off under reduced pressure. The reaction mixture was adjusted to pH 3.0 to 3.5 by adding thereto methanol, water and 1 mol/L hydrochloric acid. The organic layer was separated and the aqueous layer was extracted with chloroform three times. The organic layer and the extract were combined and dried over anhydrous magnesium sulfate, and the solvent was distilled off under reduced pressure. Ethyl acetate and hexane were added to the residue and the solid was collected by filtration and washed with water to give 13 mg of 5-cyclopropyl-2-((1-phenylisoquinolin-6-yl)amino)nicotinic acid as a yellow solid.

¹H-NMR (DMSO-d₆) δ: 0.69-0.77 (2H, m), 0.93-1.02 (2H, m), 1.94-2.06 (1H, m), 7.50-7.73 (7H, m), 7.93 (1H, d, J=9.2 Hz), 7.98 (1H, d, J=2.6 Hz), 8.39 (1H, d, J=2.6 Hz), 8.46 (1H, d, J=5.3 Hz), 8.68 (1H, d, J=2.0 Hz), 10.87 (1H, s).

MS (ESI, m/z): 382 (M+H)⁺.

Example 528

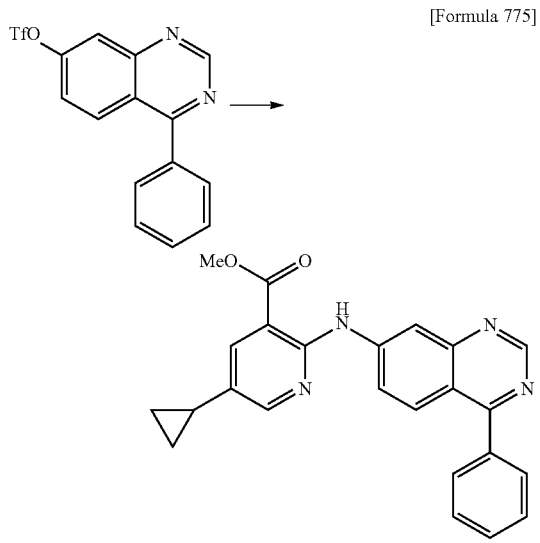

[Formula 775]

By the method similar to that of Example 526, methyl 5-cyclopropyl-2-((4-phenylquinazolin-7-yl)amino)nicotinate was obtained from 4-phenylquinazolin-7-yl trifluoromethanesulfonate and methyl 2-amino-5-cyclopropylnicotinate.

MS (ESI, m/z): 397 (M+H)⁺.

Example 529

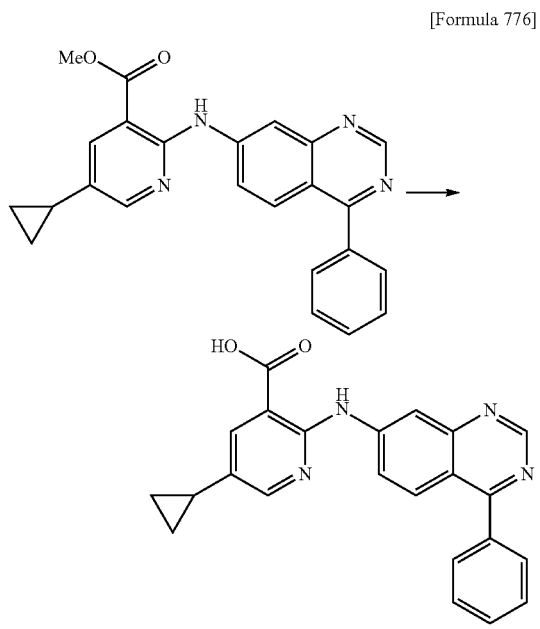

[Formula 776]

By the method similar to that of Example 527, 5-cyclopropyl-2-((4-phenylquinazolin-7-yl)amino)nicotinic acid was obtained from methyl 5-cyclopropyl-2-((4-phenylquinazolin-7-yl)amino)nicotinate.

¹H-NMR (DMSO-d₆) δ: 0.71-0.79 (2H, m), 0.94-1.04 (2H, m), 1.96-2.08 (1H, m), 7.58-7.69 (4H, m), 7.74-7.82

(2H, m), 7.94-8.02 (2H, m), 8.45 (1H, d, J=2.0 Hz), 8.89 (1H, d, J=2.6 Hz), 9.18 (1H, s), 10.93 (1H, s).

MS (ESI, m/z): 383 (M+H)+.

Example 530

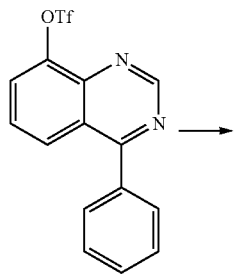

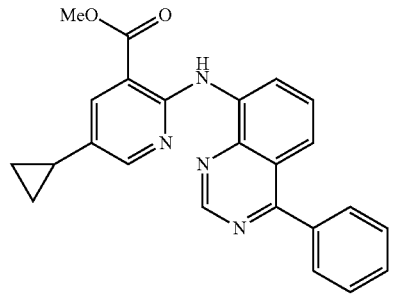

By the method similar to that of Example 526, methyl 5-cyclopropyl-2-((4-phenylquinazolin-8-yl)amino)nicotinate was obtained from 4-phenylquinazolin-8-yl trifluoromethanesulfonate and methyl 2-amino-5-cyclopropylnicotinate.

MS (ESI, m/z): 397 (M+H)+.

Example 531

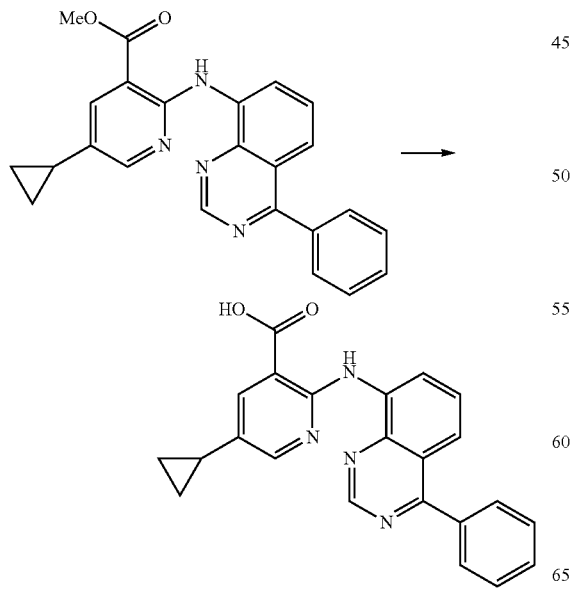

Example 532

By the method similar to that of Example 527, 5-cyclopropyl-2-((4-phenylquinazolin-8-yl)amino)nicotinic acid was obtained from methyl 5-cyclopropyl-2-((4-phenylquinazolin-8-yl)amino)nicotinate.

1H-NMR (DMSO-d6) δ: 0.70-0.78 (2H, m), 0.94-1.03 (2H, m), 1.94-2.07 (1H, m), 7.54-7.73 (5H, m), 7.77-7.86 (2H, m), 8.02 (1H, d, J=2.6 Hz), 8.41 (1H, d, J=2.6 Hz), 9.27-9.34 (1H, m), 9.39 (1H, s), 12.19 (1H, s).

MS (ESI, m/z): 383 (M+H)+.

Example 532

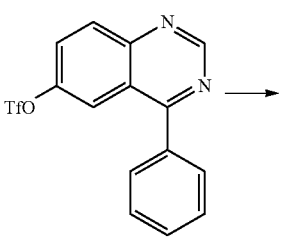

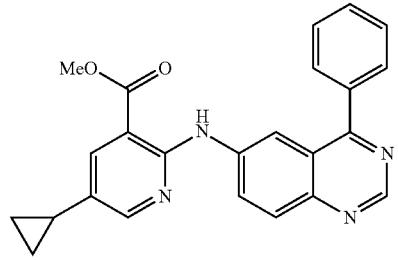

By the method similar to that of Example 526, methyl 5-cyclopropyl-2-((4-phenylquinazolin-6-yl)amino)nicotinate was obtained from 4-phenylquinazolin-6-yl trifluoromethanesulfonate and methyl 2-amino-5-cyclopropylnicotinate.

MS (ESI, m/z): 397 (M+H)+.

Example 533

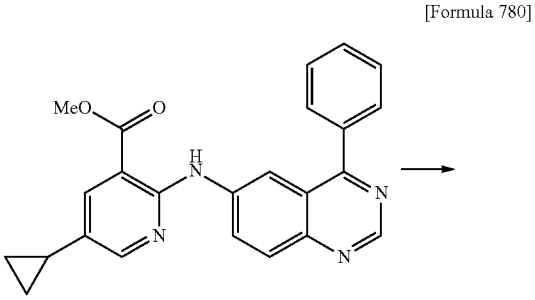

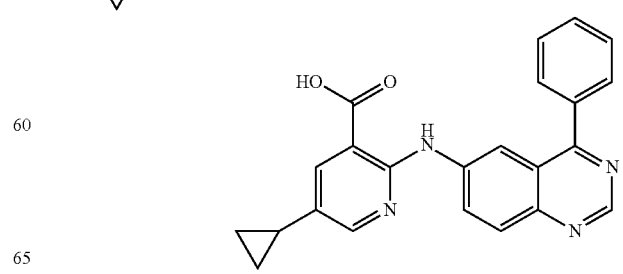

By the method similar to that of Example 527, 5-cyclopropyl-2-((4-phenylquinazolin-6-yl)amino)nicotinic acid was obtained from methyl 5-cyclopropyl-2-((4-phenylquinazolin-6-yl)amino)nicotinate.

$^1$H-NMR (DMSO-d$_6$) δ: 0.64-0.72 (2H, m), 0.91-1.01 (2H, m), 1.92-2.04 (1H, m), 7.62-7.73 (3H, m), 7.86-7.94 (3H, m), 7.98-8.09 (2H, m), 8.20 (1H, d, J=2.6 Hz), 8.97 (1H, d, J=2.0 Hz), 9.20 (1H, s), 10.82 (1H, s).

MS (ESI, m/z): 383 (M+H)$^+$.

Example 534

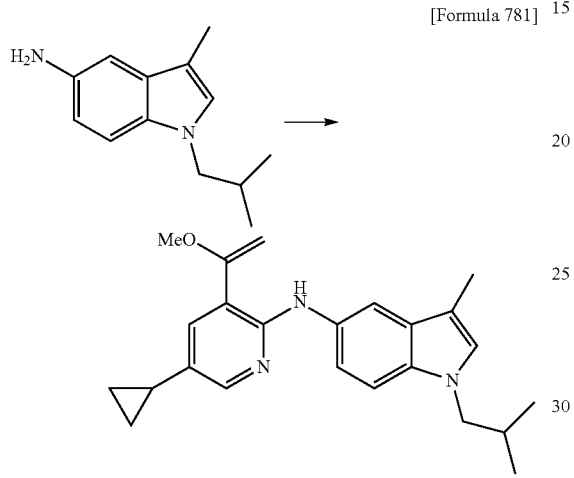

[Formula 781]

By the method similar to that of Example 221, methyl 5-cyclopropyl-2-((1-isobutyl-3-methyl-1H-indol-5-yl)amino)nicotinate was obtained from 1-isobutyl-3-methyl-1H-indol-5-amine and methyl 2-chloro-5-cyclopropylnicotinate.

MS (ESI, m/z): 378 (M+H)$^+$.

Example 535

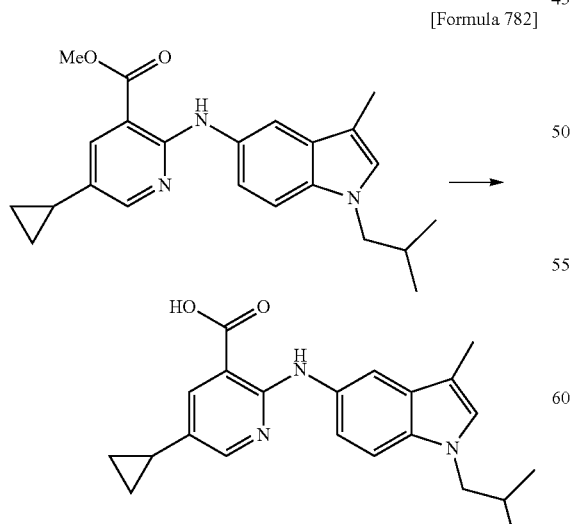

[Formula 782]

By the method similar to that of Example 222, 5-cyclopropyl-2-((1-isobutyl-3-methyl-1H-indol-5-yl)amino)nicotinic acid was obtained from methyl 5-cyclopropyl-2-((1-isobutyl-3-methyl-1H-indol-5-yl)amino)nicotinate.

$^1$H-NMR (DMSO-d$_6$) δ: 0.61-0.69 (2H, m), 0.80-0.95 (8H, m), 1.85-1.96 (1H, m), 2.00-2.16 (1H, m), 2.23 (3H, s), 3.88 (2H, d, J=7.3 Hz), 7.08 (1H, s), 7.22 (1H, dd, J=8.6, 2.0 Hz), 7.35 (1H, d, J=8.6 Hz), 7.75 (1H, d, J=2.0 Hz), 7.89 (1H, d, J=2.0 Hz), 8.15 (1H, d, J=2.6 Hz), 10.11 (1H, s).

MS (ESI, m/z): 364 (M+H)$^+$.

Example 536

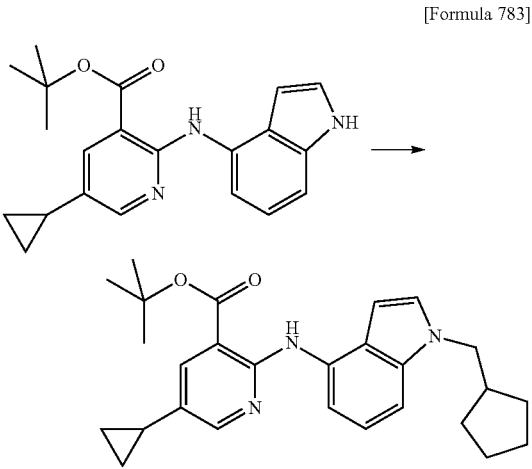

[Formula 783]

By the method similar to that of Reference Example 82, tert-butyl 2-((1-(cyclopentylmethyl)-1H-indol-4-yl)amino)-5-cyclopropylnicotinate was obtained from tert-butyl 5-cyclopropyl-2-(1H-indol-4-ylamino)nicotinate and (iodomethyl)cyclopentane.

MS (ESI, m/z): 432 (M+H)$^+$.

Example 537

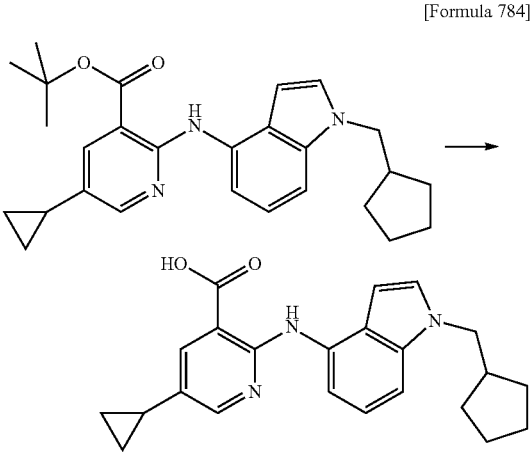

[Formula 784]

By the method similar to that of Example 222, 2-((1-(Cyclopentylmethyl)-1H-indol-4-yl)amino)-5-cyclopropylnicotinic acid was obtained from tert-butyl 2-((1-(cyclopentylmethyl)-1H-indol-4-yl)amino)-5-cyclopropylnicotinate.

¹H-NMR (DMSO-d₆) δ: 0.64-0.72 (2H, m), 0.89-0.98 (2H, m), 1.15-1.35 (2H, m), 1.40-1.74 (6H, m), 1.88-2.00 (1H, m), 2.32-2.45 (1H, m), 4.07 (2H, d, J=7.9 Hz), 6.48 (1H, d, J=2.6 Hz), 7.03-7.16 (2H, m), 7.37 (1H, d, J=3.3 Hz), 7.93 (1H, d, J=2.6 Hz), 8.18 (1H, dd, J=7.3, 1.3 Hz), 8.29 (1H, d, J=2.6 Hz), 10.93 (1H, s).

MS (ESI, m/z): 376 (M+H)⁺.

Example 538

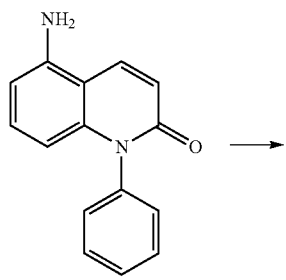

[Formula 785]

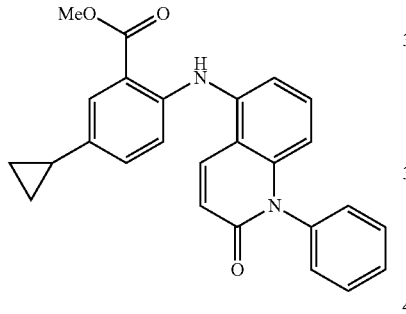

By the method similar to that of Example 221, methyl 5-cyclopropyl-2-((2-oxo-1-phenyl-1,2-dihydroquinolin-5-yl)amino)benzoate was obtained from 5-amino-1-phenylquinolin-2(1H)-one and methyl 2-bromo-5-cyclopropylbenzoate.

MS (ESI, m/z): 411 (M+H)⁺.

Example 539

[Formula 786]

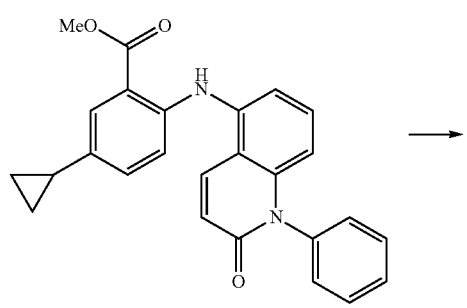

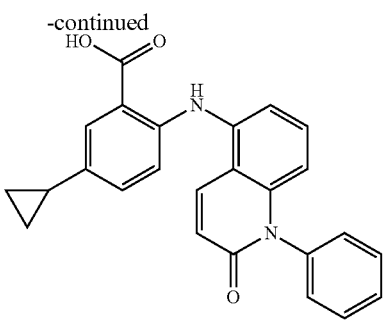

By the method similar to that of Example 222, 5-cyclopropyl-2-((2-oxo-1-phenyl-1,2-dihydroquinolin-5-yl)amino)benzoic acid was obtained from methyl 5-cyclopropyl-2-((2-oxo-1-phenyl-1,2-dihydroquinolin-5-yl)amino)benzoate.

¹H-NMR (DMSO-d₆) δ: 0.55-0.64 (2H, m), 0.86-0.94 (2H, m), 1.84-1.96 (1H, m), 6.23 (1H, d, J=8.6 Hz), 6.69 (1H, d, J=9.9 Hz), 6.95 (1H, d, J=8.6 Hz), 7.10-7.19 (2H, m), 7.30-7.41 (3H, m), 7.51-7.71 (4H, m), 8.06 (1H, d, J=9.9 Hz), 9.79 (1H, s).

MS (ESI, m/z): 397 (M+H)⁺.

Example 540

[Formula 787]

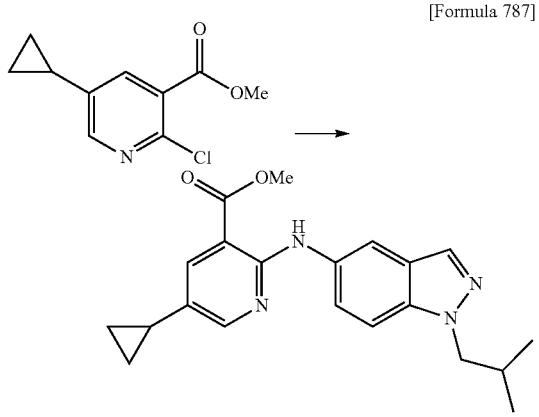

The mixture of 80 mg of methyl 2-chloro-5-cyclopropylnicotinate, 75 mg of 1-isobutyl-1H-indazol-5-amine, 17 mg of tris(dibenzylideneacetone)dipalladium(0), 22 mg of 4,5'-bis(diphenylphosphino)-9,9'-dimethylxanthene, 246 mg of cesium carbonate, and 3 mL of butyl acetate, was stirred at 130° C. for three hours and 45 minutes under a nitrogen atmosphere. The reaction mixture was cooled to room temperature and ethyl acetate and water were then added thereto. The organic layer was separated, washed with a saturated aqueous sodium chloride solution and dried over anhydrous sodium sulfate, and the solvent was distilled off under reduced pressure. The obtained residue was purified by silica gel column chromatography (gradient elution with hexane:ethyl acetate=100:0-60:40) to give 128 mg of methyl 5-cyclopropyl-2-((1-isobutyl-1H-indazol-5-yl)amino)nicotinate as a yellow oil.

¹H-NMR (DMSO-d₆) δ: 0.63-0.69 (2H, m), 0.85 (6H, d, J=6.6 Hz), 0.89-0.96 (2H, m), 1.88-1.98 (1H, m), 2.22 (1H, sep, J=6.6 Hz), 3.90 (3H, s), 4.19 (2H, d, J=6.9 Hz), 7.41

(1H, dd, J=8.6, 2.0 Hz), 7.62 (1H, d, J=9.2 Hz), 7.91 (1H, d, J=2.6 Hz), 7.99 (1H, s), 8.21 (1H, d, J=2.0 Hz), 8.26 (1H, d, J=2.6 Hz), 9.92 (1H, s).

MS (ESI, m/z): 365 (M+H)+.

Example 541

[Formual 788]

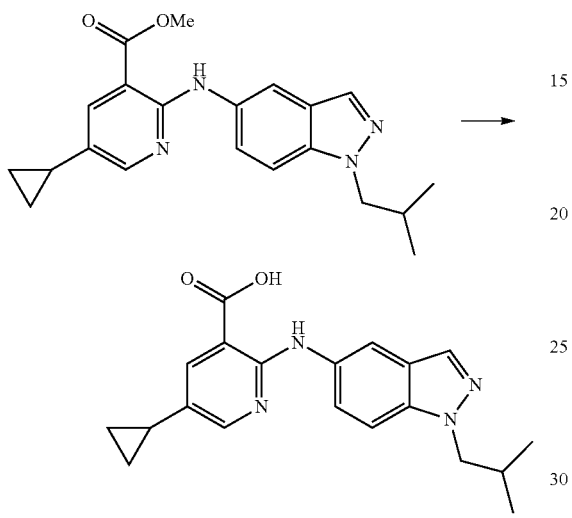

To the solution of 128 mg of methyl 5-cyclopropyl-2-((1-isobutyl-1H-indazol-5-yl)amino)nicotinate in 3 mL of tetrahydrofuran and 1.5 mL of methanol, 100 μL of a 5 mol/L aqueous sodium hydroxide solution was added, and the resultant was stirred for 14 hours and 50 minutes and then at 50° C. for one hour and 40 minutes. After 100 μL of 5 mol/L hydrochloric acid was added to the reaction mixture and the solvent was distilled off under reduced pressure, a water-methanol mixed solution was added thereto, and the solid was collected by filtration to give 96 mg of 5-cyclopropyl-2-((1-isobutyl-1H-indazol-5-yl)amino)nicotinic acid as a light orange solid.

1H-NMR (DMSO-d6) δ: 0.63-0.69 (2H, m), 0.85 (6H, d, J=6.6 Hz), 0.88-0.96 (2H, m), 1.86-1.97 (1H, m), 2.22 (1H, sep, J=7.2 Hz), 4.19 (2H, d, J=7.3 Hz), 7.40 (1H, dd, J=8.6, 2.0 Hz), 7.61 (1H, d, J=9.2 Hz), 7.90 (1H, d, J=2.6 Hz), 7.98 (1H, s), 8.21-8.26 (2H, m), 10.28 (1H, s), 13.53 (1H, brs).

MS (ESI, m/z): 351 (M+H)+, 349 (M−H)−.

Example 542

[Formula 789]

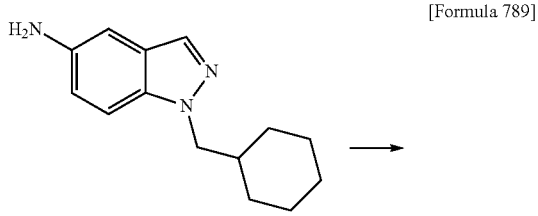

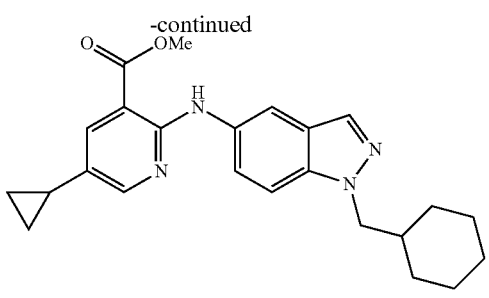

By the method similar to that of Example 540, methyl 2-((1-(cyclohexylmethyl)-1H-indazol-5-yl)amino)-5-cyclopropylnicotinate was obtained from 1-(cyclohexylmethyl)-1H-indazol-5-amine and methyl 2-chloro-5-cyclopropylnicotinate.

1H-NMR (DMSO-d6) δ: 0.63-0.70 (2H, m), 0.88-0.96 (2H, m), 0.96-1.19 (5H, m), 1.43-1.52 (2H, m), 1.55-1.70 (3H, m), 1.84-1.98 (2H, m), 3.90 (3H, s), 4.22 (2H, d, J=7.3 Hz), 7.40 (1H, dd, J=8.6, 2.0 Hz), 7.61 (1H, d, J=9.2 Hz), 7.91 (1H, d, J=2.0 Hz), 7.98 (1H, s), 8.20 (1H, d, J=1.3 Hz), 8.25 (1H, d, J=2.6 Hz), 9.92 (1H, s).

MS (ESI, m/z): 405 (M+H)+.

Example 543

[Formula 790]

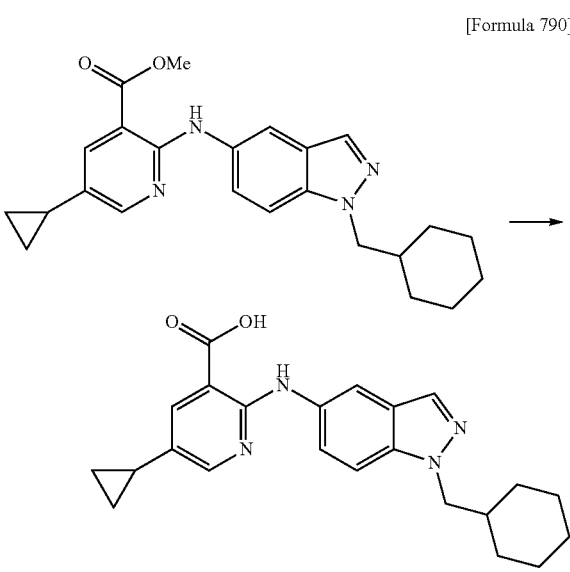

By the method similar to that of Example 541, 2-((1-(cyclohexylmethyl)-1H-indazol-5-yl)amino)-5-cyclopropylnicotinic acid was obtained from methyl 2-((1-(cyclohexylmethyl)-1H-indazol-5-yl)amino)-5-cyclopropylnicotinate.

1H-NMR (DMSO-d6) δ: 0.63-0.70 (2H, m), 0.88-0.96 (2H, m), 0.96-1.19 (5H, m), 1.43-1.53 (2H, m), 1.53-1.69 (3H, m), 1.83-1.99 (2H, m), 4.22 (2H, d, J=7.3 Hz), 7.39 (1H, dd, J=8.9, 1.7 Hz), 7.61 (1H, d, J=8.6 Hz), 7.90 (1H, d, J=2.6 Hz), 7.97 (1H, s), 8.20-8.24 (2H, m), 10.24 (1H, s), 13.51 (1H, brs).

MS (ESI, m/z): 391 (M+H)+, 389 (M−H)−.

Example 544

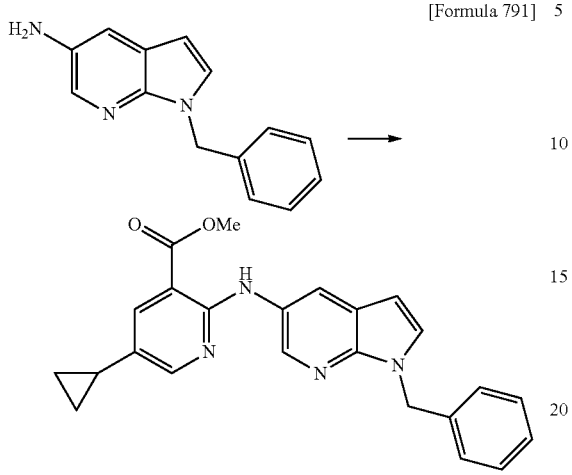

By the method similar to that of Example 540, methyl 2-((1-benzyl-1H-pyrrolo(2,3-b)pyridin-5-yl)amino)-5-cyclopropylnicotinate was obtained from 1-benzyl-1H-pyrrolo(2,3-b)pyridin-5-amine and methyl 2-chloro-5-cyclopropylnicotinate.

$^1$H-NMR (DMSO-d$_6$) δ: 0.61-0.68 (2H, m), 0.87-0.95 (2H, m), 1.86-1.96 (1H, m), 3.90 (3H, s), 5.47 (2H, s), 6.48 (1H, d, J=3.3 Hz), 7.21-7.34 (5H, m), 7.61 (1H, d, J=4.0 Hz), 7.89 (1H, d, J=2.6 Hz), 8.19 (1H, d, J=2.6 Hz), 8.29-8.32 (2H, m), 9.76 (1H, s).

MS (ESI, m/z): 399 (M+H)$^+$.

Example 545

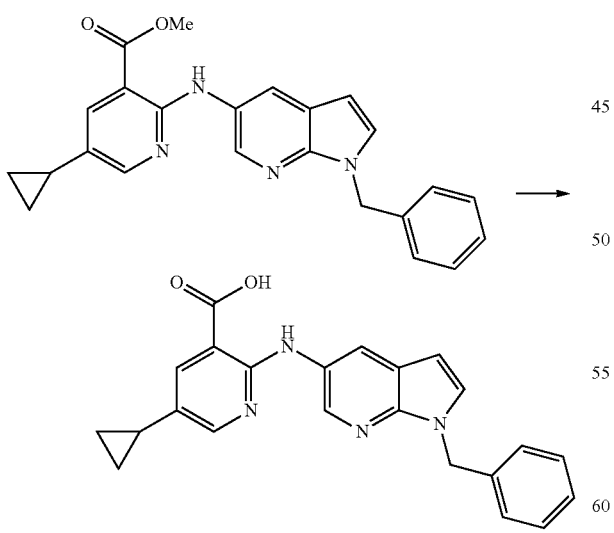

The mixture of 73 mg of methyl 2-((1-benzyl-1H-pyrrolo(2,3-b)pyridin-5-yl)amino)-5-cyclopropylnicotinate, 100 μL of a 5 mol/L aqueous sodium hydroxide solution, 3 mL of tetrahydrofuran, and 1 mL of methanol, was stirred at 50° C. for three hours and 30 minutes. After cooling the reaction mixture, 100 μL of 5 mol/L hydrochloric acid was added thereto, and the solvent was distilled off under reduced pressure. A water-methanol mixed solution was then added thereto, and the solid was collected by filtration to give 58 mg of 2-((1-benzyl-1H-pyrrolo(2,3-b)pyridin-5-yl)amino)-5-cyclopropylnicotinic acid as a yellow solid.

$^1$H-NMR (DMSO-d$_6$) δ: 0.61-0.68 (2H, m), 0.87-0.95 (2H, m), 1.86-1.96 (1H, m), 5.47 (2H, s), 6.48 (1H, d, J=3.3 Hz), 7.21-7.34 (5H, m), 7.61 (1H, d, J=4.0 Hz), 7.90 (1H, d, J=2.0 Hz), 8.16 (1H, d, J=2.0 Hz), 8.29-8.34 (2H, m), 10.08 (1H, s).

MS (ESI, m/z): 385 (M+H)$^+$, 383 (M−H)$^-$.

Example 546

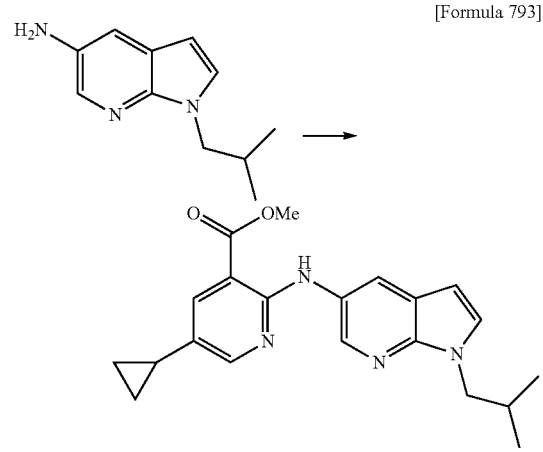

By the method similar to that of Example 540, methyl 5-cyclopropyl-2-((1-isobutyl-1H-pyrrolo(2,3-b)pyridin-5-yl)amino)nicotinate was obtained from 1-isobutyl-1H-pyrrolo(2,3-b)pyridin-5-amine and methyl 2-chloro-5-cyclopropylnicotinate.

$^1$H-NMR (DMSO-d$_6$) δ: 0.61-0.68 (2H, m), 0.85 (6H, d, J=6.6 Hz), 0.88-0.95 (2H, m), 1.86-1.97 (1H, m), 2.21 (1H, sep, J=6.6 Hz), 3.90 (3H, s), 4.05 (2H, d, J=7.3 Hz), 6.42 (1H, d, J=3.3 Hz), 7.51 (1H, d, J=3.3 Hz), 7.90 (1H, d, J=2.6 Hz), 8.20 (1H, d, J=2.0 Hz), 8.25-8.30 (2H, m), 9.75 (1H, s)

MS (ESI, m/z): 365 (M+H)$^+$.

Example 547

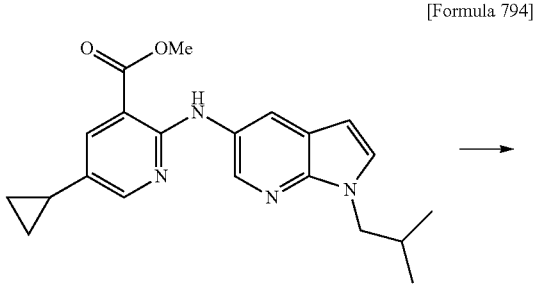

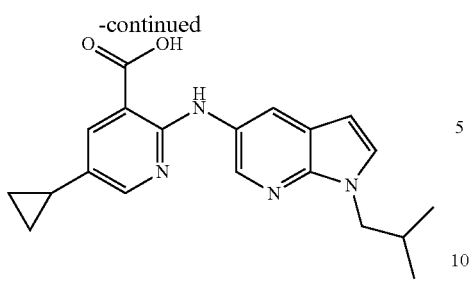

By the method similar to that of Example 545, 5-cyclopropyl-2-((1-isobutyl-1H-pyrrolo(2,3-b)pyridin-5-yl)amino)nicotinic acid was obtained from methyl 5-cyclopropyl-2-((1-isobutyl-1H-pyrrolo(2,3-b)pyridin-5-yl)amino)nicotinate.

$^1$H-NMR (DMSO-$d_6$) δ: 0.61-0.68 (2H, m), 0.85 (6H, d, J=6.6 Hz), 0.87-0.95 (2H, m), 1.86-1.95 (1H, m), 2.21 (1H, sep, J=6.6 Hz), 4.04 (2H, d, J=7.3 Hz), 6.42 (1H, d, J=4.0 Hz), 7.51 (1H, d, J=3.3 Hz), 7.89 (1H, d, J=2.6 Hz), 8.17 (1H, d, J=2.6 Hz), 8.27 (1H, d, J=2.3 Hz), 8.30 (1H, d, J=2.3 Hz), 10.04 (1H, s)

MS (ESI, m/z): 351 (M+H)$^+$, 349 (M−H)$^-$.

Example 548

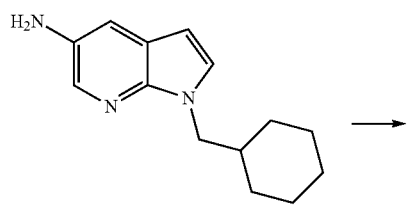

[Formula 795]

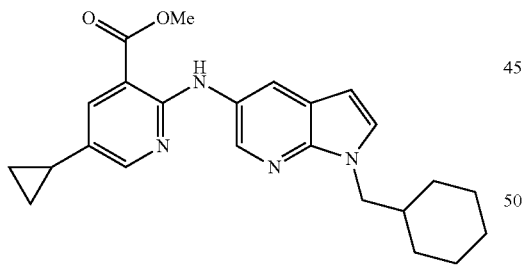

By the method similar to that of Example 540, methyl 2-((1-cyclohexylmethyl)-1H-pyrrolo(2,3-b)pyridin-5-yl)amino)-5-cyclopropylnicotinate was obtained from 1-(cyclohexylmethyl)-1H-pyrrolo(2,3-b)pyridin-5-amine and methyl 2-chloro-5-cyclopropylnicotinate.

$^1$H-NMR (DMSO-$d_6$) δ: 0.61-0.68 (2H, m), 0.87-1.07 (4H, m), 1.07-1.19 (3H, m), 1.44-1.54 (2H, m), 1.54-1.70 (3H, m), 1.85-1.95 (2H, m), 3.90 (3H, s), 4.07 (2H, d, J=7.3 Hz), 6.41 (1H, d, J=4.0 Hz), 7.49 (1H, d, J=3.3 Hz), 7.90 (1H, d, J=2.0 Hz), 8.19 (1H, d, J=2.6 Hz), 8.27 (2H, s), 9.74 (1H, s).

MS (ESI, m/z): 405 (M+H)$^+$.

Example 549

[Formula 796]

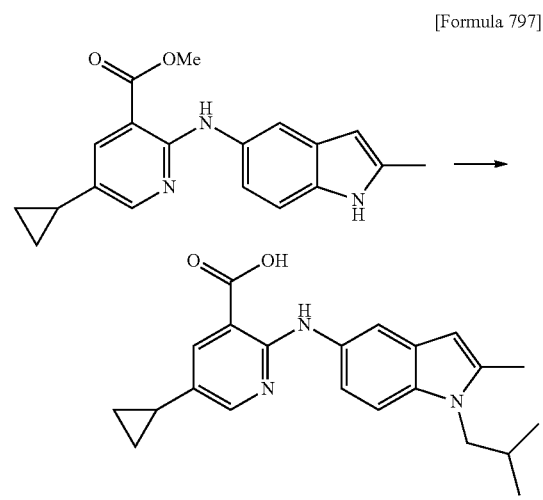

By the method similar to that of Example 545, 2-((1-cyclohexylmethyl)-1H-pyrrolo(2,3-b)pyridin-5-yl)amino)-5-cyclopropylnicotinic acid was obtained from methyl 2-((1-cyclohexylmethyl)-1H-pyrrolo(2,3-b)pyridin-5-yl)amino)-5-cyclopropylnicotinate.

$^1$H-NMR (DMSO-$d_6$) δ: 0.61-0.68 (2H, m), 0.83-1.19 (7H, m), 1.44-1.55 (2H, m), 1.56-1.71 (3H, m), 1.83-1.96 (2H, m), 4.07 (2H; d, J=7.3 Hz), 6.40 (1H, d, J=4.0 Hz), 7.48 (1H, d, J=3.3 Hz), 7.88 (1H, d, J=2.6 Hz), 8.16 (1H, d, J=2.6 Hz), 8.27 (1H, d, J=2.0 Hz), 8.30 (1H, d, J=2.0 Hz), 10.13 (1H, s).

MS (ESI, m/z): 391 (M+H)$^+$, 389 (M−H)$^-$.

Example 550

[Formula 797]

To the solution of 40 mg of methyl 5-cyclopropyl-2-((2-methyl-1H-indol-5-yl)amino)nicotinate in 1 mL of N,N-dimethylacetamide, 21 mg of potassium tert-butoxide and 20 µL, of 1-bromo-2-methylpropane were added under ice-cooling, and the resultant was stirred at room temperature for one hour and five minutes. 21 mg of potassium tert-butoxide and 20 µL of 1-bromo-2-methylpropane were added thereto under ice-cooling, and such resultant was stirred at room temperature for two hours and 25 minutes. 21 mg of potassium tert-butoxide and 40 µL of 1-bromo-2-methylpropane were added thereto under ice-cooling, and the resultant was stirred at room temperature for one hour and 45 minutes. 21 mg of potassium tert-butoxide and 20 µL of 1-bromo-2-methylpropane were added thereto under ice-cooling, and the resultant was stirred at room temperature for one hour and 50 minutes. After ethyl acetate, 175 µL of 5 mol/L hydrochloric acid and water were added to the reaction mixture, the organic layer was separated, washed with a saturated sodium chloride aqueous solution and dried over anhydrous sodium sulfate, and the solvent was distilled off under reduced pressure. The obtained residue was purified by silica gel column chromatography (gradient elution with hexane:ethyl acetate=100:0-50:50), and a water-methanol mixed solution was added to the thus obtained residue, and the solid was collected by filtration to give 10 mg of 5-cyclopropyl-2-((1-isobutyl-2-methyl-1H-indol-5-yl)amino)nicotinic acid as a light yellow solid.

$^1$H-NMR (DMSO-d$_6$) δ: 0.61-0.67 (2H, m), 0.83-0.94 (8H, m), 1.84-1.95 (1H, m), 2.11 (1H, sep, J=6.6 Hz), 2.38 (3H, s), 3.89 (2H, d, J=7.9 Hz), 6.15 (1H, s), 7.11 (1H, dd, J=8.6, 2.0 Hz), 7.29 (1H, d, J=8.6 Hz), 7.80 (1H, d, J=1.3 Hz), 7.86 (1H, d, J=2.0 Hz), 8.17 (1H, d, J=2.0 Hz), 10.12 (1H, s).

MS (ESI, m/z): 364 (M+H)$^+$, 362 (M−H)$^−$.

Example 551

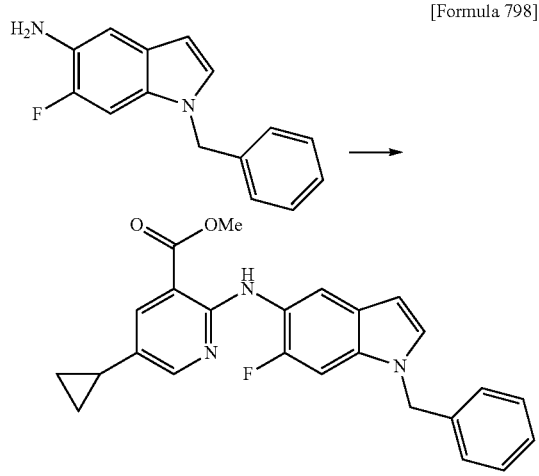

[Formula 798]

By the method similar to that of Example 540, methyl 2-((1-benzyl-6-fluoro-1H-indol-5-yl)amino)-5-cyclopropylnicotinate was obtained from 1-benzyl-6-fluoro-1H-indol-5-amine and methyl 2-chloro-5-cyclopropylnicotinate.

$^1$H-NMR (DMSO-d$_6$) δ: 0.63-0.69 (2H, m), 0.88-0.96 (2H, m), 1.87-1.97 (1H, m), 3.89 (3H, s), 5.38 (2H, s), 6.48 (1H, d, J=2.6 Hz), 7.20-7.37 (5H, m), 7.44 (1H, d, J=11.9 Hz), 7.48 (1H, d, J=3.3 Hz), 7.91 (1H, d, J=2.6 Hz), 8.26 (1H, d, J=2.6 Hz), 8.43 (1H, d, J=7.9 Hz), 9.95 (1H, d, J=2.6 Hz).

MS (ESI, m/z): 416 (M+H)$^+$.

Example 552

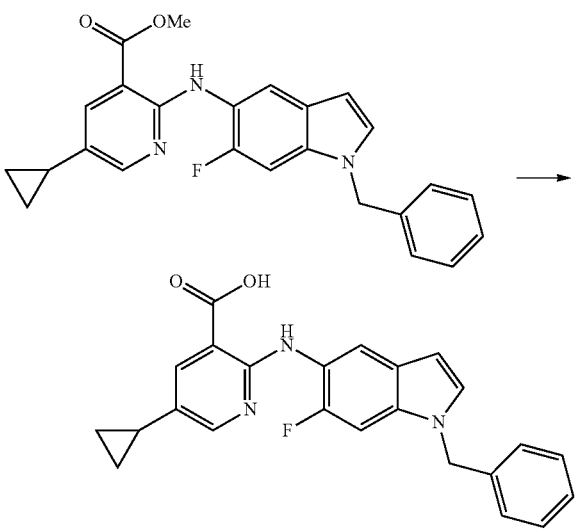

[Formula 799]

By the method similar to that of Example 545, 2-((1-benzyl-6-fluoro-1H-indol-5-yl)amino)-5-cyclopropylnicotinic acid was obtained from methyl 2-((1-benzyl-6-fluoro-1H-indol-5-yl)amino)-5-cyclopropylnicotinate.

$^1$H-NMR (DMSO-d$_6$) δ: 0.62-0.69 (2H, m), 0.87-0.95 (2H, m), 1.86-1.96 (1H, m), 5.38 (2H, s), 6.47 (1H, d, J=2.6 Hz), 7.19-7.37 (5H, m), 7.43 (1H, d, J=11.9 Hz), 7.47 (1H, d, J=3.3 Hz), 7.89 (1H, d, J=2.6 Hz), 8.22 (1H, d, J=2.6 Hz), 8.47 (1H, d, J=7.9 Hz), 10.24 (1H, s), 13.50 (1H, brs).

MS (ESI, m/z): 402 (M+H)$^+$, 400 (M−H)$^−$.

Example 553

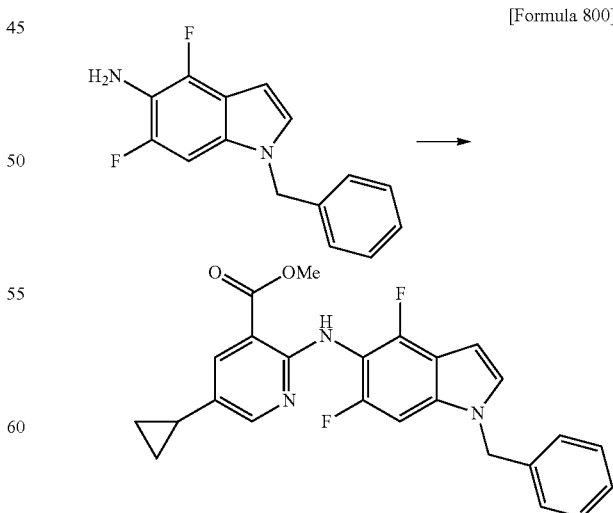

[Formula 800]

By the method similar to that of Example 540, methyl 2-((1-benzyl-4,6-difluoro-1H-indol-5-yl)amino)-5-cyclopropylnicotinate was obtained from 1-benzyl-4,6-difluoro-1H-indol-5-amine and methyl 2-chloro-5-cyclopropylnicotinate.

$^1$H-NMR (DMSO-d$_6$) δ: 0.57-0.64 (2H, m), 0.85-0.91 (2H, m), 1.81-1.92 (1H, m), 3.90 (3H, s), 5.43 (2H, s), 6.55 (1H, d, J=2.6 Hz), 7.24-7.37 (6H, m), 7.58 (1H, d, J=3.3 Hz), 7.86 (1H, d, J=2.0 Hz), 8.04 (1H, d, J=2.0 Hz), 8.93 (1H, s).

MS (ESI, m/z): 434 (M+H)$^+$.

Example 554

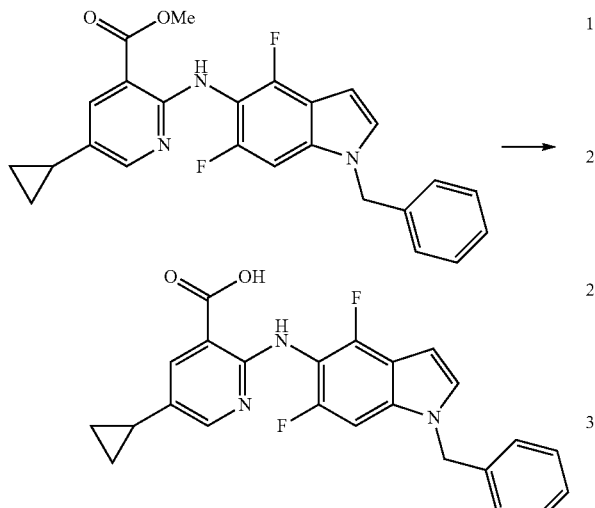

[Formula 801]

By the method similar to that of Example 545, 2-((1-benzyl-4,6-difluoro-1H-indol-5-yl)amino)-5-cyclopropylnicotinic acid was obtained from methyl 2-((1-benzyl-4,6-difluoro-1H-indol-5-yl)amino)-5-cyclopropylnicotinate.

$^1$H-NMR (DMSO-d$_6$) δ: 0.57-0.64 (2H, m), 0.84-0.92 (2H, m), 1.80-1.91 (1H, m), 5.42 (2H, s), 6.55 (1H, d, J=3.3 Hz), 7.24-7.37 (6H, m), 7.58 (1H, d, J=3.3 Hz), 7.85 (1H, d, J=2.6 Hz), 8.00 (1H, d, J=2.6 Hz), 9.16 (1H, s).

MS (ESI, m/z): 420 (M+H)$^+$, 418 (M−H)$^−$.

Example 555

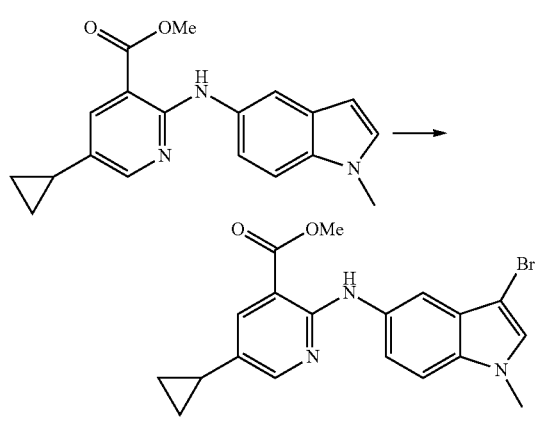

[Formula 802]

To the solution of 700 mg of methyl 5-cyclopropyl-2-((1-methyl-1H-indol-5-yl)amino)nicotinate in 20 mL of tetrahydrofuran, 388 mg of N-bromosuccinimide was added under ice-cooling, and the resultant was stirred for 10 minutes. The solvent was distilled off from the reaction mixture under reduced pressure, methanol was added to the obtained residue, and the solid was collected by filtration. The solid was washed with water to give 680 mg of methyl 2-((3-bromo-1-methyl-1H-indol-5-yl)amino)-5-cyclopropylnicotinate as a yellow solid.

$^1$H-NMR (DMSO-d$_6$) δ: 0.64-0.71 (2H, m), 0.88-0.95 (2H, m), 1.87-1.98 (1H, m), 3.78 (3H, s), 3.90 (3H, s), 7.29 (1H, dd, J=9.2, 2.0 Hz), 7.45 (1H, d, J=9.2 Hz), 7.52 (1H, s), 7.91 (1H, d, J=2.7 Hz), 7.92 (1H, d, J=1.8 Hz), 8.26 (1H, d, J=2.6 Hz), 9.95 (1H, s).

MS (ESI, m/z): 402 (M+H)$^+$.

Example 556

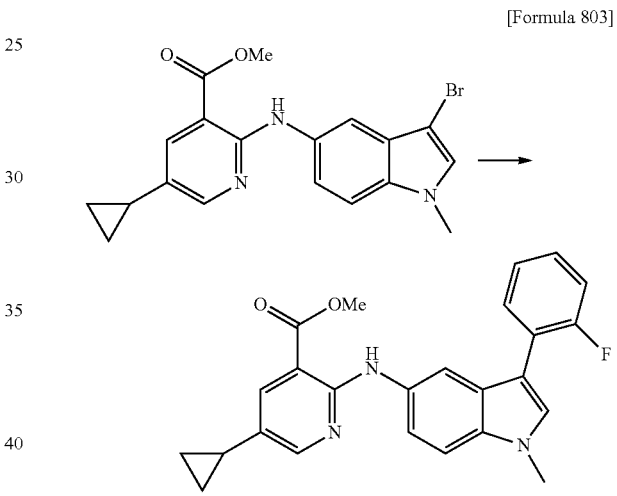

[Formula 803]

The mixture of 70 mg of methyl 2-((3-bromo-1-methyl-1H-indol-5-yl)amino)-5-cyclopropylnicotinate, 56 mg of 2-fluorophenylboronic acid, 6 mg of bis(di-tert-butyl(4-dimethylaminophenyl)phosphine)dichloropalladium(II), 80 mg of potassium carbonate, 2 mL of toluene, and 200 μL of water, was stirred at 120° C. for three hours under a nitrogen atmosphere. After ethyl acetate and water were added to the reaction mixture, the organic layer was separated, washed with a saturated aqueous sodium chloride solution and dried over anhydrous sodium sulfate, and the solvent was distilled off under reduced pressure. The obtained residue was purified by silica gel column chromatography (gradient elution with hexane:ethyl acetate=100:0-70:30) to give 59 mg of methyl 5-cyclopropyl-2-((3-(2-fluorophenyl)-1-methyl-1H-indol-5-yl)amino)nicotinate as a yellow oil.

$^1$H-NMR (DMSO-d$_6$) δ: 0.61-0.68 (2H, m), 0.87-0.94 (2H, m), 1.85-1.95 (1H, m), 3.86 (3H, s), 3.90 (3H, s), 7.27-7.34 (3H, m), 7.40 (1H, dd, J=8.7, 2.1 Hz), 7.47 (1H, d, J=9.3 Hz), 7.63 (1H, d, J=2.0 Hz), 7.67-7.74 (1H, m), 7.88 (1H, d, J=2.0 Hz), 8.04 (1H, s), 8.19 (1H, d, J=2.0 Hz), 9.88 (1H, s).

MS (ESI, m/z): 416 (M+H)$^+$.

Example 557

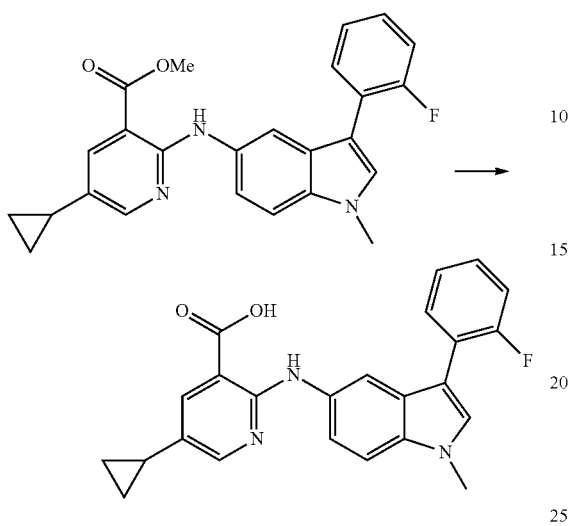

[Formula 804]

By the method similar to that of Example 545, 5-cyclopropyl-2-((3-(2-fluorophenyl)-1-methyl-1H-indol-5-yl)amino)nicotinic acid was obtained from methyl 5-cyclopropyl-2-((3-(2-fluorophenyl)-1-methyl-1H-indol-5-yl)amino)nicotinate.

$^1$H-NMR (DMSO-$d_6$) δ: 0.62-0.68 (2H, m), 0.87-0.94 (2H, m), 1.86-1.96 (1H, m), 3.86 (3H, s), 7.27-7.34 (3H, m), 7.36 (1H, dd, J=8.7, 2.1 Hz), 7.49 (1H, d, J=8.6 Hz), 7.64 (1H, d, J=2.0 Hz), 7.67-7.74 (1H, m), 7.92 (1H, d, J=2.0 Hz), 8.05 (1H, s), 8.12 (1H, d, J=2.0 Hz), 10.21 (1H, s).

MS (ESI, m/z): 402 (M+H)$^+$, 400 (M−H)$^−$.

Example 558

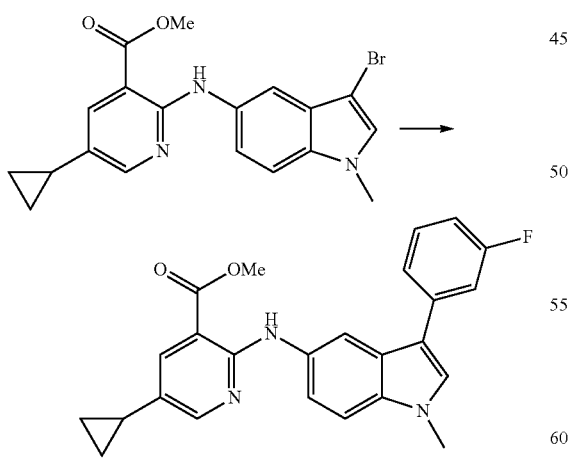

[Formula 805]

By the method similar to that of Example 556, methyl 5-cyclopropyl-2-((3-(3-fluorophenyl)-1-methyl-1H-indol-5-yl)amino)nicotinate was obtained from methyl 2-((3-bromo-1-methyl-1H-indol-5-yl)amino)-5-cyclopropylnicotinate and 3-fluorophenylboronic acid.

$^1$H-NMR (DMSO-$d_6$) δ: 0.62-0.68 (2H, m), 0.87-0.95 (2H, m), 1.87-1.97 (1H, m), 3.84 (3H, s), 3.90 (3H, s), 6.99-7.08 (1H, m), 7.36-7.55 (5H, m), 7.78 (1H, s), 7.89 (1H, d, J=2.6 Hz), 8.21 (1H, d, J=2.6 Hz), 8.25 (1H, d, J=2.0 Hz). 9.90 (1H, s).

MS (ESI, m/z): 416 (M+H)$^+$.

Example 559

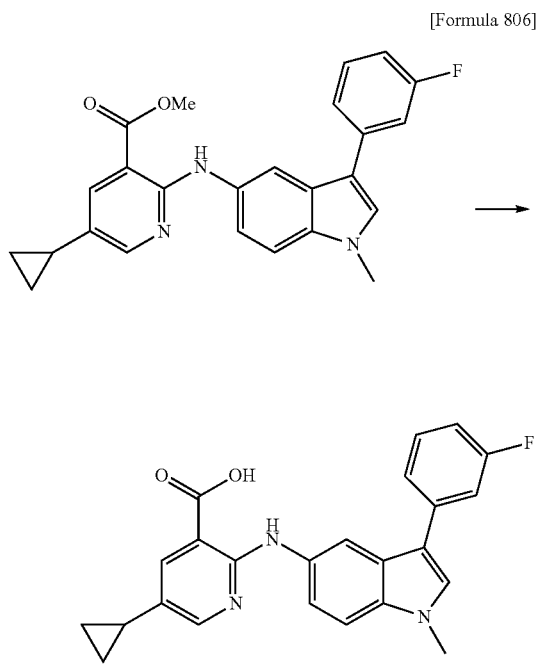

[Formula 806]

By the method similar to that of Example 545, 5-Cyclopropyl-2-((3-(3-fluorophenyl)-1-methyl-1H-indol-5-yl)amino)nicotinic acid was obtained from methyl 5-cyclopropyl-2-((3-(3-fluorophenyl)-1-methyl-1H-indol-5-yl)amino)nicotinate.

$^1$H-NMR (DMSO-$d_6$) δ: 0.62-0.68 (2H, m), 0.87-0.95 (2H, m), 1.87-1.97 (1H, m), 3.84 (3H, s), 6.99-7.08 (1H, m), 7.35 (1H, dd, J=8.6, 2.0 Hz), 7.41-7.55 (4H, m), 7.78 (1H, s), 7.91 (1H, d, J=2.6 Hz), 8.15 (1H, d, J=2.0 Hz), 8.28 (1H, d, J=2.0 Hz), 10.21 (1H, s).

MS (ESI, m/z): 402 (M+H)$^+$, 400 (M−H)$^−$.

Example 560

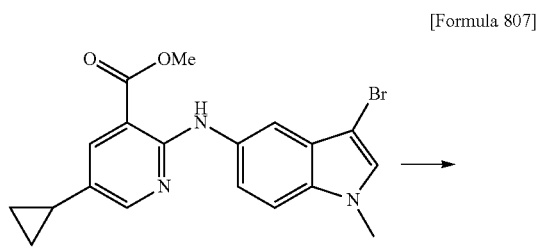

[Formula 807]

-continued

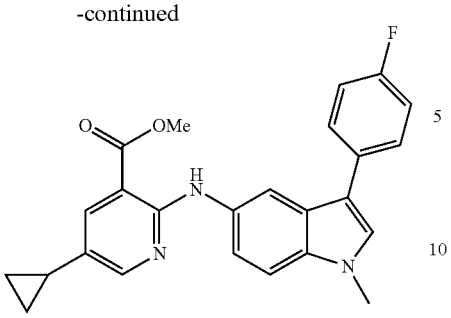

By the method similar to that of Example 556, methyl 5-cyclopropyl-2-((3-(4-fluorophenyl)-1-methyl-1H-indol-5-yl)amino)nicotinate was obtained from methyl 2-((3-bromo-1-methyl-1H-indol-5-yl)amino)-5-cyclopropylnicotinate and 4-fluorophenylboronic acid.

$^1$H-NMR (DMSO-$d_6$) δ: 0.62-0.68 (2H, m), 0.87-0.95 (2H, m), 1.86-1.96 (1H, m), 3.83 (3H, s), 3.90 (3H, s), 7.24-7.32 (2H, m), 7.37 (1H, dd, J=8.7, 2.1 Hz). 7.45 d, J=8.7 Hz), 7.63-7.69 (3H, m), 7.89 (1H, d, J=8.9 Hz), 8.19-8.22 (2H, m), 9.89 (1H, s).

MS (ESI, m/z): 416 (M+H)$^+$.

Example 561

[Formula 808]

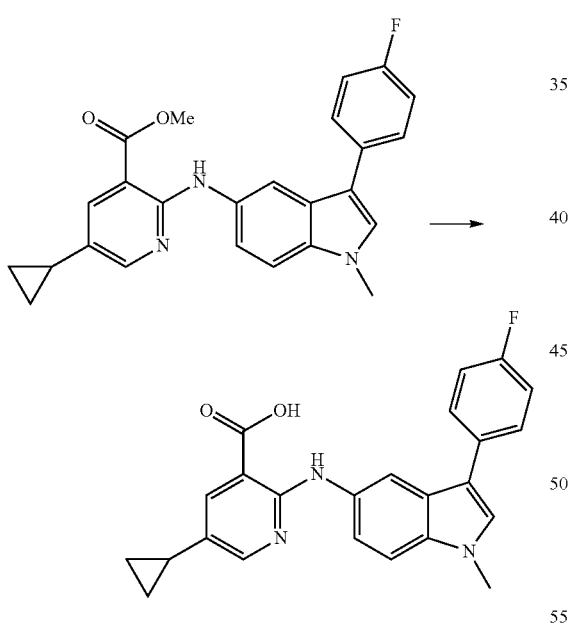

By the method similar to that of Example 545, 5-cyclopropyl-2-((3-(4-fluorophenyl)-1-methyl-1H-indol-5-yl)amino)nicotinic acid was obtained from methyl 5-cyclopropyl-2-((3-(4-fluorophenyl)-1-methyl-1H-indol-5-yl)amino)nicotinate.

$^1$H-NMR (DMSO-$d_6$) δ: 0.63-0.69 (2H, m), 0.87-0.95 (2H, m), 1.87-1.97 (1H, m), 3.84 (3H, s), 7.24-7.35 (3H, m), 7.48 (1H, d, J=8.6 Hz), 7.63-7.70 (3H, m), 7.93 (1H, d, J=2.0 Hz), 8.13 (1H, d, J=2.0 Hz), 8.19-8.22 (1H, m), 10.22 (1H, s).

MS (ESI, m/z): 402 (M+H)$^+$, 400 (M−H)$^−$.

Example 562

[Formula 809]

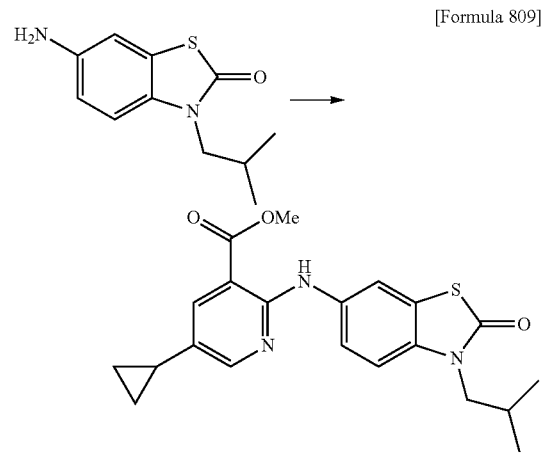

By the method similar to that of Example 540, methyl 5-cyclopropyl-2-((3-isobutyl-2-oxo-2,3-dihydro-1,3-benzothiazol-6-yl)amino)nicotinate was obtained from 6-amino-3-isobutyl-1,3-benzothiazol-2(3H)-one and methyl 2-chloro-5-cyclopropylnicotinate.

$^1$H-NMR (DMSO-$d_6$) δ: 0.63-0.70 (2H, m), 0.88-0.97 (8H, m), 1.88-1.98 (1H, m), 2.12 (1H, sep, J=7.3 Hz), 3.75 (2H, d, J=7.9 Hz), 3.90 (3H, s), 7.32 (1H, d, J=8.6 Hz), 7.51 (1H, dd, J=8.9, 2.3 Hz), 7.91 (1H, d, J=2.6 Hz), 8.13 (1H, d, J=2.6 Hz), 8.25 (1H, d, J=2.6 Hz), 9.91 (1H, s).

MS (ESI, m/z): 398 (M+H)$^+$.

Example 563

[Formula 810]

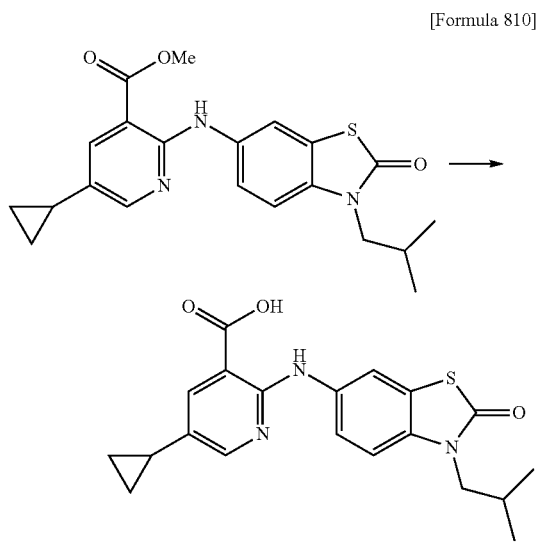

5-Cyclopropyl-2-((3-isobutyl-2-oxo-2,3-dihydro-1,3-benzothiazol-6-yl)amino)nicotinic acid was obtained from methyl 5-cyclopropyl-2-((3-isobutyl-2-oxo-2,3-dihydro-1,3-benzothiazol-6-yl)amino)nicotinate.

$^1$H-NMR (DMSO-$d_6$) δ: 0.63-0.69 (2H, m), 0.88-0.96 (8H, m), 1.87-1.97 (1H, m), 2.12 (1H, sep, J=6.6 Hz), 3.75 (2H, d, J=7.3 Hz), 7.31 (1H, d, J=8.6 Hz), 7.51 (1H, dd, J=8.6, 2.0 Hz), 7.90 (1H, d, J=2.6 Hz), 8.13 (1H, d, J=2.0 Hz), 8.22 (1H, d, J=2.6 Hz), 10.23 (1H, s), 13.58 (1H, brs).
MS (ESI, m/z): 384 (M+H)⁺, 382 (M−H)⁻.

Example 564

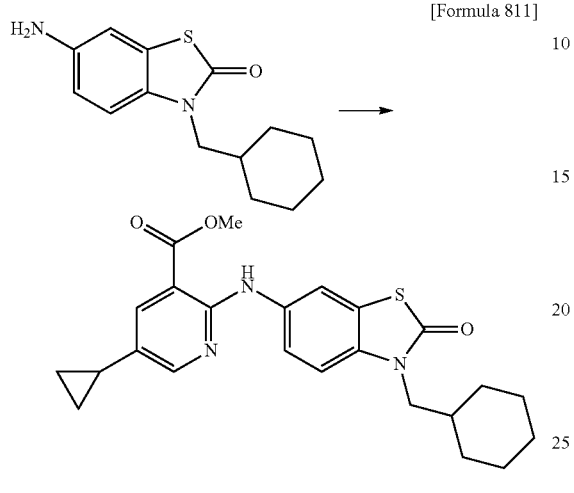

[Formula 811]

By the method similar to that of Example 540, methyl 2-((3-(cyclohexylmethyl)-2-oxo-2,3-dihydro-1,3-benzothiazol-6-yl)amino)-5-cyclopropylnicotinate was obtained from 6-amino-3-(cyclohexylmethyl)-1,3-benzothiazol-2(3H)-one and methyl 2-chloro-5-cyclopropylnicotinate.

¹H-NMR (DMSO-d₆) δ: 0.63-0.70 (2H, m), 0.89-0.97 (2H, m), 0.97-1.22 (5H, m), 1.54-1.72 (5H, m), 1.73-1.83 (1H, m), 1.88-1.98 (1H, m), 3.78 (2H, d, J=7.3 Hz), 3.90 (3H, s), 7.31 (1H, d, J=8.6 Hz), 7.50 (1H, dd, J=8.6, 2.6 Hz), 7.91 (1H, d, J=2.6 Hz), 8.12 (1H, d, J=2.0 Hz), 8.25 (1H, d, J=2.0 Hz), 9.90 (1H, s).
MS (ESI, m/z): 438 (M+H)⁺.

Example 565

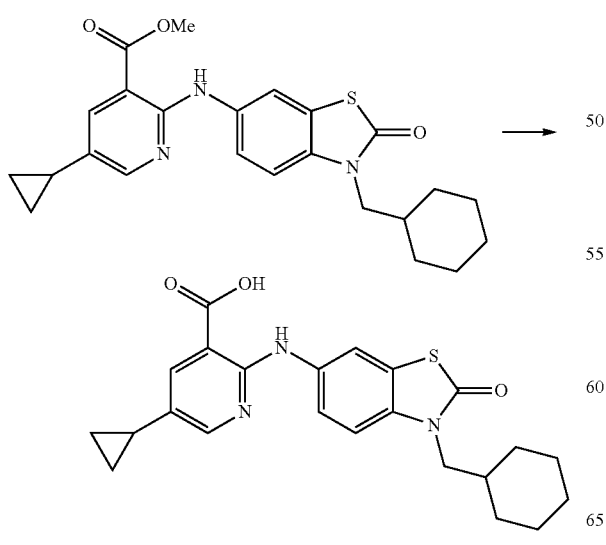

[Formula 812]

By the method similar to that of Example 545, 2-((3-(cyclohexylmethyl)-2-oxo-2,3-dihydro-1,3-benzothiazol-6-yl)amino)-5-cyclopropylnicotinic acid was obtained from methyl 2-((3-(cyclohexylmethyl)-2-oxo-2,3-dihydro-1,3-benzothiazol-6-yl)amino)-5-cyclopropylnicotinate.

¹H-NMR (DMSO-d₆) δ: 0.63-0.70 (2H, m), 0.89-0.97 (2H, m), 0.97-1.20 (5H, m), 1.55-1.72 (5H, m), 1.73-1.84 (1H, m), 1.87-1.98 (1H, m), 3.78 (2H, d, J=7.3 Hz), 7.30 (1H, d, J=8.6 Hz), 7.51 (1H, dd, J=8.9, 2.3 Hz), 7.90 (1H, d, J=2.6 Hz), 8.12 (1H, d, J=2.0 Hz), 8.22 (1H, d, J=2.6 Hz), 10.23 (1H, s), 13.59 (1H, brs).
MS (ESI, m/z): 424 (M+H)⁺, 422 (M−H)⁻.

Example 566

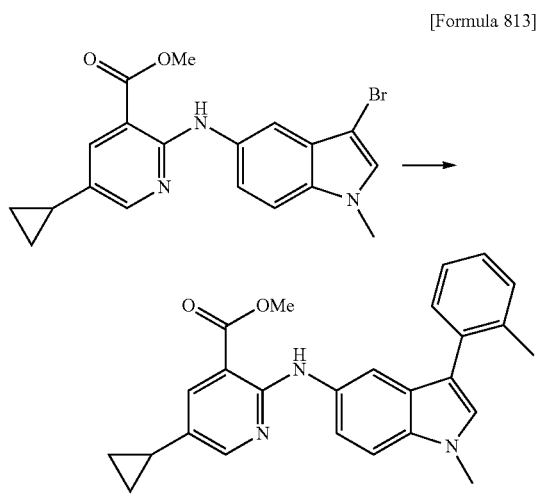

[Formula 813]

By the method similar to that of Example 556, methyl 5-cyclopropyl-2-((1-methyl-3-(2-methylphenyl)-1H-indol-5-yl)amino)nicotinate was obtained from methyl 2-((3-bromo-1-methyl-1H-indol-5-yl)amino)-5-cyclopropylnicotinate and 2-methylphenylboronic acid.

¹H-NMR (DMSO-d₆) δ: 0.60-0.66 (2H, m), 0.85-0.93 (2H, m), 1.84-1.94 (1H, m), 2.33 (3H, s), 3.84 (3H, s), 3.88 (3H, s), 7.18-7.29 (2H, m), 7.29-7.39 (3H, m), 7.41 (1H, s), 7.44 (1H, d, J=8.6 Hz), 7.77 (1H, d, J=1.3 Hz), 7.86 (1H, d, J=2.6 Hz), 8.15 (1H, d, J=2.6 Hz), 9.84 (1H, s).
MS (ESI, m/z): 412 (M+H)⁺.

Example 567

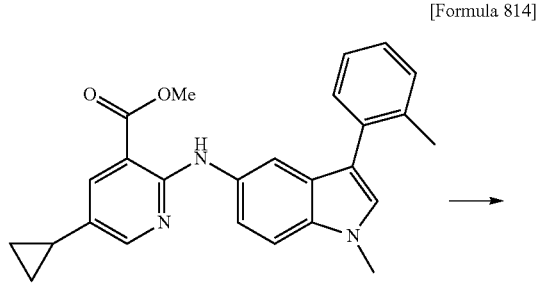

[Formula 814]

-continued

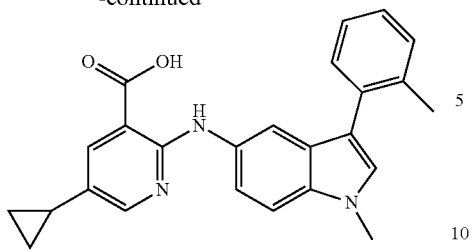

By the method similar to that of Example 545, 5-cyclopropyl-2-((1-methyl-3-(2-methylphenyl)-1H-indol-5-yl)amino)nicotinic acid was obtained from methyl 5-cyclopropyl-2-((1-methyl-3-(2-methylphenyl)-1H-indol-5-yl)amino)nicotinate.

$^1$H-NMR (DMSO-$d_6$) δ: 0.59-0.66 (2H, m), 0.85-0.93 (2H, m), 1.83-1.94 (1H, m), 2.33 (3H, s), 3.84 (3H, s), 7.18-7.39 (5H, m), 7.42 (1H, s), 7.45 (1H, d, J=8.4 Hz), 7.78 (1H, d, J=1.3 Hz), 7.88 (1H, d, J=2.0 Hz), 8.09 (1H, d, J=2.6 Hz), 10.16 (1H, s).

MS (ESI, m/z): 398 (M+H)$^+$, 396 (M−H)$^−$.

Example 568

[Formula 815]

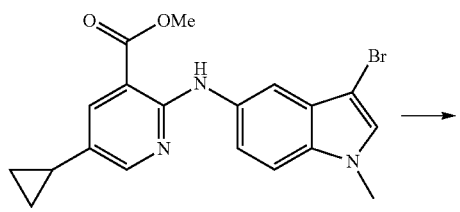

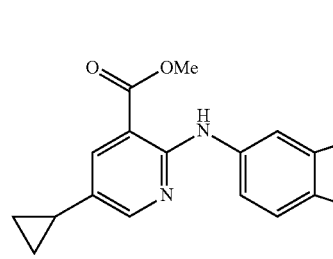

By the method similar to that of Example 556, methyl 5-cyclopropyl-2-((1-methyl-3-(3-methylphenyl)-1H-indol-5-yl)amino)nicotinate was obtained from methyl 2-((3-bromo-1-methyl-1H-indol-5-yl)amino)-5-cyclopropylnicotinate and 3-methylphenylboronic acid.

$^1$H-NMR (DMSO-$d_6$) δ: 0.62-0.68 (2H, m), 0.87-0.95 (2H, m), 1.86-1.97 (1H, m), 2.38 (3H, s), 3.83 (3H, s), 3.90 (3H, s), 7.01-7.07 (1H, m), 7.29-7.36 (2H, m), 7.42-7.49 (3H, m), 7.64 (1H, s), 7.89 (1H, d, J=2.6 Hz), 8.20 (1H, d, J=2.6 Hz), 8.26 (1H, d, J=2.0 Hz), 9.88 (1H, s).

MS (ESI, m/z): 412 (M+H)$^+$.

Example 569

[Formula 816]

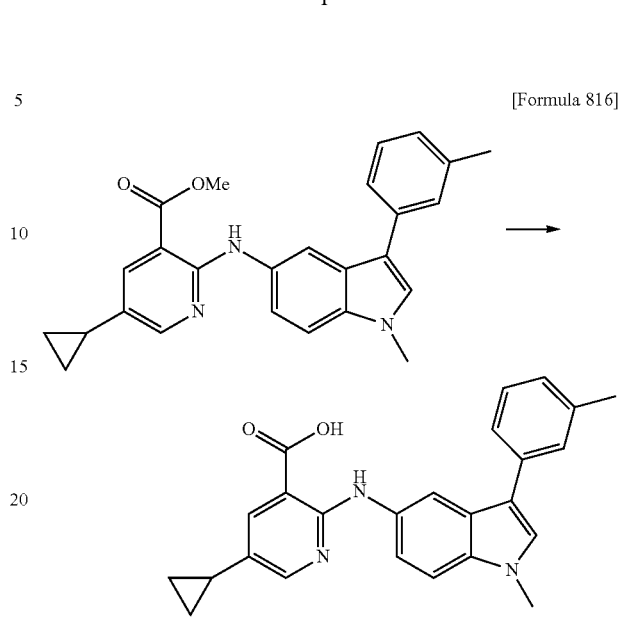

By the method similar to that of Example 545, 5-cyclopropyl-2-((1-methyl-3-(3-methylphenyl)-1H-indol-5-yl)amino)nicotinic acid was obtained from methyl 5-cyclopropyl-2-((1-methyl-3-(3-methylphenyl)-1H-indol-5-yl)amino)nicotinate.

$^1$H-NMR (DMSO-$d_6$) δ: 0.61-0.67 (2H, m), 0.87-0.94 (2H, m), 1.85-1.96 (1H, m), 2.38 (3H, s), 3.83 (3H, s), 7.04 (1H, d, J=7.3 Hz), 7.28-7.36 (2H, m), 7.41-7.49 (3H, m), 7.63 (1H, s), 7.88 (1H, d, J=2.6 Hz), 8.17 (1H, d, J=2.6 Hz), 8.30 (1H, d, J=2.0 Hz), 10.17 (1H, s), 13.43 (1H, brs).

MS (ESI, m/z): 398 (M+H)$^+$, 396 (M−H)$^−$.

Example 570

[Formula 817]

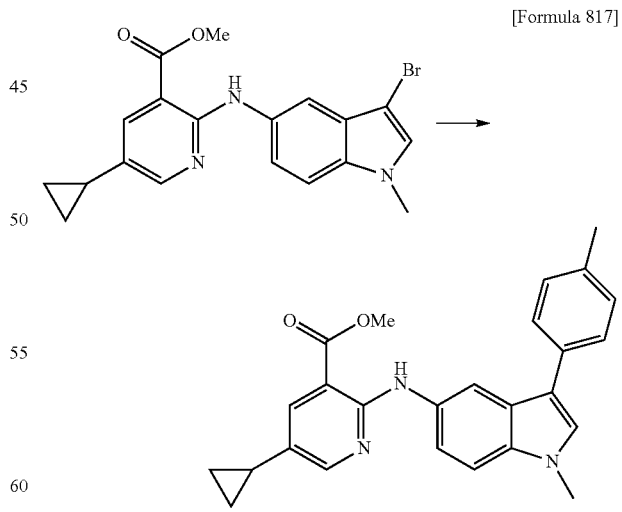

By the method similar to that of Example 556, methyl 5-cyclopropyl-2-((1-methyl-3-(4-methylphenyl)-1H-indol-5-yl)amino)nicotinate was obtained from methyl 2-((3-bromo-1-methyl-1H-indol-5-yl)amino)-5-cyclopropylnicotinate and 4-methylphenylboronic acid.

¹H-NMR (DMSO-d₆) δ: 0.62-0.68 (2H, m), 0.87-0.94 (2H, m), 1.86-1.96 (1H, m), 2.33 (3H, s), 3.82 (3H, s), 3.90 (3H, s), 7.25 (2H, d, J=7.9 Hz), 7.34 (1H, dd, J=8.6, 2.0 Hz), 7.44 (1H, d, J=9.2 Hz), 7.54 (2H, d, J=7.9 Hz), 7.60 (1H, s), 7.89 (1H, d, J=2.6 Hz), 8.19-8.23 (2H, m), 9.88 (1H, s).

MS (ESI, m/z): 412 (M+H)⁺.

Example 571

[Formula 818]

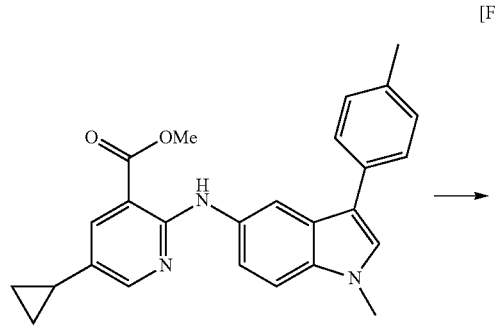

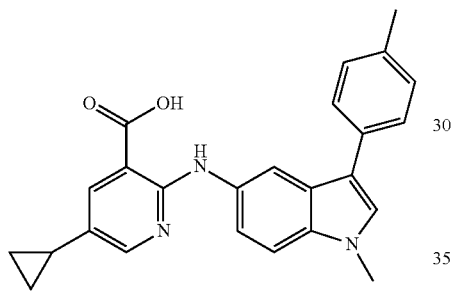

By the method similar to that of Example 545, 5-cyclopropyl-2-((1-methyl-3-(4-methylphenyl)-1H-indol-5-yl)amino)nicotinic acid was obtained from methyl 5-cyclopropyl-2-((1-methyl-3-(4-methylphenyl)-1H-indol-5-yl)amino)nicotinate.

¹H-NMR (DMSO-d₆) δ: 0.61-0.68 (2H, m), 0.86-0.94 (2H, m), 1.85-1.96 (1H, m), 2.30 (3H, s), 3.82 (3H, s), 7.25 (2H, d, J=7.9 Hz), 7.31 (1H, dd, J=8.9, 1.7 Hz), 7.43 (1H, d, J=9.2 Hz), 7.54 (2H, d, J=7.9 Hz), 7.60 (1H, s), 7.89 (1H, d, J=2.6 Hz), 8.17 (1H, d, J=2.0 Hz), 8.24 (1H, d, J=2.0 Hz), 10.18 (1H, s), 13.45 (1H, brs).

MS (ESI, m/z): 398 (M+H)⁺, 396 (M−H)⁻.

Example 572

[Formula 819]

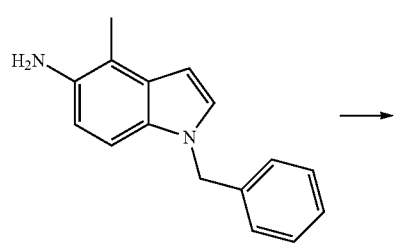

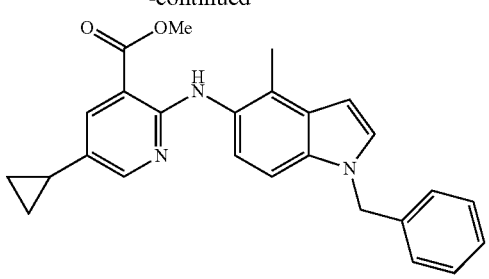

By the method similar to that of Example 540, methyl 2-((1-benzyl-4-methyl-1H-indol-5-yl)amino)-5-cyclopropylnicotinate was obtained from 1-benzyl-4-methyl-1H-indol-5-amine and methyl 2-chloro-5-cyclopropylnicotinate.

¹H-NMR (DMSO-d₆) δ: 0.56-0.63 (2H, m), 0.84-0.92 (2H, m), 1.80-1.91 (1H, m), 2.32 (3H, s), 3.89 (3H, s), 5.40 (2H, s), 6.52 (1H, d, J=3.3 Hz), 7.17-7.34 (7H, m), 7.49 (1H, d, J=3.3 Hz), 7.84 (1H, d, J=2.6 Hz), 8.05 (1H, d, J=2.0 Hz), 9.42 (1H, s).

MS (ESI, m/z): 412 (M+H)⁺.

Example 573

[Formula 820]

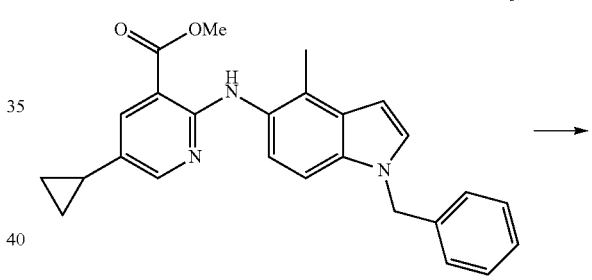

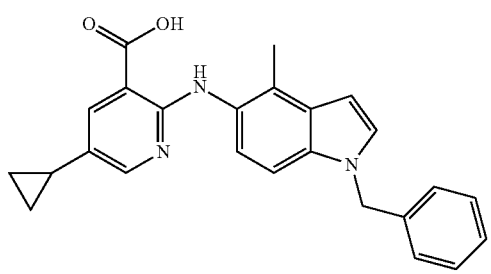

By the method similar to that of Example 545, 2-(1-benzyl-4-methyl-1H-indol-5-yl)amino)-5-cyclopropylnicotinic acid was obtained from methyl 2-((1-benzyl-4-methyl-1H-indol-5-yl)amino)-5-cyclopropylnicotinate.

¹H-NMR (DMSO-d₆) δ: 0.58-0.65 (2H, m), 0.85-0.93 (2H, m), 1.83-1.94 (1H, m), 2.33 (3H, s), 5.41 (2H, s), 6.55 (1H, d, J=2.7 Hz), 7.19-7.34 (7H, m), 7.52 (1H, d, J=3.3 Hz), 7.91-7.97 (2H, m), 9.84 (1H, s).

MS (ESI, m/z): 398 (M+H)⁺, 396 (M−H)⁻.

Example 574

[Formula 821]

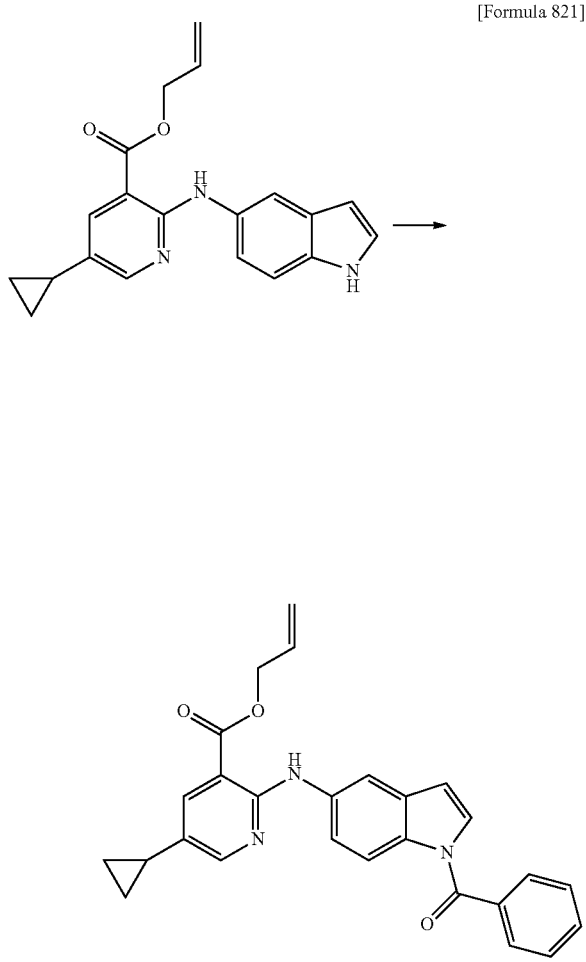

The mixture of 50 mg of allyl 5-cyclopropyl-2-(1H-indol-5-ylamino)nicotinate, 105 μL of benzoyl chloride, 250 μL of triethylamine, 18 mg of N,N-dimethyl-4-aminopyridine, and 3 mL of dichloromethane, was stirred at room temperature for nine hours and five minutes. After a saturated aqueous sodium bicarbonate solution and ethyl acetate were added to the reaction mixture, the organic layer was separated, washed with a saturated aqueous sodium chloride solution and dried over anhydrous sodium sulfate, and the solvent was distilled off under reduced pressure. The obtained residue was purified by silica gel column chromatography (gradient elution with hexane:ethyl acetate=100:0-30:70) to give 64 mg of allyl 2-((1-benzoyl-1H-indol-5-yl)amino)-5-cyclopropylnicotinate as a yellow oil.

$^1$H-NMR (DMSO-$d_6$) δ: 0.65-0.72 (2H, m), 0.92-0.98 (2H, m), 1.91-2.02 (1H, m), 4.87 (2H, d, J=5.9 Hz), 5.32 (1H, dd, J=10.2, 1.7 Hz), 5.45 (1H, dd, J=17.2, 1.3 Hz), 6.03-6.17 (1H, m), 6.74 (1H, d, J=4.0 Hz), 7.36 (1H, d, J=4.0 Hz), 7.48 (1H, dd, J=8.9, 2.3 Hz), 7.57-7.64 (2H, m), 7.66-7.73 (1H, m), 7.74-7.79 (2H, m), 7.94 (1H, d, J=6.6 Hz), 8.18-8.23 (2H, m), 8.30 (1H, d, J=2.6 Hz), 10.07 (1H, s).

MS (ESI, m/z): 438 (M+H)$^+$.

Example 575

[Formula 822]

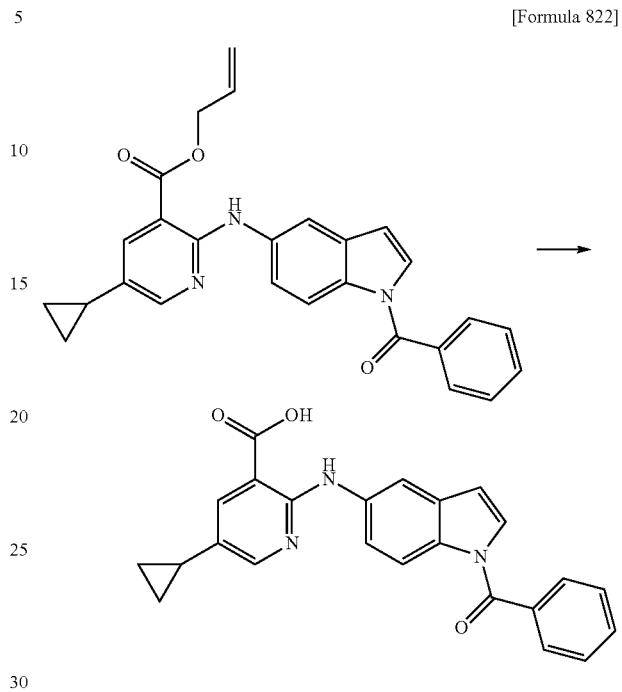

The mixture of 62 mg of allyl 2-((1-benzoyl-1H-indol-5-yl)amino)-5-cyclopropylnicotinate, 23 μL of pyrrolidine, 8 mg of tetrakistriphenylphosphinepalladium and 2 mL acetonitrile was stirred at room temperature for two hours and 50 minutes under a nitrogen atmosphere. 1 mol/L hydrochloric acid and ethyl acetate were added to the reaction mixture and the organic layer was separated. The organic layer was washed with a saturated aqueous sodium chloride solution and dried over anhydrous sodium sulfate, and the solvent was distilled off under reduced pressure. A water-methanol mixed solution was added to the obtained residue, and the solid was collected by filtration to give 45 mg of 2-((1-benzoyl-1H-indol-5-yl)amino)-5-cyclopropylnicotinic acid as a light yellow solid.

$^1$H-NMR (DMSO-$d_6$) δ: 0.64-0.71 (2H, m), 0.89-0.97 (2H, m), 1.88-1.99 (1H, m), 6.74 (1H, d, J=4.0 Hz), 7.35 (1H, d, J=4.0 Hz), 7.47 (1H, dd, J=8.6, 2.0 Hz), 7.57-7.70 (4H, m), 7.74-7.80 (2H, m), 7.92 (1H, d, J=2.6 Hz), 8.21 (1H, d, J=8.6 Hz), 8.25 (1H, dd, J=8.6, 2.0 Hz), 10.45 (1H, s).

MS (ESI, m/z): 398 (M+H)$^+$, 396 (M−H)$^−$.

Example 576

[Formula 823]

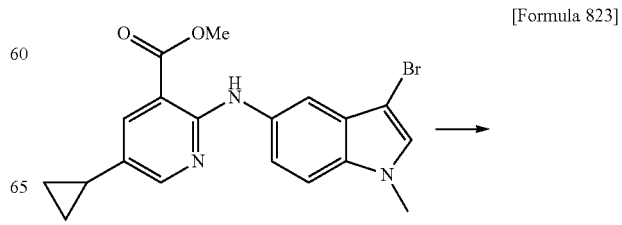

523

-continued

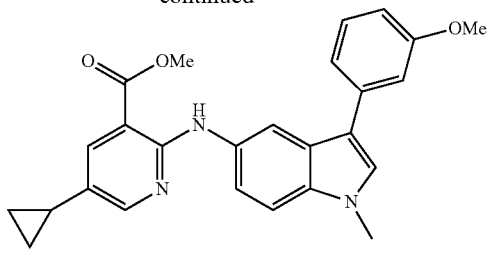

By the method similar to that of Example 556, methyl 5-cyclopropyl-2-((3-(3-methoxyphenyl)-1-methyl-1H-indol-5-yl)amino)nicotinate was obtained from methyl 2-((3-bromo-1-methyl-1H-indol-5-yl)amino)-5-cyclopropylnicotinate and 3-methoxyphenylboronic acid.

MS (ESI, m/z): 428 (M+H)+.

Example 577

[Formula 824]

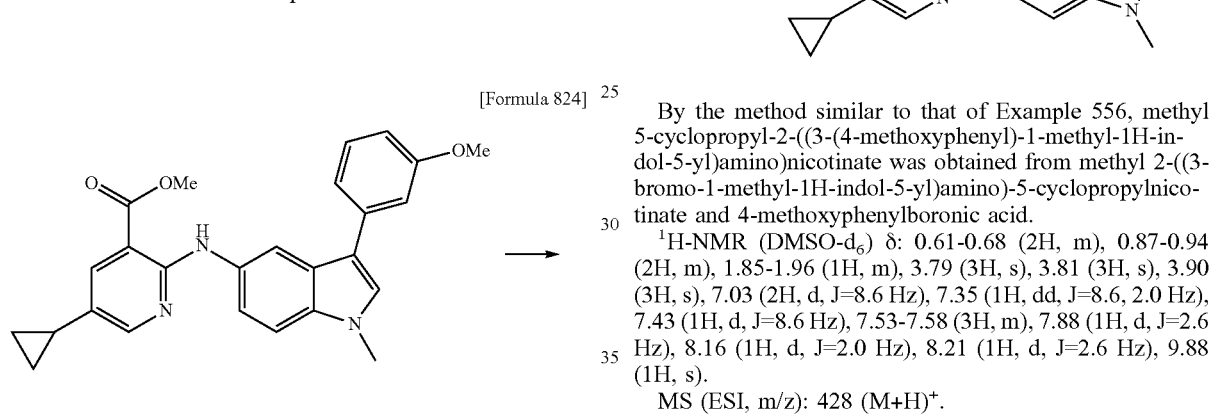

By the method similar to that of Example 545, 5-cyclopropyl-2-((3-(3-methoxyphenyl)-1-methyl-1H-indol-5-yl)amino)nicotinic acid was obtained from methyl 5-cyclopropyl-2-((3-(3-methoxyphenyl)-1-methyl-1H-indol-5-yl)amino)nicotinate.

$^1$H-NMR (DMSO-$d_6$) δ: 0.62-0.68 (2H, m), 0.87-0.95 (2H, m), 1.87-1.97 (1H, m), 3.83 (3H, s), 3.84 (3H, s), 6.81 (1H, dd, J=7.9, 2.0 Hz), 7.17-7.38 (4H, m), 7.47 (1H, d, J=9.2 Hz), 7.70 (1H, s), 7.93 (1H, d, J=2.6 Hz), 8.12 (1H, d, J=2.0 Hz), 8.29 (1H, s), 10.25 (1H, s).

MS (ESI, m/z): 414 (M+H)+, 412 (M−H)−.

524

Example 578

[Formula 825]

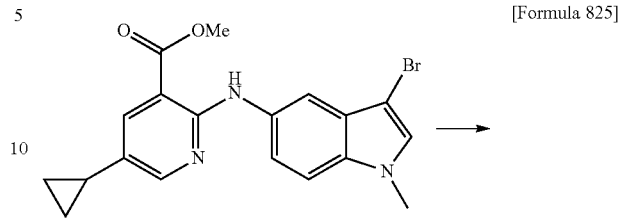

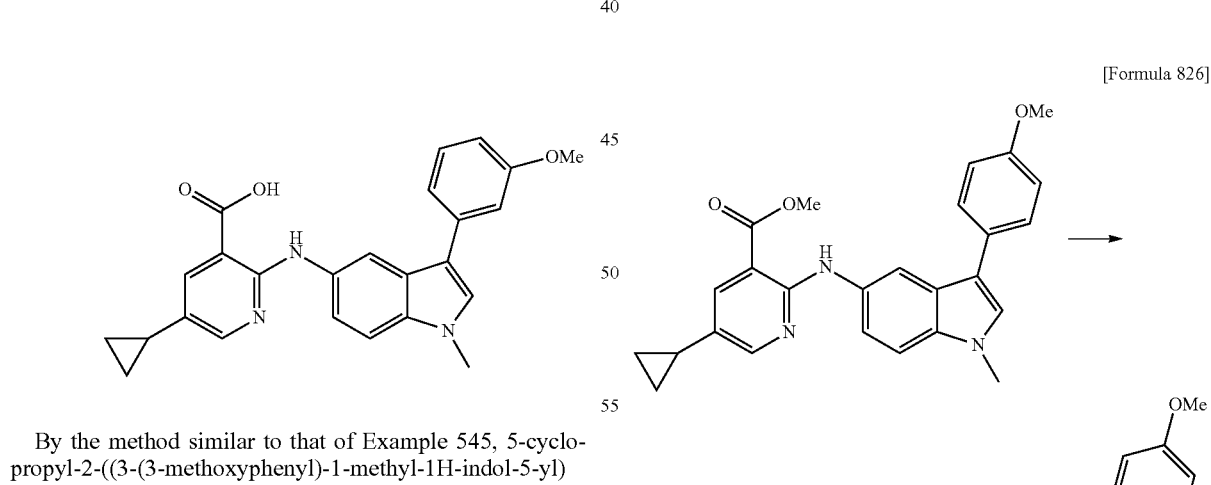

By the method similar to that of Example 556, methyl 5-cyclopropyl-2-((3-(4-methoxyphenyl)-1-methyl-1H-indol-5-yl)amino)nicotinate was obtained from methyl 2-((3-bromo-1-methyl-1H-indol-5-yl)amino)-5-cyclopropylnicotinate and 4-methoxyphenylboronic acid.

$^1$H-NMR (DMSO-$d_6$) δ: 0.61-0.68 (2H, m), 0.87-0.94 (2H, m), 1.85-1.96 (1H, m), 3.79 (3H, s), 3.81 (3H, s), 3.90 (3H, s), 7.03 (2H, d, J=8.6 Hz), 7.35 (1H, dd, J=8.6, 2.0 Hz), 7.43 (1H, d, J=8.6 Hz), 7.53-7.58 (3H, m), 7.88 (1H, d, J=2.6 Hz), 8.16 (1H, d, J=2.0 Hz), 8.21 (1H, d, J=2.6 Hz), 9.88 (1H, s).

MS (ESI, m/z): 428 (M+H)+.

Example 579

[Formula 826]

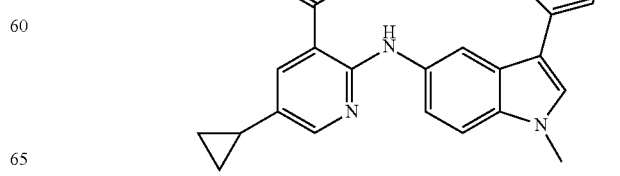

By the method similar to that of Example 545, 5-cyclopropyl-2-((3-(4-methoxyphenyl)-1-methyl-1H-indol-5-yl)amino)nicotinic acid was obtained from methyl 5-cyclopropyl-2-((3-(4-methoxyphenyl)-1-methyl-1H-indol-5-yl)amino)nicotinate.

$^1$H-NMR (DMSO-$d_6$) δ: 0.61-0.68 (2H, m), 0.86-0.94 (2H, m), 1.84-1.96 (1H, m), 3.79 (3H, s), 3.81 (3H, s), 7.03 (2H, d, J=8.6 Hz), 7.32 (1H, dd, J=8.9, 1.7 Hz), 7.42 (1H, d, J=8.6 Hz), 7.52-7.59 (3H, m), 7.87 (1H, d, J=2.0 Hz), 8.15-8.22 (2H, m), 10.15 (1H, s), 13.41 (1H, brs).

MS (ESI, m/z): 414 (M+H)$^+$, 412 (M−H)$^−$.

Example 580

[Formula 827]

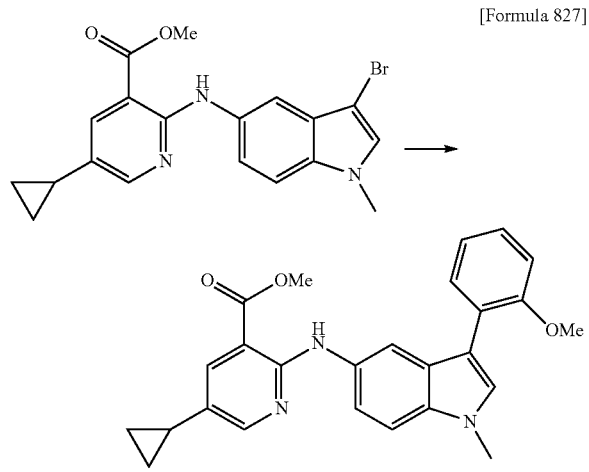

By the method similar to that of Example 556, methyl 5-cyclopropyl-2-((3-(2-methoxyphenyl)-1-methyl-1H-indol-5-yl)amino)nicotinate was obtained from methyl 2-((3-bromo-1-methyl-1H-indol-5-yl)amino)-5-cyclopropylnicotinate and 2-methoxyphenylboronic acid.

MS (ESI, m/z): 428 (M+H)$^+$.

Example 581

[Formula 828]

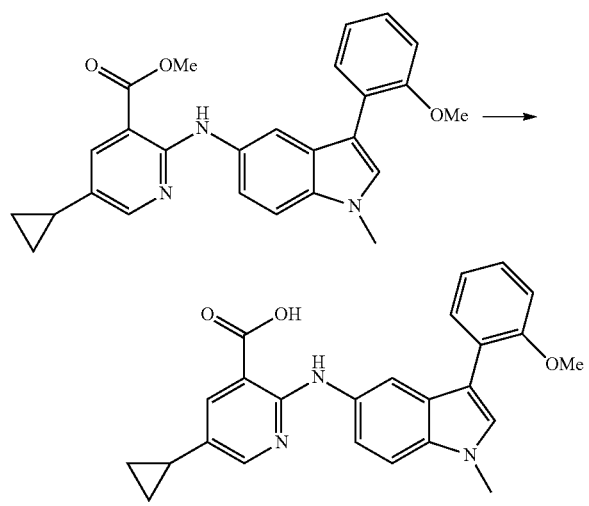

By the method similar to that of Example 545, 5-cyclopropyl-2-((3-(2-methoxyphenyl)-1-methyl-1H-indol-5-yl)amino)nicotinic acid was obtained from methyl 5-cyclopropyl-2-((3-(2-methoxyphenyl)-1-methyl-1H-indol-5-yl)amino)nicotinate.

$^1$H-NMR (DMSO-$d_6$) δ: 0.61-0.67 (2H, m), 0.85-0.94 (2H, m), 1.85-1.95 (1H, m), 3.81 (3H, s), 3.83 (3H, s), 7.00-7.07 (1H, m), 7.11 (1H, d, J=7.3 Hz), 7.22-7.31 (2H, m), 7.42 (1H, d, J=8.6 Hz), 7.50-7.55 (2H, m), 7.87 (1H, d, J=2.6 Hz), 8.02 (1H, d, J=2.0 Hz), 8.14 (1H, d, J=2.0 Hz), 10.16 (1H, s).

MS (ESI, m/z): 414 (M+H)$^+$, 412 (M−H)$^−$.

Example 582

[Formula 829]

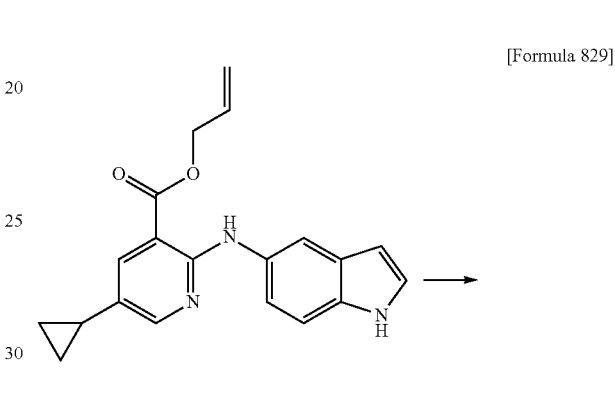

By the method similar to that of Example 574, allyl 2-((1-(cyclohexylcarbonyl)-1H-indol-5-yl)amino)-5-cyclopropylnicotinate was obtained from allyl 5-cyclopropyl-2-((1H-indol-5-ylamino)nicotinate and cyclohexanecarbonyl chloride.

$^1$H-NMR (DMSO-$d_6$) δ: 0.64-0.71 (2H, m), 0.90-0.97 (2H, m), 1.15-2.00 (12H, m), 4.84-4.89 (2H, m), 5.32 (1H, dd, J=10.6, 1.3 Hz), 5.44 dd, J=17.2, 1.3 Hz), 6.02-6.16 (1H, m), 6.73 (1H, d, J=4.0 Hz), 7.41 (1H, dd, J=8.9, 2.3 Hz), 7.97 (1H, d, J=2.4 Hz), 7.99 (1H, d, J=3.9 Hz), 8.14 (1H, d, J=2.0 Hz), 8.25-8.30 (2H, m), 10.01 (1H, s).

MS (ESI, m/z): 444 (M+H)$^+$.

Example 583

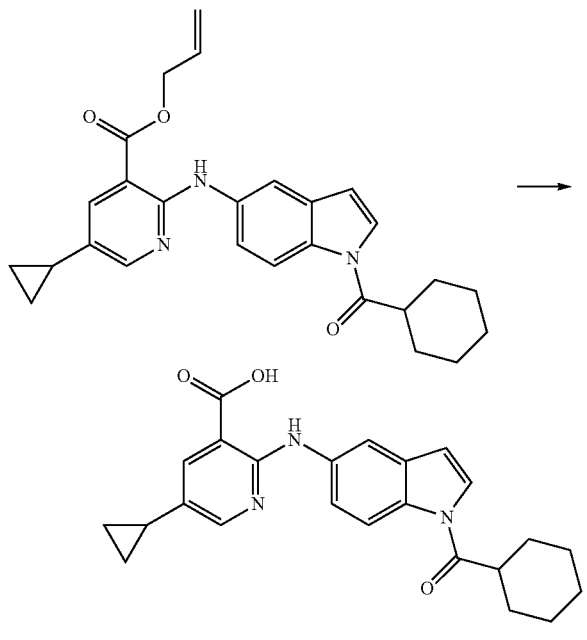
[Formula 830]

By the method similar to that of Example 575, 2-((1-(cyclohexylcarbonyl)-1H-indol-5-yl)amino)-5-cyclopropylnicotinic acid was obtained from Allyl 2-((1-(cyclohexylcarbonyl)-1H-indol-5-yl)amino)-5-cyclopropylnicotinate.

MS (ESI, m/z): 404 (M+H)$^+$, 402 (M–H)$^-$.

Example 584

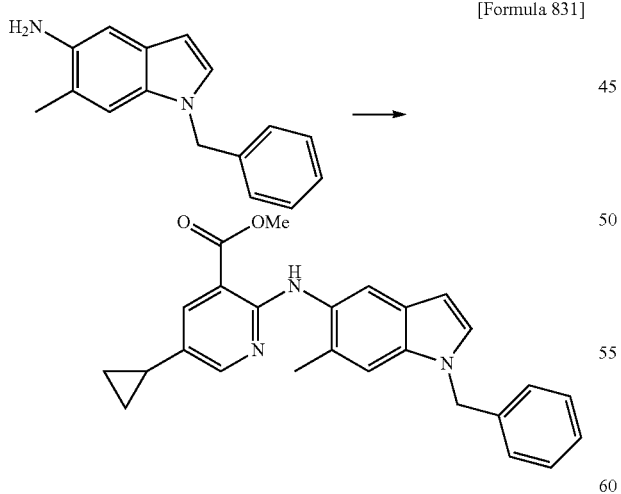
[Formula 831]

By the method similar to that of Example 540, methyl 2-((1-benzyl-6-methyl-1H-indol-5-yl)amino)-5-cyclopropylnicotinate was obtained from 1-benzyl-6-methyl-1H-indol-5-amine and methyl 2-chloro-5-cyclopropylnicotinate.

$^1$H-NMR (DMSO-d$_6$) δ: 0.60-0.66 (2H, m), 0.86-0.93 (2H, m), 1.83-1.94 (1H, m), 2.28 (3H, s), 3.89 (3H, s), 5.38 (2H, s), 6.40 (1H, d, J=3.3 Hz), 7.16-7.35 (6H, m), 7.40 (1H, d, J=3.3 Hz), 7.88 (1H, d, J=2.0 Hz), 8.05 (1H, s), 8.16 (1H, d, J=2.6 Hz), 9.60 (1H, s).

MS (ESI, m/z): 412 (M+H)$^+$.

Example 585

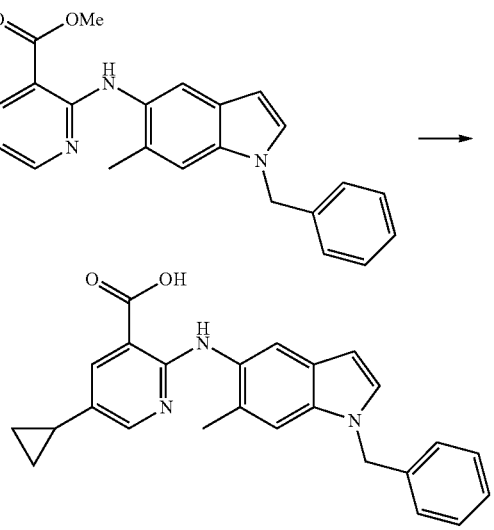
[Formula 832]

By the method similar to that of Example 545, 2-((1-benzyl-6-methyl-1H-indol-5-yl)amino)-5-cyclopropylnicotinic acid was obtained from methyl 2-((1-benzyl-6-methyl-1H-indol-5-yl)amino)-5-cyclopropylnicotinate.

$^1$H-NMR (DMSO-d$_6$) δ: 0.61-0.67 (2H, m), 0.87-0.95 (2H, m), 1.85-1.96 (1H, m), 2.28 (3H, s), 5.39 (2H, s), 6.42 (1H, d, J=2.6 Hz), 7.17-7.36 (6H, m), 7.43 (1H, d, J=3.3 Hz), 7.95 (1H, s), 8.02 (1H, s), 8.06 (1H, s), 9.99 (1H, s).

MS (ESI, m/z): 398 (M+H)$^+$, 396 (M–H)$^-$.

Example 586

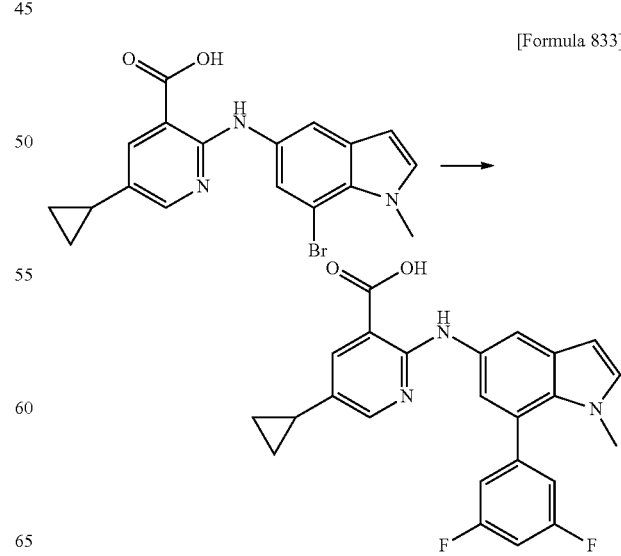
[Formula 833]

529

By the method similar to that of Example 463, 5-cyclopropyl-2-((7-(3,5-difluorophenyl)-1-methyl-1H-indol-5-yl)amino)nicotinic acid was obtained from 2-((7-bromo-1-methyl-1H-indol-5-yl)amino)-5-cyclopropylnicotinic acid and (3,5-difluorophenyl)boronic acid.

¹H-NMR (DMSO-d₆) δ: 0.62-0.68 (2H, m), 0.87-0.94 (2H, m), 1.86-1.94 (1H, m), 3.25-3.40 (3H, m), 6.47 (1H, d, J=2.9 Hz), 7.05 (1H, d, J=2.2 Hz), 7.21-7.38 (4H, m), 7.88 (1H, d, J=2.4 Hz), 8.10 (1H, d, J=2.0 Hz), 8.21 (1H, d, J=2.4 Hz), 10.22 (1H, s).

MS (ESI, m/z): 420 (M+H)⁺

Example 587

[Formula 834]

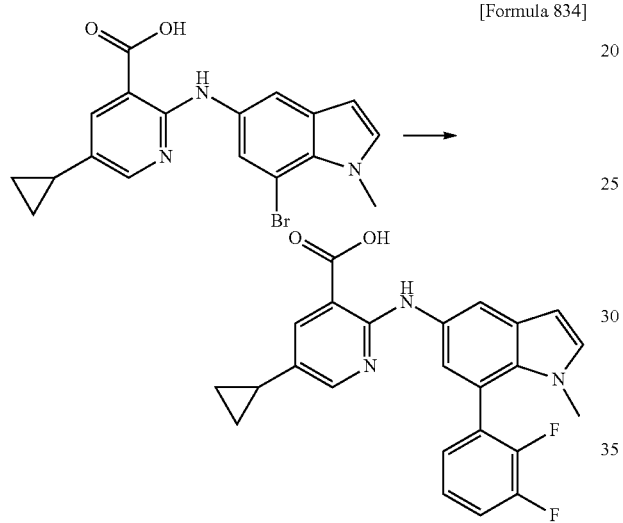

By the method similar to that of Example 463, 5-cyclopropyl-2-((7-(2,3-difluorophenyl)-1-methyl-1H-indol-5-yl)amino)nicotinic acid was obtained from 2-((7-bromo-1-methyl-1H-indol-5-yl)amino)-5-cyclopropylnicotinic acid and (2,3-difluorophenyl)boronic acid.

¹H-NMR (DMSO-d₆) δ: 0.60-0.70 (2H, m), 0.86-0.94 (2H, m), 1.86-1.95 (1H, m), 3.30 (3H, s), 6.47 (1H, d, J=2.9 Hz), 7.10 (1H, d, J=2.2 Hz), 7.27 (1H, d, J=3.2 Hz), 7.30-7.38 (2H, m), 7.48-7.52 (1H, m), 7.88 (1H, d, J=2.4 Hz), 8.11 (1H, d, J=2.2 Hz), 8.21 (1H, d, J=2.4 Hz), 10.24 (1H, s).

MS (ESI, m/z): 420 (M+H)⁺, 418 (M−H)⁻.

Example 588

[Formula 835]

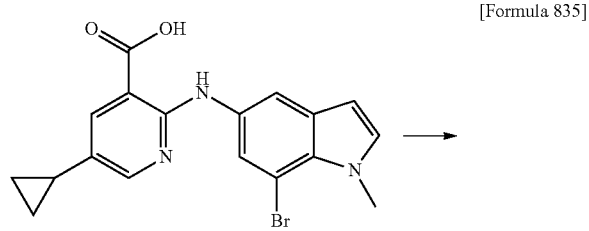

530

-continued

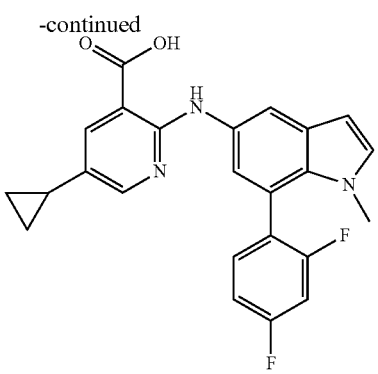

By the method similar to that of Example 463, 5-cyclopropyl-2-((7-(2,4-difluorophenyl)-1-methyl-1H-indol-5-yl)amino)nicotinic acid was obtained from 2-((7-bromo-1-methyl-1H-indol-5-yl)amino)-5-cyclopropylnicotinic acid and (2,4-difluorophenyl)boronic acid.

¹H-NMR (DMSO-d₆) δ: 0.60-0.70 (2H, m), 0.82-0.96 (2H, m), 1.84-1.94 (1H, m), 3.30 (3H, s), 6.45 (1H, d, J=2.9 Hz), 7.05 (1H, d, J=2.0 Hz), 7.16-7.28 (2H, m), 7.36-7.46 (1H, m), 7.50-7.62 (1H, m), 7.88 (1H, d, J=2.4 Hz), 8.09 (1H, d, J=2.0 Hz), 8.21 (1H, d, J=2.4 Hz), 10.22 (1H, s).

MS (ESI, m/z): 420 (M+H)⁺.

Example 589

[Formula 836]

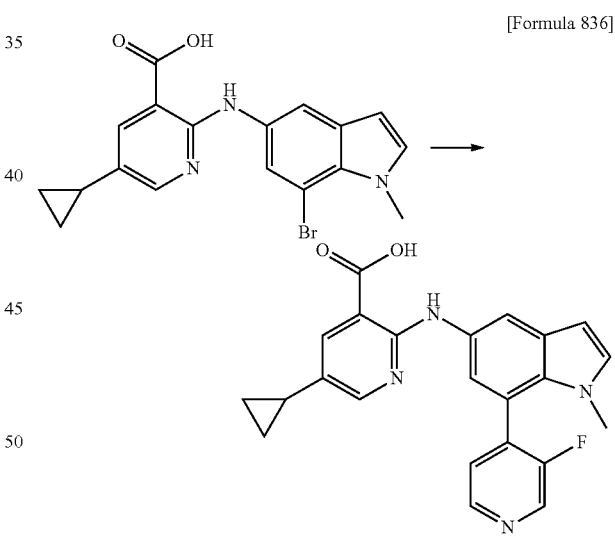

By the method similar to that of Example 463, 5-cyclopropyl-2-((7-(3-fluoropyridin-4-yl)-1-methyl-1H-indol-5-yl)amino)nicotinic acid was obtained from 2-((7-bromo-1-methyl-1H-indol-5-yl)amino)-5-cyclopropylnicotinic acid and (3-fluoropyridin-4-yl)boronic acid.

¹H-NMR (DMSO-d₆) δ: 0.60-0.73 (2H, m), 0.85-0.98 (2H, m), 1.84-1.98 (1H, m), 3.20-3.50 (3H, m), 6.45-6.55 (1H, m), 7.11-7.20 (1H, m), 7.26-7.35 (1H, m), 7.60-7.70 (1H, m), 7.84-7.94 (1H, m), 8.10-8.26 (2H, m), 8.52-8.61 (1H, m), 8.69-8.76 (1H, m), 10.23 (1H, s).

MS (ESI, m/z): 403 (M+H)⁺, 401 (M−H)⁻.

Example 590

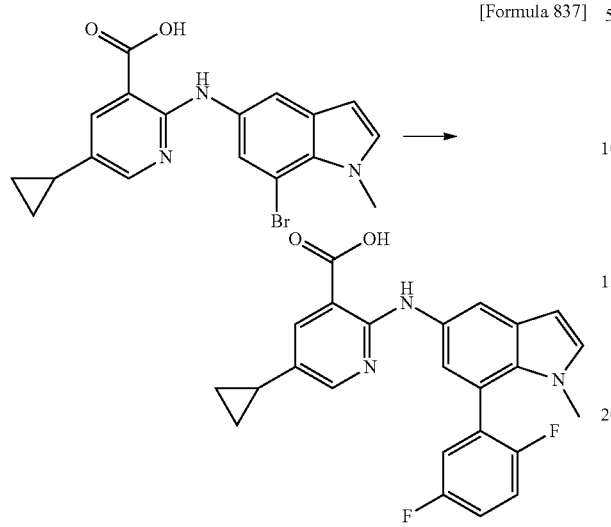

[Formula 837]

By the method similar to that of Example 463, 5-cyclopropyl-2-((7-(2,5-difluorophenyl)-1-methyl-1H-indol-5-yl)amino)nicotinic acid was obtained from 2-((7-bromo-1-methyl-1H-indol-5-yl)amino)-5-cyclopropylnicotinic acid and (2,5-difluorophenyl)boronic acid.

$^1$H-NMR (DMSO-d$_6$) δ: 0.61-0.68 (2H, m), 0.86-0.95 (2H, m), 1.85-1.95 (1H, m), 3.30 (3H, s), 6.46 (1H, d, J=3.2 Hz), 7.09 (1H, d, J=2.0 Hz), 7.27 (1H, d, J=3.2 Hz), 7.32-7.46 (3H, m), 7.89 (1H, d, J=2.4 Hz), 8.10 (1H, d, J=2,0 Hz), 8.22 (1H, d, J=2.7 Hz).

MS (ESI, m/z): 420 (M+H)$^+$, 418 (M−H)$^−$.

Example 591

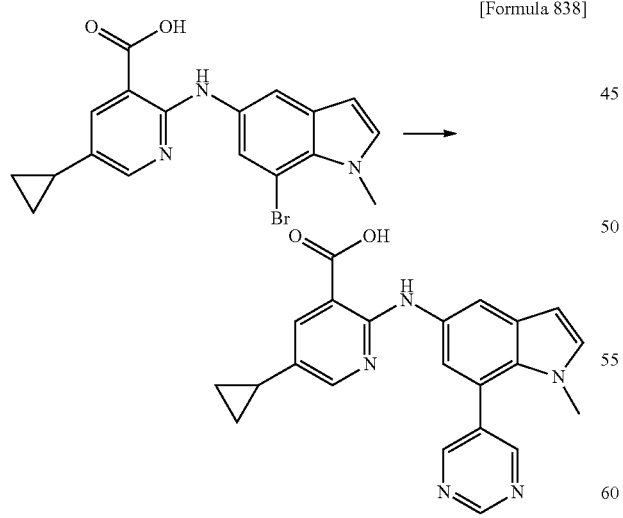

[Formula 838]

By the method similar to that of Example 463, 5-cyclopropyl-2-((1-methyl-7-(pyrimidin-5-yl)-1H-indol-5-yl)amino)nicotinic acid was obtained from 2-((7-bromo-1-methyl-1H-indol-5-yl)amino)-5-cyclopropylnicotinic acid and pyrimidin-5-ylboronic acid.

$^1$H-NMR (DMSO-d$_6$) δ: 0.59-0.70 (2H, m), 0.82-0.95 (2H, m), 1.82-1.95 (1H, m), 3.27-3.37 (3H, m), 6.44-6.52 (1H, m), 7.07-7.14 (1H, m), 7.25-7.34 (1H, m), 7.84-7.92 (1H, m), 8.12-8.25 (2H, m), 8.98 (2H, s), 9.25 (1H, s), 10.23 (1H, s).

MS (ESI, m/z): 386 (M+H)$^+$, 384 (M−H)$^−$.

Example 592

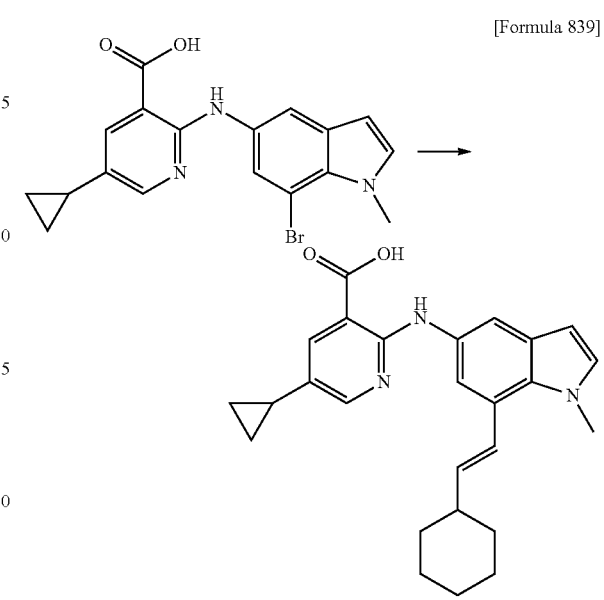

[Formula 839]

By the method similar to that of Example 463, 2-((7-((E)-2-cyclohexylethenyl)-1-methyl-1H-indol-5-yl)amino)-5-cyclopropylnicotinic acid was obtained from 2-((7-bromo-1-methyl-1H-indol-5-yl)amino)-5-cyclopropylnicotinic acid and ((E)-2-cyclohexylethenyl)boronic acid.

$^1$H-NMR (DMSO-d$_6$) δ: 0.60-0.68 (2H, m), 0.80-0.95 (3H, m), 1.10-1.40 (5H, m), 1.60-1.95 (6H, m), 3.96 (3H, s), 6.00 (1H, dd, J=15.6, 6.8 Hz), 6.33 (1H, d, J=3.2 Hz), 7.02 (1H, d, J=2.0 Hz), 7.15 (1H, d, J=15.4 Hz), 7.19 (1H, d, J=2.9 Hz), 7.87 (1H, d, J=2.4 Hz), 7.94 (1H, d, J=1.7 Hz), 8.19 (1H, d, J=2.4 Hz), 10.14 (1H, s).

MS (ESI, m/z): 416 (M+H)$^+$.

Example 593

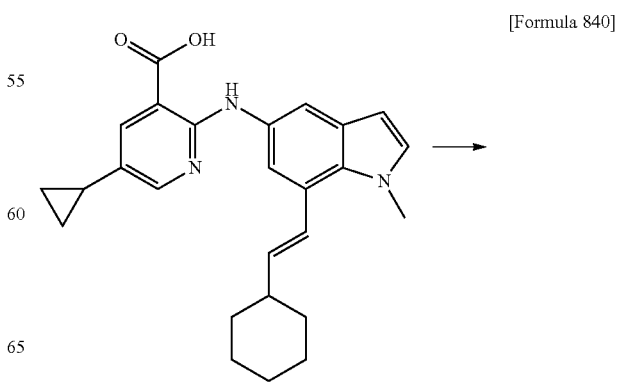

[Formula 840]

-continued

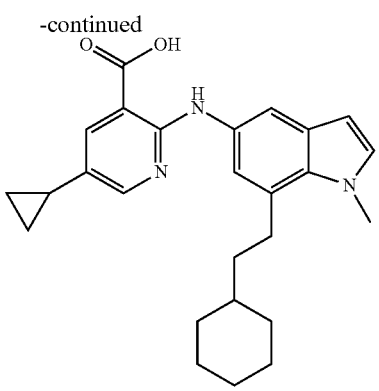

To the solution of 0.06 g of 2-((7-((E)-2-cyclohexylethenyl)-1-methyl-1H-indol-5-yl)amino)-5-cyclopropylnicotinic acid in 5 mL of methanol, 0.02 g of 10% palladium on carbon was added, and the resultant was stirred at room temperature for eight hours and 45 minutes under a hydrogen atmosphere. The insoluble matter was filtered off and the solvent was distilled off under reduced pressure. The obtained residue was purified by silica gel column chromatography (gradient elution with hexane:ethyl acetate=90:10-60:40) to give 0.026 g of 2-((7-(2-cyclohexylethyl)-1-methyl-1H-indol-5-yl)amino)-5-cyclopropylnicotinic acid as a yellow solid.

$^{1}$H-NMR (DMSO-d$_6$) δ: 0.60-0.66 (2H, m), 0.81-1.94 (16H, m), 2.91-3.06 (2H, m), 3.95 (3H, s), 6.30 (1H, d, J=3.2 Hz), 6.80-6.86 (1H, m), 7.15 (1H, d, J=3.2 Hz), 7.85 (1H, d, J=2.4 Hz), 7.88-7.94 (1H, m), 8.19 (1H, d, J=2.2 Hz), 10.09 (1H, s).

MS (ESI, m/z): 418 (M+H)$^+$, 416 (M−H)$^-$.

Example 594

[Formula 841]

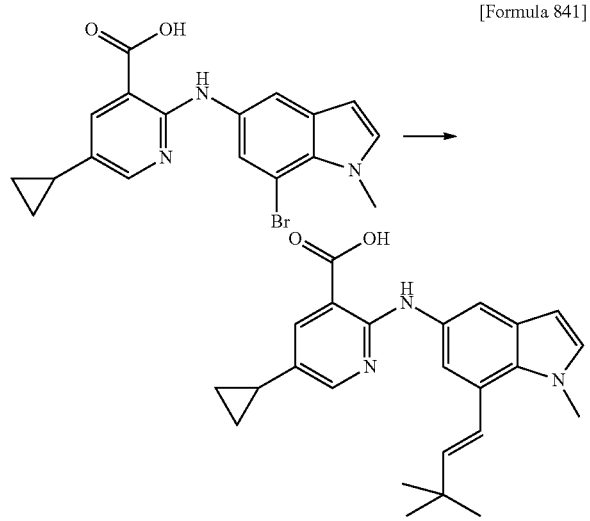

By the method similar to that of Example 463, 5-cyclopropyl-2-((7-((1E)-3,3-dimethylbut-1-en-1-yl)-1-methyl-1H-indol-5-yl)amino)nicotinic acid was obtained from 2-((7-bromo-1-methyl-1H-indol-5-yl)amino)-5-cyclopropylnicotinic acid and ((1E)-3,3-dimethylbut-1-en-1-yl)boronic acid.

$^{1}$H-NMR (DMSO-d$_6$) δ: 0.59-0.67 (2H, m), 0.77-0.94 (2H, m), 1.14 (9H, s), 1.83-1.93 (1H, m), 3.95 (3H, s), 6.05 (1H, d, J=15.9 Hz), 6.32 (1H, d, J=3.2 Hz), 6.97 (1H, d, J=2.0 Hz), 7.09 (1H, d, J=15.6 Hz), 7.18 (1H, d, J=3.2 Hz), 7.85 (1H, d, J 2.7 Hz), 7.93 (1H, d, J=2.0 Hz), 8.18 (1H, d, J=2.4 Hz), 10.11 (1H, s).

MS (ESI, m/z): 390 (M+H)$^+$.

Example 595

[Formula 842]

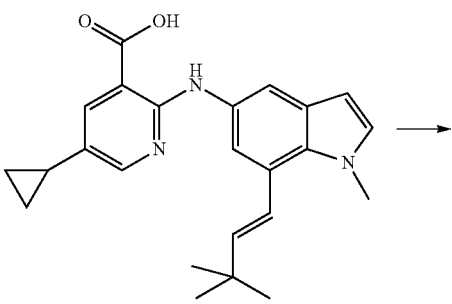

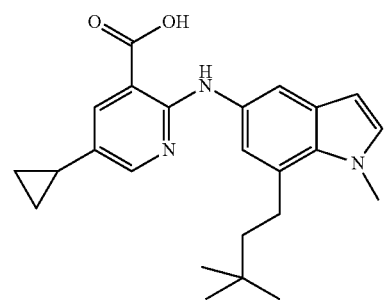

To the solution of 0.078 g of 5-cyclopropyl-2-((7-((1E)-3,3-dimethylbut-1-en-1-yl)-1-methyl-1H-indol-5-yl)amino) nicotinic acid in 5 mL of methanol, 0.025 g of 10% palladium hydroxide on carbon was added, and the resultant was stirred at room temperature for four hours under a hydrogen atmosphere. The insoluble matter was filtered off and the solvent was distilled off under reduced pressure. 5 mL of methanol and 0.028 g of 10% palladium hydroxide on carbon were added to the obtained residue, and the resultant was stirred at room temperature for four hours and 35 minutes under a hydrogen atmosphere. The insoluble matter was filtered off and the solvent was distilled off under reduced pressure. The thus obtained residue was purified by silica gel column chromatography (gradient elution with hexane:ethyl acetate=90:10-60:40) to give 0.013 g of 5-Cyclopropyl-2-((7-(3,3-dimethylbutyl)-1-methyl-1H-indol-5-yl)amino)nicotinic acid as a yellow solid.

$^{1}$H-NMR (DMSO-d$_6$) δ: 0.60-0.68 (2H, m), 0.81-0.94 (2H, m), 1.01 (9H, s), 1.48-1.60 (2H, m), 1.84-1.95 (1H, m), 2.90-3.02 (2H, m), 3.98 (3H, s), 6.32 (1H, d, J=2.9 Hz), 6.81 (1H, d, J=1.7 Hz), 7.18 (1H, d, J=3.2 Hz), 7.87 (1H, d, J=2.4 Hz), 7.92-7.98 (1H, m), 8.20 (1H, d, J=2.4 Hz), 10.10 (1H, s).

MS (ESI, m/z): 392 (M+H)$^+$.

Example 596

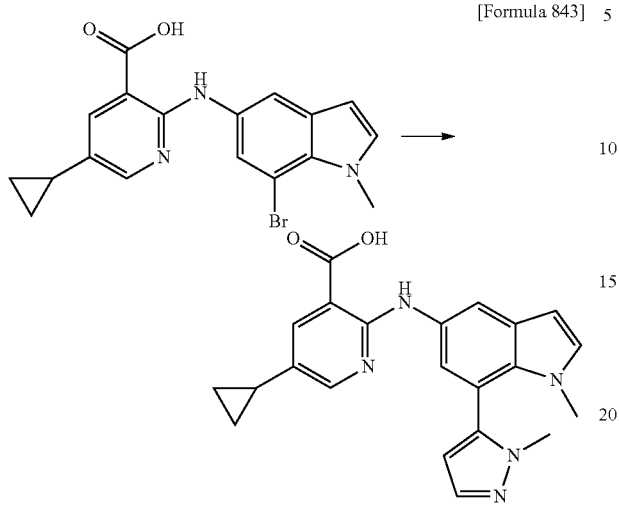

[Formula 843]

By the method similar to that of Example 463, 5-cyclopropyl-2-((1-methyl-7-(1-methyl-1H-pyrazol-5-yl)-1H-indol-5-yl)amino)nicotinic acid was obtained from 2-((7-bromo-1-methyl-1H-indol-5-yl)amino)-5-cyclopropylnicotinic acid and 1-methyl-5-(4,4,5,5-tetramethyl-1,3,2-dioxaborolan-2-yl)-1H-pyrazole.

$^1$H-NMR (DMSO-d$_6$) δ: 0.56-0.67 (2H, m), 0.80-0.93 (2H, m), 1.80-1.93 (1H, m), 3.21 (3H, s), 3.58 (3H, s), 6.38-6.49 (2H, m), 7.11-7.18 (1H, m), 7.22-7.29 (1H, m), 7.50-7.57 (1H, m), 7.83-7.90 (1H, m), 8.03-8.10 (1H, m), 8.14-8.22 (1H, m), 10.24 (1H, s).

MS (ESI, m/z): 388 (M+H)$^+$, 386 (M−H)$^-$.

Example 597

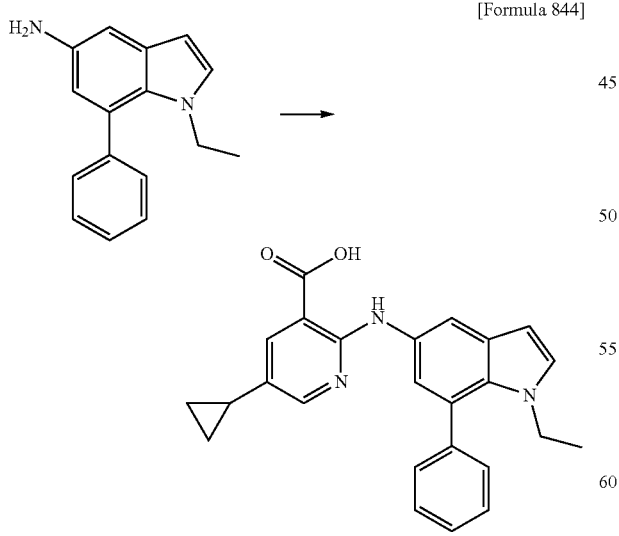

[Formula 844]

By the method similar to that of Example 462, 5-cyclopropyl-2-((1-ethyl-7-phenyl-1H-indol-5-yl)amino)nicotinic acid was obtained from 1-ethyl-7-phenyl-1H-indol-5-amine and 2-chloro-5-cyclopropylnicotinic acid.

$^1$H-NMR (DMSO-d$_6$) δ: 0.62-0.68 (2H, m), 0.78-0.94 (5H, m), 1.84-1.94 (1H, m), 3.68 (2H, q, J=7.1 Hz), 6.49 (1H, d, J=3.2 Hz), 6.98 (1H, d, J=2.0 Hz), 7.32 (1H, d, J=2.9 Hz), 7.42-7.50 (5H, m), 7.88 (1H, d, J=2.4 Hz), 8.03 (1H, d, J=2.0 Hz), 8.20 (1H, d, J=2.7 Hz), 10.23 (1H, s).

MS (ESI, m/z): 398 (M+H)$^+$, 396 (M−H)$^-$.

Example 598

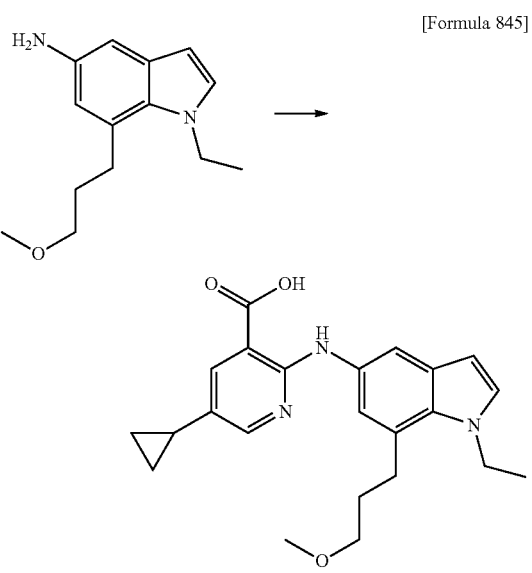

[Formula 845]

By the method similar to that of Example 462, 5-cyclopropyl-2-((1-ethyl-7-(3-methoxypropyl)-1H-indol-5-yl)amino)nicotinic acid was obtained from 1-ethyl-7-(3-methoxypropyl)-1H-indol-5-amine and 2-chloro-5-cyclopropylnicotinic acid.

$^1$H-NMR (DMSO-d$_6$) δ: 0.60-0.68 (2H, m), 0.86-0.94 (2H, m), 1.28-1.34 (3H, m), 1.80-1.94 (3H, m), 2.90-3.02 (2H, m), 3.27 (3H, s), 3.38-3.44 (2H, m), 4.24-4.34 (2H, m), 6.32-6.40 (1H, m), 6.84-6.92 (1H, m), 7.22-7.30 (1H, m), 7.82-7.88 (1H, m), 7.90-7.94 (1H, m), 8.16-8.22 (1H, m), 10.14 (1H, s).

MS (ESI, m/z): 394 (M+H)$^+$, 392 (M−H)$^-$.

Example 599

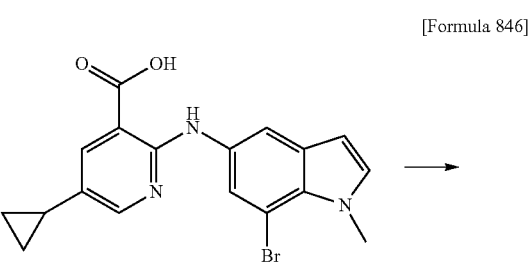

[Formula 846]

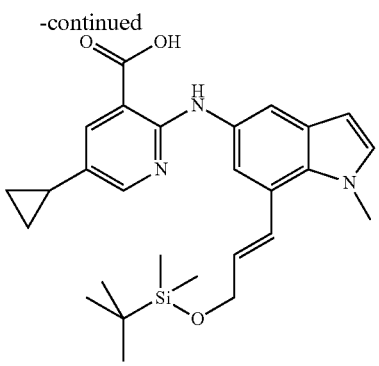

By the method similar to that of Example 463, 2-((7-((1E)-3-((tert-butyl(dimethyl)silyl)oxy)prop-1-en-1-yl)-1-methyl-1H-indol-5-yl)amino)-5-cyclopropylnicotinic acid was obtained from 2-((7-bromo-1-methyl-1H-indol-5-yl)amino)-5-cyclopropylnicotinic acid and ((1E)-3-((tert-butyl(dimethyl)silyl)oxy)prop-1-en-1-yl)boronic acid.

$^1$H-NMR (DMSO-$d_6$) δ: 0.12 (6H, s), 0.60-0.67 (2H, m), 0.88-0.94 (11H, m), 1.85-1.95 (1H, m), 3.96 (3H, s), 4.39 (2H, dd, J=4.6, 1.7 Hz), 6.17 (1H, dt, J=15.3, 4.6 Hz), 6.34 (1H, d, J=3.0 Hz), 7.17 (1H, d, J=2.0 Hz), 7.20 (1H, d, J=3.2 Hz), 7.39 (1H, d, J=15.3 Hz), 7.87 (1H, d, J=2.4 Hz), 7.95 (1H, d, J=2.0 Hz), 8.19 (1H, d, J=2.4 Hz).

MS (ESI, m/z): 478 (M+H)$^+$, 476 (M−H)$^−$.

Example 600

[Formula 847]

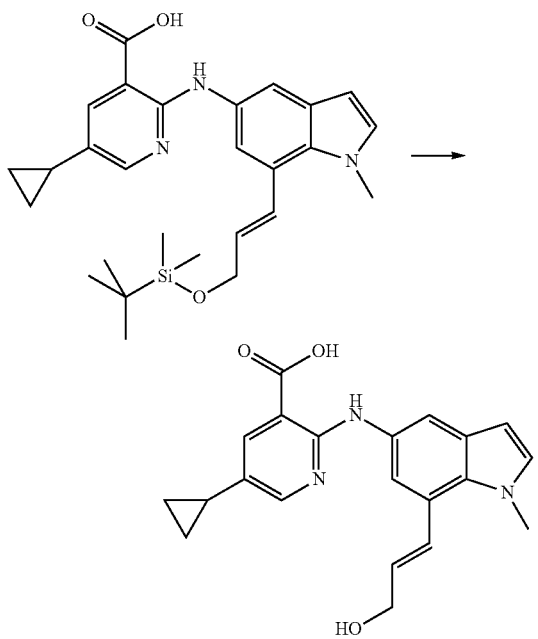

To the solution of 0.10 g of 2-((7-((1E)-3-((tert-butyl(dimethyl)silyl)oxy)prop-1-en-1-yl)-1-methyl-1H-indol-5-yl)amino)-5-cyclopropylnicotinic acid in 5 mL of methanol, 1 mL of 6 mol/L hydrochloric acid was added, and the resultant was stirred at room temperature for 10 minutes. The reaction mixture was adjusted to pH 2.3 by adding thereto ethyl acetate, water and a 2 mol/L aqueous sodium hydroxide solution, and the organic layer was separated and the aqueous layer was extracted with ethyl acetate. The organic layer and the extract were combined, washed with a saturated aqueous sodium chloride solution and dried over anhydrous sodium sulfate, and the solvent was distilled off under reduced pressure. Ethyl acetate was added to the obtained residue, and the solid was collected by filtration to give 0.006 g of 5-cyclopropyl-2-((7-((1E)-3-hydroxyprop-1-en-1-yl)-1-methyl-1H-indol-5-yl)amino)nicotinic acid as a yellow solid.

$^1$H-NMR (DMSO-$d_6$) δ: 0.60-0.69 (2H, m), 0.80-0.95 (2H, m), 1.86-1.96 (1H, m), 3.97 (3H, s), 4.18 (2H, dd, J=4.9, 1.7 Hz), 6.17 (1H, dt, J=15.4, 4.9 Hz), 6.35 (1H, d, J=3.2 Hz), 7.15 (1H, d, J=2.0 Hz), 7.22 (1H, d, J=3.0 Hz), 7.36 (1H, d, J=15.4 Hz), 7.88-7.93 (2H, m), 8.18 (1H, d, J=2.2 Hz), 10.16 (1H, s).

MS (ESI, m/z): 364 (M+H)$^+$, 362 (M−H)$^−$.

Example 601

[Formula 848]

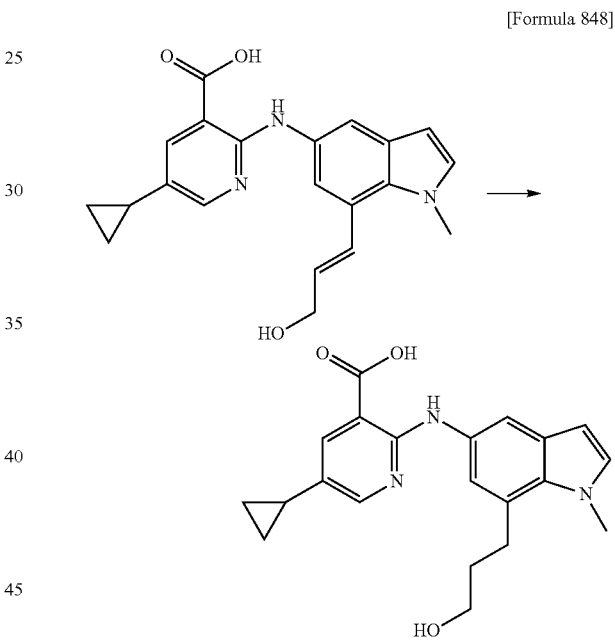

To the solution of 0.083 g of 5-cyclopropyl-2-((7-((1E)-3-hydroxyprop-1-en-1-yl)-1-methyl-1H-indol-5-yl)amino)nicotinic acid in 5 mL of methanol, 0.04 g of 10% palladium on carbon was added, and the resultant was stirred at room temperature for nine hours under a hydrogen atmosphere. The insoluble matter was filtered off and the solvent was distilled off under reduced pressure. The obtained residue was purified by silica gel column chromatography (gradient elution with hexane:ethyl acetate=80:20-0:100), and ethyl acetate and hexane were added to the thus obtained residue, and the solid was collected by filtration to give 0.006 g of 5-cyclopropyl-2-((7-(3-hydroxypropyl)-1-methyl-1H-indol-5-yl)amino)nicotinic acid as a yellow solid.

$^1$H-NMR (DMSO-$d_6$) δ: 0.61-0.67 (2H, m), 0.83-0.93 (2H, m), 1.74-1.94 (3H, m), 3.00-3.08 (2H, m), 3.48-3.56 (2H, m), 3.98 (3H, s), 6.29-6.32 (1H, m), 6.83-6.87 (1H, m), 7.12-7.22 (1H, m), 7.84-7.88 (1H, m), 7.92-7.96 (1H, m), 8.17-8.20 (1H, m), 10.25 (1H, brs).

MS (ESI, m/z): 366 (M+H)$^+$, 364 (M−H)$^−$.

Example 602

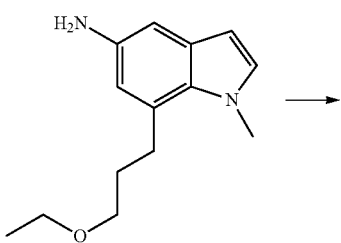

[Formula 849]

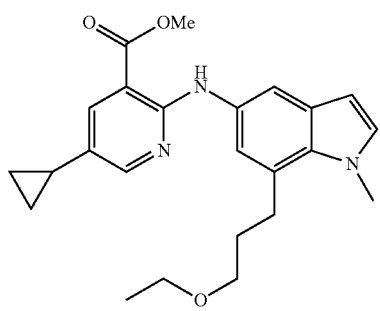

By the method similar to that of Example 223, methyl 5-cyclopropyl-2-((7-(3-ethoxypropyl)-1-methyl-1H-indol-5-yl)amino)nicotinate was obtained from 7-(3-ethoxypropyl)-1-methyl-1H-indol-5-amine and methyl 2-chloro-5-cyclopropylnicotinate.

$^1$H-NMR (DMSO-d$_6$) δ: 0.59-0.66 (2H, m), 0.86-0.95 (2H, m), 1.21 (3H, t, J=6.8 Hz), 1.76-1.86 (1H, m), 1.92-2.05 (2H, m), 3.13 (2H, t, J=7.6 Hz), 3.45-3.54 (4H, m), 3.92 (3H, s), 4.00 (3H, s), 6.41 (1H, d, J=3.2 Hz), 6.91 (1H, d, J=2.9 Hz), 7.00 (1H, d, J=2.0 Hz), 7.85 (1H, d, J=2.0 Hz), 7.89 (1H, d, J=2.7 Hz), 8.20 (1H, d, J=2.4 Hz), 9.80 (1H, s).

MS (ESI, m/z): 408 (M+H)$^+$.

Example 603

[Formula 850]

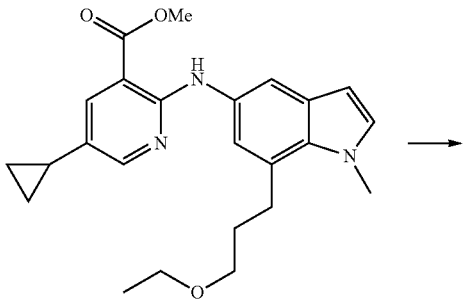

-continued

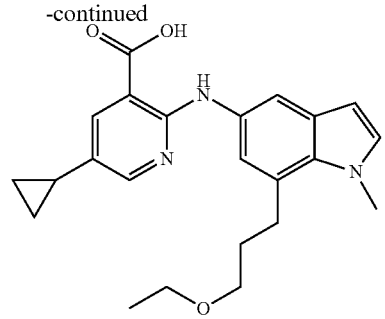

To the solution of 0.044 g of methyl 5-cyclopropyl-2-((7-(3-ethoxypropyl)-1-methyl-1H-indol-5-yl)amino)nicotinate in 0.5 mL of methanol and 1 mL of tetrahydrofuran, 0.05 mL of a 5 mol/L aqueous sodium hydroxide solution was added, and the resultant was heated at reflux at 50 to 52° C. for two hours and 10 minutes. The reaction mixture was cooled to room temperature and then adjusted to pH 2.1 by adding thereto 6 mol/L hydrochloric acid. The solvent was distilled off under reduced pressure, and methanol and water were added to the residue and the solid was collected by filtration to give 0.006 g of 5-cyclopropyl-2-((7-(3-ethoxypropyl)-1-methyl-1H-indol-5-yl)amino)nicotinic acid as a yellow solid.

$^1$H-NMR (DMSO-d$_6$) δ: 0.60-0.69 (2H, m), 0.86-0.95 (2H, m), 1.35 (3H, t, J=6.8 Hz), 1.80-1.95 (3H, m), 3.00-3.10 (2H, m), 3.40-3.48 (4H, m), 3.97 (3H, s), 6.32 (1H, d, J=2.9 Hz), 6.84-6.89 (1H, m) 7.18 (1H, d, J=2.9 Hz), 7.87 (1H, d, J=2.2 Hz), 7.90-7.95 (1H, m), 8.20 (1H, d, J=2.2 Hz), 10.12 (1H, s).

MS (ESI, m/z): 394 (M+H)$^+$, 392 (M−H)$^-$.

Example 604

[Formula 851]

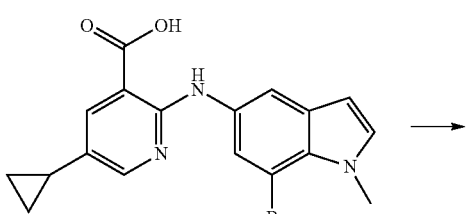

By the method similar to that of Example 463, 5-cyclopropyl-2-((7-((E)-2-ethoxyethenyl)-1-methyl-1H-indol-5-yl)amino)nicotinic acid was obtained from 2-((7-bromo-1-methyl-1H-indol-5-yl)amino)-5-cyclopropylnicotinic acid and 2-((E)-2-ethoxyethenyl-4,4,5,5-tetramethyl-1,3,2-dioxaborolane.

¹H-NMR (DMSO-d₆) δ: 0.60-0.68 (2H, m), 0.85-0.95 (2H, m), 1.29 (3H, t, J=7.1 Hz), 1.85-1.95 (1H, m), 3.91-4.00 (5H, m), 6.30 (1H, d, J=3.0 Hz), 6.55 (1H, d, J=12.5 Hz), 6.87 (1H, d, J=12.4 Hz), 6.96 (1H, d, J=1.9 Hz), 7.17 (1H, d, J=3.0 Hz), 7.87 (1H, d, J=2.4 Hz), 7.89 (1H, d, J=1.7 Hz), 8.20 (1H, d, J=2.4 Hz), 10.10 (1H, s).

MS (ESI, m/z): 378 (M+H)⁺, 376 (M−H)⁻.

Example 605

[Formula 852]

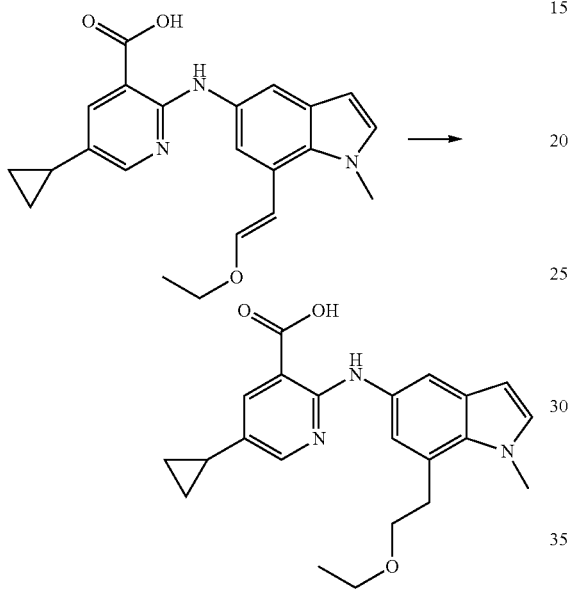

By the method similar to that of Example 601, 5-cyclopropyl-2-((7-(2-ethoxyethyl)-1-methyl-1H-indol-5-yl)amino)nicotinic acid was obtained from 5-cyclopropyl-2-((7-((E)-2-ethoxyethenyl)-1-methyl-1H-indol-5-yl)amino)nicotinic acid.

¹H-NMR (DMSO-d₆) δ: 0.61-0.68 (2H, m), 0.85-0.95 (2H, m), 1.11 (3H, t, J=7.1 Hz), 1.85-1.95 (1H, m), 3.26 (2H, t, J=7.2 Hz), 3.47 (2H, q, J=7.0 Hz), 3.67 (2H, t, J=7.1 Hz), 3.99 (3H, s), 6.32 (1H, d, J=2.9 Hz), 6.91 (1H, d, J=1.7 Hz), 7.18 (1H, d, J=2.9 Hz), 7.87 (1H, d, J=2.4 Hz), 7.97 (1H, d, J=2.0 Hz), 8.21 (1H, d, J=2.4 Hz), 10.14 (1H, s).

MS (ESI, m/z): 380 (M+H)⁺, 378 (M−H)⁻.

Example 606

[Formula 853]

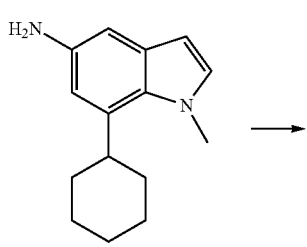

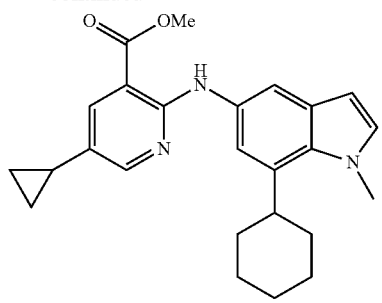

By the method similar to that of Example 223, methyl 2-((7-cyclohexyl-1-methyl-1H-indol-5-yl)amino)-5-cyclopropylnicotinate was obtained from 7-cyclohexyl-1-methyl-1H-indol-5-amine and methyl 2-chloro-5-cyclopropylnicotinate.

¹H-NMR (DMSO-d₆) δ: 0.62-0.69 (2H, m), 0.87-0.95 (2H, m), 1.42-1.61 (3H, m), 1.62-1.96 (9H, m), 3.89 (3H, s), 3.99 (3H, s), 6.32 (1H, d, J=3.2 Hz), 6.93 (1H, d, J=2.0 Hz), 7.18 (1H, d, J=2.9 Hz), 7.88 (1H, d, J=2.7 Hz), 7.93 (1H, d, J=2.2 Hz), 8.24 (1H, d, J=2.4 Hz), 9.85 (1H, s).

Example 607

[Formula 854]

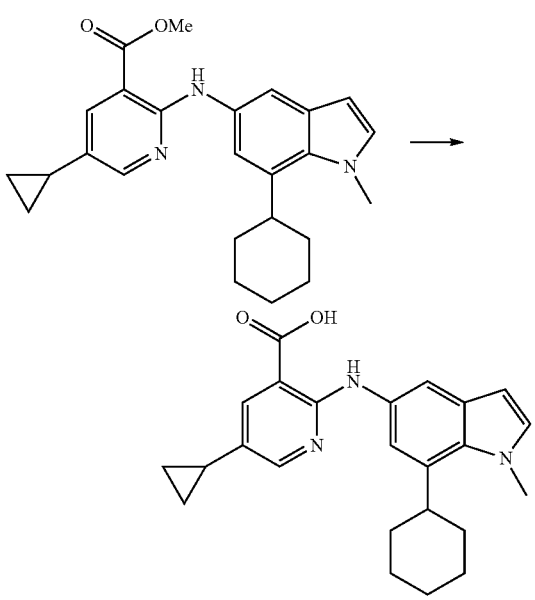

By the method similar to that of Example 603, 2-((7-cyclohexyl-1-methyl-1H-indol-5-yl)amino)-5-cyclopropylnicotinic acid was obtained from methyl 2-((7-cyclohexyl-1-methyl-1H-indol-5-yl)amino)-5-cyclopropylnicotinate.

¹H-NMR (DMSO-d₆) δ: 0.60-0.69 (2H, m), 0.86-0.94 (2H, m), 1.42-1.60 (5H, m), 1.69-1.97 (7H, m), 3.99 (3H, s), 6.28-6.35 (1H, m), 6.90-6.97 (1H, m), 7.14-7.20 (1H, m), 7.84-7.90 (1H, m), 7.90-7.95 (1H, m), 8.16-8.25 (1H, m), 10.12 (1H, s).

MS (ESI, m/z): 390 (M+H)⁺, 388 (M−H)⁻.

Example 608

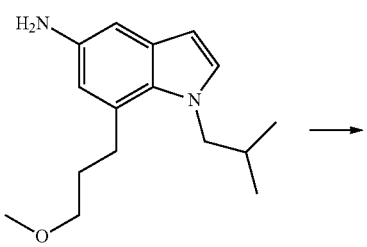

[Formula 855]

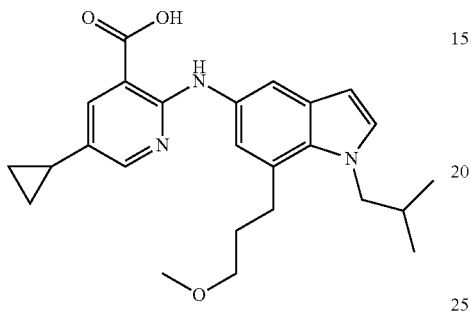

By the method similar to that of Example 462, 5-cyclopropyl-2-((7-(3-methoxypropyl)-1-(2-methylpropyl)-1H-indol-5-yl)amino)nicotinic acid was obtained from 7-(3-methoxypropyl)-1-(2-methylpropyl)-1H-indol-5-amine and 2-chloro-5-cyclopropylnicotinic acid.

¹H-NMR (DMSO-d₆) δ: 0.61-0.68 (2H, m), 0.80-0.87 (6H, m), 0.87-0.94 (2H, m), 1.76-2.02 (4H, m), 2.90-2.98 (2H, m), 3.28 (3H, s), 3.39-3.45 (2H, m), 4.03 (2H, d, J=7.3 Hz), 6.34 (1H, d, J=3.2 Hz), 6.90 (1H, d, J=2.0 Hz), 7.23 (1H, d, J=3.2 Hz), 7.87 (1H, d, J=2.7 Hz), 7.92 (1H, d, J=2.0 Hz), 8.20 (1H, d, J=2.4 Hz), 10.13 (1H, s).

MS (ESI, m/z): 422 (M+H)⁺, 420 (M−H)⁻.

Example 609

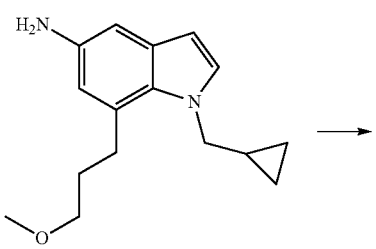

[Formula 856]

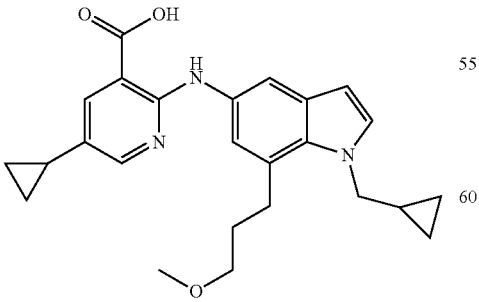

By the method similar to that of Example 462, 5-cyclopropyl-2-((1-(cyclopropylmethyl)-7-(3-methoxypropyl)-1H-indol-5-yl)amino)nicotinic acid was obtained from 1-(cyclopropylmethyl)-7-(3-methoxypropyl)-1H-indol-5-amine and 2-chloro-5-cyclopropylnicotinic acid.

¹H-NMR (DMSO-d₆) δ: 0.30-0.37 (2H, m), 0.44-0.53 (2H, m), 0.60-0.68 (2H, m), 0.86-0.94 (2H, m), 1.13-1.25 (1H, m), 1.80-1.94 (3H, m), 2.98-3.08 (2H, m), 3.28 (3H, s), 3.38-3.45 (2H, m), 4.15 (2H, d, J=6.6 Hz), 6.36 (1H, d, J=2.4 Hz), 6.90 (1H, d, J=2.0 Hz), 7.31 (1H, d, J=2.9 Hz), 7.87 (1H, d, J=2.4 Hz), 7.93 (1H, d, J=2.0 Hz), 8.20 (1H, d, J=2.2 Hz), 10.15 (1H, s).

MS (DART, m/z): 420 (M+H)⁺, 418 (M−H)⁻.

Example 610

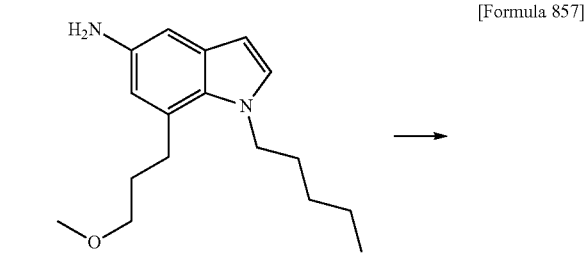

[Formula 857]

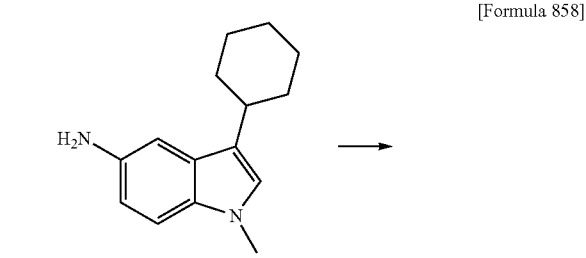

By the method similar to that of Example 462, 5-cyclopropyl-2-((7-(3-methoxypropyl)-1-pentyl-1H-indol-5-yl)amino)nicotinic acid was obtained from 7-(3-methoxypropyl)-1-pentyl-1H-indol-5-amine and 2-chloro-5-cyclopropylnicotinic acid.

¹H-NMR (DMSO-d₆) δ: 0.61-0.68 (2H, m), 0.82-0.93 (5H, m), 1.20-1.36 (4H, m), 1.60-1.74 (2H, m), 1.78-1.94 (3H, m), 2.90-3.00 (2H, m), 3.28 (3H, s), 3.42 (2H, t, J=6.0 Hz), 4.22 (2H, t, J=7.3 Hz), 6.35 (1H, d, J=3.2 Hz), 6.89 (1H, d, J=2.0 Hz), 7.25 (1H, d, J=3.2 Hz), 7.87 (1H, d, J=2.4 Hz), 7.91 (1H, d, J=2.0 Hz), 8.20 (1H, d, J=2.4 Hz), 10.14 (1H, s).

MS (DART, m/z): 436 (M+H)⁺, 434 (M−H)⁻.

Example 611

[Formula 858]

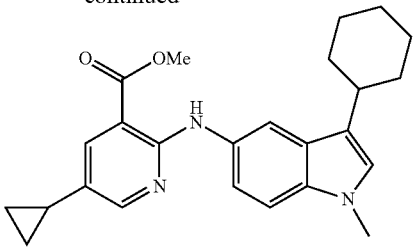

The mixture of 0.75 g of 3-cyclohexyl-1-methyl-1H-indol-5-amine, 0.68 g of methyl 2-chloro-5-cyclopropylnicotinate, 0.15 g of tris(dibenzylideneacetone)dipalladium (0), 0.19 g of 4,5'-bis(diphenylphosphino)-9,9'-dimethylxanthene, 2.15 g of cesium carbonate, and 7.5 mL of butyl acetate, was heated at reflux for four hours and 30 minutes under a nitrogen atmosphere. After cooling the reaction mixture to room temperature, the insoluble matter was filtered off and ethyl acetate and water were added to the filtrate. The organic layer was separated and the aqueous layer was extracted with ethyl acetate. The organic layer and the extract were combined, washed with a saturated aqueous sodium chloride solution and dried over anhydrous sodium sulfate, and the solvent was distilled off under reduced pressure. The obtained residue was purified by silica gel column chromatography (gradient elution with hexane:ethyl acetate=100:0-85:15) to give 1.08 g of methyl 2-((3-cyclohexyl-1-methyl-1H-indol-5-yl)amino)-5-cyclopropylnicotinate as a yellow solid.

$^1$H-NMR (DMSO-$d_6$) δ: 0.61-0.68 (2H, m), 0.85-0.94 (2H, m), 1.15-1.32 (1H, m), 1.34-1.50 (4H, m), 1.68-2.05 (6H, m), 2.66-2.79 (1H, m), 3.71 (3H, s), 3.89 (3H, s), 7.02 (1H, s), 7.28-7.32 (2H, m), 7.76 (1H, s), 7.87 (1H, d, J=2.4 Hz), 8.19 (1H, d, J=2.4 Hz), 9.79 (1H, s).

MS (ESI, m/z): 404 (M+H)$^+$.

Example 612

[Formula 859]

To the solution of 1.08 g of methyl 2-((3-cyclohexyl-1-methyl-1H-indol-5-yl)amino)-5-cyclopropylnicotinate in 11 mL of methanol and 22 mL of tetrahydrofuran, 1.1 mL of a 5 mol/L aqueous sodium hydroxide solution was added at room temperature, and the resultant was stirred at 55° C. for one hour and 30 minutes. After the reaction mixture was cooled to room temperature, water was added thereto, and the resultant was adjusted to pH 1.4 with 6 mol/L hydrochloric acid. Ethyl acetate was added thereto, and the organic layer was separated, washed with a saturated aqueous sodium chloride solution and dried over anhydrous sodium sulfate, and the solvent was distilled off under reduced pressure. The obtained residue was purified by silica gel column chromatography (gradient elution with hexane:ethyl acetate=90:10-40:60), and water and methanol were added to the thus obtained residue, and the solid was collected by filtration to give 0.26 g of 2-((3-cyclohexyl-1-methyl-1H-indol-5-yl)amino)-5-cyclopropylnicotinic acid as a yellow solid.

$^1$H-NMR (DMSO-$d_6$) δ: 0.60-0.67 (2H, m), 0.85-0.94 (2H, m), 1.18-1.50 (5H, m), 1.66-104 (6H, m), 2.65-2.79 (1H, m), 3.70 (3H, s), 7.01 (1H, s), 7.26-7.32 (2H, m), 7.78 (1H, s), 7.86 (1H, d, J=2.4 Hz), 8.16 (1H, d, J=2.4 Hz), 10.06 (1H, s).

MS (ESI, m/z): 390 (M+H)$^+$, 388 (M−H)$^−$.

Example 613

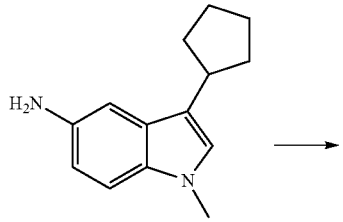

[Formula 860]

By the method similar to that of Example 611, methyl 2-((3-cyclopentyl-1-methyl-1H-indol-5-yl)amino)-5-cyclopropylnicotinate was obtained from 3-cyclopentyl-1-methyl-1H-indol-5-amine and methyl 2-chloro-5-cyclopropylnicotinate.

$^1$H-NMR (DMSO-$d_6$) δ: 0.60-0.68 (2H, m), 0.87-0.94 (2H, m), 1.55-1.82 (6H, m), 1.85-1.96 (1H, m), 2.01-2.14 (2H, m), 3.10-3.21 (1H, m), 3.70 (3H, s), 3.89 (3H, s), 7.06 (1H, s), 7.25-7.33 (2H, m), 7.83 (1H, d, J=1.2 Hz), 7.88 (1H, d, J=2.4 Hz), 8.20 (1H, d, J=2.4 Hz), 9.82 (1H, s).

MS (ESI, m/z): 390 (M+H)$^+$.

Example 614

[Formula 861]

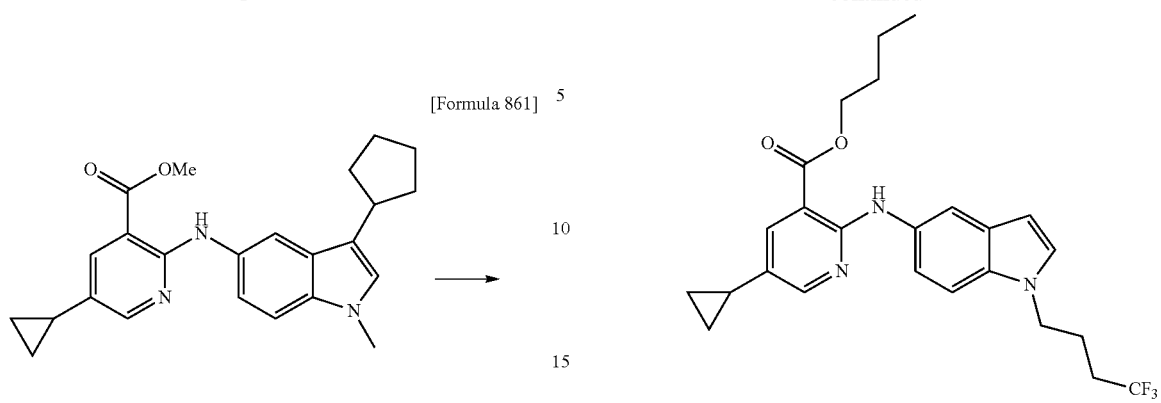

By the method similar to that of Example 612, 2-((3-cyclopentyl-1-methyl-1H-indol-5-yl)amino)-5-cyclopropyl-nicotinic acid was obtained from methyl 2-((3-cyclopentyl-1-methyl-1H-indol-5-yl)amino)-5-cyclopropylnicotinate.

$^1$H-NMR (DMSO-$d_6$) δ: 0.60-0.68 (2H, m), 0.85-0.94 (2H, m), 1.55-1.83 (6H, m), 1.85-1.95 (1H, m), 2.05-2.13 (2H, m), 3.10-3.22 (1H, m), 3.70 (3H, s), 7.05 (1H, s), 7.23-7.32 (2H, m), 7.84-7.88 (2H, m), 8.17 (1H, d, J=2.7 Hz), 10.09 (1H, s).

MS (ESI, m/z): 376 (M+H)$^+$, 374 (M−H)$^−$.

Example 615

[Formula 862]

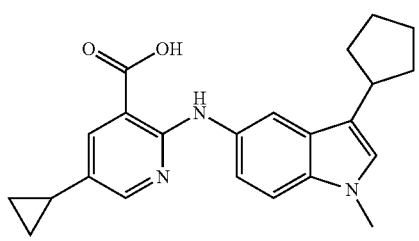

To the solution of 0.1 g of butyl 2-((1H-indol-5-yl)amino)-5-cyclopropylnicotinate in 1 mL of N,N-dimethylformamide, 0.072 g of potassium tert-butoxide and 0.074 mL of 1,1,1-trifluoro-4-iodobutane were added, and the resultant was stirred at room temperature for 45 minutes and then at 80° C. for five hours. The reaction mixture was cooled to room temperature, and ethyl acetate and water were added thereto. The organic layer was separated, washed with a saturated aqueous sodium chloride solution and dried over anhydrous sodium sulfate, and the solvent was distilled off under reduced pressure. The obtained residue was purified by silica gel column chromatography (gradient elution with hexane:ethyl acetate=100:0-70:30) to give 0.048 g of butyl 5-cyclopropyl-2-((1-(4,4,4-trifluorobutyl)-1H-indol-5-yl)amino)nicotinate as a yellow oil.

$^1$H-NMR (DMSO-$d_6$) δ: 0.61-0.68 (2H, m), 0.88-0.99 (5H, m), 1.38-1.50 (2H, m), 1.68-1.79 (2H, m), 1.86-2.03 (3H, m), 2.12-2.30 (2H, m), 4.25 (2H, t, J=6.6 Hz), 4.32 (2H, t, J=6.6 Hz), 6.40 (1H, d, J=3.2 Hz), 7.21 (1H, dd, J=8.8, 2.0 Hz), 7.37 (1H, d, J=3.0 Hz), 7.45 (1H, d, J=8.8 Hz), 7.90 (1H, d, J=2.4 Hz), 7.96 (1H, d, J=2.2 Hz), 8.21 (1H, d, J=2.7 Hz), 9.85 (1H, s).

MS (ESI, m/z): 460 (M+H)$^+$.

Example 616

[Formula 863]

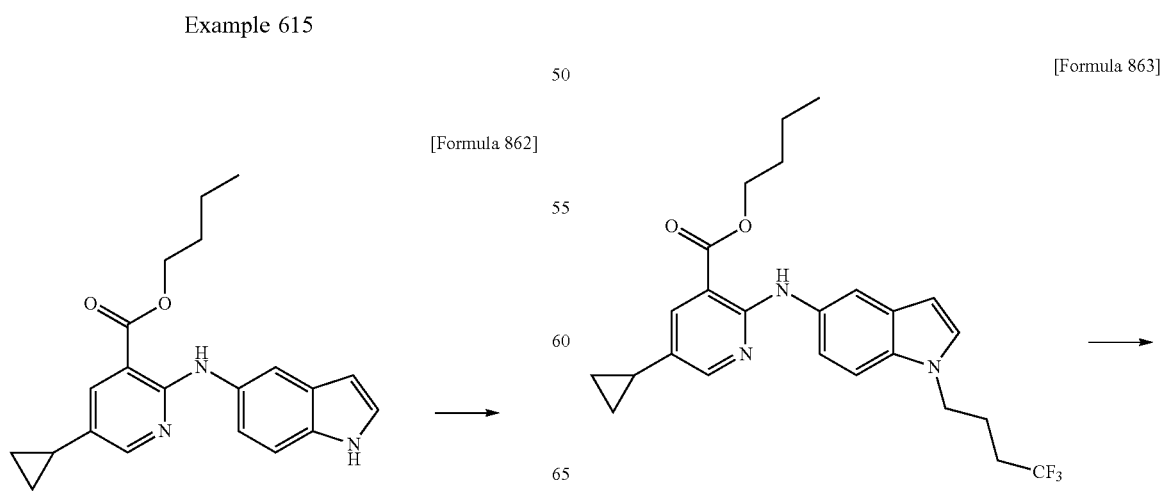

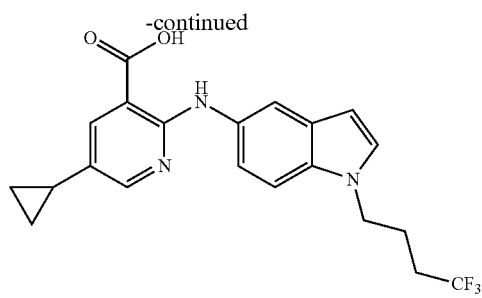

By the method similar to that of Example 612, 5-cyclopropyl-2-((1-(4,4,4-trifluorobutyl)-1H-indol-5-yl)amino)nicotinic acid was obtained from butyl 5-cyclopropyl-2-((1-(4,4,4-trifluorobutyl)-1H-indol-5-yl)amino)nicotinate.

$^1$H-NMR (DMSO-$d_6$) δ: 0.60-0.68 (2H, m), 0.85-0.94 (2H, m), 1.84-2.03 (3H, m), 2.14-2.29 (2H, m), 4.24 (2H, t, J=6.8 Hz), 6.40 (1H, d, J=2.9 Hz), 7.22 (1H, dd, J=8.8, 2.0 Hz), 7.37 (1H, d, J=3.2 Hz), 7.44 (1H, d, J=9.0 Hz), 7.87 (1H, d, J=2.4 Hz), 7.98 (1H, d, J=1.7 Hz), 8.19 (1H, d, J=2.7 Hz), 10.14 (1H, s).

MS (ESI, m/z): 404 (M+H)$^+$, 402 (M−H)$^−$.

Example 617

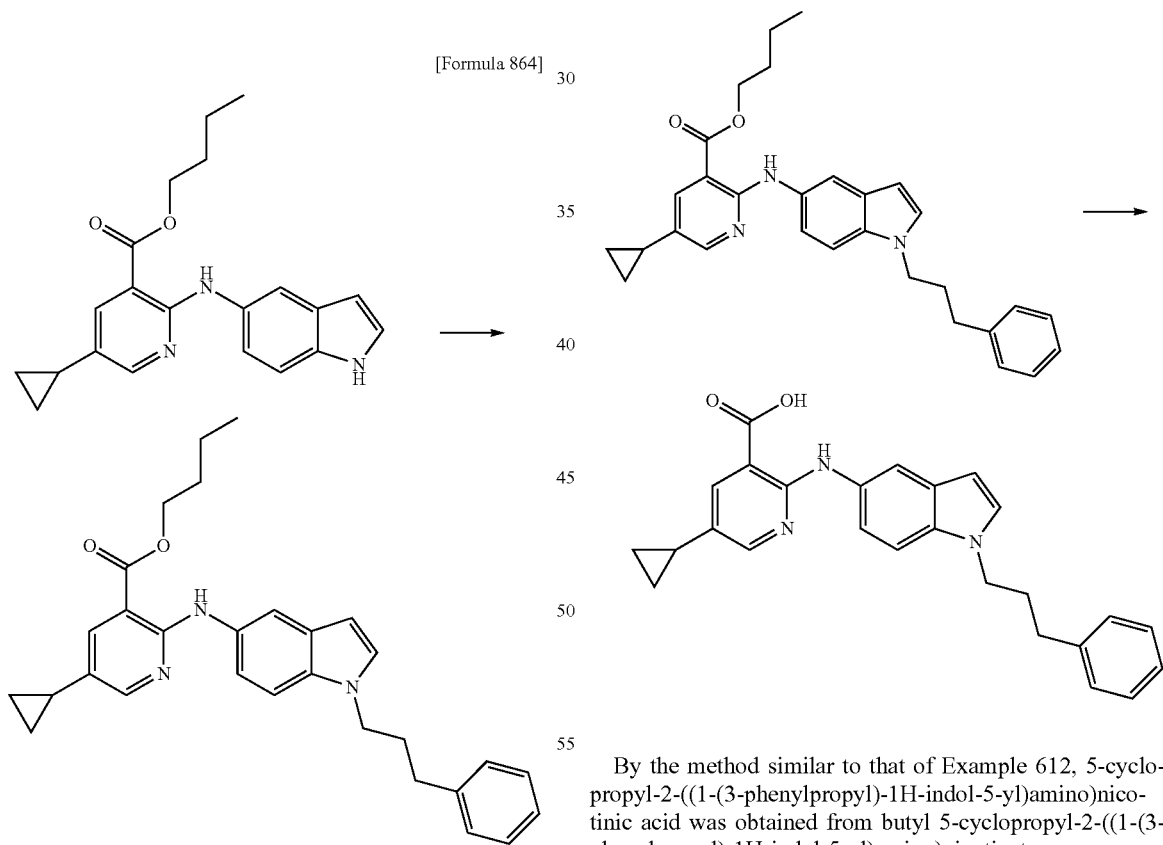

To the solution of 0.1 g of butyl 2-((1H-indol-5-yl)amino)-5-cyclopropylnicotinate in 1 mL of N,N-dimethylformamide, 0.039 g of potassium tert-butoxide was added under ice-cooling, and the resultant was stirred for five minutes. 0.053 mL of (3-bromopropyl)benzene was added thereto, and the resultant was stirred for 20 minutes and then stirred at room temperature for one hour and 15 minutes. Water, ethyl acetate and 2 mol/L hydrochloric acid were added to the reaction mixture, and the organic layer was separated, washed with a saturated aqueous sodium chloride solution and dried over anhydrous sodium sulfate, and the solvent was distilled off under reduced pressure. The obtained residue was purified by silica gel column chromatography (gradient elution with hexane:ethyl acetate=100:0-85:15) to give 0.086 g of butyl 5-cyclopropyl-2-((1-(3-phenylpropyl)-1H-indol-5-yl)amino)nicotinate as a yellow oil.

$^1$H-NMR (DMSO-$d_6$) δ: 0.60-0.68 (2H, m), 0.88-0.99 (5H, m), 1.38-1.50 (2H, m), 1.68-1.89 (2H, m), 1.87-1.96 (1H, m), 2.02-2.12 (2H, m), 2.54-2.60 (2H, m), 4.18 (2H, t, J=7.1 Hz), 4.32 (2H, t, J=6.6 Hz), 6.39 (1H, d, J=3.0 Hz), 7.15-7.23 (4H, m), 7.25-7.31 (2H, m), 7.34-7.39 (2H, m), 7.90 (1H, d, J=2.4 Hz), 7.95 (1H, d, J=2.0 Hz), 8.20 (1H, d, J=2.7 Hz), 9.85 (1H, s).

MS (ESI, m/z): 468 (M+H)$^+$.

Example 618

By the method similar to that of Example 612, 5-cyclopropyl-2-((1-(3-phenylpropyl)-1H-indol-5-yl)amino)nicotinic acid was obtained from butyl 5-cyclopropyl-2-((1-(3-phenylpropyl)-1H-indol-5-yl)amino)nicotinate.

$^1$H-NMR (DMSO-$d_6$) δ: 0.61-0.68 (2H, m), 0.86-0.94 (2H, m), 1.85-1.95 (1H, m), 2.02-2.13 (2H, m), 2.54-2.60 (2H, m), 4.17 (2H, t, J=7.2 Hz), 6.39 (1H, d, J=2.8 Hz), 7.15-7.23 (4H, m), 7.25-7.33 (2H, m), 7.35-7.40 (2H, m), 7.87 (1H, d, J=2.4 Hz), 7.97 (1H, d, J=1.6 Hz), 8.19 (1H, d, J=2.4 Hz), 10.15 (1H, s).

MS (ESI, m/z): 412 (M+H)$^+$, 410 (M−H)$^−$.

Example 619

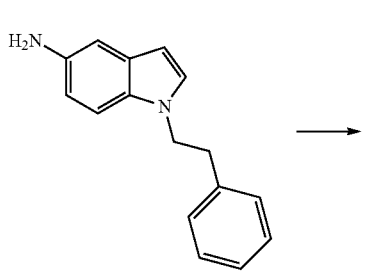

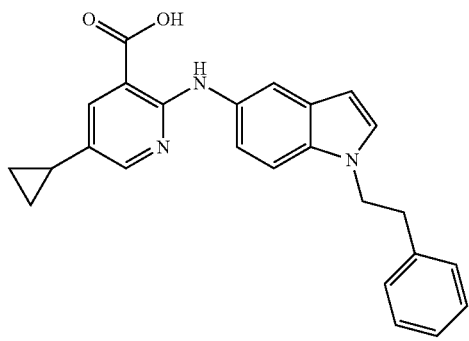

The mixture of 1.1 g of 1-(2-phenylethyl)-1H-indol-5-amine, 1.9 g of 2-chloro-5-cyclopropylnicotinic acid, 0.36 g of p-toluenesulfonic acid monohydrate, 5 mL of isopropyl alcohol, 2.5 mL of water, and 2.5 mL of 6 mol/L hydrochloric acid, was heated at reflux for 13 hours and 10 minutes. After cooling the reaction mixture to room temperature, ethyl acetate and a saturated aqueous sodium bicarbonate solution were added thereto, and the organic layer was separated and the aqueous layer was extracted with ethyl acetate. The organic layer and the extract were combined, washed with a saturated aqueous sodium bicarbonate solution and adjusted to pH 1.7 with 2 mol/L hydrochloric acid. The resultant was washed with a saturated aqueous sodium chloride solution and dried over anhydrous sodium sulfate, and the solvent was distilled off under reduced pressure. The obtained residue was purified by silica gel column chromatography (gradient elution with hexane: ethyl acetate=90:10-40:60), and hexane and ethyl acetate were added to the thus obtained residue, and the solid was collected by filtration to give 0.39 g of 5-cyclopropyl-2-((1-(2-phenylethyl)-1H-indol-5-yl)amino)nicotinic acid as a yellow solid.

$^1$H-NMR (DMSO-$d_6$) δ: 0.60-0.64 (2H, m), 0.82-0.88 (2H, m), 1.83-1.88 (1H, m), 3.06 (2H, t, J=7.3 Hz), 4.38 (2H, t, J=7.3 Hz), 6.33 (1H, d, J=3.0 Hz), 7.18-7.26 (7H, m), 7.43 (1H, d, J=8.8 Hz), 7.87 (1H, d, J=2.4 Hz), 7.94 (1H, d, J=1.7 Hz), 8.19 (1H, d, J=2.4 Hz), 10.12 (1H, s).

MS (ESI, m/z): 398 (M+H)$^+$, 396 (M−H)$^−$.

Example 620

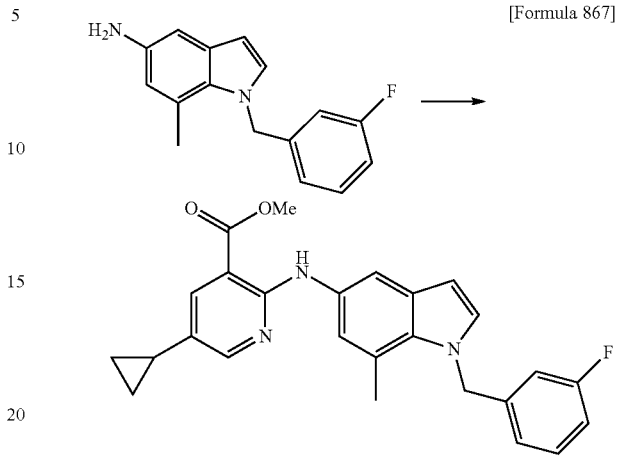

The mixture of 0.62 g of 1-(3-fluorobenzyl)-7-methyl-1H-indol-5-amine, 0.52 g of methyl 2-chloro-5-cyclopropylnicotinate, 0.11 g of tris(dibenzylideneacetone)dipalladium(0), 0.14 g of 4,5'-bis(diphenylphosphino)-9,9'-dimethylxanthene, 1.99 g of cesium carbonate, and 6 mL of butyl acetate, was heated at reflux for 11 hours under a nitrogen atmosphere. After cooling the reaction mixture to room temperature, the insoluble matter was filtered off and the filter cake was washed with ethyl acetate. The filtrate and the washings were combined, water was added thereto, the organic layer was separated and the aqueous layer was extracted with ethyl acetate. The organic layer and the extract were combined, washed with a saturated aqueous sodium chloride solution and dried over anhydrous sodium sulfate, and the solvent was distilled off under reduced pressure. The obtained residue was purified by silica gel column chromatography (gradient elution with hexane:ethyl acetate=100:0-80:20) to give 0.76 g of methyl 5-cyclopropyl-2-((1-(3-fluorobenzyl)-7-methyl-1H-indol-5-yl)amino)nicotinate as a yellow solid.

$^1$H-NMR (DMSO-$d_6$) δ: 0.62-0.68 (2H, m), 0.87-0.95 (2H, m), 1.86-1.96 (1H, m), 2.40 (3H, s), 3.89 (3H, s), 5.64 (2H, s), 6.48 (1H, d, J=2.9 Hz), 6.60-6.66 (1H, m), 6.67-6.74 (1H, m), 6.82-6.87 (1H, m), 7.02-7.11 (1H, m), 7.31-7.39 (1H, m), 7.41 (1H, d, J=2.9 Hz), 7.89 (1H, d, J=2.7 Hz), 7.92 (1H, d, J=1.9 Hz), 8.24 (1H, d, J=2.4 Hz), 9.80 (1H, s).

MS (ESI, m/z): 430 (M+H)$^+$.

Example 621

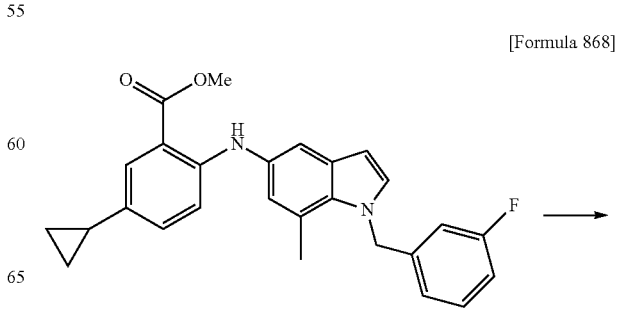

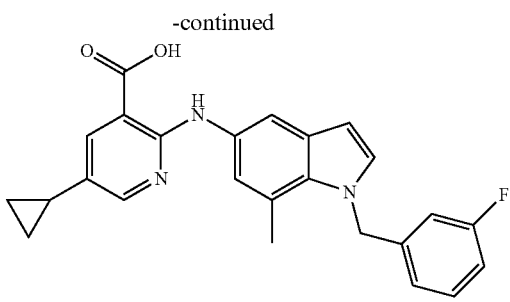

To the solution of 0.76 g of methyl 5-cyclopropyl-2-((1-(3-fluorobenzyl)-7-methyl-1H-indol-5-yl)amino)nicotinate in 15.2 mL of methanol and 10.6 mL of tetrahydrofuran, 0.76 mL of a 5 mol/L aqueous sodium hydroxide solution was added at room temperature, and the resultant was stirred at 55 to 60° C. for two hours. The reaction mixture was cooled to room temperature and then adjusted to pH 1.8 with 2 mol/L hydrochloric acid. Ethyl acetate was added thereto, and the organic layer was separated and the aqueous layer was extracted with ethyl acetate. The organic layer and the extract were combined, washed with a saturated aqueous sodium chloride solution and dried over anhydrous sodium sulfate, and the solvent was distilled off under reduced pressure. The obtained residue was purified by silica gel column chromatography (gradient elution with hexane:ethyl acetate=90:10-40:60), and water and methanol were added to the thus obtained residue, and the solid was collected by filtration to give 0.55 g of 5-cyclopropyl-2-((1-(3-fluorobenzyl)-7-methyl-1H-indol-5-yl)amino)nicotinic acid as a yellow solid.

$^1$H-NMR (DMSO-$d_6$) δ: 0.60-0.69 (2H, m), 0.86-0.96 (2H, m), 1.84-1.95 (1H, m), 2.40 (3H, s), 5.63 (2H, s), 6.47 (1H, d, J=2.8 Hz), 6.59-6.65 (1H, m), 6.67-6.75 (1H, m), 6.83 (1H, m), 7.01-7.12 (1H, m), 7.30-7.43 (2H, m), 7.87 (1H, d, J=2.4 Hz), 7.95 (1H, s), 8.21 (1H, d, J=2.0 Hz), 10.10 (1H, s).

MS (ESI, m/z): 416 (M+H)$^+$, 414 (M−H)$^−$.

Example 622

[Formula 869]

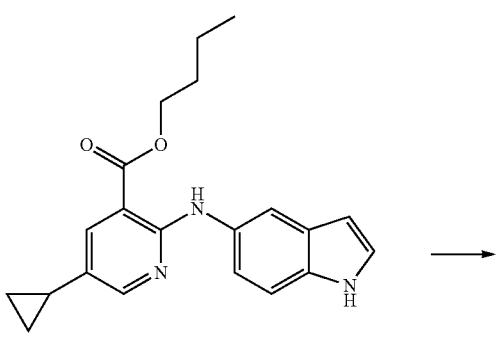

By the method similar to that of Example 617, butyl 5-cyclopropyl-2-((1-(4-methoxybenzyl)-1H-indol-5-yl)amino)nicotinate was obtained from butyl 2-((1H-indol-5-yl)amino)-5-cyclopropylnicotinate and 4-methoxybenzyl chloride.

$^1$H-NMR (DMSO-$d_6$) δ: 0.60-0.66 (2H, m), 0.87-0.98 (5H, m), 1.38-1.50 (2H, m), 1.68-1.79 (2H, m), 1.86-1.95 (1H, m), 3.70 (3H, s), 4.31 (2H, t, J=6.6 Hz), 5.31 (2H, s), 6.41 (1H, d, J=3.2 Hz), 6.83-6.90 (2H, m), 7.12-7.24 (3H, m), 7.38 (1H, d, J=8.8 Hz), 7.45 (1H, d, J=2.9 Hz), 7.89 (1H, d, J=2.4 Hz), 7.93 (1H, d, J=1.9 Hz), 8.19 (1H, d, J=2.4 Hz), 9.81 (1H, s).

MS (ESI, m/z): 470 (M+H)$^+$.

Example 623

[Formula 870]

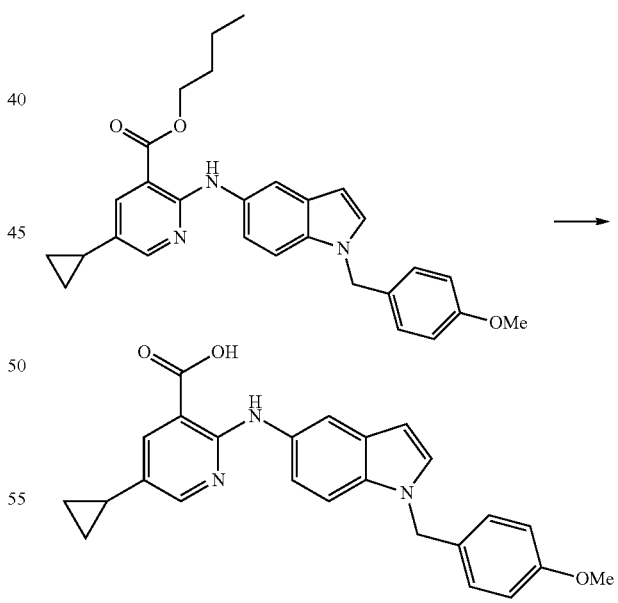

By the method similar to that of Example 612, 5-cyclopropyl-2-((1-(4-methoxybenzyl)-1H-indol-5-yl)amino)nicotinic acid was obtained from butyl 5-cyclopropyl-2-((1-(4-methoxybenzyl)-1H-indol-5-yl)amino)nicotinate.

$^1$H-NMR (DMSO-$d_6$) δ: 0.60-0.67 (2H, m), 0.82-0.95 (2H, m), 1.84-1.96 (1H, m), 3.70 (3H, s), 5.31 (2H, s), 6.41 OK d, J=2.7 Hz), 6.83-6.90 (2H, m), 7.12-7.24 (3H, m), 7.38

(1H, d, J=9.0 Hz), 7.45 (1H, d, J=3.2 Hz), 7.87 (1H, d, J=2.2 Hz), 7.94 (1H, d, J=1.7 Hz), 8.17 (1H, d, J=2.2 Hz), 10.09 (1H, s).

MS (ESI, m/z): 414 (M+H)⁺, 412 (M−H)⁻.

Example 624

[Formula 871]

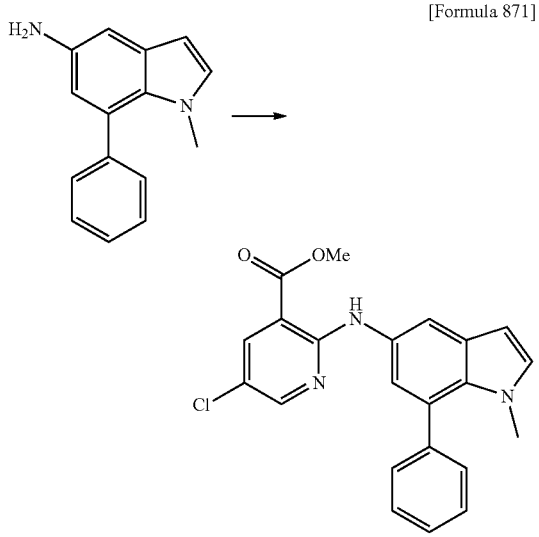

The mixture of 0.10 g of 1-methyl-7-phenyl-1H-indol-5-amine, 0.089 g of methyl 2,5-dichloronicotinate, 0.021 g of tris(dibenzylideneacetone)dipalladium(0), 0.026 g of 4,5'-bis(diphenylphosphino)-9,9'-dimethylxanthene, 0.37 g of cesium carbonate, and 1 mL of butyl acetate, was heated at reflux for five hours under a nitrogen atmosphere. The reaction mixture was cooled to room temperature, and ethyl acetate and water were then added thereto. The organic layer was separated, washed with a saturated aqueous sodium chloride solution and dried over anhydrous sodium sulfate, and the solvent was distilled off under reduced pressure. The obtained residue was purified by silica gel column chromatography (gradient elution with hexane:ethyl acetate=100:0-90:10) to give 0.049 g of methyl 5-chloro-2-((1-methyl-7-phenyl-1H-indol-5-yl)amino)nicotinate as a yellow oil.

¹H-NMR (DMSO-d₆) δ: 3.27 (3H, s), 3.90 (3H, s), 6.48 (1H, d, J=3.2 Hz), 6.98-7.03 (1H, m), 7.27 (1H, d, J=3.2 Hz), 7.40-7.51 (5H, m), 7.91-7.96 (1H, m), 8.19 (1H, d, J=2.2 Hz), 8.41 (1H, d, J=2.7 Hz), 9.96 (1H, s).

MS (ESI, m/z): 392 (M+H)⁺.

Example 625

[Formula 872]

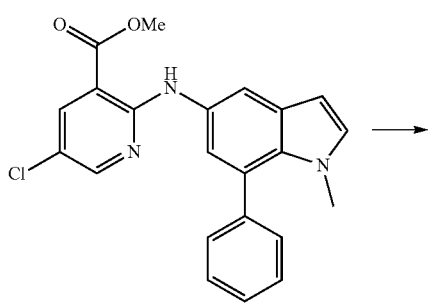

-continued

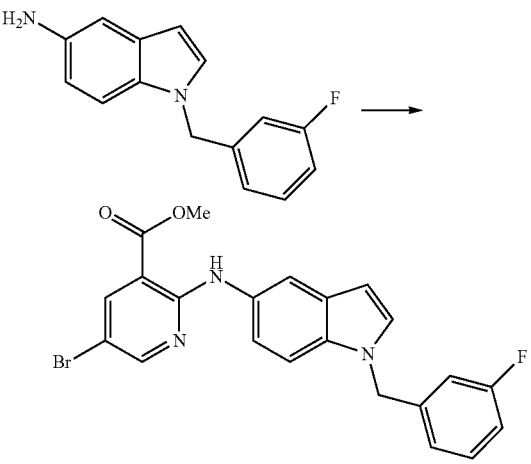

By the method similar to that of Example 612, 5-chloro-2-((1-methyl-7-phenyl-1H-indol-5-yl)amino)nicotinic acid was obtained from methyl 5-chloro-2-((1-methyl-7-phenyl-1H-indol-5-yl)amino)nicotinate.

¹H-NMR (DMSO-d₆) δ: 3.26 (3H, s), 6, 47 (1H, d, J=3.0 Hz), 6.96-7.01 (1H, m), 7.26 (1H, d, J=2.9 Hz), 7.43-7.50 (5H, m), 7.99 (1H, d, J=1.7 Hz), 8.16 (1H, d, J=2.7 Hz), 8.39 (1H, d, J=2.7 Hz), 10.34 (1H, s).

MS (ESI, m/z): 378 (M+H)⁺, 376 (M−H)⁻.

Example 626

[Formula 873]

The mixture of 8.9 g of 1-(3-fluorobenzyl)-1H-indol-5-amine, 8.8 g of methyl 5-bromo-2-chloronicotinate, 8.6 mL of 2,6-lutidine, 36 mL of xylene, and 9 mL of N,N-dimethylacetamide, was stirred at 140° C. for four hours. After cooling the reaction mixture to room temperature, the insoluble matter was filtered off and the filter cake was washed with chloroform. The filtrate and the washings were combined and the solvent was distilled off under reduced pressure. Water and ethyl acetate were added to the residue, the organic layer was separated, sequentially washed with 2 mol/L hydrochloric acid, water and a saturated aqueous sodium chloride solution and dried over anhydrous sodium sulfate, and the solvent was distilled off under reduced pressure. Ethyl acetate and hexane were added to the obtained residue, and the solid was collected by filtration to give 2.6 g of methyl 5-bromo-2-((1-(3-fluorobenzyl)-1H-indol-5-yl)amino)nicotinate as a yellow solid.

¹H-NMR (DMSO-d₆) δ: 3.90 (3H, s), 5.44 (2H, s), 6.45-6.50 (1H, m), 6.97-7.12 (3H, m), 7.17 (1H, dd, J=8.8, 2.2 Hz), 7.32-7.45 (2H, m), 7.54 (1H, d, J=3.2 Hz), 7.88 (1H, d, J=2.0 Hz), 8.28 (1H, d, J=2.4 Hz), 8.43 (1H, d, J=2.7 Hz), 9.89 (1H, s).
MS (ESI, m/z): 454 (M+H)⁺.

Example 627

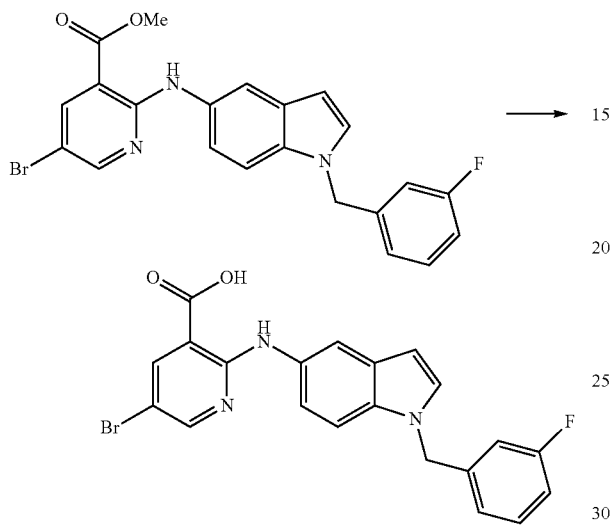

[Formula 874]

By the method similar to that of Example 612, 5-bromo-2-((1-(3-fluorobenzyl)-1H-indol-5-yl)amino)nicotinic acid was obtained from methyl 5-bromo-2-((1-(3-fluorobenzyl)-1H-indol-5-yl)amino)nicotinate.
¹H-NMR (DMSO-d₆) δ: 5.44 (2H, s), 6.45-6.49 (1H, m), 6.97-7.12 (3H, m), 7.18 (1H, dd, J=8.8, 2.2 Hz), 7.32-7.44 (2H, m), 7.52 (1H, d, J=3.2 Hz), 7.90 (1H, d, J=2.0 Hz), 8.26 (1H, d, J=2.7 Hz), 8.40 (1H, d, J=2.7 Hz), 10.21 (1H, s).
MS (ESI, m/z): 442 (M+H)⁺, 440 (M−H)⁻.

Example 628

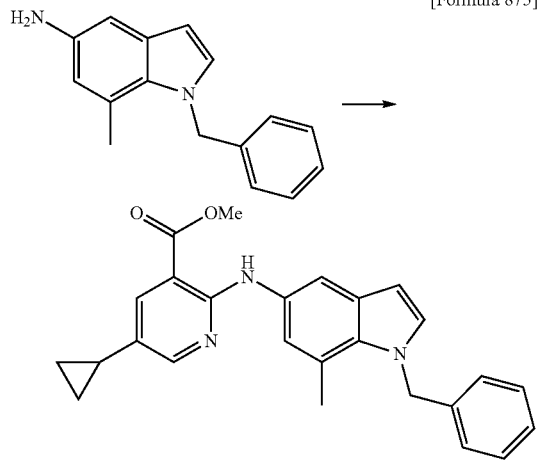

[Formula 875]

The mixture of 0.55 g of 1-benzyl-7-methyl-1H-indol-5-amine, 0.47 g of methyl 2-chloro-5-cyclopropylnicotinate, 0.026 g of palladium(II) acetate, 0.072 g of (S)-(−)-2,2'-bis(diphenylphosphino)-1,1'-binaphthyl, 0.64 g of potassium carbonate, and 5.5 mL of butyl acetate, was heated at reflux for two hours under a nitrogen atmosphere. After the reaction mixture was cooled to room temperature, ethyl acetate and water were added thereto, the organic layer was separated and the aqueous layer was extracted with ethyl acetate. The organic layer and the extract were combined, washed with a saturated aqueous sodium chloride solution and dried over anhydrous sodium sulfate, and the solvent was distilled off under reduced pressure. The obtained residue was purified by silica gel column chromatography (gradient elution with hexane:ethyl acetate=100:0-85:15) to give 0.72 g of methyl 2-((1-benzyl-7-methyl-1H-indol-5-yl)amino)-5-cyclopropylnicotinate as a yellow oil.
¹H-NMR (DMSO-d₆) δ: 0.60-0.68 (2H, m), 0.86-0.95 (2H, m), 1.85-1.95 (1H, m), 2.40 (3H, s), 3.88 (3H, s), 5.61 (2H, s), 6.46 (1H, d, J=2.9 Hz), 6.80-6.84 (1H, m), 6.84-6.90 (2H, m), 7.18-7.25 (1H, m), 7.26-7.33 (2H, m), 7.39 (1H, d, J=3.2 Hz), 7.88 (1H, d, J=2.4 Hz), 7.91 (1H, d, J=2.0 Hz), 8.23 (1H, d, J=2.4 Hz), 9.80 (1H, s).
MS (ESI, m/z): 412 (M+H)⁺.

Example 629

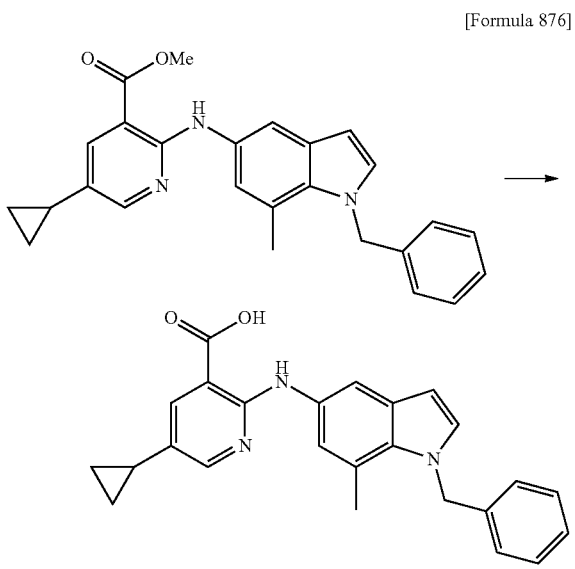

[Formula 876]

To the solution of 0.65 g of methyl 2-((1-benzyl-7-methyl-1H-indol-5-yl)amino)-5-cyclopropylnicotinate in 3 mL of methanol and 3 mL of tetrahydrofuran, 0.63 mL of a 5 mol/L aqueous sodium hydroxide solution was added at room temperature, and the resultant was stirred at 60° C. for three hours and 25 minutes. The reaction mixture was cooled to room temperature and then adjusted to pH 2.1 with 2 mol/L hydrochloric acid. Ethyl acetate was added thereto, the organic layer was separated, sequentially washed with a saturated aqueous sodium carbonate solution, 2 mol/L hydrochloric acid and a saturated aqueous sodium chloride solution and dried over anhydrous sodium sulfate, and the solvent was distilled off under reduced pressure. The obtained residue was purified by silica gel column chromatography (gradient elution with chloroform:methanol=100:0-93:7) and the thus obtained residue was sequentially washed with water and methanol, methanol, and ethyl acetate and methanol and then purified by Silica gel column chromatography (gradient elution with chloroform:methanol=100:0-95:5). Water and methanol were added to the further obtained residue, and the solid was collected by filtration to give 0.22 g of 2-((1-benzyl-7-methyl-1H-indol-5-yl)amino)-5-cyclopropylnicotinic acid as a yellow solid.

$^1$H-NMR (DMSO-d$_6$) δ: 0.60-0.68 (2H, m), 0.86-0.94 (2H, m), 1.84-1.94 (1H, m), 2.40 (3H, s), 5.61 (2H, s), 6.45 (1H, d, J=2.9 Hz), 6.81 (1H, s), 6.84-6.90 (2H, m), 7.20-7.33 (3H, m), 7.38 (1H, d, J=3.2 Hz), 7.87 (1H, d, J=2.7 Hz), 7.93 (1H, d, J=1.7 Hz), 8.20 (1H, d, J=2.4 Hz), 10.11 (1H, s).

MS (ESI, m/z): 398 (M+H)$^+$, 396 (M−H)$^−$.

Example 630

[Formula 877]

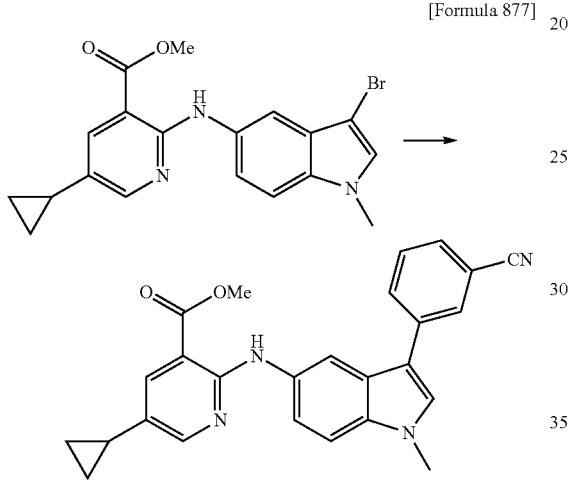

The mixture of 80 mg of methyl 2-((3-bromo-1-methyl-1H-indol-5-yl)amino)-5-cyclopropylnicotinate, 59 mg of 3-cyanophenylboronic acid, 7 mg of bis(di-tert-butyl(4-dimethylaminophenyl)phosphine)dichloropalladium(II), 83 mg of potassium carbonate, 2 mL of toluene, and 200 μL, of water, was heated at reflux for three hours and 15 minutes under a nitrogen atmosphere. The reaction mixture was purified by silica gel column chromatography (gradient elution with hexane:ethyl acetate=100:0-50:50) to give 15 mg of methyl 2-((3-((3-cyanophenyl)-1-methyl-1H-indol-5-yl)amino)-5-cyclopropylnicotinate as a yellow oil.

Example 631

[Formula 878]

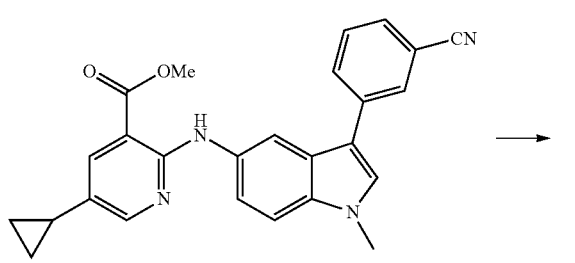

-continued

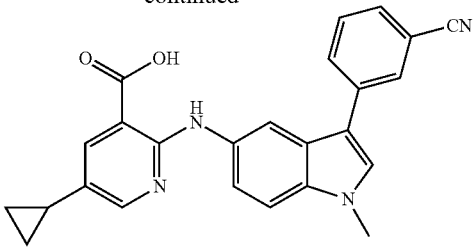

The mixture of 15 mg of methyl 2-((3-(3-cyanophenyl)-1-methyl-1H-indol-5-yl)amino)-5-cyclopropylnicotinate, 1 mL of methanol, 1 mL of tetrahydrofuran, and 100 μL of a 5 mol/L aqueous sodium hydroxide solution, was stirred at room temperature for five hours. The reaction mixture was adjusted to pH 2 by adding thereto 2 mol/L hydrochloric acid, and the solvent was then distilled off under reduced pressure. A water-methanol mixed solution was added to the obtained residue, and the solid was collected by filtration to give 10 mg of 2-((3-(3-cyanophenyl)-1-methyl-1H-indol-5-yl)amino)-5-cyclopropylnicotinic acid as a brown solid.

$^1$H-NMR (DMSO-d$_6$) δ: 0.63-0.68 (2H, m), 0.88-0.94 (2H, m), 1.87-1.95 (1H, m), 3.85 (3H, s), 7.36 (1H, dd, J=8.7, 1.8 Hz), 7.48 (1H, d, J=8.8 Hz), 7.64-7.67 (2H, m), 7.87 (1H, s), 7.91 (1H, d, J=2.7 Hz), 8.00-8.04 (1H, m), 8.08 (1H, s), 8.18 (1H, d, J=2.7 Hz), 8.38 (1H, d, J=1.7 Hz), 10.20 (1H, s), 13.46 (1H, brs).

MS (ESI, m/z): 410 (M+H)$^+$, 408 (M−H)$^−$.

Example 632

[Formula 879]

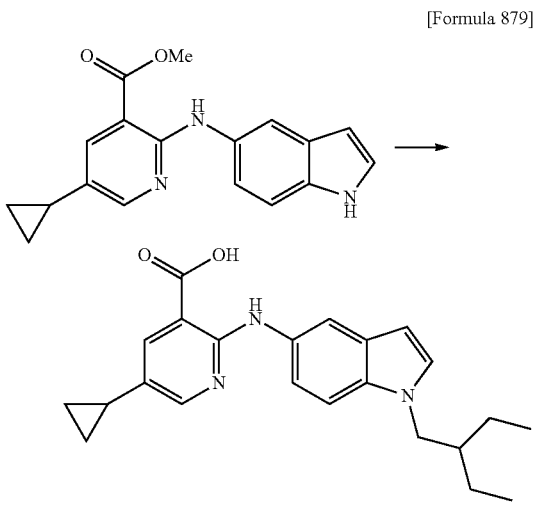

To the solution of 80 mg of methyl 5-cyclopropyl-2-(1H-indol-5-ylamino)nicotinate in 2 mL of N,N-dimethylformamide, 29 mg of potassium tert-butoxide and 36 μL of 1-bromo-2-ethylbutane were added, and the resultant was stirred at room temperature for one hour and 15 minutes. 15 mg of potassium tert-butoxide and 18 μL of 1-bromo-2-ethylbutane were further added thereto, and the resultant was stirred for 45 minutes. 15 mg of potassium tert-butoxide and 18 μL of 1-bromo-2-ethylbutane were added thereto, and the resultant was stirred for 50 minutes. 15 mg of potassium tert-butoxide and 18 μL of 1-bromo-2-ethylbutane were added thereto, and the resultant was stirred for one hour and 10 minutes. After the reaction mixture was allowed to stand overnight, 200 μL of a 5 mol/L aqueous sodium hydroxide solution was added thereto, and the resultant was stirred for three hours and 30 minutes. The reaction mixture was adjusted to pH 2 by adding thereto 350 μL of 6 mol/L hydrochloric acid, followed by addition of ethyl acetate and water. The organic layer was separated, washed with a saturated aqueous sodium chloride solution and dried over anhydrous sodium sulfate, and the solvent was distilled off under reduced pressure. The obtained residue was purified by silica gel column chromatography (gradient elution with hexane:ethyl acetate=100:0-50:50). A water-methanol mixed solution was added to the thus obtained residue, and the solid was collected by filtration to give 56 mg of 5-cyclopropyl-2-((1-(2-ethylbutyl)-1H-indol-5-yl)amino) nicotinic acid as a light orange solid.

$^1$H-NMR (DMSO-d$_6$) δ: 0.62-0.67 (2H, m), 0.85 (6H, t, J=7.6 Hz), 0.87-0.93 (2H, m), 1.24 (4H, quin, J=7.1 Hz), 1.76-1.84 (1H, m), 1.86-1.94 (1H, m), 4.03 (2H, d, J=7.3 Hz), 6.37 (1H, d, J=2.9 Hz), 7.19 (1H, dd, J=8.8, 2.0 Hz), 7.31 (1H, d, J=3.2 Hz), 7.36 (1H, d, J=8.8 Hz), 7.87 (1H, d, J=2.4 Hz), 7.94 (1H, d, J=1.7 Hz), 8.18 (1H, d, J=2.4 Hz), 10.12 (1H, s).

Example 633

[Formula 880]

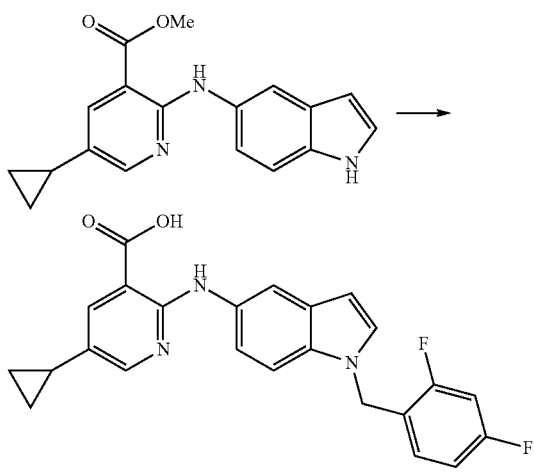

After the mixture of 80 mg of methyl 5-cyclopropyl-2-(1H-indol-5-ylamino)nicotinate, 38 mg of potassium tert-butoxide, 43 μL of 2,4-difluorobenzylbromide, and 2 mL of N,N-dimethylformamide, was stirred at room temperature for one hour and 30 minutes, 200 μL of a 5 mol/L aqueous sodium hydroxide solution was added thereto, and the resultant was stirred overnight. The reaction mixture was adjusted to pH 2 by adding thereto 6 mol/L hydrochloric acid, followed by addition of ethyl acetate and water. The organic layer was separated, washed with a saturated aqueous sodium chloride solution and dried over anhydrous sodium sulfate, and the solvent was distilled off under reduced pressure. The obtained residue was purified by silica gel column chromatography (gradient elution with hexane: ethyl acetate=100:0-50:50). A water-methanol mixed solution was added to the thus obtained residue, and the solid was collected by filtration to give 69 mg of 5-cyclopropyl-2-((1-(2,4-difluorobenzyl)-1H-indol-5-yl)amino)nicotinic acid as a pale yellow solid.

$^1$H-NMR (DMSO-d$_6$) δ: 0.61-0.66 (2H, m), 0.86-0.93 (2H, m), 1.85-1.94 (1H, m), 5.43 (2H, s), 6.44 (1H, d, J=2.9 Hz), 6.99-7.06 (1H, m), 7.09-7.16 (1H, m), 7.19 (1H, dd, J=8.8, 2.0 Hz), 7.24-7.32 (1H, m), 7.37-7.43 (2H, m), 7.86 (1H, d, J=2.4 Hz), 7.97 (1H, d, J=1.7 Hz), 8.18 (1H, d, J=2.4 Hz), 10.13 (1H, s).

MS (ESI, m/z): 420 (M+H)$^+$.

Example 634

[Formula 881]

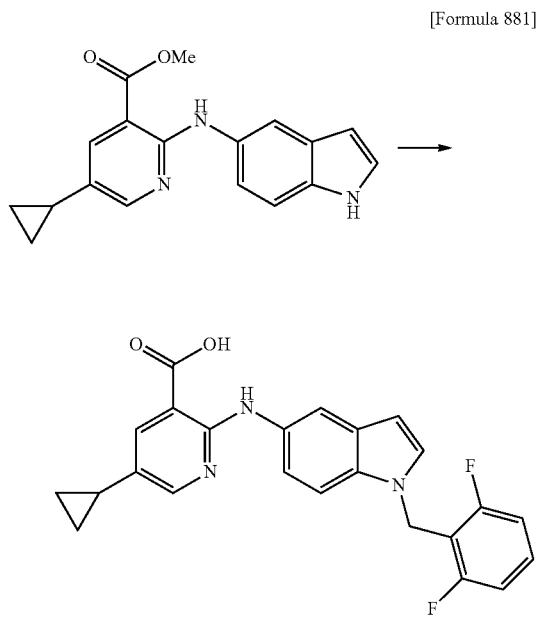

By the method similar to that of Example 633, 5-cyclopropyl-2-((1-(2,6-difluorobenzyl)-1H-indol-5-yl)amino) nicotinic acid was obtained from methyl 5-cyclopropyl-2-(1H-indol-5-ylamino)nicotinate and 2,6-difluorobenzyl bromide.

$^1$H-NMR (DMSO-d$_6$) δ: 0.61-0.66 (2H, m), 0.87-0.94 (2H, m), 1.85-1.93 (1H, m), 5.43 (2H, s), 6.40 (1H, d, J=3.2 Hz), 7.12-7.19 (2H, m), 7.23 (1H, dd, J=8.7, 1.8 Hz), 7.32 (1H, d, J=2.7 Hz), 7.40-7.48 (2H, m), 7.86 (1H, d, J=2.4 Hz), 7.95 (1H, d, J=1.7 Hz), 8.17 (1H, d, J=2.4 Hz), 10.12 (1H, s), 13.41 (1H, brs).

MS (ESI, m/z): 420 (M+H)$^+$.

Example 635

[Formula 882]

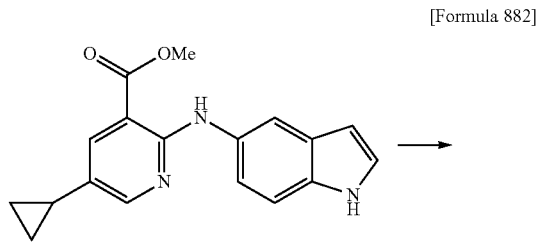

-continued

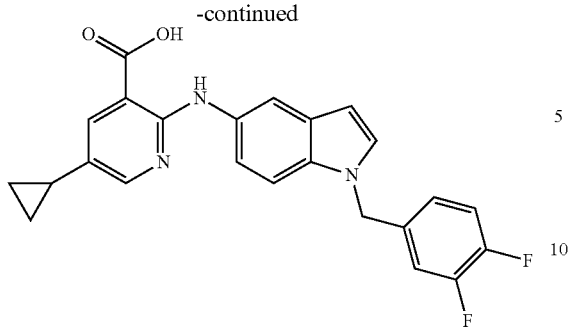

By the method similar to that of Example 633, 5-cyclopropyl-2-((1-(3,4-difluorobenzyl)-1H-indol-5-yl)amino)nicotinic acid was obtained from methyl 5-cyclopropyl-2-(1H-indol-5-ylamino)nicotinate and 3,4-difluorobenzyl bromide.

$^1$H-NMR (DMSO-$d_6$) δ: 0.61-0.67 (2H, m), 0.88-0.94 (2H, m), 1.86-1.94 (1H, m), 5.40 (2H, s), 6.45 (1H, d, J=3.2 Hz), 7.00-7.06 (1H, m), 7.18 (1H, d, J=8.8 Hz), 7.26-7.33 (1H, m), 7.33-7.42 (2H, m), 7.50 (1H, d, J=2.9 Hz), 7.87 (1H, d, J=2.2 Hz), 7.98 (1H, s), 8.18 (1H, d, J=1.7 Hz), 10.12 (1H, s), 13.42 (1H, brs).

MS (ESI, m/z): 420 (M+H)$^+$, 418 (M−H)$^-$.

Example 636

[Formula 883]

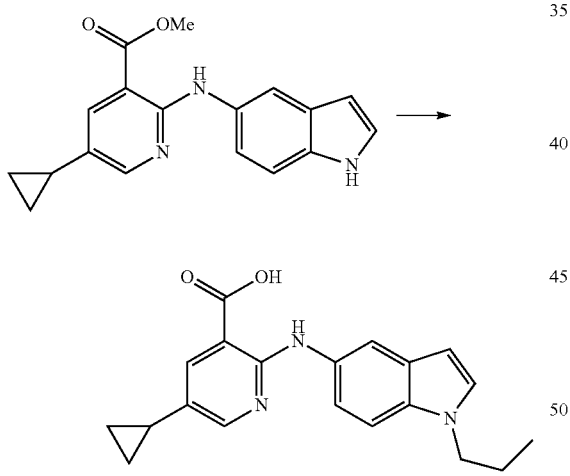

By the method similar to that of Example 633, 5-cyclopropyl-2-((1-propyl-1H-indol-5-yl)amino)nicotinic acid was obtained from methyl 5-cyclopropyl-2-(1H-indol-5-ylamino)nicotinate and 1-bromopropane.

$^1$H-NMR (DMSO-$d_6$) δ: 0.61-0.67 (2H, m), 0.84 (3H, t, J=7.3 Hz), 0.87-0.93 (2H, m), 1.77 (2H, sext, J=7.3 Hz), 1.86-1.93 (1H, m), 4.11 (2H, t, J=6.8 Hz), 6.36 (1H, d, J=2.9 Hz), 7.19 (1H, dd, J=8.5, 1.7 Hz), 7.33 (1H, d, J=2, 9 Hz), 7.40 (1H, d, J=8.8 Hz), 7.87 (1H, d, J=2.4 Hz), 7.95 (1H, d, J=1.7 Hz), 8.19 (1H, d, J=2.4 Hz), 10.12 (1H, s), 13.40 (1H, brs).

MS (ESI, m/z): 336 (M+H)$^+$, 334 (M−H)$^-$.

Example 637

[Formula 884]

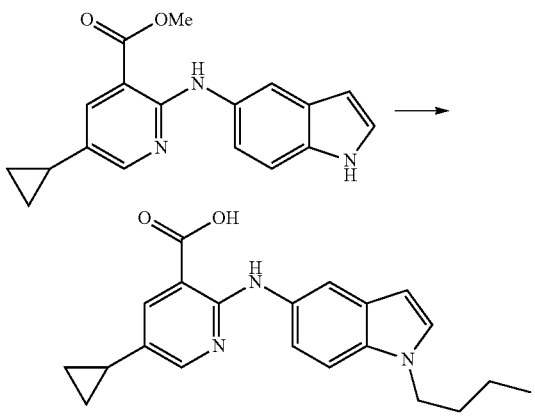

By the method similar to that of Example 633, 2-((1-butyl-1H-indol-5-yl)amino)-5-cyclopropylnicotinic acid was obtained from methyl 5-cyclopropyl-2-(1H-indol-5-ylamino)nicotinate and 1-bromobutane.

$^1$H-NMR (DMSO-$d_6$) δ: 0.61-0.67 (2H, m), 0.86-0.93 (5H, m), 1.20-1.29 (2H, m), 1.73 (2H, quin, J=7.3 Hz), 1.86-1.94 (1H, m), 4.14 (2H, t, J=7.0 Hz), 6.36 (1H, d, J=2.9 Hz), 7.19 (1H, dd, J=8.7, 1.8 Hz), 7.32 (1H, d, J=2.9 Hz), 7.39 (1H, d, J=8.5 Hz), 7.87 (1H, d, J=2.4 Hz), 7.94 (1H, d, J=2.0 Hz), 8.18 (1H, d, J=2.7 Hz), 10.14 (1H, s), 13.40 (1H, brs).

Example 638

[Formula 885]

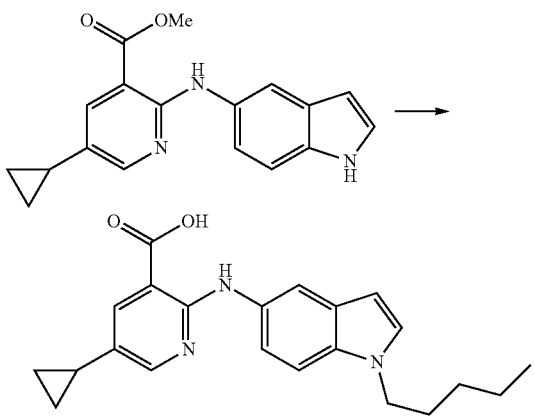

By the method similar to that of Example 633, 5-cyclopropyl-2-((1-pentyl-1H-indol-5-yl)amino)nicotinic acid was obtained from methyl 5-cyclopropyl-2-(1H-indol-5-ylamino)nicotinate and 1-bromopentane.

$^1$H-NMR (DMSO-$d_6$) δ: 0.62-0.67 (2H, m), 0.84 (3H, t, J=7.1 Hz), 0.88-0.94 (2H, m), 1.22-1.34 (4H, m), 1.75 (2H, quin, J=7.3 Hz), 1.91-1.99 (1H, m), 4.13 (2H, t, J=7.0 Hz), 6.36 (1H, d, J=2.9 Hz), 7.19 (1H, d, J=8.8 Hz), 7.33 (1H, d, =2.9 Hz), 7.39 (1H, d, J=8.5 Hz), 7.87 (1H, d, J=2.0 Hz), 7.95 (1H, s), 8.19 (1H, d, J=2.2 Hz), 10.12 (1H, s), 13.39 (1H, brs).

Example 639

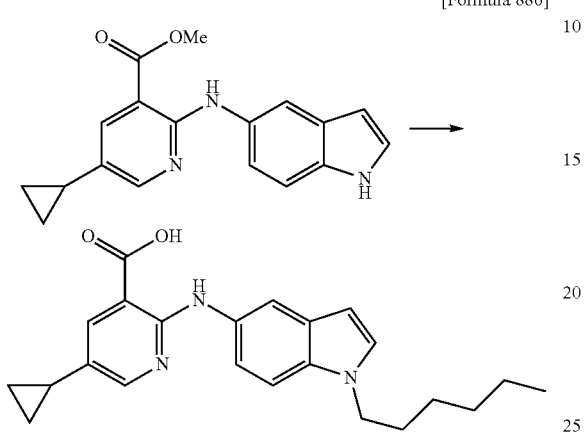

[Formula 886]

By the method similar to that of Example 633, 5-cyclopropyl-2-((1-hexyl-1H-indol-5-yl)amino)nicotinic acid was obtained from methyl 5-cyclopropyl-2-(1H-indol-5-ylamino)nicotinate and 1-bromohexane.

$^1$H-NMR (DMSO-d$_6$) δ: 0.62-0.67 (2H, m), 0.81-0.86 (3H, m), 0.88-0.94 (2H, m), 1.25-1.33 (6H, m), 1.66-1.79 (2H, m), 1.86-1.94 (1H, m), 4.13 (2H, t, J=7.0 Hz), 6.36 (1H, d, J=2.7 Hz), 7.19 (1H, dd, J=8.8, 1.7 Hz), 7.32 (1H, d, J=2.9 Hz), 7.39 (1H, d, J=8.5 Hz), 7.87 (1H, d, J=2.4 Hz), 7.95 (1H, d, J=1.7 Hz), 8.19 (1H, d, J=2.4 Hz), 10.12 (1H, s), 13.40 (1H, brs).

Example 640

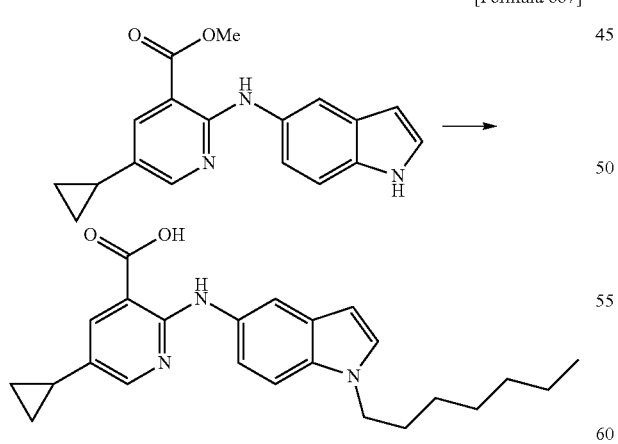

[Formula 887]

By the method similar to that of Example 633, 5-cyclopropyl-2-((1-heptyl-1H-indol-5-yl)amino)nicotinic acid was obtained from methyl 5-cyclopropyl-2-(1H-indol-5-ylamino)nicotinate and 1-bromoheptane.

$^1$H-NMR (DMSO-d$_6$) δ: 0.62-0.67 (2H, m), 0.84 (3H, t, J=6.8 Hz), 0.87-0.94 (2H, m), 1.22-1.31 (8H, m), 1.70-1.79 (2H, m), 1.91-1.99 (1H, m), 4.13 (2H, t, J=7.0 Hz), 6.36 (1H, d, J=2.9 Hz), 7.19 (1H, dd, J=8.8, 2.0 Hz), 7.32 (1H, d, J=2.9 Hz), 7.38 (1H, d, J=8.8 Hz), 7.87 (1H, d, J=2.7 Hz), 7.94 (1H, d, J=1.7 Hz), 8.19 (1H, d, J=2.4 Hz), 10.11 (1H, s), 13.39 (1H, brs).

MS (ESI, m/z): 393 (M+H)$^+$, 391 (M–H)$^-$.

Example 641

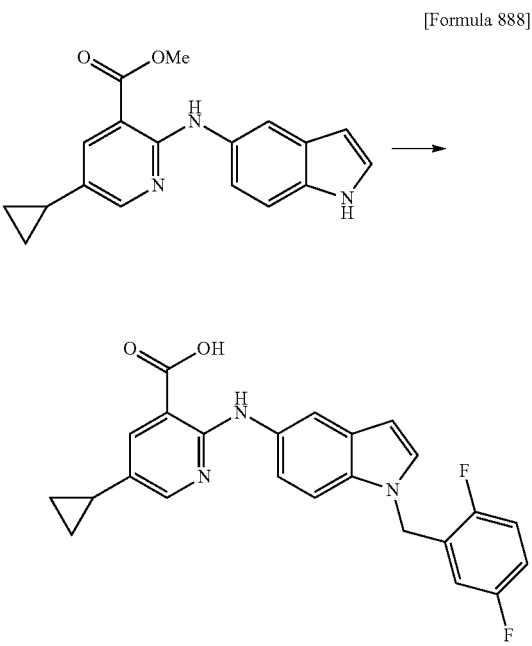

[Formula 888]

By the method similar to that of Example 633, 5-cyclopropyl-2-((1-(2,5-difluorobenzyl)-1H-indol-5-yl)amino) nicotinic acid was obtained from methyl 5-cyclopropyl-2-(1H-indol-5-ylamino)nicotinate and 2,5-difluorobenzyl bromide.

$^1$H-NMR (DMSO-d$_6$) δ: 0.62-0.67 (2H, m), 0.88-0.94 (2H, m), 1.85-1.95 (1H, m), 5.45 (2H, s), 6.46 (1H, d, J=2.9 Hz), 6.78-6.84 (1H, m), 7.15-7.23 (2H, m), 7.27-7.34 (1H, m), 7.41 (1H, d, J=8.8 Hz), 7.45 (1H, d, J=3.2 Hz), 7.87 (1H, d, J=2.7 Hz), 7.99 (1H, d, J=2.0 Hz), 8.19 (1H, d, J=2.4 Hz), 10.13 (1H, s), 13.42 (1H, brs).

MS (ESI, m/z): 420 (M+H)$^+$, 418 (M–H)$^-$.

Example 642

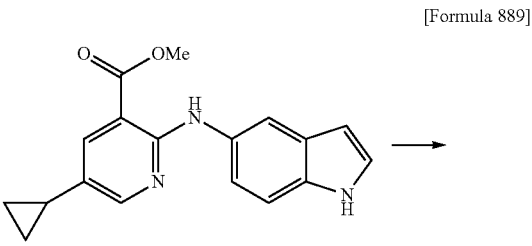

[Formula 889]

-continued

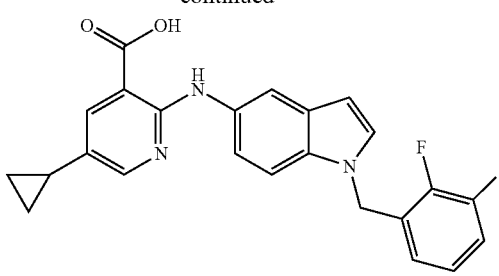

By the method similar to that of Example 633, 5-cyclopropyl-2-((1-(2,3-difluorobenzyl)-1H-indol-5-yl)amino)nicotinic acid was obtained from methyl 5-cyclopropyl-2-(1H-indol-5-ylamino)nicotinate and 2,3-difluorobenzyl bromide.

$^1$H-NMR (DMSO-d$_6$) δ: 0.62-0.67 (2H, m), 0.88-0.94 (2H, m), 1.87-1.96 (1H, m), 5.53 (2H, s), 6.47 (1H, d, J=2.9 Hz), 6.79-6.85 (1H, m), 7.09-7.17 (1H, m), 7.19 (1H, dd, J=8.7, 2.1 Hz), 7.31-7.39 (1H, m), 7.42 (1H, d, J=8.5 Hz), 7.45 (1H, d, J=2.9 Hz), 7.91 (1H, d, J=2.2 Hz), 7.95 (1H, d, J=2.0 Hz), 8.14 (1H, d, J=2.4 Hz), 10.16 (1H, s).

MS (ESI, m/z): 420 (M+H)$^+$, 418 (M−H)$^−$.

Example 643

[Formula 890]

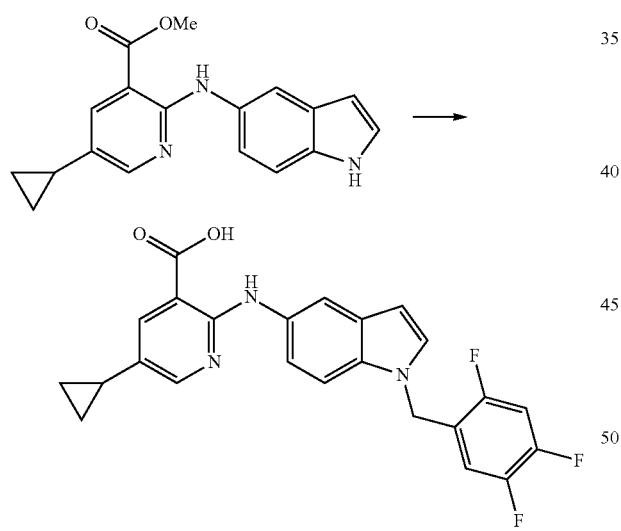

By the method similar to that of Example 633, 5-cyclopropyl-2-((1-(2,4,5-trifluorobenzyl)-1H-indol-5-yl)amino)nicotinic acid was obtained from methyl 5-cyclopropyl-2-(1H-indol-5-ylamino)nicotinate and 2,4,5-trifluorobenzyl bromide.

$^1$H-NMR (DMSO-d$_6$) δ: 0.61-0.66 (2H, m), 0.88-0.93 (2H, m), 1.85-1.93 (1H, m), 5.42 (2H, s), 6.45 (1H, d, J=3.2 Hz), 7.17-7.25 (2H, m), 7.41-7.45 (2H, m), 7.56-7.64 (1H, m), 7.87 (1H, d, J=2.4 Hz), 7.98 (1H, d, J=2.0 Hz), 8.18 (1H, d, J=2.4 Hz), 10.13 (1H, s).

MS (ESI, m/z): 438 (M+H)$^+$, 436 (M−H)$^−$.

Example 644

[Formula 891]

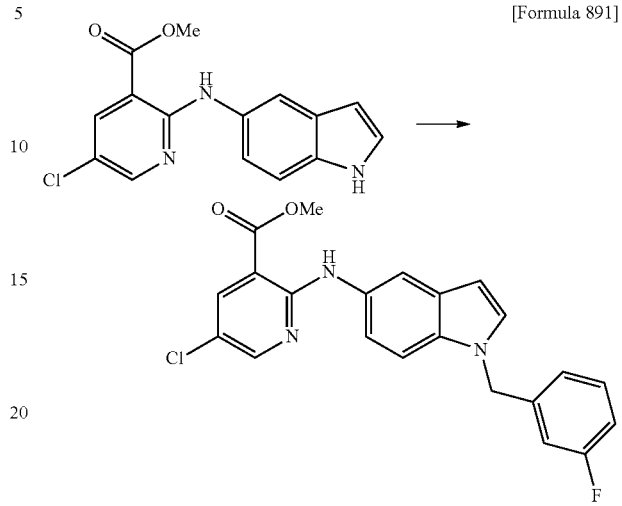

By the method similar to that of Example 633, methyl 5-chloro-2-((1-(3-fluorobenzyl)-1H-indol-5-yl)amino)nicotinate was obtained from methyl 5-chloro-2-((1H-indol-5-ylamino)nicotinate and 3-fluorobenzyl bromide.

Example 645

[Formula 892]

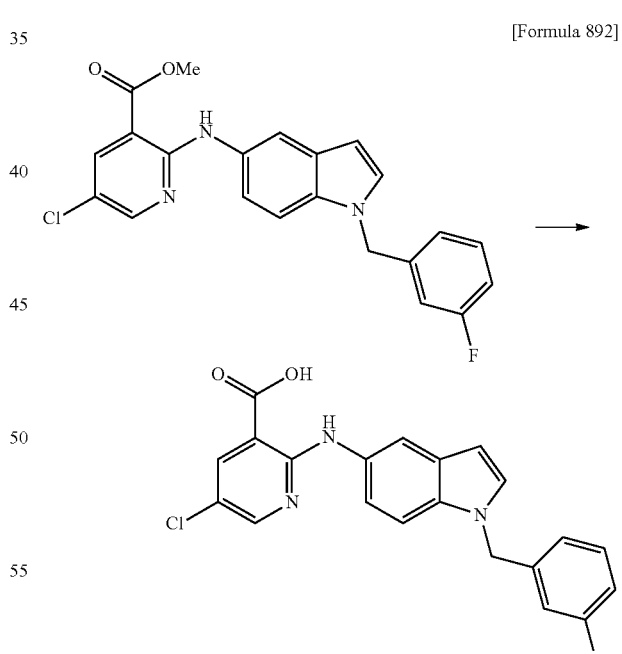

By the method similar to that of Example 631, 5-chloro-2-((1-(3-fluorobenzyl)-1H-indol-5-yl)amino)nicotinic acid was obtained from methyl 5-chloro-2-((1-(3-fluorobenzyl)-1H-indol-5-yl)amino)nicotinate.

$^1$H-NMR (DMSO-d$_6$) δ: 5.44 (2H, s), 6.47 (1H, d, J=3.2 Hz), 6.98-7.04 (2H, m), 7.05-7.11 (1H, m), 7.16-7.20 (1H, m), 7.32-7.42 (2H, m), 7.52 (1H, d, J=2.7 Hz), 7.89-7.92

(1H, m), 8.16 (1H, dd, J=3.9, 1.0 Hz), 8.35 (1H, d, J=2.7 Hz), 10.20 (1H, s), 13.86 (1H, brs).

MS (ESI, m/z): 397 (M+H)⁺, 395 (M−H)⁻.

Example 646

[Formula 893]

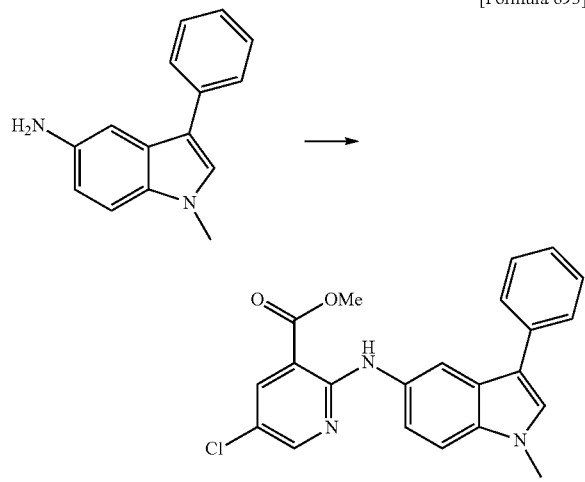

The mixture of 89 mg of 1-methyl-3-phenyl-1H-indol-5-amine, 80 mg of methyl 2,5-dichloronicotinate, 17 mg of tris(dibenzylideneacetone)dipalladium(0), 23 mg of 4,5'-bis(diphenylphosphino)-9,9'-dimethylxanthene, 253 mg of cesium carbonate, and 3 mL of butyl acetate, was heated at reflux for four hours under a nitrogen atmosphere. The reaction mixture was cooled to room temperature and then purified by silica gel column chromatography (gradient elution with hexane:ethyl acetate=100:0-30:70), and methanol was added to the obtained residue, and the solid was collected by filtration to give 80 mg of methyl 5-chloro-2-((1-methyl-3-phenyl-1H-indol-5-yl)amino)nicotinate as a yellow solid.

Example 647

[Formula 894]

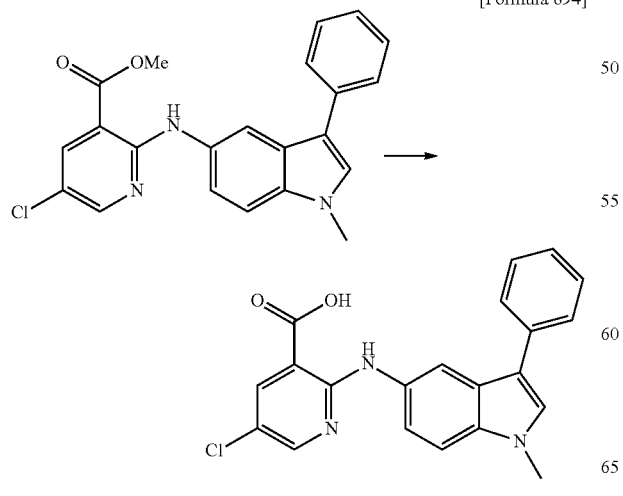

By the method similar to that of Example 631, 5-chloro-2-((1-methyl-3-phenyl-1H-indol-5-yl)amino)nicotinic acid was obtained from methyl 5-chloro-2-((1-methyl-3-phenyl-1H-indol-5-yl)amino)nicotinate.

¹H-NMR (DMSO-d₆) δ: 3.84 (3H, s), 7.20-7.25 (1H, m), 7.33 (1H, dd, J=8.9, 1.8 Hz), 7.41-7.48 (3H, m), 7.62-7.67 (2H, m), 7.67 (1H, s), 8.15-8.18 (2H, m), 8.34 (1H, d, J=2.7 Hz), 10.23 (1H, s).

MS (ESI, m/z): 379 (M+H)⁺, 377 (M−H)⁻.

Next, utility of representative compounds of the present invention will be described with reference to the following Test Examples.

Test Example 1

Cell Proliferation Inhibition Test $2 \times 10^3$ normal human neonatal foreskin epidermal keratinocytes (NHEK-F) (Kurabo, KK-4009) were suspended in 100 µL of Humedia-EG2 (Kurabo, KK-2150S) medium, plated in a 96-well plate and incubated overnight. The test compound was added on the following day and the cells were incubated for further three days. The cell count was determined using ATPlite (PerkinElmer, 6016739) or CellTiterGlo (Promega, G7573).

The inhibition rate was calculated from the following formula to determine the concentration of the compound at which the cell count is reduced by 50% ($IC_{50}$).

Inhibition rate (%)=100−(cell count in the presence of test compound/cell count in the absence of test compound)×100

The results are shown in Tables 1-1, 1-2 and 1-3.
Abbreviations in the tables have the following meanings.
A: $IC_{50} \leq 10$ nmol/L
B: 10 nmol/L$<IC_{50} \leq 100$ nmol/L
C: 100 nmol/L$<IC_{50} \leq 1000$ nmol/L

TABLE 1-1

| Example No. | |
|---|---|
| 2 | A |
| 4 | C |
| 6 | B |
| 9 | B |
| 11 | B |
| 14 | A |
| 17 | A |
| 19 | A |
| 21 | A |
| 25 | B |
| 27 | A |
| 29 | A |
| 32 | A |
| 35 | A |
| 37 | A |
| 39 | A |
| 41 | B |
| 43 | B |
| 45 | B |
| 47 | A |
| 49 | B |
| 59 | A |
| 61 | B |
| 65 | C |
| 67 | B |
| 69 | C |
| 71 | A |
| 73 | A |
| 75 | A |
| 78 | B |
| 80 | B |

TABLE 1-1-continued

| Example No. | |
|---|---|
| 82 | B |
| 84 | A |
| 86 | C |
| 88 | B |
| 90 | B |
| 94 | A |
| 96 | B |
| 98 | B |
| 100 | C |
| 102 | B |
| 104 | A |
| 107 | B |
| 108 | B |
| 110 | B |
| 112 | A |
| 114 | A |
| 116 | A |
| 121 | C |
| 123 | B |
| 125 | B |
| 126 | A |
| 129 | C |
| 130 | A |
| 132 | B |
| 133 | A |
| 137 | B |
| 138 | A |
| 142 | B |
| 146 | B |
| 148 | C |
| 149 | B |
| 153 | B |
| 156 | C |
| 157 | C |
| 158 | B |
| 159 | B |
| 166 | C |
| 170 | B |
| 175 | C |
| 177 | A |
| 179 | A |
| 181 | A |
| 183 | B |
| 185 | A |
| 187 | A |
| 189 | A |
| 191 | A |
| 194 | A |
| 196 | B |
| 198 | A |
| 202 | A |
| 204 | B |
| 206 | A |
| 208 | B |
| 210 | B |
| 218 | B |
| 222 | A |
| 224 | A |
| 227 | B |
| 229 | B |
| 231 | A |
| 233 | A |
| 237 | B |
| 239 | A |
| 241 | A |
| 249 | A |
| 251 | B |
| 255 | B |
| 257 | A |
| 269 | A |
| 271 | B |
| 275 | A |
| 277 | A |
| 281 | C |
| 283 | A |
| 296 | B |
| 298 | A |
| 300 | B |
| 302 | B |
| 311 | A |
| 313 | C |
| 315 | B |
| 317 | A |
| 319 | B |
| 331 | A |
| 333 | A |
| 335 | A |
| 337 | A |
| 339 | A |

TABLE 1-2

| Example No. | |
|---|---|
| 341 | B |
| 347 | B |
| 349 | C |
| 354 | B |
| 357 | B |
| 359 | B |
| 361 | B |
| 363 | A |
| 367 | A |
| 369 | C |
| 371 | C |
| 373 | A |
| 375 | A |
| 377 | B |
| 379 | B |
| 381 | B |
| 387 | B |
| 389 | C |
| 391 | C |
| 393 | B |
| 395 | B |
| 399 | C |
| 401 | C |
| 405 | B |
| 409 | B |
| 411 | B |
| 413 | B |
| 414 | B |
| 419 | B |
| 423 | B |
| 427 | B |
| 429 | A |
| 431 | A |
| 433 | A |
| 435 | B |
| 437 | B |
| 439 | A |
| 448 | A |
| 449 | B |
| 450 | A |
| 451 | B |
| 452 | B |
| 453 | B |
| 454 | B |
| 455 | A |
| 456 | A |
| 457 | A |
| 458 | A |
| 459 | A |
| 460 | A |
| 461 | A |
| 463 | A |
| 464 | A |
| 465 | A |
| 466 | A |
| 467 | B |
| 468 | B |
| 469 | A |
| 470 | A |

TABLE 1-2-continued

| Example No. | |
|---|---|
| 471 | A |
| 473 | B |
| 475 | C |
| 476 | A |
| 477 | A |
| 478 | A |
| 479 | A |
| 480 | A |
| 481 | A |
| 482 | A |
| 483 | A |
| 484 | A |
| 485 | A |
| 486 | A |
| 487 | A |
| 488 | A |
| 489 | A |
| 490 | A |
| 491 | A |
| 492 | A |
| 493 | A |
| 496 | B |
| 497 | A |
| 498 | A |
| 499 | A |
| 500 | B |
| 504 | A |
| 505 | A |
| 506 | A |
| 508 | A |
| 509 | A |
| 510 | A |
| 511 | A |
| 519 | B |
| 521 | A |
| 523 | A |
| 525 | A |
| 527 | A |
| 529 | B |
| 531 | B |
| 533 | C |
| 535 | A |
| 537 | A |
| 539 | A |
| 541 | B |
| 543 | A |
| 545 | A |
| 547 | B |
| 549 | A |
| 550 | B |
| 552 | A |
| 554 | A |
| 557 | B |
| 559 | B |
| 561 | B |
| 563 | B |
| 565 | A |
| 567 | B |
| 569 | C |
| 571 | B |
| 573 | A |
| 575 | B |
| 577 | C |
| 579 | C |
| 581 | B |
| 583 | B |
| 585 | A |

TABLE 1-3

| Example No. | |
|---|---|
| 586 | A |
| 587 | A |
| 588 | A |
| 589 | B |
| 590 | A |
| 591 | C |
| 593 | A |
| 594 | A |
| 595 | A |
| 596 | A |
| 597 | A |
| 598 | B |
| 603 | B |
| 604 | B |
| 605 | B |
| 607 | A |
| 608 | A |
| 609 | A |
| 610 | A |
| 612 | B |
| 614 | B |
| 616 | B |
| 618 | A |
| 619 | A |
| 621 | A |
| 623 | B |
| 625 | B |
| 627 | B |
| 629 | A |
| 630 | C |
| 632 | A |
| 633 | A |
| 634 | A |
| 635 | A |
| 636 | B |
| 637 | B |
| 638 | B |
| 639 | A |
| 640 | B |
| 641 | A |
| 642 | A |
| 643 | A |
| 645 | B |
| 647 | B |

The compounds of the present invention exhibited the excellent effect of inhibiting cell proliferation.

Test Example 2

TNFα Production Inhibition Test $7 \times 10^4$ mouse macrophage-derived cell line Raw264.7 cells were suspended in 100 μL of RPMI1640 medium containing 10% fetal bovine serum, plated in a 96-well plate and incubated overnight. The culture supernatant was removed and the test compound diluted in RPMI1640 medium containing 1% fetal bovine serum (final concentration: 1 μmol/L) was added. One hour after the addition, LPS (B4:0111) (Sigma-Aldrich, L2630) was added to a final concentration of 1 μg/mL. 16 hours after the stimulation, the culture supernatant was collected and the amount of TNFα produced in the culture supernatant was determined using ELISA kit (R&D Systems, MTA00B).

The inhibition rate was calculated from the following formula.

Inhibition rate (%)=100−(amount of TNFα produced in the presence of test compound/amount of TNFα produced in the absence of test compound)×100

The compounds of Example 2, Example 11, Example 14, Example 17, Example 21, Example 27, Example 29, Example 32, Example 35, Example 37, Example 39, Example 59, Example 61, Example 63, Example 65, Example 67, Example 69, Example 71, Example 73, Example 75, Example 78, Example 80, Example 82, Example 84, Example 90, Example 94, Example 96, Example 98, Example 102, Example 104, Example 106-1, Example 106-2, Example 107, Example 108, Example 110, Example 112, Example 194, Example 196, Example 198, Example 202, Example 255, Example 265, Example 267, Example 269, Example 275, Example 277, Example 281, Example 283, Example 287, Example 298, Example 300, Example 331, Example 333, Example 335, Example 337, Example 339, Example 354, Example 357, Example 361, Example 363, Example 373 and Example 375 inhibited the production of TNFα by 50% or more at 1 µmol/L.

The compounds of the present invention were highly effective in inhibiting the production of TNFα.

Test Example 3

Mouse TPA-Induced Ear-Swelling Model

Seven-week-old female Balb/c mice (Charles River Laboratories Japan) were used. 20 µL of a 20 ng/mL solution of TPA (Wako Pure Chemical Industries, 162-23591) dissolved in 5% DMSO/acetone was applied to the outer side of the mouse ear on day 0, day 2, day 4, day 7 and day 9 to induce ear edema and acanthosis. The test compound was dissolved in a 5% DMSO/acetone solution (concentration: 1% w/v) and 20 µL of the resulting solution was applied to the outer side of the ear once a day from day 0 to day 9. For the control group, a 5% DMSO/acetone solution was similarly applied. The TPA solution and the test compound solution were mixed and applied on the days for TPA application (day 0, day 2, day 4, day 7 and day 9). The ear thickness was chronologically measured on days 0-4 and days 7-10 using a micrometer (Mitutoyo, MDC-25MJT). The change in ear thickness and the inhibition rate were determined by the following formulas.

Change in ear thickness=(ear thickness measured on day 10)−(ear thickness measured on day 0 before TPA application)

Inhibition rate (%)=100−(change in ear thickness for test compound group/change in ear thickness for control group)×100

The inhibition rate on day 10 was 20% or more for the compounds of Example 29, Example 32, Example 35, Example 37, Example 39, Example 71, Example 75, Example 90, Example 94, Example 126, Example 128, Example 130, Example 133, Example 138, Example 142, Example 149, Example 153, Example 189, Example 206, Example 208, Example 222, Example 224, Example 233, Example 237, Example 239, Example 241, Example 275, Example 411, Example 439, Example 448, Example 450, Example 453, Example 455, Example 456, Example 457, Example 458, Example 460, Example 464, Example 466, Example 468, Example 470, Example 482, Example 484, Example 485, Example 497, Example 523, Example 543, Example 557, Example 565, Example 585, Example 588, Example 595, Example 596, Example 597, Example 598, Example 619, Example 621, Example 632, Example 633, Example 635, Example 637, Example 638, Example 639, Example 641 and Example 642.

It was shown that the compounds of the present invention have the effect of reducing ear thickness and therefore are useful for treatment such as prevention or therapy of psoriasis.

INDUSTRIAL APPLICABILITY

The novel amine derivatives or the salts thereof according to the present invention are useful for treatment such as prevention or therapy of the diseases involved in the overproliferation of keratinocytes or overproduction of TNFα, because they are highly effective in inhibiting the proliferation of keratinocytes and highly effective in inhibiting the production of TNFα.

The invention claimed is:

1. A compound of formula (1) or a salt thereof:

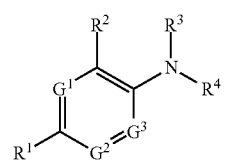

(1)

wherein
$G^1$, $G^2$ and $G^3$ are identical or different and are CH or a nitrogen atom;
$R^1$ is a chlorine atom, a bromine atom, an iodine atom, an unsubstituted or substituted $C_{1-6}$ alkyl group, an unsubstituted or substituted $C_{3-8}$ cycloalkyl group, an unsubstituted or substituted aryl group, an unsubstituted or substituted $C_{1-6}$ alkoxy group, an unsubstituted or substituted aryloxy group, an unsubstituted or substituted $C_{1-6}$ alkylthio group, an unsubstituted or substituted arylthio group, an unsubstituted or substituted $C_{1-6}$ alkylamino group, an unsubstituted or substituted di($C_{1-6}$ alkyl)amino group or an unsubstituted or substituted heterocyclic group;
$R^2$ is —COOR$^5$ wherein $R^5$ is a hydrogen atom or a carboxyl protecting group, or —C(O)N(R$^6$)SO$_2$R$^7$ wherein $R^6$ is a hydrogen atom, an ar-$C_{1-6}$ alkyl group, a $C_{1-6}$ alkoxy-$C_{1-6}$ alkyl group, an acyl group, a $C_{1-6}$ alkoxycarbonyl group, an ar-$C_{1-6}$ alkoxycarbonyl group, an aryloxycarbonyl group, a $C_{1-6}$ alkylsulfonyl group, an arylsulfonyl group or a silyl group; and $R^7$ is an unsubstituted or substituted $C_{1-6}$ alkyl group or an unsubstituted or substituted $C_{3-8}$ cycloalkyl group;
$R^3$ is a hydrogen atom, an ar-$C_{1-6}$ alkyl group, a $C_{1-6}$ alkoxy-$C_{1-6}$ alkyl group, an acyl group, a $C_{1-6}$ alkoxycarbonyl group, an ar-$C_{1-6}$ alkoxycarbonyl group, an aryloxycarbonyl group, a $C_{1-6}$ alkylsulfonyl group, an arylsulfonyl group or a silyl group; and
$R^4$ is an unsubstituted or substituted naphthyl group, an unsubstituted or substituted fused tricyclic hydrocarbon ring group, an unsubstituted or substituted bicyclic heterocyclic group or an unsubstituted or substituted tricyclic heterocyclic group,
provided that
when $R^4$ is an unsubstituted or substituted naphthyl group, then $G^3$ is a nitrogen atom; and
when $G^1$ is CH, $G^2$ is CH, $G^3$ is CH, $R^1$ is a chlorine atom, a bromine atom, an iodine atom, a $C_{1-4}$ alkyl group, a trifluoromethyl group, a dibutylamino group, a methoxy group or a substituted phenyloxy group, $R^2$ is —COOH and $R^3$ is a hydrogen atom, then $R^4$ is a group of any one of formulas (2-1) to (2-4):

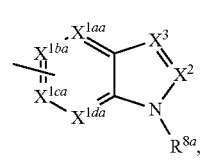

(2-1)

-continued

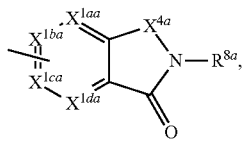
(2-2)

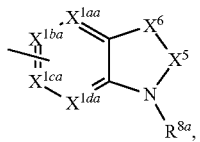
(2-3)

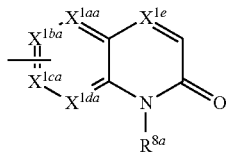
(2-4)

wherein
$X^{1aa}$, $X^{1ba}$, $X^{1ca}$, $X^{1da}$ and $X^{1e}$ are identical or different and are $CR^{9a}$ wherein $R^{9a}$ is a hydrogen atom, a halogen atom, an unsubstituted or substituted $C_{1-6}$ alkyl group, an unsubstituted or substituted $C_{3-8}$ cycloalkyl group or an unsubstituted or substituted aryl group, or a nitrogen atom;
$X^2$ is $CR^{10}$ wherein $R^{10}$ is a hydrogen atom, an unprotected or protected carboxyl group, an unsubstituted or substituted carbamoyl group, an unsubstituted or substituted $C_{1-6}$ alkyl group or an unsubstituted or substituted aryl group, or a nitrogen atom;
$X^3$ is $CR^{11}$ wherein $R^{11}$ is a hydrogen atom, an unsubstituted or substituted $C_{1-6}$ alkyl group, an unsubstituted or substituted $C_{3-8}$ cycloalkyl group, an unsubstituted or substituted aryl group, an unsubstituted or substituted ar-$C_{1-6}$ alkyl group or an unsubstituted or substituted acyl group, or a nitrogen atom;
$X^4$ is $CH_2$, $CH_2$—$CH_2$, C=O, an oxygen atom or a sulfur atom;
$X^5$ is $CH_2$ or C=O;
$X^6$ is $CH_2$, $CH_2$—$CH_2$, C=O, $NR^{12}$ wherein $R^{12}$ is a hydrogen atom, an ar-$C_{1-6}$ alkyl group, a $C_{1-6}$ alkoxy-$C_{1-6}$ alkyl group, an acyl group, a $C_{1-6}$ alkoxycarbonyl group, an ar-$C_{1-6}$ alkoxycarbonyl group, an aryloxycarbonyl group, a $C_{1-6}$ alkylsulfonyl group, an arylsulfonyl group, a silyl group, an unsubstituted or substituted $C_{1-6}$ alkyl group, an unsubstituted or substituted $C_{3-8}$ cycloalkyl group or an unsubstituted or substituted $C_{3-8}$ cycloalkyl-$C_{1-6}$ alkyl group, an oxygen atom or a sulfur atom; and
$R^{8a}$ is an unsubstituted or substituted $C_{3-6}$ alkyl group, an unsubstituted or substituted $C_{3-8}$ cycloalkyl group, an unsubstituted or substituted $C_{3-8}$ cycloalkyl-$C_{1-6}$ alkyl group, an unsubstituted or substituted aryl group, an unsubstituted or substituted ar-$C_{1-6}$ alkyl group, an unsubstituted or substituted acyl group, an unsubstituted or substituted heterocyclic group or an unsubstituted or substituted heterocyclic $C_{1-6}$ alkyl group.

2. The compound of claim 1,
wherein $R^1$ is a chlorine atom, a bromine atom, an unsubstituted or substituted $C_{1-6}$ alkyl group, an unsubstituted or substituted $C_{3-8}$ cycloalkyl group, an unsubstituted or substituted aryl group, an unsubstituted or substituted aryloxy group, an unsubstituted or substituted $C_{1-6}$ alkylthio group or an unsubstituted or substituted heterocyclic group, or a salt thereof.

3. The compound of claim 1,
wherein $R^1$ is a chlorine atom, a bromine atom, a $C_{1-6}$ alkyl group, a $C_{3-8}$ cycloalkyl group, an aryl group, an unsubstituted aryloxy group, an aryloxy group substituted with a methylsulfonyl group, a $C_{1-6}$ alkylthio group or a heterocyclic group,
or a salt thereof.

4. The compound of claim 1,
wherein $R^2$ is COOH,
or a salt thereof.

5. The compound of claim 1,
wherein $R^3$ is a hydrogen atom,
or a salt thereof.

6. The compound of claim 1,
wherein $R^4$ is an unsubstituted or substituted bicyclic heterocyclic group,
or a salt thereof.

7. The compound of claim 1,
wherein $R^1$ is a chlorine atom or a $C_{3-8}$ cycloalkyl group,
or a salt thereof.

8. The compound of claim 1,
wherein $R^4$ is a group of any one of formulas (3-1) to (3-3):

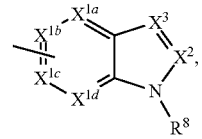
(3-1)

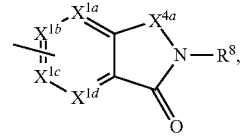
(3-2)

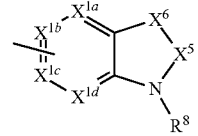
(3-3)

wherein
$X^{1a}$, $X^{1b}$, $X^{1c}$ and $X^{1d}$ are identical or different and are $CR^9$ wherein $R^9$ is a hydrogen atom, a halogen atom, an unsubstituted or substituted $C_{1-6}$ alkyl group, an unsubstituted or substituted $C_{2-6}$ alkenyl group, an unsubstituted or substituted $C_{3-8}$ cycloalkyl group, an unsubstituted or substituted $C_{4-8}$ cycloalkenyl group, an unsubstituted or substituted $C_{3-8}$ cycloalkyl-$C_{1-6}$ alkyl group or an unsubstituted or substituted aryl group, or a nitrogen atom;
$X^2$ is $CR^{10}$ wherein $R^{10}$ is a hydrogen atom, an unprotected or protected carboxyl group, an unsubstituted or substituted carbamoyl group, an unsubstituted or substituted $C_{1-6}$ alkyl group or an unsubstituted or substituted aryl group, or a nitrogen atom;
$X^3$ is $CR^{11}$ wherein $R^{11}$ is a hydrogen atom, an unsubstituted or substituted $C_{1-6}$ alkyl group, an unsubstituted or substituted $C_{3-8}$ cycloalkyl group, an unsubstituted or substituted aryl group, an unsubstituted or substituted ar-$C_{1-6}$ alkyl group or an unsubstituted or substituted acyl group, or a nitrogen atom;

$X^{4a}$ is $CH_2$, $CH_2$—$CH_2$ or C=O;

$X^5$ is $CH_2$ or C=O;

$X^6$ is $CH_2$, $CH_2$—$CH_2$, C=O, $NR^{12}$ wherein $R^{12}$ is a hydrogen atom, an ar-$C_{1-6}$ alkyl group, a $C_{1-6}$ alkoxy-$C_{1-6}$ alkyl group, an acyl group, a $C_{1-6}$ alkoxycarbonyl group, an ar-$C_{1-6}$ alkoxycarbonyl group, an aryloxycarbonyl group, a $C_{1-6}$ alkylsulfonyl group, an arylsulfonyl group, a silyl group, an unsubstituted or substituted $C_{1-6}$ alkyl group, an unsubstituted or substituted $C_{3-8}$ cycloalkyl group or an unsubstituted or substituted $C_{3-8}$ cycloalkyl-$C_{1-6}$ alkyl group, an oxygen atom or a sulfur atom; and $R^8$ is a hydrogen atom, an unsubstituted or substituted $C_{1-6}$ alkyl group, an unsubstituted or substituted $C_{3-8}$ cycloalkyl group, an unsubstituted or substituted $C_{3-8}$ cycloalkyl-$C_{1-6}$ alkyl group, an unsubstituted or substituted aryl group, an unsubstituted or substituted ar-$C_{1-6}$ alkyl group, an unsubstituted or substituted acyl group, an unsubstituted or substituted heterocyclic group or an unsubstituted or substituted heterocyclic $C_{1-6}$ alkyl group, provided that when $G^1$ is CH, $G^2$ is CH, $G^3$ is CH, $R^1$ is a chlorine atom, a bromine atom, an iodine atom, a $C_{1-4}$ alkyl group, a trifluoromethyl group, a dibutylamino group, a methoxy group or a substituted phenyloxy group, $R^2$ is —COOH and $R^3$ is a hydrogen atom, then $R^4$ is a group of any one of formulas (3-1a) to (3-3a):

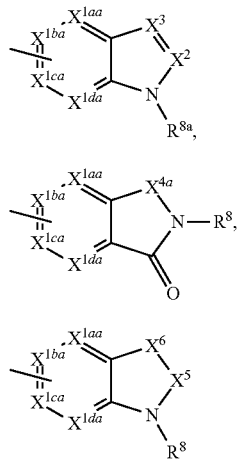

(3-1a)

(3-2a)

(3-3a)

wherein $X^{1aa}$, $X^{1ba}$, $X^{1ca}$ and $X^{1da}$ are identical or different and are $CR^{9a}$ wherein $R^{9a}$ is a hydrogen atom, a halogen atom, an unsubstituted or substituted $C_{1-6}$ alkyl group, an unsubstituted or substituted $C_{3-8}$ cycloalkyl group or an unsubstituted or substituted aryl group, or a nitrogen atom;

$X^2$ is $CR^{10}$ wherein $R^{10}$ is a hydrogen atom, an unprotected or protected carboxyl group, an unsubstituted or substituted carbamoyl group, an unsubstituted or substituted $C_{1-6}$ alkyl group or an unsubstituted or substituted aryl group, or a nitrogen atom;

$X^3$ is $CR^{11}$ wherein $R^{11}$ is a hydrogen atom, an unsubstituted or substituted $C_{1-6}$ alkyl group, an unsubstituted or substituted $C_{3-8}$ cycloalkyl group, an unsubstituted or substituted aryl group, an unsubstituted or substituted ar-$C_{1-6}$ alkyl group or an unsubstituted or substituted acyl group, or a nitrogen atom;

$X^5$ is $CH_2$ or C=O;

$X^6$ is $CH_2$, $CH_2$—$CH_2$, C=O, $NR^{12}$ wherein $R^{12}$ is a hydrogen atom, an ar-$C_{1-6}$ alkyl group, a $C_{1-6}$ alkoxy-$C_{1-6}$ alkyl group, an acyl group, a $C_{1-6}$ alkoxycarbonyl group, an ar-$C_{1-6}$ alkoxycarbonyl group, an aryloxycarbonyl group, a $C_{1-6}$ alkylsulfonyl group, an arylsulfonyl group, a silyl group, an unsubstituted or substituted $C_{1-6}$ alkyl group, an unsubstituted or substituted $C_{3-8}$ cycloalkyl group or an unsubstituted or substituted $C_{3-8}$ cycloalkyl-$C_{1-6}$ alkyl group, an oxygen atom or a sulfur atom;

$R^{8a}$ is an unsubstituted or substituted $C_{3-6}$ alkyl group, an unsubstituted or substituted $C_{3-8}$ cycloalkyl group, an unsubstituted or substituted $C_{3-8}$ cycloalkyl-$C_{1-6}$ alkyl group, an unsubstituted or substituted aryl group, an unsubstituted or substituted ar-$C_{1-6}$ alkyl group, an unsubstituted or substituted acyl group, an unsubstituted or substituted heterocyclic group or an unsubstituted or substituted heterocyclic $C_{1-6}$ alkyl group; and $X^{4a}$ is $CH_2$, $CH_2$—$CH_2$ or C=O, or a salt thereof.

9. The compound of claim 1, wherein $R^4$ is a group of any one of formula (4-1) or (4-2):

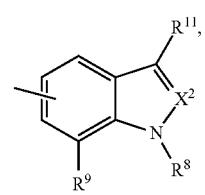

(4-1)

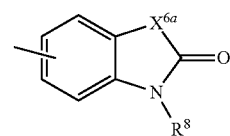

(4-2)

wherein $X^2$ is $CR^{10}$ wherein $R^{10}$ is a hydrogen atom, an unsubstituted or protected carboxyl group, an unsubstituted or substituted carbamoyl group, an unsubstituted or substituted $C_{1-6}$ alkyl group or an unsubstituted or substituted aryl group, or a nitrogen atom;

$X^{6a}$ is $CH_2$, C=O, $NR^{12}$ wherein $R^{12}$ is a hydrogen atom, an ar-$C_{1-6}$ alkyl group, a $C_{1-6}$ alkoxy-$C_{1-6}$ alkyl group, an acyl group, a $C_{1-6}$ alkoxycarbonyl group, an ar-$C_{1-6}$ alkoxycarbonyl group, an aryloxycarbonyl group, a $C_{1-6}$ alkylsulfonyl group, an arylsulfonyl group, a silyl group, an unsubstituted or substituted $C_{1-6}$ alkyl group, an unsubstituted or substituted $C_{3-8}$ cycloalkyl group or an unsubstituted or substituted $C_{3-8}$ cycloalkyl-$C_{1-6}$ alkyl group, an oxygen atom or a sulfur atom;

$R^8$ is a hydrogen atom, an unsubstituted or substituted $C_{1-6}$ alkyl group, an unsubstituted or substituted $C_{3-8}$ cycloalkyl group, an unsubstituted or substituted $C_{3-8}$ cycloalkyl-$C_{1-6}$ alkyl group, an unsubstituted or substituted aryl group, an unsubstituted or substituted ar-$C_{1-6}$ alkyl group, an unsubstituted or substituted acyl group, an unsubstituted or substituted heterocyclic group or an unsubstituted or substituted heterocyclic $C_{1-6}$ alkyl group;

$R^9$ is a hydrogen atom, a halogen atom, an unsubstituted or substituted $C_{1-6}$ alkyl group, an unsubstituted or substituted $C_{2-6}$ alkenyl group, an unsubstituted or substituted $C_{3-8}$ cycloalkyl group, an unsubstituted or substituted $C_{4-8}$ cycloalkenyl group, an unsubstituted or substituted $C_{3-8}$ cycloalkyl-$C_{1-6}$ alkyl group or an unsubstituted or substituted aryl group; and $R^{11}$ is a hydrogen atom, an unsubstituted or substituted $C_{1-6}$ alkyl group, an unsubstituted or substituted $C_{3-8}$ cycloalkyl group, an unsubstituted or substituted aryl group, an unsubstituted or substituted ar-$C_{1-6}$ alkyl group or an unsubstituted or substituted acyl group, provided that when $G^1$ is CH, $G^2$ is CH, $G^3$ is CH, $R^1$ is a chlorine atom, a bromine atom, an iodine atom, a $C_{1-4}$ alkyl group, a trifluoromethyl group, a dibutylamino group, a methoxy group or a substituted phenyloxy group, $R^2$ is —COOH and $R^3$ is a hydrogen atom, then $R^4$ is a group of formula (4-1a) or (4-2a):

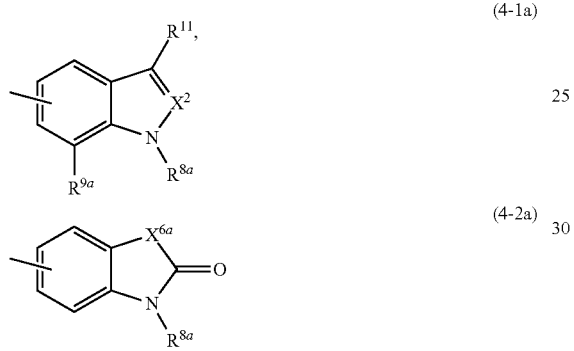

wherein $R^{8a}$ is an unsubstituted or substituted $C_{3-6}$ alkyl group, an unsubstituted or substituted $C_{3-8}$ cycloalkyl group, an unsubstituted or substituted $C_{3-8}$ cycloalkyl-$C_{1-6}$ alkyl group, an unsubstituted or substituted aryl group, an unsubstituted or substituted ar-$C_{1-6}$ alkyl group, an unsubstituted or substituted acyl group, an unsubstituted or substituted heterocyclic group or an unsubstituted or substituted heterocyclic $C_{1-6}$ alkyl group;

$R^{9a}$ is a hydrogen atom, a halogen atom, an unsubstituted or substituted $C_{1-6}$ alkyl group, an unsubstituted or substituted $C_{3-8}$ cycloalkyl group or an unsubstituted or substituted aryl group;

$R^{11}$ is a hydrogen atom, an unsubstituted or substituted $C_{1-6}$ alkyl group, an unsubstituted or substituted $C_{3-8}$ cycloalkyl group, an unsubstituted or substituted aryl group, an unsubstituted or substituted ar-$C_{1-6}$ alkyl group or an unsubstituted or substituted acyl group;

$X^2$ is $CR^{10}$ wherein $R^{10}$ is a hydrogen atom, an unprotected or protected carboxyl group, an unsubstituted or substituted carbamoyl group, an unsubstituted or substituted $C_{1-6}$ alkyl group or an unsubstituted or substituted aryl group, or a nitrogen atom;

$X^{4a}$ is $CH_2$, $CH_2$—$CH_2$ or C=O; and $X^{6a}$ is $CH_2$, C=O, $NR^{12}$ wherein $R^{12}$ is a hydrogen atom, an ar-$C_{1-6}$ alkyl group, a $C_{1-6}$ alkoxy-$C_{1-6}$ alkyl group, an acyl group, a $C_{1-6}$ alkoxycarbonyl group, an ar-$C_{1-6}$ alkoxycarbonyl group, an aryloxycarbonyl group, a $C_{1-6}$ alkylsulfonyl group, an arylsulfonyl group, a silyl group, an unsubstituted or substituted $C_{1-6}$ alkyl group, an unsubstituted or substituted $C_{3-8}$ cycloalkyl group or an unsubstituted or substituted $C_{3-8}$ cycloalkyl-$C_{1-6}$ alkyl group, an oxygen atom or a sulfur atom, or a salt thereof.

10. The compound of claim 1, wherein $G^1$ and $G^2$ are CH; $G^3$ is a nitrogen atom; and $R^4$ is a group of (5-1):

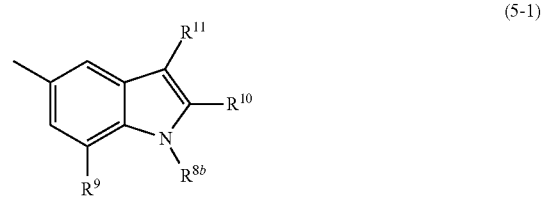

wherein $R^{8b}$ is an unsubstituted or substituted $C_{1-6}$ alkyl group, an unsubstituted or substituted $C_{3-8}$ cycloalkyl group, an unsubstituted or substituted $C_{3-8}$ cycloalkyl-$C_{1-6}$ alkyl group, an unsubstituted or substituted aryl group or an unsubstituted or substituted ar-$C_{1-6}$ alkyl group;

$R^9$ is a hydrogen atom, a halogen atom, an unsubstituted or substituted $C_{1-6}$ alkyl group, an unsubstituted or substituted $C_{2-6}$ alkenyl group, an unsubstituted or substituted $C_{3-8}$ cycloalkyl group, an unsubstituted or substituted $C_{4-8}$ cycloalkenyl group, an unsubstituted or substituted $C_{3-8}$ cycloalkyl-$C_{1-6}$ alkyl group or an unsubstituted or substituted aryl group;

$R^{10}$ is a hydrogen atom, an unprotected or protected carboxyl group, an unsubstituted or substituted carbamoyl group, an unsubstituted or substituted $C_{1-6}$ alkyl group or an unsubstituted or substituted aryl group; and $R^{11}$ is a hydrogen atom, an unsubstituted or substituted $C_{1-6}$ alkyl group, an unsubstituted or substituted $C_{3-8}$ cycloalkyl group, an unsubstituted or substituted aryl group, an unsubstituted or substituted ar-$C_{1-6}$ alkyl group or an unsubstituted or substituted acyl group, or a salt thereof.

11. The compound of claim 1, wherein $G^1$ and $G^2$ are CH; $G^3$ is a nitrogen atom; and $R^4$ is a group of formula (5-1a):

wherein $R^{8b}$ is an unsubstituted or substituted $C_{1-6}$ alkyl group, an unsubstituted or substituted $C_{3-8}$ cycloalkyl group, an unsubstituted or substituted $C_{3-8}$ cycloalkyl-$C_{1-6}$ alkyl group, an unsubstituted or substituted aryl group or an unsubstituted or substituted ar-$C_{1-6}$ alkyl group, or a salt thereof.

12. The compound of claim 1, wherein $G^1$ and $G^2$ are CH; $G^3$ is a nitrogen atom; and $R^4$ is a group of formula (5-1b):

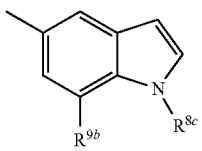

(5-1b)

wherein

R^{8c} is an unsubstituted or substituted $C_{1-6}$ alkyl group; and
R^{9b} is an unsubstituted or substituted $C_{1-6}$ alkyl group, an unsubstituted or substituted $C_{3-8}$ cycloalkyl group, an unsubstituted or substituted $C_{3-8}$ cycloalkyl-$C_{1-6}$ alkyl group or an unsubstituted or substituted aryl group,
or a salt thereof.

13. The compound of claim 1,
wherein $G^1$ and $G^2$ are CH; $G^3$ is a nitrogen atom; and $R^4$ is a group of (5-1c):

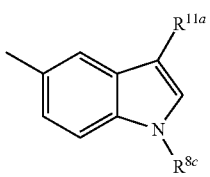

(5-1c)

wherein
R^{8c} is an unsubstituted or substituted $C_{1-6}$ alkyl group; and
R^{11a} is an unsubstituted or substituted aryl group,
or a salt thereof.

14. The compound of claim 1,
wherein the compound is at least one selected from the group consisting of 5-cyclopropyl-2-((1-(3-fluorobenzyl)-1H-indol-5-yl)amino)nicotinic acid, 5-cyclopropyl-2-((1-(2-fluorobenzyl)-1H-indol-5-yl)amino)nicotinic acid, 5-cyclopropyl-2-(1-methyl-3-phenyl-1H-indol-5-yl)amino)nicotinic acid, 5-cyclopropyl-2-((1-methyl-7-phenyl-1H-indol-5-yl)amino)nicotinic acid, 2-((7-(2-cyanophenyl)-1-methyl-1H-indol-5-yl)amino)-5-cyclopropylnicotinic acid, 2-((1-benzyl-1H-indol-5-yl)amino)-5-cyclopropylnicotinic acid, 5-cyclopropyl-2-((1-ethyl-2-phenyl-1H-indol-5-yl)amino)nicotinic acid, 5-cyclopropyl-2-(1-isopentyl-1H-indol-5-ylamino)nicotinic acid, 2-((1-(cyclohexylmethyl)-1H-indol-5-yl)amino)-5-cyclopropylnicotinic acid, 2-((1-(cyclobutylmethyl)-1H-indol-5-yl)amino)-5-cyclopropylnicotinic acid, 2-((7-(4-cyanophenyl)-1-methyl-1H-indol-5-yl)amino)-5-cyclopropylnicotinic acid, 5-cyclopropyl-2-((7-(2-methoxyphenyl)-1-methyl-1H-indol-5-yl)amino)nicotinic acid, 5-cyclopropyl-2-((1-phenyl-1H-indol-5-yl)amino)nicotinic acid, 2-((1-(cyclopentylmethyl)-1H-indol-5-yl)amino)-5-cyclopropylnicotinic acid, 5-cyclopropyl-2-((1-(4-fluorobenzyl)-1H-indol-5-yl)amino)nicotinic acid, 5-cyclopropyl-2-((1-(3-(trifluoromethyl)benzyl)-1H-indol-5-yl)amino)nicotinic acid, 2-((1-(cyclohexylmethyl)-1H-indazol-5-yl)amino)-5-cyclopropylnicotinic acid, 5-cyclopropyl-2-((1-(4-fluorophenyl)-1H-indol-5-yl)amino)nicotinic acid, 2-((1-benzyl-1H-indol-5-yl)amino)-5-cyclopropylbenzoic acid, 3-((1-benzyl-1H-indol-5-yl)amino)-6-cyclopropylpyrazine-2-carboxylic acid, 5-cyclopropyl-2-((3-(2-fluorophenyl)-1-methyl-1H-indol-5-yl)amino)nicotinic acid, 5-cyclopropyl-2-((7-(4-fluorophenyl)-1-methyl-1H-indol-5-yl)amino)nicotinic acid, 2-((1-isobutyl-1H-indol-5-yl)amino)-5-cyclopropylnicotinic acid, 5-cyclopropyl-2-((7-(2-fluorophenyl)-1-methyl-1H-indol-5-yl)amino)nicotinic acid, 5-cyclopropyl-2-((7-(3-methoxypropyl)-1-methyl-1H-indol-5-yl)amino)nicotinic acid, 5-cyclopropyl-2-((7-(2-cyclopropylethyl)-1-methyl-1H-indol-5-yl)amino)nicotinic acid, 5-cyclopropyl-2-((7-isopropyl-1-methyl-1H-indol-5-yl)amino)nicotinic acid, 2-((1-benzyl-1H-indol-5-yl)amino)-5-cyclopropyl-N-(methylsulfonyl)nicotinamide, 2-((3-benzyl-2-oxo-2,3-dihydrobenzo[d]thiazol-6-yl)amino)-5-cyclopropylnicotinic acid and 2-((1-(cyclobutylmethyl)-1H-indol-4-yl)amino)-5-cyclopropylnicotinic acid,
or a salt thereof.

15. A pharmaceutical composition, comprising:
the compound of claim 1 or a salt thereof; and
a formulation aid selected from the group consisting of an excipient, a carrier, a diluent, and a combination thereof.

16. A compound of formula (1) or a salt thereof:

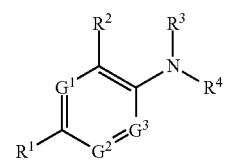

(1)

wherein
$G^1$, $G^2$ and $G^3$ are identical or different and are CH or a nitrogen atom;
$R^1$ is a chlorine atom, a bromine atom, an iodine atom, an unsubstituted or substituted $C_{1-6}$ alkyl group, an unsubstituted or substituted $C_{3-8}$ cycloalkyl group, an unsubstituted or substituted aryl group, an unsubstituted or substituted $C_{1-6}$ alkoxy group, an unsubstituted or substituted aryloxy group, an unsubstituted or substituted $C_{1-6}$ alkylthio group, an unsubstituted or substituted arylthio group, an unsubstituted or substituted $C_{1-6}$ alkylamino group, an unsubstituted or substituted di($C_{1-6}$ alkyl)amino group or an unsubstituted or substituted heterocyclic group;
$R^2$ is —COOH;
$R^3$ is a hydrogen atom, an ar-$C_{1-6}$ alkyl group, a $C_{1-6}$ alkoxy-$C_{1-6}$ alkyl group, an acyl group, a $C_{1-6}$ alkoxycarbonyl group, an ar-$C_{1-6}$ alkoxycarbonyl group, an aryloxycarbonyl group, a $C_{1-6}$ alkylsulfonyl group, an arylsulfonyl group, or a silyl group; and
$R^4$ is an unsubstituted or substituted fused bicyclic hydrocarbon ring group, an unsubstituted or substituted fused tricyclic hydrocarbon ring group, an unsubstituted or substituted bicyclic heterocyclic group or an unsubstituted or substituted tricyclic heterocyclic group,
provided that
when $R^4$ is an unsubstituted or substituted fused bicyclic hydrocarbon ring group, then $G^3$ is a nitrogen atom; and
when $G^1$ is CH, $G^2$ is CH, $G^3$ is CH, $R^1$ is a chlorine atom, a bromine atom, an iodine atom, a $C_{1-4}$ alkyl group, a trifluoromethyl group, a dibutylamino group, a methoxy group or a substituted phenyloxy group, $R^2$ is —COOH and $R^3$ is a hydrogen atom, then $R^4$ is a group of any one of formulas (2-1) to (2-4):

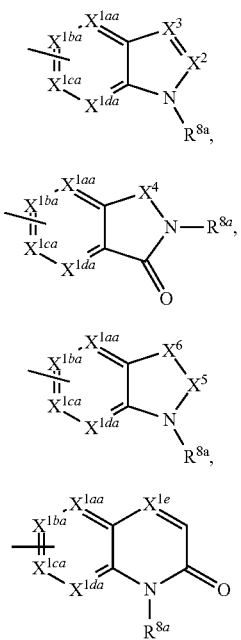

wherein
$X^{1aa}$, $X^{1ba}$, $X^{1ca}$, $X^{1da}$ and $X^{1c}$ are identical or different and are $CR^{9a}$ wherein $R^{9a}$ is a hydrogen atom, a halogen atom, an unsubstituted or substituted $C_{1-6}$ alkyl group, an unsubstituted or substituted $C_{3-8}$ cycloalkyl group or an unsubstituted or substituted aryl group, or a nitrogen atom;

$X^2$ is $CR^{10}$ wherein $R^{10}$ is a hydrogen atom, an unprotected or protected carboxyl group, an unsubstituted or substituted carbamoyl group, an unsubstituted or substituted $C_{1-6}$ alkyl group or an unsubstituted or substituted aryl group, or a nitrogen atom;

$X^3$ is $CR^{11}$ wherein $R^{11}$ is a hydrogen atom, an unsubstituted or substituted $C_{1-6}$ alkyl group, an unsubstituted or substituted $C_{3-8}$ cycloalkyl group, an unsubstituted or substituted aryl group, an unsubstituted or substituted ar-$C_{1-6}$ alkyl group or an unsubstituted or substituted acyl group, or a nitrogen atom;

$X^4$ is $CH_2$, $CH_2$—$CH_2$, $C$=$O$, an oxygen atom or a sulfur atom;

$X^5$ is $CH_2$ or $C$=$O$;

$X^6$ is $CH_2$, $CH_2$—$CH_2$, $C$=$O$, $NR^{12}$ wherein $R^{12}$ is a hydrogen atom, an ar-$C_{1-6}$ alkyl group, a $C_{1-6}$ alkoxy-$C_{1-6}$ alkyl group, an acyl group, a $C_{1-6}$ alkoxycarbonyl group, an ar-$C_{1-6}$ alkoxycarbonyl group, an aryloxycarbonyl group, a $C_{1-6}$ alkylsulfonyl group, an arylsulfonyl group, a silyl group, an unsubstituted or substituted $C_{1-6}$ alkyl group, an unsubstituted or substituted $C_{3-8}$ cycloalkyl group or an unsubstituted or substituted $C_{3-8}$ cycloalkyl-$C_{1-6}$ alkyl group, an oxygen atom or a sulfur atom; and $R^{8a}$ is an unsubstituted or substituted $C_{3-6}$ alkyl group, an unsubstituted or substituted $C_{3-8}$ cycloalkyl group, an unsubstituted or substituted $C_{3-8}$ cycloalkyl-$C_{1-6}$ alkyl group, an unsubstituted or substituted aryl group, an unsubstituted or substituted ar-$C_{1-6}$ alkyl group, an unsubstituted or substituted acyl group, an unsubstituted or substituted heterocyclic group or an unsubstituted or substituted heterocyclic $C_{1-6}$ alkyl group, or a salt thereof.

17. A method for inhibiting keratinocyte proliferation, comprising:
administering to a subject in need thereof the compound of claim 1 or a salt thereof.

18. A method for therapeutically treating a disease involved in overproliferation of keratinocytes, comprising:
administering to a subject in need thereof the compound of claim 1 or a salt thereof,
wherein the disease involved in overproliferation of keratinocytes is at least one of skin cancer, psoriasis, immunologic and allergic skin diseases, and chronic wound.

19. A method for inhibiting TNFα production, comprising:
administering to a subject in need thereof the compound of claim 1 or a salt thereof.

20. A method for therapeutically treating a disease involved in overproduction of TNFα, comprising:
administering to a subject in need thereof the compound of claim 1 or a salt thereof,
wherein the disease involved in overproduction of TNFα is at least one of septic shock, systemic lupus erythematosus, rheumatoid arthritis, psoriasis, inflammatory bowel disease, multiple sclerosis, ankylosing spondylitis, allergic disease, arteriosclerosis, insulin-resistant diabetes, graft-versus-host disease, viral hepatitis, and HIV infection.

* * * * *